(12) United States Patent
Luecke et al.

(10) Patent No.: US 7,083,961 B1
(45) Date of Patent: Aug. 1, 2006

(54) **CRYSTAL STRUCTURES OF *T. FOETUS* INOSINE MONOPHOSPHATE DEHYDROGENASE IN COMPLEX WITH SUBSTRATE, COFACTOR AND ANALOGS AND USES THEREOF**

(75) Inventors: Hartmut Luecke, Irvine, CA (US); Glen Prosise, Long Beach, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 10/663,347

(22) Filed: Sep. 15, 2003

Related U.S. Application Data

(60) Provisional application No. 60/410,523, filed on Sep. 13, 2002, provisional application No. 60/412,044, filed on Sep. 18, 2002.

(51) Int. Cl.
*C12N 9/02* (2006.01)
(52) U.S. Cl. .................. 435/189; 435/183; 536/28.7
(58) Field of Classification Search ............... 435/183, 435/189; 536/28.7
See application file for complete search history.

(56) References Cited

OTHER PUBLICATIONS

Prosise, G.L., Crystal Structure of *Tritrichomonas foetus* inosine monophosphate dehydrogenase in complex with the inhibitor ribavirin monophosphate reveals a catalysis-dependent ion-binding site. 2002. Jrnl of Biol Chem. 277(52):50654-59.*
Beck et al., "Cloning, sequencing, and structural analysis of the DNA encoding inosine monophosphate dehydrogenase (EC 1.1.1.205) from *Tritrichomonas foetus*," *Exp. Parasitol* 78(1):101-112 (1994).
Brunger et al., "Crystallography & NMR system: A new software suite for macromolecular structure determination," *Acta. Crystallogr D. Biol. Crystallogr.* 54 (Pt 5):905-21 (1998).
Chin et al., "Isolation, sequencing and expression of the gene encoding hypoxanthine-guanine-xanthine phosphoribosyltransferase of *Tritrichomonas foetus*," *Mol. Biochem. Parasitol.* 63(2):221-9 (1994).
Colby et al., "Crystal structure of human type II inosine monophosphate dehydrogenase: implications for ligand binding and drug design," *Proc. Natl. Acad. Sci. U S A* 96(7):3531-6 (1999).
Digits et al., "Kinetic mechanism of *Tritrichomonas foetus* inosine 5'-monophosphate dehydrogenase," *Biochemistry* 38(8):2295-306 (1999).
Digits et al., "Drug selectivity is determined by coupling across the NAD+ site of IMP dehydrogenase," *Biochemistry* 39(7):1771-7 (2000).

Hager et al., "Recombinant Human inosine monophosphate dehydrogenase type I and type II proteins. Purification and characterization of inhibitor binding," *Biochem Pharmacol.* 49(9):1323-9 1995.
Jones et al., "Improved methods for building protein models in electron density maps and the location of errors in these models," *Acta, Crytallogr A.* 47 (Pt 2):110-9 (1991).
Kerr et al., "Monovalent cation activation in *Escherichia coli* inosine 5'-monophosphate dehydrogenase,"*Arch. Biochem. Biophys.* 375(1):131-7 (2000).
Kuntz et al., "A geometric approach to macromolecule-ligand interactions," *J. Mol. Biol.* 161(2):269-88 (1982).
Laskowski et al., "Computer Programs," *J. App. Cryst.* 26:283-291 (1993).
Luecke et al., "*Tritrichomonas foetus* : a strategy for structure-based inhibitor design of a protozoan inosine-5'-monophosphate dehydrogenase," *Exp Parasitol.* 87(3):203-11 (1997).
Metz et al., "Inosine-5'-monophosphate dehydrogenase is required for mitogenic competence of transformed pancreatic beta cells", *Endocrinology* 142(1):193-204 (2001).
Schuller et al., "The allosteric ligand site in the Vmax-type cooperative enzyme phosphoglycerate dehydrogenase," *Nat. Struct. Biol.* 2(1):69-76(1995).
Sintchak et al., "Structure and mechanism of inosine monophospate dehydrogenase in complex with the immunosuppressant mycophenolic acid", *Cell.* 85(6):921-30 (1996).
Stehle et al., "Structure of NADH peroxidase from *Streptococcus faecalis* 10C1 refined at 2.16 A resolution", *J. Mol. Biol.* 221(4):1325-44 (1991).

(Continued)

*Primary Examiner*—Francisco C. Prats
*Assistant Examiner*—Susan E. Fernandez
(74) *Attorney, Agent, or Firm*—McDermott Will & Emery

(57) ABSTRACT

The invention provides a crystalline complex containing *T. foetus* IMPDH in complex with inosine monophosphate (IMP), the complex specified by disclosed atomic coordinates. Also provided are crystalline complexes of containing *T. foetus* IMPDH with both inosine monophosphate (IMP) and mycophenolic acid, with both xanthosine monophosphate (XMP) and mycophenolic acid, with both xanthosine monophosphate (XMP) and nicotinic adenine dinucleotide (NAD), with ribovirin (1-β-D-ribofuranosyl-1,2,4-triazole-3-carboxamide, and with both ribovirin and mycophenolic acid, each complex specified by disclosed atomic coordinates. Also provided by the invention are the atomic coordinates for these complexes. Further provided by the invention are methods for identifying modulations of IMPDH that employ the atomic coordinates of the invention.

2 Claims, 17 Drawing Sheets

OTHER PUBLICATIONS van Aalten et al, "PRODRG, a program for generating molecular topologies and unique molecular descriptors from coordinates of small molecules", *J. Comput. Aided Mol. Des.* 10(3):255-62 (1996).

Verham et al., "Purification, characterization, and kinetic analysis of inosine 5'-monophosphate dehydrogenase of *Tritrichomonas foetus*", *Mol Biochem Parasitol.* 24(1):1-12 (1987).

Whitby et al., "Crystal structure of *Tritrichomonas foetus* inosine-5'-monophosphate dehydrogenase and the enzyme-product complex", *Biochemistry.* 36(35):10666-74 (1997).

Wilson et al., "Amplification and molecular cloning of the IMP dehydrogenase gene of *Leishmania donovani*", *J. Biol. Chem.* 266(3):1665-71 (1991).

* cited by examiner

SEQUENCE LISTING

<160> NUMBER OF SEQ ID NOS: 2

<210> SEQ ID NO 1
<211> LENGTH: 503
<212> TYPE: PRT
<213> ORGANISM: Tritrichomonas foetus

<400> SEQUENCE: 1

```
Met Ala Lys Tyr Tyr Asn Glu Pro Cys His Thr Phe Asn Glu Tyr Leu
 1               5                   10                  15

Leu Ile Pro Gly Leu Ser Thr Val Asp Cys Ile Pro Ser Asn Val Asn
            20                  25                  30

Leu Ser Thr Pro Leu Val Lys Phe Gln Lys Gly Gln Gln Ser Glu Ile
        35                  40                  45

Asn Leu Lys Ile Pro Leu Val Ser Ala Ile Met Gln Ser Val Ser Gly
    50                  55                  60

Glu Lys Met Ala Ile Ala Leu Ala Arg Glu Gly Gly Ile Ser Phe Ile
65                  70                  75                  80

Phe Gly Ser Gln Ser Ile Glu Ser Gln Ala Ala Met Val His Ala Val
                85                  90                  95

Lys Asn Phe Lys Ala Gly Phe Val Val Ser Asp Ser Asn Val Lys Pro
            100                 105                 110
```

```
Asp Gln Thr Phe Ala Asp Val Leu Ala Ile Ser Gln Arg Thr Thr His
        115                 120                 125

Asn Thr Val Ala Val Thr Asp Asp Gly Thr Pro His Gly Val Leu Leu
130                 135                 140

Gly Leu Val Thr Gln Arg Asp Tyr Pro Ile Asp Leu Thr Gln Thr Glu
145                 150                 155                 160

Thr Lys Val Ser Asp Met Met Thr Pro Phe Ser Lys Leu Val Thr Ala
                165                 170                 175

His Gln Asp Thr Lys Leu Ser Glu Ala Asn Lys Ile Ile Trp Glu Lys
            180                 185                 190

Lys Leu Asn Ala Leu Pro Ile Ile Asp Asp Gln His Leu Arg Tyr
        195                 200                 205

Ile Val Phe Arg Lys Asp Tyr Asp Arg Ser Gln Val Cys His Asn Glu
        210                 215                 220

Leu Val Asp Ser Gln Lys Arg Tyr Leu Val Gly Ala Gly Ile Asn Thr
225                 230                 235                 240

Arg Asp Phe Arg Glu Arg Val Pro Ala Leu Val Glu Ala Gly Ala Asp
                245                 250                 255

Val Leu Cys Ile Asp Ser Ser Asp Gly Phe Ser Glu Trp Gln Lys Ile
                260                 265                 270

Thr Ile Gly Trp Ile Arg Glu Lys Tyr Gly Asp Lys Val Lys Val Gly
            275                 280                 285

Ala Gly Asn Ile Val Asp Gly Glu Gly Phe Arg Tyr Leu Ala Asp Ala
            290                 295                 300

Gly Ala Asp Phe Ile Lys Ile Gly Ile Gly Gly Ser Ile Cys Ile
305                 310                 315                 320

Thr Arg Glu Gln Lys Gly Ile Gly Arg Gly Gln Ala Thr Ala Val Ile
                325                 330                 335

Asp Val Val Ala Glu Arg Asn Lys Tyr Phe Glu Glu Thr Gly Ile Tyr
            340                 345                 350

Ile Pro Val Cys Ser Asp Gly Gly Ile Val Tyr Asp Tyr His Met Thr
        355                 360                 365

Leu Ala Leu Ala Met Gly Ala Asp Phe Ile Met Leu Gly Arg Tyr Phe
370                 375                 380

Ala Arg Phe Glu Glu Ser Pro Thr Arg Lys Val Thr Ile Asn Gly Ser
385                 390                 395                 400

Val Met Lys Glu Tyr Trp Gly Glu Gly Ser Ser Arg Ala Arg Asn Trp
                405                 410                 415

Gln Arg Tyr Asp Leu Gly Gly Lys Gln Lys Leu Ser Phe Glu Glu Gly
            420                 425                 430

Val Asp Ser Tyr Val Pro Tyr Ala Gly Lys Leu Lys Asp Asn Val Glu
        435                 440                 445

Ala Ser Leu Asn Lys Val Lys Ser Thr Met Cys Asn Cys Gly Ala Leu
450                 455                 460

Thr Ile Pro Gln Leu Gln Ser Lys Ala Lys Ile Thr Leu Val Ser Ser
465                 470                 475                 480

Val Ser Ile Val Glu Gly Gly Ala His Asp Val Ile Val Lys Asp Arg
                485                 490                 495

Ile Asn Asp Tyr His Pro Lys
            500
```

```
<210> SEQ ID NO 2
<211> LENGTH: 503
<212> TYPE: PRT
<213> ORGANISM: Tritrichomonas foetus
<220> FEATURE:
<221> NAME/KEY: MOD_RES
<222> LOCATION: 319
<223> OTHER INFORMATION: Xaa = S-Hydroxycysteine

<400> SEQUENCE: 2

Met Ala Lys Tyr Tyr Asn Glu Pro Cys His Thr Phe Asn Glu Tyr Leu
  1               5                  10                  15

Leu Ile Pro Gly Leu Ser Thr Val Asp Cys Ile Pro Ser Asn Val Asn
             20                  25                  30

Leu Ser Thr Pro Leu Val Lys Phe Gln Lys Gly Gln Gln Ser Glu Ile
         35                  40                  45

Asn Leu Lys Ile Pro Leu Val Ser Ala Ile Met Gln Ser Val Ser Gly
 50                  55                  60

Glu Lys Met Ala Ile Ala Leu Ala Arg Glu Gly Ile Ser Phe Ile
 65                  70                  75                  80

Phe Gly Ser Gln Ser Ile Glu Ser Gln Ala Ala Met Val His Ala Val
             85                  90                  95

Lys Asn Phe Lys Ala Gly Phe Val Ser Asp Ser Asn Val Lys Pro
            100                 105                 110

Asp Gln Thr Phe Ala Asp Val Leu Ala Ile Ser Gln Arg Thr Thr His
            115                 120                 125

Asn Thr Val Ala Val Thr Asp Asp Gly Thr Pro His Gly Val Leu Leu
130                 135                 140

Gly Leu Val Thr Gln Arg Asp Tyr Pro Ile Asp Leu Thr Gln Thr Glu
145                 150                 155                 160

Thr Lys Val Ser Asp Met Met Thr Pro Phe Ser Lys Leu Val Thr Ala
                165                 170                 175

His Gln Asp Thr Lys Leu Ser Glu Ala Asn Lys Ile Ile Trp Glu Lys
            180                 185                 190

Lys Leu Asn Ala Leu Pro Ile Ile Asp Asp Gln His Leu Arg Tyr
            195                 200                 205

Ile Val Phe Arg Lys Asp Tyr Asp Arg Ser Gln Val Cys His Asn Glu
210                 215                 220

Leu Val Asp Ser Gln Lys Arg Tyr Leu Val Gly Ala Gly Ile Asn Thr
225                 230                 235                 240

Arg Asp Phe Arg Glu Arg Val Pro Ala Leu Val Glu Ala Gly Ala Asp
                245                 250                 255

Val Leu Cys Ile Asp Ser Ser Asp Gly Phe Ser Glu Trp Gln Lys Ile
            260                 265                 270

Thr Ile Gly Trp Ile Arg Glu Lys Tyr Gly Asp Lys Val Lys Val Gly
        275                 280                 285

Ala Gly Asn Ile Val Asp Gly Glu Gly Phe Arg Tyr Leu Ala Asp Ala
    290                 295                 300

Gly Ala Asp Phe Ile Lys Ile Gly Ile Gly Gly Ser Ile Xaa Ile
305                 310                 315                 320

Thr Arg Glu Gln Lys Gly Ile Gly Arg Gly Gln Ala Thr Ala Val Ile
                325                 330                 335

Asp Val Val Ala Glu Arg Asn Lys Tyr Phe Glu Glu Thr Gly Ile Tyr
            340                 345                 350

Ile Pro Val Cys Ser Asp Gly Gly Ile Val Tyr Asp Tyr His Met Thr
        355                 360                 365
```

-continued

```
Leu Ala Leu Ala Met Gly Ala Asp Phe Ile Met Leu Gly Arg Tyr Phe
    370             375             380

Ala Arg Phe Glu Glu Ser Pro Thr Arg Lys Val Thr Ile Asn Gly Ser
385             390             395             400

Val Met Lys Glu Tyr Trp Gly Glu Gly Ser Ser Arg Ala Arg Asn Trp
            405             410             415

Gln Arg Tyr Asp Leu Gly Gly Lys Gln Lys Leu Ser Phe Glu Glu Gly
        420             425             430

Val Asp Ser Tyr Val Pro Tyr Ala Gly Lys Leu Lys Asp Asn Val Glu
        435             440             445

Ala Ser Leu Asn Lys Val Lys Ser Thr Met Cys Asn Cys Gly Ala Leu
    450             455             460

Thr Ile Pro Gln Leu Gln Ser Lys Ala Lys Ile Thr Leu Val Ser Ser
465             470             475             480

Val Ser Ile Val Glu Gly Gly Ala His Asp Val Ile Val Lys Asp Arg
            485             490             495

Ile Asn Asp Tyr His Pro Lys
        500
```

CRYSTAL STRUCTURES OF *T. FOETUS* INOSINE MONOPHOSPHATE DEHYDROGENASE IN COMPLEX WITH SUBSTRATE, COFACTOR AND ANALOGS AND USES THEREOF

This application claims benefit of the filing date of U.S. Provisional Application No. 60/410,523, filed Sep. 13, 2002, and U.S. Provisional Application No. 60/412,044, filed Sep. 18, 2002, both of which are incorporated herein by reference.

This invention was made in part with U.S. Government support under Grant No. R01-GM56445, awarded by the National Institutes of Health. The U.S. Government has certain rights in this invention.

BACKGROUND OF THE INVENTION

This invention relates generally to drug development and, more specifically, to designing compounds that modulate inosine monophosphate dehydrogenase.

The enzyme inosine monophosphate dehydrogenase (IMPDH) is responsible for the rate-limiting step in guanine nucleotide biosynthesis. Because it is up-regulated in rapidly proliferating cells, human type II IMPDH is actively targeted for immunosuppressive, anticancer, and antiviral chemotherapy. The enzyme employs a random-in ordered-out kinetic mechanism where substrate or cofactor can bind first but product is only released after the cofactor leaves. Due to structural and kinetic differences between mammalian and microbial enzymes, most drugs that are successful in the inhibition of mammalian IMPDH are far less effective against the microbial forms of the enzyme. However, with greater knowledge of the structural mechanism of the microbial enzymes, more effective and selective inhibitors of microbial IMPDH can be developed for use as anti-microbial drugs.

Thus, there exists a need for identifying and designing compounds that modulate IMPDH activity. The present invention satisfies this need and provides related advantages as well.

SUMMARY OF THE INVENTION

The invention provides a crystalline complex containing *T. foetus* inosine monophospate dehydrogenase (IMPDH) in complex with inosine monophosphate (IMP), the complex specified by disclosed atomic coordinates. Also provided are crystalline complexes of containing *T. foetus* IMPDH with both inosine monophosphate (IMP) and mycophenolic acid, with both xanthosine monophosphate (XMP) and mycophenolic acid, with both xanthosine monophosphate (XMP) and nicotinic adenine dinucleotide (NAD), with ribavirin (1-β-D-ribofuranosyl-1,2,4-triazole-3-carboxamide), and with both ribavirin and mycophenolic acid, each complex specified by disclosed atomic coordinates. The *T. foetus* IMPDH structures have complete active sites. Also provided by the invention are the atomic coordinates for these complexes. Further provided by the invention are methods for identifying a modulator of IMPDH that employ the atomic coordinates of the invention.

The invention provides methods for identifying an inhibitor of IMPDH. In one embodiment, a method of the invention involves displaying a structure for IMPDH, or a portion thereof, wherein the structure has a set of atomic coordinates shown in Tables 2–7; (b) docking a structure of a candidate inhibitor to the structure of IMPDH, or the portion thereof; and (c) identifying an inhibitor of IMPDH, wherein the inhibitor has a structure that docks favorably to the structure of IMPDH, or the portion thereof. In one embodiment, the method is used to identify an inhibitor that targets the substrate binding site to which IMP or XMP binds. In another embodiment, the method is used to identify an inhibitor that targets the NAD cofactor binding site to which NAD or MOA binds. In a further embodiment, the method can include docking a candidate inhibitor to a second IMPDH structure.

In another embodiment, the invention provides a method of identifying an inhibitor of IMPDH that involves displaying the structure for the bound complex of *T. foetus* IMPDH with NAD set forth in Table 5, (b) docking a structure of a candidate inhibitor to said structure, or portion thereof; and identifying a compound that binds Asp-358 and Asp-261, wherein said compound has a structure that docks favorably to said structure, or portion thereof.

In a further embodiment, the invention provides a method of identifying an inhibitor of IMPDH that involves (a) selecting a candidate compound by performing rational drug design with a set of atomic coordinates set forth in Tables 2–7, wherein said selecting is performed in conjunction with computer modeling; (b) contacting said compound with IMPDH, and (c) determining the ability of said compound to reduce IMPDH activity, wherein a compound that reduces IMPDH activity is an inhibitor of IMPDH.

DETAILED DESCRIPTION OF THE INVENTION

Figure 1:
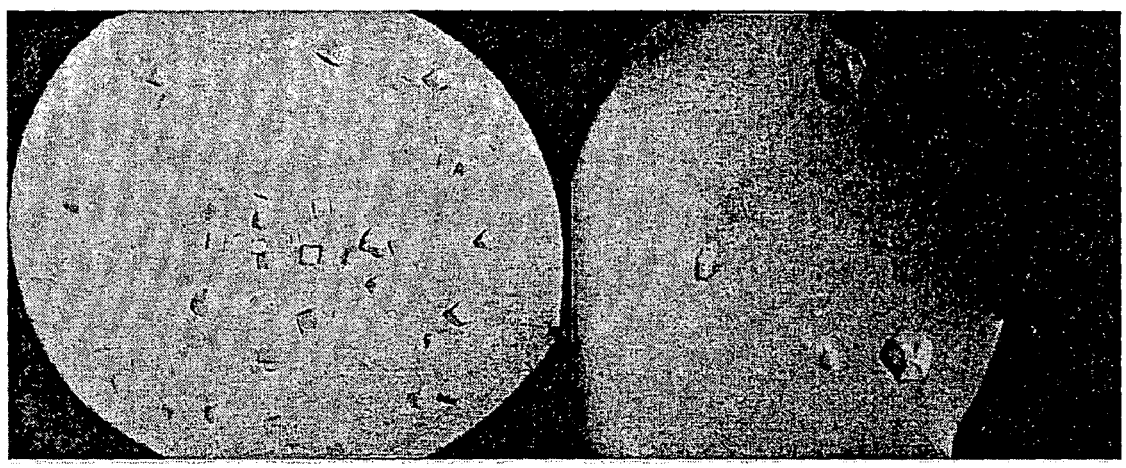
FIG. 1 shows IMPDH crystals from the original ammonium sulfate condition (left) compared with those grown from the sodium malonate (right). In malonate, the crystals grew to 0.4–0.8 mm in length while the sulfate crystals grew to between 0.1 and 0.4 mm. The sulfate-grown crystals were also much more fragile. Further, the malonate in the mother liquor acted as a cryoprotectant. No detectable needle-shaped crystals, which were observed in the sulfate condition, were observed in the malonate condition.

This invention relates to crystalline compositions of *Tritrichomonas foetus* (*T. foetus*) inosine monophospate dehydrogenase (IMPDH) complexes with its natural substrate, product, cofactor and inhibitors. The invention further relates to the discovery of high resolution crystal structures of different complexes of IMPDH, including complexes with its substrate IMP; with IMP and inhibitor mycophenolic acid (MPA); with inhibitor ribavirin; with MOA and ribavirin; with the product XMP and MOA; and with XMP and the cofactor NAD+.

As disclosed herein, six complexes of *T. foetus* IMPDH bound with IMP, IMP+MPA, XMP+MPA, XMP+NAD$^+$, ribavirin and ribavirin+MOA. In particular, the high-resolution crystal structures of four *T. foetus* IMPDH complexes with substrate, cofactor, and inhibitors—IMP, XMP+NAD$^+$, IMP+MPA, and XMP+MPA-represent the first *T. foetus* structures with a complete active site, the first IMPDH structure with the NAD$^+$ cofactor bound, and the first with MOA bound in addition to unreacted substrate, and product. As is described in Example IV, a novel monovalent cation bound at the dimer interface that is likely unique to *T. foetus* and can contribute to the stability of the cofactor binding site. The active site cation appears to be present only in the covalent substrate-complex and conformations further along the catalytic cycle for most eukaryotic organisms, but it is already present in prokaryotic organisms upon substrate binding.

Current development of drugs that bind IMPDH has focused on developing highly potent inhibitors of the human form of the enzyme. The invention provides structural information useful for development of inhibitors of microbial IMPDH. Compounds designed as inhibitors of microbial IMPDH are useful for treating diseases caused by a variety of microbes, including for example, bacteria, viruses and parasites.

In one embodiment, the invention provides atomic coordinates for the bound complex of *T. foetus* inosine monophosphate dehydrogenase (IMPDH) (SEQ ID NO:2) with inosine monophosphate (IMP). The atomic coordinates for the IMPDH-IMP complex are provided in Table 2.

In another embodiment, the invention provides atomic coordinates for the bound complex of *T. foetus* IMPDH (SEQ ID NO:2) with IMP and mycophenolic acid (also referred to herein as MOA or MOA). The atomic coordinates for the IMPDH-IMP-MOA ternary complex are provided in Table 3.

In a further embodiment, this invention further provides atomic coordinates for the bound complex of *T. foetus* IMPDH (SEQ ID NO:1) with xanthosine monophosphate (XMP) and MOA. The atomic coordinates for the IMPDH-XMP-MOA ternary complex are provided in Table 4.

Also provided by the invention are atomic coordinates for the bound complex of *T. foetus* IMPDH (SEQ ID NO:1) with xanthosine monophosphate (XMP) and nicotinic adenine dinucleotide (NAD). The atomic coordinates for the IMPDH-XMP-NAD ternary complex are provided in Table 5.

The invention further provides atomic coordinates for the bound complex of *T. foetus* IMPDH with ribavirin (1-β-D-ribofuranosyl-1,2,4-triazole-3-carboxamide). The atomic coordinates for the IMPDH-ribavirin complex are provided in Table 7.

The invention further provides atomic coordinates for the bound complex of *T. foetus* IMPDH with ribavirin and MOA. The atomic coordinates for the IMPDH-ribavirin complex are provided in Table 6.

As used herein, the term "atomic coordinates" means Cartesian structure coordinates derived from mathematical equations relating to the patterns obtained on diffraction of a monochromatic beam of X-rays by the atoms (scattering centers) of IMPDH complexes in crystal form. The diffraction data are used to calculate an electron density map of the repeating unit of the crystal. The electron density maps are then used to establish the positions of the individual atoms of the IMPDH complexes. Those of skill in the art will understand that a set of atomic coordinates for an enzyme or an enzyme-complex or portion thereof, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above can be generated because of mathematical manipulations of the atomic coordinates. For example, the atomic coordinates set forth in Tables 2–7, can be manipulated by crystallographic permutations of the atomic coordinates, fractionalization of the atomic coordinates, rotation of the atomic coordinates, integer additions or subtractions to sets of the atomic coordinates, invention of the atomic coordinates or any combination of the above.

Alternatively, modifications in the crystal structure due to mutations, additions, substitutions, and or deletions of amino acids, or other changes in any of the components that make up the crystal could also account for variations in structure coordinates. If such variations are within an acceptable standard error as compared to the original coordinates, the resulting three-dimensional shape is considered to be the same.

The atomic coordinates of the invention can be stored in a memory or computer readable medium. A memory or computer readable medium can be a hard disk, floppy disc, compact disc, magneto-optical disc, Random Access Memory, Read Only Memory or Flash Memory and the like. A computer system that contains the memory or computer readable medium used in the invention can be a single computer or multiple computers distributed in a network.

The atomic coordinates of the invention are useful for viewing or manipulating the structure of IMPDH in a conformation that binds IMP, XMP, MOA, NAD, ribavirin, and combinations thereof. The atomic coordinates shown in Tables 2–7 can be readily modified to remove one or more atoms in the structure including, for example, the atomic coordinates for IMP, XMP, MOA, NAD, ribavirin, or any combination thereof such that only a portion of the structure is viewed or manipulated. Other portions of the structures represented in Tables 2–7 that are useful in the invention include atoms of IMPDH that interact with IMP, XMP, MOA, NAD or ribavirin, such as those present in the active site loop, active site flap, or in other residues that interact with the ligands as described herein; IMP or atoms thereof that interact with IMPDH; XMP or atoms thereof that interact with IMPDH; NAD or atoms thereof that interact with IMPDH; MOA or atoms thereof that interact with IMPDH; ribavirin or atoms thereof that interact with IMPDH. A portion of the atomic coordinates useful in the invention need not be a contiguous fragment of IMPDH or its bound ligands. The atomic coordinates can be manipulated or structures viewed on any computer that supports molecular modeling software such as a personal computer, silicon graphics workstation or super computer.

Portions of IMPDH or its bound ligands can be represented as pharmacophores. As used herein the term "pharmacophore" is intended to mean a representation of relative position for two or more atoms based on their positions in a molecular structure. In addition to relative position a pharmacophore can represent other characteristics of the atoms including, for example, charge or hydrophobicity. A representation in a pharmacophore can be a point indicating, for example, the center of the atom or the representation can be a volume indicating, for example, an area in which the atom can reside making a favorable interaction with another atom. A pharmacophore can also include a volume representing locations where an atom is disallowed, for example, due to unfavorable interactions with another atom.

The atomic coordinates of the invention can be used in a variety of methods for rational drug design, such as in methods for identifying an inhibitor of IMPDH. Thus, the invention provides a method of identifying an inhibitor of IMPDH. The method includes steps of: (a) displaying a structure for IMPDH, or a portion thereof, wherein the structure has atomic coordinates shown in Tables 2–7; (b) docking a structure of a candidate inhibitor to the structure of IMPDH, or the portion thereof; and (c) identifying an inhibitor of IMPDH, wherein the inhibitor has a structure that docks favorably to the structure of IMPDH, or the portion thereof. A structure of IMPDH can be represented with a pharmacophore of an IMPDH binding site.

As used herein, the term "docking" means a computational means for performing a fitting operation between the candidate inhibitor and a portion of the structure of IMPDH. Such a portion of the structure of IMPDH can be, for example, a binding pocket.

In one embodiment, the method is used to identify an inhibitor that targets the substrate binding site to which IMP or XMP bind. Accordingly, the method can be used with a portion of IMPDH that includes atoms that interact with IMP or XMP such as those described in Examples IV and VII. The method can also be used to identify an inhibitor that targets the NAD cofactor binding site to which NAD or MOA bind. A portion of IMPDH that interacts with MOA and that is useful in a method of the invention can include, for example, atoms that interact with NAD or MOA as described in Examples V and VII. Any portion of the IMPDH structures including, for example, the active site loop, active site flap or others described herein can be used in a method of the invention.

A structure of a candidate inhibitor can be docked to a binding site of IMPDH to identify an inhibitor that is complementary in shape to the binding site or has favorable electrostatic interactions with the charged groups in the binding site. A candidate inhibitor can be identified based on structural similarity to IMP, XMP, NAD, MOA or ribavirin.

For example, a molecular structure database such as the Cambridge Structure Database can be searched to identify molecules having a particular structural attribute of IMP, XMP, NAD, MOA or ribavirin or any other inhibitor that binds to IMPDH.

In one embodiment, the method is used to identify an inhibitor that targets the substrate binding site to which RIBAVIRIN binds. Accordingly, the method can be used with a portion of IMPDH that includes atoms that interact with RIBAVIRIN such as Ser317 hydroxyl, Tyr405 hydroxyl, main chain nitrogen of Ser317, main chain nitrogen of Gly381, main chain nitrogen of Arg382, the carboxylate of Asp358, the side chain of Ile318, hydrogen of Glu408 or hydrogen of Gly409. The method can also be used to identify an inhibitor that targets the NAD cofactor binding site to which MOA binds. A portion of IMPDH that interacts with MOA and that is useful in a method of the invention can include, for example, the carbonyl oxygen of Gly312, the amide nitrogen of Gly314 or the sulfhydryl of Cys319. Any portion of the IMPDH structures including, for example, the active site loop, active site flap or others described herein can be used in a method of the invention.

A structure of a candidate ligand can be docked using algorithms available in the art including, for example, those available in the software applications DOCK (Kuntz et al., *J. Mol. Biol.* 161:269–288 (1982)) or INSIGHT98 (Molecular Simulations Inc., San Diego, Calif.). Methods for screening a structural database to identify molecules that bind to IMPDH are described, for example, in Luecke et al., *Exp. Parasitology* 87:203–211 (1997).

Figure 10:
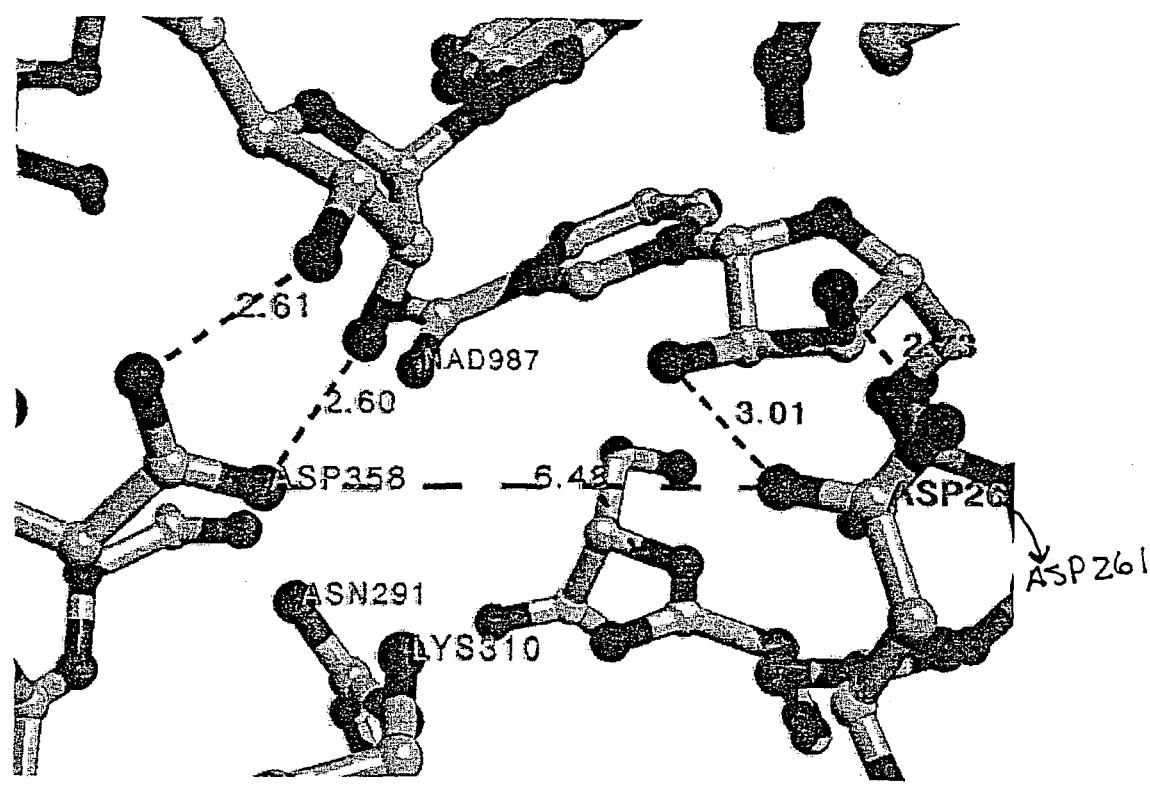
FIG. 10 shows a 2Fo-Fc electron density map contoured at 0.6 σ reveals that Π stacking is involved in forming the crystallographic dimer interface and that Trp416 from each monomer may occupy a position at the two-fold interface at 50% occupancy.

An inhibitor that targets IMPDH can be designed to contain a moiety from a ligand that binds the substrate binding site of IMPDH and a moiety from a ligand that binds to the cofactor binding site of IMPDH. The moieties included in such an inhibitor can be portions of ligands that are bound in the structures disclosed herein or can be analogs of any portion of these ligands, so long as the portion or analog is capable of binding to IMPDH when present in the inhibitor. Accordingly, the moieties of an inhibitor so designed will function as binding moieties. The binding moieties can be linked by a third moiety that is capable of taking on a conformation that places the binding moieties in relative orientations similar to those observed in a crystal structure disclosed herein such as those having coordinates set forth in Tables 2–7. As an example, hydroxyl groups on the ribose rings of XMP and NAD, when bound in a ternary complex with IMPDH, both interact with aspartate residues of IMPDH. In particular Asp358 binds to the ribose hydroxyl of IMP or XMP and ASP261 binds to the NAD(H) nicotinamide ribose hydroxyls as shown in FIG. 10. The two aspartate residues are about 6.5 angstroms apart at the closest point as shown in FIG. 10. Accordingly, an inhibitor can be designed having two ribose moieties, or analogs thereof, linked to each other such that they can attain a conformation where they interact with these aspartates in IMPDH.

A method of the invention can further include a step of docking a candidate inhibitor to a second IMPDH structure. A second IMPDH structure used in a method of the invention can be a different conformation of the same IMPDH obtained, for example, by binding to different ligands. As described herein, the conformation of *T. foetus* IMPDH differs for the complexes described herein. Furthermore there are differences between the conformations of IMPDH disclosed herein and those for IMPDH bound to ribavirin phosphate and for IMPDH structures known in the art as set forth herein. Comparison of docking results for two or more different IMPDH conformations can be used to identify an inhibitor that has favorable binding interactions with IMPDH in multiple conformations. As described herein, the conformation of *T. foetus* IMPDH in a IMPDH-ribavirin complex differs from its conformation in an IMPDH-ribavirin -MOA ternary complex. Furthermore, the conformation of *T. foetus* IMPDH in a IMPDH-ribavirin complex differs from its conformation in apo IMPDH, IMPDH-IMP complex, IMPDH-XMP, IMPDH-XMP-MOA ternary complex, or IMPDH-XMP-NAD$^+$ ternary complex. Comparison of docking results for two or more different IMPDH conformations can be used to identify an inhibitor that has favorable binding interactions with IMPDH in multiple conformations. A structure of apo IMPDH is available in the protein databank (PDB) under PDB code 1AK5. A structures of IMPDH bound to ribavirin phosphate and a structure of IMPDH bound to ribavirin and MOA in a ternary complex are described herein.

The crystal structures described herein reveal aspects of IMPDH structure and association with substrate, products and inhibitors previously unrecognized. Based on particular structural features revealed, an inhibitor of IMPDH activity can be designed. Therefore, in one embodiment, the invention provides a method of the invention for identifying an inhibitor of IMPDH can involve displaying a structure for the bound complex of *T. foetus* IMPDH with NAD set forth in Table 5; (b) docking a structure of a candidate inhibitor to said structure, or the portion thereof; and (c) identifying a compound that binds Asp-358 and Asp-261, wherein said compound has a structure that docks favorably to said structure, or portion thereof.

A second IMPDH structure used in a method of the invention can be from a different organism. By comparing docking interactions for a candidate inhibitor with IMPDH from different organisms, an inhibitor can be identified that is specific for a particular organism. For example, an inhibitor that is specific to *T. foetus* IMPDH compared to IMPDH from a mammal can be identified based on favorable docking of the candidate inhibitor to *T. foetus* IMPDH and less favorable or even unfavorable docking with IMPDH from the mammal. Such an inhibitor can be useful as a therapeutic agent to treat a cow infected with *T. foetus* as set forth below. Alternatively, comparison of docking results for IMPDH structures from two or more different organisms can be used to identify an inhibitor that has favorable docking with multiple IMPDH proteins, thereby identifying an inhibitor having relatively broad specificity. Structures for IMPDH from other organisms that are useful in the invention include, but are not limited to, those for IMPDH from mammals including, for example, humans, primates, non-human primates, Chinese hamster, agricultural animals such as cow, horse, sheep, goats, pigs; invertebrates, yeast, bacteria, or protozoa. Examples of IMPDH structures from other organisms that are useful in the invention include human type II IMPDH in a ternary complex with 6-Cl-Imp and selenazole adenine dinucleotide (PDB code 1B30); IMPDH from *S. pyogenes* (PDB code 1ZFJ) and Chinese hamster IMPDH in complex with MOA (PDB code 1Jr1).

The invention provides another method of identifying an inhibitor of IMPDH. The method involves (a) selecting a candidate compound by performing rational drug design with a set of atomic coordinates set forth in Tables 2–7, wherein said selecting is performed in conjunction with computer modeling; (b) contacting said compound with IMPDH, and (c) determining the ability of said compound to reduce IMPDH activity, wherein a compound that reduces IMPDH activity is an inhibitor of IMPDH.

The ability of a compound to reduce IMPDH activity can be determined using a variety of well known methods. Such methods include those described in Metz et al. *Endocrinology* 142:193–204 (2001) and Wilson et al. *J. Biol. Chem.* 266(3):1665–1671 (1991). Computer modeling can be performed using a variety of well known methods, including commercial modeling packages, such as those described herein above.

It is understood that the atomic coordinates of IMPDH disclosed herein can also be used for identifying a compound that increases the activity of IMPDH. Such a compound can be useful, for example, for increasing the viability of a microbe or as a therapeutic agent used to treat a disease or condition that is mediated by IMPDH or that can be reduced by increasing IMPDH activity.

An IMPDH inhibitor identified by a method of the invention can be used as a therapeutic agent. A therapeutic agent identified using the methods of the invention can be used to treat a disease or condition that is mediated by IMPDH or that is reduced by inhibitors of this enzyme such as ribavirin or MOA. Such an agent can be used to treat a mammal, agricultural animal, human, dog, cat or horse. For example, an inhibitor of *T. foetus* IMPDH can be used to treat cows infected with the *T. foetus* protozoan. A therapeutic agent identified using the methods of the invention can be used as an antiproliferative, antiviral, anticancer or immunosuppressive agent. A therapeutic agent identified using a method of the invention can be useful for treating a cancer such as those causing a benign or malignant tumor of the breast, prostate, colon, lung, brain or ovary. A therapeutic agent identified using a method of the invention can be useful for treating a viral infection such as one caused by hepatitis A, B or C; respiratory syncytial virus, HIV or hanta virus. A therapeutic agent identified using a method of the invention can be useful for treating a fungal infection such as one caused by *Aspergillus, Penicillium, Alternaria, Cladosporium*, and *Fusarium*. A therapeutic agent identified using a method fungal viral infection such as one caused by *Aspergillus, Penicillium, Alternaria, Cladosporium*, and *Fusarium*. A therapeutic agent identified using a method of the invention can be useful for treating a bacterial infection such as one caused by *Staphylococcus* spp., *Streptococcus* spp., *Haemophilus influenzae, Pseudomonas aeruginosa*, enteric Gram-negative *bacilli, Moraxella lacunata, Acinetobacter* spp., *Neisseria gonorrhoeaei, Branhamella catarrhalisi, Clamydia trachomatis*, and anaerobes. A therapeutic agent identified using a method of the invention can be useful for treating a parasitic infection such as one caused by *Acanthamoeba* and *Toxoplasma gondii*. A therapeutic agent identified using a method of the invention can be useful in combination with other treatments, for example, as an immunosuppressive agent administered following organ or cell transplantation.

It is understood that modifications which do not substantially affect the activity of the various embodiments of this invention are also included within the definition of the invention provided herein. Accordingly, the following examples are intended to illustrate but not limit the present invention.

EXAMPLE I

Cystallization of *T. foetus* IMPDH with Bound Substrate, Cofactor and Analogs

This example shows expression, purification, and crystallization of *T. foetus* IMPDH with bound IMP, IMP+MPA, XMP+MPA, and XMP+NAD$^+$.

Protein expression and subsequent purification yielded approximately 90 mg of pure and active protein as determined by Coomassie stained SDS PAGE gels and a spectrophotometrically observed increase of NADH when enzyme is added to IMP and NAD$^+$ using previously described methods (Digits and Hedstrom, *Biochem.* 38:2295–2306 (1999)). This yield could be increased substantially by optimizing the fermentation parameters, in particular by supplementing oxygen, as this was the limiting factor.

A pBAce plasmid (Chin and Wang, *Mol. Biochem. Parasitol.* 63:221–229 (1994)) containing *T. foetus* IMPDH (Beck et al., *Exp. Parsitol.* 78:101–112 (1994)) was transformed into *Escherichia coli* strain H712 (*E. coli* Stock Center, Yale University, New Haven, Conn.). This bacterial strain is deficient in native IMPDH and requires rich media for growth unless supplemented with a source of GMP or guanosine. Expression of *T. foetus* IMPDH was achieved by activation of the PhoA promoter under low phosphate conditions using supplemented MOPS minimal media using a modified version of previously published protocols (Craig et al., *Proc. Natl. Acad. Sci. USA* 88:2500–2504 (1991); Neidhardt et al., *J. Bacteriol.* 119:736–747 (1974); Yuan et al., *J. Biol. Chem.* 265:13528–13532 (1990)). Briefly, the cells were grown in MOPS media in a 19-liter fermentor (Wheaton Science Products, Millville, N.J.) inoculated with 0.5 liters of overnight MOPS culture of H712 containing the IMPDH plasmid. Temperature was maintained at 37° C., dissolved oxygen (DO) was maintained at greater than 40% with aeration, stirring, and glucose addition. The cells were harvested at 8 hours when the DO dropped to below 20% at roughly OD600 =1.5.

The cells were concentrated to 0.5 L by tangential flow filtration (Millipore, Inc., Bedford, Ma.), pelleted by centrifugation at 6,000 g, then re-suspended in a three fold volume of buffer A (50 mM Tris pH 8, 50 mM KCl, 10% glycerol, and 1 mM 2-mercaptoethanol) supplemented with protease inhibitors and 1 mM EDTA. The cells were then flash frozen in liquid nitrogen before storage at ~85° C. This mixture was lysed by French Press and clarified by centrifugation at 20,000 g. The resulting lysate was then run over a Cibacron blue column on an AKTA FPLC (Amersham-Pharmacia). Cibacron blue is a dye ligand that selectively binds many proteins that use NAD$^+$ as a cofactor. The protein was found to elute from the column in a broad peak with a gradient of 50 mM–1M KCl over 20 column volumes. Protein elution from the column was optimized by eliminating the gradient and eluting the protein in 1 M KCl. This was followed by dialysis into buffer A and concentration to 15 mg/ml. The protein was then passed through a monoQ column (Amersham-Pharmacia) using a gradient from 50 mM to 500 mM KCl over 20 column volumes. The resulting protein was >90% pure and was dialyzed in buffer A and concentrated to 30 mg/ml for storage at −85° C.

The protein was first crystallized by optimizing previously published conditions (Whitby et al., *Proteins* 36:10666–10674 (1995)) by mixing 10–15 mg/ml protein in buffer A into 2.4 M ammonium sulfate, 100 mM Tris pH 8.0, 10% glycerol, 4 mM PEG 400, and 1 mM 2-mercaptoethanol well solution in 6 μl sitting drops in a 1:1 ratio of well solution to protein at 20° C. Crystals diffracting to higher resolution were obtained with the substitution of 42% saturated sodium malonate for 2.4 M ammonium sulfate. Additionally, the crystals grew to a larger size without increased mosaicity, and the malonate provided excellent cryo-protection as no other additives were necessary.

EXAMPLE II

Crystalography Data Collection for of T. foetus IMPDH Complexes

This example describes data collection for T. foetus IMPDH crystal structures with bound IMP, IMP+MPA, XMP+MPA, and XMP+NAD$^+$.

All of the ligands were co-crystallized with the exception of NAD$^+$ and XMP. In the NAD$^+$+XMP structure, the NAD$^+$ and XMP were added to five to seven day old crystals and allowed to soak for five days before data collection. Attempts were made to generate XMP covalently attached to the active site cysteine (E-XMP*) by addition of IMP to IMPDH in a reaction buffer containing NAD$^+$ and MOA using methods previously described. The resulting x-ray structure was identical to the XMP+MPA co-crystal structure: there was clearly an oxygen atom on the C2 of XMP, but no covalent bond with the active site cysteine could be discerned.

Diffraction quality crystals grew within five days and although the crystal morphology changed due to the substitution of malonate for sulfate, the space group remained P432 (FIG. 1). The cryo-frozen crystals diffracted from 1.95 to 2.2 Å using synchrotron radiation. A randomly selected test set of diffraction data (5% of all structure factors) was set aside for $R_{free}$ calculations. All model building was carried out with the program O, and the program CNS was used for refinement. The original T. foetus apo structure was used as the initial model for all structures allowing unbiased building of the active site loop and flap. One round of rigid body refinement and simulated annealing was followed by several rounds of energy minimization, B factor refinement, model building, and water picking. Composite omit, $2F_o-F_c$, and $F_o-F_c$ maps were generated to guide model building. The program PROCHECK was used to validate the structures (Laskowski et al., J. App. Cryst. 26:283–291 (1993)). Crystal, refinement, and PROCHECK statistics are presented in Table 1.

Initial diffraction of T. foetus IMPDH using the published ammonium sulfate crystallization conditions only reached 3.2 Å using a RAXIS IV detector. The modified conditions improved resolution to 2.45 and resolution was further improved using synchrotron radiation. Synchrotron data were collected at the Stanford Synchrotron radiation laboratory (SSRL) beam line 9-1 and at The Advanced Light Source, Lawrence Berkeley National Laboratory (ALS) beam line 5.0.2. X-ray data collection, reduction and refinement statistics can be found in Table 1. Diffraction data were collected under cryo conditions using colorless crystals ranging in size from 0.4 to 0.8 mm. The crystals were loop-mounted and flash-cooled to –170° C. in the nitrogen stream. The data were collected from single crystals and integrated and scaled in the Denzo-Scalepack package (Otwinowski, Data Collection and Processing, SERC Daresbury Laboratory, Warrington, UK, pp. 56–62 (1993)). The published apo structure (Whitby et al., Biochem. 36:10666–10674 (1997)) was used as an initial model for all co-crystals, followed by rigid body and simulated annealing refinement. Several rounds of model building, energy minimization and B-factor refinement were then performed with the programs O (Jones et al., Acta Cryst. A47:110–119 (1991)) and CNS (Brunger et al., Akta Cyrst. D54:905–921 (1998)).

EXAMPLE III

Model Building for T. foetus IMPDH with bound IMP, IMP+MPA, XMP+MPA, and XMP+NAD$^+$ This example describes model building for T. foetus IMPDH with bound IMP, IMP+MPA, XMP+MPA, and XMP+NAD$^+$.

Figure 2:
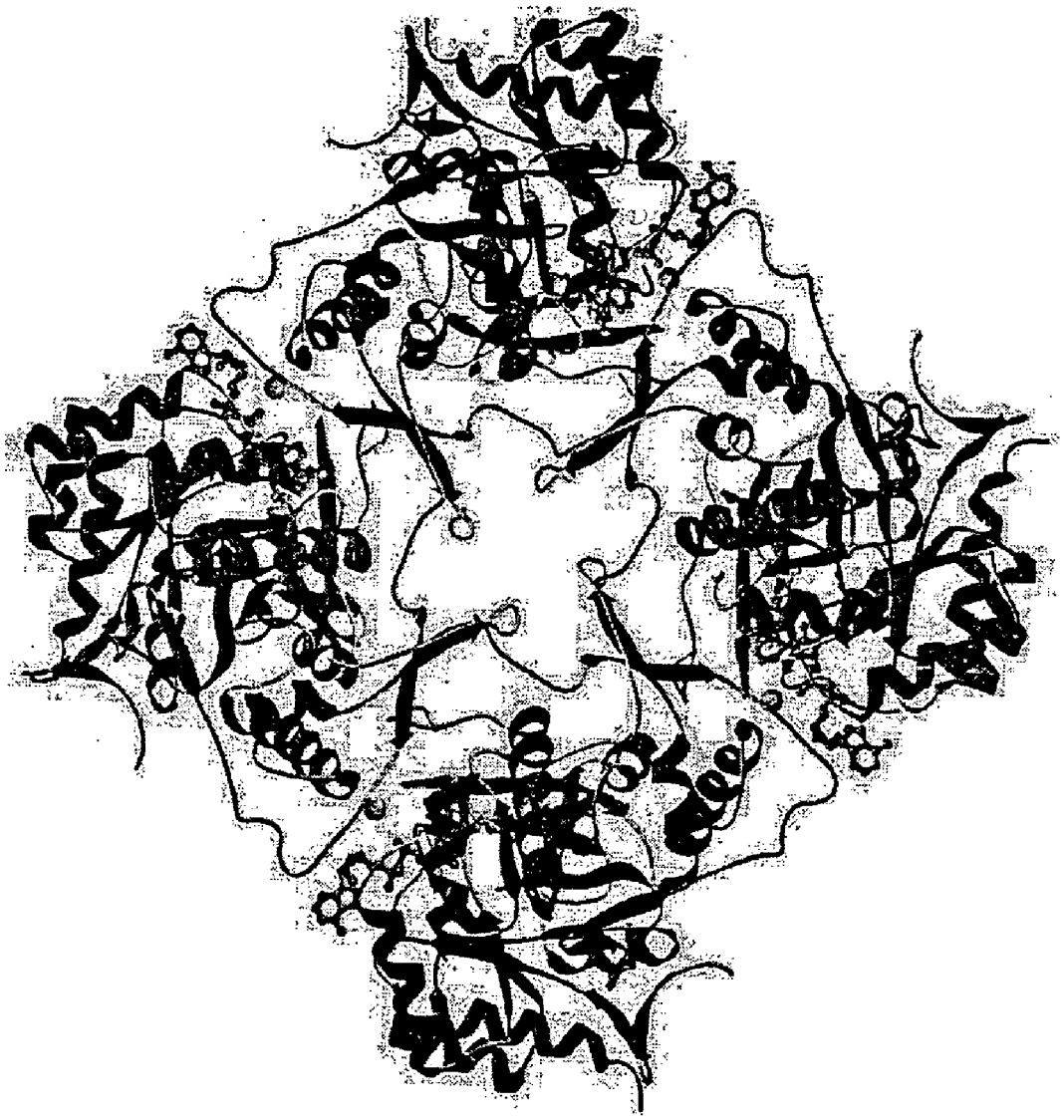
FIG. 2 shows a ribbon diagram of the IMPDH tetramer viewed along the four-fold axis. The enzyme is in complex with the product XMP (light shading), the cofactor $NAD^+$ (dark shading) and the potassium. Although the cofactor lies along the dimer interface, it does not make contact with the neighboring monomer. All molecular images were prepared with the program Deepview and rendered in POVRAY 3.5 beta.
Figure 3:
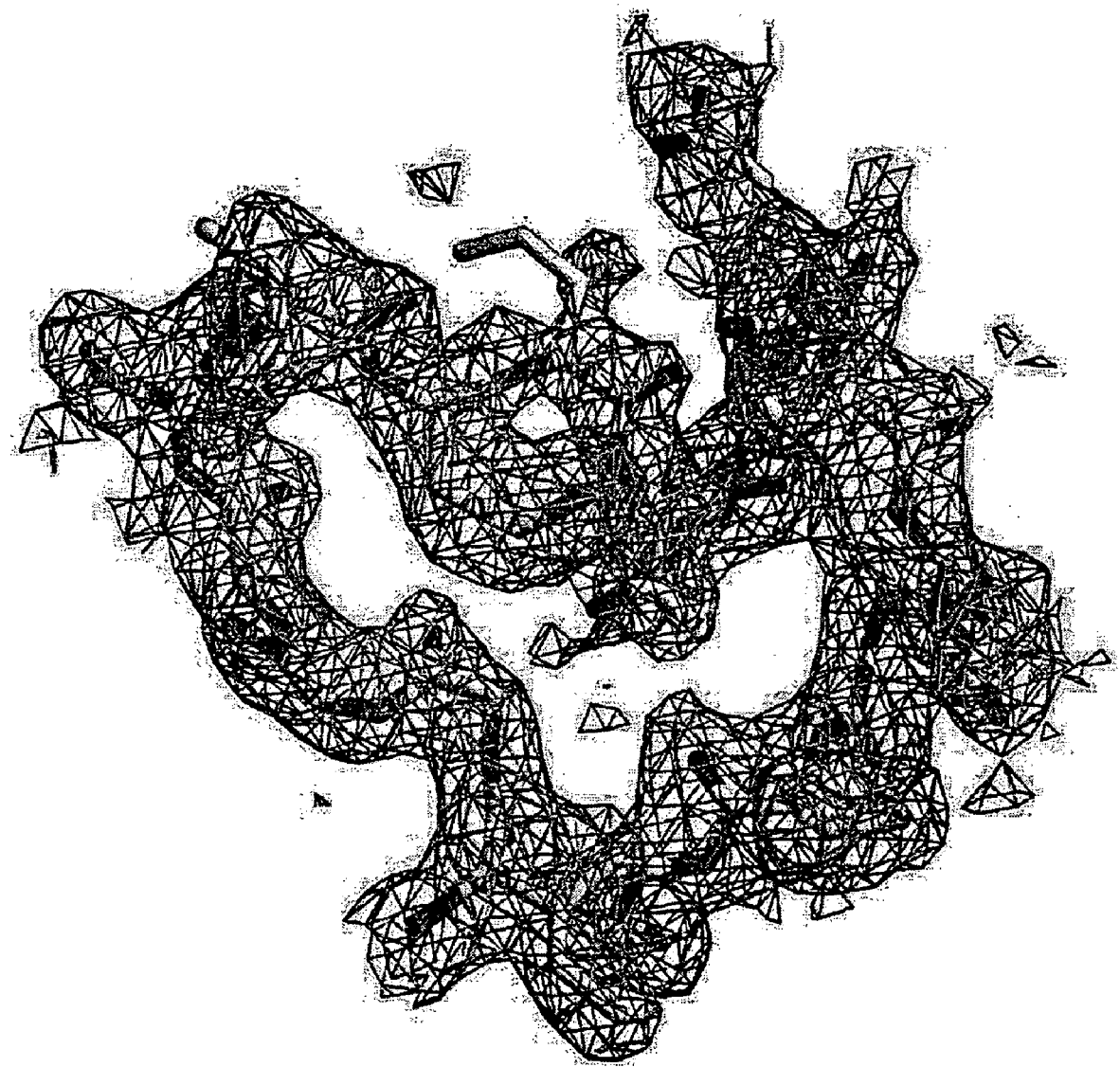
FIG. 3 shows the active site loop of *T. foetus* IMPDH. A 2.2 Å resolution $2F_o-F_c$ electron density map contoured at 0.5 σ surrounds a model of the active site loop from the IMP-bound structure. The low contouring level is necessary to obtain continuous electron density.

All IMPDH are homotetramers in solution under physiological conditions. In the cubic P432 spacegroup, this catalytic tetramer is formed by the crystallographic four-fold axis (FIG. 2). The active site loop, residues 313–330, was modeled in all but the XMP+NAD$^+$ bound structure, which lacks residues 318–321. This loop is highly mobile, in part due to three glycine residues (residues 314–316) near the active site cysteine. Additionally, this loop has not been stabilized by covalently binding a substrate intermediate or inhibitor, resulting in weak electron density and high B factors. Visualization using electron density maps at lower contouring levels (0.5–0.8 σ) resulted in continuous or nearly continuous density throughout backbone of the active site loop (FIG. 3) with the exception of the NAD$^+$ structure.

Furthermore, a larger portion of the active site flap (residues 408–433) was ordered in these structures in comparison to previous T. foetus structures. However, the distal portion of this loop was not modeled. Although there was scattered density for the 120-residue CBS domain, it was not contiguous and despite the improved resolution, this domain was not included in the model. Only the S. pyogenes structure contains the entire CBS domain (Zhang et al., Biochem. 38:4691–4700 (1999)).

The substrate IMP, product XMP, cofactor NAD$^+$, and inhibitor MOA hetero-atoms in the structures presented here were placed into the apo model only when positive density was observed in $F_o-F_c$, $2F_o-F_c$, and composite omit maps. The XMP was taken from the original T. foetus XMP structure (Whitby et al., supra, (1997)) and the IMP model was derived from this XMP structure. The NAD$^+$ model was obtained from the phosphoglycerate dehydrogenase structure (Schuller et al., Nat. Struct. Biol. 2:69–76 (1995)) and the MOA model from the Chinese hamster IMPDH structure (Sintchak et al., Cell 85:921–930 (1996)). The IMP, XMP, and MOA hetero-atoms were fitted into density using 0 and minimized in CNS. The coordinates for NAD$^+$ were fitted as above and subsequently submitted to the Dundee PRODRG Server (van Aalten et al., J. of Computer Aided Mol. Design 10:255–262 (1996)) for minimization and CNS topology file generation prior to refinement in CNS.

A cis peptide bond not previously described for IMPDH was located in all structures between Gly290 and Asn291 and is located within 7 Å of the nicotinamide portion of the NAD$^+$ cofactor. This was present but not described in the T. foetus model co-crystallized with XMP (Whitby et al., supra, (1997)) but absent in all other structures to date. The cis bond appears to cause the chain to turn away from the active site, preventing it from entering the active site. All other IMPDH x-ray structures have this same turn but a cis peptide has not been reported in those structures.

Figure 4:
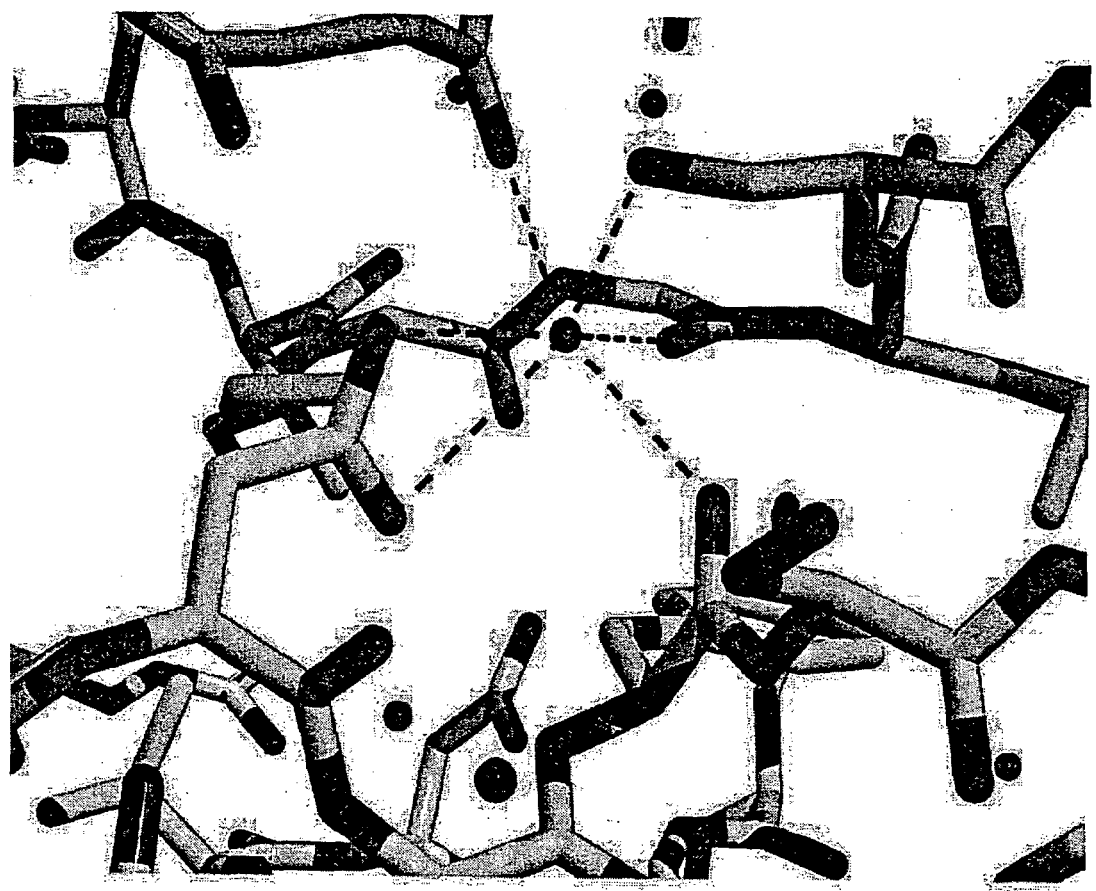
FIG. 4 shows that a potassium ion was located at the dimer interface near the cofactor binding site. The carbon atoms of the neighboring monomer are shaded and waters are shown as spheres. The ion's hydrogen bonding partners and bond distances, clockwise from Asp264, are 2.94 Å and 2.49 Å, Asn460 (2.66 Å), Ser22 (2.57 Å), Gly20 (2.30 Å), and Phe260 (2.64 Å).
Figure 5:
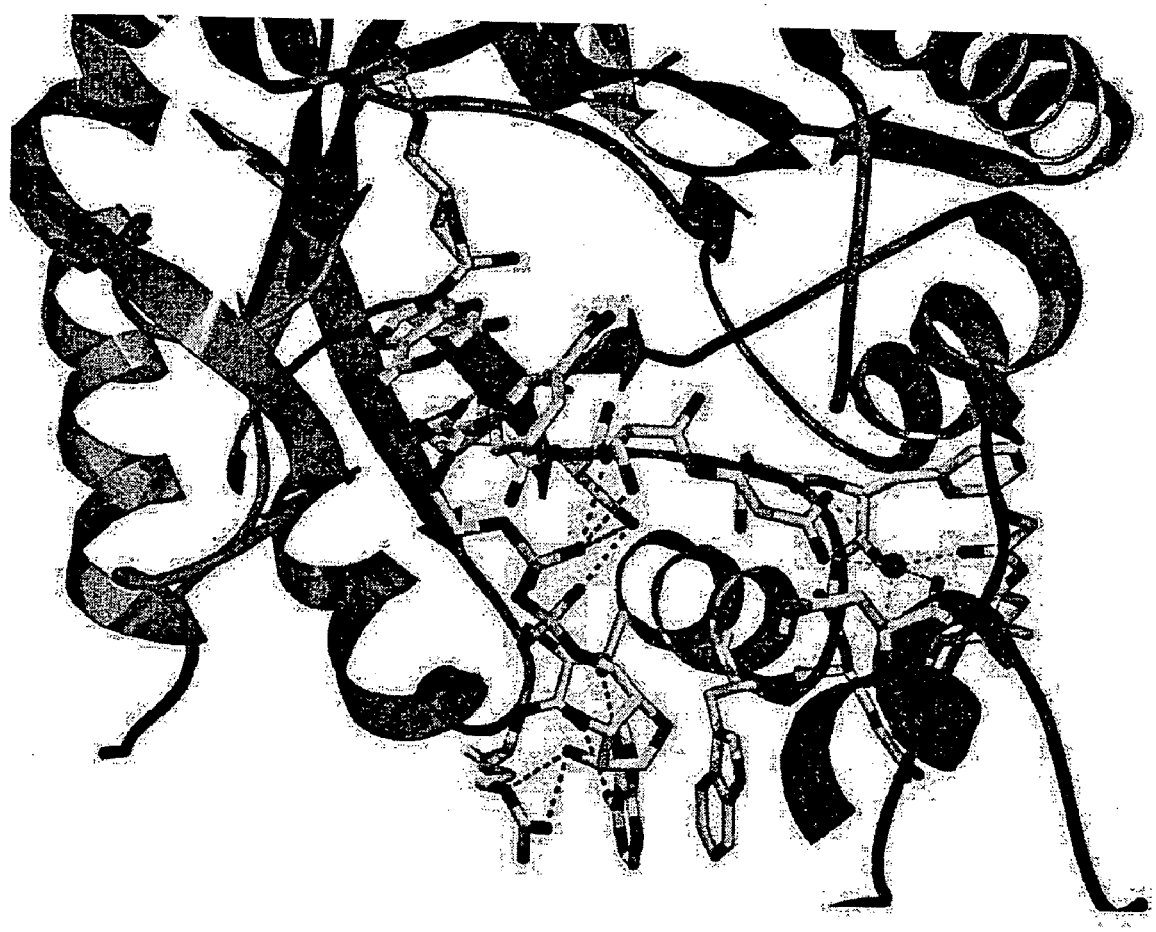
FIG. 5 shows a ribbon diagram of one IMPDH monomer looking down the barrel of the protein with bound, XMP, $NAD^+$ (both in CPK), and the potassium ion.

A novel potassium ion was also identified in all structures, approximately 9 Å away from the cis peptide. This ion is coordinated by the backbone carbonyl of Phe266, the side chain carboxyl oxygens of Asp264, and the following atoms of a neighboring monomer: backbone carbonyls of Gly20 and Asn420, and the Ser22 hydroxyloxygen (FIG. 4). The potassium ion also lies near the NAD$^+$ binding site and appears to stabilize the monomer—monomer interface as well as the cofactor binding site, but it does not make direct contact with NAD$^+$ (FIG. 5).

A strong electron density peak was found extending from the active site cysteine thyol in the IMP and IMP+MPA bound structures. This appears to be a result of oxidation to sulfenic acid (Cys-SOH) from oxygen exposure during crystal formation and extended incubation prior to cryo-cooling for data collection. This type of oxidation has been previously described for NADH peroxidase (Stehle et al., *J. Mol. Biol.* 221:1325–1344 (1991)). Although it is interesting that the cysteine was modified only in the IMP-bound structures, this could be an artifact of crystallization as the active site cysteine was not resolved in the XMP+NAD structure, and the XMP+MPA structure had poor density around the cysteine.

EXAMPLE IV

Substrate and Product Binding to *T. foetus* IMPDH

This examples describes substrate and product binding to *T. foetus* IMPDH.

In all complex structures presented herein, the substrate/product sugar hydroxyls are hydrogen bonded to the carboxyl side chain of Asp358 as well as two waters. The purine O6 accepts a hydrogen-bond from the amide nitrogens of Glu408 and Gly409. The side chain of Ile318 makes van der Waals contact with the base. The nucleotide phosphate group is coordinated by the hydroxyl of Tyr405, backbone nitrogens of Ser317 Gly381, and Arg382, and three waters.

In the IMP complex structure, the purine N1 and N3 both form hydrogen bonds with waters. The water in contact with N1 is bridging it to the backbone carbonyl of Glu431, which is 4.79 Å from the N1 as well as Gln324. This portion of the active site flap was modeled into relatively poor density but the water is clearly observed, as well as the backbone from residue 429–431. The water on N3 is bridging it to the backbone nitrogen of Gly316. The phosphate group is coordinated by the hydroxyl and the main chain nitrogen of Ser317. The IMP+MPA complex differs from the IMP structure in that the purine N1 is forming a direct hydrogen bond with the Glu431 carboxylate oxygen. The other Glu431 carboxylate oxygen is in contact with the MOA ring hydroxyl.

Only in the XMP+MPA structure is the backbone carboxyl of Glu431 in direct contact with N1 and the active site flap is not shifted in this structure. The XMP+NAD$^+$ complex structure is also characterized by the backbone carbonyl of Glu431 in direct contact with the purine N1. As in the IMP bound structure, the hydroxyl of Ser317 is pointing toward the XMP phosphate. However, the main chain nitrogen of Ser317, which was coordinating the water hydrogen bonding with N3 in the IMP structure, has moved 0.37 Å further away from the substrate and the water is no longer present.

Binding in the substrate-binding pocket is characterized by subtle conformational changes when binding IMP vs. XMP. Furthermore, a comparison with other IMPDH structures reveals few changes to the active site across species. IMP binds to the *S. pyogenes* enzyme in a nearly identical fashion as it binds to the *T. foetus* enzyme. Most noticeably, the purine ring system of the *S. pyogenes* IMP is rotated away from the catalytic Cys310. In *T. foetus* IMPDH, the ring system does not rotate away. Instead, it is the active site Cys319 that is displaced 1.3 Å from the catalytically active conformation. A structural alignment of *T. foetus, S. pyogenes*, and Chinese hamster IMPDH shows that the active site loops are almost identically positioned. Based on surrounding charges, bond distances, and geometry, we believe that there is a cation present in the bacterial structure at the position marked as water 179 in the coordinate entry (Zhang et al., supra, (1999)). Because the active site cysteine is displaced in the IMP-bound structure of the protist, the Cys319 backbone carbonyl disrupts the ion binding pocket. In the *T. foetus* XMP+MPA structure, the XMP C2 keto group causes the active site cysteine to move even further into the cation binding pocket.

Human type II IMPDH has the *T. foetus* Lys310 and Glu431 substituted with arginine and glutamine, accounting for part of the difference in sensitivity to MOA (Digits and Hedstrom, supra, (1999)). Glu431 is located near the N1 nitrogen of the IMP. In the structures presented here, only the IMP+MPA structure shows the side chain interacting with partially positively charged groups on both the IMP and MOA rings. In the other *T. foetus* structures, as well as the Chinese hamster and human type II structures, Glu431 is pointed away from the IMP, and toward the MOA or SAD inhibitors, leaving the main chain carbonyl pointed at the IMP, XMP, or 6-Cl IMP. The hamster Gln441 side chain is within hydrogen bonding distance of the MOA ring hydroxyl. The lysine or corresponding arginine is pointing between the IMP sugar hydroxyls and the MOA or cofactor. Because the arginine side chain is longer, they are near hydrogen bonding distance with one of the ribose hydroxyls of IMP and near the methyl group on the MOA ring.

RMS alignments of the substrate and product complex structures show very little movement in the core of the protein as well as the ordered portions of the active site flap. Unfortunately, the structures presented here have 10 to 14 residues missing from the active site flap, making characterization difficult. A possible explanation for this disorder is described below. The majority of conformational differences are located at the active site loop. The active site loop was resolved in all structures with the exception of the NAD$^+$ XMP co-crystal. In all cases, the loop is not well ordered with high B-factors, but overall, little movement is observed in the protein backbone of these structures with the exception of the IMP+MPA complex.

In the IMP+MPA structure, the side chains of the active site flap residues 431 to 434 move away from the active site to allow Glu431 to rotate around the Ca-C main chain bond and form hydrogen bonds with the IMP N1 and the MOA ring hydroxyl. The active site loop residues 320 to 323 shift away from the substrate+inhibitor complex with the Arg322 alpha carbon moving 7.5 Å from its position in the XMP+MPA model. It is unclear from these structures what is driving this movement of the loop, as these residues do not appear to be directly involved in substrate or cofactor binding. The nearest of these residues, Thr321, is 6.6 Å away from the MOA in the XMP+MPA structure. This complex is unlikely to occur under physiological conditions since NAD$^+$ has a far greater binding affinity than MOA. However, MOA does make a useful cofactor analog for the nicotinamide portion of the NAD$^+$ binding site. This unique pairing may be useful in structure based drug design since a structure containing unreacted substrate and cofactor may be more difficult to obtain.

EXAMPLE IV

Cofactor and Inhibitor Binding to *T. foetus* IMPDH
This example describes cofactor and inhibitor binding to *T. foetus* IMPDH.

Figure 6:
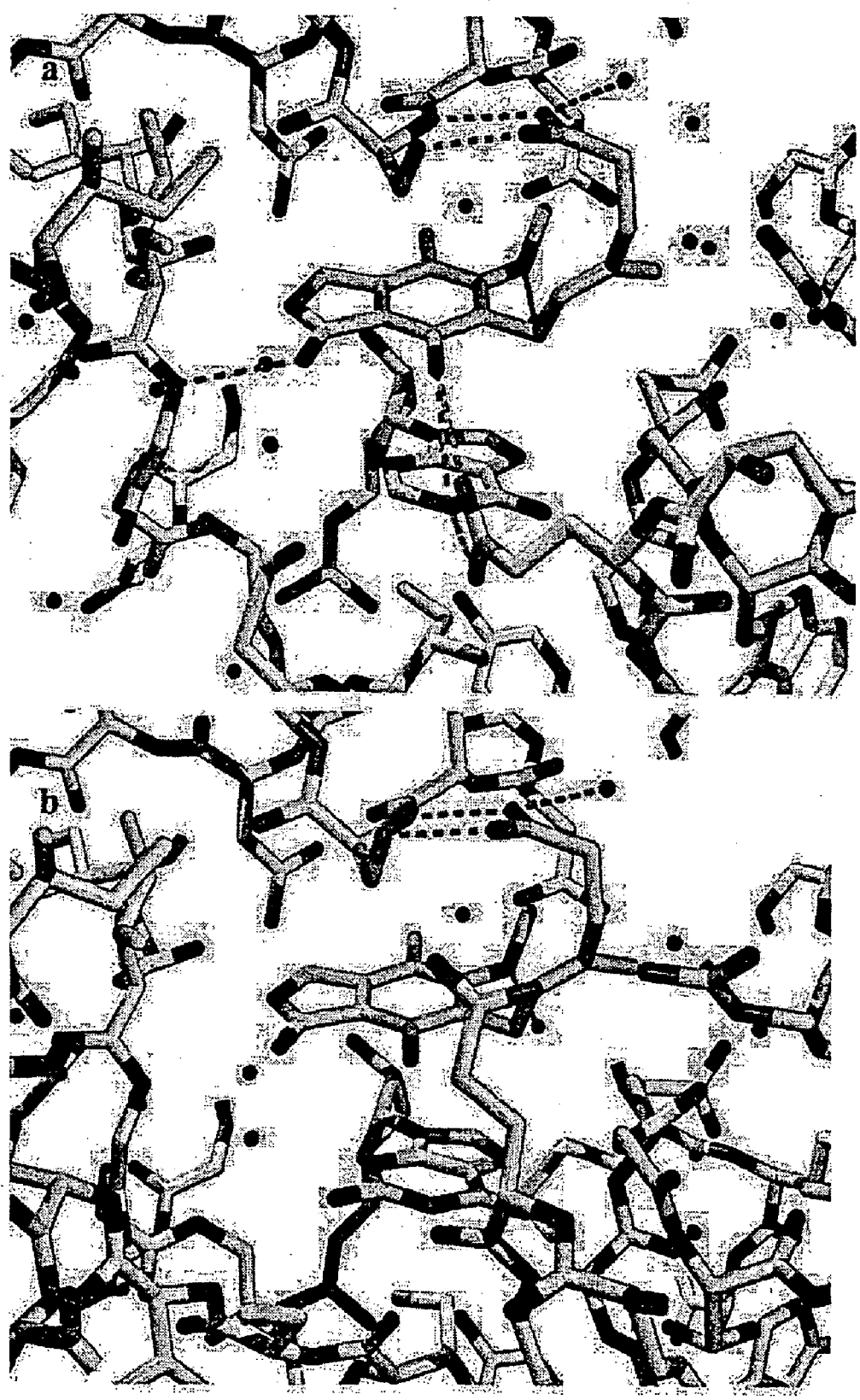
FIG. 6 shows binding of the inhibitor MOA to IMPDH showing bonds (a) with IMP (substrate) and (b) with XMP (product). A notable difference is the movement of the Glu431 side chain, which binds both the substrate and the inhibitor in the IMP-bound structure.
Figure 7:
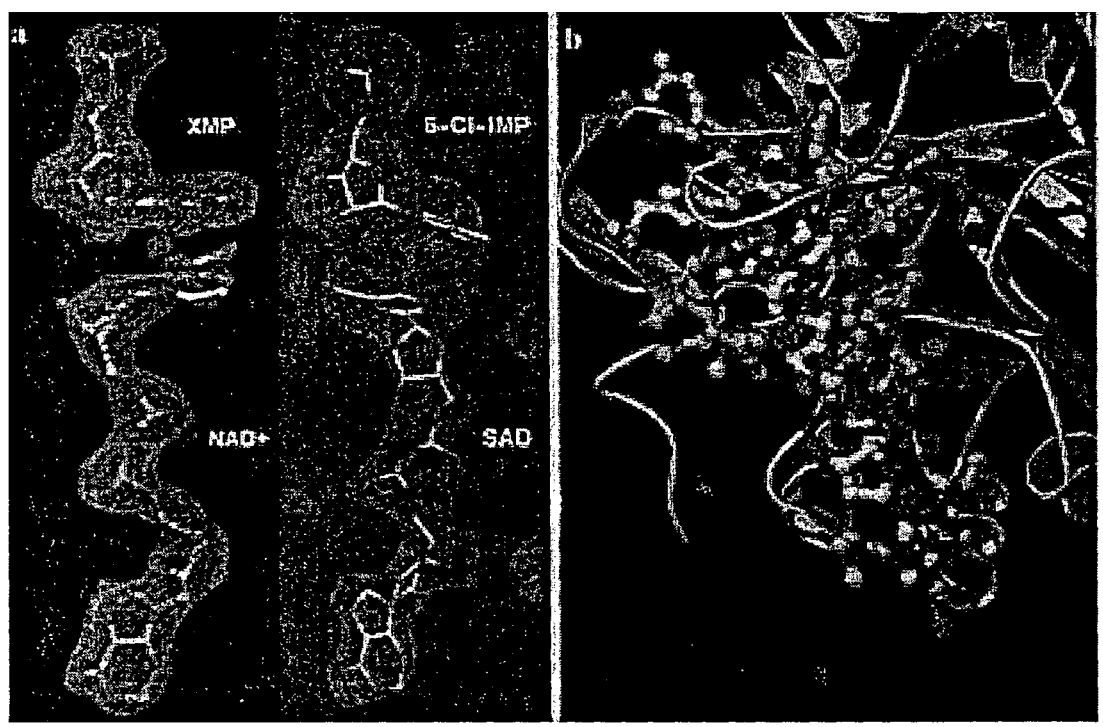
FIG. 7 shows a comparison of the active site loop of the *B. burgdorferi* apo structure (purple) with those of *T. foetus* IMP-bound (yellow), IMP+MPA (blue), XMP+MPA (green), and XMP+NAD$^+$ (red) shows a high degree of stability throughout the core domain of the enzyme as well as the resolved portion of active site flap during substrate and product binding. Also pictured are XMP and NAD$^+$ in CPK and the potassium ion in gray.

In the two MOA complex structures (IMP+MPA and XMP+MPA), the inhibitor is bound in a similar manner (FIGS. 6a and b). One difference, however, is that the side chain of Glu431, which is hydrogen bonding with both the IMP and MOA, is shifted away from the product-inhibitor complex in the XMP+MPA structure. This may be caused by the stronger partial negative charge on the XMP due to the keto group at the C2 position of the base. The main chain nitrogen of Gly314 has moved from 3.26 Å to 3.64 Å away from the MOA ring O1. The nicotinamide portion of the NAD+ cofactor stacks with the XMP purine moiety and the nicotinamide oxygen hydrogen-bonds with the Gly314 nitrogen in the same manner as the MOA inhibitor. Additionally, the nicotinamide phosphate forms bonds with the hydroxyls of Ser262 and Ser263, as well as the main chain nitrogen of Ser263. The carboxylic acid tail of MOA also binds the Ser263 hydroxyl and nitrogen. The nicotinamide sugar hydroxyls form hydrogen bonds with Asp261. The NAD+ adenosine ring stacks between the side chains of Trp269 and Arg241. Arg241 also forms hydrogen bonds with the adenosine phosphate group.

Figure 8:
FIG. 8 shows a comparison of the fit of the *T. foetus* product XMP and NAD$^+$ into electron density. On the left, the *T. foetus* structure is shown with a 2Fo–Fc electron density map contoured at 1.0 σ, and on the right, the published human structure with 6-Cl IMP and the cofactor analog, SAD, uses a σA-weighted Fo–Fc omit map. Panel b illustrates the binding of NAD$^+$ to the cofactor binding site of *T. foetus* IMPDH. NAD$^+$ makes extensive use of hydrogen bonds with IMPDH and ordered waters. The nicotinamide ring n-bonds with the purine ring of XMP while the adenosine ring stacks between Trp269 and Arg241.

Shown herein is the first IMPDH structure with both the XMP product and the NAD$_+$ cofactor bound. Although the human type II structure has 6-Cl IMP and the NAD+ analog SAD bound in the respective substrate and cofactor binding sites, the 2.9 Å structure left some ambiguity in the positioning of the SAD molecule (Colby et al., *Proc. Natl. Acad. Sci. USA* 96:3531–3536 (1999)). At 2.15 Å and with good electron density in the cofactor binding site, we were able to accurately place the cofactor (FIG. 8). Although the cofactor lies near the monomer—monomer interface, it does not make contact with the neighboring subunit in the *T. foetus* tetramer. The nearest residue is Ile27, 4.7 Å away from the adenosine portion of the cofactor. This is in contrast to the human structure where the neighboring monomer makes contact with the adenosine ring. The nicotinamide sugar hydroxyls in the *T. foetus* structure form hydrogen bonds with Asp261 and two waters in the same manner as the substrate ribose hydroxyls interact with Asp358. Asp261 is completely conserved across species. In the human structure the cofactor sugar is further from the nicotinamide plane and one of its hydroxyls is out of reach of the human Asp274.

The proximal portion of the active site flap lies near the cofactor but the electron density is too ambiguous to discern any contacts. Similarly to the human type II structure, the adenosine portion of the cofactor is stacked between Arg241 and Trp269. These residues correspond to His253 and Phe282 of human type II IMPDH, and Arg253 and Tyr282 of human type I IMPDH. It is clear that this stacking is conserved in both the mammalian and *T. foetus* structures. Interestingly, the *S. pyogenes* model contains threonine and glycine in these positions, and with the exception of *P. furious*, which contains arginine and lysine residues, respectively, no bacterial sequence contains a stacking partner for the IMPDH cofactor at this location. This suggests that bacterial enzymes may have an alternate cofactor binding mechanism and may be the reason why the bacterial enzyme has a lower affinity for NAD+. If the NAD+adenosine ring is indeed not involved in base stacking in the bacterial structure, an effective inhibitor may be a mono-nucleotide nicotinamide derivative.

MPA does not appear to trap the covalently bound product. The inhibitor MOA binds to IMPDH in the nicotinamide portion of the cofactor-binding pocket using many of the same binding partners as the cofactor. The cofactor NAD+ binds to IMPDH with many more interactions and therefore has a greater binding affinity to the enzyme when substrate is bound. Our failure to generate the covalent intermediate may be due to *T. foetus* IMPDH having a far faster release of E-XMP* than the mammalian enzyme (Digits and Hedstrom, supra, (1999)) or it may simply be that MOA does not inhibit XMP disassociation from *T. foetus* IMPDH. MOA does bind the *T. foetus* enzyme with significantly lower affinity than the mammalian form.

A novel potassium binding site was also identified. A high positive difference density peak in the $F_o$–$F_c$ electron density map was observed at a dimer interface near the cofactor-binding site. This peak was surrounded by four backbone carbonyl oxygens and the carboxylate of Asp264 (FIG. 4). The charge environment indicates a cation, and the coordination and B factor are a probable indication of a potassium ion. This potassium is located too far from the substrate and cofactor to affect catalysis or to directly affect binding (FIG. 5). However, it may aid in cofactor binding by stabilizing adjacent residues, which are involved in cofactor binding. Additionally, the monovalent cation likely stabilizes the dimer interface. This ion is present in all structures presented here (FIG. 9a). The ion was not noted in the previous *T. foetus* structures (Whitby et al., supra, (1995); Whitby et al., supra, (1997)), but there was a water molecule placed at that location in the *T. foetus* XMP-bound structure. It is possible that the previous *T. foetus* structures were not at sufficient resolution to detect the ion.

Figure 9:
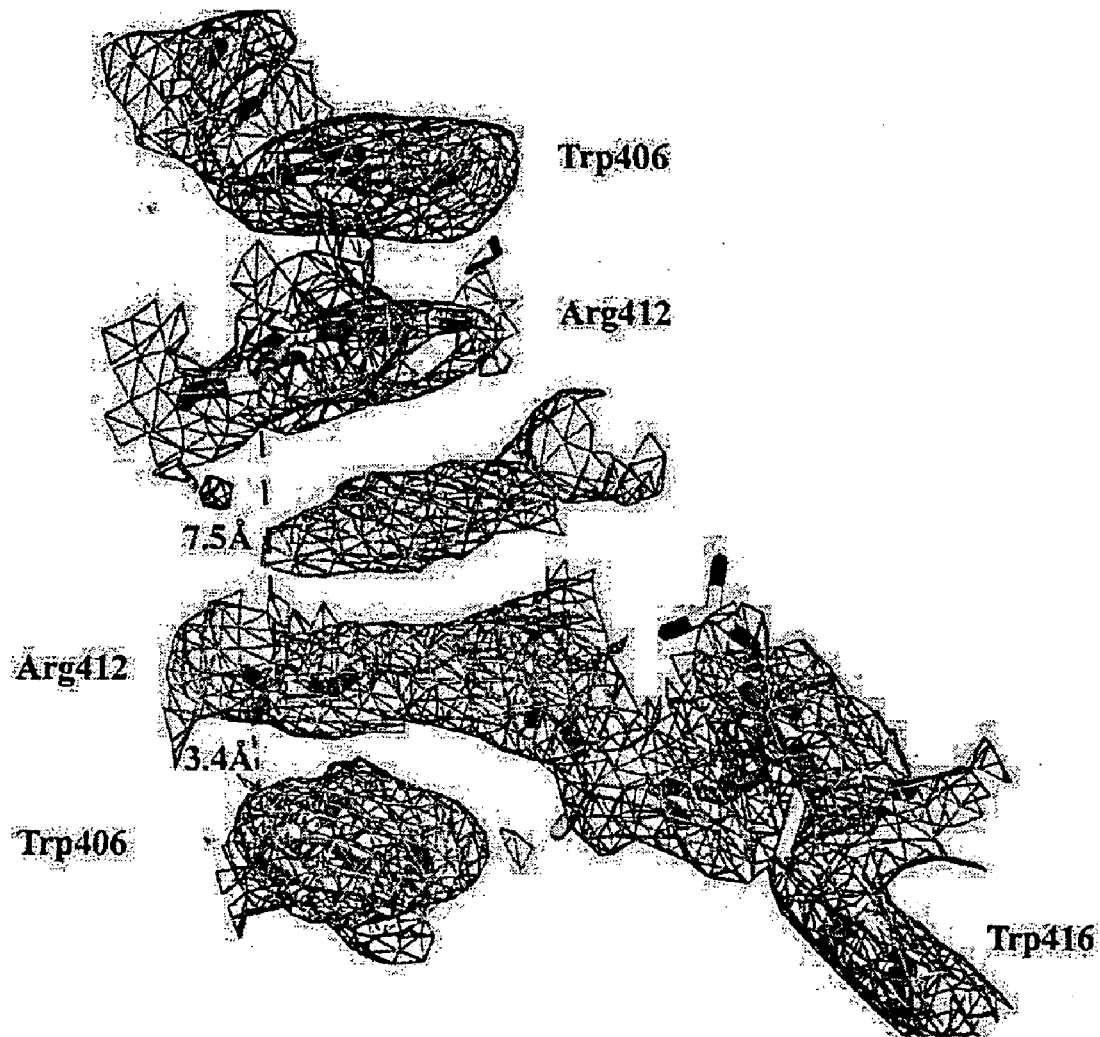
FIG. 9 shows a structural alignment demonstrates that potassium binding is conserved through all *T. foetus* structures presented here. The carbon atoms of a neighboring monomer are shown in dark gray. The *T. foetus* structure contains an aspartate at 264 while the mammalian enzyme (purple oxygens) has substituted a glutamine (b) and the bacterial enzyme (also purple oxygens) substitutes a histidine (c). Both of these side chains leave no room for the ion. An alignment of the *T. foetus* structure (blue), human structure (yellow) and *S. pyogenes* structure (green) shows that this does not appear to uniquely alter the dimer interface (d).

This ion appears to be unique to *T. foetus* IMPDH and is not likely to represent the second ion binding site proposed for the *E. coli* enzyme (Kerr et al., *Arch. Biochem. Biophys.* 375:131–137 (2000)). A protein alignment shows that the *T. foetus* Asp264 is substituted with glutamine in most eukaryotic IMPDH and with histidine in prokaryotic IMPDH. A structural alignment with the human and bacterial structures (Colby et al., supra, (1999); Zhang et al., supra, (1999)) shows that the substitutions would cause steric and charge clashes with the potassium (FIGS. 9 b and c). Absence of this ion does not appear to affect the secondary structure of either human or bacterial IMPDH (FIG. 9d). The potassium ion reported in Chinese hamster IMPDH was not detected in these structures. This is likely due to the highly mobile nature of the active site loop that forms part of the *T. foetus* IMPDH potassium binding site. Additionally, *T. foetus* IMPDH retains 80% of its activity in the absence of potassium (Verham et al., *Mol. Biochem. Parasitol.* 24:1–12 (1987)) and it has been shown that other cations can activate bacterial IMPDH (Kerr et al., supra, (2000)). It is possible that this ion only binds in the covalently bound intermediate or similar conformations.

Possible Π stacking at crystal contacts disorder the active site flap. The entire active site flap has not been resolved in any IMPDH structure to date. It had been hypothesized that a *T. foetus* structure bound with substrate and MOA would resolve this loop (Digits and Hedstrom, *Biochem.* 39:1771–1777 (2000)). This was based on fluorescence assays where a single tryptophan on the active site flap was monitored under increasing concentrations of MOA. The resulting decrease in fluorescence suggested the tryptophan, as well as the flap, may have become ordered. Unfortunately, the flap remained disordered in all structures presented here. The reason for this may be that Trp416 is involved in Π stacking with Trp406, Arg412, and the corresponding residues of a neighboring, symmetry related monomer. This symmetry related monomer is not part of the catalytic tetramer and the space occupied by Trp416 is on a crystallographic two-fold axis, implying that each monomer can only occupy this site at 50%. Although this area has weak electron density, density large enough to fit the tryptophan side chain and the resulting spacing is reasonable for a single copy of Trp416 to fit in this space. Additional density suggests an alternate conformation for this tryptophan, adjacent to the peptide bond between Ser83 and Gln84 (FIG. 10). This tryptophan is physically able to fit in either position; however, residues 414 and 415, which also move as a result of the two conformations, have little density in either conformation and there is no usable density beyond Trp416 in either conformation. We believe that the residues beyond Trp416 are disordered, in part, because of the multiple conformations of this tryptophan. Mutation of this residue may aid in resolving this loop but it is also likely to inhibit crystallization due to the loss of this crystal contact. Furthermore, the tryptophan may be stabilizing the active site flap residues preceding it, and a mutation may cause a loss in resolution of a greater portion of the loop as is the case in most other IMPDH structures. It is possible that addition of adenosine or its analogs to this mutant protein could bridge the Π systems of the two monomers, however this hypothesis has not been tested.

EXAMPLE V

Proposed Structural Mechanism for *T. foetus* IMPDH

This example describes the proposed structural mechanism for *T. foetus* IMPDH.

An improvement upon the original *T. foetus* 2.3 Å apo structure structure showing the active site loop would increase the understanding of the catalytic mechanism of IMPDH. This is likely due to the increased flexibility of the *T. foetus* loop due to the three consecutive glycine residues present in the loop. The *T. foetus* Gly315 is substituted with a proline in *B. burgdorferi*, likely providing the active site loop with increased stability. It appears that the *T. foetus* loop is stabilized only by occupation of the active site. If the apo *T. foetus* active site loop conformation is similar to that of the *B. burgdorferi* loop, a hypothesis of the IMPDH structural mechanism can begin to be described.

Figure 11:
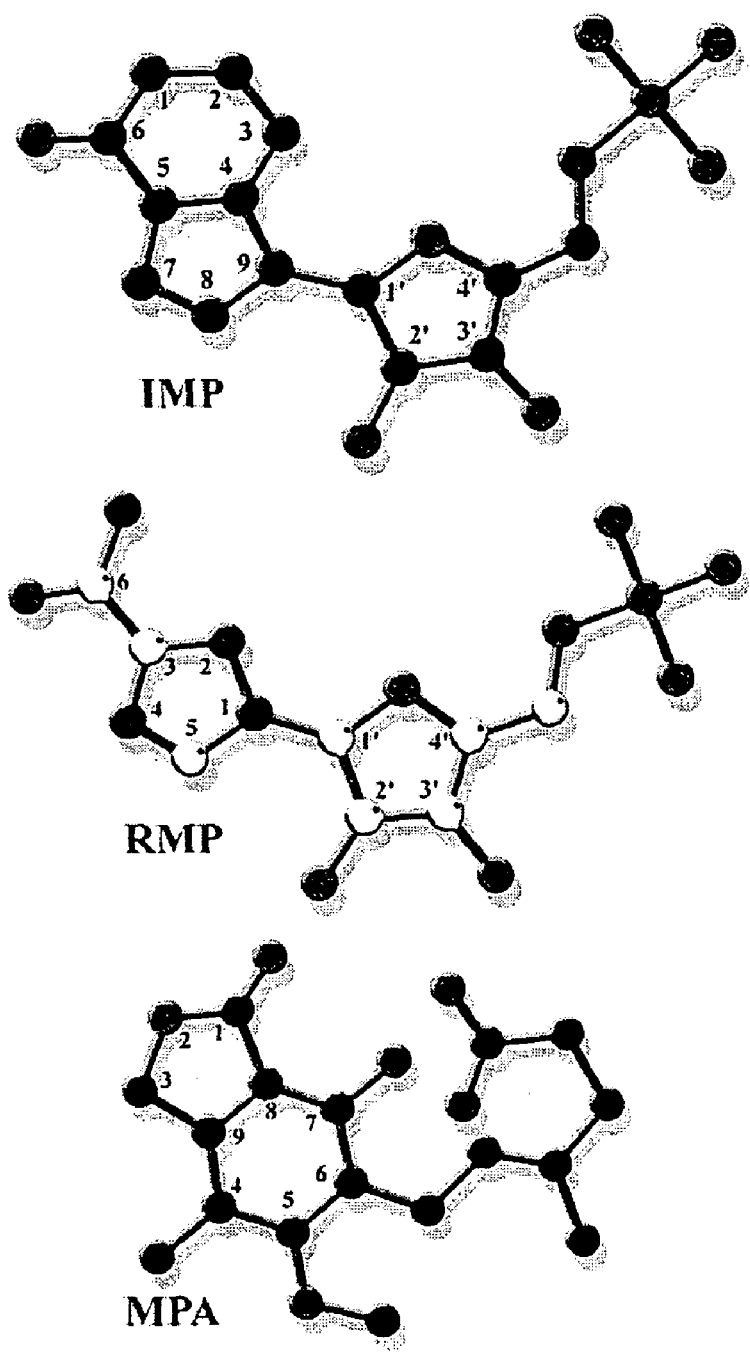
FIG. 11 shows structural formulas of the indicated compounds. The product XMP contains an additional keto group at the C2 position of the substrate IMP. This figure was created with Ligplot (Wallace et al., *Prot. Eng.* 8:127–134 (1995)) and Photoshop (Adobe Systems, San Jose, Calif.).

The kinetic mechanism is random-in ordered-out with NADH leaving before XMP is released from the enzyme. When IMP binds the enzyme first, the enzyme is in an open conformation and IMP has easy access to the active site. When NAD$^+$ binds first, the nicotinamide group blocks one entrance to the active site. Now, IMP must instead use the opening defined by the active site loop in its open configuration. An alignment of the apo *B. burgdorferi* structure and the *T. foetus* IMP-bound structure reveals an opening leading to the active site that is approximately 10 Å wide and 12 Å tall between the loop and the flap (FIG. 11). This opening, together with the flexible nature of the loop and the flap, would allow access to the active site. Additionally, Ser317 and the hydrophobic Ile318 are solvent-exposed. These two amino acids may serve as a bait to draw IMP into the structure. When IMP binds in the active site, it causes the loop to close and Ser317 to bind to the phosphate, while the Ile318 side chain forms hydrophobic interactions with the purine ring. This, in effect, closes the lid, and the substrate IMP or the product XMP must wait for NADH to leave before either nucleotide can dissociate from the enzyme.

With the exception of the IMP+MPA structure, there are no active-site bonds present in the IMP structure that are not present in the product+inhibitor or product+cofactor structure. It appears that the enzyme relies on the release of the cofactor and subsequent solvent exposure of the product with its newly formed keto group and the corresponding partial negative charge, in order for product to be released. This observation confirms kinetic studies of the *T. foetus* enzyme that show the off-rate of IMP at 7.7 s–1 and that of XMP at 17 s–1 without cofactor bound (Digits and Hedstrom, supra, (1999)). Additionally, the nicotinamide ring of NADH would lie near the O2 carbonyl of the product XMP; this newly developed partial charge may act to push the now less polar ring out of the active pocket.

The identification of a cation at the active site of the Chinese hamster structure and the possibility of a cation in the same location in the *S. pyogenes* structure are intriguing. An ion present when the substrate is bound but unreacted and still present when product is covalently bound might indicate that this ion is important in placing the active site cysteine in an orientation required for catalysis.

In the bacterial structure, Thr310 makes hydrogen bonds with an ordered water and the Glu420 main chain. This creates a stabilizing effect for several residues in the loop as well as the C-terminal portion of the active site flap. Examination of the other bacterial structure, *B. burgdorferi* in the apo conformation, reveals that the threonine is not in position to form bonds with the active site flap, resulting in a larger section of the C-terminal portion of the flap to be disordered. It appears that this increased stability in the *S. pyogenes* active site loop, and of Cys310 in particular, causes the purine to rotate away from the active site cysteine. In the *T. foetus* structure, Thr310 is substituted with Ile320 and this hydrophobic residue is likely to destabilize the active site loop in this conformation, allowing the cysteine to move rather than the purine. This threonine is conserved in prokaryotes while most eukaryotes carry the isoleucine. Apparently, it is the covalent bond with the substrate that is the stabilizing factor in the Chinese hamster model and it would not be surprising to find that the Ile-Thr substitution plays a role in prokaryote vs. eukaryotic enzyme kinetics.

EXAMPLE VI

Steady State Kinetic Analysis of *T. foetus* IMPDH

Figure 12:
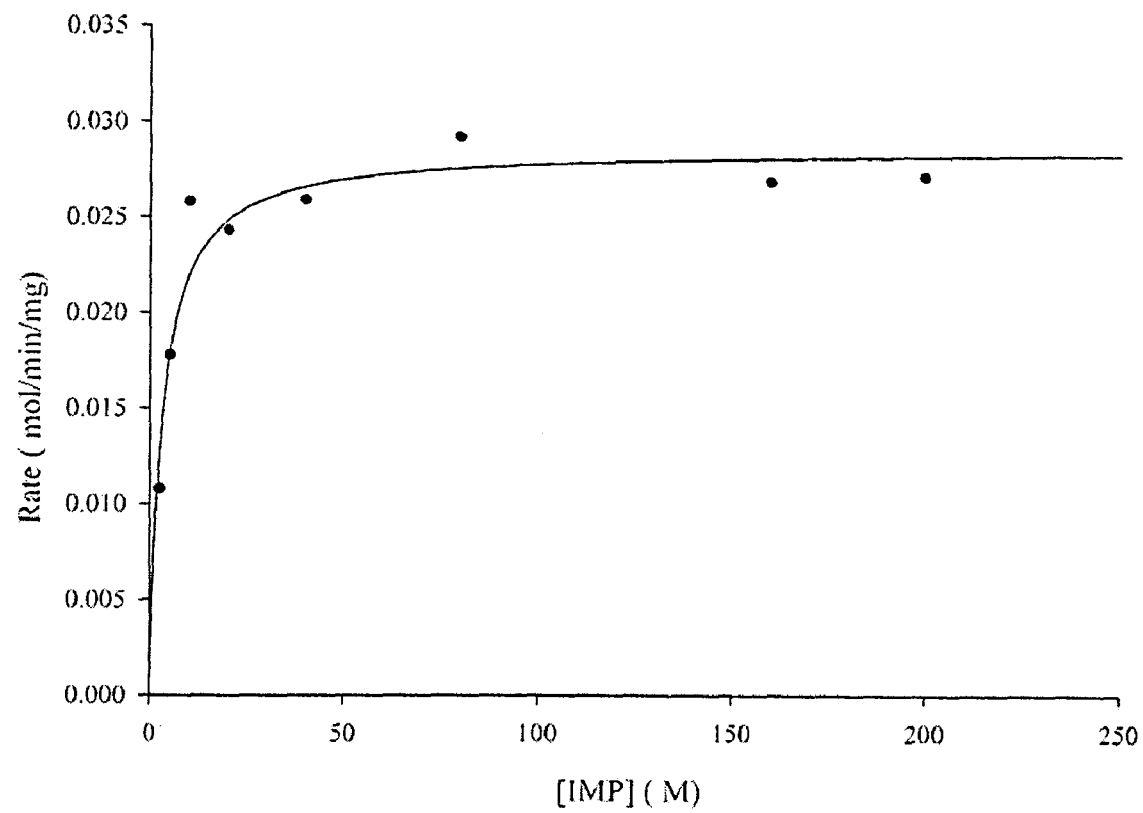
FIG. 12 shows a Michaelis-Menten graph. The initial velocity increases with increasing concentration of substrate. The concentrations of enzyme and cofactor were held constant.

Steady-state kinetic analysis of to *T. foetus* IMPDH using IMP as a substrate was performed using a spectroscopic method. Initial velocity measurements were taken with increasing amounts of IMP and plotted as a Michaelis-Menten graph (FIG. 12).

Figure 13:
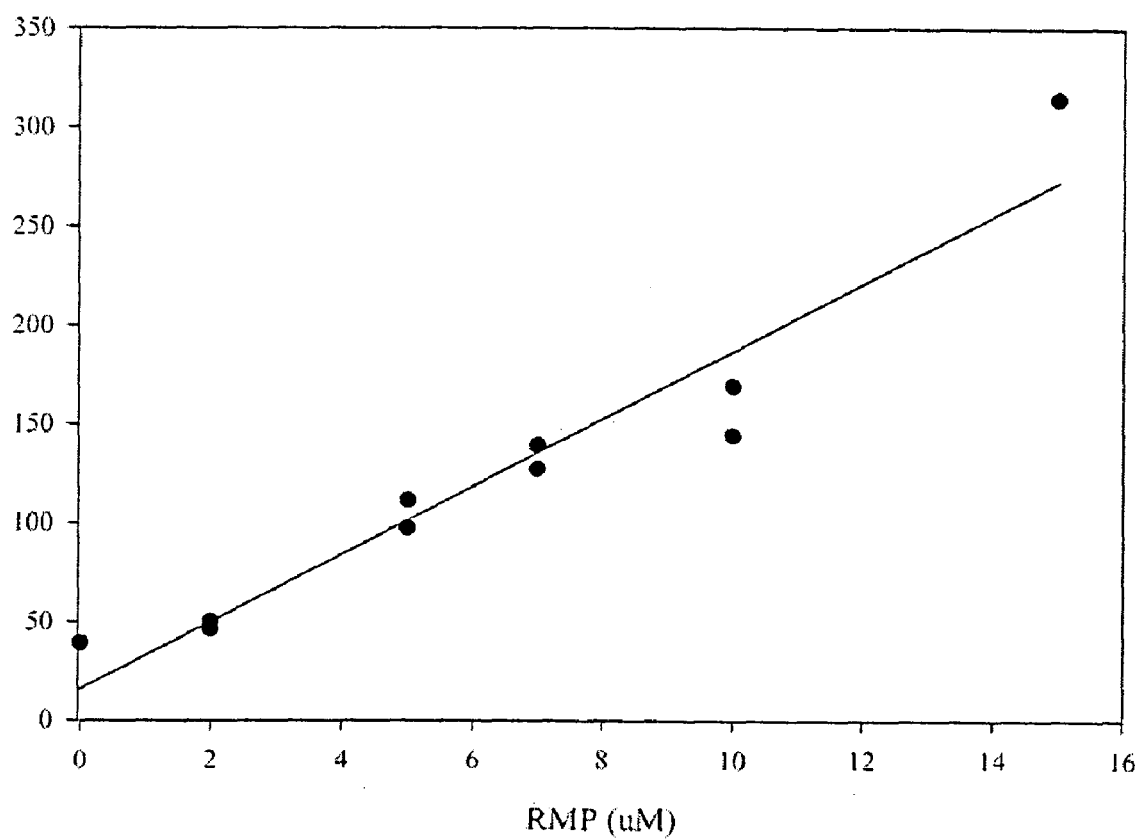
FIG. 13 is a plot showing IMPDH inhibition with increasing concentration of RMP. The concentrations of IMP, NAD$^+$, and enzyme are constant.

From the plot, an apparent Km of 3.0 M was calculated for IMP. RMP, a competitive inhibitor for the substrate IMP, was then assayed for inhibition of the protozoan enzyme with increasing concentrations of RMP. These data were graphed as a Dixon plot (FIG. 13). The apparent Ki for RMP was determined to be 65 nM.

Steady-state kinetic analysis of *T. foetus* IMPDH was performed with 4.5 M enzyme in a reaction buffer containing 100 mM KCL, 50 mM Tris pH 8.0, 1 mM DTT and 1 mM NAD$^+$. Reactions were initiated with the addition of IMP, and the production of NADH was monitored spectrophotometrically at 340 nm (340=6.22 mM$^{-1}$ cm$^{-1}$) using a Perkin Elmer Lambda 40 (EG&G, Inc., Wellesley, Ma) spectrophotometer at 25° C. For determination of the apparent Km value for IMP, the concentration of IMP was varied from Km/2 to 10 Km with the NAD$^+$ concentration fixed at 1 mM. The initial velocity at various IMP concentrations was measured and was fit to the Michaelis-Menten equation by Sigma plot (SPSS Inc., Chicago, Ill.). Since RMP is known to be a competitive inhibitor with IMP, the apparent inhibition constant Ki of RMP was estimated using a Dixon plot. In the experiments, RMP concentration was varied while IMP concentration remained fixed at 40 M, and the NAD+ concentration was 1 mM. The initial velocities at various RMP concentrations were determined by the extraction of the linear portion of the reaction time-course. By plotting 1/v vs. inhibitor concentration, the apparent inhibition constant Ki was calculated using the following equation:

$$1/v=(K_m/V_{max})(K_i[\text{IMP}])\ [\text{RMP}]+1/V_{max}(1+(K_m/[\text{IMP}]))$$

EXAMPLE VII

Crystallization to *T. foetus* IMPDH with Ribavirin

Diffraction quality IMPDH crystals in the space group P432 grew within five days. The cryo-colored crystals diffracted to 1.90 Å for the RMP co-crystal and to 2.15 Å for the crystal with RMP and MOA using synchrotron radiation. A randomly selected test set of diffraction data (5% of all-structure factors) was set aside for Rfree monitoring. The published isomorphous *T. foetus* apo structure (PDB code 1AK5) was used as the initial model for both structures allowing unbiased building of the active site loop and the active site flap. One round of rigid body refinement and simulated annealing was followed by several rounds of energy minimization, B factor refinement, model building, and water picking. Composite $2F_o-F_c$ and $F_o-F_c$ omit maps were generated to aid in model building. The program PROCHECK was used to validate the structures (Laskowski et al., *J. App. Cryst.* 26:283–291 (1993)). Crystal, refinement, and PROCHECK statistics are shown in Table 9.

Figure 14:
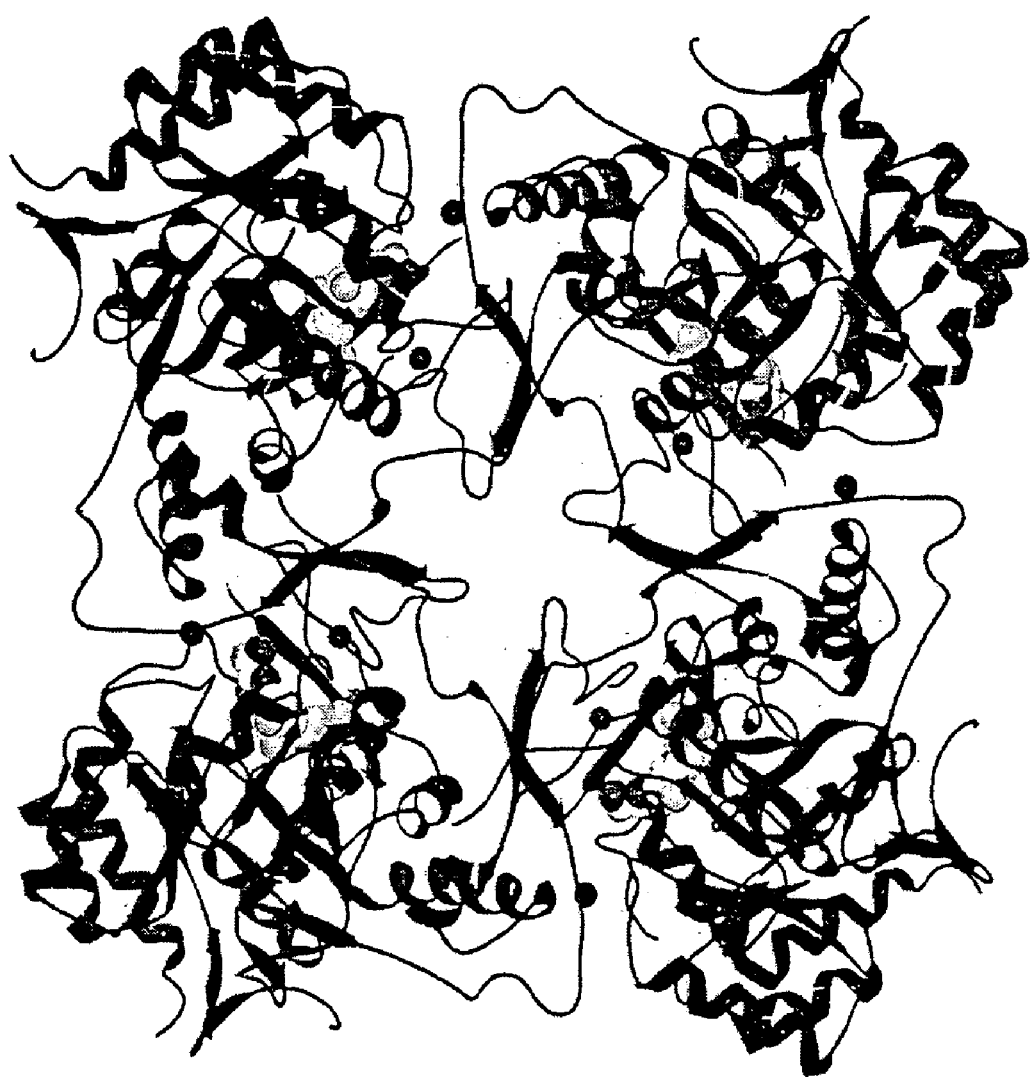
FIG. 14 shows a ribbon diagram of the IMPDH tetramer viewed looking down the four fold axis. The enzyme is in complex with the inhibitor RMP (CPK) and a sodium ion (green). A potassium ion (blue) lies in the dimer interface near the cofactor binding site. This image was made in Deepview (Guex and Peitsch, *Electrophoresis* 18:2714–2723 (1997)) and rendered in POVRAY 3.5 beta (www.povray.org).
Figure 15:
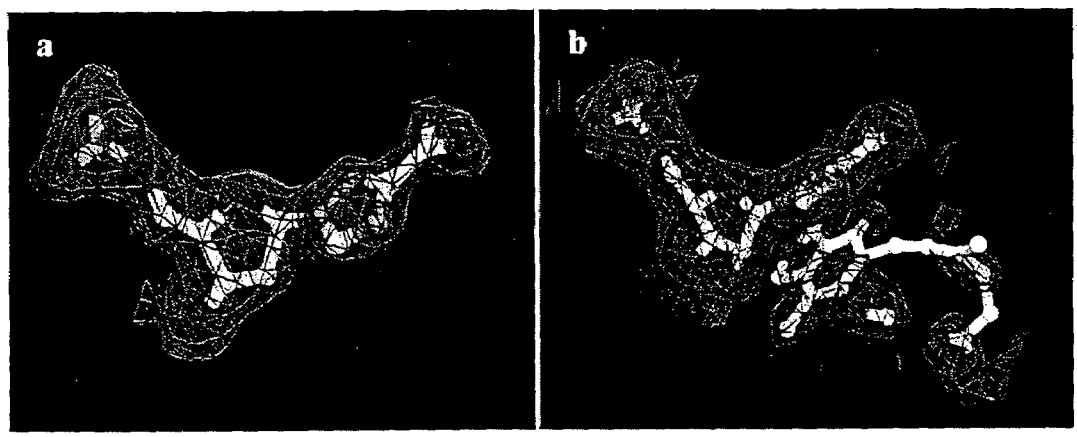
FIG. 15 shows composite annealed omit electron density maps at 1.9 Å resolution surrounding the inhibitor RMP (a) contoured at 1.8 σ. The MOA-soaked RMP co-crystal structure (b) at 2.2 Å shows nearly complete density for MOA only when contoured at 0.5 σ despite soaking in saturating amounts of MOA. Soaking for longer periods did not improve occupancy.

IMPDH crystallized as a homotetramer with monomers related by the four-fold crystallographic axis (FIG. 14). The active site loop, residues 313–330, was modeled in both the RMP and RMP+MPA structures. The proximal portion of the active site flap (residues 408 to 416 and 431 to 433) was modeled, while the distal portion (residues 417–430) was disordered. Poor density in the region of the CBS domain was observed and no attempts were made at modeling this domain. The C-terminal amino acids 484–492 were also added to the original *T. foetus* model and although these nine residues do not appear to make direct contact with substrate or product, they do lie near the active site of a neighboring monomer in the catalytic tetramer and the backbone carbonyls of residues 485–487 from part of the active site cation binding pocket. Although RMP was clearly observable in the electron density of both crystal structures, density for MOA, even with saturating concentrations in the crystallization drop, was weak and was therefore modeled at 50% occupancy (FIG. 15). B factors for MOA at this level of occupancy were in agreement with the neighboring RMP atoms.

A cis peptide bond was modeled in both structures between Gly290 and Asn291. It is located near the cofactor binding site but does not appear to be close enough to directly influence cofactor binding. In addition, a strong peak of electron density was found extending from the active site cysteine sulfur in the RMP bound structure. This appears to be a result of the thiol oxidized to sulfenic acid (Cys-SOH), likely caused by exposure to oxygen during crystal formation prior to freezing.

Figure 16:
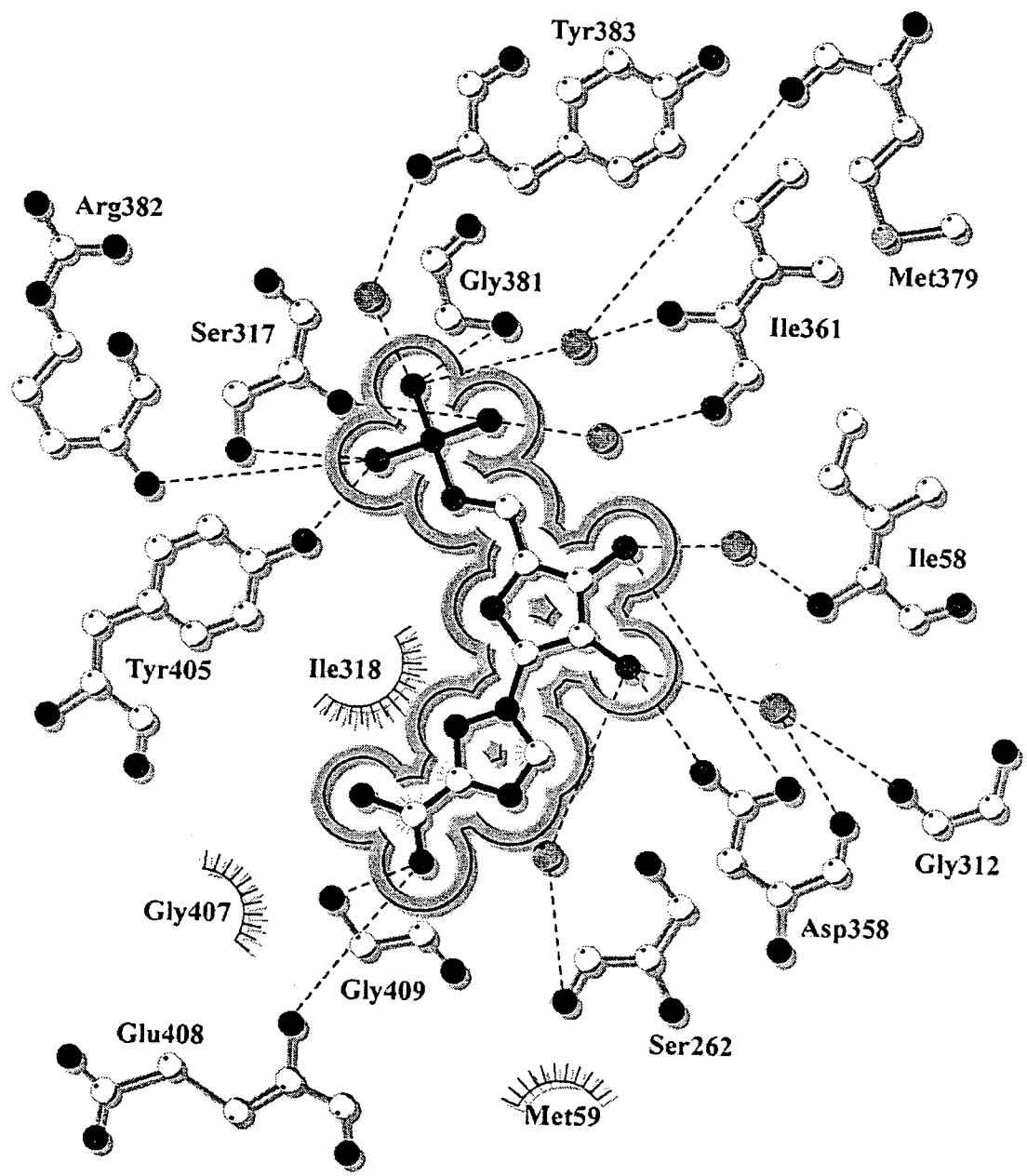
FIG. 16 shows a diagram of RMP hydrogen bonds with IMPDH. Like IMP, RMP makes many bonds with ordered waters and main chain atoms. Only the Tyr405 hydroxyl and the Asp358 carboxylate side chains make contact with the inhibitor. Additionally, Met59, Ile318, and Gly407 make hydrophobic contacts. Solvent accessibility is indicated by the yellow border around RMP, where lighter color indicates greater accessibility. This figure was created with NAC-CESS (Hubbard and Thornton, University College London, Department of Biochemistry and Molecular Biology, (1993)), HBPLUS (McDonald and Thornton, *J. Mol. Biol.* 238:777–793 (1994)), and LIGPLOT.

As was observed in the IMP bound structure, the phosphate is coordinated with hydroxyls from Ser317 and Tyr405 as well as main chain nitrogens from residues 317, 381, and 382 (FIG. 16). Three solvent waters also form hydrogen bonds with the phosphate. As in all IMPDH structures, the substrate sugar hydroxyls form strong hydrogen bonds with a conserved aspartate carboxylate (Asp358). Ile318, which in the substrate and product complexes forms hydrophobic interactions with the purine ring, has moved 1.2 Å away from the RMP inhibitor. The RMP amide oxygen forms hydrogen bonds with Glu408 and Gly409. In the RMP+MPA structure the amide nitrogen is hydrogen-bonding to the MOA ring hydroxyl and the MOA inhibitor has moved 0.6 Å from its position in the XMP+MPA structure in the direction of the RMP purine ring derivative. In this position, the MOA ring O2 makes a hydrogen bond with the backbone nitrogen of Gly314, and the C3 oxygen hydrogen bonds with the catalytic sulfhydryl of Cys319.

Figure 17:
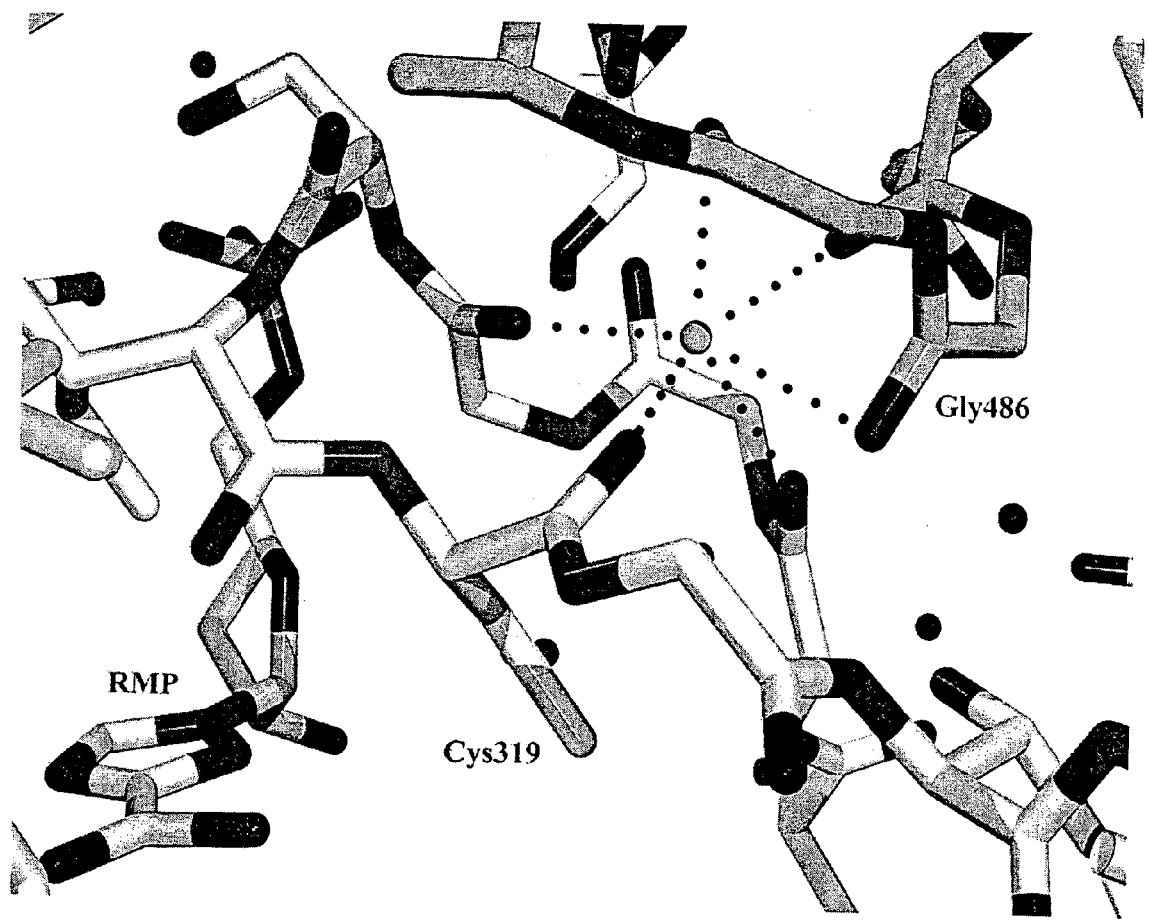
FIG. 17 shows that the ion binding site (green) is composed of backbone carbonyls from the active site loop residues, including the active site cysteine, and residues from the C-terminus of the neighboring catalytic monomer (gray carbons).

The conformation of the active site loop in the RMP as well as the RMP+MPA structure is different from the loop conformation of the structures with bound substrate or product, resulting in a pocket surrounded by backbone carbonyl oxygens from Gly314, Gly316, and the active site Cys319, as well as carbonyls from Glu485, Gly486 and Gly487 in the neighboring catalytic monomer. A high (7.7 sigma) difference density peak was observed at the center of this pocket indicating the presence of a cation. Both Na+ and K+ ions were modeled into this site and minimized in CNS. A large peak of negative difference density was observed when K+ was modeled as well as high B factors. Because of the high concentration of sodium in the crystallization buffer, the previous observation that a sodium ion binds competitively with K+ in microbial IMPDH (Kerr et al., *Arch. Biochem. Biophys.* 375:131–137 (2000)), and B factors that are near that of the neighboring atoms, a Na+ ion was placed in the final model (FIG. 17).

As is described above, *T. foetus* IMPDH binds ribavirin in the active site substrate pocket. The RMP+MPA complex was difficult to obtain, as the MOA inhibitor was only observed with saturating amounts of MOA present in the crystallization drop. Attempts to obtain a co-crystal rather than an MOA soak were unsuccessful as the levels of MOA necessary to form the complex inhibited crystal formation. Although no data have been reported on the additive effects of ribavirin and MOA, it is unlikely that both inhibitors would occupy the substrate and cofactor binding pockets of the active site simultaneously, despite their distinct binding sites. The reason might be that MOA appears to rely on stacking its ring against the product XMP purine ring to bind to IMPDH and the RMP ring is probably too small for effective stacking.

A structure of RMP bound to human IMPDH has not been made available for direct comparison; however, we were able to compare the *T. foetus* RMP structure with the Chinese hamster structure that contains a covalently bound substrate intermediate (Sintchak et al., supra, (1996)). These structures show a high degree of similarity in the conformation of the active site loop, recruitment of a catalytic ion, as well as incorporation of the C terminal residues of the neighboring catalytic monomer to create the ion pocket. The reasons behind this appear to be the lack of the IMP C2 and N3 in the RMP inhibitor, which cause the hydrophobic Ile318, which normally forms hydrophobic contacts with the purine ring of the substrate or product, to move away from the more polar, less hydrophobic purine derivative. More importantly, with this portion of the purine ring absent, it is now more favorable for the active site cysteine (Cys319) to move into its catalytic position without the need for the NAD+ cofactor to bind and for catalysis to occur. This would not be the case with substrate or product present as the Cys319 sulfhydryl would be within 2.8 of the C2 position of IMP or within 1.5 of the oxygen bound to the C2 position of XMP.

It appears that in mammalian IMPDH and the presented *T. foetus* structures, the covalent intermdiate is necessary to recruit the ion to the active site whereas the inhibitor ribavirin allows the active site loop to occupy this position without forming a covalent bond with the enzyme. No ion was found in our *T. foetus* IMP bound structure. In the human IMPDH structure with the covalently bound inhibitor 6-Cl IMP, no cation was present because it was necessary for the active site loop to move from the purine ring C2 position to the inhibitor C6 position in order for the active site cysteine to form a covalent bond with the inhibitor. This movement in the loop prevented formation of the ion-binding pocket. Furthermore, the acitve site loop in the apo *S. pyogenes* structure is in this cation-binding conformation without a covalent intermediate and a possible ion, designated water 179 (PDB accession code IZFJ), appears to occupy the same cation position as in the Chinese hamster (PDB accession code 1JR1) and the *T. foetus* structures presented here. The IMP in the bacterial structure is not covalently bound and the C2 of the purine ring is rotated slightly away from the active site cysteine. In the *T. foetus* IMP structure, it is the loop that moves slightly away from C2 of IMP when compared to the hamster covalently bound structure and the *B. burgdorferi* apo structure.

The bacterial acitve site loop appears to be stabilized upon substrate binding by Thr310, which also makes hydrogen bonds with the active site flap, both directly and through an ordered water. This threonine is conserved in bacteria but is substituted with an isoleucine in eukaryotes, which appears to disrupt the structural coupling of the active site loop to the active site flap. This results in a partial destabilization of the active site loop allowing the active site cysteine to be displaced instead of the substrate. The bacterial acitve site loop is in the catalytic position immediately following substrate binding, and this could explain the ten fold higher Kcat compared to the mammalian and *T. foetus* enzymes (24, 2, 1.8 and 4 s–1 for *S. pyogenes*, *T. foetus*, and human type I and II, respectively) (Digits and Hedstrom, supra, (1999); Zhang et al., supra, (1999); Hager et al., *Biochem. Pharmacol.* 49:1323–1329 (1995)).

The mammalian and *T. foetus* enzymes, at some point after substrate binding, must first move the active site loop into position; recruit the active site cation and C-terminal residues of the neighboring monomer before catalysis is possible. These steps may be coupled to cofactor binding. If the positively charged NAD$^+$ binds over the C2 position of IMP it may expose the substrate C2 to the active site cysteine thiol for subsequent nucleophilic attack. A role for the active site ion may be in stabilization of the active site loop during catalysis. The carbonyl oxygen from the active site Cys319 forms part of the cation binding site. When this site is occupied, the cysteine is in an ideal position to form a covalent bond with the C2 carbon of IMP. The cation-binding site appears to be formed before covalent bonding in bacterial IMPDH but likely occurs during covalent bond formation in mammalian and *T. foetus* IMPDH.

In the steady-state kinetic analysis of *T. foetus* IMPDH, an apparent Km of 3.0 µM for IMP was observed. This is consistent with the previously published Km value of 1.7 µM from a detailed bisubstrate kinetic analysis (Digits and Hedstrom, supra, (1999)). This value is much smaller than the Km of 14.2 and 9.2 µM, respectively, for human type I and II IMPDH (Hager et al., supra, (1995)) as well as the Km of 62 µM for *S. pyogenes* enzyme (Zhang et al., supra, (1999)). This result indicates the IMP binds to *T. foetus* IMPDH about 3 to 5-fold tighter than to mammalian enzymes. Interestingly, RMP, a nucleotide inhibitor, was shown to have a Ki of 65 nM for *T. foetus* IMPDH. This is about 5 to 10-fold lower than the Ki for human type I and II IMPDH, where the values are 650 nM and 390 nM, respectively (Hager et al., supra, (1995)). And it is considerably lower than the Ki of 6 µM for *S. pyogenes* IMPDH (Zhang et al., supra, (1999)). This result is consistent with steady-state kinetic analysis that shows that *T. foetus* IMPDH binds IMP (or the IMP analog RMP) more tightly than IMPDH from other species. Furthermore, the inhibition studies with RMP demonstrated that specifies specificity for an inhibitor does not occur in IMPDH. Our in vitro studies showed that RMP is a potent nanomolar inhibitor for *T. foetus* IMPDH and it appears that RMP is more effective against the protist form of IMPDH than the human and bacterial forms. A structural explanation for the 100 fold difference in Ki between *T. foetus* and *S. pyogenes* IMPDH could not be established from the highly conserved substrate binding site. The differences in Ki may be related, at least in part, to the kinetic mechanism. Further in vivo experiments are needed to address whether there is any clinical significance and pharmacological effects of ribavirin on *T. foetus*-infected cows.

Methods for Expression, Purification, and Crystallization of *T. foetus* IMPDH.

Recombinant *T. foetus* IMPDH enzyme was produced from a pBAce plasmid (Chin and Wang, supra, (1994)) containing the gene for *T. foetus* IMPDH (Beck et al., *Exp. Parasitol.* 78:101–112 (1994)) that was transformed into *Escherichia coli* strain H712 (*E. coli* Stock Center, Yale University, New Haven, Conn.). Expression of *T. foetus* IMPDH was achieved by modifying previously published protocols (Craig et al., *Proc. Natl. Acad. Sci. USA*, 88:2500–2504 (1991); Neidhardt et al., *J. Bacteriol.* 119: 736–747 (1974); Yuan et al., *J. Biol. Chem.* 265:13528–13532(1990)). Briefly, the cells were grown in MOPS media in a 19-liter fermentor (Wheaton Science Products, Millville, N.J.) and were inoculated with 0.5 liters of overnight MOPS culture of H712 containing the IMPDH plasmid. The fermentation was kept at 37° C. and was maintained by aeration, stirring and glucose addition. The dissolved oxygen (DO) was maintained at greater than 40%. The cells were harvested at 8 hours when the DO dropped to below 20% at an OD$_{600}$ of roughly 1.5.

The cells were concentrated to 0.5 L by tangential flow filtration (Millipore, Inc., Bedford, Mass.) and pelleted by centrifugation at 6,000 g. The pellet was re-suspended in a three fold volume of buffer A (50 mM Tris pH 8, 50 mM KCl, 10% gycerol, and 1 mM 2-mercaptoethanol) supplemented with protease inhibitors and 1 mM EDTA, and was then flash frozen in liquid nitrogen before storage at –85° C. This mixture was lysed by French Press and the lysate was clarified by centrifugation at 20,000 g. The supernatant was then run over a cibacron blue column on an AKTA FPLC (Amersham-Pharmacia). Protein was eluted from the column with 1 M KCl. This was followed by dialysis into buffer A and concentration to 15 mg/ml. The protein was then passed through a monoQ column (Amersham-Pharmacia) using a gradient from 50 to 500 mM KCl over 20 column volumes. The resulting protein was >90% pure and was dialyzed in buffer A and concentrated to 30 mg/ml for storage at –85° C.

The protein was crystallized at 20° C. by mixing 15 mg/ml protein in buffer A into 42% of saturated sodium malonate, 100 mM Tris pH 8.0, 4 mM PEG 400, and 1 mM 2-mercaptoethanol in 6 µl sitting drops in a 1:1 ration of well solution to protein. The protein was also co-crystallized with a ten-fold molar excess of RMP. For the efforts to co-crystallize both RMP and MOA with IMPDH, saturating levels of MOA were added to newly formed RMP bound crystals. These crystals were allowed to soak for several hours to several days before cryo-mounting.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

TABLE 1

Data collection and refinement statistics.

| Structure | IMP | IMP + MPA | XMP + MPA | NAD⁺ + XMP |
|---|---|---|---|---|
| Wavelength (Å) | 0.97 | 0.97 | 0.97 | 1.00 |
| Resolution Range (Å) | 50–2.2 | 50–1.95 | 50–2.2 | 20–2.15 |
| Resolution of outer shell (Å) | 2.2–2.34 | 1.95–2.07 | 2.2–2.34 | 2.15–2.28 |
| R ($R_{free}$) (%) | 24.9 (27.1) | 24.0 (26.8) | 22.5 (25.6) | 22.3 (24.6) |
| Unique reflections | 32,418 | 45,540 | 32,987 | 33,857 |
| Total observations | 996,397 | 1,036,471 | 407,857 | 734,853 |
| $I/\sigma_I$ all/outer shell | 21.7/2.13 | 25.88/1.82 | 21.38/2.88 | 19.03/2.22 |
| $R_{sym}$ all/outer shell (%) | 6.4/59.6 | 5.7/66.8 | 6.6/53.8 | 8.0/57.8 |
| Completeness all/outer shell (%) | 99.9/99.8 | 99.0/95.7 | 99.5/98.7 | 98.4/95.9 |
| Degrees collected | 37.5 | 37.5 | 20 | 30 |
| Amino acid residues in model | 2–101, 222–416, 431–483 | 2–106, 222–416, 430–483 | 2–101, 222–417, 428–483 | 2–101, 222–317, 322–416, 428–483 |
| Number of water molecules | 159 | 202 | 183 | 172 |
| Cell dimensions a = b = c (Å) | 154.4 | 153.5 | 155.1 | 153.8 |
| Bond length dev. (Å) | 0.006 | 0.006 | 0.005 | 0.007 |
| Bond angle dev. (°) | 1.2 | 1.2 | 1.1 | 1.3 |
| Dihedral angle dev. (°) | 22.9 | 22.2 | 22.5 | 23.0 |
| Improper angle dev. (°) | 0.71 | 0.70 | 0.67 | 0.80 |
| Ramachandran core/allowed/ generously allowed (%) | 91.9/7.8/0.3 | 92.1/7.9/0.0 | 90.7/9.0/0.3 | 91.7/7.9/0.3 |
| Mosaicity (°) | 0.60 | 0.65 | 0.40 | 0.70 |

TABLE 2

| | | | | | |
|---|---|---|---|---|---|
| HEADER | | OXIDOREDUCTASE | | 08-AUG-02 | 1ME9 |
| TITLE | | INOSINE MONOPHOSPHATE DEHYDROGENASE (IMPDH) FROM | | | |
| TITLE | 2 | *TRITRICHOMONAS FOETUS* WITH IMP BOUND | | | |
| COMPND | | MOL_ID: 1; | | | |
| COMPND | 2 | MOLECULE: INOSINE-5'-MONOPHOSPHATE DEHYDROGENASE; | | | |
| COMPND | 3 | CHAIN: A; | | | |
| COMPND | 4 | SYNONYM: IMP DEHYDROGENASE, IMPDH; | | | |
| COMPND | 5 | EC: 1.1.1.205; | | | |
| COMPND | 6 | ENGINEERED: YES | | | |
| SOURCE | | MOL_ID: 1; | | | |
| SOURCE | 2 | ORGANISM_SCIENTIFIC: *TRITRICHOMONAS FOETUS*; | | | |
| SOURCE | 3 | GENE: IMPDH; | | | |
| SOURCE | 4 | EXPRESSION_SYSTEM: *ESCHERICHIA COLI*; | | | |
| SOURCE | 5 | EXPRESSION_SYSTEM_COMMON: BACTERIA; | | | |
| SOURCE | 6 | EXPRESSION_SYSTEM_STRAIN: H712; | | | |
| SOURCE | 7 | EXPRESSION_SYSTEM_VECTOR_TYPE: PLASMID; | | | |
| SOURCE | 8 | EXPRESSION_SYSTEM_PLASMID: PBACE | | | |
| KEYWDS | | ALPHA BETA BARREL | | | |
| EXPDTA | | X-RAY DIFFRACTION | | | |
| AUTHOR | | G. L. PROSISE, H. LUECKE | | | |
| JRNL | | AUTH | G. L. PROSISE, H. LUECKE | | |
| JRNL | | TITL | CRYSTAL STRUCTURE OF *T. FOETUS* INOSINE | | |
| JRNL | | TITL 2 | MONOPHOSPHATE DEHYDROGENASE IN COMPLEX WITH | | |
| JRNL | | TITL 3 | SUBSTRATE, COFACTOR, AND ANALOGS:STRUCTURAL BASIS | | |
| JRNL | | TITL 4 | FOR THE RANDOM-IN ORDERED-OUT KINETIC MECHANISM | | |
| JRNL | | REF | TO BE PUBLISHED | | |
| JRNL | | REFN | | | |
| REMARK | 1 | | | | |
| REMARK | 2 | | | | |
| REMARK | 2 | RESOLUTION. 2.20 ANGSTROMS. | | | |
| REMARK | 3 | | | | |
| REMARK | 3 | REFINEMENT. | | | |
| REMARK | 3 | PROGRAM | : CNS 1.1 | | |
| REMARK | 3 | AUTHORS | : BRUNGER, ADAMS, CLORE, DELANO, GROS, GROSSE- | | |
| REMARK | 3 | | : KUNSTLEVE, JIANG, KUSZEWSKI, NILGES, PANNU, | | |
| REMARK | 3 | | : READ, RICE, SIMONSON, WARREN | | |
| REMARK | 3 | | | | |

TABLE 2-continued

| REMARK | 3 | REFINEMENT TARGET : ENGH & HUBER | | |
|---|---|---|---|---|
| REMARK | 3 | | | |
| REMARK | 3 | DATA USED IN REFINEMENT. | | |
| REMARK | 3 | RESOLUTION RANGE HIGH | (ANGSTROMS) | : 2.20 |
| REMARK | 3 | RESOLUTION RANGE LOW | (ANGSTROMS) | : 19.77 |
| REMARK | 3 | DATA CUTOFF | (SIGMA(F)) | : 0.000 |
| REMARK | 3 | OUTLIER CUTOFF HIGH | (RMS(ABS(F))) | : NULL |
| REMARK | 3 | COMPLETENESS (WORKING+TEST) | (%) | : 99.8 |
| REMARK | 3 | NUMBER OF REFLECTIONS | | : 32418 |
| REMARK | 3 | | | |
| REMARK | 3 | FIT TO DATA USED IN REFINEMENT. | | |
| REMARK | 3 | CROSS-VALIDATION METHOD | | : THROUGHOUT |
| REMARK | 3 | FREE R VALUE TEST SET SELECTION | | : RANDOM |
| REMARK | 3 | R VALUE | (WORKING SET) | : 0.248 |
| REMARK | 3 | FREE R VALUE | | : 0.273 |
| REMARK | 3 | FREE R VALUE TEST SET SIZE | (%) | : 5.200 |
| REMARK | 3 | FREE R VALUE TEST SET COUNT | | : 1691 |
| REMARK | 3 | ESTIMATED ERROR OF FREE R VALUE | | : 0.007 |
| REMARK | 3 | | | |
| REMARK | 3 | FIT IN THE HIGHEST RESOLUTION BIN. | | |
| REMARK | 3 | TOTAL NUMBER OF BINS USED | | : 6 |
| REMARK | 3 | BIN RESOLUTION RANGE HIGH | (A) | : 2.20 |
| REMARK | 3 | BIN RESOLUTION RANGE LOW | (A) | : 2.34 |
| REMARK | 3 | BIN COMPLETENESS (WORKING+TEST) | (%) | : 99.80 |
| REMARK | 3 | REFLECTIONS IN BIN | (WORKING SET) | : 5035 |
| REMARK | 3 | BIN R VALUE | (WORKING SET) | : 0.2770 |
| REMARK | 3 | BIN FREE R VALUE | | : 0.3040 |
| REMARK | 3 | BIN FREE R VALUE TEST SET SIZE | (%) | : 4.90 |
| REMARK | 3 | BIN FREE R VALUE TEST SET COUNT | | : 262 |
| REMARK | 3 | ESTIMATED ERROR OF BIN FREE R VALUE | | : 0.019 |
| REMARK | 3 | | | |
| REMARK | 3 | NUMBER OF NON-HYDROGEN ATOMS USED IN REFINEMENT. | | |
| REMARK | 3 | PROTEIN ATOMS | : 2685 | |
| REMARK | 3 | NUCLEIC ACID ATOMS | : 0 | |
| REMARK | 3 | HETEROGEN ATOMS | : 24 | |
| REMARK | 3 | SOLVENT ATOMS | : 145 | |
| REMARK | 3 | | | |
| REMARK | 3 | B VALUES. | | |
| REMARK | 3 | FROM WILSON PLOT | $(A^{**}2)$ | : 28.10 |
| REMARK | 3 | MEAN B VALUE | (OVERALL, $A^{**}2$) | : 40.20 |
| REMARK | 3 | OVERALL ANISOTROPIC B VALUE. | | |
| REMARK | 3 | B11 $(A^{**}2)$ | : 0.00000 | |
| REMARK | 3 | B22 $(A^{**}2)$ | : 0.00000 | |
| REMARK | 3 | B33 $(A^{**}2)$ | : 0.00000 | |
| REMARK | 3 | B12 $(A^{**}2)$ | : 0.00000 | |
| REMARK | 3 | B13 $(A^{**}2)$ | : 0.00000 | |
| REMARK | 3 | B23 $(A^{**}2)$ | : 0.00000 | |
| REMARK | 3 | | | |
| REMARK | 3 | ESTIMATED COORDINATE ERROR. | | |
| REMARK | 3 | ESD FROM LUZZATI PLOT | (A) | : 0.30 |
| REMARK | 3 | ESD FROM SIGMAA | (A) | : 0.22 |
| REMARK | 3 | LOW RESOLUTION CUTOFF | (A) | : 5.00 |
| REMARK | 3 | | | |
| REMARK | 3 | CROSS-VALIDATED ESTIMATED COORDINATE ERROR. | | |
| REMARK | 3 | ESD FROM C-V LUZZATI PLOT | (A) | : 0.34 |
| REMARK | 3 | ESD FROM C-V SIGMAA | (A) | : 0.25 |
| REMARK | 3 | | | |
| REMARK | 3 | RMS DEVIATIONS FROM IDEAL VALUES. | | |
| REMARK | 3 | BOND LENGTHS | (A) | : 0.006 |
| REMARK | 3 | BOND ANGLES | (DEGREES) | : 1.20 |
| REMARK | 3 | DIHEDRAL ANGLES | (DEGREES) | : 22.80 |
| REMARK | 3 | IMPROPER ANGLES | (DEGREES) | : 0.72 |
| REMARK | 3 | | | |
| REMARK | 3 | ISOTROPIC THERMAL MODEL : RESTRAINED | | |
| REMARK | 3 | | | |
| REMARK | 3 | ISOTROPIC THERMAL FACTOR RESTRAINTS. | RMS | SIGMA |
| REMARK | 3 | MAIN-CHAIN BOND | $(A^{**}2)$ : 1.270 | ; 1.500 |
| REMARK | 3 | MAIN-CHAIN ANGLE | $(A^{**}2)$ : 2.150 | ; 2.000 |
| REMARK | 3 | SIDE-CHAIN BOND | $(A^{**}2)$ : 1.930 | ; 2.000 |
| REMARK | 3 | SIDE-CHAIN ANGLE | $(A^{**}2)$ : 2.840 | ; 2.500 |
| REMARK | 3 | | | |

TABLE 2-continued

| | | | | |
|---|---|---|---|---|
| REMARK | 3 | BULK SOLVENT MODELING. | | |
| REMARK | 3 | METHOD USED | : FLAT MODEL | |
| REMARK | 3 | KSOL | : 0.36 | |
| REMARK | 3 | BSOL | : 40.24 | |
| REMARK | 3 | | | |
| REMARK | 3 | NCS MODEL : NULL | | |
| REMARK | 3 | | | |
| REMARK | 3 | NCS RESTRAINTS. | RMS | SIGMA/WEIGHT |
| REMARK | 3 | GROUP 1 POSITIONAL | (A) : NULL ; | NULL |
| REMARK | 3 | GROUP 1 B-FACTOR | (A**2) : NULL ; | NULL |
| REMARK | 3 | | | |
| REMARK | 3 | PARAMETER FILE 1 | : PROTEIN_REP.PARAM | |
| REMARK | 3 | PARAMETER FILE 2 | : PARAM.GNSOL | |
| REMARK | 3 | PARAMETER FILE 3 | : CIS_PEPTIDE.PARAM | |
| REMARK | 3 | PARAMETER FILE 4 | : IMP.PAR | |
| REMARK | 3 | PARAMETER FILE 5 | : ION.PARAM | |
| REMARK | 3 | PARAMETER FILE 6 | : NULL | |
| REMARK | 3 | TOPOLOGY FILE 1 | : PROTEIN.TOP | |
| REMARK | 3 | TOPOLOGY FILE 2 | : IMP.TOP | |
| REMARK | 3 | TOPOLOGY FILE 3 | : MPA.TOP | |
| REMARK | 3 | TOPOLOGY FILE 4 | : ION.TOP | |
| REMARK | 3 | TOPOLOGY FILE 5 | : TOPH.GNSOL | |
| REMARK | 3 | TOPOLOGY FILE 6 | : NULL | |
| REMARK | 3 | | | |
| REMARK | 3 | OTHER REFINEMENT REMARKS: NULL | | |
| REMARK | 4 | | | |
| REMARK | 4 | 1ME9 COMPLIES WITH FORMAT V. 2.3, 09-JULY-1998 | | |
| REMARK | 100 | | | |
| REMARK | 100 | THIS ENTRY HAS BEEN PROCESSED BY RCSB ON 09-AUG-2002. | | |
| REMARK | 100 | THE RCSB ID CODE IS RCSB016851. | | |
| REMARK | 200 | | | |
| REMARK | 200 | EXPERIMENTAL DETAILS | | |
| REMARK | 200 | EXPERIMENT TYPE | : X-RAY DIFFRACTION | |
| REMARK | 200 | DATE OF DATA COLLECTION | : 11-APR-2001 | |
| REMARK | 200 | TEMPERATURE (KELVIN) | : 100.0 | |
| REMARK | 200 | PH | : 7.50 | |
| REMARK | 200 | NUMBER OF CRYSTALS USED | : 1 | |
| REMARK | 200 | | | |
| REMARK | 200 | SYNCHROTRON (Y/N) | : Y | |
| REMARK | 200 | RADIATION SOURCE | : SSRL | |
| REMARK | 200 | BEAMLINE | : 9-1 | |
| REMARK | 200 | X-RAY GENERATOR MODEL | : NULL | |
| REMARK | 200 | MONOCHROMATIC OR LAUE (M/L) | : M | |
| REMARK | 200 | WAVELENGTH OR RANGE (A) | : 0.97 | |
| REMARK | 200 | MONOCHROMATOR | : NULL | |
| REMARK | 200 | OPTICS | : NULL | |
| REMARK | 200 | | | |
| REMARK | 200 | DETECTOR TYPE | : IMAGE PLATE | |
| REMARK | 200 | DETECTOR MANUFACTURER | : MARRESEARCH | |
| REMARK | 200 | INTENSITY-INTEGRATION SOFTWARE | : DENZO | |
| REMARK | 200 | DATA SCALING SOFTWARE | : SCALEPACK | |
| REMARK | 200 | | | |
| REMARK | 200 | NUMBER OF UNIQUE REFLECTIONS | : 32513 | |
| REMARK | 200 | RESOLUTION RANGE HIGH (A) | : 2.200 | |
| REMARK | 200 | RESOLUTION RANGE LOW (A) | : 20.000 | |
| REMARK | 200 | REJECTION CRITERIA (SIGMA(I)) | : 0.000 | |
| REMARK | 200 | | | |
| REMARK | 200 | OVERALL. | | |
| REMARK | 200 | COMPLETENESS FOR RANGE (%) | : 99.9 | |
| REMARK | 200 | DATA REDUNDANCY | : 6.700 | |
| REMARK | 200 | R MERGE (I) | : 0.06400 | |
| REMARK | 200 | R SYM (I) | : NULL | |
| REMARK | 200 | <I/SIGMA(I)> FOR THE DATA SET | : 21.7000 | |
| REMARK | 200 | | | |
| REMARK | 200 | IN THE HIGHEST RESOLUTION SHELL. | | |
| REMARK | 200 | HIGHEST RESOLUTION SHELL, RANGE HIGH (A) | : 2.20 | |
| REMARK | 200 | HIGHEST RESOLUTION SHELL, RANGE LOW (A) | : 2.24 | |
| REMARK | 200 | COMPLETENESS FOR SHELL (%) | : 99.8 | |
| REMARK | 200 | DATA REDUNDANCY IN SHELL | : NULL | |
| REMARK | 200 | R MERGE FOR SHELL (I) | : 0.59600 | |
| REMARK | 200 | R SYM FOR SHELL (I) | : NULL | |
| REMARK | 200 | <I/SIGMA(I)> FOR SHELL | : 2.130 | |
| REMARK | 200 | | | |

TABLE 2-continued

| | | | | | | |
|---|---|---|---|---|---|---|
| REMARK 200 | DIFFRACTION PROTOCOL: SINGLE WAVELENGTH | | | | | |
| REMARK 200 | METHOD USED TO DETERMINE THE STRUCTURE: FOURIER SYNTHESIS | | | | | |
| REMARK 200 | SOFTWARE USED: CNS | | | | | |
| REMARK 200 | STARTING MODEL: PDB ENTRY 1AK5 | | | | | |
| REMARK 200 | | | | | | |
| REMARK 200 | REMARK: NULL | | | | | |
| REMARK 280 | | | | | | |
| REMARK 280 | CRYSTAL | | | | | |
| REMARK 280 | SOLVENT CONTENT, VS (%): NULL | | | | | |
| REMARK 280 | MATTHEWS COEFFICIENT, VM (ANGSTROMS**3/DA): NULL | | | | | |
| REMARK 280 | | | | | | |
| REMARK 280 | CRYSTALLIZATION CONDITIONS: SODIUM MALONATE, TRIS, 2-MERCAPTOETHANOL, EDTA, GLYCEROL | | | | | |
| REMARK 290 | | | | | | |
| REMARK 290 | CRYSTALLOGRAPHIC SYMMETRY | | | | | |
| REMARK 290 | SYMMETRY OPERATORS FOR SPACE GROUP: P 4 3 2 | | | | | |
| REMARK 290 | | | | | | |
| REMARK 290 | SYMOP NNNMMM | SYMMETRY OPERATOR | | | | |
| REMARK 290 | 1555 | X, Y, Z | | | | |
| REMARK 290 | 2555 | −X, −Y, Z | | | | |
| REMARK 290 | 3555 | −X, Y, −Z | | | | |
| REMARK 290 | 4555 | X, −Y, −Z | | | | |
| REMARK 290 | 5555 | Z, X, Y | | | | |
| REMARK 290 | 6555 | Z, −X, −Y | | | | |
| REMARK 290 | 7555 | −Z, −X, Y | | | | |
| REMARK 290 | 8555 | −Z, X, −Y | | | | |
| REMARK 290 | 9555 | Y, Z, X | | | | |
| REMARK 290 | 10555 | −Y, Z, −X | | | | |
| REMARK 290 | 11555 | Y, −Z, −X | | | | |
| REMARK 290 | 12555 | −Y, −Z, X | | | | |
| REMARK 290 | 13555 | Y, X, −Z | | | | |
| REMARK 290 | 14555 | −Y, −X, −Z | | | | |
| REMARK 290 | 15555 | Y, −X, Z | | | | |
| REMARK 290 | 16555 | −Y, X, Z | | | | |
| REMARK 290 | 17555 | X, Z, −Y | | | | |
| REMARK 290 | 18555 | −X, Z, Y | | | | |
| REMARK 290 | 19555 | −X, −Z, −Y | | | | |
| REMARK 290 | 20555 | X, −Z, Y | | | | |
| REMARK 290 | 21555 | Z, Y, −X | | | | |
| REMARK 290 | 22555 | Z, −Y, X | | | | |
| REMARK 290 | 23555 | −Z, Y, X | | | | |
| REMARK 290 | 24555 | −Z, −Y, −X | | | | |
| REMARK 290 | | | | | | |
| REMARK 290 | WHERE NNN −> OPERATOR NUMBER | | | | | |
| REMARK 290 | MMM −> TRANSLATION VECTOR | | | | | |
| REMARK 290 | | | | | | |
| REMARK 290 | CRYSTALLOGRAPHIC SYMMETRY TRANSFORMATIONS | | | | | |
| REMARK 290 | THE FOLLOWING TRANSFORMATIONS OPERATE ON THE ATOM/HETATM | | | | | |
| REMARK 290 | RECORDS IN THIS ENTRY TO PRODUCE CRYSTALLOGRAPHICALLY | | | | | |
| REMARK 290 | RELATED MOLECULES. | | | | | |
| REMARK 290 | SMTRY1 | 1 | 1.000000 | 0.000000 | 0.000000 | 0.00000 |
| REMARK 290 | SMTRY2 | 1 | 0.000000 | 1.000000 | 0.000000 | 0.00000 |
| REMARK 290 | SMTRY3 | 1 | 0.000000 | 0.000000 | 1.000000 | 0.00000 |
| REMARK 290 | SMTRY1 | 2 | −1.000000 | 0.000000 | 0.000000 | 0.00000 |
| REMARK 290 | SMTRY2 | 2 | 0.000000 | −1.000000 | 0.000000 | 0.00000 |
| REMARK 290 | SMTRY3 | 2 | 0.000000 | 0.000000 | 1.000000 | 0.00000 |
| REMARK 290 | SMTRY1 | 3 | −1.000000 | 0.000000 | 0.000000 | 0.00000 |
| REMARK 290 | SMTRY2 | 3 | 0.000000 | 1.000000 | 0.000000 | 0.00000 |
| REMARK 290 | SMTRY3 | 3 | 0.000000 | 0.000000 | −1.000000 | 0.00000 |
| REMARK 290 | SMTRY1 | 4 | 1.000000 | 0.000000 | 0.000000 | 0.00000 |
| REMARK 290 | SMTRY2 | 4 | 0.000000 | −1.000000 | 0.000000 | 0.00000 |
| REMARK 290 | SMTRY3 | 4 | 0.000000 | 0.000000 | −1.000000 | 0.00000 |
| REMARK 290 | SMTRY1 | 5 | 0.000000 | 0.000000 | 1.000000 | 0.00000 |
| REMARK 290 | SMTRY2 | 5 | 1.000000 | 0.000000 | 0.000000 | 0.00000 |
| REMARK 290 | SMTRY3 | 5 | 0.000000 | 1.000000 | 0.000000 | 0.00000 |
| REMARK 290 | SMTRY1 | 6 | 0.000000 | 0.000000 | 1.000000 | 0.00000 |
| REMARK 290 | SMTRY2 | 6 | −1.000000 | 0.000000 | 0.000000 | 0.00000 |
| REMARK 290 | SMTRY3 | 6 | 0.000000 | −1.000000 | 0.000000 | 0.00000 |
| REMARK 290 | SMTRY1 | 7 | 0.000000 | 0.000000 | −1.000000 | 0.00000 |
| REMARK 290 | SMTRY2 | 7 | −1.000000 | 0.000000 | 0.000000 | 0.00000 |
| REMARK 290 | SMTRY3 | 7 | 0.000000 | 1.000000 | 0.000000 | 0.00000 |
| REMARK 290 | SMTRY1 | 8 | 0.000000 | 0.000000 | −1.000000 | 0.00000 |
| REMARK 290 | SMTRY2 | 8 | 1.000000 | 0.000000 | 0.000000 | 0.00000 |
| REMARK 290 | SMTRY3 | 8 | 0.000000 | −1.000000 | 0.000000 | 0.00000 |

TABLE 2-continued

| | | | | | | |
|---|---|---|---|---|---|---|
| REMARK 290 | SMTRY1 | 9 | 0.000000 | 1.000000 | 0.000000 | 0.00000 |
| REMARK 290 | SMTRY2 | 9 | 0.000000 | 0.000000 | 1.000000 | 0.00000 |
| REMARK 290 | SMTRY3 | 9 | 1.000000 | 0.000000 | 0.000000 | 0.00000 |
| REMARK 290 | SMTRY1 | 10 | 0.000000 | −1.000000 | 0.000000 | 0.00000 |
| REMARK 290 | SMTRY2 | 10 | 0.000000 | 0.000000 | 1.000000 | 0.00000 |
| REMARK 290 | SMTRY3 | 10 | −1.000000 | 0.000000 | 0.000000 | 0.00000 |
| REMARK 290 | SMTRY1 | 11 | 0.000000 | 1.000000 | 0.000000 | 0.00000 |
| REMARK 290 | SMTRY2 | 11 | 0.000000 | 0.000000 | −1.000000 | 0.00000 |
| REMARK 290 | SMTRY3 | 11 | −1.000000 | 0.000000 | 0.000000 | 0.00000 |
| REMARK 290 | SMTRY1 | 12 | 0.000000 | −1.000000 | 0.000000 | 0.00000 |
| REMARK 290 | SMTRY2 | 12 | 0.000000 | 0.000000 | −1.000000 | 0.00000 |
| REMARK 290 | SMTRY3 | 12 | 1.000000 | 0.000000 | 0.000000 | 0.00000 |
| REMARK 290 | SMTRY1 | 13 | 0.000000 | 1.000000 | 0.000000 | 0.00000 |
| REMARK 290 | SMTRY2 | 13 | 1.000000 | 0.000000 | 0.000000 | 0.00000 |
| REMARK 290 | SMTRY3 | 13 | 0.000000 | 0.000000 | −1.000000 | 0.00000 |
| REMARK 290 | SMTRY1 | 14 | 0.000000 | −1.000000 | 0.000000 | 0.00000 |
| REMARK 290 | SMTRY2 | 14 | −1.000000 | 0.000000 | 0.000000 | 0.00000 |
| REMARK 290 | SMTRY3 | 14 | 0.000000 | 0.000000 | −1.000000 | 0.00000 |
| REMARK 290 | SMTRY1 | 15 | 0.000000 | 1.000000 | 0.000000 | 0.00000 |
| REMARK 290 | SMTRY2 | 15 | −1.000000 | 0.000000 | 0.000000 | 0.00000 |
| REMARK 290 | SMTRY3 | 15 | 0.000000 | 0.000000 | 1.000000 | 0.00000 |
| REMARK 290 | SMTRY1 | 16 | 0.000000 | −1.000000 | 0.000000 | 0.00000 |
| REMARK 290 | SMTRY2 | 16 | 1.000000 | 0.000000 | 0.000000 | 0.00000 |
| REMARK 290 | SMTRY3 | 16 | 0.000000 | 0.000000 | 1.000000 | 0.00000 |
| REMARK 290 | SMTRY1 | 17 | 1.000000 | 0.000000 | 0.000000 | 0.00000 |
| REMARK 290 | SMTRY2 | 17 | 0.000000 | 0.000000 | 1.000000 | 0.00000 |
| REMARK 290 | SMTRY3 | 17 | 0.000000 | −1.000000 | 0.000000 | 0.00000 |
| REMARK 290 | SMTRY1 | 18 | −1.000000 | 0.000000 | 0.000000 | 0.00000 |
| REMARK 290 | SMTRY2 | 18 | 0.000000 | 0.000000 | 1.000000 | 0.00000 |
| REMARK 290 | SMTRY3 | 18 | 0.000000 | 1.000000 | 0.000000 | 0.00000 |
| REMARK 290 | SMTRY1 | 19 | −1.000000 | 0.000000 | 0.000000 | 0.00000 |
| REMARK 290 | SMTRY2 | 19 | 0.000000 | 0.000000 | −1.000000 | 0.00000 |
| REMARK 290 | SMTRY3 | 19 | 0.000000 | −1.000000 | 0.000000 | 0.00000 |
| REMARK 290 | SMTRY1 | 20 | 1.000000 | 0.000000 | 0.000000 | 0.00000 |
| REMARK 290 | SMTRY2 | 20 | 0.000000 | 0.000000 | −1.000000 | 0.00000 |
| REMARK 290 | SMTRY3 | 20 | 0.000000 | 1.000000 | 0.000000 | 0.00000 |
| REMARK 290 | SMTRY1 | 21 | 0.000000 | 0.000000 | 1.000000 | 0.00000 |
| REMARK 290 | SMTRY2 | 21 | 0.000000 | 1.000000 | 0.000000 | 0.00000 |
| REMARK 290 | SMTRY3 | 21 | −1.000000 | 0.000000 | 0.000000 | 0.00000 |
| REMARK 290 | SMTRY1 | 22 | 0.000000 | 0.000000 | 1.000000 | 0.00000 |
| REMARK 290 | SMTRY2 | 22 | 0.000000 | −1.000000 | 0.000000 | 0.00000 |
| REMARK 290 | SMTRY3 | 22 | 1.000000 | 0.000000 | 0.000000 | 0.00000 |
| REMARK 290 | SMTRY1 | 23 | 0.000000 | 0.000000 | −1.000000 | 0.00000 |
| REMARK 290 | SMTRY2 | 23 | 0.000000 | 1.000000 | 0.000000 | 0.00000 |
| REMARK 290 | SMTRY3 | 23 | 1.000000 | 0.000000 | 0.000000 | 0.00000 |
| REMARK 290 | SMTRY1 | 24 | 0.000000 | 0.000000 | −1.000000 | 0.00000 |
| REMARK 290 | SMTRY2 | 24 | 0.000000 | −1.000000 | 0.000000 | 0.00000 |
| REMARK 290 | SMTRY3 | 24 | −1.000000 | 0.000000 | 0.000000 | 0.00000 |
| REMARK 290 | | | | | | |
| REMARK 290 | REMARK: NULL | | | | | |
| REMARK 300 | | | | | | |
| REMARK 300 | BIOMOLECULE: 1 | | | | | |
| REMARK 300 | THIS ENTRY CONTAINS THE CRYSTALLOGRAPHIC ASYMMETRIC UNIT | | | | | |
| REMARK 300 | WHICH CONSISTS OF 1 CHAIN(S). SEE REMARK 350 FOR | | | | | |
| REMARK 300 | INFORMATION ON GENERATING THE BIOLOGICAL MOLECULE(S). | | | | | |
| REMARK 350 | | | | | | |
| REMARK 350 | GENERATING THE BIOMOLECULE | | | | | |
| REMARK 350 | COORDINATES FOR A COMPLETE MULTIMER REPRESENTING THE KNOWN | | | | | |
| REMARK 350 | BIOLOGICALLY SIGNIFICANT OLIGOMERIZATION STATE OF THE | | | | | |
| REMARK 350 | MOLECULE CAN BE GENERATED BY APPLYING BIOMT TRANSFORMATIONS | | | | | |
| REMARK 350 | GIVEN BELOW. BOTH NON-CRYSTALLOGRAPHIC AND | | | | | |
| REMARK 350 | CRYSTALLOGRAPHIC OPERATIONS ARE GIVEN. | | | | | |
| REMARK 350 | | | | | | |
| REMARK 350 | BIOMOLECULE: 1 | | | | | |
| REMARK 350 | APPLY THE FOLLOWING TO CHAINS: A | | | | | |
| REMARK 350 | BIOMT1 | 1 | 1.000000 | 0.000000 | 0.000000 | 0.00000 |
| REMARK 350 | BIOMT2 | 1 | 0.000000 | 1.000000 | 0.000000 | 0.00000 |
| REMARK 350 | BIOMT3 | 1 | 0.000000 | 0.000000 | 1.000000 | 0.00000 |
| REMARK 350 | BIOMT1 | 2 | −1.000000 | 0.000000 | 0.000000 | 154.41200 |
| REMARK 350 | BIOMT2 | 2 | 0.000000 | −1.000000 | 0.000000 | 154.41200 |
| REMARK 350 | BIOMT3 | 2 | 0.000000 | 0.000000 | 1.000000 | 0.00000 |
| REMARK 350 | BIOMT1 | 3 | 0.000000 | 1.000000 | 0.000000 | 0.00000 |
| REMARK 350 | BIOMT2 | 3 | −1.000000 | 0.000000 | 0.000000 | 154.41200 |
| REMARK 350 | BIOMT3 | 3 | 0.000000 | 0.000000 | 1.000000 | 0.00000 |
| REMARK 350 | BIOMT1 | 4 | 0.000000 | −1.000000 | 0.000000 | 154.41200 |
| REMARK 350 | BIOMT2 | 4 | 1.000000 | 0.000000 | 0.000000 | 0.00000 |
| REMARK 350 | BIOMT3 | 4 | 0.000000 | 0.000000 | 1.000000 | 0.00000 |
| REMARK 465 | | | | | | |

TABLE 2-continued

| | | | | |
|---|---|---|---|---|
| REMARK | 465 | MISSING RESIDUES | | |
| REMARK | 465 | THE FOLLOWING RESIDUES WERE NOT LOCATED IN THE | | |
| REMARK | 465 | EXPERIMENT. (M=MODEL NUMBER; RES=RESIDUE NAME; C=CHAIN | | |
| REMARK | 465 | IDENTIFIER; SSSEQ=SEQUENCE NUMBER; I=INSERTION CODE.) | | |
| REMARK | 465 | | | |
| REMARK | 465 | M  RES C | SSSEQI | |
| REMARK | 465 | MET A | 1 | |
| REMARK | 465 | GLY A | 102 | |
| REMARK | 465 | PHE A | 103 | |
| REMARK | 465 | VAL A | 104 | |
| REMARK | 465 | VAL A | 105 | |
| REMARK | 465 | SER A | 106 | |
| REMARK | 465 | ASP A | 107 | |
| REMARK | 465 | SER A | 108 | |
| REMARK | 465 | ASN A | 109 | |
| REMARK | 465 | VAL A | 110 | |
| REMARK | 465 | LYS A | 111 | |
| REMARK | 465 | PRO A | 112 | |
| REMARK | 465 | ASP A | 113 | |
| REMARK | 465 | GLN A | 114 | |
| REMARK | 465 | THR A | 115 | |
| REMARK | 465 | PHE A | 116 | |
| REMARK | 465 | ALA A | 117 | |
| REMARK | 465 | ASP A | 118 | |
| REMARK | 465 | VAL A | 119 | |
| REMARK | 465 | LEU A | 120 | |
| REMARK | 465 | ALA A | 121 | |
| REMARK | 465 | ILE A | 122 | |
| REMARK | 465 | SER A | 123 | |
| REMARK | 465 | GLN A | 124 | |
| REMARK | 465 | ARG A | 125 | |
| REMARK | 465 | THR A | 126 | |
| REMARK | 465 | THR A | 127 | |
| REMARK | 465 | HIS A | 128 | |
| REMARK | 465 | ASN A | 129 | |
| REMARK | 465 | THR A | 130 | |
| REMARK | 465 | VAL A | 131 | |
| REMARK | 465 | ALA A | 132 | |
| REMARK | 465 | VAL A | 133 | |
| REMARK | 465 | THR A | 134 | |
| REMARK | 465 | ASP A | 135 | |
| REMARK | 465 | ASP A | 136 | |
| REMARK | 465 | GLY A | 137 | |
| REMARK | 465 | THR A | 138 | |
| REMARK | 465 | PRO A | 139 | |
| REMARK | 465 | HIS A | 140 | |
| REMARK | 465 | GLY A | 141 | |
| REMARK | 465 | VAL A | 142 | |
| REMARK | 465 | LEU A | 143 | |
| REMARK | 465 | LEU A | 144 | |
| REMARK | 465 | GLY A | 145 | |
| REMARK | 465 | LEU A | 146 | |
| REMARK | 465 | VAL A | 147 | |
| REMARK | 465 | THR A | 148 | |
| REMARK | 465 | GLN A | 149 | |
| REMARK | 465 | ARG A | 150 | |
| REMARK | 465 | ASP A | 151 | |
| REMARK | 465 | TYR A | 152 | |
| REMARK | 465 | PRO A | 153 | |
| REMARK | 465 | ILE A | 154 | |
| REMARK | 465 | ASP A | 155 | |
| REMARK | 465 | LEU A | 156 | |
| REMARK | 465 | THR A | 157 | |
| REMARK | 465 | GLN A | 158 | |
| REMARK | 465 | THR A | 159 | |
| REMARK | 465 | GLU A | 160 | |
| REMARK | 465 | THR A | 161 | |
| REMARK | 465 | LYS A | 162 | |
| REMARK | 465 | VAL A | 163 | |
| REMARK | 465 | SER A | 164 | |
| REMARK | 465 | ASP A | 165 | |
| REMARK | 465 | MET A | 166 | |
| REMARK | 465 | MET A | 167 | |
| REMARK | 465 | THR A | 168 | |
| REMARK | 465 | PRO A | 169 | |
| REMARK | 465 | PHE A | 170 | |
| REMARK | 465 | SER A | 171 | |
| REMARK | 465 | LYS A | 172 | |
| REMARK | 465 | LEU A | 173 | |

TABLE 2-continued

| | | | |
|---|---|---|---|
| REMARK 465 | VAL | A | 174 |
| REMARK 465 | THR | A | 175 |
| REMARK 465 | ALA | A | 176 |
| REMARK 465 | HIS | A | 177 |
| REMARK 465 | GLN | A | 178 |
| REMARK 465 | ASP | A | 179 |
| REMARK 465 | THR | A | 180 |
| REMARK 465 | LYS | A | 181 |
| REMARK 465 | LEU | A | 182 |
| REMARK 465 | SER | A | 183 |
| REMARK 465 | GLU | A | 184 |
| REMARK 465 | ALA | A | 185 |
| REMARK 465 | ASN | A | 186 |
| REMARK 465 | LYS | A | 187 |
| REMARK 465 | ILE | A | 188 |
| REMARK 465 | ILE | A | 189 |
| REMARK 465 | TRP | A | 190 |
| REMARK 465 | GLU | A | 191 |
| REMARK 465 | LYS | A | 192 |
| REMARK 465 | LYS | A | 193 |
| REMARK 465 | LEU | A | 194 |
| REMARK 465 | ASN | A | 195 |
| REMARK 465 | ALA | A | 196 |
| REMARK 465 | LEU | A | 197 |
| REMARK 465 | PRO | A | 198 |
| REMARK 465 | ILE | A | 199 |
| REMARK 465 | ILE | A | 200 |
| REMARK 465 | ASP | A | 201 |
| REMARK 465 | ASP | A | 202 |
| REMARK 465 | ASP | A | 203 |
| REMARK 465 | GLN | A | 204 |
| REMARK 465 | HIS | A | 205 |
| REMARK 465 | LEU | A | 206 |
| REMARK 465 | ARG | A | 207 |
| REMARK 465 | TYR | A | 208 |
| REMARK 465 | ILE | A | 209 |
| REMARK 465 | VAL | A | 210 |
| REMARK 465 | PHE | A | 211 |
| REMARK 465 | ARG | A | 212 |
| REMARK 465 | LYS | A | 213 |
| REMARK 465 | ASP | A | 214 |
| REMARK 465 | TYR | A | 215 |
| REMARK 465 | ASP | A | 216 |
| REMARK 465 | ARG | A | 217 |
| REMARK 465 | SER | A | 218 |
| REMARK 465 | GLN | A | 219 |
| REMARK 465 | VAL | A | 220 |
| REMARK 465 | CYS | A | 221 |
| REMARK 465 | GLN | A | 417 |
| REMARK 465 | ARG | A | 418 |
| REMARK 465 | TYR | A | 419 |
| REMARK 465 | ASP | A | 420 |
| REMARK 465 | LEU | A | 421 |
| REMARK 465 | GLY | A | 422 |
| REMARK 465 | GLY | A | 423 |
| REMARK 465 | LYS | A | 424 |
| REMARK 465 | GLN | A | 425 |
| REMARK 465 | LYS | A | 426 |
| REMARK 465 | LEU | A | 427 |
| REMARK 465 | SER | A | 428 |
| REMARK 465 | VAL | A | 484 |
| REMARK 465 | GLU | A | 485 |
| REMARK 465 | GLY | A | 486 |
| REMARK 465 | GLY | A | 487 |
| REMARK 465 | ALA | A | 488 |
| REMARK 465 | HIS | A | 489 |
| REMARK 465 | ASP | A | 490 |
| REMARK 465 | VAL | A | 491 |
| REMARK 465 | ILE | A | 492 |
| REMARK 465 | VAL | A | 493 |
| REMARK 465 | LYS | A | 494 |
| REMARK 465 | ASP | A | 495 |
| REMARK 465 | ARG | A | 496 |
| REMARK 465 | ILE | A | 497 |
| REMARK 465 | ASN | A | 498 |
| REMARK 465 | ASP | A | 499 |

TABLE 2-continued

| | | | | | | | | | | | | | | |
|---|---|---|---|---|---|---|---|---|---|---|---|---|---|---|
| REMARK | 465 | | | TYR A | 500 | | | | | | | | | |
| REMARK | 465 | | | HIS A | 501 | | | | | | | | | |
| REMARK | 465 | | | PRO A | 502 | | | | | | | | | |
| REMARK | 465 | | | LYS A | 503 | | | | | | | | | |
| REMARK | 500 | | | | | | | | | | | | | |
| REMARK | 500 | GEOMETRY AND STEREOCHEMISTRY | | | | | | | | | | | | | |
| REMARK | 500 | SUBTOPIC: CLOSE CONTACTS | | | | | | | | | | | | | |
| REMARK | 500 | | | | | | | | | | | | | |
| REMARK | 500 | THE FOLLOWING ATOMS THAT ARE RELATED BY CRYSTALLOGRAPHIC | | | | | | | | | | | | | |
| REMARK | 500 | SYMMETRY ARE IN CLOSE CONTACT. AN ATOM LOCATED WITHIN 0.15 | | | | | | | | | | | | | |
| REMARK | 500 | ANGSTROMS OF A SYMMETRY RELATED ATOM IS ASSUMED TO BE ON A | | | | | | | | | | | | | |
| REMARK | 500 | SPECIAL POSITION AND IS, THEREFORE, LISTED IN REMARK 375 | | | | | | | | | | | | | |
| REMARK | 500 | INSTEAD OF REMARK 500. ATOMS WITH NON-BLANK ALTERNATE | | | | | | | | | | | | | |
| REMARK | 500 | LOCATION INDICATORS ARE NOT INCLUDED IN THE CALCULATIONS. | | | | | | | | | | | | | |
| REMARK | 500 | | | | | | | | | | | | | |
| REMARK | 500 | DISTANCE CUTOFF: | | | | | | | | | | | | | |
| REMARK | 500 | 2.2 ANGSTROMS FOR CONTACTS NOT INVOLVING HYDROGEN ATOMS | | | | | | | | | | | | | |
| REMARK | 500 | 1.6 ANGSTROMS FOR CONTACTS INVOLVING HYDROGEN ATOMS | | | | | | | | | | | | | |
| REMARK | 500 | | | | | | | | | | | | | |
| REMARK | 500 | | ATM1 | RES C | SSEQI | ATM2 | RES C | SSEQI | SSYMOP | DISTANCE | | | | | |
| REMARK | 500 | | O | GLY A | 20 | K | K | A | 900 | 16655 | 2.18 | | | | |
| REMARK | 500 | | | | | | | | | | | | | |
| REMARK | 500 | GEOMETRY AND STEREOCHEMISTRY | | | | | | | | | | | | | |
| REMARK | 500 | SUBTOPIC: COVALENT BOND ANGLES | | | | | | | | | | | | | |
| REMARK | 500 | | | | | | | | | | | | | |
| REMARK | 500 | THE STEREOCHEMICAL PARAMETERS OF THE FOLLOWING RESIDUES | | | | | | | | | | | | | |
| REMARK | 500 | HAVE VALUES WHICH DEVIATE FROM EXPECTED VALUES BY MORE | | | | | | | | | | | | | |
| REMARK | 500 | THAN 6*RMSD (M=MODEL NUMBER; RES=RESIDUE NAME; C=CHAIN | | | | | | | | | | | | | |
| REMARK | 500 | IDENTIFIER; SSEQ=SEQUENCE NUMBER; I=INSERTION CODE). | | | | | | | | | | | | | |
| REMARK | 500 | | | | | | | | | | | | | |
| REMARK | 500 | STANDARD TABLE: | | | | | | | | | | | | | |
| REMARK | 500 | FORMAT: (10X,I3,1X,A3,1X,A1,I4,A1,3(1X,A4,2X),12X,F5.1) | | | | | | | | | | | | | |
| REMARK | 500 | | | | | | | | | | | | | |
| REMARK | 500 | EXPECTED VALUES: ENGH AND HUBER, 1991 | | | | | | | | | | | | | |
| REMARK | 500 | | | | | | | | | | | | | |
| REMARK | 500 | | M | RES C | SSEQI | ATM1 | | ATM2 | | ATM3 | | | | | |
| REMARK | 500 | | | ILE A | 27 | N | – | CA | – | C | ANGL. DEV. = –8.1 DEGREES | | | | |
| REMARK | 500 | | | SER A | 63 | N | – | CA | – | C | ANGL. DEV. = 7.9 DEGREES | | | | |
| REMARK | 500 | | | GLY A | 305 | N | – | CA | – | C | ANGL. DEV. = 7.8 DEGREES | | | | |
| REMARK | 500 | | | GLY A | 312 | N | – | CA | – | C | ANGL. DEV. = 7.2 DEGREES | | | | |
| REMARK | 500 | | | SER A | 357 | N | – | CA | – | C | ANGL. DEV. = –7.4 DEGREES | | | | |
| REMARK | 500 | | | LYS A | 472 | N | – | CA | – | C | ANGL. DEV. = 8.0 DEGREES | | | | |
| REMARK | 500 | | | LYS A | 474 | N | – | CA | – | C | ANGL. DEV. = –9.2 DEGREES | | | | |
| REMARK | 500 | | | LEU A | 477 | N | – | CA | – | C | ANGL. DEV. = –7.8 DEGREES | | | | |
| REMARK | 900 | | | | | | | | | | | | | |
| REMARK | 900 | RELATED ENTRIES | | | | | | | | | | | | | |
| REMARK | 900 | RELATED ID: 1AK5 | | | RELATED DB: PDB | | | | | | | | | | |
| REMARK | 900 | INOSINE MONOPHOSPHATE DEHYDROGENASE (IMPDH) FROM | | | | | | | | | | | | | |
| REMARK | 900 | *TRITRICHOMONAS FOETUS* | | | | | | | | | | | | | |
| REMARK | 900 | RELATED ID: 1ME7 | | | RELATED DB: PDB | | | | | | | | | | |
| REMARK | 900 | 1ME7 CONTAINS THE SAME PROTEIN WITH RMP AND MPA BOUND | | | | | | | | | | | | | |
| REMARK | 900 | RELATED ID: 1ME8 | | | RELATED DB: PDB | | | | | | | | | | |
| REMARK | 900 | 1ME8 CONTAINS THE SAME PROTEIN WITH RMP BOUND | | | | | | | | | | | | | |
| REMARK | 900 | RELATED ID: 1MEH | | | RELATED DB: PDB | | | | | | | | | | |
| REMARK | 900 | 1MEH CONTAINS THE SAME PROTEIN WITH IMP AND MPA BOUND | | | | | | | | | | | | | |
| REMARK | 900 | RELATED ID: 1MEI | | | RELATED DB: PDB | | | | | | | | | | |
| REMARK | 900 | 1MEI CONTAINS THE SAME PROTEIN WITH XMP AND MYCOPHENOLIC | | | | | | | | | | | | | |
| REMARK | 900 | ACID BOUND | | | | | | | | | | | | | |
| REMARK | 900 | RELATED ID: 1MEW | | | RELATED DB: PDB | | | | | | | | | | |
| REMARK | 900 | 1MEW CONTAINS THE SAME PROTEIN WITH XMP AND NAD BOUND | | | | | | | | | | | | | |
| DBREF | 1ME9 A | 1 | 503 | SWS | P50097 | IMDH_TRIFO | | 1 | 503 | | | | | | |
| SEQADV | 1ME9 CSO A | 319 | SWS | P50097 | CYS | 319 | MODIFIED RESIDUE | | | | | | | | |
| SEQRES | 1 | A | 503 | MET | ALA | LYS | TYR | TYR | ASN | GLU | PRO | CYS | HIS | THR | PHE | ASN |
| SEQRES | 2 | A | 503 | GLU | TYR | LEU | LEU | ILE | PRO | GLY | LEU | SER | THR | VAL | ASP | CYS |
| SEQRES | 3 | A | 503 | ILE | PRO | SER | ASN | VAL | ASN | LEU | SER | THR | PRO | LEU | VAL | LYS |
| SEQRES | 4 | A | 503 | PHE | GLN | LYS | GLY | GLN | GLN | SER | GLU | ILE | ASN | LEU | LYS | ILE |
| SEQRES | 5 | A | 503 | PRO | LEU | VAL | SER | ALA | ILE | MET | GLN | SER | VAL | SER | GLY | GLU |
| SEQRES | 6 | A | 503 | LYS | MET | ALA | ILE | ALA | LEU | ALA | ARG | GLU | GLY | GLY | ILE | SER |
| SEQRES | 7 | A | 503 | PHE | ILE | PHE | GLY | SER | GLN | SER | ILE | GLU | SER | GLN | ALA | ALA |
| SEQRES | 8 | A | 503 | MET | VAL | HIS | ALA | VAL | LYS | ASN | PHE | LYS | ALA | GLY | PHE | VAL |
| SEQRES | 9 | A | 503 | VAL | SER | ASP | SER | ASN | VAL | LYS | PRO | ASP | GLN | THR | PHE | ALA |
| SEQRES | 10 | A | 503 | ASP | VAL | LEU | ALA | ILE | SER | GLN | ARG | THR | THR | HIS | ASN | THR |
| SEQRES | 11 | A | 503 | VAL | ALA | VAL | THR | ASP | ASP | GLY | THR | PRO | HIS | GLY | VAL | LEU |
| SEQRES | 12 | A | 503 | LEU | GLY | LEU | VAL | THR | GLN | ARG | ASP | TYR | PRO | ILE | ASP | VAL |
| SEQRES | 13 | A | 503 | THR | GLN | THR | GLU | THR | LYS | VAL | SER | ASP | MET | MET | THR | PRO |
| SEQRES | 14 | A | 503 | PHE | SER | LYS | LEU | VAL | THR | ALA | HIS | GLN | ASP | THR | LYS | LEU |
| SEQRES | 15 | A | 503 | SER | GLU | ALA | ASN | LYS | ILE | ILE | TRP | GLU | LYS | LYS | LEU | ASN |
| SEQRES | 16 | A | 503 | ALA | LEU | PRO | ILE | ILE | ASP | ASP | ASP | GLN | HIS | LEU | ARG | TYR |
| SEQRES | 17 | A | 503 | ILE | VAL | PHE | ARG | LYS | ASP | TYR | ASP | ARG | SER | GLN | VAL | CYS |

TABLE 2-continued

```
SEQRES   18 A  503  HIS ASN GLU LEU VAL ASP SER GLN LYS ARG TYR LEU VAL
SEQRES   19 A  503  GLY ALA GLY ILE ASN THR ARG ASP PHE ARG GLU ARG VAL
SEQRES   20 A  503  PRO ALA LEU VAL GLU ALA GLY ALA ASP VAL LEU CYS ILE
SEQRES   21 A  503  ASP SER SER ASP GLY PHE SER ILE GLU TRP GLN LYS ILE THR
SEQRES   22 A  503  ILE GLY TRP ILE ARG GLU LYS TYR GLY ASP LYS VAL LYS
SEQRES   23 A  503  VAL GLY ALA GLY ASN ILE VAL ASP GLY GLU GLY PHE ARG
SEQRES   24 A  503  TYR LEU ALA ASP ALA GLY ALA ASP PHE ILE LYS ILE GLY
SEQRES   25 A  503  ILE GLY GLY GLY SER ILE CSO ILE THR ARG GLU GLN LYS
SEQRES   26 A  503  GLY ILE GLY ARG GLY GLN ALA THR ALA VAL ILE ASP VAL
SEQRES   27 A  503  VAL ALA GLU ARG ASN LYS TYR PHE GLU GLU THR GLY ILE
SEQRES   28 A  503  TYR ILE PRO VAL CYS SER ASP GLY GLY ILE VAL TYR ASP
SEQRES   29 A  503  TYR HIS MET THR LEU ALA LEU ALA MET GLY ALA ASP PHE
SEQRES   30 A  503  ILE MET LEU GLY ARG TYR PHE ALA ARG PHE GLU GLU SER
SEQRES   31 A  503  PRO THR ARG LYS VAL THR ILE ASN GLY SER VAL MET LYS
SEQRES   32 A  503  GLU TYR TRP GLY GLU GLY SER SER ARG ALA ARG ASN TRP
SEQRES   33 A  503  GLN ARG TYR ASP LEU GLY LYS LYS LEU SER PHE
SEQRES   34 A  503  GLU GLU GLY VAL ASP SER TYR VAL PRO TYR ALA GLY LYS
SEQRES   35 A  503  LEU LYS ASP ASN VAL GLU ALA SER LEU ASN LYS VAL LYS
SEQRES   36 A  503  SER THR MET CYS ASN CYS GLY ALA LEU THR ILE PRO GLN
SEQRES   37 A  503  LEU GLN SER LYS ALA LYS ILE THR LEU VAL SER SER VAL
SEQRES   38 A  503  SER ILE VAL GLU GLY GLY ALA HIS ASP VAL ILE VAL LYS
SEQRES   39 A  503  ASP ARG ILE ASN ASP TYR HIS PRO LYS
MODRES   1ME9 CSO A   319   CYS   S-HYDROXYCYSTEINE
HET        CSO A  319       7
HET        K   A  900       1
HET        IMP    602      23
HETNAM     CSO S-HYDROXYCYSTEINE
HETNAM     K   POTASSIUM ION
HETNAM     IMP INOSINIC ACID
FORMUL   1        CSO    C3 H7 N1 O3 S1
FORMUL   2        K      K1 1+
FORMUL   3        IMP    C10 H13 N4 O8 P1
FORMUL   4        HOH    *145(H2 O1)
HELIX    1   1 THR A   11  ASN A   13  5                                   3
HELIX    2   2 ILE A   27  VAL A   31  5                                   5
HELIX    3   3 GLY A   64  GLU A   74  1                                  11
HELIX    4   4 SER A   85  ASN A   98  1                                  14
HELIX    5   5 ASP A  242  GLY A  254  1                                  13
HELIX    6   6 SER A  267  GLY A  282  1                                  16
HELIX    7   7 ASP A  283  VAL A  285  5                                   3
HELIX    8   8 ASP A  294  ALA A  304  1                                  11
HELIX    9   9 GLY A  330  GLY A  350  1                                  21
HELIX   10  10 TYR A  363  MET A  373  1                                  11
HELIX   11  11 GLY A  381  ARG A  386  1                                   6
HELIX   12  12 SER A  410  ASN A  415  1                                   6
HELIX   13  13 LYS A  442  CYS A  461  1                                  20
HELIX   14  14 THR A  465  ALA A  473  1                                   9
SHEET    1 A 2 TYR A   15  LEU A   17  0
SHEET    2 A 2 ILE A  475  LEU A  477 -1  O  THR A  476   N  LEU A   16
SHEET    1 B 2 THR A   35  PRO A   36  0
SHEET    2 B 2 ASN A   49  LEU A   50 -1  O  LEU A   50   N  THR A   35
SHEET    1 C 2 PHE A   40  GLN A   41  0
SHEET    2 C 2 ILE A  351  TYR A  352 -1  O  TYR A  352   N  PHE A   40
SHEET    1 D 9 LEU A   54  SER A   56  0
SHEET    2 D 9 ILE A   77  ILE A   80  1  O  ILE A   77   N  SER A   56
SHEET    3 D 9 GLY A  235  ILE A  238  1  O  GLY A  237   N  ILE A   80
SHEET    4 D 9 VAL A  257  ILE A  260  1  O  CYS A  259   N  ILE A  238
SHEET    5 D 9 VAL A  287  ILE A  292  1  O  GLY A  288   N  LEU A  258
SHEET    6 D 9 PHE A  308  ILE A  311  1  O  LYS A  310   N  ALA A  289
SHEET    7 D 9 VAL A  355  ASP A  358  1  O  CYS A  356   N  ILE A  311
SHEET    8 D 9 PHE A  377  LEU A  380  1  O  MET A  379   N  SER A  357
SHEET    9 D 9 LEU A   54  SER A   56  1  N  VAL A   55   O  ILE A  378
SHEET    1 E 3 LYS A  394  ILE A  397  0
SHEET    2 E 3 SER A  400  TRP A  406 -1  O  SER A  400   N  ILE A  397
SHEET    3 E 3 ASP A  434  PRO A  438  1  O  SER A  435   N  TYR A  405
SSBOND   1 CYS A   26  CYS A  459
CISPEP   1 GLY A  290  ASN A  291      0       0.99
CRYST1  154.412 154.412 154.412  90.00  90.00  90.00 P 4 3 2       24
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.006476  0.000000  0.000000        0.00000
SCALE2      0.000000  0.006476  0.000000        0.00000
SCALE3      0.000000  0.000000  0.006476        0.00000
ATOM         1  N    ALA A    2      55.031  74.792  36.719  1.00  34.77           N
ATOM         2  CA   ALA A    2      55.778  73.707  36.025  1.00  35.14           C
ATOM         3  C    ALA A    2      57.099  73.393  36.732  1.00  35.76           C
ATOM         4  O    ALA A    2      57.541  74.137  37.609  1.00  33.95           O
ATOM         5  CB   ALA A    2      56.041  74.107  34.583  1.00  34.68           C
```

TABLE 2-continued

| ATOM | 6 | N | LYS A | 3 | 57.724 | 72.288 | 36.340 | 1.00 | 35.35 | N |
|---|---|---|---|---|---|---|---|---|---|---|
| ATOM | 7 | CA | LYS A | 3 | 58.992 | 71.873 | 36.927 | 1.00 | 37.15 | C |
| ATOM | 8 | C | LYS A | 3 | 60.102 | 72.070 | 35.899 | 1.00 | 36.78 | C |
| ATOM | 9 | O | LYS A | 3 | 59.954 | 71.708 | 34.735 | 1.00 | 38.00 | O |
| ATOM | 10 | CB | LYS A | 3 | 58.899 | 70.403 | 37.363 | 1.00 | 39.80 | C |
| ATOM | 11 | CG | LYS A | 3 | 60.157 | 69.806 | 37.997 | 1.00 | 44.47 | C |
| ATOM | 12 | CD | LYS A | 3 | 61.036 | 69.120 | 36.954 | 1.00 | 48.61 | C |
| ATOM | 13 | CE | LYS A | 3 | 61.897 | 68.023 | 37.579 | 1.00 | 49.58 | C |
| ATOM | 14 | NZ | LYS A | 3 | 62.832 | 68.555 | 38.611 | 1.00 | 52.93 | N |
| ATOM | 15 | N | TYR A | 4 | 61.206 | 72.662 | 36.339 | 1.00 | 36.47 | N |
| ATOM | 16 | CA | TYR A | 4 | 62.351 | 72.934 | 35.479 | 1.00 | 36.96 | C |
| ATOM | 17 | C | TYR A | 4 | 63.577 | 72.172 | 35.977 | 1.00 | 38.55 | C |
| ATOM | 18 | O | TYR A | 4 | 63.591 | 71.670 | 37.096 | 1.00 | 37.91 | O |
| ATOM | 19 | CB | TYR A | 4 | 62.635 | 74.442 | 35.472 | 1.00 | 35.25 | C |
| ATOM | 20 | CG | TYR A | 4 | 61.519 | 75.245 | 34.848 | 1.00 | 34.15 | C |
| ATOM | 21 | CD1 | TYR A | 4 | 61.394 | 75.337 | 33.464 | 1.00 | 32.56 | C |
| ATOM | 22 | CD2 | TYR A | 4 | 60.554 | 75.866 | 35.637 | 1.00 | 34.18 | C |
| ATOM | 23 | CE1 | TYR A | 4 | 60.330 | 76.029 | 32.879 | 1.00 | 33.21 | C |
| ATOM | 24 | CE2 | TYR A | 4 | 59.484 | 76.561 | 35.061 | 1.00 | 33.54 | C |
| ATOM | 25 | CZ | TYR A | 4 | 59.380 | 76.637 | 33.684 | 1.00 | 32.10 | C |
| ATOM | 26 | OH | TYR A | 4 | 58.328 | 77.310 | 33.111 | 1.00 | 30.26 | O |
| ATOM | 27 | N | TYR A | 5 | 64.608 | 72.091 | 35.144 | 1.00 | 40.78 | N |
| ATOM | 28 | CA | TYR A | 5 | 65.823 | 71.383 | 35.520 | 1.00 | 42.88 | C |
| ATOM | 29 | C | TYR A | 5 | 67.023 | 72.320 | 35.609 | 1.00 | 44.40 | C |
| ATOM | 30 | O | TYR A | 5 | 67.062 | 73.368 | 34.957 | 1.00 | 44.26 | O |
| ATOM | 31 | CB | TYR A | 5 | 66.104 | 70.251 | 34.527 | 1.00 | 42.67 | C |
| ATOM | 32 | CG | TYR A | 5 | 64.970 | 69.255 | 34.423 | 1.00 | 42.51 | C |
| ATOM | 33 | CD1 | TYR A | 5 | 63.796 | 69.579 | 33.745 | 1.00 | 43.00 | C |
| ATOM | 34 | CD2 | TYR A | 5 | 65.058 | 67.997 | 35.030 | 1.00 | 43.01 | C |
| ATOM | 35 | CE1 | TYR A | 5 | 62.735 | 68.682 | 33.670 | 1.00 | 43.13 | C |
| ATOM | 36 | CE2 | TYR A | 5 | 64.005 | 67.090 | 34.963 | 1.00 | 42.79 | C |
| ATOM | 37 | CZ | TYR A | 5 | 62.845 | 67.440 | 34.281 | 1.00 | 43.79 | C |
| ATOM | 38 | OH | TYR A | 5 | 61.794 | 66.556 | 34.202 | 1.00 | 42.47 | O |
| ATOM | 39 | N | ASN A | 6 | 67.996 | 71.934 | 36.429 | 1.00 | 45.72 | N |
| ATOM | 40 | CA | ASN A | 6 | 69.201 | 72.729 | 36.636 | 1.00 | 45.99 | C |
| ATOM | 41 | C | ASN A | 6 | 70.163 | 72.704 | 35.453 | 1.00 | 45.21 | C |
| ATOM | 42 | O | ASN A | 6 | 70.883 | 73.673 | 35.218 | 1.00 | 46.34 | O |
| ATOM | 43 | CB | ASN A | 6 | 69.926 | 72.243 | 37.893 | 1.00 | 48.66 | C |
| ATOM | 44 | CG | ASN A | 6 | 69.147 | 72.530 | 39.163 | 1.00 | 51.75 | C |
| ATOM | 45 | OD1 | ASN A | 6 | 69.264 | 71.805 | 40.153 | 1.00 | 52.73 | O |
| ATOM | 46 | ND2 | ASN A | 6 | 68.356 | 73.601 | 39.147 | 1.00 | 53.06 | N |
| ATOM | 47 | N | GLU A | 7 | 70.177 | 71.605 | 34.707 | 1.00 | 43.47 | N |
| ATOM | 48 | CA | GLU A | 7 | 71.079 | 71.486 | 33.564 | 1.00 | 41.57 | C |
| ATOM | 49 | C | GLU A | 7 | 70.346 | 71.136 | 32.284 | 1.00 | 38.29 | C |
| ATOM | 50 | O | GLU A | 7 | 69.314 | 70.472 | 32.315 | 1.00 | 37.72 | O |
| ATOM | 51 | CB | GLU A | 7 | 72.127 | 70.393 | 33.817 | 1.00 | 43.70 | C |
| ATOM | 52 | CG | GLU A | 7 | 73.090 | 70.645 | 34.973 | 1.00 | 46.76 | C |
| ATOM | 53 | CD | GLU A | 7 | 73.898 | 71.919 | 34.802 | 1.00 | 47.87 | C |
| ATOM | 54 | OE1 | GLU A | 7 | 74.359 | 72.193 | 33.670 | 1.00 | 49.12 | O |
| ATOM | 55 | OE2 | GLU A | 7 | 74.082 | 72.641 | 35.805 | 1.00 | 50.03 | O |
| ATOM | 56 | N | PRO A | 8 | 70.871 | 71.577 | 31.135 | 1.00 | 35.40 | N |
| ATOM | 57 | CA | PRO A | 8 | 70.208 | 71.252 | 29.871 | 1.00 | 34.46 | C |
| ATOM | 58 | C | PRO A | 8 | 70.554 | 69.795 | 29.540 | 1.00 | 33.72 | C |
| ATOM | 59 | O | PRO A | 8 | 71.523 | 69.267 | 30.073 | 1.00 | 33.53 | O |
| ATOM | 60 | CB | PRO A | 8 | 70.835 | 72.240 | 28.895 | 1.00 | 34.81 | C |
| ATOM | 61 | CG | PRO A | 8 | 72.234 | 72.402 | 29.433 | 1.00 | 33.93 | C |
| ATOM | 62 | CD | PRO A | 8 | 72.018 | 72.481 | 30.923 | 1.00 | 35.69 | C |
| ATOM | 63 | N | CYS A | 9 | 69.769 | 69.139 | 28.690 | 1.00 | 32.35 | N |
| ATOM | 64 | CA | CYS A | 9 | 70.080 | 67.760 | 28.330 | 1.00 | 32.79 | C |
| ATOM | 65 | C | CYS A | 9 | 71.159 | 67.727 | 27.240 | 1.00 | 30.89 | C |
| ATOM | 66 | O | CYS A | 9 | 71.332 | 68.694 | 26.501 | 1.00 | 30.36 | O |
| ATOM | 67 | CB | CYS A | 9 | 68.814 | 67.012 | 27.884 | 1.00 | 35.10 | C |
| ATOM | 68 | SG | CYS A | 9 | 67.853 | 67.729 | 26.524 | 1.00 | 42.35 | S |
| ATOM | 69 | N | HIS A | 10 | 71.888 | 66.618 | 27.157 | 1.00 | 30.90 | N |
| ATOM | 70 | CA | HIS A | 10 | 72.979 | 66.462 | 26.193 | 1.00 | 29.93 | C |
| ATOM | 71 | C | HIS A | 10 | 72.848 | 65.184 | 25.371 | 1.00 | 30.71 | C |
| ATOM | 72 | O | HIS A | 10 | 72.257 | 64.207 | 25.825 | 1.00 | 30.16 | O |
| ATOM | 73 | CB | HIS A | 10 | 74.315 | 66.419 | 26.933 | 1.00 | 29.59 | C |
| ATOM | 74 | CG | HIS A | 10 | 74.582 | 67.624 | 27.773 | 1.00 | 30.61 | C |
| ATOM | 75 | ND1 | HIS A | 10 | 74.945 | 68.840 | 27.236 | 1.00 | 30.69 | N |
| ATOM | 76 | CD2 | HIS A | 10 | 74.533 | 67.804 | 29.115 | 1.00 | 30.16 | C |
| ATOM | 77 | CE1 | HIS A | 10 | 75.109 | 69.716 | 28.210 | 1.00 | 30.34 | C |
| ATOM | 78 | NE2 | HIS A | 10 | 74.864 | 69.112 | 29.359 | 1.00 | 31.65 | N |
| ATOM | 79 | N | THR A | 11 | 73.405 | 65.199 | 24.164 | 1.00 | 30.01 | N |
| ATOM | 80 | CA | THR A | 11 | 73.368 | 64.032 | 23.286 | 1.00 | 30.68 | C |
| ATOM | 81 | C | THR A | 11 | 74.696 | 63.287 | 23.412 | 1.00 | 29.38 | C |
| ATOM | 82 | O | THR A | 11 | 75.639 | 63.803 | 24.006 | 1.00 | 29.12 | O |
| ATOM | 83 | CB | THR A | 11 | 73.194 | 64.437 | 21.816 | 1.00 | 31.25 | C |
| ATOM | 84 | OG1 | THR A | 11 | 74.303 | 65.251 | 21.419 | 1.00 | 33.58 | O |

TABLE 2-continued

| | | | | | | | | | | |
|---|---|---|---|---|---|---|---|---|---|---|
| ATOM | 85 | CG2 | THR A | 11 | 71.903 | 65.220 | 21.621 | 1.00 | 34.80 | C |
| ATOM | 86 | N | PHE A | 12 | 74.768 | 62.085 | 22.846 | 1.00 | 29.78 | N |
| ATOM | 87 | CA | PHE A | 12 | 75.991 | 61.278 | 22.894 | 1.00 | 31.09 | C |
| ATOM | 88 | C | PHE A | 12 | 77.208 | 61.973 | 22.287 | 1.00 | 31.77 | C |
| ATOM | 89 | O | PHE A | 12 | 78.334 | 61.771 | 22.747 | 1.00 | 30.24 | O |
| ATOM | 90 | CB | PHE A | 12 | 75.789 | 59.943 | 22.173 | 1.00 | 28.84 | C |
| ATOM | 91 | CG | PHE A | 12 | 74.853 | 59.003 | 22.877 | 1.00 | 29.84 | C |
| ATOM | 92 | CD1 | PHE A | 12 | 74.966 | 58.782 | 24.247 | 1.00 | 28.95 | C |
| ATOM | 93 | CD2 | PHE A | 12 | 73.904 | 58.284 | 22.156 | 1.00 | 29.11 | C |
| ATOM | 94 | CE1 | PHE A | 12 | 74.153 | 57.853 | 24.888 | 1.00 | 30.30 | C |
| ATOM | 95 | CE2 | PHE A | 12 | 73.082 | 57.348 | 22.788 | 1.00 | 30.62 | C |
| ATOM | 96 | CZ | PHE A | 12 | 73.207 | 57.130 | 24.154 | 1.00 | 28.11 | C |
| ATOM | 97 | N | ASN A | 13 | 76.984 | 62.770 | 21.243 | 1.00 | 33.09 | N |
| ATOM | 98 | CA | ASN A | 13 | 78.071 | 63.496 | 20.582 | 1.00 | 33.64 | C |
| ATOM | 99 | C | ASN A | 13 | 78.783 | 64.499 | 21.487 | 1.00 | 32.75 | C |
| ATOM | 100 | O | ASN A | 13 | 79.884 | 64.944 | 21.168 | 1.00 | 33.53 | O |
| ATOM | 101 | CB | ASN A | 13 | 77.554 | 64.238 | 19.344 | 1.00 | 37.76 | C |
| ATOM | 102 | CG | ASN A | 13 | 77.564 | 63.377 | 18.098 | 1.00 | 42.14 | C |
| ATOM | 103 | OD1 | ASN A | 13 | 78.553 | 62.701 | 17.804 | 1.00 | 46.22 | O |
| ATOM | 104 | ND2 | ASN A | 13 | 76.471 | 63.408 | 17.348 | 1.00 | 44.81 | N |
| ATOM | 105 | N | GLU A | 14 | 78.163 | 64.861 | 22.607 | 1.00 | 31.62 | N |
| ATOM | 106 | CA | GLU A | 14 | 78.771 | 65.818 | 23.531 | 1.00 | 31.09 | C |
| ATOM | 107 | C | GLU A | 14 | 79.655 | 65.155 | 24.581 | 1.00 | 31.08 | C |
| ATOM | 108 | O | GLU A | 14 | 80.097 | 65.801 | 25.527 | 1.00 | 31.33 | O |
| ATOM | 109 | CB | GLU A | 14 | 77.684 | 66.629 | 24.232 | 1.00 | 31.42 | C |
| ATOM | 110 | CG | GLU A | 14 | 76.804 | 67.400 | 23.272 | 1.00 | 32.57 | C |
| ATOM | 111 | CD | GLU A | 14 | 75.692 | 68.138 | 23.971 | 1.00 | 31.00 | C |
| ATOM | 112 | OE1 | GLU A | 14 | 75.995 | 68.988 | 24.831 | 1.00 | 32.14 | O |
| ATOM | 113 | OE2 | GLU A | 14 | 74.516 | 67.864 | 23.660 | 1.00 | 32.39 | O |
| ATOM | 114 | N | TYR A | 15 | 79.928 | 63.869 | 24.418 | 1.00 | 29.84 | N |
| ATOM | 115 | CA | TYR A | 15 | 80.746 | 63.176 | 25.397 | 1.00 | 29.38 | C |
| ATOM | 116 | C | TYR A | 15 | 81.916 | 62.432 | 24.792 | 1.00 | 29.40 | C |
| ATOM | 117 | O | TYR A | 15 | 81.906 | 62.064 | 23.616 | 1.00 | 30.63 | O |
| ATOM | 118 | CB | TYR A | 15 | 79.889 | 62.177 | 26.184 | 1.00 | 29.52 | C |
| ATOM | 119 | CG | TYR A | 15 | 78.909 | 62.805 | 27.147 | 1.00 | 30.93 | C |
| ATOM | 120 | CD1 | TYR A | 15 | 79.296 | 63.131 | 28.446 | 1.00 | 30.83 | C |
| ATOM | 121 | CD2 | TYR A | 15 | 77.593 | 63.074 | 26.759 | 1.00 | 30.10 | C |
| ATOM | 122 | CE1 | TYR A | 15 | 78.400 | 63.706 | 29.341 | 1.00 | 32.23 | C |
| ATOM | 123 | CE2 | TYR A | 15 | 76.688 | 63.653 | 27.646 | 1.00 | 32.13 | C |
| ATOM | 124 | CZ | TYR A | 15 | 77.099 | 63.967 | 28.934 | 1.00 | 32.37 | C |
| ATOM | 125 | OH | TYR A | 15 | 76.225 | 64.565 | 29.809 | 1.00 | 35.93 | O |
| ATOM | 126 | N | LEU A | 16 | 82.929 | 62.216 | 25.620 | 1.00 | 30.01 | N |
| ATOM | 127 | CA | LEU A | 16 | 84.107 | 61.457 | 25.229 | 1.00 | 30.13 | C |
| ATOM | 128 | C | LEU A | 16 | 84.514 | 60.664 | 26.463 | 1.00 | 28.66 | C |
| ATOM | 129 | O | LEU A | 16 | 84.207 | 61.048 | 27.592 | 1.00 | 26.73 | O |
| ATOM | 130 | CB | LEU A | 16 | 85.260 | 62.374 | 24.788 | 1.00 | 31.28 | C |
| ATOM | 131 | CG | LEU A | 16 | 85.169 | 63.110 | 23.440 | 1.00 | 32.96 | C |
| ATOM | 132 | CD1 | LEU A | 16 | 86.432 | 63.925 | 23.241 | 1.00 | 34.63 | C |
| ATOM | 133 | CD2 | LEU A | 16 | 85.011 | 62.126 | 22.287 | 1.00 | 33.72 | C |
| ATOM | 134 | N | LEU A | 17 | 85.182 | 59.543 | 26.239 | 1.00 | 29.11 | N |
| ATOM | 135 | CA | LEU A | 17 | 85.652 | 58.696 | 27.327 | 1.00 | 30.34 | C |
| ATOM | 136 | C | LEU A | 17 | 87.129 | 58.990 | 27.618 | 1.00 | 30.21 | C |
| ATOM | 137 | O | LEU A | 17 | 87.943 | 59.094 | 26.698 | 1.00 | 31.80 | O |
| ATOM | 138 | CB | LEU A | 17 | 85.502 | 57.224 | 26.935 | 1.00 | 29.21 | C |
| ATOM | 139 | CG | LEU A | 17 | 84.082 | 56.655 | 26.892 | 1.00 | 28.59 | C |
| ATOM | 140 | CD1 | LEU A | 17 | 84.051 | 55.435 | 25.990 | 1.00 | 25.58 | C |
| ATOM | 141 | CD2 | LEU A | 17 | 83.622 | 56.315 | 28.304 | 1.00 | 25.80 | C |
| ATOM | 142 | N | ILE A | 18 | 87.466 | 59.144 | 28.892 | 1.00 | 31.07 | N |
| ATOM | 143 | CA | ILE A | 18 | 88.852 | 59.385 | 29.282 | 1.00 | 30.21 | C |
| ATOM | 144 | C | ILE A | 18 | 89.418 | 58.024 | 29.677 | 1.00 | 29.84 | C |
| ATOM | 145 | O | ILE A | 18 | 88.859 | 57.345 | 30.536 | 1.00 | 29.71 | O |
| ATOM | 146 | CB | ILE A | 18 | 88.939 | 60.359 | 30.472 | 1.00 | 30.01 | C |
| ATOM | 147 | CG1 | ILE A | 18 | 88.464 | 61.748 | 30.035 | 1.00 | 30.69 | C |
| ATOM | 148 | CG2 | ILE A | 18 | 90.375 | 60.428 | 30.991 | 1.00 | 28.88 | C |
| ATOM | 149 | CD1 | ILE A | 18 | 88.447 | 62.774 | 31.145 | 1.00 | 31.89 | C |
| ATOM | 150 | N | PRO A | 19 | 90.528 | 57.601 | 29.045 | 1.00 | 29.50 | N |
| ATOM | 151 | CA | PRO A | 19 | 91.140 | 56.303 | 29.350 | 1.00 | 30.06 | C |
| ATOM | 152 | C | PRO A | 19 | 91.482 | 56.059 | 30.818 | 1.00 | 29.17 | C |
| ATOM | 153 | O | PRO A | 19 | 91.777 | 56.989 | 31.570 | 1.00 | 30.34 | O |
| ATOM | 154 | CB | PRO A | 19 | 92.389 | 56.285 | 28.460 | 1.00 | 30.87 | C |
| ATOM | 155 | CG | PRO A | 19 | 91.978 | 57.136 | 27.284 | 1.00 | 30.83 | C |
| ATOM | 156 | CD | PRO A | 19 | 91.265 | 58.285 | 27.966 | 1.00 | 29.93 | C |
| ATOM | 157 | N | GLY A | 20 | 91.415 | 54.792 | 31.210 | 1.00 | 27.42 | N |
| ATOM | 158 | CA | GLY A | 20 | 91.745 | 54.398 | 32.566 | 1.00 | 27.95 | C |
| ATOM | 159 | C | GLY A | 20 | 92.936 | 53.469 | 32.445 | 1.00 | 27.30 | C |
| ATOM | 160 | O | GLY A | 20 | 93.543 | 53.402 | 31.386 | 1.00 | 26.88 | O |
| ATOM | 161 | N | LEU A | 21 | 93.275 | 52.739 | 33.497 | 1.00 | 29.16 | N |
| ATOM | 162 | CA | LEU A | 21 | 94.422 | 51.838 | 33.424 | 1.00 | 29.56 | C |
| ATOM | 163 | C | LEU A | 21 | 94.130 | 50.584 | 32.611 | 1.00 | 29.75 | C |

TABLE 2-continued

| | | | | | | | | | | |
|---|---|---|---|---|---|---|---|---|---|---|
| ATOM | 164 | O | LEU A | 21 | 93.212 | 49.831 | 32.920 | 1.00 | 29.91 | O |
| ATOM | 165 | CB | LEU A | 21 | 94.885 | 51.435 | 34.834 | 1.00 | 30.32 | C |
| ATOM | 166 | CG | LEU A | 21 | 96.026 | 50.403 | 34.888 | 1.00 | 30.63 | C |
| ATOM | 167 | CD1 | LEU A | 21 | 97.262 | 50.967 | 34.183 | 1.00 | 25.74 | C |
| ATOM | 168 | CD2 | LEU A | 21 | 96.342 | 50.047 | 36.348 | 1.00 | 31.08 | C |
| ATOM | 169 | N | SER A | 22 | 94.917 | 50.370 | 31.564 | 1.00 | 31.55 | N |
| ATOM | 170 | CA | SER A | 22 | 94.762 | 49.191 | 30.726 | 1.00 | 32.64 | C |
| ATOM | 171 | C | SER A | 22 | 95.789 | 48.167 | 31.189 | 1.00 | 34.68 | C |
| ATOM | 172 | O | SER A | 22 | 96.993 | 48.439 | 31.185 | 1.00 | 32.90 | O |
| ATOM | 173 | CB | SER A | 22 | 95.008 | 49.531 | 29.256 | 1.00 | 32.66 | C |
| ATOM | 174 | OG | SER A | 22 | 94.090 | 50.505 | 28.793 | 1.00 | 31.63 | O |
| ATOM | 175 | N | THR A | 23 | 95.305 | 46.998 | 31.600 | 1.00 | 36.61 | N |
| ATOM | 176 | CA | THR A | 23 | 96.170 | 45.923 | 32.075 | 1.00 | 37.91 | C |
| ATOM | 177 | C | THR A | 23 | 96.550 | 44.997 | 30.927 | 1.00 | 38.68 | C |
| ATOM | 178 | O | THR A | 23 | 95.882 | 44.978 | 29.892 | 1.00 | 39.48 | O |
| ATOM | 179 | CB | THR A | 23 | 95.478 | 45.107 | 33.174 | 1.00 | 37.72 | C |
| ATOM | 180 | OG1 | THR A | 23 | 94.187 | 44.701 | 32.718 | 1.00 | 41.28 | O |
| ATOM | 181 | CG2 | THR A | 23 | 95.311 | 45.936 | 34.431 | 1.00 | 38.84 | C |
| ATOM | 182 | N | VAL A | 24 | 97.624 | 44.232 | 31.117 | 1.00 | 39.25 | N |
| ATOM | 183 | CA | VAL A | 24 | 98.118 | 43.311 | 30.095 | 1.00 | 39.40 | C |
| ATOM | 184 | C | VAL A | 24 | 97.105 | 42.274 | 29.611 | 1.00 | 40.18 | C |
| ATOM | 185 | O | VAL A | 24 | 97.178 | 41.820 | 28.470 | 1.00 | 39.57 | O |
| ATOM | 186 | CB | VAL A | 24 | 99.390 | 42.559 | 30.582 | 1.00 | 40.21 | C |
| ATOM | 187 | CG1 | VAL A | 24 | 100.555 | 43.537 | 30.721 | 1.00 | 38.74 | C |
| ATOM | 188 | CG2 | VAL A | 24 | 99.115 | 41.863 | 31.912 | 1.00 | 40.04 | C |
| ATOM | 189 | N | ASP A | 25 | 96.160 | 41.896 | 30.464 | 1.00 | 41.79 | N |
| ATOM | 190 | CA | ASP A | 25 | 95.170 | 40.903 | 30.066 | 1.00 | 45.39 | C |
| ATOM | 191 | C | ASP A | 25 | 94.021 | 41.455 | 29.225 | 1.00 | 45.56 | C |
| ATOM | 192 | O | ASP A | 25 | 93.233 | 40.684 | 28.681 | 1.00 | 45.92 | O |
| ATOM | 193 | CB | ASP A | 25 | 94.592 | 40.185 | 31.294 | 1.00 | 48.41 | C |
| ATOM | 194 | CG | ASP A | 25 | 93.943 | 41.140 | 32.283 | 1.00 | 51.92 | C |
| ATOM | 195 | OD1 | ASP A | 25 | 93.010 | 40.724 | 33.005 | 1.00 | 54.02 | O |
| ATOM | 196 | OD2 | ASP A | 25 | 94.375 | 42.304 | 32.355 | 1.00 | 53.64 | O |
| ATOM | 197 | N | CYS A | 26 | 93.912 | 42.774 | 29.096 | 1.00 | 45.84 | N |
| ATOM | 198 | CA | CYS A | 26 | 92.808 | 43.308 | 28.309 | 1.00 | 45.30 | C |
| ATOM | 199 | C | CYS A | 26 | 93.109 | 43.487 | 26.838 | 1.00 | 45.23 | C |
| ATOM | 200 | O | CYS A | 26 | 93.730 | 44.463 | 26.426 | 1.00 | 44.99 | O |
| ATOM | 201 | CB | CYS A | 26 | 92.301 | 44.641 | 28.867 | 1.00 | 44.12 | C |
| ATOM | 202 | SG | CYS A | 26 | 90.582 | 45.050 | 28.364 | 1.00 | 43.07 | S |
| ATOM | 203 | N | ILE A | 27 | 92.663 | 42.521 | 26.049 | 1.00 | 46.24 | N |
| ATOM | 204 | CA | ILE A | 27 | 92.807 | 42.573 | 24.608 | 1.00 | 47.19 | C |
| ATOM | 205 | C | ILE A | 27 | 91.403 | 42.280 | 24.110 | 1.00 | 47.45 | C |
| ATOM | 206 | O | ILE A | 27 | 90.651 | 41.553 | 24.763 | 1.00 | 46.02 | O |
| ATOM | 207 | CB | ILE A | 27 | 93.796 | 41.507 | 24.077 | 1.00 | 49.39 | C |
| ATOM | 208 | CG1 | ILE A | 27 | 93.511 | 40.151 | 24.728 | 1.00 | 49.86 | C |
| ATOM | 209 | CG2 | ILE A | 27 | 95.229 | 41.964 | 24.329 | 1.00 | 49.14 | C |
| ATOM | 210 | CD1 | ILE A | 27 | 94.444 | 39.039 | 24.270 | 1.00 | 52.58 | C |
| ATOM | 211 | N | PRO A | 28 | 91.025 | 42.857 | 22.962 | 1.00 | 47.37 | N |
| ATOM | 212 | CA | PRO A | 28 | 89.703 | 42.674 | 22.363 | 1.00 | 47.25 | C |
| ATOM | 213 | C | PRO A | 28 | 89.120 | 41.265 | 22.436 | 1.00 | 47.37 | C |
| ATOM | 214 | O | PRO A | 28 | 87.972 | 41.088 | 22.842 | 1.00 | 46.21 | O |
| ATOM | 215 | CB | PRO A | 28 | 89.919 | 43.146 | 20.929 | 1.00 | 48.82 | C |
| ATOM | 216 | CG | PRO A | 28 | 90.865 | 44.289 | 21.121 | 1.00 | 47.38 | C |
| ATOM | 217 | CD | PRO A | 28 | 91.866 | 43.722 | 22.111 | 1.00 | 48.12 | C |
| ATOM | 218 | N | SER A | 29 | 89.908 | 40.264 | 22.057 | 1.00 | 47.34 | N |
| ATOM | 219 | CA | SER A | 29 | 89.426 | 38.888 | 22.063 | 1.00 | 46.68 | C |
| ATOM | 220 | C | SER A | 29 | 89.015 | 38.355 | 23.435 | 1.00 | 45.41 | C |
| ATOM | 221 | O | SER A | 29 | 88.294 | 37.361 | 23.524 | 1.00 | 45.14 | O |
| ATOM | 222 | CB | SER A | 29 | 90.469 | 37.952 | 21.429 | 1.00 | 48.70 | C |
| ATOM | 223 | OG | SER A | 29 | 91.665 | 37.887 | 22.188 | 1.00 | 51.82 | O |
| ATOM | 224 | N | ASN A | 30 | 89.460 | 38.999 | 24.507 | 1.00 | 43.78 | N |
| ATOM | 225 | CA | ASN A | 30 | 89.079 | 38.528 | 25.832 | 1.00 | 42.85 | C |
| ATOM | 226 | C | ASN A | 30 | 87.923 | 39.330 | 26.427 | 1.00 | 40.38 | C |
| ATOM | 227 | O | ASN A | 30 | 87.454 | 39.033 | 27.528 | 1.00 | 40.36 | O |
| ATOM | 228 | CB | ASN A | 30 | 90.271 | 38.560 | 26.789 | 1.00 | 45.40 | C |
| ATOM | 229 | CG | ASN A | 30 | 91.397 | 37.656 | 26.341 | 1.00 | 48.87 | C |
| ATOM | 230 | OD1 | ASN A | 30 | 91.165 | 36.604 | 25.739 | 1.00 | 50.85 | O |
| ATOM | 231 | ND2 | ASN A | 30 | 92.629 | 38.052 | 26.644 | 1.00 | 50.41 | N |
| ATOM | 232 | N | VAL A | 31 | 87.461 | 40.342 | 25.703 | 1.00 | 35.43 | N |
| ATOM | 233 | CA | VAL A | 31 | 86.355 | 41.153 | 26.196 | 1.00 | 34.43 | C |
| ATOM | 234 | C | VAL A | 31 | 85.030 | 40.405 | 26.046 | 1.00 | 32.47 | C |
| ATOM | 235 | O | VAL A | 31 | 84.719 | 39.858 | 24.990 | 1.00 | 31.37 | O |
| ATOM | 236 | CB | VAL A | 31 | 86.288 | 42.516 | 25.460 | 1.00 | 34.64 | C |
| ATOM | 237 | CG1 | VAL A | 31 | 85.055 | 43.296 | 25.907 | 1.00 | 34.16 | C |
| ATOM | 238 | CG2 | VAL A | 31 | 87.554 | 43.325 | 25.763 | 1.00 | 33.50 | C |
| ATOM | 239 | N | ASN A | 32 | 84.262 | 40.376 | 27.125 | 1.00 | 32.26 | N |
| ATOM | 240 | CA | ASN A | 32 | 82.972 | 39.695 | 27.155 | 1.00 | 31.85 | C |
| ATOM | 241 | C | ASN A | 32 | 81.865 | 40.737 | 27.009 | 1.00 | 31.43 | C |
| ATOM | 242 | O | ASN A | 32 | 81.731 | 41.614 | 27.855 | 1.00 | 31.95 | O |

TABLE 2-continued

| | | | | | | | | | | |
|---|---|---|---|---|---|---|---|---|---|---|
| ATOM | 243 | CB | ASN A | 32 | 82.837 | 38.959 | 28.494 | 1.00 | 33.05 | C |
| ATOM | 244 | CG | ASN A | 32 | 81.543 | 38.173 | 28.618 | 1.00 | 34.40 | C |
| ATOM | 245 | OD1 | ASN A | 32 | 80.616 | 38.330 | 27.826 | 1.00 | 31.77 | O |
| ATOM | 246 | ND2 | ASN A | 32 | 81.476 | 37.325 | 29.641 | 1.00 | 36.34 | N |
| ATOM | 247 | N | LEU A | 33 | 81.070 | 40.638 | 25.944 | 1.00 | 31.73 | N |
| ATOM | 248 | CA | LEU A | 33 | 79.986 | 41.595 | 25.710 | 1.00 | 31.12 | C |
| ATOM | 249 | C | LEU A | 33 | 78.604 | 41.067 | 26.088 | 1.00 | 32.02 | C |
| ATOM | 250 | O | LEU A | 33 | 77.582 | 41.607 | 25.661 | 1.00 | 32.34 | O |
| ATOM | 251 | CB | LEU A | 33 | 79.979 | 42.040 | 24.244 | 1.00 | 32.07 | C |
| ATOM | 252 | CG | LEU A | 33 | 81.202 | 42.819 | 23.763 | 1.00 | 33.24 | C |
| ATOM | 253 | CD1 | LEU A | 33 | 81.030 | 43.165 | 22.300 | 1.00 | 33.95 | C |
| ATOM | 254 | CD2 | LEU A | 33 | 81.380 | 44.091 | 24.601 | 1.00 | 33.50 | C |
| ATOM | 255 | N | SER A | 34 | 78.574 | 40.003 | 26.878 | 1.00 | 31.24 | N |
| ATOM | 256 | CA | SER A | 34 | 77.316 | 39.419 | 27.326 | 1.00 | 31.29 | C |
| ATOM | 257 | C | SER A | 34 | 76.559 | 40.452 | 28.180 | 1.00 | 30.51 | C |
| ATOM | 258 | O | SER A | 34 | 77.172 | 41.284 | 28.850 | 1.00 | 30.18 | O |
| ATOM | 259 | CB | SER A | 34 | 77.613 | 38.154 | 28.136 | 1.00 | 31.20 | C |
| ATOM | 260 | OG | SER A | 34 | 76.447 | 37.653 | 28.758 | 1.00 | 39.13 | O |
| ATOM | 261 | N | THR A | 35 | 75.231 | 40.403 | 28.161 | 1.00 | 29.56 | N |
| ATOM | 262 | CA | THR A | 35 | 74.445 | 41.364 | 28.923 | 1.00 | 26.77 | C |
| ATOM | 263 | C | THR A | 35 | 73.013 | 40.869 | 29.167 | 1.00 | 27.05 | C |
| ATOM | 264 | O | THR A | 35 | 72.435 | 40.168 | 28.336 | 1.00 | 27.90 | O |
| ATOM | 265 | CB | THR A | 35 | 74.416 | 42.737 | 28.181 | 1.00 | 27.30 | C |
| ATOM | 266 | OG1 | THR A | 35 | 74.121 | 43.788 | 29.110 | 1.00 | 25.66 | O |
| ATOM | 267 | CG2 | THR A | 35 | 73.363 | 42.738 | 27.085 | 1.00 | 26.06 | C |
| ATOM | 268 | N | PRO A | 36 | 72.423 | 41.233 | 30.318 | 1.00 | 26.43 | N |
| ATOM | 269 | CA | PRO A | 36 | 71.058 | 40.815 | 30.653 | 1.00 | 26.22 | C |
| ATOM | 270 | C | PRO A | 36 | 69.955 | 41.534 | 29.866 | 1.00 | 27.39 | C |
| ATOM | 271 | O | PRO A | 36 | 70.018 | 42.745 | 29.641 | 1.00 | 26.32 | O |
| ATOM | 272 | CB | PRO A | 36 | 70.971 | 41.094 | 32.153 | 1.00 | 26.70 | C |
| ATOM | 273 | CG | PRO A | 36 | 71.839 | 42.318 | 32.305 | 1.00 | 25.86 | C |
| ATOM | 274 | CD | PRO A | 36 | 73.036 | 41.988 | 31.429 | 1.00 | 24.23 | C |
| ATOM | 275 | N | LEU A | 37 | 68.942 | 40.770 | 29.468 | 1.00 | 27.00 | N |
| ATOM | 276 | CA | LEU A | 37 | 67.815 | 41.295 | 28.716 | 1.00 | 28.26 | C |
| ATOM | 277 | C | LEU A | 37 | 66.590 | 41.525 | 29.600 | 1.00 | 29.30 | C |
| ATOM | 278 | O | LEU A | 37 | 65.852 | 42.489 | 29.396 | 1.00 | 29.95 | O |
| ATOM | 279 | CB | LEU A | 37 | 67.444 | 40.334 | 27.580 | 1.00 | 28.03 | C |
| ATOM | 280 | CG | LEU A | 37 | 66.334 | 40.796 | 26.631 | 1.00 | 27.43 | C |
| ATOM | 281 | CD1 | LEU A | 37 | 66.879 | 41.891 | 25.699 | 1.00 | 26.44 | C |
| ATOM | 282 | CD2 | LEU A | 37 | 65.821 | 39.615 | 25.813 | 1.00 | 27.22 | C |
| ATOM | 283 | N | VAL A | 38 | 66.375 | 40.650 | 30.583 | 1.00 | 28.72 | N |
| ATOM | 284 | CA | VAL A | 38 | 65.214 | 40.768 | 31.464 | 1.00 | 27.01 | C |
| ATOM | 285 | C | VAL A | 38 | 65.588 | 40.778 | 32.944 | 1.00 | 28.83 | C |
| ATOM | 286 | O | VAL A | 38 | 66.633 | 40.263 | 33.340 | 1.00 | 30.63 | O |
| ATOM | 287 | CB | VAL A | 38 | 64.187 | 39.635 | 31.178 | 1.00 | 28.13 | C |
| ATOM | 288 | CG1 | VAL A | 38 | 63.710 | 39.731 | 29.723 | 1.00 | 24.82 | C |
| ATOM | 289 | CG2 | VAL A | 38 | 64.815 | 38.265 | 31.428 | 1.00 | 25.61 | C |
| ATOM | 290 | N | LYS A | 39 | 64.715 | 41.364 | 33.755 | 1.00 | 27.51 | N |
| ATOM | 291 | CA | LYS A | 39 | 64.950 | 41.516 | 35.183 | 1.00 | 29.76 | C |
| ATOM | 292 | C | LYS A | 39 | 65.127 | 40.247 | 36.006 | 1.00 | 30.05 | C |
| ATOM | 293 | O | LYS A | 39 | 64.584 | 39.196 | 35.684 | 1.00 | 30.31 | O |
| ATOM | 294 | CB | LYS A | 39 | 63.830 | 42.350 | 35.812 | 1.00 | 29.02 | C |
| ATOM | 295 | CG | LYS A | 39 | 62.456 | 41.677 | 35.757 | 1.00 | 29.38 | C |
| ATOM | 296 | CD | LYS A | 39 | 61.439 | 42.441 | 36.583 | 1.00 | 30.04 | C |
| ATOM | 297 | CE | LYS A | 39 | 60.065 | 41.781 | 36.528 | 1.00 | 31.85 | C |
| ATOM | 298 | NZ | LYS A | 39 | 59.125 | 42.424 | 37.483 | 1.00 | 31.72 | N |
| ATOM | 299 | N | PHE A | 40 | 65.887 | 40.388 | 37.088 | 1.00 | 30.48 | N |
| ATOM | 300 | CA | PHE A | 40 | 66.172 | 39.309 | 38.019 | 1.00 | 31.44 | C |
| ATOM | 301 | C | PHE A | 40 | 66.417 | 39.922 | 39.392 | 1.00 | 32.56 | C |
| ATOM | 302 | O | PHE A | 40 | 66.522 | 41.143 | 39.518 | 1.00 | 33.92 | O |
| ATOM | 303 | CB | PHE A | 40 | 67.411 | 38.516 | 37.575 | 1.00 | 29.74 | C |
| ATOM | 304 | CG | PHE A | 40 | 68.624 | 39.369 | 37.298 | 1.00 | 28.15 | C |
| ATOM | 305 | CD1 | PHE A | 40 | 68.802 | 39.971 | 36.050 | 1.00 | 28.42 | C |
| ATOM | 306 | CD2 | PHE A | 40 | 69.591 | 39.562 | 38.279 | 1.00 | 27.09 | C |
| ATOM | 307 | CE1 | PHE A | 40 | 69.928 | 40.747 | 35.788 | 1.00 | 26.56 | C |
| ATOM | 308 | CE2 | PHE A | 40 | 70.723 | 40.336 | 38.031 | 1.00 | 26.08 | C |
| ATOM | 309 | CZ | PHE A | 40 | 70.894 | 40.930 | 36.783 | 1.00 | 27.19 | C |
| ATOM | 310 | N | GLN A | 41 | 66.502 | 39.078 | 40.415 | 1.00 | 33.34 | N |
| ATOM | 311 | CA | GLN A | 41 | 66.740 | 39.538 | 41.778 | 1.00 | 35.08 | C |
| ATOM | 312 | C | GLN A | 41 | 68.226 | 39.523 | 42.084 | 1.00 | 32.98 | C |
| ATOM | 313 | O | GLN A | 41 | 68.999 | 38.848 | 41.411 | 1.00 | 32.25 | O |
| ATOM | 314 | CB | GLN A | 41 | 66.039 | 38.624 | 42.797 | 1.00 | 38.64 | C |
| ATOM | 315 | CG | GLN A | 41 | 64.528 | 38.606 | 42.729 | 1.00 | 45.39 | C |
| ATOM | 316 | CD | GLN A | 41 | 63.918 | 39.959 | 43.043 | 1.00 | 48.32 | C |
| ATOM | 317 | OE1 | GLN A | 41 | 64.168 | 40.538 | 44.105 | 1.00 | 51.57 | O |
| ATOM | 318 | NE2 | GLN A | 41 | 63.113 | 40.469 | 42.122 | 1.00 | 49.79 | N |
| ATOM | 319 | N | LYS A | 42 | 68.605 | 40.268 | 43.116 | 1.00 | 32.94 | N |
| ATOM | 320 | CA | LYS A | 42 | 69.985 | 40.341 | 43.580 | 1.00 | 34.24 | C |
| ATOM | 321 | C | LYS A | 42 | 70.530 | 38.925 | 43.835 | 1.00 | 34.61 | C |

TABLE 2-continued

| | | | | | | | | | | |
|---|---|---|---|---|---|---|---|---|---|---|
| ATOM | 322 | O | LYS A | 42 | 69.847 | 38.083 | 44.429 | 1.00 | 32.73 | O |
| ATOM | 323 | CB | LYS A | 42 | 70.031 | 41.148 | 44.874 | 1.00 | 35.33 | C |
| ATOM | 324 | CG | LYS A | 42 | 71.390 | 41.217 | 45.521 | 1.00 | 39.95 | C |
| ATOM | 325 | CD | LYS A | 42 | 71.305 | 41.933 | 46.855 | 1.00 | 42.65 | C |
| ATOM | 326 | CE | LYS A | 42 | 72.661 | 42.007 | 47.524 | 1.00 | 44.06 | C |
| ATOM | 327 | NZ | LYS A | 42 | 72.561 | 42.711 | 48.829 | 1.00 | 48.33 | N |
| ATOM | 328 | N | GLY A | 43 | 71.752 | 38.666 | 43.381 | 1.00 | 34.34 | N |
| ATOM | 329 | CA | GLY A | 43 | 72.348 | 37.355 | 43.572 | 1.00 | 33.96 | C |
| ATOM | 330 | C | GLY A | 43 | 72.056 | 36.394 | 42.438 | 1.00 | 33.07 | C |
| ATOM | 331 | O | GLY A | 43 | 72.717 | 35.365 | 42.301 | 1.00 | 32.56 | O |
| ATOM | 332 | N | GLN A | 44 | 71.066 | 36.726 | 41.618 | 1.00 | 33.56 | N |
| ATOM | 333 | CA | GLN A | 44 | 70.695 | 35.883 | 40.484 | 1.00 | 33.80 | C |
| ATOM | 334 | C | GLN A | 44 | 71.315 | 36.362 | 39.176 | 1.00 | 34.40 | C |
| ATOM | 335 | O | GLN A | 44 | 72.039 | 37.353 | 39.140 | 1.00 | 33.77 | O |
| ATOM | 336 | CB | GLN A | 44 | 69.174 | 35.867 | 40.311 | 1.00 | 35.69 | C |
| ATOM | 337 | CG | GLN A | 44 | 68.406 | 35.347 | 41.507 | 1.00 | 38.03 | C |
| ATOM | 338 | CD | GLN A | 44 | 66.898 | 35.438 | 41.324 | 1.00 | 40.01 | C |
| ATOM | 339 | OE1 | GLN A | 44 | 66.135 | 34.847 | 42.093 | 1.00 | 39.88 | O |
| ATOM | 340 | NE2 | GLN A | 44 | 66.461 | 36.186 | 40.310 | 1.00 | 35.88 | N |
| ATOM | 341 | N | GLN A | 45 | 71.021 | 35.626 | 38.110 | 1.00 | 35.41 | N |
| ATOM | 342 | CA | GLN A | 45 | 71.465 | 35.936 | 36.758 | 1.00 | 36.43 | C |
| ATOM | 343 | C | GLN A | 45 | 70.174 | 36.046 | 35.957 | 1.00 | 34.87 | C |
| ATOM | 344 | O | GLN A | 45 | 69.170 | 35.438 | 36.319 | 1.00 | 33.83 | O |
| ATOM | 345 | CB | GLN A | 45 | 72.312 | 34.800 | 36.170 | 1.00 | 40.80 | C |
| ATOM | 346 | CG | GLN A | 45 | 73.682 | 34.634 | 36.801 | 1.00 | 46.43 | C |
| ATOM | 347 | CD | GLN A | 45 | 74.527 | 35.881 | 36.657 | 1.00 | 50.68 | C |
| ATOM | 348 | OE1 | GLN A | 45 | 74.757 | 36.360 | 35.543 | 1.00 | 54.30 | O |
| ATOM | 349 | NE2 | GLN A | 45 | 74.995 | 36.418 | 37.784 | 1.00 | 50.86 | N |
| ATOM | 350 | N | SER A | 46 | 70.194 | 36.820 | 34.881 | 1.00 | 32.16 | N |
| ATOM | 351 | CA | SER A | 46 | 69.009 | 36.976 | 34.056 | 1.00 | 32.64 | C |
| ATOM | 352 | C | SER A | 46 | 68.721 | 35.690 | 33.289 | 1.00 | 33.23 | C |
| ATOM | 353 | O | SER A | 46 | 69.643 | 35.015 | 32.836 | 1.00 | 32.72 | O |
| ATOM | 354 | CB | SER A | 46 | 69.204 | 38.120 | 33.059 | 1.00 | 30.63 | C |
| ATOM | 355 | OG | SER A | 46 | 68.058 | 38.282 | 32.252 | 1.00 | 30.42 | O |
| ATOM | 356 | N | GLU A | 47 | 67.441 | 35.364 | 33.133 | 1.00 | 33.48 | N |
| ATOM | 357 | CA | GLU A | 47 | 67.047 | 34.167 | 32.399 | 1.00 | 34.97 | C |
| ATOM | 358 | C | GLU A | 47 | 67.453 | 34.269 | 30.936 | 1.00 | 34.59 | C |
| ATOM | 359 | O | GLU A | 47 | 67.588 | 33.261 | 30.251 | 1.00 | 34.40 | O |
| ATOM | 360 | CB | GLU A | 47 | 65.536 | 33.963 | 32.492 | 1.00 | 36.97 | C |
| ATOM | 361 | CG | GLU A | 47 | 65.048 | 33.634 | 33.884 | 1.00 | 40.19 | C |
| ATOM | 362 | CD | GLU A | 47 | 63.541 | 33.663 | 33.982 | 1.00 | 43.59 | C |
| ATOM | 363 | OE1 | GLU A | 47 | 62.884 | 32.836 | 33.313 | 1.00 | 46.14 | O |
| ATOM | 364 | OE2 | GLU A | 47 | 63.010 | 34.519 | 34.726 | 1.00 | 45.57 | O |
| ATOM | 365 | N | ILE A | 48 | 67.633 | 35.494 | 30.452 | 1.00 | 34.08 | N |
| ATOM | 366 | CA | ILE A | 48 | 68.032 | 35.702 | 29.066 | 1.00 | 32.00 | C |
| ATOM | 367 | C | ILE A | 48 | 69.188 | 36.698 | 28.991 | 1.00 | 31.52 | C |
| ATOM | 368 | O | ILE A | 48 | 69.075 | 37.847 | 29.418 | 1.00 | 30.71 | O |
| ATOM | 369 | CB | ILE A | 48 | 66.851 | 36.231 | 28.204 | 1.00 | 32.81 | C |
| ATOM | 370 | CG1 | ILE A | 48 | 65.671 | 35.254 | 28.264 | 1.00 | 33.69 | C |
| ATOM | 371 | CG2 | ILE A | 48 | 67.307 | 36.419 | 26.764 | 1.00 | 32.09 | C |
| ATOM | 372 | CD1 | ILE A | 48 | 64.439 | 35.718 | 27.503 | 1.00 | 34.71 | C |
| ATOM | 373 | N | ASN A | 49 | 70.306 | 36.241 | 28.449 | 1.00 | 30.86 | N |
| ATOM | 374 | CA | ASN A | 49 | 71.483 | 37.076 | 28.308 | 1.00 | 31.23 | C |
| ATOM | 375 | C | ASN A | 49 | 71.892 | 37.131 | 26.851 | 1.00 | 31.45 | C |
| ATOM | 376 | O | ASN A | 49 | 72.070 | 36.095 | 26.214 | 1.00 | 31.67 | O |
| ATOM | 377 | CB | ASN A | 49 | 72.636 | 36.514 | 29.154 | 1.00 | 30.33 | C |
| ATOM | 378 | CG | ASN A | 49 | 72.393 | 36.676 | 30.640 | 1.00 | 31.43 | C |
| ATOM | 379 | OD1 | ASN A | 49 | 72.573 | 37.757 | 31.193 | 1.00 | 28.79 | O |
| ATOM | 380 | ND2 | ASN A | 49 | 71.958 | 35.602 | 31.292 | 1.00 | 32.52 | N |
| ATOM | 381 | N | LEU A | 50 | 72.017 | 38.343 | 26.321 | 1.00 | 30.27 | N |
| ATOM | 382 | CA | LEU A | 50 | 72.440 | 38.523 | 24.937 | 1.00 | 30.28 | C |
| ATOM | 383 | C | LEU A | 50 | 73.947 | 38.255 | 24.904 | 1.00 | 30.37 | C |
| ATOM | 384 | O | LEU A | 50 | 74.624 | 38.437 | 25.916 | 1.00 | 30.24 | O |
| ATOM | 385 | CB | LEU A | 50 | 72.174 | 39.965 | 24.476 | 1.00 | 28.53 | C |
| ATOM | 386 | CG | LEU A | 50 | 70.755 | 40.537 | 24.591 | 1.00 | 30.96 | C |
| ATOM | 387 | CD1 | LEU A | 50 | 70.767 | 42.022 | 24.227 | 1.00 | 30.43 | C |
| ATOM | 388 | CD2 | LEU A | 50 | 69.807 | 39.769 | 23.673 | 1.00 | 30.05 | C |
| ATOM | 389 | N | LYS A | 51 | 74.461 | 37.821 | 23.755 | 1.00 | 30.78 | N |
| ATOM | 390 | CA | LYS A | 51 | 75.896 | 37.572 | 23.590 | 1.00 | 32.78 | C |
| ATOM | 391 | C | LYS A | 51 | 76.563 | 38.904 | 23.231 | 1.00 | 31.15 | C |
| ATOM | 392 | O | LYS A | 51 | 77.740 | 39.120 | 23.516 | 1.00 | 31.86 | O |
| ATOM | 393 | CB | LYS A | 51 | 76.157 | 36.549 | 22.470 | 1.00 | 33.00 | C |
| ATOM | 394 | CG | LYS A | 51 | 76.430 | 35.127 | 22.945 | 1.00 | 37.03 | C |
| ATOM | 395 | CD | LYS A | 51 | 75.265 | 34.540 | 23.694 | 1.00 | 39.28 | C |
| ATOM | 396 | CE | LYS A | 51 | 75.548 | 33.103 | 24.116 | 1.00 | 42.58 | C |
| ATOM | 397 | NZ | LYS A | 51 | 75.773 | 32.190 | 22.957 | 1.00 | 43.64 | N |
| ATOM | 398 | N | ILE A | 52 | 75.802 | 39.777 | 22.571 | 1.00 | 29.58 | N |
| ATOM | 399 | CA | ILE A | 52 | 76.266 | 41.114 | 22.209 | 1.00 | 28.26 | C |
| ATOM | 400 | C | ILE A | 52 | 75.126 | 42.049 | 22.607 | 1.00 | 28.67 | C |

TABLE 2-continued

| | | | | | | | | | | |
|---|---|---|---|---|---|---|---|---|---|---|
| ATOM | 401 | O | ILE A | 52 | 73.954 | 41.700 | 22.476 | 1.00 | 30.64 | O |
| ATOM | 402 | CB | ILE A | 52 | 76.597 | 41.248 | 20.689 | 1.00 | 29.21 | C |
| ATOM | 403 | CG1 | ILE A | 52 | 75.369 | 40.926 | 19.832 | 1.00 | 29.71 | C |
| ATOM | 404 | CG2 | ILE A | 52 | 77.768 | 40.317 | 20.326 | 1.00 | 28.36 | C |
| ATOM | 405 | CD1 | ILE A | 52 | 75.591 | 41.184 | 18.343 | 1.00 | 25.96 | C |
| ATOM | 406 | N | PRO A | 53 | 75.451 | 43.253 | 23.091 | 1.00 | 27.43 | N |
| ATOM | 407 | CA | PRO A | 53 | 74.436 | 44.217 | 23.521 | 1.00 | 27.51 | C |
| ATOM | 408 | C | PRO A | 53 | 73.665 | 44.991 | 22.453 | 1.00 | 28.48 | C |
| ATOM | 409 | O | PRO A | 53 | 73.321 | 46.152 | 22.667 | 1.00 | 28.86 | O |
| ATOM | 410 | CB | PRO A | 53 | 75.231 | 45.140 | 24.431 | 1.00 | 25.91 | C |
| ATOM | 411 | CG | PRO A | 53 | 76.535 | 45.245 | 23.685 | 1.00 | 27.35 | C |
| ATOM | 412 | CD | PRO A | 53 | 76.808 | 43.810 | 23.255 | 1.00 | 27.52 | C |
| ATOM | 413 | N | LEU A | 54 | 73.376 | 44.360 | 21.319 | 1.00 | 27.64 | N |
| ATOM | 414 | CA | LEU A | 54 | 72.639 | 45.048 | 20.266 | 1.00 | 28.10 | C |
| ATOM | 415 | C | LEU A | 54 | 71.310 | 44.369 | 19.933 | 1.00 | 28.75 | C |
| ATOM | 416 | O | LEU A | 54 | 71.233 | 43.142 | 19.847 | 1.00 | 29.19 | O |
| ATOM | 417 | CB | LEU A | 54 | 73.486 | 45.135 | 18.989 | 1.00 | 26.86 | C |
| ATOM | 418 | CG | LEU A | 54 | 74.898 | 45.720 | 19.078 | 1.00 | 27.96 | C |
| ATOM | 419 | CD1 | LEU A | 54 | 75.549 | 45.652 | 17.707 | 1.00 | 25.98 | C |
| ATOM | 420 | CD2 | LEU A | 54 | 74.857 | 47.159 | 19.584 | 1.00 | 28.24 | C |
| ATOM | 421 | N | VAL A | 55 | 70.261 | 45.171 | 19.770 | 1.00 | 27.85 | N |
| ATOM | 422 | CA | VAL A | 55 | 68.957 | 44.649 | 19.388 | 1.00 | 28.01 | C |
| ATOM | 423 | C | VAL A | 55 | 68.426 | 45.554 | 18.276 | 1.00 | 29.53 | C |
| ATOM | 424 | O | VAL A | 55 | 68.649 | 46.768 | 18.299 | 1.00 | 30.35 | O |
| ATOM | 425 | CB | VAL A | 55 | 67.947 | 44.605 | 20.579 | 1.00 | 26.85 | C |
| ATOM | 426 | CG1 | VAL A | 55 | 68.531 | 43.797 | 21.725 | 1.00 | 25.48 | C |
| ATOM | 427 | CG2 | VAL A | 55 | 67.569 | 45.998 | 21.021 | 1.00 | 26.54 | C |
| ATOM | 428 | N | SER A | 56 | 67.765 | 44.961 | 17.284 | 1.00 | 28.53 | N |
| ATOM | 429 | CA | SER A | 56 | 67.224 | 45.735 | 16.174 | 1.00 | 28.75 | C |
| ATOM | 430 | C | SER A | 56 | 65.855 | 46.310 | 16.533 | 1.00 | 27.91 | C |
| ATOM | 431 | O | SER A | 56 | 65.070 | 45.694 | 17.253 | 1.00 | 29.11 | O |
| ATOM | 432 | CB | SER A | 56 | 67.166 | 44.878 | 14.897 | 1.00 | 28.24 | C |
| ATOM | 433 | OG | SER A | 56 | 66.443 | 43.676 | 15.091 | 1.00 | 30.49 | O |
| ATOM | 434 | N | ALA A | 57 | 65.594 | 47.512 | 16.037 | 1.00 | 27.60 | N |
| ATOM | 435 | CA | ALA A | 57 | 64.363 | 48.241 | 16.318 | 1.00 | 27.21 | C |
| ATOM | 436 | C | ALA A | 57 | 63.062 | 47.574 | 15.876 | 1.00 | 29.66 | C |
| ATOM | 437 | O | ALA A | 57 | 63.030 | 46.784 | 14.931 | 1.00 | 29.73 | O |
| ATOM | 438 | CB | ALA A | 57 | 64.460 | 49.640 | 15.721 | 1.00 | 25.06 | C |
| ATOM | 439 | N | ILE A | 58 | 61.990 | 47.911 | 16.581 | 1.00 | 28.79 | N |
| ATOM | 440 | CA | ILE A | 58 | 60.660 | 47.379 | 16.302 | 1.00 | 30.03 | C |
| ATOM | 441 | C | ILE A | 58 | 60.085 | 48.199 | 15.148 | 1.00 | 30.02 | C |
| ATOM | 442 | O | ILE A | 58 | 59.148 | 48.983 | 15.327 | 1.00 | 30.35 | O |
| ATOM | 443 | CB | ILE A | 58 | 59.765 | 47.524 | 17.546 | 1.00 | 28.25 | C |
| ATOM | 444 | CG1 | ILE A | 58 | 60.560 | 47.095 | 18.788 | 1.00 | 27.95 | C |
| ATOM | 445 | CG2 | ILE A | 58 | 58.508 | 46.677 | 17.390 | 1.00 | 27.16 | C |
| ATOM | 446 | CD1 | ILE A | 58 | 59.785 | 47.176 | 20.078 | 1.00 | 28.05 | C |
| ATOM | 447 | N | MET A | 59 | 60.661 | 47.998 | 13.965 | 1.00 | 30.49 | N |
| ATOM | 448 | CA | MET A | 59 | 60.275 | 48.743 | 12.772 | 1.00 | 31.82 | C |
| ATOM | 449 | C | MET A | 59 | 60.088 | 47.877 | 11.530 | 1.00 | 32.36 | C |
| ATOM | 450 | O | MET A | 59 | 60.864 | 46.954 | 11.282 | 1.00 | 31.48 | O |
| ATOM | 451 | CB | MET A | 59 | 61.341 | 49.799 | 12.479 | 1.00 | 30.41 | C |
| ATOM | 452 | CG | MET A | 59 | 61.619 | 50.738 | 13.635 | 1.00 | 28.79 | C |
| ATOM | 453 | SD | MET A | 59 | 62.996 | 51.827 | 13.284 | 1.00 | 31.66 | S |
| ATOM | 454 | CE | MET A | 59 | 62.278 | 52.935 | 12.079 | 1.00 | 26.93 | C |
| ATOM | 455 | N | GLN A | 60 | 59.072 | 48.208 | 10.736 | 1.00 | 34.40 | N |
| ATOM | 456 | CA | GLN A | 60 | 58.772 | 47.459 | 9.512 | 1.00 | 36.49 | C |
| ATOM | 457 | C | GLN A | 60 | 59.974 | 47.433 | 8.582 | 1.00 | 36.55 | C |
| ATOM | 458 | O | GLN A | 60 | 60.208 | 46.447 | 7.885 | 1.00 | 37.12 | O |
| ATOM | 459 | CB | GLN A | 60 | 57.604 | 48.092 | 8.741 | 1.00 | 36.94 | C |
| ATOM | 460 | CG | GLN A | 60 | 56.360 | 48.433 | 9.546 | 1.00 | 37.40 | C |
| ATOM | 461 | CD | GLN A | 60 | 55.273 | 49.031 | 8.666 | 1.00 | 40.00 | C |
| ATOM | 462 | OE1 | GLN A | 60 | 55.562 | 49.808 | 7.753 | 1.00 | 39.70 | O |
| ATOM | 463 | NE2 | GLN A | 60 | 54.018 | 48.677 | 8.936 | 1.00 | 40.59 | N |
| ATOM | 464 | N | SER A | 61 | 60.730 | 48.526 | 8.572 | 1.00 | 36.66 | N |
| ATOM | 465 | CA | SER A | 61 | 61.890 | 48.645 | 7.694 | 1.00 | 36.60 | C |
| ATOM | 466 | C | SER A | 61 | 63.196 | 48.130 | 8.286 | 1.00 | 36.12 | C |
| ATOM | 467 | O | SER A | 61 | 64.274 | 48.388 | 7.738 | 1.00 | 36.48 | O |
| ATOM | 468 | CB | SER A | 61 | 62.073 | 50.105 | 7.280 | 1.00 | 35.62 | C |
| ATOM | 469 | OG | SER A | 61 | 62.314 | 50.921 | 8.414 | 1.00 | 41.10 | O |
| ATOM | 470 | N | VAL A | 62 | 63.111 | 47.393 | 9.386 | 1.00 | 34.72 | N |
| ATOM | 471 | CA | VAL A | 62 | 64.320 | 46.893 | 10.020 | 1.00 | 33.57 | C |
| ATOM | 472 | C | VAL A | 62 | 64.273 | 45.444 | 10.472 | 1.00 | 33.65 | C |
| ATOM | 473 | O | VAL A | 62 | 65.067 | 44.625 | 10.022 | 1.00 | 35.33 | O |
| ATOM | 474 | CB | VAL A | 62 | 64.692 | 47.757 | 11.253 | 1.00 | 32.43 | C |
| ATOM | 475 | CG1 | VAL A | 62 | 65.900 | 47.160 | 11.970 | 1.00 | 32.00 | C |
| ATOM | 476 | CG2 | VAL A | 62 | 64.983 | 49.189 | 10.820 | 1.00 | 32.49 | C |
| ATOM | 477 | N | SER A | 63 | 63.337 | 45.133 | 11.361 | 1.00 | 34.80 | N |
| ATOM | 478 | CA | SER A | 63 | 63.245 | 43.799 | 11.926 | 1.00 | 34.50 | C |
| ATOM | 479 | C | SER A | 63 | 62.258 | 42.804 | 11.322 | 1.00 | 35.59 | C |

TABLE 2-continued

| | | | | | | | | | | |
|---|---|---|---|---|---|---|---|---|---|---|
| ATOM | 480 | O | SER A | 63 | 61.149 | 42.610 | 11.830 | 1.00 | 33.23 | O |
| ATOM | 481 | CB | SER A | 63 | 62.999 | 43.916 | 13.431 | 1.00 | 33.57 | C |
| ATOM | 482 | OG | SER A | 63 | 64.061 | 44.620 | 14.062 | 1.00 | 32.53 | O |
| ATOM | 483 | N | GLY A | 64 | 62.686 | 42.168 | 10.240 | 1.00 | 36.21 | N |
| ATOM | 484 | CA | GLY A | 64 | 61.874 | 41.154 | 9.602 | 1.00 | 37.02 | C |
| ATOM | 485 | C | GLY A | 64 | 62.487 | 39.815 | 9.979 | 1.00 | 39.12 | C |
| ATOM | 486 | O | GLY A | 64 | 63.403 | 39.764 | 10.811 | 1.00 | 36.38 | O |
| ATOM | 487 | N | GLU A | 65 | 62.011 | 38.736 | 9.364 | 1.00 | 39.92 | N |
| ATOM | 488 | CA | GLU A | 65 | 62.522 | 37.405 | 9.665 | 1.00 | 42.75 | C |
| ATOM | 489 | C | GLU A | 65 | 64.015 | 37.240 | 9.395 | 1.00 | 42.41 | C |
| ATOM | 490 | O | GLU A | 65 | 64.731 | 36.649 | 10.201 | 1.00 | 41.59 | O |
| ATOM | 491 | CB | GLU A | 65 | 61.735 | 36.332 | 8.892 | 1.00 | 46.22 | C |
| ATOM | 492 | CG | GLU A | 65 | 61.608 | 36.565 | 7.385 | 1.00 | 51.45 | C |
| ATOM | 493 | CD | GLU A | 65 | 60.419 | 37.448 | 7.007 | 1.00 | 55.41 | C |
| ATOM | 494 | OE1 | GLU A | 65 | 60.438 | 38.668 | 7.305 | 1.00 | 55.84 | O |
| ATOM | 495 | OE2 | GLU A | 65 | 59.456 | 36.915 | 6.405 | 1.00 | 57.74 | O |
| ATOM | 496 | N | LYS A | 66 | 64.485 | 37.764 | 8.268 | 1.00 | 42.65 | N |
| ATOM | 497 | CA | LYS A | 66 | 65.895 | 37.647 | 7.914 | 1.00 | 44.04 | C |
| ATOM | 498 | C | LYS A | 66 | 66.801 | 38.387 | 8.897 | 1.00 | 41.64 | C |
| ATOM | 499 | O | LYS A | 66 | 67.854 | 37.879 | 9.287 | 1.00 | 39.47 | O |
| ATOM | 500 | CB | LYS A | 66 | 66.132 | 38.169 | 6.494 | 1.00 | 46.38 | C |
| ATOM | 501 | CG | LYS A | 66 | 65.289 | 37.488 | 5.415 | 1.00 | 52.36 | C |
| ATOM | 502 | CD | LYS A | 66 | 65.540 | 35.975 | 5.309 | 1.00 | 56.28 | C |
| ATOM | 503 | CE | LYS A | 66 | 64.795 | 35.174 | 6.387 | 1.00 | 58.02 | C |
| ATOM | 504 | NZ | LYS A | 66 | 64.957 | 33.692 | 6.235 | 1.00 | 57.63 | N |
| ATOM | 505 | N | MET A | 67 | 66.393 | 39.588 | 9.289 | 1.00 | 39.83 | N |
| ATOM | 506 | CA | MET A | 67 | 67.168 | 40.376 | 10.237 | 1.00 | 37.79 | C |
| ATOM | 507 | C | MET A | 67 | 67.305 | 39.592 | 11.541 | 1.00 | 37.63 | C |
| ATOM | 508 | O | MET A | 67 | 68.409 | 39.413 | 12.061 | 1.00 | 36.92 | O |
| ATOM | 509 | CB | MET A | 67 | 66.472 | 41.710 | 10.512 | 1.00 | 37.57 | C |
| ATOM | 510 | CG | MET A | 67 | 67.214 | 42.614 | 11.485 | 1.00 | 37.05 | C |
| ATOM | 511 | SD | MET A | 67 | 68.849 | 43.062 | 10.880 | 1.00 | 36.99 | S |
| ATOM | 512 | CE | MET A | 67 | 68.422 | 44.225 | 9.565 | 1.00 | 34.40 | C |
| ATOM | 513 | N | ALA A | 68 | 66.173 | 39.111 | 12.047 | 1.00 | 35.24 | N |
| ATOM | 514 | CA | ALA A | 68 | 66.133 | 38.356 | 13.290 | 1.00 | 35.08 | C |
| ATOM | 515 | C | ALA A | 68 | 67.079 | 37.157 | 13.296 | 1.00 | 35.81 | C |
| ATOM | 516 | O | ALA A | 68 | 67.714 | 36.868 | 14.310 | 1.00 | 34.68 | O |
| ATOM | 517 | CB | ALA A | 68 | 64.707 | 37.901 | 13.571 | 1.00 | 34.00 | C |
| ATOM | 518 | N | ILE A | 69 | 67.169 | 36.460 | 12.167 | 1.00 | 35.92 | N |
| ATOM | 519 | CA | ILE A | 69 | 68.043 | 35.298 | 12.063 | 1.00 | 36.63 | C |
| ATOM | 520 | C | ILE A | 69 | 69.510 | 35.729 | 12.016 | 1.00 | 35.80 | C |
| ATOM | 521 | O | ILE A | 69 | 70.344 | 35.204 | 12.754 | 1.00 | 37.14 | O |
| ATOM | 522 | CB | ILE A | 69 | 67.694 | 34.456 | 10.804 | 1.00 | 38.10 | C |
| ATOM | 523 | CG1 | ILE A | 69 | 66.314 | 33.814 | 10.982 | 1.00 | 39.72 | C |
| ATOM | 524 | CG2 | ILE A | 69 | 68.739 | 33.375 | 10.580 | 1.00 | 37.50 | C |
| ATOM | 525 | CD1 | ILE A | 69 | 65.712 | 33.259 | 9.695 | 1.00 | 40.53 | C |
| ATOM | 526 | N | ALA A | 70 | 69.816 | 36.697 | 11.160 | 1.00 | 34.80 | N |
| ATOM | 527 | CA | ALA A | 70 | 71.179 | 37.194 | 11.027 | 1.00 | 34.57 | C |
| ATOM | 528 | C | ALA A | 70 | 71.727 | 37.773 | 12.332 | 1.00 | 34.76 | C |
| ATOM | 529 | O | ALA A | 70 | 72.897 | 37.563 | 12.665 | 1.00 | 34.89 | O |
| ATOM | 530 | CB | ALA A | 70 | 71.244 | 38.246 | 9.932 | 1.00 | 33.76 | C |
| ATOM | 531 | N | LEU A | 71 | 70.886 | 38.501 | 13.066 | 1.00 | 34.07 | N |
| ATOM | 532 | CA | LEU A | 71 | 71.315 | 39.113 | 14.318 | 1.00 | 32.78 | C |
| ATOM | 533 | C | LEU A | 71 | 71.451 | 38.095 | 15.436 | 1.00 | 33.19 | C |
| ATOM | 534 | O | LEU A | 71 | 72.390 | 38.164 | 16.223 | 1.00 | 32.88 | O |
| ATOM | 535 | CB | LEU A | 71 | 70.348 | 40.223 | 14.737 | 1.00 | 31.82 | C |
| ATOM | 536 | CG | LEU A | 71 | 70.677 | 41.001 | 16.021 | 1.00 | 31.91 | C |
| ATOM | 537 | CD1 | LEU A | 71 | 72.140 | 41.434 | 16.021 | 1.00 | 31.18 | C |
| ATOM | 538 | CD2 | LEU A | 71 | 69.758 | 42.226 | 16.127 | 1.00 | 30.99 | C |
| ATOM | 539 | N | ALA A | 72 | 70.515 | 37.151 | 15.506 | 1.00 | 33.38 | N |
| ATOM | 540 | CA | ALA A | 72 | 70.566 | 36.120 | 16.534 | 1.00 | 34.54 | C |
| ATOM | 541 | C | ALA A | 72 | 71.820 | 35.272 | 16.354 | 1.00 | 36.16 | C |
| ATOM | 542 | O | ALA A | 72 | 72.385 | 34.775 | 17.332 | 1.00 | 35.90 | O |
| ATOM | 543 | CB | ALA A | 72 | 69.318 | 35.234 | 16.468 | 1.00 | 32.94 | C |
| ATOM | 544 | N | ARG A | 73 | 72.242 | 35.103 | 15.102 | 1.00 | 37.20 | N |
| ATOM | 545 | CA | ARG A | 73 | 73.433 | 34.316 | 14.791 | 1.00 | 40.02 | C |
| ATOM | 546 | C | ARG A | 73 | 74.685 | 34.954 | 15.376 | 1.00 | 40.27 | C |
| ATOM | 547 | O | ARG A | 73 | 75.641 | 34.259 | 15.711 | 1.00 | 39.91 | O |
| ATOM | 548 | CB | ARG A | 73 | 73.618 | 34.177 | 13.276 | 1.00 | 42.94 | C |
| ATOM | 549 | CG | ARG A | 73 | 72.702 | 33.172 | 12.595 | 1.00 | 45.30 | C |
| ATOM | 550 | CD | ARG A | 73 | 72.948 | 33.169 | 11.090 | 1.00 | 48.88 | C |
| ATOM | 551 | NE | ARG A | 73 | 72.151 | 32.162 | 10.401 | 1.00 | 53.31 | N |
| ATOM | 552 | CZ | ARG A | 73 | 71.960 | 32.126 | 9.084 | 1.00 | 55.75 | C |
| ATOM | 553 | NH1 | ARG A | 73 | 72.509 | 33.049 | 8.300 | 1.00 | 56.63 | N |
| ATOM | 554 | NH2 | ARG A | 73 | 71.216 | 31.166 | 8.549 | 1.00 | 56.55 | N |
| ATOM | 555 | N | GLU A | 74 | 74.676 | 36.281 | 15.488 | 1.00 | 40.14 | N |
| ATOM | 556 | CA | GLU A | 74 | 75.819 | 37.003 | 16.025 | 1.00 | 38.77 | C |
| ATOM | 557 | C | GLU A | 74 | 75.711 | 37.229 | 17.531 | 1.00 | 36.73 | C |
| ATOM | 558 | O | GLU A | 74 | 76.634 | 37.750 | 18.144 | 1.00 | 37.21 | O |

TABLE 2-continued

| | | | | | | | | | | |
|---|---|---|---|---|---|---|---|---|---|---|
| ATOM | 559 | CB | GLU A | 74 | 75.979 | 38.347 | 15.310 | 1.00 | 40.15 | C |
| ATOM | 560 | CG | GLU A | 74 | 76.113 | 38.239 | 13.796 | 1.00 | 42.93 | C |
| ATOM | 561 | CD | GLU A | 74 | 77.234 | 37.301 | 13.357 | 1.00 | 44.79 | C |
| ATOM | 562 | OE1 | GLU A | 74 | 78.397 | 37.518 | 13.762 | 1.00 | 47.17 | O |
| ATOM | 563 | OE2 | GLU A | 74 | 76.948 | 36.347 | 12.601 | 1.00 | 46.07 | O |
| ATOM | 564 | N | GLY A | 75 | 74.586 | 36.851 | 18.127 | 1.00 | 35.85 | N |
| ATOM | 565 | CA | GLY A | 75 | 74.436 | 37.026 | 19.562 | 1.00 | 35.85 | C |
| ATOM | 566 | C | GLY A | 75 | 73.429 | 38.056 | 20.044 | 1.00 | 35.01 | C |
| ATOM | 567 | O | GLY A | 75 | 73.169 | 38.148 | 21.243 | 1.00 | 34.48 | O |
| ATOM | 568 | N | GLY A | 76 | 72.875 | 38.840 | 19.126 | 1.00 | 34.39 | N |
| ATOM | 569 | CA | GLY A | 76 | 71.887 | 39.834 | 19.513 | 1.00 | 33.62 | C |
| ATOM | 570 | C | GLY A | 76 | 70.483 | 39.299 | 19.281 | 1.00 | 32.89 | C |
| ATOM | 571 | O | GLY A | 76 | 70.315 | 38.101 | 19.025 | 1.00 | 32.03 | O |
| ATOM | 572 | N | ILE A | 77 | 69.475 | 40.165 | 19.374 | 1.00 | 31.21 | N |
| ATOM | 573 | CA | ILE A | 77 | 68.096 | 39.735 | 19.151 | 1.00 | 31.46 | C |
| ATOM | 574 | C | ILE A | 77 | 67.282 | 40.820 | 18.439 | 1.00 | 32.84 | C |
| ATOM | 575 | O | ILE A | 77 | 67.531 | 42.021 | 18.611 | 1.00 | 31.99 | O |
| ATOM | 576 | CB | ILE A | 77 | 67.400 | 39.369 | 20.484 | 1.00 | 30.05 | C |
| ATOM | 577 | CG1 | ILE A | 77 | 66.190 | 38.470 | 20.213 | 1.00 | 29.38 | C |
| ATOM | 578 | CG2 | ILE A | 77 | 66.954 | 40.644 | 21.220 | 1.00 | 27.82 | C |
| ATOM | 579 | CD1 | ILE A | 77 | 65.442 | 38.047 | 21.474 | 1.00 | 26.08 | C |
| ATOM | 580 | N | SER A | 78 | 66.312 | 40.390 | 17.637 | 1.00 | 32.97 | N |
| ATOM | 581 | CA | SER A | 78 | 65.456 | 41.317 | 16.904 | 1.00 | 32.44 | C |
| ATOM | 582 | C | SER A | 78 | 64.049 | 41.320 | 17.472 | 1.00 | 32.06 | C |
| ATOM | 583 | O | SER A | 78 | 63.592 | 40.322 | 18.016 | 1.00 | 34.00 | O |
| ATOM | 584 | CB | SER A | 78 | 65.382 | 40.930 | 15.424 | 1.00 | 30.67 | C |
| ATOM | 585 | OG | SER A | 78 | 66.616 | 41.134 | 14.768 | 1.00 | 30.87 | O |
| ATOM | 586 | N | PHE A | 79 | 63.369 | 42.453 | 17.351 | 1.00 | 32.02 | N |
| ATOM | 587 | CA | PHE A | 79 | 61.998 | 42.562 | 17.816 | 1.00 | 31.78 | C |
| ATOM | 588 | C | PHE A | 79 | 61.105 | 42.740 | 16.596 | 1.00 | 31.81 | C |
| ATOM | 589 | O | PHE A | 79 | 60.896 | 43.854 | 16.130 | 1.00 | 33.21 | O |
| ATOM | 590 | CB | PHE A | 79 | 61.830 | 43.747 | 18.780 | 1.00 | 30.40 | C |
| ATOM | 591 | CG | PHE A | 79 | 62.408 | 43.500 | 20.145 | 1.00 | 29.75 | C |
| ATOM | 592 | CD1 | PHE A | 79 | 63.754 | 43.732 | 20.401 | 1.00 | 31.91 | C |
| ATOM | 593 | CD2 | PHE A | 79 | 61.611 | 42.994 | 21.169 | 1.00 | 30.82 | C |
| ATOM | 594 | CE1 | PHE A | 79 | 64.302 | 43.462 | 21.663 | 1.00 | 32.55 | C |
| ATOM | 595 | CE2 | PHE A | 79 | 62.145 | 42.719 | 22.428 | 1.00 | 29.78 | C |
| ATOM | 596 | CZ | PHE A | 79 | 63.490 | 42.953 | 22.676 | 1.00 | 30.40 | C |
| ATOM | 597 | N | ILE A | 80 | 60.603 | 41.628 | 16.071 | 1.00 | 32.06 | N |
| ATOM | 598 | CA | ILE A | 80 | 59.726 | 41.651 | 14.902 | 1.00 | 32.86 | C |
| ATOM | 599 | C | ILE A | 80 | 58.677 | 42.748 | 15.075 | 1.00 | 32.33 | C |
| ATOM | 600 | O | ILE A | 80 | 57.963 | 42.781 | 16.084 | 1.00 | 32.22 | O |
| ATOM | 601 | CB | ILE A | 80 | 59.015 | 40.282 | 14.717 | 1.00 | 32.80 | C |
| ATOM | 602 | CG1 | ILE A | 80 | 60.056 | 39.175 | 14.529 | 1.00 | 33.69 | C |
| ATOM | 603 | CG2 | ILE A | 80 | 58.082 | 40.329 | 13.508 | 1.00 | 35.09 | C |
| ATOM | 604 | CD1 | ILE A | 80 | 60.974 | 39.387 | 13.347 | 1.00 | 32.85 | C |
| ATOM | 605 | N | PHE A | 81 | 58.581 | 43.643 | 14.095 | 1.00 | 32.37 | N |
| ATOM | 606 | CA | PHE A | 81 | 57.627 | 44.740 | 14.186 | 1.00 | 33.33 | C |
| ATOM | 607 | C | PHE A | 81 | 56.188 | 44.274 | 14.368 | 1.00 | 34.02 | C |
| ATOM | 608 | O | PHE A | 81 | 55.771 | 43.271 | 13.792 | 1.00 | 33.19 | O |
| ATOM | 609 | CB | PHE A | 81 | 57.731 | 45.676 | 12.966 | 1.00 | 33.82 | C |
| ATOM | 610 | CG | PHE A | 81 | 57.438 | 45.016 | 11.643 | 1.00 | 34.92 | C |
| ATOM | 611 | CD1 | PHE A | 81 | 58.376 | 44.191 | 11.033 | 1.00 | 35.21 | C |
| ATOM | 612 | CD2 | PHE A | 81 | 56.224 | 45.241 | 10.995 | 1.00 | 36.11 | C |
| ATOM | 613 | CE1 | PHE A | 81 | 58.113 | 43.600 | 9.791 | 1.00 | 34.85 | C |
| ATOM | 614 | CE2 | PHE A | 81 | 55.947 | 44.658 | 9.756 | 1.00 | 36.53 | C |
| ATOM | 615 | CZ | PHE A | 81 | 56.895 | 43.836 | 9.153 | 1.00 | 36.94 | C |
| ATOM | 616 | N | GLY A | 82 | 55.441 | 45.014 | 15.184 | 1.00 | 33.59 | N |
| ATOM | 617 | CA | GLY A | 82 | 54.055 | 44.675 | 15.439 | 1.00 | 34.64 | C |
| ATOM | 618 | C | GLY A | 82 | 53.078 | 45.472 | 14.596 | 1.00 | 35.83 | C |
| ATOM | 619 | O | GLY A | 82 | 51.870 | 45.283 | 14.708 | 1.00 | 36.22 | O |
| ATOM | 620 | N | SER A | 83 | 53.594 | 46.363 | 13.753 | 1.00 | 35.37 | N |
| ATOM | 621 | CA | SER A | 83 | 52.744 | 47.173 | 12.886 | 1.00 | 35.72 | C |
| ATOM | 622 | C | SER A | 83 | 52.379 | 46.393 | 11.618 | 1.00 | 36.39 | C |
| ATOM | 623 | O | SER A | 83 | 52.701 | 46.791 | 10.496 | 1.00 | 35.68 | O |
| ATOM | 624 | CB | SER A | 83 | 53.456 | 48.476 | 12.522 | 1.00 | 34.36 | C |
| ATOM | 625 | OG | SER A | 83 | 54.710 | 48.208 | 11.928 | 1.00 | 35.50 | O |
| ATOM | 626 | N | GLN A | 84 | 51.714 | 45.264 | 11.826 | 1.00 | 37.28 | N |
| ATOM | 627 | CA | GLN A | 84 | 51.270 | 44.387 | 10.753 | 1.00 | 38.09 | C |
| ATOM | 628 | C | GLN A | 84 | 50.229 | 43.474 | 11.394 | 1.00 | 38.74 | C |
| ATOM | 629 | O | GLN A | 84 | 50.021 | 43.542 | 12.604 | 1.00 | 37.63 | O |
| ATOM | 630 | CB | GLN A | 84 | 52.445 | 43.569 | 10.214 | 1.00 | 39.17 | C |
| ATOM | 631 | CG | GLN A | 84 | 53.074 | 42.636 | 11.235 | 1.00 | 40.30 | C |
| ATOM | 632 | CD | GLN A | 84 | 54.255 | 41.877 | 10.668 | 1.00 | 43.44 | C |
| ATOM | 633 | OE1 | GLN A | 84 | 54.155 | 41.259 | 9.607 | 1.00 | 45.87 | O |
| ATOM | 634 | NE2 | GLN A | 84 | 55.383 | 41.912 | 11.375 | 1.00 | 43.38 | N |
| ATOM | 635 | N | SER A | 85 | 49.577 | 42.626 | 10.605 | 1.00 | 39.77 | N |
| ATOM | 636 | CA | SER A | 85 | 48.556 | 41.739 | 11.163 | 1.00 | 40.71 | C |
| ATOM | 637 | C | SER A | 85 | 49.138 | 40.766 | 12.182 | 1.00 | 41.13 | C |

TABLE 2-continued

| | | | | | | | | | | |
|---|---|---|---|---|---|---|---|---|---|---|
| ATOM | 638 | O | SER A | 85 | 50.301 | 40.373 | 12.088 | 1.00 | 41.44 | O |
| ATOM | 639 | CB | SER A | 85 | 47.868 | 40.938 | 10.055 | 1.00 | 40.69 | C |
| ATOM | 640 | OG | SER A | 85 | 48.608 | 39.771 | 9.743 | 1.00 | 41.94 | O |
| ATOM | 641 | N | ILE A | 86 | 48.314 | 40.377 | 13.150 | 1.00 | 41.34 | N |
| ATOM | 642 | CA | ILE A | 86 | 48.721 | 39.437 | 14.187 | 1.00 | 43.32 | C |
| ATOM | 643 | C | ILE A | 86 | 49.213 | 38.134 | 13.552 | 1.00 | 45.69 | C |
| ATOM | 644 | O | ILE A | 86 | 50.207 | 37.550 | 13.992 | 1.00 | 45.58 | O |
| ATOM | 645 | CB | ILE A | 86 | 47.540 | 39.117 | 15.132 | 1.00 | 42.04 | C |
| ATOM | 646 | CG1 | ILE A | 86 | 47.139 | 40.379 | 15.904 | 1.00 | 42.78 | C |
| ATOM | 647 | CG2 | ILE A | 86 | 47.913 | 37.986 | 16.075 | 1.00 | 40.93 | C |
| ATOM | 648 | CD1 | ILE A | 86 | 45.948 | 40.191 | 16.833 | 1.00 | 40.98 | C |
| ATOM | 649 | N | GLU A | 87 | 48.511 | 37.690 | 12.513 | 1.00 | 46.91 | N |
| ATOM | 650 | CA | GLU A | 87 | 48.860 | 36.460 | 11.809 | 1.00 | 48.52 | C |
| ATOM | 651 | C | GLU A | 87 | 50.201 | 36.612 | 11.104 | 1.00 | 46.94 | C |
| ATOM | 652 | O | GLU A | 87 | 51.025 | 35.700 | 11.098 | 1.00 | 47.16 | O |
| ATOM | 653 | CB | GLU A | 87 | 47.784 | 36.117 | 10.767 | 1.00 | 50.61 | C |
| ATOM | 654 | CG | GLU A | 87 | 46.364 | 35.944 | 11.318 | 1.00 | 54.49 | C |
| ATOM | 655 | CD | GLU A | 87 | 45.799 | 37.214 | 11.955 | 1.00 | 57.21 | C |
| ATOM | 656 | OE1 | GLU A | 87 | 45.896 | 38.300 | 11.337 | 1.00 | 57.37 | O |
| ATOM | 657 | OE2 | GLU A | 87 | 45.241 | 37.121 | 13.074 | 1.00 | 59.49 | O |
| ATOM | 658 | N | SER A | 88 | 50.408 | 37.778 | 10.508 | 1.00 | 46.26 | N |
| ATOM | 659 | CA | SER A | 88 | 51.637 | 38.064 | 9.778 | 1.00 | 45.86 | C |
| ATOM | 660 | C | SER A | 88 | 52.865 | 38.124 | 10.692 | 1.00 | 44.29 | C |
| ATOM | 661 | O | SER A | 88 | 53.921 | 37.584 | 10.363 | 1.00 | 43.79 | O |
| ATOM | 662 | CB | SER A | 88 | 51.480 | 39.384 | 9.024 | 1.00 | 46.24 | C |
| ATOM | 663 | OG | SER A | 88 | 52.551 | 39.587 | 8.126 | 1.00 | 50.64 | O |
| ATOM | 664 | N | GLN A | 89 | 52.725 | 38.781 | 11.838 | 1.00 | 42.05 | N |
| ATOM | 665 | CA | GLN A | 89 | 53.831 | 38.902 | 12.784 | 1.00 | 41.12 | C |
| ATOM | 666 | C | GLN A | 89 | 54.164 | 37.534 | 13.378 | 1.00 | 40.97 | C |
| ATOM | 667 | O | GLN A | 89 | 55.331 | 37.147 | 13.464 | 1.00 | 41.60 | O |
| ATOM | 668 | CB | GLN A | 89 | 53.474 | 39.895 | 13.904 | 1.00 | 37.36 | C |
| ATOM | 669 | CG | GLN A | 89 | 54.563 | 40.076 | 14.967 | 1.00 | 34.71 | C |
| ATOM | 670 | CD | GLN A | 89 | 54.182 | 41.087 | 16.042 | 1.00 | 32.75 | C |
| ATOM | 671 | OE1 | GLN A | 89 | 53.004 | 41.260 | 16.354 | 1.00 | 29.71 | O |
| ATOM | 672 | NE2 | GLN A | 89 | 55.183 | 41.740 | 16.630 | 1.00 | 30.65 | N |
| ATOM | 673 | N | ALA A | 90 | 53.132 | 36.798 | 13.778 | 1.00 | 41.05 | N |
| ATOM | 674 | CA | ALA A | 90 | 53.326 | 35.478 | 14.363 | 1.00 | 40.85 | C |
| ATOM | 675 | C | ALA A | 90 | 54.027 | 34.536 | 13.386 | 1.00 | 40.83 | C |
| ATOM | 676 | O | ALA A | 90 | 54.828 | 33.697 | 13.790 | 1.00 | 42.16 | O |
| ATOM | 677 | CB | ALA A | 90 | 51.988 | 34.896 | 14.790 | 1.00 | 40.56 | C |
| ATOM | 678 | N | ALA A | 91 | 53.733 | 34.676 | 12.099 | 1.00 | 40.30 | N |
| ATOM | 679 | CA | ALA A | 91 | 54.364 | 33.822 | 11.106 | 1.00 | 41.24 | C |
| ATOM | 680 | C | ALA A | 91 | 55.873 | 34.065 | 11.106 | 1.00 | 41.52 | C |
| ATOM | 681 | O | ALA A | 91 | 56.661 | 33.124 | 11.032 | 1.00 | 42.19 | O |
| ATOM | 682 | CB | ALA A | 91 | 53.776 | 34.092 | 9.714 | 1.00 | 38.85 | C |
| ATOM | 683 | N | MET A | 92 | 56.278 | 35.327 | 11.192 | 1.00 | 41.97 | N |
| ATOM | 684 | CA | MET A | 92 | 57.702 | 35.651 | 11.208 | 1.00 | 42.09 | C |
| ATOM | 685 | C | MET A | 92 | 58.386 | 35.064 | 12.438 | 1.00 | 41.02 | C |
| ATOM | 686 | O | MET A | 92 | 59.513 | 34.579 | 12.360 | 1.00 | 40.61 | O |
| ATOM | 687 | CB | MET A | 92 | 57.910 | 37.165 | 11.181 | 1.00 | 42.37 | C |
| ATOM | 688 | CG | MET A | 92 | 57.542 | 37.806 | 9.867 | 1.00 | 41.26 | C |
| ATOM | 689 | SD | MET A | 92 | 57.939 | 39.549 | 9.851 | 1.00 | 41.37 | S |
| ATOM | 690 | CE | MET A | 92 | 56.946 | 40.100 | 8.458 | 1.00 | 41.08 | C |
| ATOM | 691 | N | VAL A | 93 | 57.702 | 35.116 | 13.574 | 1.00 | 41.53 | N |
| ATOM | 692 | CA | VAL A | 93 | 58.256 | 34.578 | 14.808 | 1.00 | 41.04 | C |
| ATOM | 693 | C | VAL A | 93 | 58.434 | 33.077 | 14.645 | 1.00 | 42.35 | C |
| ATOM | 694 | O | VAL A | 93 | 59.480 | 32.524 | 14.979 | 1.00 | 42.28 | O |
| ATOM | 695 | CB | VAL A | 93 | 57.325 | 34.857 | 16.004 | 1.00 | 41.44 | C |
| ATOM | 696 | CG1 | VAL A | 93 | 57.777 | 34.058 | 17.222 | 1.00 | 39.20 | C |
| ATOM | 697 | CG2 | VAL A | 93 | 57.324 | 36.350 | 16.315 | 1.00 | 39.63 | C |
| ATOM | 698 | N | HIS A | 94 | 57.401 | 32.426 | 14.119 | 1.00 | 43.29 | N |
| ATOM | 699 | CA | HIS A | 94 | 57.421 | 30.984 | 13.898 | 1.00 | 43.16 | C |
| ATOM | 700 | C | HIS A | 94 | 58.579 | 30.600 | 12.982 | 1.00 | 42.12 | C |
| ATOM | 701 | O | HIS A | 94 | 59.320 | 29.657 | 13.261 | 1.00 | 41.10 | O |
| ATOM | 702 | CB | HIS A | 94 | 56.100 | 30.538 | 13.263 | 1.00 | 45.51 | C |
| ATOM | 703 | CG | HIS A | 94 | 55.983 | 29.056 | 13.087 | 1.00 | 46.61 | C |
| ATOM | 704 | ND1 | HIS A | 94 | 55.628 | 28.210 | 14.116 | 1.00 | 46.66 | N |
| ATOM | 705 | CD2 | HIS A | 94 | 56.193 | 28.268 | 12.006 | 1.00 | 46.86 | C |
| ATOM | 706 | CE1 | HIS A | 94 | 55.624 | 26.965 | 13.677 | 1.00 | 46.63 | C |
| ATOM | 707 | NE2 | HIS A | 94 | 55.964 | 26.972 | 12.400 | 1.00 | 47.89 | N |
| ATOM | 708 | N | ALA A | 95 | 58.727 | 31.339 | 11.888 | 1.00 | 41.47 | N |
| ATOM | 709 | CA | ALA A | 95 | 59.788 | 31.080 | 10.921 | 1.00 | 41.48 | C |
| ATOM | 710 | C | ALA A | 95 | 61.168 | 31.132 | 11.567 | 1.00 | 42.50 | C |
| ATOM | 711 | O | ALA A | 95 | 62.017 | 30.282 | 11.306 | 1.00 | 42.88 | O |
| ATOM | 712 | CB | ALA A | 95 | 59.712 | 32.088 | 9.783 | 1.00 | 40.24 | C |
| ATOM | 713 | N | VAL A | 96 | 61.394 | 32.138 | 12.407 | 1.00 | 42.32 | N |
| ATOM | 714 | CA | VAL A | 96 | 62.680 | 32.289 | 13.074 | 1.00 | 40.88 | C |
| ATOM | 715 | C | VAL A | 96 | 62.923 | 31.140 | 14.049 | 1.00 | 41.55 | C |
| ATOM | 716 | O | VAL A | 96 | 64.011 | 30.566 | 14.086 | 1.00 | 41.75 | O |

TABLE 2-continued

| | | | | | | | | | | |
|---|---|---|---|---|---|---|---|---|---|---|
| ATOM | 717 | CB | VAL A | 96 | 62.755 | 33.635 | 13.837 | 1.00 | 40.31 | C |
| ATOM | 718 | CG1 | VAL A | 96 | 64.044 | 33.719 | 14.643 | 1.00 | 38.83 | C |
| ATOM | 719 | CG2 | VAL A | 96 | 62.684 | 34.787 | 12.849 | 1.00 | 40.30 | C |
| ATOM | 720 | N | LYS A | 97 | 61.897 | 30.802 | 14.823 | 1.00 | 42.33 | N |
| ATOM | 721 | CA | LYS A | 97 | 61.989 | 29.735 | 15.810 | 1.00 | 44.12 | C |
| ATOM | 722 | C | LYS A | 97 | 62.197 | 28.349 | 15.206 | 1.00 | 46.23 | C |
| ATOM | 723 | O | LYS A | 97 | 62.787 | 27.475 | 15.843 | 1.00 | 46.86 | O |
| ATOM | 724 | CB | LYS A | 97 | 60.730 | 29.718 | 16.686 | 1.00 | 43.33 | C |
| ATOM | 725 | CG | LYS A | 97 | 60.484 | 31.004 | 17.471 | 1.00 | 42.58 | C |
| ATOM | 726 | CD | LYS A | 97 | 61.669 | 31.349 | 18.374 | 1.00 | 40.95 | C |
| ATOM | 727 | CE | LYS A | 97 | 61.894 | 30.305 | 19.461 | 1.00 | 39.70 | C |
| ATOM | 728 | NZ | LYS A | 97 | 63.158 | 30.559 | 20.212 | 1.00 | 38.22 | N |
| ATOM | 729 | N | ASN A | 98 | 61.713 | 28.143 | 13.985 | 1.00 | 48.10 | N |
| ATOM | 730 | CA | ASN A | 98 | 61.844 | 26.842 | 13.338 | 1.00 | 51.26 | C |
| ATOM | 731 | C | ASN A | 98 | 62.675 | 26.897 | 12.062 | 1.00 | 52.29 | C |
| ATOM | 732 | O | ASN A | 98 | 62.383 | 26.192 | 11.096 | 1.00 | 53.51 | O |
| ATOM | 733 | CB | ASN A | 98 | 60.456 | 26.274 | 13.023 | 1.00 | 52.57 | C |
| ATOM | 734 | CG | ASN A | 98 | 59.599 | 26.102 | 14.264 | 1.00 | 54.13 | C |
| ATOM | 735 | OD1 | ASN A | 98 | 59.898 | 25.286 | 15.139 | 1.00 | 56.37 | O |
| ATOM | 736 | ND2 | ASN A | 98 | 58.527 | 26.876 | 14.349 | 1.00 | 55.61 | N |
| ATOM | 737 | N | PHE A | 99 | 63.713 | 27.728 | 12.063 | 1.00 | 53.22 | N |
| ATOM | 738 | CA | PHE A | 99 | 64.579 | 27.872 | 10.897 | 1.00 | 54.26 | C |
| ATOM | 739 | C | PHE A | 99 | 65.526 | 26.686 | 10.731 | 1.00 | 54.80 | C |
| ATOM | 740 | O | PHE A | 99 | 65.886 | 26.332 | 9.611 | 1.00 | 54.79 | O |
| ATOM | 741 | CB | PHE A | 99 | 65.398 | 29.160 | 11.005 | 1.00 | 53.75 | C |
| ATOM | 742 | CG | PHE A | 99 | 66.234 | 29.457 | 9.786 | 1.00 | 54.18 | C |
| ATOM | 743 | CD1 | PHE A | 99 | 65.633 | 29.777 | 8.573 | 1.00 | 53.83 | C |
| ATOM | 744 | CD2 | PHE A | 99 | 67.624 | 29.437 | 9.858 | 1.00 | 53.66 | C |
| ATOM | 745 | CE1 | PHE A | 99 | 66.404 | 30.075 | 7.447 | 1.00 | 53.53 | C |
| ATOM | 746 | CE2 | PHE A | 99 | 68.403 | 29.732 | 8.743 | 1.00 | 53.55 | C |
| ATOM | 747 | CZ | PHE A | 99 | 67.792 | 30.052 | 7.534 | 1.00 | 53.92 | C |
| ATOM | 748 | N | LYS A | 100 | 65.927 | 26.078 | 11.845 | 1.00 | 55.84 | N |
| ATOM | 749 | CA | LYS A | 100 | 66.848 | 24.940 | 11.809 | 1.00 | 57.08 | C |
| ATOM | 750 | C | LYS A | 100 | 66.159 | 23.588 | 11.633 | 1.00 | 58.33 | C |
| ATOM | 751 | O | LYS A | 100 | 66.811 | 22.546 | 11.722 | 1.00 | 58.42 | O |
| ATOM | 752 | CB | LYS A | 100 | 67.691 | 24.893 | 13.086 | 1.00 | 55.72 | C |
| ATOM | 753 | CG | LYS A | 100 | 68.611 | 26.083 | 13.298 | 1.00 | 55.04 | C |
| ATOM | 754 | CD | LYS A | 100 | 69.353 | 25.929 | 14.616 | 1.00 | 53.54 | C |
| ATOM | 755 | CE | LYS A | 100 | 70.352 | 27.045 | 14.855 | 1.00 | 51.61 | C |
| ATOM | 756 | NZ | LYS A | 100 | 71.015 | 26.867 | 16.172 | 1.00 | 50.36 | N |
| ATOM | 757 | N | ALA A | 101 | 64.850 | 23.601 | 11.395 | 1.00 | 59.54 | N |
| ATOM | 758 | CA | ALA A | 101 | 64.095 | 22.363 | 11.213 | 1.00 | 60.39 | C |
| ATOM | 759 | C | ALA A | 101 | 64.471 | 21.672 | 9.904 | 1.00 | 60.69 | C |
| ATOM | 760 | O | ALA A | 101 | 65.016 | 22.298 | 8.995 | 1.00 | 60.89 | O |
| ATOM | 761 | CB | ALA A | 101 | 62.596 | 22.652 | 11.237 | 1.00 | 60.64 | C |
| ATOM | 762 | N | HIS A | 222 | 79.198 | 30.290 | 16.950 | 1.00 | 63.01 | N |
| ATOM | 763 | CA | HIS A | 222 | 79.815 | 30.312 | 18.273 | 1.00 | 62.71 | C |
| ATOM | 764 | C | HIS A | 222 | 79.103 | 31.282 | 19.214 | 1.00 | 60.87 | C |
| ATOM | 765 | O | HIS A | 222 | 78.923 | 30.994 | 20.399 | 1.00 | 60.68 | O |
| ATOM | 766 | CB | HIS A | 222 | 81.296 | 30.695 | 18.167 | 1.00 | 65.58 | C |
| ATOM | 767 | CG | HIS A | 222 | 82.137 | 29.677 | 17.460 | 1.00 | 69.22 | C |
| ATOM | 768 | ND1 | HIS A | 222 | 82.251 | 28.373 | 17.896 | 1.00 | 70.94 | N |
| ATOM | 769 | CD2 | HIS A | 222 | 82.903 | 29.769 | 16.346 | 1.00 | 70.61 | C |
| ATOM | 770 | CE1 | HIS A | 222 | 83.049 | 27.706 | 17.080 | 1.00 | 71.60 | C |
| ATOM | 771 | NE2 | HIS A | 222 | 83.458 | 28.530 | 16.131 | 1.00 | 71.43 | N |
| ATOM | 772 | N | ASN A | 223 | 78.698 | 32.432 | 18.686 | 1.00 | 57.42 | N |
| ATOM | 773 | CA | ASN A | 223 | 78.012 | 33.422 | 19.503 | 1.00 | 55.31 | C |
| ATOM | 774 | C | ASN A | 223 | 76.518 | 33.511 | 19.219 | 1.00 | 52.14 | C |
| ATOM | 775 | O | ASN A | 223 | 75.888 | 34.525 | 19.520 | 1.00 | 49.94 | O |
| ATOM | 776 | CB | ASN A | 223 | 78.657 | 34.797 | 19.317 | 1.00 | 57.68 | C |
| ATOM | 777 | CG | ASN A | 223 | 79.984 | 34.925 | 20.050 | 1.00 | 60.74 | C |
| ATOM | 778 | OD1 | ASN A | 223 | 80.713 | 35.904 | 19.870 | 1.00 | 64.29 | O |
| ATOM | 779 | ND2 | ASN A | 223 | 80.299 | 33.942 | 20.890 | 1.00 | 61.50 | N |
| ATOM | 780 | N | GLU A | 224 | 75.948 | 32.453 | 18.648 | 1.00 | 48.44 | N |
| ATOM | 781 | CA | GLU A | 224 | 74.520 | 32.462 | 18.351 | 1.00 | 46.42 | C |
| ATOM | 782 | C | GLU A | 224 | 73.699 | 32.516 | 19.631 | 1.00 | 43.23 | C |
| ATOM | 783 | O | GLU A | 224 | 74.041 | 31.889 | 20.631 | 1.00 | 42.87 | O |
| ATOM | 784 | CB | GLU A | 224 | 74.109 | 31.226 | 17.538 | 1.00 | 47.17 | C |
| ATOM | 785 | CG | GLU A | 224 | 74.383 | 29.892 | 18.217 | 1.00 | 49.19 | C |
| ATOM | 786 | CD | GLU A | 224 | 73.622 | 28.735 | 17.581 | 1.00 | 50.18 | C |
| ATOM | 787 | OE1 | GLU A | 224 | 73.410 | 28.755 | 16.346 | 1.00 | 51.65 | O |
| ATOM | 788 | OE2 | GLU A | 224 | 73.246 | 27.799 | 18.318 | 1.00 | 49.83 | O |
| ATOM | 789 | N | LEU A | 225 | 72.615 | 33.279 | 19.590 | 1.00 | 40.90 | N |
| ATOM | 790 | CA | LEU A | 225 | 71.733 | 33.410 | 20.734 | 1.00 | 38.88 | C |
| ATOM | 791 | C | LEU A | 225 | 70.565 | 32.457 | 20.516 | 1.00 | 38.25 | C |
| ATOM | 792 | O | LEU A | 225 | 69.747 | 32.664 | 19.621 | 1.00 | 36.15 | O |
| ATOM | 793 | CB | LEU A | 225 | 71.232 | 34.851 | 20.848 | 1.00 | 37.76 | C |
| ATOM | 794 | CG | LEU A | 225 | 70.380 | 35.166 | 22.077 | 1.00 | 37.49 | C |
| ATOM | 795 | CD1 | LEU A | 225 | 71.196 | 34.932 | 23.340 | 1.00 | 37.19 | C |

TABLE 2-continued

| ATOM | 796 | CD2 | LEU A | 225 | 69.898 | 36.602 | 22.007 | 1.00 | 36.97 | C |
|---|---|---|---|---|---|---|---|---|---|---|
| ATOM | 797 | N | VAL A | 226 | 70.492 | 31.416 | 21.341 | 1.00 | 38.35 | N |
| ATOM | 798 | CA | VAL A | 226 | 69.435 | 30.415 | 21.215 | 1.00 | 39.11 | C |
| ATOM | 799 | C | VAL A | 226 | 68.830 | 29.993 | 22.551 | 1.00 | 40.13 | C |
| ATOM | 800 | O | VAL A | 226 | 69.337 | 30.345 | 23.617 | 1.00 | 40.81 | O |
| ATOM | 801 | CB | VAL A | 226 | 69.969 | 29.133 | 20.533 | 1.00 | 38.58 | C |
| ATOM | 802 | CG1 | VAL A | 226 | 70.373 | 29.420 | 19.094 | 1.00 | 35.25 | C |
| ATOM | 803 | CG2 | VAL A | 226 | 71.154 | 28.595 | 21.326 | 1.00 | 38.53 | C |
| ATOM | 804 | N | ASP A | 227 | 67.737 | 29.237 | 22.475 | 1.00 | 40.83 | N |
| ATOM | 805 | CA | ASP A | 227 | 67.067 | 28.728 | 23.661 | 1.00 | 41.94 | C |
| ATOM | 806 | C | ASP A | 227 | 67.601 | 27.323 | 23.970 | 1.00 | 43.67 | C |
| ATOM | 807 | O | ASP A | 227 | 68.501 | 26.828 | 23.288 | 1.00 | 43.28 | O |
| ATOM | 808 | CB | ASP A | 227 | 65.545 | 28.679 | 23.452 | 1.00 | 42.33 | C |
| ATOM | 809 | CG | ASP A | 227 | 65.139 | 27.889 | 22.210 | 1.00 | 42.71 | C |
| ATOM | 810 | OD1 | ASP A | 227 | 65.753 | 26.838 | 21.924 | 1.00 | 43.47 | O |
| ATOM | 811 | OD2 | ASP A | 227 | 64.185 | 28.314 | 21.525 | 1.00 | 40.79 | O |
| ATOM | 812 | N | SER A | 228 | 67.036 | 26.681 | 24.990 | 1.00 | 46.46 | N |
| ATOM | 813 | CA | SER A | 228 | 67.467 | 25.342 | 25.395 | 1.00 | 48.86 | C |
| ATOM | 814 | C | SER A | 228 | 67.336 | 24.291 | 24.287 | 1.00 | 50.18 | C |
| ATOM | 815 | O | SER A | 228 | 67.953 | 23.226 | 24.358 | 1.00 | 50.85 | O |
| ATOM | 816 | CB | SER A | 228 | 66.682 | 24.891 | 26.631 | 1.00 | 48.09 | C |
| ATOM | 817 | OG | SER A | 228 | 65.289 | 24.897 | 26.378 | 1.00 | 49.20 | O |
| ATOM | 818 | N | GLN A | 229 | 66.537 | 24.596 | 23.268 | 1.00 | 50.81 | N |
| ATOM | 819 | CA | GLN A | 229 | 66.331 | 23.685 | 22.148 | 1.00 | 51.37 | C |
| ATOM | 820 | C | GLN A | 229 | 67.229 | 24.081 | 20.984 | 1.00 | 50.93 | C |
| ATOM | 821 | O | GLN A | 229 | 67.103 | 23.548 | 19.878 | 1.00 | 49.76 | O |
| ATOM | 822 | CB | GLN A | 229 | 64.865 | 23.723 | 21.699 | 1.00 | 53.18 | C |
| ATOM | 823 | CG | GLN A | 229 | 63.873 | 23.346 | 22.784 | 1.00 | 55.38 | C |
| ATOM | 824 | CD | GLN A | 229 | 62.434 | 23.565 | 22.353 | 1.00 | 58.59 | C |
| ATOM | 825 | OE1 | GLN A | 229 | 61.971 | 22.979 | 21.369 | 1.00 | 60.22 | O |
| ATOM | 826 | NE2 | GLN A | 229 | 61.716 | 24.413 | 23.087 | 1.00 | 58.58 | N |
| ATOM | 827 | N | LYS A | 230 | 68.131 | 25.026 | 21.242 | 1.00 | 50.37 | N |
| ATOM | 828 | CA | LYS A | 230 | 69.065 | 25.515 | 20.231 | 1.00 | 48.94 | C |
| ATOM | 829 | C | LYS A | 230 | 68.407 | 26.325 | 19.116 | 1.00 | 46.73 | C |
| ATOM | 830 | O | LYS A | 230 | 68.991 | 26.513 | 18.048 | 1.00 | 47.20 | O |
| ATOM | 831 | CB | LYS A | 230 | 69.856 | 24.349 | 19.626 | 1.00 | 51.73 | C |
| ATOM | 832 | CG | LYS A | 230 | 70.992 | 23.825 | 20.507 | 1.00 | 54.62 | C |
| ATOM | 833 | CD | LYS A | 230 | 72.073 | 24.889 | 20.705 | 1.00 | 57.67 | C |
| ATOM | 834 | CE | LYS A | 230 | 73.357 | 24.307 | 21.302 | 1.00 | 59.53 | C |
| ATOM | 835 | NZ | LYS A | 230 | 73.161 | 23.692 | 22.653 | 1.00 | 59.91 | N |
| ATOM | 836 | N | ARG A | 231 | 67.195 | 26.811 | 19.362 | 1.00 | 45.43 | N |
| ATOM | 837 | CA | ARG A | 231 | 66.494 | 27.621 | 18.368 | 1.00 | 43.78 | C |
| ATOM | 838 | C | ARG A | 231 | 66.851 | 29.087 | 18.595 | 1.00 | 41.98 | C |
| ATOM | 839 | O | ARG A | 231 | 67.013 | 29.524 | 19.735 | 1.00 | 40.65 | O |
| ATOM | 840 | CB | ARG A | 231 | 64.979 | 27.445 | 18.495 | 1.00 | 45.11 | C |
| ATOM | 841 | CG | ARG A | 231 | 64.494 | 26.006 | 18.362 | 1.00 | 46.09 | C |
| ATOM | 842 | CD | ARG A | 231 | 62.990 | 25.927 | 18.557 | 1.00 | 47.94 | C |
| ATOM | 843 | NE | ARG A | 231 | 62.587 | 26.465 | 19.854 | 1.00 | 49.46 | N |
| ATOM | 844 | CZ | ARG A | 231 | 61.326 | 26.555 | 20.273 | 1.00 | 52.08 | C |
| ATOM | 845 | NH1 | ARG A | 231 | 60.328 | 26.144 | 19.498 | 1.00 | 50.02 | N |
| ATOM | 846 | NH2 | ARG A | 231 | 61.063 | 27.058 | 21.476 | 1.00 | 53.40 | N |
| ATOM | 847 | N | TYR A | 232 | 66.981 | 29.841 | 17.510 | 1.00 | 40.54 | N |
| ATOM | 848 | CA | TYR A | 232 | 67.312 | 31.253 | 17.607 | 1.00 | 38.76 | C |
| ATOM | 849 | C | TYR A | 232 | 66.284 | 32.005 | 18.451 | 1.00 | 38.33 | C |
| ATOM | 850 | O | TYR A | 232 | 65.086 | 31.706 | 18.418 | 1.00 | 37.07 | O |
| ATOM | 851 | CB | TYR A | 232 | 67.377 | 31.882 | 16.217 | 1.00 | 39.12 | C |
| ATOM | 852 | CG | TYR A | 232 | 68.502 | 31.363 | 15.353 | 1.00 | 41.29 | C |
| ATOM | 853 | CD1 | TYR A | 232 | 69.821 | 31.371 | 15.809 | 1.00 | 41.57 | C |
| ATOM | 854 | CD2 | TYR A | 232 | 68.253 | 30.883 | 14.070 | 1.00 | 41.51 | C |
| ATOM | 855 | CE1 | TYR A | 232 | 70.867 | 30.915 | 15.002 | 1.00 | 43.44 | C |
| ATOM | 856 | CE2 | TYR A | 232 | 69.288 | 30.425 | 13.257 | 1.00 | 44.33 | C |
| ATOM | 857 | CZ | TYR A | 232 | 70.591 | 30.444 | 13.727 | 1.00 | 44.76 | C |
| ATOM | 858 | OH | TYR A | 232 | 71.612 | 30.003 | 12.913 | 1.00 | 47.05 | O |
| ATOM | 859 | N | LEU A | 233 | 66.764 | 32.970 | 19.228 | 1.00 | 36.38 | N |
| ATOM | 860 | CA | LEU A | 233 | 65.879 | 33.775 | 20.052 | 1.00 | 35.39 | C |
| ATOM | 861 | C | LEU A | 233 | 65.296 | 34.876 | 19.176 | 1.00 | 33.69 | C |
| ATOM | 862 | O | LEU A | 233 | 65.937 | 35.338 | 18.230 | 1.00 | 33.90 | O |
| ATOM | 863 | CB | LEU A | 233 | 66.650 | 34.390 | 21.226 | 1.00 | 35.98 | C |
| ATOM | 864 | CG | LEU A | 233 | 66.395 | 33.765 | 22.602 | 1.00 | 39.07 | C |
| ATOM | 865 | CD1 | LEU A | 233 | 66.503 | 32.252 | 22.519 | 1.00 | 37.64 | C |
| ATOM | 866 | CD2 | LEU A | 233 | 67.384 | 34.325 | 23.616 | 1.00 | 38.75 | C |
| ATOM | 867 | N | VAL A | 234 | 64.072 | 35.279 | 19.475 | 1.00 | 32.47 | N |
| ATOM | 868 | CA | VAL A | 234 | 63.433 | 36.334 | 18.710 | 1.00 | 31.96 | C |
| ATOM | 869 | C | VAL A | 234 | 62.465 | 37.080 | 19.613 | 1.00 | 31.91 | C |
| ATOM | 870 | O | VAL A | 234 | 61.883 | 36.502 | 20.529 | 1.00 | 31.40 | O |
| ATOM | 871 | CB | VAL A | 234 | 62.676 | 35.767 | 17.476 | 1.00 | 31.95 | C |
| ATOM | 872 | CG1 | VAL A | 234 | 61.402 | 35.048 | 17.913 | 1.00 | 29.55 | C |
| ATOM | 873 | CG2 | VAL A | 234 | 62.371 | 36.888 | 16.498 | 1.00 | 29.80 | C |
| ATOM | 874 | N | GLY A | 235 | 62.319 | 38.375 | 19.366 | 1.00 | 32.16 | N |

TABLE 2-continued

| | | | | | | | | | | |
|---|---|---|---|---|---|---|---|---|---|---|
| ATOM | 875 | CA | GLY A | 235 | 61.416 | 39.174 | 20.163 | 1.00 | 31.96 | C |
| ATOM | 876 | C | GLY A | 235 | 60.308 | 39.689 | 19.277 | 1.00 | 32.19 | C |
| ATOM | 877 | O | GLY A | 235 | 60.396 | 39.604 | 18.050 | 1.00 | 32.58 | O |
| ATOM | 878 | N | ALA A | 236 | 59.259 | 40.225 | 19.886 | 1.00 | 31.00 | N |
| ATOM | 879 | CA | ALA A | 236 | 58.154 | 40.746 | 19.109 | 1.00 | 31.50 | C |
| ATOM | 880 | C | ALA A | 236 | 57.535 | 41.973 | 19.766 | 1.00 | 30.43 | C |
| ATOM | 881 | O | ALA A | 236 | 57.275 | 41.981 | 20.965 | 1.00 | 32.80 | O |
| ATOM | 882 | CB | ALA A | 236 | 57.095 | 39.653 | 18.911 | 1.00 | 32.43 | C |
| ATOM | 883 | N | GLY A | 237 | 57.311 | 43.013 | 18.973 | 1.00 | 30.90 | N |
| ATOM | 884 | CA | GLY A | 237 | 56.710 | 44.218 | 19.504 | 1.00 | 32.34 | C |
| ATOM | 885 | C | GLY A | 237 | 55.206 | 44.067 | 19.618 | 1.00 | 32.69 | C |
| ATOM | 886 | O | GLY A | 237 | 54.595 | 43.345 | 18.837 | 1.00 | 34.22 | O |
| ATOM | 887 | N | ILE A | 238 | 54.607 | 44.723 | 20.606 | 1.00 | 32.45 | N |
| ATOM | 888 | CA | ILE A | 238 | 53.161 | 44.668 | 20.774 | 1.00 | 32.44 | C |
| ATOM | 889 | C | ILE A | 238 | 52.646 | 46.077 | 21.074 | 1.00 | 32.79 | C |
| ATOM | 890 | O | ILE A | 238 | 53.422 | 46.976 | 21.400 | 1.00 | 32.08 | O |
| ATOM | 891 | CB | ILE A | 238 | 52.739 | 43.709 | 21.927 | 1.00 | 33.39 | C |
| ATOM | 892 | CG1 | ILE A | 238 | 53.212 | 44.253 | 23.278 | 1.00 | 34.02 | C |
| ATOM | 893 | CG2 | ILE A | 238 | 53.309 | 42.320 | 21.686 | 1.00 | 32.20 | C |
| ATOM | 894 | CD1 | ILE A | 238 | 52.721 | 43.433 | 24.483 | 1.00 | 32.19 | C |
| ATOM | 895 | N | ASN A | 239 | 51.341 | 46.276 | 20.946 | 1.00 | 32.14 | N |
| ATOM | 896 | CA | ASN A | 239 | 50.768 | 47.579 | 21.221 | 1.00 | 31.92 | C |
| ATOM | 897 | C | ASN A | 239 | 49.769 | 47.462 | 22.358 | 1.00 | 33.41 | C |
| ATOM | 898 | O | ASN A | 239 | 49.391 | 46.357 | 22.759 | 1.00 | 32.91 | O |
| ATOM | 899 | CB | ASN A | 239 | 50.111 | 48.161 | 19.958 | 1.00 | 32.71 | C |
| ATOM | 900 | CG | ASN A | 239 | 48.978 | 47.300 | 19.428 | 1.00 | 32.73 | C |
| ATOM | 901 | OD1 | ASN A | 239 | 47.941 | 47.162 | 20.070 | 1.00 | 33.18 | O |
| ATOM | 902 | ND2 | ASN A | 239 | 49.175 | 46.717 | 18.249 | 1.00 | 31.34 | N |
| ATOM | 903 | N | THR A | 240 | 49.351 | 48.608 | 22.878 | 1.00 | 34.02 | N |
| ATOM | 904 | CA | THR A | 240 | 48.414 | 48.658 | 23.989 | 1.00 | 35.67 | C |
| ATOM | 905 | C | THR A | 240 | 46.949 | 48.476 | 23.596 | 1.00 | 36.91 | C |
| ATOM | 906 | O | THR A | 240 | 46.061 | 48.629 | 24.435 | 1.00 | 35.65 | O |
| ATOM | 907 | CB | THR A | 240 | 48.555 | 49.995 | 24.739 | 1.00 | 34.88 | C |
| ATOM | 908 | OG1 | THR A | 240 | 48.330 | 51.074 | 23.823 | 1.00 | 34.88 | O |
| ATOM | 909 | CG2 | THR A | 240 | 49.952 | 50.125 | 25.343 | 1.00 | 33.05 | C |
| ATOM | 910 | N | ARG A | 241 | 46.691 | 48.135 | 22.338 | 1.00 | 39.01 | N |
| ATOM | 911 | CA | ARG A | 241 | 45.312 | 47.972 | 21.889 | 1.00 | 43.02 | C |
| ATOM | 912 | C | ARG A | 241 | 44.821 | 46.538 | 21.708 | 1.00 | 42.60 | C |
| ATOM | 913 | O | ARG A | 241 | 43.926 | 46.093 | 22.429 | 1.00 | 41.68 | O |
| ATOM | 914 | CB | ARG A | 241 | 45.087 | 48.752 | 20.588 | 1.00 | 46.62 | C |
| ATOM | 915 | CG | ARG A | 241 | 43.702 | 48.546 | 19.976 | 1.00 | 52.95 | C |
| ATOM | 916 | CD | ARG A | 241 | 43.469 | 49.420 | 18.740 | 1.00 | 57.47 | C |
| ATOM | 917 | NE | ARG A | 241 | 42.889 | 50.725 | 19.069 | 1.00 | 61.95 | N |
| ATOM | 918 | CZ | ARG A | 241 | 43.504 | 51.681 | 19.763 | 1.00 | 63.53 | C |
| ATOM | 919 | NH1 | ARG A | 241 | 44.738 | 51.496 | 20.218 | 1.00 | 64.10 | N |
| ATOM | 920 | NH2 | ARG A | 241 | 42.883 | 52.831 | 19.999 | 1.00 | 63.47 | N |
| ATOM | 921 | N | ASP A | 242 | 45.396 | 45.820 | 20.748 | 1.00 | 42.26 | N |
| ATOM | 922 | CA | ASP A | 242 | 44.974 | 44.450 | 20.473 | 1.00 | 43.86 | C |
| ATOM | 923 | C | ASP A | 242 | 45.832 | 43.360 | 21.119 | 1.00 | 43.63 | C |
| ATOM | 924 | O | ASP A | 242 | 45.930 | 42.258 | 20.585 | 1.00 | 44.69 | O |
| ATOM | 925 | CB | ASP A | 242 | 44.930 | 44.214 | 18.957 | 1.00 | 43.42 | C |
| ATOM | 926 | CG | ASP A | 242 | 46.295 | 44.361 | 18.295 | 1.00 | 45.14 | C |
| ATOM | 927 | OD1 | ASP A | 242 | 47.320 | 44.022 | 18.931 | 1.00 | 44.30 | O |
| ATOM | 928 | OD2 | ASP A | 242 | 46.344 | 44.799 | 17.123 | 1.00 | 45.01 | O |
| ATOM | 929 | N | PHE A | 243 | 46.433 | 43.655 | 22.266 | 1.00 | 43.34 | N |
| ATOM | 930 | CA | PHE A | 243 | 47.298 | 42.686 | 22.939 | 1.00 | 43.11 | C |
| ATOM | 931 | C | PHE A | 243 | 46.612 | 41.409 | 23.434 | 1.00 | 43.36 | C |
| ATOM | 932 | O | PHE A | 243 | 47.244 | 40.354 | 23.504 | 1.00 | 43.21 | O |
| ATOM | 933 | CB | PHE A | 243 | 48.043 | 43.368 | 24.097 | 1.00 | 40.53 | C |
| ATOM | 934 | CG | PHE A | 243 | 47.147 | 43.890 | 25.179 | 1.00 | 38.93 | C |
| ATOM | 935 | CD1 | PHE A | 243 | 46.662 | 43.042 | 26.170 | 1.00 | 38.45 | C |
| ATOM | 936 | CD2 | PHE A | 243 | 46.795 | 45.236 | 25.216 | 1.00 | 38.69 | C |
| ATOM | 937 | CE1 | PHE A | 243 | 45.842 | 43.524 | 27.185 | 1.00 | 38.00 | C |
| ATOM | 938 | CE2 | PHE A | 243 | 45.974 | 45.731 | 26.226 | 1.00 | 38.21 | C |
| ATOM | 939 | CZ | PHE A | 243 | 45.497 | 44.872 | 27.215 | 1.00 | 38.78 | C |
| ATOM | 940 | N | ARG A | 244 | 45.328 | 41.497 | 23.772 | 1.00 | 43.84 | N |
| ATOM | 941 | CA | ARG A | 244 | 44.598 | 40.325 | 24.253 | 1.00 | 44.76 | C |
| ATOM | 942 | C | ARG A | 244 | 44.549 | 39.225 | 23.197 | 1.00 | 44.01 | C |
| ATOM | 943 | O | ARG A | 244 | 44.455 | 38.047 | 23.526 | 1.00 | 44.85 | O |
| ATOM | 944 | CB | ARG A | 244 | 43.176 | 40.713 | 24.685 | 1.00 | 44.23 | C |
| ATOM | 945 | CG | ARG A | 244 | 43.148 | 41.654 | 25.880 | 1.00 | 43.24 | C |
| ATOM | 946 | CD | ARG A | 244 | 41.735 | 41.931 | 26.362 | 1.00 | 44.43 | C |
| ATOM | 947 | NE | ARG A | 244 | 41.721 | 42.938 | 27.420 | 1.00 | 45.36 | N |
| ATOM | 948 | CZ | ARG A | 244 | 41.970 | 44.231 | 27.224 | 1.00 | 46.55 | C |
| ATOM | 949 | NH1 | ARG A | 244 | 42.247 | 44.678 | 26.003 | 1.00 | 44.24 | N |
| ATOM | 950 | NH2 | ARG A | 244 | 41.953 | 45.077 | 28.248 | 1.00 | 45.03 | N |
| ATOM | 951 | N | GLU A | 245 | 44.614 | 39.610 | 21.929 | 1.00 | 44.30 | N |
| ATOM | 952 | CA | GLU A | 245 | 44.599 | 38.634 | 20.849 | 1.00 | 45.31 | C |
| ATOM | 953 | C | GLU A | 245 | 46.001 | 38.448 | 20.275 | 1.00 | 44.68 | C |

TABLE 2-continued

| ATOM | 954 | O | GLU A | 245 | 46.363 | 37.358 | 19.826 | 1.00 | 44.64 | O |
|---|---|---|---|---|---|---|---|---|---|---|
| ATOM | 955 | CB | GLU A | 245 | 43.640 | 39.071 | 19.733 | 1.00 | 48.37 | C |
| ATOM | 956 | CG | GLU A | 245 | 42.153 | 38.931 | 20.084 | 1.00 | 53.41 | C |
| ATOM | 957 | CD | GLU A | 245 | 41.647 | 39.993 | 21.059 | 1.00 | 57.52 | C |
| ATOM | 958 | OE1 | GLU A | 245 | 40.635 | 39.725 | 21.746 | 1.00 | 59.50 | O |
| ATOM | 959 | OE2 | GLU A | 245 | 42.239 | 41.099 | 21.132 | 1.00 | 59.64 | O |
| ATOM | 960 | N | ARG A | 246 | 46.794 | 39.514 | 20.309 | 1.00 | 42.77 | N |
| ATOM | 961 | CA | ARG A | 246 | 48.152 | 39.479 | 19.771 | 1.00 | 41.08 | C |
| ATOM | 962 | C | ARG A | 246 | 49.163 | 38.714 | 20.629 | 1.00 | 39.13 | C |
| ATOM | 963 | O | ARG A | 246 | 49.964 | 37.944 | 20.111 | 1.00 | 37.89 | O |
| ATOM | 964 | CB | ARG A | 246 | 48.649 | 40.907 | 19.553 | 1.00 | 42.28 | C |
| ATOM | 965 | CG | ARG A | 246 | 49.936 | 40.997 | 18.770 | 1.00 | 44.41 | C |
| ATOM | 966 | CD | ARG A | 246 | 50.355 | 42.442 | 18.584 | 1.00 | 46.22 | C |
| ATOM | 967 | NE | ARG A | 246 | 50.638 | 42.723 | 17.185 | 1.00 | 50.24 | N |
| ATOM | 968 | CZ | ARG A | 246 | 49.723 | 43.062 | 16.287 | 1.00 | 48.88 | C |
| ATOM | 969 | NH1 | ARG A | 246 | 48.454 | 43.175 | 16.638 | 1.00 | 51.93 | N |
| ATOM | 970 | NH2 | ARG A | 246 | 50.076 | 43.269 | 15.031 | 1.00 | 50.28 | N |
| ATOM | 971 | N | VAL A | 247 | 49.134 | 38.928 | 21.939 | 1.00 | 37.97 | N |
| ATOM | 972 | CA | VAL A | 247 | 50.075 | 38.246 | 22.822 | 1.00 | 38.70 | C |
| ATOM | 973 | C | VAL A | 247 | 49.977 | 36.716 | 22.746 | 1.00 | 39.69 | C |
| ATOM | 974 | O | VAL A | 247 | 50.980 | 36.041 | 22.499 | 1.00 | 40.53 | O |
| ATOM | 975 | CB | VAL A | 247 | 49.901 | 38.717 | 24.285 | 1.00 | 36.45 | C |
| ATOM | 976 | CG1 | VAL A | 247 | 50.735 | 37.867 | 25.217 | 1.00 | 35.80 | C |
| ATOM | 977 | CG2 | VAL A | 247 | 50.315 | 40.184 | 24.402 | 1.00 | 36.49 | C |
| ATOM | 978 | N | PRO A | 248 | 48.770 | 36.148 | 22.955 | 1.00 | 39.79 | N |
| ATOM | 979 | CA | PRO A | 248 | 48.615 | 34.688 | 22.895 | 1.00 | 38.65 | C |
| ATOM | 980 | C | PRO A | 248 | 49.149 | 34.104 | 21.588 | 1.00 | 37.90 | C |
| ATOM | 981 | O | PRO A | 248 | 49.773 | 33.044 | 21.579 | 1.00 | 38.24 | O |
| ATOM | 982 | CB | PRO A | 248 | 47.107 | 34.498 | 23.050 | 1.00 | 40.03 | C |
| ATOM | 983 | CG | PRO A | 248 | 46.727 | 35.633 | 23.951 | 1.00 | 39.42 | C |
| ATOM | 984 | CD | PRO A | 248 | 47.499 | 36.790 | 23.340 | 1.00 | 37.60 | C |
| ATOM | 985 | N | ALA A | 249 | 48.905 | 34.808 | 20.488 | 1.00 | 38.13 | N |
| ATOM | 986 | CA | ALA A | 249 | 49.369 | 34.372 | 19.178 | 1.00 | 38.44 | C |
| ATOM | 987 | C | ALA A | 249 | 50.899 | 34.403 | 19.100 | 1.00 | 40.66 | C |
| ATOM | 988 | O | ALA A | 249 | 51.519 | 33.508 | 18.505 | 1.00 | 40.90 | O |
| ATOM | 989 | CB | ALA A | 249 | 48.777 | 35.257 | 18.103 | 1.00 | 38.28 | C |
| ATOM | 990 | N | LEU A | 250 | 51.502 | 35.433 | 19.698 | 1.00 | 39.69 | N |
| ATOM | 991 | CA | LEU A | 250 | 52.956 | 35.570 | 19.699 | 1.00 | 39.26 | C |
| ATOM | 992 | C | LEU A | 250 | 53.585 | 34.501 | 20.587 | 1.00 | 39.24 | C |
| ATOM | 993 | O | LEU A | 250 | 54.600 | 33.908 | 20.232 | 1.00 | 38.60 | O |
| ATOM | 994 | CB | LEU A | 250 | 53.357 | 36.974 | 20.176 | 1.00 | 39.22 | C |
| ATOM | 995 | CG | LEU A | 250 | 53.642 | 38.057 | 19.119 | 1.00 | 39.75 | C |
| ATOM | 996 | CD1 | LEU A | 250 | 53.046 | 37.699 | 17.772 | 1.00 | 37.78 | C |
| ATOM | 997 | CD2 | LEU A | 250 | 53.099 | 39.387 | 19.610 | 1.00 | 39.06 | C |
| ATOM | 998 | N | VAL A | 251 | 52.974 | 34.256 | 21.740 | 1.00 | 40.54 | N |
| ATOM | 999 | CA | VAL A | 251 | 53.469 | 33.243 | 22.665 | 1.00 | 42.59 | C |
| ATOM | 1000 | C | VAL A | 251 | 53.413 | 31.878 | 21.985 | 1.00 | 43.82 | C |
| ATOM | 1001 | O | VAL A | 251 | 54.406 | 31.153 | 21.942 | 1.00 | 43.85 | O |
| ATOM | 1002 | CB | VAL A | 251 | 52.616 | 33.201 | 23.946 | 1.00 | 42.12 | C |
| ATOM | 1003 | CG1 | VAL A | 251 | 53.101 | 32.088 | 24.865 | 1.00 | 43.50 | C |
| ATOM | 1004 | CG2 | VAL A | 251 | 52.691 | 34.543 | 24.653 | 1.00 | 44.13 | C |
| ATOM | 1005 | N | GLU A | 252 | 52.243 | 31.537 | 21.451 | 1.00 | 45.33 | N |
| ATOM | 1006 | CA | GLU A | 252 | 52.055 | 30.268 | 20.759 | 1.00 | 46.43 | C |
| ATOM | 1007 | C | GLU A | 252 | 53.068 | 30.096 | 19.629 | 1.00 | 44.48 | C |
| ATOM | 1008 | O | GLU A | 252 | 53.568 | 28.996 | 19.398 | 1.00 | 44.67 | O |
| ATOM | 1009 | CB | GLU A | 252 | 50.634 | 30.172 | 20.183 | 1.00 | 49.48 | C |
| ATOM | 1010 | CG | GLU A | 252 | 49.629 | 29.457 | 21.081 | 1.00 | 55.40 | C |
| ATOM | 1011 | CD | GLU A | 252 | 49.072 | 30.334 | 22.188 | 1.00 | 57.85 | C |
| ATOM | 1012 | OE1 | GLU A | 252 | 47.945 | 30.858 | 22.029 | 1.00 | 57.96 | O |
| ATOM | 1013 | OE2 | GLU A | 252 | 49.762 | 30.500 | 23.216 | 1.00 | 60.59 | O |
| ATOM | 1014 | N | ALA A | 253 | 53.363 | 31.183 | 18.923 | 1.00 | 41.46 | N |
| ATOM | 1015 | CA | ALA A | 253 | 54.315 | 31.135 | 17.820 | 1.00 | 39.92 | C |
| ATOM | 1016 | C | ALA A | 253 | 55.748 | 30.896 | 18.306 | 1.00 | 39.79 | C |
| ATOM | 1017 | O | ALA A | 253 | 56.638 | 30.587 | 17.509 | 1.00 | 39.66 | O |
| ATOM | 1018 | CB | ALA A | 253 | 54.239 | 32.421 | 17.009 | 1.00 | 38.59 | C |
| ATOM | 1019 | N | GLY A | 254 | 55.971 | 31.046 | 19.609 | 1.00 | 38.49 | N |
| ATOM | 1020 | CA | GLY A | 254 | 57.297 | 30.813 | 20.156 | 1.00 | 40.23 | C |
| ATOM | 1021 | C | GLY A | 254 | 58.139 | 32.043 | 20.472 | 1.00 | 39.89 | C |
| ATOM | 1022 | O | GLY A | 254 | 59.355 | 31.936 | 20.619 | 1.00 | 39.63 | O |
| ATOM | 1023 | N | ALA A | 255 | 57.506 | 33.207 | 20.575 | 1.00 | 39.17 | N |
| ATOM | 1024 | CA | ALA A | 255 | 58.232 | 34.432 | 20.888 | 1.00 | 38.09 | C |
| ATOM | 1025 | C | ALA A | 255 | 58.933 | 34.287 | 22.238 | 1.00 | 36.72 | C |
| ATOM | 1026 | O | ALA A | 255 | 58.324 | 33.872 | 23.223 | 1.00 | 35.94 | O |
| ATOM | 1027 | CB | ALA A | 255 | 57.276 | 35.612 | 20.916 | 1.00 | 37.70 | C |
| ATOM | 1028 | N | ASP A | 256 | 60.214 | 34.634 | 22.283 | 1.00 | 35.80 | N |
| ATOM | 1029 | CA | ASP A | 256 | 60.977 | 34.520 | 23.523 | 1.00 | 35.28 | C |
| ATOM | 1030 | C | ASP A | 256 | 60.809 | 35.725 | 24.437 | 1.00 | 33.72 | C |
| ATOM | 1031 | O | ASP A | 256 | 60.921 | 35.610 | 25.656 | 1.00 | 32.72 | O |
| ATOM | 1032 | CB | ASP A | 256 | 62.451 | 34.307 | 23.199 | 1.00 | 34.79 | C |

TABLE 2-continued

| ATOM | 1033 | CG | ASP A | 256 | 62.682 | 33.041 | 22.404 | 1.00 | 37.41 | C |
|---|---|---|---|---|---|---|---|---|---|---|
| ATOM | 1034 | OD1 | ASP A | 256 | 62.584 | 31.948 | 23.003 | 1.00 | 38.37 | O |
| ATOM | 1035 | OD2 | ASP A | 256 | 62.944 | 33.137 | 21.185 | 1.00 | 34.51 | O |
| ATOM | 1036 | N | VAL A | 257 | 60.538 | 36.881 | 23.845 | 1.00 | 32.63 | N |
| ATOM | 1037 | CA | VAL A | 257 | 60.354 | 38.096 | 24.625 | 1.00 | 32.40 | C |
| ATOM | 1038 | C | VAL A | 257 | 59.502 | 39.085 | 23.845 | 1.00 | 31.76 | C |
| ATOM | 1039 | O | VAL A | 257 | 59.520 | 39.100 | 22.617 | 1.00 | 32.06 | O |
| ATOM | 1040 | CB | VAL A | 257 | 61.720 | 38.748 | 24.986 | 1.00 | 29.73 | C |
| ATOM | 1041 | CG1 | VAL A | 257 | 62.435 | 39.181 | 23.730 | 1.00 | 30.67 | C |
| ATOM | 1042 | CG2 | VAL A | 257 | 61.514 | 39.920 | 25.924 | 1.00 | 29.01 | C |
| ATOM | 1043 | N | LEU A | 258 | 58.749 | 39.899 | 24.572 | 1.00 | 30.18 | N |
| ATOM | 1044 | CA | LEU A | 258 | 57.886 | 40.894 | 23.957 | 1.00 | 31.57 | C |
| ATOM | 1045 | C | LEU A | 258 | 58.308 | 42.286 | 24.405 | 1.00 | 31.09 | C |
| ATOM | 1046 | O | LEU A | 258 | 59.036 | 42.441 | 25.384 | 1.00 | 31.25 | O |
| ATOM | 1047 | CB | LEU A | 258 | 56.427 | 40.665 | 24.374 | 1.00 | 29.78 | C |
| ATOM | 1048 | CG | LEU A | 258 | 55.852 | 39.263 | 24.175 | 1.00 | 31.14 | C |
| ATOM | 1049 | CD1 | LEU A | 258 | 54.440 | 39.223 | 24.729 | 1.00 | 33.95 | C |
| ATOM | 1050 | CD2 | LEU A | 258 | 55.870 | 38.887 | 22.696 | 1.00 | 30.48 | C |
| ATOM | 1051 | N | CYS A | 259 | 57.849 | 43.298 | 23.680 | 1.00 | 31.62 | N |
| ATOM | 1052 | CA | CYS A | 259 | 58.149 | 44.675 | 24.042 | 1.00 | 31.37 | C |
| ATOM | 1053 | C | CYS A | 259 | 57.070 | 45.613 | 23.521 | 1.00 | 30.31 | C |
| ATOM | 1054 | O | CYS A | 259 | 56.798 | 45.650 | 22.324 | 1.00 | 31.18 | O |
| ATOM | 1055 | CB | CYS A | 259 | 59.503 | 45.114 | 23.485 | 1.00 | 28.99 | C |
| ATOM | 1056 | SG | CYS A | 259 | 60.014 | 46.724 | 24.132 | 1.00 | 29.97 | S |
| ATOM | 1057 | N | ILE A | 260 | 56.456 | 46.362 | 24.428 | 1.00 | 30.30 | N |
| ATOM | 1058 | CA | ILE A | 260 | 55.431 | 47.317 | 24.042 | 1.00 | 31.13 | C |
| ATOM | 1059 | C | ILE A | 260 | 56.147 | 48.408 | 23.248 | 1.00 | 33.06 | C |
| ATOM | 1060 | O | ILE A | 260 | 57.157 | 48.959 | 23.693 | 1.00 | 32.27 | O |
| ATOM | 1061 | CB | ILE A | 260 | 54.752 | 47.921 | 25.276 | 1.00 | 30.72 | C |
| ATOM | 1062 | CG1 | ILE A | 260 | 54.132 | 46.796 | 26.110 | 1.00 | 29.75 | C |
| ATOM | 1063 | CG2 | ILE A | 260 | 53.695 | 48.946 | 24.851 | 1.00 | 27.83 | C |
| ATOM | 1064 | CD1 | ILE A | 260 | 53.567 | 47.256 | 27.440 | 1.00 | 30.89 | C |
| ATOM | 1065 | N | ASP A | 261 | 55.620 | 48.701 | 22.068 | 1.00 | 33.30 | N |
| ATOM | 1066 | CA | ASP A | 261 | 56.204 | 49.682 | 21.172 | 1.00 | 34.73 | C |
| ATOM | 1067 | C | ASP A | 261 | 55.482 | 51.032 | 21.222 | 1.00 | 35.90 | C |
| ATOM | 1068 | O | ASP A | 261 | 54.372 | 51.171 | 20.706 | 1.00 | 37.40 | O |
| ATOM | 1069 | CB | ASP A | 261 | 56.183 | 49.090 | 19.762 | 1.00 | 34.92 | C |
| ATOM | 1070 | CG | ASP A | 261 | 56.704 | 50.036 | 18.712 | 1.00 | 36.01 | C |
| ATOM | 1071 | OD1 | ASP A | 261 | 57.519 | 50.924 | 19.041 | 1.00 | 34.62 | O |
| ATOM | 1072 | OD2 | ASP A | 261 | 56.303 | 49.871 | 17.541 | 1.00 | 37.89 | O |
| ATOM | 1073 | N | SER A | 262 | 56.117 | 52.031 | 21.831 | 1.00 | 35.46 | N |
| ATOM | 1074 | CA | SER A | 262 | 55.504 | 53.354 | 21.946 | 1.00 | 35.41 | C |
| ATOM | 1075 | C | SER A | 262 | 56.538 | 54.453 | 22.172 | 1.00 | 35.72 | C |
| ATOM | 1076 | O | SER A | 262 | 57.599 | 54.203 | 22.748 | 1.00 | 35.63 | O |
| ATOM | 1077 | CB | SER A | 262 | 54.499 | 53.339 | 23.101 | 1.00 | 35.49 | C |
| ATOM | 1078 | OG | SER A | 262 | 53.993 | 54.629 | 23.377 | 1.00 | 35.23 | O |
| ATOM | 1079 | N | SER A | 263 | 56.240 | 55.671 | 21.722 | 1.00 | 34.24 | N |
| ATOM | 1080 | CA | SER A | 263 | 57.183 | 56.770 | 21.922 | 1.00 | 35.35 | C |
| ATOM | 1081 | C | SER A | 263 | 57.056 | 57.337 | 23.334 | 1.00 | 34.38 | C |
| ATOM | 1082 | O | SER A | 263 | 58.021 | 57.862 | 23.886 | 1.00 | 36.61 | O |
| ATOM | 1083 | CB | SER A | 263 | 56.982 | 57.876 | 20.873 | 1.00 | 35.88 | C |
| ATOM | 1084 | OG | SER A | 263 | 55.638 | 58.326 | 20.822 | 1.00 | 39.99 | O |
| ATOM | 1085 | N | ASP A | 264 | 55.872 | 57.224 | 23.925 | 1.00 | 31.64 | N |
| ATOM | 1086 | CA | ASP A | 264 | 55.664 | 57.707 | 25.289 | 1.00 | 30.91 | C |
| ATOM | 1087 | C | ASP A | 264 | 55.128 | 56.564 | 26.155 | 1.00 | 30.07 | C |
| ATOM | 1088 | O | ASP A | 264 | 53.917 | 56.353 | 26.247 | 1.00 | 29.83 | O |
| ATOM | 1089 | CB | ASP A | 264 | 54.692 | 58.898 | 25.296 | 1.00 | 29.57 | C |
| ATOM | 1090 | CG | ASP A | 264 | 54.281 | 59.325 | 26.706 | 1.00 | 29.79 | C |
| ATOM | 1091 | OD1 | ASP A | 264 | 54.945 | 58.947 | 27.696 | 1.00 | 27.03 | O |
| ATOM | 1092 | OD2 | ASP A | 264 | 53.283 | 60.057 | 26.824 | 1.00 | 29.07 | O |
| ATOM | 1093 | N | GLY A | 265 | 56.042 | 55.838 | 26.792 | 1.00 | 29.18 | N |
| ATOM | 1094 | CA | GLY A | 265 | 55.659 | 54.712 | 27.627 | 1.00 | 28.22 | C |
| ATOM | 1095 | C | GLY A | 265 | 55.158 | 55.050 | 29.018 | 1.00 | 28.37 | C |
| ATOM | 1096 | O | GLY A | 265 | 54.689 | 54.169 | 29.736 | 1.00 | 28.80 | O |
| ATOM | 1097 | N | PHE A | 266 | 55.258 | 56.317 | 29.407 | 1.00 | 27.17 | N |
| ATOM | 1098 | CA | PHE A | 266 | 54.798 | 56.752 | 30.721 | 1.00 | 28.12 | C |
| ATOM | 1099 | C | PHE A | 266 | 53.275 | 56.847 | 30.584 | 1.00 | 29.95 | C |
| ATOM | 1100 | O | PHE A | 266 | 52.699 | 57.932 | 30.598 | 1.00 | 29.08 | O |
| ATOM | 1101 | CB | PHE A | 266 | 55.415 | 58.117 | 31.048 | 1.00 | 27.00 | C |
| ATOM | 1102 | CG | PHE A | 266 | 55.483 | 58.432 | 32.522 | 1.00 | 28.08 | C |
| ATOM | 1103 | CD1 | PHE A | 266 | 54.761 | 57.684 | 33.456 | 1.00 | 26.54 | C |
| ATOM | 1104 | CD2 | PHE A | 266 | 56.259 | 59.502 | 32.973 | 1.00 | 25.82 | C |
| ATOM | 1105 | CE1 | PHE A | 266 | 54.810 | 57.995 | 34.817 | 1.00 | 26.74 | C |
| ATOM | 1106 | CE2 | PHE A | 266 | 56.317 | 59.827 | 34.328 | 1.00 | 24.90 | C |
| ATOM | 1107 | CZ | PHE A | 266 | 55.593 | 59.074 | 35.257 | 1.00 | 27.12 | C |
| ATOM | 1108 | N | SER A | 267 | 52.636 | 55.684 | 30.453 | 1.00 | 31.46 | N |
| ATOM | 1109 | CA | SER A | 267 | 51.194 | 55.596 | 30.233 | 1.00 | 31.95 | C |
| ATOM | 1110 | C | SER A | 267 | 50.476 | 54.513 | 31.029 | 1.00 | 32.94 | C |
| ATOM | 1111 | O | SER A | 267 | 50.989 | 53.405 | 31.218 | 1.00 | 32.01 | O |

TABLE 2-continued

| | | | | | | | | | | |
|---|---|---|---|---|---|---|---|---|---|---|
| ATOM | 1112 | CB | SER A | 267 | 50.938 | 55.343 | 28.746 | 1.00 | 31.54 | C |
| ATOM | 1113 | OG | SER A | 267 | 49.558 | 55.219 | 28.462 | 1.00 | 34.95 | O |
| ATOM | 1114 | N | GLU A | 268 | 49.266 | 54.833 | 31.466 | 1.00 | 33.57 | N |
| ATOM | 1115 | CA | GLU A | 268 | 48.460 | 53.887 | 32.214 | 1.00 | 35.39 | C |
| ATOM | 1116 | C | GLU A | 268 | 48.162 | 52.711 | 31.284 | 1.00 | 35.05 | C |
| ATOM | 1117 | O | GLU A | 268 | 47.945 | 51.589 | 31.736 | 1.00 | 35.30 | O |
| ATOM | 1118 | CB | GLU A | 268 | 47.159 | 54.551 | 32.677 | 1.00 | 36.81 | C |
| ATOM | 1119 | CG | GLU A | 268 | 46.306 | 53.672 | 33.576 | 1.00 | 41.82 | C |
| ATOM | 1120 | CD | GLU A | 268 | 45.047 | 54.369 | 34.076 | 1.00 | 45.55 | C |
| ATOM | 1121 | OE1 | GLU A | 268 | 44.238 | 53.691 | 34.753 | 1.00 | 47.73 | O |
| ATOM | 1122 | OE2 | GLU A | 268 | 44.864 | 55.582 | 33.801 | 1.00 | 43.72 | O |
| ATOM | 1123 | N | TRP A | 269 | 48.166 | 52.973 | 29.980 | 1.00 | 33.62 | N |
| ATOM | 1124 | CA | TRP A | 269 | 47.907 | 51.925 | 29.002 | 1.00 | 35.48 | C |
| ATOM | 1125 | C | TRP A | 269 | 48.958 | 50.813 | 29.063 | 1.00 | 34.72 | C |
| ATOM | 1126 | O | TRP A | 269 | 48.632 | 49.637 | 28.873 | 1.00 | 35.26 | O |
| ATOM | 1127 | CB | TRP A | 269 | 47.858 | 52.502 | 27.584 | 1.00 | 36.38 | C |
| ATOM | 1128 | CG | TRP A | 269 | 46.659 | 53.368 | 27.322 | 1.00 | 41.33 | C |
| ATOM | 1129 | CD1 | TRP A | 269 | 46.656 | 54.711 | 27.068 | 1.00 | 40.88 | C |
| ATOM | 1130 | CD2 | TRP A | 269 | 45.289 | 52.948 | 27.272 | 1.00 | 42.34 | C |
| ATOM | 1131 | NE1 | TRP A | 269 | 45.372 | 55.150 | 26.861 | 1.00 | 42.36 | N |
| ATOM | 1132 | CE2 | TRP A | 269 | 44.513 | 54.090 | 26.981 | 1.00 | 42.40 | C |
| ATOM | 1133 | CE3 | TRP A | 269 | 44.642 | 51.715 | 27.445 | 1.00 | 43.39 | C |
| ATOM | 1134 | CZ2 | TRP A | 269 | 43.122 | 54.039 | 26.858 | 1.00 | 44.45 | C |
| ATOM | 1135 | CZ3 | TRP A | 269 | 43.258 | 51.663 | 27.322 | 1.00 | 44.28 | C |
| ATOM | 1136 | CH2 | TRP A | 269 | 42.514 | 52.821 | 27.031 | 1.00 | 44.95 | C |
| ATOM | 1137 | N | GLN A | 270 | 50.216 | 51.176 | 29.313 | 1.00 | 32.85 | N |
| ATOM | 1138 | CA | GLN A | 270 | 51.274 | 50.171 | 29.406 | 1.00 | 32.10 | C |
| ATOM | 1139 | C | GLN A | 270 | 51.134 | 49.400 | 30.717 | 1.00 | 31.09 | C |
| ATOM | 1140 | O | GLN A | 270 | 51.403 | 48.205 | 30.770 | 1.00 | 30.10 | O |
| ATOM | 1141 | CB | GLN A | 270 | 52.669 | 50.816 | 29.308 | 1.00 | 30.58 | C |
| ATOM | 1142 | CG | GLN A | 270 | 52.897 | 51.572 | 28.000 | 1.00 | 29.81 | C |
| ATOM | 1143 | CD | GLN A | 270 | 54.275 | 51.346 | 27.394 | 1.00 | 29.50 | C |
| ATOM | 1144 | OE1 | GLN A | 270 | 55.172 | 50.791 | 28.031 | 1.00 | 28.16 | O |
| ATOM | 1145 | NE2 | GLN A | 270 | 54.448 | 51.789 | 26.156 | 1.00 | 26.58 | N |
| ATOM | 1146 | N | LYS A | 271 | 50.712 | 50.085 | 31.775 | 1.00 | 32.98 | N |
| ATOM | 1147 | CA | LYS A | 271 | 50.518 | 49.416 | 33.057 | 1.00 | 35.22 | C |
| ATOM | 1148 | C | LYS A | 271 | 49.432 | 48.347 | 32.881 | 1.00 | 34.93 | C |
| ATOM | 1149 | O | LYS A | 271 | 49.566 | 47.224 | 33.365 | 1.00 | 33.86 | O |
| ATOM | 1150 | CB | LYS A | 271 | 50.097 | 50.419 | 34.137 | 1.00 | 36.36 | C |
| ATOM | 1151 | CG | LYS A | 271 | 49.780 | 49.767 | 35.481 | 1.00 | 39.94 | C |
| ATOM | 1152 | CD | LYS A | 271 | 49.633 | 50.794 | 36.608 | 1.00 | 42.24 | C |
| ATOM | 1153 | CE | LYS A | 271 | 49.393 | 50.095 | 37.951 | 1.00 | 45.21 | C |
| ATOM | 1154 | NZ | LYS A | 271 | 49.405 | 51.022 | 39.132 | 1.00 | 47.32 | N |
| ATOM | 1155 | N | ILE A | 272 | 48.373 | 48.708 | 32.159 | 1.00 | 34.90 | N |
| ATOM | 1156 | CA | ILE A | 272 | 47.257 | 47.807 | 31.897 | 1.00 | 35.34 | C |
| ATOM | 1157 | C | ILE A | 272 | 47.698 | 46.602 | 31.071 | 1.00 | 35.48 | C |
| ATOM | 1158 | O | ILE A | 272 | 47.347 | 45.466 | 31.387 | 1.00 | 36.14 | O |
| ATOM | 1159 | CB | ILE A | 272 | 46.109 | 48.545 | 31.157 | 1.00 | 35.04 | C |
| ATOM | 1160 | CG1 | ILE A | 272 | 45.467 | 49.565 | 32.101 | 1.00 | 35.36 | C |
| ATOM | 1161 | CG2 | ILE A | 272 | 45.073 | 47.539 | 30.644 | 1.00 | 34.61 | C |
| ATOM | 1162 | CD1 | ILE A | 272 | 44.485 | 50.509 | 31.431 | 1.00 | 33.49 | C |
| ATOM | 1163 | N | THR A | 273 | 48.469 | 46.851 | 30.016 | 1.00 | 34.92 | N |
| ATOM | 1164 | CA | THR A | 273 | 48.951 | 45.777 | 29.156 | 1.00 | 34.08 | C |
| ATOM | 1165 | C | THR A | 273 | 49.844 | 44.791 | 29.918 | 1.00 | 34.99 | C |
| ATOM | 1166 | O | THR A | 273 | 49.675 | 43.578 | 29.803 | 1.00 | 36.08 | O |
| ATOM | 1167 | CB | THR A | 273 | 49.741 | 46.340 | 27.958 | 1.00 | 34.19 | C |
| ATOM | 1168 | OG1 | THR A | 273 | 48.888 | 47.192 | 27.188 | 1.00 | 35.97 | O |
| ATOM | 1169 | CG2 | THR A | 273 | 50.248 | 45.216 | 27.069 | 1.00 | 32.81 | C |
| ATOM | 1170 | N | ILE A | 274 | 50.797 | 45.305 | 30.687 | 1.00 | 34.29 | N |
| ATOM | 1171 | CA | ILE A | 274 | 51.692 | 44.433 | 31.443 | 1.00 | 34.33 | C |
| ATOM | 1172 | C | ILE A | 274 | 50.900 | 43.660 | 32.493 | 1.00 | 35.70 | C |
| ATOM | 1173 | O | ILE A | 274 | 51.185 | 42.495 | 32.769 | 1.00 | 34.67 | O |
| ATOM | 1174 | CB | ILE A | 274 | 52.793 | 45.235 | 32.153 | 1.00 | 32.65 | C |
| ATOM | 1175 | CG1 | ILE A | 274 | 53.699 | 45.902 | 31.113 | 1.00 | 32.10 | C |
| ATOM | 1176 | CG2 | ILE A | 274 | 53.597 | 44.313 | 33.082 | 1.00 | 31.88 | C |
| ATOM | 1177 | CD1 | ILE A | 274 | 54.700 | 46.877 | 31.704 | 1.00 | 30.38 | C |
| ATOM | 1178 | N | GLY A | 275 | 49.907 | 44.324 | 33.076 | 1.00 | 36.56 | N |
| ATOM | 1179 | CA | GLY A | 275 | 49.082 | 43.684 | 34.085 | 1.00 | 37.75 | C |
| ATOM | 1180 | C | GLY A | 275 | 48.326 | 42.496 | 33.520 | 1.00 | 37.44 | C |
| ATOM | 1181 | O | GLY A | 275 | 48.230 | 41.456 | 34.159 | 1.00 | 38.90 | O |
| ATOM | 1182 | N | TRP A | 276 | 47.791 | 42.649 | 32.316 | 1.00 | 36.76 | N |
| ATOM | 1183 | CA | TRP A | 276 | 47.040 | 41.582 | 31.677 | 1.00 | 37.78 | C |
| ATOM | 1184 | C | TRP A | 276 | 47.952 | 40.391 | 31.416 | 1.00 | 39.15 | C |
| ATOM | 1185 | O | TRP A | 276 | 47.535 | 39.238 | 31.545 | 1.00 | 38.18 | O |
| ATOM | 1186 | CB | TRP A | 276 | 46.452 | 42.069 | 30.355 | 1.00 | 37.54 | C |
| ATOM | 1187 | CG | TRP A | 276 | 45.547 | 41.082 | 29.704 | 1.00 | 38.13 | C |
| ATOM | 1188 | CD1 | TRP A | 276 | 44.213 | 40.906 | 29.948 | 1.00 | 38.02 | C |
| ATOM | 1189 | CD2 | TRP A | 276 | 45.905 | 40.117 | 28.706 | 1.00 | 38.93 | C |
| ATOM | 1190 | NE1 | TRP A | 276 | 43.717 | 39.891 | 29.158 | 1.00 | 38.58 | N |

TABLE 2-continued

| ATOM | 1191 | CE2 | TRP A | 276 | 44.734 | 39.390 | 28.387 | 1.00 | 39.11 | C |
|---|---|---|---|---|---|---|---|---|---|---|
| ATOM | 1192 | CE3 | TRP A | 276 | 47.102 | 39.795 | 28.049 | 1.00 | 39.30 | C |
| ATOM | 1193 | CZ2 | TRP A | 276 | 44.724 | 38.360 | 27.439 | 1.00 | 39.42 | C |
| ATOM | 1194 | CZ3 | TRP A | 276 | 47.093 | 38.768 | 27.105 | 1.00 | 40.69 | C |
| ATOM | 1195 | CH2 | TRP A | 276 | 45.908 | 38.064 | 26.809 | 1.00 | 40.36 | C |
| ATOM | 1196 | N | ILE A | 277 | 49.199 | 40.675 | 31.045 | 1.00 | 38.34 | N |
| ATOM | 1197 | CA | ILE A | 277 | 50.164 | 39.621 | 30.765 | 1.00 | 38.49 | C |
| ATOM | 1198 | C | ILE A | 277 | 50.535 | 38.850 | 32.033 | 1.00 | 40.03 | C |
| ATOM | 1199 | O | ILE A | 277 | 50.704 | 37.634 | 31.995 | 1.00 | 39.95 | O |
| ATOM | 1200 | CB | ILE A | 277 | 51.444 | 40.197 | 30.113 | 1.00 | 38.18 | C |
| ATOM | 1201 | CG1 | ILE A | 277 | 51.112 | 40.752 | 28.725 | 1.00 | 37.35 | C |
| ATOM | 1202 | CG2 | ILE A | 277 | 52.520 | 39.121 | 30.016 | 1.00 | 36.41 | C |
| ATOM | 1203 | CD1 | ILE A | 277 | 52.274 | 41.440 | 28.036 | 1.00 | 35.39 | C |
| ATOM | 1204 | N | ARG A | 278 | 50.656 | 39.556 | 33.152 | 1.00 | 41.65 | N |
| ATOM | 1205 | CA | ARG A | 278 | 51.001 | 38.921 | 34.421 | 1.00 | 44.16 | C |
| ATOM | 1206 | C | ARG A | 278 | 49.871 | 38.043 | 34.950 | 1.00 | 46.24 | C |
| ATOM | 1207 | O | ARG A | 278 | 50.114 | 36.945 | 35.439 | 1.00 | 47.52 | O |
| ATOM | 1208 | CB | ARG A | 278 | 51.350 | 39.977 | 35.472 | 1.00 | 42.76 | C |
| ATOM | 1209 | CG | ARG A | 278 | 52.659 | 40.688 | 35.221 | 1.00 | 41.00 | C |
| ATOM | 1210 | CD | ARG A | 278 | 53.853 | 39.767 | 35.416 | 1.00 | 40.34 | C |
| ATOM | 1211 | NE | ARG A | 278 | 55.085 | 40.438 | 35.003 | 1.00 | 39.80 | N |
| ATOM | 1212 | CZ | ARG A | 278 | 55.819 | 40.075 | 33.957 | 1.00 | 37.53 | C |
| ATOM | 1213 | NH1 | ARG A | 278 | 55.460 | 39.035 | 33.220 | 1.00 | 36.20 | N |
| ATOM | 1214 | NH2 | ARG A | 278 | 56.895 | 40.777 | 33.628 | 1.00 | 37.01 | N |
| ATOM | 1215 | N | GLU A | 279 | 48.640 | 38.535 | 34.853 | 1.00 | 48.36 | N |
| ATOM | 1216 | CA | GLU A | 279 | 47.471 | 37.794 | 35.320 | 1.00 | 50.94 | C |
| ATOM | 1217 | C | GLU A | 279 | 47.248 | 36.513 | 34.512 | 1.00 | 50.49 | C |
| ATOM | 1218 | O | GLU A | 279 | 46.799 | 35.500 | 35.045 | 1.00 | 50.81 | O |
| ATOM | 1219 | CB | GLU A | 279 | 46.222 | 38.681 | 35.225 | 1.00 | 54.09 | C |
| ATOM | 1220 | CG | GLU A | 279 | 44.889 | 37.951 | 35.431 | 1.00 | 60.56 | C |
| ATOM | 1221 | CD | GLU A | 279 | 44.637 | 37.514 | 36.874 | 1.00 | 64.23 | C |
| ATOM | 1222 | OE1 | GLU A | 279 | 43.642 | 36.788 | 37.106 | 1.00 | 65.99 | O |
| ATOM | 1223 | OE2 | GLU A | 279 | 45.419 | 37.897 | 37.777 | 1.00 | 66.30 | O |
| ATOM | 1224 | N | LYS A | 280 | 47.586 | 36.567 | 33.230 | 1.00 | 49.08 | N |
| ATOM | 1225 | CA | LYS A | 280 | 47.399 | 35.444 | 32.323 | 1.00 | 48.34 | C |
| ATOM | 1226 | C | LYS A | 280 | 48.596 | 34.489 | 32.246 | 1.00 | 47.43 | C |
| ATOM | 1227 | O | LYS A | 280 | 48.423 | 33.286 | 32.061 | 1.00 | 47.48 | O |
| ATOM | 1228 | CB | LYS A | 280 | 47.084 | 36.000 | 30.928 | 1.00 | 50.57 | C |
| ATOM | 1229 | CG | LYS A | 280 | 46.280 | 35.093 | 30.003 | 1.00 | 53.00 | C |
| ATOM | 1230 | CD | LYS A | 280 | 47.125 | 33.994 | 29.392 | 1.00 | 55.48 | C |
| ATOM | 1231 | CE | LYS A | 280 | 46.372 | 33.274 | 28.270 | 1.00 | 56.67 | C |
| ATOM | 1232 | NZ | LYS A | 280 | 45.161 | 32.558 | 28.763 | 1.00 | 57.35 | N |
| ATOM | 1233 | N | TYR A | 281 | 49.805 | 35.019 | 32.403 | 1.00 | 45.34 | N |
| ATOM | 1234 | CA | TYR A | 281 | 51.012 | 34.208 | 32.297 | 1.00 | 41.45 | C |
| ATOM | 1235 | C | TYR A | 281 | 51.987 | 34.331 | 33.457 | 1.00 | 40.66 | C |
| ATOM | 1236 | O | TYR A | 281 | 53.025 | 33.672 | 33.457 | 1.00 | 40.87 | O |
| ATOM | 1237 | CB | TYR A | 281 | 51.773 | 34.580 | 31.028 | 1.00 | 40.75 | C |
| ATOM | 1238 | CG | TYR A | 281 | 50.998 | 34.455 | 29.742 | 1.00 | 40.09 | C |
| ATOM | 1239 | CD1 | TYR A | 281 | 50.798 | 33.211 | 29.144 | 1.00 | 40.34 | C |
| ATOM | 1240 | CD2 | TYR A | 281 | 50.507 | 35.587 | 29.091 | 1.00 | 39.82 | C |
| ATOM | 1241 | CE1 | TYR A | 281 | 50.139 | 33.099 | 27.928 | 1.00 | 39.98 | C |
| ATOM | 1242 | CE2 | TYR A | 281 | 49.841 | 35.484 | 27.877 | 1.00 | 40.22 | C |
| ATOM | 1243 | CZ | TYR A | 281 | 49.665 | 34.237 | 27.300 | 1.00 | 40.45 | C |
| ATOM | 1244 | OH | TYR A | 281 | 49.032 | 34.127 | 26.089 | 1.00 | 43.40 | O |
| ATOM | 1245 | N | GLY A | 282 | 51.679 | 35.165 | 34.440 | 1.00 | 39.75 | N |
| ATOM | 1246 | CA | GLY A | 282 | 52.617 | 35.333 | 35.533 | 1.00 | 40.40 | C |
| ATOM | 1247 | C | GLY A | 282 | 53.931 | 35.851 | 34.961 | 1.00 | 41.42 | C |
| ATOM | 1248 | O | GLY A | 282 | 53.929 | 36.614 | 33.991 | 1.00 | 38.40 | O |
| ATOM | 1249 | N | ASP A | 283 | 55.053 | 35.433 | 35.541 | 1.00 | 43.07 | N |
| ATOM | 1250 | CA | ASP A | 283 | 56.369 | 35.863 | 35.074 | 1.00 | 45.04 | C |
| ATOM | 1251 | C | ASP A | 283 | 56.955 | 34.932 | 34.008 | 1.00 | 44.74 | C |
| ATOM | 1252 | O | ASP A | 283 | 58.155 | 34.938 | 33.768 | 1.00 | 45.50 | O |
| ATOM | 1253 | CB | ASP A | 283 | 57.333 | 35.961 | 36.262 | 1.00 | 47.26 | C |
| ATOM | 1254 | CG | ASP A | 283 | 56.936 | 37.049 | 37.253 | 1.00 | 51.59 | C |
| ATOM | 1255 | OD1 | ASP A | 283 | 56.921 | 38.243 | 36.865 | 1.00 | 52.49 | O |
| ATOM | 1256 | OD2 | ASP A | 283 | 56.639 | 36.713 | 38.424 | 1.00 | 53.68 | O |
| ATOM | 1257 | N | LYS A | 284 | 56.103 | 34.143 | 33.363 | 1.00 | 45.94 | N |
| ATOM | 1258 | CA | LYS A | 284 | 56.542 | 33.197 | 32.334 | 1.00 | 46.43 | C |
| ATOM | 1259 | C | LYS A | 284 | 56.751 | 33.889 | 30.988 | 1.00 | 44.34 | C |
| ATOM | 1260 | O | LYS A | 284 | 57.530 | 33.432 | 30.152 | 1.00 | 45.10 | O |
| ATOM | 1261 | CB | LYS A | 284 | 55.510 | 32.067 | 32.182 | 1.00 | 50.03 | C |
| ATOM | 1262 | CG | LYS A | 284 | 55.898 | 30.981 | 31.181 | 1.00 | 54.57 | C |
| ATOM | 1263 | CD | LYS A | 284 | 54.819 | 29.892 | 31.055 | 1.00 | 57.10 | C |
| ATOM | 1264 | CE | LYS A | 284 | 53.656 | 30.317 | 30.157 | 1.00 | 58.56 | C |
| ATOM | 1265 | NZ | LYS A | 284 | 54.064 | 30.449 | 28.717 | 1.00 | 57.77 | N |
| ATOM | 1266 | N | VAL A | 285 | 56.036 | 34.984 | 30.775 | 1.00 | 41.89 | N |
| ATOM | 1267 | CA | VAL A | 285 | 56.163 | 35.741 | 29.539 | 1.00 | 38.65 | C |
| ATOM | 1268 | C | VAL A | 285 | 56.865 | 37.052 | 29.870 | 1.00 | 37.26 | C |
| ATOM | 1269 | O | VAL A | 285 | 56.445 | 37.785 | 30.768 | 1.00 | 36.50 | O |

TABLE 2-continued

| | | | | | | | | | | |
|---|---|---|---|---|---|---|---|---|---|---|
| ATOM | 1270 | CB | VAL A | 285 | 54.784 | 36.024 | 28.918 | 1.00 | 38.41 | C |
| ATOM | 1271 | CG1 | VAL A | 285 | 54.935 | 36.904 | 27.681 | 1.00 | 36.80 | C |
| ATOM | 1272 | CG2 | VAL A | 285 | 54.113 | 34.710 | 28.552 | 1.00 | 37.51 | C |
| ATOM | 1273 | N | LYS A | 286 | 57.947 | 37.332 | 29.151 | 1.00 | 35.95 | N |
| ATOM | 1274 | CA | LYS A | 286 | 58.724 | 38.542 | 29.382 | 1.00 | 34.21 | C |
| ATOM | 1275 | C | LYS A | 286 | 58.260 | 39.677 | 28.485 | 1.00 | 32.46 | C |
| ATOM | 1276 | O | LYS A | 286 | 58.006 | 39.482 | 27.296 | 1.00 | 32.56 | O |
| ATOM | 1277 | CB | LYS A | 286 | 60.215 | 38.262 | 29.151 | 1.00 | 34.13 | C |
| ATOM | 1278 | CG | LYS A | 286 | 60.755 | 37.082 | 29.955 | 1.00 | 34.78 | C |
| ATOM | 1279 | CD | LYS A | 286 | 60.443 | 37.214 | 31.439 | 1.00 | 33.84 | C |
| ATOM | 1280 | CE | LYS A | 286 | 61.080 | 36.077 | 32.238 | 1.00 | 33.85 | C |
| ATOM | 1281 | NZ | LYS A | 286 | 60.846 | 36.204 | 33.710 | 1.00 | 34.7& | N |
| ATOM | 1282 | N | VAL A | 287 | 58.154 | 40.867 | 29.062 | 1.00 | 30.53 | N |
| ATOM | 1283 | CA | VAL A | 287 | 57.702 | 42.028 | 28.311 | 1.00 | 29.76 | C |
| ATOM | 1284 | C | VAL A | 287 | 58.419 | 43.317 | 28.697 | 1.00 | 28.61 | C |
| ATOM | 1285 | O | VAL A | 287 | 58.390 | 43.744 | 29.856 | 1.00 | 29.71 | O |
| ATOM | 1286 | CB | VAL A | 287 | 56.160 | 42.221 | 28.472 | 1.00 | 28.44 | C |
| ATOM | 1287 | CG1 | VAL A | 287 | 55.785 | 42.274 | 29.938 | 1.00 | 29.00 | C |
| ATOM | 1288 | CG2 | VAL A | 287 | 55.707 | 43.487 | 27.769 | 1.00 | 28.47 | C |
| ATOM | 1289 | N | GLY A | 288 | 59.078 | 43.920 | 27.716 | 1.00 | 29.14 | N |
| ATOM | 1290 | CA | GLY A | 288 | 59.766 | 45.177 | 27.941 | 1.00 | 28.04 | C |
| ATOM | 1291 | C | GLY A | 288 | 58.759 | 46.288 | 27.721 | 1.00 | 28.71 | C |
| ATOM | 1292 | O | GLY A | 288 | 57.760 | 46.089 | 27.023 | 1.00 | 29.59 | O |
| ATOM | 1293 | N | ALA A | 289 | 59.007 | 47.454 | 28.310 | 1.00 | 28.36 | N |
| ATOM | 1294 | CA | ALA A | 289 | 58.090 | 48.585 | 28.174 | 1.00 | 28.55 | C |
| ATOM | 1295 | C | ALA A | 289 | 58.855 | 49.883 | 27.902 | 1.00 | 29.25 | C |
| ATOM | 1296 | O | ALA A | 289 | 60.075 | 49.921 | 28.034 | 1.00 | 30.12 | O |
| ATOM | 1297 | CB | ALA A | 289 | 57.242 | 48.720 | 29.444 | 1.00 | 26.88 | C |
| ATOM | 1298 | N | GLY A | 290 | 58.136 | 50.938 | 27.525 | 1.00 | 28.43 | N |
| ATOM | 1299 | CA | GLY A | 290 | 58.779 | 52.209 | 27.232 | 1.00 | 28.28 | C |
| ATOM | 1300 | C | GLY A | 290 | 58.137 | 52.867 | 26.021 | 1.00 | 29.46 | C |
| ATOM | 1301 | O | GLY A | 290 | 57.142 | 52.357 | 25.512 | 1.00 | 29.19 | O |
| ATOM | 1302 | N | ASN A | 291 | 58.700 | 53.969 | 25.523 | 1.00 | 28.11 | N |
| ATOM | 1303 | CA | ASM A | 291 | 59.918 | 54.586 | 26.053 | 1.00 | 27.63 | C |
| ATOM | 1304 | C | ASN A | 291 | 59.689 | 55.673 | 27.101 | 1.00 | 27.03 | C |
| ATOM | 1305 | O | ASN A | 291 | 58.656 | 56.336 | 27.113 | 1.00 | 26.50 | O |
| ATOM | 1306 | CB | ASN A | 291 | 60.723 | 55.200 | 24.902 | 1.00 | 24.57 | C |
| ATOM | 1307 | CG | ASN A | 291 | 61.251 | 54.163 | 23.946 | 1.00 | 27.24 | C |
| ATOM | 1308 | OD1 | ASN A | 291 | 60.850 | 52.994 | 23.990 | 1.00 | 28.22 | O |
| ATOM | 1309 | ND2 | ASN A | 291 | 62.157 | 54.577 | 23.069 | 1.00 | 24.45 | N |
| ATOM | 1310 | N | ILE A | 292 | 60.676 | 55.848 | 27.974 | 1.00 | 25.83 | N |
| ATOM | 1311 | CA | ILE A | 292 | 60.634 | 56.884 | 28.996 | 1.00 | 26.30 | C |
| ATOM | 1312 | C | ILE A | 292 | 62.000 | 57.576 | 29.002 | 1.00 | 26.52 | C |
| ATOM | 1313 | O | ILE A | 292 | 62.943 | 57.082 | 28.376 | 1.00 | 27.26 | O |
| ATOM | 1314 | CB | ILE A | 292 | 60.286 | 56.304 | 30.399 | 1.00 | 26.90 | C |
| ATOM | 1315 | CG1 | ILE A | 292 | 61.132 | 55.066 | 30.705 | 1.00 | 27.05 | C |
| ATOM | 1316 | CG2 | ILE A | 292 | 58.801 | 55.967 | 30.458 | 1.00 | 26.39 | C |
| ATOM | 1317 | CD1 | ILE A | 292 | 62.564 | 55.368 | 31.104 | 1.00 | 28.87 | C |
| ATOM | 1318 | N | VAL A | 293 | 62.115 | 58.707 | 29.695 | 1.00 | 26.68 | N |
| ATOM | 1319 | CA | VAL A | 293 | 63.376 | 59.443 | 29.719 | 1.00 | 26.19 | C |
| ATOM | 1320 | C | VAL A | 293 | 63.856 | 59.935 | 31.080 | 1.00 | 26.51 | C |
| ATOM | 1321 | O | VAL A | 293 | 64.876 | 60.619 | 31.161 | 1.00 | 27.91 | O |
| ATOM | 1322 | CB | VAL A | 293 | 63.323 | 60.668 | 28.776 | 1.00 | 26.56 | C |
| ATOM | 1323 | CG1 | VAL A | 293 | 63.327 | 60.216 | 27.331 | 1.00 | 24.86 | C |
| ATOM | 1324 | CG2 | VAL A | 293 | 62.079 | 61.493 | 29.068 | 1.00 | 25.40 | C |
| ATOM | 1325 | N | ASP A | 294 | 63.127 | 59.618 | 32.143 | 1.00 | 26.19 | N |
| ATOM | 1326 | CA | ASP A | 294 | 63.547 | 60.039 | 33.477 | 1.00 | 27.16 | C |
| ATOM | 1327 | C | ASP A | 294 | 63.233 | 58.988 | 34.535 | 1.00 | 26.65 | C |
| ATOM | 1328 | O | ASP A | 294 | 62.595 | 57.980 | 34.245 | 1.00 | 27.20 | O |
| ATOM | 1329 | CB | ASP A | 294 | 62.909 | 61.388 | 33.860 | 1.00 | 26.43 | C |
| ATOM | 1330 | CG | ASP A | 294 | 61.385 | 61.347 | 33.903 | 1.00 | 29.29 | C |
| ATOM | 1331 | OD1 | ASP A | 294 | 60.770 | 60.309 | 33.581 | 1.00 | 29.96 | O |
| ATOM | 1332 | OD2 | ASP A | 294 | 60.791 | 62.383 | 34.262 | 1.00 | 31.71 | O |
| ATOM | 1333 | N | GLY A | 295 | 63.693 | 59.232 | 35.757 | 1.00 | 27.62 | N |
| ATOM | 1334 | CA | GLY A | 295 | 63.462 | 58.303 | 36.846 | 1.00 | 29.92 | C |
| ATOM | 1335 | C | GLY A | 295 | 62.004 | 57.997 | 37.127 | 1.00 | 30.82 | C |
| ATOM | 1336 | O | GLY A | 295 | 61.661 | 56.861 | 37.445 | 1.00 | 30.01 | O |
| ATOM | 1337 | N | GLU A | 296 | 61.146 | 59.009 | 37.025 | 1.00 | 32.13 | N |
| ATOM | 1338 | CA | GLU A | 296 | 59.713 | 58.831 | 37.265 | 1.00 | 31.92 | C |
| ATOM | 1339 | C | GLU A | 296 | 59.111 | 57.859 | 36.263 | 1.00 | 29.81 | C |
| ATOM | 1340 | O | GLU A | 296 | 58.331 | 56.989 | 36.631 | 1.00 | 30.09 | O |
| ATOM | 1341 | CB | GLU A | 296 | 58.977 | 60.169 | 37.157 | 1.00 | 35.45 | C |
| ATOM | 1342 | CG | GLU A | 296 | 58.989 | 61.006 | 38.413 | 1.00 | 42.92 | C |
| ATOM | 1343 | CD | GLU A | 296 | 58.284 | 62.338 | 38.215 | 1.00 | 48.68 | C |
| ATOM | 1344 | OE1 | GLU A | 296 | 57.151 | 62.350 | 37.669 | 1.00 | 50.17 | O |
| ATOM | 1345 | OE2 | GLU A | 296 | 58.865 | 63.375 | 38.609 | 1.00 | 51.29 | O |
| ATOM | 1346 | N | GLY A | 297 | 59.471 | 58.024 | 34.994 | 1.00 | 29.22 | N |
| ATOM | 1347 | CA | GLY A | 297 | 58.961 | 57.146 | 33.954 | 1.00 | 29.30 | C |
| ATOM | 1348 | C | GLY A | 297 | 59.453 | 55.721 | 34.150 | 1.00 | 28.85 | C |

TABLE 2-continued

| | | | | | | | | | | |
|---|---|---|---|---|---|---|---|---|---|---|
| ATOM | 1349 | O | GLY A | 297 | 58.703 | 54.764 | 33.950 | 1.00 | 30.00 | O |
| ATOM | 1350 | N | PHE A | 298 | 60.721 | 55.585 | 34.529 | 1.00 | 27.55 | N |
| ATOM | 1351 | CA | PHE A | 298 | 61.325 | 54.276 | 34.783 | 1.00 | 28.20 | C |
| ATOM | 1352 | C | PHE A | 298 | 60.572 | 53.592 | 35.921 | 1.00 | 28.81 | C |
| ATOM | 1353 | O | PHE A | 298 | 60.127 | 52.453 | 35.797 | 1.00 | 29.70 | O |
| ATOM | 1354 | CB | PHE A | 298 | 62.793 | 54.432 | 35.205 | 1.00 | 26.54 | C |
| ATOM | 1355 | CG | PHE A | 298 | 63.403 | 53.164 | 35.747 | 1.00 | 27.42 | C |
| ATOM | 1356 | CD1 | PHE A | 298 | 63.930 | 52.206 | 34.890 | 1.00 | 25.96 | C |
| ATOM | 1357 | CD2 | PHE A | 298 | 63.380 | 52.895 | 37.112 | 1.00 | 28.67 | C |
| ATOM | 1358 | CE1 | PHE A | 298 | 64.419 | 50.995 | 35.381 | 1.00 | 27.00 | C |
| ATOM | 1359 | CE2 | PHE A | 298 | 63.865 | 51.687 | 37.615 | 1.00 | 29.28 | C |
| ATOM | 1360 | CZ | PHE A | 298 | 64.385 | 50.732 | 36.745 | 1.00 | 26.48 | C |
| ATOM | 1361 | N | ARG A | 299 | 60.460 | 54.319 | 37.030 | 1.00 | 29.81 | N |
| ATOM | 1362 | CA | ARG A | 299 | 59.801 | 53.868 | 38.252 | 1.00 | 31.20 | C |
| ATOM | 1363 | C | ARG A | 299 | 58.372 | 53.388 | 38.000 | 1.00 | 31.34 | C |
| ATOM | 1364 | O | ARG A | 299 | 57.948 | 52.355 | 38.529 | 1.00 | 30.36 | O |
| ATOM | 1365 | CB | ARG A | 299 | 59.811 | 55.020 | 39.257 | 1.00 | 33.79 | C |
| ATOM | 1366 | CG | ARG A | 299 | 58.887 | 54.867 | 40.443 | 1.00 | 39.24 | C |
| ATOM | 1367 | CD | ARG A | 299 | 59.563 | 54.163 | 41.591 | 1.00 | 43.20 | C |
| ATOM | 1368 | NE | ARG A | 299 | 60.787 | 54.835 | 42.029 | 1.00 | 46.01 | N |
| ATOM | 1369 | CZ | ARG A | 299 | 61.578 | 54.359 | 42.989 | 1.00 | 46.27 | C |
| ATOM | 1370 | NH1 | ARG A | 299 | 61.261 | 53.226 | 43.597 | 1.00 | 46.49 | N |
| ATOM | 1371 | NH2 | ARG A | 299 | 62.691 | 54.996 | 43.329 | 1.00 | 46.82 | N |
| ATOM | 1372 | N | TYR A | 300 | 57.630 | 54.135 | 37.192 | 1.00 | 29.36 | N |
| ATOM | 1373 | CA | TYR A | 300 | 56.263 | 53.752 | 36.886 | 1.00 | 30.10 | C |
| ATOM | 1374 | C | TYR A | 300 | 56.209 | 52.406 | 36.160 | 1.00 | 29.41 | C |
| ATOM | 1375 | O | TYR A | 300 | 55.416 | 51.538 | 36.510 | 1.00 | 29.12 | O |
| ATOM | 1376 | CB | TYR A | 300 | 55.584 | 54.813 | 36.025 | 1.00 | 28.91 | C |
| ATOM | 1377 | CG | TYR A | 300 | 54.123 | 54.518 | 35.770 | 1.00 | 28.90 | C |
| ATOM | 1378 | CD1 | TYR A | 300 | 53.152 | 54.795 | 36.737 | 1.00 | 27.98 | C |
| ATOM | 1379 | CD2 | TYR A | 300 | 53.712 | 53.960 | 34.562 | 1.00 | 27.83 | C |
| ATOM | 1380 | CE1 | TYR A | 300 | 51.799 | 54.526 | 36.497 | 1.00 | 28.93 | C |
| ATOM | 1381 | CE2 | TYR A | 300 | 52.368 | 53.687 | 34.314 | 1.00 | 29.78 | C |
| ATOM | 1382 | CZ | TYR A | 300 | 51.419 | 53.974 | 35.284 | 1.00 | 28.36 | C |
| ATOM | 1383 | OH | TYR A | 300 | 50.098 | 53.722 | 35.019 | 1.00 | 28.95 | O |
| ATOM | 1384 | N | LEU A | 301 | 57.047 | 52.230 | 35.145 | 1.00 | 29.18 | N |
| ATOM | 1385 | CA | LEU A | 301 | 57.037 | 50.970 | 34.416 | 1.00 | 29.02 | C |
| ATOM | 1386 | C | LEU A | 301 | 57.645 | 49.845 | 35.257 | 1.00 | 29.33 | C |
| ATOM | 1387 | O | LEU A | 301 | 57.286 | 48.685 | 35.098 | 1.00 | 30.06 | O |
| ATOM | 1388 | CB | LEU A | 301 | 57.768 | 51.119 | 33.079 | 1.00 | 25.76 | C |
| ATOM | 1389 | CG | LEU A | 301 | 57.063 | 52.069 | 32.093 | 1.00 | 26.66 | C |
| ATOM | 1390 | CD1 | LEU A | 301 | 57.839 | 52.143 | 30.770 | 1.00 | 20.87 | C |
| ATOM | 1391 | CD2 | LEU A | 301 | 55.631 | 51.577 | 31.848 | 1.00 | 24.96 | C |
| ATOM | 1392 | N | ALA A | 302 | 58.551 | 50.192 | 36.163 | 1.00 | 29.71 | N |
| ATOM | 1393 | CA | ALA A | 302 | 59.165 | 49.184 | 37.019 | 1.00 | 31.15 | C |
| ATOM | 1394 | C | ALA A | 302 | 58.093 | 48.588 | 37.946 | 1.00 | 31.17 | C |
| ATOM | 1395 | O | ALA A | 302 | 57.913 | 47.371 | 38.003 | 1.00 | 31.11 | O |
| ATOM | 1396 | CB | ALA A | 302 | 60.300 | 49.804 | 37.835 | 1.00 | 27.53 | C |
| ATOM | 1397 | N | ASP A | 303 | 57.381 | 49.455 | 38.660 | 1.00 | 31.61 | N |
| ATOM | 1398 | CA | ASP A | 303 | 56.327 | 49.016 | 39.565 | 1.00 | 32.39 | C |
| ATOM | 1399 | C | ASP A | 303 | 55.221 | 48.296 | 38.811 | 1.00 | 32.86 | C |
| ATOM | 1400 | O | ASP A | 303 | 54.541 | 47.442 | 39.381 | 1.00 | 33.19 | O |
| ATOM | 1401 | CB | ASP A | 303 | 55.723 | 50.201 | 40.328 | 1.00 | 33.54 | C |
| ATOM | 1402 | CG | ASP A | 303 | 56.701 | 50.831 | 41.301 | 1.00 | 36.75 | C |
| ATOM | 1403 | OD1 | ASP A | 303 | 57.613 | 50.123 | 41.785 | 1.00 | 37.27 | O |
| ATOM | 1404 | OD2 | ASP A | 303 | 56.546 | 52.033 | 41.601 | 1.00 | 39.52 | O |
| ATOM | 1405 | N | ALA A | 304 | 55.034 | 48.649 | 37.540 | 1.00 | 31.74 | N |
| ATOM | 1406 | CA | ALA A | 304 | 54.010 | 48.017 | 36.708 | 1.00 | 31.41 | C |
| ATOM | 1407 | C | ALA A | 304 | 54.434 | 46.596 | 36.310 | 1.00 | 31.41 | C |
| ATOM | 1408 | O | ALA A | 304 | 53.621 | 45.813 | 35.818 | 1.00 | 30.05 | O |
| ATOM | 1409 | CB | ALA A | 304 | 53.741 | 48.858 | 35.460 | 1.00 | 30.00 | C |
| ATOM | 1410 | N | GLY A | 305 | 55.711 | 46.272 | 36.505 | 1.00 | 31.95 | N |
| ATOM | 1411 | CA | GLY A | 305 | 56.179 | 44.929 | 36.195 | 1.00 | 31.25 | C |
| ATOM | 1412 | C | GLY A | 305 | 57.000 | 44.673 | 34.944 | 1.00 | 32.68 | C |
| ATOM | 1413 | O | GLY A | 305 | 57.279 | 43.513 | 34.620 | 1.00 | 33.06 | O |
| ATOM | 1414 | N | ALA A | 306 | 57.397 | 45.727 | 34.236 | 1.00 | 31.70 | N |
| ATOM | 1415 | CA | ALA A | 306 | 58.192 | 45.560 | 33.018 | 1.00 | 31.42 | C |
| ATOM | 1416 | C | ALA A | 306 | 59.463 | 44.744 | 33.294 | 1.00 | 30.89 | C |
| ATOM | 1417 | O | ALA A | 306 | 60.067 | 44.875 | 34.358 | 1.00 | 30.03 | O |
| ATOM | 1418 | CB | ALA A | 306 | 58.564 | 46.934 | 32.450 | 1.00 | 30.33 | C |
| ATOM | 1419 | N | ASP A | 307 | 59.864 | 43.911 | 32.334 | 1.00 | 30.79 | N |
| ATOM | 1420 | CA | ASP A | 307 | 61.070 | 43.085 | 32.472 | 1.00 | 30.22 | C |
| ATOM | 1421 | C | ASP A | 307 | 62.337 | 43.837 | 32.044 | 1.00 | 29.80 | C |
| ATOM | 1422 | O | ASP A | 307 | 63.449 | 43.468 | 32.407 | 1.00 | 29.77 | O |
| ATOM | 1423 | CB | ASP A | 307 | 60.908 | 41.790 | 31.673 | 1.00 | 29.98 | C |
| ATOM | 1424 | CG | ASP A | 307 | 59.931 | 40.835 | 32.328 | 1.00 | 31.85 | C |
| ATOM | 1425 | OD1 | ASP A | 307 | 60.267 | 40.310 | 33.407 | 1.00 | 30.41 | O |
| ATOM | 1426 | OD2 | ASP A | 307 | 58.826 | 40.626 | 31.783 | 1.00 | 32.28 | O |
| ATOM | 1427 | N | PHE A | 308 | 62.153 | 44.876 | 31.242 | 1.00 | 28.99 | N |

TABLE 2-continued

| | | | | | | | | | | |
|---|---|---|---|---|---|---|---|---|---|---|
| ATOM | 1428 | CA | PHE A | 308 | 63.243 | 45.742 | 30.819 | 1.00 | 28.95 | C |
| ATOM | 1429 | C | PHE A | 308 | 62.560 | 47.025 | 30.362 | 1.00 | 29.95 | C |
| ATOM | 1430 | O | PHE A | 308 | 61.395 | 47.009 | 29.958 | 1.00 | 29.34 | O |
| ATOM | 1431 | CB | PHE A | 308 | 64.141 | 45.087 | 29.742 | 1.00 | 27.92 | C |
| ATOM | 1432 | CG | PHE A | 308 | 63.582 | 45.092 | 28.339 | 1.00 | 29.45 | C |
| ATOM | 1433 | CD1 | PHE A | 308 | 63.520 | 46.272 | 27.594 | 1.00 | 29.48 | C |
| ATOM | 1434 | CD2 | PHE A | 308 | 63.193 | 43.894 | 27.729 | 1.00 | 29.25 | C |
| ATOM | 1435 | CE1 | PHE A | 308 | 63.085 | 46.259 | 26.263 | 1.00 | 28.89 | C |
| ATOM | 1436 | CE2 | PHE A | 308 | 62.757 | 43.870 | 26.398 | 1.00 | 28.70 | C |
| ATOM | 1437 | CZ | PHE A | 308 | 62.704 | 45.056 | 25.664 | 1.00 | 29.12 | C |
| ATOM | 1438 | N | ILE A | 309 | 63.266 | 48.141 | 30.475 | 1.00 | 29.18 | N |
| ATOM | 1439 | CA | ILE A | 309 | 62.685 | 49.425 | 30.127 | 1.00 | 29.21 | C |
| ATOM | 1440 | C | ILE A | 309 | 63.497 | 50.150 | 29.061 | 1.00 | 27.84 | C |
| ATOM | 1441 | O | ILE A | 309 | 64.719 | 50.258 | 29.172 | 1.00 | 26.04 | O |
| ATOM | 1442 | CB | ILE A | 309 | 62.539 | 50.284 | 31.422 | 1.00 | 27.91 | C |
| ATOM | 1443 | CG1 | ILE A | 309 | 61.524 | 49.602 | 32.353 | 1.00 | 26.47 | C |
| ATOM | 1444 | CG2 | ILE A | 309 | 62.123 | 51.703 | 31.082 | 1.00 | 27.10 | C |
| ATOM | 1445 | CD1 | ILE A | 309 | 61.390 | 50.207 | 33.733 | 1.00 | 25.58 | C |
| ATOM | 1446 | N | LYS A | 310 | 62.813 | 50.616 | 28.015 | 1.00 | 27.18 | N |
| ATOM | 1447 | CA | LYS A | 310 | 63.480 | 51.322 | 26.926 | 1.00 | 28.54 | C |
| ATOM | 1448 | C | LYS A | 310 | 63.537 | 52.827 | 27.149 | 1.00 | 27.05 | C |
| ATOM | 1449 | O | LYS A | 310 | 62.550 | 53.460 | 27.529 | 1.00 | 26.03 | O |
| ATOM | 1450 | CB | LYS A | 310 | 62.817 | 51.030 | 25.573 | 1.00 | 28.97 | C |
| ATOM | 1451 | CG | LYS A | 310 | 63.170 | 49.671 | 25.012 | 1.00 | 32.45 | C |
| ATOM | 1452 | CD | LYS A | 310 | 63.175 | 49.652 | 23.488 | 1.00 | 28.69 | C |
| ATOM | 1453 | CE | LYS A | 310 | 61.783 | 49.797 | 22.894 | 1.00 | 30.25 | C |
| ATOM | 1454 | NZ | LYS A | 310 | 61.577 | 51.156 | 22.318 | 1.00 | 30.02 | N |
| ATOM | 1455 | N | ILE A | 311 | 64.713 | 53.380 | 26.880 | 1.00 | 26.50 | N |
| ATOM | 1456 | CA | ILE A | 311 | 64.988 | 54.799 | 27.061 | 1.00 | 25.97 | C |
| ATOM | 1457 | C | ILE A | 311 | 65.140 | 55.546 | 25.744 | 1.00 | 26.10 | C |
| ATOM | 1458 | O | ILE A | 311 | 65.875 | 55.115 | 24.854 | 1.00 | 24.93 | O |
| ATOM | 1459 | CB | ILE A | 311 | 66.297 | 54.995 | 27.851 | 1.00 | 24.14 | C |
| ATOM | 1460 | CG1 | ILE A | 311 | 66.229 | 54.208 | 29.162 | 1.00 | 23.37 | C |
| ATOM | 1461 | CG2 | ILE A | 311 | 66.541 | 56.493 | 28.113 | 1.00 | 21.90 | C |
| ATOM | 1462 | CD1 | ILE A | 311 | 67.585 | 53.999 | 29.821 | 1.00 | 22.04 | C |
| ATOM | 1463 | N | GLY A | 312 | 64.440 | 56.668 | 25.619 | 1.00 | 27.44 | N |
| ATOM | 1464 | CA | GLY A | 312 | 64.587 | 57.453 | 24.417 | 1.00 | 29.07 | C |
| ATOM | 1465 | C | GLY A | 312 | 63.364 | 58.017 | 23.740 | 1.00 | 31.30 | C |
| ATOM | 1466 | O | GLY A | 312 | 62.499 | 57.284 | 23.281 | 1.00 | 32.02 | O |
| ATOM | 1467 | N | ILE A | 313 | 63.316 | 59.342 | 23.671 | 1.00 | 34.02 | N |
| ATOM | 1468 | CA | ILE A | 313 | 62.242 | 60.063 | 23.005 | 1.00 | 35.18 | C |
| ATOM | 1469 | C | ILE A | 313 | 62.860 | 61.264 | 22.294 | 1.00 | 36.95 | C |
| ATOM | 1470 | O | ILE A | 313 | 63.446 | 62.143 | 22.937 | 1.00 | 33.67 | O |
| ATOM | 1471 | CB | ILE A | 313 | 61.184 | 60.588 | 23.991 | 1.00 | 35.37 | C |
| ATOM | 1472 | CG1 | ILE A | 313 | 60.488 | 59.419 | 24.697 | 1.00 | 37.50 | C |
| ATOM | 1473 | CG2 | ILE A | 313 | 60.161 | 61.420 | 23.236 | 1.00 | 36.43 | C |
| ATOM | 1474 | CD1 | ILE A | 313 | 59.485 | 59.848 | 25.762 | 1.00 | 34.44 | C |
| ATOM | 1475 | N | GLY A | 314 | 62.744 | 61.280 | 20.968 | 1.00 | 39.08 | N |
| ATOM | 1476 | CA | GLY A | 314 | 63.269 | 62.384 | 20.180 | 1.00 | 42.63 | C |
| ATOM | 1477 | C | GLY A | 314 | 64.709 | 62.259 | 19.711 | 1.00 | 45.06 | C |
| ATOM | 1478 | O | GLY A | 314 | 65.204 | 63.127 | 18.984 | 1.00 | 46.48 | O |
| ATOM | 1479 | N | GLY A | 315 | 65.383 | 61.186 | 20.111 | 1.00 | 45.85 | N |
| ATOM | 1480 | CA | GLY A | 315 | 66.767 | 60.997 | 19.716 | 1.00 | 47.36 | C |
| ATOM | 1481 | C | GLY A | 315 | 66.970 | 60.175 | 18.456 | 1.00 | 48.37 | C |
| ATOM | 1482 | O | GLY A | 315 | 68.067 | 60.169 | 17.901 | 1.00 | 48.87 | O |
| ATOM | 1483 | N | GLY A | 316 | 65.929 | 59.482 | 18.002 | 1.00 | 49.42 | N |
| ATOM | 1484 | CA | GLY A | 316 | 66.042 | 58.666 | 16.802 | 1.00 | 50.45 | C |
| ATOM | 1485 | C | GLY A | 316 | 66.512 | 59.444 | 15.581 | 1.00 | 52.07 | C |
| ATOM | 1486 | O | GLY A | 316 | 66.307 | 60.655 | 15.492 | 1.00 | 51.74 | O |
| ATOM | 1487 | N | SER A | 317 | 67.137 | 58.748 | 14.634 | 1.00 | 53.21 | N |
| ATOM | 1488 | CA | SER A | 317 | 67.640 | 59.384 | 13.417 | 1.00 | 55.05 | C |
| ATOM | 1489 | C | SER A | 317 | 66.513 | 59.886 | 12.519 | 1.00 | 56.78 | C |
| ATOM | 1490 | O | SER A | 317 | 66.689 | 60.855 | 11.782 | 1.00 | 57.20 | O |
| ATOM | 1491 | CB | SER A | 317 | 68.529 | 58.413 | 12.629 | 1.00 | 53.62 | C |
| ATOM | 1492 | OG | SER A | 317 | 67.769 | 57.378 | 12.034 | 1.00 | 52.76 | O |
| ATOM | 1493 | N | ILE A | 318 | 65.360 | 59.226 | 12.575 | 1.00 | 59.64 | N |
| ATOM | 1494 | CA | ILE A | 318 | 64.210 | 59.634 | 11.770 | 1.00 | 63.21 | C |
| ATOM | 1495 | C | ILE A | 318 | 63.236 | 60.457 | 12.599 | 1.00 | 65.18 | C |
| ATOM | 1496 | O | ILE A | 318 | 62.033 | 60.454 | 12.337 | 1.00 | 66.41 | O |
| ATOM | 1497 | CB | ILE A | 318 | 63.425 | 58.425 | 11.193 | 1.00 | 62.53 | C |
| ATOM | 1498 | CG1 | ILE A | 318 | 62.907 | 57.531 | 12.325 | 1.00 | 61.87 | C |
| ATOM | 1499 | CG2 | ILE A | 318 | 64.292 | 57.668 | 10.216 | 1.00 | 63.60 | C |
| ATOM | 1500 | CD1 | ILE A | 318 | 63.986 | 56.875 | 13.169 | 1.00 | 63.20 | C |
| HETATM | 1501 | N | CSO A | 319 | 63.755 | 61.160 | 13.601 | 1.00 | 67.42 | N |
| HETATM | 1502 | CA | CSO A | 319 | 62.906 | 61.974 | 14.457 | 1.00 | 69.97 | C |
| HETATM | 1503 | CB | CSO A | 319 | 62.908 | 61.424 | 15.883 | 1.00 | 69.24 | C |
| HETATM | 1504 | SG | CSO A | 319 | 61.855 | 62.386 | 17.013 | 1.00 | 71.47 | S |
| HETATM | 1505 | C | CSO A | 319 | 63.286 | 63.449 | 14.489 | 1.00 | 71.57 | C |
| HETATM | 1506 | O | CSO A | 319 | 64.383 | 63.812 | 14.916 | 1.00 | 71.62 | O |

TABLE 2-continued

| | | | | | | | | | | |
|---|---|---|---|---|---|---|---|---|---|---|
| HETATM | 1507 | OD | CSO A | 319 | 60.102 | 62.492 | 16.543 | 1.00 | 68.93 | O |
| ATOM | 1508 | N | ILE A | 320 | 62.363 | 64.292 | 14.035 | 1.00 | 73.78 | N |
| ATOM | 1509 | CA | ILE A | 320 | 62.568 | 65.736 | 14.026 | 1.00 | 75.95 | C |
| ATOM | 1510 | C | ILE A | 320 | 61.613 | 66.330 | 15.064 | 1.00 | 77.00 | C |
| ATOM | 1511 | O | ILE A | 320 | 60.712 | 67.099 | 14.730 | 1.00 | 77.56 | O |
| ATOM | 1512 | CB | ILE A | 320 | 62.250 | 66.346 | 12.636 | 1.00 | 76.42 | C |
| ATOM | 1513 | CG1 | ILE A | 320 | 62.907 | 65.512 | 11.529 | 1.00 | 76.94 | C |
| ATOM | 1514 | CG2 | ILE A | 320 | 62.740 | 67.793 | 12.577 | 1.00 | 76.02 | C |
| ATOM | 1515 | CD1 | ILE A | 320 | 64.419 | 65.396 | 11.639 | 1.00 | 77.38 | C |
| ATOM | 1516 | N | THR A | 321 | 61.821 | 65.948 | 16.322 | 1.00 | 78.28 | N |
| ATOM | 1517 | CA | THR A | 321 | 61.000 | 66.397 | 17.448 | 1.00 | 79.55 | C |
| ATOM | 1518 | C | THR A | 321 | 60.432 | 67.809 | 17.303 | 1.00 | 79.96 | C |
| ATOM | 1519 | O | THR A | 321 | 59.222 | 68.014 | 17.421 | 1.00 | 79.36 | O |
| ATOM | 1520 | CB | THR A | 321 | 61.798 | 66.340 | 18.767 | 1.00 | 79.97 | C |
| ATOM | 1521 | OG1 | THR A | 321 | 62.325 | 65.020 | 18.951 | 1.00 | 80.89 | O |
| ATOM | 1522 | CG2 | THR A | 321 | 60.902 | 66.688 | 19.942 | 1.00 | 79.20 | C |
| ATOM | 1523 | N | ARG A | 322 | 61.312 | 68.776 | 17.057 | 1.00 | 80.56 | N |
| ATOM | 1524 | CA | ARG A | 322 | 60.911 | 70.173 | 16.903 | 1.00 | 81.44 | C |
| ATOM | 1525 | C | ARG A | 322 | 60.282 | 70.402 | 15.533 | 1.00 | 80.96 | C |
| ATOM | 1526 | O | ARG A | 322 | 60.658 | 71.317 | 14.796 | 1.00 | 81.59 | O |
| ATOM | 1527 | CB | ARG A | 322 | 62.128 | 71.076 | 17.090 | 1.00 | 82.63 | C |
| ATOM | 1528 | CG | ARG A | 322 | 62.904 | 70.739 | 18.345 | 1.00 | 84.75 | C |
| ATOM | 1529 | CD | ARG A | 322 | 64.194 | 71.520 | 18.459 | 1.00 | 85.81 | C |
| ATOM | 1530 | NE | ARG A | 322 | 65.052 | 70.945 | 19.491 | 1.00 | 86.61 | N |
| ATOM | 1531 | CZ | ARG A | 322 | 66.238 | 71.432 | 19.834 | 1.00 | 87.87 | C |
| ATOM | 1532 | NH1 | ARG A | 322 | 66.711 | 72.512 | 19.226 | 1.00 | 88.28 | N |
| ATOM | 1533 | NH2 | ARG A | 322 | 66.955 | 70.831 | 20.775 | 1.00 | 88.07 | N |
| ATOM | 1534 | N | GLU A | 323 | 59.318 | 69.549 | 15.211 | 1.00 | 79.65 | N |
| ATOM | 1535 | CA | GLU A | 323 | 58.595 | 69.596 | 13.949 | 1.00 | 78.09 | C |
| ATOM | 1536 | C | GLU A | 323 | 57.395 | 68.679 | 14.153 | 1.00 | 76.08 | C |
| ATOM | 1537 | O | GLU A | 323 | 56.482 | 68.618 | 13.328 | 1.00 | 75.54 | O |
| ATOM | 1538 | CB | GLU A | 323 | 59.485 | 69.078 | 12.818 | 1.00 | 79.51 | C |
| ATOM | 1539 | CG | GLU A | 323 | 58.886 | 69.206 | 11.429 | 1.00 | 82.04 | C |
| ATOM | 1540 | CD | GLU A | 323 | 59.856 | 68.784 | 10.341 | 1.00 | 83.25 | C |
| ATOM | 1541 | OE1 | GLU A | 323 | 60.262 | 67.601 | 10.328 | 1.00 | 84.45 | O |
| ATOM | 1542 | OE2 | GLU A | 323 | 60.216 | 69.638 | 9.501 | 1.00 | 83.53 | O |
| ATOM | 1543 | N | GLN A | 324 | 57.419 | 67.969 | 15.278 | 1.00 | 73.73 | N |
| ATOM | 1544 | CA | GLN A | 324 | 56.358 | 67.047 | 15.656 | 1.00 | 70.84 | C |
| ATOM | 1545 | C | GLN A | 324 | 55.584 | 67.624 | 16.841 | 1.00 | 67.80 | C |
| ATOM | 1546 | O | GLN A | 324 | 54.752 | 68.516 | 16.665 | 1.00 | 68.23 | O |
| ATOM | 1547 | CB | GLN A | 324 | 56.951 | 65.684 | 16.028 | 1.00 | 72.52 | C |
| ATOM | 1548 | CG | GLN A | 324 | 57.667 | 64.984 | 14.883 | 1.00 | 74.98 | C |
| ATOM | 1549 | CD | GLN A | 324 | 56.732 | 64.622 | 13.740 | 1.00 | 77.08 | C |
| ATOM | 1550 | OE1 | GLN A | 324 | 56.070 | 65.485 | 13.162 | 1.00 | 78.31 | O |
| ATOM | 1551 | NE2 | GLN A | 324 | 56.678 | 63.338 | 13.407 | 1.00 | 78.07 | N |
| ATOM | 1552 | N | LYS A | 325 | 55.865 | 67.129 | 18.045 | 1.00 | 63.07 | N |
| ATOM | 1553 | CA | LYS A | 325 | 55.169 | 67.608 | 19.237 | 1.00 | 58.26 | C |
| ATOM | 1554 | C | LYS A | 325 | 56.069 | 68.271 | 20.273 | 1.00 | 54.26 | C |
| ATOM | 1555 | O | LYS A | 325 | 55.592 | 68.754 | 21.301 | 1.00 | 53.55 | O |
| ATOM | 1556 | CB | LYS A | 325 | 54.387 | 66.466 | 19.894 | 1.00 | 58.47 | C |
| ATOM | 1557 | CG | LYS A | 325 | 53.233 | 65.959 | 19.042 | 1.00 | 57.42 | C |
| ATOM | 1558 | CD | LYS A | 325 | 52.221 | 65.177 | 19.862 | 1.00 | 57.29 | C |
| ATOM | 1559 | CE | LYS A | 325 | 52.836 | 63.949 | 20.508 | 1.00 | 55.50 | C |
| ATOM | 1560 | NZ | LYS A | 325 | 51.779 | 63.110 | 21.124 | 1.00 | 55.85 | N |
| ATOM | 1561 | N | GLY A | 326 | 57.369 | 68.292 | 20.005 | 1.00 | 49.91 | N |
| ATOM | 1562 | CA | GLY A | 326 | 58.288 | 68.924 | 20.929 | 1.00 | 46.08 | C |
| ATOM | 1563 | C | GLY A | 326 | 58.462 | 68.239 | 22.271 | 1.00 | 44.72 | C |
| ATOM | 1564 | O | GLY A | 326 | 58.571 | 68.909 | 23.300 | 1.00 | 42.35 | O |
| ATOM | 1565 | N | ILE A | 327 | 58.472 | 66.908 | 22.269 | 1.00 | 42.55 | N |
| ATOM | 1566 | CA | ILE A | 327 | 58.676 | 66.151 | 23.496 | 1.00 | 41.64 | C |
| ATOM | 1567 | C | ILE A | 327 | 59.998 | 65.398 | 23.351 | 1.00 | 40.52 | C |
| ATOM | 1568 | O | ILE A | 327 | 60.387 | 65.011 | 22.248 | 1.00 | 39.17 | O |
| ATOM | 1569 | CB | ILE A | 327 | 57.526 | 65.136 | 23.764 | 1.00 | 43.00 | C |
| ATOM | 1570 | CG1 | ILE A | 327 | 57.530 | 64.026 | 22.713 | 1.00 | 43.54 | C |
| ATOM | 1571 | CG2 | ILE A | 327 | 56.179 | 65.859 | 23.752 | 1.00 | 43.95 | C |
| ATOM | 1572 | CD1 | ILE A | 327 | 56.507 | 62.920 | 22.986 | 1.00 | 45.42 | C |
| ATOM | 1573 | N | GLY A | 328 | 60.706 | 65.206 | 24.455 | 1.00 | 39.74 | N |
| ATOM | 1574 | CA | GLY A | 328 | 61.963 | 64.490 | 24.362 | 1.00 | 38.49 | C |
| ATOM | 1575 | C | GLY A | 328 | 63.040 | 64.952 | 25.321 | 1.00 | 37.48 | C |
| ATOM | 1576 | O | GLY A | 328 | 62.810 | 65.790 | 26.201 | 1.00 | 33.46 | O |
| ATOM | 1577 | N | ARG A | 329 | 64.233 | 64.399 | 25.132 | 1.00 | 35.76 | N |
| ATOM | 1578 | CA | ARG A | 329 | 65.361 | 64.723 | 25.981 | 1.00 | 34.21 | C |
| ATOM | 1579 | C | ARG A | 329 | 66.625 | 64.178 | 25.333 | 1.00 | 32.60 | C |
| ATOM | 1580 | O | ARG A | 329 | 66.592 | 63.117 | 24.719 | 1.00 | 33.20 | O |
| ATOM | 1581 | CB | ARG A | 329 | 65.152 | 64.070 | 27.353 | 1.00 | 34.78 | C |
| ATOM | 1582 | CG | ARG A | 329 | 66.083 | 64.550 | 28.441 | 1.00 | 32.95 | C |
| ATOM | 1583 | CD | ARG A | 329 | 65.843 | 63.788 | 29.726 | 1.00 | 32.61 | C |
| ATOM | 1584 | NE | ARG A | 329 | 66.249 | 64.578 | 30.881 | 1.00 | 32.32 | N |
| ATOM | 1585 | CZ | ARG A | 329 | 66.174 | 64.166 | 32.142 | 1.00 | 33.26 | C |

TABLE 2-continued

| | | | | | | | | | | |
|---|---|---|---|---|---|---|---|---|---|---|
| ATOM | 1586 | NH1 | ARG A | 329 | 65.708 | 62.956 | 32.431 | 1.00 | 31.12 | N |
| ATOM | 1587 | NH2 | ARG A | 329 | 66.561 | 64.975 | 33.118 | 1.00 | 34.83 | N |
| ATOM | 1588 | N | GLY A | 330 | 67.733 | 64.908 | 25.452 | 1.00 | 32.13 | N |
| ATOM | 1589 | CA | GLY A | 330 | 68.978 | 64.419 | 24.893 | 1.00 | 29.42 | C |
| ATOM | 1590 | C | GLY A | 330 | 69.146 | 62.988 | 25.382 | 1.00 | 27.97 | C |
| ATOM | 1591 | O | GLY A | 330 | 68.986 | 62.718 | 26.569 | 1.00 | 26.61 | O |
| ATOM | 1592 | N | GLN A | 331 | 69.455 | 62.076 | 24.469 | 1.00 | 28.50 | N |
| ATOM | 1593 | CA | GLN A | 331 | 69.611 | 60.667 | 24.801 | 1.00 | 28.43 | C |
| ATOM | 1594 | C | GLN A | 331 | 70.586 | 60.394 | 25.947 | 1.00 | 28.88 | C |
| ATOM | 1595 | O | GLN A | 331 | 70.294 | 59.570 | 26.819 | 1.00 | 29.14 | O |
| ATOM | 1596 | CB | GLN A | 331 | 70.049 | 59.876 | 23.561 | 1.00 | 28.74 | C |
| ATOM | 1597 | CG | GLN A | 331 | 69.975 | 58.362 | 23.734 | 1.00 | 30.37 | C |
| ATOM | 1598 | CD | GLN A | 331 | 68.540 | 57.846 | 23.795 | 1.00 | 34.54 | C |
| ATOM | 1599 | OE1 | GLN A | 331 | 68.288 | 56.727 | 24.250 | 1.00 | 34.07 | O |
| ATOM | 1600 | NE2 | GLN A | 331 | 67.596 | 58.655 | 23.324 | 1.00 | 32.56 | N |
| ATOM | 1601 | N | ALA A | 332 | 71.733 | 61.073 | 25.951 | 1.00 | 26.91 | N |
| ATOM | 1602 | CA | ALA A | 332 | 72.732 | 60.857 | 26.999 | 1.00 | 27.04 | C |
| ATOM | 1603 | C | ALA A | 332 | 72.165 | 61.146 | 28.389 | 1.00 | 26.51 | C |
| ATOM | 1604 | O | ALA A | 332 | 72.235 | 60.304 | 29.289 | 1.00 | 24.75 | O |
| ATOM | 1605 | CB | ALA A | 332 | 73.981 | 61.725 | 26.743 | 1.00 | 26.35 | C |
| ATOM | 1606 | N | THR A | 333 | 71.602 | 62.337 | 28.555 | 1.00 | 25.80 | N |
| ATOM | 1607 | CA | THR A | 333 | 71.021 | 62.735 | 29.828 | 1.00 | 26.22 | C |
| ATOM | 1608 | C | THR A | 333 | 69.921 | 61.763 | 30.251 | 1.00 | 26.29 | C |
| ATOM | 1609 | O | THR A | 333 | 69.798 | 61.427 | 31.430 | 1.00 | 24.39 | O |
| ATOM | 1610 | CB | THR A | 333 | 70.421 | 64.145 | 29.740 | 1.00 | 27.31 | C |
| ATOM | 1611 | OG1 | THR A | 333 | 71.440 | 65.071 | 29.336 | 1.00 | 28.44 | O |
| ATOM | 1612 | CG2 | THR A | 333 | 69.863 | 64.566 | 31.094 | 1.00 | 27.55 | C |
| ATOM | 1613 | N | ALA A | 334 | 69.128 | 61.321 | 29.276 | 1.00 | 25.58 | N |
| ATOM | 1614 | CA | ALA A | 334 | 68.040 | 60.384 | 29.520 | 1.00 | 25.32 | C |
| ATOM | 1615 | C | ALA A | 334 | 68.570 | 59.079 | 30.125 | 1.00 | 24.79 | C |
| ATOM | 1616 | O | ALA A | 334 | 68.064 | 58.603 | 31.146 | 1.00 | 24.60 | O |
| ATOM | 1617 | CB | ALA A | 334 | 67.303 | 60.094 | 28.210 | 1.00 | 24.05 | C |
| ATOM | 1618 | N | VAL A | 335 | 69.588 | 58.506 | 29.491 | 1.00 | 24.43 | N |
| ATOM | 1619 | CA | VAL A | 335 | 70.181 | 57.256 | 29.964 | 1.00 | 24.60 | C |
| ATOM | 1620 | C | VAL A | 335 | 70.774 | 57.420 | 31.362 | 1.00 | 25.20 | C |
| ATOM | 1621 | O | VAL A | 335 | 70.484 | 56.635 | 32.271 | 1.00 | 26.11 | O |
| ATOM | 1622 | CB | VAL A | 335 | 71.288 | 56.765 | 28.995 | 1.00 | 26.29 | C |
| ATOM | 1623 | CG1 | VAL A | 335 | 71.986 | 55.527 | 29.564 | 1.00 | 25.97 | C |
| ATOM | 1624 | CG2 | VAL A | 335 | 70.678 | 56.442 | 27.640 | 1.00 | 24.78 | C |
| ATOM | 1625 | N | ILE A | 336 | 71.600 | 58.448 | 31.533 | 1.00 | 25.74 | N |
| ATOM | 1626 | CA | ILE A | 336 | 72.238 | 58.713 | 32.815 | 1.00 | 26.05 | C |
| ATOM | 1627 | C | ILE A | 336 | 71.213 | 58.842 | 33.945 | 1.00 | 27.20 | C |
| ATOM | 1628 | O | ILE A | 336 | 71.395 | 58.287 | 35.030 | 1.00 | 26.21 | O |
| ATOM | 1629 | CB | ILE A | 336 | 73.084 | 59.998 | 32.744 | 1.00 | 25.46 | C |
| ATOM | 1630 | CG1 | ILE A | 336 | 74.275 | 59.769 | 31.806 | 1.00 | 24.75 | C |
| ATOM | 1631 | CG2 | ILE A | 336 | 73.552 | 60.409 | 34.141 | 1.00 | 22.41 | C |
| ATOM | 1632 | CD1 | ILE A | 336 | 75.078 | 61.022 | 31.519 | 1.00 | 26.47 | C |
| ATOM | 1633 | N | ASP A | 337 | 70.130 | 59.565 | 33.681 | 1.00 | 27.99 | N |
| ATOM | 1634 | CA | ASP A | 337 | 69.090 | 59.769 | 34.686 | 1.00 | 28.97 | C |
| ATOM | 1635 | C | ASP A | 337 | 68.318 | 58.476 | 35.001 | 1.00 | 29.22 | C |
| ATOM | 1636 | O | ASP A | 337 | 68.057 | 58.160 | 36.165 | 1.00 | 27.09 | O |
| ATOM | 1637 | CB | ASP A | 337 | 68.110 | 60.845 | 34.209 | 1.00 | 31.92 | C |
| ATOM | 1638 | CG | ASP A | 337 | 67.111 | 61.234 | 35.279 | 1.00 | 35.94 | C |
| ATOM | 1639 | OD1 | ASP A | 337 | 66.026 | 61.755 | 34.937 | 1.00 | 39.65 | O |
| ATOM | 1640 | OD2 | ASP A | 337 | 67.416 | 61.026 | 36.472 | 1.00 | 40.82 | O |
| ATOM | 1641 | N | VAL A | 338 | 67.950 | 57.739 | 33.956 | 1.00 | 27.65 | N |
| ATOM | 1642 | CA | VAL A | 338 | 67.205 | 56.502 | 34.133 | 1.00 | 26.39 | C |
| ATOM | 1643 | C | VAL A | 338 | 68.058 | 55.470 | 34.854 | 1.00 | 25.81 | C |
| ATOM | 1644 | O | VAL A | 338 | 67.575 | 54.780 | 35.748 | 1.00 | 25.37 | O |
| ATOM | 1645 | CB | VAL A | 338 | 66.720 | 55.930 | 32.771 | 1.00 | 24.93 | C |
| ATOM | 1646 | CG1 | VAL A | 338 | 66.113 | 54.545 | 32.971 | 1.00 | 23.01 | C |
| ATOM | 1647 | CG2 | VAL A | 338 | 65.677 | 56.870 | 32.155 | 1.00 | 23.63 | C |
| ATOM | 1648 | N | VAL A | 339 | 69.323 | 55.375 | 34.460 | 1.00 | 25.47 | N |
| ATOM | 1649 | CA | VAL A | 339 | 70.252 | 54.440 | 35.075 | 1.00 | 25.33 | C |
| ATOM | 1650 | C | VAL A | 339 | 70.413 | 54.711 | 36.572 | 1.00 | 27.56 | C |
| ATOM | 1651 | O | VAL A | 339 | 70.493 | 53.773 | 37.362 | 1.00 | 29.02 | O |
| ATOM | 1652 | CB | VAL A | 339 | 71.633 | 54.500 | 34.383 | 1.00 | 24.83 | C |
| ATOM | 1653 | CG1 | VAL A | 339 | 72.701 | 53.830 | 35.246 | 1.00 | 23.64 | C |
| ATOM | 1654 | CG2 | VAL A | 339 | 71.549 | 53.809 | 33.031 | 1.00 | 22.84 | C |
| ATOM | 1655 | N | ALA A | 340 | 70.458 | 55.982 | 36.962 | 1.00 | 27.28 | N |
| ATOM | 1656 | CA | ALA A | 340 | 70.596 | 56.330 | 38.374 | 1.00 | 28.29 | C |
| ATOM | 1657 | C | ALA A | 340 | 69.360 | 55.861 | 39.141 | 1.00 | 29.41 | C |
| ATOM | 1658 | O | ALA A | 340 | 69.461 | 55.348 | 40.260 | 1.00 | 29.34 | O |
| ATOM | 1659 | CB | ALA A | 340 | 70.775 | 57.835 | 38.536 | 1.00 | 25.77 | C |
| ATOM | 1660 | N | GLU A | 341 | 68.192 | 56.031 | 38.531 | 1.00 | 28.19 | N |
| ATOM | 1661 | CA | GLU A | 341 | 66.949 | 55.619 | 39.168 | 1.00 | 29.67 | C |
| ATOM | 1662 | C | GLU A | 341 | 66.878 | 54.093 | 39.245 | 1.00 | 28.17 | C |
| ATOM | 1663 | O | GLU A | 341 | 66.419 | 53.543 | 40.236 | 1.00 | 27.43 | O |
| ATOM | 1664 | CB | GLU A | 341 | 65.750 | 56.151 | 38.384 | 1.00 | 30.31 | C |

TABLE 2-continued

| | | | | | | | | | | |
|---|---|---|---|---|---|---|---|---|---|---|
| ATOM | 1665 | CG | GLU A | 341 | 64.433 | 56.116 | 39.153 | 1.00 | 33.93 | C |
| ATOM | 1666 | CD | GLU A | 341 | 64.441 | 57.036 | 40.368 | 1.00 | 36.33 | C |
| ATOM | 1667 | OE1 | GLU A | 341 | 65.031 | 58.137 | 40.294 | 1.00 | 37.90 | O |
| ATOM | 1668 | OE2 | GLU A | 341 | 63.843 | 56.668 | 41.395 | 1.00 | 37.92 | O |
| ATOM | 1669 | N | ARG A | 342 | 67.335 | 53.420 | 38.192 | 1.00 | 28.17 | N |
| ATOM | 1670 | CA | ARG A | 342 | 67.328 | 51.959 | 38.140 | 1.00 | 27.23 | C |
| ATOM | 1671 | C | ARG A | 342 | 68.220 | 51.382 | 39.241 | 1.00 | 26.35 | C |
| ATOM | 1672 | O | ARG A | 342 | 67.861 | 50.394 | 39.875 | 1.00 | 27.18 | O |
| ATOM | 1673 | CB | ARG A | 342 | 67.799 | 51.481 | 36.756 | 1.00 | 26.16 | C |
| ATOM | 1674 | CG | ARG A | 342 | 67.736 | 49.961 | 36.513 | 1.00 | 25.81 | C |
| ATOM | 1675 | CD | ARG A | 342 | 68.988 | 49.223 | 37.006 | 1.00 | 22.94 | C |
| ATOM | 1676 | NE | ARG A | 342 | 70.230 | 49.706 | 36.405 | 1.00 | 23.37 | N |
| ATOM | 1677 | CZ | ARG A | 342 | 70.606 | 49.502 | 35.141 | 1.00 | 22.98 | C |
| ATOM | 1678 | NH1 | ARG A | 342 | 69.837 | 48.816 | 34.304 | 1.00 | 22.05 | N |
| ATOM | 1679 | NH2 | ARG A | 342 | 71.771 | 49.977 | 34.713 | 1.00 | 22.35 | N |
| ATOM | 1680 | N | ASN A | 343 | 69.372 | 52.005 | 39.472 | 1.00 | 26.04 | N |
| ATOM | 1681 | CA | ASN A | 343 | 70.288 | 51.542 | 40.510 | 1.00 | 27.90 | C |
| ATOM | 1682 | C | ASN A | 343 | 69.715 | 51.821 | 41.902 | 1.00 | 30.25 | C |
| ATOM | 1683 | O | ASN A | 343 | 69.891 | 51.030 | 42.827 | 1.00 | 31.34 | O |
| ATOM | 1684 | CB | ASN A | 343 | 71.662 | 52.202 | 40.353 | 1.00 | 25.88 | C |
| ATOM | 1685 | CG | ASN A | 343 | 72.379 | 51.755 | 39.086 | 1.00 | 28.08 | C |
| ATOM | 1686 | OD1 | ASN A | 343 | 72.029 | 50.729 | 38.494 | 1.00 | 26.63 | O |
| ATOM | 1687 | ND2 | ASN A | 343 | 73.396 | 52.510 | 38.674 | 1.00 | 26.34 | N |
| ATOM | 1688 | N | LYS A | 344 | 69.017 | 52.941 | 42.043 | 1.00 | 31.32 | N |
| ATOM | 1689 | CA | LYS A | 344 | 68.392 | 53.296 | 43.308 | 1.00 | 34.03 | C |
| ATOM | 1690 | C | LYS A | 344 | 67.296 | 52.260 | 43.561 | 1.00 | 33.69 | C |
| ATOM | 1691 | O | LYS A | 344 | 67.151 | 51.736 | 44.668 | 1.00 | 34.47 | O |
| ATOM | 1692 | CB | LYS A | 344 | 67.791 | 54.705 | 43.209 | 1.00 | 36.27 | C |
| ATOM | 1693 | CG | LYS A | 344 | 67.106 | 55.221 | 44.467 | 1.00 | 42.99 | C |
| ATOM | 1694 | CD | LYS A | 344 | 66.596 | 56.654 | 44.257 | 1.00 | 46.73 | C |
| ATOM | 1695 | CE | LYS A | 344 | 65.820 | 57.178 | 45.469 | 1.00 | 49.48 | C |
| ATOM | 1696 | NZ | LYS A | 344 | 66.664 | 57.318 | 46.702 | 1.00 | 53.65 | N |
| ATOM | 1697 | N | TYR A | 345 | 66.541 | 51.956 | 42.512 | 1.00 | 32.48 | N |
| ATOM | 1698 | CA | TYR A | 345 | 65.463 | 50.979 | 42.590 | 1.00 | 32.33 | C |
| ATOM | 1699 | C | TYR A | 345 | 66.008 | 49.599 | 42.989 | 1.00 | 32.68 | C |
| ATOM | 1700 | O | TYR A | 345 | 65.413 | 48.901 | 43.811 | 1.00 | 32.28 | O |
| ATOM | 1701 | CB | TYR A | 345 | 64.764 | 50.878 | 41.241 | 1.00 | 30.33 | C |
| ATOM | 1702 | CG | TYR A | 345 | 63.474 | 50.092 | 41.273 | 1.00 | 31.92 | C |
| ATOM | 1703 | CD1 | TYR A | 345 | 62.291 | 50.685 | 41.702 | 1.00 | 32.27 | C |
| ATOM | 1704 | CD2 | TYR A | 345 | 63.427 | 48.767 | 40.830 | 1.00 | 31.10 | C |
| ATOM | 1705 | CE1 | TYR A | 345 | 61.090 | 49.988 | 41.681 | 1.00 | 32.84 | C |
| ATOM | 1706 | CE2 | TYR A | 345 | 62.230 | 48.061 | 40.805 | 1.00 | 32.54 | C |
| ATOM | 1707 | CZ | TYR A | 345 | 61.066 | 48.683 | 41.228 | 1.00 | 33.59 | C |
| ATOM | 1708 | OH | TYR A | 345 | 59.869 | 48.022 | 41.152 | 1.00 | 35.30 | O |
| ATOM | 1709 | N | PHE A | 346 | 67.133 | 49.211 | 42.396 | 1.00 | 32.82 | N |
| ATOM | 1710 | CA | PHE A | 346 | 67.759 | 47.928 | 42.703 | 1.00 | 34.48 | C |
| ATOM | 1711 | C | PHE A | 346 | 68.103 | 47.840 | 44.193 | 1.00 | 35.77 | C |
| ATOM | 1712 | O | PHE A | 346 | 67.859 | 46.827 | 44.843 | 1.00 | 34.19 | O |
| ATOM | 1713 | CB | PHE A | 346 | 69.037 | 47.751 | 41.881 | 1.00 | 34.20 | C |
| ATOM | 1714 | CG | PHE A | 346 | 69.817 | 46.518 | 42.232 | 1.00 | 35.55 | C |
| ATOM | 1715 | CD1 | PHE A | 346 | 69.302 | 45.254 | 41.964 | 1.00 | 34.50 | C |
| ATOM | 1716 | CD2 | PHE A | 346 | 71.060 | 46.620 | 42.850 | 1.00 | 37.04 | C |
| ATOM | 1717 | CE1 | PHE A | 346 | 70.010 | 44.107 | 42.304 | 1.00 | 35.77 | C |
| ATOM | 1718 | CE2 | PHE A | 346 | 71.779 | 45.478 | 43.198 | 1.00 | 38.55 | C |
| ATOM | 1719 | CZ | PHE A | 346 | 71.250 | 44.217 | 42.923 | 1.00 | 38.73 | C |
| ATOM | 1720 | N | GLU A | 347 | 68.660 | 48.921 | 44.723 | 1.00 | 37.60 | N |
| ATOM | 1721 | CA | GLU A | 347 | 69.054 | 48.986 | 46.122 | 1.00 | 40.87 | C |
| ATOM | 1722 | C | GLU A | 347 | 67.875 | 48.954 | 47.091 | 1.00 | 40.71 | C |
| ATOM | 1723 | O | GLU A | 347 | 68.014 | 48.483 | 48.218 | 1.00 | 41.55 | O |
| ATOM | 1724 | CB | GLU A | 347 | 69.887 | 50.247 | 46.361 | 1.00 | 42.18 | C |
| ATOM | 1725 | CG | GLU A | 347 | 71.112 | 50.334 | 45.461 | 1.00 | 49.56 | C |
| ATOM | 1726 | CD | GLU A | 347 | 72.249 | 49.423 | 45.901 | 1.00 | 54.08 | C |
| ATOM | 1727 | OE1 | GLU A | 347 | 71.994 | 48.244 | 46.240 | 1.00 | 57.12 | O |
| ATOM | 1728 | OE2 | GLU A | 347 | 73.412 | 49.887 | 45.899 | 1.00 | 57.88 | O |
| ATOM | 1729 | N | GLU A | 348 | 66.717 | 49.446 | 46.656 | 1.00 | 39.71 | N |
| ATOM | 1730 | CA | GLU A | 348 | 65.543 | 49.464 | 47.523 | 1.00 | 39.97 | C |
| ATOM | 1731 | C | GLU A | 348 | 64.782 | 48.149 | 47.503 | 1.00 | 38.48 | C |
| ATOM | 1732 | O | GLU A | 348 | 64.283 | 47.705 | 48.529 | 1.00 | 38.26 | O |
| ATOM | 1733 | CB | GLU A | 348 | 64.543 | 50.550 | 47.100 | 1.00 | 41.21 | C |
| ATOM | 1734 | CG | GLU A | 348 | 65.120 | 51.879 | 46.664 | 1.00 | 44.97 | C |
| ATOM | 1735 | CD | GLU A | 348 | 64.044 | 52.828 | 46.141 | 1.00 | 45.86 | C |
| ATOM | 1736 | OE1 | GLU A | 348 | 63.112 | 52.360 | 45.454 | 1.00 | 46.60 | O |
| ATOM | 1737 | OE2 | GLU A | 348 | 64.135 | 54.043 | 46.405 | 1.00 | 48.18 | O |
| ATOM | 1738 | N | THR A | 349 | 64.696 | 47.536 | 46.327 | 1.00 | 37.21 | N |
| ATOM | 1739 | CA | THR A | 349 | 63.922 | 46.314 | 46.146 | 1.00 | 35.37 | C |
| ATOM | 1740 | C | THR A | 349 | 64.677 | 45.019 | 45.849 | 1.00 | 35.43 | C |
| ATOM | 1741 | O | THR A | 349 | 64.093 | 43.943 | 45.910 | 1.00 | 36.36 | O |
| ATOM | 1742 | CB | THR A | 349 | 62.906 | 46.507 | 45.004 | 1.00 | 35.82 | C |
| ATOM | 1743 | OG1 | THR A | 349 | 63.613 | 46.564 | 43.755 | 1.00 | 33.52 | O |

TABLE 2-continued

| ATOM | 1744 | CG2 | THR A | 349 | 62.116 | 47.812 | 45.190 | 1.00 | 34.32 | C |
|---|---|---|---|---|---|---|---|---|---|---|
| ATOM | 1745 | N | GLY A | 350 | 65.957 | 45.114 | 45.513 | 1.00 | 35.89 | N |
| ATOM | 1746 | CA | GLY A | 350 | 66.715 | 43.917 | 45.183 | 1.00 | 34.68 | C |
| ATOM | 1747 | C | GLY A | 350 | 66.415 | 43.442 | 43.766 | 1.00 | 33.95 | C |
| ATOM | 1748 | O | GLY A | 350 | 66.870 | 42.381 | 43.339 | 1.00 | 35.21 | O |
| ATOM | 1749 | N | ILE A | 351 | 65.639 | 44.231 | 43.029 | 1.00 | 33.01 | N |
| ATOM | 1750 | CA | ILE A | 351 | 65.283 | 43.885 | 41.654 | 1.00 | 30.90 | C |
| ATOM | 1751 | C | ILE A | 351 | 66.124 | 44.690 | 40.665 | 1.00 | 29.41 | C |
| ATOM | 1752 | O | ILE A | 351 | 66.117 | 45.911 | 40.699 | 1.00 | 27.96 | O |
| ATOM | 1753 | CB | ILE A | 351 | 63.795 | 44.197 | 41.356 | 1.00 | 33.21 | C |
| ATOM | 1754 | CG1 | ILE A | 351 | 62.885 | 43.471 | 42.355 | 1.00 | 34.74 | C |
| ATOM | 1755 | CG2 | ILE A | 351 | 63.455 | 43.779 | 39.930 | 1.00 | 32.48 | C |
| ATOM | 1756 | CD1 | ILE A | 351 | 61.424 | 43.894 | 42.262 | 1.00 | 34.70 | C |
| ATOM | 1757 | N | TYR A | 352 | 66.842 | 44.005 | 39.785 | 1.00 | 28.99 | N |
| ATOM | 1758 | CA | TYR A | 352 | 67.655 | 44.685 | 38.787 | 1.00 | 28.73 | C |
| ATOM | 1759 | C | TYR A | 352 | 66.907 | 44.657 | 37.464 | 1.00 | 28.49 | C |
| ATOM | 1760 | O | TYR A | 352 | 66.651 | 43.588 | 36.921 | 1.00 | 27.67 | O |
| ATOM | 1761 | CB | TYR A | 352 | 69.004 | 43.991 | 38.593 | 1.00 | 27.77 | C |
| ATOM | 1762 | CG | TYR A | 352 | 69.899 | 44.726 | 37.617 | 1.00 | 27.14 | C |
| ATOM | 1763 | CD1 | TYR A | 352 | 70.688 | 45.799 | 38.038 | 1.00 | 23.99 | C |
| ATOM | 1764 | CD2 | TYR A | 352 | 69.925 | 44.376 | 36.267 | 1.00 | 26.25 | C |
| ATOM | 1765 | CE1 | TYR A | 352 | 71.481 | 46.504 | 37.139 | 1.00 | 24.83 | C |
| ATOM | 1766 | CE2 | TYR A | 352 | 70.715 | 45.076 | 35.358 | 1.00 | 26.68 | C |
| ATOM | 1767 | CZ | TYR A | 352 | 71.492 | 46.138 | 35.804 | 1.00 | 24.57 | C |
| ATOM | 1768 | OH | TYR A | 352 | 72.302 | 46.809 | 34.923 | 1.00 | 26.41 | O |
| ATOM | 1769 | N | ILE A | 353 | 66.554 | 45.831 | 36.948 | 1.00 | 28.02 | N |
| ATOM | 1770 | CA | ILE A | 353 | 65.843 | 45.897 | 35.681 | 1.00 | 26.70 | C |
| ATOM | 1771 | C | ILE A | 353 | 66.761 | 46.407 | 34.575 | 1.00 | 27.00 | C |
| ATOM | 1772 | O | ILE A | 353 | 67.247 | 47.536 | 34.631 | 1.00 | 27.67 | O |
| ATOM | 1773 | CB | ILE A | 353 | 64.620 | 46.826 | 35.780 | 1.00 | 28.56 | C |
| ATOM | 1774 | CG1 | ILE A | 353 | 63.702 | 46.346 | 36.915 | 1.00 | 29.44 | C |
| ATOM | 1775 | CG2 | ILE A | 353 | 63.875 | 46.840 | 34.443 | 1.00 | 28.04 | C |
| ATOM | 1776 | CD1 | ILE A | 353 | 62.450 | 47.169 | 37.103 | 1.00 | 27.09 | C |
| ATOM | 1777 | N | PRO A | 354 | 67.020 | 45.574 | 33.556 | 1.00 | 26.94 | N |
| ATOM | 1778 | CA | PRO A | 354 | 67.892 | 45.999 | 32.456 | 1.00 | 25.14 | C |
| ATOM | 1779 | C | PRO A | 354 | 67.246 | 47.162 | 31.711 | 1.00 | 25.78 | C |
| ATOM | 1780 | O | PRO A | 354 | 66.020 | 47.210 | 31.578 | 1.00 | 24.81 | O |
| ATOM | 1781 | CB | PRO A | 354 | 67.988 | 44.748 | 31.582 | 1.00 | 23.53 | C |
| ATOM | 1782 | CG | PRO A | 354 | 67.734 | 43.614 | 32.558 | 1.00 | 24.17 | C |
| ATOM | 1783 | CD | PRO A | 354 | 66.612 | 44.167 | 33.392 | 1.00 | 25.08 | C |
| ATOM | 1784 | N | VAL A | 355 | 68.061 | 48.106 | 31.242 | 1.00 | 25.52 | N |
| ATOM | 1785 | CA | VAL A | 355 | 67.524 | 49.237 | 30.498 | 1.00 | 24.60 | C |
| ATOM | 1786 | C | VAL A | 355 | 68.152 | 49.287 | 29.124 | 1.00 | 24.64 | C |
| ATOM | 1787 | O | VAL A | 355 | 69.309 | 48.914 | 28.937 | 1.00 | 24.59 | O |
| ATOM | 1788 | CB | VAL A | 355 | 67.727 | 50.596 | 31.233 | 1.00 | 24.72 | C |
| ATOM | 1789 | CG1 | VAL A | 355 | 66.987 | 50.566 | 32.560 | 1.00 | 23.24 | C |
| ATOM | 1790 | CG2 | VAL A | 355 | 69.209 | 50.905 | 31.425 | 1.00 | 22.37 | C |
| ATOM | 1791 | N | CYS A | 356 | 67.365 | 49.746 | 28.163 | 1.00 | 24.56 | N |
| ATOM | 1792 | CA | CYS A | 356 | 67.794 | 49.819 | 26.783 | 1.00 | 24.50 | C |
| ATOM | 1793 | C | CYS A | 356 | 67.869 | 51.245 | 26.263 | 1.00 | 24.85 | C |
| ATOM | 1794 | O | CYS A | 356 | 66.901 | 51.998 | 26.368 | 1.00 | 25.28 | O |
| ATOM | 1795 | CB | CYS A | 356 | 66.816 | 49.018 | 25.919 | 1.00 | 24.42 | C |
| ATOM | 1796 | SG | CYS A | 356 | 67.077 | 49.153 | 24.147 | 1.00 | 27.02 | S |
| ATOM | 1797 | N | SER A | 357 | 69.017 | 51.614 | 25.704 | 1.00 | 24.06 | N |
| ATOM | 1798 | CA | SER A | 357 | 69.172 | 52.944 | 25.123 | 1.00 | 24.90 | C |
| ATOM | 1799 | C | SER A | 357 | 68.681 | 52.774 | 23.694 | 1.00 | 24.81 | C |
| ATOM | 1800 | O | SER A | 357 | 69.300 | 52.076 | 22.897 | 1.00 | 24.49 | O |
| ATOM | 1801 | CB | SER A | 357 | 70.629 | 53.394 | 25.110 | 1.00 | 23.83 | C |
| ATOM | 1802 | OG | SER A | 357 | 70.717 | 54.691 | 24.539 | 1.00 | 26.00 | O |
| ATOM | 1803 | N | ASP A | 358 | 67.562 | 53.414 | 23.389 | 1.00 | 25.07 | N |
| ATOM | 1804 | CA | ASP A | 358 | 66.927 | 53.308 | 22.085 | 1.00 | 26.86 | C |
| ATOM | 1805 | C | ASP A | 358 | 67.067 | 54.547 | 21.200 | 1.00 | 26.28 | C |
| ATOM | 1806 | O | ASP A | 358 | 66.510 | 55.598 | 21.504 | 1.00 | 25.81 | O |
| ATOM | 1807 | CB | ASP A | 358 | 65.442 | 52.986 | 22.309 | 1.00 | 26.49 | C |
| ATOM | 1808 | CG | ASP A | 358 | 64.672 | 52.770 | 21.021 | 1.00 | 26.81 | C |
| ATOM | 1809 | OD1 | ASP A | 358 | 65.293 | 52.598 | 19.949 | 1.00 | 28.14 | O |
| ATOM | 1810 | OD2 | ASP A | 358 | 63.425 | 52.757 | 21.099 | 1.00 | 25.32 | O |
| ATOM | 1811 | N | GLY A | 359 | 67.811 | 54.409 | 20.106 | 1.00 | 28.28 | N |
| ATOM | 1812 | CA | GLY A | 359 | 67.975 | 55.509 | 19.174 | 1.00 | 30.20 | C |
| ATOM | 1813 | C | GLY A | 359 | 69.098 | 56.486 | 19.460 | 1.00 | 33.11 | C |
| ATOM | 1814 | O | GLY A | 359 | 69.637 | 56.539 | 20.564 | 1.00 | 32.49 | O |
| ATOM | 1815 | N | GLY A | 360 | 69.456 | 57.260 | 18.442 | 1.00 | 34.01 | N |
| ATOM | 1816 | CA | GLY A | 360 | 70.504 | 58.243 | 18.602 | 1.00 | 36.30 | C |
| ATOM | 1817 | C | GLY A | 360 | 71.916 | 57.755 | 18.357 | 1.00 | 37.16 | C |
| ATOM | 1818 | O | GLY A | 360 | 72.849 | 58.538 | 18.482 | 1.00 | 39.18 | O |
| ATOM | 1819 | N | ILE A | 361 | 72.096 | 56.481 | 18.021 | 1.00 | 38.47 | N |
| ATOM | 1820 | CA | ILE A | 361 | 73.442 | 55.976 | 17.762 | 1.00 | 40.22 | C |
| ATOM | 1821 | C | ILE A | 361 | 73.856 | 56.399 | 16.359 | 1.00 | 42.51 | C |
| ATOM | 1822 | O | ILE A | 361 | 73.296 | 55.922 | 15.369 | 1.00 | 42.14 | O |

TABLE 2-continued

| | | | | | | | | | | |
|---|---|---|---|---|---|---|---|---|---|---|
| ATOM | 1823 | CB | ILE A | 361 | 73.527 | 54.430 | 17.848 | 1.00 | 40.03 | C |
| ATOM | 1824 | CG1 | ILE A | 361 | 73.133 | 53.945 | 19.247 | 1.00 | 38.70 | C |
| ATOM | 1825 | CG2 | ILE A | 361 | 74.953 | 53.974 | 17.527 | 1.00 | 39.30 | C |
| ATOM | 1826 | CD1 | ILE A | 361 | 74.077 | 54.379 | 20.352 | 1.00 | 38.35 | C |
| ATOM | 1827 | N | VAL A | 362 | 74.835 | 57.297 | 16.284 | 1.00 | 44.13 | N |
| ATOM | 1828 | CA | VAL A | 362 | 75.326 | 57.799 | 15.007 | 1.00 | 45.18 | C |
| ATOM | 1829 | C | VAL A | 362 | 76.688 | 57.200 | 14.659 | 1.00 | 46.18 | C |
| ATOM | 1830 | O | VAL A | 362 | 76.943 | 56.875 | 13.498 | 1.00 | 47.54 | O |
| ATOM | 1831 | CB | VAL A | 362 | 75.437 | 59.336 | 15.030 | 1.00 | 46.11 | C |
| ATOM | 1832 | CG1 | VAL A | 362 | 75.853 | 59.856 | 13.653 | 1.00 | 47.64 | C |
| ATOM | 1833 | CG2 | VAL A | 362 | 74.099 | 59.940 | 15.440 | 1.00 | 47.33 | C |
| ATOM | 1834 | N | TYR A | 363 | 77.552 | 57.052 | 15.665 | 1.00 | 44.63 | N |
| ATOM | 1835 | CA | TYR A | 363 | 78.889 | 56.482 | 15.473 | 1.00 | 42.52 | C |
| ATOM | 1836 | C | TYR A | 363 | 79.087 | 55.265 | 16.370 | 1.00 | 39.50 | C |
| ATOM | 1837 | O | TYR A | 363 | 78.395 | 55.109 | 17.373 | 1.00 | 38.80 | O |
| ATOM | 1838 | CB | TYR A | 363 | 79.960 | 57.519 | 15.803 | 1.00 | 44.72 | C |
| ATOM | 1839 | CG | TYR A | 363 | 79.838 | 58.794 | 15.010 | 1.00 | 48.91 | C |
| ATOM | 1840 | CD1 | TYR A | 363 | 79.930 | 58.782 | 13.619 | 1.00 | 51.13 | C |
| ATOM | 1841 | CD2 | TYR A | 363 | 79.639 | 60.016 | 15.649 | 1.00 | 50.12 | C |
| ATOM | 1842 | CE1 | TYR A | 363 | 79.829 | 59.957 | 12.882 | 1.00 | 53.53 | C |
| ATOM | 1843 | CE2 | TYR A | 363 | 79.538 | 61.199 | 14.921 | 1.00 | 52.91 | C |
| ATOM | 1844 | CZ | TYR A | 363 | 79.636 | 61.162 | 13.539 | 1.00 | 53.71 | C |
| ATOM | 1845 | OH | TYR A | 363 | 79.567 | 62.330 | 12.813 | 1.00 | 56.33 | O |
| ATOM | 1846 | N | ASP A | 364 | 80.040 | 54.409 | 16.024 | 1.00 | 37.74 | N |
| ATOM | 1847 | CA | ASP A | 364 | 80.289 | 53.221 | 16.831 | 1.00 | 37.31 | C |
| ATOM | 1848 | C | ASP A | 364 | 80.610 | 53.556 | 18.282 | 1.00 | 36.24 | C |
| ATOM | 1849 | O | ASP A | 364 | 80.175 | 52.852 | 19.192 | 1.00 | 37.36 | O |
| ATOM | 1850 | CB | ASP A | 364 | 81.441 | 52.389 | 16.259 | 1.00 | 39.54 | C |
| ATOM | 1851 | CG | ASP A | 364 | 81.104 | 51.746 | 14.926 | 1.00 | 41.10 | C |
| ATOM | 1852 | OD1 | ASP A | 364 | 79.976 | 51.235 | 14.763 | 1.00 | 40.94 | O |
| ATOM | 1853 | OD2 | ASP A | 364 | 81.985 | 51.738 | 14.042 | 1.00 | 44.42 | O |
| ATOM | 1854 | N | TYR A | 365 | 81.359 | 54.631 | 18.508 | 1.00 | 33.86 | N |
| ATOM | 1855 | CA | TYR A | 365 | 81.733 | 54.989 | 19.870 | 1.00 | 33.09 | C |
| ATOM | 1856 | C | TYR A | 365 | 80.544 | 55.418 | 20.733 | 1.00 | 31.64 | C |
| ATOM | 1857 | O | TYR A | 365 | 80.646 | 55.456 | 21.955 | 1.00 | 30.06 | O |
| ATOM | 1858 | CB | TYR A | 365 | 82.828 | 56.066 | 19.859 | 1.00 | 31.22 | C |
| ATOM | 1859 | CG | TYR A | 365 | 82.342 | 57.493 | 19.813 | 1.00 | 34.92 | C |
| ATOM | 1860 | CD1 | TYR A | 365 | 82.131 | 58.216 | 20.987 | 1.00 | 35.27 | C |
| ATOM | 1861 | CD2 | TYR A | 365 | 82.136 | 58.140 | 18.595 | 1.00 | 36.06 | C |
| ATOM | 1862 | CE1 | TYR A | 365 | 81.735 | 59.549 | 20.948 | 1.00 | 37.45 | C |
| ATOM | 1863 | CE2 | TYR A | 365 | 81.738 | 59.476 | 18.545 | 1.00 | 38.40 | C |
| ATOM | 1864 | CZ | TYR A | 365 | 81.543 | 60.173 | 19.724 | 1.00 | 38.62 | C |
| ATOM | 1865 | OH | TYR A | 365 | 81.174 | 61.500 | 19.676 | 1.00 | 43.03 | O |
| ATOM | 1866 | N | HIS A | 366 | 79.420 | 55.737 | 20.098 | 1.00 | 31.37 | N |
| ATOM | 1867 | CA | HIS A | 366 | 78.231 | 56.110 | 20.855 | 1.00 | 30.85 | C |
| ATOM | 1868 | C | HIS A | 366 | 77.743 | 54.859 | 21.571 | 1.00 | 28.97 | C |
| ATOM | 1869 | O | HIS A | 366 | 77.130 | 54.947 | 22.630 | 1.00 | 28.47 | O |
| ATOM | 1870 | CB | HIS A | 366 | 77.125 | 56.635 | 19.926 | 1.00 | 31.13 | C |
| ATOM | 1871 | CG | HIS A | 366 | 77.373 | 58.016 | 19.406 | 1.00 | 31.77 | C |
| ATOM | 1872 | ND1 | HIS A | 366 | 78.311 | 58.862 | 19.957 | 1.00 | 33.13 | N |
| ATOM | 1873 | CD2 | HIS A | 366 | 76.765 | 58.719 | 18.422 | 1.00 | 31.89 | C |
| ATOM | 1874 | CE1 | HIS A | 366 | 78.267 | 60.028 | 19.339 | 1.00 | 31.00 | C |
| ATOM | 1875 | NE2 | HIS A | 366 | 77.337 | 59.968 | 18.405 | 1.00 | 32.26 | N |
| ATOM | 1876 | N | MET A | 367 | 78.017 | 53.697 | 20.979 | 1.00 | 27.68 | N |
| ATOM | 1877 | CA | MET A | 367 | 77.633 | 52.419 | 21.580 | 1.00 | 28.37 | C |
| ATOM | 1878 | C | MET A | 367 | 78.372 | 52.283 | 22.909 | 1.00 | 26.83 | C |
| ATOM | 1879 | O | MET A | 367 | 77.774 | 51.998 | 23.938 | 1.00 | 27.33 | O |
| ATOM | 1880 | CB | MET A | 367 | 78.027 | 51.240 | 20.678 | 1.00 | 26.41 | C |
| ATOM | 1881 | CG | MET A | 367 | 77.301 | 51.164 | 19.333 | 1.00 | 29.28 | C |
| ATOM | 1882 | SD | MET A | 367 | 77.864 | 49.737 | 18.350 | 1.00 | 31.67 | S |
| ATOM | 1883 | CE | MET A | 367 | 76.804 | 49.861 | 16.903 | 1.00 | 31.17 | C |
| ATOM | 1884 | N | THR A | 368 | 79.686 | 52.485 | 22.868 | 1.00 | 27.26 | N |
| ATOM | 1885 | CA | THR A | 368 | 80.519 | 52.393 | 24.062 | 1.00 | 27.02 | C |
| ATOM | 1886 | C | THR A | 368 | 80.035 | 53.402 | 25.106 | 1.00 | 26.24 | C |
| ATOM | 1887 | O | THR A | 368 | 79.960 | 53.092 | 26.288 | 1.00 | 26.81 | O |
| ATOM | 1888 | CB | THR A | 368 | 81.998 | 52.667 | 23.713 | 1.00 | 27.29 | C |
| ATOM | 1889 | OG1 | THR A | 368 | 82.350 | 51.907 | 22.548 | 1.00 | 28.57 | O |
| ATOM | 1890 | CG2 | THR A | 368 | 82.912 | 52.252 | 24.861 | 1.00 | 26.87 | C |
| ATOM | 1891 | N | LEU A | 369 | 79.701 | 54.610 | 24.664 | 1.00 | 25.92 | N |
| ATOM | 1892 | CA | LEU A | 369 | 79.205 | 55.636 | 25.578 | 1.00 | 27.25 | C |
| ATOM | 1893 | C | LEU A | 369 | 77.913 | 55.206 | 26.263 | 1.00 | 25.90 | C |
| ATOM | 1894 | O | LEU A | 369 | 77.805 | 55.280 | 27.483 | 1.00 | 26.13 | O |
| ATOM | 1895 | CB | LEU A | 369 | 78.956 | 56.949 | 24.835 | 1.00 | 27.34 | C |
| ATOM | 1896 | CG | LEU A | 369 | 80.177 | 57.813 | 24.525 | 1.00 | 30.74 | C |
| ATOM | 1897 | CD1 | LEU A | 369 | 79.731 | 59.030 | 23.718 | 1.00 | 30.74 | C |
| ATOM | 1898 | CD2 | LEU A | 369 | 80.855 | 58.244 | 25.823 | 1.00 | 27.53 | C |
| ATOM | 1899 | N | ALA A | 370 | 76.946 | 54.755 | 25.464 | 1.00 | 25.24 | N |
| ATOM | 1900 | CA | ALA A | 370 | 75.644 | 54.313 | 25.966 | 1.00 | 25.58 | C |
| ATOM | 1901 | C | ALA A | 370 | 75.804 | 53.233 | 27.037 | 1.00 | 23.76 | C |

TABLE 2-continued

| ATOM | 1902 | O | ALA A | 370 | 75.192 | 53.294 | 28.099 | 1.00 | 24.01 | O |
|------|------|---|-------|-----|--------|--------|--------|------|-------|---|
| ATOM | 1903 | CB | ALA A | 370 | 74.792 | 53.787 | 24.809 | 1.00 | 20.78 | C |
| ATOM | 1904 | N | LEU A | 371 | 76.638 | 52.248 | 26.745 | 1.00 | 24.06 | N |
| ATOM | 1905 | CA | LEU A | 371 | 76.892 | 51.162 | 27.677 | 1.00 | 24.06 | C |
| ATOM | 1906 | C | LEU A | 371 | 77.599 | 51.698 | 28.926 | 1.00 | 24.64 | C |
| ATOM | 1907 | O | LEU A | 371 | 77.223 | 51.360 | 30.042 | 1.00 | 24.05 | O |
| ATOM | 1908 | CB | LEU A | 371 | 77.750 | 50.086 | 26.990 | 1.00 | 22.32 | C |
| ATOM | 1909 | CG | LEU A | 371 | 77.084 | 49.415 | 25.772 | 1.00 | 25.62 | C |
| ATOM | 1910 | CD1 | LEU A | 371 | 78.104 | 48.572 | 25.004 | 1.00 | 24.75 | C |
| ATOM | 1911 | CD2 | LEU A | 371 | 75.909 | 48.553 | 26.227 | 1.00 | 23.36 | C |
| ATOM | 1912 | N | ALA A | 372 | 78.607 | 52.549 | 28.732 | 1.00 | 23.99 | N |
| ATOM | 1913 | CA | ALA A | 372 | 79.367 | 53.109 | 29.844 | 1.00 | 24.54 | C |
| ATOM | 1914 | C | ALA A | 372 | 78.484 | 53.911 | 30.774 | 1.00 | 26.37 | C |
| ATOM | 1915 | O | ALA A | 372 | 78.699 | 53.920 | 31.984 | 1.00 | 26.64 | O |
| ATOM | 1916 | CB | ALA A | 372 | 80.505 | 53.989 | 29.329 | 1.00 | 23.23 | C |
| ATOM | 1917 | N | MET A | 373 | 77.496 | 54.598 | 30.207 | 1.00 | 26.85 | N |
| ATOM | 1918 | CA | MET A | 373 | 76.591 | 55.395 | 31.017 | 1.00 | 26.45 | C |
| ATOM | 1919 | C | MET A | 373 | 75.617 | 54.514 | 31.795 | 1.00 | 25.55 | C |
| ATOM | 1920 | O | MET A | 373 | 74.883 | 55.009 | 32.634 | 1.00 | 26.24 | O |
| ATOM | 1921 | CB | MET A | 373 | 75.834 | 56.402 | 30.145 | 1.00 | 25.35 | C |
| ATOM | 1922 | CG | MET A | 373 | 76.704 | 57.547 | 29.626 | 1.00 | 27.17 | C |
| ATOM | 1923 | SD | MET A | 373 | 75.865 | 58.517 | 28.344 | 1.00 | 27.74 | S |
| ATOM | 1924 | CE | MET A | 373 | 77.157 | 59.681 | 27.884 | 1.00 | 26.78 | C |
| ATOM | 1925 | N | GLY A | 374 | 75.603 | 53.212 | 31.518 | 1.00 | 25.87 | N |
| ATOM | 1926 | CA | GLY A | 374 | 74.725 | 52.327 | 32.269 | 1.00 | 24.01 | C |
| ATOM | 1927 | C | GLY A | 374 | 73.710 | 51.500 | 31.506 | 1.00 | 24.90 | C |
| ATOM | 1928 | O | GLY A | 374 | 73.120 | 50.581 | 32.073 | 1.00 | 26.82 | O |
| ATOM | 1929 | N | ALA A | 375 | 73.472 | 51.818 | 30.241 | 1.00 | 23.59 | N |
| ATOM | 1930 | CA | ALA A | 375 | 72.521 | 51.035 | 29.468 | 1.00 | 24.75 | C |
| ATOM | 1931 | C | ALA A | 375 | 73.061 | 49.611 | 29.345 | 1.00 | 25.43 | C |
| ATOM | 1932 | O | ALA A | 375 | 74.255 | 49.411 | 29.116 | 1.00 | 25.89 | O |
| ATOM | 1933 | CB | ALA A | 375 | 72.325 | 51.644 | 28.085 | 1.00 | 21.49 | C |
| ATOM | 1934 | N | ASP A | 376 | 72.182 | 48.627 | 29.506 | 1.00 | 25.62 | N |
| ATOM | 1935 | CA | ASP A | 376 | 72.571 | 47.221 | 29.406 | 1.00 | 26.07 | C |
| ATOM | 1936 | C | ASP A | 376 | 72.671 | 46.809 | 27.945 | 1.00 | 25.46 | C |
| ATOM | 1937 | O | ASP A | 376 | 73.531 | 46.017 | 27.573 | 1.00 | 25.47 | O |
| ATOM | 1938 | CB | ASP A | 376 | 71.559 | 46.355 | 30.147 | 1.00 | 24.89 | C |
| ATOM | 1939 | CG | ASP A | 376 | 71.472 | 46.713 | 31.616 | 1.00 | 25.22 | C |
| ATOM | 1940 | OD1 | ASP A | 376 | 72.272 | 46.174 | 32.413 | 1.00 | 25.77 | O |
| ATOM | 1941 | OD2 | ASP A | 376 | 70.616 | 47.549 | 31.971 | 1.00 | 25.29 | O |
| ATOM | 1942 | N | PHE A | 377 | 71.779 | 47.339 | 27.117 | 1.00 | 26.78 | N |
| ATOM | 1943 | CA | PHE A | 377 | 71.834 | 47.053 | 25.695 | 1.00 | 26.93 | C |
| ATOM | 1944 | C | PHE A | 377 | 71.331 | 48.236 | 24.876 | 1.00 | 26.74 | C |
| ATOM | 1945 | O | PHE A | 377 | 70.791 | 49.205 | 25.416 | 1.00 | 25.26 | O |
| ATOM | 1946 | CB | PHE A | 377 | 71.108 | 45.742 | 25.327 | 1.00 | 26.14 | C |
| ATOM | 1947 | CG | PHE A | 377 | 69.704 | 45.638 | 25.836 | 1.00 | 28.33 | C |
| ATOM | 1948 | CD1 | PHE A | 377 | 69.451 | 45.223 | 27.141 | 1.00 | 28.91 | C |
| ATOM | 1949 | CD2 | PHE A | 377 | 68.626 | 45.898 | 24.992 | 1.00 | 26.99 | C |
| ATOM | 1950 | CE1 | PHE A | 377 | 68.137 | 45.064 | 27.597 | 1.00 | 29.14 | C |
| ATOM | 1951 | CE2 | PHE A | 377 | 67.316 | 45.742 | 25.438 | 1.00 | 27.18 | C |
| ATOM | 1952 | CZ | PHE A | 377 | 67.072 | 45.323 | 26.741 | 1.00 | 28.12 | C |
| ATOM | 1953 | N | ILE A | 378 | 71.526 | 48.150 | 23.567 | 1.00 | 26.27 | N |
| ATOM | 1954 | CA | ILE A | 378 | 71.188 | 49.241 | 22.669 | 1.00 | 27.14 | C |
| ATOM | 1955 | C | ILE A | 378 | 70.242 | 48.824 | 21.556 | 1.00 | 27.25 | C |
| ATOM | 1956 | O | ILE A | 378 | 70.423 | 47.774 | 20.947 | 1.00 | 28.04 | O |
| ATOM | 1957 | CB | ILE A | 378 | 72.497 | 49.788 | 22.032 | 1.00 | 27.66 | C |
| ATOM | 1958 | CG1 | ILE A | 378 | 73.491 | 50.146 | 23.137 | 1.00 | 28.26 | C |
| ATOM | 1959 | CG2 | ILE A | 378 | 72.217 | 51.011 | 21.159 | 1.00 | 28.62 | C |
| ATOM | 1960 | CD1 | ILE A | 378 | 74.915 | 50.248 | 22.644 | 1.00 | 30.77 | C |
| ATOM | 1961 | N | MET A | 379 | 69.226 | 49.641 | 21.301 | 1.00 | 26.60 | N |
| ATOM | 1962 | CA | MET A | 379 | 68.293 | 49.346 | 20.217 | 1.00 | 27.52 | C |
| ATOM | 1963 | C | MET A | 379 | 68.654 | 50.271 | 19.054 | 1.00 | 27.68 | C |
| ATOM | 1964 | O | MET A | 379 | 68.784 | 51.478 | 19.232 | 1.00 | 26.96 | O |
| ATOM | 1965 | CB | MET A | 379 | 66.838 | 49.581 | 20.645 | 1.00 | 26.96 | C |
| ATOM | 1966 | CG | MET A | 379 | 65.844 | 49.295 | 19.524 | 1.00 | 28.29 | C |
| ATOM | 1967 | SD | MET A | 379 | 64.114 | 49.244 | 20.007 | 1.00 | 26.79 | S |
| ATOM | 1968 | CE | MET A | 379 | 63.985 | 47.548 | 20.606 | 1.00 | 27.87 | C |
| ATOM | 1969 | N | LEU A | 380 | 68.829 | 49.701 | 17.868 | 1.00 | 29.02 | N |
| ATOM | 1970 | CA | LEU A | 380 | 69.181 | 50.503 | 16.706 | 1.00 | 29.48 | C |
| ATOM | 1971 | C | LEU A | 380 | 68.279 | 50.225 | 15.516 | 1.00 | 29.03 | C |
| ATOM | 1972 | O | LEU A | 380 | 67.880 | 49.086 | 15.275 | 1.00 | 29.34 | O |
| ATOM | 1973 | CB | LEU A | 380 | 70.642 | 50.258 | 16.301 | 1.00 | 29.79 | C |
| ATOM | 1974 | CG | LEU A | 380 | 71.722 | 50.470 | 17.368 | 1.00 | 30.01 | C |
| ATOM | 1975 | CD1 | LEU A | 380 | 71.783 | 49.227 | 18.259 | 1.00 | 31.49 | C |
| ATOM | 1976 | CD2 | LEU A | 380 | 73.079 | 50.693 | 16.714 | 1.00 | 30.65 | C |
| ATOM | 1977 | N | GLY A | 381 | 67.960 | 51.283 | 14.780 | 1.00 | 30.37 | N |
| ATOM | 1978 | CA | GLY A | 381 | 67.122 | 51.155 | 13.602 | 1.00 | 31.25 | C |
| ATOM | 1979 | C | GLY A | 381 | 67.941 | 51.401 | 12.348 | 1.00 | 30.92 | C |
| ATOM | 1980 | O | GLY A | 381 | 68.210 | 50.485 | 11.581 | 1.00 | 30.18 | O |

TABLE 2-continued

| | | | | | | | | | | |
|---|---|---|---|---|---|---|---|---|---|---|
| ATOM | 1981 | N | ARG A | 382 | 68.351 | 52.646 | 12.147 | 1.00 | 33.69 | N |
| ATOM | 1982 | CA | ARG A | 382 | 69.142 | 53.014 | 10.977 | 1.00 | 36.36 | C |
| ATOM | 1983 | C | ARG A | 382 | 70.371 | 52.125 | 10.772 | 1.00 | 36.33 | C |
| ATOM | 1984 | O | ARG A | 382 | 70.645 | 51.681 | 9.656 | 1.00 | 35.82 | O |
| ATOM | 1985 | CB | ARG A | 382 | 69.585 | 54.472 | 11.084 | 1.00 | 38.87 | C |
| ATOM | 1986 | CG | ARG A | 382 | 70.584 | 54.858 | 10.023 | 1.00 | 45.32 | C |
| ATOM | 1987 | CD | ARG A | 382 | 71.228 | 56.211 | 10.282 | 1.00 | 50.37 | C |
| ATOM | 1988 | NE | ARG A | 382 | 72.434 | 56.333 | 9.470 | 1.00 | 54.70 | N |
| ATOM | 1989 | CZ | ARG A | 382 | 73.548 | 55.638 | 9.685 | 1.00 | 55.84 | C |
| ATOM | 1990 | NH1 | ARG A | 382 | 73.614 | 54.780 | 10.700 | 1.00 | 56.30 | N |
| ATOM | 1991 | NH2 | ARG A | 382 | 74.582 | 55.774 | 8.863 | 1.00 | 56.90 | N |
| ATOM | 1992 | N | TYR A | 383 | 71.109 | 51.877 | 11.851 | 1.00 | 35.02 | N |
| ATOM | 1993 | CA | TYR A | 383 | 72.311 | 51.044 | 11.808 | 1.00 | 33.31 | C |
| ATOM | 1994 | C | TYR A | 383 | 72.059 | 49.714 | 11.093 | 1.00 | 32.20 | C |
| ATOM | 1995 | O | TYR A | 383 | 72.818 | 49.323 | 10.209 | 1.00 | 32.03 | O |
| ATOM | 1996 | CB | TYR A | 383 | 72.808 | 50.781 | 13.237 | 1.00 | 31.93 | C |
| ATOM | 1997 | CG | TYR A | 383 | 74.023 | 49.884 | 13.333 | 1.00 | 30.42 | C |
| ATOM | 1998 | CD1 | TYR A | 383 | 75.316 | 50.413 | 13.303 | 1.00 | 30.08 | C |
| ATOM | 1999 | CD2 | TYR A | 383 | 73.879 | 48.501 | 13.445 | 1.00 | 29.35 | C |
| ATOM | 2000 | CE1 | TYR A | 383 | 76.431 | 49.586 | 13.384 | 1.00 | 29.62 | C |
| ATOM | 2001 | CE2 | TYR A | 383 | 74.983 | 47.665 | 13.527 | 1.00 | 27.30 | C |
| ATOM | 2002 | CZ | TYR A | 383 | 76.254 | 48.210 | 13.495 | 1.00 | 29.91 | C |
| ATOM | 2003 | OH | TYR A | 383 | 77.342 | 47.373 | 13.556 | 1.00 | 29.92 | O |
| ATOM | 2004 | N | PHE A | 384 | 70.988 | 49.029 | 11.477 | 1.00 | 30.96 | N |
| ATOM | 2005 | CA | PHE A | 384 | 70.635 | 47.741 | 10.884 | 1.00 | 32.01 | C |
| ATOM | 2006 | C | PHE A | 384 | 69.907 | 47.827 | 9.533 | 1.00 | 33.62 | C |
| ATOM | 2007 | O | PHE A | 384 | 69.951 | 46.886 | 8.744 | 1.00 | 33.74 | O |
| ATOM | 2008 | CB | PHE A | 384 | 69.773 | 46.939 | 11.862 | 1.00 | 30.96 | C |
| ATOM | 2009 | CG | PHE A | 384 | 70.526 | 46.421 | 13.063 | 1.00 | 32.53 | C |
| ATOM | 2010 | CD1 | PHE A | 384 | 71.443 | 45.375 | 12.931 | 1.00 | 29.92 | C |
| ATOM | 2011 | CD2 | PHE A | 384 | 70.301 | 46.963 | 14.330 | 1.00 | 28.33 | C |
| ATOM | 2012 | CE1 | PHE A | 384 | 72.123 | 44.874 | 14.045 | 1.00 | 30.70 | C |
| ATOM | 2013 | CE2 | PHE A | 384 | 70.971 | 46.471 | 15.444 | 1.00 | 30.80 | C |
| ATOM | 2014 | CZ | PHE A | 384 | 71.886 | 45.421 | 15.303 | 1.00 | 28.49 | C |
| ATOM | 2015 | N | ALA A | 385 | 69.234 | 48.943 | 9.269 | 1.00 | 35.08 | N |
| ATOM | 2016 | CA | ALA A | 385 | 68.504 | 49.104 | 8.010 | 1.00 | 36.64 | C |
| ATOM | 2017 | C | ALA A | 385 | 69.441 | 49.035 | 6.805 | 1.00 | 38.11 | C |
| ATOM | 2018 | O | ALA A | 385 | 69.051 | 48.586 | 5.731 | 1.00 | 38.07 | O |
| ATOM | 2019 | CB | ALA A | 385 | 67.752 | 50.429 | 8.009 | 1.00 | 35.59 | C |
| ATOM | 2020 | N | ARG A | 386 | 70.682 | 49.475 | 7.004 | 1.00 | 39.97 | N |
| ATOM | 2021 | CA | ARG A | 386 | 71.701 | 49.491 | 5.958 | 1.00 | 39.58 | C |
| ATOM | 2022 | C | ARG A | 386 | 72.150 | 48.109 | 5.488 | 1.00 | 40.10 | C |
| ATOM | 2023 | O | ARG A | 386 | 72.819 | 47.989 | 4.457 | 1.00 | 39.76 | O |
| ATOM | 2024 | CB | ARG A | 386 | 72.945 | 50.232 | 6.449 | 1.00 | 40.19 | C |
| ATOM | 2025 | CG | ARG A | 386 | 72.755 | 51.685 | 6.835 | 1.00 | 43.04 | C |
| ATOM | 2026 | CA | ARG A | 386 | 74.036 | 52.170 | 7.499 | 1.00 | 45.06 | C |
| ATOM | 2027 | NE | ARG A | 386 | 74.404 | 51.264 | 8.585 | 1.00 | 46.41 | N |
| ATOM | 2028 | CZ | ARG A | 386 | 75.644 | 51.055 | 9.015 | 1.00 | 45.80 | C |
| ATOM | 2029 | NH1 | ARG A | 386 | 76.667 | 51.690 | 8.455 | 1.00 | 45.90 | N |
| ATOM | 2030 | NH2 | ARG A | 386 | 75.860 | 50.190 | 9.996 | 1.00 | 44.95 | N |
| ATOM | 2031 | N | PHE A | 387 | 71.798 | 47.071 | 6.238 | 1.00 | 40.02 | N |
| ATOM | 2032 | CA | PHE A | 387 | 72.229 | 45.726 | 5.883 | 1.00 | 40.37 | C |
| ATOM | 2033 | C | PHE A | 387 | 71.346 | 44.966 | 4.892 | 1.00 | 41.94 | C |
| ATOM | 2034 | O | PHE A | 387 | 70.143 | 45.207 | 4.769 | 1.00 | 41.59 | O |
| ATOM | 2035 | CB | PHE A | 387 | 72.417 | 44.877 | 7.149 | 1.00 | 39.91 | C |
| ATOM | 2036 | CG | PHE A | 387 | 73.319 | 45.506 | 8.183 | 1.00 | 40.02 | C |
| ATOM | 2037 | CD1 | PHE A | 387 | 74.411 | 46.283 | 7.801 | 1.00 | 39.37 | C |
| ATOM | 2038 | CD2 | PHE A | 387 | 73.084 | 45.308 | 9.544 | 1.00 | 39.37 | C |
| ATOM | 2039 | CE1 | PHE A | 387 | 75.255 | 46.855 | 8.755 | 1.00 | 40.23 | C |
| ATOM | 2040 | CE2 | PHE A | 387 | 73.921 | 45.872 | 10.510 | 1.00 | 38.11 | C |
| ATOM | 2041 | CZ | PHE A | 387 | 75.009 | 46.648 | 10.117 | 1.00 | 39.23 | C |
| ATOM | 2042 | N | GLU A | 388 | 71.985 | 44.040 | 4.190 | 1.00 | 42.30 | N |
| ATOM | 2043 | CA | GLU A | 388 | 71.340 | 43.194 | 3.200 | 1.00 | 42.95 | C |
| ATOM | 2044 | C | GLU A | 388 | 70.103 | 42.530 | 3.784 | 1.00 | 41.98 | C |
| ATOM | 2045 | O | GLU A | 388 | 69.080 | 42.401 | 3.108 | 1.00 | 41.50 | O |
| ATOM | 2046 | CB | GLU A | 388 | 72.331 | 42.118 | 2.740 | 1.00 | 44.78 | C |
| ATOM | 2047 | CG | GLU A | 388 | 71.786 | 41.096 | 1.749 | 1.00 | 48.50 | C |
| ATOM | 2048 | CD | GLU A | 388 | 71.457 | 41.708 | 0.400 | 1.00 | 51.34 | C |
| ATOM | 2049 | OE1 | GLU A | 388 | 72.306 | 42.458 | −0.130 | 1.00 | 52.78 | O |
| ATOM | 2050 | OE2 | GLU A | 388 | 70.359 | 41.435 | −0.134 | 1.00 | 53.13 | O |
| ATOM | 2051 | N | GLU A | 389 | 70.200 | 42.128 | 5.049 | 1.00 | 40.73 | N |
| ATOM | 2052 | CA | GLU A | 389 | 69.107 | 41.441 | 5.722 | 1.00 | 39.64 | C |
| ATOM | 2053 | C | GLU A | 389 | 67.884 | 42.266 | 6.125 | 1.00 | 38.63 | C |
| ATOM | 2054 | O | GLU A | 389 | 66.879 | 41.699 | 6.541 | 1.00 | 38.65 | O |
| ATOM | 2055 | CB | GLU A | 389 | 69.648 | 40.678 | 6.937 | 1.00 | 39.65 | C |
| ATOM | 2056 | CG | GLU A | 389 | 70.631 | 39.577 | 6.567 | 1.00 | 39.31 | C |
| ATOM | 2057 | CD | GLU A | 389 | 72.088 | 39.993 | 6.699 | 1.00 | 39.13 | C |
| ATOM | 2058 | OE1 | GLU A | 389 | 72.409 | 41.184 | 6.511 | 1.00 | 37.80 | O |
| ATOM | 2059 | OE2 | GLU A | 389 | 72.924 | 39.112 | 6.982 | 1.00 | 38.72 | O |

TABLE 2-continued

| | | | | | | | | | | |
|---|---|---|---|---|---|---|---|---|---|---|
| ATOM | 2060 | N | SER A | 390 | 67.951 | 43.589 | 6.020 | 1.00 | 38.90 | N |
| ATOM | 2061 | CA | SER A | 390 | 66.783 | 44.398 | 6.362 | 1.00 | 42.49 | C |
| ATOM | 2062 | C | SER A | 390 | 65.734 | 44.108 | 5.276 | 1.00 | 44.51 | C |
| ATOM | 2063 | O | SER A | 390 | 66.069 | 44.008 | 4.092 | 1.00 | 44.30 | O |
| ATOM | 2064 | CB | SER A | 390 | 67.130 | 45.886 | 6.393 | 1.00 | 41.33 | C |
| ATOM | 2065 | OG | SER A | 390 | 67.521 | 46.348 | 5.116 | 1.00 | 46.43 | O |
| ATOM | 2066 | N | PRO A | 391 | 64.454 | 43.985 | 5.669 | 1.00 | 45.30 | N |
| ATOM | 2067 | CA | PRO A | 391 | 63.317 | 43.691 | 4.785 | 1.00 | 47.36 | C |
| ATOM | 2068 | C | PRO A | 391 | 62.956 | 44.730 | 3.725 | 1.00 | 48.75 | C |
| ATOM | 2069 | O | PRO A | 391 | 61.909 | 44.625 | 3.089 | 1.00 | 50.35 | O |
| ATOM | 2070 | CB | PRO A | 391 | 62.176 | 43.478 | 5.775 | 1.00 | 46.19 | C |
| ATOM | 2071 | CG | PRO A | 391 | 62.473 | 44.525 | 6.804 | 1.00 | 44.91 | C |
| ATOM | 2072 | CD | PRO A | 391 | 63.975 | 44.374 | 7.010 | 1.00 | 44.19 | C |
| ATOM | 2073 | N | THR A | 392 | 63.806 | 45.727 | 3.529 | 1.00 | 49.99 | N |
| ATOM | 2074 | CA | THR A | 392 | 63.507 | 46.755 | 2.549 | 1.00 | 51.23 | C |
| ATOM | 2075 | C | THR A | 392 | 64.213 | 46.535 | 1.217 | 1.00 | 53.82 | C |
| ATOM | 2076 | O | THR A | 392 | 65.077 | 45.665 | 1.083 | 1.00 | 54.85 | O |
| ATOM | 2077 | CB | THR A | 392 | 63.863 | 48.152 | 3.084 | 1.00 | 49.99 | C |
| ATOM | 2078 | OG1 | THR A | 392 | 65.261 | 48.209 | 3.375 | 1.00 | 50.17 | O |
| ATOM | 2079 | CG2 | THR A | 392 | 63.070 | 48.450 | 4.351 | 1.00 | 49.74 | C |
| ATOM | 2080 | N | ARG A | 393 | 63.835 | 47.336 | 0.230 | 1.00 | 55.66 | N |
| ATOM | 2081 | CA | ARG A | 393 | 64.407 | 47.224 | −1.098 | 1.00 | 58.14 | C |
| ATOM | 2082 | C | ARG A | 393 | 65.744 | 47.930 | −1.238 | 1.00 | 58.48 | C |
| ATOM | 2083 | O | ARG A | 393 | 65.950 | 49.023 | −0.709 | 1.00 | 57.12 | O |
| ATOM | 2084 | CB | ARG A | 393 | 63.419 | 47.766 | −2.134 | 1.00 | 59.64 | C |
| ATOM | 2085 | CG | ARG A | 393 | 62.178 | 46.895 | −2.315 | 1.00 | 62.55 | C |
| ATOM | 2086 | CD | ARG A | 393 | 61.092 | 47.637 | −3.073 | 1.00 | 64.17 | C |
| ATOM | 2087 | NE | ARG A | 393 | 61.646 | 48.361 | −4.210 | 1.00 | 65.75 | N |
| ATOM | 2088 | CZ | ARG A | 393 | 61.462 | 49.659 | −4.423 | 1.00 | 67.27 | C |
| ATOM | 2089 | NH1 | ARG A | 393 | 60.732 | 50.372 | −3.576 | 1.00 | 66.89 | N |
| ATOM | 2090 | NH2 | ARG A | 393 | 62.024 | 50.248 | −5.472 | 1.00 | 68.47 | N |
| ATOM | 2091 | N | LYS A | 394 | 66.650 | 47.276 | −1.957 | 1.00 | 59.95 | N |
| ATOM | 2092 | CA | LYS A | 394 | 67.979 | 47.805 | −2.217 | 1.00 | 61.71 | C |
| ATOM | 2093 | C | LYS A | 394 | 67.835 | 48.647 | −3.479 | 1.00 | 63.80 | C |
| ATOM | 2094 | O | LYS A | 394 | 67.576 | 48.116 | −4.555 | 1.00 | 64.78 | O |
| ATOM | 2095 | CB | LYS A | 394 | 68.953 | 46.652 | −2.456 | 1.00 | 59.47 | C |
| ATOM | 2096 | CG | LYS A | 394 | 70.408 | 47.017 | −2.271 | 1.00 | 57.65 | C |
| ATOM | 2097 | CD | LYS A | 394 | 71.316 | 45.886 | −2.715 | 1.00 | 56.24 | C |
| ATOM | 2098 | CE | LYS A | 394 | 71.039 | 44.606 | −1.958 | 1.00 | 54.65 | C |
| ATOM | 2099 | NZ | LYS A | 394 | 71.894 | 43.500 | −2.462 | 1.00 | 53.21 | N |
| ATOM | 2100 | N | VAL A | 395 | 67.994 | 49.959 | −3.343 | 1.00 | 66.61 | N |
| ATOM | 2101 | CA | VAL A | 395 | 67.840 | 50.863 | −4.474 | 1.00 | 69.32 | C |
| ATOM | 2102 | C | VAL A | 395 | 69.118 | 51.577 | −4.896 | 1.00 | 71.12 | C |
| ATOM | 2103 | O | VAL A | 395 | 69.663 | 52.384 | −4.145 | 1.00 | 71.80 | O |
| ATOM | 2104 | CB | VAL A | 395 | 66.775 | 51.935 | −4.168 | 1.00 | 69.81 | C |
| ATOM | 2105 | CG1 | VAL A | 395 | 66.653 | 52.901 | −5.338 | 1.00 | 71.62 | C |
| ATOM | 2106 | CG2 | VAL A | 395 | 65.438 | 51.270 | −3.884 | 1.00 | 70.98 | C |
| ATOM | 2107 | N | THR A | 396 | 69.581 | 51.287 | −6.109 | 1.00 | 73.05 | N |
| ATOM | 2108 | CA | THR A | 396 | 70.783 | 51.921 | −6.644 | 1.00 | 74.05 | C |
| ATOM | 2109 | C | THR A | 396 | 70.409 | 53.303 | −7.163 | 1.00 | 74.87 | C |
| ATOM | 2110 | O | THR A | 396 | 69.793 | 53.428 | −8.222 | 1.00 | 75.03 | O |
| ATOM | 2111 | CB | THR A | 396 | 71.381 | 51.106 | −7.804 | 1.00 | 74.00 | C |
| ATOM | 2112 | OG1 | THR A | 396 | 71.715 | 49.791 | −7.343 | 1.00 | 74.43 | O |
| ATOM | 2113 | CG2 | THR A | 396 | 72.638 | 51.781 | −8.336 | 1.00 | 74.35 | C |
| ATOM | 2114 | N | ILE A | 397 | 70.784 | 54.335 | −6.415 | 1.00 | 75.83 | N |
| ATOM | 2115 | CA | ILE A | 397 | 70.472 | 55.710 | −6.788 | 1.00 | 76.89 | C |
| ATOM | 2116 | C | ILE A | 397 | 71.681 | 56.521 | −7.251 | 1.00 | 77.53 | C |
| ATOM | 2117 | O | ILE A | 397 | 72.537 | 56.897 | −6.449 | 1.00 | 77.96 | O |
| ATOM | 2118 | CB | ILE A | 397 | 69.817 | 56.466 | −5.612 | 1.00 | 77.21 | C |
| ATOM | 2119 | CG1 | ILE A | 397 | 68.525 | 55.761 | −5.196 | 1.00 | 77.37 | C |
| ATOM | 2120 | CG2 | ILE A | 397 | 69.538 | 57.911 | −6.010 | 1.00 | 76.96 | C |
| ATOM | 2121 | CD1 | ILE A | 397 | 67.820 | 56.415 | −4.025 | 1.00 | 78.15 | C |
| ATOM | 2122 | N | ASN A | 398 | 71.736 | 56.793 | −8.551 | 1.00 | 78.03 | N |
| ATOM | 2123 | CA | ASN A | 398 | 72.814 | 57.583 | −9.131 | 1.00 | 77.85 | C |
| ATOM | 2124 | C | ASN A | 398 | 74.200 | 57.051 | −8.758 | 1.00 | 76.64 | C |
| ATOM | 2125 | O | ASN A | 398 | 75.036 | 57.787 | −8.229 | 1.00 | 76.51 | O |
| ATOM | 2126 | CB | ASN A | 398 | 72.667 | 59.042 | −8.679 | 1.00 | 79.57 | C |
| ATOM | 2127 | CG | ASN A | 398 | 73.387 | 60.019 | −9.595 | 1.00 | 82.07 | C |
| ATOM | 2128 | OD1 | ASN A | 398 | 74.617 | 60.007 | −9.700 | 1.00 | 83.51 | O |
| ATOM | 2129 | ND2 | ASN A | 398 | 72.618 | 60.874 | −10.266 | 1.00 | 82.25 | N |
| ATOM | 2130 | N | GLY A | 399 | 74.434 | 55.768 | −9.026 | 1.00 | 75.00 | N |
| ATOM | 2131 | CA | GLY A | 399 | 75.724 | 55.165 | −8.730 | 1.00 | 72.65 | C |
| ATOM | 2132 | C | GLY A | 399 | 75.916 | 54.587 | −7.336 | 1.00 | 71.38 | C |
| ATOM | 2133 | O | GLY A | 399 | 76.745 | 53.695 | −7.143 | 1.00 | 71.58 | O |
| ATOM | 2134 | N | SER A | 400 | 75.163 | 55.087 | −6.361 | 1.00 | 69.39 | N |
| ATOM | 2135 | CA | SER A | 400 | 75.283 | 54.609 | −4.985 | 1.00 | 66.71 | C |
| ATOM | 2136 | C | SER A | 400 | 74.121 | 53.723 | −4.565 | 1.00 | 64.95 | C |
| ATOM | 2137 | O | SER A | 400 | 72.958 | 54.084 | −4.734 | 1.00 | 65.32 | O |
| ATOM | 2138 | CB | SER A | 400 | 75.381 | 55.794 | −4.023 | 1.00 | 66.11 | C |

TABLE 2-continued

| ATOM | 2139 | OG | SER A | 400 | 76.546 | 56.557 | -4.273 | 1.00 | 66.69 | O |
|---|---|---|---|---|---|---|---|---|---|---|
| ATOM | 2140 | N | VAL A | 401 | 74.440 | 52.561 | -4.011 | 1.00 | 62.49 | N |
| ATOM | 2141 | CA | VAL A | 401 | 73.412 | 51.639 | -3.557 | 1.00 | 60.52 | C |
| ATOM | 2142 | C | VAL A | 401 | 72.905 | 52.092 | -2.190 | 1.00 | 60.36 | C |
| ATOM | 2143 | O | VAL A | 401 | 73.689 | 52.313 | -1.261 | 1.00 | 60.61 | O |
| ATOM | 2144 | CB | VAL A | 401 | 73.960 | 50.203 | -3.453 | 1.00 | 59.89 | C |
| ATOM | 2145 | CG1 | VAL A | 401 | 72.869 | 49.261 | -2.978 | 1.00 | 58.28 | C |
| ATOM | 2146 | CG2 | VAL A | 401 | 74.496 | 49.758 | -4.805 | 1.00 | 59.96 | C |
| ATOM | 2147 | N | MET A | 402 | 71.588 | 52.237 | -2.079 | 1.00 | 58.65 | N |
| ATOM | 2148 | CA | MET A | 402 | 70.957 | 52.672 | -0.841 | 1.00 | 56.16 | C |
| ATOM | 2149 | C | MET A | 402 | 69.885 | 51.671 | -0.435 | 1.00 | 54.18 | C |
| ATOM | 2150 | O | MET A | 402 | 69.568 | 50.747 | -1.186 | 1.00 | 53.12 | O |
| ATOM | 2151 | CB | MET A | 402 | 70.297 | 54.038 | -1.038 | 1.00 | 58.26 | C |
| ATOM | 2152 | CG | MET A | 402 | 71.168 | 55.081 | -1.713 | 1.00 | 59.17 | C |
| ATOM | 2153 | SD | MET A | 402 | 72.561 | 55.584 | -0.705 | 1.00 | 63.98 | S |
| ATOM | 2154 | CE | MET A | 402 | 71.781 | 56.836 | 0.332 | 1.00 | 60.67 | C |
| ATOM | 2155 | N | LYS A | 403 | 69.340 | 51.856 | 0.764 | 1.00 | 51.25 | N |
| ATOM | 2156 | CA | LYS A | 403 | 68.267 | 51.007 | 1.267 | 1.00 | 48.15 | C |
| ATOM | 2157 | C | LYS A | 403 | 67.185 | 51.913 | 1.828 | 1.00 | 47.01 | C |
| ATOM | 2158 | O | LYS A | 403 | 67.473 | 52.981 | 2.369 | 1.00 | 46.14 | O |
| ATOM | 2159 | CB | LYS A | 403 | 68.760 | 50.049 | 2.357 | 1.00 | 47.38 | C |
| ATOM | 2160 | CG | LYS A | 403 | 69.675 | 48.948 | 1.850 | 1.00 | 46.96 | C |
| ATOM | 2161 | CD | LYS A | 403 | 69.389 | 47.602 | 2.514 | 1.00 | 46.69 | C |
| ATOM | 2162 | CE | LYS A | 403 | 68.052 | 47.027 | 2.054 | 1.00 | 45.74 | C |
| ATOM | 2163 | NZ | LYS A | 403 | 67.823 | 45.633 | 2.534 | 1.00 | 43.06 | N |
| ATOM | 2164 | N | GLU A | 404 | 65.937 | 51.491 | 1.683 | 1.00 | 46.11 | N |
| ATOM | 2165 | CA | GLU A | 404 | 64.817 | 52.276 | 2.171 | 1.00 | 46.13 | C |
| ATOM | 2166 | C | GLU A | 404 | 64.767 | 52.246 | 3.689 | 1.00 | 44.64 | C |
| ATOM | 2167 | O | GLU A | 404 | 65.107 | 51.243 | 4.316 | 1.00 | 43.82 | O |
| ATOM | 2168 | CB | GLU A | 404 | 63.506 | 51.725 | 1.616 | 1.00 | 47.95 | C |
| ATOM | 2169 | CG | GLU A | 404 | 63.453 | 51.663 | 0.101 | 1.00 | 52.21 | C |
| ATOM | 2170 | CD | GLU A | 404 | 62.145 | 51.099 | -0.405 | 1.00 | 53.46 | C |
| ATOM | 2171 | OE1 | GLU A | 404 | 61.875 | 49.900 | -0.160 | 1.00 | 54.61 | O |
| ATOM | 2172 | OE2 | GLU A | 404 | 61.386 | 51.860 | -1.042 | 1.00 | 54.88 | O |
| ATOM | 2173 | N | TYR A | 405 | 64.336 | 53.354 | 4.272 | 1.00 | 43.31 | N |
| ATOM | 2174 | CA | TYR A | 405 | 64.228 | 53.454 | 5.714 | 1.00 | 42.00 | C |
| ATOM | 2175 | C | TYR A | 405 | 63.190 | 54.501 | 6.056 | 1.00 | 40.73 | C |
| ATOM | 2176 | O | TYR A | 405 | 63.323 | 55.662 | 5.688 | 1.00 | 41.74 | O |
| ATOM | 2177 | CB | TYR A | 405 | 65.577 | 53.837 | 6.328 | 1.00 | 41.52 | C |
| ATOM | 2178 | CG | TYR A | 405 | 65.571 | 53.885 | 7.839 | 1.00 | 40.73 | C |
| ATOM | 2179 | CD1 | TYR A | 405 | 65.154 | 52.787 | 8.588 | 1.00 | 39.95 | C |
| ATOM | 2180 | CD2 | TYR A | 405 | 66.002 | 55.020 | 8.521 | 1.00 | 40.92 | C |
| ATOM | 2181 | CE1 | TYR A | 405 | 65.167 | 52.817 | 9.983 | 1.00 | 40.74 | C |
| ATOM | 2182 | CE2 | TYR A | 405 | 66.019 | 55.061 | 9.913 | 1.00 | 40.89 | C |
| ATOM | 2183 | CZ | TYR A | 405 | 65.599 | 53.957 | 10.637 | 1.00 | 40.10 | C |
| ATOM | 2184 | OH | TYR A | 405 | 65.596 | 54.003 | 12.011 | 1.00 | 39.70 | O |
| ATOM | 2185 | N | TRP A | 406 | 62.150 | 54.082 | 6.760 | 1.00 | 39.11 | N |
| ATOM | 2186 | CA | TRP A | 406 | 61.091 | 54.993 | 7.153 | 1.00 | 37.83 | C |
| ATOM | 2187 | C | TRP A | 406 | 60.708 | 54.695 | 8.594 | 1.00 | 36.75 | C |
| ATOM | 2188 | O | TRP A | 406 | 60.862 | 53.566 | 9.057 | 1.00 | 36.18 | O |
| ATOM | 2189 | CB | TRP A | 406 | 59.887 | 54.829 | 6.209 | 1.00 | 34.87 | C |
| ATOM | 2190 | CG | TRP A | 406 | 59.258 | 53.464 | 6.225 | 1.00 | 32.13 | C |
| ATOM | 2191 | CD1 | TRP A | 406 | 58.274 | 53.030 | 7.061 | 1.00 | 31.21 | C |
| ATOM | 2192 | CD2 | TRP A | 406 | 59.574 | 52.357 | 5.371 | 1.00 | 31.79 | C |
| ATOM | 2193 | NE1 | TRP A | 406 | 57.954 | 51.729 | 6.784 | 1.00 | 31.89 | N |
| ATOM | 2194 | CE2 | TRP A | 406 | 58.736 | 51.287 | 5.752 | 1.00 | 31.65 | C |
| ATOM | 2195 | CE3 | TRP A | 406 | 60.483 | 52.165 | 4.322 | 1.00 | 32.48 | C |
| ATOM | 2196 | CZ2 | TRP A | 406 | 58.776 | 50.034 | 5.119 | 1.00 | 32.31 | C |
| ATOM | 2197 | CZ3 | TRP A | 406 | 60.524 | 50.915 | 3.690 | 1.00 | 33.57 | C |
| ATOM | 2198 | CH2 | TRP A | 406 | 59.674 | 49.869 | 4.094 | 1.00 | 32.43 | C |
| ATOM | 2199 | N | GLY A | 407 | 60.229 | 55.717 | 9.298 | 1.00 | 37.66 | N |
| ATOM | 2200 | CA | GLY A | 407 | 59.835 | 55.554 | 10.685 | 1.00 | 38.09 | C |
| ATOM | 2201 | C | GLY A | 407 | 58.446 | 54.963 | 10.858 | 1.00 | 39.18 | C |
| ATOM | 2202 | O | GLY A | 407 | 57.629 | 54.993 | 9.939 | 1.00 | 38.93 | O |
| ATOM | 2203 | N | GLU A | 408 | 58.183 | 54.419 | 12.042 | 1.00 | 39.46 | N |
| ATOM | 2204 | CA | GLU A | 408 | 56.888 | 53.822 | 12.350 | 1.00 | 40.78 | C |
| ATOM | 2205 | C | GLU A | 408 | 55.792 | 54.880 | 12.425 | 1.00 | 42.44 | C |
| ATOM | 2206 | O | GLU A | 408 | 54.607 | 54.563 | 12.370 | 1.00 | 43.17 | O |
| ATOM | 2207 | CB | GLU A | 408 | 56.963 | 53.062 | 13.674 | 1.00 | 39.22 | C |
| ATOM | 2208 | CG | GLU A | 408 | 57.763 | 51.777 | 13.589 | 1.00 | 37.81 | C |
| ATOM | 2209 | CD | GLU A | 408 | 57.106 | 50.743 | 12.681 | 1.00 | 37.71 | C |
| ATOM | 2210 | OE1 | GLU A | 408 | 56.007 | 50.266 | 13.022 | 1.00 | 37.89 | O |
| ATOM | 2211 | OE2 | GLU A | 408 | 57.685 | 50.408 | 11.628 | 1.00 | 37.24 | O |
| ATOM | 2212 | N | GLY A | 409 | 56.200 | 56.139 | 12.543 | 1.00 | 44.48 | N |
| ATOM | 2213 | CA | GLY A | 409 | 55.242 | 57.227 | 12.623 | 1.00 | 46.13 | C |
| ATOM | 2214 | C | GLY A | 409 | 54.866 | 57.805 | 11.269 | 1.00 | 47.54 | C |
| ATOM | 2215 | O | GLY A | 409 | 53.909 | 58.566 | 11.166 | 1.00 | 47.48 | O |
| ATOM | 2216 | N | SER A | 410 | 55.611 | 57.450 | 10.227 | 1.00 | 49.11 | N |
| ATOM | 2217 | CA | SER A | 410 | 55.316 | 57.956 | 8.893 | 1.00 | 51.17 | C |

TABLE 2-continued

| | | | | | | | | | | |
|---|---|---|---|---|---|---|---|---|---|---|
| ATOM | 2218 | C | SER A | 410 | 54.028 | 57.319 | 8.381 | 1.00 | 53.44 | C |
| ATOM | 2219 | O | SER A | 410 | 53.676 | 56.205 | 8.777 | 1.00 | 52.20 | O |
| ATOM | 2220 | CB | SER A | 410 | 56.465 | 57.646 | 7.928 | 1.00 | 50.64 | C |
| ATOM | 2221 | OG | SER A | 410 | 56.489 | 56.273 | 7.580 | 1.00 | 52.23 | O |
| ATOM | 2222 | N | SER A | 411 | 53.328 | 58.033 | 7.503 | 1.00 | 55.87 | N |
| ATOM | 2223 | CA | SER A | 411 | 52.074 | 57.547 | 6.937 | 1.00 | 58.48 | C |
| ATOM | 2224 | C | SER A | 411 | 52.303 | 56.253 | 6.170 | 1.00 | 59.75 | C |
| ATOM | 2225 | O | SER A | 411 | 51.425 | 55.393 | 6.100 | 1.00 | 59.90 | O |
| ATOM | 2226 | CB | SER A | 411 | 51.481 | 58.605 | 6.006 | 1.00 | 59.49 | C |
| ATOM | 2227 | OG | SER A | 411 | 52.433 | 59.025 | 5.042 | 1.00 | 60.32 | O |
| ATOM | 2228 | N | ARG A | 412 | 53.498 | 56.122 | 5.605 | 1.00 | 61.10 | N |
| ATOM | 2229 | CA | ARG A | 412 | 53.867 | 54.939 | 4.841 | 1.00 | 62.63 | C |
| ATOM | 2230 | C | ARG A | 412 | 53.824 | 53.667 | 5.686 | 1.00 | 64.23 | C |
| ATOM | 2231 | O | ARG A | 412 | 54.057 | 52.572 | 5.177 | 1.00 | 63.68 | O |
| ATOM | 2232 | CB | ARG A | 412 | 55.273 | 55.114 | 4.254 | 1.00 | 60.98 | C |
| ATOM | 2233 | CG | ARG A | 412 | 55.772 | 53.904 | 3.483 | 1.00 | 59.74 | C |
| ATOM | 2234 | CD | ARG A | 412 | 57.137 | 54.136 | 2.871 | 1.00 | 58.42 | C |
| ATOM | 2235 | NE | ARG A | 412 | 57.566 | 52.982 | 2.086 | 1.00 | 57.23 | N |
| ATOM | 2236 | CZ | ARG A | 412 | 58.706 | 52.918 | 1.406 | 1.00 | 57.66 | C |
| ATOM | 2237 | NH1 | ARG A | 412 | 59.547 | 53.944 | 1.409 | 1.00 | 56.64 | N |
| ATOM | 2238 | NH2 | ARG A | 412 | 59.002 | 51.825 | 0.718 | 1.00 | 58.20 | N |
| ATOM | 2239 | N | ALA A | 413 | 53.514 | 53.806 | 6.972 | 1.00 | 67.55 | N |
| ATOM | 2240 | CA | ALA A | 413 | 53.480 | 52.643 | 7.851 | 1.00 | 70.19 | C |
| ATOM | 2241 | C | ALA A | 413 | 52.367 | 52.630 | 8.894 | 1.00 | 72.70 | C |
| ATOM | 2242 | O | ALA A | 413 | 51.812 | 51.573 | 9.189 | 1.00 | 72.87 | O |
| ATOM | 2243 | CB | ALA A | 413 | 54.828 | 52.496 | 8.548 | 1.00 | 70.18 | C |
| ATOM | 2244 | N | ARG A | 414 | 52.045 | 53.794 | 9.456 | 1.00 | 76.29 | N |
| ATOM | 2245 | CA | ARG A | 414 | 51.020 | 53.864 | 10.492 | 1.00 | 79.14 | C |
| ATOM | 2246 | C | ARG A | 414 | 49.605 | 53.528 | 10.021 | 1.00 | 80.91 | C |
| ATOM | 2247 | O | ARG A | 414 | 48.799 | 53.012 | 10.803 | 1.00 | 80.83 | O |
| ATOM | 2248 | CB | ARG A | 414 | 51.033 | 55.237 | 11.184 | 1.00 | 79.31 | C |
| ATOM | 2249 | CG | ARG A | 414 | 50.589 | 56.425 | 10.341 | 1.00 | 80.51 | C |
| ATOM | 2250 | CD | ARG A | 414 | 50.376 | 57.644 | 11.245 | 1.00 | 81.22 | C |
| ATOM | 2251 | NE | ARG A | 414 | 49.912 | 58.836 | 10.532 | 1.00 | 81.34 | N |
| ATOM | 2252 | CZ | ARG A | 414 | 50.676 | 59.603 | 9.757 | 1.00 | 81.51 | C |
| ATOM | 2253 | NH1 | ARG A | 414 | 51.959 | 59.310 | 9.583 | 1.00 | 80.79 | N |
| ATOM | 2254 | NH2 | ARG A | 414 | 50.158 | 60.671 | 9.161 | 1.00 | 80.72 | N |
| ATOM | 2255 | N | ASN A | 415 | 49.294 | 53.814 | 8.758 | 1.00 | 81.82 | N |
| ATOM | 2256 | CA | ASN A | 415 | 47.965 | 53.499 | 8.240 | 1.00 | 83.15 | C |
| ATOM | 2257 | C | ASN A | 415 | 47.967 | 52.029 | 7.797 | 1.00 | 83.41 | C |
| ATOM | 2258 | O | ASN A | 415 | 47.862 | 51.733 | 6.602 | 1.00 | 84.28 | O |
| ATOM | 2259 | CB | ASN A | 415 | 47.598 | 54.394 | 7.036 | 1.00 | 83.73 | C |
| ATOM | 2260 | CG | ASN A | 415 | 47.997 | 55.861 | 7.227 | 1.00 | 84.65 | C |
| ATOM | 2261 | OD1 | ASN A | 415 | 47.436 | 56.589 | 8.076 | 1.00 | 84.65 | O |
| ATOM | 2262 | ND2 | ASN A | 415 | 48.969 | 56.310 | 6.429 | 1.00 | 85.41 | N |
| ATOM | 2263 | N | TRP A | 416 | 48.101 | 51.116 | 8.758 | 1.00 | 82.63 | N |
| ATOM | 2264 | CA | TRP A | 416 | 48.118 | 49.682 | 8.465 | 1.00 | 82.02 | C |
| ATOM | 2265 | C | TRP A | 416 | 46.776 | 49.027 | 8.809 | 1.00 | 82.01 | C |
| ATOM | 2266 | O | TRP A | 416 | 46.228 | 49.228 | 9.896 | 1.00 | 82.27 | O |
| ATOM | 2267 | CB | TRP A | 416 | 49.268 | 48.998 | 9.236 | 1.00 | 79.66 | C |
| ATOM | 2268 | CG | TRP A | 416 | 48.850 | 47.849 | 10.126 | 1.00 | 77.46 | C |
| ATOM | 2269 | CD1 | TRP A | 416 | 48.380 | 46.627 | 9.731 | 1.00 | 76.95 | C |
| ATOM | 2270 | CD2 | TRP A | 416 | 48.806 | 47.849 | 11.560 | 1.00 | 76.39 | C |
| ATOM | 2271 | NE1 | TRP A | 416 | 48.040 | 45.871 | 10.828 | 1.00 | 75.11 | N |
| ATOM | 2272 | CE2 | TRP A | 416 | 48.290 | 46.595 | 11.963 | 1.00 | 75.43 | C |
| ATOM | 2273 | CE3 | TRP A | 416 | 49.149 | 48.788 | 12.544 | 1.00 | 75.87 | C |
| ATOM | 2274 | CZ2 | TRP A | 416 | 48.107 | 46.256 | 13.309 | 1.00 | 75.55 | C |
| ATOM | 2275 | CZ3 | TRP A | 416 | 48.965 | 48.449 | 13.884 | 1.00 | 76.10 | C |
| ATOM | 2276 | CH2 | TRP A | 416 | 48.448 | 47.193 | 14.251 | 1.00 | 75.60 | C |
| ATOM | 2277 | N | PHE A | 429 | 48.725 | 67.124 | 8.023 | 1.00 | 82.88 | N |
| ATOM | 2278 | CA | PHE A | 429 | 49.810 | 67.001 | 8.991 | 1.00 | 82.94 | C |
| ATOM | 2279 | C | PHE A | 429 | 50.394 | 65.588 | 8.957 | 1.00 | 82.92 | C |
| ATOM | 2280 | O | PHE A | 429 | 49.681 | 64.621 | 8.683 | 1.00 | 82.79 | O |
| ATOM | 2281 | CB | PHE A | 429 | 49.292 | 67.335 | 10.408 | 1.00 | 83.53 | C |
| ATOM | 2282 | CG | PHE A | 429 | 48.135 | 66.455 | 10.870 | 1.00 | 83.27 | C |
| ATOM | 2283 | CD1 | PHE A | 429 | 48.310 | 65.082 | 11.041 | 1.00 | 82.47 | C |
| ATOM | 2284 | CD2 | PHE A | 429 | 46.883 | 67.010 | 11.141 | 1.00 | 82.83 | C |
| ATOM | 2285 | CE1 | PHE A | 429 | 47.263 | 64.261 | 11.473 | 1.00 | 81.70 | C |
| ATOM | 2286 | CE2 | PHE A | 429 | 45.819 | 66.202 | 11.580 | 1.00 | 82.89 | C |
| ATOM | 2287 | CZ | PHE A | 429 | 46.014 | 64.819 | 11.745 | 1.00 | 82.38 | C |
| ATOM | 2288 | N | GLU A | 430 | 51.693 | 65.468 | 9.221 | 1.00 | 82.60 | N |
| ATOM | 2289 | CA | GLU A | 430 | 52.327 | 64.157 | 9.229 | 1.00 | 82.03 | C |
| ATOM | 2290 | C | GLU A | 430 | 53.060 | 63.870 | 10.528 | 1.00 | 81.40 | C |
| ATOM | 2291 | O | GLU A | 430 | 53.285 | 64.769 | 11.340 | 1.00 | 81.74 | O |
| ATOM | 2292 | CB | GLU A | 430 | 53.302 | 64.011 | 8.069 | 1.00 | 80.59 | C |
| ATOM | 2293 | CG | GLU A | 430 | 53.725 | 62.546 | 7.846 | 1.00 | 80.58 | C |
| ATOM | 2294 | CD | GLU A | 430 | 54.143 | 62.283 | 6.421 | 1.00 | 79.33 | C |
| ATOM | 2295 | OE1 | GLU A | 430 | 55.063 | 62.985 | 5.936 | 1.00 | 79.26 | O |
| ATOM | 2296 | OE2 | GLU A | 430 | 53.547 | 61.382 | 5.773 | 1.00 | 78.51 | O |

TABLE 2-continued

| | | | | | | | | | | |
|---|---|---|---|---|---|---|---|---|---|---|
| ATOM | 2297 | N | GLU A | 431 | 53.456 | 62.614 | 10.712 | 1.00 | 79.43 | N |
| ATOM | 2298 | CA | GLU A | 431 | 54.133 | 62.214 | 11.941 | 1.00 | 77.44 | C |
| ATOM | 2299 | C | GLU A | 431 | 55.365 | 61.338 | 11.724 | 1.00 | 75.89 | C |
| ATOM | 2300 | O | GLU A | 431 | 55.739 | 60.568 | 12.606 | 1.00 | 75.77 | O |
| ATOM | 2301 | CB | GLU A | 431 | 53.129 | 61.482 | 12.841 | 1.00 | 76.96 | C |
| ATOM | 2302 | CG | GLU A | 431 | 51.677 | 61.970 | 12.631 | 1.00 | 76.64 | C |
| ATOM | 2303 | CD | GLU A | 431 | 50.767 | 61.647 | 13.795 | 1.00 | 77.02 | C |
| ATOM | 2304 | OE1 | GLU A | 431 | 50.818 | 60.496 | 14.301 | 1.00 | 76.77 | O |
| ATOM | 2305 | OE2 | GLU A | 431 | 49.984 | 62.546 | 14.214 | 1.00 | 77.41 | O |
| ATOM | 2306 | N | GLY A | 432 | 56.000 | 61.462 | 10.562 | 1.00 | 74.32 | N |
| ATOM | 2307 | CA | GLY A | 432 | 57.179 | 60.660 | 10.297 | 1.00 | 72.21 | C |
| ATOM | 2308 | C | GLY A | 432 | 57.936 | 61.058 | 9.047 | 1.00 | 70.77 | C |
| ATOM | 2309 | O | GLY A | 432 | 57.540 | 61.985 | 8.337 | 1.00 | 71.05 | O |
| ATOM | 2310 | N | VAL A | 433 | 59.032 | 60.352 | 8.776 | 1.00 | 68.86 | N |
| ATOM | 2311 | CA | VAL A | 433 | 59.855 | 60.629 | 7.603 | 1.00 | 66.42 | C |
| ATOM | 2312 | C | VAL A | 433 | 60.245 | 59.353 | 6.852 | 1.00 | 64.76 | C |
| ATOM | 2313 | O | VAL A | 433 | 60.353 | 58.275 | 7.442 | 1.00 | 63.75 | O |
| ATOM | 2314 | CB | VAL A | 433 | 61.139 | 61.397 | 7.998 | 1.00 | 66.53 | C |
| ATOM | 2315 | CG1 | VAL A | 433 | 60.776 | 62.757 | 8.567 | 1.00 | 66.43 | C |
| ATOM | 2316 | CG2 | VAL A | 433 | 61.928 | 60.600 | 9.016 | 1.00 | 66.47 | C |
| ATOM | 2317 | N | ASP A | 434 | 60.445 | 59.498 | 5.544 | 1.00 | 62.35 | N |
| ATOM | 2318 | CA | ASP A | 434 | 60.824 | 58.399 | 4.656 | 1.00 | 60.25 | C |
| ATOM | 2319 | C | ASP A | 434 | 62.173 | 58.780 | 4.052 | 1.00 | 58.31 | C |
| ATOM | 2320 | O | ASP A | 434 | 62.333 | 59.891 | 3.549 | 1.00 | 58.55 | O |
| ATOM | 2321 | CB | ASP A | 434 | 59.780 | 58.260 | 3.539 | 1.00 | 61.48 | C |
| ATOM | 2322 | CG | ASP A | 434 | 59.952 | 56.994 | 2.715 | 1.00 | 62.63 | C |
| ATOM | 2323 | OD1 | ASP A | 434 | 61.091 | 56.500 | 2.578 | 1.00 | 65.25 | O |
| ATOM | 2324 | OD2 | ASP A | 434 | 58.936 | 56.499 | 2.186 | 1.00 | 63.34 | O |
| ATOM | 2325 | N | SER A | 435 | 63.143 | 57.873 | 4.095 | 1.00 | 55.86 | N |
| ATOM | 2326 | CA | SER A | 435 | 64.459 | 58.182 | 3.548 | 1.00 | 53.85 | C |
| ATOM | 2327 | C | SER A | 435 | 65.260 | 56.977 | 3.069 | 1.00 | 51.23 | C |
| ATOM | 2328 | O | SER A | 435 | 64.753 | 55.859 | 2.996 | 1.00 | 50.16 | O |
| ATOM | 2329 | CB | SER A | 435 | 65.279 | 58.952 | 4.583 | 1.00 | 53.87 | C |
| ATOM | 2330 | OG | SER A | 435 | 65.363 | 58.220 | 5.792 | 1.00 | 56.33 | O |
| ATOM | 2331 | N | TYR A | 436 | 66.523 | 57.230 | 2.744 | 1.00 | 49.98 | N |
| ATOM | 2332 | CA | TYR A | 436 | 67.436 | 56.203 | 2.263 | 1.00 | 49.61 | C |
| ATOM | 2333 | C | TYR A | 436 | 68.712 | 56.158 | 3.104 | 1.00 | 48.71 | C |
| ATOM | 2334 | O | TYR A | 436 | 69.174 | 57.187 | 3.602 | 1.00 | 48.91 | O |
| ATOM | 2335 | CB | TYR A | 436 | 67.817 | 56.485 | 0.806 | 1.00 | 51.63 | C |
| ATOM | 2336 | CG | TYR A | 436 | 66.691 | 56.313 | −0.188 | 1.00 | 52.47 | C |
| ATOM | 2337 | CD1 | TYR A | 436 | 66.256 | 55.044 | −0.562 | 1.00 | 52.86 | C |
| ATOM | 2338 | CD2 | TYR A | 436 | 66.058 | 57.420 | −0.752 | 1.00 | 54.05 | C |
| ATOM | 2339 | CE1 | TYR A | 436 | 65.219 | 54.878 | −1.475 | 1.00 | 55.19 | C |
| ATOM | 2340 | CE2 | TYR A | 436 | 65.015 | 57.267 | −1.668 | 1.00 | 55.67 | C |
| ATOM | 2341 | CZ | TYR A | 436 | 64.602 | 55.992 | −2.023 | 1.00 | 55.33 | C |
| ATOM | 2342 | OH | TYR A | 436 | 63.569 | 55.825 | −2.916 | 1.00 | 57.47 | O |
| ATOM | 2343 | N | VAL A | 437 | 69.272 | 54.963 | 3.263 | 1.00 | 45.78 | N |
| ATOM | 2344 | CA | VAL A | 437 | 70.514 | 54.794 | 4.008 | 1.00 | 44.47 | C |
| ATOM | 2345 | C | VAL A | 437 | 71.501 | 54.059 | 3.114 | 1.00 | 44.14 | C |
| ATOM | 2346 | O | VAL A | 437 | 71.120 | 53.167 | 2.357 | 1.00 | 43.85 | O |
| ATOM | 2347 | CB | VAL A | 437 | 70.318 | 53.984 | 5.316 | 1.00 | 43.82 | C |
| ATOM | 2348 | CG1 | VAL A | 437 | 69.389 | 54.736 | 6.255 | 1.00 | 42.73 | C |
| ATOM | 2349 | CG2 | VAL A | 437 | 69.778 | 52.598 | 5.004 | 1.00 | 41.37 | C |
| ATOM | 2350 | N | PRO A | 438 | 72.788 | 54.429 | 3.186 | 1.00 | 44.43 | N |
| ATOM | 2351 | CA | PRO A | 438 | 73.798 | 53.770 | 2.352 | 1.00 | 43.91 | C |
| ATOM | 2352 | C | PRO A | 438 | 73.930 | 52.285 | 2.654 | 1.00 | 43.14 | C |
| ATOM | 2353 | O | PRO A | 438 | 73.975 | 51.883 | 3.816 | 1.00 | 43.63 | O |
| ATOM | 2354 | CB | PRO A | 438 | 75.073 | 54.556 | 2.667 | 1.00 | 44.21 | C |
| ATOM | 2355 | CG | PRO A | 438 | 74.849 | 55.003 | 4.085 | 1.00 | 44.54 | C |
| ATOM | 2356 | CD | PRO A | 438 | 73.403 | 55.436 | 4.070 | 1.00 | 43.37 | C |
| ATOM | 2357 | N | TYR A | 439 | 73.971 | 51.480 | 1.597 | 1.00 | 42.30 | N |
| ATOM | 2358 | CA | TYR A | 439 | 74.103 | 50.034 | 1.713 | 1.00 | 41.24 | C |
| ATOM | 2359 | C | TYR A | 439 | 75.441 | 49.711 | 2.362 | 1.00 | 42.01 | C |
| ATOM | 2360 | O | TYR A | 439 | 76.477 | 50.233 | 1.956 | 1.00 | 41.44 | O |
| ATOM | 2361 | CB | TYR A | 439 | 74.025 | 49.391 | 0.323 | 1.00 | 39.97 | C |
| ATOM | 2362 | CG | TYR A | 439 | 74.174 | 47.884 | 0.302 | 1.00 | 37.05 | C |
| ATOM | 2363 | CD1 | TYR A | 439 | 73.341 | 47.067 | 1.063 | 1.00 | 37.13 | C |
| ATOM | 2364 | CD2 | TYR A | 439 | 75.134 | 47.273 | −0.506 | 1.00 | 38.06 | C |
| ATOM | 2365 | CE1 | TYR A | 439 | 73.458 | 45.675 | 1.019 | 1.00 | 37.56 | C |
| ATOM | 2366 | CE2 | TYR A | 439 | 75.260 | 45.887 | −0.557 | 1.00 | 36.89 | C |
| ATOM | 2367 | CZ | TYR A | 439 | 74.419 | 45.094 | 0.206 | 1.00 | 38.34 | C |
| ATOM | 2368 | OH | TYR A | 439 | 74.544 | 43.723 | 0.158 | 1.00 | 39.52 | O |
| ATOM | 2369 | N | ALA A | 440 | 75.415 | 48.841 | 3.366 | 1.00 | 42.74 | N |
| ATOM | 2370 | CA | ALA A | 440 | 76.632 | 48.473 | 4.078 | 1.00 | 42.66 | C |
| ATOM | 2371 | C | ALA A | 440 | 76.991 | 47.007 | 3.907 | 1.00 | 42.37 | C |
| ATOM | 2372 | O | ALA A | 440 | 77.982 | 46.540 | 4.462 | 1.00 | 43.02 | O |
| ATOM | 2373 | CB | ALA A | 440 | 76.480 | 48.799 | 5.561 | 1.00 | 42.72 | C |
| ATOM | 2374 | N | GLY A | 441 | 76.190 | 46.282 | 3.139 | 1.00 | 41.94 | N |
| ATOM | 2375 | CA | GLY A | 441 | 76.465 | 44.872 | 2.940 | 1.00 | 41.40 | C |

TABLE 2-continued

| ATOM | 2376 | C | GLY A | 441 | 75.788 | 44.014 | 3.991 | 1.00 | 42.16 | C |
|---|---|---|---|---|---|---|---|---|---|---|
| ATOM | 2377 | O | GLY A | 441 | 74.776 | 44.410 | 4.568 | 1.00 | 42.14 | O |
| ATOM | 2378 | N | LYS A | 442 | 76.351 | 42.838 | 4.246 | 1.00 | 42.68 | N |
| ATOM | 2379 | CA | LYS A | 442 | 75.799 | 41.909 | 5.225 | 1.00 | 42.67 | C |
| ATOM | 2380 | C | LYS A | 442 | 76.048 | 42.345 | 6.675 | 1.00 | 41.33 | C |
| ATOM | 2381 | O | LYS A | 442 | 77.086 | 42.924 | 7.000 | 1.00 | 39.63 | O |
| ATOM | 2382 | CB | LYS A | 442 | 76.384 | 40.515 | 4.990 | 1.00 | 45.23 | C |
| ATOM | 2383 | CG | LYS A | 442 | 76.063 | 39.949 | 3.612 | 1.00 | 49.35 | C |
| ATOM | 2384 | CD | LYS A | 442 | 74.990 | 38.864 | 3.670 | 1.00 | 51.07 | C |
| ATOM | 2385 | CE | LYS A | 442 | 75.563 | 37.563 | 4.226 | 1.00 | 54.09 | C |
| ATOM | 2386 | NZ | LYS A | 442 | 74.589 | 36.429 | 4.216 | 1.00 | 55.56 | N |
| ATOM | 2387 | N | LEU A | 443 | 75.078 | 42.055 | 7.534 | 1.00 | 40.11 | N |
| ATOM | 2388 | CA | LEU A | 443 | 75.140 | 42.395 | 8.951 | 1.00 | 38.38 | C |
| ATOM | 2389 | C | LEU A | 443 | 76.422 | 41.932 | 9.657 | 1.00 | 38.75 | C |
| ATOM | 2390 | O | LEU A | 443 | 77.085 | 42.717 | 10.329 | 1.00 | 36.60 | O |
| ATOM | 2391 | CB | LEU A | 443 | 73.917 | 41.805 | 9.659 | 1.00 | 35.66 | C |
| ATOM | 2392 | CG | LEU A | 443 | 73.769 | 41.987 | 11.173 | 1.00 | 34.22 | C |
| ATOM | 2393 | CD1 | LEU A | 443 | 72.311 | 41.806 | 11.567 | 1.00 | 31.06 | C |
| ATOM | 2394 | CD2 | LEU A | 443 | 74.660 | 40.991 | 11.904 | 1.00 | 33.38 | C |
| ATOM | 2395 | N | LYS A | 444 | 76.763 | 40.659 | 9.489 | 1.00 | 39.50 | N |
| ATOM | 2396 | CA | LYS A | 444 | 77.939 | 40.065 | 10.125 | 1.00 | 42.18 | C |
| ATOM | 2397 | C | LYS A | 444 | 79.232 | 40.890 | 10.156 | 1.00 | 41.66 | C |
| ATOM | 2398 | O | LYS A | 444 | 79.745 | 41.200 | 11.229 | 1.00 | 42.08 | O |
| ATOM | 2399 | CB | LYS A | 444 | 78.237 | 38.702 | 9.493 | 1.00 | 43.45 | C |
| ATOM | 2400 | CG | LYS A | 444 | 79.237 | 37.878 | 10.285 | 1.00 | 48.67 | C |
| ATOM | 2401 | CD | LYS A | 444 | 79.460 | 36.511 | 9.663 | 1.00 | 51.53 | C |
| ATOM | 2402 | CE | LYS A | 444 | 80.285 | 35.630 | 10.585 | 1.00 | 52.97 | C |
| ATOM | 2403 | NZ | LYS A | 444 | 81.600 | 36.254 | 10.907 | 1.00 | 53.80 | N |
| ATOM | 2404 | N | ASP A | 445 | 79.757 | 41.240 | 8.988 | 1.00 | 41.15 | N |
| ATOM | 2405 | CA | ASP A | 445 | 81.005 | 41.991 | 8.901 | 1.00 | 41.12 | C |
| ATOM | 2406 | C | ASP A | 445 | 80.951 | 43.355 | 9.567 | 1.00 | 40.48 | C |
| ATOM | 2407 | O | ASP A | 445 | 81.936 | 43.810 | 10.149 | 1.00 | 39.71 | O |
| ATOM | 2408 | CB | ASP A | 445 | 81.412 | 42.164 | 7.436 | 1.00 | 44.73 | C |
| ATOM | 2409 | CG | ASP A | 445 | 81.511 | 40.841 | 6.698 | 1.00 | 47.59 | C |
| ATOM | 2410 | OD1 | ASP A | 445 | 82.364 | 40.008 | 7.077 | 1.00 | 48.96 | O |
| ATOM | 2411 | OD2 | ASP A | 445 | 80.726 | 40.636 | 5.746 | 1.00 | 50.74 | O |
| ATOM | 2412 | N | ASN A | 446 | 79.802 | 44.012 | 9.471 | 1.00 | 38.11 | N |
| ATOM | 2413 | CA | ASN A | 446 | 79.637 | 45.332 | 10.058 | 1.00 | 37.61 | C |
| ATOM | 2414 | C | ASN A | 446 | 79.543 | 45.289 | 11.579 | 1.00 | 37.06 | C |
| ATOM | 2415 | O | ASN A | 446 | 80.122 | 46.136 | 12.261 | 1.00 | 35.82 | O |
| ATOM | 2416 | CB | ASN A | 446 | 78.405 | 46.000 | 9.469 | 1.00 | 38.33 | C |
| ATOM | 2417 | CG | ASN A | 446 | 78.605 | 46.388 | 8.023 | 1.00 | 39.42 | C |
| ATOM | 2418 | OD1 | ASN A | 446 | 79.106 | 47.473 | 7.725 | 1.00 | 39.50 | O |
| ATOM | 2419 | ND2 | ASN A | 446 | 78.232 | 45.493 | 7.112 | 1.00 | 38.24 | N |
| ATOM | 2420 | N | VAL A | 447 | 78.815 | 44.309 | 12.106 | 1.00 | 35.62 | N |
| ATOM | 2421 | CA | VAL A | 447 | 78.676 | 44.165 | 13.547 | 1.00 | 36.21 | C |
| ATOM | 2422 | C | VAL A | 447 | 80.030 | 43.786 | 14.160 | 1.00 | 36.80 | C |
| ATOM | 2423 | O | VAL A | 447 | 80.419 | 44.314 | 15.199 | 1.00 | 36.29 | O |
| ATOM | 2424 | CB | VAL A | 447 | 77.629 | 43.087 | 13.901 | 1.00 | 35.55 | C |
| ATOM | 2425 | CG1 | VAL A | 447 | 77.741 | 42.707 | 15.373 | 1.00 | 34.78 | C |
| ATOM | 2426 | CG2 | VAL A | 447 | 76.229 | 43.612 | 13.598 | 1.00 | 34.46 | C |
| ATOM | 2427 | N | GLU A | 448 | 80.746 | 42.876 | 13.505 | 1.00 | 37.04 | N |
| ATOM | 2428 | CA | GLU A | 448 | 82.048 | 42.451 | 13.994 | 1.00 | 38.35 | C |
| ATOM | 2429 | C | GLU A | 448 | 82.967 | 43.667 | 14.076 | 1.00 | 36.95 | C |
| ATOM | 2430 | O | GLU A | 448 | 83.655 | 43.864 | 15.075 | 1.00 | 35.90 | O |
| ATOM | 2431 | CB | GLU A | 448 | 82.656 | 41.392 | 13.062 | 1.00 | 40.48 | C |
| ATOM | 2432 | CG | GLU A | 448 | 83.949 | 40.772 | 13.586 | 1.00 | 45.60 | C |
| ATOM | 2433 | CD | GLU A | 448 | 84.553 | 39.739 | 12.634 | 1.00 | 50.26 | C |
| ATOM | 2434 | OE1 | GLU A | 448 | 85.094 | 40.133 | 11.573 | 1.00 | 51.53 | O |
| ATOM | 2435 | OE2 | GLU A | 448 | 84.482 | 38.529 | 12.950 | 1.00 | 52.94 | O |
| ATOM | 2436 | N | ALA A | 449 | 82.960 | 44.485 | 13.028 | 1.00 | 34.49 | N |
| ATOM | 2437 | CA | ALA A | 449 | 83.793 | 45.683 | 12.982 | 1.00 | 34.45 | C |
| ATOM | 2438 | C | ALA A | 449 | 83.417 | 46.670 | 14.089 | 1.00 | 33.89 | C |
| ATOM | 2439 | O | ALA A | 449 | 84.282 | 47.195 | 14.790 | 1.00 | 33.96 | O |
| ATOM | 2440 | CB | ALA A | 449 | 83.665 | 46.361 | 11.616 | 1.00 | 34.26 | C |
| ATOM | 2441 | N | SER A | 450 | 82.123 | 46.924 | 14.233 | 1.00 | 31.81 | N |
| ATOM | 2442 | CA | SER A | 450 | 81.638 | 47.841 | 15.252 | 1.00 | 32.08 | C |
| ATOM | 2443 | C | SER A | 450 | 82.023 | 47.380 | 16.657 | 1.00 | 31.86 | C |
| ATOM | 2444 | O | SER A | 450 | 82.531 | 48.166 | 17.463 | 1.00 | 29.55 | O |
| ATOM | 2445 | CB | SER A | 450 | 80.112 | 47.969 | 15.167 | 1.00 | 30.70 | C |
| ATOM | 2446 | OG | SER A | 450 | 79.724 | 48.753 | 14.056 | 1.00 | 31.66 | O |
| ATOM | 2447 | N | LEU A | 451 | 81.784 | 46.103 | 16.941 | 1.00 | 31.11 | N |
| ATOM | 2448 | CA | LEU A | 451 | 82.077 | 45.556 | 18.259 | 1.00 | 32.52 | C |
| ATOM | 2449 | C | LEU A | 451 | 83.565 | 45.413 | 18.559 | 1.00 | 33.63 | C |
| ATOM | 2450 | O | LEU A | 451 | 83.959 | 45.383 | 19.723 | 1.00 | 33.14 | O |
| ATOM | 2451 | CB | LEU A | 451 | 81.347 | 44.227 | 18.449 | 1.00 | 30.21 | C |
| ATOM | 2452 | CG | LEU A | 451 | 79.824 | 44.407 | 18.426 | 1.00 | 30.73 | C |
| ATOM | 2453 | CD1 | LEU A | 451 | 79.143 | 43.096 | 18.766 | 1.00 | 27.89 | C |
| ATOM | 2454 | CD2 | LEU A | 451 | 79.411 | 45.501 | 19.416 | 1.00 | 28.68 | C |

TABLE 2-continued

| | | | | | | | | | | |
|---|---|---|---|---|---|---|---|---|---|---|
| ATOM | 2455 | N | ASN A | 452 | 84.392 | 45.331 | 17.521 | 1.00 | 35.18 | N |
| ATOM | 2456 | CA | ASN A | 452 | 85.831 | 45.251 | 17.732 | 1.00 | 35.86 | C |
| ATOM | 2457 | C | ASN A | 452 | 86.294 | 46.601 | 18.274 | 1.00 | 35.32 | C |
| ATOM | 2458 | O | ASN A | 452 | 87.176 | 46.665 | 19.134 | 1.00 | 34.79 | O |
| ATOM | 2459 | CB | ASN A | 452 | 86.581 | 44.941 | 16.429 | 1.00 | 37.41 | C |
| ATOM | 2460 | CG | ASN A | 452 | 86.632 | 43.459 | 16.125 | 1.00 | 41.69 | C |
| ATOM | 2461 | OD1 | ASN A | 452 | 86.668 | 42.626 | 17.037 | 1.00 | 45.32 | O |
| ATOM | 2462 | ND2 | ASN A | 452 | 86.656 | 43.117 | 14.841 | 1.00 | 44.05 | N |
| ATOM | 2463 | N | LYS A | 453 | 85.695 | 47.680 | 17.774 | 1.00 | 34.56 | N |
| ATOM | 2464 | CA | LYS A | 453 | 86.069 | 49.012 | 18.235 | 1.00 | 35.20 | C |
| ATOM | 2465 | C | LYS A | 453 | 85.568 | 49.255 | 19.651 | 1.00 | 32.43 | C |
| ATOM | 2466 | O | LYS A | 453 | 86.237 | 49.915 | 20.442 | 1.00 | 31.92 | O |
| ATOM | 2467 | CB | LYS A | 453 | 85.533 | 50.098 | 17.292 | 1.00 | 36.51 | C |
| ATOM | 2468 | CG | LYS A | 453 | 86.090 | 49.988 | 15.877 | 1.00 | 42.24 | C |
| ATOM | 2469 | CD | LYS A | 453 | 86.165 | 51.338 | 15.160 | 1.00 | 43.06 | C |
| ATOM | 2470 | CE | LYS A | 453 | 84.835 | 52.050 | 15.172 | 1.00 | 45.98 | C |
| ATOM | 2471 | NZ | LYS A | 453 | 84.889 | 53.331 | 14.419 | 1.00 | 46.25 | N |
| ATOM | 2472 | N | VAL A | 454 | 84.391 | 48.724 | 19.968 | 1.00 | 30.18 | N |
| ATOM | 2473 | CA | VAL A | 454 | 83.836 | 48.878 | 21.303 | 1.00 | 28.56 | C |
| ATOM | 2474 | C | VAL A | 454 | 84.741 | 48.143 | 22.295 | 1.00 | 29.40 | C |
| ATOM | 2475 | O | VAL A | 454 | 85.100 | 48.690 | 23.338 | 1.00 | 26.82 | O |
| ATOM | 2476 | CB | VAL A | 454 | 82.401 | 48.306 | 21.390 | 1.00 | 29.78 | C |
| ATOM | 2477 | CG1 | VAL A | 454 | 81.943 | 48.247 | 22.855 | 1.00 | 26.04 | C |
| ATOM | 2478 | CG2 | VAL A | 454 | 81.444 | 49.181 | 20.572 | 1.00 | 29.03 | C |
| ATOM | 2479 | N | LYS A | 455 | 85.111 | 46.910 | 21.953 | 1.00 | 28.71 | N |
| ATOM | 2480 | CA | LYS A | 455 | 85.984 | 46.095 | 22.799 | 1.00 | 30.25 | C |
| ATOM | 2481 | C | LYS A | 455 | 87.330 | 46.774 | 23.020 | 1.00 | 30.25 | C |
| ATOM | 2482 | O | LYS A | 455 | 87.864 | 46.779 | 24.125 | 1.00 | 29.71 | O |
| ATOM | 2483 | CB | LYS A | 455 | 86.225 | 44.725 | 22.159 | 1.00 | 29.78 | C |
| ATOM | 2484 | CG | LYS A | 455 | 85.048 | 43.776 | 22.199 | 1.00 | 31.31 | C |
| ATOM | 2485 | CD | LYS A | 455 | 85.354 | 42.555 | 21.340 | 1.00 | 34.36 | C |
| ATOM | 2486 | CE | LYS A | 455 | 84.234 | 41.536 | 21.385 | 1.00 | 38.66 | C |
| ATOM | 2487 | NZ | LYS A | 455 | 84.480 | 40.397 | 20.448 | 1.00 | 40.02 | N |
| ATOM | 2488 | N | SER A | 456 | 87.876 | 47.338 | 21.950 | 1.00 | 31.20 | N |
| ATOM | 2489 | CA | SER A | 456 | 89.159 | 48.020 | 22.012 | 1.00 | 32.66 | C |
| ATOM | 2490 | C | SER A | 456 | 89.063 | 49.232 | 22.939 | 1.00 | 32.37 | C |
| ATOM | 2491 | O | SER A | 456 | 89.938 | 49.461 | 23.786 | 1.00 | 32.02 | O |
| ATOM | 2492 | CB | SER A | 456 | 89.583 | 48.453 | 20.601 | 1.00 | 33.72 | C |
| ATOM | 2493 | OG | SER A | 456 | 90.866 | 49.044 | 20.615 | 1.00 | 36.70 | O |
| ATOM | 2494 | N | THR A | 457 | 87.994 | 50.009 | 22.776 | 1.00 | 29.64 | N |
| ATOM | 2495 | CA | THR A | 457 | 87.787 | 51.178 | 23.614 | 1.00 | 29.25 | C |
| ATOM | 2496 | C | THR A | 457 | 87.595 | 50.733 | 25.060 | 1.00 | 28.90 | C |
| ATOM | 2497 | O | THR A | 457 | 88.086 | 51.380 | 25.981 | 1.00 | 28.75 | O |
| ATOM | 2498 | CB | THR A | 457 | 86.561 | 51.982 | 23.158 | 1.00 | 29.05 | C |
| ATOM | 2499 | OG1 | THR A | 457 | 86.757 | 52.393 | 21.805 | 1.00 | 32.49 | O |
| ATOM | 2500 | CG2 | THR A | 457 | 86.369 | 53.216 | 24.022 | 1.00 | 26.06 | C |
| ATOM | 2501 | N | MET A | 458 | 86.884 | 49.625 | 25.259 | 1.00 | 28.56 | N |
| ATOM | 2502 | CA | MET A | 458 | 86.663 | 49.111 | 26.603 | 1.00 | 27.60 | C |
| ATOM | 2503 | C | MET A | 458 | 87.993 | 48.832 | 27.288 | 1.00 | 28.20 | C |
| ATOM | 2504 | O | MET A | 458 | 88.167 | 49.155 | 28.459 | 1.00 | 28.30 | O |
| ATOM | 2505 | CB | MET A | 458 | 85.792 | 47.853 | 26.560 | 1.00 | 27.08 | C |
| ATOM | 2506 | CG | MET A | 458 | 84.306 | 48.170 | 26.380 | 1.00 | 26.92 | C |
| ATOM | 2507 | SD | MET A | 458 | 83.227 | 46.746 | 26.210 | 1.00 | 28.93 | S |
| ATOM | 2508 | CE | MET A | 458 | 83.415 | 45.945 | 27.805 | 1.00 | 27.06 | C |
| ATOM | 2509 | N | CYS A | 459 | 88.944 | 48.252 | 26.561 | 1.00 | 29.24 | N |
| ATOM | 2510 | CA | CYS A | 459 | 90.254 | 47.982 | 27.141 | 1.00 | 30.30 | C |
| ATOM | 2511 | C | CYS A | 459 | 91.009 | 49.273 | 27.466 | 1.00 | 30.36 | C |
| ATOM | 2512 | O | CYS A | 459 | 91.818 | 49.303 | 28.397 | 1.00 | 28.82 | O |
| ATOM | 2513 | CB | CYS A | 459 | 91.092 | 47.100 | 26.212 | 1.00 | 32.96 | C |
| ATOM | 2514 | SG | CYS A | 459 | 90.670 | 45.337 | 26.352 | 1.00 | 36.19 | S |
| ATOM | 2515 | N | ASN A | 460 | 90.757 | 50.335 | 26.702 | 1.00 | 28.82 | N |
| ATOM | 2516 | CA | ASN A | 460 | 91.411 | 51.609 | 26.986 | 1.00 | 29.47 | C |
| ATOM | 2517 | C | ASN A | 460 | 90.884 | 52.087 | 28.334 | 1.00 | 28.59 | C |
| ATOM | 2518 | O | ASN A | 460 | 91.586 | 52.756 | 29.079 | 1.00 | 29.35 | O |
| ATOM | 2519 | CB | ASN A | 460 | 91.078 | 52.677 | 25.937 | 1.00 | 29.43 | C |
| ATOM | 2520 | CG | ASN A | 460 | 91.756 | 52.434 | 24.610 | 1.00 | 32.45 | C |
| ATOM | 2521 | OD1 | ASN A | 460 | 91.097 | 52.161 | 23.612 | 1.00 | 33.79 | O |
| ATOM | 2522 | ND2 | ASN A | 460 | 93.080 | 52.536 | 24.589 | 1.00 | 31.89 | N |
| ATOM | 2523 | N | CYS A | 461 | 89.636 | 51.735 | 28.633 | 1.00 | 28.48 | N |
| ATOM | 2524 | CA | CYS A | 461 | 88.993 | 52.143 | 29.878 | 1.00 | 27.53 | C |
| ATOM | 2525 | C | CYS A | 461 | 89.204 | 51.138 | 31.010 | 1.00 | 27.92 | C |
| ATOM | 2526 | O | CYS A | 461 | 88.633 | 51.289 | 32.086 | 1.00 | 27.95 | O |
| ATOM | 2527 | CB | CYS A | 461 | 87.486 | 52.355 | 29.646 | 1.00 | 29.51 | C |
| ATOM | 2528 | SG | CYS A | 461 | 87.070 | 53.620 | 28.389 | 1.00 | 32.81 | S |
| ATOM | 2529 | N | GLY A | 462 | 90.021 | 50.119 | 30.762 | 1.00 | 27.78 | N |
| ATOM | 2530 | CA | GLY A | 462 | 90.293 | 49.106 | 31.767 | 1.00 | 27.70 | C |
| ATOM | 2531 | C | GLY A | 462 | 89.133 | 48.163 | 32.052 | 1.00 | 28.72 | C |
| ATOM | 2532 | O | GLY A | 462 | 88.987 | 47.674 | 33.176 | 1.00 | 29.35 | O |
| ATOM | 2533 | N | ALA A | 463 | 88.315 | 47.881 | 31.043 | 1.00 | 27.30 | N |

TABLE 2-continued

| | | | | | | | | | | |
|---|---|---|---|---|---|---|---|---|---|---|
| ATOM | 2534 | CA | ALA A | 463 | 87.163 | 47.012 | 31.248 | 1.00 | 27.53 | C |
| ATOM | 2535 | C | ALA A | 463 | 87.121 | 45.785 | 30.352 | 1.00 | 27.82 | C |
| ATOM | 2536 | O | ALA A | 463 | 87.288 | 45.886 | 29.139 | 1.00 | 27.55 | O |
| ATOM | 2537 | CB | ALA A | 463 | 85.879 | 47.820 | 31.069 | 1.00 | 26.38 | C |
| ATOM | 2538 | N | LEU A | 464 | 86.884 | 44.628 | 30.961 | 1.00 | 28.56 | N |
| ATOM | 2539 | CA | LEU A | 464 | 86.785 | 43.369 | 30.223 | 1.00 | 30.06 | C |
| ATOM | 2540 | C | LEU A | 464 | 85.330 | 42.963 | 30.014 | 1.00 | 29.07 | C |
| ATOM | 2541 | O | LEU A | 464 | 85.043 | 42.046 | 29.246 | 1.00 | 31.05 | O |
| ATOM | 2542 | CB | LEU A | 464 | 87.512 | 42.237 | 30.961 | 1.00 | 31.49 | C |
| ATOM | 2543 | CG | LEU A | 464 | 88.993 | 42.025 | 30.640 | 1.00 | 33.97 | C |
| ATOM | 2544 | CD1 | LEU A | 464 | 89.150 | 41.723 | 29.158 | 1.00 | 36.04 | C |
| ATOM | 2545 | CD2 | LEU A | 464 | 89.788 | 43.265 | 31.004 | 1.00 | 38.27 | C |
| ATOM | 2546 | N | THR A | 465 | 84.419 | 43.633 | 30.712 | 1.00 | 27.77 | N |
| ATOM | 2547 | CA | THR A | 465 | 82.996 | 43.338 | 30.595 | 1.00 | 27.41 | C |
| ATOM | 2548 | C | THR A | 465 | 82.197 | 44.630 | 30.674 | 1.00 | 27.20 | C |
| ATOM | 2549 | O | THR A | 465 | 82.709 | 45.664 | 31.107 | 1.00 | 26.83 | O |
| ATOM | 2550 | CB | THR A | 465 | 82.494 | 42.417 | 31.736 | 1.00 | 27.84 | C |
| ATOM | 2551 | OG1 | THR A | 465 | 82.536 | 43.133 | 32.975 | 1.00 | 28.30 | O |
| ATOM | 2552 | CG2 | THR A | 465 | 83.355 | 41.159 | 31.838 | 1.00 | 28.72 | C |
| ATOM | 2553 | N | ILE A | 466 | 80.936 | 44.567 | 30.260 | 1.00 | 25.31 | N |
| ATOM | 2554 | CA | ILE A | 466 | 80.085 | 45.743 | 30.298 | 1.00 | 25.03 | C |
| ATOM | 2555 | C | ILE A | 466 | 79.898 | 46.236 | 31.732 | 1.00 | 24.87 | C |
| ATOM | 2556 | O | ILE A | 466 | 79.985 | 47.430 | 31.993 | 1.00 | 27.04 | O |
| ATOM | 2557 | CB | ILE A | 466 | 78.724 | 45.456 | 29.629 | 1.00 | 25.22 | C |
| ATOM | 2558 | CG1 | ILE A | 466 | 78.939 | 45.313 | 28.114 | 1.00 | 24.45 | C |
| ATOM | 2559 | CG2 | ILE A | 466 | 77.726 | 46.565 | 29.944 | 1.00 | 22.53 | C |
| ATOM | 2560 | CD1 | ILE A | 466 | 77.699 | 44.908 | 27.350 | 1.00 | 25.70 | C |
| ATOM | 2561 | N | PRO A | 467 | 79.638 | 45.327 | 32.684 | 1.00 | 25.57 | N |
| ATOM | 2562 | CA | PRO A | 467 | 79.468 | 45.805 | 34.058 | 1.00 | 25.31 | C |
| ATOM | 2563 | C | PRO A | 467 | 80.730 | 46.506 | 34.570 | 1.00 | 26.95 | C |
| ATOM | 2564 | O | PRO A | 467 | 80.649 | 47.499 | 35.292 | 1.00 | 27.35 | O |
| ATOM | 2565 | CB | PRO A | 467 | 79.149 | 44.525 | 34.828 | 1.00 | 25.79 | C |
| ATOM | 2566 | CG | PRO A | 467 | 78.393 | 43.723 | 33.811 | 1.00 | 24.45 | C |
| ATOM | 2567 | CD | PRO A | 467 | 79.258 | 43.909 | 32.577 | 1.00 | 23.17 | C |
| ATOM | 2568 | N | GLN A | 468 | 81.897 | 46.003 | 34.186 | 1.00 | 27.99 | N |
| ATOM | 2569 | CA | GLN A | 468 | 83.137 | 46.623 | 34.630 | 1.00 | 28.59 | C |
| ATOM | 2570 | C | GLN A | 468 | 83.320 | 47.995 | 33.976 | 1.00 | 29.85 | C |
| ATOM | 2571 | O | GLN A | 468 | 83.844 | 48.926 | 34.594 | 1.00 | 29.02 | O |
| ATOM | 2572 | CB | GLN A | 468 | 84.320 | 45.710 | 34.323 | 1.00 | 29.66 | C |
| ATOM | 2573 | CG | GLN A | 468 | 85.623 | 46.216 | 34.879 | 1.00 | 30.83 | C |
| ATOM | 2574 | CD | GLN A | 468 | 86.722 | 45.175 | 34.834 | 1.00 | 29.49 | C |
| ATOM | 2575 | OE1 | GLN A | 468 | 86.806 | 44.380 | 33.900 | 1.00 | 27.39 | O |
| ATOM | 2576 | NE2 | GLN A | 468 | 87.589 | 45.194 | 35.839 | 1.00 | 32.22 | N |
| ATOM | 2577 | N | LEU A | 469 | 82.872 | 48.124 | 32.729 | 1.00 | 28.18 | N |
| ATOM | 2578 | CA | LEU A | 469 | 82.961 | 49.395 | 32.025 | 1.00 | 26.94 | C |
| ATOM | 2579 | C | LEU A | 469 | 82.029 | 50.413 | 32.676 | 1.00 | 27.29 | C |
| ATOM | 2580 | O | LEU A | 469 | 82.379 | 51.587 | 32.815 | 1.00 | 26.46 | O |
| ATOM | 2581 | CB | LEU A | 469 | 82.566 | 49.232 | 30.554 | 1.00 | 27.22 | C |
| ATOM | 2582 | CG | LEU A | 469 | 82.343 | 50.536 | 29.777 | 1.00 | 28.28 | C |
| ATOM | 2583 | CD1 | LEU A | 469 | 83.683 | 51.232 | 29.552 | 1.00 | 25.24 | C |
| ATOM | 2584 | CD2 | LEU A | 469 | 81.657 | 50.238 | 28.438 | 1.00 | 27.64 | C |
| ATOM | 2585 | N | GLN A | 470 | 80.845 | 49.959 | 33.076 | 1.00 | 26.40 | N |
| ATOM | 2586 | CA | GLN A | 470 | 79.864 | 50.851 | 33.685 | 1.00 | 28.89 | C |
| ATOM | 2587 | C | GLN A | 470 | 80.344 | 51.351 | 35.038 | 1.00 | 29.84 | C |
| ATOM | 2588 | O | GLN A | 470 | 80.001 | 52.444 | 35.480 | 1.00 | 28.12 | O |
| ATOM | 2589 | CB | GLN A | 470 | 78.513 | 50.132 | 33.807 | 1.00 | 27.17 | C |
| ATOM | 2590 | CG | GLN A | 470 | 77.962 | 49.716 | 32.434 | 1.00 | 27.68 | C |
| ATOM | 2591 | CD | GLN A | 470 | 76.666 | 48.938 | 32.506 | 1.00 | 28.13 | C |
| ATOM | 2592 | OE1 | GLN A | 470 | 76.449 | 48.166 | 33.432 | 1.00 | 28.58 | O |
| ATOM | 2593 | NE2 | GLN A | 470 | 75.803 | 49.122 | 31.508 | 1.00 | 26.29 | N |
| ATOM | 2594 | N | SER A | 471 | 81.173 | 50.543 | 35.676 | 1.00 | 31.64 | N |
| ATOM | 2595 | CA | SER A | 471 | 81.712 | 50.880 | 36.976 | 1.00 | 31.86 | C |
| ATOM | 2596 | C | SER A | 471 | 82.949 | 51.783 | 36.887 | 1.00 | 32.13 | C |
| ATOM | 2597 | O | SER A | 471 | 83.081 | 52.742 | 37.646 | 1.00 | 32.18 | O |
| ATOM | 2598 | CB | SER A | 471 | 82.050 | 49.585 | 37.722 | 1.00 | 30.51 | C |
| ATOM | 2599 | OG | SER A | 471 | 82.831 | 49.842 | 38.870 | 1.00 | 33.39 | O |
| ATOM | 2600 | N | LYS A | 472 | 83.830 | 51.493 | 35.936 | 1.00 | 32.80 | N |
| ATOM | 2601 | CA | LYS A | 472 | 85.081 | 52.234 | 35.783 | 1.00 | 33.19 | C |
| ATOM | 2602 | C | LYS A | 472 | 85.148 | 53.388 | 34.781 | 1.00 | 32.28 | C |
| ATOM | 2603 | O | LYS A | 472 | 86.097 | 54.163 | 34.813 | 1.00 | 32.33 | O |
| ATOM | 2604 | CB | LYS A | 472 | 86.201 | 51.245 | 35.452 | 1.00 | 34.04 | C |
| ATOM | 2605 | CG | LYS A | 472 | 86.335 | 50.127 | 36.466 | 1.00 | 36.23 | C |
| ATOM | 2606 | CD | LYS A | 472 | 87.335 | 49.075 | 36.019 | 1.00 | 38.07 | C |
| ATOM | 2607 | CE | LYS A | 472 | 88.755 | 49.592 | 36.059 | 1.00 | 39.38 | C |
| ATOM | 2608 | NZ | LYS A | 472 | 89.723 | 48.517 | 35.698 | 1.00 | 41.01 | N |
| ATOM | 2609 | N | ALA A | 473 | 84.170 | 53.506 | 33.889 | 1.00 | 31.34 | N |
| ATOM | 2610 | CA | ALA A | 473 | 84.201 | 54.572 | 32.892 | 1.00 | 30.17 | C |
| ATOM | 2611 | C | ALA A | 473 | 84.324 | 55.987 | 33.461 | 1.00 | 30.11 | C |
| ATOM | 2612 | O | ALA A | 473 | 83.718 | 56.334 | 34.480 | 1.00 | 30.70 | O |

TABLE 2-continued

| | | | | | | | | | | |
|---|---|---|---|---|---|---|---|---|---|---|
| ATOM | 2613 | CB | ALA A | 473 | 82.971 | 54.489 | 31.986 | 1.00 | 29.13 | C |
| ATOM | 2614 | N | LYS A | 474 | 85.136 | 56.788 | 32.781 | 1.00 | 30.05 | N |
| ATOM | 2615 | CA | LYS A | 474 | 85.362 | 58.184 | 33.129 | 1.00 | 29.85 | C |
| ATOM | 2616 | C | LYS A | 474 | 84.772 | 58.909 | 31.928 | 1.00 | 29.93 | C |
| ATOM | 2617 | O | LYS A | 474 | 85.302 | 58.833 | 30.816 | 1.00 | 29.14 | O |
| ATOM | 2618 | CB | LYS A | 474 | 86.862 | 58.441 | 33.277 | 1.00 | 28.50 | C |
| ATOM | 2619 | CG | LYS A | 474 | 87.460 | 57.684 | 34.471 | 1.00 | 28.70 | C |
| ATOM | 2620 | CD | LYS A | 474 | 88.943 | 57.375 | 34.279 | 1.00 | 27.54 | C |
| ATOM | 2621 | CE | LYS A | 474 | 89.803 | 58.620 | 34.334 | 1.00 | 29.17 | C |
| ATOM | 2622 | NZ | LYS A | 474 | 91.222 | 58.265 | 34.018 | 1.00 | 28.64 | N |
| ATOM | 2623 | N | ILE A | 475 | 83.660 | 59.597 | 32.150 | 1.00 | 29.12 | N |
| ATOM | 2624 | CA | ILE A | 475 | 82.968 | 60.254 | 31.056 | 1.00 | 29.85 | C |
| ATOM | 2625 | C | ILE A | 475 | 82.935 | 61.764 | 31.176 | 1.00 | 29.94 | C |
| ATOM | 2626 | O | ILE A | 475 | 82.444 | 62.314 | 32.166 | 1.00 | 30.35 | O |
| ATOM | 2627 | CB | ILE A | 475 | 81.524 | 59.703 | 30.943 | 1.00 | 29.86 | C |
| ATOM | 2628 | CG1 | ILE A | 475 | 81.564 | 58.164 | 30.940 | 1.00 | 29.42 | C |
| ATOM | 2629 | CG2 | ILE A | 475 | 80.867 | 60.213 | 29.666 | 1.00 | 29.91 | C |
| ATOM | 2630 | CD1 | ILE A | 475 | 80.205 | 57.470 | 30.951 | 1.00 | 23.94 | C |
| ATOM | 2631 | N | THR A | 476 | 83.459 | 62.429 | 30.153 | 1.00 | 29.56 | N |
| ATOM | 2632 | CA | THR A | 476 | 83.511 | 63.881 | 30.141 | 1.00 | 29.14 | C |
| ATOM | 2633 | C | THR A | 476 | 82.686 | 64.506 | 29.042 | 1.00 | 28.15 | C |
| ATOM | 2634 | O | THR A | 476 | 82.582 | 63.986 | 27.932 | 1.00 | 26.60 | O |
| ATOM | 2635 | CB | THR A | 476 | 84.962 | 64.414 | 29.981 | 1.00 | 28.25 | C |
| ATOM | 2636 | OG1 | THR A | 476 | 84.953 | 65.844 | 30.066 | 1.00 | 32.24 | O |
| ATOM | 2637 | CG2 | THR A | 476 | 85.535 | 64.022 | 28.629 | 1.00 | 26.65 | C |
| ATOM | 2638 | N | LEU A | 477 | 82.105 | 65.644 | 29.381 | 1.00 | 29.09 | N |
| ATOM | 2639 | CA | LEU A | 477 | 81.312 | 66.424 | 28.456 | 1.00 | 32.22 | C |
| ATOM | 2640 | C | LEU A | 477 | 82.352 | 67.281 | 27.731 | 1.00 | 32.43 | C |
| ATOM | 2641 | O | LEU A | 477 | 83.395 | 67.592 | 28.304 | 1.00 | 32.10 | O |
| ATOM | 2642 | CB | LEU A | 477 | 80.352 | 67.312 | 29.256 | 1.00 | 33.05 | C |
| ATOM | 2643 | CG | LEU A | 477 | 79.239 | 68.097 | 28.566 | 1.00 | 35.08 | C |
| ATOM | 2644 | CD1 | LEU A | 477 | 78.264 | 67.138 | 27.910 | 1.00 | 32.98 | C |
| ATOM | 2645 | CD2 | LEU A | 477 | 78.526 | 68.966 | 29.604 | 1.00 | 35.36 | C |
| ATOM | 2646 | N | VAL A | 478 | 82.093 | 67.635 | 26.477 | 1.00 | 33.80 | N |
| ATOM | 2647 | CA | VAL A | 478 | 83.018 | 68.480 | 25.726 | 1.00 | 35.55 | C |
| ATOM | 2648 | C | VAL A | 478 | 82.280 | 69.767 | 25.365 | 1.00 | 35.88 | C |
| ATOM | 2649 | O | VAL A | 478 | 81.052 | 69.787 | 25.304 | 1.00 | 35.41 | O |
| ATOM | 2650 | CB | VAL A | 478 | 83.516 | 67.796 | 24.422 | 1.00 | 36.48 | C |
| ATOM | 2651 | CG1 | VAL A | 478 | 83.960 | 66.370 | 24.718 | 1.00 | 37.57 | C |
| ATOM | 2652 | CG2 | VAL A | 478 | 82.428 | 67.822 | 23.363 | 1.00 | 38.80 | C |
| ATOM | 2653 | N | SER A | 479 | 83.028 | 70.839 | 25.132 | 1.00 | 37.26 | N |
| ATOM | 2654 | CA | SER A | 479 | 82.432 | 72.127 | 24.794 | 1.00 | 39.38 | C |
| ATOM | 2655 | C | SER A | 479 | 81.806 | 72.119 | 23.406 | 1.00 | 40.82 | C |
| ATOM | 2656 | O | SER A | 479 | 82.200 | 71.341 | 22.537 | 1.00 | 41.28 | O |
| ATOM | 2657 | CB | SER A | 479 | 83.488 | 73.230 | 24.869 | 1.00 | 38.01 | C |
| ATOM | 2658 | OG | SER A | 479 | 84.515 | 72.999 | 23.924 | 1.00 | 38.36 | O |
| ATOM | 2659 | N | SER A | 480 | 80.825 | 72.990 | 23.203 | 1.00 | 44.34 | N |
| ATOM | 2660 | CA | SER A | 480 | 80.152 | 73.083 | 21.912 | 1.00 | 48.75 | C |
| ATOM | 2661 | C | SER A | 480 | 81.149 | 73.491 | 20.828 | 1.00 | 50.10 | C |
| ATOM | 2662 | O | SER A | 480 | 81.088 | 73.005 | 19.698 | 1.00 | 50.70 | O |
| ATOM | 2663 | CB | SER A | 480 | 79.017 | 74.104 | 21.986 | 1.00 | 49.74 | C |
| ATOM | 2664 | OG | SER A | 480 | 79.516 | 75.382 | 22.326 | 1.00 | 52.76 | O |
| ATOM | 2665 | N | VAL A | 481 | 82.074 | 74.377 | 21.187 | 1.00 | 52.36 | N |
| ATOM | 2666 | CA | VAL A | 481 | 83.096 | 74.856 | 20.262 | 1.00 | 54.26 | C |
| ATOM | 2667 | C | VAL A | 481 | 83.975 | 73.729 | 19.720 | 1.00 | 55.31 | C |
| ATOM | 2668 | O | VAL A | 481 | 84.319 | 73.721 | 18.537 | 1.00 | 55.24 | O |
| ATOM | 2669 | CB | VAL A | 481 | 84.017 | 75.901 | 20.937 | 1.00 | 54.94 | C |
| ATOM | 2670 | CG1 | VAL A | 481 | 85.189 | 76.234 | 20.021 | 1.00 | 55.96 | C |
| ATOM | 2671 | CG2 | VAL A | 481 | 83.229 | 77.162 | 21.256 | 1.00 | 55.59 | C |
| ATOM | 2672 | N | SER A | 482 | 84.343 | 72.788 | 20.586 | 1.00 | 56.16 | N |
| ATOM | 2673 | CA | SER A | 482 | 85.190 | 71.670 | 20.183 | 1.00 | 58.27 | C |
| ATOM | 2674 | C | SER A | 482 | 84.491 | 70.750 | 19.184 | 1.00 | 60.34 | C |
| ATOM | 2675 | O | SER A | 482 | 85.144 | 69.962 | 18.493 | 1.00 | 60.26 | O |
| ATOM | 2676 | CB | SER A | 482 | 85.620 | 70.855 | 21.408 | 1.00 | 57.59 | C |
| ATOM | 2677 | OG | SER A | 482 | 84.518 | 70.189 | 21.998 | 1.00 | 57.44 | O |
| ATOM | 2678 | N | ILE A | 483 | 83.166 | 70.851 | 19.107 | 1.00 | 61.66 | N |
| ATOM | 2679 | CA | ILE A | 483 | 82.395 | 70.016 | 18.192 | 1.00 | 64.37 | C |
| ATOM | 2680 | C | ILE A | 483 | 82.307 | 70.637 | 16.795 | 1.00 | 65.60 | C |
| ATOM | 2681 | O | ILE A | 483 | 82.290 | 71.886 | 16.692 | 1.00 | 65.96 | O |
| ATOM | 2682 | CB | ILE A | 483 | 80.959 | 69.786 | 18.728 | 1.00 | 64.32 | C |
| ATOM | 2683 | CG1 | ILE A | 483 | 81.023 | 69.252 | 20.161 | 1.00 | 64.61 | C |
| ATOM | 2684 | CG2 | ILE A | 483 | 80.215 | 68.796 | 17.835 | 1.00 | 64.26 | C |
| ATOM | 2685 | CD1 | ILE A | 483 | 79.670 | 68.993 | 20.789 | 1.00 | 64.99 | C |
| TER | 2686 | | ILE A | 483 | | | | | | |
| HETATM | 2687 | K | K A | 900 | 52.942 | 60.264 | 29.342 | 0.75 | 35.52 | K |
| HETATM | 2688 | P | IMP | 602 | 67.729 | 55.171 | 15.018 | 1.00 | 32.01 | P |
| HETATM | 2689 | O1P | IMP | 602 | 67.318 | 55.116 | 13.589 | 1.00 | 35.06 | O |
| HETATM | 2690 | O2P | IMP | 602 | 68.541 | 53.958 | 15.324 | 1.00 | 37.34 | O |
| HETATM | 2691 | O3P | IMP | 602 | 68.509 | 56.460 | 15.351 | 1.00 | 34.23 | O |

TABLE 2-continued

| | | | | | | | | | | |
|---|---|---|---|---|---|---|---|---|---|---|
| HETATM | 2692 | O5* | IMP | 602 | 66.513 | 55.208 | 16.042 | 1.00 | 32.49 | O |
| HETATM | 2693 | C5* | IMP | 602 | 65.484 | 54.230 | 15.900 | 1.00 | 28.06 | C |
| HETATM | 2694 | C4* | IMP | 602 | 64.416 | 54.369 | 16.948 | 1.00 | 29.30 | C |
| HETATM | 2695 | O4* | IMP | 602 | 63.654 | 55.545 | 16.512 | 1.00 | 28.92 | O |
| HETATM | 2696 | C3* | IMP | 602 | 63.350 | 53.301 | 17.112 | 1.00 | 27.97 | C |
| HETATM | 2697 | O3* | IMP | 602 | 63.765 | 52.190 | 17.882 | 1.00 | 29.87 | O |
| HETATM | 2698 | C2* | IMP | 602 | 62.219 | 54.048 | 17.747 | 1.00 | 28.37 | C |
| HETATM | 2699 | O2* | IMP | 602 | 62.308 | 54.094 | 19.151 | 1.00 | 28.77 | O |
| HETATM | 2700 | C1* | IMP | 602 | 62.341 | 55.422 | 17.066 | 1.00 | 29.44 | C |
| HETATM | 2701 | N9 | IMP | 602 | 61.392 | 55.563 | 15.918 | 1.00 | 31.97 | N |
| HETATM | 2702 | C8 | IMP | 602 | 60.890 | 54.644 | 15.016 | 1.00 | 32.78 | C |
| HETATM | 2703 | N7 | IMP | 602 | 60.086 | 55.173 | 14.154 | 1.00 | 32.55 | N |
| HETATM | 2704 | C5 | IMP | 602 | 60.027 | 56.497 | 14.463 | 1.00 | 34.42 | C |
| HETATM | 2705 | C6 | IMP | 602 | 59.302 | 57.582 | 13.855 | 1.00 | 35.14 | C |
| HETATM | 2706 | O6 | IMP | 602 | 58.555 | 57.521 | 12.883 | 1.00 | 36.42 | O |
| HETATM | 2707 | N1 | IMP | 602 | 59.516 | 58.848 | 14.495 | 1.00 | 36.83 | N |
| HETATM | 2708 | C2 | IMP | 602 | 60.355 | 59.011 | 15.609 | 1.00 | 38.21 | C |
| HETATM | 2709 | N3 | IMP | 602 | 61.034 | 57.973 | 16.170 | 1.00 | 35.63 | N |
| HETATM | 2710 | C4 | IMP | 602 | 60.832 | 56.774 | 15.563 | 1.00 | 34.37 | C |
| HETATM | 2711 | O | HOH | 1 | 63.019 | 58.881 | 18.340 | 1.00 | 44.26 | O |
| HETATM | 2712 | O | HOH | 2 | 52.277 | 57.766 | 28.053 | 1.00 | 120.54 | O |
| HETATM | 2713 | O | HOH | 3 | 66.605 | 47.974 | 38.976 | 1.00 | 25.54 | O |
| HETATM | 2714 | O | HOH | 4 | 59.386 | 45.205 | 36.943 | 1.00 | 29.43 | O |
| HETATM | 2715 | O | HOH | 5 | 79.662 | 41.845 | 29.507 | 1.00 | 22.13 | O |
| HETATM | 2716 | O | HOH | 6 | 65.938 | 60.529 | 24.679 | 1.00 | 31.17 | O |
| HETATM | 2717 | O | HOH | 7 | 74.980 | 45.671 | 32.871 | 1.00 | 30.42 | O |
| HETATM | 2718 | O | HOH | 8 | 57.548 | 58.753 | 28.347 | 1.00 | 28.92 | O |
| HETATM | 2719 | O | HOH | 9 | 70.703 | 54.421 | 21.919 | 1.00 | 26.74 | O |
| HETATM | 2720 | O | HOH | 10 | 70.985 | 53.252 | 14.290 | 1.00 | 27.12 | O |
| HETATM | 2721 | O | HOH | 11 | 45.680 | 44.301 | 11.265 | 1.00 | 103.96 | O |
| HETATM | 2722 | O | HOH | 12 | 77.744 | 53.946 | 34.272 | 1.00 | 32.08 | O |
| HETATM | 2723 | O | HOH | 13 | 58.727 | 51.272 | 23.006 | 1.00 | 27.53 | O |
| HETATM | 2724 | O | HOH | 14 | 62.326 | 38.666 | 34.100 | 1.00 | 27.41 | O |
| HETATM | 2725 | O | HOH | 15 | 56.691 | 78.735 | 34.475 | 1.00 | 29.79 | O |
| HETATM | 2726 | O | HOH | 16 | 88.368 | 53.773 | 33.242 | 1.00 | 29.09 | O |
| HETATM | 2727 | O | HOH | 17 | 72.567 | 38.252 | 33.805 | 1.00 | 32.29 | O |
| HETATM | 2728 | O | HOH | 18 | 87.198 | 55.495 | 31.179 | 1.00 | 28.25 | O |
| HETATM | 2729 | O | HOH | 19 | 49.308 | 44.270 | 21.126 | 1.00 | 33.03 | O |
| HETATM | 2730 | O | HOH | 20 | 78.730 | 48.078 | 37.343 | 1.00 | 33.84 | O |
| HETATM | 2731 | O | HOH | 21 | 73.616 | 57.426 | 36.203 | 1.00 | 27.28 | O |
| HETATM | 2732 | O | HOH | 22 | 56.311 | 77.113 | 37.092 | 1.00 | 34.13 | O |
| HETATM | 2733 | O | HOH | 23 | 74.197 | 59.875 | 37.788 | 1.00 | 40.63 | O |
| HETATM | 2734 | O | HOH | 24 | 64.449 | 41.371 | 7.872 | 1.00 | 35.33 | O |
| HETATM | 2735 | O | HOH | 25 | 76.108 | 43.846 | 30.984 | 1.00 | 26.68 | O |
| HETATM | 2736 | O | HOH | 26 | 70.175 | 33.467 | 27.535 | 1.00 | 36.79 | O |
| HETATM | 2737 | O | HOH | 27 | 84.289 | 53.139 | 21.052 | 1.00 | 32.01 | O |
| HETATM | 2738 | O | HOH | 28 | 56.502 | 57.506 | 38.867 | 1.00 | 42.20 | O |
| HETATM | 2739 | O | HOH | 29 | 48.256 | 54.233 | 36.924 | 1.00 | 41.83 | O |
| HETATM | 2740 | O | HOH | 30 | 75.042 | 38.867 | 31.153 | 1.00 | 33.27 | O |
| HETATM | 2741 | O | HOH | 31 | 69.348 | 62.804 | 21.515 | 1.00 | 38.19 | O |
| HETATM | 2742 | O | HOH | 32 | 92.355 | 40.593 | 20.080 | 1.00 | 59.23 | O |
| HETATM | 2743 | O | HOH | 33 | 59.908 | 50.926 | 20.187 | 1.00 | 37.89 | O |
| HETATM | 2744 | O | HOH | 34 | 53.040 | 51.707 | 38.077 | 1.00 | 33.13 | O |
| HETATN | 2745 | O | HOH | 35 | 58.612 | 45.227 | 6.010 | 1.00 | 41.56 | O |
| HETATM | 2746 | O | HOH | 36 | 69.127 | 67.876 | 32.847 | 1.00 | 41.45 | O |
| HETATM | 2747 | O | HOH | 37 | 63.999 | 56.486 | 20.273 | 1.00 | 37.87 | O |
| HETATM | 2748 | O | HOH | 38 | 52.165 | 53.830 | 25.868 | 1.00 | 36.90 | O |
| HETATM | 2749 | O | HOH | 39 | 65.226 | 36.648 | 34.797 | 1.00 | 33.52 | O |
| HETATM | 2750 | O | HOH | 40 | 67.969 | 38.369 | 46.331 | 1.00 | 38.33 | O |
| HETATM | 2751 | O | HOH | 41 | 76.432 | 41.259 | 32.168 | 1.00 | 31.45 | O |
| HETATM | 2752 | O | HOH | 42 | 58.931 | 42.035 | 5.988 | 1.00 | 51.68 | O |
| HETATM | 2753 | O | HOH | 43 | 58.873 | 38.279 | 34.683 | 1.00 | 31.39 | O |
| HETATM | 2754 | O | HOH | 44 | 91.268 | 41.892 | 34.973 | 1.00 | 45.58 | O |
| HETATM | 2755 | O | HOH | 45 | 87.214 | 67.124 | 30.708 | 1.00 | 29.61 | O |
| HETATM | 2756 | O | HOH | 46 | 61.767 | 50.507 | 18.007 | 1.00 | 29.58 | O |
| HETATM | 2757 | O | HOH | 47 | 53.679 | 55.874 | 20.408 | 1.00 | 48.69 | O |
| HETATM | 2758 | O | HOH | 48 | 56.278 | 41.477 | 37.489 | 1.00 | 44.57 | O |
| HETATM | 2759 | O | HOH | 49 | 59.791 | 59.574 | 31.027 | 1.00 | 52.11 | O |
| HETATM | 2760 | O | HOH | 50 | 62.820 | 39.505 | 6.099 | 1.00 | 44.52 | O |
| HETATM | 2761 | O | HOH | 51 | 49.843 | 43.256 | 7.770 | 1.00 | 52.85 | O |
| HETATM | 2762 | O | HOH | 52 | 58.407 | 35.678 | 26.960 | 1.00 | 39.42 | O |
| HETATM | 2763 | O | HOH | 53 | 59.608 | 51.214 | 9.860 | 1.00 | 33.11 | O |
| HETATM | 2764 | O | HOH | 54 | 59.577 | 51.575 | 16.371 | 1.00 | 31.46 | O |
| HETATM | 2765 | O | HOH | 55 | 74.077 | 50.717 | 36.341 | 1.00 | 43.49 | O |
| HETATM | 2766 | O | HOH | 56 | 79.182 | 38.296 | 17.383 | 1.00 | 40.40 | O |
| HETATM | 2767 | O | HOH | 57 | 75.288 | 70.156 | 31.710 | 1.00 | 40.54 | O |
| HETATM | 2768 | O | HOH | 58 | 64.697 | 73.440 | 32.795 | 1.00 | 34.94 | O |
| HETATM | 2769 | O | HOH | 59 | 66.251 | 37.651 | 16.856 | 1.00 | 33.53 | O |
| HETATM | 2770 | O | HOH | 60 | 63.282 | 31.611 | 25.681 | 1.00 | 44.64 | O |

TABLE 2-continued

| | | | | | | | | | | |
|---|---|---|---|---|---|---|---|---|---|---|
| HETATM | 2771 | O | HOH | 61 | 71.430 | 55.918 | 41.920 | 1.00 | 36.49 | O |
| HETATM | 2772 | O | HOH | 62 | 65.638 | 58.677 | 21.385 | 1.00 | 35.26 | O |
| HETATM | 2773 | O | HOH | 63 | 55.080 | 46.995 | 17.425 | 1.00 | 53.19 | O |
| HETATM | 2774 | O | HOH | 64 | 50.562 | 31.766 | 16.460 | 1.00 | 43.10 | O |
| HETATM | 2775 | O | HOH | 65 | 74.644 | 37.157 | 10.791 | 1.00 | 39.58 | O |
| HETATM | 2776 | O | HOH | 66 | 62.315 | 61.756 | 37.610 | 1.00 | 36.98 | O |
| HETATM | 2777 | O | HOH | 67 | 73.617 | 64.778 | 30.740 | 1.00 | 42.65 | O |
| HETATM | 2778 | O | HOH | 68 | 55.753 | 71.270 | 16.210 | 1.00 | 37.70 | O |
| HETATM | 2779 | O | HOH | 69 | 60.894 | 73.990 | 38.995 | 1.00 | 52.68 | O |
| HETATM | 2780 | O | HOH | 70 | 54.230 | 73.527 | 38.967 | 1.00 | 53.01 | O |
| HETATM | 2781 | O | HOH | 71 | 85.347 | 49.247 | 39.609 | 1.00 | 46.03 | O |
| HETATM | 2782 | O | HOH | 72 | 90.366 | 44.868 | 34.983 | 1.00 | 60.08 | O |
| HETATM | 2783 | O | HOH | 73 | 74.553 | 34.802 | 40.308 | 1.00 | 42.36 | O |
| HETATM | 2784 | O | HOH | 74 | 92.253 | 47.877 | 34.577 | 1.00 | 48.24 | O |
| HETATM | 2785 | O | HOH | 75 | 62.333 | 64.301 | 35.516 | 1.00 | 42.55 | O |
| HETATM | 2786 | O | HOH | 76 | 75.293 | 38.619 | 8.177 | 1.00 | 42.95 | O |
| HETATM | 2787 | O | HOH | 77 | 74.834 | 47.737 | 35.645 | 1.00 | 45.47 | O |
| HETATM | 2788 | O | HOH | 78 | 43.248 | 43.725 | 23.511 | 1.00 | 41.40 | O |
| HETATM | 2789 | O | HOH | 79 | 92.749 | 48.847 | 23.299 | 1.00 | 48.74 | O |
| HETATM | 2790 | O | HOH | 80 | 81.622 | 38.388 | 24.165 | 1.00 | 48.40 | O |
| HETATM | 2791 | O | HOH | 81 | 69.535 | 35.845 | 7.684 | 1.00 | 44.93 | O |
| HETATM | 2792 | O | HOH | 82 | 66.021 | 28.568 | 15.079 | 1.00 | 43.38 | O |
| HETATM | 2793 | O | HOH | 83 | 63.363 | 58.444 | 43.595 | 1.00 | 60.19 | O |
| HETATM | 2794 | O | HOH | 84 | 50.760 | 46.222 | 35.814 | 1.00 | 40.54 | O |
| HETATM | 2795 | O | HOH | 85 | 73.050 | 33.188 | 26.343 | 1.00 | 59.24 | O |
| HETATM | 2796 | O | HOH | 86 | 60.595 | 29.978 | 22.680 | 1.00 | 52.27 | O |
| HETATM | 2797 | O | HOH | 87 | 69.555 | 45.175 | 46.108 | 1.00 | 47.35 | O |
| HETATM | 2798 | O | HOH | 88 | 91.680 | 50.881 | 35.482 | 1.00 | 58.01 | O |
| HETATM | 2799 | O | HOH | 89 | 54.754 | 33.372 | 37.626 | 1.00 | 47.38 | O |
| HETATM | 2800 | O | HOH | 90 | 70.270 | 53.925 | 17.757 | 1.00 | 43.71 | O |
| HETATM | 2801 | O | HOH | 91 | 86.174 | 38.632 | 29.884 | 1.00 | 51.68 | O |
| HETATM | 2802 | O | HOH | 92 | 50.223 | 32.982 | 11.986 | 1.00 | 53.26 | O |
| HETATM | 2803 | O | HOH | 93 | 69.797 | 32.727 | 38.335 | 1.00 | 48.52 | O |
| HETATM | 2804 | O | HOH | 94 | 45.294 | 44.791 | 32.974 | 1.00 | 45.93 | O |
| HETATM | 2805 | O | HOH | 95 | 50.957 | 50.719 | 21.814 | 1.00 | 47.04 | O |
| HETATM | 2806 | O | HOH | 96 | 67.427 | 59.503 | 38.921 | 1.00 | 51.20 | O |
| HETATM | 2807 | O | HOH | 97 | 45.814 | 48.859 | 27.359 | 1.00 | 52.57 | O |
| HETATM | 2808 | O | HOH | 98 | 67.272 | 72.374 | 31.829 | 1.00 | 43.34 | O |
| HETATM | 2809 | O | HOH | 99 | 81.547 | 54.867 | 13.482 | 1.00 | 56.22 | O |
| HETATM | 2810 | O | HOH | 100 | 73.436 | 41.135 | 42.320 | 1.00 | 51.99 | O |
| HETATM | 2811 | O | HOH | 101 | 45.438 | 41.435 | 12.889 | 1.00 | 51.81 | O |
| HETATM | 2812 | O | HOH | 102 | 72.135 | 31.364 | 23.780 | 1.00 | 49.13 | O |
| HETATM | 2813 | O | HOH | 103 | 64.895 | 66.481 | 39.105 | 1.00 | 64.76 | O |
| HETATM | 2814 | O | HOH | 104 | 67.577 | 69.286 | 38.086 | 1.00 | 45.89 | O |
| HETATM | 2815 | O | HOH | 105 | 69.612 | 68.635 | 35.879 | 1.00 | 63.93 | O |
| HETATM | 2816 | O | HOH | 106 | 72.031 | 67.254 | 32.046 | 1.00 | 48.47 | O |
| HETATM | 2817 | O | HOH | 107 | 72.305 | 61.345 | 21.016 | 1.00 | 44.10 | O |
| HETATM | 2818 | O | HOH | 108 | 74.756 | 62.694 | 19.263 | 1.00 | 48.65 | O |
| HETATM | 2819 | O | HOH | 109 | 95.910 | 46.347 | 27.675 | 1.00 | 53.29 | O |
| HETATM | 2820 | O | HOH | 110 | 94.046 | 48.897 | 25.977 | 1.00 | 51.23 | O |
| HETATM | 2821 | O | HOH | 111 | 97.282 | 43.405 | 26.308 | 1.00 | 55.88 | O |
| HETATM | 2822 | O | HOH | 112 | 96.131 | 51.037 | 25.453 | 1.00 | 43.15 | O |
| HETATM | 2823 | O | HOH | 113 | 79.236 | 36.729 | 24.882 | 1.00 | 50.87 | O |
| HETATM | 2824 | O | HOH | 114 | 79.234 | 40.387 | 31.965 | 1.00 | 38.53 | O |
| HETATM | 2825 | O | HOH | 115 | 81.670 | 39.064 | 21.018 | 1.00 | 60.16 | O |
| HETATM | 2826 | O | HOH | 116 | 60.063 | 41.314 | 40.014 | 1.00 | 53.39 | O |
| HETATM | 2827 | O | HOH | 117 | 68.407 | 44.274 | 48.786 | 1.00 | 58.93 | O |
| HETATM | 2828 | O | HOH | 118 | 73.852 | 38.881 | 40.464 | 1.00 | 54.08 | O |
| HETATM | 2829 | O | HOH | 119 | 66.435 | 34.694 | 36.949 | 1.00 | 50.41 | O |
| HETATM | 2830 | O | HOH | 120 | 68.667 | 31.549 | 25.842 | 1.00 | 64.44 | O |
| HETATM | 2831 | O | HOH | 121 | 65.857 | 31.082 | 26.881 | 1.00 | 40.73 | O |
| HETATM | 2832 | O | HOH | 122 | 62.672 | 33.363 | 29.890 | 1.00 | 48.58 | O |
| HETATM | 2833 | O | HOH | 123 | 61.493 | 33.436 | 27.087 | 1.00 | 48.36 | O |
| HETATM | 2834 | O | HOH | 124 | 69.854 | 28.735 | 27.500 | 1.00 | 61.68 | O |
| HETATM | 2835 | O | HOH | 125 | 64.874 | 31.147 | 29.825 | 1.00 | 60.07 | O |
| HETATM | 2836 | O | HOH | 126 | 71.711 | 32.640 | 30.005 | 1.00 | 47.37 | O |
| HETATM | 2837 | O | HOH | 127 | 52.466 | 50.282 | 19.032 | 1.00 | 52.65 | O |
| HETATM | 2838 | O | HOH | 128 | 49.739 | 53.604 | 24.073 | 1.00 | 61.02 | O |
| HETATM | 2839 | O | HOH | 129 | 48.481 | 31.684 | 25.480 | 1.00 | 54.44 | O |
| HETATM | 2840 | O | HOH | 130 | 65.224 | 61.485 | 37.955 | 1.00 | 47.75 | O |
| HETATM | 2841 | O | HOH | 131 | 72.681 | 36.196 | 7.328 | 1.00 | 60.10 | O |
| HETATM | 2842 | O | HOH | 132 | 54.600 | 53.590 | 40.349 | 1.00 | 61.76 | O |
| HETATM | 2843 | O | HOH | 133 | 55.212 | 44.260 | 39.797 | 1.00 | 54.33 | O |
| HETATM | 2844 | O | HOH | 134 | 58.628 | 61.370 | 13.634 | 1.00 | 55.77 | O |
| HETATM | 2845 | O | HOH | 135 | 78.074 | 50.966 | 38.251 | 1.00 | 55.68 | O |
| HETATM | 2846 | O | HOH | 136 | 76.140 | 52.648 | 36.261 | 1.00 | 34.66 | O |
| HETATM | 2847 | O | HOH | 137 | 66.486 | 54.699 | 47.835 | 1.00 | 67.66 | O |
| HETATM | 2848 | O | HOH | 138 | 74.079 | 55.395 | 38.640 | 1.00 | 55.76 | O |
| HETATM | 2849 | O | HOH | 139 | 72.037 | 53.724 | 43.983 | 1.00 | 49.73 | O |

TABLE 2-continued

| | | | | | | | | | | |
|---|---|---|---|---|---|---|---|---|---|---|
| HETATM | 2850 | O | HOH | 140 | 89.745 | 53.305 | 35.869 | 1.00 | 47.56 | O |
| HETATM | 2851 | O | HOH | 141 | 66.701 | 41.042 | 2.783 | 1.00 | 58.40 | O |
| HETATM | 2852 | O | HOH | 142 | 92.676 | 53.997 | 36.233 | 1.00 | 50.74 | O |
| HETATM | 2853 | O | HOH | 143 | 70.897 | 57.476 | 14.491 | 1.00 | 45.37 | O |
| HETATM | 2854 | O | HOH | 144 | 68.797 | 43.869 | 0.416 | 1.00 | 57.30 | O |
| HETATM | 2855 | O | HOH | 145 | 63.760 | 40.147 | 3.283 | 1.00 | 60.15 | O |
| CONECT | 202 2514 | | | | | | | | | |
| CONECT | 1501 1502 | | | | | | | | | |
| CONECT | 1502 1501 1503 1505 | | | | | | | | | |
| CONECT | 1503 1502 1504 | | | | | | | | | |
| CONECT | 1504 1503 1507 | | | | | | | | | |
| CONECT | 1505 1502 1506 | | | | | | | | | |
| CONECT | 1506 1505 | | | | | | | | | |
| CONECT | 1507 1504 | | | | | | | | | |
| CONECT | 2514 202 | | | | | | | | | |
| CONECT | 2688 2689 2690 2691 2692 | | | | | | | | | |
| CONECT | 2689 2688 | | | | | | | | | |
| CONECT | 2690 2688 | | | | | | | | | |
| CONECT | 2691 2688 | | | | | | | | | |
| CONECT | 2692 2688 2693 | | | | | | | | | |
| CONECT | 2693 2692 2694 | | | | | | | | | |
| CONECT | 2694 2693 2695 2696 | | | | | | | | | |
| CONECT | 2695 2694 2700 | | | | | | | | | |
| CONECT | 2696 2694 2697 2698 | | | | | | | | | |
| CONECT | 2697 2696 | | | | | | | | | |
| CONECT | 2698 2696 2699 2700 | | | | | | | | | |
| CONECT | 2699 2698 | | | | | | | | | |
| CONECT | 2700 2695 2698 2701 | | | | | | | | | |
| CONECT | 2701 2700 2702 2710 | | | | | | | | | |
| CONECT | 2702 2701 2703 | | | | | | | | | |
| CONECT | 2703 2702 2704 | | | | | | | | | |
| CONECT | 2704 2703 2705 2710 | | | | | | | | | |
| CONECT | 2705 2704 2706 2707 | | | | | | | | | |
| CONECT | 2706 2705 | | | | | | | | | |
| CONECT | 2707 2705 2708 | | | | | | | | | |
| CONECT | 2708 2707 2709 | | | | | | | | | |
| CONECT | 2709 2708 2710 | | | | | | | | | |
| CONECT | 2710 2701 2704 2709 | | | | | | | | | |
| MASTER | 521 0 3 14 18 0 0 6 2854 1 32 39 | | | | | | | | | |
| END | | | | | | | | | | | |

Figure 11
P-UC 5440
Page 1

TABLE 3

| | | |
|---|---|---|
| HEADER | OXIDOREDUCTASE 08-AUG-02 1MEH | |
| TITLE | INOSINE MONOPHOSPHATE DEHYDROGENASE (IMPDH) FROM | |
| TITLE | 2 | *TRITRICHOMONAS FOETUS* WITH IMP AND MOA BOUND |
| COMPND | MOL_ID: 1; | |
| COMPND | 2 | MOLECULE: INOSINE-5'-MONOPHOSPHATE DEHYDROGENASE; |
| COMPND | 3 | CHAIN: A; |
| COMPND | 4 | SYNONYM: IMP DEHYDROGENASE, IMPDH; |
| COMPND | 5 | EC: 1.1.1.205; |
| COMPND | 6 | ENGINEERED: YES |
| SOURCE | MOL_ID: 1; | |
| SOURCE | 2 | ORGANISM_SCIENTIFIC: *TRITRICHOMONAS FOETUS*; |
| SOURCE | 3 | GENE: IMPDH; |
| SOURCE | 4 | EXPRESSION_SYSTEM: *ESCHERICHIA COLI*; |
| SOURCE | 5 | EXPRESSION_SYSTEM_COMMON: BACTERIA; |
| SOURCE | 6 | EXPRESSION_SYSTEM_STRAIN: H712; |
| SOURCE | 7 | EXPRESSION_SYSTEM_VECTOR_TYPE: PLASMID; |
| SOURCE | 8 | EXPRESSION_SYSTEM_PLASMID: PBACE |
| KEYWDS | ALPHA BETA BARREL | |
| EXPDTA | X-RAY DIFFRACTION | |
| AUTHOR | G. L. PROSISE, H. LUECKE | |
| JRNL | AUTH | G. L. PROSISE, H. LUECKE |
| JRNL | TITL | CRYSTAL STRUCTURE OF *T. FOETUS* INOSINE |
| JRNL | TITL 2 | MONOPHOSPHATE DEHYDROGENASE IN COMPLEX WITH |
| JRNL | TITL 3 | SUBSTRATE, COFACTOR, AND ANALOGS:STRUCTURAL BASIS |
| JRNL | TITL 4 | FOR THE RANDOM-IN ORDERED-OUT KINETIC MECHANISM |
| JRNL | REF | TO BE PUBLISHED |
| JRNL | REFN | |

TABLE 3-continued

```
REMARK   1
REMARK   2
REMARK   2   RESOLUTION. 1.95 ANGSTROMS.
REMARK   3
REMARK   3   REFINEMENT.
REMARK   3         PROGRAM     : CNS 1.1
REMARK   3         AUTHORS     : BRUNGER, ADAMS, CLORE, DELANO, GROS, GROSSE-
REMARK   3                     : KUNSTLEVE, JIANG, KUSZEWSKI, NILGES, PANNU,
REMARK   3                     : READ, RICE, SIMONSON, WARREN
REMARK   3
REMARK   3         REFINEMENT TARGET : ENGH & HUBER
REMARK   3
REMARK   3         DATA USED IN REFINEMENT.
REMARK   3            RESOLUTION RANGE HIGH       (ANGSTROMS) : 1.95
REMARK   3            RESOLUTION RANGE LOW        (ANGSTROMS) : 19.98
REMARK   3            DATA CUTOFF                  (SIGMA(F)) : 0.000
REMARK   3            OUTLIER CUTOFF HIGH        (RMS(ABS(F))) : NULL
REMARK   3            COMPLETENESS (WORKING+TEST)        (%) : 98.6
REMARK   3            NUMBER OF REFLECTIONS                  : 44863
REMARK   3
REMARK   3         FIT TO DATA USED IN REFINEMENT.
REMARK   3            CROSS-VALIDATION METHOD            : THROUGHOUT
REMARK   3            FREE R VALUE TEST SET SELECTION    : RANDOM
REMARK   3            R VALUE            (WORKING SET) : 0.243
REMARK   3            FREE R VALUE                     : 0.272
REMARK   3            FREE R VALUE TEST SET SIZE   (%) : 5.100
REMARK   3            FREE R VALUE TEST SET COUNT      : 2294
REMARK   3            ESTIMATED ERROR OF FREE R VALUE  : 0.006
REMARK   3
REMARK   3         FIT IN THE HIGHEST RESOLUTION BIN.
REMARK   3            TOTAL NUMBER OF BINS USED             : 6
REMARK   3            BIN RESOLUTION RANGE HIGH        (A) : 1.95
REMARK   3            BIN RESOLUTION RANGE LOW         (A) : 2.07
REMARK   3            BIN COMPLETENESS (WORKING+TEST)  (%) : 96.70
REMARK   3            REFLECTIONS IN BIN      (WORKING SET) : 6852
REMARK   3            BIN R VALUE             (WORKING SET) : 0.2630
REMARK   3            BIN FREE R VALUE                     : 0.2960
REMARK   3            BIN FREE R VALUE TEST SET SIZE   (%) : 4.60
REMARK   3            BIN FREE R VALUE TEST SET COUNT      : 333
REMARK   3            ESTIMATED ERROR OF BIN FREE R VALUE  : 0.016
REMARK   3
REMARK   3         NUMBER OF NON-HYDROGEN ATOMS USED IN REFINEMENT.
REMARK   3            PROTEIN ATOMS          : 2709
REMARK   3            NUCLEIC ACID ATOMS     : 0
REMARK   3            HETEROGEN ATOMS        : 47
REMARK   3            SOLVENT ATOMS          : 193
REMARK   3
REMARK   3         B VALUES.
REMARK   3            FROM WILSON PLOT             (A**2) : 19.90
REMARK   3            MEAN B VALUE        (OVERALL, A**2) : 32.70
REMARK   3            OVERALL ANISOTROPIC B VALUE.
REMARK   3              B11 (A**2) : 0.00000
REMARK   3              B22 (A**2) : 0.00000
REMARK   3              B33 (A**2) : 0.00000
REMARK   3              B12 (A**2) : 0.00000
REMARK   3              B13 (A**2) : 0.00000
REMARK   3              B23 (A**2) : 0.00000
REMARK   3
REMARK   3         ESTIMATED COORDINATE ERROR.
REMARK   3            ESD FROM LUZZATI PLOT           (A) : 0.25
REMARK   3            ESD FROM SIGMAA                 (A) : 0.15
REMARK   3            LOW RESOLUTION CUTOFF           (A) : 5.00
REMARK   3
REMARK   3         CROSS-VALIDATED ESTIMATED COORDINATE ERROR.
REMARK   3            ESD FROM C-V LUZZATI PLOT       (A) : 0.29
REMARK   3            ESD FROM C-V SIGMAA             (A) : 0.18
REMARK   3
REMARK   3         RMS DEVIATIONS FROM IDEAL VALUES.
REMARK   3            BOND LENGTHS                    (A) : 0.006
REMARK   3            BOND ANGLES               (DEGREES) : 1.20
REMARK   3            DIHEDRAL ANGLES           (DEGREES) : 22.30
REMARK   3            IMPROPER ANGLES           (DEGREES) : 0.70
REMARK   3
REMARK   3         ISOTROPIC THERMAL MODEL : RESTRAINED
REMARK   3
```

TABLE 3-continued

| | | | | |
|---|---|---|---|---|
| REMARK | 3 | ISOTROPIC THERMAL FACTOR RESTRAINTS. | RMS | SIGMA |
| REMARK | 3 | MAIN-CHAIN BOND | (A**2) : 0.810 | ; 1.500 |
| REMARK | 3 | MAIN-CHAIN ANGLE | (A**2) : 1.440 | ; 2.000 |
| REMARK | 3 | SIDE-CHAIN BOND | (A**2) : 1.060 | ; 2.000 |
| REMARK | 3 | SIDE-CHAIN ANGLE | (A**2) : 1.700 | ; 2.500 |
| REMARK | 3 | | | |
| REMARK | 3 | BULK SOLVENT MODELING. | | |
| REMARK | 3 | METHOD USED   : FLAT MODEL | | |
| REMARK | 3 | KSOL          : 0.40 | | |
| REMARK | 3 | BSOL          : 48.93 | | |
| REMARK | 3 | | | |
| REMARK | 3 | NCS MODEL : NULL | | |
| REMARK | 3 | | | |
| REMARK | 3 | NCS RESTRAINTS. | RMS | SIGMA/WEIGHT |
| REMARK | 3 | GROUP 1 POSITIONAL | (A) : NULL | ; NULL |
| REMARK | 3 | GROUP 1 B-FACTOR | (A**2) : NULL | ; NULL |
| REMARK | 3 | | | |
| REMARK | 3 | PARAMETER FILE 1   : PROTEIN_REP.PARAM | | |
| REMARK | 3 | PARAMETER FILE 2   : PARAM.GNSOL | | |
| REMARK | 3 | PARAMETER FILE 3   : CIS_PEPTIDE.PARAM | | |
| REMARK | 3 | PARAMETER FILE 4   : MPA.PAR | | |
| REMARK | 3 | PARAMETER FILE 5   : IMP.PAR | | |
| REMARK | 3 | PARAMETER FILE 6   : NULL | | |
| REMARK | 3 | TOPOLOGY FILE 1    : PROTEIN.TOP | | |
| REMARK | 3 | TOPOLOGY FILE 2    : IMP.TOP | | |
| REMARK | 3 | TOPOLOGY FILE 3    : MPA.TOP | | |
| REMARK | 3 | TOPOLOGY FILE 4    : K.TOP | | |
| REMARK | 3 | TOPOLOGY FILE 5    : TOPH.GNSOL | | |
| REMARK | 3 | TOPOLOGY FILE 6    : NULL | | |
| REMARK | 3 | | | |
| REMARK | 3 | OTHER REFINEMENT REMARKS: NULL | | |
| REMARK | 4 | | | |
| REMARK | 4 | 1MEH COMPLIES WITH FORMAT V. 2.3, 09-JULY-1998 | | |
| REMARK | 100 | | | |
| REMARK | 100 | THIS ENTRY HAS BEEN PROCESSED BY RCSB ON 16-AUG-2002. | | |
| REMARK | 100 | THE RCSB ID CODE IS RCSB016852. | | |
| REMARK | 200 | | | |
| REMARK | 200 | EXPERIMENTAL DETAILS | | |
| REMARK | 200 | EXPERIMENT TYPE | : X-RAY DIFFRACTION | |
| REMARK | 200 | DATE OF DATA COLLECTION | : 11-APR-2001 | |
| REMARK | 200 | TEMPERATURE                       (KELVIN) | : 100.0 | |
| REMARK | 200 | PH | : 7.50 | |
| REMARK | 200 | NUMBER OF CRYSTALS USED | : 1 | |
| REMARK | 200 | | | |
| REMARK | 200 | SYNCHROTRON                       (Y/N) | : Y | |
| REMARK | 200 | RADIATION SOURCE | : SSRL | |
| REMARK | 200 | BEAMLINE | : 9-1 | |
| REMARK | 200 | X-RAY GENERATOR MODEL | : NULL | |
| REMARK | 200 | MONOCHROMATIC OR LAUE             (M/L) | : M | |
| REMARK | 200 | WAVELENGTH OR RANGE               (A) | : 0.97 | |
| REMARK | 200 | MONOCHROMATOR | : NULL | |
| REMARK | 200 | OPTICS | : NULL | |
| REMARK | 200 | | | |
| REMARK | 200 | DETECTOR TYPE | : IMAGE PLATE | |
| REMARK | 200 | DETECTOR MANUFACTURER | : MARRESEARCH | |
| REMARK | 200 | INTENSITY-INTEGRATION SOFTWARE | : DENZO | |
| REMARK | 200 | DATA SCALING SOFTWARE | : SCALEPACK | |
| REMARK | 200 | | | |
| REMARK | 200 | NUMBER OF UNIQUE REFLECTIONS | : 44997 | |
| REMARK | 200 | RESOLUTION RANGE HIGH             (A) | : 1.950 | |
| REMARK | 200 | RESOLUTION RANGE LOW              (A) | : 20.000 | |
| REMARK | 200 | REJECTION CRITERIA                (SIGMA(I)) | : NULL | |
| REMARK | 200 | | | |
| REMARK | 200 | OVERALL. | | |
| REMARK | 200 | COMPLETENESS FOR RANGE            (%) | : 99.0 | |
| REMARK | 200 | DATA REDUNDANCY | : 5.400 | |
| REMARK | 200 | R MERGE                           (I) | : 0.05700 | |
| REMARK | 200 | R SYM                             (I) | : NULL | |
| REMARK | 200 | <I/SIGMA(I)> FOR THE DATA SET | : 25.9000 | |
| REMARK | 200 | | | |
| REMARK | 200 | IN THE HIGHEST RESOLUTION SHELL. | | |
| REMARK | 200 | HIGHEST RESOLUTION SHELL, RANGE HIGH  (A) | : 1.95 | |
| REMARK | 200 | HIGHEST RESOLUTION SHELL, RANGE LOW   (A) | : 1.98 | |
| REMARK | 200 | COMPLETENESS FOR SHELL            (%) | : 95.7 | |
| REMARK | 200 | DATA REDUNDANCY IN SHELL | : NULL | |
| REMARK | 200 | R MERGE FOR SHELL                 (I) | : 0.66000 | |
| REMARK | 200 | R SYM FOR SHELL                   (I) | : NULL | |
| REMARK | 200 | <I/SIGMA(I)> FOR SHELL | : 1.820 | |
| REMARK | 200 | | | |

TABLE 3-continued

```
REMARK  200  DIFFRACTION PROTOCOL: SINGLE WAVELENGTH
REMARK  200  METHOD USED TO DETERMINE THE STRUCTURE: FOURIER SYNTHESIS
REMARK  200  SOFTWARE USED: CNS
REMARK  200  STARTING MODEL: PDB ENTRY 1AK5
REMARK  200
REMARK  200  REMARK: NULL
REMARK  280
REMARK  280  CRYSTAL
REMARK  280  SOLVENT CONTENT, VS (%) : NULL
REMARK  280  MATTHEWS COEFFICIENT, VM (ANGSTROMS**3/DA) : NULL
REMARK  280
REMARK  280  CRYSTALLIZATION CONDITIONS: SODIUM MALONATE, TRIS, 2-
REMARK  280    MERCAPTOETHANOL, EDTA, GLYCEROL
REMARK  290
REMARK  290  CRYSTALLOGRAPHIC SYMMETRY
REMARK  290  SYMMETRY OPERATORS FOR SPACE GROUP: P 4 3 2
REMARK  290
REMARK  290          SYMOP  SYMMETRY
REMARK  290          NNNMMM OPERATOR
REMARK  290           1555  X,Y,Z
REMARK  290           2555  -X,-Y,Z
REMARK  290           3555  -X,Y,-Z
REMARK  290           4555  X,-Y,-Z
REMARK  290           5555  Z,X,Y
REMARK  290           6555  Z,-X,-Y
REMARK  290           7555  -Z,-X,Y
REMARK  290           8555  -Z,X,-Y
REMARK  290           9555  Y,Z,X
REMARK  290          10555  -Y,Z,-X
REMARK  290          11555  Y,-Z,-X
REMARK  290          12555  -Y,-Z,X
REMARK  290          13555  Y,X,-Z
REMARK  290          14555  -Y,-X,-Z
REMARK  290          15555  Y,-X,Z
REMARK  290          16555  -Y,X,Z
REMARK  290          17555  X,Z,-Y
REMARK  290          18555  -X,Z,Y
REMARK  290          19555  -X,-Z,-Y
REMARK  290          20555  X,-Z,Y
REMARK  290          21555  Z,Y,-X
REMARK  290          22555  Z,-Y,X
REMARK  290          23555  -Z,Y,X
REMARK  290          24555  -Z,-Y,-X
REMARK  290
REMARK  290     WHERE    NNN --> OPERATOR NUMBER
REMARK  290              MMM --> TRANSLATION VECTOR
REMARK  290
REMARK  290  CRYSTALLOGRAPHIC SYMMETRY TRANSFORMATIONS
REMARK  290  THE FOLLOWING TRANSFORMATIONS OPERATE ON THE ATOM/HETATM
REMARK  290  RECORDS IN THIS ENTRY TO PRODUCE CRYSTALLOGRAPHICALLY
REMARK  290  RELATED MOLECULES.
REMARK  290     SMTRY1   1    1.000000   0.000000   0.000000   0.00000
REMARK  290     SMTRY2   1    0.000000   1.000000   0.000000   0.00000
REMARK  290     SMTRY3   1    0.000000   0.000000   1.000000   0.00000
REMARK  290     SMTRY1   2   -1.000000   0.000000   0.000000   0.00000
REMARK  290     SMTRY2   2    0.000000  -1.000000   0.000000   0.00000
REMARK  290     SMTRY3   2    0.000000   0.000000   1.000000   0.00000
REMARK  290     SMTRY1   3   -1.000000   0.000000   0.000000   0.00000
REMARK  290     SMTRY2   3    0.000000   1.000000   0.000000   0.00000
REMARK  290     SMTRY3   3    0.000000   0.000000  -1.000000   0.00000
REMARK  290     SMTRY1   4    1.000000   0.000000   0.000000   0.00000
REMARK  290     SMTRY2   4    0.000000  -1.000000   0.000000   0.00000
REMARK  290     SMTRY3   4    0.000000   0.000000  -1.000000   0.00000
REMARK  290     SMTRY1   5    0.000000   0.000000   1.000000   0.00000
REMARK  290     SMTRY2   5    1.000000   0.000000   0.000000   0.00000
REMARK  290     SMTRY3   5    0.000000   1.000000   0.000000   0.00000
REMARK  290     SMTRY1   6    0.000000   0.000000   1.000000   0.00000
REMARK  290     SMTRY2   6   -1.000000   0.000000   0.000000   0.00000
REMARK  290     SMTRY3   6    0.000000  -1.000000   0.000000   0.00000
REMARK  290     SMTRY1   7    0.000000   0.000000  -1.000000   0.00000
REMARK  290     SMTRY2   7   -1.000000   0.000000   0.000000   0.00000
REMARK  290     SMTRY3   7    0.000000   1.000000   0.000000   0.00000
REMARK  290     SMTRY1   8    0.000000   0.000000  -1.000000   0.00000
REMARK  290     SMTRY2   8    1.000000   0.000000   0.000000   0.00000
REMARK  290     SMTRY3   8    0.000000  -1.000000   0.000000   0.00000
REMARK  290     SMTRY1   9    0.000000   1.000000   0.000000   0.00000
REMARK  290     SMTRY2   9    0.000000   0.000000   1.000000   0.00000
REMARK  290     SMTRY3   9    1.000000   0.000000   0.000000   0.00000
REMARK  290     SMTRY1  10    0.000000  -1.000000   0.000000   0.00000
```

TABLE 3-continued

| | | | | | | | |
|---|---|---|---|---|---|---|---|
| REMARK | 290 | SMTRY2 | 10 | 0.000000 | 0.000000 | 1.000000 | 0.00000 |
| REMARK | 290 | SMTRY3 | 10 | −1.000000 | 0.000000 | 0.000000 | 0.00000 |
| REMARK | 290 | SMTRY1 | 11 | 0.000000 | 1.000000 | 0.000000 | 0.00000 |
| REMARK | 290 | SMTRY2 | 11 | 0.000000 | 0.000000 | −1.000000 | 0.00000 |
| REMARK | 290 | SMTRY3 | 11 | −1.000000 | 0.000000 | 0.000000 | 0.00000 |
| REMARK | 290 | SMTRY1 | 12 | 0.000000 | −1.000000 | 0.000000 | 0.00000 |
| REMARK | 290 | SMTRY2 | 12 | 0.000000 | 0.000000 | −1.000000 | 0.00000 |
| REMARK | 290 | SMTRY3 | 12 | 1.000000 | 0.000000 | 0.000000 | 0.00000 |
| REMARK | 290 | SMTRY1 | 13 | 0.000000 | 1.000000 | 0.000000 | 0.00000 |
| REMARK | 290 | SMTRY2 | 13 | 1.000000 | 0.000000 | 0.000000 | 0.00000 |
| REMARK | 290 | SMTRY3 | 13 | 0.000000 | 0.000000 | −1.000000 | 0.00000 |
| REMARK | 290 | SMTRY1 | 14 | 0.000000 | −1.000000 | 0.000000 | 0.00000 |
| REMARK | 290 | SMTRY2 | 14 | −1.000000 | 0.000000 | 0.000000 | 0.00000 |
| REMARK | 290 | SMTRY3 | 14 | 0.000000 | 0.000000 | −1.000000 | 0.00000 |
| REMARK | 290 | SMTRY1 | 15 | 0.000000 | 1.000000 | 0.000000 | 0.00000 |
| REMARK | 290 | SMTRY2 | 15 | −1.000000 | 0.000000 | 0.000000 | 0.00000 |
| REMARK | 290 | SMTRY3 | 15 | 0.000000 | 0.000000 | 1.000000 | 0.00000 |
| REMARK | 290 | SMTRY1 | 16 | 0.000000 | −1.000000 | 0.000000 | 0.00000 |
| REMARK | 290 | SMTRY2 | 16 | 1.000000 | 0.000000 | 0.000000 | 0.00000 |
| REMARK | 290 | SMTRY3 | 16 | 0.000000 | 0.000000 | 1.000000 | 0.00000 |
| REMARK | 290 | SMTRY1 | 17 | 1.000000 | 0.000000 | 0.000000 | 0.00000 |
| REMARK | 290 | SMTRY2 | 17 | 0.000000 | 0.000000 | 1.000000 | 0.00000 |
| REMARK | 290 | SMTRY3 | 17 | 0.000000 | −1.000000 | 0.000000 | 0.00000 |
| REMARK | 290 | SMTRY1 | 18 | −1.000000 | 0.000000 | 0.000000 | 0.00000 |
| REMARK | 290 | SMTRY2 | 18 | 0.000000 | 0.000000 | 1.000000 | 0.00000 |
| REMARK | 290 | SMTRY3 | 18 | 0.000000 | 1.000000 | 0.000000 | 0.00000 |
| REMARK | 290 | SMTRY1 | 19 | −1.000000 | 0.000000 | 0.000000 | 0.00000 |
| REMARK | 290 | SMTRY2 | 19 | 0.000000 | 0.000000 | −1.000000 | 0.00000 |
| REMARK | 290 | SMTRY3 | 19 | 0.000000 | −1.000000 | 0.000000 | 0.00000 |
| REMARK | 290 | SMTRY1 | 20 | 1.000000 | 0.000000 | 0.000000 | 0.00000 |
| REMARK | 290 | SMTRY2 | 20 | 0.000000 | 0.000000 | −1.000000 | 0.00000 |
| REMARK | 290 | SMTRY3 | 20 | 0.000000 | 1.000000 | 0.000000 | 0.00000 |
| REMARK | 290 | SMTRY1 | 21 | 0.000000 | 0.000000 | 1.000000 | 0.00000 |
| REMARK | 290 | SMTRY2 | 21 | 0.000000 | 1.000000 | 0.000000 | 0.00000 |
| REMARK | 290 | SMTRY3 | 21 | −1.000000 | 0.000000 | 0.000000 | 0.00000 |
| REMARK | 290 | SMTRY1 | 22 | 0.000000 | 0.000000 | 1.000000 | 0.00000 |
| REMARK | 290 | SMTRY2 | 22 | 0.000000 | −1.000000 | 0.000000 | 0.00000 |
| REMARK | 290 | SMTRY3 | 22 | 1.000000 | 0.000000 | 0.000000 | 0.00000 |
| REMARK | 290 | SMTRY1 | 23 | 0.000000 | 0.000000 | −1.000000 | 0.00000 |
| REMARK | 290 | SMTRY2 | 23 | 0.000000 | 1.000000 | 0.000000 | 0.00000 |
| REMARK | 290 | SMTRY3 | 23 | 1.000000 | 0.000000 | 0.000000 | 0.00000 |
| REMARK | 290 | SMTRY1 | 24 | 0.000000 | 0.000000 | −1.000000 | 0.00000 |
| REMARK | 290 | SMTRY2 | 24 | 0.000000 | −1.000000 | 0.000000 | 0.00000 |
| REMARK | 290 | SMTRY3 | 24 | −1.000000 | 0.000000 | 0.000000 | 0.00000 |
| REMARK | 290 | | | | | | |
| REMARK | 290 | REMARK: NULL | | | | | |
| REMARK | 300 | | | | | | |
| REMARK | 300 | BIOMOLECULE: 1 | | | | | |
| REMARK | 300 | THIS ENTRY CONTAINS THE CRYSTALLOGRAPHIC ASYMMETRIC UNIT | | | | | |
| REMARK | 300 | WHICH CONSISTS OF 1 CHAIN(S). SEE REMARK 350 FOR | | | | | |
| REMARK | 300 | INFORMATION ON GENERATING THE BIOLOGICAL MOLECULE(S). | | | | | |
| REMARK | 350 | | | | | | |
| REMARK | 350 | GENERATING THE BIOMOLECULE | | | | | |
| REMARK | 350 | COORDINATES FOR A COMPLETE MULTIMER REPRESENTING THE KNOWN | | | | | |
| REMARK | 350 | BIOLOGICALLY SIGNIFICANT OLIGOMERIZATION STATE OF THE | | | | | |
| REMARK | 350 | MOLECULE CAN BE GENERATED BY APPLYING BIOMT TRANSFORMATIONS | | | | | |
| REMARK | 350 | GIVEN BELOW. BOTH NON-CRYSTALLOGRAPHIC AND | | | | | |
| REMARK | 350 | CRYSTALLOGRAPHIC OPERATIONS ARE GIVEN. | | | | | |
| REMARK | 350 | | | | | | |
| REMARK | 350 | BIOMOLECULE: 1 | | | | | |
| REMARK | 350 | APPLY THE FOLLOWING TO CHAINS: A | | | | | |
| REMARK | 350 | BIOMT1 | 1 | 1.000000 | 0.000000 | 0.000000 | 0.00000 |
| REMARK | 350 | BIOMT2 | 1 | 0.000000 | 1.000000 | 0.000000 | 0.00000 |
| REMARK | 350 | BIOMT3 | 1 | 0.000000 | 0.000000 | 1.000000 | 0.00000 |
| REMARK | 350 | BIOMT1 | 2 | −1.000000 | 0.000000 | 0.000000 | 153.48000 |
| REMARK | 350 | BIOMT2 | 2 | 0.000000 | −1.000000 | 0.000000 | 153.48000 |
| REMARK | 350 | BIOMT3 | 2 | 0.000000 | 0.000000 | 1.000000 | 0.00000 |
| REMARK | 350 | BIOMT1 | 3 | 0.000000 | 1.000000 | 0.000000 | 0.00000 |
| REMARK | 350 | BIOMT2 | 3 | −1.000000 | 0.000000 | 0.000000 | 153.48000 |
| REMARK | 350 | BIOMT3 | 3 | 0.000000 | 0.000000 | 1.000000 | 0.00000 |
| REMARK | 350 | BIOMT1 | 4 | 0.000000 | −1.000000 | 0.000000 | 153.48000 |
| REMARK | 350 | BIOMT2 | 4 | 1.000000 | 0.000000 | 0.000000 | 0.00000 |
| REMARK | 350 | BIOMT3 | 4 | 0.000000 | 0.000000 | 1.000000 | 0.00000 |
| REMARK | 465 | | | | | | |
| REMARK | 465 | MISSING RESIDUES | | | | | |
| REMARK | 465 | THE FOLLOWING RESIDUES WERE NOT LOCATED IN THE | | | | | |
| REMARK | 465 | EXPERIMENT. (M=MODEL NUMBER; RES=RESIDUE NAME; C=CHAIN | | | | | |
| REMARK | 465 | IDENTIFIER; SSSEQ=SEQUENCE NUMBER; I=INSERTION CODE.) | | | | | |
| REMARK | 465 | | | | | | |

TABLE 3-continued

| | | | | | |
|---|---|---|---|---|---|
| REMARK | 465 | M | RES | C | SSSEQI |
| REMARK | 465 | | MET | A | 1 |
| REMARK | 465 | | ASP | A | 107 |
| REMARK | 465 | | SER | A | 108 |
| REMARK | 465 | | ASN | A | 109 |
| REMARK | 465 | | VAL | A | 110 |
| REMARK | 465 | | LYS | A | 111 |
| REMARK | 465 | | PRO | A | 112 |
| REMARK | 465 | | ASP | A | 113 |
| REMARK | 465 | | GLN | A | 114 |
| REMARK | 465 | | THR | A | 115 |
| REMARK | 465 | | PHE | A | 116 |
| REMARK | 465 | | ALA | A | 117 |
| REMARK | 465 | | ASP | A | 118 |
| REMARK | 465 | | VAL | A | 119 |
| REMARK | 465 | | LEU | A | 120 |
| REMARK | 465 | | ALA | A | 121 |
| REMARK | 465 | | ILE | A | 122 |
| REMARK | 465 | | SER | A | 123 |
| REMARK | 465 | | GLN | A | 124 |
| REMARK | 465 | | ARG | A | 125 |
| REMARK | 465 | | THR | A | 126 |
| REMARK | 465 | | THR | A | 127 |
| REMARK | 465 | | HIS | A | 128 |
| REMARK | 465 | | ASN | A | 129 |
| REMARK | 465 | | THR | A | 130 |
| REMARK | 465 | | VAL | A | 131 |
| REMARK | 465 | | ALA | A | 132 |
| REMARK | 465 | | VAL | A | 133 |
| REMARK | 465 | | THR | A | 134 |
| REMARK | 465 | | ASP | A | 135 |
| REMARK | 465 | | ASP | A | 136 |
| REMARK | 465 | | GLY | A | 137 |
| REMARK | 465 | | THR | A | 138 |
| REMARK | 465 | | PRO | A | 139 |
| REMARK | 465 | | HIS | A | 140 |
| REMARK | 465 | | GLY | A | 141 |
| REMARK | 465 | | VAL | A | 142 |
| REMARK | 465 | | LEU | A | 143 |
| REMARK | 465 | | LEU | A | 144 |
| REMARK | 465 | | GLY | A | 145 |
| REMARK | 465 | | LEU | A | 146 |
| REMARK | 465 | | VAL | A | 147 |
| REMARK | 465 | | THR | A | 148 |
| REMARK | 465 | | GLN | A | 149 |
| REMARK | 465 | | ARG | A | 150 |
| REMARK | 465 | | ASP | A | 151 |
| REMARK | 465 | | TYR | A | 152 |
| REMARK | 465 | | PRO | A | 153 |
| REMARK | 465 | | ILE | A | 154 |
| REMARK | 465 | | ASP | A | 155 |
| REMARK | 465 | | LEU | A | 156 |
| REMARK | 465 | | THR | A | 157 |
| REMARK | 465 | | GLN | A | 158 |
| REMARK | 465 | | THR | A | 159 |
| REMARK | 465 | | GLU | A | 160 |
| REMARK | 465 | | THR | A | 161 |
| REMARK | 465 | | LYS | A | 162 |
| REMARK | 465 | | VAL | A | 163 |
| REMARK | 465 | | SER | A | 164 |
| REMARK | 465 | | ASP | A | 165 |
| REMARK | 465 | | MET | A | 166 |
| REMARK | 465 | | MET | A | 167 |
| REMARK | 465 | | THR | A | 168 |
| REMARK | 465 | | PRO | A | 169 |
| REMARK | 465 | | PHE | A | 170 |
| REMARK | 465 | | SER | A | 171 |
| REMARK | 465 | | LYS | A | 172 |
| REMARK | 465 | | LEU | A | 173 |
| REMARK | 465 | | VAL | A | 174 |
| REMARK | 465 | | THR | A | 175 |
| REMARK | 465 | | ALA | A | 176 |
| REMARK | 465 | | HIS | A | 177 |
| REMARK | 465 | | GLN | A | 178 |
| REMARK | 465 | | ASP | A | 179 |

TABLE 3-continued

| | | | | |
|---|---|---|---|---|
| REMARK | 465 | THR | A | 180 |
| REMARK | 465 | LYS | A | 181 |
| REMARK | 465 | LEU | A | 182 |
| REMARK | 465 | SER | A | 183 |
| REMARK | 465 | GLU | A | 184 |
| REMARK | 465 | ALA | A | 185 |
| REMARK | 465 | ASN | A | 186 |
| REMARK | 465 | LYS | A | 187 |
| REMARK | 465 | ILE | A | 188 |
| REMARK | 465 | ILE | A | 189 |
| REMARK | 465 | TRP | A | 190 |
| REMARK | 465 | GLU | A | 191 |
| REMARK | 465 | LYS | A | 192 |
| REMARK | 465 | LYS | A | 193 |
| REMARK | 465 | LEU | A | 194 |
| REMARK | 465 | ASN | A | 195 |
| REMARK | 465 | ALA | A | 196 |
| REMARK | 465 | LEU | A | 197 |
| REMARK | 465 | PRO | A | 198 |
| REMARK | 465 | ILE | A | 199 |
| REMARK | 465 | ILE | A | 200 |
| REMARK | 465 | ASP | A | 201 |
| REMARK | 465 | ASP | A | 202 |
| REMARK | 465 | ASP | A | 203 |
| REMARK | 465 | GLN | A | 204 |
| REMARK | 465 | HIS | A | 205 |
| REMARK | 465 | LEU | A | 206 |
| REMARK | 465 | ARG | A | 207 |
| REMARK | 465 | TYR | A | 208 |
| REMARK | 465 | ILE | A | 209 |
| REMARK | 465 | VAL | A | 210 |
| REMARK | 465 | PHE | A | 211 |
| REMARK | 465 | ARG | A | 212 |
| REMARK | 465 | LYS | A | 213 |
| REMARK | 465 | ASP | A | 214 |
| REMARK | 465 | TYR | A | 215 |
| REMARK | 465 | ASP | A | 216 |
| REMARK | 465 | ARG | A | 217 |
| REMARK | 465 | SER | A | 218 |
| REMARK | 465 | GLN | A | 219 |
| REMARK | 465 | VAL | A | 220 |
| REMARK | 465 | CYS | A | 221 |
| REMARK | 465 | GLN | A | 417 |
| REMARK | 465 | ARG | A | 418 |
| REMARK | 465 | TYR | A | 419 |
| REMARK | 465 | ASP | A | 420 |
| REMARK | 465 | LEU | A | 421 |
| REMARK | 465 | GLY | A | 422 |
| REMARK | 465 | GLY | A | 423 |
| REMARK | 465 | LYS | A | 424 |
| REMARK | 465 | GLN | A | 425 |
| REMARK | 465 | LYS | A | 426 |
| REMARK | 465 | LEU | A | 427 |
| REMARK | 465 | SER | A | 428 |
| REMARK | 465 | PHE | A | 429 |
| REMARK | 465 | VAL | A | 484 |
| REMARK | 465 | GLU | A | 485 |
| REMARK | 465 | GLY | A | 486 |
| REMARK | 465 | GLY | A | 487 |
| REMARK | 465 | ALA | A | 488 |
| REMARK | 465 | HIS | A | 489 |
| REMARK | 465 | ASP | A | 490 |
| REMARK | 465 | VAL | A | 491 |
| REMARK | 465 | ILE | A | 492 |
| REMARK | 465 | VAL | A | 493 |
| REMARK | 465 | LYS | A | 494 |
| REMARK | 465 | ASP | A | 495 |
| REMARK | 465 | ARG | A | 496 |
| REMARK | 465 | ILE | A | 497 |
| REMARK | 465 | ASN | A | 498 |
| REMARK | 465 | ASP | A | 499 |
| REMARK | 465 | TYR | A | 500 |
| REMARK | 465 | HIS | A | 501 |
| REMARK | 465 | PRO | A | 502 |
| REMARK | 465 | LYS | A | 503 |
| REMARK | 500 | | | |

TABLE 3-continued

```
REMARK   500   GEOMETRY AND STEREOCHEMISTRY
REMARK   500   SUBTOPIC: COVALENT BOND LENGTHS
REMARK   500
REMARK   500   THE STEREOCHEMICAL PARAMETERS OF THE FOLLOWING RESIDUES
REMARK   500   HAVE VALUES WHICH DEVIATE FROM EXPECTED VALUES BY MORE
REMARK   500   THAN 6*RMSD (M=MODEL NUMBER; RES=RESIDUE NAME; C=CHAIN
REMARK   500   IDENTIFIER; SSEQ=SEQUENCE NUMBER; I=INSERTION CODE).
REMARK   500
REMARK   500   STANDARD TABLE:
REMARK   500   FORMAT: (10X,I3,1X,2(A3,1X,A1,I4,A1,1X,A4,3X),F6.3)
REMARK   500
REMARK   500   EXPECTED VALUES: ENGH AND HUBER, 1991
REMARK   500
REMARK   500        M   RES   CSSEQI   ATM1   RES   CSSEQI   ATM2   DEVIATION
REMARK   500            PRO   A 354    CG     PRO   A 354    CB     0.033
REMARK   500            MET   A 373    CE     MET   A 373    SD     0.035
REMARK   500
REMARK   500   GEOMETRY AND STEREOCHEMISTRY
REMARK   500   SUBTOPIC: COVALENT BOND ANGLES
REMARK   500
REMARK   500   THE STEREOCHEMICAL PARAMETERS OF THE FOLLOWING RESIDUES
REMARK   500   HAVE VALUES WHICH DEVIATE FROM EXPECTED VALUES BY MORE
REMARK   500   THAN 6*RMSD (M=MODEL NUMBER; RES=RESIDUE NAME; C=CHAIN
REMARK   500   IDENTIFIER; SSEQ=SEQUENCE NUMBER; I=INSERTION CODE).
REMARK   500
REMARK   500   STANDARD TABLE:
REMARK   500   FORMAT: (10X,I3,1X,A3,1X,A1,I4,A1,3(1X,A4,2X),12X,F5.1)
REMARK   500
REMARK   500   EXPECTED VALUES: ENGH AND HUBER, 1991
REMARK   500
REMARK   500        M   RES   CSSEQI     ATM1       ATM2       ATM3
REMARK   500            GLY   A  20       N    -    CA    -    C     ANGL. DEV. = -8.3 DEGREES
REMARK   500            ILE   A  27       N    -    CA    -    C     ANGL. DEV. = -8.2 DEGREES
REMARK   500            GLN   A  45       N    -    CA    -    C     ANGL. DEV. = -8.3 DEGREES
REMARK   500            ILE   A  52       N    -    CA    -    C     ANGL. DEV. = -7.8 DEGREES
REMARK   500            PRO   A  53       N    -    CA    -    C     ANGL. DEV. =  7.0 DEGREES
REMARK   500            SER   A  63       N    -    CA    -    C     ANGL. DEV. =  8.6 DEGREES
REMARK   500            PHE   A 266       N    -    CA    -    C     ANGL. DEV. = -8.1 DEGREES
REMARK   500            LYS   A 394       N    -    CA    -    C     ANGL. DEV. = -7.7 DEGREES
REMARK   500            LYS   A 472       N    -    CA    -    C     ANGL. DEV. =  7.3 DEGREES
REMARK   500            LYS   A 474       N    -    CA    -    C     ANGL. DEV. = -8.1 DEGREES
REMARK   500            LEU   A 477       N    -    CA    -    C     ANGL. DEV. = -7.0 DEGREES
REMARK   900
REMARK   900   RELATED ENTRIES
REMARK   900   RELATED ID: 1AK5        RELATED DB: PDB
REMARK   900   INOSINE MONOPHOSPHATE DEHYDROGENASE (IMPDH) FROM
REMARK   900   TRITRICHOMONAS FOETUS
REMARK   900   RELATED ID: 1ME7        RELATED DB: PDB
REMARK   900   1ME7 CONTAINS THE SAME PROTEIN WITH RVP AND MOA BOUND
REMARK   900   RELATED ID: 1ME8        RELATED DB: PDB
REMARK   900   1ME8 CONTAINS THE SAME PROTEIN WITH RVP BOUND
REMARK   900   RELATED ID: 1ME9        RELATED DB: PDB
REMARK   900   1ME9 CONTAINS THE SAME PROTEIN WITH IMP BOUND
REMARK   900   RELATED ID: 1MEI        RELATED DB: PDB
REMARK   900   1MEI CONTAINS THE SAME PROTEIN WITH XMP AND MYCOPHENOLIC
REMARK   900   ACID BOUND
REMARK   900   RELATED ID: 1MEW        RELATED DB: PDB
REMARK   900   1MEW CONTAINS THE SAME PROTEIN WITH XMP AND NAD BOUND
DBREF    1MEH     A     1    503    SWS   P50097   IMDH_TRIFO     1     503
SEQADV   1MEH     CSO   A   319    SWS   P50097   CYS      319 MODIFIED RESIDUE
SEQRES     1     A   503   MET   ALA   LYS   TYR   TYR   ASN   GLU   PRO   CYS   HIS   THR   PHE   ASN
SEQRES     2     A   503   GLU   TYR   LEU   LEU   ILE   PRO   GLY   LEU   SER   THR   VAL   ASP   CYS
SEQRES     3     A   503   ILE   PRO   SER   ASN   VAL   ASN   LEU   SER   THR   PRO   LEU   VAL   LYS
SEQRES     4     A   503   PHE   GLN   LYS   GLY   GLN   GLN   SER   GLU   ILE   ASN   LEU   LYS   ILE
SEQRES     5     A   503   PRO   LEU   VAL   SER   ALA   ILE   MET   GLN   SER   VAL   SER   GLY   GLU
SEQRES     6     A   503   LYS   MET   ALA   ILE   ALA   LEU   ALA   ARG   GLU   GLY   GLY   ILE   SER
SEQRES     7     A   503   PHE   ILE   PHE   GLY   SER   GLN   SER   ILE   GLU   SER   GLN   ALA   ALA
SEQRES     8     A   503   MET   VAL   HIS   ALA   VAL   LYS   ASN   PHE   LYS   ALA   GLY   PHE   VAL
SEQRES     9     A   503   VAL   SER   ASP   SER   ASN   VAL   LYS   PRO   ASP   GLN   THR   PHE   ALA
SEQRES    10     A   503   ASP   VAL   LEU   ALA   ILE   SER   GLN   ARG   THR   THR   HIS   ASN   THR
SEQRES    11     A   503   VAL   ALA   VAL   THR   ASP   ASP   GLY   THR   PRO   HIS   GLY   VAL   LEU
SEQRES    12     A   503   LEU   GLY   LEU   VAL   THR   GLN   ARG   ASP   TYR   PRO   ILE   ASP   LEU
SEQRES    13     A   503   THR   GLN   THR   GLU   THR   LYS   VAL   SER   ASP   MET   MET   THR   PRO
SEQRES    14     A   503   PHE   SER   LYS   LEU   VAL   THR   ALA   HIS   GLN   ASP   THR   LYS   LEU
SEQRES    15     A   503   SER   GLU   ALA   ASN   LYS   ILE   ILE   TRP   GLU   LYS   LYS   LEU   ASN
SEQRES    16     A   503   ALA   LEU   PRO   ILE   ILE   ASP   ASP   ASP   GLN   HIS   LEU   ARG   TYR
SEQRES    17     A   503   ILE   VAL   PHE   ARG   LYS   ASP   TYR   ASP   ARG   SER   GLN   VAL   CYS
SEQRES    18     A   503   HIS   ASN   GLU   LEU   VAL   ASP   SER   GLN   LYS   ARG   TYR   LEU   VAL
SEQRES    19     A   503   GLY   ALA   GLY   ILE   ASN   THR   ARG   ASP   PHE   ARG   GLU   ARG   VAL
```

TABLE 3-continued

| | | | | | | | | | | | | | | |
|---|---|---|---|---|---|---|---|---|---|---|---|---|---|---|
| SEQRES | 20 | A | 503 | PRO | ALA | LEU | VAL | GLU | ALA | GLY | ALA | ASP | VAL | LEU | CYS | ILE |
| SEQRES | 21 | A | 503 | ASP | SER | SER | ASP | GLY | PHE | SER | GLU | TRP | GLN | LYS | ILE | THR |
| SEQRES | 22 | A | 503 | ILE | GLY | TRP | ILE | ARG | GLU | LYS | TYR | GLY | ASP | LYS | VAL | LYS |
| SEQRES | 23 | A | 503 | VAL | GLY | ALA | GLY | ASN | ILE | VAL | ASP | GLY | GLU | GLY | PHE | ARG |
| SEQRES | 24 | A | 503 | TYR | LEU | ALA | ASP | ALA | GLY | ALA | ASP | PHE | ILE | LYS | ILE | GLY |
| SEQRES | 25 | A | 503 | ILE | GLY | GLY | GLY | SER | ILE | CSO | ILE | THR | ARG | GLU | GLN | LYS |
| SEQRES | 26 | A | 503 | GLY | ILE | GLY | ARG | GLY | GLN | ALA | THR | ALA | VAL | ILE | ASP | VAL |
| SEQRES | 27 | A | 503 | VAL | ALA | GLU | ARG | ASN | LYS | TYR | PHE | GLU | GLU | THR | GLY | ILE |
| SEQRES | 28 | A | 503 | TYR | ILE | PRO | VAL | CYS | SER | ASP | GLY | GLY | ILE | VAL | TYR | ASP |
| SEQRES | 29 | A | 503 | TYR | HIS | MET | THR | LEU | ALA | LEU | ALA | MET | GLY | ALA | ASP | PHE |
| SEQRES | 30 | A | 503 | ILE | MET | LEU | GLY | ARG | TYR | PHE | ALA | ARG | PHE | GLU | GLU | SER |
| SEQRES | 31 | A | 503 | PRO | THR | ARG | LYS | VAL | THR | ILE | ASN | GLY | SER | VAL | MET | LYS |
| SEQRES | 32 | A | 503 | GLU | TYR | TRP | GLY | GLU | GLY | SER | SER | ARG | ALA | ARG | ASN | TRP |
| SEQRES | 33 | A | 503 | GLN | ARG | TYR | ASP | LEU | GLY | GLY | LYS | GLN | LYS | LEU | SER | PHE |
| SEQRES | 34 | A | 503 | GLU | GLU | GLY | VAL | ASP | SER | TYR | VAL | PRO | TYR | ALA | GLY | LYS |
| SEQRES | 35 | A | 503 | LEU | LYS | ASP | ASN | VAL | GLU | ALA | SER | LEU | ASN | LYS | VAL | LYS |
| SEQRES | 36 | A | 503 | SER | THR | MET | CYS | ASN | CYS | GLY | ALA | LEU | THR | ILE | PRO | GLN |
| SEQRES | 37 | A | 503 | LEU | GLN | SER | LYS | ALA | LYS | ILE | THR | LEU | VAL | SER | SER | VAL |
| SEQRES | 38 | A | 503 | SER | ILE | VAL | GLU | GLY | GLY | ALA | HIS | ASP | VAL | ILE | VAL | LYS |
| SEQRES | 39 | A | 503 | ASP | ARG | ILE | ASN | ASP | TYR | HIS | PRO | LYS | | | | |
| MODRES | 1MEH | CSO A | | 319 | | CYS | | S-HYDROXYCYSTEINE | | | | | | | |
| HET | CSO | | A 319 | | 7 | | | | | | | | | | |
| HET | K | | A 900 | | 1 | | | | | | | | | | |
| HET | IMP | | 602 | | 23 | | | | | | | | | | |
| HET | MOA | | 600 | | 23 | | | | | | | | | | |
| HETNAM | | CSO | S-HYDROXYCYSTEINE | | | | | | | | | | | | |
| HETNAM | | K | POTASSIUM ION | | | | | | | | | | | | |
| HETNAM | | IMP | INOSINIC ACID | | | | | | | | | | | | |
| HETNAM | | MOA | MYCOPHENOLIC ACID | | | | | | | | | | | | |
| HETSYN | | MOA | 6-(1,3-DIHYDRO-7-HYDROXY-5-METHOXY-4-METHYL-1- | | | | | | | | | | | | |
| HETSYN | 2 | MOA | OXOISOBENZOFURAN-6-YL)-4-METHYL-4-HEXANOIC ACID | | | | | | | | | | | | |
| FORMUL | 1 | CSO | C3 H7 N1 O3 S1 | | | | | | | | | | | | |
| FORMUL | 2 | K | K1 1+ | | | | | | | | | | | | |
| FORMUL | 3 | IMP | C10 H13 N4 O8 P1 | | | | | | | | | | | | |
| FORMUL | 4 | MOA | C17 H20 O6 | | | | | | | | | | | | |
| FORMUL | 5 | HOH | *193(H2 O1) | | | | | | | | | | | | |
| HELIX | 1 | | 1 THR | A | 11 | ASN | A | 13 | 5 | | | | | | 3 |
| HELIX | 2 | | 2 ILE | A | 27 | VAL | A | 31 | 5 | | | | | | 5 |
| HELIX | 3 | | 3 GLY | A | 64 | GLU | A | 74 | 1 | | | | | | 11 |
| HELIX | 4 | | 4 SER | A | 85 | ASN | A | 98 | 1 | | | | | | 14 |
| HELIX | 5 | | 5 ASP | A | 242 | GLY | A | 254 | 1 | | | | | | 13 |
| HELIX | 6 | | 6 SER | A | 267 | GLY | A | 282 | 1 | | | | | | 16 |
| HELIX | 7 | | 7 ASP | A | 283 | VAL | A | 285 | 5 | | | | | | 3 |
| HELIX | 8 | | 8 ASP | A | 294 | GLY | A | 305 | 1 | | | | | | 12 |
| HELIX | 9 | | 9 GLY | A | 316 | ARG | A | 322 | 5 | | | | | | 7 |
| HELIX | 10 | | 10 GLY | A | 330 | GLY | A | 350 | 1 | | | | | | 21 |
| HELIX | 11 | | 11 TYR | A | 363 | MET | A | 373 | 1 | | | | | | 11 |
| HELIX | 12 | | 12 GLY | A | 381 | ARG | A | 386 | 1 | | | | | | 6 |
| HELIX | 13 | | 13 LYS | A | 442 | CYS | A | 461 | 1 | | | | | | 20 |
| HELIX | 14 | | 14 THR | A | 465 | ALA | A | 473 | 1 | | | | | | 9 |
| SHEET | 1 | | A 2 TYR | A 15 | LEU | A | 17 | 0 | | | | | | | |
| SHEET | 2 | | A 2 ILE | A 475 | LEU | A | 477 | -1 O | THR | A | 476 N | LEU | A | 16 | |
| SHEET | 1 | | B 2 THR | A 35 | PRO | A | 36 | 0 | | | | | | | |
| SHEET | 2 | | B 2 ASN | A 49 | LEU | A | 50 | -1 O | LEU | A | 50 N | THR | A | 35 | |
| SHEET | 1 | | C 2 PHE | A 40 | GLN | A | 41 | 0 | | | | | | | |
| SHEET | 2 | | C 2 ILE | A 351 | TYR | A | 352 | -1 O | TYR | A | 352 N | PHE | A | 40 | |
| SHEET | 1 | | D 9 LEU | A 54 | SER | A | 56 | 0 | | | | | | | |
| SHEET | 2 | | D 9 ILE | A 77 | ILE | A | 80 | 1 O | ILE | A | 77 N | SER | A | 56 | |
| SHEET | 3 | | D 9 GLY | A 235 | ILE | A | 238 | 1 O | GLY | A | 237 N | ILE | A | 80 | |
| SHEET | 4 | | D 9 VAL | A 257 | ILE | A | 260 | 1 O | CYS | A | 259 N | ILE | A | 238 | |
| SHEET | 5 | | D 9 VAL | A 287 | ILE | A | 292 | 1 O | GLY | A | 288 N | LEU | A | 258 | |
| SHEET | 6 | | D 9 ILE | A 309 | ILE | A | 311 | 1 O | LYS | A | 310 N | ALA | A | 289 | |
| SHEET | 7 | | D 9 VAL | A 355 | ASP | A | 358 | 1 O | CYS | A | 356 N | ILE | A | 311 | |
| SHEET | 8 | | D 9 PHE | A 377 | LEU | A | 380 | 1 O | MET | A | 379 N | SER | A | 357 | |
| SHEET | 9 | | D 9 LEU | A 54 | SER | A | 56 | 1 N | VAL | A | 55 O | ILE | A | 378 | |
| SHEET | 1 | | E 3 LYS | A 394 | ILE | A | 397 | 0 | | | | | | | |
| SHEET | 2 | | E 3 SER | A 400 | TRP | A | 406 | -1 O | MET | A | 402 N | VAL | A | 395 | |
| SHEET | 3 | | E 3 ASP | A 434 | PRO | A | 438 | -1 O | SER | A | 435 N | TYR | A | 405 | |
| SSBOND | 1 | | CYS A | 26 | CYS | A | 459 | | | | | | | | |
| CISPEP | 1 | | GLY A | 290 | ASN | A | 291 | | 0 | | 1.32 | | | | |
| CRYST1 | 153.480 | | 153.480 | 153.480 | 90.00 | | 90.00 | 90.00 | P 4 3 2 | | 24 | | | | |
| ORIGX1 | | 1.000000 | 0.000000 | 0.000000 | | 0.00000 | | | | | | | | | |
| ORIGX2 | | 0.000000 | 1.000000 | 0.000000 | | 0.00000 | | | | | | | | | |
| ORIGX3 | | 0.000000 | 0.000000 | 1.000000 | | 0.00000 | | | | | | | | | |
| SCALE1 | | 0.006516 | 0.000000 | 0.000000 | | 0.00000 | | | | | | | | | |
| SCALE2 | | 0.000000 | 0.006516 | 0.000000 | | 0.00000 | | | | | | | | | |
| SCALE3 | | 0.000000 | 0.000000 | 0.006516 | | 0.00000 | | | | | | | | | |
| ATOM | 1 | N | ALA | A | 2 | 54.528 | 74.306 | 36.657 | 1.00 | 34.86 | | | | N | |
| ATOM | 2 | CA | ALA | A | 2 | 55.364 | 73.391 | 35.830 | 1.00 | 34.91 | | | | C | |

TABLE 3-continued

| ATOM | 3 | C | ALA | A | 2 | 56.681 | 73.065 | 36.533 | 1.00 | 35.04 | C |
|---|---|---|---|---|---|---|---|---|---|---|---|
| ATOM | 4 | O | ALA | A | 2 | 57.152 | 73.829 | 37.373 | 1.00 | 34.42 | O |
| ATOM | 5 | CB | ALA | A | 2 | 55.650 | 74.032 | 34.477 | 1.00 | 34.75 | C |
| ATOM | 6 | N | LYS | A | 3 | 57.264 | 71.925 | 36.179 | 1.00 | 35.15 | N |
| ATOM | 7 | CA | LYS | A | 3 | 58.535 | 71.498 | 36.749 | 1.00 | 35.98 | C |
| ATOM | 8 | C | LYS | A | 3 | 59.629 | 71.674 | 35.700 | 1.00 | 35.70 | C |
| ATOM | 9 | O | LYS | A | 3 | 59.467 | 71.259 | 34.552 | 1.00 | 35.42 | O |
| ATOM | 10 | CB | LYS | A | 3 | 58.459 | 70.029 | 37.187 | 1.00 | 36.70 | C |
| ATOM | 11 | CG | LYS | A | 3 | 59.819 | 69.387 | 37.449 | 1.00 | 38.59 | C |
| ATOM | 12 | CD | LYS | A | 3 | 59.689 | 67.979 | 38.016 | 1.00 | 39.69 | C |
| ATOM | 13 | CE | LYS | A | 3 | 61.003 | 67.211 | 37.901 | 1.00 | 40.42 | C |
| ATOM | 14 | NZ | LYS | A | 3 | 62.157 | 67.940 | 38.510 | 1.00 | 40.89 | N |
| ATOM | 15 | N | TYR | A | 4 | 60.733 | 72.298 | 36.099 | 1.00 | 35.51 | N |
| ATOM | 16 | CA | TYR | A | 4 | 61.864 | 72.539 | 35.210 | 1.00 | 36.45 | C |
| ATOM | 17 | C | TYR | A | 4 | 63.081 | 71.752 | 35.695 | 1.00 | 37.94 | C |
| ATOM | 18 | O | TYR | A | 4 | 63.055 | 71.166 | 36.775 | 1.00 | 38.19 | O |
| ATOM | 19 | CB | TYR | A | 4 | 62.182 | 74.040 | 35.171 | 1.00 | 34.85 | C |
| ATOM | 20 | CG | TYR | A | 4 | 61.071 | 74.870 | 34.566 | 1.00 | 33.25 | C |
| ATOM | 21 | CD1 | TYR | A | 4 | 60.904 | 74.944 | 33.182 | 1.00 | 32.63 | C |
| ATOM | 22 | CD2 | TYR | A | 4 | 60.158 | 75.545 | 35.375 | 1.00 | 32.51 | C |
| ATOM | 23 | CE1 | TYR | A | 4 | 59.850 | 75.670 | 32.618 | 1.00 | 31.87 | C |
| ATOM | 24 | CE2 | TYR | A | 4 | 59.099 | 76.273 | 34.821 | 1.00 | 32.01 | C |
| ATOM | 25 | CZ | TYR | A | 4 | 58.953 | 76.328 | 33.445 | 1.00 | 31.47 | C |
| ATOM | 26 | OH | TYR | A | 4 | 57.900 | 77.024 | 32.896 | 1.00 | 31.76 | O |
| ATOM | 27 | N | TYR | A | 5 | 64.144 | 71.733 | 34.898 | 1.00 | 40.06 | N |
| ATOM | 28 | CA | TYR | A | 5 | 65.351 | 70.998 | 35.272 | 1.00 | 41.80 | C |
| ATOM | 29 | C | TYR | A | 5 | 66.588 | 71.888 | 35.355 | 1.00 | 42.70 | C |
| ATOM | 30 | O | TYR | A | 5 | 66.654 | 72.941 | 34.719 | 1.00 | 42.98 | O |
| ATOM | 31 | CB | TYR | A | 5 | 65.596 | 69.850 | 34.286 | 1.00 | 42.18 | C |
| ATOM | 32 | CG | TYR | A | 5 | 64.446 | 68.871 | 34.224 | 1.00 | 42.27 | C |
| ATOM | 33 | CD1 | TYR | A | 5 | 63.238 | 69.225 | 33.630 | 1.00 | 42.61 | C |
| ATOM | 34 | CD2 | TYR | A | 5 | 64.551 | 67.603 | 34.797 | 1.00 | 42.57 | C |
| ATOM | 35 | CE1 | TYR | A | 5 | 62.160 | 68.347 | 33.611 | 1.00 | 42.81 | C |
| ATOM | 36 | CE2 | TYR | A | 5 | 63.478 | 66.715 | 34.783 | 1.00 | 42.46 | C |
| ATOM | 37 | CZ | TYR | A | 5 | 62.285 | 67.096 | 34.188 | 1.00 | 42.90 | C |
| ATOM | 38 | OH | TYR | A | 5 | 61.211 | 66.234 | 34.173 | 1.00 | 42.71 | O |
| ATOM | 39 | N | ASN | A | 6 | 67.561 | 71.455 | 36.153 | 1.00 | 43.48 | N |
| ATOM | 40 | CA | ASN | A | 6 | 68.802 | 72.199 | 36.349 | 1.00 | 44.29 | C |
| ATOM | 41 | C | ASN | A | 6 | 69.702 | 72.229 | 35.117 | 1.00 | 44.03 | C |
| ATOM | 42 | O | ASN | A | 6 | 70.291 | 73.263 | 34.800 | 1.00 | 44.49 | O |
| ATOM | 43 | CB | ASN | A | 6 | 69.575 | 71.615 | 37.534 | 1.00 | 45.28 | C |
| ATOM | 44 | CG | ASN | A | 6 | 68.911 | 71.909 | 38.867 | 1.00 | 46.42 | C |
| ATOM | 45 | OD1 | ASN | A | 6 | 69.164 | 71.229 | 39.863 | 1.00 | 47.16 | O |
| ATOM | 46 | ND2 | ASN | A | 6 | 68.065 | 72.935 | 38.895 | 1.00 | 46.63 | N |
| ATOM | 47 | N | GLU | A | 7 | 69.812 | 71.102 | 34.421 | 1.00 | 43.48 | N |
| ATOM | 48 | CA | GLU | A | 7 | 70.659 | 71.039 | 33.233 | 1.00 | 42.70 | C |
| ATOM | 49 | C | GLU | A | 7 | 69.882 | 70.632 | 31.986 | 1.00 | 41.37 | C |
| ATOM | 50 | O | GLU | A | 7 | 68.858 | 69.955 | 32.073 | 1.00 | 40.86 | O |
| ATOM | 51 | CB | GLU | A | 7 | 71.803 | 70.041 | 33.446 | 1.00 | 44.08 | C |
| ATOM | 52 | CG | GLU | A | 7 | 72.774 | 70.384 | 34.577 | 1.00 | 45.95 | C |
| ATOM | 53 | CD | GLU | A | 7 | 73.516 | 71.695 | 34.358 | 1.00 | 46.95 | C |
| ATOM | 54 | OE1 | GLU | A | 7 | 74.048 | 71.911 | 33.246 | 1.00 | 47.35 | O |
| ATOM | 55 | OE2 | GLU | A | 7 | 73.575 | 72.507 | 35.307 | 1.00 | 48.10 | O |
| ATOM | 56 | N | PRO | A | 8 | 70.364 | 71.050 | 30.803 | 1.00 | 39.91 | N |
| ATOM | 57 | CA | PRO | A | 8 | 69.704 | 70.711 | 29.540 | 1.00 | 38.65 | C |
| ATOM | 58 | C | PRO | A | 8 | 70.048 | 69.265 | 29.203 | 1.00 | 37.69 | C |
| ATOM | 59 | O | PRO | A | 8 | 71.039 | 68.738 | 29.707 | 1.00 | 37.18 | O |
| ATOM | 60 | CB | PRO | A | 8 | 70.324 | 71.698 | 28.559 | 1.00 | 38.70 | C |
| ATOM | 61 | CG | PRO | A | 8 | 71.731 | 71.816 | 29.074 | 1.00 | 39.39 | C |
| ATOM | 62 | CD | PRO | A | 8 | 71.529 | 71.926 | 30.570 | 1.00 | 39.63 | C |
| ATOM | 63 | N | CYS | A | 9 | 69.235 | 68.616 | 28.372 | 1.00 | 36.47 | N |
| ATOM | 64 | CA | CYS | A | 9 | 69.517 | 67.235 | 28.005 | 1.00 | 35.60 | C |
| ATOM | 65 | C | CYS | A | 9 | 70.554 | 67.179 | 26.882 | 1.00 | 34.44 | C |
| ATOM | 66 | O | CYS | A | 9 | 70.712 | 68.138 | 26.116 | 1.00 | 34.18 | O |
| ATOM | 67 | CB | CYS | A | 9 | 68.226 | 66.497 | 27.617 | 1.00 | 36.20 | C |
| ATOM | 68 | SG | CYS | A | 9 | 67.191 | 67.270 | 26.369 | 1.00 | 39.57 | S |
| ATOM | 69 | N | HIS | A | 10 | 71.269 | 66.060 | 26.799 | 1.00 | 32.73 | N |
| ATOM | 70 | CA | HIS | A | 10 | 72.327 | 65.882 | 25.808 | 1.00 | 31.17 | C |
| ATOM | 71 | C | HIS | A | 10 | 72.184 | 64.600 | 24.990 | 1.00 | 30.48 | C |
| ATOM | 72 | O | HIS | A | 10 | 71.527 | 63.650 | 25.413 | 1.00 | 29.49 | O |
| ATOM | 73 | CB | HIS | A | 10 | 73.684 | 65.852 | 26.513 | 1.00 | 31.38 | C |
| ATOM | 74 | CG | HIS | A | 10 | 73.953 | 67.049 | 27.368 | 1.00 | 31.58 | C |
| ATOM | 75 | ND1 | HIS | A | 10 | 74.340 | 68.264 | 26.847 | 1.00 | 32.08 | N |
| ATOM | 76 | CD2 | HIS | A | 10 | 73.893 | 67.217 | 28.710 | 1.00 | 32.22 | C |
| ATOM | 77 | CE1 | HIS | A | 10 | 74.511 | 69.129 | 27.832 | 1.00 | 31.71 | C |
| ATOM | 78 | NE2 | HIS | A | 10 | 74.245 | 68.518 | 28.972 | 1.00 | 32.26 | N |
| ATOM | 79 | N | THR | A | 11 | 72.823 | 64.580 | 23.822 | 1.00 | 29.90 | N |
| ATOM | 80 | CA | THR | A | 11 | 72.796 | 63.417 | 22.936 | 1.00 | 29.38 | C |
| ATOM | 81 | C | THR | A | 11 | 74.134 | 62.681 | 23.054 | 1.00 | 28.79 | C |

TABLE 3-continued

| | | | | | | | | | | | |
|---|---|---|---|---|---|---|---|---|---|---|---|
| ATOM | 82 | O | THR | A | 11 | 75.057 | 63.175 | 23.699 | 1.00 | 28.16 | O |
| ATOM | 83 | CB | THR | A | 11 | 72.594 | 63.836 | 21.470 | 1.00 | 30.26 | C |
| ATOM | 84 | OG1 | THR | A | 11 | 73.709 | 64.626 | 21.045 | 1.00 | 31.91 | O |
| ATOM | 85 | CG2 | THR | A | 11 | 71.311 | 64.660 | 21.316 | 1.00 | 31.15 | C |
| ATOM | 86 | N | PHE | A | 12 | 74.240 | 61.510 | 22.433 | 1.00 | 28.35 | N |
| ATOM | 87 | CA | PHE | A | 12 | 75.474 | 60.730 | 22.493 | 1.00 | 28.54 | C |
| ATOM | 88 | C | PHE | A | 12 | 76.684 | 61.440 | 21.883 | 1.00 | 28.64 | C |
| ATOM | 89 | O | PHE | A | 12 | 77.813 | 61.252 | 22.340 | 1.00 | 27.98 | O |
| ATOM | 90 | CB | PHE | A | 12 | 75.282 | 59.367 | 21.816 | 1.00 | 27.87 | C |
| ATOM | 91 | CG | PHE | A | 12 | 74.379 | 58.428 | 22.578 | 1.00 | 27.50 | C |
| ATOM | 92 | CD1 | PHE | A | 12 | 74.549 | 58.232 | 23.946 | 1.00 | 27.53 | C |
| ATOM | 93 | CD2 | PHE | A | 12 | 73.374 | 57.724 | 21.923 | 1.00 | 27.61 | C |
| ATOM | 94 | CE1 | PHE | A | 12 | 73.729 | 57.348 | 24.652 | 1.00 | 26.85 | C |
| ATOM | 95 | CE2 | PHE | A | 12 | 72.549 | 56.834 | 22.621 | 1.00 | 27.24 | C |
| ATOM | 96 | CZ | PHE | A | 12 | 72.729 | 56.648 | 23.985 | 1.00 | 26.78 | C |
| ATOM | 97 | N | ASN | A | 13 | 76.449 | 62.246 | 20.851 | 1.00 | 28.52 | N |
| ATOM | 98 | CA | ASN | A | 13 | 77.527 | 62.988 | 20.191 | 1.00 | 29.04 | C |
| ATOM | 99 | C | ASN | A | 13 | 78.243 | 63.954 | 21.131 | 1.00 | 28.55 | C |
| ATOM | 100 | O | ASN | A | 13 | 79.339 | 64.428 | 20.829 | 1.00 | 28.82 | O |
| ATOM | 101 | CB | ASN | A | 13 | 76.969 | 63.792 | 19.016 | 1.00 | 30.99 | C |
| ATOM | 102 | CG | ASN | A | 13 | 76.995 | 63.027 | 17.716 | 1.00 | 32.29 | C |
| ATOM | 103 | OD1 | ASN | A | 13 | 76.291 | 63.379 | 16.772 | 1.00 | 34.44 | O |
| ATOM | 104 | ND2 | ASN | A | 13 | 77.823 | 61.990 | 17.647 | 1.00 | 32.33 | N |
| ATOM | 105 | N | GLU | A | 14 | 77.625 | 64.255 | 22.265 | 1.00 | 27.53 | N |
| ATOM | 106 | CA | GLU | A | 14 | 78.218 | 65.190 | 23.212 | 1.00 | 27.62 | C |
| ATOM | 107 | C | GLU | A | 14 | 79.093 | 64.530 | 24.278 | 1.00 | 26.94 | C |
| ATOM | 108 | O | GLU | A | 14 | 79.548 | 65.199 | 25.203 | 1.00 | 27.17 | O |
| ATOM | 109 | CB | GLU | A | 14 | 77.114 | 66.003 | 23.890 | 1.00 | 28.36 | C |
| ATOM | 110 | CG | GLU | A | 14 | 76.224 | 66.769 | 22.912 | 1.00 | 29.57 | C |
| ATOM | 111 | CD | GLU | A | 14 | 75.134 | 67.557 | 23.608 | 1.00 | 30.53 | C |
| ATOM | 112 | OE1 | GLU | A | 14 | 75.468 | 68.455 | 24.411 | 1.00 | 31.64 | O |
| ATOM | 113 | OE2 | GLU | A | 14 | 73.941 | 67.281 | 23.352 | 1.00 | 31.42 | O |
| ATOM | 114 | N | TYR | A | 15 | 79.343 | 63.231 | 24.140 | 1.00 | 26.43 | N |
| ATOM | 115 | CA | TYR | A | 15 | 80.150 | 62.509 | 25.123 | 1.00 | 26.24 | C |
| ATOM | 116 | C | TYR | A | 15 | 81.325 | 61.721 | 24.555 | 1.00 | 26.03 | C |
| ATOM | 117 | O | TYR | A | 15 | 81.325 | 61.315 | 23.393 | 1.00 | 25.65 | O |
| ATOM | 118 | CB | TYR | A | 15 | 79.264 | 61.538 | 25.909 | 1.00 | 26.61 | C |
| ATOM | 119 | CG | TYR | A | 15 | 78.257 | 62.197 | 26.818 | 1.00 | 27.62 | C |
| ATOM | 120 | CD1 | TYR | A | 15 | 78.604 | 62.578 | 28.112 | 1.00 | 28.33 | C |
| ATOM | 121 | CD2 | TYR | A | 15 | 76.954 | 62.447 | 26.383 | 1.00 | 28.22 | C |
| ATOM | 122 | CE1 | TYR | A | 15 | 77.682 | 63.188 | 28.958 | 1.00 | 29.62 | C |
| ATOM | 123 | CE2 | TYR | A | 15 | 76.023 | 63.063 | 27.222 | 1.00 | 29.03 | C |
| ATOM | 124 | CZ | TYR | A | 15 | 76.395 | 63.429 | 28.505 | 1.00 | 29.97 | C |
| ATOM | 125 | OH | TYR | A | 15 | 75.495 | 64.057 | 29.335 | 1.00 | 31.38 | O |
| ATOM | 126 | N | LEU | A | 16 | 82.323 | 61.509 | 25.408 | 1.00 | 26.11 | N |
| ATOM | 127 | CA | LEU | A | 16 | 83.507 | 60.730 | 25.071 | 1.00 | 26.06 | C |
| ATOM | 128 | C | LEU | A | 16 | 83.925 | 59.997 | 26.336 | 1.00 | 25.29 | C |
| ATOM | 129 | O | LEU | A | 16 | 83.606 | 60.430 | 27.444 | 1.00 | 24.34 | O |
| ATOM | 130 | CB | LEU | A | 16 | 84.660 | 61.628 | 24.607 | 1.00 | 26.91 | C |
| ATOM | 131 | CG | LEU | A | 16 | 84.570 | 62.300 | 23.233 | 1.00 | 28.35 | C |
| ATOM | 132 | CD1 | LEU | A | 16 | 85.820 | 63.150 | 23.016 | 1.00 | 27.97 | C |
| ATOM | 133 | CD2 | LEU | A | 16 | 84.452 | 61.246 | 22.134 | 1.00 | 28.15 | C |
| ATOM | 134 | N | LEU | A | 17 | 84.634 | 58.889 | 26.165 | 1.00 | 24.72 | N |
| ATOM | 135 | CA | LEU | A | 17 | 85.119 | 58.097 | 27.290 | 1.00 | 24.73 | C |
| ATOM | 136 | C | LEU | A | 17 | 86.592 | 58.405 | 27.558 | 1.00 | 24.51 | C |
| ATOM | 137 | O | LEU | A | 17 | 87.386 | 58.553 | 26.626 | 1.00 | 24.84 | O |
| ATOM | 138 | CB | LEU | A | 17 | 84.970 | 56.603 | 26.983 | 1.00 | 24.74 | C |
| ATOM | 139 | CG | LEU | A | 17 | 83.551 | 56.029 | 26.964 | 1.00 | 25.01 | C |
| ATOM | 140 | CD1 | LEU | A | 17 | 83.526 | 54.730 | 26.166 | 1.00 | 25.67 | C |
| ATOM | 141 | CD2 | LEU | A | 17 | 83.086 | 55.796 | 28.391 | 1.00 | 25.40 | C |
| ATOM | 142 | N | ILE | A | 18 | 86.950 | 58.512 | 28.831 | 1.00 | 24.38 | N |
| ATOM | 143 | CA | ILE | A | 18 | 88.330 | 58.770 | 29.219 | 1.00 | 24.63 | C |
| ATOM | 144 | C | ILE | A | 18 | 88.900 | 57.408 | 29.613 | 1.00 | 24.85 | C |
| ATOM | 145 | O | ILE | A | 18 | 88.315 | 56.694 | 30.429 | 1.00 | 25.12 | O |
| ATOM | 146 | CB | ILE | A | 18 | 88.395 | 59.765 | 30.406 | 1.00 | 25.11 | C |
| ATOM | 147 | CG1 | ILE | A | 18 | 87.927 | 61.147 | 29.926 | 1.00 | 25.53 | C |
| ATOM | 148 | CG2 | ILE | A | 18 | 89.820 | 59.838 | 30.972 | 1.00 | 24.64 | C |
| ATOM | 149 | CD1 | ILE | A | 18 | 87.909 | 62.211 | 31.010 | 1.00 | 27.24 | C |
| ATOM | 150 | N | PRO | A | 19 | 90.039 | 57.020 | 29.023 | 1.00 | 25.20 | N |
| ATOM | 151 | CA | PRO | A | 19 | 90.652 | 55.723 | 29.332 | 1.00 | 25.63 | C |
| ATOM | 152 | C | PRO | A | 19 | 90.914 | 55.433 | 30.805 | 1.00 | 25.58 | C |
| ATOM | 153 | O | PRO | A | 19 | 91.147 | 56.339 | 31.602 | 1.00 | 25.92 | O |
| ATOM | 154 | CB | PRO | A | 19 | 91.949 | 55.746 | 28.520 | 1.00 | 25.89 | C |
| ATOM | 155 | CG | PRO | A | 19 | 91.597 | 56.623 | 27.346 | 1.00 | 26.34 | C |
| ATOM | 156 | CD | PRO | A | 19 | 90.828 | 57.744 | 28.009 | 1.00 | 25.19 | C |
| ATOM | 157 | N | GLY | A | 20 | 90.847 | 54.150 | 31.149 | 1.00 | 25.25 | N |
| ATOM | 158 | CA | GLY | A | 20 | 91.121 | 53.705 | 32.505 | 1.00 | 25.27 | C |
| ATOM | 159 | C | GLY | A | 20 | 92.328 | 52.800 | 32.362 | 1.00 | 25.31 | C |
| ATOM | 160 | O | GLY | A | 20 | 92.926 | 52.766 | 31.293 | 1.00 | 24.89 | O |

TABLE 3-continued

| | | | | | | | | | | | |
|---|---|---|---|---|---|---|---|---|---|---|---|
| ATOM | 161 | N | LEU | A | 21 | 92.701 | 52.067 | 33.402 | 1.00 | 25.69 | N |
| ATOM | 162 | CA | LEU | A | 21 | 93.858 | 51.184 | 33.293 | 1.00 | 26.65 | C |
| ATOM | 163 | C | LEU | A | 21 | 93.558 | 49.946 | 32.453 | 1.00 | 26.91 | C |
| ATOM | 164 | O | LEU | A | 21 | 92.641 | 49.185 | 32.761 | 1.00 | 26.58 | O |
| ATOM | 165 | CB | LEU | A | 21 | 94.341 | 50.752 | 34.685 | 1.00 | 26.99 | C |
| ATOM | 166 | CG | LEU | A | 21 | 95.498 | 49.739 | 34.720 | 1.00 | 27.71 | C |
| ATOM | 167 | CD1 | LEU | A | 21 | 96.721 | 50.297 | 34.003 | 1.00 | 27.95 | C |
| ATOM | 168 | CD2 | LEU | A | 21 | 95.838 | 49.412 | 36.174 | 1.00 | 28.33 | C |
| ATOM | 169 | N | SER | A | 22 | 94.328 | 49.756 | 31.383 | 1.00 | 27.24 | N |
| ATOM | 170 | CA | SER | A | 22 | 94.165 | 48.593 | 30.516 | 1.00 | 28.46 | C |
| ATOM | 171 | C | SER | A | 22 | 95.145 | 47.515 | 30.977 | 1.00 | 29.50 | C |
| ATOM | 172 | O | SER | A | 22 | 96.353 | 47.747 | 31.011 | 1.00 | 28.90 | O |
| ATOM | 173 | CB | SER | A | 22 | 94.468 | 48.952 | 29.060 | 1.00 | 28.09 | C |
| ATOM | 174 | OG | SER | A | 22 | 93.577 | 49.931 | 28.573 | 1.00 | 27.34 | O |
| ATOM | 175 | N | THR | A | 23 | 94.621 | 46.342 | 31.323 | 1.00 | 30.24 | N |
| ATOM | 176 | CA | THR | A | 23 | 95.448 | 45.231 | 31.790 | 1.00 | 31.35 | C |
| ATOM | 177 | C | THR | A | 23 | 95.902 | 44.337 | 30.642 | 1.00 | 31.61 | C |
| ATOM | 178 | O | THR | A | 23 | 95.257 | 44.283 | 29.595 | 1.00 | 32.12 | O |
| ATOM | 179 | CB | THR | A | 23 | 94.682 | 44.369 | 32.810 | 1.00 | 31.67 | C |
| ATOM | 180 | OG1 | THR | A | 23 | 93.384 | 44.061 | 32.286 | 1.00 | 33.18 | O |
| ATOM | 181 | CG2 | THR | A | 23 | 94.532 | 45.105 | 34.126 | 1.00 | 32.36 | C |
| ATOM | 182 | N | VAL | A | 24 | 97.011 | 43.628 | 30.842 | 1.00 | 32.54 | N |
| ATOM | 183 | CA | VAL | A | 24 | 97.537 | 42.746 | 29.805 | 1.00 | 33.28 | C |
| ATOM | 184 | C | VAL | A | 24 | 96.516 | 41.691 | 29.378 | 1.00 | 34.33 | C |
| ATOM | 185 | O | VAL | A | 24 | 96.585 | 41.166 | 28.269 | 1.00 | 34.00 | O |
| ATOM | 186 | CB | VAL | A | 24 | 98.837 | 42.025 | 30.267 | 1.00 | 33.25 | C |
| ATOM | 187 | CG1 | VAL | A | 24 | 99.934 | 43.049 | 30.552 | 1.00 | 32.51 | C |
| ATOM | 188 | CG2 | VAL | A | 24 | 98.563 | 41.185 | 31.499 | 1.00 | 33.40 | C |
| ATOM | 189 | N | ASP | A | 25 | 95.563 | 41.392 | 30.253 | 1.00 | 36.01 | N |
| ATOM | 190 | CA | ASP | A | 25 | 94.552 | 40.389 | 29.945 | 1.00 | 38.28 | C |
| ATOM | 191 | C | ASP | A | 25 | 93.382 | 40.901 | 29.106 | 1.00 | 38.45 | C |
| ATOM | 192 | O | ASP | A | 25 | 92.550 | 40.114 | 28.668 | 1.00 | 38.94 | O |
| ATOM | 193 | CB | ASP | A | 25 | 94.023 | 39.761 | 31.241 | 1.00 | 40.34 | C |
| ATOM | 194 | CG | ASP | A | 25 | 93.159 | 40.713 | 32.048 | 1.00 | 42.35 | C |
| ATOM | 195 | OD1 | ASP | A | 25 | 91.955 | 40.834 | 31.745 | 1.00 | 44.31 | O |
| ATOM | 196 | OD2 | ASP | A | 25 | 93.684 | 41.348 | 32.985 | 1.00 | 44.56 | O |
| ATOM | 197 | N | CYS | A | 26 | 93.311 | 42.206 | 28.860 | 1.00 | 38.57 | N |
| ATOM | 198 | CA | CYS | A | 26 | 92.195 | 42.714 | 28.070 | 1.00 | 38.08 | C |
| ATOM | 199 | C | CYS | A | 26 | 92.480 | 42.930 | 26.597 | 1.00 | 38.07 | C |
| ATOM | 200 | O | CYS | A | 26 | 93.094 | 43.923 | 26.204 | 1.00 | 38.02 | O |
| ATOM | 201 | CB | CYS | A | 26 | 91.652 | 44.026 | 28.639 | 1.00 | 37.39 | C |
| ATOM | 202 | SG | CYS | A | 26 | 89.947 | 44.430 | 28.092 | 1.00 | 36.98 | S |
| ATOM | 203 | N | ILE | A | 27 | 92.025 | 41.982 | 25.789 | 1.00 | 37.71 | N |
| ATOM | 204 | CA | ILE | A | 27 | 92.144 | 42.070 | 24.347 | 1.00 | 37.96 | C |
| ATOM | 205 | C | ILE | A | 27 | 90.721 | 41.819 | 23.871 | 1.00 | 37.64 | C |
| ATOM | 206 | O | ILE | A | 27 | 89.965 | 41.100 | 24.526 | 1.00 | 37.26 | O |
| ATOM | 207 | CB | ILE | A | 27 | 93.099 | 40.999 | 23.765 | 1.00 | 38.64 | C |
| ATOM | 208 | CG1 | ILE | A | 27 | 92.780 | 39.627 | 24.361 | 1.00 | 38.53 | C |
| ATOM | 209 | CG2 | ILE | A | 27 | 94.548 | 41.407 | 24.020 | 1.00 | 38.05 | C |
| ATOM | 210 | CD1 | ILE | A | 27 | 93.629 | 38.504 | 23.789 | 1.00 | 39.94 | C |
| ATOM | 211 | N | PRO | A | 28 | 90.329 | 42.424 | 22.742 | 1.00 | 37.48 | N |
| ATOM | 212 | CA | PRO | A | 28 | 88.985 | 42.267 | 22.185 | 1.00 | 37.27 | C |
| ATOM | 213 | C | PRO | A | 28 | 88.399 | 40.862 | 22.281 | 1.00 | 37.00 | C |
| ATOM | 214 | O | PRO | A | 28 | 87.245 | 40.696 | 22.675 | 1.00 | 36.24 | O |
| ATOM | 215 | CB | PRO | A | 28 | 89.165 | 42.726 | 20.741 | 1.00 | 37.74 | C |
| ATOM | 216 | CG | PRO | A | 28 | 90.147 | 43.838 | 20.892 | 1.00 | 37.23 | C |
| ATOM | 217 | CD | PRO | A | 28 | 91.165 | 43.259 | 21.858 | 1.00 | 37.69 | C |
| ATOM | 218 | N | SER | A | 29 | 89.195 | 39.854 | 21.934 | 1.00 | 36.71 | N |
| ATOM | 219 | CA | SER | A | 29 | 88.724 | 38.473 | 21.960 | 1.00 | 36.44 | C |
| ATOM | 220 | C | SER | A | 29 | 88.358 | 37.934 | 23.340 | 1.00 | 35.69 | C |
| ATOM | 221 | O | SER | A | 29 | 87.608 | 36.964 | 23.444 | 1.00 | 35.87 | O |
| ATOM | 222 | CB | SER | A | 29 | 89.747 | 37.543 | 21.291 | 1.00 | 37.16 | C |
| ATOM | 223 | OG | SER | A | 29 | 91.019 | 37.620 | 21.907 | 1.00 | 38.53 | O |
| ATOM | 224 | N | ASN | A | 30 | 88.874 | 38.547 | 24.400 | 1.00 | 34.53 | N |
| ATOM | 225 | CA | ASN | A | 30 | 88.541 | 38.084 | 25.744 | 1.00 | 33.29 | C |
| ATOM | 226 | C | ASN | A | 30 | 87.358 | 38.850 | 26.342 | 1.00 | 31.44 | C |
| ATOM | 227 | O | ASN | A | 30 | 86.903 | 38.526 | 27.436 | 1.00 | 31.19 | O |
| ATOM | 228 | CB | ASN | A | 30 | 89.747 | 38.195 | 26.686 | 1.00 | 35.35 | C |
| ATOM | 229 | CG | ASN | A | 30 | 90.819 | 37.158 | 26.396 | 1.00 | 37.30 | C |
| ATOM | 230 | OD1 | ASN | A | 30 | 90.517 | 36.011 | 26.061 | 1.00 | 38.46 | O |
| ATOM | 231 | ND2 | ASN | A | 30 | 92.078 | 37.552 | 26.544 | 1.00 | 37.96 | N |
| ATOM | 232 | N | VAL | A | 31 | 86.861 | 39.858 | 25.628 | 1.00 | 28.79 | N |
| ATOM | 233 | CA | VAL | A | 31 | 85.730 | 40.645 | 26.119 | 1.00 | 27.05 | C |
| ATOM | 234 | C | VAL | A | 31 | 84.408 | 39.897 | 25.955 | 1.00 | 26.82 | C |
| ATOM | 235 | O | VAL | A | 31 | 84.095 | 39.394 | 24.880 | 1.00 | 26.06 | O |
| ATOM | 236 | CB | VAL | A | 31 | 85.637 | 42.011 | 25.400 | 1.00 | 26.53 | C |
| ATOM | 237 | CG1 | VAL | A | 31 | 84.345 | 42.724 | 25.797 | 1.00 | 25.95 | C |
| ATOM | 238 | CG2 | VAL | A | 31 | 86.845 | 42.873 | 25.773 | 1.00 | 24.71 | C |
| ATOM | 239 | N | ASN | A | 32 | 83.645 | 39.835 | 27.041 | 1.00 | 26.34 | N |

TABLE 3-continued

| | | | | | | | | | | | |
|---|---|---|---|---|---|---|---|---|---|---|---|
| ATOM | 240 | CA | ASN | A | 32 | 82.355 | 39.140 | 27.082 | 1.00 | 26.00 | C |
| ATOM | 241 | C | ASN | A | 32 | 81.227 | 40.164 | 26.965 | 1.00 | 25.15 | C |
| ATOM | 242 | O | ASN | A | 32 | 81.080 | 41.016 | 27.842 | 1.00 | 25.29 | O |
| ATOM | 243 | CB | ASN | A | 32 | 82.240 | 38.396 | 28.420 | 1.00 | 26.75 | C |
| ATOM | 244 | CG | ASN | A | 32 | 80.958 | 37.583 | 28.549 | 1.00 | 28.49 | C |
| ATOM | 245 | OD1 | ASN | A | 32 | 79.957 | 37.851 | 27.884 | 1.00 | 28.21 | O |
| ATOM | 246 | ND2 | ASN | A | 32 | 80.984 | 36.591 | 29.434 | 1.00 | 29.77 | N |
| ATOM | 247 | N | LEU | A | 33 | 80.429 | 40.079 | 25.901 | 1.00 | 24.40 | N |
| ATOM | 248 | CA | LEU | A | 33 | 79.329 | 41.024 | 25.700 | 1.00 | 24.28 | C |
| ATOM | 249 | C | LEU | A | 33 | 77.947 | 40.492 | 26.094 | 1.00 | 23.96 | C |
| ATOM | 250 | O | LEU | A | 33 | 76.922 | 41.024 | 25.664 | 1.00 | 23.48 | O |
| ATOM | 251 | CB | LEU | A | 33 | 79.300 | 41.511 | 24.242 | 1.00 | 24.79 | C |
| ATOM | 252 | CG | LEU | A | 33 | 80.520 | 42.316 | 23.774 | 1.00 | 25.38 | C |
| ATOM | 253 | CD1 | LEU | A | 33 | 80.321 | 42.761 | 22.333 | 1.00 | 25.52 | C |
| ATOM | 254 | CD2 | LEU | A | 33 | 80.721 | 43.529 | 24.675 | 1.00 | 25.70 | C |
| ATOM | 255 | N | SER | A | 34 | 77.920 | 39.445 | 26.913 | 1.00 | 23.29 | N |
| ATOM | 256 | CA | SER | A | 34 | 76.653 | 38.882 | 27.375 | 1.00 | 23.29 | C |
| ATOM | 257 | C | SER | A | 34 | 75.916 | 39.961 | 28.168 | 1.00 | 22.23 | C |
| ATOM | 258 | O | SER | A | 34 | 76.544 | 40.817 | 28.780 | 1.00 | 22.07 | O |
| ATOM | 259 | CB | SER | A | 34 | 76.909 | 37.670 | 28.278 | 1.00 | 23.70 | C |
| ATOM | 260 | OG | SER | A | 34 | 75.698 | 37.216 | 28.861 | 1.00 | 27.20 | O |
| ATOM | 261 | N | THR | A | 35 | 74.588 | 39.923 | 28.170 | 1.00 | 21.87 | N |
| ATOM | 262 | CA | THR | A | 35 | 73.822 | 40.925 | 28.902 | 1.00 | 20.75 | C |
| ATOM | 263 | C | THR | A | 35 | 72.396 | 40.419 | 29.149 | 1.00 | 20.94 | C |
| ATOM | 264 | O | THR | A | 35 | 71.826 | 39.699 | 28.320 | 1.00 | 21.27 | O |
| ATOM | 265 | CB | THR | A | 35 | 73.814 | 42.277 | 28.112 | 1.00 | 21.38 | C |
| ATOM | 266 | OG1 | THR | A | 35 | 73.523 | 43.368 | 29.001 | 1.00 | 21.23 | O |
| ATOM | 267 | CG2 | THR | A | 35 | 72.786 | 42.239 | 26.991 | 1.00 | 20.66 | C |
| ATOM | 268 | N | PRO | A | 36 | 71.801 | 40.786 | 30.296 | 1.00 | 20.32 | N |
| ATOM | 269 | CA | PRO | A | 36 | 70.440 | 40.354 | 30.636 | 1.00 | 20.69 | C |
| ATOM | 270 | C | PRO | A | 36 | 69.338 | 41.049 | 29.841 | 1.00 | 20.70 | C |
| ATOM | 271 | O | PRO | A | 36 | 69.404 | 42.251 | 29.581 | 1.00 | 21.51 | O |
| ATOM | 272 | CB | PRO | A | 36 | 70.350 | 40.662 | 32.128 | 1.00 | 19.89 | C |
| ATOM | 273 | CG | PRO | A | 36 | 71.153 | 41.919 | 32.239 | 1.00 | 19.69 | C |
| ATOM | 274 | CD | PRO | A | 36 | 72.372 | 41.614 | 31.377 | 1.00 | 20.06 | C |
| ATOM | 275 | N | LEU | A | 37 | 68.317 | 40.285 | 29.471 | 1.00 | 21.00 | N |
| ATOM | 276 | CA | LEU | A | 37 | 67.197 | 40.830 | 28.718 | 1.00 | 21.84 | C |
| ATOM | 277 | C | LEU | A | 37 | 65.980 | 41.072 | 29.609 | 1.00 | 21.93 | C |
| ATOM | 278 | O | LEU | A | 37 | 65.257 | 42.049 | 29.416 | 1.00 | 21.26 | O |
| ATOM | 279 | CB | LEU | A | 37 | 66.798 | 39.882 | 27.582 | 1.00 | 22.24 | C |
| ATOM | 280 | CG | LEU | A | 37 | 65.696 | 40.404 | 26.650 | 1.00 | 22.01 | C |
| ATOM | 281 | CD1 | LEU | A | 37 | 66.269 | 41.525 | 25.787 | 1.00 | 22.09 | C |
| ATOM | 282 | CD2 | LEU | A | 37 | 65.164 | 39.289 | 25.777 | 1.00 | 22.26 | C |
| ATOM | 283 | N | VAL | A | 38 | 65.758 | 40.193 | 30.585 | 1.00 | 21.79 | N |
| ATOM | 284 | CA | VAL | A | 38 | 64.598 | 40.328 | 31.466 | 1.00 | 22.14 | C |
| ATOM | 285 | C | VAL | A | 38 | 64.950 | 40.384 | 32.950 | 1.00 | 22.71 | C |
| ATOM | 286 | O | VAL | A | 38 | 65.973 | 39.846 | 33.386 | 1.00 | 22.81 | O |
| ATOM | 287 | CB | VAL | A | 38 | 63.577 | 39.188 | 31.216 | 1.00 | 22.25 | C |
| ATOM | 288 | CG1 | VAL | A | 38 | 63.064 | 39.267 | 29.776 | 1.00 | 22.95 | C |
| ATOM | 289 | CG2 | VAL | A | 38 | 64.220 | 37.832 | 31.469 | 1.00 | 22.56 | C |
| ATOM | 290 | N | LYS | A | 39 | 64.081 | 41.032 | 33.719 | 1.00 | 22.22 | N |
| ATOM | 291 | CA | LYS | A | 39 | 64.296 | 41.230 | 35.144 | 1.00 | 22.61 | C |
| ATOM | 292 | C | LYS | A | 39 | 64.525 | 39.970 | 35.972 | 1.00 | 22.81 | C |
| ATOM | 293 | O | LYS | A | 39 | 64.018 | 38.892 | 35.655 | 1.00 | 22.94 | O |
| ATOM | 294 | CB | LYS | A | 39 | 63.130 | 42.019 | 35.750 | 1.00 | 22.84 | C |
| ATOM | 295 | CG | LYS | A | 39 | 61.814 | 41.259 | 35.802 | 1.00 | 23.34 | C |
| ATOM | 296 | CD | LYS | A | 39 | 60.751 | 42.061 | 36.548 | 1.00 | 25.09 | C |
| ATOM | 297 | CE | LYS | A | 39 | 59.425 | 41.313 | 36.606 | 1.00 | 25.38 | C |
| ATOM | 298 | NZ | LYS | A | 39 | 58.393 | 42.105 | 37.328 | 1.00 | 26.79 | N |
| ATOM | 299 | N | PHE | A | 40 | 65.297 | 40.140 | 37.041 | 1.00 | 23.12 | N |
| ATOM | 300 | CA | PHE | A | 40 | 65.620 | 39.065 | 37.973 | 1.00 | 24.28 | C |
| ATOM | 301 | C | PHE | A | 40 | 65.900 | 39.689 | 39.342 | 1.00 | 25.44 | C |
| ATOM | 302 | O | PHE | A | 40 | 66.044 | 40.914 | 39.456 | 1.00 | 26.48 | O |
| ATOM | 303 | CB | PHE | A | 40 | 66.848 | 38.272 | 37.492 | 1.00 | 22.73 | C |
| ATOM | 304 | CG | PHE | A | 40 | 68.061 | 39.123 | 37.217 | 1.00 | 22.77 | C |
| ATOM | 305 | CD1 | PHE | A | 40 | 68.251 | 39.709 | 35.965 | 1.00 | 22.17 | C |
| ATOM | 306 | CD2 | PHE | A | 40 | 69.011 | 39.347 | 38.212 | 1.00 | 22.45 | C |
| ATOM | 307 | CE1 | PHE | A | 40 | 69.369 | 40.504 | 35.709 | 1.00 | 22.24 | C |
| ATOM | 308 | CE2 | PHE | A | 40 | 70.133 | 40.139 | 37.971 | 1.00 | 22.30 | C |
| ATOM | 309 | CZ | PHE | A | 40 | 70.313 | 40.721 | 36.713 | 1.00 | 23.25 | C |
| ATOM | 310 | N | GLN | A | 41 | 65.968 | 38.850 | 40.373 | 1.00 | 25.99 | N |
| ATOM | 311 | CA | GLN | A | 41 | 66.233 | 39.300 | 41.741 | 1.00 | 27.32 | C |
| ATOM | 312 | C | GLN | A | 41 | 67.722 | 39.323 | 42.021 | 1.00 | 26.58 | C |
| ATOM | 313 | O | GLN | A | 41 | 68.494 | 38.644 | 41.350 | 1.00 | 26.05 | O |
| ATOM | 314 | CB | GLN | A | 41 | 65.580 | 38.360 | 42.767 | 1.00 | 28.63 | C |
| ATOM | 315 | CG | GLN | A | 41 | 64.073 | 38.418 | 42.811 | 1.00 | 32.62 | C |
| ATOM | 316 | CD | GLN | A | 41 | 63.568 | 39.766 | 43.273 | 1.00 | 34.57 | C |
| ATOM | 317 | OE1 | GLN | A | 41 | 63.767 | 40.164 | 44.429 | 1.00 | 37.98 | O |
| ATOM | 318 | NE2 | GLN | A | 41 | 62.915 | 40.485 | 42.375 | 1.00 | 35.13 | N |

TABLE 3-continued

| | | | | | | | | | | | |
|---|---|---|---|---|---|---|---|---|---|---|---|
| ATOM | 319 | N | LYS | A | 42 | 68.112 | 40.091 | 43.035 | 1.00 | 26.17 | N |
| ATOM | 320 | CA | LYS | A | 42 | 69.511 | 40.189 | 43.432 | 1.00 | 26.88 | C |
| ATOM | 321 | C | LYS | A | 42 | 70.104 | 38.790 | 43.624 | 1.00 | 26.18 | C |
| ATOM | 322 | O | LYS | A | 42 | 69.506 | 37.936 | 44.284 | 1.00 | 25.24 | O |
| ATOM | 323 | CB | LYS | A | 42 | 69.620 | 40.984 | 44.738 | 1.00 | 28.70 | C |
| ATOM | 324 | CG | LYS | A | 42 | 71.020 | 41.076 | 45.320 | 1.00 | 30.39 | C |
| ATOM | 325 | CD | LYS | A | 42 | 71.018 | 41.936 | 46.581 | 1.00 | 32.90 | C |
| ATOM | 326 | CE | LYS | A | 42 | 72.414 | 42.059 | 47.174 | 1.00 | 34.17 | C |
| ATOM | 327 | NZ | LYS | A | 42 | 72.429 | 42.982 | 48.349 | 1.00 | 36.34 | N |
| ATOM | 328 | N | GLY | A | 43 | 71.271 | 38.561 | 43.031 | 1.00 | 25.61 | N |
| ATOM | 329 | CA | GLY | A | 43 | 71.929 | 37.272 | 43.157 | 1.00 | 25.50 | C |
| ATOM | 330 | C | GLY | A | 43 | 71.574 | 36.267 | 42.079 | 1.00 | 24.98 | C |
| ATOM | 331 | O | GLY | A | 43 | 72.260 | 35.260 | 41.916 | 1.00 | 25.00 | O |
| ATOM | 332 | N | GLN | A | 44 | 70.500 | 36.523 | 41.343 | 1.00 | 24.55 | N |
| ATOM | 333 | CA | GLN | A | 44 | 70.092 | 35.606 | 40.287 | 1.00 | 24.65 | C |
| ATOM | 334 | C | GLN | A | 44 | 70.707 | 36.017 | 38.961 | 1.00 | 25.02 | C |
| ATOM | 335 | O | GLN | A | 44 | 71.394 | 37.029 | 38.868 | 1.00 | 24.74 | O |
| ATOM | 336 | CB | GLN | A | 44 | 68.569 | 35.610 | 40.117 | 1.00 | 24.79 | C |
| ATOM | 337 | CG | GLN | A | 44 | 67.766 | 35.374 | 41.390 | 1.00 | 24.46 | C |
| ATOM | 338 | CD | GLN | A | 44 | 66.270 | 35.328 | 41.124 | 1.00 | 25.55 | C |
| ATOM | 339 | OE1 | GLN | A | 44 | 65.758 | 36.043 | 40.255 | 1.00 | 24.07 | O |
| ATOM | 340 | NE2 | GLN | A | 44 | 65.557 | 34.499 | 41.884 | 1.00 | 24.73 | N |
| ATOM | 341 | N | GLN | A | 45 | 70.452 | 35.208 | 37.942 | 1.00 | 25.65 | N |
| ATOM | 342 | CA | GLN | A | 45 | 70.894 | 35.490 | 36.584 | 1.00 | 26.47 | C |
| ATOM | 343 | C | GLN | A | 45 | 69.584 | 35.679 | 35.834 | 1.00 | 25.54 | C |
| ATOM | 344 | O | GLN | A | 45 | 68.559 | 35.137 | 36.242 | 1.00 | 24.56 | O |
| ATOM | 345 | CB | GLN | A | 45 | 71.650 | 34.298 | 35.982 | 1.00 | 28.94 | C |
| ATOM | 346 | CG | GLN | A | 45 | 73.051 | 34.092 | 36.532 | 1.00 | 31.95 | C |
| ATOM | 347 | CD | GLN | A | 45 | 73.946 | 35.287 | 36.280 | 1.00 | 34.21 | C |
| ATOM | 348 | OE1 | GLN | A | 45 | 74.117 | 35.716 | 35.137 | 1.00 | 36.26 | O |
| ATOM | 349 | NE2 | GLN | A | 45 | 74.525 | 35.834 | 37.348 | 1.00 | 35.09 | N |
| ATOM | 350 | N | SER | A | 46 | 69.597 | 36.458 | 34.759 | 1.00 | 24.88 | N |
| ATOM | 351 | CA | SER | A | 46 | 68.379 | 36.643 | 33.986 | 1.00 | 24.59 | C |
| ATOM | 352 | C | SER | A | 46 | 68.038 | 35.329 | 33.287 | 1.00 | 25.11 | C |
| ATOM | 353 | O | SER | A | 46 | 68.937 | 34.576 | 32.907 | 1.00 | 24.15 | O |
| ATOM | 354 | CB | SER | A | 46 | 68.567 | 37.732 | 32.931 | 1.00 | 23.51 | C |
| ATOM | 355 | OG | SER | A | 46 | 67.375 | 37.895 | 32.188 | 1.00 | 22.66 | O |
| ATOM | 356 | N | GLU | A | 47 | 66.747 | 35.052 | 33.122 | 1.00 | 26.17 | N |
| ATOM | 357 | CA | GLU | A | 47 | 66.318 | 33.831 | 32.443 | 1.00 | 27.54 | C |
| ATOM | 358 | C | GLU | A | 47 | 66.708 | 33.896 | 30.970 | 1.00 | 27.30 | C |
| ATOM | 359 | O | GLU | A | 47 | 66.831 | 32.871 | 30.303 | 1.00 | 27.84 | O |
| ATOM | 360 | CB | GLU | A | 47 | 64.803 | 33.649 | 32.564 | 1.00 | 29.20 | C |
| ATOM | 361 | CG | GLU | A | 47 | 64.330 | 33.359 | 33.977 | 1.00 | 32.39 | C |
| ATOM | 362 | CD | GLU | A | 47 | 62.821 | 33.411 | 34.104 | 1.00 | 34.34 | C |
| ATOM | 363 | OE1 | GLU | A | 47 | 62.145 | 32.508 | 33.566 | 1.00 | 35.91 | O |
| ATOM | 364 | OE2 | GLU | A | 47 | 62.314 | 34.363 | 34.735 | 1.00 | 35.54 | O |
| ATOM | 365 | N | ILE | A | 48 | 66.890 | 35.109 | 30.458 | 1.00 | 26.04 | N |
| ATOM | 366 | CA | ILE | A | 48 | 67.284 | 35.284 | 29.063 | 1.00 | 25.89 | C |
| ATOM | 367 | C | ILE | A | 48 | 68.454 | 36.254 | 28.971 | 1.00 | 25.55 | C |
| ATOM | 368 | O | ILE | A | 48 | 68.353 | 37.409 | 29.387 | 1.00 | 25.22 | O |
| ATOM | 369 | CB | ILE | A | 48 | 66.133 | 35.844 | 28.193 | 1.00 | 26.14 | C |
| ATOM | 370 | CG1 | ILE | A | 48 | 64.913 | 34.921 | 28.255 | 1.00 | 27.04 | C |
| ATOM | 371 | CG2 | ILE | A | 48 | 66.604 | 35.977 | 26.747 | 1.00 | 25.69 | C |
| ATOM | 372 | CD1 | ILE | A | 48 | 63.686 | 35.502 | 27.561 | 1.00 | 28.89 | C |
| ATOM | 373 | N | ASN | A | 49 | 69.567 | 35.775 | 28.431 | 1.00 | 24.84 | N |
| ATOM | 374 | CA | ASN | A | 49 | 70.750 | 36.603 | 28.277 | 1.00 | 24.41 | C |
| ATOM | 375 | C | ASN | A | 49 | 71.148 | 36.668 | 26.813 | 1.00 | 24.16 | C |
| ATOM | 376 | O | ASN | A | 49 | 71.297 | 35.637 | 26.157 | 1.00 | 24.28 | O |
| ATOM | 377 | CB | ASN | A | 49 | 71.914 | 36.030 | 29.095 | 1.00 | 24.39 | C |
| ATOM | 378 | CG | ASN | A | 49 | 71.693 | 36.157 | 30.592 | 1.00 | 25.36 | C |
| ATOM | 379 | OD1 | ASN | A | 49 | 71.883 | 37.227 | 31.175 | 1.00 | 23.83 | O |
| ATOM | 380 | ND2 | ASN | A | 49 | 71.273 | 35.065 | 31.219 | 1.00 | 25.54 | N |
| ATOM | 381 | N | LEU | A | 50 | 71.298 | 37.879 | 26.292 | 1.00 | 23.32 | N |
| ATOM | 382 | CA | LEU | A | 50 | 71.724 | 38.045 | 24.909 | 1.00 | 23.00 | C |
| ATOM | 383 | C | LEU | A | 50 | 73.222 | 37.769 | 24.916 | 1.00 | 23.10 | C |
| ATOM | 384 | O | LEU | A | 50 | 73.873 | 37.953 | 25.945 | 1.00 | 22.63 | O |
| ATOM | 385 | CB | LEU | A | 50 | 71.492 | 39.484 | 24.442 | 1.00 | 22.34 | C |
| ATOM | 386 | CG | LEU | A | 50 | 70.087 | 40.075 | 24.569 | 1.00 | 22.93 | C |
| ATOM | 387 | CD1 | LEU | A | 50 | 70.100 | 41.515 | 24.045 | 1.00 | 23.23 | C |
| ATOM | 388 | CD2 | LEU | A | 50 | 69.093 | 39.221 | 23.787 | 1.00 | 23.68 | C |
| ATOM | 389 | N | LYS | A | 51 | 73.769 | 37.322 | 23.788 | 1.00 | 23.53 | N |
| ATOM | 390 | CA | LYS | A | 51 | 75.201 | 37.074 | 23.707 | 1.00 | 24.58 | C |
| ATOM | 391 | C | LYS | A | 51 | 75.900 | 38.353 | 23.240 | 1.00 | 24.53 | C |
| ATOM | 392 | O | LYS | A | 51 | 77.099 | 38.525 | 23.448 | 1.00 | 24.51 | O |
| ATOM | 393 | CB | LYS | A | 51 | 75.492 | 35.878 | 22.789 | 1.00 | 26.26 | C |
| ATOM | 394 | CG | LYS | A | 51 | 75.057 | 34.561 | 23.438 | 1.00 | 27.65 | C |
| ATOM | 395 | CD | LYS | A | 51 | 75.469 | 33.337 | 22.639 | 1.00 | 29.52 | C |
| ATOM | 396 | CE | LYS | A | 51 | 74.978 | 32.065 | 23.324 | 1.00 | 30.43 | C |
| ATOM | 397 | NZ | LYS | A | 51 | 75.354 | 30.839 | 22.555 | 1.00 | 32.78 | N |

TABLE 3-continued

| | | | | | | | | | | | |
|---|---|---|---|---|---|---|---|---|---|---|---|
| ATOM | 398 | N | ILE | A | 52 | 75.139 | 39.240 | 22.596 | 1.00 | 23.97 | N |
| ATOM | 399 | CA | ILE | A | 52 | 75.641 | 40.555 | 22.192 | 1.00 | 23.86 | C |
| ATOM | 400 | C | ILE | A | 52 | 74.496 | 41.505 | 22.570 | 1.00 | 23.49 | C |
| ATOM | 401 | O | ILE | A | 52 | 73.322 | 41.143 | 22.469 | 1.00 | 24.41 | O |
| ATOM | 402 | CB | ILE | A | 52 | 75.985 | 40.667 | 20.678 | 1.00 | 24.09 | C |
| ATOM | 403 | CG1 | ILE | A | 52 | 74.760 | 40.365 | 19.815 | 1.00 | 24.55 | C |
| ATOM | 404 | CG2 | ILE | A | 52 | 77.174 | 39.749 | 20.352 | 1.00 | 24.63 | C |
| ATOM | 405 | CD1 | ILE | A | 52 | 74.985 | 40.668 | 18.337 | 1.00 | 25.99 | C |
| ATOM | 406 | N | PRO | A | 53 | 74.821 | 42.722 | 23.019 | 1.00 | 22.93 | N |
| ATOM | 407 | CA | PRO | A | 53 | 73.827 | 43.720 | 23.437 | 1.00 | 22.98 | C |
| ATOM | 408 | C | PRO | A | 53 | 73.051 | 44.482 | 22.363 | 1.00 | 23.03 | C |
| ATOM | 409 | O | PRO | A | 53 | 72.673 | 45.631 | 22.586 | 1.00 | 23.64 | O |
| ATOM | 410 | CB | PRO | A | 53 | 74.654 | 44.657 | 24.305 | 1.00 | 22.57 | C |
| ATOM | 411 | CG | PRO | A | 53 | 75.944 | 44.714 | 23.542 | 1.00 | 23.54 | C |
| ATOM | 412 | CD | PRO | A | 53 | 76.190 | 43.246 | 23.194 | 1.00 | 23.09 | C |
| ATOM | 413 | N | LEU | A | 54 | 72.798 | 43.853 | 21.220 | 1.00 | 22.71 | N |
| ATOM | 414 | CA | LEU | A | 54 | 72.073 | 44.521 | 20.138 | 1.00 | 23.22 | C |
| ATOM | 415 | C | LEU | A | 54 | 70.760 | 43.834 | 19.777 | 1.00 | 22.95 | C |
| ATOM | 416 | O | LEU | A | 54 | 70.715 | 42.615 | 19.596 | 1.00 | 22.05 | O |
| ATOM | 417 | CB | LEU | A | 54 | 72.940 | 44.589 | 18.870 | 1.00 | 23.59 | C |
| ATOM | 418 | CG | LEU | A | 54 | 74.366 | 45.141 | 18.963 | 1.00 | 23.98 | C |
| ATOM | 419 | CD1 | LEU | A | 54 | 75.015 | 45.095 | 17.583 | 1.00 | 24.50 | C |
| ATOM | 420 | CD2 | LEU | A | 54 | 74.343 | 46.567 | 19.494 | 1.00 | 24.21 | C |
| ATOM | 421 | N | VAL | A | 55 | 69.695 | 44.625 | 19.675 | 1.00 | 22.53 | N |
| ATOM | 422 | CA | VAL | A | 55 | 68.392 | 44.104 | 19.284 | 1.00 | 22.49 | C |
| ATOM | 423 | C | VAL | A | 55 | 67.871 | 45.017 | 18.170 | 1.00 | 22.61 | C |
| ATOM | 424 | O | VAL | A | 55 | 68.116 | 46.229 | 18.183 | 1.00 | 22.47 | O |
| ATOM | 425 | CB | VAL | A | 55 | 67.387 | 44.060 | 20.475 | 1.00 | 22.79 | C |
| ATOM | 426 | CG1 | VAL | A | 55 | 68.032 | 43.361 | 21.673 | 1.00 | 22.48 | C |
| ATOM | 427 | CG2 | VAL | A | 55 | 66.924 | 45.452 | 20.845 | 1.00 | 22.85 | C |
| ATOM | 428 | N | SER | A | 56 | 67.180 | 44.438 | 17.193 | 1.00 | 22.42 | N |
| ATOM | 429 | CA | SER | A | 56 | 66.665 | 45.232 | 16.080 | 1.00 | 22.42 | C |
| ATOM | 430 | C | SER | A | 56 | 65.300 | 45.823 | 16.410 | 1.00 | 22.63 | C |
| ATOM | 431 | O | SER | A | 56 | 64.485 | 45.200 | 17.094 | 1.00 | 23.01 | O |
| ATOM | 432 | CB | SER | A | 56 | 66.611 | 44.389 | 14.794 | 1.00 | 22.36 | C |
| ATOM | 433 | OG | SER | A | 56 | 65.832 | 43.220 | 14.959 | 1.00 | 23.60 | O |
| ATOM | 434 | N | ALA | A | 57 | 65.076 | 47.039 | 15.921 | 1.00 | 22.62 | N |
| ATOM | 435 | CA | ALA | A | 57 | 63.853 | 47.799 | 16.163 | 1.00 | 22.97 | C |
| ATOM | 436 | C | ALA | A | 57 | 62.557 | 47.117 | 15.730 | 1.00 | 23.76 | C |
| ATOM | 437 | O | ALA | A | 57 | 62.533 | 46.338 | 14.781 | 1.00 | 24.23 | O |
| ATOM | 438 | CB | ALA | A | 57 | 63.971 | 49.174 | 15.496 | 1.00 | 21.89 | C |
| ATOM | 439 | N | ILE | A | 58 | 61.480 | 47.430 | 16.444 | 1.00 | 24.06 | N |
| ATOM | 440 | CA | ILE | A | 58 | 60.161 | 46.860 | 16.174 | 1.00 | 24.95 | C |
| ATOM | 441 | C | ILE | A | 58 | 59.552 | 47.647 | 15.016 | 1.00 | 25.14 | C |
| ATOM | 442 | O | ILE | A | 58 | 58.567 | 48.369 | 15.189 | 1.00 | 25.13 | O |
| ATOM | 443 | CB | ILE | A | 58 | 59.259 | 46.984 | 17.427 | 1.00 | 25.04 | C |
| ATOM | 444 | CG1 | ILE | A | 58 | 60.035 | 46.504 | 18.661 | 1.00 | 25.04 | C |
| ATOM | 445 | CG2 | ILE | A | 58 | 57.992 | 46.149 | 17.260 | 1.00 | 25.28 | C |
| ATOM | 446 | CD1 | ILE | A | 58 | 59.239 | 46.529 | 19.950 | 1.00 | 24.84 | C |
| ATOM | 447 | N | MET | A | 59 | 60.143 | 47.483 | 13.834 | 1.00 | 25.33 | N |
| ATOM | 448 | CA | MET | A | 59 | 59.716 | 48.220 | 12.647 | 1.00 | 25.63 | C |
| ATOM | 449 | C | MET | A | 59 | 59.521 | 47.358 | 11.398 | 1.00 | 25.77 | C |
| ATOM | 450 | O | MET | A | 59 | 60.257 | 46.397 | 11.171 | 1.00 | 25.17 | O |
| ATOM | 451 | CB | MET | A | 59 | 60.750 | 49.310 | 12.354 | 1.00 | 25.44 | C |
| ATOM | 452 | CG | MET | A | 59 | 61.021 | 50.234 | 13.540 | 1.00 | 24.70 | C |
| ATOM | 453 | SD | MET | A | 59 | 62.394 | 51.382 | 13.288 | 1.00 | 24.28 | S |
| ATOM | 454 | CE | MET | A | 59 | 61.721 | 52.448 | 11.981 | 1.00 | 24.30 | C |
| ATOM | 455 | N | GLN | A | 60 | 58.533 | 47.724 | 10.585 | 1.00 | 26.54 | N |
| ATOM | 456 | CA | GLN | A | 60 | 58.234 | 47.005 | 9.345 | 1.00 | 27.32 | C |
| ATOM | 457 | C | GLN | A | 60 | 59.464 | 46.961 | 8.443 | 1.00 | 27.38 | C |
| ATOM | 458 | O | GLN | A | 60 | 59.719 | 45.963 | 7.771 | 1.00 | 27.43 | O |
| ATOM | 459 | CB | GLN | A | 60 | 57.109 | 47.701 | 8.564 | 1.00 | 27.95 | C |
| ATOM | 460 | CG | GLN | A | 60 | 55.838 | 47.994 | 9.337 | 1.00 | 29.68 | C |
| ATOM | 461 | CD | GLN | A | 60 | 54.802 | 48.717 | 8.482 | 1.00 | 31.25 | C |
| ATOM | 462 | OE1 | GLN | A | 60 | 55.149 | 49.525 | 7.616 | 1.00 | 31.26 | O |
| ATOM | 463 | NE2 | GLN | A | 60 | 53.526 | 48.442 | 8.735 | 1.00 | 31.01 | N |
| ATOM | 464 | N | SER | A | 61 | 60.220 | 48.053 | 8.427 | 1.00 | 27.19 | N |
| ATOM | 465 | CA | SER | A | 61 | 61.398 | 48.145 | 7.573 | 1.00 | 27.60 | C |
| ATOM | 466 | C | SER | A | 61 | 62.682 | 47.598 | 8.193 | 1.00 | 27.60 | C |
| ATOM | 467 | O | SER | A | 61 | 63.773 | 47.818 | 7.662 | 1.00 | 28.23 | O |
| ATOM | 468 | CB | SER | A | 61 | 61.620 | 49.602 | 7.152 | 1.00 | 27.83 | C |
| ATOM | 469 | OG | SER | A | 61 | 61.955 | 50.422 | 8.261 | 1.00 | 29.04 | O |
| ATOM | 470 | N | VAL | A | 62 | 62.560 | 46.867 | 9.296 | 1.00 | 26.86 | N |
| ATOM | 471 | CA | VAL | A | 62 | 63.745 | 46.337 | 9.957 | 1.00 | 26.42 | C |
| ATOM | 472 | C | VAL | A | 62 | 63.665 | 44.883 | 10.402 | 1.00 | 26.63 | C |
| ATOM | 473 | O | VAL | A | 62 | 64.432 | 44.045 | 9.938 | 1.00 | 27.23 | O |
| ATOM | 474 | CB | VAL | A | 62 | 64.098 | 47.181 | 11.210 | 1.00 | 26.30 | C |
| ATOM | 475 | CG1 | VAL | A | 62 | 65.342 | 46.618 | 11.893 | 1.00 | 25.75 | C |
| ATOM | 476 | CG2 | VAL | A | 62 | 64.310 | 48.631 | 10.820 | 1.00 | 25.78 | C |

TABLE 3-continued

| | | | | | | | | | | | |
|---|---|---|---|---|---|---|---|---|---|---|---|
| ATOM | 477 | N | SER | A | 63 | 62.725 | 44.585 | 11.291 | 1.00 | 26.87 | N |
| ATOM | 478 | CA | SER | A | 63 | 62.621 | 43.248 | 11.849 | 1.00 | 26.97 | C |
| ATOM | 479 | C | SER | A | 63 | 61.630 | 42.252 | 11.253 | 1.00 | 27.37 | C |
| ATOM | 480 | O | SER | A | 63 | 60.534 | 42.048 | 11.778 | 1.00 | 26.24 | O |
| ATOM | 481 | CB | SER | A | 63 | 62.394 | 43.364 | 13.359 | 1.00 | 27.27 | C |
| ATOM | 482 | OG | SER | A | 63 | 63.447 | 44.106 | 13.965 | 1.00 | 27.97 | O |
| ATOM | 483 | N | GLY | A | 64 | 62.049 | 41.627 | 10.158 | 1.00 | 27.73 | N |
| ATOM | 484 | CA | GLY | A | 64 | 61.248 | 40.610 | 9.507 | 1.00 | 28.60 | C |
| ATOM | 485 | C | GLY | A | 64 | 61.899 | 39.284 | 9.859 | 1.00 | 29.32 | C |
| ATOM | 486 | O | GLY | A | 64 | 62.870 | 39.257 | 10.623 | 1.00 | 28.30 | O |
| ATOM | 487 | N | GLU | A | 65 | 61.387 | 38.190 | 9.304 | 1.00 | 29.97 | N |
| ATOM | 488 | CA | GLU | A | 65 | 61.912 | 36.855 | 9.584 | 1.00 | 31.24 | C |
| ATOM | 489 | C | GLU | A | 65 | 63.413 | 36.688 | 9.339 | 1.00 | 30.93 | C |
| ATOM | 490 | O | GLU | A | 65 | 64.131 | 36.167 | 10.188 | 1.00 | 30.06 | O |
| ATOM | 491 | CB | GLU | A | 65 | 61.147 | 35.811 | 8.760 | 1.00 | 33.66 | C |
| ATOM | 492 | CG | GLU | A | 65 | 60.983 | 36.196 | 7.292 | 1.00 | 37.41 | C |
| ATOM | 493 | CD | GLU | A | 65 | 59.788 | 37.106 | 7.051 | 1.00 | 39.43 | C |
| ATOM | 494 | OE1 | GLU | A | 65 | 58.650 | 36.587 | 7.069 | 1.00 | 41.83 | O |
| ATOM | 495 | OE2 | GLU | A | 65 | 59.978 | 38.331 | 6.846 | 1.00 | 40.38 | O |
| ATOM | 496 | N | LYS | A | 66 | 63.884 | 37.123 | 8.176 | 1.00 | 30.29 | N |
| ATOM | 497 | CA | LYS | A | 66 | 65.295 | 36.996 | 7.837 | 1.00 | 30.29 | C |
| ATOM | 498 | C | LYS | A | 66 | 66.221 | 37.768 | 8.781 | 1.00 | 29.26 | C |
| ATOM | 499 | O | LYS | A | 66 | 67.294 | 37.284 | 9.140 | 1.00 | 28.41 | O |
| ATOM | 500 | CB | LYS | A | 66 | 65.528 | 37.423 | 6.380 | 1.00 | 31.58 | C |
| ATOM | 501 | CG | LYS | A | 66 | 64.731 | 38.637 | 5.917 | 1.00 | 33.89 | C |
| ATOM | 502 | CD | LYS | A | 66 | 63.214 | 38.395 | 5.941 | 1.00 | 34.74 | C |
| ATOM | 503 | CE | LYS | A | 66 | 62.489 | 39.441 | 5.136 | 1.00 | 35.36 | C |
| ATOM | 504 | NZ | LYS | A | 66 | 62.985 | 39.417 | 3.718 | 1.00 | 34.63 | N |
| ATOM | 505 | N | MET | A | 67 | 65.807 | 38.962 | 9.185 | 1.00 | 28.14 | N |
| ATOM | 506 | CA | MET | A | 67 | 66.606 | 39.765 | 10.104 | 1.00 | 26.95 | C |
| ATOM | 507 | C | MET | A | 67 | 66.722 | 39.019 | 11.433 | 1.00 | 26.58 | C |
| ATOM | 508 | O | MET | A | 67 | 67.812 | 38.889 | 11.997 | 1.00 | 25.12 | O |
| ATOM | 509 | CB | MET | A | 67 | 65.939 | 41.125 | 10.327 | 1.00 | 27.01 | C |
| ATOM | 510 | CG | MET | A | 67 | 66.628 | 42.020 | 11.347 | 1.00 | 25.99 | C |
| ATOM | 511 | SD | MET | A | 67 | 68.293 | 42.472 | 10.859 | 1.00 | 26.26 | S |
| ATOM | 512 | CE | MET | A | 67 | 67.950 | 43.550 | 9.432 | 1.00 | 25.77 | C |
| ATOM | 513 | N | ALA | A | 68 | 65.587 | 38.513 | 11.910 | 1.00 | 26.72 | N |
| ATOM | 514 | CA | ALA | A | 68 | 65.524 | 37.791 | 13.174 | 1.00 | 26.82 | C |
| ATOM | 515 | C | ALA | A | 68 | 66.457 | 36.590 | 13.203 | 1.00 | 27.20 | C |
| ATOM | 516 | O | ALA | A | 68 | 67.092 | 36.315 | 14.217 | 1.00 | 27.21 | O |
| ATOM | 517 | CB | ALA | A | 68 | 64.092 | 37.350 | 13.452 | 1.00 | 26.91 | C |
| ATOM | 518 | N | ILE | A | 69 | 66.532 | 35.867 | 12.092 | 1.00 | 27.20 | N |
| ATOM | 519 | CA | ILE | A | 69 | 67.403 | 34.702 | 12.011 | 1.00 | 27.15 | C |
| ATOM | 520 | C | ILE | A | 69 | 68.870 | 35.125 | 11.980 | 1.00 | 26.50 | C |
| ATOM | 521 | O | ILE | A | 69 | 69.700 | 34.568 | 12.695 | 1.00 | 27.23 | O |
| ATOM | 522 | CB | ILE | A | 69 | 67.089 | 33.867 | 10.747 | 1.00 | 27.71 | C |
| ATOM | 523 | CG1 | ILE | A | 69 | 65.692 | 33.250 | 10.870 | 1.00 | 28.00 | C |
| ATOM | 524 | CG2 | ILE | A | 69 | 68.144 | 32.787 | 10.558 | 1.00 | 27.79 | C |
| ATOM | 525 | CD1 | ILE | A | 69 | 65.121 | 32.737 | 9.547 | 1.00 | 29.43 | C |
| ATOM | 526 | N | ALA | A | 70 | 69.184 | 36.116 | 11.154 | 1.00 | 25.73 | N |
| ATOM | 527 | CA | ALA | A | 70 | 70.556 | 36.592 | 11.029 | 1.00 | 25.41 | C |
| ATOM | 528 | C | ALA | A | 70 | 71.109 | 37.181 | 12.325 | 1.00 | 25.00 | C |
| ATOM | 529 | O | ALA | A | 70 | 72.260 | 36.936 | 12.683 | 1.00 | 24.51 | O |
| ATOM | 530 | CB | ALA | A | 70 | 70.645 | 37.627 | 9.914 | 1.00 | 25.47 | C |
| ATOM | 531 | N | LEU | A | 71 | 70.292 | 37.961 | 13.025 | 1.00 | 24.62 | N |
| ATOM | 532 | CA | LEU | A | 71 | 70.736 | 38.580 | 14.266 | 1.00 | 24.36 | C |
| ATOM | 533 | C | LEU | A | 71 | 70.878 | 37.541 | 15.372 | 1.00 | 24.81 | C |
| ATOM | 534 | O | LEU | A | 71 | 71.850 | 37.562 | 16.121 | 1.00 | 25.09 | O |
| ATOM | 535 | CB | LEU | A | 71 | 69.759 | 39.680 | 14.690 | 1.00 | 23.62 | C |
| ATOM | 536 | CG | LEU | A | 71 | 70.116 | 40.466 | 15.960 | 1.00 | 23.09 | C |
| ATOM | 537 | CD1 | LEU | A | 71 | 71.583 | 40.872 | 15.932 | 1.00 | 22.51 | C |
| ATOM | 538 | CD2 | LEU | A | 71 | 69.220 | 41.701 | 16.053 | 1.00 | 22.83 | C |
| ATOM | 539 | N | ALA | A | 72 | 69.916 | 36.629 | 15.471 | 1.00 | 25.59 | N |
| ATOM | 540 | CA | ALA | A | 72 | 69.982 | 35.583 | 16.490 | 1.00 | 26.49 | C |
| ATOM | 541 | C | ALA | A | 72 | 71.246 | 34.742 | 16.284 | 1.00 | 27.18 | C |
| ATOM | 542 | O | ALA | A | 72 | 71.868 | 34.287 | 17.249 | 1.00 | 26.99 | O |
| ATOM | 543 | CB | ALA | A | 72 | 68.739 | 34.699 | 16.421 | 1.00 | 26.25 | C |
| ATOM | 544 | N | ARG | A | 73 | 71.624 | 34.540 | 15.025 | 1.00 | 27.93 | N |
| ATOM | 545 | CA | ARG | A | 73 | 72.822 | 33.765 | 14.707 | 1.00 | 28.79 | C |
| ATOM | 546 | C | ARG | A | 73 | 74.084 | 34.417 | 15.267 | 1.00 | 28.77 | C |
| ATOM | 547 | O | ARG | A | 73 | 75.058 | 33.729 | 15.573 | 1.00 | 28.68 | O |
| ATOM | 548 | CB | ARG | A | 73 | 72.965 | 33.596 | 13.191 | 1.00 | 30.52 | C |
| ATOM | 549 | CG | ARG | A | 73 | 72.054 | 32.535 | 12.601 | 1.00 | 31.89 | C |
| ATOM | 550 | CD | ARG | A | 73 | 72.198 | 32.469 | 11.089 | 1.00 | 33.48 | C |
| ATOM | 551 | NE | ARG | A | 73 | 71.517 | 31.303 | 10.534 | 1.00 | 35.10 | N |
| ATOM | 552 | CZ | ARG | A | 73 | 71.257 | 31.135 | 9.241 | 1.00 | 36.83 | C |
| ATOM | 553 | NH1 | ARG | A | 73 | 71.618 | 32.061 | 8.360 | 1.00 | 37.07 | N |
| ATOM | 554 | NH2 | ARG | A | 73 | 70.642 | 30.034 | 8.825 | 1.00 | 37.30 | N |
| ATOM | 555 | N | GLU | A | 74 | 74.064 | 35.741 | 15.401 | 1.00 | 28.39 | N |

TABLE 3-continued

| ATOM | 556 | CA | GLU | A | 74 | 75.210 | 36.470 | 15.933 | 1.00 | 28.09 | C |
|---|---|---|---|---|---|---|---|---|---|---|---|
| ATOM | 557 | C | GLU | A | 74 | 75.100 | 36.720 | 17.444 | 1.00 | 27.22 | C |
| ATOM | 558 | O | GLU | A | 74 | 75.977 | 37.342 | 18.034 | 1.00 | 27.15 | O |
| ATOM | 559 | CB | GLU | A | 74 | 75.378 | 37.804 | 15.195 | 1.00 | 30.01 | C |
| ATOM | 560 | CG | GLU | A | 74 | 75.546 | 37.668 | 13.679 | 1.00 | 32.33 | C |
| ATOM | 561 | CD | GLU | A | 74 | 76.686 | 36.741 | 13.283 | 1.00 | 33.71 | C |
| ATOM | 562 | OE1 | GLU | A | 74 | 77.836 | 36.984 | 13.704 | 1.00 | 36.00 | O |
| ATOM | 563 | OE2 | GLU | A | 74 | 76.431 | 35.768 | 12.543 | 1.00 | 35.10 | O |
| ATOM | 564 | N | GLY | A | 75 | 74.021 | 36.251 | 18.066 | 1.00 | 26.36 | N |
| ATOM | 565 | CA | GLY | A | 75 | 73.872 | 36.427 | 19.504 | 1.00 | 25.20 | C |
| ATOM | 566 | C | GLY | A | 75 | 72.872 | 37.461 | 19.993 | 1.00 | 24.86 | C |
| ATOM | 567 | O | GLY | A | 75 | 72.677 | 37.607 | 21.200 | 1.00 | 24.26 | O |
| ATOM | 568 | N | GLY | A | 76 | 72.238 | 38.179 | 19.070 | 1.00 | 24.23 | N |
| ATOM | 569 | CA | GLY | A | 76 | 71.266 | 39.186 | 19.464 | 1.00 | 24.11 | C |
| ATOM | 570 | C | GLY | A | 76 | 69.848 | 38.706 | 19.237 | 1.00 | 23.43 | C |
| ATOM | 571 | O | GLY | A | 76 | 69.627 | 37.531 | 18.963 | 1.00 | 23.27 | O |
| ATOM | 572 | N | ILE | A | 77 | 68.876 | 39.604 | 19.346 | 1.00 | 23.31 | N |
| ATOM | 573 | CA | ILE | A | 77 | 67.494 | 39.205 | 19.127 | 1.00 | 22.63 | C |
| ATOM | 574 | C | ILE | A | 77 | 66.718 | 40.293 | 18.391 | 1.00 | 23.12 | C |
| ATOM | 575 | O | ILE | A | 77 | 66.984 | 41.487 | 18.563 | 1.00 | 22.23 | O |
| ATOM | 576 | CB | ILE | A | 77 | 66.797 | 38.873 | 20.470 | 1.00 | 22.89 | C |
| ATOM | 577 | CG1 | ILE | A | 77 | 65.535 | 38.044 | 20.212 | 1.00 | 22.47 | C |
| ATOM | 578 | CG2 | ILE | A | 77 | 66.465 | 40.163 | 21.230 | 1.00 | 22.43 | C |
| ATOM | 579 | CD1 | ILE | A | 77 | 64.847 | 37.547 | 21.474 | 1.00 | 21.82 | C |
| ATOM | 580 | N | SER | A | 78 | 65.771 | 39.873 | 17.556 | 1.00 | 23.10 | N |
| ATOM | 581 | CA | SER | A | 78 | 64.942 | 40.813 | 16.809 | 1.00 | 23.37 | C |
| ATOM | 582 | C | SER | A | 78 | 63.526 | 40.796 | 17.362 | 1.00 | 23.52 | C |
| ATOM | 583 | O | SER | A | 78 | 63.044 | 39.762 | 17.820 | 1.00 | 24.10 | O |
| ATOM | 584 | CB | SER | A | 78 | 64.877 | 40.434 | 15.321 | 1.00 | 23.20 | C |
| ATOM | 585 | OG | SER | A | 78 | 66.125 | 40.583 | 14.671 | 1.00 | 24.07 | O |
| ATOM | 586 | N | PHE | A | 79 | 62.863 | 41.944 | 17.328 | 1.00 | 23.99 | N |
| ATOM | 587 | CA | PHE | A | 79 | 61.483 | 42.020 | 17.777 | 1.00 | 24.76 | C |
| ATOM | 588 | C | PHE | A | 79 | 60.617 | 42.208 | 16.534 | 1.00 | 24.96 | C |
| ATOM | 589 | O | PHE | A | 79 | 60.474 | 43.321 | 16.031 | 1.00 | 24.87 | O |
| ATOM | 590 | CB | PHE | A | 79 | 61.284 | 43.183 | 18.760 | 1.00 | 24.45 | C |
| ATOM | 591 | CG | PHE | A | 79 | 61.820 | 42.905 | 20.137 | 1.00 | 24.94 | C |
| ATOM | 592 | CD1 | PHE | A | 79 | 63.161 | 43.126 | 20.438 | 1.00 | 25.40 | C |
| ATOM | 593 | CD2 | PHE | A | 79 | 60.993 | 42.367 | 21.121 | 1.00 | 25.21 | C |
| ATOM | 594 | CE1 | PHE | A | 79 | 63.674 | 42.812 | 21.699 | 1.00 | 25.47 | C |
| ATOM | 595 | CE2 | PHE | A | 79 | 61.496 | 42.050 | 22.382 | 1.00 | 25.32 | C |
| ATOM | 596 | CZ | PHE | A | 79 | 62.839 | 42.272 | 22.670 | 1.00 | 24.97 | C |
| ATOM | 597 | N | ILE | A | 80 | 60.060 | 41.108 | 16.033 | 1.00 | 25.49 | N |
| ATOM | 598 | CA | ILE | A | 80 | 59.212 | 41.134 | 14.837 | 1.00 | 25.86 | C |
| ATOM | 599 | C | ILE | A | 80 | 58.160 | 42.236 | 14.964 | 1.00 | 25.66 | C |
| ATOM | 600 | O | ILE | A | 80 | 57.435 | 42.294 | 15.961 | 1.00 | 24.99 | O |
| ATOM | 601 | CB | ILE | A | 80 | 58.496 | 39.775 | 14.634 | 1.00 | 26.44 | C |
| ATOM | 602 | CG1 | ILE | A | 80 | 59.527 | 38.640 | 14.575 | 1.00 | 26.91 | C |
| ATOM | 603 | CG2 | ILE | A | 80 | 57.658 | 39.810 | 13.353 | 1.00 | 26.85 | C |
| ATOM | 604 | CD1 | ILE | A | 80 | 60.497 | 38.729 | 13.410 | 1.00 | 27.62 | C |
| ATOM | 605 | N | PHE | A | 81 | 58.064 | 43.101 | 13.955 | 1.00 | 25.74 | N |
| ATOM | 606 | CA | PHE | A | 81 | 57.107 | 44.202 | 14.020 | 1.00 | 26.34 | C |
| ATOM | 607 | C | PHE | A | 81 | 55.665 | 43.759 | 14.221 | 1.00 | 26.79 | C |
| ATOM | 608 | O | PHE | A | 81 | 55.234 | 42.737 | 13.688 | 1.00 | 26.54 | O |
| ATOM | 609 | CB | PHE | A | 81 | 57.221 | 45.123 | 12.787 | 1.00 | 27.27 | C |
| ATOM | 610 | CG | PHE | A | 81 | 56.931 | 44.453 | 11.470 | 1.00 | 27.76 | C |
| ATOM | 611 | CD1 | PHE | A | 81 | 57.864 | 43.610 | 10.877 | 1.00 | 27.97 | C |
| ATOM | 612 | CD2 | PHE | A | 81 | 55.733 | 44.706 | 10.801 | 1.00 | 28.39 | C |
| ATOM | 613 | CE1 | PHE | A | 81 | 57.614 | 43.027 | 9.631 | 1.00 | 28.62 | C |
| ATOM | 614 | CE2 | PHE | A | 81 | 55.471 | 44.129 | 9.553 | 1.00 | 28.30 | C |
| ATOM | 615 | CZ | PHE | A | 81 | 56.414 | 43.290 | 8.969 | 1.00 | 28.84 | C |
| ATOM | 616 | N | GLY | A | 82 | 54.930 | 44.540 | 15.009 | 1.00 | 27.50 | N |
| ATOM | 617 | CA | GLY | A | 82 | 53.543 | 44.230 | 15.303 | 1.00 | 28.54 | C |
| ATOM | 618 | C | GLY | A | 82 | 52.553 | 45.047 | 14.496 | 1.00 | 29.14 | C |
| ATOM | 619 | O | GLY | A | 82 | 51.342 | 44.898 | 14.661 | 1.00 | 28.33 | O |
| ATOM | 620 | N | SER | A | 83 | 53.068 | 45.914 | 13.629 | 1.00 | 29.58 | N |
| ATOM | 621 | CA | SER | A | 83 | 52.222 | 46.746 | 12.780 | 1.00 | 30.10 | C |
| ATOM | 622 | C | SER | A | 83 | 51.858 | 45.966 | 11.515 | 1.00 | 30.82 | C |
| ATOM | 623 | O | SER | A | 83 | 52.172 | 46.368 | 10.393 | 1.00 | 30.41 | O |
| ATOM | 624 | CB | SER | A | 83 | 52.947 | 48.046 | 12.423 | 1.00 | 29.96 | C |
| ATOM | 625 | OG | SER | A | 83 | 54.228 | 47.778 | 11.889 | 1.00 | 29.80 | O |
| ATOM | 626 | N | GLN | A | 84 | 51.202 | 44.832 | 11.732 | 1.00 | 31.40 | N |
| ATOM | 627 | CA | GLN | A | 84 | 50.752 | 43.941 | 10.674 | 1.00 | 31.71 | C |
| ATOM | 628 | C | GLN | A | 84 | 49.694 | 43.059 | 11.328 | 1.00 | 32.16 | C |
| ATOM | 629 | O | GLN | A | 84 | 49.489 | 43.140 | 12.543 | 1.00 | 32.26 | O |
| ATOM | 630 | CB | GLN | A | 84 | 51.915 | 43.093 | 10.147 | 1.00 | 31.73 | C |
| ATOM | 631 | CG | GLN | A | 84 | 52.525 | 42.130 | 11.165 | 1.00 | 31.03 | C |
| ATOM | 632 | CD | GLN | A | 84 | 53.658 | 41.307 | 10.579 | 1.00 | 31.51 | C |
| ATOM | 633 | OE1 | GLN | A | 84 | 53.500 | 40.679 | 9.532 | 1.00 | 31.44 | O |
| ATOM | 634 | NE2 | GLN | A | 84 | 54.809 | 41.299 | 11.255 | 1.00 | 30.10 | N |

TABLE 3-continued

| | | | | | | | | | | | |
|---|---|---|---|---|---|---|---|---|---|---|---|
| ATOM | 635 | N | SER | A | 85 | 49.021 | 42.221 | 10.547 | 1.00 | 32.25 | N |
| ATOM | 636 | CA | SER | A | 85 | 47.986 | 41.365 | 11.115 | 1.00 | 32.76 | C |
| ATOM | 637 | C | SER | A | 85 | 48.568 | 40.370 | 12.113 | 1.00 | 33.10 | C |
| ATOM | 638 | O | SER | A | 85 | 49.736 | 39.988 | 12.020 | 1.00 | 33.02 | O |
| ATOM | 639 | CB | SER | A | 85 | 47.243 | 40.604 | 10.010 | 1.00 | 32.36 | C |
| ATOM | 640 | OG | SER | A | 85 | 48.034 | 39.553 | 9.489 | 1.00 | 32.58 | O |
| ATOM | 641 | N | ILE | A | 86 | 47.741 | 39.965 | 13.072 | 1.00 | 33.27 | N |
| ATOM | 642 | CA | ILE | A | 86 | 48.138 | 39.005 | 14.092 | 1.00 | 33.73 | C |
| ATOM | 643 | C | ILE | A | 86 | 48.637 | 37.732 | 13.412 | 1.00 | 34.65 | C |
| ATOM | 644 | O | ILE | A | 86 | 49.670 | 37.167 | 13.785 | 1.00 | 34.09 | O |
| ATOM | 645 | CB | ILE | A | 86 | 46.935 | 38.662 | 15.008 | 1.00 | 33.67 | C |
| ATOM | 646 | CG1 | ILE | A | 86 | 46.553 | 39.889 | 15.842 | 1.00 | 33.78 | C |
| ATOM | 647 | CG2 | ILE | A | 86 | 47.267 | 37.479 | 15.898 | 1.00 | 33.45 | C |
| ATOM | 648 | CD1 | ILE | A | 86 | 45.321 | 39.696 | 16.704 | 1.00 | 34.30 | C |
| ATOM | 649 | N | GLU | A | 87 | 47.896 | 37.297 | 12.397 | 1.00 | 34.81 | N |
| ATOM | 650 | CA | GLU | A | 87 | 48.235 | 36.093 | 11.650 | 1.00 | 35.57 | C |
| ATOM | 651 | C | GLU | A | 87 | 49.582 | 36.220 | 10.946 | 1.00 | 34.64 | C |
| ATOM | 652 | O | GLU | A | 87 | 50.399 | 35.301 | 10.975 | 1.00 | 34.19 | O |
| ATOM | 653 | CB | GLU | A | 87 | 47.143 | 35.800 | 10.617 | 1.00 | 37.45 | C |
| ATOM | 654 | CG | GLU | A | 87 | 45.768 | 35.485 | 11.210 | 1.00 | 40.12 | C |
| ATOM | 655 | CD | GLU | A | 87 | 45.205 | 36.609 | 12.076 | 1.00 | 42.17 | C |
| ATOM | 656 | OE1 | GLU | A | 87 | 45.205 | 37.779 | 11.629 | 1.00 | 42.59 | O |
| ATOM | 657 | OE2 | GLU | A | 87 | 44.751 | 36.316 | 13.206 | 1.00 | 43.96 | O |
| ATOM | 658 | N | SER | A | 88 | 49.806 | 37.365 | 10.313 | 1.00 | 34.00 | N |
| ATOM | 659 | CA | SER | A | 88 | 51.045 | 37.619 | 9.592 | 1.00 | 34.14 | C |
| ATOM | 660 | C | SER | A | 88 | 52.264 | 37.630 | 10.523 | 1.00 | 33.33 | C |
| ATOM | 661 | O | SER | A | 88 | 53.291 | 37.015 | 10.225 | 1.00 | 33.84 | O |
| ATOM | 662 | CB | SER | A | 88 | 50.941 | 38.955 | 8.850 | 1.00 | 34.56 | C |
| ATOM | 663 | OG | SER | A | 88 | 52.106 | 39.207 | 8.086 | 1.00 | 37.63 | O |
| ATOM | 664 | N | GLN | A | 89 | 52.148 | 38.329 | 11.647 | 1.00 | 32.36 | N |
| ATOM | 665 | CA | GLN | A | 89 | 53.247 | 38.416 | 12.609 | 1.00 | 31.38 | C |
| ATOM | 666 | C | GLN | A | 89 | 53.538 | 37.064 | 13.255 | 1.00 | 31.34 | C |
| ATOM | 667 | O | GLN | A | 89 | 54.697 | 36.688 | 13.433 | 1.00 | 30.83 | O |
| ATOM | 668 | CB | GLN | A | 89 | 52.923 | 39.448 | 13.696 | 1.00 | 30.40 | C |
| ATOM | 669 | CG | GLN | A | 89 | 53.986 | 39.546 | 14.786 | 1.00 | 29.25 | C |
| ATOM | 670 | CD | GLN | A | 89 | 53.629 | 40.544 | 15.877 | 1.00 | 28.00 | C |
| ATOM | 671 | OE1 | GLN | A | 89 | 52.470 | 40.658 | 16.275 | 1.00 | 26.78 | O |
| ATOM | 672 | NE2 | GLN | A | 89 | 54.632 | 41.258 | 16.378 | 1.00 | 26.79 | N |
| ATOM | 673 | N | ALA | A | 90 | 52.486 | 36.333 | 13.608 | 1.00 | 31.60 | N |
| ATOM | 674 | CA | ALA | A | 90 | 52.654 | 35.022 | 14.225 | 1.00 | 31.80 | C |
| ATOM | 675 | C | ALA | A | 90 | 53.379 | 34.079 | 13.265 | 1.00 | 32.05 | C |
| ATOM | 676 | O | ALA | A | 90 | 54.178 | 33.245 | 13.686 | 1.00 | 32.08 | O |
| ATOM | 677 | CB | ALA | A | 90 | 51.297 | 34.447 | 14.613 | 1.00 | 31.91 | C |
| ATOM | 678 | N | ALA | A | 91 | 53.105 | 34.224 | 11.971 | 1.00 | 32.10 | N |
| ATOM | 679 | CA | ALA | A | 91 | 53.738 | 33.386 | 10.958 | 1.00 | 32.03 | C |
| ATOM | 680 | C | ALA | A | 91 | 55.248 | 33.614 | 10.934 | 1.00 | 32.05 | C |
| ATOM | 681 | O | ALA | A | 91 | 56.026 | 32.666 | 10.818 | 1.00 | 31.83 | O |
| ATOM | 682 | CB | ALA | A | 91 | 53.137 | 33.678 | 9.578 | 1.00 | 32.23 | C |
| ATOM | 683 | N | MET | A | 92 | 55.664 | 34.873 | 11.038 | 1.00 | 31.86 | N |
| ATOM | 684 | CA | MET | A | 92 | 57.090 | 35.190 | 11.037 | 1.00 | 31.76 | C |
| ATOM | 685 | C | MET | A | 92 | 57.762 | 34.598 | 12.270 | 1.00 | 31.37 | C |
| ATOM | 686 | O | MET | A | 92 | 58.860 | 34.053 | 12.185 | 1.00 | 31.68 | O |
| ATOM | 687 | CB | MET | A | 92 | 57.311 | 36.702 | 11.024 | 1.00 | 31.76 | C |
| ATOM | 688 | CG | MET | A | 92 | 56.857 | 37.392 | 9.759 | 1.00 | 32.23 | C |
| ATOM | 689 | SD | MET | A | 92 | 57.284 | 39.134 | 9.784 | 1.00 | 32.24 | S |
| ATOM | 690 | CE | MET | A | 92 | 56.701 | 39.656 | 8.159 | 1.00 | 32.37 | C |
| ATOM | 691 | N | VAL | A | 93 | 57.100 | 34.718 | 13.418 | 1.00 | 31.37 | N |
| ATOM | 692 | CA | VAL | A | 93 | 57.639 | 34.185 | 14.667 | 1.00 | 30.84 | C |
| ATOM | 693 | C | VAL | A | 93 | 57.828 | 32.678 | 14.526 | 1.00 | 31.49 | C |
| ATOM | 694 | O | VAL | A | 93 | 58.901 | 32.142 | 14.805 | 1.00 | 31.13 | O |
| ATOM | 695 | CB | VAL | A | 93 | 56.686 | 34.472 | 15.849 | 1.00 | 30.30 | C |
| ATOM | 696 | CG1 | VAL | A | 93 | 57.131 | 33.699 | 17.086 | 1.00 | 29.35 | C |
| ATOM | 697 | CG2 | VAL | A | 93 | 56.662 | 35.971 | 16.138 | 1.00 | 29.04 | C |
| ATOM | 698 | N | HIS | A | 94 | 56.775 | 32.003 | 14.076 | 1.00 | 32.42 | N |
| ATOM | 699 | CA | HIS | A | 94 | 56.812 | 30.557 | 13.884 | 1.00 | 33.18 | C |
| ATOM | 700 | C | HIS | A | 94 | 57.929 | 30.173 | 12.909 | 1.00 | 32.93 | C |
| ATOM | 701 | O | HIS | A | 94 | 58.667 | 29.217 | 13.147 | 1.00 | 33.48 | O |
| ATOM | 702 | CB | HIS | A | 94 | 55.447 | 30.078 | 13.369 | 1.00 | 34.65 | C |
| ATOM | 703 | CG | HIS | A | 94 | 55.280 | 28.591 | 13.374 | 1.00 | 35.98 | C |
| ATOM | 704 | ND1 | HIS | A | 94 | 55.796 | 27.778 | 12.388 | 1.00 | 36.93 | N |
| ATOM | 705 | CD2 | HIS | A | 94 | 54.656 | 27.768 | 14.251 | 1.00 | 36.50 | C |
| ATOM | 706 | CE1 | HIS | A | 94 | 55.497 | 26.519 | 12.657 | 1.00 | 36.90 | C |
| ATOM | 707 | NE2 | HIS | A | 94 | 54.806 | 26.486 | 13.782 | 1.00 | 37.15 | N |
| ATOM | 708 | N | ALA | A | 95 | 58.067 | 30.928 | 11.823 | 1.00 | 32.80 | N |
| ATOM | 709 | CA | ALA | A | 95 | 59.109 | 30.649 | 10.834 | 1.00 | 32.63 | C |
| ATOM | 710 | C | ALA | A | 95 | 60.507 | 30.700 | 11.453 | 1.00 | 32.64 | C |
| ATOM | 711 | O | ALA | A | 95 | 61.383 | 29.903 | 11.107 | 1.00 | 32.76 | O |
| ATOM | 712 | CB | ALA | A | 95 | 59.019 | 31.641 | 9.677 | 1.00 | 32.50 | C |
| ATOM | 713 | N | VAL | A | 96 | 60.721 | 31.642 | 12.365 | 1.00 | 32.04 | N |

TABLE 3-continued

| | | | | | | | | | | | |
|---|---|---|---|---|---|---|---|---|---|---|---|
| ATOM | 714 | CA | VAL | A | 96 | 62.023 | 31.770 | 13.011 | 1.00 | 31.47 | C |
| ATOM | 715 | C | VAL | A | 96 | 62.262 | 30.620 | 13.981 | 1.00 | 31.55 | C |
| ATOM | 716 | O | VAL | A | 96 | 63.329 | 30.007 | 13.976 | 1.00 | 31.64 | O |
| ATOM | 717 | CB | VAL | A | 96 | 62.142 | 33.105 | 13.783 | 1.00 | 30.96 | C |
| ATOM | 718 | CG1 | VAL | A | 96 | 63.479 | 33.176 | 14.508 | 1.00 | 30.67 | C |
| ATOM | 719 | CG2 | VAL | A | 96 | 62.009 | 34.266 | 12.824 | 1.00 | 31.22 | C |
| ATOM | 720 | N | LYS | A | 97 | 61.261 | 30.327 | 14.805 | 1.00 | 32.04 | N |
| ATOM | 721 | CA | LYS | A | 97 | 61.358 | 29.256 | 15.792 | 1.00 | 33.20 | C |
| ATOM | 722 | C | LYS | A | 97 | 61.543 | 27.872 | 15.169 | 1.00 | 34.86 | C |
| ATOM | 723 | O | LYS | A | 97 | 62.171 | 26.999 | 15.767 | 1.00 | 34.76 | O |
| ATOM | 724 | CB | LYS | A | 97 | 60.108 | 29.240 | 16.681 | 1.00 | 32.12 | C |
| ATOM | 725 | CG | LYS | A | 97 | 59.868 | 30.523 | 17.477 | 1.00 | 31.22 | C |
| ATOM | 726 | CD | LYS | A | 97 | 61.064 | 30.874 | 18.360 | 1.00 | 29.75 | C |
| ATOM | 727 | CE | LYS | A | 97 | 61.404 | 29.751 | 19.333 | 1.00 | 29.19 | C |
| ATOM | 728 | NZ | LYS | A | 97 | 62.616 | 30.076 | 20.141 | 1.00 | 29.12 | N |
| ATOM | 729 | N | ASN | A | 98 | 61.000 | 27.671 | 13.972 | 1.00 | 36.75 | N |
| ATOM | 730 | CA | ASN | A | 98 | 61.108 | 26.375 | 13.308 | 1.00 | 39.34 | C |
| ATOM | 731 | C | ASN | A | 98 | 61.978 | 26.386 | 12.055 | 1.00 | 40.41 | C |
| ATOM | 732 | O | ASN | A | 98 | 61.781 | 25.571 | 11.150 | 1.00 | 40.41 | O |
| ATOM | 733 | CB | ASN | A | 98 | 59.711 | 25.850 | 12.955 | 1.00 | 40.86 | C |
| ATOM | 734 | CG | ASN | A | 98 | 58.870 | 25.553 | 14.185 | 1.00 | 42.24 | C |
| ATOM | 735 | OD1 | ASN | A | 98 | 58.468 | 26.461 | 14.912 | 1.00 | 44.16 | O |
| ATOM | 736 | ND2 | ASN | A | 98 | 58.605 | 24.275 | 14.427 | 1.00 | 43.29 | N |
| ATOM | 737 | N | PHE | A | 99 | 62.950 | 27.293 | 12.010 | 1.00 | 41.32 | N |
| ATOM | 738 | CA | PHE | A | 99 | 63.837 | 27.410 | 10.854 | 1.00 | 42.37 | C |
| ATOM | 739 | C | PHE | A | 99 | 64.779 | 26.225 | 10.654 | 1.00 | 43.23 | C |
| ATOM | 740 | O | PHE | A | 99 | 65.086 | 25.860 | 9.519 | 1.00 | 43.09 | O |
| ATOM | 741 | CB | PHE | A | 99 | 64.680 | 28.682 | 10.957 | 1.00 | 42.31 | C |
| ATOM | 742 | CG | PHE | A | 99 | 65.533 | 28.941 | 9.746 | 1.00 | 42.53 | C |
| ATOM | 743 | CD1 | PHE | A | 99 | 64.955 | 29.335 | 8.544 | 1.00 | 42.50 | C |
| ATOM | 744 | CD2 | PHE | A | 99 | 66.913 | 28.780 | 9.803 | 1.00 | 42.81 | C |
| ATOM | 745 | CE1 | PHE | A | 99 | 65.742 | 29.566 | 7.414 | 1.00 | 42.79 | C |
| ATOM | 746 | CE2 | PHE | A | 99 | 67.707 | 29.009 | 8.681 | 1.00 | 42.73 | C |
| ATOM | 747 | CZ | PHE | A | 99 | 67.120 | 29.403 | 7.485 | 1.00 | 42.71 | C |
| ATOM | 748 | N | LYS | A | 100 | 65.246 | 25.639 | 11.752 | 1.00 | 44.14 | N |
| ATOM | 749 | CA | LYS | A | 100 | 66.173 | 24.512 | 11.678 | 1.00 | 45.76 | C |
| ATOM | 750 | C | LYS | A | 100 | 65.520 | 23.178 | 11.337 | 1.00 | 47.12 | C |
| ATOM | 751 | O | LYS | A | 100 | 66.214 | 22.185 | 11.130 | 1.00 | 47.59 | O |
| ATOM | 752 | CB | LYS | A | 100 | 66.941 | 24.372 | 12.996 | 1.00 | 45.30 | C |
| ATOM | 753 | CG | LYS | A | 100 | 67.867 | 25.541 | 13.304 | 1.00 | 44.67 | C |
| ATOM | 754 | CD | LYS | A | 100 | 68.619 | 25.319 | 14.604 | 1.00 | 44.01 | C |
| ATOM | 755 | CE | LYS | A | 100 | 69.645 | 26.417 | 14.840 | 1.00 | 43.17 | C |
| ATOM | 756 | NZ | LYS | A | 100 | 70.359 | 26.229 | 16.128 | 1.00 | 42.38 | N |
| ATOM | 757 | N | ALA | A | 101 | 64.193 | 23.152 | 11.279 | 1.00 | 48.59 | N |
| ATOM | 758 | CA | ALA | A | 101 | 63.472 | 21.924 | 10.960 | 1.00 | 50.30 | C |
| ATOM | 759 | C | ALA | A | 101 | 63.843 | 21.416 | 9.570 | 1.00 | 51.59 | C |
| ATOM | 760 | O | ALA | A | 101 | 64.125 | 22.202 | 8.666 | 1.00 | 51.58 | O |
| ATOM | 761 | CB | ALA | A | 101 | 61.967 | 22.162 | 11.043 | 1.00 | 49.96 | C |
| ATOM | 762 | N | GLY | A | 102 | 63.846 | 20.095 | 9.401 | 1.00 | 53.11 | N |
| ATOM | 763 | CA | GLY | A | 102 | 64.175 | 19.504 | 8.126 | 1.00 | 54.99 | C |
| ATOM | 764 | C | GLY | A | 102 | 62.909 | 19.190 | 7.356 | 1.00 | 56.36 | C |
| ATOM | 765 | O | GLY | A | 102 | 62.401 | 20.035 | 6.617 | 1.00 | 56.47 | O |
| ATOM | 766 | N | PHE | A | 103 | 62.396 | 17.975 | 7.524 | 1.00 | 57.72 | N |
| ATOM | 767 | CA | PHE | A | 103 | 61.167 | 17.580 | 6.848 | 1.00 | 59.15 | C |
| ATOM | 768 | C | PHE | A | 103 | 59.987 | 18.171 | 7.609 | 1.00 | 59.91 | C |
| ATOM | 769 | O | PHE | A | 103 | 59.771 | 17.853 | 8.779 | 1.00 | 60.20 | O |
| ATOM | 770 | CB | PHE | A | 103 | 61.036 | 16.054 | 6.797 | 1.00 | 59.55 | C |
| ATOM | 771 | CG | PHE | A | 103 | 62.114 | 15.377 | 5.996 | 1.00 | 59.88 | C |
| ATOM | 772 | CD1 | PHE | A | 103 | 63.409 | 15.269 | 6.495 | 1.00 | 60.13 | C |
| ATOM | 773 | CD2 | PHE | A | 103 | 61.835 | 14.854 | 4.739 | 1.00 | 59.99 | C |
| ATOM | 774 | CE1 | PHE | A | 103 | 64.411 | 14.649 | 5.753 | 1.00 | 60.20 | C |
| ATOM | 775 | CE2 | PHE | A | 103 | 62.830 | 14.232 | 3.988 | 1.00 | 60.34 | C |
| ATOM | 776 | CZ | PHE | A | 103 | 64.122 | 14.130 | 4.497 | 1.00 | 60.26 | C |
| ATOM | 777 | N | VAL | A | 104 | 59.229 | 19.035 | 6.942 | 1.00 | 60.70 | N |
| ATOM | 778 | CA | VAL | A | 104 | 58.078 | 19.673 | 7.566 | 1.00 | 61.34 | C |
| ATOM | 779 | C | VAL | A | 104 | 56.764 | 19.239 | 6.924 | 1.00 | 61.90 | C |
| ATOM | 780 | O | VAL | A | 104 | 56.666 | 19.111 | 5.702 | 1.00 | 61.92 | O |
| ATOM | 781 | CB | VAL | A | 104 | 58.185 | 21.212 | 7.479 | 1.00 | 61.42 | C |
| ATOM | 782 | CG1 | VAL | A | 104 | 56.991 | 21.858 | 8.169 | 1.00 | 61.56 | C |
| ATOM | 783 | CG2 | VAL | A | 104 | 59.485 | 21.679 | 8.118 | 1.00 | 61.49 | C |
| ATOM | 784 | N | VAL | A | 105 | 55.757 | 19.014 | 7.761 | 1.00 | 62.35 | N |
| ATOM | 785 | CA | VAL | A | 105 | 54.440 | 18.604 | 7.292 | 1.00 | 62.87 | C |
| ATOM | 786 | C | VAL | A | 105 | 53.715 | 19.808 | 6.697 | 1.00 | 63.08 | C |
| ATOM | 787 | O | VAL | A | 105 | 53.411 | 20.771 | 7.403 | 1.00 | 63.17 | O |
| ATOM | 788 | CB | VAL | A | 105 | 53.591 | 18.034 | 8.450 | 1.00 | 62.93 | C |
| ATOM | 789 | CG1 | VAL | A | 105 | 52.234 | 17.585 | 7.931 | 1.00 | 63.00 | C |
| ATOM | 790 | CG2 | VAL | A | 105 | 54.324 | 16.876 | 9.109 | 1.00 | 62.99 | C |
| ATOM | 791 | N | SER | A | 106 | 53.445 | 19.751 | 5.397 | 1.00 | 63.19 | N |
| ATOM | 792 | CA | SER | A | 106 | 52.759 | 20.839 | 4.710 | 1.00 | 63.34 | C |

TABLE 3-continued

| ATOM | 793 | C | SER | A | 106 | 51.372 | 21.071 | 5.298 | 1.00 | 63.37 | C |
| --- | --- | --- | --- | --- | --- | --- | --- | --- | --- | --- | --- |
| ATOM | 794 | O | SER | A | 106 | 51.163 | 22.011 | 6.065 | 1.00 | 63.55 | O |
| ATOM | 795 | CB | SER | A | 106 | 52.638 | 20.527 | 3.217 | 1.00 | 63.52 | C |
| ATOM | 796 | OG | SER | A | 106 | 51.969 | 21.570 | 2.530 | 1.00 | 63.46 | O |
| ATOM | 797 | N | HIS | A | 222 | 78.549 | 29.753 | 16.811 | 1.00 | 46.50 | N |
| ATOM | 798 | CA | HIS | A | 222 | 79.214 | 29.762 | 18.111 | 1.00 | 46.34 | C |
| ATOM | 799 | C | HIS | A | 222 | 78.515 | 30.714 | 19.076 | 1.00 | 45.23 | C |
| ATOM | 800 | O | HIS | A | 222 | 78.376 | 30.423 | 20.263 | 1.00 | 45.39 | O |
| ATOM | 801 | CB | HIS | A | 222 | 80.679 | 30.185 | 17.962 | 1.00 | 47.77 | C |
| ATOM | 802 | CG | HIS | A | 222 | 81.512 | 29.225 | 17.170 | 1.00 | 49.66 | C |
| ATOM | 803 | ND1 | HIS | A | 222 | 81.651 | 27.897 | 17.515 | 1.00 | 50.29 | N |
| ATOM | 804 | CD2 | HIS | A | 222 | 82.269 | 29.406 | 16.061 | 1.00 | 50.09 | C |
| ATOM | 805 | CE1 | HIS | A | 222 | 82.457 | 27.302 | 16.653 | 1.00 | 50.69 | C |
| ATOM | 806 | NE2 | HIS | A | 222 | 82.847 | 28.195 | 15.761 | 1.00 | 50.78 | N |
| ATOM | 807 | N | ASN | A | 223 | 78.079 | 31.857 | 18.560 | 1.00 | 43.45 | N |
| ATOM | 808 | CA | ASN | A | 223 | 77.402 | 32.843 | 19.386 | 1.00 | 41.69 | C |
| ATOM | 809 | C | ASN | A | 223 | 75.906 | 32.910 | 19.120 | 1.00 | 39.79 | C |
| ATOM | 810 | O | ASN | A | 223 | 75.266 | 33.908 | 19.444 | 1.00 | 38.70 | O |
| ATOM | 811 | CB | ASN | A | 223 | 78.024 | 34.225 | 19.171 | 1.00 | 43.26 | C |
| ATOM | 812 | CG | ASN | A | 223 | 79.314 | 34.408 | 19.946 | 1.00 | 44.91 | C |
| ATOM | 813 | OD1 | ASN | A | 223 | 79.305 | 34.509 | 21.177 | 1.00 | 45.63 | O |
| ATOM | 814 | ND2 | ASN | A | 223 | 80.433 | 34.446 | 19.232 | 1.00 | 45.69 | N |
| ATOM | 815 | N | GLU | A | 224 | 75.345 | 31.852 | 18.537 | 1.00 | 37.33 | N |
| ATOM | 816 | CA | GLU | A | 224 | 73.915 | 31.836 | 18.254 | 1.00 | 35.82 | C |
| ATOM | 817 | C | GLU | A | 224 | 73.110 | 31.935 | 19.540 | 1.00 | 33.98 | C |
| ATOM | 818 | O | GLU | A | 224 | 73.464 | 31.338 | 20.555 | 1.00 | 34.05 | O |
| ATOM | 819 | CB | GLU | A | 224 | 73.508 | 30.560 | 17.499 | 1.00 | 36.85 | C |
| ATOM | 820 | CG | GLU | A | 224 | 73.919 | 29.250 | 18.173 | 1.00 | 38.61 | C |
| ATOM | 821 | CD | GLU | A | 224 | 73.188 | 28.035 | 17.613 | 1.00 | 39.59 | C |
| ATOM | 822 | OE1 | GLU | A | 224 | 72.843 | 28.032 | 16.411 | 1.00 | 40.09 | O |
| ATOM | 823 | OE2 | GLU | A | 224 | 72.967 | 27.072 | 18.377 | 1.00 | 40.45 | O |
| ATOM | 824 | N | LEU | A | 225 | 72.032 | 32.707 | 19.496 | 1.00 | 32.23 | N |
| ATOM | 825 | CA | LEU | A | 225 | 71.162 | 32.869 | 20.651 | 1.00 | 31.01 | C |
| ATOM | 826 | C | LEU | A | 225 | 69.988 | 31.928 | 20.443 | 1.00 | 30.52 | C |
| ATOM | 827 | O | LEU | A | 225 | 69.142 | 32.164 | 19.578 | 1.00 | 29.48 | O |
| ATOM | 828 | CB | LEU | A | 225 | 70.660 | 34.311 | 20.750 | 1.00 | 30.04 | C |
| ATOM | 829 | CG | LEU | A | 225 | 69.753 | 34.608 | 21.947 | 1.00 | 29.97 | C |
| ATOM | 830 | CD1 | LEU | A | 225 | 70.505 | 34.321 | 23.250 | 1.00 | 29.58 | C |
| ATOM | 831 | CD2 | LEU | A | 225 | 69.294 | 36.056 | 21.899 | 1.00 | 28.91 | C |
| ATOM | 832 | N | VAL | A | 226 | 69.938 | 30.863 | 21.238 | 1.00 | 30.37 | N |
| ATOM | 833 | CA | VAL | A | 226 | 68.874 | 29.875 | 21.107 | 1.00 | 30.90 | C |
| ATOM | 834 | C | VAL | A | 226 | 68.249 | 29.459 | 22.436 | 1.00 | 31.48 | C |
| ATOM | 835 | O | VAL | A | 226 | 68.767 | 29.782 | 23.512 | 1.00 | 31.51 | O |
| ATOM | 836 | CB | VAL | A | 226 | 69.405 | 28.604 | 20.414 | 1.00 | 30.86 | C |
| ATOM | 837 | CG1 | VAL | A | 226 | 69.837 | 28.924 | 18.997 | 1.00 | 30.18 | C |
| ATOM | 838 | CG2 | VAL | A | 226 | 70.579 | 28.040 | 21.209 | 1.00 | 31.20 | C |
| ATOM | 839 | N | ASP | A | 227 | 67.130 | 28.743 | 22.352 | 1.00 | 31.82 | N |
| ATOM | 840 | CA | ASP | A | 227 | 66.446 | 28.257 | 23.543 | 1.00 | 32.90 | C |
| ATOM | 841 | C | ASP | A | 227 | 66.961 | 26.857 | 23.874 | 1.00 | 34.23 | C |
| ATOM | 842 | O | ASP | A | 227 | 67.891 | 26.365 | 23.231 | 1.00 | 34.23 | O |
| ATOM | 843 | CB | ASP | A | 227 | 64.921 | 28.225 | 23.339 | 1.00 | 32.40 | C |
| ATOM | 844 | CG | ASP | A | 227 | 64.486 | 27.355 | 22.158 | 1.00 | 32.01 | C |
| ATOM | 845 | OD1 | ASP | A | 227 | 65.177 | 26.369 | 21.829 | 1.00 | 31.77 | O |
| ATOM | 846 | OD2 | ASP | A | 227 | 63.426 | 27.652 | 21.569 | 1.00 | 31.75 | O |
| ATOM | 847 | N | SER | A | 228 | 66.354 | 26.219 | 24.871 | 1.00 | 35.88 | N |
| ATOM | 848 | CA | SER | A | 228 | 66.767 | 24.881 | 25.289 | 1.00 | 37.61 | C |
| ATOM | 849 | C | SER | A | 228 | 66.675 | 23.846 | 24.169 | 1.00 | 38.35 | C |
| ATOM | 850 | O | SER | A | 228 | 67.330 | 22.805 | 24.227 | 1.00 | 38.93 | O |
| ATOM | 851 | CB | SER | A | 228 | 65.927 | 24.421 | 26.486 | 1.00 | 37.87 | C |
| ATOM | 852 | OG | SER | A | 228 | 64.547 | 24.377 | 26.159 | 1.00 | 39.04 | O |
| ATOM | 853 | N | GLN | A | 229 | 65.868 | 24.135 | 23.152 | 1.00 | 39.18 | N |
| ATOM | 854 | CA | GLN | A | 229 | 65.698 | 23.227 | 22.021 | 1.00 | 39.80 | C |
| ATOM | 855 | C | GLN | A | 229 | 66.566 | 23.622 | 20.828 | 1.00 | 39.23 | C |
| ATOM | 856 | O | GLN | A | 229 | 66.348 | 23.151 | 19.712 | 1.00 | 39.37 | O |
| ATOM | 857 | CB | GLN | A | 229 | 64.232 | 23.192 | 21.584 | 1.00 | 41.24 | C |
| ATOM | 858 | CG | GLN | A | 229 | 63.250 | 22.883 | 22.703 | 1.00 | 43.62 | C |
| ATOM | 859 | CD | GLN | A | 229 | 61.819 | 22.778 | 22.207 | 1.00 | 45.00 | C |
| ATOM | 860 | OE1 | GLN | A | 229 | 60.871 | 22.836 | 22.992 | 1.00 | 45.95 | O |
| ATOM | 861 | NE2 | GLN | A | 229 | 61.656 | 22.613 | 20.898 | 1.00 | 46.15 | N |
| ATOM | 862 | N | LYS | A | 230 | 67.544 | 24.492 | 21.065 | 1.00 | 38.50 | N |
| ATOM | 863 | CA | LYS | A | 230 | 68.451 | 24.949 | 20.013 | 1.00 | 37.74 | C |
| ATOM | 864 | C | LYS | A | 230 | 67.765 | 25.765 | 18.920 | 1.00 | 36.23 | C |
| ATOM | 865 | O | LYS | A | 230 | 68.303 | 25.921 | 17.824 | 1.00 | 36.06 | O |
| ATOM | 866 | CB | LYS | A | 230 | 69.176 | 23.756 | 19.376 | 1.00 | 39.35 | C |
| ATOM | 867 | CG | LYS | A | 230 | 70.046 | 22.964 | 20.342 | 1.00 | 41.26 | C |
| ATOM | 868 | CD | LYS | A | 230 | 71.113 | 23.843 | 20.984 | 1.00 | 43.12 | C |
| ATOM | 869 | CE | LYS | A | 230 | 71.938 | 23.060 | 21.997 | 1.00 | 44.34 | C |
| ATOM | 870 | NZ | LYS | A | 230 | 72.907 | 23.933 | 22.723 | 1.00 | 45.01 | N |
| ATOM | 871 | N | ARG | A | 231 | 66.579 | 26.283 | 19.217 | 1.00 | 34.84 | N |

TABLE 3-continued

| | | | | | | | | | | | |
|---|---|---|---|---|---|---|---|---|---|---|---|
| ATOM | 872 | CA | ARG | A | 231 | 65.844 | 27.099 | 18.257 | 1.00 | 34.03 | C |
| ATOM | 873 | C | ARG | A | 231 | 66.203 | 28.565 | 18.499 | 1.00 | 32.95 | C |
| ATOM | 874 | O | ARG | A | 231 | 66.289 | 29.001 | 19.646 | 1.00 | 31.96 | O |
| ATOM | 875 | CB | ARG | A | 231 | 64.335 | 26.910 | 18.442 | 1.00 | 34.65 | C |
| ATOM | 876 | CG | ARG | A | 231 | 63.864 | 25.460 | 18.369 | 1.00 | 35.93 | C |
| ATOM | 877 | CD | ARG | A | 231 | 62.362 | 25.367 | 18.593 | 1.00 | 36.99 | C |
| ATOM | 878 | NE | ARG | A | 231 | 61.977 | 25.904 | 19.897 | 1.00 | 38.07 | N |
| ATOM | 879 | CZ | ARG | A | 231 | 60.720 | 26.085 | 20.292 | 1.00 | 39.08 | C |
| ATOM | 880 | NH1 | ARG | A | 231 | 59.716 | 25.774 | 19.484 | 1.00 | 39.24 | N |
| ATOM | 881 | NH2 | ARG | A | 231 | 60.467 | 26.582 | 21.498 | 1.00 | 40.03 | N |
| ATOM | 882 | N | TYR | A | 232 | 66.414 | 29.320 | 17.424 | 1.00 | 31.73 | N |
| ATOM | 883 | CA | TYR | A | 232 | 66.754 | 30.733 | 17.548 | 1.00 | 30.36 | C |
| ATOM | 884 | C | TYR | A | 232 | 65.701 | 31.473 | 18.364 | 1.00 | 29.68 | C |
| ATOM | 885 | O | TYR | A | 232 | 64.504 | 31.206 | 18.237 | 1.00 | 28.90 | O |
| ATOM | 886 | CB | TYR | A | 232 | 66.843 | 31.393 | 16.172 | 1.00 | 31.11 | C |
| ATOM | 887 | CG | TYR | A | 232 | 67.909 | 30.824 | 15.268 | 1.00 | 31.38 | C |
| ATOM | 888 | CD1 | TYR | A | 232 | 69.246 | 30.798 | 15.661 | 1.00 | 31.61 | C |
| ATOM | 889 | CD2 | TYR | A | 232 | 67.582 | 30.320 | 14.013 | 1.00 | 31.87 | C |
| ATOM | 890 | CE1 | TYR | A | 232 | 70.233 | 30.279 | 14.820 | 1.00 | 32.53 | C |
| ATOM | 891 | CE2 | TYR | A | 232 | 68.557 | 29.801 | 13.167 | 1.00 | 32.60 | C |
| ATOM | 892 | CZ | TYR | A | 232 | 69.877 | 29.784 | 13.576 | 1.00 | 32.81 | C |
| ATOM | 893 | OH | TYR | A | 232 | 70.838 | 29.280 | 12.730 | 1.00 | 34.16 | O |
| ATOM | 894 | N | LEU | A | 233 | 66.148 | 32.401 | 19.205 | 1.00 | 28.53 | N |
| ATOM | 895 | CA | LEU | A | 233 | 65.218 | 33.185 | 20.003 | 1.00 | 28.15 | C |
| ATOM | 896 | C | LEU | A | 233 | 64.666 | 34.306 | 19.136 | 1.00 | 27.30 | C |
| ATOM | 897 | O | LEU | A | 233 | 65.333 | 34.783 | 18.216 | 1.00 | 27.41 | O |
| ATOM | 898 | CB | LEU | A | 233 | 65.913 | 33.801 | 21.224 | 1.00 | 28.49 | C |
| ATOM | 899 | CG | LEU | A | 233 | 66.443 | 32.883 | 22.328 | 1.00 | 29.33 | C |
| ATOM | 900 | CD1 | LEU | A | 233 | 66.808 | 33.738 | 23.535 | 1.00 | 29.80 | C |
| ATOM | 901 | CD2 | LEU | A | 233 | 65.396 | 31.855 | 22.724 | 1.00 | 28.86 | C |
| ATOM | 902 | N | VAL | A | 234 | 63.444 | 34.725 | 19.431 | 1.00 | 26.70 | N |
| ATOM | 903 | CA | VAL | A | 234 | 62.830 | 35.804 | 18.684 | 1.00 | 26.26 | C |
| ATOM | 904 | C | VAL | A | 234 | 61.821 | 36.512 | 19.564 | 1.00 | 25.94 | C |
| ATOM | 905 | O | VAL | A | 234 | 61.172 | 35.892 | 20.407 | 1.00 | 26.26 | O |
| ATOM | 906 | CB | VAL | A | 234 | 62.120 | 35.288 | 17.407 | 1.00 | 26.74 | C |
| ATOM | 907 | CG1 | VAL | A | 234 | 60.919 | 34.429 | 17.782 | 1.00 | 25.97 | C |
| ATOM | 908 | CG2 | VAL | A | 234 | 61.693 | 36.466 | 16.543 | 1.00 | 25.98 | C |
| ATOM | 909 | N | GLY | A | 235 | 61.711 | 37.821 | 19.378 | 1.00 | 25.83 | N |
| ATOM | 910 | CA | GLY | A | 235 | 60.766 | 38.599 | 20.152 | 1.00 | 25.73 | C |
| ATOM | 911 | C | GLY | A | 235 | 59.698 | 39.117 | 19.215 | 1.00 | 25.81 | C |
| ATOM | 912 | O | GLY | A | 235 | 59.823 | 38.976 | 17.999 | 1.00 | 26.03 | O |
| ATOM | 913 | N | ALA | A | 236 | 58.655 | 39.724 | 19.771 | 1.00 | 25.58 | N |
| ATOM | 914 | CA | ALA | A | 236 | 57.567 | 40.255 | 18.962 | 1.00 | 24.80 | C |
| ATOM | 915 | C | ALA | A | 236 | 56.956 | 41.480 | 19.628 | 1.00 | 24.47 | C |
| ATOM | 916 | O | ALA | A | 236 | 56.724 | 41.494 | 20.838 | 1.00 | 23.49 | O |
| ATOM | 917 | CB | ALA | A | 236 | 56.500 | 39.183 | 18.759 | 1.00 | 24.63 | C |
| ATOM | 918 | N | GLY | A | 237 | 56.694 | 42.509 | 18.832 | 1.00 | 23.78 | N |
| ATOM | 919 | CA | GLY | A | 237 | 56.104 | 43.711 | 19.381 | 1.00 | 23.62 | C |
| ATOM | 920 | C | GLY | A | 237 | 54.597 | 43.582 | 19.482 | 1.00 | 24.13 | C |
| ATOM | 921 | O | GLY | A | 237 | 53.968 | 42.900 | 18.671 | 1.00 | 23.90 | O |
| ATOM | 922 | N | ILE | A | 238 | 54.015 | 44.210 | 20.497 | 1.00 | 24.19 | N |
| ATOM | 923 | CA | ILE | A | 238 | 52.570 | 44.188 | 20.654 | 1.00 | 24.84 | C |
| ATOM | 924 | C | ILE | A | 238 | 52.113 | 45.610 | 20.932 | 1.00 | 25.64 | C |
| ATOM | 925 | O | ILE | A | 238 | 52.931 | 46.496 | 21.196 | 1.00 | 24.88 | O |
| ATOM | 926 | CB | ILE | A | 238 | 52.110 | 43.274 | 21.816 | 1.00 | 24.90 | C |
| ATOM | 927 | CG1 | ILE | A | 238 | 52.669 | 43.782 | 23.147 | 1.00 | 24.94 | C |
| ATOM | 928 | CG2 | ILE | A | 238 | 52.537 | 41.841 | 21.550 | 1.00 | 24.38 | C |
| ATOM | 929 | CD1 | ILE | A | 238 | 52.192 | 42.969 | 24.360 | 1.00 | 25.52 | C |
| ATOM | 930 | N | ASN | A | 239 | 50.807 | 45.831 | 20.854 | 1.00 | 26.34 | N |
| ATOM | 931 | CA | ASN | A | 239 | 50.251 | 47.147 | 21.116 | 1.00 | 27.12 | C |
| ATOM | 932 | C | ASN | A | 239 | 49.239 | 47.032 | 22.248 | 1.00 | 27.64 | C |
| ATOM | 933 | O | ASN | A | 239 | 48.820 | 45.932 | 22.610 | 1.00 | 27.63 | O |
| ATOM | 934 | CB | ASN | A | 239 | 49.598 | 47.715 | 19.849 | 1.00 | 27.57 | C |
| ATOM | 935 | CG | ASN | A | 239 | 48.478 | 46.841 | 19.325 | 1.00 | 27.88 | C |
| ATOM | 936 | OD1 | ASN | A | 239 | 47.419 | 46.731 | 19.941 | 1.00 | 28.35 | O |
| ATOM | 937 | ND2 | ASN | A | 239 | 48.708 | 46.211 | 18.181 | 1.00 | 28.71 | N |
| ATOM | 938 | N | THR | A | 240 | 48.858 | 48.172 | 22.808 | 1.00 | 28.33 | N |
| ATOM | 939 | CA | THR | A | 240 | 47.916 | 48.210 | 23.916 | 1.00 | 29.57 | C |
| ATOM | 940 | C | THR | A | 240 | 46.456 | 48.037 | 23.496 | 1.00 | 31.11 | C |
| ATOM | 941 | O | THR | A | 240 | 45.553 | 48.160 | 24.324 | 1.00 | 31.21 | O |
| ATOM | 942 | CB | THR | A | 240 | 48.056 | 49.538 | 24.686 | 1.00 | 29.04 | C |
| ATOM | 943 | OG1 | THR | A | 240 | 47.813 | 50.632 | 23.792 | 1.00 | 29.08 | O |
| ATOM | 944 | CG2 | THR | A | 240 | 49.468 | 49.678 | 25.262 | 1.00 | 27.94 | C |
| ATOM | 945 | N | ARG | A | 241 | 46.217 | 47.736 | 22.223 | 1.00 | 32.81 | N |
| ATOM | 946 | CA | ARG | A | 241 | 44.843 | 47.584 | 21.749 | 1.00 | 34.67 | C |
| ATOM | 947 | C | ARG | A | 241 | 44.326 | 46.161 | 21.532 | 1.00 | 34.16 | C |
| ATOM | 948 | O | ARG | A | 241 | 43.360 | 45.752 | 22.174 | 1.00 | 34.43 | O |
| ATOM | 949 | CB | ARG | A | 241 | 44.635 | 48.395 | 20.464 | 1.00 | 36.65 | C |
| ATOM | 950 | CG | ARG | A | 241 | 43.247 | 48.215 | 19.851 | 1.00 | 39.95 | C |

TABLE 3-continued

| | | | | | | | | | | |
|---|---|---|---|---|---|---|---|---|---|---|
| ATOM | 951 | CD | ARG | A | 241 | 42.994 | 49.151 | 18.671 | 1.00 | 42.38 | C |
| ATOM | 952 | NE | ARG | A | 241 | 42.483 | 50.457 | 19.088 | 1.00 | 45.23 | N |
| ATOM | 953 | CZ | ARG | A | 241 | 43.212 | 51.418 | 19.648 | 1.00 | 46.14 | C |
| ATOM | 954 | NH1 | ARG | A | 241 | 44.509 | 51.238 | 19.870 | 1.00 | 47.33 | N |
| ATOM | 955 | NH2 | ARG | A | 241 | 42.642 | 52.566 | 19.990 | 1.00 | 46.48 | N |
| ATOM | 956 | N | ASP | A | 242 | 44.955 | 45.408 | 20.636 | 1.00 | 33.84 | N |
| ATOM | 957 | CA | ASP | A | 242 | 44.493 | 44.050 | 20.349 | 1.00 | 33.74 | C |
| ATOM | 958 | C | ASP | A | 242 | 45.275 | 42.926 | 21.026 | 1.00 | 33.27 | C |
| ATOM | 959 | O | ASP | A | 242 | 45.270 | 41.796 | 20.547 | 1.00 | 33.34 | O |
| ATOM | 960 | CB | ASP | A | 242 | 44.483 | 43.803 | 18.830 | 1.00 | 33.77 | C |
| ATOM | 961 | CG | ASP | A | 242 | 45.874 | 43.869 | 18.206 | 1.00 | 33.91 | C |
| ATOM | 962 | OD1 | ASP | A | 242 | 46.869 | 43.553 | 18.891 | 1.00 | 34.63 | O |
| ATOM | 963 | OD2 | ASP | A | 242 | 45.975 | 44.220 | 17.012 | 1.00 | 34.44 | O |
| ATOM | 964 | N | PHE | A | 243 | 45.929 | 43.228 | 22.143 | 1.00 | 33.23 | N |
| ATOM | 965 | CA | PHE | A | 243 | 46.725 | 42.228 | 22.854 | 1.00 | 33.10 | C |
| ATOM | 966 | C | PHE | A | 243 | 45.977 | 40.971 | 23.305 | 1.00 | 33.10 | C |
| ATOM | 967 | O | PHE | A | 243 | 46.553 | 39.883 | 23.330 | 1.00 | 32.90 | O |
| ATOM | 968 | CB | PHE | A | 243 | 47.428 | 42.878 | 24.056 | 1.00 | 32.51 | C |
| ATOM | 969 | CG | PHE | A | 243 | 46.494 | 43.438 | 25.089 | 1.00 | 31.55 | C |
| ATOM | 970 | CD1 | PHE | A | 243 | 45.956 | 42.620 | 26.078 | 1.00 | 31.75 | C |
| ATOM | 971 | CD2 | PHE | A | 243 | 46.155 | 44.785 | 25.077 | 1.00 | 31.51 | C |
| ATOM | 972 | CE1 | PHE | A | 243 | 45.095 | 43.136 | 27.041 | 1.00 | 31.53 | C |
| ATOM | 973 | CE2 | PHE | A | 243 | 45.293 | 45.314 | 26.037 | 1.00 | 31.87 | C |
| ATOM | 974 | CZ | PHE | A | 243 | 44.763 | 44.487 | 27.022 | 1.00 | 32.20 | C |
| ATOM | 975 | N | ARG | A | 244 | 44.703 | 41.104 | 23.660 | 1.00 | 33.75 | N |
| ATOM | 976 | CA | ARG | A | 244 | 43.937 | 39.942 | 24.105 | 1.00 | 34.29 | C |
| ATOM | 977 | C | ARG | A | 244 | 43.920 | 38.850 | 23.042 | 1.00 | 34.39 | C |
| ATOM | 978 | O | ARG | A | 244 | 43.801 | 37.666 | 23.355 | 1.00 | 34.22 | O |
| ATOM | 979 | CB | ARG | A | 244 | 42.507 | 40.347 | 24.478 | 1.00 | 34.64 | C |
| ATOM | 980 | CG | ARG | A | 244 | 42.444 | 41.300 | 25.662 | 1.00 | 35.99 | C |
| ATOM | 981 | CD | ARG | A | 244 | 41.012 | 41.616 | 26.074 | 1.00 | 36.99 | C |
| ATOM | 982 | NE | ARG | A | 244 | 40.968 | 42.595 | 27.157 | 1.00 | 37.44 | N |
| ATOM | 983 | CZ | ARG | A | 244 | 41.260 | 43.884 | 27.012 | 1.00 | 38.60 | C |
| ATOM | 984 | NH1 | ARG | A | 244 | 41.616 | 44.361 | 25.825 | 1.00 | 38.28 | N |
| ATOM | 985 | NH2 | ARG | A | 244 | 41.200 | 44.699 | 28.058 | 1.00 | 39.02 | N |
| ATOM | 986 | N | GLU | A | 245 | 44.048 | 39.247 | 21.782 | 1.00 | 34.77 | N |
| ATOM | 987 | CA | GLU | A | 245 | 44.066 | 38.281 | 20.693 | 1.00 | 35.05 | C |
| ATOM | 988 | C | GLU | A | 245 | 45.473 | 38.075 | 20.138 | 1.00 | 34.00 | C |
| ATOM | 989 | O | GLU | A | 245 | 45.853 | 36.955 | 19.803 | 1.00 | 33.63 | O |
| ATOM | 990 | CB | GLU | A | 245 | 43.128 | 38.725 | 19.561 | 1.00 | 36.92 | C |
| ATOM | 991 | CG | GLU | A | 245 | 41.643 | 38.667 | 19.921 | 1.00 | 40.34 | C |
| ATOM | 992 | CD | GLU | A | 245 | 41.188 | 39.805 | 20.829 | 1.00 | 42.35 | C |
| ATOM | 993 | OE1 | GLU | A | 245 | 40.089 | 39.688 | 21.415 | 1.00 | 44.16 | O |
| ATOM | 994 | OE2 | GLU | A | 245 | 41.912 | 40.821 | 20.949 | 1.00 | 43.70 | O |
| ATOM | 995 | N | ARG | A | 246 | 46.249 | 39.151 | 20.051 | 1.00 | 32.70 | N |
| ATOM | 996 | CA | ARG | A | 246 | 47.605 | 39.060 | 19.512 | 1.00 | 31.63 | C |
| ATOM | 997 | C | ARG | A | 246 | 48.569 | 38.278 | 20.403 | 1.00 | 31.12 | C |
| ATOM | 998 | O | ARG | A | 246 | 49.349 | 37.467 | 19.908 | 1.00 | 30.59 | O |
| ATOM | 999 | CB | ARG | A | 246 | 48.167 | 40.464 | 19.251 | 1.00 | 31.59 | C |
| ATOM | 1000 | CG | ARG | A | 246 | 49.547 | 40.475 | 18.593 | 1.00 | 31.32 | C |
| ATOM | 1001 | CD | ARG | A | 246 | 50.027 | 41.901 | 18.325 | 1.00 | 31.90 | C |
| ATOM | 1002 | NE | ARG | A | 246 | 49.162 | 42.624 | 17.392 | 1.00 | 32.03 | N |
| ATOM | 1003 | CZ | ARG | A | 246 | 49.171 | 42.461 | 16.072 | 1.00 | 31.59 | C |
| ATOM | 1004 | NH1 | ARG | A | 246 | 50.004 | 41.597 | 15.506 | 1.00 | 31.30 | N |
| ATOM | 1005 | NH2 | ARG | A | 246 | 48.348 | 43.171 | 15.315 | 1.00 | 32.08 | N |
| ATOM | 1006 | N | VAL | A | 247 | 48.514 | 38.511 | 21.712 | 1.00 | 30.54 | N |
| ATOM | 1007 | CA | VAL | A | 247 | 49.411 | 37.822 | 22.638 | 1.00 | 30.81 | C |
| ATOM | 1008 | C | VAL | A | 247 | 49.299 | 36.296 | 22.600 | 1.00 | 31.06 | C |
| ATOM | 1009 | O | VAL | A | 247 | 50.304 | 35.603 | 22.439 | 1.00 | 31.19 | O |
| ATOM | 1010 | CB | VAL | A | 247 | 49.215 | 38.339 | 24.087 | 1.00 | 30.61 | C |
| ATOM | 1011 | CG1 | VAL | A | 247 | 49.955 | 37.460 | 25.070 | 1.00 | 29.27 | C |
| ATOM | 1012 | CG2 | VAL | A | 247 | 49.742 | 39.772 | 24.189 | 1.00 | 30.03 | C |
| ATOM | 1013 | N | PRO | A | 248 | 48.080 | 35.749 | 22.754 | 1.00 | 31.23 | N |
| ATOM | 1014 | CA | PRO | A | 248 | 47.944 | 34.289 | 22.717 | 1.00 | 31.12 | C |
| ATOM | 1015 | C | PRO | A | 248 | 48.504 | 33.704 | 21.420 | 1.00 | 30.88 | C |
| ATOM | 1016 | O | PRO | A | 248 | 49.142 | 32.650 | 21.421 | 1.00 | 30.83 | O |
| ATOM | 1017 | CB | PRO | A | 248 | 46.434 | 34.084 | 22.846 | 1.00 | 31.29 | C |
| ATOM | 1018 | CG | PRO | A | 248 | 46.026 | 35.237 | 23.719 | 1.00 | 30.86 | C |
| ATOM | 1019 | CD | PRO | A | 248 | 46.802 | 36.388 | 23.118 | 1.00 | 30.24 | C |
| ATOM | 1020 | N | ALA | A | 249 | 48.272 | 34.402 | 20.313 | 1.00 | 31.01 | N |
| ATOM | 1021 | CA | ALA | A | 249 | 48.751 | 33.953 | 19.012 | 1.00 | 30.71 | C |
| ATOM | 1022 | C | ALA | A | 249 | 50.277 | 33.926 | 18.960 | 1.00 | 30.92 | C |
| ATOM | 1023 | O | ALA | A | 249 | 50.871 | 32.989 | 18.421 | 1.00 | 30.39 | O |
| ATOM | 1024 | CB | ALA | A | 249 | 48.211 | 34.859 | 17.919 | 1.00 | 31.05 | C |
| ATOM | 1025 | N | LEU | A | 250 | 50.909 | 34.957 | 19.516 | 1.00 | 30.74 | N |
| ATOM | 1026 | CA | LEU | A | 250 | 52.367 | 35.035 | 19.521 | 1.00 | 30.84 | C |
| ATOM | 1027 | C | LEU | A | 250 | 52.952 | 33.987 | 20.459 | 1.00 | 31.45 | C |
| ATOM | 1028 | O | LEU | A | 250 | 53.995 | 33.403 | 20.172 | 1.00 | 31.01 | O |
| ATOM | 1029 | CB | LEU | A | 250 | 52.827 | 36.437 | 19.935 | 1.00 | 30.44 | C |

TABLE 3-continued

| ATOM | 1030 | CG | LEU | A | 250 | 52.442 | 37.553 | 18.952 | 1.00 | 30.49 | C |
| --- | --- | --- | --- | --- | --- | --- | --- | --- | --- | --- | --- |
| ATOM | 1031 | CD1 | LEU | A | 250 | 52.899 | 38.901 | 19.491 | 1.00 | 29.78 | C |
| ATOM | 1032 | CD2 | LEU | A | 250 | 53.071 | 37.279 | 17.590 | 1.00 | 29.75 | C |
| ATOM | 1033 | N | VAL | A | 251 | 52.275 | 33.752 | 21.579 | 1.00 | 32.58 | N |
| ATOM | 1034 | CA | VAL | A | 251 | 52.724 | 32.755 | 22.546 | 1.00 | 33.79 | C |
| ATOM | 1035 | C | VAL | A | 251 | 52.683 | 31.378 | 21.884 | 1.00 | 34.44 | C |
| ATOM | 1036 | O | VAL | A | 251 | 53.632 | 30.598 | 21.987 | 1.00 | 34.16 | O |
| ATOM | 1037 | CB | VAL | A | 251 | 51.818 | 32.742 | 23.799 | 1.00 | 34.18 | C |
| ATOM | 1038 | CG1 | VAL | A | 251 | 52.183 | 31.569 | 24.703 | 1.00 | 35.25 | C |
| ATOM | 1039 | CG2 | VAL | A | 251 | 51.965 | 34.055 | 24.554 | 1.00 | 35.24 | C |
| ATOM | 1040 | N | GLU | A | 252 | 51.580 | 31.094 | 21.196 | 1.00 | 34.83 | N |
| ATOM | 1041 | CA | GLU | A | 252 | 51.411 | 29.818 | 20.509 | 1.00 | 35.52 | C |
| ATOM | 1042 | C | GLU | A | 252 | 52.488 | 29.645 | 19.442 | 1.00 | 34.61 | C |
| ATOM | 1043 | O | GLU | A | 252 | 53.032 | 28.557 | 19.277 | 1.00 | 34.77 | O |
| ATOM | 1044 | CB | GLU | A | 252 | 50.031 | 29.742 | 19.845 | 1.00 | 37.32 | C |
| ATOM | 1045 | CG | GLU | A | 252 | 49.752 | 28.398 | 19.162 | 1.00 | 40.99 | C |
| ATOM | 1046 | CD | GLU | A | 252 | 48.561 | 28.429 | 18.203 | 1.00 | 43.11 | C |
| ATOM | 1047 | OE1 | GLU | A | 252 | 48.090 | 27.335 | 17.814 | 1.00 | 44.94 | O |
| ATOM | 1048 | OE2 | GLU | A | 252 | 48.102 | 29.532 | 17.823 | 1.00 | 44.42 | O |
| ATOM | 1049 | N | ALA | A | 253 | 52.784 | 30.723 | 18.719 | 1.00 | 33.41 | N |
| ATOM | 1050 | CA | ALA | A | 253 | 53.793 | 30.691 | 17.663 | 1.00 | 32.41 | C |
| ATOM | 1051 | C | ALA | A | 253 | 55.198 | 30.428 | 18.201 | 1.00 | 31.93 | C |
| ATOM | 1052 | O | ALA | A | 253 | 56.104 | 30.078 | 17.441 | 1.00 | 31.99 | O |
| ATOM | 1053 | CB | ALA | A | 253 | 53.773 | 31.999 | 16.884 | 1.00 | 32.46 | C |
| ATOM | 1054 | N | GLY | A | 254 | 55.384 | 30.613 | 19.504 | 1.00 | 30.81 | N |
| ATOM | 1055 | CA | GLY | A | 254 | 56.684 | 30.366 | 20.098 | 1.00 | 29.67 | C |
| ATOM | 1056 | C | GLY | A | 254 | 57.527 | 31.587 | 20.431 | 1.00 | 28.80 | C |
| ATOM | 1057 | O | GLY | A | 254 | 58.723 | 31.452 | 20.686 | 1.00 | 28.19 | O |
| ATOM | 1058 | N | ALA | A | 255 | 56.929 | 32.775 | 20.429 | 1.00 | 28.28 | N |
| ATOM | 1059 | CA | ALA | A | 255 | 57.690 | 33.984 | 20.752 | 1.00 | 27.64 | C |
| ATOM | 1060 | C | ALA | A | 255 | 58.349 | 33.807 | 22.112 | 1.00 | 27.07 | C |
| ATOM | 1061 | O | ALA | A | 255 | 57.721 | 33.341 | 23.059 | 1.00 | 27.00 | O |
| ATOM | 1062 | CB | ALA | A | 255 | 56.776 | 35.203 | 20.769 | 1.00 | 27.72 | C |
| ATOM | 1063 | N | ASP | A | 256 | 59.617 | 34.183 | 22.205 | 1.00 | 26.96 | N |
| ATOM | 1064 | CA | ASP | A | 256 | 60.368 | 34.049 | 23.446 | 1.00 | 26.98 | C |
| ATOM | 1065 | C | ASP | A | 256 | 60.197 | 35.244 | 24.380 | 1.00 | 26.65 | C |
| ATOM | 1066 | O | ASP | A | 256 | 60.354 | 35.124 | 25.594 | 1.00 | 26.61 | O |
| ATOM | 1067 | CB | ASP | A | 256 | 61.845 | 33.848 | 23.117 | 1.00 | 27.66 | C |
| ATOM | 1068 | CG | ASP | A | 256 | 62.085 | 32.590 | 22.312 | 1.00 | 28.65 | C |
| ATOM | 1069 | OD1 | ASP | A | 256 | 62.063 | 31.497 | 22.908 | 1.00 | 29.35 | O |
| ATOM | 1070 | OD2 | ASP | A | 256 | 62.275 | 32.690 | 21.081 | 1.00 | 29.48 | O |
| ATOM | 1071 | N | VAL | A | 257 | 59.873 | 36.397 | 23.808 | 1.00 | 25.89 | N |
| ATOM | 1072 | CA | VAL | A | 257 | 59.683 | 37.608 | 24.594 | 1.00 | 25.16 | C |
| ATOM | 1073 | C | VAL | A | 257 | 58.841 | 38.589 | 23.786 | 1.00 | 24.93 | C |
| ATOM | 1074 | O | VAL | A | 257 | 58.880 | 38.581 | 22.556 | 1.00 | 24.52 | O |
| ATOM | 1075 | CB | VAL | A | 257 | 61.053 | 38.255 | 24.950 | 1.00 | 25.36 | C |
| ATOM | 1076 | CG1 | VAL | A | 257 | 61.850 | 38.514 | 23.684 | 1.00 | 26.06 | C |
| ATOM | 1077 | CG2 | VAL | A | 257 | 60.847 | 39.550 | 25.725 | 1.00 | 24.98 | C |
| ATOM | 1078 | N | LEU | A | 258 | 58.072 | 39.415 | 24.487 | 1.00 | 24.27 | N |
| ATOM | 1079 | CA | LEU | A | 258 | 57.220 | 40.413 | 23.851 | 1.00 | 24.81 | C |
| ATOM | 1080 | C | LEU | A | 258 | 57.652 | 41.801 | 24.319 | 1.00 | 25.12 | C |
| ATOM | 1081 | O | LEU | A | 258 | 58.377 | 41.936 | 25.304 | 1.00 | 25.19 | O |
| ATOM | 1082 | CB | LEU | A | 258 | 55.758 | 40.200 | 24.253 | 1.00 | 24.78 | C |
| ATOM | 1083 | CG | LEU | A | 258 | 55.165 | 38.798 | 24.097 | 1.00 | 25.27 | C |
| ATOM | 1084 | CD1 | LEU | A | 258 | 53.738 | 38.804 | 24.625 | 1.00 | 26.64 | C |
| ATOM | 1085 | CD2 | LEU | A | 258 | 55.201 | 38.367 | 22.636 | 1.00 | 25.42 | C |
| ATOM | 1086 | N | CYS | A | 259 | 57.202 | 42.829 | 23.612 | 1.00 | 24.79 | N |
| ATOM | 1087 | CA | CYS | A | 259 | 57.518 | 44.195 | 23.999 | 1.00 | 25.27 | C |
| ATOM | 1088 | C | CYS | A | 259 | 56.447 | 45.139 | 23.486 | 1.00 | 25.48 | C |
| ATOM | 1089 | O | CYS | A | 259 | 56.146 | 45.150 | 22.297 | 1.00 | 25.28 | O |
| ATOM | 1090 | CB | CYS | A | 259 | 58.883 | 44.628 | 23.448 | 1.00 | 25.05 | C |
| ATOM | 1091 | SG | CYS | A | 259 | 59.397 | 46.260 | 24.055 | 1.00 | 24.98 | S |
| ATOM | 1092 | N | ILE | A | 260 | 55.864 | 45.920 | 24.389 | 1.00 | 26.39 | N |
| ATOM | 1093 | CA | ILE | A | 260 | 54.846 | 46.884 | 23.996 | 1.00 | 27.80 | C |
| ATOM | 1094 | C | ILE | A | 260 | 55.571 | 48.017 | 23.275 | 1.00 | 29.01 | C |
| ATOM | 1095 | O | ILE | A | 260 | 56.492 | 48.627 | 23.816 | 1.00 | 29.15 | O |
| ATOM | 1096 | CB | ILE | A | 260 | 54.108 | 47.462 | 25.210 | 1.00 | 27.85 | C |
| ATOM | 1097 | CG1 | ILE | A | 260 | 53.585 | 46.325 | 26.088 | 1.00 | 27.74 | C |
| ATOM | 1098 | CG2 | ILE | A | 260 | 52.943 | 48.340 | 24.734 | 1.00 | 27.65 | C |
| ATOM | 1099 | CD1 | ILE | A | 260 | 52.992 | 46.796 | 27.406 | 1.00 | 29.12 | C |
| ATOM | 1100 | N | ASP | A | 261 | 55.136 | 48.287 | 22.054 | 1.00 | 30.05 | N |
| ATOM | 1101 | CA | ASP | A | 261 | 55.726 | 49.307 | 21.195 | 1.00 | 31.69 | C |
| ATOM | 1102 | C | ASP | A | 261 | 54.914 | 50.611 | 21.272 | 1.00 | 31.11 | C |
| ATOM | 1103 | O | ASP | A | 261 | 53.747 | 50.624 | 20.901 | 1.00 | 31.52 | O |
| ATOM | 1104 | CB | ASP | A | 261 | 55.760 | 48.721 | 19.773 | 1.00 | 33.20 | C |
| ATOM | 1105 | CG | ASP | A | 261 | 56.363 | 49.653 | 18.746 | 1.00 | 35.95 | C |
| ATOM | 1106 | OD1 | ASP | A | 261 | 57.279 | 50.427 | 19.080 | 1.00 | 37.14 | O |
| ATOM | 1107 | OD2 | ASP | A | 261 | 55.925 | 49.586 | 17.576 | 1.00 | 37.53 | O |
| ATOM | 1108 | N | SER | A | 262 | 55.524 | 51.692 | 21.769 | 1.00 | 30.51 | N |

TABLE 3-continued

| ATOM | 1109 | CA | SER | A | 262 | 54.829 | 52.985 | 21.896 | 1.00 | 30.28 | C |
|------|------|----|----|---|-----|--------|--------|--------|------|-------|---|
| ATOM | 1110 | C | SER | A | 262 | 55.742 | 54.207 | 22.054 | 1.00 | 29.74 | C |
| ATOM | 1111 | O | SER | A | 262 | 56.801 | 54.123 | 22.673 | 1.00 | 29.61 | O |
| ATOM | 1112 | CB | SER | A | 262 | 53.863 | 52.937 | 23.087 | 1.00 | 31.07 | C |
| ATOM | 1113 | OG | SER | A | 262 | 53.352 | 54.226 | 23.389 | 1.00 | 31.39 | O |
| ATOM | 1114 | N | SER | A | 263 | 55.313 | 55.350 | 21.515 | 1.00 | 29.06 | N |
| ATOM | 1115 | CA | SER | A | 263 | 56.093 | 56.585 | 21.608 | 1.00 | 28.10 | C |
| ATOM | 1116 | C | SER | A | 263 | 56.027 | 57.203 | 23.005 | 1.00 | 27.79 | C |
| ATOM | 1117 | O | SER | A | 263 | 56.822 | 58.079 | 23.345 | 1.00 | 28.25 | O |
| ATOM | 1118 | CB | SER | A | 263 | 55.611 | 57.615 | 20.574 | 1.00 | 28.95 | C |
| ATOM | 1119 | OG | SER | A | 263 | 54.300 | 58.073 | 20.857 | 1.00 | 29.45 | O |
| ATOM | 1120 | N | ASP | A | 264 | 55.073 | 56.749 | 23.809 | 1.00 | 26.48 | N |
| ATOM | 1121 | CA | ASP | A | 264 | 54.923 | 57.245 | 25.173 | 1.00 | 25.78 | C |
| ATOM | 1122 | C | ASP | A | 264 | 54.400 | 56.107 | 26.043 | 1.00 | 25.45 | C |
| ATOM | 1123 | O | ASP | A | 264 | 53.191 | 55.891 | 26.144 | 1.00 | 25.07 | O |
| ATOM | 1124 | CB | ASP | A | 264 | 53.959 | 58.440 | 25.202 | 1.00 | 25.30 | C |
| ATOM | 1125 | CG | ASP | A | 264 | 53.616 | 58.900 | 26.619 | 1.00 | 24.43 | C |
| ATOM | 1126 | OD1 | ASP | A | 264 | 54.333 | 58.559 | 27.586 | 1.00 | 23.75 | O |
| ATOM | 1127 | OD2 | ASP | A | 264 | 52.618 | 59.629 | 26.760 | 1.00 | 24.33 | O |
| ATOM | 1128 | N | GLY | A | 265 | 55.331 | 55.378 | 26.652 | 1.00 | 24.58 | N |
| ATOM | 1129 | CA | GLY | A | 265 | 54.985 | 54.253 | 27.500 | 1.00 | 24.14 | C |
| ATOM | 1130 | C | GLY | A | 265 | 54.505 | 54.603 | 28.896 | 1.00 | 24.38 | C |
| ATOM | 1131 | O | GLY | A | 265 | 54.105 | 53.718 | 29.655 | 1.00 | 23.84 | O |
| ATOM | 1132 | N | PHE | A | 266 | 54.554 | 55.884 | 29.250 | 1.00 | 24.38 | N |
| ATOM | 1133 | CA | PHE | A | 266 | 54.095 | 56.321 | 30.562 | 1.00 | 24.40 | C |
| ATOM | 1134 | C | PHE | A | 266 | 52.584 | 56.429 | 30.382 | 1.00 | 24.85 | C |
| ATOM | 1135 | O | PHE | A | 266 | 52.035 | 57.523 | 30.275 | 1.00 | 23.66 | O |
| ATOM | 1136 | CB | PHE | A | 266 | 54.700 | 57.685 | 30.902 | 1.00 | 24.77 | C |
| ATOM | 1137 | CG | PHE | A | 266 | 54.758 | 57.987 | 32.383 | 1.00 | 25.09 | C |
| ATOM | 1138 | CD1 | PHE | A | 266 | 54.030 | 57.233 | 33.302 | 1.00 | 24.80 | C |
| ATOM | 1139 | CD2 | PHE | A | 266 | 55.530 | 59.047 | 32.851 | 1.00 | 24.88 | C |
| ATOM | 1140 | CE1 | PHE | A | 266 | 54.071 | 57.533 | 34.665 | 1.00 | 25.40 | C |
| ATOM | 1141 | CE2 | PHE | A | 266 | 55.580 | 59.360 | 34.210 | 1.00 | 24.97 | C |
| ATOM | 1142 | CZ | PHE | A | 266 | 54.849 | 58.601 | 35.121 | 1.00 | 25.68 | C |
| ATOM | 1143 | N | SER | A | 267 | 51.924 | 55.274 | 30.348 | 1.00 | 25.48 | N |
| ATOM | 1144 | CA | SER | A | 267 | 50.486 | 55.203 | 30.112 | 1.00 | 26.23 | C |
| ATOM | 1145 | C | SER | A | 267 | 49.777 | 54.078 | 30.855 | 1.00 | 26.64 | C |
| ATOM | 1146 | O | SER | A | 267 | 50.306 | 52.971 | 30.983 | 1.00 | 25.99 | O |
| ATOM | 1147 | CB | SER | A | 267 | 50.241 | 55.016 | 28.616 | 1.00 | 26.26 | C |
| ATOM | 1148 | OG | SER | A | 267 | 48.898 | 54.647 | 28.356 | 1.00 | 28.51 | O |
| ATOM | 1149 | N | GLU | A | 268 | 48.567 | 54.363 | 31.321 | 1.00 | 27.32 | N |
| ATOM | 1150 | CA | GLU | A | 268 | 47.776 | 53.363 | 32.021 | 1.00 | 28.41 | C |
| ATOM | 1151 | C | GLU | A | 268 | 47.486 | 52.195 | 31.089 | 1.00 | 28.35 | C |
| ATOM | 1152 | O | GLU | A | 268 | 47.276 | 51.070 | 31.544 | 1.00 | 27.34 | O |
| ATOM | 1153 | CB | GLU | A | 268 | 46.454 | 53.964 | 32.513 | 1.00 | 30.40 | C |
| ATOM | 1154 | CG | GLU | A | 268 | 46.594 | 54.834 | 33.754 | 1.00 | 33.77 | C |
| ATOM | 1155 | CD | GLU | A | 268 | 45.255 | 55.298 | 34.320 | 1.00 | 35.87 | C |
| ATOM | 1156 | OE1 | GLU | A | 268 | 45.246 | 55.792 | 35.471 | 1.00 | 37.72 | O |
| ATOM | 1157 | OE2 | GLU | A | 268 | 44.221 | 55.177 | 33.623 | 1.00 | 35.03 | O |
| ATOM | 1158 | N | TRP | A | 269 | 47.471 | 52.464 | 29.785 | 1.00 | 28.35 | N |
| ATOM | 1159 | CA | TRP | A | 269 | 47.204 | 51.417 | 28.806 | 1.00 | 29.40 | C |
| ATOM | 1160 | C | TRP | A | 269 | 48.275 | 50.332 | 28.857 | 1.00 | 29.06 | C |
| ATOM | 1161 | O | TRP | A | 269 | 47.976 | 49.154 | 28.653 | 1.00 | 29.12 | O |
| ATOM | 1162 | CB | TRP | A | 269 | 47.121 | 51.995 | 27.388 | 1.00 | 30.30 | C |
| ATOM | 1163 | CG | TRP | A | 269 | 45.916 | 52.861 | 27.150 | 1.00 | 32.00 | C |
| ATOM | 1164 | CD1 | TRP | A | 269 | 45.908 | 54.202 | 26.892 | 1.00 | 32.39 | C |
| ATOM | 1165 | CD2 | TRP | A | 269 | 44.543 | 52.443 | 27.146 | 1.00 | 32.75 | C |
| ATOM | 1166 | NE1 | TRP | A | 269 | 44.617 | 54.644 | 26.727 | 1.00 | 33.20 | N |
| ATOM | 1167 | CE2 | TRP | A | 269 | 43.760 | 53.586 | 26.877 | 1.00 | 33.15 | C |
| ATOM | 1168 | CE3 | TRP | A | 269 | 43.899 | 51.212 | 27.343 | 1.00 | 33.57 | C |
| ATOM | 1169 | CZ2 | TRP | A | 269 | 42.363 | 53.539 | 26.798 | 1.00 | 33.93 | C |
| ATOM | 1170 | CZ3 | TRP | A | 269 | 42.507 | 51.164 | 27.266 | 1.00 | 34.42 | C |
| ATOM | 1171 | CH2 | TRP | A | 269 | 41.757 | 52.323 | 26.994 | 1.00 | 34.51 | C |
| ATOM | 1172 | N | GLN | A | 270 | 49.519 | 50.726 | 29.122 | 1.00 | 28.51 | N |
| ATOM | 1173 | CA | GLN | A | 270 | 50.610 | 49.755 | 29.209 | 1.00 | 28.61 | C |
| ATOM | 1174 | C | GLN | A | 270 | 50.460 | 48.941 | 30.490 | 1.00 | 28.10 | C |
| ATOM | 1175 | O | GLN | A | 270 | 50.699 | 47.736 | 30.499 | 1.00 | 28.60 | O |
| ATOM | 1176 | CB | GLN | A | 270 | 51.977 | 50.457 | 29.205 | 1.00 | 28.36 | C |
| ATOM | 1177 | CG | GLN | A | 270 | 52.238 | 51.315 | 27.977 | 1.00 | 28.23 | C |
| ATOM | 1178 | CD | GLN | A | 270 | 53.519 | 50.943 | 27.244 | 1.00 | 28.01 | C |
| ATOM | 1179 | OE1 | GLN | A | 270 | 54.445 | 50.374 | 27.825 | 1.00 | 27.19 | O |
| ATOM | 1180 | NE2 | GLN | A | 270 | 53.581 | 51.282 | 25.963 | 1.00 | 26.48 | N |
| ATOM | 1181 | N | LYS | A | 271 | 50.072 | 49.604 | 31.575 | 1.00 | 28.37 | N |
| ATOM | 1182 | CA | LYS | A | 271 | 49.878 | 48.915 | 32.846 | 1.00 | 28.70 | C |
| ATOM | 1183 | C | LYS | A | 271 | 48.784 | 47.858 | 32.671 | 1.00 | 27.88 | C |
| ATOM | 1184 | O | LYS | A | 271 | 48.917 | 46.734 | 33.144 | 1.00 | 27.93 | O |
| ATOM | 1185 | CB | LYS | A | 271 | 49.476 | 49.912 | 33.941 | 1.00 | 29.92 | C |
| ATOM | 1186 | CG | LYS | A | 271 | 49.092 | 49.260 | 35.266 | 1.00 | 32.48 | C |
| ATOM | 1187 | CD | LYS | A | 271 | 48.701 | 50.309 | 36.300 | 1.00 | 34.72 | C |

TABLE 3-continued

| | | | | | | | | | | |
|---|---|---|---|---|---|---|---|---|---|---|
| ATOM | 1188 | CE | LYS | A | 271 | 48.207 | 49.671 | 37.590 | 1.00 | 36.23 | C |
| ATOM | 1189 | NZ | LYS | A | 271 | 49.269 | 48.881 | 38.274 | 1.00 | 38.61 | N |
| ATOM | 1190 | N | ILE | A | 272 | 47.712 | 48.231 | 31.979 | 1.00 | 27.39 | N |
| ATOM | 1191 | CA | ILE | A | 272 | 46.592 | 47.326 | 31.726 | 1.00 | 27.48 | C |
| ATOM | 1192 | C | ILE | A | 272 | 47.036 | 46.124 | 30.902 | 1.00 | 26.99 | C |
| ATOM | 1193 | O | ILE | A | 272 | 46.668 | 44.989 | 31.195 | 1.00 | 27.02 | O |
| ATOM | 1194 | CB | ILE | A | 272 | 45.447 | 48.057 | 30.978 | 1.00 | 27.22 | C |
| ATOM | 1195 | CG1 | ILE | A | 272 | 44.786 | 49.064 | 31.922 | 1.00 | 27.67 | C |
| ATOM | 1196 | CG2 | ILE | A | 272 | 44.422 | 47.046 | 30.447 | 1.00 | 27.76 | C |
| ATOM | 1197 | CD1 | ILE | A | 272 | 43.836 | 50.030 | 31.231 | 1.00 | 27.85 | C |
| ATOM | 1198 | N | THR | A | 273 | 47.831 | 46.377 | 29.868 | 1.00 | 26.65 | N |
| ATOM | 1199 | CA | THR | A | 273 | 48.322 | 45.306 | 29.010 | 1.00 | 26.53 | C |
| ATOM | 1200 | C | THR | A | 273 | 49.202 | 44.331 | 29.792 | 1.00 | 26.14 | C |
| ATOM | 1201 | O | THR | A | 273 | 49.041 | 43.114 | 29.694 | 1.00 | 25.79 | O |
| ATOM | 1202 | CB | THR | A | 273 | 49.120 | 45.878 | 27.824 | 1.00 | 26.74 | C |
| ATOM | 1203 | OG1 | THR | A | 273 | 48.270 | 46.744 | 27.059 | 1.00 | 27.53 | O |
| ATOM | 1204 | CG2 | THR | A | 273 | 49.626 | 44.752 | 26.928 | 1.00 | 27.26 | C |
| ATOM | 1205 | N | ILE | A | 274 | 50.134 | 44.863 | 30.571 | 1.00 | 26.20 | N |
| ATOM | 1206 | CA | ILE | A | 274 | 51.010 | 44.003 | 31.357 | 1.00 | 26.20 | C |
| ATOM | 1207 | C | ILE | A | 274 | 50.175 | 43.230 | 32.377 | 1.00 | 26.66 | C |
| ATOM | 1208 | O | ILE | A | 274 | 50.411 | 42.045 | 32.616 | 1.00 | 26.11 | O |
| ATOM | 1209 | CB | ILE | A | 274 | 52.080 | 44.821 | 32.096 | 1.00 | 25.86 | C |
| ATOM | 1210 | CG1 | ILE | A | 274 | 52.942 | 45.581 | 31.082 | 1.00 | 26.16 | C |
| ATOM | 1211 | CG2 | ILE | A | 274 | 52.950 | 43.895 | 32.945 | 1.00 | 25.61 | C |
| ATOM | 1212 | CD1 | ILE | A | 274 | 53.895 | 46.583 | 31.715 | 1.00 | 27.00 | C |
| ATOM | 1213 | N | GLY | A | 275 | 49.194 | 43.908 | 32.966 | 1.00 | 26.98 | N |
| ATOM | 1214 | CA | GLY | A | 275 | 48.335 | 43.266 | 33.949 | 1.00 | 28.29 | C |
| ATOM | 1215 | C | GLY | A | 275 | 47.599 | 42.064 | 33.382 | 1.00 | 28.55 | C |
| ATOM | 1216 | O | GLY | A | 275 | 47.537 | 41.009 | 34.015 | 1.00 | 28.98 | O |
| ATOM | 1217 | N | TRP | A | 276 | 47.041 | 42.222 | 32.187 | 1.00 | 28.87 | N |
| ATOM | 1218 | CA | TRP | A | 276 | 46.312 | 41.145 | 31.526 | 1.00 | 28.90 | C |
| ATOM | 1219 | C | TRP | A | 276 | 47.246 | 39.963 | 31.270 | 1.00 | 29.40 | C |
| ATOM | 1220 | O | TRP | A | 276 | 46.864 | 38.802 | 31.453 | 1.00 | 29.24 | O |
| ATOM | 1221 | CB | TRP | A | 276 | 45.735 | 41.633 | 30.197 | 1.00 | 29.68 | C |
| ATOM | 1222 | CG | TRP | A | 276 | 44.847 | 40.631 | 29.531 | 1.00 | 30.48 | C |
| ATOM | 1223 | CD1 | TRP | A | 276 | 43.513 | 40.429 | 29.766 | 1.00 | 30.71 | C |
| ATOM | 1224 | CD2 | TRP | A | 276 | 45.230 | 39.673 | 28.539 | 1.00 | 30.72 | C |
| ATOM | 1225 | NE1 | TRP | A | 276 | 43.043 | 39.405 | 28.977 | 1.00 | 30.48 | N |
| ATOM | 1226 | CE2 | TRP | A | 276 | 44.075 | 38.922 | 28.214 | 1.00 | 31.35 | C |
| ATOM | 1227 | CE3 | TRP | A | 276 | 46.437 | 39.373 | 27.891 | 1.00 | 31.18 | C |
| ATOM | 1228 | CZ2 | TRP | A | 276 | 44.092 | 37.890 | 27.268 | 1.00 | 31.27 | C |
| ATOM | 1229 | CZ3 | TRP | A | 276 | 46.455 | 38.344 | 26.951 | 1.00 | 31.86 | C |
| ATOM | 1230 | CH2 | TRP | A | 276 | 45.287 | 37.616 | 26.649 | 1.00 | 31.77 | C |
| ATOM | 1231 | N | ILE | A | 277 | 48.472 | 40.256 | 30.844 | 1.00 | 28.84 | N |
| ATOM | 1232 | CA | ILE | A | 277 | 49.440 | 39.197 | 30.585 | 1.00 | 28.97 | C |
| ATOM | 1233 | C | ILE | A | 277 | 49.774 | 38.442 | 31.878 | 1.00 | 29.36 | C |
| ATOM | 1234 | O | ILE | A | 277 | 49.822 | 37.213 | 31.886 | 1.00 | 28.83 | O |
| ATOM | 1235 | CB | ILE | A | 277 | 50.740 | 39.765 | 29.950 | 1.00 | 28.28 | C |
| ATOM | 1236 | CG1 | ILE | A | 277 | 50.442 | 40.296 | 28.542 | 1.00 | 28.37 | C |
| ATOM | 1237 | CG2 | ILE | A | 277 | 51.802 | 38.678 | 29.867 | 1.00 | 28.02 | C |
| ATOM | 1238 | CD1 | ILE | A | 277 | 51.604 | 41.054 | 27.890 | 1.00 | 27.79 | C |
| ATOM | 1239 | N | ARG | A | 278 | 49.988 | 39.174 | 32.969 | 1.00 | 30.21 | N |
| ATOM | 1240 | CA | ARG | A | 278 | 50.312 | 38.551 | 34.254 | 1.00 | 31.53 | C |
| ATOM | 1241 | C | ARG | A | 278 | 49.173 | 37.683 | 34.776 | 1.00 | 33.21 | C |
| ATOM | 1242 | O | ARG | A | 278 | 49.400 | 36.609 | 35.334 | 1.00 | 33.46 | O |
| ATOM | 1243 | CB | ARG | A | 278 | 50.643 | 39.616 | 35.304 | 1.00 | 30.82 | C |
| ATOM | 1244 | CG | ARG | A | 278 | 51.957 | 40.335 | 35.071 | 1.00 | 30.23 | C |
| ATOM | 1245 | CD | ARG | A | 278 | 53.143 | 39.393 | 35.206 | 1.00 | 29.99 | C |
| ATOM | 1246 | NE | ARG | A | 278 | 54.382 | 40.066 | 34.832 | 1.00 | 28.97 | N |
| ATOM | 1247 | CZ | ARG | A | 278 | 55.148 | 39.711 | 33.806 | 1.00 | 28.64 | C |
| ATOM | 1248 | NH1 | ARG | A | 278 | 54.812 | 38.677 | 33.044 | 1.00 | 26.58 | N |
| ATOM | 1249 | NH2 | ARG | A | 278 | 56.243 | 40.409 | 33.530 | 1.00 | 27.89 | N |
| ATOM | 1250 | N | GLU | A | 279 | 47.949 | 38.168 | 34.597 | 1.00 | 34.74 | N |
| ATOM | 1251 | CA | GLU | A | 279 | 46.754 | 37.466 | 35.043 | 1.00 | 36.51 | C |
| ATOM | 1252 | C | GLU | A | 279 | 46.553 | 36.166 | 34.268 | 1.00 | 36.74 | C |
| ATOM | 1253 | O | GLU | A | 279 | 46.101 | 35.162 | 34.819 | 1.00 | 36.85 | O |
| ATOM | 1254 | CB | GLU | A | 279 | 45.541 | 38.384 | 34.859 | 1.00 | 38.13 | C |
| ATOM | 1255 | CG | GLU | A | 279 | 44.204 | 37.819 | 35.314 | 1.00 | 41.43 | C |
| ATOM | 1256 | CD | GLU | A | 279 | 43.065 | 38.828 | 35.182 | 1.00 | 43.32 | C |
| ATOM | 1257 | OE1 | GLU | A | 279 | 41.902 | 38.449 | 35.442 | 1.00 | 44.56 | O |
| ATOM | 1258 | OE2 | GLU | A | 279 | 43.327 | 40.002 | 34.823 | 1.00 | 44.56 | O |
| ATOM | 1259 | N | LYS | A | 280 | 46.915 | 36.183 | 32.991 | 1.00 | 36.37 | N |
| ATOM | 1260 | CA | LYS | A | 280 | 46.742 | 35.019 | 32.133 | 1.00 | 36.81 | C |
| ATOM | 1261 | C | LYS | A | 280 | 47.941 | 34.071 | 32.107 | 1.00 | 36.04 | C |
| ATOM | 1262 | O | LYS | A | 280 | 47.773 | 32.854 | 32.038 | 1.00 | 35.58 | O |
| ATOM | 1263 | CB | LYS | A | 280 | 46.433 | 35.495 | 30.710 | 1.00 | 38.33 | C |
| ATOM | 1264 | CG | LYS | A | 280 | 45.519 | 34.591 | 29.895 | 1.00 | 40.96 | C |
| ATOM | 1265 | CD | LYS | A | 280 | 46.185 | 33.281 | 29.512 | 1.00 | 42.35 | C |
| ATOM | 1266 | CE | LYS | A | 280 | 45.280 | 32.456 | 28.601 | 1.00 | 42.90 | C |

TABLE 3-continued

| | | | | | | | | | | | |
|---|---|---|---|---|---|---|---|---|---|---|---|
| ATOM | 1267 | NZ | LYS | A | 280 | 44.954 | 33.184 | 27.341 | 1.00 | 42.89 | N |
| ATOM | 1268 | N | TYR | A | 281 | 49.146 | 34.627 | 32.185 | 1.00 | 34.52 | N |
| ATOM | 1269 | CA | TYR | A | 281 | 50.362 | 33.826 | 32.100 | 1.00 | 33.39 | C |
| ATOM | 1270 | C | TYR | A | 281 | 51.328 | 33.919 | 33.274 | 1.00 | 33.09 | C |
| ATOM | 1271 | O | TYR | A | 281 | 52.334 | 33.214 | 33.297 | 1.00 | 33.09 | O |
| ATOM | 1272 | CB | TYR | A | 281 | 51.124 | 34.209 | 30.834 | 1.00 | 32.75 | C |
| ATOM | 1273 | CG | TYR | A | 281 | 50.356 | 34.016 | 29.549 | 1.00 | 32.31 | C |
| ATOM | 1274 | CD1 | TYR | A | 281 | 50.221 | 32.752 | 28.976 | 1.00 | 32.30 | C |
| ATOM | 1275 | CD2 | TYR | A | 281 | 49.785 | 35.103 | 28.889 | 1.00 | 32.48 | C |
| ATOM | 1276 | CE1 | TYR | A | 281 | 49.541 | 32.577 | 27.774 | 1.00 | 32.47 | C |
| ATOM | 1277 | CE2 | TYR | A | 281 | 49.104 | 34.939 | 27.691 | 1.00 | 32.55 | C |
| ATOM | 1278 | CZ | TYR | A | 281 | 48.987 | 33.674 | 27.138 | 1.00 | 32.49 | C |
| ATOM | 1279 | OH | TYR | A | 281 | 48.328 | 33.512 | 25.941 | 1.00 | 33.37 | O |
| ATOM | 1280 | N | GLY | A | 282 | 51.043 | 34.780 | 34.240 | 1.00 | 32.83 | N |
| ATOM | 1281 | CA | GLY | A | 282 | 51.961 | 34.919 | 35.355 | 1.00 | 32.77 | C |
| ATOM | 1282 | C | GLY | A | 282 | 53.284 | 35.449 | 34.826 | 1.00 | 33.10 | C |
| ATOM | 1283 | O | GLY | A | 282 | 53.305 | 36.220 | 33.863 | 1.00 | 32.17 | O |
| ATOM | 1284 | N | ASP | A | 283 | 54.391 | 35.041 | 35.436 | 1.00 | 33.13 | N |
| ATOM | 1285 | CA | ASP | A | 283 | 55.699 | 35.501 | 34.986 | 1.00 | 33.88 | C |
| ATOM | 1286 | C | ASP | A | 283 | 56.322 | 34.574 | 33.945 | 1.00 | 33.49 | C |
| ATOM | 1287 | O | ASP | A | 283 | 57.519 | 34.647 | 33.674 | 1.00 | 34.01 | O |
| ATOM | 1288 | CB | ASP | A | 283 | 56.637 | 35.665 | 36.184 | 1.00 | 34.83 | C |
| ATOM | 1289 | CG | ASP | A | 283 | 56.242 | 36.833 | 37.072 | 1.00 | 36.88 | C |
| ATOM | 1290 | OD1 | ASP | A | 283 | 56.206 | 37.978 | 36.569 | 1.00 | 38.24 | O |
| ATOM | 1291 | OD2 | ASP | A | 283 | 55.965 | 36.615 | 38.270 | 1.00 | 38.21 | O |
| ATOM | 1292 | N | LYS | A | 284 | 55.504 | 33.711 | 33.352 | 1.00 | 33.24 | N |
| ATOM | 1293 | CA | LYS | A | 284 | 55.985 | 32.773 | 32.342 | 1.00 | 33.02 | C |
| ATOM | 1294 | C | LYS | A | 284 | 56.118 | 33.426 | 30.968 | 1.00 | 32.02 | C |
| ATOM | 1295 | O | LYS | A | 284 | 56.838 | 32.931 | 30.105 | 1.00 | 32.97 | O |
| ATOM | 1296 | CB | LYS | A | 284 | 55.058 | 31.551 | 32.275 | 1.00 | 34.39 | C |
| ATOM | 1297 | CG | LYS | A | 284 | 55.260 | 30.568 | 33.433 | 1.00 | 36.82 | C |
| ATOM | 1298 | CD | LYS | A | 284 | 55.284 | 31.281 | 34.783 | 1.00 | 38.42 | C |
| ATOM | 1299 | CE | LYS | A | 284 | 55.742 | 30.359 | 35.910 | 1.00 | 39.93 | C |
| ATOM | 1300 | NZ | LYS | A | 284 | 56.028 | 31.120 | 37.168 | 1.00 | 39.68 | N |
| ATOM | 1301 | N | VAL | A | 285 | 55.410 | 34.530 | 30.761 | 1.00 | 29.89 | N |
| ATOM | 1302 | CA | VAL | A | 285 | 55.510 | 35.259 | 29.502 | 1.00 | 28.50 | C |
| ATOM | 1303 | C | VAL | A | 285 | 56.233 | 36.566 | 29.813 | 1.00 | 27.10 | C |
| ATOM | 1304 | O | VAL | A | 285 | 55.816 | 37.326 | 30.691 | 1.00 | 27.10 | O |
| ATOM | 1305 | CB | VAL | A | 285 | 54.122 | 35.559 | 28.895 | 1.00 | 28.58 | C |
| ATOM | 1306 | CG1 | VAL | A | 285 | 54.259 | 36.563 | 27.748 | 1.00 | 27.74 | C |
| ATOM | 1307 | CG2 | VAL | A | 285 | 53.502 | 34.264 | 28.375 | 1.00 | 28.28 | C |
| ATOM | 1308 | N | LYS | A | 286 | 57.327 | 36.815 | 29.101 | 1.00 | 25.90 | N |
| ATOM | 1309 | CA | LYS | A | 286 | 58.125 | 38.014 | 29.317 | 1.00 | 24.52 | C |
| ATOM | 1310 | C | LYS | A | 286 | 57.671 | 39.148 | 28.410 | 1.00 | 24.47 | C |
| ATOM | 1311 | O | LYS | A | 286 | 57.419 | 38.944 | 27.222 | 1.00 | 24.28 | O |
| ATOM | 1312 | CB | LYS | A | 286 | 59.601 | 37.697 | 29.076 | 1.00 | 25.16 | C |
| ATOM | 1313 | CG | LYS | A | 286 | 60.112 | 36.510 | 29.893 | 1.00 | 24.27 | C |
| ATOM | 1314 | CD | LYS | A | 286 | 59.926 | 36.746 | 31.388 | 1.00 | 24.81 | C |
| ATOM | 1315 | CE | LYS | A | 286 | 60.396 | 35.544 | 32.204 | 1.00 | 25.83 | C |
| ATOM | 1316 | NZ | LYS | A | 286 | 60.194 | 35.749 | 33.670 | 1.00 | 24.86 | N |
| ATOM | 1317 | N | VAL | A | 287 | 57.574 | 40.347 | 28.972 | 1.00 | 24.27 | N |
| ATOM | 1318 | CA | VAL | A | 287 | 57.120 | 41.495 | 28.202 | 1.00 | 24.13 | C |
| ATOM | 1319 | C | VAL | A | 287 | 57.779 | 42.813 | 28.597 | 1.00 | 23.84 | C |
| ATOM | 1320 | O | VAL | A | 287 | 57.687 | 43.255 | 29.743 | 1.00 | 23.87 | O |
| ATOM | 1321 | CB | VAL | A | 287 | 55.573 | 41.644 | 28.308 | 1.00 | 24.31 | C |
| ATOM | 1322 | CG1 | VAL | A | 287 | 55.146 | 41.662 | 29.769 | 1.00 | 25.02 | C |
| ATOM | 1323 | CG2 | VAL | A | 287 | 55.114 | 42.923 | 27.609 | 1.00 | 24.49 | C |
| ATOM | 1324 | N | GLY | A | 288 | 58.456 | 43.428 | 27.634 | 1.00 | 23.20 | N |
| ATOM | 1325 | CA | GLY | A | 288 | 59.097 | 44.707 | 27.882 | 1.00 | 22.85 | C |
| ATOM | 1326 | C | GLY | A | 288 | 58.077 | 45.801 | 27.643 | 1.00 | 22.44 | C |
| ATOM | 1327 | O | GLY | A | 288 | 57.018 | 45.548 | 27.063 | 1.00 | 22.27 | O |
| ATOM | 1328 | N | ALA | A | 289 | 58.383 | 47.014 | 28.088 | 1.00 | 22.59 | N |
| ATOM | 1329 | CA | ALA | A | 289 | 57.468 | 48.139 | 27.922 | 1.00 | 23.01 | C |
| ATOM | 1330 | C | ALA | A | 289 | 58.248 | 49.422 | 27.682 | 1.00 | 23.15 | C |
| ATOM | 1331 | O | ALA | A | 289 | 59.438 | 49.498 | 27.976 | 1.00 | 23.72 | O |
| ATOM | 1332 | CB | ALA | A | 289 | 56.573 | 48.287 | 29.168 | 1.00 | 23.19 | C |
| ATOM | 1333 | N | GLY | A | 290 | 57.565 | 50.427 | 27.144 | 1.00 | 23.69 | N |
| ATOM | 1334 | CA | GLY | A | 290 | 58.205 | 51.698 | 26.856 | 1.00 | 23.22 | C |
| ATOM | 1335 | C | GLY | A | 290 | 57.432 | 52.435 | 25.775 | 1.00 | 23.29 | C |
| ATOM | 1336 | O | GLY | A | 290 | 56.397 | 51.945 | 25.320 | 1.00 | 22.89 | O |
| ATOM | 1337 | N | ASN | A | 291 | 57.937 | 53.582 | 25.324 | 1.00 | 22.88 | N |
| ATOM | 1338 | CA | ASN | A | 291 | 59.199 | 54.155 | 25.787 | 1.00 | 22.55 | C |
| ATOM | 1339 | C | ASN | A | 291 | 59.028 | 55.263 | 26.817 | 1.00 | 22.60 | C |
| ATOM | 1340 | O | ASN | A | 291 | 58.024 | 55.974 | 26.817 | 1.00 | 22.43 | O |
| ATOM | 1341 | CB | ASN | A | 291 | 59.977 | 54.727 | 24.592 | 1.00 | 22.24 | C |
| ATOM | 1342 | CG | ASN | A | 291 | 60.565 | 53.651 | 23.708 | 1.00 | 22.60 | C |
| ATOM | 1343 | OD1 | ASN | A | 291 | 60.148 | 52.493 | 23.758 | 1.00 | 21.74 | O |
| ATOM | 1344 | ND2 | ASN | A | 291 | 61.538 | 54.029 | 22.884 | 1.00 | 21.50 | N |
| ATOM | 1345 | N | ILE | A | 292 | 60.028 | 55.404 | 27.685 | 1.00 | 22.32 | N |

TABLE 3-continued

| ATOM | 1346 | CA | ILE | A | 292 | 60.031 | 56.448 | 28.702 | 1.00 | 22.58 | C |
|---|---|---|---|---|---|---|---|---|---|---|---|
| ATOM | 1347 | C | ILE | A | 292 | 61.391 | 57.144 | 28.669 | 1.00 | 22.53 | C |
| ATOM | 1348 | O | ILE | A | 292 | 62.327 | 56.651 | 28.033 | 1.00 | 22.76 | O |
| ATOM | 1349 | CB | ILE | A | 292 | 59.722 | 55.879 | 30.123 | 1.00 | 22.99 | C |
| ATOM | 1350 | CG1 | ILE | A | 292 | 60.591 | 54.655 | 30.437 | 1.00 | 22.90 | C |
| ATOM | 1351 | CG2 | ILE | A | 292 | 58.243 | 55.506 | 30.208 | 1.00 | 23.43 | C |
| ATOM | 1352 | CD1 | ILE | A | 292 | 62.040 | 54.972 | 30.767 | 1.00 | 23.93 | C |
| ATOM | 1353 | N | VAL | A | 293 | 61.502 | 58.296 | 29.322 | 1.00 | 22.08 | N |
| ATOM | 1354 | CA | VAL | A | 293 | 62.765 | 59.028 | 29.320 | 1.00 | 22.29 | C |
| ATOM | 1355 | C | VAL | A | 293 | 63.201 | 59.555 | 30.678 | 1.00 | 22.70 | C |
| ATOM | 1356 | O | VAL | A | 293 | 64.187 | 60.282 | 30.766 | 1.00 | 22.85 | O |
| ATOM | 1357 | CB | VAL | A | 293 | 62.720 | 60.228 | 28.346 | 1.00 | 22.95 | C |
| ATOM | 1358 | CG1 | VAL | A | 293 | 62.595 | 59.730 | 26.906 | 1.00 | 22.15 | C |
| ATOM | 1359 | CG2 | VAL | A | 293 | 61.550 | 61.148 | 28.706 | 1.00 | 22.40 | C |
| ATOM | 1360 | N | ASP | A | 294 | 62.474 | 59.209 | 31.736 | 1.00 | 22.82 | N |
| ATOM | 1361 | CA | ASP | A | 294 | 62.851 | 59.680 | 33.060 | 1.00 | 23.34 | C |
| ATOM | 1362 | C | ASP | A | 294 | 62.532 | 58.660 | 34.145 | 1.00 | 23.54 | C |
| ATOM | 1363 | O | ASP | A | 294 | 61.897 | 57.634 | 33.880 | 1.00 | 23.02 | O |
| ATOM | 1364 | CB | ASP | A | 294 | 62.181 | 61.040 | 33.365 | 1.00 | 23.61 | C |
| ATOM | 1365 | CG | ASP | A | 294 | 60.680 | 60.934 | 33.635 | 1.00 | 24.61 | C |
| ATOM | 1366 | OD1 | ASP | A | 294 | 60.057 | 59.898 | 33.323 | 1.00 | 25.36 | O |
| ATOM | 1367 | OD2 | ASP | A | 294 | 60.115 | 61.921 | 34.158 | 1.00 | 24.53 | O |
| ATOM | 1368 | N | GLY | A | 295 | 62.991 | 58.943 | 35.359 | 1.00 | 23.57 | N |
| ATOM | 1369 | CA | GLY | A | 295 | 62.762 | 58.043 | 36.474 | 1.00 | 24.71 | C |
| ATOM | 1370 | C | GLY | A | 295 | 61.300 | 57.752 | 36.756 | 1.00 | 24.99 | C |
| ATOM | 1371 | O | GLY | A | 295 | 60.943 | 56.611 | 37.038 | 1.00 | 24.55 | O |
| ATOM | 1372 | N | GLU | A | 296 | 60.455 | 58.777 | 36.692 | 1.00 | 25.66 | N |
| ATOM | 1373 | CA | GLU | A | 296 | 59.022 | 58.603 | 36.943 | 1.00 | 26.31 | C |
| ATOM | 1374 | C | GLU | A | 296 | 58.413 | 57.575 | 36.001 | 1.00 | 25.52 | C |
| ATOM | 1375 | O | GLU | A | 296 | 57.635 | 56.715 | 36.421 | 1.00 | 24.66 | O |
| ATOM | 1376 | CB | GLU | A | 296 | 58.269 | 59.924 | 36.759 | 1.00 | 28.85 | C |
| ATOM | 1377 | CG | GLU | A | 296 | 58.342 | 60.889 | 37.927 | 1.00 | 33.07 | C |
| ATOM | 1378 | CD | GLU | A | 296 | 57.642 | 62.208 | 37.621 | 1.00 | 36.15 | C |
| ATOM | 1379 | OE1 | GLU | A | 296 | 56.485 | 62.181 | 37.130 | 1.00 | 37.36 | O |
| ATOM | 1380 | OE2 | GLU | A | 296 | 58.250 | 63.272 | 37.871 | 1.00 | 38.01 | O |
| ATOM | 1381 | N | GLY | A | 297 | 58.750 | 57.687 | 34.721 | 1.00 | 25.01 | N |
| ATOM | 1382 | CA | GLY | A | 297 | 58.227 | 56.761 | 33.733 | 1.00 | 24.76 | C |
| ATOM | 1383 | C | GLY | A | 297 | 58.735 | 55.353 | 33.981 | 1.00 | 24.56 | C |
| ATOM | 1384 | O | GLY | A | 297 | 57.976 | 54.384 | 33.891 | 1.00 | 24.54 | O |
| ATOM | 1385 | N | PHE | A | 298 | 60.026 | 55.238 | 34.279 | 1.00 | 23.53 | N |
| ATOM | 1386 | CA | PHE | A | 298 | 60.628 | 53.938 | 34.559 | 1.00 | 23.73 | C |
| ATOM | 1387 | C | PHE | A | 298 | 59.904 | 53.288 | 35.737 | 1.00 | 23.95 | C |
| ATOM | 1388 | O | PHE | A | 298 | 59.470 | 52.140 | 35.659 | 1.00 | 23.92 | O |
| ATOM | 1389 | CB | PHE | A | 298 | 62.107 | 54.091 | 34.926 | 1.00 | 22.70 | C |
| ATOM | 1390 | CG | PHE | A | 298 | 62.710 | 52.844 | 35.510 | 1.00 | 22.74 | C |
| ATOM | 1391 | CD1 | PHE | A | 298 | 63.206 | 51.841 | 34.685 | 1.00 | 22.49 | C |
| ATOM | 1392 | CD2 | PHE | A | 298 | 62.702 | 52.636 | 36.885 | 1.00 | 22.82 | C |
| ATOM | 1393 | CE1 | PHE | A | 298 | 63.680 | 50.645 | 35.223 | 1.00 | 22.80 | C |
| ATOM | 1394 | CE2 | PHE | A | 298 | 63.171 | 51.447 | 37.433 | 1.00 | 22.71 | C |
| ATOM | 1395 | CZ | PHE | A | 298 | 63.659 | 50.448 | 36.599 | 1.00 | 22.47 | C |
| ATOM | 1396 | N | ARG | A | 299 | 59.800 | 54.043 | 36.829 | 1.00 | 24.49 | N |
| ATOM | 1397 | CA | ARG | A | 299 | 59.158 | 53.588 | 38.062 | 1.00 | 25.88 | C |
| ATOM | 1398 | C | ARG | A | 299 | 57.736 | 53.090 | 37.833 | 1.00 | 25.06 | C |
| ATOM | 1399 | O | ARG | A | 299 | 57.323 | 52.074 | 38.402 | 1.00 | 24.51 | O |
| ATOM | 1400 | CB | ARG | A | 299 | 59.154 | 54.735 | 39.080 | 1.00 | 28.63 | C |
| ATOM | 1401 | CG | ARG | A | 299 | 58.300 | 54.510 | 40.313 | 1.00 | 32.44 | C |
| ATOM | 1402 | CD | ARG | A | 299 | 59.044 | 53.764 | 41.400 | 1.00 | 35.12 | C |
| ATOM | 1403 | NE | ARG | A | 299 | 60.302 | 54.414 | 41.772 | 1.00 | 37.30 | N |
| ATOM | 1404 | CZ | ARG | A | 299 | 61.032 | 54.061 | 42.827 | 1.00 | 37.36 | C |
| ATOM | 1405 | NH1 | ARG | A | 299 | 60.620 | 53.077 | 43.614 | 1.00 | 37.31 | N |
| ATOM | 1406 | NH2 | ARG | A | 299 | 62.186 | 54.665 | 43.079 | 1.00 | 37.90 | N |
| ATOM | 1407 | N | TYR | A | 300 | 56.987 | 53.804 | 36.998 | 1.00 | 23.80 | N |
| ATOM | 1408 | CA | TYR | A | 300 | 55.615 | 53.413 | 36.717 | 1.00 | 23.18 | C |
| ATOM | 1409 | C | TYR | A | 300 | 55.549 | 52.050 | 36.022 | 1.00 | 22.98 | C |
| ATOM | 1410 | O | TYR | A | 300 | 54.760 | 51.189 | 36.405 | 1.00 | 22.25 | O |
| ATOM | 1411 | CB | TYR | A | 300 | 54.929 | 54.460 | 35.837 | 1.00 | 23.21 | C |
| ATOM | 1412 | CG | TYR | A | 300 | 53.474 | 54.153 | 35.573 | 1.00 | 23.56 | C |
| ATOM | 1413 | CD1 | TYR | A | 300 | 52.505 | 54.362 | 36.560 | 1.00 | 24.05 | C |
| ATOM | 1414 | CD2 | TYR | A | 300 | 53.066 | 53.632 | 34.349 | 1.00 | 23.81 | C |
| ATOM | 1415 | CE1 | TYR | A | 300 | 51.164 | 54.059 | 36.325 | 1.00 | 24.38 | C |
| ATOM | 1416 | CE2 | TYR | A | 300 | 51.734 | 53.325 | 34.105 | 1.00 | 24.00 | C |
| ATOM | 1417 | CZ | TYR | A | 300 | 50.790 | 53.540 | 35.094 | 1.00 | 23.95 | C |
| ATOM | 1418 | OH | TYR | A | 300 | 49.474 | 53.239 | 34.845 | 1.00 | 24.48 | O |
| ATOM | 1419 | N | LEU | A | 301 | 56.372 | 51.857 | 34.996 | 1.00 | 21.97 | N |
| ATOM | 1420 | CA | LEU | A | 301 | 56.366 | 50.592 | 34.274 | 1.00 | 22.14 | C |
| ATOM | 1421 | C | LEU | A | 301 | 56.991 | 49.463 | 35.102 | 1.00 | 22.14 | C |
| ATOM | 1422 | O | LEU | A | 301 | 56.625 | 48.298 | 34.947 | 1.00 | 22.36 | O |
| ATOM | 1423 | CB | LEU | A | 301 | 57.081 | 50.741 | 32.920 | 1.00 | 21.32 | C |
| ATOM | 1424 | CG | LEU | A | 301 | 56.381 | 51.668 | 31.909 | 1.00 | 21.51 | C |

TABLE 3-continued

| | | | | | | | | | | | |
|---|---|---|---|---|---|---|---|---|---|---|---|
| ATOM | 1425 | CD1 | LEU | A | 301 | 57.204 | 51.757 | 30.618 | 1.00 | 21.05 | C |
| ATOM | 1426 | CD2 | LEU | A | 301 | 54.972 | 51.136 | 31.607 | 1.00 | 21.05 | C |
| ATOM | 1427 | N | ALA | A | 302 | 57.925 | 49.808 | 35.984 | 1.00 | 22.39 | N |
| ATOM | 1428 | CA | ALA | A | 302 | 58.559 | 48.799 | 36.833 | 1.00 | 23.49 | C |
| ATOM | 1429 | C | ALA | A | 302 | 57.500 | 48.240 | 37.790 | 1.00 | 24.06 | C |
| ATOM | 1430 | O | ALA | A | 302 | 57.357 | 47.022 | 37.937 | 1.00 | 23.67 | O |
| ATOM | 1431 | CB | ALA | A | 302 | 59.708 | 49.415 | 37.625 | 1.00 | 22.59 | C |
| ATOM | 1432 | N | ASP | A | 303 | 56.760 | 49.138 | 38.432 | 1.00 | 24.53 | N |
| ATOM | 1433 | CA | ASP | A | 303 | 55.709 | 48.734 | 39.360 | 1.00 | 26.12 | C |
| ATOM | 1434 | C | ASP | A | 303 | 54.589 | 48.010 | 38.614 | 1.00 | 26.16 | C |
| ATOM | 1435 | O | ASP | A | 303 | 53.891 | 47.179 | 39.194 | 1.00 | 26.12 | O |
| ATOM | 1436 | CB | ASP | A | 303 | 55.121 | 49.948 | 40.094 | 1.00 | 27.14 | C |
| ATOM | 1437 | CG | ASP | A | 303 | 56.086 | 50.560 | 41.103 | 1.00 | 28.94 | C |
| ATOM | 1438 | OD1 | ASP | A | 303 | 56.998 | 49.856 | 41.586 | 1.00 | 30.42 | O |
| ATOM | 1439 | OD2 | ASP | A | 303 | 55.916 | 51.751 | 41.432 | 1.00 | 30.69 | O |
| ATOM | 1440 | N | ALA | A | 304 | 54.416 | 48.333 | 37.332 | 1.00 | 25.47 | N |
| ATOM | 1441 | CA | ALA | A | 304 | 53.386 | 47.695 | 36.517 | 1.00 | 25.15 | C |
| ATOM | 1442 | C | ALA | A | 304 | 53.755 | 46.246 | 36.196 | 1.00 | 25.19 | C |
| ATOM | 1443 | O | ALA | A | 304 | 52.895 | 45.451 | 35.811 | 1.00 | 24.86 | O |
| ATOM | 1444 | CB | ALA | A | 304 | 53.172 | 48.472 | 35.233 | 1.00 | 24.93 | C |
| ATOM | 1445 | N | GLY | A | 305 | 55.035 | 45.909 | 36.337 | 1.00 | 24.65 | N |
| ATOM | 1446 | CA | GLY | A | 305 | 55.461 | 44.540 | 36.086 | 1.00 | 24.64 | C |
| ATOM | 1447 | C | GLY | A | 305 | 56.306 | 44.266 | 34.851 | 1.00 | 24.36 | C |
| ATOM | 1448 | O | GLY | A | 305 | 56.597 | 43.107 | 34.547 | 1.00 | 24.74 | O |
| ATOM | 1449 | N | ALA | A | 306 | 56.711 | 45.311 | 34.140 | 1.00 | 23.62 | N |
| ATOM | 1450 | CA | ALA | A | 306 | 57.521 | 45.136 | 32.935 | 1.00 | 23.66 | C |
| ATOM | 1451 | C | ALA | A | 306 | 58.803 | 44.351 | 33.214 | 1.00 | 23.20 | C |
| ATOM | 1452 | O | ALA | A | 306 | 59.430 | 44.532 | 34.256 | 1.00 | 23.66 | O |
| ATOM | 1453 | CB | ALA | A | 306 | 57.866 | 46.499 | 32.336 | 1.00 | 22.87 | C |
| ATOM | 1454 | N | ASP | A | 307 | 59.188 | 43.490 | 32.274 | 1.00 | 23.16 | N |
| ATOM | 1455 | CA | ASP | A | 307 | 60.398 | 42.679 | 32.406 | 1.00 | 22.69 | C |
| ATOM | 1456 | C | ASP | A | 307 | 61.659 | 43.439 | 31.998 | 1.00 | 22.59 | C |
| ATOM | 1457 | O | ASP | A | 307 | 62.764 | 43.098 | 32.415 | 1.00 | 22.56 | O |
| ATOM | 1458 | CB | ASP | A | 307 | 60.243 | 41.391 | 31.601 | 1.00 | 23.45 | C |
| ATOM | 1459 | CG | ASP | A | 307 | 59.292 | 40.424 | 32.267 | 1.00 | 23.60 | C |
| ATOM | 1460 | OD1 | ASP | A | 307 | 59.626 | 39.963 | 33.375 | 1.00 | 24.19 | O |
| ATOM | 1461 | OD2 | ASP | A | 307 | 58.217 | 40.144 | 31.705 | 1.00 | 23.04 | O |
| ATOM | 1462 | N | PHE | A | 308 | 61.482 | 44.453 | 31.159 | 1.00 | 22.02 | N |
| ATOM | 1463 | CA | PHE | A | 308 | 62.571 | 45.334 | 30.756 | 1.00 | 21.84 | C |
| ATOM | 1464 | C | PHE | A | 308 | 61.903 | 46.608 | 30.264 | 1.00 | 21.93 | C |
| ATOM | 1465 | O | PHE | A | 308 | 60.755 | 46.587 | 29.809 | 1.00 | 20.69 | O |
| ATOM | 1466 | CB | PHE | A | 308 | 63.505 | 44.695 | 29.700 | 1.00 | 21.68 | C |
| ATOM | 1467 | CG | PHE | A | 308 | 62.928 | 44.596 | 28.312 | 1.00 | 22.97 | C |
| ATOM | 1468 | CD1 | PHE | A | 308 | 62.892 | 45.707 | 27.470 | 1.00 | 23.01 | C |
| ATOM | 1469 | CD2 | PHE | A | 308 | 62.487 | 43.369 | 27.820 | 1.00 | 22.89 | C |
| ATOM | 1470 | CE1 | PHE | A | 308 | 62.431 | 45.596 | 26.153 | 1.00 | 23.45 | C |
| ATOM | 1471 | CE2 | PHE | A | 308 | 62.023 | 43.245 | 26.504 | 1.00 | 23.97 | C |
| ATOM | 1472 | CZ | PHE | A | 308 | 61.998 | 44.362 | 25.669 | 1.00 | 23.35 | C |
| ATOM | 1473 | N | ILE | A | 309 | 62.609 | 47.724 | 30.381 | 1.00 | 20.99 | N |
| ATOM | 1474 | CA | ILE | A | 309 | 62.040 | 49.001 | 29.994 | 1.00 | 21.61 | C |
| ATOM | 1475 | C | ILE | A | 309 | 62.877 | 49.704 | 28.929 | 1.00 | 21.29 | C |
| ATOM | 1476 | O | ILE | A | 309 | 64.096 | 49.835 | 29.071 | 1.00 | 20.03 | O |
| ATOM | 1477 | CB | ILE | A | 309 | 61.866 | 49.881 | 31.264 | 1.00 | 21.66 | C |
| ATOM | 1478 | CG1 | ILE | A | 309 | 60.841 | 49.204 | 32.189 | 1.00 | 22.00 | C |
| ATOM | 1479 | CG2 | ILE | A | 309 | 61.444 | 51.298 | 30.886 | 1.00 | 20.92 | C |
| ATOM | 1480 | CD1 | ILE | A | 309 | 60.725 | 49.797 | 33.575 | 1.00 | 22.70 | C |
| ATOM | 1481 | N | LYS | A | 310 | 62.212 | 50.132 | 27.854 | 1.00 | 21.58 | N |
| ATOM | 1482 | CA | LYS | A | 310 | 62.884 | 50.809 | 26.745 | 1.00 | 21.98 | C |
| ATOM | 1483 | C | LYS | A | 310 | 62.919 | 52.317 | 26.942 | 1.00 | 21.74 | C |
| ATOM | 1484 | O | LYS | A | 310 | 61.907 | 52.942 | 27.271 | 1.00 | 21.19 | O |
| ATOM | 1485 | CB | LYS | A | 310 | 62.211 | 50.489 | 25.404 | 1.00 | 23.35 | C |
| ATOM | 1486 | CG | LYS | A | 310 | 62.440 | 49.071 | 24.915 | 1.00 | 26.33 | C |
| ATOM | 1487 | CD | LYS | A | 310 | 62.448 | 48.987 | 23.377 | 1.00 | 24.86 | C |
| ATOM | 1488 | CE | LYS | A | 310 | 61.072 | 49.221 | 22.764 | 1.00 | 26.09 | C |
| ATOM | 1489 | NZ | LYS | A | 310 | 60.922 | 50.568 | 22.124 | 1.00 | 25.19 | N |
| ATOM | 1490 | N | ILE | A | 311 | 64.093 | 52.890 | 26.704 | 1.00 | 20.80 | N |
| ATOM | 1491 | CA | ILE | A | 311 | 64.330 | 54.319 | 26.888 | 1.00 | 20.47 | C |
| ATOM | 1492 | C | ILE | A | 311 | 64.496 | 55.076 | 25.578 | 1.00 | 20.59 | C |
| ATOM | 1493 | O | ILE | A | 311 | 65.258 | 54.658 | 24.707 | 1.00 | 20.84 | O |
| ATOM | 1494 | CB | ILE | A | 311 | 65.625 | 54.543 | 27.695 | 1.00 | 19.79 | C |
| ATOM | 1495 | CG1 | ILE | A | 311 | 65.544 | 53.813 | 29.039 | 1.00 | 19.38 | C |
| ATOM | 1496 | CG2 | ILE | A | 311 | 65.876 | 56.037 | 27.885 | 1.00 | 19.52 | C |
| ATOM | 1497 | CD1 | ILE | A | 311 | 66.917 | 53.602 | 29.686 | 1.00 | 19.29 | C |
| ATOM | 1498 | N | GLY | A | 312 | 63.796 | 56.197 | 25.444 | 1.00 | 21.35 | N |
| ATOM | 1499 | CA | GLY | A | 312 | 63.962 | 56.992 | 24.247 | 1.00 | 22.14 | C |
| ATOM | 1500 | C | GLY | A | 312 | 62.738 | 57.526 | 23.542 | 1.00 | 22.59 | C |
| ATOM | 1501 | O | GLY | A | 312 | 61.877 | 56.771 | 23.106 | 1.00 | 22.49 | O |
| ATOM | 1502 | N | ILE | A | 313 | 62.670 | 58.847 | 23.430 | 1.00 | 23.41 | N |
| ATOM | 1503 | CA | ILE | A | 313 | 61.577 | 59.497 | 22.725 | 1.00 | 24.56 | C |

TABLE 3-continued

| | | | | | | | | | | |
|---|---|---|---|---|---|---|---|---|---|---|
| ATOM | 1504 | C | ILE | A | 313 | 62.156 | 60.654 | 21.912 | 1.00 | 25.54 | C |
| ATOM | 1505 | O | ILE | A | 313 | 62.786 | 61.553 | 22.467 | 1.00 | 24.97 | O |
| ATOM | 1506 | CB | ILE | A | 313 | 60.505 | 60.047 | 23.692 | 1.00 | 24.81 | C |
| ATOM | 1507 | CG1 | ILE | A | 313 | 59.855 | 58.896 | 24.471 | 1.00 | 24.74 | C |
| ATOM | 1508 | CG2 | ILE | A | 313 | 59.447 | 60.804 | 22.904 | 1.00 | 25.11 | C |
| ATOM | 1509 | CD1 | ILE | A | 313 | 58.854 | 59.350 | 25.526 | 1.00 | 25.63 | C |
| ATOM | 1510 | N | GLY | A | 314 | 61.962 | 60.609 | 20.596 | 1.00 | 27.37 | N |
| ATOM | 1511 | CA | GLY | A | 314 | 62.451 | 61.673 | 19.729 | 1.00 | 29.50 | C |
| ATOM | 1512 | C | GLY | A | 314 | 63.927 | 61.641 | 19.369 | 1.00 | 31.01 | C |
| ATOM | 1513 | O | GLY | A | 314 | 64.422 | 62.554 | 18.706 | 1.00 | 32.03 | O |
| ATOM | 1514 | N | GLY | A | 315 | 64.636 | 60.598 | 19.791 | 1.00 | 31.66 | N |
| ATOM | 1515 | CA | GLY | A | 315 | 66.056 | 60.505 | 19.490 | 1.00 | 32.68 | C |
| ATOM | 1516 | C | GLY | A | 315 | 66.396 | 59.643 | 18.285 | 1.00 | 33.40 | C |
| ATOM | 1517 | O | GLY | A | 315 | 67.553 | 59.576 | 17.876 | 1.00 | 33.37 | O |
| ATOM | 1518 | N | GLY | A | 316 | 65.396 | 58.985 | 17.710 | 1.00 | 34.10 | N |
| ATOM | 1519 | CA | GLY | A | 316 | 65.644 | 58.137 | 16.555 | 1.00 | 35.23 | C |
| ATOM | 1520 | C | GLY | A | 316 | 66.065 | 58.913 | 15.319 | 1.00 | 36.50 | C |
| ATOM | 1521 | O | GLY | A | 316 | 65.677 | 60.070 | 15.141 | 1.00 | 36.03 | O |
| ATOM | 1522 | N | SER | A | 317 | 66.857 | 58.276 | 14.460 | 1.00 | 37.55 | N |
| ATOM | 1523 | CA | SER | A | 317 | 67.337 | 58.911 | 13.236 | 1.00 | 39.31 | C |
| ATOM | 1524 | C | SER | A | 317 | 66.171 | 59.337 | 12.356 | 1.00 | 40.68 | C |
| ATOM | 1525 | O | SER | A | 317 | 66.295 | 60.251 | 11.543 | 1.00 | 40.52 | O |
| ATOM | 1526 | CB | SER | A | 317 | 68.240 | 57.951 | 12.453 | 1.00 | 38.70 | C |
| ATOM | 1527 | OG | SER | A | 317 | 67.512 | 56.826 | 11.980 | 1.00 | 38.86 | O |
| ATOM | 1528 | N | ILE | A | 318 | 65.040 | 58.663 | 12.522 | 1.00 | 42.85 | N |
| ATOM | 1529 | CA | ILE | A | 318 | 63.842 | 58.960 | 11.751 | 1.00 | 45.43 | C |
| ATOM | 1530 | C | ILE | A | 318 | 63.419 | 60.410 | 11.977 | 1.00 | 47.03 | C |
| ATOM | 1531 | O | ILE | A | 318 | 62.896 | 61.062 | 11.074 | 1.00 | 47.28 | O |
| ATOM | 1532 | CB | ILE | A | 318 | 62.667 | 58.043 | 12.165 | 1.00 | 45.77 | C |
| ATOM | 1533 | CG1 | ILE | A | 318 | 63.127 | 56.586 | 12.239 | 1.00 | 46.41 | C |
| ATOM | 1534 | CG2 | ILE | A | 318 | 61.541 | 58.171 | 11.171 | 1.00 | 46.37 | C |
| ATOM | 1535 | CD1 | ILE | A | 318 | 63.984 | 56.265 | 13.459 | 1.00 | 46.06 | C |
| HETATM | 1536 | N | CSO | A | 319 | 63.652 | 60.907 | 13.188 | 1.00 | 48.82 | N |
| HETATM | 1537 | CA | CSO | A | 319 | 63.290 | 62.276 | 13.544 | 1.00 | 51.09 | C |
| HETATM | 1538 | CB | CSO | A | 319 | 63.435 | 62.481 | 15.053 | 1.00 | 50.48 | C |
| HETATM | 1539 | SG | CSO | A | 319 | 62.220 | 61.534 | 16.020 | 1.00 | 49.21 | S |
| HETATM | 1540 | C | CSO | A | 319 | 64.088 | 63.347 | 12.809 | 1.00 | 52.89 | C |
| HETATM | 1541 | O | CSO | A | 319 | 63.690 | 64.513 | 12.782 | 1.00 | 53.33 | O |
| HETATM | 1542 | OD | CSO | A | 319 | 60.509 | 62.125 | 15.865 | 1.00 | 49.59 | O |
| ATOM | 1543 | N | ILE | A | 320 | 65.210 | 62.955 | 12.215 | 1.00 | 54.92 | N |
| ATOM | 1544 | CA | ILE | A | 320 | 66.048 | 63.899 | 11.484 | 1.00 | 56.96 | C |
| ATOM | 1545 | C | ILE | A | 320 | 65.262 | 64.568 | 10.360 | 1.00 | 58.10 | C |
| ATOM | 1546 | O | ILE | A | 320 | 65.443 | 65.756 | 10.083 | 1.00 | 58.63 | O |
| ATOM | 1547 | CB | ILE | A | 320 | 67.279 | 63.197 | 10.873 | 1.00 | 57.26 | C |
| ATOM | 1548 | CG1 | ILE | A | 320 | 68.121 | 62.562 | 11.983 | 1.00 | 57.57 | C |
| ATOM | 1549 | CG2 | ILE | A | 320 | 68.113 | 64.201 | 10.089 | 1.00 | 57.46 | C |
| ATOM | 1550 | CD1 | ILE | A | 320 | 69.282 | 61.731 | 11.473 | 1.00 | 57.71 | C |
| ATOM | 1551 | N | THR | A | 321 | 64.389 | 63.801 | 9.714 | 1.00 | 59.12 | N |
| ATOM | 1552 | CA | THR | A | 321 | 63.583 | 64.323 | 8.618 | 1.00 | 60.34 | C |
| ATOM | 1553 | C | THR | A | 321 | 62.103 | 64.387 | 8.985 | 1.00 | 60.84 | C |
| ATOM | 1554 | O | THR | A | 321 | 61.257 | 63.773 | 8.330 | 1.00 | 61.34 | O |
| ATOM | 1555 | CB | THR | A | 321 | 63.755 | 63.464 | 7.352 | 1.00 | 60.65 | C |
| ATOM | 1556 | OG1 | THR | A | 321 | 63.414 | 62.105 | 7.647 | 1.00 | 61.41 | O |
| ATOM | 1557 | CG2 | THR | A | 321 | 65.195 | 63.524 | 6.860 | 1.00 | 60.98 | C |
| ATOM | 1558 | N | ARG | A | 322 | 61.806 | 65.138 | 10.040 | 1.00 | 61.12 | N |
| ATOM | 1559 | CA | ARG | A | 322 | 60.441 | 65.314 | 10.523 | 1.00 | 61.24 | C |
| ATOM | 1560 | C | ARG | A | 322 | 60.445 | 66.385 | 11.606 | 1.00 | 60.69 | C |
| ATOM | 1561 | O | ARG | A | 322 | 61.501 | 66.723 | 12.145 | 1.00 | 60.84 | O |
| ATOM | 1562 | CB | ARG | A | 322 | 59.901 | 63.994 | 11.080 | 1.00 | 62.07 | C |
| ATOM | 1563 | CG | ARG | A | 322 | 58.509 | 64.074 | 11.698 | 1.00 | 63.32 | C |
| ATOM | 1564 | CD | ARG | A | 322 | 57.518 | 64.813 | 10.804 | 1.00 | 64.42 | C |
| ATOM | 1565 | NE | ARG | A | 322 | 57.486 | 64.287 | 9.442 | 1.00 | 65.37 | N |
| ATOM | 1566 | CZ | ARG | A | 322 | 56.737 | 64.792 | 8.466 | 1.00 | 65.78 | C |
| ATOM | 1567 | NH1 | ARG | A | 322 | 55.955 | 65.838 | 8.702 | 1.00 | 65.97 | N |
| ATOM | 1568 | NH2 | ARG | A | 322 | 56.774 | 64.258 | 7.253 | 1.00 | 65.94 | N |
| ATOM | 1569 | N | GLU | A | 323 | 59.272 | 66.925 | 11.919 | 1.00 | 59.94 | N |
| ATOM | 1570 | CA | GLU | A | 323 | 59.174 | 67.960 | 12.940 | 1.00 | 59.06 | C |
| ATOM | 1571 | C | GLU | A | 323 | 58.885 | 67.393 | 14.325 | 1.00 | 57.87 | C |
| ATOM | 1572 | O | GLU | A | 323 | 58.236 | 66.355 | 14.466 | 1.00 | 57.61 | O |
| ATOM | 1573 | CB | GLU | A | 323 | 58.096 | 68.981 | 12.570 | 1.00 | 59.76 | C |
| ATOM | 1574 | CG | GLU | A | 323 | 57.938 | 70.098 | 13.597 | 1.00 | 60.62 | C |
| ATOM | 1575 | CD | GLU | A | 323 | 59.243 | 70.833 | 13.897 | 1.00 | 61.14 | C |
| ATOM | 1576 | OE1 | GLU | A | 323 | 59.296 | 71.537 | 14.928 | 1.00 | 61.68 | O |
| ATOM | 1577 | OE2 | GLU | A | 323 | 60.211 | 70.719 | 13.113 | 1.00 | 61.24 | O |
| ATOM | 1578 | N | GLN | A | 324 | 59.379 | 68.091 | 15.343 | 1.00 | 56.34 | N |
| ATOM | 1579 | CA | GLN | A | 324 | 59.192 | 67.685 | 16.729 | 1.00 | 54.78 | C |
| ATOM | 1580 | C | GLN | A | 324 | 57.726 | 67.648 | 17.141 | 1.00 | 53.18 | C |
| ATOM | 1581 | O | GLN | A | 324 | 56.947 | 68.537 | 16.794 | 1.00 | 53.10 | O |
| ATOM | 1582 | CB | GLN | A | 324 | 59.956 | 68.634 | 17.658 | 1.00 | 55.79 | C |

TABLE 3-continued

| | | | | | | | | | | |
|---|---|---|---|---|---|---|---|---|---|---|
| ATOM | 1583 | CG | GLN | A | 324 | 61.319 | 68.127 | 18.094 | 1.00 | 56.75 | C |
| ATOM | 1584 | CD | GLN | A | 324 | 61.220 | 66.843 | 18.891 | 1.00 | 57.57 | C |
| ATOM | 1585 | OE1 | GLN | A | 324 | 60.430 | 66.746 | 19.830 | 1.00 | 58.20 | O |
| ATOM | 1586 | NE2 | GLN | A | 324 | 62.025 | 65.849 | 18.524 | 1.00 | 58.36 | N |
| ATOM | 1587 | N | LYS | A | 325 | 57.357 | 66.607 | 17.880 | 1.00 | 50.98 | N |
| ATOM | 1588 | CA | LYS | A | 325 | 55.992 | 66.461 | 18.367 | 1.00 | 48.78 | C |
| ATOM | 1589 | C | LYS | A | 325 | 55.860 | 67.276 | 19.651 | 1.00 | 46.62 | C |
| ATOM | 1590 | O | LYS | A | 325 | 54.757 | 67.518 | 20.140 | 1.00 | 47.07 | O |
| ATOM | 1591 | CB | LYS | A | 325 | 55.680 | 64.987 | 18.648 | 1.00 | 49.79 | C |
| ATOM | 1592 | CG | LYS | A | 325 | 54.374 | 64.759 | 19.405 | 1.00 | 50.84 | C |
| ATOM | 1593 | CD | LYS | A | 325 | 54.094 | 63.274 | 19.607 | 1.00 | 51.53 | C |
| ATOM | 1594 | CE | LYS | A | 325 | 53.023 | 63.046 | 20.668 | 1.00 | 51.83 | C |
| ATOM | 1595 | NZ | LYS | A | 325 | 51.726 | 63.694 | 20.333 | 1.00 | 52.33 | N |
| ATOM | 1596 | N | GLY | A | 326 | 56.997 | 67.701 | 20.193 | 1.00 | 43.50 | N |
| ATOM | 1597 | CA | GLY | A | 326 | 56.973 | 68.490 | 21.409 | 1.00 | 40.48 | C |
| ATOM | 1598 | C | GLY | A | 326 | 57.413 | 67.734 | 22.648 | 1.00 | 38.13 | C |
| ATOM | 1599 | O | GLY | A | 326 | 57.736 | 68.347 | 23.664 | 1.00 | 37.44 | O |
| ATOM | 1600 | N | ILE | A | 327 | 57.422 | 66.405 | 22.569 | 1.00 | 36.05 | N |
| ATOM | 1601 | CA | ILE | A | 327 | 57.836 | 65.579 | 23.696 | 1.00 | 34.00 | C |
| ATOM | 1602 | C | ILE | A | 327 | 59.153 | 64.882 | 23.381 | 1.00 | 32.98 | C |
| ATOM | 1603 | O | ILE | A | 327 | 59.400 | 64.481 | 22.244 | 1.00 | 32.36 | O |
| ATOM | 1604 | CB | ILE | A | 327 | 56.776 | 64.498 | 24.037 | 1.00 | 34.45 | C |
| ATOM | 1605 | CG1 | ILE | A | 327 | 56.576 | 63.557 | 22.845 | 1.00 | 34.20 | C |
| ATOM | 1606 | CG2 | ILE | A | 327 | 55.453 | 65.165 | 24.413 | 1.00 | 34.27 | C |
| ATOM | 1607 | CD1 | ILE | A | 327 | 55.626 | 62.390 | 23.132 | 1.00 | 35.32 | C |
| ATOM | 1608 | N | GLY | A | 328 | 60.001 | 64.741 | 24.390 | 1.00 | 31.07 | N |
| ATOM | 1609 | CA | GLY | A | 328 | 61.268 | 64.078 | 24.166 | 1.00 | 29.89 | C |
| ATOM | 1610 | C | GLY | A | 328 | 62.337 | 64.489 | 25.151 | 1.00 | 28.34 | C |
| ATOM | 1611 | O | GLY | A | 328 | 62.082 | 65.254 | 26.080 | 1.00 | 27.64 | O |
| ATOM | 1612 | N | ARG | A | 329 | 63.545 | 63.980 | 24.930 | 1.00 | 26.67 | N |
| ATOM | 1613 | CA | ARG | A | 329 | 64.669 | 64.283 | 25.797 | 1.00 | 25.93 | C |
| ATOM | 1614 | C | ARG | A | 329 | 65.940 | 63.749 | 25.142 | 1.00 | 24.65 | C |
| ATOM | 1615 | O | ARG | A | 329 | 65.904 | 62.714 | 24.485 | 1.00 | 24.97 | O |
| ATOM | 1616 | CB | ARG | A | 329 | 64.458 | 63.605 | 27.154 | 1.00 | 25.47 | C |
| ATOM | 1617 | CG | ARG | A | 329 | 65.375 | 64.095 | 28.248 | 1.00 | 25.11 | C |
| ATOM | 1618 | CD | ARG | A | 329 | 65.056 | 63.413 | 29.568 | 1.00 | 24.72 | C |
| ATOM | 1619 | NE | ARG | A | 329 | 65.626 | 64.149 | 30.692 | 1.00 | 24.50 | N |
| ATOM | 1620 | CZ | ARG | A | 329 | 65.577 | 63.743 | 31.955 | 1.00 | 25.99 | C |
| ATOM | 1621 | NH1 | ARG | A | 329 | 64.986 | 62.595 | 32.267 | 1.00 | 24.83 | N |
| ATOM | 1622 | NH2 | ARG | A | 329 | 66.104 | 64.497 | 32.909 | 1.00 | 26.04 | N |
| ATOM | 1623 | N | GLY | A | 330 | 67.054 | 64.458 | 25.304 | 1.00 | 24.47 | N |
| ATOM | 1624 | CA | GLY | A | 330 | 68.305 | 63.977 | 24.737 | 1.00 | 24.08 | C |
| ATOM | 1625 | C | GLY | A | 330 | 68.487 | 62.533 | 25.182 | 1.00 | 24.18 | C |
| ATOM | 1626 | O | GLY | A | 330 | 68.292 | 62.222 | 26.358 | 1.00 | 22.92 | O |
| ATOM | 1627 | N | GLN | A | 331 | 68.857 | 61.655 | 24.254 | 1.00 | 24.04 | N |
| ATOM | 1628 | CA | GLN | A | 331 | 69.022 | 60.230 | 24.551 | 1.00 | 24.22 | C |
| ATOM | 1629 | C | GLN | A | 331 | 70.004 | 59.909 | 25.679 | 1.00 | 24.49 | C |
| ATOM | 1630 | O | GLN | A | 331 | 69.737 | 59.033 | 26.503 | 1.00 | 24.57 | O |
| ATOM | 1631 | CB | GLN | A | 331 | 69.445 | 59.470 | 23.286 | 1.00 | 24.17 | C |
| ATOM | 1632 | CG | GLN | A | 331 | 69.411 | 57.946 | 23.436 | 1.00 | 24.47 | C |
| ATOM | 1633 | CD | GLN | A | 331 | 67.988 | 57.392 | 23.540 | 1.00 | 25.33 | C |
| ATOM | 1634 | OE1 | GLN | A | 331 | 67.777 | 56.262 | 23.989 | 1.00 | 25.75 | O |
| ATOM | 1635 | NE2 | GLN | A | 331 | 67.013 | 58.183 | 23.112 | 1.00 | 24.22 | N |
| ATOM | 1636 | N | ALA | A | 332 | 71.139 | 60.602 | 25.713 | 1.00 | 23.98 | N |
| ATOM | 1637 | CA | ALA | A | 332 | 72.138 | 60.355 | 26.746 | 1.00 | 23.64 | C |
| ATOM | 1638 | C | ALA | A | 332 | 71.576 | 60.692 | 28.124 | 1.00 | 23.77 | C |
| ATOM | 1639 | O | ALA | A | 332 | 71.673 | 59.892 | 29.058 | 1.00 | 22.81 | O |
| ATOM | 1640 | CB | ALA | A | 332 | 73.403 | 61.176 | 26.470 | 1.00 | 23.79 | C |
| ATOM | 1641 | N | THR | A | 333 | 70.982 | 61.875 | 28.245 | 1.00 | 23.32 | N |
| ATOM | 1642 | CA | THR | A | 333 | 70.401 | 62.302 | 29.510 | 1.00 | 23.16 | C |
| ATOM | 1643 | C | THR | A | 333 | 69.294 | 61.345 | 29.954 | 1.00 | 23.11 | C |
| ATOM | 1644 | O | THR | A | 333 | 69.163 | 61.040 | 31.144 | 1.00 | 22.07 | O |
| ATOM | 1645 | CB | THR | A | 333 | 69.814 | 63.717 | 29.398 | 1.00 | 23.96 | C |
| ATOM | 1646 | OG1 | THR | A | 333 | 70.838 | 64.619 | 28.960 | 1.00 | 25.42 | O |
| ATOM | 1647 | CG2 | THR | A | 333 | 69.273 | 64.179 | 30.749 | 1.00 | 24.50 | C |
| ATOM | 1648 | N | ALA | A | 334 | 68.497 | 60.884 | 28.995 | 1.00 | 22.70 | N |
| ATOM | 1649 | CA | ALA | A | 334 | 67.407 | 59.959 | 29.292 | 1.00 | 23.13 | C |
| ATOM | 1650 | C | ALA | A | 334 | 67.949 | 58.654 | 29.886 | 1.00 | 22.44 | C |
| ATOM | 1651 | O | ALA | A | 334 | 67.456 | 58.175 | 30.907 | 1.00 | 22.81 | O |
| ATOM | 1652 | CB | ALA | A | 334 | 66.602 | 59.671 | 28.020 | 1.00 | 22.10 | C |
| ATOM | 1653 | N | VAL | A | 335 | 68.965 | 58.085 | 29.251 | 1.00 | 22.20 | N |
| ATOM | 1654 | CA | VAL | A | 335 | 69.556 | 56.840 | 29.737 | 1.00 | 21.98 | C |
| ATOM | 1655 | C | VAL | A | 335 | 70.150 | 57.026 | 31.134 | 1.00 | 22.34 | C |
| ATOM | 1656 | O | VAL | A | 335 | 69.869 | 56.249 | 32.047 | 1.00 | 22.57 | O |
| ATOM | 1657 | CB | VAL | A | 335 | 70.656 | 56.334 | 28.765 | 1.00 | 23.03 | C |
| ATOM | 1658 | CG1 | VAL | A | 335 | 71.411 | 55.152 | 29.378 | 1.00 | 22.63 | C |
| ATOM | 1659 | CG2 | VAL | A | 335 | 70.015 | 55.917 | 27.440 | 1.00 | 22.29 | C |
| ATOM | 1660 | N | ILE | A | 336 | 70.952 | 58.071 | 31.302 | 1.00 | 22.70 | N |
| ATOM | 1661 | CA | ILE | A | 336 | 71.588 | 58.352 | 32.583 | 1.00 | 23.12 | C |

TABLE 3-continued

| | | | | | | | | | | | |
|---|---|---|---|---|---|---|---|---|---|---|---|
| ATOM | 1662 | C | ILE | A | 336 | 70.569 | 58.499 | 33.710 | 1.00 | 23.63 | C |
| ATOM | 1663 | O | ILE | A | 336 | 70.751 | 57.941 | 34.796 | 1.00 | 23.32 | O |
| ATOM | 1664 | CB | ILE | A | 336 | 72.437 | 59.636 | 32.498 | 1.00 | 23.30 | C |
| ATOM | 1665 | CG1 | ILE | A | 336 | 73.614 | 59.406 | 31.545 | 1.00 | 23.03 | C |
| ATOM | 1666 | CG2 | ILE | A | 336 | 72.929 | 60.044 | 33.888 | 1.00 | 23.03 | C |
| ATOM | 1667 | CD1 | ILE | A | 336 | 74.395 | 60.668 | 31.215 | 1.00 | 23.69 | C |
| ATOM | 1668 | N | ASP | A | 337 | 69.500 | 59.248 | 33.449 | 1.00 | 24.24 | N |
| ATOM | 1669 | CA | ASP | A | 337 | 68.457 | 59.471 | 34.447 | 1.00 | 24.71 | C |
| ATOM | 1670 | C | ASP | A | 337 | 67.713 | 58.179 | 34.777 | 1.00 | 24.54 | C |
| ATOM | 1671 | O | ASP | A | 337 | 67.506 | 57.849 | 35.947 | 1.00 | 24.97 | O |
| ATOM | 1672 | CB | ASP | A | 337 | 67.446 | 60.505 | 33.948 | 1.00 | 25.62 | C |
| ATOM | 1673 | CG | ASP | A | 337 | 66.441 | 60.891 | 35.016 | 1.00 | 27.13 | C |
| ATOM | 1674 | OD1 | ASP | A | 337 | 65.279 | 61.195 | 34.679 | 1.00 | 27.55 | O |
| ATOM | 1675 | OD2 | ASP | A | 337 | 66.821 | 60.902 | 36.202 | 1.00 | 29.34 | O |
| ATOM | 1676 | N | VAL | A | 338 | 67.293 | 57.455 | 33.743 | 1.00 | 23.33 | N |
| ATOM | 1677 | CA | VAL | A | 338 | 66.569 | 56.206 | 33.953 | 1.00 | 22.60 | C |
| ATOM | 1678 | C | VAL | A | 338 | 67.430 | 55.171 | 34.672 | 1.00 | 22.27 | C |
| ATOM | 1679 | O | VAL | A | 338 | 66.948 | 54.471 | 35.557 | 1.00 | 21.72 | O |
| ATOM | 1680 | CB | VAL | A | 338 | 66.075 | 55.611 | 32.615 | 1.00 | 22.51 | C |
| ATOM | 1681 | CG1 | VAL | A | 338 | 65.518 | 54.204 | 32.839 | 1.00 | 21.86 | C |
| ATOM | 1682 | CG2 | VAL | A | 338 | 64.985 | 56.514 | 32.023 | 1.00 | 21.22 | C |
| ATOM | 1683 | N | VAL | A | 339 | 68.700 | 55.078 | 34.284 | 1.00 | 22.03 | N |
| ATOM | 1684 | CA | VAL | A | 339 | 69.622 | 54.129 | 34.903 | 1.00 | 21.70 | C |
| ATOM | 1685 | C | VAL | A | 339 | 69.776 | 54.432 | 36.398 | 1.00 | 22.15 | C |
| ATOM | 1686 | O | VAL | A | 339 | 69.853 | 53.520 | 37.219 | 1.00 | 21.73 | O |
| ATOM | 1687 | CB | VAL | A | 339 | 71.015 | 54.174 | 34.214 | 1.00 | 21.11 | C |
| ATOM | 1688 | CG1 | VAL | A | 339 | 72.079 | 53.494 | 35.099 | 1.00 | 20.90 | C |
| ATOM | 1689 | CG2 | VAL | A | 339 | 70.936 | 53.465 | 32.855 | 1.00 | 20.61 | C |
| ATOM | 1690 | N | ALA | A | 340 | 69.821 | 55.712 | 36.749 | 1.00 | 21.99 | N |
| ATOM | 1691 | CA | ALA | A | 340 | 69.957 | 56.085 | 38.155 | 1.00 | 23.22 | C |
| ATOM | 1692 | C | ALA | A | 340 | 68.717 | 55.623 | 38.928 | 1.00 | 22.99 | C |
| ATOM | 1693 | O | ALA | A | 340 | 68.818 | 55.112 | 40.048 | 1.00 | 23.73 | O |
| ATOM | 1694 | CB | ALA | A | 340 | 70.140 | 57.599 | 38.283 | 1.00 | 23.33 | C |
| ATOM | 1695 | N | GLU | A | 341 | 67.549 | 55.788 | 38.320 | 1.00 | 22.81 | N |
| ATOM | 1696 | CA | GLU | A | 341 | 66.298 | 55.376 | 38.955 | 1.00 | 23.25 | C |
| ATOM | 1697 | C | GLU | A | 341 | 66.234 | 53.851 | 39.047 | 1.00 | 22.89 | C |
| ATOM | 1698 | O | GLU | A | 341 | 65.740 | 53.296 | 40.029 | 1.00 | 22.02 | O |
| ATOM | 1699 | CB | GLU | A | 341 | 65.103 | 55.885 | 38.146 | 1.00 | 23.80 | C |
| ATOM | 1700 | CG | GLU | A | 341 | 63.786 | 55.897 | 38.910 | 1.00 | 26.95 | C |
| ATOM | 1701 | CD | GLU | A | 341 | 63.827 | 56.810 | 40.130 | 1.00 | 29.07 | C |
| ATOM | 1702 | OE1 | GLU | A | 341 | 64.433 | 57.902 | 40.052 | 1.00 | 30.17 | O |
| ATOM | 1703 | OE2 | GLU | A | 341 | 63.240 | 56.441 | 41.165 | 1.00 | 30.84 | O |
| ATOM | 1704 | N | ARG | A | 342 | 66.736 | 53.179 | 38.014 | 1.00 | 22.30 | N |
| ATOM | 1705 | CA | ARG | A | 342 | 66.737 | 51.722 | 37.979 | 1.00 | 22.47 | C |
| ATOM | 1706 | C | ARG | A | 342 | 67.639 | 51.169 | 39.084 | 1.00 | 22.30 | C |
| ATOM | 1707 | O | ARG | A | 342 | 67.303 | 50.182 | 39.732 | 1.00 | 22.02 | O |
| ATOM | 1708 | CB | ARG | A | 342 | 67.205 | 51.233 | 36.598 | 1.00 | 22.21 | C |
| ATOM | 1709 | CG | ARG | A | 342 | 67.165 | 49.717 | 36.393 | 1.00 | 21.30 | C |
| ATOM | 1710 | CD | ARG | A | 342 | 68.428 | 49.027 | 36.910 | 1.00 | 21.14 | C |
| ATOM | 1711 | NE | ARG | A | 342 | 69.657 | 49.497 | 36.266 | 1.00 | 21.04 | N |
| ATOM | 1712 | CZ | ARG | A | 342 | 70.024 | 49.221 | 35.012 | 1.00 | 21.58 | C |
| ATOM | 1713 | NH1 | ARG | A | 342 | 69.260 | 48.468 | 34.227 | 1.00 | 20.91 | N |
| ATOM | 1714 | NH2 | ARG | A | 342 | 71.175 | 49.686 | 34.543 | 1.00 | 21.45 | N |
| ATOM | 1715 | N | ASN | A | 343 | 68.780 | 51.813 | 39.304 | 1.00 | 22.59 | N |
| ATOM | 1716 | CA | ASN | A | 343 | 69.697 | 51.356 | 40.343 | 1.00 | 23.77 | C |
| ATOM | 1717 | C | ASN | A | 343 | 69.096 | 51.613 | 41.721 | 1.00 | 24.38 | C |
| ATOM | 1718 | O | ASN | A | 343 | 69.274 | 50.816 | 42.643 | 1.00 | 23.51 | O |
| ATOM | 1719 | CB | ASN | A | 343 | 71.060 | 52.046 | 40.201 | 1.00 | 23.94 | C |
| ATOM | 1720 | CG | ASN | A | 343 | 71.798 | 51.608 | 38.948 | 1.00 | 24.43 | C |
| ATOM | 1721 | OD1 | ASN | A | 343 | 71.500 | 50.554 | 38.386 | 1.00 | 24.77 | O |
| ATOM | 1722 | ND2 | ASN | A | 343 | 72.775 | 52.404 | 38.513 | 1.00 | 24.50 | N |
| ATOM | 1723 | N | LYS | A | 344 | 68.368 | 52.718 | 41.849 | 1.00 | 24.94 | N |
| ATOM | 1724 | CA | LYS | A | 344 | 67.717 | 53.063 | 43.104 | 1.00 | 26.62 | C |
| ATOM | 1725 | C | LYS | A | 344 | 66.626 | 52.029 | 43.368 | 1.00 | 26.38 | C |
| ATOM | 1726 | O | LYS | A | 344 | 66.461 | 51.551 | 44.492 | 1.00 | 26.78 | O |
| ATOM | 1727 | CB | LYS | A | 344 | 67.106 | 54.465 | 43.008 | 1.00 | 29.24 | C |
| ATOM | 1728 | CG | LYS | A | 344 | 66.398 | 54.943 | 44.267 | 1.00 | 32.28 | C |
| ATOM | 1729 | CD | LYS | A | 344 | 65.866 | 56.358 | 44.078 | 1.00 | 34.61 | C |
| ATOM | 1730 | CE | LYS | A | 344 | 65.196 | 56.878 | 45.343 | 1.00 | 36.69 | C |
| ATOM | 1731 | NZ | LYS | A | 344 | 66.161 | 57.002 | 46.475 | 1.00 | 38.80 | N |
| ATOM | 1732 | N | TYR | A | 345 | 65.888 | 51.681 | 42.318 | 1.00 | 25.59 | N |
| ATOM | 1733 | CA | TYR | A | 345 | 64.811 | 50.702 | 42.412 | 1.00 | 25.49 | C |
| ATOM | 1734 | C | TYR | A | 345 | 65.366 | 49.339 | 42.841 | 1.00 | 25.79 | C |
| ATOM | 1735 | O | TYR | A | 345 | 64.746 | 48.627 | 43.635 | 1.00 | 24.45 | O |
| ATOM | 1736 | CB | TYR | A | 345 | 64.117 | 50.566 | 41.057 | 1.00 | 25.37 | C |
| ATOM | 1737 | CG | TYR | A | 345 | 62.815 | 49.801 | 41.089 | 1.00 | 25.96 | C |
| ATOM | 1738 | CD1 | TYR | A | 345 | 61.626 | 50.427 | 41.460 | 1.00 | 26.32 | C |
| ATOM | 1739 | CD2 | TYR | A | 345 | 62.764 | 48.459 | 40.713 | 1.00 | 26.30 | C |
| ATOM | 1740 | CE1 | TYR | A | 345 | 60.415 | 49.738 | 41.446 | 1.00 | 27.08 | C |

TABLE 3-continued

| ATOM | 1741 | CE2 | TYR | A | 345 | 61.558 | 47.759 | 40.697 | 1.00 | 27.11 | C |
|---|---|---|---|---|---|---|---|---|---|---|---|
| ATOM | 1742 | CZ | TYR | A | 345 | 60.391 | 48.406 | 41.061 | 1.00 | 27.19 | C |
| ATOM | 1743 | OH | TYR | A | 345 | 59.195 | 47.735 | 41.008 | 1.00 | 28.86 | O |
| ATOM | 1744 | N | PHE | A | 346 | 66.530 | 48.983 | 42.305 | 1.00 | 26.33 | N |
| ATOM | 1745 | CA | PHE | A | 346 | 67.181 | 47.713 | 42.632 | 1.00 | 27.73 | C |
| ATOM | 1746 | C | PHE | A | 346 | 67.537 | 47.684 | 44.118 | 1.00 | 28.91 | C |
| ATOM | 1747 | O | PHE | A | 346 | 67.337 | 46.679 | 44.798 | 1.00 | 28.66 | O |
| ATOM | 1748 | CB | PHE | A | 346 | 68.450 | 47.540 | 41.793 | 1.00 | 27.70 | C |
| ATOM | 1749 | CG | PHE | A | 346 | 69.269 | 46.331 | 42.163 | 1.00 | 27.99 | C |
| ATOM | 1750 | CD1 | PHE | A | 346 | 68.773 | 45.047 | 41.959 | 1.00 | 27.87 | C |
| ATOM | 1751 | CD2 | PHE | A | 346 | 70.536 | 46.480 | 42.723 | 1.00 | 28.85 | C |
| ATOM | 1752 | CE1 | PHE | A | 346 | 69.526 | 43.923 | 42.304 | 1.00 | 27.89 | C |
| ATOM | 1753 | CE2 | PHE | A | 346 | 71.303 | 45.361 | 43.076 | 1.00 | 29.71 | C |
| ATOM | 1754 | CZ | PHE | A | 346 | 70.793 | 44.080 | 42.864 | 1.00 | 29.06 | C |
| ATOM | 1755 | N | GLU | A | 347 | 68.059 | 48.798 | 44.616 | 1.00 | 30.12 | N |
| ATOM | 1756 | CA | GLU | A | 347 | 68.430 | 48.897 | 46.021 | 1.00 | 32.28 | C |
| ATOM | 1757 | C | GLU | A | 347 | 67.227 | 48.820 | 46.958 | 1.00 | 31.98 | C |
| ATOM | 1758 | O | GLU | A | 347 | 67.329 | 48.280 | 48.056 | 1.00 | 31.99 | O |
| ATOM | 1759 | CB | GLU | A | 347 | 69.189 | 50.200 | 46.280 | 1.00 | 33.95 | C |
| ATOM | 1760 | CG | GLU | A | 347 | 70.645 | 50.150 | 45.853 | 1.00 | 38.56 | C |
| ATOM | 1761 | CD | GLU | A | 347 | 71.454 | 51.319 | 46.386 | 1.00 | 41.08 | C |
| ATOM | 1762 | OE1 | GLU | A | 347 | 71.294 | 51.673 | 47.576 | 1.00 | 42.98 | O |
| ATOM | 1763 | OE2 | GLU | A | 347 | 72.265 | 51.875 | 45.619 | 1.00 | 43.56 | O |
| ATOM | 1764 | N | GLU | A | 348 | 66.091 | 49.352 | 46.522 | 1.00 | 31.64 | N |
| ATOM | 1765 | CA | GLU | A | 348 | 64.888 | 49.347 | 47.348 | 1.00 | 31.87 | C |
| ATOM | 1766 | C | GLU | A | 348 | 64.124 | 48.031 | 47.330 | 1.00 | 30.98 | C |
| ATOM | 1767 | O | GLU | A | 348 | 63.576 | 47.617 | 48.350 | 1.00 | 31.10 | O |
| ATOM | 1768 | CB | GLU | A | 348 | 63.911 | 50.439 | 46.897 | 1.00 | 33.10 | C |
| ATOM | 1769 | CG | GLU | A | 348 | 64.506 | 51.812 | 46.664 | 1.00 | 35.32 | C |
| ATOM | 1770 | CD | GLU | A | 348 | 63.494 | 52.779 | 46.059 | 1.00 | 36.44 | C |
| ATOM | 1771 | OE1 | GLU | A | 348 | 62.716 | 52.358 | 45.178 | 1.00 | 37.22 | O |
| ATOM | 1772 | OE2 | GLU | A | 348 | 63.481 | 53.961 | 46.454 | 1.00 | 38.05 | O |
| ATOM | 1773 | N | THR | A | 349 | 64.079 | 47.381 | 46.171 | 1.00 | 29.37 | N |
| ATOM | 1774 | CA | THR | A | 349 | 63.316 | 46.147 | 46.016 | 1.00 | 28.42 | C |
| ATOM | 1775 | C | THR | A | 349 | 64.107 | 44.864 | 45.790 | 1.00 | 28.26 | C |
| ATOM | 1776 | O | THR | A | 349 | 63.563 | 43.775 | 45.928 | 1.00 | 28.54 | O |
| ATOM | 1777 | CB | THR | A | 349 | 62.347 | 46.267 | 44.829 | 1.00 | 28.53 | C |
| ATOM | 1778 | OG1 | THR | A | 349 | 63.106 | 46.331 | 43.611 | 1.00 | 26.68 | O |
| ATOM | 1779 | CG2 | THR | A | 349 | 61.489 | 47.525 | 44.956 | 1.00 | 27.99 | C |
| ATOM | 1780 | N | GLY | A | 350 | 65.375 | 44.982 | 45.423 | 1.00 | 27.91 | N |
| ATOM | 1781 | CA | GLY | A | 350 | 66.153 | 43.789 | 45.148 | 1.00 | 27.45 | C |
| ATOM | 1782 | C | GLY | A | 350 | 65.860 | 43.276 | 43.743 | 1.00 | 26.56 | C |
| ATOM | 1783 | O | GLY | A | 350 | 66.367 | 42.235 | 43.339 | 1.00 | 27.60 | O |
| ATOM | 1784 | N | ILE | A | 351 | 65.034 | 44.005 | 42.995 | 1.00 | 25.92 | N |
| ATOM | 1785 | CA | ILE | A | 351 | 64.687 | 43.614 | 41.625 | 1.00 | 24.44 | C |
| ATOM | 1786 | C | ILE | A | 351 | 65.530 | 44.395 | 40.619 | 1.00 | 23.82 | C |
| ATOM | 1787 | O | ILE | A | 351 | 65.557 | 45.627 | 40.649 | 1.00 | 22.61 | O |
| ATOM | 1788 | CB | ILE | A | 351 | 63.203 | 43.913 | 41.299 | 1.00 | 25.48 | C |
| ATOM | 1789 | CG1 | ILE | A | 351 | 62.281 | 43.222 | 42.310 | 1.00 | 25.99 | C |
| ATOM | 1790 | CG2 | ILE | A | 351 | 62.880 | 43.449 | 39.873 | 1.00 | 25.21 | C |
| ATOM | 1791 | CD1 | ILE | A | 351 | 60.810 | 43.615 | 42.169 | 1.00 | 26.39 | C |
| ATOM | 1792 | N | TYR | A | 352 | 66.214 | 43.683 | 39.728 | 1.00 | 23.12 | N |
| ATOM | 1793 | CA | TYR | A | 352 | 67.024 | 44.339 | 38.708 | 1.00 | 22.28 | C |
| ATOM | 1794 | C | TYR | A | 352 | 66.274 | 44.290 | 37.389 | 1.00 | 22.46 | C |
| ATOM | 1795 | O | TYR | A | 352 | 66.033 | 43.210 | 36.845 | 1.00 | 21.68 | O |
| ATOM | 1796 | CB | TYR | A | 352 | 68.375 | 43.647 | 38.518 | 1.00 | 22.40 | C |
| ATOM | 1797 | CG | TYR | A | 352 | 69.269 | 44.375 | 37.526 | 1.00 | 22.27 | C |
| ATOM | 1798 | CD1 | TYR | A | 352 | 70.058 | 45.451 | 37.932 | 1.00 | 22.07 | C |
| ATOM | 1799 | CD2 | TYR | A | 352 | 69.296 | 44.012 | 36.176 | 1.00 | 22.89 | C |
| ATOM | 1800 | CE1 | TYR | A | 352 | 70.852 | 46.151 | 37.028 | 1.00 | 22.81 | C |
| ATOM | 1801 | CE2 | TYR | A | 352 | 70.094 | 44.714 | 35.252 | 1.00 | 22.60 | C |
| ATOM | 1802 | CZ | TYR | A | 352 | 70.868 | 45.779 | 35.691 | 1.00 | 22.45 | C |
| ATOM | 1803 | OH | TYR | A | 352 | 71.676 | 46.468 | 34.814 | 1.00 | 22.10 | O |
| ATOM | 1804 | N | ILE | A | 353 | 65.912 | 45.462 | 36.876 | 1.00 | 22.15 | N |
| ATOM | 1805 | CA | ILE | A | 353 | 65.196 | 45.556 | 35.610 | 1.00 | 22.13 | C |
| ATOM | 1806 | C | ILE | A | 353 | 66.119 | 46.052 | 34.495 | 1.00 | 21.86 | C |
| ATOM | 1807 | O | ILE | A | 353 | 66.603 | 47.188 | 34.531 | 1.00 | 21.86 | O |
| ATOM | 1808 | CB | ILE | A | 353 | 63.996 | 46.523 | 35.721 | 1.00 | 23.05 | C |
| ATOM | 1809 | CG1 | ILE | A | 353 | 63.036 | 46.030 | 36.817 | 1.00 | 23.41 | C |
| ATOM | 1810 | CG2 | ILE | A | 353 | 63.278 | 46.614 | 34.374 | 1.00 | 21.86 | C |
| ATOM | 1811 | CD1 | ILE | A | 353 | 61.863 | 46.936 | 37.063 | 1.00 | 24.85 | C |
| ATOM | 1812 | N | PRO | A | 354 | 66.388 | 45.201 | 33.495 | 1.00 | 21.74 | N |
| ATOM | 1813 | CA | PRO | A | 354 | 67.263 | 45.626 | 32.397 | 1.00 | 21.25 | C |
| ATOM | 1814 | C | PRO | A | 354 | 66.608 | 46.780 | 31.649 | 1.00 | 21.17 | C |
| ATOM | 1815 | O | PRO | A | 354 | 65.385 | 46.825 | 31.534 | 1.00 | 21.72 | O |
| ATOM | 1816 | CB | PRO | A | 354 | 67.360 | 44.373 | 31.524 | 1.00 | 21.72 | C |
| ATOM | 1817 | CG | PRO | A | 354 | 67.181 | 43.240 | 32.529 | 1.00 | 20.93 | C |
| ATOM | 1818 | CD | PRO | A | 354 | 66.051 | 43.769 | 33.382 | 1.00 | 21.57 | C |
| ATOM | 1819 | N | VAL | A | 355 | 67.406 | 47.722 | 31.159 | 1.00 | 20.15 | N |

TABLE 3-continued

| | | | | | | | | | | |
|---|---|---|---|---|---|---|---|---|---|---|
| ATOM | 1820 | CA | VAL | A | 355 | 66.841 | 48.829 | 30.396 | 1.00 | 19.73 | C |
| ATOM | 1821 | C | VAL | A | 355 | 67.482 | 48.842 | 29.022 | 1.00 | 19.50 | C |
| ATOM | 1822 | O | VAL | A | 355 | 68.629 | 48.430 | 28.851 | 1.00 | 19.88 | O |
| ATOM | 1823 | CB | VAL | A | 355 | 67.032 | 50.206 | 31.094 | 1.00 | 18.66 | C |
| ATOM | 1824 | CG1 | VAL | A | 355 | 66.254 | 50.226 | 32.394 | 1.00 | 18.46 | C |
| ATOM | 1825 | CG2 | VAL | A | 355 | 68.514 | 50.497 | 31.333 | 1.00 | 18.65 | C |
| ATOM | 1826 | N | CYS | A | 356 | 66.723 | 49.312 | 28.043 | 1.00 | 19.68 | N |
| ATOM | 1827 | CA | CYS | A | 356 | 67.185 | 49.346 | 26.666 | 1.00 | 20.26 | C |
| ATOM | 1828 | C | CYS | A | 356 | 67.273 | 50.761 | 26.110 | 1.00 | 20.70 | C |
| ATOM | 1829 | O | CYS | A | 356 | 66.297 | 51.509 | 26.161 | 1.00 | 20.96 | O |
| ATOM | 1830 | CB | CYS | A | 356 | 66.228 | 48.522 | 25.796 | 1.00 | 20.28 | C |
| ATOM | 1831 | SG | CYS | A | 356 | 66.486 | 48.701 | 24.007 | 1.00 | 22.73 | S |
| ATOM | 1832 | N | SER | A | 357 | 68.440 | 51.129 | 25.586 | 1.00 | 20.27 | N |
| ATOM | 1833 | CA | SER | A | 357 | 68.597 | 52.447 | 24.981 | 1.00 | 20.16 | C |
| ATOM | 1834 | C | SER | A | 357 | 68.088 | 52.277 | 23.553 | 1.00 | 20.30 | C |
| ATOM | 1835 | O | SER | A | 357 | 68.713 | 51.599 | 22.734 | 1.00 | 19.54 | O |
| ATOM | 1836 | CB | SER | A | 357 | 70.061 | 52.882 | 24.962 | 1.00 | 20.20 | C |
| ATOM | 1837 | OG | SER | A | 357 | 70.163 | 54.193 | 24.432 | 1.00 | 20.16 | O |
| ATOM | 1838 | N | ASP | A | 358 | 66.951 | 52.899 | 23.262 | 1.00 | 20.12 | N |
| ATOM | 1839 | CA | ASP | A | 358 | 66.327 | 52.767 | 21.955 | 1.00 | 21.37 | C |
| ATOM | 1840 | C | ASP | A | 358 | 66.441 | 54.009 | 21.070 | 1.00 | 21.92 | C |
| ATOM | 1841 | O | ASP | A | 358 | 65.862 | 55.057 | 21.367 | 1.00 | 22.18 | O |
| ATOM | 1842 | CB | ASP | A | 358 | 64.855 | 52.370 | 22.166 | 1.00 | 20.81 | C |
| ATOM | 1843 | CG | ASP | A | 358 | 64.081 | 52.214 | 20.867 | 1.00 | 22.08 | C |
| ATOM | 1844 | OD1 | ASP | A | 358 | 64.703 | 52.059 | 19.791 | 1.00 | 21.34 | O |
| ATOM | 1845 | OD2 | ASP | A | 358 | 62.834 | 52.229 | 20.937 | 1.00 | 20.69 | O |
| ATOM | 1846 | N | GLY | A | 359 | 67.204 | 53.875 | 19.986 | 1.00 | 22.92 | N |
| ATOM | 1847 | CA | GLY | A | 359 | 67.381 | 54.964 | 19.040 | 1.00 | 23.74 | C |
| ATOM | 1848 | C | GLY | A | 359 | 68.538 | 55.905 | 19.328 | 1.00 | 25.08 | C |
| ATOM | 1849 | O | GLY | A | 359 | 69.078 | 55.928 | 20.431 | 1.00 | 24.78 | O |
| ATOM | 1850 | N | GLY | A | 360 | 68.932 | 56.678 | 18.323 | 1.00 | 25.97 | N |
| ATOM | 1851 | CA | GLY | A | 360 | 70.007 | 57.633 | 18.517 | 1.00 | 27.86 | C |
| ATOM | 1852 | C | GLY | A | 360 | 71.419 | 57.132 | 18.287 | 1.00 | 28.88 | C |
| ATOM | 1853 | O | GLY | A | 360 | 72.367 | 57.904 | 18.417 | 1.00 | 29.93 | O |
| ATOM | 1854 | N | ILE | A | 361 | 71.581 | 55.855 | 17.961 | 1.00 | 29.68 | N |
| ATOM | 1855 | CA | ILE | A | 361 | 72.918 | 55.329 | 17.706 | 1.00 | 30.57 | C |
| ATOM | 1856 | C | ILE | A | 361 | 73.309 | 55.719 | 16.282 | 1.00 | 31.81 | C |
| ATOM | 1857 | O | ILE | A | 361 | 72.765 | 55.196 | 15.310 | 1.00 | 31.75 | O |
| ATOM | 1858 | CB | ILE | A | 361 | 72.971 | 53.789 | 17.838 | 1.00 | 30.18 | C |
| ATOM | 1859 | CG1 | ILE | A | 361 | 72.603 | 53.368 | 19.266 | 1.00 | 29.88 | C |
| ATOM | 1860 | CG2 | ILE | A | 361 | 74.366 | 53.282 | 17.481 | 1.00 | 30.01 | C |
| ATOM | 1861 | CD1 | ILE | A | 361 | 73.605 | 53.792 | 20.328 | 1.00 | 28.84 | C |
| ATOM | 1862 | N | VAL | A | 362 | 74.249 | 56.648 | 16.167 | 1.00 | 32.99 | N |
| ATOM | 1863 | CA | VAL | A | 362 | 74.699 | 57.110 | 14.862 | 1.00 | 33.95 | C |
| ATOM | 1864 | C | VAL | A | 362 | 76.028 | 56.463 | 14.483 | 1.00 | 34.24 | C |
| ATOM | 1865 | O | VAL | A | 362 | 76.203 | 56.015 | 13.351 | 1.00 | 35.04 | O |
| ATOM | 1866 | CB | VAL | A | 362 | 74.851 | 58.646 | 14.854 | 1.00 | 34.42 | C |
| ATOM | 1867 | CG1 | VAL | A | 362 | 75.233 | 59.131 | 13.462 | 1.00 | 34.82 | C |
| ATOM | 1868 | CG2 | VAL | A | 362 | 73.555 | 59.292 | 15.304 | 1.00 | 34.82 | C |
| ATOM | 1869 | N | TYR | A | 363 | 76.953 | 56.404 | 15.438 | 1.00 | 33.91 | N |
| ATOM | 1870 | CA | TYR | A | 363 | 78.271 | 55.813 | 15.210 | 1.00 | 33.19 | C |
| ATOM | 1871 | C | TYR | A | 363 | 78.507 | 54.649 | 16.163 | 1.00 | 31.86 | C |
| ATOM | 1872 | O | TYR | A | 363 | 77.862 | 54.561 | 17.207 | 1.00 | 31.05 | O |
| ATOM | 1873 | CB | TYR | A | 363 | 79.350 | 56.877 | 15.411 | 1.00 | 34.45 | C |
| ATOM | 1874 | CG | TYR | A | 363 | 79.142 | 58.094 | 14.544 | 1.00 | 36.04 | C |
| ATOM | 1875 | CD1 | TYR | A | 363 | 79.242 | 58.008 | 13.154 | 1.00 | 37.00 | C |
| ATOM | 1876 | CD2 | TYR | A | 363 | 78.796 | 59.323 | 15.105 | 1.00 | 36.77 | C |
| ATOM | 1877 | CE1 | TYR | A | 363 | 78.998 | 59.114 | 12.344 | 1.00 | 38.19 | C |
| ATOM | 1878 | CE2 | TYR | A | 363 | 78.548 | 60.435 | 14.304 | 1.00 | 37.90 | C |
| ATOM | 1879 | CZ | TYR | A | 363 | 78.649 | 60.323 | 12.926 | 1.00 | 38.55 | C |
| ATOM | 1880 | OH | TYR | A | 363 | 78.390 | 61.415 | 12.130 | 1.00 | 40.47 | O |
| ATOM | 1881 | N | ASP | A | 364 | 79.432 | 53.760 | 15.813 | 1.00 | 30.55 | N |
| ATOM | 1882 | CA | ASP | A | 364 | 79.717 | 52.610 | 16.668 | 1.00 | 29.67 | C |
| ATOM | 1883 | C | ASP | A | 364 | 80.055 | 52.987 | 18.108 | 1.00 | 28.54 | C |
| ATOM | 1884 | O | ASP | A | 364 | 79.621 | 52.316 | 19.043 | 1.00 | 28.30 | O |
| ATOM | 1885 | CB | ASP | A | 364 | 80.871 | 51.772 | 16.109 | 1.00 | 30.75 | C |
| ATOM | 1886 | CG | ASP | A | 364 | 80.511 | 51.052 | 14.819 | 1.00 | 31.62 | C |
| ATOM | 1887 | OD1 | ASP | A | 364 | 79.346 | 50.634 | 14.647 | 1.00 | 31.07 | O |
| ATOM | 1888 | OD2 | ASP | A | 364 | 81.413 | 50.887 | 13.981 | 1.00 | 33.54 | O |
| ATOM | 1889 | N | TYR | A | 365 | 80.828 | 54.054 | 18.293 | 1.00 | 26.82 | N |
| ATOM | 1890 | CA | TYR | A | 365 | 81.214 | 54.449 | 19.642 | 1.00 | 26.01 | C |
| ATOM | 1891 | C | TYR | A | 365 | 80.021 | 54.874 | 20.499 | 1.00 | 25.10 | C |
| ATOM | 1892 | O | TYR | A | 365 | 80.117 | 54.925 | 21.723 | 1.00 | 24.73 | O |
| ATOM | 1893 | CB | TYR | A | 365 | 82.295 | 55.541 | 19.588 | 1.00 | 25.94 | C |
| ATOM | 1894 | CG | TYR | A | 365 | 81.804 | 56.962 | 19.451 | 1.00 | 26.33 | C |
| ATOM | 1895 | CD1 | TYR | A | 365 | 81.582 | 57.751 | 20.578 | 1.00 | 25.79 | C |
| ATOM | 1896 | CD2 | TYR | A | 365 | 81.624 | 57.542 | 18.193 | 1.00 | 26.48 | C |
| ATOM | 1897 | CE1 | TYR | A | 365 | 81.203 | 59.086 | 20.459 | 1.00 | 27.08 | C |
| ATOM | 1898 | CE2 | TYR | A | 365 | 81.242 | 58.876 | 18.063 | 1.00 | 27.27 | C |

TABLE 3-continued

| ATOM | 1899 | CZ | TYR | A | 365 | 81.036 | 59.640 | 19.198 | 1.00 | 27.74 | C |
| --- | --- | --- | --- | --- | --- | --- | --- | --- | --- | --- | --- |
| ATOM | 1900 | OH | TYR | A | 365 | 80.675 | 60.962 | 19.074 | 1.00 | 29.07 | O |
| ATOM | 1901 | N | HIS | A | 366 | 78.892 | 55.164 | 19.858 | 1.00 | 24.53 | N |
| ATOM | 1902 | CA | HIS | A | 366 | 77.685 | 55.534 | 20.591 | 1.00 | 24.28 | C |
| ATOM | 1903 | C | HIS | A | 366 | 77.190 | 54.300 | 21.339 | 1.00 | 23.77 | C |
| ATOM | 1904 | O | HIS | A | 366 | 76.569 | 54.411 | 22.399 | 1.00 | 23.59 | O |
| ATOM | 1905 | CB | HIS | A | 366 | 76.589 | 56.017 | 19.641 | 1.00 | 24.35 | C |
| ATOM | 1906 | CG | HIS | A | 366 | 76.799 | 57.409 | 19.134 | 1.00 | 25.11 | C |
| ATOM | 1907 | ND1 | HIS | A | 366 | 77.870 | 58.187 | 19.517 | 1.00 | 25.78 | N |
| ATOM | 1908 | CD2 | HIS | A | 366 | 76.059 | 58.173 | 18.295 | 1.00 | 25.31 | C |
| ATOM | 1909 | CE1 | HIS | A | 366 | 77.779 | 59.372 | 18.938 | 1.00 | 25.96 | C |
| ATOM | 1910 | NE2 | HIS | A | 366 | 76.690 | 59.389 | 18.191 | 1.00 | 25.85 | N |
| ATOM | 1911 | N | MET | A | 367 | 77.463 | 53.129 | 20.773 | 1.00 | 23.23 | N |
| ATOM | 1912 | CA | MET | A | 367 | 77.062 | 51.863 | 21.388 | 1.00 | 23.44 | C |
| ATOM | 1913 | C | MET | A | 367 | 77.785 | 51.715 | 22.721 | 1.00 | 22.42 | C |
| ATOM | 1914 | O | MET | A | 367 | 77.180 | 51.385 | 23.735 | 1.00 | 21.74 | O |
| ATOM | 1915 | CB | MET | A | 367 | 77.437 | 50.672 | 20.494 | 1.00 | 23.55 | C |
| ATOM | 1916 | CG | MET | A | 367 | 76.680 | 50.582 | 19.169 | 1.00 | 25.18 | C |
| ATOM | 1917 | SD | MET | A | 367 | 77.253 | 49.158 | 18.204 | 1.00 | 26.50 | S |
| ATOM | 1918 | CE | MET | A | 367 | 76.270 | 49.323 | 16.707 | 1.00 | 25.76 | C |
| ATOM | 1919 | N | THR | A | 368 | 79.093 | 51.941 | 22.698 | 1.00 | 22.22 | N |
| ATOM | 1920 | CA | THR | A | 368 | 79.915 | 51.835 | 23.898 | 1.00 | 22.15 | C |
| ATOM | 1921 | C | THR | A | 368 | 79.445 | 52.838 | 24.952 | 1.00 | 21.97 | C |
| ATOM | 1922 | O | THR | A | 368 | 79.380 | 52.517 | 26.137 | 1.00 | 22.10 | O |
| ATOM | 1923 | CB | THR | A | 368 | 81.392 | 52.097 | 23.560 | 1.00 | 22.55 | C |
| ATOM | 1924 | OG1 | THR | A | 368 | 81.735 | 51.369 | 22.373 | 1.00 | 22.22 | O |
| ATOM | 1925 | CG2 | THR | A | 368 | 82.294 | 51.645 | 24.702 | 1.00 | 21.82 | C |
| ATOM | 1926 | N | LEU | A | 369 | 79.117 | 54.052 | 24.517 | 1.00 | 21.48 | N |
| ATOM | 1927 | CA | LEU | A | 369 | 78.640 | 55.087 | 25.431 | 1.00 | 21.65 | C |
| ATOM | 1928 | C | LEU | A | 369 | 77.318 | 54.693 | 26.096 | 1.00 | 21.14 | C |
| ATOM | 1929 | O | LEU | A | 369 | 77.163 | 54.833 | 27.306 | 1.00 | 20.89 | O |
| ATOM | 1930 | CB | LEU | A | 369 | 78.446 | 56.416 | 24.689 | 1.00 | 22.45 | C |
| ATOM | 1931 | CG | LEU | A | 369 | 79.697 | 57.209 | 24.300 | 1.00 | 24.02 | C |
| ATOM | 1932 | CD1 | LEU | A | 369 | 79.301 | 58.381 | 23.400 | 1.00 | 23.76 | C |
| ATOM | 1933 | CD2 | LEU | A | 369 | 80.397 | 57.710 | 25.567 | 1.00 | 23.98 | C |
| ATOM | 1934 | N | ALA | A | 370 | 76.371 | 54.211 | 25.296 | 1.00 | 20.39 | N |
| ATOM | 1935 | CA | ALA | A | 370 | 75.065 | 53.806 | 25.810 | 1.00 | 20.84 | C |
| ATOM | 1936 | C | ALA | A | 370 | 75.242 | 52.732 | 26.877 | 1.00 | 20.22 | C |
| ATOM | 1937 | O | ALA | A | 370 | 74.635 | 52.793 | 27.945 | 1.00 | 20.03 | O |
| ATOM | 1938 | CB | ALA | A | 370 | 74.194 | 53.279 | 24.675 | 1.00 | 20.37 | C |
| ATOM | 1939 | N | LEU | A | 371 | 76.078 | 51.748 | 26.576 | 1.00 | 20.36 | N |
| ATOM | 1940 | CA | LEU | A | 371 | 76.343 | 50.669 | 27.516 | 1.00 | 20.12 | C |
| ATOM | 1941 | C | LEU | A | 371 | 77.032 | 51.209 | 28.773 | 1.00 | 20.41 | C |
| ATOM | 1942 | O | LEU | A | 371 | 76.656 | 50.853 | 29.887 | 1.00 | 19.69 | O |
| ATOM | 1943 | CB | LEU | A | 371 | 77.222 | 49.602 | 26.854 | 1.00 | 19.81 | C |
| ATOM | 1944 | CG | LEU | A | 371 | 76.580 | 48.882 | 25.656 | 1.00 | 20.61 | C |
| ATOM | 1945 | CD1 | LEU | A | 371 | 77.592 | 47.954 | 24.999 | 1.00 | 21.12 | C |
| ATOM | 1946 | CD2 | LEU | A | 371 | 75.364 | 48.092 | 26.127 | 1.00 | 20.77 | C |
| ATOM | 1947 | N | ALA | A | 372 | 78.036 | 52.064 | 28.588 | 1.00 | 20.08 | N |
| ATOM | 1948 | CA | ALA | A | 372 | 78.772 | 52.640 | 29.712 | 1.00 | 20.58 | C |
| ATOM | 1949 | C | ALA | A | 372 | 77.868 | 53.444 | 30.641 | 1.00 | 21.51 | C |
| ATOM | 1950 | O | ALA | A | 372 | 78.064 | 53.450 | 31.858 | 1.00 | 21.21 | O |
| ATOM | 1951 | CB | ALA | A | 372 | 79.909 | 53.525 | 29.199 | 1.00 | 20.25 | C |
| ATOM | 1952 | N | MET | A | 373 | 76.883 | 54.126 | 30.065 | 1.00 | 21.00 | N |
| ATOM | 1953 | CA | MET | A | 373 | 75.947 | 54.923 | 30.852 | 1.00 | 21.56 | C |
| ATOM | 1954 | C | MET | A | 373 | 74.960 | 54.065 | 31.641 | 1.00 | 21.75 | C |
| ATOM | 1955 | O | MET | A | 373 | 74.187 | 54.588 | 32.449 | 1.00 | 21.78 | O |
| ATOM | 1956 | CB | MET | A | 373 | 75.192 | 55.892 | 29.944 | 1.00 | 21.91 | C |
| ATOM | 1957 | CG | MET | A | 373 | 76.082 | 56.987 | 29.370 | 1.00 | 22.56 | C |
| ATOM | 1958 | SD | MET | A | 373 | 75.243 | 57.985 | 28.132 | 1.00 | 24.61 | S |
| ATOM | 1959 | CE | MET | A | 373 | 76.595 | 59.086 | 27.591 | 1.00 | 23.75 | C |
| ATOM | 1960 | N | GLY | A | 374 | 74.970 | 52.754 | 31.405 | 1.00 | 21.29 | N |
| ATOM | 1961 | CA | GLY | A | 374 | 74.078 | 51.884 | 32.157 | 1.00 | 20.54 | C |
| ATOM | 1962 | C | GLY | A | 374 | 73.062 | 51.058 | 31.390 | 1.00 | 20.55 | C |
| ATOM | 1963 | O | GLY | A | 374 | 72.444 | 50.164 | 31.961 | 1.00 | 20.60 | O |
| ATOM | 1964 | N | ALA | A | 375 | 72.864 | 51.345 | 30.108 | 1.00 | 20.21 | N |
| ATOM | 1965 | CA | ALA | A | 375 | 71.910 | 50.562 | 29.332 | 1.00 | 20.36 | C |
| ATOM | 1966 | C | ALA | A | 375 | 72.448 | 49.140 | 29.228 | 1.00 | 20.12 | C |
| ATOM | 1967 | O | ALA | A | 375 | 73.644 | 48.943 | 29.011 | 1.00 | 19.79 | O |
| ATOM | 1968 | CB | ALA | A | 375 | 71.731 | 51.166 | 27.932 | 1.00 | 20.49 | C |
| ATOM | 1969 | N | ASP | A | 376 | 71.573 | 48.151 | 29.399 | 1.00 | 20.05 | N |
| ATOM | 1970 | CA | ASP | A | 376 | 71.976 | 46.744 | 29.308 | 1.00 | 20.54 | C |
| ATOM | 1971 | C | ASP | A | 376 | 72.074 | 46.303 | 27.854 | 1.00 | 20.62 | C |
| ATOM | 1972 | O | ASP | A | 376 | 72.933 | 45.498 | 27.491 | 1.00 | 20.67 | O |
| ATOM | 1973 | CB | ASP | A | 376 | 70.978 | 45.874 | 30.069 | 1.00 | 20.75 | C |
| ATOM | 1974 | CG | ASP | A | 376 | 70.900 | 46.253 | 31.530 | 1.00 | 21.21 | C |
| ATOM | 1975 | OD1 | ASP | A | 376 | 71.732 | 45.757 | 32.319 | 1.00 | 21.97 | O |
| ATOM | 1976 | OD2 | ASP | A | 376 | 70.027 | 47.073 | 31.882 | 1.00 | 21.23 | O |
| ATOM | 1977 | N | PHE | A | 377 | 71.173 | 46.813 | 27.022 | 1.00 | 21.26 | N |

TABLE 3-continued

| | | | | | | | | | | |
|---|---|---|---|---|---|---|---|---|---|---|
| ATOM | 1978 | CA | PHE | A | 377 | 71.220 | 46.501 | 25.604 | 1.00 | 21.16 | C |
| ATOM | 1979 | C | PHE | A | 377 | 70.726 | 47.683 | 24.788 | 1.00 | 21.44 | C |
| ATOM | 1980 | O | PHE | A | 377 | 70.186 | 48.647 | 25.336 | 1.00 | 21.24 | O |
| ATOM | 1981 | CB | PHE | A | 377 | 70.467 | 45.204 | 25.252 | 1.00 | 21.17 | C |
| ATOM | 1982 | CG | PHE | A | 377 | 69.056 | 45.135 | 25.758 | 1.00 | 22.60 | C |
| ATOM | 1983 | CD1 | PHE | A | 377 | 68.791 | 44.771 | 27.077 | 1.00 | 23.03 | C |
| ATOM | 1984 | CD2 | PHE | A | 377 | 67.987 | 45.371 | 24.900 | 1.00 | 21.57 | C |
| ATOM | 1985 | CE1 | PHE | A | 377 | 67.478 | 44.638 | 27.531 | 1.00 | 22.95 | C |
| ATOM | 1986 | CE2 | PHE | A | 377 | 66.669 | 45.240 | 25.345 | 1.00 | 22.51 | C |
| ATOM | 1987 | CZ | PHE | A | 377 | 66.416 | 44.872 | 26.663 | 1.00 | 22.95 | C |
| ATOM | 1988 | N | ILE | A | 378 | 70.931 | 47.600 | 23.480 | 1.00 | 20.98 | N |
| ATOM | 1989 | CA | ILE | A | 378 | 70.607 | 48.683 | 22.567 | 1.00 | 21.02 | C |
| ATOM | 1990 | C | ILE | A | 378 | 69.669 | 48.272 | 21.439 | 1.00 | 20.93 | C |
| ATOM | 1991 | O | ILE | A | 378 | 69.847 | 47.222 | 20.833 | 1.00 | 20.57 | O |
| ATOM | 1992 | CB | ILE | A | 378 | 71.923 | 49.220 | 21.936 | 1.00 | 21.28 | C |
| ATOM | 1993 | CG1 | ILE | A | 378 | 72.914 | 49.588 | 23.046 | 1.00 | 21.93 | C |
| ATOM | 1994 | CG2 | ILE | A | 378 | 71.643 | 50.439 | 21.056 | 1.00 | 21.62 | C |
| ATOM | 1995 | CD1 | ILE | A | 378 | 74.341 | 49.772 | 22.558 | 1.00 | 22.57 | C |
| ATOM | 1996 | N | MET | A | 379 | 68.669 | 49.105 | 21.166 | 1.00 | 20.84 | N |
| ATOM | 1997 | CA | MET | A | 379 | 67.743 | 48.831 | 20.073 | 1.00 | 21.55 | C |
| ATOM | 1998 | C | MET | A | 379 | 68.084 | 49.794 | 18.941 | 1.00 | 21.65 | C |
| ATOM | 1999 | O | MET | A | 379 | 68.230 | 50.998 | 19.164 | 1.00 | 21.66 | O |
| ATOM | 2000 | CB | MET | A | 379 | 66.284 | 49.028 | 20.503 | 1.00 | 21.25 | C |
| ATOM | 2001 | CG | MET | A | 379 | 65.303 | 48.766 | 19.356 | 1.00 | 21.22 | C |
| ATOM | 2002 | SD | MET | A | 379 | 63.576 | 48.745 | 19.833 | 1.00 | 22.14 | S |
| ATOM | 2003 | CE | MET | A | 379 | 63.437 | 47.038 | 20.433 | 1.00 | 22.39 | C |
| ATOM | 2004 | N | LEU | A | 380 | 68.226 | 49.262 | 17.731 | 1.00 | 22.48 | N |
| ATOM | 2005 | CA | LEU | A | 380 | 68.575 | 50.092 | 16.584 | 1.00 | 22.61 | C |
| ATOM | 2006 | C | LEU | A | 380 | 67.703 | 49.788 | 15.373 | 1.00 | 22.97 | C |
| ATOM | 2007 | O | LEU | A | 380 | 67.342 | 48.634 | 15.128 | 1.00 | 22.62 | O |
| ATOM | 2008 | CB | LEU | A | 380 | 70.041 | 49.875 | 16.192 | 1.00 | 23.11 | C |
| ATOM | 2009 | CG | LEU | A | 380 | 71.131 | 49.897 | 17.270 | 1.00 | 23.70 | C |
| ATOM | 2010 | CD1 | LEU | A | 380 | 71.193 | 48.542 | 17.966 | 1.00 | 23.80 | C |
| ATOM | 2011 | CD2 | LEU | A | 380 | 72.476 | 50.200 | 16.625 | 1.00 | 23.63 | C |
| ATOM | 2012 | N | GLY | A | 381 | 67.382 | 50.830 | 14.614 | 1.00 | 22.74 | N |
| ATOM | 2013 | CA | GLY | A | 381 | 66.576 | 50.655 | 13.419 | 1.00 | 24.26 | C |
| ATOM | 2014 | C | GLY | A | 381 | 67.414 | 50.872 | 12.172 | 1.00 | 24.94 | C |
| ATOM | 2015 | O | GLY | A | 381 | 67.648 | 49.946 | 11.397 | 1.00 | 25.50 | O |
| ATOM | 2016 | N | ARG | A | 382 | 67.882 | 52.103 | 11.992 | 1.00 | 26.09 | N |
| ATOM | 2017 | CA | ARG | A | 382 | 68.694 | 52.477 | 10.836 | 1.00 | 27.52 | C |
| ATOM | 2018 | C | ARG | A | 382 | 69.891 | 51.551 | 10.630 | 1.00 | 27.04 | C |
| ATOM | 2019 | O | ARG | A | 382 | 70.180 | 51.130 | 9.507 | 1.00 | 26.49 | O |
| ATOM | 2020 | CB | ARG | A | 382 | 69.199 | 53.911 | 10.998 | 1.00 | 29.77 | C |
| ATOM | 2021 | CG | ARG | A | 382 | 69.830 | 54.488 | 9.737 | 1.00 | 34.03 | C |
| ATOM | 2022 | CD | ARG | A | 382 | 70.702 | 55.699 | 10.034 | 1.00 | 37.28 | C |
| ATOM | 2023 | NE | ARG | A | 382 | 72.102 | 55.327 | 10.247 | 1.00 | 41.27 | N |
| ATOM | 2024 | CZ | ARG | A | 382 | 72.554 | 54.651 | 11.300 | 1.00 | 42.49 | C |
| ATOM | 2025 | NH1 | ARG | A | 382 | 71.723 | 54.267 | 12.255 | 1.00 | 44.24 | N |
| ATOM | 2026 | NH2 | ARG | A | 382 | 73.842 | 54.354 | 11.396 | 1.00 | 44.03 | N |
| ATOM | 2027 | N | TYR | A | 383 | 70.589 | 51.248 | 11.721 | 1.00 | 26.34 | N |
| ATOM | 2028 | CA | TYR | A | 383 | 71.763 | 50.380 | 11.679 | 1.00 | 25.33 | C |
| ATOM | 2029 | C | TYR | A | 383 | 71.493 | 49.062 | 10.948 | 1.00 | 24.88 | C |
| ATOM | 2030 | O | TYR | A | 383 | 72.280 | 48.639 | 10.096 | 1.00 | 24.77 | O |
| ATOM | 2031 | CB | TYR | A | 383 | 72.233 | 50.075 | 13.105 | 1.00 | 24.87 | C |
| ATOM | 2032 | CG | TYR | A | 383 | 73.466 | 49.203 | 13.179 | 1.00 | 24.53 | C |
| ATOM | 2033 | CD1 | TYR | A | 383 | 74.742 | 49.754 | 13.066 | 1.00 | 24.66 | C |
| ATOM | 2034 | CD2 | TYR | A | 383 | 73.356 | 47.823 | 13.354 | 1.00 | 24.92 | C |
| ATOM | 2035 | CE1 | TYR | A | 383 | 75.882 | 48.952 | 13.126 | 1.00 | 24.58 | C |
| ATOM | 2036 | CE2 | TYR | A | 383 | 74.491 | 47.008 | 13.413 | 1.00 | 24.77 | C |
| ATOM | 2037 | CZ | TYR | A | 383 | 75.748 | 47.581 | 13.299 | 1.00 | 25.09 | C |
| ATOM | 2038 | OH | TYR | A | 383 | 76.867 | 46.782 | 13.350 | 1.00 | 24.41 | O |
| ATOM | 2039 | N | PHE | A | 384 | 70.383 | 48.416 | 11.291 | 1.00 | 24.06 | N |
| ATOM | 2040 | CA | PHE | A | 384 | 70.015 | 47.136 | 10.694 | 1.00 | 23.93 | C |
| ATOM | 2041 | C | PHE | A | 384 | 69.289 | 47.263 | 9.357 | 1.00 | 24.44 | C |
| ATOM | 2042 | O | PHE | A | 384 | 69.320 | 46.338 | 8.542 | 1.00 | 24.13 | O |
| ATOM | 2043 | CB | PHE | A | 384 | 69.139 | 46.334 | 11.663 | 1.00 | 23.18 | C |
| ATOM | 2044 | CG | PHE | A | 384 | 69.869 | 45.847 | 12.889 | 1.00 | 22.86 | C |
| ATOM | 2045 | CD1 | PHE | A | 384 | 70.813 | 44.828 | 12.795 | 1.00 | 22.67 | C |
| ATOM | 2046 | CD2 | PHE | A | 384 | 69.606 | 46.407 | 14.139 | 1.00 | 22.33 | C |
| ATOM | 2047 | CE1 | PHE | A | 384 | 71.487 | 44.369 | 13.929 | 1.00 | 22.64 | C |
| ATOM | 2048 | CE2 | PHE | A | 384 | 70.272 | 45.958 | 15.281 | 1.00 | 21.84 | C |
| ATOM | 2049 | CZ | PHE | A | 384 | 71.216 | 44.936 | 15.176 | 1.00 | 22.26 | C |
| ATOM | 2050 | N | ALA | A | 385 | 68.629 | 48.395 | 9.138 | 1.00 | 24.36 | N |
| ATOM | 2051 | CA | ALA | A | 385 | 67.904 | 48.612 | 7.889 | 1.00 | 26.01 | C |
| ATOM | 2052 | C | ALA | A | 385 | 68.839 | 48.544 | 6.679 | 1.00 | 26.76 | C |
| ATOM | 2053 | O | ALA | A | 385 | 68.424 | 48.166 | 5.588 | 1.00 | 27.26 | O |
| ATOM | 2054 | CB | ALA | A | 385 | 67.193 | 49.964 | 7.927 | 1.00 | 25.65 | C |
| ATOM | 2055 | N | ARG | A | 386 | 70.102 | 48.908 | 6.891 | 1.00 | 28.04 | N |
| ATOM | 2056 | CA | ARG | A | 386 | 71.119 | 48.915 | 5.837 | 1.00 | 28.74 | C |

TABLE 3-continued

| | | | | | | | | | | |
|---|---|---|---|---|---|---|---|---|---|---|
| ATOM | 2057 | C | ARG | A | 386 | 71.531 | 47.529 | 5.344 | 1.00 | 28.88 | C |
| ATOM | 2058 | O | ARG | A | 386 | 72.116 | 47.401 | 4.267 | 1.00 | 29.00 | O |
| ATOM | 2059 | CB | ARG | A | 386 | 72.390 | 49.612 | 6.331 | 1.00 | 29.46 | C |
| ATOM | 2060 | CG | ARG | A | 386 | 72.241 | 51.044 | 6.813 | 1.00 | 31.77 | C |
| ATOM | 2061 | CD | ARG | A | 386 | 73.547 | 51.470 | 7.482 | 1.00 | 32.99 | C |
| ATOM | 2062 | NE | ARG | A | 386 | 73.922 | 50.500 | 8.508 | 1.00 | 34.12 | N |
| ATOM | 2063 | CZ | ARG | A | 386 | 75.170 | 50.218 | 8.871 | 1.00 | 34.01 | C |
| ATOM | 2064 | NH1 | ARG | A | 386 | 76.197 | 50.830 | 8.294 | 1.00 | 33.31 | N |
| ATOM | 2065 | NH2 | ARG | A | 386 | 75.388 | 49.313 | 9.813 | 1.00 | 34.05 | N |
| ATOM | 2066 | N | PHE | A | 387 | 71.239 | 46.495 | 6.127 | 1.00 | 28.95 | N |
| ATOM | 2067 | CA | PHE | A | 387 | 71.649 | 45.146 | 5.763 | 1.00 | 28.84 | C |
| ATOM | 2068 | C | PHE | A | 387 | 70.775 | 44.388 | 4.777 | 1.00 | 29.75 | C |
| ATOM | 2069 | O | PHE | A | 387 | 69.581 | 44.642 | 4.641 | 1.00 | 29.59 | O |
| ATOM | 2070 | CB | PHE | A | 387 | 71.833 | 44.289 | 7.021 | 1.00 | 28.17 | C |
| ATOM | 2071 | CG | PHE | A | 387 | 72.742 | 44.904 | 8.050 | 1.00 | 28.00 | C |
| ATOM | 2072 | CD1 | PHE | A | 387 | 73.851 | 45.655 | 7.663 | 1.00 | 27.77 | C |
| ATOM | 2073 | CD2 | PHE | A | 387 | 72.499 | 44.723 | 9.408 | 1.00 | 27.53 | C |
| ATOM | 2074 | CE1 | PHE | A | 387 | 74.703 | 46.218 | 8.617 | 1.00 | 27.95 | C |
| ATOM | 2075 | CE2 | PHE | A | 387 | 73.346 | 45.282 | 10.370 | 1.00 | 26.97 | C |
| ATOM | 2076 | CZ | PHE | A | 387 | 74.445 | 46.029 | 9.976 | 1.00 | 27.00 | C |
| ATOM | 2077 | N | GLU | A | 388 | 71.412 | 43.441 | 4.100 | 1.00 | 30.90 | N |
| ATOM | 2078 | CA | GLU | A | 388 | 70.773 | 42.585 | 3.112 | 1.00 | 32.08 | C |
| ATOM | 2079 | C | GLU | A | 388 | 69.544 | 41.898 | 3.691 | 1.00 | 31.92 | C |
| ATOM | 2080 | O | GLU | A | 388 | 68.539 | 41.713 | 3.001 | 1.00 | 31.55 | O |
| ATOM | 2081 | CB | GLU | A | 388 | 71.778 | 41.529 | 2.647 | 1.00 | 33.36 | C |
| ATOM | 2082 | CG | GLU | A | 388 | 71.235 | 40.528 | 1.647 | 1.00 | 37.10 | C |
| ATOM | 2083 | CD | GLU | A | 388 | 70.777 | 41.189 | 0.367 | 1.00 | 38.82 | C |
| ATOM | 2084 | OE1 | GLU | A | 388 | 71.594 | 41.898 | −0.258 | 1.00 | 40.61 | O |
| ATOM | 2085 | OE2 | GLU | A | 388 | 69.604 | 41.000 | −0.015 | 1.00 | 41.01 | O |
| ATOM | 2086 | N | GLU | A | 389 | 69.626 | 41.532 | 4.967 | 1.00 | 31.81 | N |
| ATOM | 2087 | CA | GLU | A | 389 | 68.534 | 40.837 | 5.633 | 1.00 | 31.88 | C |
| ATOM | 2088 | C | GLU | A | 389 | 67.315 | 41.667 | 6.027 | 1.00 | 31.91 | C |
| ATOM | 2089 | O | GLU | A | 389 | 66.307 | 41.103 | 6.442 | 1.00 | 31.96 | O |
| ATOM | 2090 | CB | GLU | A | 389 | 69.064 | 40.090 | 6.863 | 1.00 | 31.96 | C |
| ATOM | 2091 | CG | GLU | A | 389 | 70.092 | 39.016 | 6.523 | 1.00 | 31.96 | C |
| ATOM | 2092 | CD | GLU | A | 389 | 71.527 | 39.515 | 6.568 | 1.00 | 31.52 | C |
| ATOM | 2093 | OE1 | GLU | A | 389 | 71.764 | 40.735 | 6.447 | 1.00 | 32.44 | O |
| ATOM | 2094 | OE2 | GLU | A | 389 | 72.431 | 38.676 | 6.715 | 1.00 | 32.19 | O |
| ATOM | 2095 | N | SER | A | 390 | 67.385 | 42.991 | 5.920 | 1.00 | 32.24 | N |
| ATOM | 2096 | CA | SER | A | 390 | 66.215 | 43.792 | 6.270 | 1.00 | 33.25 | C |
| ATOM | 2097 | C | SER | A | 390 | 65.147 | 43.453 | 5.218 | 1.00 | 34.01 | C |
| ATOM | 2098 | O | SER | A | 390 | 65.474 | 43.169 | 4.064 | 1.00 | 33.38 | O |
| ATOM | 2099 | CB | SER | A | 390 | 66.544 | 45.290 | 6.264 | 1.00 | 33.16 | C |
| ATOM | 2100 | OG | SER | A | 390 | 66.764 | 45.776 | 4.954 | 1.00 | 34.84 | O |
| ATOM | 2101 | N | PRO | A | 391 | 63.860 | 43.484 | 5.604 | 1.00 | 34.79 | N |
| ATOM | 2102 | CA | PRO | A | 391 | 62.737 | 43.165 | 4.713 | 1.00 | 35.94 | C |
| ATOM | 2103 | C | PRO | A | 391 | 62.322 | 44.209 | 3.681 | 1.00 | 37.25 | C |
| ATOM | 2104 | O | PRO | A | 391 | 61.208 | 44.153 | 3.167 | 1.00 | 38.09 | O |
| ATOM | 2105 | CB | PRO | A | 391 | 61.611 | 42.883 | 5.697 | 1.00 | 35.46 | C |
| ATOM | 2106 | CG | PRO | A | 391 | 61.850 | 43.944 | 6.725 | 1.00 | 34.53 | C |
| ATOM | 2107 | CD | PRO | A | 391 | 63.363 | 43.892 | 6.933 | 1.00 | 34.40 | C |
| ATOM | 2108 | N | THR | A | 392 | 63.196 | 45.157 | 3.373 | 1.00 | 38.30 | N |
| ATOM | 2109 | CA | THR | A | 392 | 62.849 | 46.185 | 2.403 | 1.00 | 39.78 | C |
| ATOM | 2110 | C | THR | A | 392 | 63.551 | 45.958 | 1.072 | 1.00 | 41.04 | C |
| ATOM | 2111 | O | THR | A | 392 | 64.460 | 45.131 | 0.969 | 1.00 | 40.81 | O |
| ATOM | 2112 | CB | THR | A | 392 | 63.210 | 47.581 | 2.920 | 1.00 | 39.64 | C |
| ATOM | 2113 | OG1 | THR | A | 392 | 64.629 | 47.674 | 3.085 | 1.00 | 40.34 | O |
| ATOM | 2114 | CG2 | THR | A | 392 | 62.528 | 47.844 | 4.259 | 1.00 | 39.79 | C |
| ATOM | 2115 | N | ARG | A | 393 | 63.122 | 46.697 | 0.055 | 1.00 | 42.49 | N |
| ATOM | 2116 | CA | ARG | A | 393 | 63.707 | 46.566 | −1.271 | 1.00 | 44.24 | C |
| ATOM | 2117 | C | ARG | A | 393 | 65.072 | 47.214 | −1.372 | 1.00 | 44.65 | C |
| ATOM | 2118 | O | ARG | A | 393 | 65.306 | 48.298 | −0.834 | 1.00 | 44.87 | O |
| ATOM | 2119 | CB | ARG | A | 393 | 62.806 | 47.196 | −2.337 | 1.00 | 45.06 | C |
| ATOM | 2120 | CG | ARG | A | 393 | 61.425 | 46.587 | −2.464 | 1.00 | 46.87 | C |
| ATOM | 2121 | CD | ARG | A | 393 | 60.966 | 46.622 | −3.919 | 1.00 | 48.41 | C |
| ATOM | 2122 | NE | ARG | A | 393 | 61.374 | 47.850 | −4.597 | 1.00 | 49.42 | N |
| ATOM | 2123 | CZ | ARG | A | 393 | 60.971 | 49.068 | −4.253 | 1.00 | 49.97 | C |
| ATOM | 2124 | NH1 | ARG | A | 393 | 60.138 | 49.231 | −3.233 | 1.00 | 50.58 | N |
| ATOM | 2125 | NH2 | ARG | A | 393 | 61.410 | 50.125 | −4.925 | 1.00 | 50.50 | N |
| ATOM | 2126 | N | LYS | A | 394 | 65.973 | 46.535 | −2.069 | 1.00 | 45.28 | N |
| ATOM | 2127 | CA | LYS | A | 394 | 67.309 | 47.056 | −2.296 | 1.00 | 46.21 | C |
| ATOM | 2128 | C | LYS | A | 394 | 67.171 | 47.833 | −3.598 | 1.00 | 46.79 | C |
| ATOM | 2129 | O | LYS | A | 394 | 66.911 | 47.242 | −4.645 | 1.00 | 47.04 | O |
| ATOM | 2130 | CB | LYS | A | 394 | 68.304 | 45.913 | −2.478 | 1.00 | 45.89 | C |
| ATOM | 2131 | CG | LYS | A | 394 | 69.744 | 46.366 | −2.558 | 1.00 | 46.14 | C |
| ATOM | 2132 | CD | LYS | A | 394 | 70.649 | 45.254 | −3.055 | 1.00 | 46.46 | C |
| ATOM | 2133 | CE | LYS | A | 394 | 70.618 | 44.049 | −2.140 | 1.00 | 46.54 | C |
| ATOM | 2134 | NZ | LYS | A | 394 | 71.498 | 42.968 | −2.658 | 1.00 | 46.60 | N |
| ATOM | 2135 | N | VAL | A | 395 | 67.316 | 49.151 | −3.533 | 1.00 | 47.31 | N |

TABLE 3-continued

| ATOM | 2136 | CA | VAL | A | 395 | 67.183 | 49.977 | -4.726 | 1.00 | 48.01 | C |
|---|---|---|---|---|---|---|---|---|---|---|---|
| ATOM | 2137 | C | VAL | A | 395 | 68.489 | 50.671 | -5.078 | 1.00 | 48.58 | C |
| ATOM | 2138 | O | VAL | A | 395 | 69.209 | 51.136 | -4.197 | 1.00 | 48.67 | O |
| ATOM | 2139 | CB | VAL | A | 395 | 66.086 | 51.049 | -4.543 | 1.00 | 48.06 | C |
| ATOM | 2140 | CG1 | VAL | A | 395 | 64.757 | 50.379 | -4.223 | 1.00 | 48.03 | C |
| ATOM | 2141 | CG2 | VAL | A | 395 | 66.473 | 52.014 | -3.435 | 1.00 | 47.99 | C |
| ATOM | 2142 | N | THR | A | 396 | 68.792 | 50.736 | -6.370 | 1.00 | 49.08 | N |
| ATOM | 2143 | CA | THR | A | 396 | 70.014 | 51.380 | -6.831 | 1.00 | 49.73 | C |
| ATOM | 2144 | C | THR | A | 396 | 69.691 | 52.708 | -7.493 | 1.00 | 50.27 | C |
| ATOM | 2145 | O | THR | A | 396 | 69.007 | 52.759 | -8.516 | 1.00 | 50.30 | O |
| ATOM | 2146 | CB | THR | A | 396 | 70.770 | 50.497 | -7.835 | 1.00 | 49.70 | C |
| ATOM | 2147 | OG1 | THR | A | 396 | 71.053 | 49.228 | -7.234 | 1.00 | 49.67 | O |
| ATOM | 2148 | CG2 | THR | A | 396 | 72.080 | 51.159 | -8.240 | 1.00 | 49.85 | C |
| ATOM | 2149 | N | ILE | A | 397 | 70.192 | 53.784 | -6.899 | 1.00 | 50.84 | N |
| ATOM | 2150 | CA | ILE | A | 397 | 69.953 | 55.122 | -7.416 | 1.00 | 51.13 | C |
| ATOM | 2151 | C | ILE | A | 397 | 71.261 | 55.795 | -7.821 | 1.00 | 51.21 | C |
| ATOM | 2152 | O | ILE | A | 397 | 72.043 | 56.214 | -6.967 | 1.00 | 51.47 | O |
| ATOM | 2153 | CB | ILE | A | 397 | 69.260 | 56.001 | -6.358 | 1.00 | 51.32 | C |
| ATOM | 2154 | CG1 | ILE | A | 397 | 68.033 | 55.276 | -5.800 | 1.00 | 51.51 | C |
| ATOM | 2155 | CG2 | ILE | A | 397 | 68.855 | 57.333 | -6.977 | 1.00 | 51.27 | C |
| ATOM | 2156 | CD1 | ILE | A | 397 | 67.325 | 56.029 | -4.691 | 1.00 | 51.49 | C |
| ATOM | 2157 | N | ASN | A | 398 | 71.497 | 55.889 | -9.126 | 1.00 | 51.17 | N |
| ATOM | 2158 | CA | ASN | A | 398 | 72.702 | 56.528 | -9.644 | 1.00 | 50.97 | C |
| ATOM | 2159 | C | ASN | A | 398 | 73.987 | 55.852 | -9.174 | 1.00 | 50.29 | C |
| ATOM | 2160 | O | ASN | A | 398 | 74.930 | 56.525 | -8.758 | 1.00 | 50.58 | O |
| ATOM | 2161 | CB | ASN | A | 398 | 72.730 | 58.000 | -9.228 | 1.00 | 51.92 | C |
| ATOM | 2162 | CG | ASN | A | 398 | 71.476 | 58.742 | -9.635 | 1.00 | 52.91 | C |
| ATOM | 2163 | OD1 | ASN | A | 398 | 71.150 | 58.827 | -10.819 | 1.00 | 53.63 | O |
| ATOM | 2164 | ND2 | ASN | A | 398 | 70.761 | 59.284 | -8.654 | 1.00 | 53.34 | N |
| ATOM | 2165 | N | GLY | A | 399 | 74.021 | 54.526 | -9.238 | 1.00 | 49.43 | N |
| ATOM | 2166 | CA | GLY | A | 399 | 75.209 | 53.801 | -8.824 | 1.00 | 48.10 | C |
| ATOM | 2167 | C | GLY | A | 399 | 75.308 | 53.532 | -7.334 | 1.00 | 47.22 | C |
| ATOM | 2168 | O | GLY | A | 399 | 76.228 | 52.844 | -6.887 | 1.00 | 47.45 | O |
| ATOM | 2169 | N | SER | A | 400 | 74.374 | 54.073 | -6.559 | 1.00 | 45.83 | N |
| ATOM | 2170 | CA | SER | A | 400 | 74.387 | 53.864 | -5.115 | 1.00 | 44.44 | C |
| ATOM | 2171 | C | SER | A | 400 | 73.287 | 52.916 | -4.674 | 1.00 | 43.04 | C |
| ATOM | 2172 | O | SER | A | 400 | 72.100 | 53.221 | -4.793 | 1.00 | 42.88 | O |
| ATOM | 2173 | CB | SER | A | 400 | 74.243 | 55.195 | -4.373 | 1.00 | 44.67 | C |
| ATOM | 2174 | OG | SER | A | 400 | 75.455 | 55.926 | -4.407 | 1.00 | 45.51 | O |
| ATOM | 2175 | N | VAL | A | 401 | 73.692 | 51.757 | -4.167 | 1.00 | 41.55 | N |
| ATOM | 2176 | CA | VAL | A | 401 | 72.739 | 50.768 | -3.697 | 1.00 | 40.15 | C |
| ATOM | 2177 | C | VAL | A | 401 | 72.251 | 51.225 | -2.328 | 1.00 | 39.84 | C |
| ATOM | 2178 | O | VAL | A | 401 | 73.046 | 51.445 | -1.413 | 1.00 | 39.36 | O |
| ATOM | 2179 | CB | VAL | A | 401 | 73.395 | 49.375 | -3.599 | 1.00 | 39.80 | C |
| ATOM | 2180 | CG1 | VAL | A | 401 | 72.386 | 48.348 | -3.117 | 1.00 | 38.64 | C |
| ATOM | 2181 | CG2 | VAL | A | 401 | 73.944 | 48.971 | -4.966 | 1.00 | 39.24 | C |
| ATOM | 2182 | N | MET | A | 402 | 70.938 | 51.387 | -2.206 | 1.00 | 39.55 | N |
| ATOM | 2183 | CA | MET | A | 402 | 70.329 | 51.837 | -0.961 | 1.00 | 39.09 | C |
| ATOM | 2184 | C | MET | A | 402 | 69.240 | 50.864 | -0.539 | 1.00 | 38.02 | C |
| ATOM | 2185 | O | MET | A | 402 | 68.872 | 49.962 | -1.289 | 1.00 | 37.68 | O |
| ATOM | 2186 | CB | MET | A | 402 | 69.683 | 53.213 | -1.148 | 1.00 | 40.51 | C |
| ATOM | 2187 | CG | MET | A | 402 | 70.529 | 54.244 | -1.882 | 1.00 | 42.23 | C |
| ATOM | 2188 | SD | MET | A | 402 | 71.952 | 54.787 | -0.942 | 1.00 | 45.56 | S |
| ATOM | 2189 | CE | MET | A | 402 | 71.204 | 56.039 | 0.120 | 1.00 | 43.68 | C |
| ATOM | 2190 | N | LYS | A | 403 | 68.734 | 51.059 | 0.673 | 1.00 | 36.46 | N |
| ATOM | 2191 | CA | LYS | A | 403 | 67.649 | 50.250 | 1.199 | 1.00 | 35.41 | C |
| ATOM | 2192 | C | LYS | A | 403 | 66.641 | 51.227 | 1.785 | 1.00 | 34.75 | C |
| ATOM | 2193 | O | LYS | A | 403 | 67.016 | 52.298 | 2.265 | 1.00 | 34.48 | O |
| ATOM | 2194 | CB | LYS | A | 403 | 68.153 | 49.275 | 2.266 | 1.00 | 35.62 | C |
| ATOM | 2195 | CG | LYS | A | 403 | 69.086 | 48.205 | 1.710 | 1.00 | 35.12 | C |
| ATOM | 2196 | CD | LYS | A | 403 | 68.847 | 46.848 | 2.346 | 1.00 | 35.57 | C |
| ATOM | 2197 | CE | LYS | A | 403 | 67.466 | 46.315 | 2.009 | 1.00 | 35.05 | C |
| ATOM | 2198 | NZ | LYS | A | 403 | 67.242 | 44.936 | 2.521 | 1.00 | 33.99 | N |
| ATOM | 2199 | N | GLU | A | 404 | 65.364 | 50.869 | 1.727 | 1.00 | 34.23 | N |
| ATOM | 2200 | CA | GLU | A | 404 | 64.305 | 51.734 | 2.235 | 1.00 | 34.40 | C |
| ATOM | 2201 | C | GLU | A | 404 | 64.259 | 51.735 | 3.754 | 1.00 | 33.56 | C |
| ATOM | 2202 | O | GLU | A | 404 | 64.590 | 50.740 | 4.394 | 1.00 | 33.40 | O |
| ATOM | 2203 | CB | GLU | A | 404 | 62.947 | 51.268 | 1.718 | 1.00 | 35.68 | C |
| ATOM | 2204 | CG | GLU | A | 404 | 62.879 | 51.034 | 0.225 | 1.00 | 38.04 | C |
| ATOM | 2205 | CD | GLU | A | 404 | 61.547 | 50.453 | -0.193 | 1.00 | 39.70 | C |
| ATOM | 2206 | OE1 | GLU | A | 404 | 61.264 | 49.284 | 0.159 | 1.00 | 40.89 | O |
| ATOM | 2207 | OE2 | GLU | A | 404 | 60.778 | 51.171 | -0.864 | 1.00 | 40.74 | O |
| ATOM | 2208 | N | TYR | A | 405 | 63.833 | 52.855 | 4.325 | 1.00 | 32.74 | N |
| ATOM | 2209 | CA | TYR | A | 405 | 63.714 | 52.975 | 5.770 | 1.00 | 32.04 | C |
| ATOM | 2210 | C | TYR | A | 405 | 62.665 | 54.027 | 6.092 | 1.00 | 31.67 | C |
| ATOM | 2211 | O | TYR | A | 405 | 62.782 | 55.179 | 5.677 | 1.00 | 32.05 | O |
| ATOM | 2212 | CB | TYR | A | 405 | 65.059 | 53.365 | 6.392 | 1.00 | 31.13 | C |
| ATOM | 2213 | CG | TYR | A | 405 | 65.049 | 53.387 | 7.905 | 1.00 | 30.72 | C |
| ATOM | 2214 | CD1 | TYR | A | 405 | 64.643 | 52.269 | 8.636 | 1.00 | 29.79 | C |

TABLE 3-continued

| | | | | | | | | | | |
|---|---|---|---|---|---|---|---|---|---|---|
| ATOM | 2215 | CD2 | TYR | A | 405 | 65.451 | 54.523 | 8.607 | 1.00 | 29.90 | C |
| ATOM | 2216 | CE1 | TYR | A | 405 | 64.638 | 52.282 | 10.033 | 1.00 | 30.48 | C |
| ATOM | 2217 | CE2 | TYR | A | 405 | 65.449 | 54.546 | 10.001 | 1.00 | 30.64 | C |
| ATOM | 2218 | CZ | TYR | A | 405 | 65.041 | 53.423 | 10.707 | 1.00 | 30.22 | C |
| ATOM | 2219 | OH | TYR | A | 405 | 65.029 | 53.448 | 12.085 | 1.00 | 30.03 | O |
| ATOM | 2220 | N | TRP | A | 406 | 61.632 | 53.627 | 6.822 | 1.00 | 31.08 | N |
| ATOM | 2221 | CA | TRP | A | 406 | 60.574 | 54.555 | 7.186 | 1.00 | 30.89 | C |
| ATOM | 2222 | C | TRP | A | 406 | 60.134 | 54.345 | 8.629 | 1.00 | 31.03 | C |
| ATOM | 2223 | O | TRP | A | 406 | 60.190 | 53.231 | 9.150 | 1.00 | 30.22 | O |
| ATOM | 2224 | CB | TRP | A | 406 | 59.384 | 54.401 | 6.227 | 1.00 | 29.70 | C |
| ATOM | 2225 | CG | TRP | A | 406 | 58.715 | 53.059 | 6.267 | 1.00 | 28.77 | C |
| ATOM | 2226 | CD1 | TRP | A | 406 | 57.695 | 52.675 | 7.090 | 1.00 | 28.91 | C |
| ATOM | 2227 | CD2 | TRP | A | 406 | 59.018 | 51.924 | 5.448 | 1.00 | 28.70 | C |
| ATOM | 2228 | NE1 | TRP | A | 406 | 57.342 | 51.374 | 6.833 | 1.00 | 29.02 | N |
| ATOM | 2229 | CE2 | TRP | A | 406 | 58.139 | 50.887 | 5.831 | 1.00 | 28.47 | C |
| ATOM | 2230 | CE3 | TRP | A | 406 | 59.947 | 51.681 | 4.426 | 1.00 | 28.73 | C |
| ATOM | 2231 | CZ2 | TRP | A | 406 | 58.158 | 49.624 | 5.228 | 1.00 | 28.64 | C |
| ATOM | 2232 | CZ3 | TRP | A | 406 | 59.967 | 50.423 | 3.825 | 1.00 | 29.12 | C |
| ATOM | 2233 | CH2 | TRP | A | 406 | 59.075 | 49.411 | 4.231 | 1.00 | 29.01 | C |
| ATOM | 2234 | N | GLY | A | 407 | 59.708 | 55.428 | 9.270 | 1.00 | 31.77 | N |
| ATOM | 2235 | CA | GLY | A | 407 | 59.270 | 55.349 | 10.652 | 1.00 | 32.35 | C |
| ATOM | 2236 | C | GLY | A | 407 | 57.927 | 54.665 | 10.816 | 1.00 | 32.51 | C |
| ATOM | 2237 | O | GLY | A | 407 | 57.124 | 54.619 | 9.887 | 1.00 | 32.50 | O |
| ATOM | 2238 | N | GLU | A | 408 | 57.685 | 54.125 | 12.005 | 1.00 | 32.68 | N |
| ATOM | 2239 | CA | GLU | A | 408 | 56.428 | 53.450 | 12.296 | 1.00 | 32.74 | C |
| ATOM | 2240 | C | GLU | A | 408 | 55.302 | 54.465 | 12.443 | 1.00 | 33.30 | C |
| ATOM | 2241 | O | GLU | A | 408 | 54.127 | 54.106 | 12.447 | 1.00 | 33.00 | O |
| ATOM | 2242 | CB | GLU | A | 408 | 56.562 | 52.625 | 13.576 | 1.00 | 32.42 | C |
| ATOM | 2243 | CG | GLU | A | 408 | 57.342 | 51.343 | 13.382 | 1.00 | 32.27 | C |
| ATOM | 2244 | CD | GLU | A | 408 | 56.618 | 50.373 | 12.460 | 1.00 | 32.10 | C |
| ATOM | 2245 | OE1 | GLU | A | 408 | 55.511 | 49.930 | 12.824 | 1.00 | 31.95 | O |
| ATOM | 2246 | OE2 | GLU | A | 408 | 57.149 | 50.059 | 11.376 | 1.00 | 31.80 | O |
| ATOM | 2247 | N | GLY | A | 409 | 55.670 | 55.736 | 12.563 | 1.00 | 34.53 | N |
| ATOM | 2248 | CA | GLY | A | 409 | 54.677 | 56.784 | 12.702 | 1.00 | 36.36 | C |
| ATOM | 2249 | C | GLY | A | 409 | 54.250 | 57.358 | 11.362 | 1.00 | 37.80 | C |
| ATOM | 2250 | O | GLY | A | 409 | 53.313 | 58.148 | 11.291 | 1.00 | 37.85 | O |
| ATOM | 2251 | N | SER | A | 410 | 54.934 | 56.965 | 10.293 | 1.00 | 39.37 | N |
| ATOM | 2252 | CA | SER | A | 410 | 54.598 | 57.462 | 8.963 | 1.00 | 41.45 | C |
| ATOM | 2253 | C | SER | A | 410 | 53.291 | 56.839 | 8.485 | 1.00 | 43.20 | C |
| ATOM | 2254 | O | SER | A | 410 | 52.945 | 55.723 | 8.876 | 1.00 | 42.83 | O |
| ATOM | 2255 | CB | SER | A | 410 | 55.715 | 57.135 | 7.971 | 1.00 | 40.60 | C |
| ATOM | 2256 | OG | SER | A | 410 | 55.795 | 55.740 | 7.738 | 1.00 | 40.47 | O |
| ATOM | 2257 | N | SER | A | 411 | 52.564 | 57.566 | 7.642 | 1.00 | 45.39 | N |
| ATOM | 2258 | CA | SER | A | 411 | 51.300 | 57.065 | 7.120 | 1.00 | 47.54 | C |
| ATOM | 2259 | C | SER | A | 411 | 51.556 | 55.777 | 6.347 | 1.00 | 48.82 | C |
| ATOM | 2260 | O | SER | A | 411 | 50.699 | 54.897 | 6.287 | 1.00 | 48.87 | O |
| ATOM | 2261 | CB | SER | A | 411 | 50.642 | 58.113 | 6.212 | 1.00 | 47.83 | C |
| ATOM | 2262 | OG | SER | A | 411 | 51.518 | 58.534 | 5.180 | 1.00 | 48.13 | O |
| ATOM | 2263 | N | ARG | A | 412 | 52.750 | 55.669 | 5.770 | 1.00 | 50.57 | N |
| ATOM | 2264 | CA | ARG | A | 412 | 53.125 | 54.483 | 5.009 | 1.00 | 52.38 | C |
| ATOM | 2265 | C | ARG | A | 412 | 53.169 | 53.244 | 5.895 | 1.00 | 53.64 | C |
| ATOM | 2266 | O | ARG | A | 412 | 52.940 | 52.130 | 5.426 | 1.00 | 53.63 | O |
| ATOM | 2267 | CB | ARG | A | 412 | 54.495 | 54.677 | 4.351 | 1.00 | 52.24 | C |
| ATOM | 2268 | CG | ARG | A | 412 | 55.008 | 53.420 | 3.652 | 1.00 | 52.42 | C |
| ATOM | 2269 | CD | ARG | A | 412 | 56.351 | 53.628 | 2.971 | 1.00 | 52.24 | C |
| ATOM | 2270 | NE | ARG | A | 412 | 56.789 | 52.412 | 2.286 | 1.00 | 52.01 | N |
| ATOM | 2271 | CZ | ARG | A | 412 | 57.920 | 52.298 | 1.596 | 1.00 | 52.09 | C |
| ATOM | 2272 | NH1 | ARG | A | 412 | 58.747 | 53.329 | 1.487 | 1.00 | 51.74 | N |
| ATOM | 2273 | NH2 | ARG | A | 412 | 58.226 | 51.145 | 1.014 | 1.00 | 52.05 | N |
| ATOM | 2274 | N | ALA | A | 413 | 53.465 | 53.445 | 7.176 | 1.00 | 55.35 | N |
| ATOM | 2275 | CA | ALA | A | 413 | 53.555 | 52.344 | 8.128 | 1.00 | 57.35 | C |
| ATOM | 2276 | C | ALA | A | 413 | 52.196 | 51.934 | 8.682 | 1.00 | 58.87 | C |
| ATOM | 2277 | O | ALA | A | 413 | 51.760 | 50.799 | 8.501 | 1.00 | 58.87 | O |
| ATOM | 2278 | CB | ALA | A | 413 | 54.483 | 52.725 | 9.278 | 1.00 | 56.92 | C |
| ATOM | 2279 | N | ARG | A | 414 | 51.532 | 52.858 | 9.368 | 1.00 | 61.25 | N |
| ATOM | 2280 | CA | ARG | A | 414 | 50.232 | 52.558 | 9.945 | 1.00 | 63.66 | C |
| ATOM | 2281 | C | ARG | A | 414 | 49.102 | 52.862 | 8.968 | 1.00 | 64.89 | C |
| ATOM | 2282 | O | ARG | A | 414 | 48.824 | 54.018 | 8.648 | 1.00 | 65.40 | O |
| ATOM | 2283 | CB | ARG | A | 414 | 50.040 | 53.330 | 11.259 | 1.00 | 64.13 | C |
| ATOM | 2284 | CG | ARG | A | 414 | 50.007 | 54.843 | 11.139 | 1.00 | 65.06 | C |
| ATOM | 2285 | CD | ARG | A | 414 | 49.833 | 55.477 | 12.511 | 1.00 | 65.70 | C |
| ATOM | 2286 | NE | ARG | A | 414 | 49.344 | 56.850 | 12.427 | 1.00 | 66.48 | N |
| ATOM | 2287 | CZ | ARG | A | 414 | 49.075 | 57.614 | 13.481 | 1.00 | 66.77 | C |
| ATOM | 2288 | NH1 | ARG | A | 414 | 49.250 | 57.143 | 14.709 | 1.00 | 66.88 | N |
| ATOM | 2289 | NH2 | ARG | A | 414 | 48.615 | 58.846 | 13.311 | 1.00 | 67.02 | N |
| ATOM | 2290 | N | ASN | A | 415 | 48.467 | 51.799 | 8.486 | 1.00 | 66.35 | N |
| ATOM | 2291 | CA | ASN | A | 415 | 47.361 | 51.907 | 7.542 | 1.00 | 67.56 | C |
| ATOM | 2292 | C | ASN | A | 415 | 46.837 | 50.495 | 7.276 | 1.00 | 67.89 | C |
| ATOM | 2293 | O | ASN | A | 415 | 46.002 | 50.282 | 6.397 | 1.00 | 68.21 | O |

TABLE 3-continued

| | | | | | | | | | | |
|---|---|---|---|---|---|---|---|---|---|---|
| ATOM | 2294 | CB | ASN | A | 415 | 47.840 | 52.552 | 6.233 | 1.00 | 68.15 | C |
| ATOM | 2295 | CG | ASN | A | 415 | 46.701 | 53.155 | 5.418 | 1.00 | 68.99 | C |
| ATOM | 2296 | OD1 | ASN | A | 415 | 45.788 | 52.454 | 4.978 | 1.00 | 69.44 | O |
| ATOM | 2297 | ND2 | ASN | A | 415 | 46.756 | 54.466 | 5.215 | 1.00 | 69.28 | N |
| ATOM | 2298 | N | TRP | A | 416 | 47.343 | 49.534 | 8.045 | 1.00 | 68.11 | N |
| ATOM | 2299 | CA | TRP | A | 416 | 46.932 | 48.140 | 7.915 | 1.00 | 68.12 | C |
| ATOM | 2300 | C | TRP | A | 416 | 45.656 | 47.901 | 8.719 | 1.00 | 68.17 | C |
| ATOM | 2301 | O | TRP | A | 416 | 44.616 | 47.529 | 8.171 | 1.00 | 68.31 | O |
| ATOM | 2302 | CB | TRP | A | 416 | 48.040 | 47.209 | 8.424 | 1.00 | 68.13 | C |
| ATOM | 2303 | CG | TRP | A | 416 | 48.339 | 47.382 | 9.886 | 1.00 | 67.91 | C |
| ATOM | 2304 | CD1 | TRP | A | 416 | 49.047 | 48.397 | 10.465 | 1.00 | 67.92 | C |
| ATOM | 2305 | CD2 | TRP | A | 416 | 47.868 | 46.558 | 10.960 | 1.00 | 67.76 | C |
| ATOM | 2306 | NE1 | TRP | A | 416 | 49.040 | 48.259 | 11.834 | 1.00 | 67.80 | N |
| ATOM | 2307 | CE2 | TRP | A | 416 | 48.323 | 47.139 | 12.164 | 1.00 | 67.78 | C |
| ATOM | 2308 | CE3 | TRP | A | 416 | 47.101 | 45.388 | 11.021 | 1.00 | 67.62 | C |
| ATOM | 2309 | CZ2 | TRP | A | 416 | 48.036 | 46.588 | 13.419 | 1.00 | 67.74 | C |
| ATOM | 2310 | CZ3 | TRP | A | 416 | 46.815 | 44.839 | 12.268 | 1.00 | 67.75 | C |
| ATOM | 2311 | CH2 | TRP | A | 416 | 47.282 | 45.441 | 13.450 | 1.00 | 67.77 | C |
| ATOM | 2312 | N | GLU | A | 430 | 49.118 | 63.275 | 11.644 | 1.00 | 73.03 | N |
| ATOM | 2313 | CA | GLU | A | 430 | 50.037 | 62.232 | 12.086 | 1.00 | 72.84 | C |
| ATOM | 2314 | C | GLU | A | 430 | 51.464 | 62.554 | 11.659 | 1.00 | 72.49 | C |
| ATOM | 2315 | O | GLU | A | 430 | 51.709 | 63.560 | 10.992 | 1.00 | 72.57 | O |
| ATOM | 2316 | CB | GLU | A | 430 | 49.622 | 60.882 | 11.499 | 1.00 | 73.23 | C |
| ATOM | 2317 | CG | GLU | A | 430 | 49.699 | 60.809 | 9.981 | 1.00 | 73.60 | C |
| ATOM | 2318 | CD | GLU | A | 430 | 49.250 | 59.466 | 9.439 | 1.00 | 73.90 | C |
| ATOM | 2319 | OE1 | GLU | A | 430 | 49.840 | 58.437 | 9.831 | 1.00 | 73.94 | O |
| ATOM | 2320 | OE2 | GLU | A | 430 | 48.308 | 59.439 | 8.619 | 1.00 | 74.25 | O |
| ATOM | 2321 | N | GLU | A | 431 | 52.403 | 61.695 | 12.046 | 1.00 | 71.87 | N |
| ATOM | 2322 | CA | GLU | A | 431 | 53.803 | 61.891 | 11.692 | 1.00 | 71.10 | C |
| ATOM | 2323 | C | GLU | A | 431 | 54.066 | 61.249 | 10.333 | 1.00 | 70.43 | C |
| ATOM | 2324 | O | GLU | A | 431 | 53.136 | 60.792 | 9.666 | 1.00 | 70.43 | O |
| ATOM | 2325 | CB | GLU | A | 431 | 54.714 | 61.254 | 12.744 | 1.00 | 71.29 | C |
| ATOM | 2326 | CG | GLU | A | 431 | 56.138 | 61.783 | 12.716 | 1.00 | 71.71 | C |
| ATOM | 2327 | CD | GLU | A | 431 | 57.111 | 60.917 | 13.493 | 1.00 | 71.87 | C |
| ATOM | 2328 | OE1 | GLU | A | 431 | 56.854 | 60.632 | 14.684 | 1.00 | 72.06 | O |
| ATOM | 2329 | OE2 | GLU | A | 431 | 58.141 | 60.528 | 12.907 | 1.00 | 71.88 | O |
| ATOM | 2330 | N | GLY | A | 432 | 55.331 | 61.211 | 9.926 | 1.00 | 69.40 | N |
| ATOM | 2331 | CA | GLY | A | 432 | 55.667 | 60.614 | 8.647 | 1.00 | 67.99 | C |
| ATOM | 2332 | C | GLY | A | 432 | 57.101 | 60.847 | 8.215 | 1.00 | 66.90 | C |
| ATOM | 2333 | O | GLY | A | 432 | 57.524 | 61.987 | 8.030 | 1.00 | 67.35 | O |
| ATOM | 2334 | N | VAL | A | 433 | 57.853 | 59.763 | 8.054 | 1.00 | 65.49 | N |
| ATOM | 2335 | CA | VAL | A | 433 | 59.246 | 59.851 | 7.631 | 1.00 | 63.66 | C |
| ATOM | 2336 | C | VAL | A | 433 | 59.611 | 58.651 | 6.760 | 1.00 | 62.12 | C |
| ATOM | 2337 | O | VAL | A | 433 | 59.537 | 57.503 | 7.200 | 1.00 | 61.66 | O |
| ATOM | 2338 | CB | VAL | A | 433 | 60.198 | 59.891 | 8.840 | 1.00 | 64.04 | C |
| ATOM | 2339 | CG1 | VAL | A | 433 | 61.624 | 60.100 | 8.366 | 1.00 | 64.18 | C |
| ATOM | 2340 | CG2 | VAL | A | 433 | 59.784 | 60.994 | 9.797 | 1.00 | 64.08 | C |
| ATOM | 2341 | N | ASP | A | 434 | 60.008 | 58.930 | 5.522 | 1.00 | 60.25 | N |
| ATOM | 2342 | CA | ASP | A | 434 | 60.377 | 57.892 | 4.566 | 1.00 | 58.26 | C |
| ATOM | 2343 | C | ASP | A | 434 | 61.718 | 58.280 | 3.947 | 1.00 | 56.78 | C |
| ATOM | 2344 | O | ASP | A | 434 | 61.881 | 59.405 | 3.475 | 1.00 | 56.70 | O |
| ATOM | 2345 | CB | ASP | A | 434 | 59.311 | 57.805 | 3.470 | 1.00 | 58.76 | C |
| ATOM | 2346 | CG | ASP | A | 434 | 59.280 | 56.456 | 2.783 | 1.00 | 58.92 | C |
| ATOM | 2347 | OD1 | ASP | A | 434 | 60.357 | 55.902 | 2.487 | 1.00 | 59.73 | O |
| ATOM | 2348 | OD2 | ASP | A | 434 | 58.168 | 55.955 | 2.525 | 1.00 | 59.23 | O |
| ATOM | 2349 | N | SER | A | 435 | 62.676 | 57.359 | 3.944 | 1.00 | 54.66 | N |
| ATOM | 2350 | CA | SER | A | 435 | 63.988 | 57.664 | 3.382 | 1.00 | 52.26 | C |
| ATOM | 2351 | C | SER | A | 435 | 64.779 | 56.437 | 2.938 | 1.00 | 50.24 | C |
| ATOM | 2352 | O | SER | A | 435 | 64.263 | 55.319 | 2.913 | 1.00 | 49.77 | O |
| ATOM | 2353 | CB | SER | A | 435 | 64.815 | 58.454 | 4.400 | 1.00 | 52.83 | C |
| ATOM | 2354 | OG | SER | A | 435 | 65.010 | 57.701 | 5.586 | 1.00 | 53.50 | O |
| ATOM | 2355 | N | TYR | A | 436 | 66.040 | 56.668 | 2.586 | 1.00 | 47.86 | N |
| ATOM | 2356 | CA | TYR | A | 436 | 66.935 | 55.609 | 2.140 | 1.00 | 45.83 | C |
| ATOM | 2357 | C | TYR | A | 436 | 68.198 | 55.593 | 2.993 | 1.00 | 43.91 | C |
| ATOM | 2358 | O | TYR | A | 436 | 68.622 | 56.626 | 3.513 | 1.00 | 43.83 | O |
| ATOM | 2359 | CB | TYR | A | 436 | 67.333 | 55.825 | 0.677 | 1.00 | 46.59 | C |
| ATOM | 2360 | CG | TYR | A | 436 | 66.196 | 55.715 | −0.312 | 1.00 | 47.13 | C |
| ATOM | 2361 | CD1 | TYR | A | 436 | 65.599 | 54.485 | −0.585 | 1.00 | 47.53 | C |
| ATOM | 2362 | CD2 | TYR | A | 436 | 65.713 | 56.843 | −0.974 | 1.00 | 47.79 | C |
| ATOM | 2363 | CE1 | TYR | A | 436 | 64.547 | 54.380 | −1.493 | 1.00 | 48.14 | C |
| ATOM | 2364 | CE2 | TYR | A | 436 | 64.661 | 56.751 | −1.882 | 1.00 | 48.43 | C |
| ATOM | 2365 | CZ | TYR | A | 436 | 64.083 | 55.517 | −2.136 | 1.00 | 48.48 | C |
| ATOM | 2366 | OH | TYR | A | 436 | 63.036 | 55.424 | −3.024 | 1.00 | 49.29 | O |
| ATOM | 2367 | N | VAL | A | 437 | 68.786 | 54.412 | 3.140 | 1.00 | 41.44 | N |
| ATOM | 2368 | CA | VAL | A | 437 | 70.018 | 54.251 | 3.901 | 1.00 | 39.25 | C |
| ATOM | 2369 | C | VAL | A | 437 | 70.997 | 53.500 | 3.010 | 1.00 | 37.73 | C |
| ATOM | 2370 | O | VAL | A | 437 | 70.604 | 52.608 | 2.261 | 1.00 | 37.14 | O |
| ATOM | 2371 | CB | VAL | A | 437 | 69.786 | 53.455 | 5.209 | 1.00 | 38.97 | C |
| ATOM | 2372 | CG1 | VAL | A | 437 | 68.841 | 54.225 | 6.119 | 1.00 | 39.50 | C |

TABLE 3-continued

| | | | | | | | | | | |
|---|---|---|---|---|---|---|---|---|---|---|
| ATOM | 2373 | CG2 | VAL | A | 437 | 69.221 | 52.084 | 4.901 | 1.00 | 38.52 | C |
| ATOM | 2374 | N | PRO | A | 438 | 72.289 | 53.852 | 3.075 | 1.00 | 37.00 | N |
| ATOM | 2375 | CA | PRO | A | 438 | 73.280 | 53.169 | 2.239 | 1.00 | 35.94 | C |
| ATOM | 2376 | C | PRO | A | 438 | 73.390 | 51.682 | 2.547 | 1.00 | 34.96 | C |
| ATOM | 2377 | O | PRO | A | 438 | 73.442 | 51.282 | 3.710 | 1.00 | 34.43 | O |
| ATOM | 2378 | CB | PRO | A | 438 | 74.569 | 53.929 | 2.543 | 1.00 | 36.50 | C |
| ATOM | 2379 | CG | PRO | A | 438 | 74.377 | 54.345 | 3.981 | 1.00 | 37.42 | C |
| ATOM | 2380 | CD | PRO | A | 438 | 72.935 | 54.813 | 3.988 | 1.00 | 37.02 | C |
| ATOM | 2381 | N | TYR | A | 439 | 73.412 | 50.872 | 1.492 | 1.00 | 33.53 | N |
| ATOM | 2382 | CA | TYR | A | 439 | 73.526 | 49.423 | 1.619 | 1.00 | 32.47 | C |
| ATOM | 2383 | C | TYR | A | 439 | 74.858 | 49.089 | 2.284 | 1.00 | 31.86 | C |
| ATOM | 2384 | O | TYR | A | 439 | 75.881 | 49.681 | 1.959 | 1.00 | 31.19 | O |
| ATOM | 2385 | CB | TYR | A | 439 | 73.459 | 48.778 | 0.232 | 1.00 | 31.92 | C |
| ATOM | 2386 | CG | TYR | A | 439 | 73.590 | 47.273 | 0.230 | 1.00 | 31.72 | C |
| ATOM | 2387 | CD1 | TYR | A | 439 | 72.683 | 46.476 | 0.925 | 1.00 | 31.68 | C |
| ATOM | 2388 | CD2 | TYR | A | 439 | 74.601 | 46.643 | −0.497 | 1.00 | 31.71 | C |
| ATOM | 2389 | CE1 | TYR | A | 439 | 72.775 | 45.087 | 0.896 | 1.00 | 32.18 | C |
| ATOM | 2390 | CE2 | TYR | A | 439 | 74.702 | 45.254 | −0.533 | 1.00 | 32.39 | C |
| ATOM | 2391 | CZ | TYR | A | 439 | 73.784 | 44.484 | 0.165 | 1.00 | 32.74 | C |
| ATOM | 2392 | OH | TYR | A | 439 | 73.863 | 43.112 | 0.124 | 1.00 | 34.28 | O |
| ATOM | 2393 | N | ALA | A | 440 | 74.847 | 48.133 | 3.208 | 1.00 | 31.96 | N |
| ATOM | 2394 | CA | ALA | A | 440 | 76.070 | 47.765 | 3.913 | 1.00 | 32.22 | C |
| ATOM | 2395 | C | ALA | A | 440 | 76.429 | 46.297 | 3.758 | 1.00 | 32.05 | C |
| ATOM | 2396 | O | ALA | A | 440 | 77.465 | 45.856 | 4.244 | 1.00 | 32.90 | O |
| ATOM | 2397 | CB | ALA | A | 440 | 75.938 | 48.115 | 5.396 | 1.00 | 31.52 | C |
| ATOM | 2398 | N | GLY | A | 441 | 75.577 | 45.538 | 3.080 | 1.00 | 32.08 | N |
| ATOM | 2399 | CA | GLY | A | 441 | 75.857 | 44.127 | 2.899 | 1.00 | 32.00 | C |
| ATOM | 2400 | C | GLY | A | 441 | 75.250 | 43.262 | 3.991 | 1.00 | 32.35 | C |
| ATOM | 2401 | O | GLY | A | 441 | 74.248 | 43.639 | 4.602 | 1.00 | 31.44 | O |
| ATOM | 2402 | N | LYS | A | 442 | 75.867 | 42.106 | 4.231 | 1.00 | 32.08 | N |
| ATOM | 2403 | CA | LYS | A | 442 | 75.411 | 41.147 | 5.235 | 1.00 | 32.60 | C |
| ATOM | 2404 | C | LYS | A | 442 | 75.531 | 41.671 | 6.664 | 1.00 | 31.49 | C |
| ATOM | 2405 | O | LYS | A | 442 | 76.495 | 42.350 | 7.012 | 1.00 | 31.52 | O |
| ATOM | 2406 | CB | LYS | A | 442 | 76.216 | 39.848 | 5.129 | 1.00 | 34.46 | C |
| ATOM | 2407 | CG | LYS | A | 442 | 76.072 | 39.097 | 3.814 | 1.00 | 37.78 | C |
| ATOM | 2408 | CD | LYS | A | 442 | 74.734 | 38.377 | 3.714 | 1.00 | 39.58 | C |
| ATOM | 2409 | CE | LYS | A | 442 | 74.725 | 37.415 | 2.527 | 1.00 | 41.54 | C |
| ATOM | 2410 | NZ | LYS | A | 442 | 73.453 | 36.640 | 2.425 | 1.00 | 42.55 | N |
| ATOM | 2411 | N | LEU | A | 443 | 74.548 | 41.332 | 7.491 | 1.00 | 30.52 | N |
| ATOM | 2412 | CA | LEU | A | 443 | 74.538 | 41.751 | 8.887 | 1.00 | 29.23 | C |
| ATOM | 2413 | C | LEU | A | 443 | 75.790 | 41.271 | 9.624 | 1.00 | 29.23 | C |
| ATOM | 2414 | O | LEU | A | 443 | 76.430 | 42.040 | 10.343 | 1.00 | 28.36 | O |
| ATOM | 2415 | CB | LEU | A | 443 | 73.281 | 41.208 | 9.582 | 1.00 | 28.43 | C |
| ATOM | 2416 | CG | LEU | A | 443 | 73.124 | 41.454 | 11.087 | 1.00 | 28.11 | C |
| ATOM | 2417 | CD1 | LEU | A | 443 | 71.648 | 41.409 | 11.471 | 1.00 | 27.84 | C |
| ATOM | 2418 | CD2 | LEU | A | 443 | 73.920 | 40.408 | 11.863 | 1.00 | 28.16 | C |
| ATOM | 2419 | N | LYS | A | 444 | 76.136 | 40.003 | 9.423 | 1.00 | 29.23 | N |
| ATOM | 2420 | CA | LYS | A | 444 | 77.282 | 39.382 | 10.083 | 1.00 | 30.71 | C |
| ATOM | 2421 | C | LYS | A | 444 | 78.583 | 40.179 | 10.103 | 1.00 | 30.91 | C |
| ATOM | 2422 | O | LYS | A | 444 | 79.124 | 40.453 | 11.174 | 1.00 | 30.45 | O |
| ATOM | 2423 | CB | LYS | A | 444 | 77.562 | 38.002 | 9.477 | 1.00 | 31.85 | C |
| ATOM | 2424 | CG | LYS | A | 444 | 78.712 | 37.262 | 10.164 | 1.00 | 34.22 | C |
| ATOM | 2425 | CD | LYS | A | 444 | 78.908 | 35.868 | 9.587 | 1.00 | 36.27 | C |
| ATOM | 2426 | CE | LYS | A | 444 | 80.016 | 35.126 | 10.314 | 1.00 | 37.68 | C |
| ATOM | 2427 | NZ | LYS | A | 444 | 81.325 | 35.828 | 10.197 | 1.00 | 38.57 | N |
| ATOM | 2428 | N | ASP | A | 445 | 79.087 | 40.542 | 8.927 | 1.00 | 30.82 | N |
| ATOM | 2429 | CA | ASP | A | 445 | 80.344 | 41.280 | 8.829 | 1.00 | 31.15 | C |
| ATOM | 2430 | C | ASP | A | 445 | 80.303 | 42.662 | 9.462 | 1.00 | 30.19 | C |
| ATOM | 2431 | O | ASP | A | 445 | 81.296 | 43.125 | 10.022 | 1.00 | 29.83 | O |
| ATOM | 2432 | CB | ASP | A | 445 | 80.757 | 41.412 | 7.363 | 1.00 | 33.63 | C |
| ATOM | 2433 | CG | ASP | A | 445 | 80.781 | 40.079 | 6.650 | 1.00 | 35.59 | C |
| ATOM | 2434 | OD1 | ASP | A | 445 | 81.474 | 39.158 | 7.136 | 1.00 | 36.48 | O |
| ATOM | 2435 | OD2 | ASP | A | 445 | 80.102 | 39.953 | 5.610 | 1.00 | 37.86 | O |
| ATOM | 2436 | N | ASN | A | 446 | 79.157 | 43.321 | 9.366 | 1.00 | 28.50 | N |
| ATOM | 2437 | CA | ASN | A | 446 | 79.005 | 44.657 | 9.922 | 1.00 | 28.18 | C |
| ATOM | 2438 | C | ASN | A | 446 | 78.957 | 44.660 | 11.450 | 1.00 | 27.76 | C |
| ATOM | 2439 | O | ASN | A | 446 | 79.575 | 45.506 | 12.092 | 1.00 | 27.67 | O |
| ATOM | 2440 | CB | ASN | A | 446 | 77.750 | 45.306 | 9.347 | 1.00 | 28.54 | C |
| ATOM | 2441 | CG | ASN | A | 446 | 77.938 | 45.755 | 7.909 | 1.00 | 28.71 | C |
| ATOM | 2442 | OD1 | ASN | A | 446 | 78.508 | 46.815 | 7.652 | 1.00 | 29.83 | O |
| ATOM | 2443 | ND2 | ASN | A | 446 | 77.473 | 44.945 | 6.967 | 1.00 | 27.87 | N |
| ATOM | 2444 | N | VAL | A | 447 | 78.222 | 43.714 | 12.023 | 1.00 | 27.34 | N |
| ATOM | 2445 | CA | VAL | A | 447 | 78.105 | 43.600 | 13.474 | 1.00 | 27.67 | C |
| ATOM | 2446 | C | VAL | A | 447 | 79.461 | 43.220 | 14.071 | 1.00 | 28.37 | C |
| ATOM | 2447 | O | VAL | A | 447 | 79.878 | 43.770 | 15.088 | 1.00 | 28.42 | O |
| ATOM | 2448 | CB | VAL | A | 447 | 77.043 | 42.542 | 13.850 | 1.00 | 27.28 | C |
| ATOM | 2449 | CG1 | VAL | A | 447 | 77.154 | 42.172 | 15.324 | 1.00 | 26.67 | C |
| ATOM | 2450 | CG2 | VAL | A | 447 | 75.657 | 43.091 | 13.553 | 1.00 | 26.56 | C |
| ATOM | 2451 | N | GLU | A | 448 | 80.151 | 42.287 | 13.426 | 1.00 | 28.89 | N |

TABLE 3-continued

| | | | | | | | | | | |
|---|---|---|---|---|---|---|---|---|---|---|
| ATOM | 2452 | CA | GLU | A | 448 | 81.464 | 41.861 | 13.897 | 1.00 | 30.04 | C |
| ATOM | 2453 | C | GLU | A | 448 | 82.412 | 43.061 | 13.971 | 1.00 | 29.13 | C |
| ATOM | 2454 | O | GLU | A | 448 | 83.127 | 43.239 | 14.960 | 1.00 | 28.39 | O |
| ATOM | 2455 | CB | GLU | A | 448 | 82.029 | 40.790 | 12.959 | 1.00 | 32.21 | C |
| ATOM | 2456 | CG | GLU | A | 448 | 83.451 | 40.343 | 13.273 | 1.00 | 35.95 | C |
| ATOM | 2457 | CD | GLU | A | 448 | 83.912 | 39.210 | 12.365 | 1.00 | 38.46 | C |
| ATOM | 2458 | OE1 | GLU | A | 448 | 83.834 | 39.364 | 11.124 | 1.00 | 40.14 | O |
| ATOM | 2459 | OE2 | GLU | A | 448 | 84.351 | 38.163 | 12.890 | 1.00 | 40.41 | O |
| ATOM | 2460 | N | ALA | A | 449 | 82.404 | 43.889 | 12.930 | 1.00 | 27.90 | N |
| ATOM | 2461 | CA | ALA | A | 449 | 83.265 | 45.069 | 12.893 | 1.00 | 27.67 | C |
| ATOM | 2462 | C | ALA | A | 449 | 82.870 | 46.080 | 13.974 | 1.00 | 27.21 | C |
| ATOM | 2463 | O | ALA | A | 449 | 83.725 | 46.612 | 14.685 | 1.00 | 26.68 | O |
| ATOM | 2464 | CB | ALA | A | 449 | 83.203 | 45.722 | 11.513 | 1.00 | 28.18 | C |
| ATOM | 2465 | N | SER | A | 450 | 81.573 | 46.343 | 14.097 | 1.00 | 26.17 | N |
| ATOM | 2466 | CA | SER | A | 450 | 81.090 | 47.279 | 15.105 | 1.00 | 26.52 | C |
| ATOM | 2467 | C | SER | A | 450 | 81.487 | 46.829 | 16.511 | 1.00 | 26.58 | C |
| ATOM | 2468 | O | SER | A | 450 | 82.062 | 47.603 | 17.281 | 1.00 | 26.69 | O |
| ATOM | 2469 | CB | SER | A | 450 | 79.562 | 47.408 | 15.032 | 1.00 | 26.11 | C |
| ATOM | 2470 | OG | SER | A | 450 | 79.154 | 48.048 | 13.833 | 1.00 | 25.91 | O |
| ATOM | 2471 | N | LEU | A | 451 | 81.186 | 45.575 | 16.839 | 1.00 | 25.76 | N |
| ATOM | 2472 | CA | LEU | A | 451 | 81.490 | 45.045 | 18.163 | 1.00 | 26.02 | C |
| ATOM | 2473 | C | LEU | A | 451 | 82.986 | 44.910 | 18.450 | 1.00 | 26.55 | C |
| ATOM | 2474 | O | LEU | A | 451 | 83.404 | 44.961 | 19.611 | 1.00 | 25.99 | O |
| ATOM | 2475 | CB | LEU | A | 451 | 80.767 | 43.709 | 18.372 | 1.00 | 25.37 | C |
| ATOM | 2476 | CG | LEU | A | 451 | 79.238 | 43.840 | 18.305 | 1.00 | 25.01 | C |
| ATOM | 2477 | CD1 | LEU | A | 451 | 78.586 | 42.524 | 18.693 | 1.00 | 24.99 | C |
| ATOM | 2478 | CD2 | LEU | A | 451 | 78.773 | 44.962 | 19.232 | 1.00 | 25.24 | C |
| ATOM | 2479 | N | ASN | A | 452 | 83.796 | 44.747 | 17.407 | 1.00 | 26.96 | N |
| ATOM | 2480 | CA | ASN | A | 452 | 85.240 | 44.661 | 17.618 | 1.00 | 28.17 | C |
| ATOM | 2481 | C | ASN | A | 452 | 85.722 | 46.016 | 18.133 | 1.00 | 27.59 | C |
| ATOM | 2482 | O | ASN | A | 452 | 86.624 | 46.094 | 18.968 | 1.00 | 26.76 | O |
| ATOM | 2483 | CB | ASN | A | 452 | 85.977 | 44.310 | 16.320 | 1.00 | 30.23 | C |
| ATOM | 2484 | CG | ASN | A | 452 | 86.089 | 42.815 | 16.099 | 1.00 | 33.77 | C |
| ATOM | 2485 | OD1 | ASN | A | 452 | 86.244 | 42.048 | 17.050 | 1.00 | 36.57 | O |
| ATOM | 2486 | ND2 | ASN | A | 452 | 86.034 | 42.393 | 14.839 | 1.00 | 35.31 | N |
| ATOM | 2487 | N | LYS | A | 453 | 85.104 | 47.081 | 17.632 | 1.00 | 27.29 | N |
| ATOM | 2488 | CA | LYS | A | 453 | 85.453 | 48.435 | 18.043 | 1.00 | 27.38 | C |
| ATOM | 2489 | C | LYS | A | 453 | 84.962 | 48.684 | 19.465 | 1.00 | 26.33 | C |
| ATOM | 2490 | O | LYS | A | 453 | 85.654 | 49.305 | 20.267 | 1.00 | 25.74 | O |
| ATOM | 2491 | CB | LYS | A | 453 | 84.835 | 49.453 | 17.076 | 1.00 | 29.18 | C |
| ATOM | 2492 | CG | LYS | A | 453 | 85.374 | 49.322 | 15.651 | 1.00 | 31.57 | C |
| ATOM | 2493 | CD | LYS | A | 453 | 84.545 | 50.103 | 14.637 | 1.00 | 33.43 | C |
| ATOM | 2494 | CE | LYS | A | 453 | 84.630 | 51.604 | 14.856 | 1.00 | 34.79 | C |
| ATOM | 2495 | NZ | LYS | A | 453 | 83.781 | 52.334 | 13.861 | 1.00 | 35.78 | N |
| ATOM | 2496 | N | VAL | A | 454 | 83.764 | 48.197 | 19.772 | 1.00 | 25.19 | N |
| ATOM | 2497 | CA | VAL | A | 454 | 83.200 | 48.351 | 21.104 | 1.00 | 24.18 | C |
| ATOM | 2498 | C | VAL | A | 454 | 84.108 | 47.638 | 22.114 | 1.00 | 24.77 | C |
| ATOM | 2499 | O | VAL | A | 454 | 84.455 | 48.194 | 23.159 | 1.00 | 23.53 | O |
| ATOM | 2500 | CB | VAL | A | 454 | 81.770 | 47.741 | 21.180 | 1.00 | 24.45 | C |
| ATOM | 2501 | CG1 | VAL | A | 454 | 81.293 | 47.691 | 22.627 | 1.00 | 23.62 | C |
| ATOM | 2502 | CG2 | VAL | A | 454 | 80.800 | 48.574 | 20.338 | 1.00 | 23.76 | C |
| ATOM | 2503 | N | LYS | A | 455 | 84.501 | 46.409 | 21.791 | 1.00 | 24.44 | N |
| ATOM | 2504 | CA | LYS | A | 455 | 85.355 | 45.634 | 22.683 | 1.00 | 24.98 | C |
| ATOM | 2505 | C | LYS | A | 455 | 86.728 | 46.266 | 22.878 | 1.00 | 25.10 | C |
| ATOM | 2506 | O | LYS | A | 455 | 87.273 | 46.254 | 23.984 | 1.00 | 24.49 | O |
| ATOM | 2507 | CB | LYS | A | 455 | 85.477 | 44.194 | 22.168 | 1.00 | 25.62 | C |
| ATOM | 2508 | CG | LYS | A | 455 | 84.136 | 43.465 | 22.213 | 1.00 | 27.11 | C |
| ATOM | 2509 | CD | LYS | A | 455 | 84.249 | 41.968 | 21.985 | 1.00 | 28.53 | C |
| ATOM | 2510 | CE | LYS | A | 455 | 84.339 | 41.611 | 20.517 | 1.00 | 29.62 | C |
| ATOM | 2511 | NZ | LYS | A | 455 | 84.059 | 40.156 | 20.315 | 1.00 | 30.79 | N |
| ATOM | 2512 | N | SER | A | 456 | 87.282 | 46.831 | 21.810 | 1.00 | 24.87 | N |
| ATOM | 2513 | CA | SER | A | 456 | 88.583 | 47.478 | 21.895 | 1.00 | 26.04 | C |
| ATOM | 2514 | C | SER | A | 456 | 88.477 | 48.690 | 22.831 | 1.00 | 25.43 | C |
| ATOM | 2515 | O | SER | A | 456 | 89.337 | 48.908 | 23.689 | 1.00 | 25.09 | O |
| ATOM | 2516 | CB | SER | A | 456 | 89.046 | 47.920 | 20.501 | 1.00 | 27.09 | C |
| ATOM | 2517 | OG | SER | A | 456 | 90.355 | 48.454 | 20.559 | 1.00 | 30.80 | O |
| ATOM | 2518 | N | THR | A | 457 | 87.414 | 49.471 | 22.671 | 1.00 | 24.22 | N |
| ATOM | 2519 | CA | THR | A | 457 | 87.214 | 50.640 | 23.520 | 1.00 | 24.20 | C |
| ATOM | 2520 | C | THR | A | 457 | 86.999 | 50.197 | 24.968 | 1.00 | 23.77 | C |
| ATOM | 2521 | O | THR | A | 457 | 87.484 | 50.835 | 25.900 | 1.00 | 23.17 | O |
| ATOM | 2522 | CB | THR | A | 457 | 86.013 | 51.470 | 23.035 | 1.00 | 24.69 | C |
| ATOM | 2523 | OG1 | THR | A | 457 | 86.268 | 51.918 | 21.699 | 1.00 | 25.52 | O |
| ATOM | 2524 | CG2 | THR | A | 457 | 85.791 | 52.680 | 23.934 | 1.00 | 24.52 | C |
| ATOM | 2525 | N | MET | A | 458 | 86.285 | 49.092 | 25.155 | 1.00 | 23.48 | N |
| ATOM | 2526 | CA | MET | A | 458 | 86.054 | 48.582 | 26.500 | 1.00 | 23.69 | C |
| ATOM | 2527 | C | MET | A | 458 | 87.395 | 48.265 | 27.160 | 1.00 | 23.66 | C |
| ATOM | 2528 | O | MET | A | 458 | 87.582 | 48.522 | 28.351 | 1.00 | 23.57 | O |
| ATOM | 2529 | CB | MET | A | 458 | 85.157 | 47.339 | 26.453 | 1.00 | 22.39 | C |
| ATOM | 2530 | CG | MET | A | 458 | 83.680 | 47.680 | 26.256 | 1.00 | 22.53 | C |

TABLE 3-continued

| ATOM | 2531 | SD  | MET | A | 458 | 82.608 | 46.247 | 26.043 | 1.00 | 23.32 | S |
| ATOM | 2532 | CE  | MET | A | 458 | 82.688 | 45.515 | 27.705 | 1.00 | 22.32 | C |
| ATOM | 2533 | N   | CYS | A | 459 | 88.332 | 47.716 | 26.393 | 1.00 | 24.05 | N |
| ATOM | 2534 | CA  | CYS | A | 459 | 89.649 | 47.413 | 26.947 | 1.00 | 25.56 | C |
| ATOM | 2535 | C   | CYS | A | 459 | 90.409 | 48.701 | 27.281 | 1.00 | 25.13 | C |
| ATOM | 2536 | O   | CYS | A | 459 | 91.214 | 48.725 | 28.215 | 1.00 | 24.61 | O |
| ATOM | 2537 | CB  | CYS | A | 459 | 90.465 | 46.548 | 25.985 | 1.00 | 28.49 | C |
| ATOM | 2538 | SG  | CYS | A | 459 | 90.054 | 44.772 | 26.089 | 1.00 | 33.40 | S |
| ATOM | 2539 | N   | ASN | A | 460 | 90.160 | 49.766 | 26.519 | 1.00 | 24.08 | N |
| ATOM | 2540 | CA  | ASN | A | 460 | 90.804 | 51.047 | 26.793 | 1.00 | 24.35 | C |
| ATOM | 2541 | C   | ASN | A | 460 | 90.302 | 51.515 | 28.155 | 1.00 | 24.02 | C |
| ATOM | 2542 | O   | ASN | A | 460 | 91.029 | 52.148 | 28.915 | 1.00 | 23.20 | O |
| ATOM | 2543 | CB  | ASN | A | 460 | 90.412 | 52.110 | 25.759 | 1.00 | 24.60 | C |
| ATOM | 2544 | CG  | ASN | A | 460 | 91.081 | 51.909 | 24.415 | 1.00 | 25.78 | C |
| ATOM | 2545 | OD1 | ASN | A | 460 | 90.405 | 51.787 | 23.399 | 1.00 | 27.02 | O |
| ATOM | 2546 | ND2 | ASN | A | 460 | 92.410 | 51.889 | 24.399 | 1.00 | 24.46 | N |
| ATOM | 2547 | N   | CYS | A | 461 | 89.042 | 51.205 | 28.448 | 1.00 | 23.87 | N |
| ATOM | 2548 | CA  | CYS | A | 461 | 88.422 | 51.611 | 29.704 | 1.00 | 24.41 | C |
| ATOM | 2549 | C   | CYS | A | 461 | 88.660 | 50.633 | 30.848 | 1.00 | 24.32 | C |
| ATOM | 2550 | O   | CYS | A | 461 | 88.180 | 50.852 | 31.958 | 1.00 | 25.56 | O |
| ATOM | 2551 | CB  | CYS | A | 461 | 86.918 | 51.806 | 29.496 | 1.00 | 24.60 | C |
| ATOM | 2552 | SG  | CYS | A | 461 | 86.525 | 53.116 | 28.308 | 1.00 | 26.96 | S |
| ATOM | 2553 | N   | GLY | A | 462 | 89.389 | 49.556 | 30.570 | 1.00 | 24.32 | N |
| ATOM | 2554 | CA  | GLY | A | 462 | 89.685 | 48.558 | 31.587 | 1.00 | 24.60 | C |
| ATOM | 2555 | C   | GLY | A | 462 | 88.547 | 47.600 | 31.907 | 1.00 | 25.06 | C |
| ATOM | 2556 | O   | GLY | A | 462 | 88.465 | 47.076 | 33.024 | 1.00 | 24.53 | O |
| ATOM | 2557 | N   | ALA | A | 463 | 87.682 | 47.343 | 30.929 | 1.00 | 24.46 | N |
| ATOM | 2558 | CA  | ALA | A | 463 | 86.539 | 46.463 | 31.147 | 1.00 | 24.56 | C |
| ATOM | 2559 | C   | ALA | A | 463 | 86.489 | 45.254 | 30.234 | 1.00 | 24.52 | C |
| ATOM | 2560 | O   | ALA | A | 463 | 86.647 | 45.372 | 29.018 | 1.00 | 24.90 | O |
| ATOM | 2561 | CB  | ALA | A | 463 | 85.246 | 47.257 | 31.000 | 1.00 | 24.47 | C |
| ATOM | 2562 | N   | LEU | A | 464 | 86.246 | 44.092 | 30.834 | 1.00 | 24.58 | N |
| ATOM | 2563 | CA  | LEU | A | 464 | 86.139 | 42.840 | 30.096 | 1.00 | 24.71 | C |
| ATOM | 2564 | C   | LEU | A | 464 | 84.683 | 42.423 | 29.927 | 1.00 | 23.91 | C |
| ATOM | 2565 | O   | LEU | A | 464 | 84.387 | 41.458 | 29.224 | 1.00 | 24.47 | O |
| ATOM | 2566 | CB  | LEU | A | 464 | 86.887 | 41.720 | 30.823 | 1.00 | 25.91 | C |
| ATOM | 2567 | CG  | LEU | A | 464 | 88.397 | 41.634 | 30.616 | 1.00 | 27.36 | C |
| ATOM | 2568 | CD1 | LEU | A | 464 | 88.947 | 40.476 | 31.448 | 1.00 | 28.44 | C |
| ATOM | 2569 | CD2 | LEU | A | 464 | 88.702 | 41.420 | 29.147 | 1.00 | 27.33 | C |
| ATOM | 2570 | N   | THR | A | 465 | 83.782 | 43.131 | 30.596 | 1.00 | 22.92 | N |
| ATOM | 2571 | CA  | THR | A | 465 | 82.354 | 42.831 | 30.512 | 1.00 | 22.25 | C |
| ATOM | 2572 | C   | THR | A | 465 | 81.568 | 44.129 | 30.548 | 1.00 | 21.44 | C |
| ATOM | 2573 | O   | THR | A | 465 | 82.104 | 45.177 | 30.891 | 1.00 | 20.34 | O |
| ATOM | 2574 | CB  | THR | A | 465 | 81.862 | 41.981 | 31.699 | 1.00 | 22.45 | C |
| ATOM | 2575 | OG1 | THR | A | 465 | 81.932 | 42.762 | 32.899 | 1.00 | 22.22 | O |
| ATOM | 2576 | CG2 | THR | A | 465 | 82.710 | 40.726 | 31.858 | 1.00 | 22.79 | C |
| ATOM | 2577 | N   | ILE | A | 466 | 80.288 | 44.052 | 30.214 | 1.00 | 21.19 | N |
| ATOM | 2578 | CA  | ILE | A | 466 | 79.447 | 45.236 | 30.230 | 1.00 | 20.76 | C |
| ATOM | 2579 | C   | ILE | A | 466 | 79.254 | 45.736 | 31.666 | 1.00 | 20.40 | C |
| ATOM | 2580 | O   | ILE | A | 466 | 79.358 | 46.929 | 31.927 | 1.00 | 19.90 | O |
| ATOM | 2581 | CB  | ILE | A | 466 | 78.098 | 44.944 | 29.530 | 1.00 | 21.19 | C |
| ATOM | 2582 | CG1 | ILE | A | 466 | 78.356 | 44.780 | 28.022 | 1.00 | 21.38 | C |
| ATOM | 2583 | CG2 | ILE | A | 466 | 77.100 | 46.073 | 29.792 | 1.00 | 21.25 | C |
| ATOM | 2584 | CD1 | ILE | A | 466 | 77.152 | 44.290 | 27.219 | 1.00 | 22.58 | C |
| ATOM | 2585 | N   | PRO | A | 467 | 78.995 | 44.828 | 32.626 | 1.00 | 20.68 | N |
| ATOM | 2586 | CA  | PRO | A | 467 | 78.822 | 45.333 | 33.991 | 1.00 | 20.34 | C |
| ATOM | 2587 | C   | PRO | A | 467 | 80.094 | 46.009 | 34.510 | 1.00 | 21.02 | C |
| ATOM | 2588 | O   | PRO | A | 467 | 80.025 | 47.006 | 35.216 | 1.00 | 21.23 | O |
| ATOM | 2589 | CB  | PRO | A | 467 | 78.461 | 44.076 | 34.782 | 1.00 | 20.94 | C |
| ATOM | 2590 | CG  | PRO | A | 467 | 77.717 | 43.250 | 33.750 | 1.00 | 20.39 | C |
| ATOM | 2591 | CD  | PRO | A | 467 | 78.606 | 43.411 | 32.538 | 1.00 | 19.76 | C |
| ATOM | 2592 | N   | GLN | A | 468 | 81.259 | 45.475 | 34.160 | 1.00 | 21.22 | N |
| ATOM | 2593 | CA  | GLN | A | 468 | 82.491 | 46.093 | 34.627 | 1.00 | 21.96 | C |
| ATOM | 2594 | C   | GLN | A | 468 | 82.648 | 47.477 | 33.992 | 1.00 | 22.09 | C |
| ATOM | 2595 | O   | GLN | A | 468 | 83.108 | 48.412 | 34.644 | 1.00 | 22.10 | O |
| ATOM | 2596 | CB  | GLN | A | 468 | 83.709 | 45.217 | 34.308 | 1.00 | 22.23 | C |
| ATOM | 2597 | CG  | GLN | A | 468 | 85.015 | 45.839 | 34.780 | 1.00 | 22.84 | C |
| ATOM | 2598 | CD  | GLN | A | 468 | 86.211 | 44.908 | 34.692 | 1.00 | 22.48 | C |
| ATOM | 2599 | OE1 | GLN | A | 468 | 86.355 | 44.141 | 33.740 | 1.00 | 22.48 | O |
| ATOM | 2600 | NE2 | GLN | A | 468 | 87.097 | 44.997 | 35.683 | 1.00 | 22.38 | N |
| ATOM | 2601 | N   | LEU | A | 469 | 82.264 | 47.603 | 32.722 | 1.00 | 21.64 | N |
| ATOM | 2602 | CA  | LEU | A | 469 | 82.344 | 48.886 | 32.027 | 1.00 | 21.89 | C |
| ATOM | 2603 | C   | LEU | A | 469 | 81.434 | 49.905 | 32.714 | 1.00 | 22.01 | C |
| ATOM | 2604 | O   | LEU | A | 469 | 81.818 | 51.051 | 32.925 | 1.00 | 21.53 | O |
| ATOM | 2605 | CB  | LEU | A | 469 | 81.904 | 48.735 | 30.564 | 1.00 | 21.51 | C |
| ATOM | 2606 | CG  | LEU | A | 469 | 81.761 | 50.027 | 29.745 | 1.00 | 22.03 | C |
| ATOM | 2607 | CD1 | LEU | A | 469 | 83.134 | 50.627 | 29.484 | 1.00 | 21.95 | C |
| ATOM | 2608 | CD2 | LEU | A | 469 | 81.056 | 49.727 | 28.414 | 1.00 | 22.12 | C |
| ATOM | 2609 | N   | GLN | A | 470 | 80.225 | 49.473 | 33.058 | 1.00 | 22.00 | N |

TABLE 3-continued

| ATOM | 2610 | CA | GLN | A | 470 | 79.254 | 50.349 | 33.696 | 1.00 | 23.44 | C |
|---|---|---|---|---|---|---|---|---|---|---|---|
| ATOM | 2611 | C | GLN | A | 470 | 79.743 | 50.838 | 35.055 | 1.00 | 24.51 | C |
| ATOM | 2612 | O | GLN | A | 470 | 79.377 | 51.922 | 35.513 | 1.00 | 25.02 | O |
| ATOM | 2613 | CB | GLN | A | 470 | 77.917 | 49.612 | 33.817 | 1.00 | 23.09 | C |
| ATOM | 2614 | CG | GLN | A | 470 | 77.402 | 49.156 | 32.439 | 1.00 | 23.12 | C |
| ATOM | 2615 | CD | GLN | A | 470 | 76.092 | 48.397 | 32.492 | 1.00 | 22.83 | C |
| ATOM | 2616 | OE1 | GLN | A | 470 | 75.855 | 47.613 | 33.406 | 1.00 | 23.32 | O |
| ATOM | 2617 | NE2 | GLN | A | 470 | 75.242 | 48.610 | 31.488 | 1.00 | 21.97 | N |
| ATOM | 2618 | N | SER | A | 471 | 80.590 | 50.039 | 35.687 | 1.00 | 25.04 | N |
| ATOM | 2619 | CA | SER | A | 471 | 81.139 | 50.391 | 36.983 | 1.00 | 26.85 | C |
| ATOM | 2620 | C | SER | A | 471 | 82.378 | 51.284 | 36.863 | 1.00 | 27.29 | C |
| ATOM | 2621 | O | SER | A | 471 | 82.530 | 52.246 | 37.614 | 1.00 | 27.87 | O |
| ATOM | 2622 | CB | SER | A | 471 | 81.500 | 49.115 | 37.749 | 1.00 | 27.07 | C |
| ATOM | 2623 | OG | SER | A | 471 | 82.193 | 49.422 | 38.943 | 1.00 | 30.83 | O |
| ATOM | 2624 | N | LYS | A | 472 | 83.244 | 50.981 | 35.900 | 1.00 | 27.53 | N |
| ATOM | 2625 | CA | LYS | A | 472 | 84.496 | 51.723 | 35.732 | 1.00 | 28.78 | C |
| ATOM | 2626 | C | LYS | A | 472 | 84.519 | 52.903 | 34.768 | 1.00 | 27.72 | C |
| ATOM | 2627 | O | LYS | A | 472 | 85.421 | 53.733 | 34.840 | 1.00 | 27.66 | O |
| ATOM | 2628 | CB | LYS | A | 472 | 85.604 | 50.752 | 35.316 | 1.00 | 29.70 | C |
| ATOM | 2629 | CG | LYS | A | 472 | 85.789 | 49.598 | 36.274 | 1.00 | 33.23 | C |
| ATOM | 2630 | CD | LYS | A | 472 | 86.819 | 48.602 | 35.768 | 1.00 | 33.84 | C |
| ATOM | 2631 | CE | LYS | A | 472 | 88.218 | 49.184 | 35.759 | 1.00 | 34.76 | C |
| ATOM | 2632 | NZ | LYS | A | 472 | 89.209 | 48.107 | 35.470 | 1.00 | 34.52 | N |
| ATOM | 2633 | N | ALA | A | 473 | 83.548 | 52.976 | 33.865 | 1.00 | 26.96 | N |
| ATOM | 2634 | CA | ALA | A | 473 | 83.522 | 54.045 | 32.870 | 1.00 | 26.73 | C |
| ATOM | 2635 | C | ALA | A | 473 | 83.663 | 55.472 | 33.395 | 1.00 | 26.34 | C |
| ATOM | 2636 | O | ALA | A | 473 | 83.045 | 55.853 | 34.389 | 1.00 | 26.04 | O |
| ATOM | 2637 | CB | ALA | A | 473 | 82.250 | 53.936 | 32.023 | 1.00 | 26.80 | C |
| ATOM | 2638 | N | LYS | A | 474 | 84.502 | 56.248 | 32.713 | 1.00 | 26.28 | N |
| ATOM | 2639 | CA | LYS | A | 474 | 84.712 | 57.656 | 33.034 | 1.00 | 26.69 | C |
| ATOM | 2640 | C | LYS | A | 474 | 84.166 | 58.376 | 31.807 | 1.00 | 26.49 | C |
| ATOM | 2641 | O | LYS | A | 474 | 84.724 | 58.278 | 30.712 | 1.00 | 25.96 | O |
| ATOM | 2642 | CB | LYS | A | 474 | 86.202 | 57.955 | 33.241 | 1.00 | 27.26 | C |
| ATOM | 2643 | CG | LYS | A | 474 | 86.777 | 57.279 | 34.485 | 1.00 | 28.54 | C |
| ATOM | 2644 | CD | LYS | A | 474 | 88.207 | 57.724 | 34.778 | 1.00 | 30.16 | C |
| ATOM | 2645 | CE | LYS | A | 474 | 89.177 | 57.220 | 33.745 | 1.00 | 30.74 | C |
| ATOM | 2646 | NZ | LYS | A | 474 | 90.571 | 57.651 | 34.057 | 1.00 | 30.36 | N |
| ATOM | 2647 | N | ILE | A | 475 | 83.067 | 59.095 | 31.995 | 1.00 | 26.72 | N |
| ATOM | 2648 | CA | ILE | A | 475 | 82.403 | 59.763 | 30.885 | 1.00 | 27.59 | C |
| ATOM | 2649 | C | ILE | A | 475 | 82.413 | 61.281 | 30.960 | 1.00 | 28.14 | C |
| ATOM | 2650 | O | ILE | A | 475 | 81.900 | 61.871 | 31.910 | 1.00 | 28.29 | O |
| ATOM | 2651 | CB | ILE | A | 475 | 80.943 | 59.278 | 30.794 | 1.00 | 27.25 | C |
| ATOM | 2652 | CG1 | ILE | A | 475 | 80.919 | 57.743 | 30.797 | 1.00 | 27.67 | C |
| ATOM | 2653 | CG2 | ILE | A | 475 | 80.281 | 59.832 | 29.537 | 1.00 | 27.73 | C |
| ATOM | 2654 | CD1 | ILE | A | 475 | 79.522 | 57.134 | 30.885 | 1.00 | 26.56 | C |
| ATOM | 2655 | N | THR | A | 476 | 82.982 | 61.912 | 29.941 | 1.00 | 28.53 | N |
| ATOM | 2656 | CA | THR | A | 476 | 83.045 | 63.364 | 29.916 | 1.00 | 29.40 | C |
| ATOM | 2657 | C | THR | A | 476 | 82.184 | 63.974 | 28.820 | 1.00 | 29.85 | C |
| ATOM | 2658 | O | THR | A | 476 | 82.029 | 63.407 | 27.734 | 1.00 | 28.69 | O |
| ATOM | 2659 | CB | THR | A | 476 | 84.488 | 63.865 | 29.722 | 1.00 | 29.27 | C |
| ATOM | 2660 | OG1 | THR | A | 476 | 84.501 | 65.293 | 29.813 | 1.00 | 30.19 | O |
| ATOM | 2661 | CG2 | THR | A | 476 | 85.027 | 63.445 | 28.353 | 1.00 | 28.75 | C |
| ATOM | 2662 | N | LEU | A | 477 | 81.615 | 65.133 | 29.126 | 1.00 | 30.92 | N |
| ATOM | 2663 | CA | LEU | A | 477 | 80.791 | 65.863 | 28.176 | 1.00 | 33.43 | C |
| ATOM | 2664 | C | LEU | A | 477 | 81.792 | 66.681 | 27.363 | 1.00 | 34.68 | C |
| ATOM | 2665 | O | LEU | A | 477 | 82.829 | 67.084 | 27.887 | 1.00 | 34.58 | O |
| ATOM | 2666 | CB | LEU | A | 477 | 79.831 | 66.795 | 28.925 | 1.00 | 34.07 | C |
| ATOM | 2667 | CG | LEU | A | 477 | 78.671 | 67.452 | 28.173 | 1.00 | 35.06 | C |
| ATOM | 2668 | CD1 | LEU | A | 477 | 77.683 | 66.393 | 27.716 | 1.00 | 34.39 | C |
| ATOM | 2669 | CD2 | LEU | A | 477 | 77.975 | 68.449 | 29.094 | 1.00 | 35.94 | C |
| ATOM | 2670 | N | VAL | A | 478 | 81.497 | 66.910 | 26.089 | 1.00 | 36.01 | N |
| ATOM | 2671 | CA | VAL | A | 478 | 82.388 | 67.688 | 25.234 | 1.00 | 37.55 | C |
| ATOM | 2672 | C | VAL | A | 478 | 81.741 | 69.041 | 24.929 | 1.00 | 38.64 | C |
| ATOM | 2673 | O | VAL | A | 478 | 80.517 | 69.151 | 24.884 | 1.00 | 37.96 | O |
| ATOM | 2674 | CB | VAL | A | 478 | 82.681 | 66.929 | 23.919 | 1.00 | 37.92 | C |
| ATOM | 2675 | CG1 | VAL | A | 478 | 83.612 | 67.732 | 23.046 | 1.00 | 38.33 | C |
| ATOM | 2676 | CG2 | VAL | A | 478 | 83.308 | 65.577 | 24.234 | 1.00 | 38.01 | C |
| ATOM | 2677 | N | SER | A | 479 | 82.559 | 70.073 | 24.733 | 1.00 | 40.23 | N |
| ATOM | 2678 | CA | SER | A | 479 | 82.034 | 71.408 | 24.452 | 1.00 | 42.03 | C |
| ATOM | 2679 | C | SER | A | 479 | 81.414 | 71.483 | 23.062 | 1.00 | 43.58 | C |
| ATOM | 2680 | O | SER | A | 479 | 81.868 | 70.818 | 22.130 | 1.00 | 43.18 | O |
| ATOM | 2681 | CB | SER | A | 479 | 83.139 | 72.465 | 24.572 | 1.00 | 41.76 | C |
| ATOM | 2682 | OG | SER | A | 479 | 84.069 | 72.363 | 23.508 | 1.00 | 41.31 | O |
| ATOM | 2683 | N | SER | A | 480 | 80.373 | 72.299 | 22.930 | 1.00 | 45.81 | N |
| ATOM | 2684 | CA | SER | A | 480 | 79.688 | 72.465 | 21.653 | 1.00 | 48.45 | C |
| ATOM | 2685 | C | SER | A | 480 | 80.615 | 73.067 | 20.602 | 1.00 | 49.80 | C |
| ATOM | 2686 | O | SER | A | 480 | 80.426 | 72.859 | 19.402 | 1.00 | 50.06 | O |
| ATOM | 2687 | CB | SER | A | 480 | 78.450 | 73.352 | 21.830 | 1.00 | 48.66 | C |
| ATOM | 2688 | OG | SER | A | 480 | 78.778 | 74.574 | 22.468 | 1.00 | 50.04 | O |

TABLE 3-continued

| | | | | | | | | | | | |
|---|---|---|---|---|---|---|---|---|---|---|---|
| ATOM | 2689 | N | VAL | A | 481 | 81.622 | 73.805 | 21.062 | 1.00 | 51.44 | N |
| ATOM | 2690 | CA | VAL | A | 481 | 82.584 | 74.442 | 20.168 | 1.00 | 53.08 | C |
| ATOM | 2691 | C | VAL | A | 481 | 83.452 | 73.408 | 19.462 | 1.00 | 53.99 | C |
| ATOM | 2692 | O | VAL | A | 481 | 83.755 | 73.544 | 18.277 | 1.00 | 54.37 | O |
| ATOM | 2693 | CB | VAL | A | 481 | 83.515 | 75.402 | 20.936 | 1.00 | 53.14 | C |
| ATOM | 2694 | CG1 | VAL | A | 481 | 84.397 | 76.161 | 19.958 | 1.00 | 53.54 | C |
| ATOM | 2695 | CG2 | VAL | A | 481 | 82.698 | 76.363 | 21.775 | 1.00 | 53.62 | C |
| ATOM | 2696 | N | SER | A | 482 | 83.858 | 72.379 | 20.199 | 1.00 | 55.12 | N |
| ATOM | 2697 | CA | SER | A | 482 | 84.695 | 71.324 | 19.642 | 1.00 | 56.25 | C |
| ATOM | 2698 | C | SER | A | 482 | 83.890 | 70.412 | 18.722 | 1.00 | 57.11 | C |
| ATOM | 2699 | O | SER | A | 482 | 84.454 | 69.577 | 18.012 | 1.00 | 57.33 | O |
| ATOM | 2700 | CB | SER | A | 482 | 85.319 | 70.499 | 20.767 | 1.00 | 56.17 | C |
| ATOM | 2701 | OG | SER | A | 482 | 84.315 | 69.924 | 21.581 | 1.00 | 56.14 | O |
| ATOM | 2702 | N | ILE | A | 483 | 82.571 | 70.572 | 18.742 | 1.00 | 57.97 | N |
| ATOM | 2703 | CA | ILE | A | 483 | 81.693 | 69.769 | 17.899 | 1.00 | 58.92 | C |
| ATOM | 2704 | C | ILE | A | 483 | 81.319 | 70.545 | 16.639 | 1.00 | 59.33 | C |
| ATOM | 2705 | O | ILE | A | 483 | 81.588 | 70.028 | 15.535 | 1.00 | 59.84 | O |
| ATOM | 2706 | CB | ILE | A | 483 | 80.399 | 69.375 | 18.645 | 1.00 | 59.00 | C |
| ATOM | 2707 | CG1 | ILE | A | 483 | 80.744 | 68.544 | 19.883 | 1.00 | 59.10 | C |
| ATOM | 2708 | CG2 | ILE | A | 483 | 79.485 | 68.585 | 17.716 | 1.00 | 59.45 | C |
| ATOM | 2709 | CD1 | ILE | A | 483 | 79.543 | 68.155 | 20.718 | 1.00 | 59.17 | C |
| TER | 2710 | | ILE | A | 483 | | | | | | |
| HETATM | 2711 | K | K | A | 900 | 52.243 | 59.799 | 29.172 | 0.75 | 29.54 | K |
| HETATM | 2712 | P | IMP | | 602 | 67.273 | 54.643 | 14.906 | 1.00 | 25.76 | P |
| HETATM | 2713 | O1P | IMP | | 602 | 66.861 | 54.580 | 13.478 | 1.00 | 26.22 | O |
| HETATM | 2714 | O2P | IMP | | 602 | 68.037 | 53.408 | 15.254 | 1.00 | 26.63 | O |
| HETATM | 2715 | O3P | IMP | | 602 | 68.090 | 55.908 | 15.218 | 1.00 | 25.72 | O |
| HETATM | 2716 | O5* | IMP | | 602 | 66.048 | 54.751 | 15.914 | 1.00 | 25.69 | O |
| HETATM | 2717 | C5* | IMP | | 602 | 65.054 | 53.735 | 15.819 | 1.00 | 23.90 | C |
| HETATM | 2718 | C4* | IMP | | 602 | 63.955 | 53.909 | 16.822 | 1.00 | 23.17 | C |
| HETATM | 2719 | O4* | IMP | | 602 | 63.226 | 55.091 | 16.335 | 1.00 | 22.32 | O |
| HETATM | 2720 | C3* | IMP | | 602 | 62.855 | 52.875 | 16.958 | 1.00 | 22.53 | C |
| HETATM | 2721 | O3* | IMP | | 602 | 63.229 | 51.710 | 17.687 | 1.00 | 21.85 | O |
| HETATM | 2722 | C2* | IMP | | 602 | 61.776 | 53.670 | 17.629 | 1.00 | 22.98 | C |
| HETATM | 2723 | O2* | IMP | | 602 | 61.948 | 53.736 | 19.029 | 1.00 | 22.76 | O |
| HETATM | 2724 | C1* | IMP | | 602 | 61.928 | 55.030 | 16.924 | 1.00 | 23.55 | C |
| HETATM | 2725 | N9 | IMP | | 602 | 60.928 | 55.202 | 15.816 | 1.00 | 24.16 | N |
| HETATM | 2726 | C8 | IMP | | 602 | 60.310 | 54.298 | 14.971 | 1.00 | 25.51 | C |
| HETATM | 2727 | N7 | IMP | | 602 | 59.490 | 54.866 | 14.137 | 1.00 | 25.39 | N |
| HETATM | 2728 | C5 | IMP | | 602 | 59.548 | 56.197 | 14.417 | 1.00 | 25.42 | C |
| HETATM | 2729 | C6 | IMP | | 602 | 58.866 | 57.320 | 13.831 | 1.00 | 26.39 | C |
| HETATM | 2730 | O6 | IMP | | 602 | 58.049 | 57.295 | 12.909 | 1.00 | 27.34 | O |
| HETATM | 2731 | N1 | IMP | | 602 | 59.213 | 58.576 | 14.425 | 1.00 | 26.64 | N |
| HETATM | 2732 | C2 | IMP | | 602 | 60.131 | 58.702 | 15.478 | 1.00 | 26.89 | C |
| HETATM | 2733 | N3 | IMP | | 602 | 60.765 | 57.630 | 16.021 | 1.00 | 25.55 | N |
| HETATM | 2734 | C4 | IMP | | 602 | 60.437 | 56.438 | 15.458 | 1.00 | 25.01 | C |
| HETATM | 2735 | C1 | MOA | | 600 | 59.312 | 58.341 | 19.371 | 1.00 | 30.41 | C |
| HETATM | 2736 | C2 | MOA | | 600 | 54.700 | 56.341 | 16.455 | 1.00 | 32.49 | C |
| HETATM | 2737 | C3 | MOA | | 600 | 53.578 | 55.627 | 16.198 | 1.00 | 33.53 | C |
| HETATM | 2738 | C4 | MOA | | 600 | 52.262 | 56.261 | 16.628 | 1.00 | 34.60 | C |
| HETATM | 2739 | C5 | MOA | | 600 | 51.704 | 55.529 | 17.856 | 1.00 | 35.56 | C |
| HETATM | 2740 | C6 | MOA | | 600 | 52.413 | 55.880 | 19.153 | 1.00 | 36.42 | C |
| HETATM | 2741 | C7 | MOA | | 600 | 58.717 | 53.456 | 19.827 | 1.00 | 29.24 | C |
| HETATM | 2742 | C8 | MOA | | 600 | 55.639 | 53.144 | 18.309 | 1.00 | 29.52 | C |
| HETATM | 2743 | C9 | MOA | | 600 | 53.564 | 54.254 | 15.513 | 1.00 | 33.79 | C |
| HETATM | 2744 | C10 | MOA | | 600 | 59.889 | 56.364 | 20.539 | 1.00 | 29.78 | C |
| HETATM | 2745 | C11 | MOA | | 600 | 58.905 | 56.011 | 19.445 | 1.00 | 29.43 | C |
| HETATM | 2746 | C12 | MOA | | 600 | 58.347 | 54.721 | 19.086 | 1.00 | 29.74 | C |
| HETATM | 2747 | C13 | MOA | | 600 | 57.416 | 54.689 | 17.974 | 1.00 | 30.13 | C |
| HETATM | 2748 | C14 | MOA | | 600 | 57.077 | 55.910 | 17.275 | 1.00 | 30.94 | C |
| HETATM | 2749 | C15 | MOA | | 600 | 57.655 | 57.164 | 17.672 | 1.00 | 30.68 | C |
| HETATM | 2750 | C16 | MOA | | 600 | 58.569 | 57.183 | 18.763 | 1.00 | 30.24 | C |
| HETATM | 2751 | C17 | MOA | | 600 | 56.107 | 55.881 | 16.099 | 1.00 | 32.03 | C |
| HETATM | 2752 | O1 | MOA | | 600 | 59.306 | 59.497 | 19.082 | 1.00 | 30.18 | O |
| HETATM | 2753 | O2 | MOA | | 600 | 60.036 | 57.818 | 20.365 | 1.00 | 29.58 | O |
| HETATM | 2754 | O3 | MOA | | 600 | 56.876 | 53.479 | 17.608 | 1.00 | 30.38 | O |
| HETATM | 2755 | O4 | MOA | | 600 | 57.314 | 58.318 | 16.987 | 1.00 | 32.33 | O |
| HETATM | 2756 | O5 | MOA | | 600 | 52.401 | 57.074 | 19.536 | 1.00 | 37.48 | O |
| HETATM | 2757 | O6 | MOA | | 600 | 52.985 | 54.959 | 19.780 | 1.00 | 35.87 | O |
| HETATM | 2758 | O | HOH | | 1 | 59.924 | 29.679 | 22.414 | 1.00 | 50.51 | O |
| HETATM | 2759 | O | HOH | | 2 | 79.013 | 41.426 | 29.423 | 1.00 | 18.90 | O |
| HETATM | 2760 | O | HOH | | 3 | 58.751 | 44.934 | 36.922 | 1.00 | 19.77 | O |
| HETATM | 2761 | O | HOH | | 4 | 70.195 | 53.954 | 21.764 | 1.00 | 22.57 | O |
| HETATM | 2762 | O | HOH | | 5 | 65.251 | 60.127 | 24.411 | 1.00 | 21.78 | O |
| HETATM | 2763 | O | HOH | | 6 | 75.493 | 43.370 | 30.924 | 1.00 | 20.48 | O |
| HETATM | 2764 | O | HOH | | 7 | 56.253 | 78.397 | 34.291 | 1.00 | 25.40 | O |
| HETATM | 2765 | O | HOH | | 8 | 66.025 | 47.704 | 38.822 | 1.00 | 22.86 | O |
| HETATM | 2766 | O | HOH | | 9 | 56.894 | 58.199 | 28.230 | 1.00 | 22.26 | O |
| HETATM | 2767 | O | HOH | | 10 | 70.506 | 52.801 | 14.222 | 1.00 | 25.03 | O |

TABLE 3-continued

| | | | | | | | | | | |
|---|---|---|---|---|---|---|---|---|---|---|
| HETATM | 2768 | O | HOH | 11 | 63.871 | 40.741 | 7.794 | 1.00 | 24.61 | O |
| HETATM | 2769 | O | HOH | 12 | 60.616 | 40.963 | 2.773 | 1.00 | 57.79 | O |
| HETATM | 2770 | O | HOH | 13 | 72.961 | 57.112 | 35.993 | 1.00 | 22.52 | O |
| HETATM | 2771 | O | HOH | 14 | 74.407 | 45.323 | 32.761 | 1.00 | 26.87 | O |
| HETATM | 2772 | O | HOH | 15 | 86.443 | 54.944 | 31.105 | 1.00 | 24.24 | O |
| HETATM | 2773 | O | HOH | 16 | 64.957 | 58.145 | 21.206 | 1.00 | 26.57 | O |
| HETATM | 2774 | O | HOH | 17 | 58.226 | 37.978 | 34.604 | 1.00 | 28.06 | O |
| HETATM | 2775 | O | HOH | 18 | 65.737 | 37.023 | 16.608 | 1.00 | 23.81 | O |
| HETATM | 2776 | O | HOH | 19 | 71.973 | 37.555 | 33.842 | 1.00 | 27.82 | O |
| HETATM | 2777 | O | HOH | 20 | 61.772 | 38.247 | 34.046 | 1.00 | 22.62 | O |
| HETATM | 2778 | O | HOH | 21 | 52.301 | 52.152 | 19.306 | 1.00 | 49.95 | O |
| HETATM | 2779 | O | HOH | 22 | 87.828 | 53.279 | 33.165 | 1.00 | 28.88 | O |
| HETATM | 2780 | O | HOH | 23 | 81.359 | 62.610 | 21.058 | 1.00 | 27.37 | O |
| HETATM | 2781 | O | HOH | 24 | 75.817 | 40.774 | 32.087 | 1.00 | 26.13 | O |
| HETATM | 2782 | O | HOH | 25 | 58.057 | 34.952 | 27.087 | 1.00 | 28.97 | O |
| HETATM | 2783 | O | HOH | 26 | 83.688 | 52.415 | 20.816 | 1.00 | 30.28 | O |
| HETATM | 2784 | O | HOH | 27 | 77.149 | 53.162 | 34.368 | 1.00 | 29.69 | O |
| HETATM | 2785 | O | HOH | 28 | 56.074 | 56.906 | 38.662 | 1.00 | 37.23 | O |
| HETATM | 2786 | O | HOH | 29 | 49.870 | 31.480 | 16.451 | 1.00 | 33.88 | O |
| HETATM | 2787 | O | HOH | 30 | 73.925 | 34.558 | 39.925 | 1.00 | 28.68 | O |
| HETATM | 2788 | O | HOH | 31 | 78.589 | 39.852 | 31.836 | 1.00 | 26.69 | O |
| HETATM | 2789 | O | HOH | 32 | 59.193 | 50.825 | 9.635 | 1.00 | 30.48 | O |
| HETATM | 2790 | O | HOH | 33 | 48.757 | 43.664 | 20.942 | 1.00 | 29.46 | O |
| HETATM | 2791 | O | HOH | 34 | 63.470 | 55.921 | 20.034 | 1.00 | 28.45 | O |
| HETATM | 2792 | O | HOH | 35 | 64.748 | 36.350 | 34.843 | 1.00 | 29.99 | O |
| HETATM | 2793 | O | HOH | 36 | 74.476 | 38.378 | 31.025 | 1.00 | 30.13 | O |
| HETATM | 2794 | O | HOH | 37 | 51.517 | 53.493 | 25.810 | 1.00 | 33.48 | O |
| HETATM | 2795 | O | HOH | 38 | 67.426 | 38.071 | 46.103 | 1.00 | 30.22 | O |
| HETATM | 2796 | O | HOH | 39 | 73.458 | 50.410 | 36.144 | 1.00 | 28.96 | O |
| HETATM | 2797 | O | HOH | 40 | 48.967 | 53.101 | 24.116 | 1.00 | 49.76 | O |
| HETATM | 2798 | O | HOH | 41 | 70.826 | 32.483 | 29.970 | 1.00 | 39.88 | O |
| HETATM | 2799 | O | HOH | 42 | 61.107 | 50.022 | 17.672 | 1.00 | 23.40 | O |
| HETATM | 2800 | O | HOH | 43 | 73.974 | 36.418 | 10.780 | 1.00 | 31.43 | O |
| HETATM | 2801 | O | HOH | 44 | 50.211 | 45.778 | 35.694 | 1.00 | 31.02 | O |
| HETATM | 2802 | O | HOH | 45 | 63.973 | 35.222 | 38.133 | 1.00 | 49.08 | O |
| HETATM | 2803 | O | HOH | 46 | 52.459 | 51.210 | 38.008 | 1.00 | 33.23 | O |
| HETATM | 2804 | O | HOH | 47 | 68.639 | 62.467 | 21.428 | 1.00 | 33.95 | O |
| HETATM | 2805 | O | HOH | 48 | 69.432 | 33.097 | 27.354 | 1.00 | 32.47 | O |
| HETATM | 2806 | O | HOH | 49 | 74.578 | 37.941 | 8.159 | 1.00 | 32.47 | O |
| HETATM | 2807 | O | HOH | 50 | 58.916 | 51.450 | 16.416 | 1.00 | 29.63 | O |
| HETATM | 2808 | O | HOH | 51 | 69.598 | 53.385 | 17.586 | 1.00 | 29.79 | O |
| HETATM | 2809 | O | HOH | 52 | 47.572 | 53.766 | 36.762 | 1.00 | 39.69 | O |
| HETATM | 2810 | O | HOH | 53 | 84.793 | 48.751 | 39.168 | 1.00 | 43.51 | O |
| HETATM | 2811 | O | HOH | 54 | 59.544 | 49.841 | 20.045 | 1.00 | 33.31 | O |
| HETATM | 2812 | O | HOH | 55 | 64.161 | 25.507 | 14.641 | 1.00 | 30.60 | O |
| HETATM | 2813 | O | HOH | 56 | 55.066 | 70.757 | 16.127 | 1.00 | 32.83 | O |
| HETATM | 2814 | O | HOH | 57 | 74.182 | 47.486 | 35.548 | 1.00 | 31.59 | O |
| HETATM | 2815 | O | HOH | 58 | 62.583 | 34.645 | 41.460 | 1.00 | 39.46 | O |
| HETATM | 2816 | O | HOH | 59 | 51.561 | 30.405 | 13.105 | 1.00 | 57.09 | O |
| HETATM | 2817 | O | HOH | 60 | 47.880 | 31.075 | 25.095 | 1.00 | 39.60 | O |
| HETATM | 2818 | O | HOH | 61 | 53.997 | 32.961 | 37.361 | 1.00 | 38.91 | O |
| HETATM | 2819 | O | HOH | 62 | 84.739 | 38.545 | 32.721 | 1.00 | 34.80 | O |
| HETATM | 2820 | O | HOH | 63 | 70.499 | 56.677 | 14.512 | 1.00 | 31.54 | O |
| HETATM | 2821 | O | HOH | 64 | 96.766 | 42.780 | 26.087 | 1.00 | 48.54 | O |
| HETATM | 2822 | O | HOH | 65 | 48.178 | 56.536 | 26.666 | 1.00 | 44.06 | O |
| HETATM | 2823 | O | HOH | 66 | 55.822 | 40.800 | 37.347 | 1.00 | 41.31 | O |
| HETATM | 2824 | O | HOH | 67 | 62.651 | 58.499 | 18.259 | 1.00 | 30.38 | O |
| HETATM | 2825 | O | HOH | 68 | 78.584 | 37.867 | 17.336 | 1.00 | 35.48 | O |
| HETATM | 2826 | O | HOH | 69 | 73.741 | 59.595 | 37.699 | 1.00 | 46.66 | O |
| HETATM | 2827 | O | HOH | 70 | 61.930 | 61.268 | 37.149 | 1.00 | 35.16 | O |
| HETATM | 2828 | O | HOH | 71 | 64.600 | 31.307 | 29.524 | 1.00 | 40.08 | O |
| HETATM | 2829 | O | HOH | 72 | 68.630 | 35.309 | 7.689 | 1.00 | 35.28 | O |
| HETATM | 2830 | O | HOH | 73 | 74.821 | 69.567 | 31.440 | 1.00 | 45.20 | O |
| HETATM | 2831 | O | HOH | 74 | 60.851 | 32.866 | 26.981 | 1.00 | 36.07 | O |
| HETATM | 2832 | O | HOH | 75 | 78.209 | 47.346 | 37.269 | 1.00 | 42.78 | O |
| HETATM | 2833 | O | HOH | 76 | 78.477 | 34.764 | 30.567 | 1.00 | 40.04 | O |
| HETATM | 2834 | O | HOH | 77 | 71.498 | 30.722 | 23.744 | 1.00 | 35.11 | O |
| HETATM | 2835 | O | HOH | 78 | 64.709 | 27.584 | 26.706 | 1.00 | 39.53 | O |
| HETATM | 2836 | O | HOH | 79 | 58.218 | 44.875 | 5.808 | 1.00 | 39.15 | O |
| HETATM | 2837 | O | HOH | 80 | 91.925 | 40.314 | 20.235 | 1.00 | 47.22 | O |
| HETATM | 2838 | O | HOH | 81 | 65.374 | 28.271 | 14.859 | 1.00 | 33.66 | O |
| HETATM | 2839 | O | HOH | 82 | 86.254 | 46.969 | 13.548 | 1.00 | 42.09 | O |
| HETATM | 2840 | O | HOH | 83 | 86.599 | 66.411 | 30.817 | 1.00 | 28.92 | O |
| HETATM | 2841 | O | HOH | 84 | 62.054 | 33.096 | 29.810 | 1.00 | 43.30 | O |
| HETATM | 2842 | O | HOH | 85 | 95.032 | 45.638 | 27.312 | 1.00 | 44.01 | O |
| HETATM | 2843 | O | HOH | 86 | 50.747 | 50.260 | 21.915 | 1.00 | 33.76 | O |
| HETATM | 2844 | O | HOH | 87 | 64.754 | 61.086 | 37.994 | 1.00 | 43.01 | O |
| HETATM | 2845 | O | HOH | 88 | 70.920 | 55.587 | 41.621 | 1.00 | 30.53 | O |
| HETATM | 2846 | O | HOH | 89 | 87.356 | 35.892 | 30.913 | 1.00 | 54.42 | O |

TABLE 3-continued

| | | | | | | | | | | |
|---|---|---|---|---|---|---|---|---|---|---|
| HETATM | 2847 | O | HOH | 90 | 58.062 | 50.894 | 22.714 | 1.00 | 36.70 | O |
| HETATM | 2848 | O | HOH | 91 | 66.375 | 33.870 | 36.838 | 1.00 | 36.70 | O |
| HETATM | 2849 | O | HOH | 92 | 80.489 | 54.081 | 12.959 | 1.00 | 34.92 | O |
| HETATM | 2850 | O | HOH | 93 | 49.688 | 32.577 | 11.671 | 1.00 | 44.86 | O |
| HETATM | 2851 | O | HOH | 94 | 59.901 | 34.059 | 37.276 | 1.00 | 46.67 | O |
| HETATM | 2852 | O | HOH | 95 | 60.124 | 37.261 | 37.104 | 1.00 | 40.44 | O |
| HETATM | 2853 | O | HOH | 96 | 68.062 | 43.325 | 0.440 | 1.00 | 40.55 | O |
| HETATM | 2854 | O | HOH | 97 | 92.043 | 48.470 | 23.328 | 1.00 | 41.20 | O |
| HETATM | 2855 | O | HOH | 98 | 91.696 | 47.559 | 34.606 | 1.00 | 36.60 | O |
| HETATM | 2856 | O | HOH | 99 | 72.456 | 40.842 | 41.613 | 1.00 | 38.50 | O |
| HETATM | 2857 | O | HOH | 100 | 56.000 | 31.198 | 23.572 | 1.00 | 40.79 | O |
| HETATM | 2858 | O | HOH | 101 | 49.154 | 42.288 | 7.689 | 1.00 | 40.98 | O |
| HETATM | 2859 | O | HOH | 102 | 73.470 | 34.115 | 8.839 | 1.00 | 54.10 | O |
| HETATM | 2860 | O | HOH | 103 | 61.679 | 22.463 | 5.705 | 1.00 | 52.66 | O |
| HETATM | 2861 | O | HOH | 104 | 77.579 | 33.064 | 16.137 | 1.00 | 47.51 | O |
| HETATM | 2862 | O | HOH | 105 | 44.253 | 34.815 | 19.536 | 1.00 | 42.37 | O |
| HETATM | 2863 | O | HOH | 106 | 45.451 | 48.437 | 27.057 | 1.00 | 38.64 | O |
| HETATM | 2864 | O | HOH | 107 | 59.592 | 41.005 | 40.036 | 1.00 | 41.25 | O |
| HETATM | 2865 | O | HOH | 108 | 72.057 | 60.543 | 20.606 | 1.00 | 36.69 | O |
| HETATM | 2866 | O | HOH | 109 | 55.706 | 47.432 | 14.991 | 1.00 | 42.24 | O |
| HETATM | 2867 | O | HOH | 110 | 62.531 | 31.016 | 25.446 | 1.00 | 42.66 | O |
| HETATM | 2868 | O | HOH | 111 | 73.718 | 48.291 | 39.771 | 1.00 | 53.04 | O |
| HETATM | 2869 | O | HOH | 112 | 83.522 | 36.024 | 30.729 | 1.00 | 43.33 | O |
| HETATM | 2870 | O | HOH | 113 | 45.028 | 41.039 | 12.802 | 1.00 | 37.34 | O |
| HETATM | 2871 | O | HOH | 114 | 69.524 | 61.101 | 18.831 | 1.00 | 49.35 | O |
| HETATM | 2872 | O | HOH | 115 | 44.452 | 44.556 | 32.827 | 1.00 | 42.61 | O |
| HETATM | 2873 | O | HOH | 116 | 54.399 | 50.470 | 15.469 | 1.00 | 48.43 | O |
| HETATM | 2874 | O | HOH | 117 | 61.680 | 63.886 | 35.352 | 1.00 | 38.29 | O |
| HETATM | 2875 | O | HOH | 118 | 77.475 | 37.083 | 32.225 | 1.00 | 42.79 | O |
| HETATM | 2876 | O | HOH | 119 | 53.086 | 57.730 | 38.200 | 1.00 | 44.72 | O |
| HETATM | 2877 | O | HOH | 120 | 79.877 | 44.361 | 4.154 | 1.00 | 44.06 | O |
| HETATM | 2878 | O | HOH | 121 | 57.773 | 49.349 | 44.295 | 1.00 | 43.42 | O |
| HETATM | 2879 | O | HOH | 122 | 81.021 | 37.925 | 24.041 | 1.00 | 40.18 | O |
| HETATM | 2880 | O | HOH | 123 | 92.237 | 46.682 | 19.335 | 1.00 | 49.83 | O |
| HETATM | 2881 | O | HOH | 124 | 80.220 | 47.967 | 11.064 | 1.00 | 40.72 | O |
| HETATM | 2882 | O | HOH | 125 | 73.280 | 38.459 | 40.030 | 1.00 | 48.09 | O |
| HETATM | 2883 | O | HOH | 126 | 75.038 | 35.191 | 27.031 | 1.00 | 35.93 | O |
| HETATM | 2884 | O | HOH | 127 | 54.075 | 73.213 | 39.117 | 1.00 | 50.72 | O |
| HETATM | 2885 | O | HOH | 128 | 53.079 | 51.663 | 12.707 | 1.00 | 36.75 | O |
| HETATM | 2886 | O | HOH | 129 | 60.212 | 50.703 | 45.884 | 1.00 | 49.07 | O |
| HETATM | 2887 | O | HOH | 130 | 85.493 | 38.286 | 29.721 | 1.00 | 45.03 | O |
| HETATM | 2888 | O | HOH | 131 | 72.246 | 32.952 | 26.073 | 1.00 | 44.35 | O |
| HETATM | 2889 | O | HOH | 132 | 74.333 | 61.925 | 18.775 | 1.00 | 48.91 | O |
| HETATM | 2890 | O | HOH | 133 | 78.475 | 36.361 | 24.540 | 1.00 | 37.31 | O |
| HETATM | 2891 | O | HOH | 134 | 70.535 | 25.345 | 24.416 | 1.00 | 53.34 | O |
| HETATM | 2892 | O | HOH | 135 | 81.081 | 38.943 | 20.640 | 1.00 | 56.12 | O |
| HETATM | 2893 | O | HOH | 136 | 60.987 | 73.452 | 38.941 | 1.00 | 44.96 | O |
| HETATM | 2894 | O | HOH | 137 | 72.007 | 45.634 | 46.667 | 1.00 | 47.04 | O |
| HETATM | 2895 | O | HOH | 138 | 54.881 | 54.255 | 40.087 | 1.00 | 47.22 | O |
| HETATM | 2896 | O | HOH | 139 | 64.127 | 73.162 | 32.500 | 1.00 | 39.03 | O |
| HETATM | 2897 | O | HOH | 140 | 91.015 | 51.135 | 35.563 | 1.00 | 54.84 | O |
| HETATM | 2898 | O | HOH | 141 | 44.237 | 42.950 | 15.139 | 1.00 | 48.61 | O |
| HETATM | 2899 | O | HOH | 142 | 84.958 | 38.682 | 22.430 | 1.00 | 41.83 | O |
| HETATM | 2900 | O | HOH | 143 | 58.380 | 41.590 | 5.816 | 1.00 | 48.19 | O |
| HETATM | 2901 | O | HOH | 144 | 83.941 | 42.401 | 9.407 | 1.00 | 45.78 | O |
| HETATM | 2902 | O | HOH | 145 | 48.035 | 32.860 | 14.382 | 1.00 | 49.29 | O |
| HETATM | 2903 | O | HOH | 146 | 62.470 | 25.629 | 24.500 | 1.00 | 47.15 | O |
| HETATM | 2904 | O | HOH | 147 | 65.188 | 30.631 | 26.633 | 1.00 | 37.87 | O |
| HETATM | 2905 | O | HOH | 148 | 77.128 | 50.319 | 38.016 | 1.00 | 50.84 | O |
| HETATM | 2906 | O | HOH | 149 | 42.757 | 43.332 | 23.225 | 1.00 | 33.93 | O |
| HETATM | 2907 | O | HOH | 150 | 58.953 | 59.302 | 30.126 | 1.00 | 39.39 | O |
| HETATM | 2908 | O | HOH | 151 | 55.806 | 76.784 | 37.029 | 1.00 | 43.89 | O |
| HETATM | 2909 | O | HOH | 152 | 90.603 | 36.990 | 30.793 | 1.00 | 49.14 | O |
| HETATM | 2910 | O | HOH | 153 | 73.243 | 28.912 | 13.776 | 1.00 | 44.78 | O |
| HETATM | 2911 | O | HOH | 154 | 67.670 | 43.878 | 49.116 | 1.00 | 67.50 | O |
| HETATM | 2912 | O | HOH | 155 | 65.834 | 40.753 | 2.745 | 1.00 | 47.30 | O |
| HETATM | 2913 | O | HOH | 156 | 73.843 | 26.459 | 21.225 | 1.00 | 51.06 | O |
| HETATM | 2914 | O | HOH | 157 | 47.543 | 41.292 | 37.139 | 1.00 | 43.81 | O |
| HETATM | 2915 | O | HOH | 158 | 68.949 | 44.995 | 46.463 | 1.00 | 50.27 | O |
| HETATM | 2916 | O | HOH | 159 | 65.492 | 48.526 | 5.504 | 1.00 | 49.51 | O |
| HETATM | 2917 | O | HOH | 160 | 61.797 | 59.722 | 40.006 | 1.00 | 48.68 | O |
| HETATM | 2918 | O | HOH | 161 | 55.273 | 30.697 | 8.635 | 1.00 | 52.97 | O |
| HETATM | 2919 | O | HOH | 162 | 50.769 | 46.331 | 39.662 | 1.00 | 54.24 | O |
| HETATM | 2920 | O | HOH | 163 | 55.705 | 37.312 | 5.362 | 1.00 | 48.34 | O |
| HETATM | 2921 | O | HOH | 164 | 71.788 | 35.831 | 6.649 | 1.00 | 44.94 | O |
| HETATM | 2922 | O | HOH | 165 | 56.757 | 27.304 | 17.057 | 1.00 | 47.57 | O |
| HETATM | 2923 | O | HOH | 166 | 65.426 | 40.295 | 46.540 | 1.00 | 43.83 | O |
| HETATM | 2924 | O | HOH | 167 | 55.456 | 40.561 | 4.913 | 1.00 | 53.90 | O |
| HETATM | 2925 | O | HOH | 168 | 66.954 | 59.058 | 38.463 | 1.00 | 50.46 | O |

TABLE 3-continued

| | | | | | | | | | | | |
|---|---|---|---|---|---|---|---|---|---|---|---|
| HETATM | 2926 | O | | HOH | 169 | 71.615 | 66.882 | 31.700 | 1.00 | 48.78 | O |
| HETATM | 2927 | O | | HOH | 170 | 73.024 | 64.238 | 30.477 | 1.00 | 52.09 | O |
| HETATM | 2928 | O | | HOH | 171 | 64.066 | 49.499 | 51.024 | 1.00 | 64.01 | O |
| HETATM | 2929 | O | | HOH | 172 | 53.222 | 41.567 | 6.859 | 1.00 | 49.28 | O |
| HETATM | 2930 | O | | HOH | 173 | 70.234 | 41.586 | −4.830 | 1.00 | 59.58 | O |
| HETATM | 2931 | O | | HOH | 174 | 66.709 | 49.280 | −8.054 | 1.00 | 53.26 | O |
| HETATM | 2932 | O | | HOH | 175 | 61.589 | 53.016 | −3.167 | 1.00 | 53.96 | O |
| HETATM | 2933 | O | | HOH | 176 | 66.692 | 71.708 | 31.475 | 1.00 | 48.45 | O |
| HETATM | 2934 | O | | HOH | 177 | 71.233 | 53.697 | 43.927 | 1.00 | 52.05 | O |
| HETATM | 2935 | O | | HOH | 178 | 72.743 | 64.308 | 17.573 | 1.00 | 54.16 | O |
| HETATM | 2936 | O | | HOH | 179 | 89.336 | 53.769 | 35.871 | 1.00 | 53.70 | O |
| HETATM | 2937 | O | | HOH | 180 | 54.353 | 46.276 | 17.782 | 1.00 | 54.59 | O |
| HETATM | 2938 | O | | HOH | 181 | 68.022 | 31.001 | 25.937 | 1.00 | 44.50 | O |
| HETATM | 2939 | O | | HOH | 182 | 52.980 | 29.445 | 10.465 | 1.00 | 50.22 | O |
| HETATM | 2940 | O | | HOH | 183 | 56.686 | 28.215 | 9.903 | 1.00 | 56.33 | O |
| HETATM | 2941 | O | | HOH | 184 | 77.977 | 49.876 | 10.573 | 1.00 | 53.98 | O |
| HETATM | 2942 | O | | HOH | 185 | 82.562 | 49.900 | 11.756 | 1.00 | 57.59 | O |
| HETATM | 2943 | O | | HOH | 186 | 81.326 | 47.021 | 8.192 | 1.00 | 51.32 | O |
| HETATM | 2944 | O | | HOH | 187 | 76.430 | 51.542 | −3.718 | 1.00 | 42.16 | O |
| HETATM | 2945 | O | | HOH | 188 | 75.167 | 53.201 | −1.226 | 1.00 | 44.07 | O |
| HETATM | 2946 | O | | HOH | 189 | 62.348 | 54.827 | 1.013 | 1.00 | 51.43 | O |
| HETATM | 2947 | O | | HOH | 190 | 59.995 | 64.398 | 17.439 | 1.00 | 60.65 | O |
| HETATM | 2948 | O | | HOH | 191 | 97.267 | 51.029 | 39.970 | 1.00 | 58.50 | O |
| HETATM | 2949 | O | | HOH | 192 | 97.537 | 47.953 | 39.149 | 1.00 | 64.57 | O |
| HETATM | 2950 | O | | HOH | 193 | 93.132 | 47.026 | 37.250 | 1.00 | 46.96 | O |
| CONECT | 202 | 2538 | | | | | | | | | |
| CONECT | 1536 | 1537 | | | | | | | | | |
| CONECT | 1537 | 1536 | 1538 | 1540 | | | | | | | |
| CONECT | 1538 | 1537 | 1539 | | | | | | | | |
| CONECT | 1539 | 1538 | 1542 | | | | | | | | |
| CONECT | 1540 | 1537 | 1541 | | | | | | | | |
| CONECT | 1541 | 1540 | | | | | | | | | |
| CONECT | 1542 | 1539 | | | | | | | | | |
| CONECT | 2538 | 202 | | | | | | | | | |
| CONECT | 2712 | 2713 | 2714 | 2715 | 2716 | | | | | | |
| CONECT | 2713 | 2712 | | | | | | | | | |
| CONECT | 2714 | 2712 | | | | | | | | | |
| CONECT | 2715 | 2712 | | | | | | | | | |
| CONECT | 2716 | 2712 | 2717 | | | | | | | | |
| CONECT | 2717 | 2716 | 2718 | | | | | | | | |
| CONECT | 2718 | 2717 | 2719 | 2720 | | | | | | | |
| CONECT | 2719 | 2718 | 2724 | | | | | | | | |
| CONECT | 2720 | 2718 | 2721 | 2722 | | | | | | | |
| CONECT | 2721 | 2720 | | | | | | | | | |
| CONECT | 2722 | 2720 | 2723 | 2724 | | | | | | | |
| CONECT | 2723 | 2722 | | | | | | | | | |
| CONECT | 2724 | 2719 | 2722 | 2725 | | | | | | | |
| CONECT | 2725 | 2724 | 2726 | 2734 | | | | | | | |
| CONECT | 2726 | 2725 | 2727 | | | | | | | | |
| CONECT | 2727 | 2726 | 2728 | | | | | | | | |
| CONECT | 2728 | 2727 | 2729 | 2734 | | | | | | | |
| CONECT | 2729 | 2728 | 2730 | 2731 | | | | | | | |
| CONECT | 2730 | 2729 | | | | | | | | | |
| CONECT | 2731 | 2729 | 2732 | | | | | | | | |
| CONECT | 2732 | 2731 | 2733 | | | | | | | | |
| CONECT | 2733 | 2732 | 2734 | | | | | | | | |
| CONECT | 2734 | 2725 | 2728 | 2733 | | | | | | | |
| CONECT | 2735 | 2750 | 2752 | 2753 | | | | | | | |
| CONECT | 2736 | 2737 | 2751 | | | | | | | | |
| CONECT | 2737 | 2736 | 2738 | 2743 | | | | | | | |
| CONECT | 2738 | 2737 | 2739 | | | | | | | | |
| CONECT | 2739 | 2738 | 2740 | | | | | | | | |
| CONECT | 2740 | 2739 | 2756 | 2757 | | | | | | | |
| CONECT | 2741 | 2746 | | | | | | | | | |
| CONECT | 2742 | 2754 | | | | | | | | | |
| CONECT | 2743 | 2737 | | | | | | | | | |
| CONECT | 2744 | 2745 | 2753 | | | | | | | | |
| CONECT | 2745 | 2744 | 2746 | 2750 | | | | | | | |
| CONECT | 2746 | 2741 | 2745 | 2747 | | | | | | | |
| CONECT | 2747 | 2746 | 2748 | 2754 | | | | | | | |
| CONECT | 2748 | 2747 | 2749 | 2751 | | | | | | | |
| CONECT | 2749 | 2748 | 2750 | 2755 | | | | | | | |
| CONECT | 2750 | 2735 | 2745 | 2749 | | | | | | | |
| CONECT | 2751 | 2736 | 2748 | | | | | | | | |
| CONECT | 2752 | 2735 | | | | | | | | | |
| CONECT | 2753 | 2735 | 2744 | | | | | | | | |
| CONECT | 2754 | 2742 | 2747 | | | | | | | | |

TABLE 3-continued

| | | |
|---|---|---|
| CONECT | 2755 | 2749 |
| CONECT | 2756 | 2740 |
| CONECT | 2757 | 2740 |
| MASTER | 520 0 4 14 18 0 0 6 2949 1 55 39 | |
| END | | |
| FIG. 12 | | |
| P-UC 5440 | | |
| Page 69 | | |
| 6876 | | |
| 62 | | |
| TABLE 3 | | |

TABLE 4

| | | |
|---|---|---|
| HEADER | | OXIDOREDUCTASE 08-AUG-02 1MEI |
| TITLE | | INOSINE MONOPHOSPHATE DEHYDROGENASE (IMPDH) FROM |
| TITLE | 2 | *TRITRICHOMONAS FOETUS* WITH XMP AND MYCOPHENOLIC ACID BOUND |
| COMPND | | MOL_ID: 1; |
| COMPND | 2 | MOLECULE: INOSINE-5'-MONOPHOSPHATE DEHYDROGENASE; |
| COMPND | 3 | CHAIN: A; |
| COMPND | 4 | SYNONYM: IMP DEHYDROGENASE, IMPDH; |
| COMPND | S | EC: 1.1.1.205; |
| COMPND | 6 | ENGINEERED: YES |
| SOURCE | | MOL ID: 1; |
| SOURCE | 2 | ORGANISM_SCIENTIFIC: *TRITRICHOMONAS FOETUS*; |
| SOURCE | 3 | GENE: IMPDH; |
| SOURCE | 4 | EXPRESSION_SYSTEM: *ESCHERICHIA COLI*; |
| SOURCE | 5 | EXPRESSION_SYSTEM_COMMON: BACTERIA; |
| SOURCE | 6 | EXPRESSION_SYSTEM_STRAIN: H712; |
| SOURCE | 7 | EXPRESSION_SYSTEM_VECTOR_TYPE: PLASMID; |
| SOURCE | 8 | EXPRESSION_SYSTEM_PLASMID: PBACE |
| KEYWDS | | ALPHA BETA BARREL |
| EXPDTA | | X-RAY DIFFRACTION |
| AUTHOR | | G. L. PROSISE, H. LUECKE |
| JRNL | | AUTH    G. L. PROSISE, H. LUECKE |
| JRNL | | TITL     CRYSTAL STRUCTURE OF *T. FOETUS* INOSINE |
| JRNL | | TITL  2  MONOPHOSPHATE DEHYDROGENASE IN COMPLEX WITH |
| JRNL | | TITL  3  SUBSTRATE, COFACTOR, AND ANALOGS:STRUCTURAL BASIS |
| JRNL | | TITL  4  FOR THE RANDOM-IN ORDERED-OUT KINETIC MECHANISM |
| JRNL | | REF     TO BE PUBLISHED |
| JRNL | | REFN |
| REMARK | 1 | |
| REMARK | 2 | |
| REMARK | 2 | RESOLUTION. 2.20 ANGSTROMS. |
| REMARK | 3 | |
| REMARK | 3 | REFINEMENT. |
| REMARK | 3 |   PROGRAM    :  CNS 1.1 |
| REMARK | 3 |   AUTHORS    :  BRUNGER, ADAMS, CLORE, DELANO, GROS, GROSSE- |
| REMARK | 3 |                      :  KUNSTLEVE, JIANG, KUSZEWSKI, NILGES, PANNU, |
| REMARK | 3 |                      :  READ, RICE, SIMONSON, WARREN |
| REMARK | 3 | |
| REMARK | 3 | REFINEMENT TARGET : ENGH & HUBER |
| REMARK | 3 | |
| REMARK | 3 | DATA USED IN REFINEMENT. |
| REMARK | 3 |   RESOLUTION RANGE HIGH     (ANGSTROMS) :  2.20 |
| REMARK | 3 |   RESOLUTION RANGE LOW      (ANGSTROMS) :  33.06 |
| REMARK | 3 |   DATA CUTOFF               (SIGMA(F)) :  0.000 |
| REMARK | 3 |   OUTLIER CUTOFF HIGH      (RMS(ABS(F))) :  NULL |
| REMARK | 3 |   COMPLETENESS (WORKING+TEST)    (%) :  99.5 |
| REMARK | 3 |   NUMBER OF REFLECTIONS          : 32648 |
| REMARK | 3 | |
| REMARK | 3 | FIT TO DATA USED IN REFINEMENT. |
| REMARK | 3 |   CROSS-VALIDATION METHOD         : THROUGHOUT |
| REMARK | 3 |   FREE R VALUE TEST SET SELECTION  : RANDOM |
| REMARK | 3 |   R VALUE                  (WORKING SET) : 0.227 |
| REMARK | 3 |   FREE R VALUE                       : 0.257 |
| REMARK | 3 |   FREE R VALUE TEST SET SIZE     (%) : 5.200 |
| REMARK | 3 |   FREE R VALUE TEST SET COUNT     : 1709 |
| REMARK | 3 |   ESTIMATED ERROR OF FREE R VALUE  : 0.006 |
| REMARK | 3 | |
| REMARK | 3 | FIT IN THE HIGHEST RESOLUTION BIN. |
| REMARK | 3 |   TOTAL NUMBER OF BINS USED       : 6 |
| REMARK | 3 |   BIN RESOLUTION RANGE HIGH    (A) : 2.20 |
| REMARK | 3 |   BIN RESOLUTION RANGE LOW     (A) : 2.34 |
| REMARK | 3 |   BIN COMPLETENESS (WORKING+TEST)  (%) : 96.60 |
| REMARK | 3 |   REFLECTIONS IN BIN      (WORKING SET) : 4936 |

TABLE 4-continued

| | | | | | |
|---|---|---|---|---|---|
| REMARK | 3 | BIN R VALUE | (WORKING SET) : | 0.2710 | |
| REMARK | 3 | BIN FREE R VALUE | : | 0.2930 | |
| REMARK | 3 | BIN FREE R VALUE TEST SET SIZE | (%) : | 5.00 | |
| REMARK | 3 | BIN FREE R VALUE TEST SET COUNT | : | 259 | |
| REMARK | 3 | ESTIMATED ERROR OF BINFREE R VALUE | : | 0.018 | |
| REMARK | 3 | | | | |
| REMARK | 3 | NUMBER OF NON-HYDROGEN ATOMS USED INREFINEMENT. | | | |
| REMARK | 3 | PROTEIN ATOMS | : | 2690 | |
| REMARK | 3 | NUCLEIC ACID ATOMS | : | 0 | |
| REMARK | 3 | HETEROGEN ATOMS | : | 48 | |
| REMARK | 3 | SOLVENT ATOMS | : | 180 | |
| REMARK | 3 | | | | |
| REMARK | 3 | B VALUES. | | | |
| REMARK | 3 | FROM WILSON PLOT | (A**2) : | 27.40 | |
| REMARK | 3 | MEAN B VALUE | (OVERALL, A**2) : | 37.30 | |
| REMARK | 3 | OVERALL ANISOTROPIC B VALUE. | | | |
| REMARK | 3 | B11 (A**2) : | 0.00000 | | |
| REMARK | 3 | B22 (A**2) : | 0.00000 | | |
| REMARK | 3 | B33 (A**2) : | 0.00000 | | |
| REMARK | 3 | B12 (A**2) : | 0.00000 | | |
| REMARK | 3 | B13 (A**2) : | 0.00000 | | |
| REMARK | 3 | B23 (A**2) : | 0.00000 | | |
| REMARK | 3 | | | | |
| REMARK | 3 | ESTIMATED COORDINATE ERROR. | | | |
| REMARK | 3 | ESD FROM LUZZATI PLOT | (A) : | 0.27 | |
| REMARK | 3 | ESD FROM SIGMAA | (A) : | 0.23 | |
| REMARK | 3 | LOW RESOLUTION CUTOFF | (A) : | 5.00 | |
| REMARK | 3 | | | | |
| REMARK | 3 | CROSS-VALIDATED ESTIMATED COORDINATEERROR. | | | |
| REMARK | 3 | ESD FROM C-V LUZZATI PLOT | (A) : | 0.32 | |
| REMARK | 3 | ESD FROM C-V SIGMAA | (A) : | 0.28 | |
| REMARK | 3 | | | | |
| REMARK | 3 | RMS DEVIATIONS FROM IDEAL VALUES. | | | |
| REMARK | 3 | BOND LENGTHS | (A) : | 0.006 | |
| REMARK | 3 | BOND ANGLES | (DEGREES) : | 1.20 | |
| REMARK | 3 | DIHEDRAL ANGLES | (DEGREES) : | 22.50 | |
| REMARK | 3 | IMPROPER ANGLES | (DEGREES) : | 0.68 | |
| REMARK | 3 | | | | |
| REMARK | 3 | ISOTROPIC THERMAL MODEL : RESTRAINED | | | |
| REMARK | 3 | | | | |
| REMARK | 3 | ISOTROPIC THERMAL FACTOR RESTRAINTS. | | RMS | SIGMA |
| REMARK | 3 | MAIN-CHAIN BOND | (A**2) : | 1.230 ; | 1.500 |
| REMARK | 3 | MAIN-CHAIN ANGLE | (A**2) : | 2.190 ; | 2.000 |
| REMARK | 3 | SIDE-CHAIN BOND | (A**2) : | 1.610 ; | 2.000 |
| REMARK | 3 | SIDE-CHAIN ANGLE | (A**2) : | 2.520 ; | 2.500 |
| REMARK | 3 | | | | |
| REMARK | 3 | BULK SOLVENT MODELING. | | | |
| REMARK | 3 | METHOD USED : | FLAT MODEL | | |
| REMARK | 3 | KSOL : | 0.34 | | |
| REMARK | 3 | BSOL : | 35.45 | | |
| REMARK | 3 | | | | |
| REMARK | 3 | NCS MODEL : NULL | | | |
| REMARK | 3 | | | | |
| REMARK | 3 | NCS RESTRAINTS. | | RMS | SIGMA/WEIGHT |
| REMARK | 3 | GROUP 1 POSITIONAL | (A) : | NULL ; | NULL |
| REMARK | 3 | GROUP 2 B-FACTOR | (A**2) : | NULL ; | NULL |
| REMARK | 3 | | | | |
| REMARK | 3 | PARAMETER FILE 1 : | PROTEIN_REP.PARAM | | |
| REMARK | 3 | PARAMETER FILE 2 : | PARAM.GNSOL | | |
| REMARK | 3 | PARAMETER FILE 3 : | CIS_PEPTIDE.PARAM | | |
| REMARK | 3 | PARAMETER FILE 4 : | MPA.PAR | | |
| REMARK | 3 | PARAMETER FILE 5 : | XMP.PAR | | |
| REMARK | 3 | PARAMETER FILE 6 : | NULL | | |
| REMARK | 3 | TOPOLOGY FILE 1 : | PROTEIN.TOP | | |
| REMARK | 3 | TOPOLOGY FILE 2 : | XMP.TOP | | |
| REMARK | 3 | TOPOLOGY FILE 3 : | MPA.TOP | | |
| REMARK | 3 | TOPOLOGY FILE 4 : | K.TOP | | |
| REMARK | 3 | TOPOLOGY FILE 5 : | TOPH.GNSOL | | |
| REMARK | 3 | TOPOLOGY FILE 6 : | NULL | | |
| REMARK | 3 | | | | |
| REMARK | 3 | OTHER REFINEMENT REMARKS: NULL | | | |
| REMARK | 4 | | | | |
| REMARK | 4 | 1MEI COMPLIES WITH FORMAT V. 2.3, 09-JULY-1998 | | | |
| REMARK | 100 | | | | |
| REMARK | 100 | THIS ENTRY HAS BEEN PROCESSED BY RCSB ON 16-AUG-2002. | | | |
| REMARK | 100 | THE RCSB ID CODE IS RCSB016853. | | | |
| REMARK | 200 | | | | |

TABLE 4-continued

```
REMARK   200  EXPERIMENTAL DETAILS
REMARK   200    EXPERIMENT TYPE                         :  X-RAY DIFFRACTION
REMARK   200    DATE OF DATA COLLECTION                 :  11-APR-2001
REMARK   200    TEMPERATURE              (KELVIN) :        100.0
REMARK   200    PH                                      :  7.50
REMARK   200    NUMBER OF CRYSTALS USED                 :  1
REMARK   200
REMARK   200    SYNCHROTRON              (Y/N) :           Y
REMARK   200    RADIATION SOURCE                        :  SSRL
REMARK   200    BEAMLINE                                :  9-1
REMARK   200    X-RAY GENERATOR MODEL                   :  NULL
REMARK   200    MONOCHROMATIC OR LAUE    (M/L) :           M
REMARK   200    WAVELENGTH OR RANGE      (A) :             0.97
REMARK   200    MONOCHROMATOR                           :  NULL
REMARK   200    OPTICS                                  :  NULL
REMARK   200
REMARK   200    DETECTOR TYPE                           :  IMAGE PLATE
REMARK   200    DETECTOR MANUFACTURER                   :  MARRESEARCH
REMARK   200    INTENSITY-INTEGRATION SOFTWARE   :         DENZO
REMARK   200    DATA SCALING SOFTWARE            :         SCALEPACK
REMARK   200
REMARK   200    NUMBER OF UNIQUE REFLECTIONS    :          32815
REMARK   200    RESOLUTION RANGE HIGH    (A) :             2.200
REMARK   200    RESOLUTION RANGE LOW     (A) :             99.000
REMARK   200    REJECTION CRITERIA       (SIGMA(I)) :      NULL
REMARK   200
REMARK   200  OVERALL.
REMARK   200    COMPLETENESS FOR RANGE   (%) :             99.5
REMARK   200    DATA REDUNDANCY                     :      4.700
REMARK   200    R MERGE                  (I) :             0.06600
REMARK   200    R SYM                    (I) :             NULL
REMARK   200    <I/SIGMA(I)> FOR THE DATA SET       :      21.4000
REMARK   200
REMARK   200  IN THE HIGHEST RESOLUTION SHELL.
REMARK   200    HIGHEST RESOLUTION SHELL, RANGE HIGH  (A) :   2.20
REMARK   200    HIGHEST RESOLUTION SHELL, RANGE LOW   (A) :   2.24
REMARK   200    COMPLETENESS FOR SHELL   (%) :             98.7
REMARK   200    DATA REDUNDANCY IN SHELL            :      NULL
REMARK   200    R MERGE FOR SHELL        (I) :             0.50000
REMARK   200    R SYM FOR SHELL          (I) :             NULL
REMARK   200    <I/SIGMA(I)> FOR SHELL              :      2.900
REMARK   200
REMARK   200  DIFFRACTION PROTOCOL: SINGLE WAVELENGTH
REMARK   200  METHOD USED TO DETERMINE THE STRUCTURE: FOURIER SYNTHESIS
REMARK   200  SOFTWARE USED: CNS
REMARK   200  STARTING MODEL: PDB ENTRY 1AK5
REMARK   200
REMARK   200  REMARK: NULL
REMARK   280
REMARK   280  CRYSTAL
REMARK   280  SOLVENT CONTENT, VS     (%) :  NULL
REMARK   280  MATTHEWS COEFFICIENT, VM   (ANGSTROMS**3/DA) :   NULL
REMARK   280
REMARK   280  CRYSTALLIZATION CONDITIONS: SODIUM MALONATE, TRIS, 2-
REMARK   280    MERCAPTOETHANOL, EDTA, GLYCEROL
REMARK   290
REMARK   290  CRYSTALLOGRAPHIC SYMMETRY
REMARK   290  SYMMETRY OPERATORS FOR SPACE GROUP: P 4 3 2
REMARK   290
REMARK   290         SYMOP     SYMMETRY
REMARK   290         NNNMMM    OPERATOR
REMARK   290          1555     X, Y, Z
REMARK   290          2555     -X, -Y, Z
REMARK   290          3555     -X, Y, -Z
REMARK   290          4555     X, -Y, -Z
REMARK   290          5555     Z, X, Y
REMARK   290          6555     Z, -X, -Y
REMARK   290          7555     -Z, -X, Y
REMARK   290          8555     -Z, X, -Y
REMARK   290          9555     Y, Z, X
REMARK   290         10555     -Y, Z, -X
REMARK   290         11555     Y, -Z, -X
REMARK   290         12555     -Y, -Z, X
REMARK   290         13555     Y, X, -Z
REMARK   290         14555     -Y, -X, -Z
REMARK   290         15555     Y, -X, Z
REMARK   290         16555     -Y, X, Z
REMARK   290         17555     X, Z, -Y
REMARK   290         18555     X, Z, Y
```

TABLE 4-continued

| | | | | | | | |
|---|---|---|---|---|---|---|---|
| REMARK | 290 | | 19555 | −X, −Z, −Y | | | |
| REMARK | 290 | | 20555 | X, −Z, Y | | | |
| REMARK | 290 | | 21555 | Z, Y, −X | | | |
| REMARK | 290 | | 22555 | Z, −Y, X | | | |
| REMARK | 290 | | 23555 | −Z, Y, X | | | |
| REMARK | 290 | | 24555 | −Z, −Y, −X | | | |
| REMARK | 290 | | | | | | |
| REMARK | 290 | | WHERE | NNN −> OPERATOR NUMBER | | | |
| REMARK | 290 | | | MMM −> TRANSLATION VECTOR | | | |
| REMARK | 290 | | | | | | |
| REMARK | 290 | CRYSTALLOGRAPHIC SYMMETRY TRANSFORMATIONS | | | | | |
| REMARK | 290 | THE FOLLOWING TRANSFORMATIONS OPERATE ON THE ATOM/HETATM | | | | | |
| REMARK | 290 | RECORDS IN THIS ENTRY TO PRODUCE CRYSTALLOGRAPHICALLY | | | | | |
| REMARK | 290 | RELATED MOLECULES. | | | | | |
| REMARK | 290 | SMTRY1 | 1 | 1.000000 | 0.000000 | 0.000000 | 0.00000 |
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | −1.000000 | 0.000000 | 0.000000 | 0.00000 |
| REMARK | 290 | SMTRY2 | 2 | 0.000000 | −1.000000 | 0.000000 | 0.00000 |
| REMARK | 290 | SMTRY3 | 2 | 0.000000 | 0.000000 | 1.000000 | 0.00000 |
| REMARK | 290 | SMTRY1 | 3 | −1.000000 | 0.000000 | 0.000000 | 0.00000 |
| REMARK | 290 | SMTRY2 | 3 | 0.000000 | 1.000000 | 0.000000 | 0.00000 |
| REMARK | 290 | SMTRY3 | 3 | 0.000000 | 0.000000 | −1.000000 | 0.00000 |
| REMARK | 290 | SMTRY1 | 4 | 1.000000 | 0.000000 | 0.000000 | 0.00000 |
| REMARK | 290 | SMTRY2 | 4 | 0.000000 | −1.000000 | 0.000000 | 0.00000 |
| REMARK | 290 | SMTRY3 | 4 | 0.000000 | 0.000000 | −1.000000 | 0.00000 |
| REMARK | 290 | SMTRY1 | 5 | 0.000000 | 0.000000 | 1.000000 | 0.00000 |
| REMARK | 290 | SMTRY2 | 5 | 1.000000 | 0.000000 | 0.000000 | 0.00000 |
| REMARK | 290 | SMTRY3 | 5 | 0.000000 | 1.000000 | 0.000000 | 0.00000 |
| REMARK | 290 | SMTRY1 | 6 | 0.000000 | 0.000000 | 1.000000 | 0.00000 |
| REMARK | 290 | SMTRY2 | 6 | −1.000000 | 0.000000 | 0.000000 | 0.00000 |
| REMARK | 290 | SMTRY3 | 6 | 0.000000 | −1.000000 | 0.000000 | 0.00000 |
| REMARK | 290 | SMTRY1 | 7 | 0.000000 | 0.000000 | −1.000000 | 0.00000 |
| REMARK | 290 | SMTRY2 | 7 | −1.000000 | 0.000000 | 0.000000 | 0.00000 |
| REMARK | 290 | SMTRY3 | 7 | 0.000000 | 1.000000 | 0.000000 | 0.00000 |
| REMARK | 290 | SMTRY1 | 8 | 0.000000 | 0.000000 | −1.000000 | 0.00000 |
| REMARK | 290 | SMTRY2 | 8 | 1.000000 | 0.000000 | 0.000000 | 0.00000 |
| REMARK | 290 | SMTRY3 | 8 | 0.000000 | −1.000000 | 0.000000 | 0.00000 |
| REMARK | 290 | SMTRY1 | 9 | 0.000000 | 1.000000 | 0.000000 | 0.00000 |
| REMARK | 290 | SMTRY2 | 9 | 0.000000 | 0.000000 | 1.000000 | 0.00000 |
| REMARK | 290 | SMTRY3 | 9 | 1.000000 | 0.000000 | 0.000000 | 0.00000 |
| REMARK | 290 | SMTRY1 | 10 | 0.000000 | −1.000000 | 0.000000 | 0.00000 |
| REMARK | 290 | SMTRY2 | 10 | 0.000000 | 0.000000 | 1.000000 | 0.00000 |
| REMARK | 290 | SMTRY3 | 10 | −1.000000 | 0.000000 | 0.000000 | 0.00000 |
| REMARK | 290 | SMTRY1 | 11 | 0.000000 | 1.000000 | 0.000000 | 0.00000 |
| REMARK | 290 | SMTRY2 | 11 | 0.000000 | 0.000000 | −1.000000 | 0.00000 |
| REMARK | 290 | SMTRY3 | 11 | −1.000000 | 0.000000 | 0.000000 | 0.00000 |
| REMARK | 290 | SMTRY1 | 12 | 0.000000 | −1.000000 | 0.000000 | 0.00000 |
| REMARK | 290 | SMTRY2 | 12 | 0.000000 | 0.000000 | −1.000000 | 0.00000 |
| REMARK | 290 | SMTRY3 | 12 | 1.000000 | 0.000000 | 0.000000 | 0.00000 |
| REMARK | 290 | SMTRY1 | 13 | 0.000000 | 1.000000 | 0.000000 | 0.00000 |
| REMARK | 290 | SMTRY2 | 13 | 1.000000 | 0.000000 | 0.000000 | 0.00000 |
| REMARK | 290 | SMTRY3 | 13 | 0.000000 | 0.000000 | −1.000000 | 0.00000 |
| REMARK | 290 | SMTRY1 | 14 | 0.000000 | −1.000000 | 0.000000 | 0.00000 |
| REMARK | 290 | SMTRY2 | 14 | −1.000000 | 0.000000 | 0.000000 | 0.00000 |
| REMARK | 290 | SMTRY3 | 14 | 0.000000 | 0.000000 | −1.000000 | 0.00000 |
| REMARK | 290 | SMTRY1 | 15 | 0.000000 | 1.000000 | 0.000000 | 0.00000 |
| REMARK | 290 | SMTRY2 | 15 | −1.000000 | 0.000000 | 0.000000 | 0.00000 |
| REMARK | 290 | SMTRY3 | 15 | 0.000000 | 0.000000 | 1.000000 | 0.00000 |
| REMARK | 290 | SMTRY1 | 16 | 0.000000 | −1.000000 | 0.000000 | 0.00000 |
| REMARK | 290 | SMTRY2 | 16 | 1.000000 | 0.000000 | 0.000000 | 0.00000 |
| REMARK | 290 | SMTRY3 | 16 | 0.000000 | 0.000000 | 1.000000 | 0.00000 |
| REMARK | 290 | SMTRY1 | 17 | 1.000000 | 0.000000 | 0.000000 | 0.00000 |
| REMARK | 290 | SMTRY2 | 17 | 0.000000 | 0.000000 | 1.000000 | 0.00000 |
| REMARK | 290 | SMTRY3 | 17 | 0.000000 | −1.000000 | 0.000000 | 0.00000 |
| REMARK | 290 | SMTRY1 | 18 | −1.000000 | 0.000000 | 0.000000 | 0.00000 |
| REMARK | 290 | SMTRY2 | 18 | 0.000000 | 0.000000 | 1.000000 | 0.00000 |
| REMARK | 290 | SMTRY3 | 18 | 0.000000 | 1.000000 | 0.000000 | 0.00000 |
| REMARK | 290 | SMTRY1 | 19 | −1.000000 | 0.000000 | 0.000000 | 0.00000 |
| REMARK | 290 | SMTRY2 | 19 | 0.000000 | 0.000000 | −1.000000 | 0.00000 |
| REMARK | 290 | SMTRY3 | 19 | 0.000000 | −1.000000 | 0.000000 | 0.00000 |
| REMARK | 290 | SMTRY1 | 20 | 1.000000 | 0.000000 | 0.000000 | 0.00000 |
| REMARK | 290 | SMTRY2 | 20 | 0.000000 | 0.000000 | −1.000000 | 0.00000 |
| REMARK | 290 | SMTRY3 | 20 | 0.000000 | 1.000000 | 0.000000 | 0.00000 |
| REMARK | 290 | SMTRY1 | 21 | 0.000000 | 0.000000 | 1.000000 | 0.00000 |
| REMARK | 290 | SMTRY2 | 21 | 0.000000 | 1.000000 | 0.000000 | 0.00000 |
| REMARK | 290 | SMTRY3 | 21 | −1.000000 | 0.000000 | 0.000000 | 0.00000 |
| REMARK | 290 | SMTRY1 | 22 | 0.000000 | 0.000000 | 1.000000 | 0.00000 |
| REMARK | 290 | SMTRY2 | 22 | 0.000000 | −1.000000 | 0.000000 | 0.00000 |

TABLE 4-continued

| | | | | | | | |
|---|---|---|---|---|---|---|---|
| REMARK | 290 | SMTRY3 | 22 | 1.000000 | 0.000000 | 0.000000 | 0.00000 |
| REMARK | 290 | SMTRY1 | 23 | 0.000000 | 0.000000 | −1.000000 | 0.00000 |
| REMARK | 290 | SMTRY2 | 23 | 0.000000 | 1.000000 | 0.000000 | 0.00000 |
| REMARK | 290 | SMTRY3 | 23 | 1.000000 | 0.000000 | 0.000000 | 0.00000 |
| REMARK | 290 | SMTRY1 | 24 | 0.000000 | 0.000000 | −1.000000 | 0.00000 |
| REMARK | 290 | SMTRY2 | 24 | 0.000000 | −1.000000 | 0.000000 | 0.00000 |
| REMARK | 290 | SMTRY3 | 24 | −1.000000 | 0.000000 | 0.000000 | 0.00000 |
| REMARK | 290 | | | | | | |
| REMARK | 290 | REMARK: NULL | | | | | |
| REMARK | 300 | | | | | | |
| REMARK | 300 | BIOMOLECULE: 1 | | | | | |
| REMARK | 300 | THIS ENTRY CONTAINS THE CRYSTALLOGRAPHIC ASYMMETRIC UNIT | | | | | |
| REMARK | 300 | WHICH CONSISTS OF 1 CHAIN(S). SEE REMARK 350 FOR | | | | | |
| REMARK | 300 | INFORMATION ON GENERATING THE BIOLOGICAL MOLECULE(S). | | | | | |
| REMARK | 350 | | | | | | |
| REMARK | 350 | GENERATING THE BIOMOLECULE | | | | | |
| REMARK | 350 | COORDINATES FOR A COMPLETE MULTIMER REPRESENTING THE KNOWN | | | | | |
| REMARK | 350 | BIOLOGICALLY SIGNIFICANT OLIGOMERIZATION STATE OF THE | | | | | |
| REMARK | 350 | MOLECULE CAN BE GENERATED BY APPLYING BIOMT TRANSFORMATIONS | | | | | |
| REMARK | 350 | GIVEN BELOW. BOTH NON-CRYSTALLOGRAPHIC AND | | | | | |
| REMARK | 350 | CRYSTALLOGRAPHIC OPERATIONS ARE GIVEN. | | | | | |
| REMARK | 350 | | | | | | |
| REMARK | 350 | BIOMOLECULE: 1 | | | | | |
| REMARK | 350 | APPLY THE FOLLOWING TO CHAINS: A | | | | | |
| REMARK | 350 | BIOMT1 | 1 | 1.000000 | 0.000000 | 0.000000 | 0.00000 |
| REMARK | 350 | BIOMT2 | 1 | 0.000000 | 1.000000 | 0.000000 | 0.00000 |
| REMARK | 350 | BIOMT3 | 1 | 0.000000 | 0.000000 | 1.000000 | 0.00000 |
| REMARK | 350 | BIOMT1 | 2 | −1.000000 | 0.000000 | 0.000000 | 155.07000 |
| REMARK | 350 | BIOMT2 | 2 | 0.000000 | −1.000000 | 0.000000 | 155.07000 |
| REMARK | 350 | BIOMT3 | 2 | 0.000000 | 0.000000 | 1.000000 | 0.00000 |
| REMARK | 350 | BIOMT1 | 3 | 0.000000 | 1.000000 | 0.000000 | 0.00000 |
| REMARK | 350 | BIOMT2 | 3 | −1.000000 | 0.000000 | 0.000000 | 155.07000 |
| REMARK | 350 | BIOMT3 | 3 | 0.000000 | 0.000000 | 1.000000 | 0.00000 |
| REMARK | 350 | BIOMT1 | 4 | 0.000000 | −1.000000 | 0.000000 | 155.07000 |
| REMARK | 350 | BIOMT2 | 4 | 1.000000 | 0.000000 | 0.000000 | 0.00000 |
| REMARK | 350 | BIOMT3 | 4 | 0.000000 | 0.000000 | 1.000000 | 0.00000 |
| REMARK | 375 | | | | | | |
| REMARK | 375 | SPECIAL POSITION | | | | | |
| REMARK | 375 | THE FOLLOWING ATOMS ARE FOUND TO BE WITHIN 0.15 ANGSTROMS | | | | | |
| REMARK | 375 | OF A SYMMETRY RELATEDATOM AND ARE ASSUMED TO BE ON SPECIAL | | | | | |
| REMARK | 375 | POSITIONS. | | | | | |
| REMARK | 375 | | | | | | |
| REMARK | 375 | ATOM RES CSSEQI | | | | | |
| REMARK | 375 | HOH 131 LIES ON A SPECIAL POSITION. | | | | | |
| REMARK | 465 | | | | | | |
| REMARK | 465 | MISSING RESIDUES | | | | | |
| REMARK | 465 | THE FOLLOWING RESIDUES WERE NOT LOCATED IN THE | | | | | |
| REMARK | 465 | EXPERIMENT. (M = MODEL NUMBER; RES = RESIDUE NAME; C = CHAIN | | | | | |
| REMARK | 465 | IDENTIFIER; SSSEQ = SEQUENCE NUMBER; I = INSERTION CODE.) | | | | | |
| REMARK | 465 | | | | | | |
| REMARK | 465 | M RES C SSSEQI | | | | | |
| REMARK | 465 | MET A 1 | | | | | |
| REMARK | 465 | GLY A 102 | | | | | |
| REMARK | 465 | PHE A 103 | | | | | |
| REMARK | 465 | VAL A 104 | | | | | |
| REMARK | 465 | VAL A 105 | | | | | |
| REMARK | 465 | SER A 106 | | | | | |
| REMARK | 465 | ASP A 107 | | | | | |
| REMARK | 465 | SER A 108 | | | | | |
| REMARK | 465 | ASN A 109 | | | | | |
| REMARK | 465 | VAL A 110 | | | | | |
| REMARK | 465 | LYS A 111 | | | | | |
| REMARK | 465 | PRO A 112 | | | | | |
| REMARK | 465 | ASP A 113 | | | | | |
| REMARK | 465 | GLN A 114 | | | | | |
| REMARK | 465 | THR A 115 | | | | | |
| REMARK | 465 | PHE A 116 | | | | | |
| REMARK | 465 | ALA A 117 | | | | | |
| REMARK | 465 | ASP A 118 | | | | | |
| REMARK | 465 | VAL A 119 | | | | | |
| REMARK | 465 | LEU A 120 | | | | | |
| REMARK | 465 | ALA A 121 | | | | | |
| REMARK | 465 | ILE A 122 | | | | | |
| REMARK | 465 | SER A 123 | | | | | |
| REMARK | 465 | GLN A 124 | | | | | |
| REMARK | 465 | ARG A 125 | | | | | |
| REMARK | 465 | THR A 126 | | | | | |
| REMARK | 465 | THR A 127 | | | | | |
| REMARK | 465 | HIS A 128 | | | | | |

TABLE 4-continued

| | | | | |
|---|---|---|---|---|
| REMARK | 465 | ASN | A | 129 |
| REMARK | 465 | THR | A | 130 |
| REMARK | 465 | VAL | A | 131 |
| REMARK | 465 | ALA | A | 132 |
| REMARK | 465 | VAL | A | 133 |
| REMARK | 465 | THR | A | 134 |
| REMARK | 465 | ASP | A | 135 |
| REMARK | 465 | ASP | A | 136 |
| REMARK | 465 | GLY | A | 137 |
| REMARK | 465 | THR | A | 138 |
| REMARK | 465 | PRO | A | 139 |
| REMARK | 465 | HIS | A | 140 |
| REMARK | 465 | GLY | A | 141 |
| REMARK | 465 | VAL | A | 142 |
| REMARK | 465 | LEU | A | 143 |
| REMARK | 465 | LEU | A | 144 |
| REMARK | 465 | GLY | A | 145 |
| REMARK | 465 | LEU | A | 146 |
| REMARK | 465 | VAL | A | 147 |
| REMARK | 465 | THR | A | 148 |
| REMARK | 465 | GLN | A | 149 |
| REMARK | 465 | ARG | A | 150 |
| REMARK | 465 | ASP | A | 151 |
| REMARK | 465 | TYR | A | 152 |
| REMARK | 465 | PRO | A | 153 |
| REMARK | 465 | ILE | A | 154 |
| REMARK | 465 | ASP | A | 155 |
| REMARK | 465 | LEU | A | 156 |
| REMARK | 465 | THR | A | 157 |
| REMARK | 465 | GLN | A | 158 |
| REMARK | 465 | THR | A | 159 |
| REMARK | 465 | GLU | A | 160 |
| REMARK | 465 | THR | A | 161 |
| REMARK | 465 | LYS | A | 162 |
| REMARK | 465 | VAL | A | 163 |
| REMARK | 465 | SER | A | 164 |
| REMARK | 465 | ASP | A | 165 |
| REMARK | 465 | MET | A | 166 |
| REMARK | 465 | MET | A | 167 |
| REMARK | 465 | THR | A | 168 |
| REMARK | 465 | PRO | A | 169 |
| REMARK | 465 | PHE | A | 170 |
| REMARK | 465 | SER | A | 171 |
| REMARK | 465 | LYS | A | 172 |
| REMARK | 465 | LEU | A | 173 |
| REMARK | 465 | VAL | A | 174 |
| REMARK | 465 | THR | A | 175 |
| REMARK | 465 | ALA | A | 176 |
| REMARK | 465 | HIS | A | 177 |
| REMARK | 465 | GLN | A | 178 |
| REMARK | 465 | ASP | A | 179 |
| REMARK | 465 | THR | A | 180 |
| REMARK | 465 | LYS | A | 181 |
| REMARK | 465 | LEU | A | 182 |
| REMARK | 465 | SER | A | 183 |
| REMARK | 465 | GLU | A | 184 |
| REMARK | 465 | ALA | A | 185 |
| REMARK | 465 | ASN | A | 186 |
| REMARK | 465 | LYS | A | 187 |
| REMARK | 465 | ILE | A | 188 |
| REMARK | 465 | ILE | A | 189 |
| REMARK | 465 | TRP | A | 190 |
| REMARK | 465 | GLU | A | 191 |
| REMARK | 465 | LYS | A | 192 |
| REMARK | 465 | LYS | A | 193 |
| REMARK | 465 | LEU | A | 194 |
| REMARK | 465 | ASN | A | 195 |
| REMARK | 465 | ALA | A | 196 |
| REMARK | 465 | LEU | A | 197 |
| REMARK | 465 | PRO | A | 198 |
| REMARK | 465 | ILE | A | 199 |
| REMARK | 465 | ILE | A | 200 |
| REMARK | 465 | ASP | A | 201 |
| REMARK | 465 | ASP | A | 202 |
| REMARK | 465 | ASP | A | 203 |
| REMARK | 465 | GLN | A | 204 |
| REMARK | 465 | HIS | A | 205 |
| REMARK | 465 | LEU | A | 206 |
| REMARK | 465 | ARG | A | 207 |

TABLE 4-continued

```
REMARK    465    TYR   A    208
REMARK    465    ILE   A    209
REMARK    465    VAL   A    210
REMARK    465    PHE   A    211
REMARK    465    ARG   A    212
REMARK    465    LYS   A    213
REMARK    465    ASP   A    214
REMARK    465    TYR   A    215
REMARK    465    ASP   A    216
REMARK    465    ARG   A    217
REMARK    465    SER   A    218
REMARK    465    GLN   A    219
REMARK    465    VAL   A    220
REMARK    465    CYS   A    221
REMARK    465    GLN   A    417
REMARK    465    ARG   A    418
REMARK    465    TYR   A    419
REMARK    465    ASP   A    420
REMARK    465    LEU   A    421
REMARK    465    GLY   A    422
REMARK    465    GLY   A    423
REMARK    465    LYS   A    424
REMARK    465    GLN   A    425
REMARK    465    LYS   A    426
REMARK    465    LEU   A    427
REMARK    465    VAL   A    484
REMARK    465    GLU   A    485
REMARK    465    GLY   A    486
REMARK    465    GLY   A    487
REMARK    465    ALA   A    488
REMARK    465    HIS   A    489
REMARK    465    ASP   A    490
REMARK    465    VAL   A    491
REMARK    465    ILE   A    492
REMARK    465    VAL   A    493
REMARK    465    LYS   A    494
REMARK    465    ASP   A    495
REMARK    465    ARG   A    496
REMARK    465    ILE   A    497
REMARK    465    ASN   A    498
REMARK    465    ASP   A    499
REMARK    465    TYR   A    500
REMARK    465    HIS   A    501
REMARK    465    PRO   A    502
REMARK    465    LYS   A    503
REMARK    500
REMARK    500  GEOMETRY AND STEREOCHEMISTRY
REMARK    500  SUBTOPIC: CLOSE CONTACTS IN SAME ASYMMETRIC UNIT
REMARK    500
REMARK    500  THE FOLLOWING ATOMS ARE IN CLOSE CONTACT.
REMARK    500
REMARK    500  ATM1    RES   C    SSEQI ATM2    RES   C    SSEQI
REMARK    500  0       GLYA 20    K      K       A    900            2.12
REMARK    500
REMARK    500  GEOMETRY AND STEREOCHEMISTRY
REMARK    500  SUBTOPIC: COVALENT BOND LENGTHS
REMARK    500
REMARK    500  THE STEREOCHEMICAL PARAMETERS OF THE FOLLOWING RESIDUES
REMARK    500  HAVE VALUES WHICH DEVIATE FROM EXPECTED VALUES BY MORE
REMARK    500  THAN 6*RMSD (M = MODEL NUMBER; RES = RESIDUE NAME; C = CHAIN
REMARK    500  IDENTIFIER; SSEQ = SEQUENCE NUMBER; I = INSERTION CODE)
REMARK    500
REMARK    500  STANDARD TABLE:
REMARK    500  FORMAT: (10X, 13, 1X, 2(A3, 1X, A1, I4, A1, 1X, A4, 3X), F6.3).
REMARK    500
REMARK    500  EXPECTED VALUES: ENGH AND HUBER, 1991
REMARK    500
REMARK    500  M   RES   CSSEQI    ATM1    RES   CSSEQI    ATM2        DEVIATION
REMARK    500      MET   A    379  CE      MET   A    379  SD                    0.037
REMARK    500
REMARK    500  GEOMETRY AND STEREOCHEMISTRY
REMARK    500  SUBTOPIC: COVALENT BOND ANGLES
REMARK    500
REMARK    500  THE STEREOCHEMICAL PARAMETERS OF THE FOLLOWING RESIDUES
REMARK    500  HAVE VALUES WHICH DEVIATE FROM EXPECTED VALUES BY MORE
REMARK    500  THAN 6*RMSD (M = MODEL NUMBER; RES = RESIDUE NAME; C = CHAIN
REMARK    500  IDENTIFIER; SSEQ = SEQUENCE NUMBER; I = INSERTION CODE).
REMARK    500
```

TABLE 4-continued

```
REMARK   500 STANDARD TABLE:
REMARK   500 FORMAT: (10X, I3, 1X, A3, 1X, A1, I4, A1, 3(1X, A4, 2X), 12X, F5.1)
REMARK   500
REMARK   500 EXPECTED VALUES: ENGH AND HUBER, 1991
REMARK   500
REMARK   500 M  RES  CSSEQI   ATM1        ATM2        ATM3
REMARK   500    ILE  A    27 N     -   CA    -   C      ANGL. DEV. =  -7.8 DEGREES
REMARK   500    GLN  A    45 N     -   CA    -   C      ANGL. DEV. =  -7.7 DEGREES
REMARK   500    SER  A    63 N     -   CA    -   C      ANGL. DEV. =   8.3 DEGREES
REMARK   500    PHE  A   266 N     -   CA    -   C      ANGL. DEV. =  -7.2 DEGREES
REMARK   500    GLY  A   312 N     -   CA    -   C      ANGL. DEV. =   7.6 DEGREES
REMARK   500    THR  A   349 N     -   CA    -   C      ANGL. DEV. =   7.3 DEGREES
REMARK   500    PRO  A   391 N     -   CA    -   C      ANGL. DEV. =   7.3 DEGREES
REMARK   500    LYS  A   394 N     -   CA    -   C      ANGL. DEV. =  -7.8 DEGREES
REMARK   500    LYS  A   472 N     -   CA    -   C      ANGL. DEV. =   8.3 DEGREES
REMARK   500    LYS  A   474 N     -   CA    -   C      ANGL. DEV. =  -8.6 DEGREES
REMARK   500    LEU  A   477 N     -   CA    -   C      ANGL. DEV. =  -7.6 DEGREES
REMARK   500
REMARK   500 GEOMETRY AND STEREOCHEMISTRY
REMARK   500 SUBTOPIC: TORSION ANGLES
REMARK   500
REMARK   500 TORSION ANGLES OUTSIDE THE EXPECTED RAMACHANDRAN REGIONS:
REMARK   500 (M = MODEL NUMBER; RES = RESIDUE NAME; C = CHAIN IDENTIFIER;
REMARK   500 SSEQ = SEQUENCE NUMBER; I = INSERTION CODE).
REMARK   500
REMARK   500 STANDARD TABLE:
REMARK   500 FORMAT: (10X, I3, 1X, A3, 1X, A1, I4, A1, 4X, F7.2, 3X, F7.2)
REMARK   500
REMARK   500 M  RES  CSSEQI      PSI      PHI
REMARK   500    GLN  A   324   -106.74 -152.50
REMARK   900
REMARK   900 RELATED ENTRIES
REMARK   900 RELATED ID: 1AK5    RELATED DB: PDB
REMARK   900 INOSINE MONOPHOSPHATE DEHYDROGENASE (IMPDH) FROM
REMARK   900 TRITRICHOMONAS FOETUS
REMARK   900 RELATED ID: 1ME7    RELATED DB: PDB
REMARK   900 1ME7 CONTAINS THE SAME PROTEIN WITH RVP AND MOA BOUND
REMARK   900 RELATED ID: 1ME8    RELATED DB: PDB
REMARK   900 1ME8 CONTAINS THE SAME PROTEIN WITH RVP BOUND
REMARK   900 RELATED ID: 1ME9    RELATED DB: PDB
REMARK   900 1ME9 CONTAINS THE SAME PROTEIN WITH IMP BOUND
REMARK   900 RELATED ID: 1MEH    RELATED DB: PDB
REMARK   900 1MEH CONTAINS THE SAME PROTEIN WITH IMP AND MOA BOUND
REMARK   900 RELATED ID: 1MEW    RELATED DB: PDB
REMARK   900 1MEW CONTAINS THE SAME PROTEIN WITH XMP AND NAD BOUND
DBREF    1MEI    A    1   503  SWS   P50097  IMDH_TRIFO   1    503
SEQRES    1A   503  MET  ALA  LYS  TYR  TYR  ASN  GLU  PRO  CYS  HIS  THR  PHE  ASN
SEQRES    2A   503  GLU  TYR  LEU  LEU  ILE  PRO  GLY  LEU  SER  THR  VAL  ASP  CYS
SEQRES    3A   503  ILE  PRO  SER  ASN  VAL  ASN  LEU  SER  THR  PRO  LEU  LEU  LYS
SEQRES    4A   503  PHE  GLN  LYS  GLY  GLN  GLN  SER  GLU  ILE  ASN  LEU  LYS  ILE
SEQRES    5A   503  PRO  LEU  VAL  SER  ALA  ILE  MET  GLN  SER  VAL  SER  GLY  GLU
SEQRES    6A   503  LYS  MET  ALA  ILE  ALA  LEU  ALA  ARG  GLU  GLY  GLY  ILE  SER
SEQRES    7A   503  PHE  ILE  PHE  GLY  SER  GLN  SER  ILE  GLU  SER  GLN  ALA  ALA
SEQRES    8A   503  MET  VAL  HIS  ALA  VAL  LYS  ASN  PHE  LYS  ALA  GLY  PHE  VAL
SEQRES    9A   503  VAL  SER  ASP  SER  ASN  VAL  LYS  PRO  ASP  GLN  THR  PHE  ALA
SEQRES   10A   503  ASP  VAL  LEU  ALA  ILE  SER  GLN  ARO  THR  THR  HIS  ASN  THR
SEQRES   11A   503  VAL  ALA  VAL  THR  ASP  ASP  GLY  THR  PRO  HIS  GLY  VAL  LEU
SEQRES   12A   503  LEU  GLY  LEU  VAL  THR  GLN  ARG  ASP  TYR  PRO  ILE  ASP  LEU
SEQRES   13A   503  THR  GLN  THR  GLU  THR  LYS  VAL  SER  ASP  MET  MET  THR  PRO
SEQRES   14A   503  PHE  SER  LYS  LEU  VAL  THR  ALA  HIS  GLN  ASP  THR  LYS  LEU
SEQRES   15A   503  SER  GLU  ALA  ASN  LYS  ILE  ILE  TRP  GLU  LYS  LYS  LEU  ASN
SEQRES   16A   503  ALA  LEU  PRO  ILE  ILE  ASP  ASP  ASP  GLN  HIS  LEU  ARG  TYR
SEQRES   17A   503  ILE  VAL  PHE  ARG  LYS  ASP  TYR  ASP  ARG  SER  GLN  VAL  CYS
SEQRES   18A   503  HIS  ASN  GLU  LEU  VAL  ASP  SER  GLN  LYS  ARG  TYR  LEU  VAL
SEQRES   19A   503  GLY  ALA  GLY  ILE  ASN  THR  ARG  ASP  PHE  ARG  GLU  ARG  VAL
SEQRES   20A   503  PRO  ALA  LEU  VAL  GLU  ALA  GLY  ALA  ASP  VAL  LEU  CYS  ILE
SEQRES   21A   503  ASP  SER  SER  ASP  GLY  PHE  SER  GLU  TRP  GLN  LYS  ILE  THR
SEQRES   22A   503  ILE  GLY  TRP  ILE  ARG  GLU  LYS  TYR  GLY  ASP  LYS  VAL  LYS
SEQRES   23A   503  VAL  GLY  ALA  GLY  ASN  ILE  VAL  ASP  GLY  GLU  GLY  PHE  ARG
SEQRES   24A   503  TYR  LEU  ALA  ASP  ALA  GLY  ALA  ASP  PHE  ILE  LYS  ILE  GLY
SEQRES   25A   503  ILE  GLY  GLY  GLY  SER  ILE  CYS  ILE  THR  ARO  GLU  GLN  LYS
SEQRES   26A   503  GLY  ILE  GLY  ARG  GLY  GLN  ALA  THR  ALA  VAL  ILE  ASP  VAL
SEQRES   27A   503  VAL  ALA  GLU  ARG  ASN  LYS  TYR  PHE  GLU  GLU  THR  GLY  ILE
SEQRES   28A   503  TYR  ILE  PRO  VAL  CYS  SER  ASP  GLY  GLY  ILE  VAL  TYR  ASP
SEQRES   29A   503  TYR  HIS  MET  THR  LEU  ALA  LEU  ALA  MET  GLY  ALA  ASP  PHE
SEQRES   30A   503  ILE  MET  LEU  GLY  ARG  TYR  PHE  ALA  ARG  PHE  GLU  GIU  SER
SEQRES   31A   503  PRO  THR  ARG  LYS  VAL  THR  ILE  ASN  GLY  SER  VAL  MET  LYS
SEQRES   32A   503  GLU  TYR  TRP  GLY  GLU  GLY  SER  SER  ARG  ALA  ARG  ASN  TRP
SEQRES   33A   503  GLN  ARG  TYR  ASP  LEU  GLY  GLY  LYS  GLN  LYS  LEU  SER  PHE
```

TABLE 4-continued

| | | | | | | | | | | | | | | | | |
|---|---|---|---|---|---|---|---|---|---|---|---|---|---|---|---|---|
| SEQRES | 34 | A | 503 | GLU | GLU | GLY | VAL | ASP | SER | TYR | VAL | PRO | TYR | ALA | GLY | LYS |
| SEQRES | 35 | A | 503 | LEU | LYS | ASP | ASN | VAL | GLU | ALA | SER | LEU | ASN | LYS | VAL | LYS |
| SEQRES | 36 | A | 503 | SER | THR | MET | CYS | ASN | CYS | GLY | ALA | LEU | THR | ILE | PRO | GLN |
| SEQRES | 37 | A | 503 | LEU | GLN | SER | LYS | ALA | LYS | ILE | THR | LEU | VAL | SER | SER | VAL |
| SEQRES | 38 | A | 503 | SER | ILE | VAL | GLU | GLY | GLY | ALA | HIS | ASP | VAL | ILE | VAL | LYS |
| SEQRES | 39 | A | 503 | ASP | ARG | ILE | ASN | ASP | TYR | HIS | PRO | LYS | | | | |
| HET | K | A | 900 | 1 | | | | | | | | | | | | |
| HET | XMP | | 602 | 24 | | | | | | | | | | | | |
| HET | MOA | | 600 | 23 | | | | | | | | | | | | |
| HETNAM | | K | POTASSIUM ION | | | | | | | | | | | | | |
| HETNAM | | XMP | XANTHOSINE-5'-MONOPHOSPHATE | | | | | | | | | | | | | |
| HETNAM | | MOA | MYCOPHENOLIC ACID | | | | | | | | | | | | | |
| HETSYN | | XMP | 5--MONOPHOSPHATE-9-BETA-D-RIBOFURANOSYL XANTHINE | | | | | | | | | | | | | |
| HETSYN | | MOA | 6-(1,3-DIHYDRO-7-HYDROXY-5-METHOXY-4-METHYL-1- | | | | | | | | | | | | | |
| HETSYN | 2 | MOA | OXOISOBENZOFURAN-6-YL)-4-METHYL-4-HEXANOIC ACID | | | | | | | | | | | | | |
| FORMUL | 2 | K | K1 | 1+ | | | | | | | | | | | | |
| FORMUL | 3 | XMP | C10 | H14 | N4 | O9 | P1 | 1+ | | | | | | | | |
| FORMUL | 4 | MOA | C17 | H20 | O6 | | | | | | | | | | | |
| FORMUL | 5 | HOH | *180(H2 O1) | | | | | | | | | | | | | |
| HELIX | 1 | 1 | THR | A | 11 | ASN | A | 13 | 5 | | | | | | | 3 |
| HELIX | 2 | 2 | ILE | A | 27 | VAL | A | 31 | 5 | | | | | | | 5 |
| HELIX | 3 | 3 | GLY | A | 64 | GLU | A | 74 | 1 | | | | | | | 11 |
| HELIX | 4 | 4 | SER | A | 85 | ASN | A | 98 | 1 | | | | | | | 14 |
| HELIX | 5 | 5 | ASP | A | 242 | GLY | A | 254 | 1 | | | | | | | 13 |
| HELIX | 6 | 6 | SER | A | 267 | GLY | A | 282 | 1 | | | | | | | 16 |
| HELIX | 7 | 7 | ASP | A | 283 | VAL | A | 285 | 5 | | | | | | | 3 |
| HELIX | 8 | 8 | ASP | A | 294 | GLY | A | 305 | 1 | | | | | | | 12 |
| HELIX | 9 | 9 | GLY | A | 330 | GLY | A | 350 | 1 | | | | | | | 21 |
| HELIX | 10 | 10 | TYR | A | 363 | MET | A | 373 | 1 | | | | | | | 11 |
| HELIX | 11 | 11 | GLY | A | 381 | ARG | A | 386 | 1 | | | | | | | 6 |
| HELIX | 12 | 12 | SER | A | 410 | ASN | A | 415 | 1 | | | | | | | 6 |
| HELIX | 13 | 13 | LYS | A | 442 | CYS | A | 461 | 1 | | | | | | | 20 |
| HELIX | 14 | 14 | THR | A | 465 | ALA | A | 473 | 1 | | | | | | | 9 |
| SHEET | 1 | A | 2 | TYR | A | 15 | ILE | A | 18 | 0 | | | | | | |
| SHEET | 2 | A | 2 | LYS | A | 474 | LEU | A | 477 | −1 | O | LYS | A | 474 | N | ILE | A | 18 |
| SHEET | 1 | B | 2 | THR | A | 35 | PRO | A | 36 | 0 | | | | | | |
| SHEET | 2 | B | 2 | ASN | A | 49 | LEU | A | 50 | −1 | O | LEU | A | 50 | N | THR | A | 35 |
| SHEET | 1 | C | 2 | PHE | A | 40 | GLN | A | 41 | 0 | | | | | | |
| SHEET | 2 | C | 2 | ILE | A | 351 | TYR | A | 352 | −1 | O | TYR | A | 352 | N | PHE | A | 40 |
| SHEET | 1 | D | 9 | LEU | A | 54 | SER | A | 56 | 0 | | | | | | |
| SHEET | 2 | D | 9 | ILE | A | 77 | ILE | A | 80 | 1 | O | ILE | A | 77 | N | SER | A | 56 |
| SHEET | 3 | D | 9 | GLY | A | 235 | ILE | A | 238 | 1 | O | GLY | A | 237 | N | ILE | A | 80 |
| SHEET | 4 | D | 9 | VAL | A | 257 | ILE | A | 260 | 1 | O | CYS | A | 259 | N | ILE | A | 238 |
| SHEET | 5 | D | 9 | VAL | A | 287 | ILE | A | 292 | 1 | O | GLY | A | 288 | N | LEU | A | 258 |
| SHEET | 6 | D | 9 | PHE | A | 308 | ILE | A | 311 | 1 | O | LYS | A | 310 | N | ALA | A | 289 |
| SHEET | 7 | D | 9 | VAL | A | 355 | ASP | A | 358 | 1 | O | CYS | A | 356 | N | ILE | A | 311 |
| SHEET | 8 | D | 9 | PHE | A | 377 | LEU | A | 380 | 1 | O | PHE | A | 377 | N | SER | A | 357 |
| SHEET | 9 | D | 9 | LEU | A | 54 | SER | A | 56 | 1 | N | VAL | A | 55 | O | ILE | A | 378 |
| SHEET | 1 | E | 3 | LYS | A | 394 | ILE | A | 397 | 0 | | | | | | |
| SHEET | 2 | E | 3 | SER | A | 400 | TRP | A | 406 | −1 | O | MET | A | 402 | N | VAL | A | 395 |
| SHEET | 3 | E | 3 | ASP | A | 434 | PRO | A | 438 | −1 | O | SER | A | 435 | N | TYR | A | 405 |
| SSBOND | 1 | CYS | A | 26 | CYS | A | | 459 | | | | | | | | |
| CISPEP | 1 | GLY | A | 290 | ASN | A | | 291 | | | 0 | | 0.82 | | | |
| CRYST1 | 155.070 | 155.070 | 155.070 | 90.00 | 90.00 | 90.00 | P 4 3 2 | 24 | | | | | | | | |
| ORIGX1 | | 1.000000 | 0.000000 | 0.000000 | | 0.00000 | | | | | | | | | | |
| ORIGX2 | | 0.000000 | 1.000000 | 0.000000 | | 0.00000 | | | | | | | | | | |
| ORIGX3 | | 0.000000 | 0.000000 | 1.000000 | | 0.00000 | | | | | | | | | | |
| SCALE1 | | 0.006449 | 0.000000 | 0.000000 | | 0.00000 | | | | | | | | | | |
| SCALE2 | | 0.000000 | 0.006449 | 0.000000 | | 0.00000 | | | | | | | | | | |
| SCALE3 | | 0.000000 | 0.000000 | 0.006449 | | 0.00000 | | | | | | | | | | |
| ATOM | 1 | N | ALA | A | 2 | 55.246 | 75.030 | 36.667 | 1.00 | 28.12 | | N | | | |
| ATOM | 2 | CA | ALA | A | 2 | 56.014 | 73.998 | 35.916 | 1.00 | 26.83 | | C | | | |
| ATOM | 3 | C | ALA | A | 2 | 57.303 | 73.637 | 36.651 | 1.00 | 27.59 | | C | | | |
| ATOM | 4 | O | ALA | A | 2 | 57.744 | 74.364 | 37.542 | 1.00 | 26.06 | | O | | | |
| ATOM | 5 | CB | ALA | A | 2 | 56.331 | 74.512 | 34.522 | 1.00 | 27.30 | | C | | | |
| ATOM | 6 | N | LYS | A | 3 | 57.901 | 72.510 | 36.272 | 1.00 | 27.55 | | N | | | |
| ATOM | 7 | CA | LYS | A | 3 | 59.139 | 72.052 | 36.891 | 1.00 | 28.66 | | C | | | |
| ATOM | 8 | C | LYS | A | 3 | 60.304 | 72.241 | 35.923 | 1.00 | 28.28 | | C | | | |
| ATOM | 9 | O | LYS | A | 3 | 60.213 | 71.877 | 34.751 | 1.00 | 28.88 | | O | | | |
| ATOM | 10 | CB | LYS | A | 3 | 59.022 | 70.571 | 37.276 | 1.00 | 30.08 | | C | | | |
| ATOM | 11 | CG | LYS | A | 3 | 60.256 | 70.001 | 37.985 | 1.00 | 34.20 | | C | | | |
| ATOM | 12 | CD | LYS | A | 3 | 60.835 | 68.809 | 37.222 | 1.00 | 37.41 | | C | | | |
| ATOM | 13 | CE | LYS | A | 3 | 61.981 | 68.154 | 37.977 | 1.00 | 38.58 | | C | | | |
| ATOM | 14 | NZ | LYS | A | 3 | 63.081 | 69.118 | 38.256 | 1.00 | 40.73 | | N | | | |
| ATOM | 15 | N | TYR | A | 4 | 61.396 | 72.809 | 36.424 | 1.00 | 27.63 | | N | | | |
| ATOM | 16 | CA | TYR | A | 4 | 62.589 | 73.060 | 35.617 | 1.00 | 27.84 | | C | | | |
| ATOM | 17 | C | TYR | A | 4 | 63.789 | 72.257 | 36.120 | 1.00 | 29.05 | | C | | | |
| ATOM | 18 | O | TYR | A | 4 | 63.729 | 71.620 | 37.168 | 1.00 | 28.98 | | O | | | |
| ATOM | 19 | CB | TYR | A | 4 | 62.906 | 74.559 | 35.635 | 1.00 | 26.14 | | C | | | |

TABLE 4-continued

| | | | | | | | | | | |
|---|---|---|---|---|---|---|---|---|---|---|
| ATOM | 20 | CG | TYR | A | 4 | 61.816 | 75.386 | 34.994 | 1.00 | 26.21 | C |
| ATOM | 21 | CD1 | TYR | A | 4 | 61.746 | 75.528 | 33.607 | 1.00 | 24.20 | C |
| ATOM | 22 | CD2 | TYR | A | 4 | 60.819 | 75.981 | 35.769 | 1.00 | 26.83 | C |
| ATOM | 23 | CE1 | TYR | A | 4 | 60.707 | 76.243 | 33.007 | 1.00 | 24.96 | C |
| ATOM | 24 | CE2 | TYR | A | 4 | 59.773 | 76.699 | 35.177 | 1.00 | 26.60 | C |
| ATOM | 25 | CZ | TYR | A | 4 | 59.726 | 76.824 | 33.799 | 1.00 | 25.65 | C |
| ATOM | 26 | OH | TYR | A | 4 | 58.698 | 77.523 | 33.215 | 1.00 | 25.82 | O |
| ATOM | 27 | N | TYR | A | 5 | 64.880 | 72.288 | 35.362 | 1.00 | 30.21 | N |
| ATOM | 28 | CA | TYR | A | 5 | 66.082 | 71.556 | 35.732 | 1.00 | 31.29 | C |
| ATOM | 29 | C | TYR | A | 5 | 67.275 | 72.487 | 35.860 | 1.00 | 32.27 | C |
| ATOM | 30 | O | TYR | A | 5 | 67.313 | 73.551 | 35.241 | 1.00 | 33.48 | O |
| ATOM | 31 | CB | TYR | A | 5 | 66.370 | 70.467 | 34.700 | 1.00 | 30.15 | C |
| ATOM | 32 | CG | TYR | A | 5 | 65.246 | 69.467 | 34.568 | 1.00 | 30.45 | C |
| ATOM | 33 | CD1 | TYR | A | 5 | 64.076 | 69.789 | 33.876 | 1.00 | 30.10 | C |
| ATOM | 34 | CD2 | TYR | A | 5 | 65.338 | 68.203 | 35.158 | 1.00 | 29.26 | C |
| ATOM | 35 | CE1 | TYR | A | 5 | 63.028 | 68.879 | 33.775 | 1.00 | 30.02 | C |
| ATOM | 36 | CE2 | TYR | A | 5 | 64.298 | 67.289 | 35.064 | 1.00 | 29.82 | C |
| ATOM | 37 | CZ | TYR | A | 5 | 63.147 | 67.632 | 34.372 | 1.00 | 30.16 | C |
| ATOM | 38 | OH | TYR | A | 5 | 62.122 | 66.728 | 34.277 | 1.00 | 29.57 | O |
| ATOM | 39 | N | ASN | A | 6 | 68.249 | 72.079 | 36.667 | 1.00 | 33.12 | N |
| ATOM | 40 | CA | ASN | A | 6 | 69.445 | 72.880 | 36.903 | 1.00 | 34.04 | C |
| ATOM | 41 | C | ASN | A | 6 | 70.421 | 72.883 | 35.732 | 1.00 | 33.43 | C |
| ATOM | 42 | O | ASN | A | 6 | 71.190 | 73.827 | 35.569 | 1.00 | 34.04 | O |
| ATOM | 43 | CB | ASN | A | 6 | 70.158 | 72.380 | 38.162 | 1.00 | 36.54 | C |
| ATOM | 44 | CG | ASN | A | 6 | 69.322 | 72.563 | 39.417 | 1.00 | 40.37 | C |
| ATOM | 45 | OD1 | ASN | A | 6 | 69.335 | 71.716 | 40.315 | 1.00 | 42.93 | O |
| ATOM | 46 | ND2 | ASN | A | 6 | 68.597 | 73.679 | 39.493 | 1.00 | 41.40 | N |
| ATOM | 47 | N | GLU | A | 7 | 70.388 | 71.839 | 34.912 | 1.00 | 32.19 | N |
| ATOM | 48 | CA | GLU | A | 7 | 71.301 | 71.749 | 33.774 | 1.00 | 30.55 | C |
| ATOM | 49 | C | GLU | A | 7 | 70.588 | 71.404 | 32.477 | 1.00 | 28.37 | C |
| ATOM | 50 | O | GLU | A | 7 | 69.563 | 70.724 | 32.483 | 1.00 | 27.97 | O |
| ATOM | 51 | CB | GLU | A | 7 | 72.365 | 70.671 | 34.030 | 1.00 | 32.84 | C |
| ATOM | 52 | CG | GLU | A | 7 | 73.323 | 70.926 | 35.203 | 1.00 | 36.46 | C |
| ATOM | 53 | CD | GLU | A | 7 | 74.235 | 72.121 | 34.978 | 1.00 | 38.59 | C |
| ATOM | 54 | OE1 | GLU | A | 7 | 74.649 | 72.348 | 33.821 | 1.00 | 39.18 | O |
| ATOM | 55 | OE2 | GLU | A | 7 | 74.552 | 72.828 | 35.961 | 1.00 | 41.76 | O |
| ATOM | 56 | N | PRO | A | 8 | 71.125 | 71.868 | 31.339 | 1.00 | 26.18 | N |
| ATOM | 57 | CA | PRO | A | 8 | 70.484 | 71.549 | 30.062 | 1.00 | 25.74 | C |
| ATOM | 58 | C | PRO | A | 8 | 70.830 | 70.098 | 29.736 | 1.00 | 25.66 | C |
| ATOM | 59 | O | PRO | A | 8 | 71.796 | 69.561 | 30.281 | 1.00 | 25.70 | O |
| ATOM | 60 | CB | PRO | A | 8 | 71.140 | 72.530 | 29.094 | 1.00 | 25.89 | C |
| ATOM | 61 | CG | PRO | A | 8 | 72.531 | 72.678 | 29.661 | 1.00 | 24.82 | C |
| ATOM | 62 | CD | PRO | A | 8 | 72.270 | 72.780 | 31.149 | 1.00 | 25.95 | C |
| ATOM | 63 | N | CYS | A | 9 | 70.053 | 69.457 | 28.869 | 1.00 | 25.32 | N |
| ATOM | 64 | CA | CYS | A | 9 | 70.342 | 68.074 | 28.501 | 1.00 | 25.12 | C |
| ATOM | 65 | C | CYS | A | 9 | 71.405 | 68.030 | 27.396 | 1.00 | 24.58 | C |
| ATOM | 66 | O | CYS | A | 9 | 71.599 | 69.009 | 26.674 | 1.00 | 24.57 | O |
| ATOM | 67 | CB | CYS | A | 9 | 69.058 | 67.354 | 28.064 | 1.00 | 25.98 | C |
| ATOM | 68 | SG | CYS | A | 9 | 68.140 | 68.110 | 26.701 | 1.00 | 28.89 | S |
| ATOM | 69 | N | HIS | A | 10 | 72.087 | 66.895 | 27.267 | 1.00 | 23.82 | N |
| ATOM | 70 | CA | HIS | A | 10 | 73.159 | 66.735 | 26.284 | 1.00 | 22.97 | C |
| ATOM | 71 | C | HIS | A | 10 | 73.016 | 65.458 | 25.450 | 1.00 | 23.29 | C |
| ATOM | 72 | O | HIS | A | 10 | 72.389 | 64.491 | 25.886 | 1.00 | 22.16 | O |
| ATOM | 73 | CB | HIS | A | 10 | 74.505 | 66.695 | 27.013 | 1.00 | 23.38 | C |
| ATOM | 74 | CG | HIS | A | 10 | 74.767 | 67.892 | 27.874 | 1.00 | 24.01 | C |
| ATOM | 75 | ND1 | HIS | A | 10 | 75.212 | 69.094 | 27.364 | 1.00 | 23.71 | N |
| ATOM | 76 | CD2 | HIS | A | 10 | 74.645 | 68.071 | 29.211 | 1.00 | 23.36 | C |
| ATOM | 77 | CE1 | HIS | A | 10 | 75.353 | 69.962 | 28.351 | 1.00 | 22.56 | C |
| ATOM | 78 | NE2 | HIS | A | 10 | 75.015 | 69.366 | 29.481 | 1.00 | 23.59 | N |
| ATOM | 79 | N | THR | A | 11 | 73.605 | 65.462 | 24.255 | 1.00 | 23.11 | N |
| ATOM | 80 | CA | THR | A | 11 | 73.573 | 64.300 | 23.362 | 1.00 | 23.58 | C |
| ATOM | 81 | C | THR | A | 11 | 74.920 | 63.571 | 23.464 | 1.00 | 23.26 | C |
| ATOM | 82 | O | THR | A | 11 | 75.858 | 64.093 | 24.061 | 1.00 | 22.66 | O |
| ATOM | 83 | CB | THR | A | 11 | 73.360 | 64.719 | 21.889 | 1.00 | 24.09 | C |
| ATOM | 84 | OG1 | THR | A | 11 | 74.439 | 65.562 | 21.475 | 1.00 | 25.91 | O |
| ATOM | 85 | CG2 | THR | A | 11 | 72.049 | 65.480 | 21.727 | 1.00 | 25.24 | C |
| ATOM | 86 | N | PHE | A | 12 | 75.017 | 62.377 | 22.881 | 1.00 | 23.30 | N |
| ATOM | 87 | CA | PHE | A | 12 | 76.262 | 61.609 | 22.931 | 1.00 | 24.87 | C |
| ATOM | 88 | C | PHE | A | 12 | 77.458 | 62.328 | 22.304 | 1.00 | 26.16 | C |
| ATOM | 89 | O | PHE | A | 12 | 78.596 | 62.112 | 22.713 | 1.00 | 26.04 | O |
| ATOM | 90 | CB | PHE | A | 12 | 76.096 | 60.243 | 22.249 | 1.00 | 23.25 | C |
| ATOM | 91 | CG | PHE | A | 12 | 75.216 | 59.284 | 23.004 | 1.00 | 23.37 | C |
| ATOM | 92 | CD1 | PHE | A | 12 | 75.362 | 59.119 | 24.377 | 1.00 | 22.09 | C |
| ATOM | 93 | CD2 | PHE | A | 12 | 74.253 | 58.537 | 22.337 | 1.00 | 22.79 | C |
| ATOM | 94 | CE1 | PHE | A | 12 | 74.560 | 58.223 | 25.078 | 1.00 | 23.40 | C |
| ATOM | 95 | CE2 | PHE | A | 12 | 73.443 | 57.634 | 23.027 | 1.00 | 24.01 | C |
| ATOM | 96 | CZ | PHE | A | 12 | 73.596 | 57.476 | 24.399 | 1.00 | 22.98 | C |
| ATOM | 97 | N | ASN | A | 13 | 77.202 | 63.173 | 21.310 | 1.00 | 26.96 | N |
| ATOM | 98 | CA | ASN | A | 13 | 78.273 | 63.905 | 20.637 | 1.00 | 28.09 | C |

TABLE 4-continued

| ATOM | 99 | C | ASN | A | 13 | 78.998 | 64.901 | 21.533 | 1.00 | 26.75 | C |
|---|---|---|---|---|---|---|---|---|---|---|---|
| ATOM | 100 | O | ASN | A | 13 | 80.044 | 65.420 | 21.152 | 1.00 | 27.23 | O |
| ATOM | 101 | CB | ASN | A | 13 | 77.734 | 64.663 | 19.417 | 1.00 | 31.04 | C |
| ATOM | 102 | CG | ASN | A | 13 | 77.622 | 63.787 | 18.183 | 1.00 | 36.11 | C |
| ATOM | 103 | OD1 | ASN | A | 13 | 78.522 | 63.000 | 17.883 | 1.00 | 39.98 | O |
| ATOM | 104 | ND2 | ASN | A | 13 | 76.526 | 63.934 | 17.448 | 1.00 | 38.57 | N |
| ATOM | 105 | N | GLU | A | 14 | 78.445 | 65.178 | 22.710 | 1.00 | 25.07 | N |
| ATOM | 106 | CA | GLU | A | 14 | 79.060 | 66.136 | 23.621 | 1.00 | 25.01 | C |
| ATOM | 107 | C | GLU | A | 14 | 79.976 | 65.483 | 24.650 | 1.00 | 25.17 | C |
| ATOM | 108 | O | GLU | A | 14 | 80.464 | 66.148 | 25.563 | 1.00 | 26.57 | O |
| ATOM | 109 | CB | GLU | A | 14 | 77.976 | 66.937 | 24.348 | 1.00 | 25.02 | C |
| ATOM | 110 | CG | GLU | A | 14 | 77.000 | 67.638 | 23.420 | 1.00 | 25.34 | C |
| ATOM | 111 | CD | GLU | A | 14 | 75.926 | 68.401 | 24.169 | 1.00 | 25.36 | C |
| ATOM | 112 | OE1 | GLU | A | 14 | 76.272 | 69.314 | 24.947 | 1.00 | 25.19 | O |
| ATOM | 113 | OE2 | GLU | A | 14 | 74.734 | 68.083 | 23.978 | 1.00 | 26.80 | O |
| ATOM | 114 | N | TYR | A | 15 | 80.229 | 64.189 | 24.499 | 1.00 | 24.38 | N |
| ATOM | 115 | CA | TYR | A | 15 | 81.067 | 63.487 | 25.455 | 1.00 | 23.13 | C |
| ATOM | 116 | C | TYR | A | 15 | 82.248 | 62.754 | 24.856 | 1.00 | 23.75 | C |
| ATOM | 117 | O | TYR | A | 15 | 82.230 | 62.360 | 23.691 | 1.00 | 24.15 | O |
| ATOM | 118 | CB | TYR | A | 15 | 80.224 | 62.478 | 26.238 | 1.00 | 22.70 | C |
| ATOM | 119 | CG | TYR | A | 15 | 79.201 | 63.097 | 27.153 | 1.00 | 23.45 | C |
| ATOM | 120 | CD1 | TYR | A | 15 | 79.519 | 63.416 | 28.474 | 1.00 | 23.71 | C |
| ATOM | 121 | CD2 | TYR | A | 15 | 77.909 | 63.361 | 26.702 | 1.00 | 24.00 | C |
| ATOM | 122 | CE1 | TYR | A | 15 | 78.571 | 63.977 | 29.326 | 1.00 | 25.23 | C |
| ATOM | 123 | CE2 | TYR | A | 15 | 76.954 | 63.927 | 27.544 | 1.00 | 25.30 | C |
| ATOM | 124 | CZ | TYR | A | 15 | 77.288 | 64.231 | 28.851 | 1.00 | 25.69 | C |
| ATOM | 125 | OH | TYR | A | 15 | 76.342 | 64.793 | 29.680 | 1.00 | 29.22 | O |
| ATOM | 126 | N | LEU | A | 16 | 83.273 | 62.570 | 25.681 | 1.00 | 24.09 | N |
| ATOM | 127 | CA | LEU | A | 16 | 84.470 | 61.830 | 25.301 | 1.00 | 24.11 | C |
| ATOM | 128 | C | LEU | A | 16 | 84.866 | 61.010 | 26.519 | 1.00 | 23.10 | C |
| ATOM | 129 | O | LEU | A | 16 | 84.525 | 61.360 | 27.649 | 1.00 | 22.07 | O |
| ATOM | 130 | CB | LEU | A | 16 | 85.625 | 62.767 | 24.922 | 1.00 | 24.98 | C |
| ATOM | 131 | CG | LEU | A | 16 | 85.590 | 63.480 | 23.569 | 1.00 | 26.50 | C |
| ATOM | 132 | CD1 | LEU | A | 16 | 86.770 | 64.421 | 23.467 | 1.00 | 28.14 | C |
| ATOM | 133 | CD2 | LEU | A | 16 | 85.635 | 62.471 | 22.444 | 1.00 | 28.66 | C |
| ATOM | 134 | N | LEU | A | 17 | 85.572 | 59.913 | 26.279 | 1.00 | 23.04 | N |
| ATOM | 135 | CA | LEU | A | 17 | 86.047 | 59.040 | 27.346 | 1.00 | 23.77 | C |
| ATOM | 136 | C | LEU | A | 17 | 87.512 | 59.362 | 27.630 | 1.00 | 23.70 | C |
| ATOM | 137 | O | LEU | A | 17 | 88.301 | 59.540 | 26.706 | 1.00 | 23.54 | O |
| ATOM | 138 | CB | LEU | A | 17 | 85.929 | 57.569 | 26.923 | 1.00 | 22.71 | C |
| ATOM | 139 | CG | LEU | A | 17 | 84.511 | 56.990 | 26.882 | 1.00 | 23.40 | C |
| ATOM | 140 | CD1 | LEU | A | 17 | 84.480 | 55.739 | 26.022 | 1.00 | 23.07 | C |
| ATOM | 141 | CD2 | LEU | A | 17 | 84.047 | 56.698 | 28.301 | 1.00 | 21.29 | C |
| ATOM | 142 | N | ILE | A | 18 | 87.860 | 59.456 | 28.909 | 1.00 | 24.51 | N |
| ATOM | 143 | CA | ILE | A | 18 | 89.236 | 59.720 | 29.313 | 1.00 | 24.55 | C |
| ATOM | 144 | C | ILE | A | 18 | 89.803 | 58.357 | 29.705 | 1.00 | 24.94 | C |
| ATOM | 145 | O | ILE | A | 18 | 89.236 | 57.670 | 30.545 | 1.00 | 25.77 | O |
| ATOM | 146 | CB | ILE | A | 18 | 89.279 | 60.687 | 30.509 | 1.00 | 24.40 | C |
| ATOM | 147 | CG1 | ILE | A | 18 | 88.798 | 62.071 | 30.054 | 1.00 | 25.23 | C |
| ATOM | 148 | CG2 | ILE | A | 18 | 90.696 | 60.750 | 31.089 | 1.00 | 24.00 | C |
| ATOM | 149 | CD1 | ILE | A | 18 | 88.754 | 63.115 | 31.149 | 1.00 | 26.14 | C |
| ATOM | 150 | N | PRO | A | 19 | 90.921 | 57.942 | 29.089 | 1.00 | 24.65 | N |
| ATOM | 151 | CA | PRO | A | 19 | 91.519 | 56.640 | 29.402 | 1.00 | 26.08 | C |
| ATOM | 152 | C | PRO | A | 19 | 91.842 | 56.372 | 30.868 | 1.00 | 26.01 | C |
| ATOM | 153 | O | PRO | A | 19 | 92.120 | 57.288 | 31.646 | 1.00 | 25.83 | O |
| ATOM | 154 | CB | PRO | A | 19 | 92.787 | 56.610 | 28.533 | 1.00 | 26.14 | C |
| ATOM | 155 | CG | PRO | A | 19 | 92.431 | 57.503 | 27.375 | 1.00 | 26.01 | C |
| ATOM | 156 | CD | PRO | A | 19 | 91.708 | 58.646 | 28.061 | 1.00 | 24.66 | C |
| ATOM | 157 | N | GLY | A | 20 | 91.792 | 55.092 | 31.221 | 1.00 | 25.78 | N |
| ATOM | 158 | CA | GLY | A | 20 | 92.118 | 54.654 | 32.564 | 1.00 | 25.89 | C |
| ATOM | 159 | C | GLY | A | 20 | 93.331 | 53.748 | 32.425 | 1.00 | 26.31 | C |
| ATOM | 160 | O | GLY | A | 20 | 93.940 | 53.671 | 31.353 | 1.00 | 26.09 | O |
| ATOM | 161 | N | LEU | A | 21 | 93.692 | 53.052 | 33.492 | 1.00 | 27.91 | N |
| ATOM | 162 | CA | LEU | A | 21 | 94.842 | 52.161 | 33.436 | 1.00 | 28.51 | C |
| ATOM | 163 | C | LEU | A | 21 | 94.522 | 50.917 | 32.626 | 1.00 | 28.22 | C |
| ATOM | 164 | O | LEU | A | 21 | 93.599 | 50.178 | 32.950 | 1.00 | 28.84 | O |
| ATOM | 165 | CB | LEU | A | 21 | 95.281 | 51.748 | 34.850 | 1.00 | 28.54 | C |
| ATOM | 166 | CG | LEU | A | 21 | 96.424 | 50.721 | 34.929 | 1.00 | 28.79 | C |
| ATOM | 167 | CD1 | LEU | A | 21 | 97.661 | 51.272 | 34.230 | 1.00 | 25.50 | C |
| ATOM | 168 | CD2 | LEU | A | 21 | 96.726 | 50.390 | 36.394 | 1.00 | 28.73 | C |
| ATOM | 169 | N | SER | A | 22 | 95.284 | 50.697 | 31.562 | 1.00 | 29.18 | N |
| ATOM | 170 | CA | SER | A | 22 | 95.099 | 49.525 | 30.725 | 1.00 | 30.50 | C |
| ATOM | 171 | C | SER | A | 22 | 96.101 | 48.467 | 31.171 | 1.00 | 32.47 | C |
| ATOM | 172 | O | SER | A | 22 | 97.310 | 48.684 | 31.107 | 1.00 | 31.83 | O |
| ATOM | 173 | CB | SER | A | 22 | 95.340 | 49.874 | 29.259 | 1.00 | 30.15 | C |
| ATOM | 174 | OG | SER | A | 22 | 94.432 | 50.858 | 28.813 | 1.00 | 31.65 | O |
| ATOM | 175 | N | THR | A | 23 | 95.595 | 47.327 | 31.630 | 1.00 | 35.11 | N |
| ATOM | 176 | CA | THR | A | 23 | 96.451 | 46.237 | 32.090 | 1.00 | 36.70 | C |
| ATOM | 177 | C | THR | A | 23 | 96.864 | 45.327 | 30.941 | 1.00 | 37.53 | C |

TABLE 4-continued

| | | | | | | | | | | | |
|---|---|---|---|---|---|---|---|---|---|---|---|
| ATOM | 178 | O | THR | A | 23 | 96.241 | 45.331 | 29.879 | 1.00 | 38.20 | O |
| ATOM | 179 | CB | THR | A | 23 | 95.741 | 45.392 | 33.155 | 1.00 | 37.23 | C |
| ATOM | 180 | OG1 | THR | A | 23 | 94.462 | 44.985 | 32.660 | 1.00 | 40.43 | O |
| ATOM | 181 | CG2 | THR | A | 23 | 95.552 | 46.191 | 34.429 | 1.00 | 37.20 | C |
| ATOM | 182 | N | VAL | A | 24 | 97.919 | 44.547 | 31.159 | 1.00 | 38.34 | N |
| ATOM | 183 | CA | VAL | A | 24 | 98.425 | 43.636 | 30.135 | 1.00 | 38.85 | C |
| ATOM | 184 | C | VAL | A | 24 | 97.396 | 42.605 | 29.666 | 1.00 | 39.73 | C |
| ATOM | 185 | O | VAL | A | 24 | 97.401 | 42.203 | 28.499 | 1.00 | 39.77 | O |
| ATOM | 186 | CB | VAL | A | 24 | 99.700 | 42.886 | 30.625 | 1.00 | 39.23 | C |
| ATOM | 187 | CG1 | VAL | A | 24 | 100.851 | 43.871 | 30.800 | 1.00 | 38.15 | C |
| ATOM | 188 | CG2 | VAL | A | 24 | 99.418 | 42.167 | 31.938 | 1.00 | 38.35 | C |
| ATOM | 189 | N | ASP | A | 25 | 96.506 | 42.186 | 30.560 | 1.00 | 40.55 | N |
| ATOM | 190 | CA | ASP | A | 25 | 95.503 | 41.195 | 30.186 | 1.00 | 43.23 | C |
| ATOM | 191 | C | ASP | A | 25 | 94.328 | 41.733 | 29.370 | 1.00 | 42.88 | C |
| ATOM | 192 | O | ASP | A | 25 | 93.485 | 40.951 | 28.933 | 1.00 | 43.24 | O |
| ATOM | 193 | CB | ASP | A | 25 | 94.956 | 40.476 | 31.425 | 1.00 | 45.78 | C |
| ATOM | 194 | CG | ASP | A | 25 | 94.301 | 41.421 | 32.405 | 1.00 | 48.75 | C |
| ATOM | 195 | OD1 | ASP | A | 25 | 93.333 | 41.010 | 33.083 | 1.00 | 49.75 | O |
| ATOM | 196 | OD2 | ASP | A | 25 | 94.764 | 42.574 | 32.503 | 1.00 | 50.54 | O |
| ATOM | 197 | N | CYS | A | 26 | 94.257 | 43.045 | 29.150 | 1.00 | 42.32 | N |
| ATOM | 198 | CA | CYS | A | 26 | 93.137 | 43.581 | 28.377 | 1.00 | 41.35 | C |
| ATOM | 199 | C | CYS | A | 26 | 93.440 | 43.763 | 26.903 | 1.00 | 41.34 | C |
| ATOM | 200 | O | CYS | A | 26 | 94.067 | 44.738 | 26.496 | 1.00 | 41.54 | O |
| ATOM | 201 | CB | CYS | A | 26 | 92.640 | 44.924 | 28.943 | 1.00 | 39.84 | C |
| ATOM | 202 | SG | CYS | A | 26 | 90.919 | 45.372 | 28.462 | 1.00 | 36.85 | S |
| ATOM | 203 | N | ILE | A | 27 | 92.992 | 42.802 | 26.108 | 1.00 | 42.52 | N |
| ATOM | 204 | CA | ILE | A | 27 | 93.142 | 42.857 | 24.664 | 1.00 | 43.62 | C |
| ATOM | 205 | C | ILE | A | 27 | 91.725 | 42.630 | 24.152 | 1.00 | 44.10 | C |
| ATOM | 206 | O | ILE | A | 27 | 90.935 | 41.930 | 24.789 | 1.00 | 43.64 | O |
| ATOM | 207 | CB | ILE | A | 27 | 94.086 | 41.748 | 24.125 | 1.00 | 45.23 | C |
| ATOM | 208 | CG1 | ILE | A | 27 | 93.613 | 40.374 | 24.601 | 1.00 | 45.47 | C |
| ATOM | 209 | CG2 | ILE | A | 27 | 95.519 | 42.019 | 24.579 | 1.00 | 44.91 | C |
| ATOM | 210 | CD1 | ILE | A | 27 | 94.479 | 39.224 | 24.114 | 1.00 | 47.61 | C |
| ATOM | 211 | N | PRO | A | 28 | 91.377 | 43.235 | 23.010 | 1.00 | 44.56 | N |
| ATOM | 212 | CA | PRO | A | 28 | 90.041 | 43.090 | 22.429 | 1.00 | 44.54 | C |
| ATOM | 213 | C | PRO | A | 28 | 89.474 | 41.673 | 22.450 | 1.00 | 44.69 | C |
| ATOM | 214 | O | PRO | A | 28 | 88.312 | 41.471 | 22.801 | 1.00 | 44.73 | O |
| ATOM | 215 | CB | PRO | A | 28 | 90.233 | 43.625 | 21.016 | 1.00 | 45.21 | C |
| ATOM | 216 | CG | PRO | A | 28 | 91.205 | 44.738 | 21.239 | 1.00 | 44.60 | C |
| ATOM | 217 | CD | PRO | A | 28 | 92.221 | 44.104 | 22.170 | 1.00 | 44.85 | C |
| ATOM | 218 | N | SER | A | 29 | 90.292 | 40.692 | 22.082 | 1.00 | 44.42 | N |
| ATOM | 219 | CA | SER | A | 29 | 89.835 | 39.307 | 22.048 | 1.00 | 43.86 | C |
| ATOM | 220 | C | SER | A | 29 | 89.390 | 38.767 | 23.405 | 1.00 | 42.44 | C |
| ATOM | 221 | O | SER | A | 29 | 88.605 | 37.821 | 23.468 | 1.00 | 43.23 | O |
| ATOM | 222 | CB | SER | A | 29 | 90.926 | 38.400 | 21.455 | 1.00 | 45.84 | C |
| ATOM | 223 | OG | SER | A | 29 | 92.107 | 38.401 | 22.241 | 1.00 | 48.98 | O |
| ATOM | 224 | N | ASN | A | 30 | 89.878 | 39.357 | 24.491 | 1.00 | 40.37 | N |
| ATOM | 225 | CA | ASN | A | 30 | 89.489 | 38.892 | 25.819 | 1.00 | 39.43 | C |
| ATOM | 226 | C | ASN | A | 30 | 88.330 | 39.695 | 26.417 | 1.00 | 37.05 | C |
| ATOM | 227 | O | ASN | A | 30 | 87.912 | 39.442 | 27.548 | 1.00 | 36.90 | O |
| ATOM | 228 | CB | ASN | A | 30 | 90.677 | 38.942 | 26.788 | 1.00 | 41.28 | C |
| ATOM | 229 | CG | ASN | A | 30 | 91.830 | 38.061 | 26.348 | 1.00 | 44.29 | C |
| ATOM | 230 | OD1 | ASN | A | 30 | 91.638 | 37.064 | 25.648 | 1.00 | 45.64 | O |
| ATOM | 231 | ND2 | ASN | A | 30 | 93.040 | 38.417 | 26.773 | 1.00 | 44.79 | N |
| ATOM | 232 | N | VAL | A | 31 | 87.817 | 40.666 | 25.668 | 1.00 | 34.05 | N |
| ATOM | 233 | CA | VAL | A | 31 | 86.716 | 41.478 | 26.169 | 1.00 | 31.36 | C |
| ATOM | 234 | C | VAL | A | 31 | 85.404 | 40.711 | 26.051 | 1.00 | 30.32 | C |
| ATOM | 235 | O | VAL | A | 31 | 85.090 | 40.149 | 25.005 | 1.00 | 28.53 | O |
| ATOM | 236 | CB | VAL | A | 31 | 86.615 | 42.823 | 25.404 | 1.00 | 31.14 | C |
| ATOM | 237 | CG1 | VAL | A | 31 | 85.429 | 43.641 | 25.919 | 1.00 | 29.88 | C |
| ATOM | 238 | CG2 | VAL | A | 31 | 87.910 | 43.612 | 25.579 | 1.00 | 29.52 | C |
| ATOM | 239 | N | ASN | A | 32 | 84.653 | 40.680 | 27.144 | 1.00 | 29.79 | N |
| ATOM | 240 | CA | ASN | A | 32 | 83.369 | 39.987 | 27.195 | 1.00 | 30.76 | C |
| ATOM | 241 | C | ASN | A | 32 | 82.246 | 41.013 | 27.030 | 1.00 | 30.01 | C |
| ATOM | 242 | O | ASN | A | 32 | 82.095 | 41.908 | 27.860 | 1.00 | 29.60 | O |
| ATOM | 243 | CB | ASN | A | 32 | 83.244 | 39.266 | 28.541 | 1.00 | 32.62 | C |
| ATOM | 244 | CG | ASN | A | 32 | 81.916 | 38.549 | 28.716 | 1.00 | 34.80 | C |
| ATOM | 245 | OD1 | ASN | A | 32 | 81.640 | 38.004 | 29.786 | 1.00 | 38.96 | O |
| ATOM | 246 | ND2 | ASN | A | 32 | 81.093 | 38.538 | 27.676 | 1.00 | 32.90 | N |
| ATOM | 247 | N | LEU | A | 33 | 81.458 | 40.872 | 25.964 | 1.00 | 29.61 | N |
| ATOM | 248 | CA | LEU | A | 33 | 80.361 | 41.798 | 25.677 | 1.00 | 29.44 | C |
| ATOM | 249 | C | LEU | A | 33 | 78.961 | 41.292 | 26.050 | 1.00 | 29.73 | C |
| ATOM | 250 | O | LEU | A | 33 | 77.955 | 41.805 | 25.555 | 1.00 | 29.64 | O |
| ATOM | 251 | CB | LEU | A | 33 | 80.397 | 42.176 | 24.191 | 1.00 | 30.47 | C |
| ATOM | 252 | CG | LEU | A | 33 | 80.910 | 43.558 | 23.761 | 1.00 | 31.37 | C |
| ATOM | 253 | CD1 | LEU | A | 33 | 81.975 | 44.091 | 24.699 | 1.00 | 30.40 | C |
| ATOM | 254 | CD2 | LEU | A | 33 | 81.439 | 43.446 | 22.350 | 1.00 | 31.39 | C |
| ATOM | 255 | N | SER | A | 34 | 78.892 | 40.289 | 26.920 | 1.00 | 28.68 | N |
| ATOM | 256 | CA | SER | A | 34 | 77.605 | 39.752 | 27.360 | 1.00 | 28.45 | C |

TABLE 4-continued

| | | | | | | | | | | | |
|---|---|---|---|---|---|---|---|---|---|---|---|
| ATOM | 257 | C | SER | A | 34 | 76.885 | 40.800 | 28.197 | 1.00 | 26.82 | C |
| ATOM | 258 | O | SER | A | 34 | 77.521 | 41.633 | 28.840 | 1.00 | 27.22 | O |
| ATOM | 259 | CB | SER | A | 34 | 77.812 | 38.502 | 28.216 | 1.00 | 28.51 | C |
| ATOM | 260 | OG | SER | A | 34 | 78.504 | 37.518 | 27.477 | 1.00 | 35.24 | O |
| ATOM | 261 | N | THR | A | 35 | 75.561 | 40.750 | 28.209 | 1.00 | 24.82 | N |
| ATOM | 262 | CA | THR | A | 35 | 74.795 | 41.709 | 28.982 | 1.00 | 23.94 | C |
| ATOM | 263 | C | THR | A | 35 | 73.380 | 41.170 | 29.201 | 1.00 | 24.11 | C |
| ATOM | 264 | O | THR | A | 35 | 72.834 | 40.470 | 28.349 | 1.00 | 25.00 | O |
| ATOM | 265 | CB | THR | A | 35 | 74.752 | 43.084 | 28.251 | 1.00 | 24.28 | C |
| ATOM | 266 | OG1 | THR | A | 35 | 74.409 | 44.117 | 29.181 | 1.00 | 24.41 | O |
| ATOM | 267 | CG2 | THR | A | 35 | 73.728 | 43.069 | 27.126 | 1.00 | 21.95 | C |
| ATOM | 268 | N | PRO | A | 36 | 72.776 | 41.478 | 30.358 | 1.00 | 23.32 | N |
| ATOM | 269 | CA | PRO | A | 36 | 71.419 | 41.023 | 30.687 | 1.00 | 22.99 | C |
| ATOM | 270 | C | PRO | A | 36 | 70.304 | 41.697 | 29.881 | 1.00 | 24.25 | C |
| ATOM | 271 | O | PRO | A | 36 | 70.321 | 42.912 | 29.670 | 1.00 | 23.91 | O |
| ATOM | 272 | CB | PRO | A | 36 | 71.309 | 41.328 | 32.177 | 1.00 | 22.91 | C |
| ATOM | 273 | CG | PRO | A | 36 | 72.159 | 42.567 | 32.321 | 1.00 | 22.08 | C |
| ATOM | 274 | CD | PRO | A | 36 | 73.370 | 42.236 | 31.475 | 1.00 | 22.10 | C |
| ATOM | 275 | N | LEU | A | 37 | 69.329 | 40.900 | 29.447 | 1.00 | 24.03 | N |
| ATOM | 276 | CA | LEU | A | 37 | 68.201 | 41.407 | 28.677 | 1.00 | 24.03 | C |
| ATOM | 277 | C | LEU | A | 37 | 66.974 | 41.670 | 29.552 | 1.00 | 24.86 | C |
| ATOM | 278 | O | LEU | A | 37 | 66.293 | 42.684 | 29.385 | 1.00 | 25.14 | O |
| ATOM | 279 | CB | LEU | A | 37 | 67.825 | 40.420 | 27.567 | 1.00 | 24.13 | C |
| ATOM | 280 | CG | LEU | A | 37 | 66.707 | 40.862 | 26.614 | 1.00 | 25.46 | C |
| ATOM | 281 | CD1 | LEU | A | 37 | 67.191 | 42.043 | 25.759 | 1.00 | 24.90 | C |
| ATOM | 282 | CD2 | LEU | A | 37 | 66.306 | 39.698 | 25.708 | 1.00 | 25.09 | C |
| ATOM | 283 | N | VAL | A | 38 | 66.691 | 40.767 | 30.487 | 1.00 | 24.24 | N |
| ATOM | 284 | CA | VAL | A | 38 | 65.525 | 40.920 | 31.347 | 1.00 | 24.00 | C |
| ATOM | 285 | C | VAL | A | 38 | 65.889 | 40.950 | 32.820 | 1.00 | 25.63 | C |
| ATOM | 286 | O | VAL | A | 38 | 66.942 | 40.454 | 33.215 | 1.00 | 26.92 | O |
| ATOM | 287 | CB | VAL | A | 38 | 64.488 | 39.802 | 31.074 | 1.00 | 24.41 | C |
| ATOM | 288 | CG1 | VAL | A | 38 | 64.014 | 39.890 | 29.623 | 1.00 | 21.19 | C |
| ATOM | 289 | CG2 | VAL | A | 38 | 65.100 | 38.427 | 31.349 | 1.00 | 23.21 | C |
| ATOM | 290 | N | LYS | A | 39 | 65.003 | 41.527 | 33.629 | 1.00 | 25.88 | N |
| ATOM | 291 | CA | LYS | A | 39 | 65.240 | 41.686 | 35.060 | 1.00 | 27.51 | C |
| ATOM | 292 | C | LYS | A | 39 | 65.422 | 40.413 | 35.869 | 1.00 | 28.51 | C |
| ATOM | 293 | O | LYS | A | 39 | 64.916 | 39.351 | 35.513 | 1.00 | 29.00 | O |
| ATOM | 294 | CB | LYS | A | 39 | 64.121 | 42.513 | 35.697 | 1.00 | 27.27 | C |
| ATOM | 295 | CG | LYS | A | 39 | 62.754 | 41.843 | 35.661 | 1.00 | 28.27 | C |
| ATOM | 296 | CD | LYS | A | 39 | 61.751 | 42.595 | 36.514 | 1.00 | 27.78 | C |
| ATOM | 297 | CE | LYS | A | 39 | 60.369 | 41.943 | 36.448 | 1.00 | 29.12 | C |
| ATOM | 298 | NZ | LYS | A | 39 | 59.401 | 42.617 | 37.361 | 1.00 | 28.02 | N |
| ATOM | 299 | N | PHE | A | 40 | 66.152 | 40.556 | 36.973 | 1.00 | 28.42 | N |
| ATOM | 300 | CA | PHE | A | 40 | 66.439 | 39.470 | 37.893 | 1.00 | 29.14 | C |
| ATOM | 301 | C | PHE | A | 40 | 66.668 | 40.063 | 39.278 | 1.00 | 30.30 | C |
| ATOM | 302 | O | PHE | A | 40 | 66.794 | 41.278 | 39.421 | 1.00 | 30.54 | O |
| ATOM | 303 | CB | PHE | A | 40 | 67.687 | 38.697 | 37.449 | 1.00 | 28.10 | C |
| ATOM | 304 | CG | PHE | A | 40 | 68.913 | 39.558 | 37.251 | 1.00 | 27.25 | C |
| ATOM | 305 | CD1 | PHE | A | 40 | 69.163 | 40.167 | 36.023 | 1.00 | 25.59 | C |
| ATOM | 306 | CD2 | PHE | A | 40 | 69.824 | 39.743 | 38.287 | 1.00 | 25.17 | C |
| ATOM | 307 | CE1 | PHE | A | 40 | 70.304 | 40.944 | 35.830 | 1.00 | 25.72 | C |
| ATOM | 308 | CE2 | PHE | A | 40 | 70.968 | 40.518 | 38.106 | 1.00 | 25.52 | C |
| ATOM | 309 | CZ | PHE | A | 40 | 71.211 | 41.120 | 36.873 | 1.00 | 26.27 | C |
| ATOM | 310 | N | GLN | A | 41 | 66.713 | 39.200 | 40.291 | 1.00 | 31.34 | N |
| ATOM | 311 | CA | GLN | A | 41 | 66.927 | 39.622 | 41.672 | 1.00 | 33.56 | C |
| ATOM | 312 | C | GLN | A | 41 | 68.408 | 39.585 | 41.998 | 1.00 | 32.76 | C |
| ATOM | 313 | O | GLN | A | 41 | 69.183 | 38.929 | 41.305 | 1.00 | 32.65 | O |
| ATOM | 314 | CB | GLN | A | 41 | 66.190 | 38.685 | 42.641 | 1.00 | 36.73 | C |
| ATOM | 315 | CG | GLN | A | 41 | 64.681 | 38.719 | 42.523 | 1.00 | 42.60 | C |
| ATOM | 316 | CD | GLN | A | 41 | 64.087 | 40.002 | 43.073 | 1.00 | 45.09 | C |
| ATOM | 317 | OE1 | GLN | A | 41 | 62.956 | 40.359 | 42.749 | 1.00 | 48.80 | O |
| ATOM | 318 | NE2 | GLN | A | 41 | 64.842 | 40.693 | 43.921 | 1.00 | 48.01 | N |
| ATOM | 319 | N | LYS | A | 42 | 68.798 | 40.280 | 43.061 | 1.00 | 32.91 | N |
| ATOM | 320 | CA | LYS | A | 42 | 70.191 | 40.291 | 43.471 | 1.00 | 34.34 | C |
| ATOM | 321 | C | LYS | A | 42 | 70.670 | 38.865 | 43.747 | 1.00 | 34.29 | C |
| ATOM | 322 | O | LYS | A | 42 | 69.934 | 38.055 | 44.311 | 1.00 | 32.99 | O |
| ATOM | 323 | CB | LYS | A | 42 | 70.382 | 41.129 | 44.731 | 1.00 | 35.20 | C |
| ATOM | 324 | CG | LYS | A | 42 | 71.849 | 41.328 | 45.053 | 1.00 | 39.21 | C |
| ATOM | 325 | CD | LYS | A | 42 | 72.079 | 42.234 | 46.244 | 1.00 | 42.37 | C |
| ATOM | 326 | CE | LYS | A | 42 | 71.760 | 41.547 | 47.549 | 1.00 | 42.56 | C |
| ATOM | 327 | NZ | LYS | A | 42 | 72.329 | 42.327 | 48.680 | 1.00 | 43.58 | N |
| ATOM | 328 | N | GLY | A | 43 | 71.902 | 38.568 | 43.345 | 1.00 | 34.17 | N |
| ATOM | 329 | CA | GLY | A | 43 | 72.457 | 37.244 | 43.565 | 1.00 | 34.57 | C |
| ATOM | 330 | C | GLY | A | 43 | 72.186 | 36.277 | 42.431 | 1.00 | 34.77 | C |
| ATOM | 331 | O | GLY | A | 43 | 72.784 | 35.202 | 42.361 | 1.00 | 34.67 | O |
| ATOM | 332 | N | GLN | A | 44 | 71.282 | 36.655 | 41.538 | 1.00 | 35.36 | N |
| ATOM | 333 | CA | GLN | A | 44 | 70.942 | 35.810 | 40.403 | 1.00 | 36.05 | C |
| ATOM | 334 | C | GLN | A | 44 | 71.551 | 36.364 | 39.123 | 1.00 | 35.80 | C |
| ATOM | 335 | O | GLN | A | 44 | 72.230 | 37.390 | 39.138 | 1.00 | 35.18 | O |

TABLE 4-continued

| | | | | | | | | | | |
|---|---|---|---|---|---|---|---|---|---|---|
| ATOM | 336 | CB | GLN | A | 44 | 69.422 | 35.740 | 40.228 | 1.00 | 38.46 | C |
| ATOM | 337 | CG | GLN | A | 44 | 68.644 | 35.556 | 41.517 | 1.00 | 42.54 | C |
| ATOM | 338 | CD | GLN | A | 44 | 67.145 | 35.481 | 41.281 | 1.00 | 44.54 | C |
| ATOM | 339 | OE1 | GLN | A | 44 | 66.583 | 36.271 | 40.517 | 1.00 | 46.34 | O |
| ATOM | 340 | NE2 | GLN | A | 44 | 66.487 | 34.539 | 41.945 | 1.00 | 44.29 | N |
| ATOM | 341 | N | GLN | A | 45 | 71.299 | 35.664 | 38.022 | 1.00 | 35.96 | N |
| ATOM | 342 | CA | GLN | A | 45 | 71.759 | 36.055 | 36.695 | 1.00 | 36.42 | C |
| ATOM | 343 | C | GLN | A | 45 | 70.469 | 36.221 | 35.907 | 1.00 | 35.19 | C |
| ATOM | 344 | O | GLN | A | 45 | 69.435 | 35.682 | 36.293 | 1.00 | 35.44 | O |
| ATOM | 345 | CB | GLN | A | 45 | 72.586 | 34.943 | 36.039 | 1.00 | 39.65 | C |
| ATOM | 346 | CG | GLN | A | 45 | 73.865 | 34.569 | 36.763 | 1.00 | 44.40 | C |
| ATOM | 347 | CD | GLN | A | 45 | 74.951 | 35.614 | 36.610 | 1.00 | 47.78 | C |
| ATOM | 348 | OE1 | GLN | A | 45 | 75.471 | 35.834 | 35.510 | 1.00 | 50.39 | O |
| ATOM | 349 | NE2 | GLN | A | 45 | 75.303 | 36.266 | 37.714 | 1.00 | 48.43 | N |
| ATOM | 350 | N | SER | A | 46 | 70.519 | 36.967 | 34.812 | 1.00 | 32.83 | N |
| ATOM | 351 | CA | SER | A | 46 | 69.333 | 37.154 | 33.995 | 1.00 | 32.14 | C |
| ATOM | 352 | C | SER | A | 46 | 69.040 | 35.856 | 33.244 | 1.00 | 32.13 | C |
| ATOM | 353 | O | SER | A | 46 | 69.962 | 35.137 | 32.864 | 1.00 | 32.53 | O |
| ATOM | 354 | CB | SER | A | 46 | 69.554 | 38.289 | 32.996 | 1.00 | 29.54 | C |
| ATOM | 355 | OG | SER | A | 46 | 68.415 | 38.451 | 32.179 | 1.00 | 28.47 | O |
| ATOM | 356 | N | GLU | A | 47 | 67.762 | 35.562 | 33.032 | 1.00 | 32.14 | N |
| ATOM | 357 | CA | GLU | A | 47 | 67.364 | 34.355 | 32.318 | 1.00 | 32.15 | C |
| ATOM | 358 | C | GLU | A | 47 | 67.768 | 34.441 | 30.856 | 1.00 | 31.61 | C |
| ATOM | 359 | O | GLU | A | 47 | 67.865 | 33.424 | 30.169 | 1.00 | 30.42 | O |
| ATOM | 360 | CB | GLU | A | 47 | 65.853 | 34.154 | 32.418 | 1.00 | 34.33 | C |
| ATOM | 361 | CG | GLU | A | 47 | 65.358 | 33.856 | 33.823 | 1.00 | 37.88 | C |
| ATOM | 362 | CD | GLU | A | 47 | 63.844 | 33.834 | 33.905 | 1.00 | 41.09 | C |
| ATOM | 363 | OE1 | GLU | A | 47 | 63.226 | 32.981 | 33.231 | 1.00 | 43.20 | O |
| ATOM | 364 | OE2 | GLU | A | 47 | 63.271 | 34.671 | 34.639 | 1.00 | 43.10 | O |
| ATOM | 365 | N | ILE | A | 48 | 67.978 | 35.663 | 30.373 | 1.00 | 30.37 | N |
| ATOM | 366 | CA | ILE | A | 48 | 68.392 | 35.871 | 28.990 | 1.00 | 29.07 | C |
| ATOM | 367 | C | ILE | A | 48 | 69.551 | 36.863 | 28.923 | 1.00 | 28.22 | C |
| ATOM | 368 | O | ILE | A | 48 | 69.434 | 38.010 | 29.354 | 1.00 | 27.33 | O |
| ATOM | 369 | CB | ILE | A | 48 | 67.241 | 36.415 | 28.113 | 1.00 | 29.02 | C |
| ATOM | 370 | CG1 | ILE | A | 48 | 66.068 | 35.430 | 28.102 | 1.00 | 29.85 | C |
| ATOM | 371 | CG2 | ILE | A | 48 | 67.744 | 36.639 | 26.687 | 1.00 | 28.61 | C |
| ATOM | 372 | CD1 | ILE | A | 48 | 64.865 | 35.915 | 27.302 | 1.00 | 29.38 | C |
| ATOM | 373 | N | ASN | A | 49 | 70.676 | 36.412 | 28.388 | 1.00 | 27.92 | N |
| ATOM | 374 | CA | ASN | A | 49 | 71.839 | 37.271 | 28.258 | 1.00 | 28.26 | C |
| ATOM | 375 | C | ASN | A | 49 | 72.251 | 37.351 | 26.798 | 1.00 | 28.80 | C |
| ATOM | 376 | O | ASN | A | 49 | 72.436 | 36.328 | 26.143 | 1.00 | 30.14 | O |
| ATOM | 377 | CB | ASN | A | 49 | 72.997 | 36.726 | 29.101 | 1.00 | 27.34 | C |
| ATOM | 378 | CG | ASN | A | 49 | 72.738 | 36.847 | 30.592 | 1.00 | 27.92 | C |
| ATOM | 379 | OD1 | ASN | A | 49 | 72.899 | 37.914 | 31.176 | 1.00 | 26.65 | O |
| ATOM | 380 | ND2 | ASN | A | 49 | 72.317 | 35.752 | 31.211 | 1.00 | 27.88 | N |
| ATOM | 381 | N | LEU | A | 50 | 72.367 | 38.569 | 26.281 | 1.00 | 28.12 | N |
| ATOM | 382 | CA | LEU | A | 50 | 72.795 | 38.760 | 24.899 | 1.00 | 27.11 | C |
| ATOM | 383 | C | LEU | A | 50 | 74.302 | 38.496 | 24.876 | 1.00 | 26.67 | C |
| ATOM | 384 | O | LEU | A | 50 | 74.964 | 38.644 | 25.900 | 1.00 | 25.35 | O |
| ATOM | 385 | CB | LEU | A | 50 | 72.530 | 40.203 | 24.454 | 1.00 | 26.25 | C |
| ATOM | 386 | CG | LEU | A | 50 | 71.098 | 40.734 | 24.549 | 1.00 | 27.50 | C |
| ATOM | 387 | CD1 | LEU | A | 50 | 71.071 | 42.216 | 24.160 | 1.00 | 25.93 | C |
| ATOM | 388 | CD2 | LEU | A | 50 | 70.190 | 39.917 | 23.632 | 1.00 | 27.40 | C |
| ATOM | 389 | N | LYS | A | 51 | 74.837 | 38.100 | 23.723 | 1.00 | 27.96 | N |
| ATOM | 390 | CA | LYS | A | 51 | 76.275 | 37.859 | 23.585 | 1.00 | 29.04 | C |
| ATOM | 391 | C | LYS | A | 51 | 76.941 | 39.189 | 23.217 | 1.00 | 27.91 | C |
| ATOM | 392 | O | LYS | A | 51 | 78.128 | 39.397 | 23.472 | 1.00 | 28.86 | O |
| ATOM | 393 | CB | LYS | A | 51 | 76.564 | 36.813 | 22.496 | 1.00 | 30.79 | C |
| ATOM | 394 | CG | LYS | A | 51 | 76.813 | 35.389 | 23.004 | 1.00 | 33.79 | C |
| ATOM | 395 | CD | LYS | A | 51 | 75.558 | 34.739 | 23.541 | 1.00 | 36.94 | C |
| ATOM | 396 | CE | LYS | A | 51 | 75.836 | 33.339 | 24.093 | 1.00 | 39.15 | C |
| ATOM | 397 | NZ | LYS | A | 51 | 76.304 | 32.377 | 23.060 | 1.00 | 40.17 | N |
| ATOM | 398 | N | ILE | A | 52 | 76.163 | 40.070 | 22.590 | 1.00 | 26.85 | N |
| ATOM | 399 | CA | ILE | A | 52 | 76.608 | 41.411 | 22.216 | 1.00 | 24.81 | C |
| ATOM | 400 | C | ILE | A | 52 | 75.442 | 42.326 | 22.590 | 1.00 | 25.02 | C |
| ATOM | 401 | O | ILE | A | 52 | 74.276 | 41.961 | 22.425 | 1.00 | 24.33 | O |
| ATOM | 402 | CB | ILE | A | 52 | 76.950 | 41.540 | 20.700 | 1.00 | 25.62 | C |
| ATOM | 403 | CG1 | ILE | A | 52 | 75.738 | 41.178 | 19.833 | 1.00 | 25.04 | C |
| ATOM | 404 | CG2 | ILE | A | 52 | 78.159 | 40.654 | 20.370 | 1.00 | 25.34 | C |
| ATOM | 405 | CD1 | ILE | A | 52 | 75.946 | 41.460 | 18.351 | 1.00 | 22.84 | C |
| ATOM | 406 | N | PRO | A | 53 | 75.742 | 43.527 | 23.102 | 1.00 | 24.40 | N |
| ATOM | 407 | CA | PRO | A | 53 | 74.732 | 44.502 | 23.526 | 1.00 | 25.22 | C |
| ATOM | 408 | C | PRO | A | 53 | 73.979 | 45.272 | 22.439 | 1.00 | 25.38 | C |
| ATOM | 409 | O | PRO | A | 53 | 73.644 | 46.438 | 22.638 | 1.00 | 25.66 | O |
| ATOM | 410 | CB | PRO | A | 53 | 75.535 | 45.432 | 24.426 | 1.00 | 23.34 | C |
| ATOM | 411 | CG | PRO | A | 53 | 76.829 | 45.526 | 23.670 | 1.00 | 24.00 | C |
| ATOM | 412 | CD | PRO | A | 53 | 77.101 | 44.079 | 23.267 | 1.00 | 23.34 | C |
| ATOM | 413 | N | LEU | A | 54 | 73.705 | 44.633 | 21.304 | 1.00 | 25.11 | N |
| ATOM | 414 | CA | LEU | A | 54 | 72.982 | 45.306 | 20.229 | 1.00 | 24.78 | C |

TABLE 4-continued

| | | | | | | | | | | |
|---|---|---|---|---|---|---|---|---|---|---|
| ATOM | 415 | C | LEU | A | 54 | 71.670 | 44.607 | 19.883 | 1.00 | 25.72 | C |
| ATOM | 416 | O | LEU | A | 54 | 71.613 | 43.375 | 19.783 | 1.00 | 25.86 | O |
| ATOM | 417 | CB | LEU | A | 54 | 73.842 | 45.382 | 18.965 | 1.00 | 24.66 | C |
| ATOM | 418 | CG | LEU | A | 54 | 75.270 | 45.925 | 19.050 | 1.00 | 24.20 | C |
| ATOM | 419 | CD1 | LEU | A | 54 | 75.865 | 45.913 | 17.660 | 1.00 | 22.76 | C |
| ATOM | 420 | CD2 | LEU | A | 54 | 75.288 | 47.333 | 19.636 | 1.00 | 23.83 | C |
| ATOM | 421 | N | VAL | A | 55 | 70.613 | 45.396 | 19.721 | 1.00 | 24.79 | N |
| ATOM | 422 | CA | VAL | A | 55 | 69.315 | 44.866 | 19.335 | 1.00 | 25.45 | C |
| ATOM | 423 | C | VAL | A | 55 | 68.803 | 45.777 | 18.220 | 1.00 | 26.67 | C |
| ATOM | 424 | O | VAL | A | 55 | 69.044 | 46.988 | 18.252 | 1.00 | 26.82 | O |
| ATOM | 425 | CB | VAL | A | 55 | 68.298 | 44.846 | 20.519 | 1.00 | 24.52 | C |
| ATOM | 426 | CG1 | VAL | A | 55 | 68.889 | 44.086 | 21.698 | 1.00 | 23.68 | C |
| ATOM | 427 | CG2 | VAL | A | 55 | 67.906 | 46.263 | 20.922 | 1.00 | 25.10 | C |
| ATOM | 428 | N | SER | A | 56 | 68.132 | 45.197 | 17.225 | 1.00 | 26.09 | N |
| ATOM | 429 | CA | SER | A | 56 | 67.603 | 45.980 | 16.111 | 1.00 | 26.11 | C |
| ATOM | 430 | C | SER | A | 56 | 66.219 | 46.532 | 16.453 | 1.00 | 25.25 | C |
| ATOM | 431 | O | SER | A | 56 | 65.418 | 45.877 | 17.121 | 1.00 | 25.67 | O |
| ATOM | 432 | CB | SER | A | 56 | 67.565 | 45.135 | 14.825 | 1.00 | 26.43 | C |
| ATOM | 433 | OG | SER | A | 56 | 66.749 | 43.988 | 14.965 | 1.00 | 27.47 | O |
| ATOM | 434 | N | ALA | A | 57 | 65.957 | 47.751 | 15.996 | 1.00 | 24.68 | N |
| ATOM | 435 | CA | ALA | A | 57 | 64.710 | 48.458 | 16.270 | 1.00 | 25.05 | C |
| ATOM | 436 | C | ALA | A | 57 | 63.407 | 47.783 | 15.820 | 1.00 | 25.91 | C |
| ATOM | 437 | O | ALA | A | 57 | 63.375 | 47.019 | 14.853 | 1.00 | 25.61 | O |
| ATOM | 438 | CB | ALA | A | 57 | 64.797 | 49.868 | 15.691 | 1.00 | 22.75 | C |
| ATOM | 439 | N | ILE | A | 58 | 62.335 | 48.091 | 16.544 | 1.00 | 25.97 | N |
| ATOM | 440 | CA | ILE | A | 58 | 61.002 | 47.555 | 16.276 | 1.00 | 27.20 | C |
| ATOM | 441 | C | ILE | A | 58 | 60.400 | 48.361 | 15.124 | 1.00 | 27.24 | C |
| ATOM | 442 | O | ILE | A | 58 | 59.417 | 49.088 | 15.297 | 1.00 | 28.19 | O |
| ATOM | 443 | CB | ILE | A | 58 | 60.114 | 47.696 | 17.535 | 1.00 | 26.40 | C |
| ATOM | 444 | CG1 | ILE | A | 58 | 60.929 | 47.293 | 18.773 | 1.00 | 26.10 | C |
| ATOM | 445 | CG2 | ILE | A | 58 | 58.869 | 46.829 | 17.403 | 1.00 | 25.39 | C |
| ATOM | 446 | CD1 | ILE | A | 58 | 60.144 | 47.268 | 20.061 | 1.00 | 25.45 | C |
| ATOM | 447 | N | MET | A | 59 | 60.998 | 48.213 | 13.945 | 1.00 | 27.31 | N |
| ATOM | 448 | CA | MET | A | 59 | 60.581 | 48.965 | 12.768 | 1.00 | 27.85 | C |
| ATOM | 449 | C | MET | A | 59 | 60.419 | 48.127 | 11.501 | 1.00 | 28.29 | C |
| ATOM | 450 | O | MET | A | 59 | 61.177 | 47.185 | 11.261 | 1.00 | 27.17 | O |
| ATOM | 451 | CB | MET | A | 59 | 61.604 | 50.072 | 12.503 | 1.00 | 27.11 | C |
| ATOM | 452 | CG | MET | A | 59 | 61.908 | 50.946 | 13.711 | 1.00 | 26.18 | C |
| ATOM | 453 | SD | MET | A | 59 | 63.235 | 52.128 | 13.373 | 1.00 | 28.54 | S |
| ATOM | 454 | CE | MET | A | 59 | 62.471 | 53.130 | 12.107 | 1.00 | 25.89 | C |
| ATOM | 455 | N | GLN | A | 60 | 59.444 | 48.505 | 10.679 | 1.00 | 29.33 | N |
| ATOM | 456 | CA | GLN | A | 60 | 59.163 | 47.806 | 9.428 | 1.00 | 30.56 | C |
| ATOM | 457 | C | GLN | A | 60 | 60.372 | 47.772 | 8.503 | 1.00 | 30.93 | C |
| ATOM | 458 | O | GLN | A | 60 | 60.576 | 46.800 | 7.783 | 1.00 | 31.46 | O |
| ATOM | 459 | CB | GLN | A | 60 | 58.006 | 48.479 | 8.674 | 1.00 | 31.20 | C |
| ATOM | 460 | CG | GLN | A | 60 | 56.741 | 48.712 | 9.491 | 1.00 | 32.68 | C |
| ATOM | 461 | CD | GLN | A | 60 | 55.654 | 49.395 | 8.680 | 1.00 | 33.85 | C |
| ATOM | 462 | OE1 | GLN | A | 60 | 55.941 | 50.208 | 7.802 | 1.00 | 36.50 | O |
| ATOM | 463 | NE2 | GLN | A | 60 | 54.401 | 49.079 | 8.979 | 1.00 | 34.24 | N |
| ATOM | 464 | N | SER | A | 61 | 61.171 | 48.834 | 8.519 | 1.00 | 30.66 | N |
| ATOM | 465 | CA | SER | A | 61 | 62.332 | 48.906 | 7.639 | 1.00 | 31.00 | C |
| ATOM | 466 | C | SER | A | 61 | 63.619 | 48.359 | 8.241 | 1.00 | 30.65 | C |
| ATOM | 467 | O | SER | A | 61 | 64.695 | 48.514 | 7.659 | 1.00 | 30.72 | O |
| ATOM | 468 | CB | SER | A | 61 | 62.553 | 50.353 | 7.185 | 1.00 | 30.89 | C |
| ATOM | 469 | OG | SER | A | 61 | 62.658 | 51.225 | 8.292 | 1.00 | 34.36 | O |
| ATOM | 470 | N | VAL | A | 62 | 63.512 | 47.698 | 9.388 | 1.00 | 30.00 | N |
| ATOM | 471 | CA | VAL | A | 62 | 64.696 | 47.165 | 10.039 | 1.00 | 29.68 | C |
| ATOM | 472 | C | VAL | A | 62 | 64.642 | 45.696 | 10.449 | 1.00 | 30.05 | C |
| ATOM | 473 | O | VAL | A | 62 | 65.413 | 44.880 | 9.948 | 1.00 | 30.69 | O |
| ATOM | 474 | CB | VAL | A | 62 | 65.046 | 47.997 | 11.306 | 1.00 | 29.93 | C |
| ATOM | 475 | CG1 | VAL | A | 62 | 66.287 | 47.418 | 11.989 | 1.00 | 30.22 | C |
| ATOM | 476 | CG2 | VAL | A | 62 | 65.280 | 49.460 | 10.926 | 1.00 | 29.24 | C |
| ATOM | 477 | N | SER | A | 63 | 63.729 | 45.364 | 11.354 | 1.00 | 30.78 | N |
| ATOM | 478 | CA | SER | A | 63 | 63.641 | 44.011 | 11.889 | 1.00 | 31.26 | C |
| ATOM | 479 | C | SER | A | 63 | 62.664 | 43.019 | 11.267 | 1.00 | 32.02 | C |
| ATOM | 480 | O | SER | A | 63 | 61.535 | 42.842 | 11.741 | 1.00 | 30.32 | O |
| ATOM | 481 | CB | SER | A | 63 | 63.389 | 44.091 | 13.400 | 1.00 | 30.76 | C |
| ATOM | 482 | OG | SER | A | 63 | 64.420 | 44.825 | 14.051 | 1.00 | 29.40 | O |
| ATOM | 483 | N | GLY | A | 64 | 63.122 | 42.361 | 10.211 | 1.00 | 32.88 | N |
| ATOM | 484 | CA | GLY | A | 64 | 62.320 | 41.352 | 9.553 | 1.00 | 33.87 | C |
| ATOM | 485 | C | GLY | A | 64 | 62.916 | 40.005 | 9.925 | 1.00 | 35.96 | C |
| ATOM | 486 | O | GLY | A | 64 | 63.761 | 39.932 | 10.823 | 1.00 | 33.92 | O |
| ATOM | 487 | N | GLU | A | 65 | 62.501 | 38.949 | 9.226 | 1.00 | 37.32 | N |
| ATOM | 488 | CA | GLU | A | 65 | 62.980 | 37.596 | 9.493 | 1.00 | 39.14 | C |
| ATOM | 489 | C | GLU | A | 65 | 64.487 | 37.461 | 9.320 | 1.00 | 37.65 | C |
| ATOM | 490 | O | GLU | A | 65 | 65.175 | 36.945 | 10.198 | 1.00 | 36.98 | O |
| ATOM | 491 | CB | GLU | A | 65 | 62.298 | 36.591 | 8.559 | 1.00 | 42.54 | C |
| ATOM | 492 | CG | GLU | A | 65 | 60.841 | 36.885 | 8.260 | 1.00 | 48.99 | C |
| ATOM | 493 | CD | GLU | A | 65 | 60.245 | 35.884 | 7.283 | 1.00 | 53.35 | C |

TABLE 4-continued

| | | | | | | | | | | |
|---|---|---|---|---|---|---|---|---|---|---|
| ATOM | 494 | OE1 | GLU | A | 65 | 60.872 | 35.654 | 6.224 | 1.00 | 55.95 | O |
| ATOM | 495 | OE2 | GLU | A | 65 | 59.155 | 35.333 | 7.568 | 1.00 | 54.54 | O |
| ATOM | 496 | N | LYS | A | 66 | 64.991 | 37.914 | 8.177 | 1.00 | 37.01 | N |
| ATOM | 497 | CA | LYS | A | 66 | 66.416 | 37.820 | 7.883 | 1.00 | 36.92 | C |
| ATOM | 498 | C | LYS | A | 66 | 67.290 | 38.597 | 8.859 | 1.00 | 34.95 | C |
| ATOM | 499 | O | LYS | A | 66 | 68.373 | 38.140 | 9.228 | 1.00 | 33.49 | O |
| ATOM | 500 | CB | LYS | A | 66 | 66.691 | 38.282 | 6.448 | 1.00 | 38.53 | C |
| ATOM | 501 | CG | LYS | A | 66 | 66.185 | 37.309 | 5.397 | 1.00 | 43.00 | C |
| ATOM | 502 | CD | LYS | A | 66 | 66.517 | 37.777 | 3.987 | 1.00 | 47.32 | C |
| ATOM | 503 | CE | LYS | A | 66 | 66.060 | 36.759 | 2.944 | 1.00 | 48.73 | C |
| ATOM | 504 | NZ | LYS | A | 66 | 66.276 | 37.246 | 1.549 | 1.00 | 49.84 | N |
| ATOM | 505 | N | MET | A | 67 | 66.826 | 39.772 | 9.272 | 1.00 | 33.11 | N |
| ATOM | 506 | CA | MET | A | 67 | 67.582 | 40.584 | 10.218 | 1.00 | 32.25 | C |
| ATOM | 507 | C | MET | A | 67 | 67.696 | 39.825 | 11.536 | 1.00 | 32.26 | C |
| ATOM | 508 | O | MET | A | 67 | 68.780 | 39.717 | 12.106 | 1.00 | 32.78 | O |
| ATOM | 509 | CB | MET | A | 67 | 66.882 | 41.927 | 10.452 | 1.00 | 31.65 | C |
| ATOM | 510 | CG | MET | A | 67 | 67.589 | 42.843 | 11.447 | 1.00 | 30.85 | C |
| ATOM | 511 | SD | MET | A | 67 | 69.259 | 43.315 | 10.933 | 1.00 | 30.60 | S |
| ATOM | 512 | CE | MET | A | 67 | 68.905 | 44.374 | 9.529 | 1.00 | 28.51 | C |
| ATOM | 513 | N | ALA | A | 68 | 66.573 | 39.286 | 12.003 | 1.00 | 30.79 | N |
| ATOM | 514 | CA | ALA | A | 68 | 66.535 | 38.548 | 13.261 | 1.00 | 30.85 | C |
| ATOM | 515 | C | ALA | A | 68 | 67.495 | 37.355 | 13.281 | 1.00 | 31.53 | C |
| ATOM | 516 | O | ALA | A | 68 | 68.158 | 37.099 | 14.286 | 1.00 | 31.47 | O |
| ATOM | 517 | CB | ALA | A | 68 | 65.114 | 38.089 | 13.542 | 1.00 | 29.40 | C |
| ATOM | 518 | N | ILE | A | 69 | 67.573 | 36.632 | 12.169 | 1.00 | 31.56 | N |
| ATOM | 519 | CA | ILE | A | 69 | 68.466 | 35.484 | 12.067 | 1.00 | 31.71 | C |
| ATOM | 520 | C | ILE | A | 69 | 69.923 | 35.952 | 12.011 | 1.00 | 31.13 | C |
| ATOM | 521 | O | ILE | A | 69 | 70.778 | 35.446 | 12.734 | 1.00 | 31.74 | O |
| ATOM | 522 | CB | ILE | A | 69 | 68.137 | 34.645 | 10.801 | 1.00 | 33.02 | C |
| ATOM | 523 | CG1 | ILE | A | 69 | 66.787 | 33.942 | 10.983 | 1.00 | 34.17 | C |
| ATOM | 524 | CG2 | ILE | A | 69 | 69.236 | 33.629 | 10.535 | 1.00 | 32.75 | C |
| ATOM | 525 | CD1 | ILE | A | 69 | 66.173 | 33.422 | 9.680 | 1.00 | 34.42 | C |
| ATOM | 526 | N | ALA | A | 70 | 70.194 | 36.933 | 12.255 | 1.00 | 30.92 | N |
| ATOM | 527 | CA | ALA | A | 70 | 71.540 | 37.468 | 11.000 | 1.00 | 29.65 | C |
| ATOM | 528 | C | ALA | A | 70 | 72.102 | 38.049 | 12.298 | 1.00 | 29.11 | C |
| ATOM | 529 | O | ALA | A | 70 | 73.278 | 37.866 | 12.602 | 1.00 | 28.78 | O |
| ATOM | 530 | CB | ALA | A | 70 | 71.550 | 38.529 | 9.914 | 1.00 | 30.07 | C |
| ATOM | 531 | N | LEU | A | 71 | 71.263 | 38.752 | 13.055 | 1.00 | 28.45 | N |
| ATOM | 532 | CA | LEU | A | 71 | 71.701 | 39.357 | 14.308 | 1.00 | 28.31 | C |
| ATOM | 533 | C | LEU | A | 71 | 71.845 | 38.324 | 15.420 | 1.00 | 29.00 | C |
| ATOM | 534 | O | LEU | A | 71 | 72.796 | 38.377 | 16.198 | 1.00 | 28.61 | O |
| ATOM | 535 | CB | LEU | A | 71 | 70.726 | 40.453 | 14.742 | 1.00 | 26.49 | C |
| ATOM | 536 | CG | LEU | A | 71 | 71.090 | 41.270 | 15.992 | 1.00 | 26.53 | C |
| ATOM | 537 | CD1 | LEU | A | 71 | 72.561 | 41.711 | 15.941 | 1.00 | 24.18 | C |
| ATOM | 538 | CD2 | LEU | A | 71 | 70.168 | 42.487 | 16.073 | 1.00 | 24.70 | C |
| ATOM | 539 | N | ALA | A | 72 | 70.899 | 37.392 | 15.502 | 1.00 | 29.36 | N |
| ATOM | 540 | CA | ALA | A | 72 | 70.966 | 36.355 | 16.526 | 1.00 | 29.89 | C |
| ATOM | 541 | C | ALA | A | 72 | 72.251 | 35.553 | 16.336 | 1.00 | 30.74 | C |
| ATOM | 542 | O | ALA | A | 72 | 72.890 | 35.147 | 17.308 | 1.00 | 29.87 | O |
| ATOM | 543 | CB | ALA | A | 72 | 69.747 | 35.429 | 16.435 | 1.00 | 28.97 | C |
| ATOM | 544 | N | ARG | A | 73 | 72.623 | 35.330 | 15.077 | 1.00 | 31.36 | N |
| ATOM | 545 | CA | ARG | A | 73 | 73.832 | 34.580 | 14.761 | 1.00 | 33.37 | C |
| ATOM | 546 | C | ARG | A | 73 | 75.082 | 35.242 | 15.321 | 1.00 | 33.97 | C |
| ATOM | 547 | O | ARG | A | 73 | 76.062 | 34.562 | 15.616 | 1.00 | 34.69 | O |
| ATOM | 548 | CB | ARG | A | 73 | 73.988 | 34.414 | 13.247 | 1.00 | 34.83 | C |
| ATOM | 549 | CG | ARG | A | 73 | 73.071 | 33.373 | 12.630 | 1.00 | 37.24 | C |
| ATOM | 550 | CD | ARG | A | 73 | 73.289 | 33.268 | 11.124 | 1.00 | 40.12 | C |
| ATOM | 551 | NE | ARG | A | 73 | 72.462 | 32.222 | 10.531 | 1.00 | 43.25 | N |
| ATOM | 552 | CZ | ARG | A | 73 | 72.258 | 32.069 | 9.225 | 1.00 | 45.18 | C |
| ATOM | 553 | NH1 | ARG | A | 73 | 72.821 | 32.899 | 8.354 | 1.00 | 44.94 | N |
| ATOM | 554 | NH2 | ARG | A | 73 | 71.484 | 31.083 | 8.789 | 1.00 | 45.96 | N |
| ATOM | 555 | N | GLU | A | 74 | 75.050 | 36.566 | 15.463 | 1.00 | 33.85 | N |
| ATOM | 556 | CA | GLU | A | 74 | 76.198 | 37.293 | 15.995 | 1.00 | 33.08 | C |
| ATOM | 557 | C | GLU | A | 74 | 76.089 | 37.514 | 17.501 | 1.00 | 31.63 | C |
| ATOM | 558 | O | GLU | A | 74 | 77.011 | 38.037 | 18.119 | 1.00 | 32.56 | O |
| ATOM | 559 | CB | GLU | A | 74 | 76.367 | 38.642 | 15.286 | 1.00 | 34.18 | C |
| ATOM | 560 | CG | GLU | A | 74 | 76.569 | 38.544 | 13.779 | 1.00 | 37.13 | C |
| ATOM | 561 | CD | GLU | A | 74 | 77.709 | 37.611 | 13.384 | 1.00 | 39.95 | C |
| ATOM | 562 | OE1 | GLU | A | 74 | 78.834 | 37.775 | 13.909 | 1.00 | 41.16 | O |
| ATOM | 563 | OE2 | GLU | A | 74 | 77.478 | 36.718 | 12.539 | 1.00 | 40.45 | O |
| ATOM | 564 | N | GLY | A | 75 | 74.964 | 37.127 | 18.095 | 1.00 | 30.42 | N |
| ATOM | 565 | CA | GLY | A | 75 | 74.820 | 37.284 | 19.533 | 1.00 | 29.77 | C |
| ATOM | 566 | C | GLY | A | 75 | 73.815 | 38.310 | 20.019 | 1.00 | 29.50 | C |
| ATOM | 567 | O | GLY | A | 75 | 73.598 | 38.439 | 21.222 | 1.00 | 29.13 | O |
| ATOM | 568 | N | GLY | A | 76 | 73.212 | 39.051 | 19.096 | 1.00 | 29.23 | N |
| ATOM | 569 | CA | GLY | A | 76 | 72.226 | 40.042 | 19.483 | 1.00 | 28.60 | C |
| ATOM | 570 | C | GLY | A | 76 | 70.831 | 39.498 | 19.245 | 1.00 | 28.37 | C |
| ATOM | 571 | O | GLY | A | 76 | 70.668 | 38.304 | 18.976 | 1.00 | 26.97 | O |
| ATOM | 572 | N | ILE | A | 77 | 69.823 | 40.361 | 19.345 | 1.00 | 27.56 | N |

TABLE 4-continued

| | | | | | | | | | | |
|---|---|---|---|---|---|---|---|---|---|---|
| ATOM | 573 | CA | ILE | A | 77 | 68.445 | 39.937 | 19.122 | 1.00 | 27.52 | C |
| ATOM | 574 | C | ILE | A | 77 | 67.643 | 41.025 | 18.409 | 1.00 | 28.94 | C |
| ATOM | 575 | O | ILE | A | 77 | 67.905 | 42.221 | 18.572 | 1.00 | 28.96 | O |
| ATOM | 576 | CB | ILE | A | 77 | 67.750 | 39.578 | 20.455 | 1.00 | 26.85 | C |
| ATOM | 577 | CG1 | ILE | A | 77 | 66.524 | 38.704 | 20.183 | 1.00 | 27.10 | C |
| ATOM | 578 | CG2 | ILE | A | 77 | 67.332 | 40.852 | 21.205 | 1.00 | 24.72 | C |
| ATOM | 579 | CD1 | ILE | A | 77 | 65.800 | 38.268 | 21.443 | 1.00 | 24.29 | C |
| ATOM | 580 | N | SER | A | 78 | 66.674 | 40.602 | 17.605 | 1.00 | 28.99 | N |
| ATOM | 581 | CA | SER | A | 78 | 65.824 | 41.529 | 16.872 | 1.00 | 28.68 | C |
| ATOM | 582 | C | SER | A | 78 | 64.409 | 41.496 | 17.423 | 1.00 | 28.78 | C |
| ATOM | 583 | O | SER | A | 78 | 63.950 | 40.469 | 17.913 | 1.00 | 30.10 | O |
| ATOM | 584 | CB | SER | A | 78 | 65.775 | 41.160 | 15.387 | 1.00 | 27.58 | C |
| ATOM | 585 | OG | SER | A | 78 | 67.004 | 41.415 | 14.743 | 1.00 | 27.37 | O |
| ATOM | 586 | N | PHE | A | 79 | 63.727 | 42.632 | 17.357 | 1.00 | 28.40 | N |
| ATOM | 587 | CA | PHE | A | 79 | 62.350 | 42.710 | 17.807 | 1.00 | 28.34 | C |
| ATOM | 588 | C | PHE | A | 79 | 61.494 | 42.893 | 16.558 | 1.00 | 28.91 | C |
| ATOM | 589 | O | PHE | A | 79 | 61.360 | 44.004 | 16.048 | 1.00 | 29.07 | O |
| ATOM | 590 | CB | PHE | A | 79 | 62.150 | 43.885 | 18.778 | 1.00 | 26.91 | C |
| ATOM | 591 | CG | PHE | A | 79 | 62.715 | 43.635 | 20.155 | 1.00 | 27.54 | C |
| ATOM | 592 | CD1 | PHE | A | 79 | 64.067 | 43.839 | 20.421 | 1.00 | 28.32 | C |
| ATOM | 593 | CD2 | PHE | A | 79 | 61.902 | 43.146 | 21.175 | 1.00 | 27.29 | C |
| ATOM | 594 | CE1 | PHE | A | 79 | 64.601 | 43.555 | 21.685 | 1.00 | 28.62 | C |
| ATOM | 595 | CE2 | PHE | A | 79 | 62.426 | 42.861 | 22.436 | 1.00 | 27.31 | C |
| ATOM | 596 | CZ | PHE | A | 79 | 63.775 | 43.065 | 22.691 | 1.00 | 27.27 | C |
| ATOM | 597 | N | ILE | A | 80 | 60.947 | 41.789 | 16.053 | 1.00 | 28.75 | N |
| ATOM | 598 | CA | ILE | A | 80 | 60.102 | 41.815 | 14.861 | 1.00 | 29.29 | C |
| ATOM | 599 | C | ILE | A | 80 | 59.054 | 42.919 | 15.011 | 1.00 | 29.89 | C |
| ATOM | 600 | O | ILE | A | 80 | 58.319 | 42.950 | 16.000 | 1.00 | 30.34 | O |
| ATOM | 601 | CB | ILE | A | 80 | 59.384 | 40.450 | 14.657 | 1.00 | 29.92 | C |
| ATOM | 602 | CG1 | ILE | A | 80 | 60.416 | 39.326 | 14.516 | 1.00 | 30.32 | C |
| ATOM | 603 | CG2 | ILE | A | 80 | 58.499 | 40.498 | 13.414 | 1.00 | 29.91 | C |
| ATOM | 604 | CD1 | ILE | A | 80 | 61.356 | 39.496 | 13.341 | 1.00 | 30.51 | C |
| ATOM | 605 | N | PHE | A | 81 | 58.981 | 43.821 | 14.035 | 1.00 | 30.13 | N |
| ATOM | 606 | CA | PHE | A | 81 | 58.027 | 44.922 | 14.120 | 1.00 | 31.72 | C |
| ATOM | 607 | C | PHE | A | 81 | 56.579 | 44.473 | 14.289 | 1.00 | 31.73 | C |
| ATOM | 608 | O | PHE | A | 81 | 56.136 | 43.510 | 13.661 | 1.00 | 32.24 | O |
| ATOM | 609 | CB | PHE | A | 81 | 58.150 | 45.861 | 12.905 | 1.00 | 32.72 | C |
| ATOM | 610 | CG | PHE | A | 81 | 57.886 | 45.203 | 11.573 | 1.00 | 34.52 | C |
| ATOM | 611 | CD1 | PHE | A | 81 | 58.857 | 44.422 | 10.959 | 1.00 | 34.19 | C |
| ATOM | 612 | CD2 | PHE | A | 81 | 56.673 | 45.396 | 10.918 | 1.00 | 35.24 | C |
| ATOM | 613 | CE1 | PHE | A | 81 | 58.625 | 43.844 | 9.708 | 1.00 | 34.16 | C |
| ATOM | 614 | CE2 | PHE | A | 81 | 56.432 | 44.823 | 9.668 | 1.00 | 35.18 | C |
| ATOM | 615 | CZ | PHE | A | 81 | 57.410 | 44.048 | 9.064 | 1.00 | 34.69 | C |
| ATOM | 616 | N | GLY | A | 82 | 55.851 | 45.179 | 15.152 | 1.00 | 31.39 | N |
| ATOM | 617 | CA | GLY | A | 82 | 54.462 | 44.851 | 15.401 | 1.00 | 32.43 | C |
| ATOM | 618 | C | GLY | A | 82 | 53.490 | 45.673 | 14.574 | 1.00 | 33.20 | C |
| ATOM | 619 | O | GLY | A | 82 | 52.277 | 45.505 | 14.688 | 1.00 | 33.41 | O |
| ATOM | 620 | N | SER | A | 83 | 54.012 | 46.567 | 13.741 | 1.00 | 33.11 | N |
| ATOM | 621 | CA | SER | A | 83 | 53.156 | 47.392 | 12.900 | 1.00 | 34.17 | C |
| ATOM | 622 | C | SER | A | 83 | 52.759 | 46.625 | 11.640 | 1.00 | 34.38 | C |
| ATOM | 623 | O | SER | A | 83 | 53.044 | 47.038 | 10.517 | 1.00 | 34.03 | O |
| ATOM | 624 | CB | SER | A | 83 | 53.867 | 48.697 | 12.534 | 1.00 | 33.42 | C |
| ATOM | 625 | OG | SER | A | 83 | 55.143 | 48.439 | 11.990 | 1.00 | 34.18 | O |
| ATOM | 626 | N | GLN | A | 84 | 52.110 | 45.487 | 11.855 | 1.00 | 35.41 | N |
| ATOM | 627 | CA | GLN | A | 84 | 51.640 | 44.625 | 10.780 | 1.00 | 36.62 | C |
| ATOM | 628 | C | GLN | A | 84 | 50.585 | 43.711 | 11.397 | 1.00 | 37.53 | C |
| ATOM | 629 | O | GLN | A | 84 | 50.373 | 43.741 | 12.611 | 1.00 | 36.60 | O |
| ATOM | 630 | CB | GLN | A | 84 | 52.794 | 43.797 | 10.201 | 1.00 | 37.29 | C |
| ATOM | 631 | CG | GLN | A | 84 | 53.412 | 42.805 | 11.174 | 1.00 | 37.90 | C |
| ATOM | 632 | CD | GLN | A | 84 | 54.568 | 42.035 | 10.563 | 1.00 | 39.55 | C |
| ATOM | 633 | OE1 | GLN | A | 84 | 54.427 | 41.416 | 9.510 | 1.00 | 41.11 | O |
| ATOM | 634 | NE2 | GLN | A | 84 | 55.720 | 42.065 | 11.228 | 1.00 | 39.70 | N |
| ATOM | 635 | N | SER | A | 85 | 49.921 | 42.908 | 10.571 | 1.00 | 38.61 | N |
| ATOM | 636 | CA | SER | A | 85 | 48.888 | 42.013 | 11.079 | 1.00 | 40.37 | C |
| ATOM | 637 | C | SER | A | 85 | 49.485 | 41.050 | 12.092 | 1.00 | 40.61 | C |
| ATOM | 638 | O | SER | A | 85 | 50.655 | 40.678 | 11.993 | 1.00 | 40.59 | O |
| ATOM | 639 | CB | SER | A | 85 | 48.249 | 41.211 | 9.943 | 1.00 | 40.55 | C |
| ATOM | 640 | OG | SER | A | 85 | 49.115 | 40.182 | 9.501 | 1.00 | 41.70 | O |
| ATOM | 641 | N | ILE | A | 86 | 48.667 | 40.657 | 13.063 | 1.00 | 40.88 | N |
| ATOM | 642 | CA | ILE | A | 86 | 49.079 | 39.732 | 14.108 | 1.00 | 41.21 | C |
| ATOM | 643 | C | ILE | A | 86 | 49.589 | 38.424 | 13.508 | 1.00 | 42.63 | C |
| ATOM | 644 | O | ILE | A | 86 | 50.578 | 37.858 | 13.977 | 1.00 | 42.00 | O |
| ATOM | 645 | CB | ILE | A | 86 | 47.899 | 39.429 | 15.061 | 1.00 | 40.49 | C |
| ATOM | 646 | CG1 | ILE | A | 86 | 47.454 | 40.722 | 15.750 | 1.00 | 39.68 | C |
| ATOM | 647 | CG2 | ILE | A | 86 | 48.299 | 38.366 | 16.079 | 1.00 | 39.80 | C |
| ATOM | 648 | CD1 | ILE | A | 86 | 46.272 | 40.558 | 16.686 | 1.00 | 38.99 | C |
| ATOM | 649 | N | GLU | A | 87 | 48.918 | 37.952 | 12.462 | 1.00 | 43.90 | N |
| ATOM | 650 | CA | GLU | A | 87 | 49.314 | 36.709 | 11.814 | 1.00 | 45.61 | C |
| ATOM | 651 | C | GLU | A | 87 | 50.604 | 36.839 | 11.009 | 1.00 | 44.76 | C |

TABLE 4-continued

| | | | | | | | | | | | |
|---|---|---|---|---|---|---|---|---|---|---|---|
| ATOM | 652 | O | GLU | A | 87 | 51.355 | 35.874 | 10.879 | 1.00 | 45.04 | O |
| ATOM | 653 | CB | GLU | A | 87 | 48.177 | 36.173 | 10.924 | 1.00 | 47.51 | C |
| ATOM | 654 | CG | GLU | A | 87 | 47.243 | 37.229 | 10.324 | 1.00 | 51.63 | C |
| ATOM | 655 | CD | GLU | A | 87 | 46.341 | 37.895 | 11.362 | 1.00 | 53.09 | C |
| ATOM | 656 | OE1 | GLU | A | 87 | 45.804 | 37.180 | 12.238 | 1.00 | 54.09 | O |
| ATOM | 657 | OE2 | GLU | A | 87 | 46.156 | 39.131 | 11.290 | 1.00 | 53.94 | O |
| ATOM | 658 | N | SER | A | 88 | 50.865 | 38.025 | 10.470 | 1.00 | 44.57 | N |
| ATOM | 659 | CA | SER | A | 88 | 52.091 | 38.246 | 9.704 | 1.00 | 44.09 | C |
| ATOM | 660 | C | SER | A | 88 | 53.295 | 38.287 | 10.643 | 1.00 | 42.16 | C |
| ATOM | 661 | O | SER | A | 88 | 54.343 | 37.720 | 10.346 | 1.00 | 41.66 | O |
| ATOM | 662 | CB | SER | A | 88 | 52.017 | 39.560 | 8.925 | 1.00 | 45.33 | C |
| ATOM | 663 | OG | SER | A | 88 | 51.076 | 39.473 | 7.875 | 1.00 | 49.27 | O |
| ATOM | 664 | N | GLN | A | 89 | 53.137 | 38.966 | 11.774 | 1.00 | 40.30 | N |
| ATOM | 665 | CA | GLN | A | 89 | 54.214 | 39.070 | 12.750 | 1.00 | 39.20 | C |
| ATOM | 666 | C | GLN | A | 89 | 54.529 | 37.696 | 13.336 | 1.00 | 38.78 | C |
| ATOM | 667 | O | GLN | A | 89 | 55.695 | 37.325 | 13.477 | 1.00 | 38.47 | O |
| ATOM | 668 | CB | GLN | A | 89 | 53.827 | 40.046 | 13.867 | 1.00 | 37.90 | C |
| ATOM | 669 | CG | GLN | A | 89 | 54.856 | 40.158 | 14.984 | 1.00 | 36.29 | C |
| ATOM | 670 | CD | GLN | A | 89 | 54.484 | 41.196 | 16.025 | 1.00 | 35.77 | C |
| ATOM | 671 | OE1 | GLN | A | 89 | 53.314 | 41.342 | 16.381 | 1.00 | 34.41 | O |
| ATOM | 672 | NE2 | GLN | A | 89 | 55.483 | 41.910 | 16.534 | 1.00 | 34.88 | N |
| ATOM | 673 | N | ALA | A | 90 | 53.487 | 36.940 | 13.668 | 1.00 | 38.89 | N |
| ATOM | 674 | CA | ALA | A | 90 | 53.665 | 35.606 | 14.236 | 1.00 | 38.52 | C |
| ATOM | 675 | C | ALA | A | 90 | 54.416 | 34.706 | 13.258 | 1.00 | 37.75 | C |
| ATOM | 676 | O | ALA | A | 90 | 55.284 | 33.932 | 13.658 | 1.00 | 37.34 | O |
| ATOM | 677 | CB | ALA | A | 90 | 52.310 | 34.996 | 14.580 | 1.00 | 38.78 | C |
| ATOM | 678 | N | ALA | A | 91 | 54.086 | 34.815 | 11.976 | 1.00 | 37.31 | N |
| ATOM | 679 | CA | ALA | A | 91 | 54.751 | 34.007 | 10.960 | 1.00 | 37.66 | C |
| ATOM | 680 | C | ALA | A | 91 | 56.259 | 34.272 | 10.972 | 1.00 | 37.59 | C |
| ATOM | 681 | O | ALA | A | 91 | 57.061 | 33.339 | 10.934 | 1.00 | 37.08 | O |
| ATOM | 682 | CB | ALA | A | 91 | 54.170 | 34.312 | 9.582 | 1.00 | 36.97 | C |
| ATOM | 683 | N | MET | A | 92 | 56.644 | 35.544 | 11.023 | 1.00 | 38.21 | N |
| ATOM | 684 | CA | MET | A | 92 | 58.063 | 35.898 | 11.052 | 1.00 | 38.30 | C |
| ATOM | 685 | C | MET | A | 92 | 58.747 | 35.311 | 12.282 | 1.00 | 37.53 | C |
| ATOM | 686 | O | MET | A | 92 | 59.841 | 34.756 | 12.188 | 1.00 | 37.70 | O |
| ATOM | 687 | CB | MET | A | 92 | 58.242 | 37.418 | 11.054 | 1.00 | 39.02 | C |
| ATOM | 688 | CG | MET | A | 92 | 57.888 | 38.093 | 9.747 | 1.00 | 39.39 | C |
| ATOM | 689 | SD | MET | A | 92 | 58.282 | 39.850 | 9.772 | 1.00 | 39.06 | S |
| ATOM | 690 | CE | MET | A | 92 | 57.340 | 40.410 | 8.355 | 1.00 | 38.06 | C |
| ATOM | 691 | N | VAL | A | 93 | 58.099 | 35.443 | 13.436 | 1.00 | 37.33 | N |
| ATOM | 692 | CA | VAL | A | 93 | 58.647 | 34.919 | 14.679 | 1.00 | 37.59 | C |
| ATOM | 693 | C | VAL | A | 93 | 58.822 | 33.416 | 14.558 | 1.00 | 38.75 | C |
| ATOM | 694 | O | VAL | A | 93 | 59.865 | 32.871 | 14.915 | 1.00 | 39.48 | O |
| ATOM | 695 | CB | VAL | A | 93 | 57.718 | 35.218 | 15.877 | 1.00 | 37.43 | C |
| ATOM | 696 | CG1 | VAL | A | 93 | 58.182 | 34.447 | 17.106 | 1.00 | 35.94 | C |
| ATOM | 697 | CG2 | VAL | A | 93 | 57.705 | 36.711 | 16.162 | 1.00 | 36.07 | C |
| ATOM | 698 | N | HIS | A | 94 | 57.795 | 32.749 | 14.042 | 1.00 | 40.16 | N |
| ATOM | 699 | CA | HIS | A | 94 | 57.833 | 31.301 | 13.875 | 1.00 | 40.66 | C |
| ATOM | 700 | C | HIS | A | 94 | 58.930 | 30.881 | 12.898 | 1.00 | 40.13 | C |
| ATOM | 701 | O | HIS | A | 94 | 59.624 | 29.888 | 13.122 | 1.00 | 40.44 | O |
| ATOM | 702 | CB | HIS | A | 94 | 56.466 | 30.797 | 13.395 | 1.00 | 42.53 | C |
| ATOM | 703 | CG | HIS | A | 94 | 56.400 | 29.312 | 13.209 | 1.00 | 43.62 | C |
| ATOM | 704 | ND1 | HIS | A | 94 | 56.844 | 28.683 | 12.065 | 1.00 | 44.37 | N |
| ATOM | 705 | CD2 | HIS | A | 94 | 55.961 | 28.331 | 14.033 | 1.00 | 43.39 | C |
| ATOM | 706 | CE1 | HIS | A | 94 | 56.680 | 27.379 | 12.191 | 1.00 | 44.17 | C |
| ATOM | 707 | NE2 | HIS | A | 94 | 56.146 | 27.139 | 13.376 | 1.00 | 44.00 | N |
| ATOM | 708 | N | ALA | A | 95 | 59.092 | 31.642 | 11.821 | 1.00 | 39.31 | N |
| ATOM | 709 | CA | ALA | A | 95 | 60.111 | 31.335 | 10.825 | 1.00 | 38.23 | C |
| ATOM | 710 | C | ALA | A | 95 | 61.516 | 31.408 | 11.425 | 1.00 | 38.43 | C |
| ATOM | 711 | O | ALA | A | 95 | 62.399 | 30.637 | 11.055 | 1.00 | 38.01 | O |
| ATOM | 712 | CB | ALA | A | 95 | 59.996 | 32.298 | 9.647 | 1.00 | 37.20 | C |
| ATOM | 713 | N | VAL | A | 96 | 61.720 | 32.341 | 12.350 | 1.00 | 38.46 | N |
| ATOM | 714 | CA | VAL | A | 96 | 63.019 | 32.504 | 12.992 | 1.00 | 37.77 | C |
| ATOM | 715 | C | VAL | A | 96 | 63.293 | 31.366 | 13.973 | 1.00 | 38.35 | C |
| ATOM | 716 | O | VAL | A | 96 | 64.383 | 30.794 | 13.983 | 1.00 | 37.59 | O |
| ATOM | 717 | CB | VAL | A | 96 | 63.103 | 33.858 | 13.748 | 1.00 | 37.72 | C |
| ATOM | 718 | CG1 | VAL | A | 96 | 64.417 | 33.959 | 14.509 | 1.00 | 36.02 | C |
| ATOM | 719 | CG2 | VAL | A | 96 | 62.985 | 35.009 | 12.757 | 1.00 | 36.81 | C |
| ATOM | 720 | N | LYS | A | 97 | 62.295 | 31.040 | 14.787 | 1.00 | 38.94 | N |
| ATOM | 721 | CA | LYS | A | 97 | 62.426 | 29.978 | 15.777 | 1.00 | 40.76 | C |
| ATOM | 722 | C | LYS | A | 97 | 62.607 | 28.599 | 15.145 | 1.00 | 42.67 | C |
| ATOM | 723 | O | LYS | A | 97 | 63.211 | 27.710 | 15.747 | 1.00 | 43.04 | O |
| ATOM | 724 | CB | LYS | A | 97 | 61.199 | 29.955 | 16.697 | 1.00 | 39.98 | C |
| ATOM | 725 | CG | LYS | A | 97 | 60.989 | 31.227 | 17.516 | 1.00 | 39.03 | C |
| ATOM | 726 | CD | LYS | A | 97 | 62.189 | 31.543 | 18.411 | 1.00 | 37.55 | C |
| ATOM | 727 | CE | LYS | A | 97 | 62.416 | 30.474 | 19.472 | 1.00 | 36.48 | C |
| ATOM | 728 | NZ | LYS | A | 97 | 63.663 | 30.739 | 20.249 | 1.00 | 34.18 | N |
| ATOM | 729 | N | ASN | A | 98 | 62.091 | 28.425 | 13.933 | 1.00 | 44.43 | N |
| ATOM | 730 | CA | ASN | A | 98 | 62.190 | 27.142 | 13.247 | 1.00 | 46.61 | C |

TABLE 4-continued

| ATOM | 731 | C | ASN | A | 98 | 63.069 | 27.188 | 12.005 | 1.00 | 46.93 | C |
|---|---|---|---|---|---|---|---|---|---|---|---|
| ATOM | 732 | O | ASN | A | 98 | 62.847 | 26.431 | 11.059 | 1.00 | 48.02 | O |
| ATOM | 733 | CB | ASN | A | 98 | 60.790 | 26.656 | 12.866 | 1.00 | 48.75 | C |
| ATOM | 734 | CG | ASN | A | 98 | 59.921 | 26.378 | 14.078 | 1.00 | 51.25 | C |
| ATOM | 735 | OD1 | ASN | A | 98 | 58.697 | 26.390 | 13.992 | 1.00 | 53.69 | O |
| ATOM | 736 | ND2 | ASN | A | 98 | 60.555 | 26.114 | 15.214 | 1.00 | 53.55 | N |
| ATOM | 737 | N | PHE | A | 99 | 64.073 | 28.060 | 12.007 | 1.00 | 46.26 | N |
| ATOM | 738 | CA | PHE | A | 99 | 64.958 | 28.182 | 10.855 | 1.00 | 46.28 | C |
| ATOM | 739 | C | PHE | A | 99 | 65.891 | 26.987 | 10.674 | 1.00 | 46.62 | C |
| ATOM | 740 | O | PHE | A | 99 | 66.232 | 26.634 | 9.548 | 1.00 | 46.35 | O |
| ATOM | 741 | CB | PHE | A | 99 | 65.799 | 29.459 | 10.952 | 1.00 | 45.12 | C |
| ATOM | 742 | CG | PHE | A | 99 | 66.577 | 29.765 | 9.699 | 1.00 | 44.39 | C |
| ATOM | 743 | CD1 | PHE | A | 99 | 65.918 | 30.122 | 8.526 | 1.00 | 44.53 | C |
| ATOM | 744 | CD2 | PHE | A | 99 | 67.964 | 29.690 | 9.689 | 1.00 | 43.94 | C |
| ATOM | 745 | CE1 | PHE | A | 99 | 66.630 | 30.401 | 7.362 | 1.00 | 44.09 | C |
| ATOM | 746 | CE2 | PHE | A | 99 | 68.685 | 29.966 | 8.529 | 1.00 | 43.84 | C |
| ATOM | 747 | CZ | PHE | A | 99 | 68.018 | 30.323 | 7.365 | 1.00 | 44.07 | C |
| ATOM | 748 | N | LYS | A | 100 | 66.303 | 26.368 | 11.775 | 1.00 | 47.68 | N |
| ATOM | 749 | CA | LYS | A | 100 | 67.214 | 25.226 | 11.708 | 1.00 | 49.23 | C |
| ATOM | 750 | C | LYS | A | 100 | 66.519 | 23.882 | 11.499 | 1.00 | 50.54 | C |
| ATOM | 751 | O | LYS | A | 100 | 67.165 | 22.834 | 11.564 | 1.00 | 50.71 | O |
| ATOM | 752 | CB | LYS | A | 100 | 68.059 | 25.146 | 12.980 | 1.00 | 48.77 | C |
| ATOM | 753 | CG | LYS | A | 100 | 68.932 | 26.364 | 13.239 | 1.00 | 47.96 | C |
| ATOM | 754 | CD | LYS | A | 100 | 69.709 | 26.180 | 14.526 | 1.00 | 46.23 | C |
| ATOM | 755 | CE | LYS | A | 100 | 70.672 | 27.320 | 14.777 | 1.00 | 44.66 | C |
| ATOM | 756 | NZ | LYS | A | 100 | 71.462 | 27.057 | 16.006 | 1.00 | 43.46 | N |
| ATOM | 757 | N | ALA | A | 101 | 65.212 | 23.909 | 11.253 | 1.00 | 51.61 | N |
| ATOM | 758 | CA | ALA | A | 101 | 64.447 | 22.683 | 11.040 | 1.00 | 52.22 | C |
| ATOM | 759 | C | ALA | A | 101 | 64.975 | 21.911 | 9.835 | 1.00 | 52.77 | C |
| ATOM | 760 | O | ALA | A | 101 | 64.961 | 22.412 | 8.711 | 1.00 | 53.93 | O |
| ATOM | 761 | CB | ALA | A | 101 | 62.974 | 23.011 | 10.840 | 1.00 | 52.31 | C |
| ATOM | 762 | N | HIS | A | 222 | 80.602 | 29.634 | 17.602 | 1.00 | 62.86 | N |
| ATOM | 763 | CA | HIS | A | 222 | 79.850 | 30.811 | 17.181 | 1.00 | 61.95 | C |
| ATOM | 764 | C | HIS | A | 222 | 79.347 | 31.556 | 18.415 | 1.00 | 60.27 | C |
| ATOM | 765 | O | HIS | A | 222 | 79.357 | 31.019 | 19.526 | 1.00 | 60.09 | O |
| ATOM | 766 | CB | HIS | A | 222 | 78.642 | 30.402 | 16.323 | 1.00 | 64.41 | C |
| ATOM | 767 | CG | HIS | A | 222 | 78.978 | 29.493 | 15.179 | 1.00 | 67.13 | C |
| ATOM | 768 | ND1 | HIS | A | 222 | 78.014 | 28.948 | 14.357 | 1.00 | 68.00 | N |
| ATOM | 769 | CD2 | HIS | A | 222 | 80.165 | 29.019 | 14.729 | 1.00 | 68.21 | C |
| ATOM | 770 | CE1 | HIS | A | 222 | 78.591 | 28.177 | 13.452 | 1.00 | 68.36 | C |
| ATOM | 771 | NE2 | HIS | A | 222 | 79.896 | 28.202 | 13.656 | 1.00 | 68.83 | N |
| ATOM | 772 | N | ASN | A | 223 | 78.915 | 32.796 | 18.220 | 1.00 | 57.17 | N |
| ATOM | 773 | CA | ASN | A | 223 | 78.378 | 33.583 | 19.319 | 1.00 | 53.95 | C |
| ATOM | 774 | C | ASN | A | 223 | 76.882 | 33.737 | 19.113 | 1.00 | 50.53 | C |
| ATOM | 775 | O | ASN | A | 223 | 76.293 | 34.746 | 19.493 | 1.00 | 48.94 | O |
| ATOM | 776 | CB | ASN | A | 223 | 79.039 | 34.960 | 19.388 | 1.00 | 55.72 | C |
| ATOM | 777 | CG | ASN | A | 223 | 80.463 | 34.895 | 19.899 | 1.00 | 57.65 | C |
| ATOM | 778 | OD1 | ASN | A | 223 | 81.380 | 34.504 | 19.173 | 1.00 | 59.28 | O |
| ATOM | 779 | ND2 | ASN | A | 223 | 80.654 | 35.262 | 21.161 | 1.00 | 57.30 | N |
| ATOM | 780 | N | GLU | A | 224 | 76.275 | 32.723 | 18.505 | 1.00 | 46.60 | N |
| ATOM | 781 | CA | GLU | A | 224 | 74.843 | 32.740 | 18.248 | 1.00 | 43.68 | C |
| ATOM | 782 | C | GLU | A | 224 | 74.057 | 32.795 | 19.548 | 1.00 | 40.12 | C |
| ATOM | 783 | O | GLU | A | 224 | 74.438 | 32.179 | 20.542 | 1.00 | 38.99 | O |
| ATOM | 784 | CB | GLU | A | 224 | 74.419 | 31.502 | 17.449 | 1.00 | 44.21 | C |
| ATOM | 785 | CG | GLU | A | 224 | 74.834 | 30.176 | 18.074 | 1.00 | 46.74 | C |
| ATOM | 786 | CD | GLU | A | 224 | 74.123 | 28.981 | 17.454 | 1.00 | 47.84 | C |
| ATOM | 787 | OE1 | GLU | A | 224 | 73.924 | 28.977 | 16.221 | 1.00 | 48.39 | O |
| ATOM | 788 | OE2 | GLU | A | 224 | 73.775 | 28.041 | 18.199 | 1.00 | 48.26 | O |
| ATOM | 789 | N | LEU | A | 225 | 72.962 | 33.546 | 19.527 | 1.00 | 37.30 | N |
| ATOM | 790 | CA | LEU | A | 225 | 72.089 | 33.681 | 20.681 | 1.00 | 35.11 | C |
| ATOM | 791 | C | LEU | A | 225 | 70.932 | 32.704 | 20.479 | 1.00 | 34.44 | C |
| ATOM | 792 | O | LEU | A | 225 | 70.088 | 32.901 | 19.603 | 1.00 | 33.50 | O |
| ATOM | 793 | CB | LEU | A | 225 | 71.561 | 35.116 | 20.775 | 1.00 | 33.83 | C |
| ATOM | 794 | CG | LEU | A | 225 | 70.675 | 35.448 | 21.979 | 1.00 | 34.33 | C |
| ATOM | 795 | CD1 | LEU | A | 225 | 71.450 | 35.194 | 23.274 | 1.00 | 34.23 | C |
| ATOM | 796 | CD2 | LEU | A | 225 | 70.220 | 36.899 | 21.899 | 1.00 | 33.89 | C |
| ATOM | 797 | N | VAL | A | 226 | 70.893 | 31.653 | 21.292 | 1.00 | 34.99 | N |
| ATOM | 798 | CA | VAL | A | 226 | 69.853 | 30.635 | 21.169 | 1.00 | 35.64 | C |
| ATOM | 799 | C | VAL | A | 226 | 69.235 | 30.197 | 22.491 | 1.00 | 37.35 | C |
| ATOM | 800 | O | VAL | A | 226 | 69.744 | 30.516 | 23.566 | 1.00 | 38.20 | O |
| ATOM | 801 | CB | VAL | A | 226 | 70.412 | 29.372 | 20.488 | 1.00 | 34.80 | C |
| ATOM | 802 | CG1 | VAL | A | 226 | 70.890 | 29.701 | 19.086 | 1.00 | 33.57 | C |
| ATOM | 803 | CG2 | VAL | A | 226 | 71.557 | 28.805 | 21.325 | 1.00 | 34.39 | C |
| ATOM | 804 | N | ASP | A | 227 | 68.128 | 29.462 | 22.397 | 1.00 | 38.54 | N |
| ATOM | 805 | CA | ASP | A | 227 | 67.453 | 28.938 | 23.575 | 1.00 | 39.28 | C |
| ATOM | 806 | C | ASP | A | 227 | 67.986 | 27.529 | 23.842 | 1.00 | 40.76 | C |
| ATOM | 807 | O | ASP | A | 227 | 68.841 | 27.032 | 23.103 | 1.00 | 39.48 | O |
| ATOM | 808 | CB | ASP | A | 227 | 65.929 | 28.897 | 23.374 | 1.00 | 39.13 | C |
| ATOM | 809 | CG | ASP | A | 227 | 65.510 | 28.134 | 22.123 | 1.00 | 39.09 | C |

TABLE 4-continued

| ATOM | 810 | OD1 | ASP | A | 227 | 66.196 | 27.164 | 21.740 | 1.00 | 39.60 | O |
| --- | --- | --- | --- | --- | --- | --- | --- | --- | --- | --- | --- |
| ATOM | 811 | OD2 | ASP | A | 227 | 64.472 | 28.498 | 21.529 | 1.00 | 38.30 | O |
| ATOM | 812 | N | SER | A | 228 | 67.478 | 26.888 | 24.891 | 1.00 | 43.19 | N |
| ATOM | 813 | CA | SER | A | 228 | 67.918 | 25.544 | 25.262 | 1.00 | 45.34 | C |
| ATOM | 814 | C | SER | A | 228 | 67.723 | 24.504 | 24.157 | 1.00 | 46.69 | C |
| ATOM | 815 | O | SER | A | 228 | 68.239 | 23.388 | 24.255 | 1.00 | 47.84 | O |
| ATOM | 816 | CB | SER | A | 228 | 67.202 | 25.088 | 26.537 | 1.00 | 45.27 | C |
| ATOM | 817 | OG | SER | A | 228 | 65.796 | 25.143 | 26.379 | 1.00 | 46.27 | O |
| ATOM | 818 | N | GLN | A | 229 | 66.988 | 24.868 | 23.110 | 1.00 | 47.37 | N |
| ATOM | 819 | CA | GLN | A | 229 | 66.746 | 23.962 | 21.990 | 1.00 | 47.48 | C |
| ATOM | 820 | C | GLN | A | 229 | 67.631 | 24.320 | 20.797 | 1.00 | 47.27 | C |
| ATOM | 821 | O | GLN | A | 229 | 67.433 | 23.812 | 19.691 | 1.00 | 46.74 | O |
| ATOM | 822 | CB | GLN | A | 229 | 65.272 | 24.014 | 21.573 | 1.00 | 48.89 | C |
| ATOM | 823 | CG | GLN | A | 229 | 64.301 | 23.525 | 22.639 | 1.00 | 50.86 | C |
| ATOM | 824 | CD | GLN | A | 229 | 62.849 | 23.622 | 22.197 | 1.00 | 53.57 | C |
| ATOM | 825 | OE1 | GLN | A | 229 | 62.439 | 22.989 | 21.221 | 1.00 | 54.79 | O |
| ATOM | 826 | NE2 | GLN | A | 229 | 62.063 | 24.421 | 22.913 | 1.00 | 54.30 | N |
| ATOM | 827 | N | LYS | A | 230 | 68.603 | 25.200 | 21.032 | 1.00 | 46.64 | N |
| ATOM | 828 | CA | LYS | A | 230 | 69.534 | 25.642 | 19.994 | 1.00 | 45.65 | C |
| ATOM | 829 | C | LYS | A | 230 | 68.876 | 26.513 | 18.925 | 1.00 | 43.41 | C |
| ATOM | 830 | O | LYS | A | 230 | 69.462 | 26.758 | 17.870 | 1.00 | 43.63 | O |
| ATOM | 831 | CB | LYS | A | 230 | 70.199 | 24.434 | 19.324 | 1.00 | 48.29 | C |
| ATOM | 832 | CG | LYS | A | 230 | 70.961 | 23.521 | 20.277 | 1.00 | 52.07 | C |
| ATOM | 833 | CD | LYS | A | 230 | 72.156 | 24.222 | 20.911 | 1.00 | 55.27 | C |
| ATOM | 834 | CE | LYS | A | 230 | 72.890 | 23.286 | 21.871 | 1.00 | 57.57 | C |
| ATOM | 835 | NZ | LYS | A | 230 | 74.090 | 23.919 | 22.492 | 1.00 | 58.56 | N |
| ATOM | 836 | N | ARG | A | 231 | 67.663 | 26.982 | 19.197 | 1.00 | 41.68 | N |
| ATOM | 837 | CA | ARG | A | 231 | 66.947 | 27.829 | 18.246 | 1.00 | 40.28 | C |
| ATOM | 838 | C | ARG | A | 231 | 67.277 | 29.302 | 18.488 | 1.00 | 38.35 | C |
| ATOM | 839 | O | ARG | A | 231 | 67.386 | 29.739 | 19.634 | 1.00 | 36.97 | O |
| ATOM | 840 | CB | ARG | A | 231 | 65.438 | 27.626 | 18.386 | 1.00 | 41.68 | C |
| ATOM | 841 | CG | ARG | A | 231 | 64.972 | 26.186 | 18.232 | 1.00 | 43.64 | C |
| ATOM | 842 | CD | ARG | A | 231 | 63.472 | 26.084 | 18.443 | 1.00 | 45.03 | C |
| ATOM | 843 | NE | ARG | A | 231 | 63.077 | 26.614 | 19.746 | 1.00 | 46.86 | N |
| ATOM | 844 | CZ | ARG | A | 231 | 61.817 | 26.753 | 20.150 | 1.00 | 48.34 | C |
| ATOM | 845 | NH1 | ARG | A | 231 | 60.814 | 26.402 | 19.354 | 1.00 | 48.72 | N |
| ATOM | 846 | NH2 | ARG | A | 231 | 61.559 | 27.248 | 21.355 | 1.00 | 49.43 | N |
| ATOM | 847 | N | TYR | A | 232 | 67.431 | 30.061 | 17.406 | 1.00 | 36.49 | N |
| ATOM | 848 | CA | TYR | A | 232 | 67.742 | 31.483 | 17.510 | 1.00 | 34.28 | C |
| ATOM | 849 | C | TYR | A | 232 | 66.713 | 32.225 | 18.352 | 1.00 | 33.16 | C |
| ATOM | 850 | O | TYR | A | 232 | 65.514 | 31.959 | 18.265 | 1.00 | 33.82 | O |
| ATOM | 851 | CS | TYR | A | 232 | 67.791 | 32.131 | 16.127 | 1.00 | 33.26 | C |
| ATOM | 852 | CG | TYR | A | 232 | 68.892 | 31.630 | 15.232 | 1.00 | 32.73 | C |
| ATOM | 853 | CD1 | TYR | A | 232 | 70.213 | 31.584 | 15.672 | 1.00 | 32.85 | C |
| ATOM | 854 | CD2 | TYR | A | 232 | 68.614 | 31.215 | 13.932 | 1.00 | 33.54 | C |
| ATOM | 855 | CE1 | TYR | A | 232 | 71.237 | 31.131 | 14.830 | 1.00 | 33.51 | C |
| ATOM | 856 | CE2 | TYR | A | 232 | 69.620 | 30.764 | 13.087 | 1.00 | 33.65 | C |
| ATOM | 857 | CZ | TYR | A | 232 | 70.927 | 30.724 | 13.540 | 1.00 | 33.53 | C |
| ATOM | 858 | OH | TYR | A | 232 | 71.910 | 30.270 | 12.695 | 1.00 | 34.70 | O |
| ATOM | 859 | N | LEU | A | 233 | 67.186 | 33.151 | 19.177 | 1.00 | 32.10 | N |
| ATOM | 860 | CA | LEU | A | 233 | 66.290 | 33.942 | 20.008 | 1.00 | 31.00 | C |
| ATOM | 861 | C | LEU | A | 233 | 65.707 | 35.036 | 19.132 | 1.00 | 29.82 | C |
| ATOM | 862 | O | LEU | A | 233 | 66.346 | 35.479 | 18.175 | 1.00 | 29.69 | O |
| ATOM | 863 | CB | LEU | A | 233 | 67.051 | 34.571 | 21.180 | 1.00 | 30.50 | C |
| ATOM | 864 | CG | LEU | A | 233 | 66.828 | 33.952 | 22.564 | 1.00 | 32.28 | C |
| ATOM | 865 | CD1 | LEU | A | 233 | 66.898 | 32.442 | 22.480 | 1.00 | 31.52 | C |
| ATOM | 866 | CD2 | LEU | A | 233 | 67.867 | 34.488 | 23.542 | 1.00 | 30.57 | C |
| ATOM | 867 | N | VAL | A | 234 | 64.491 | 35.461 | 19.446 | 1.00 | 28.87 | N |
| ATOM | 868 | CA | VAL | A | 234 | 63.855 | 36.517 | 18.675 | 1.00 | 28.85 | C |
| ATOM | 869 | C | VAL | A | 234 | 62.872 | 37.272 | 19.552 | 1.00 | 29.58 | C |
| ATOM | 870 | O | VAL | A | 234 | 62.257 | 36.699 | 20.454 | 1.00 | 29.60 | O |
| ATOM | 871 | CB | VAL | A | 234 | 63.113 | 35.952 | 17.431 | 1.00 | 28.52 | C |
| ATOM | 872 | CG1 | VAL | A | 234 | 61.924 | 35.100 | 17.861 | 1.00 | 27.33 | C |
| ATOM | 873 | CG2 | VAL | A | 234 | 62.669 | 37.091 | 16.533 | 1.00 | 26.42 | C |
| ATOM | 874 | N | GLY | A | 235 | 62.752 | 38.571 | 19.299 | 1.00 | 29.15 | N |
| ATOM | 875 | CA | GLY | A | 235 | 61.835 | 39.387 | 20.065 | 1.00 | 29.25 | C |
| ATOM | 876 | C | GLY | A | 235 | 60.701 | 39.852 | 19.178 | 1.00 | 30.00 | C |
| ATOM | 877 | O | GLY | A | 235 | 60.745 | 39.678 | 17.955 | 1.00 | 29.63 | O |
| ATOM | 878 | N | ALA | A | 236 | 59.680 | 40.444 | 19.786 | 1.00 | 29.18 | N |
| ATOM | 879 | CA | ALA | A | 236 | 58.545 | 40.932 | 19.023 | 1.00 | 29.42 | C |
| ATOM | 880 | C | ALA | A | 236 | 57.930 | 42.156 | 19.681 | 1.00 | 28.94 | C |
| ATOM | 881 | O | ALA | A | 236 | 57.700 | 42.175 | 20.887 | 1.00 | 30.25 | O |
| ATOM | 882 | CB | ALA | A | 236 | 57.502 | 39.828 | 18.880 | 1.00 | 30.04 | C |
| ATOM | 883 | N | GLY | A | 237 | 57.675 | 43.185 | 18.885 | 1.00 | 28.85 | N |
| ATOM | 884 | CA | GLY | A | 237 | 57.072 | 44.386 | 19.426 | 1.00 | 29.68 | C |
| ATOM | 885 | C | GLY | A | 237 | 55.565 | 44.232 | 19.522 | 1.00 | 30.66 | C |
| ATOM | 886 | O | GLY | A | 237 | 54.957 | 43.541 | 18.700 | 1.00 | 31.29 | O |
| ATOM | 887 | N | ILE | A | 238 | 54.969 | 44.850 | 20.540 | 1.00 | 30.86 | N |
| ATOM | 888 | CA | ILE | A | 238 | 53.524 | 44.811 | 20.734 | 1.00 | 31.71 | C |

TABLE 4-continued

| ATOM | 889 | C | ILE | A | 238 | 53.038 | 46.228 | 21.055 | 1.00 | 32.48 | C |
|---|---|---|---|---|---|---|---|---|---|---|---|
| ATOM | 890 | O | ILE | A | 238 | 53.834 | 47.106 | 21.385 | 1.00 | 31.88 | O |
| ATOM | 891 | CB | ILE | A | 238 | 53.107 | 43.869 | 21.901 | 1.00 | 32.49 | C |
| ATOM | 892 | CG1 | ILE | A | 238 | 53.631 | 44.409 | 23.233 | 1.00 | 32.43 | C |
| ATOM | 893 | CG2 | ILE | A | 238 | 53.626 | 42.458 | 21.652 | 1.00 | 31.98 | C |
| ATOM | 894 | CD1 | ILE | A | 238 | 53.098 | 43.658 | 24.452 | 1.00 | 31.48 | C |
| ATOM | 895 | N | ASN | A | 239 | 51.732 | 46.451 | 20.946 | 1.00 | 32.65 | N |
| ATOM | 896 | CA | ASN | A | 239 | 51.171 | 47.761 | 21.232 | 1.00 | 33.12 | C |
| ATOM | 897 | C | ASN | A | 239 | 50.172 | 47.661 | 22.375 | 1.00 | 34.35 | C |
| ATOM | 898 | O | ASN | A | 239 | 49.801 | 46.559 | 22.798 | 1.00 | 34.32 | O |
| ATOM | 899 | CB | ASN | A | 239 | 50.508 | 48.344 | 19.977 | 1.00 | 33.45 | C |
| ATOM | 900 | CG | ASN | A | 239 | 49.374 | 47.478 | 19.450 | 1.00 | 33.90 | C |
| ATOM | 901 | OD1 | ASN | A | 239 | 48.333 | 47.342 | 20.090 | 1.00 | 33.39 | O |
| ATOM | 902 | ND2 | ASN | A | 239 | 49.576 | 46.889 | 18.278 | 1.00 | 33.29 | N |
| ATOM | 903 | N | THR | A | 240 | 49.743 | 48.810 | 22.883 | 1.00 | 35.36 | N |
| ATOM | 904 | CA | THR | A | 240 | 48.799 | 48.847 | 23.993 | 1.00 | 35.80 | C |
| ATOM | 905 | C | THR | A | 240 | 47.337 | 48.691 | 23.576 | 1.00 | 37.42 | C |
| ATOM | 906 | O | THR | A | 240 | 46.444 | 48.870 | 24.401 | 1.00 | 36.13 | O |
| ATOM | 907 | CB | THR | A | 240 | 48.923 | 50.162 | 24.770 | 1.00 | 34.93 | C |
| ATOM | 908 | OG1 | THR | A | 240 | 48.776 | 51.257 | 23.859 | 1.00 | 34.76 | O |
| ATOM | 909 | CG2 | THR | A | 240 | 50.273 | 50.252 | 25.467 | 1.00 | 33.70 | C |
| ATOM | 910 | N | ARG | A | 241 | 47.086 | 48.349 | 22.313 | 1.00 | 39.17 | N |
| ATOM | 911 | CA | ARG | A | 241 | 45.707 | 48.208 | 21.853 | 1.00 | 42.57 | C |
| ATOM | 912 | C | ARG | A | 241 | 45.212 | 46.785 | 21.603 | 1.00 | 42.28 | C |
| ATOM | 913 | O | ARG | A | 241 | 44.262 | 46.347 | 22.247 | 1.00 | 43.14 | O |
| ATOM | 914 | CB | ARG | A | 241 | 45.484 | 49.058 | 20.598 | 1.00 | 45.89 | C |
| ATOM | 915 | CG | ARG | A | 241 | 45.948 | 50.498 | 20.767 | 1.00 | 51.37 | C |
| ATOM | 916 | CD | ARG | A | 241 | 45.095 | 51.484 | 19.983 | 1.00 | 56.20 | C |
| ATOM | 917 | NE | ARG | A | 241 | 45.628 | 52.843 | 20.084 | 1.00 | 60.59 | N |
| ATOM | 918 | CZ | ARG | A | 241 | 44.928 | 53.947 | 19.834 | 1.00 | 62.98 | C |
| ATOM | 919 | NH1 | ARG | A | 241 | 43.654 | 53.862 | 19.468 | 1.00 | 63.64 | N |
| ATOM | 920 | NH2 | ARG | A | 241 | 45.505 | 55.138 | 19.945 | 1.00 | 64.03 | N |
| ATOM | 921 | N | ASP | A | 242 | 45.843 | 46.063 | 20.682 | 1.00 | 41.72 | N |
| ATOM | 922 | CA | ASP | A | 242 | 45.410 | 44.698 | 20.373 | 1.00 | 42.47 | C |
| ATOM | 923 | C | ASP | A | 242 | 46.241 | 43.591 | 21.030 | 1.00 | 41.62 | C |
| ATOM | 924 | O | ASP | A | 242 | 46.326 | 42.488 | 20.501 | 1.00 | 41.70 | O |
| ATOM | 925 | CS | ASP | A | 242 | 45.403 | 44.478 | 18.853 | 1.00 | 42.18 | C |
| ATOM | 926 | CG | ASP | A | 242 | 46.799 | 44.528 | 18.240 | 1.00 | 44.11 | C |
| ATOM | 927 | OD1 | ASP | A | 242 | 47.791 | 44.451 | 18.998 | 1.00 | 43.54 | O |
| ATOM | 928 | OD2 | ASP | A | 242 | 46.903 | 44.631 | 16.995 | 1.00 | 42.81 | O |
| ATOM | 929 | N | PHE | A | 243 | 46.830 | 43.876 | 22.186 | 1.00 | 41.52 | N |
| ATOM | 930 | CA | PHE | A | 243 | 47.668 | 42.897 | 22.878 | 1.00 | 41.20 | C |
| ATOM | 931 | C | PHE | A | 243 | 46.966 | 41.623 | 23.352 | 1.00 | 42.11 | C |
| ATOM | 932 | O | PHE | A | 243 | 47.603 | 40.573 | 23.467 | 1.00 | 42.24 | O |
| ATOM | 933 | CB | PHE | A | 243 | 48.387 | 43.565 | 24.058 | 1.00 | 38.57 | C |
| ATOM | 934 | CG | PHE | A | 243 | 47.465 | 44.128 | 25.095 | 1.00 | 37.00 | C |
| ATOM | 935 | CD1 | PHE | A | 243 | 46.983 | 43.327 | 26.123 | 1.00 | 36.77 | C |
| ATOM | 936 | CD2 | PHE | A | 243 | 47.083 | 45.464 | 25.051 | 1.00 | 36.43 | C |
| ATOM | 937 | CE1 | PHE | A | 243 | 46.136 | 43.847 | 27.096 | 1.00 | 35.68 | C |
| ATOM | 938 | CE2 | PHE | A | 243 | 46.237 | 45.996 | 26.017 | 1.00 | 36.27 | C |
| ATOM | 939 | CZ | PHE | A | 243 | 45.762 | 45.185 | 27.044 | 1.00 | 36.83 | C |
| ATOM | 940 | N | ARG | A | 244 | 45.666 | 41.702 | 23.623 | 1.00 | 43.08 | N |
| ATOM | 941 | CA | ARG | A | 244 | 44.926 | 40.526 | 24.078 | 1.00 | 43.54 | C |
| ATOM | 942 | C | ARG | A | 244 | 44.890 | 39.447 | 22.996 | 1.00 | 43.52 | C |
| ATOM | 943 | O | ARG | A | 244 | 44.803 | 38.257 | 23.297 | 1.00 | 43.24 | O |
| ATOM | 944 | CB | ARG | A | 244 | 43.502 | 40.914 | 24.498 | 1.00 | 43.28 | C |
| ATOM | 945 | CG | ARG | A | 244 | 43.455 | 41.843 | 25.705 | 1.00 | 43.47 | C |
| ATOM | 946 | CD | ARG | A | 244 | 42.029 | 42.095 | 26.172 | 1.00 | 44.74 | C |
| ATOM | 947 | NE | ARG | A | 244 | 41.971 | 43.071 | 27.259 | 1.00 | 45.31 | N |
| ATOM | 948 | CZ | ARG | A | 244 | 42.192 | 44.376 | 27.110 | 1.00 | 46.31 | C |
| ATOM | 949 | NH1 | ARG | A | 244 | 42.485 | 44.872 | 25.914 | 1.00 | 44.51 | N |
| ATOM | 950 | NH2 | ARG | A | 244 | 42.123 | 45.188 | 28.159 | 1.00 | 44.79 | N |
| ATOM | 951 | N | GLU | A | 245 | 44.960 | 39.867 | 21.736 | 1.00 | 44.04 | N |
| ATOM | 952 | CA | GLU | A | 245 | 44.959 | 38.928 | 20.618 | 1.00 | 44.49 | C |
| ATOM | 953 | C | GLU | A | 245 | 46.371 | 38.707 | 20.078 | 1.00 | 43.54 | C |
| ATOM | 954 | O | GLU | A | 245 | 46.720 | 37.601 | 19.665 | 1.00 | 43.64 | O |
| ATOM | 955 | CB | GLU | A | 245 | 44.067 | 39.439 | 19.479 | 1.00 | 47.18 | C |
| ATOM | 956 | CG | GLU | A | 245 | 42.599 | 39.036 | 19.570 | 1.00 | 51.54 | C |
| ATOM | 957 | CD | GLU | A | 245 | 41.917 | 39.551 | 20.822 | 1.00 | 54.39 | C |
| ATOM | 958 | OE1 | GLU | A | 245 | 41.972 | 40.777 | 21.070 | 1.00 | 56.74 | O |
| ATOM | 959 | OE2 | GLU | A | 245 | 41.320 | 38.730 | 21.555 | 1.00 | 56.12 | O |
| ATOM | 960 | N | ARG | A | 246 | 47.183 | 39.761 | 20.088 | 1.00 | 41.72 | N |
| ATOM | 961 | CA | ARG | A | 246 | 48.547 | 39.679 | 19.569 | 1.00 | 40.10 | C |
| ATOM | 962 | C | ARG | A | 246 | 49.529 | 38.897 | 20.449 | 1.00 | 38.51 | C |
| ATOM | 963 | O | ARG | A | 246 | 50.305 | 38.087 | 19.943 | 1.00 | 37.50 | O |
| ATOM | 964 | CD | ARG | A | 246 | 49.093 | 41.091 | 19.314 | 1.00 | 39.02 | C |
| ATOM | 965 | CG | ARG | A | 246 | 50.417 | 41.125 | 18.558 | 1.00 | 38.76 | C |
| ATOM | 966 | CD | ARG | A | 246 | 50.877 | 42.560 | 18.333 | 1.00 | 39.34 | C |
| ATOM | 967 | NE | ARG | A | 246 | 49.978 | 43.314 | 17.460 | 1.00 | 37.43 | N |

TABLE 4-continued

| | | | | | | | | | | |
|---|---|---|---|---|---|---|---|---|---|---|
| ATOM | 968 | CZ | ARG | A | 246 | 49.985 | 43.242 | 16.132 | 1.00 | 38.30 | C |
| ATOM | 969 | NH1 | ARG | A | 246 | 50.847 | 42.450 | 15.507 | 1.00 | 37.21 | N |
| ATOM | 970 | NH2 | ARG | A | 246 | 49.129 | 43.967 | 15.422 | 1.00 | 39.33 | N |
| ATOM | 971 | N | VAL | A | 247 | 49.502 | 39.137 | 21.756 | 1.00 | 37.24 | N |
| ATOM | 972 | CA | VAL | A | 247 | 50.414 | 38.440 | 22.657 | 1.00 | 37.34 | C |
| ATOM | 973 | C | VAL | A | 247 | 50.303 | 36.918 | 22.523 | 1.00 | 38.18 | C |
| ATOM | 974 | O | VAL | A | 247 | 51.292 | 36.251 | 22.209 | 1.00 | 38.12 | O |
| ATOM | 975 | CD | VAL | A | 247 | 50.185 | 38.872 | 24.129 | 1.00 | 36.77 | C |
| ATOM | 976 | CG1 | VAL | A | 247 | 51.023 | 38.026 | 25.070 | 1.00 | 35.70 | C |
| ATOM | 977 | CG2 | VAL | A | 247 | 50.550 | 40.343 | 24.293 | 1.00 | 37.03 | C |
| ATOM | 978 | N | PRO | A | 248 | 49.100 | 36.347 | 22.747 | 1.00 | 38.57 | N |
| ATOM | 979 | CA | PRO | A | 248 | 48.934 | 34.892 | 22.631 | 1.00 | 38.12 | C |
| ATOM | 980 | C | PRO | A | 248 | 49.506 | 34.329 | 21.333 | 1.00 | 37.59 | C |
| ATOM | 981 | O | PRO | A | 248 | 50.166 | 33.293 | 21.336 | 1.00 | 37.87 | O |
| ATOM | 982 | CB | PRO | A | 248 | 47.422 | 34.714 | 22.729 | 1.00 | 38.80 | C |
| ATOM | 983 | CG | PRO | A | 248 | 47.039 | 35.791 | 23.701 | 1.00 | 38.59 | C |
| ATOM | 984 | CD | PRO | A | 248 | 47.840 | 36.979 | 23.188 | 1.00 | 38.38 | C |
| ATOM | 985 | N | ALA | A | 249 | 49.256 | 35.016 | 20.224 | 1.00 | 37.30 | N |
| ATOM | 986 | CA | ALA | A | 249 | 49.763 | 34.573 | 18.932 | 1.00 | 38.37 | C |
| ATOM | 987 | C | ALA | A | 249 | 51.292 | 34.588 | 18.923 | 1.00 | 39.52 | C |
| ATOM | 988 | O | ALA | A | 249 | 51.931 | 33.682 | 18.379 | 1.00 | 38.98 | O |
| ATOM | 989 | CB | ALA | A | 249 | 49.228 | 35.471 | 17.826 | 1.00 | 38.41 | C |
| ATOM | 990 | N | LEU | A | 250 | 51.872 | 35.625 | 19.526 | 1.00 | 39.58 | N |
| ATOM | 991 | CA | LEU | A | 250 | 53.322 | 35.761 | 19.587 | 1.00 | 39.74 | C |
| ATOM | 992 | C | LEU | A | 250 | 53.935 | 34.682 | 20.475 | 1.00 | 39.38 | C |
| ATOM | 993 | O | LEU | A | 250 | 54.951 | 34.082 | 20.123 | 1.00 | 38.34 | O |
| ATOM | 994 | CB | LEU | A | 250 | 53.695 | 37.163 | 20.092 | 1.00 | 39.96 | C |
| ATOM | 995 | CG | LEU | A | 250 | 54.043 | 38.222 | 19.029 | 1.00 | 40.83 | C |
| ATOM | 996 | CD1 | LEU | A | 250 | 53.463 | 37.859 | 17.678 | 1.00 | 39.28 | C |
| ATOM | 997 | CD2 | LEU | A | 250 | 53.540 | 39.582 | 19.487 | 1.00 | 39.93 | C |
| ATOM | 998 | N | VAL | A | 251 | 53.310 | 34.434 | 21.620 | 1.00 | 39.76 | N |
| ATOM | 999 | CA | VAL | A | 251 | 53.793 | 33.409 | 22.537 | 1.00 | 41.50 | C |
| ATOM | 1000 | C | VAL | A | 251 | 53.714 | 32.055 | 21.845 | 1.00 | 42.53 | C |
| ATOM | 1001 | O | VAL | A | 251 | 54.690 | 31.303 | 21.810 | 1.00 | 42.76 | O |
| ATOM | 1002 | CB | VAL | A | 251 | 52.940 | 33.354 | 23.818 | 1.00 | 41.62 | C |
| ATOM | 1003 | CG1 | VAL | A | 251 | 53.352 | 32.161 | 24.671 | 1.00 | 41.89 | C |
| ATOM | 1004 | CG2 | VAL | A | 251 | 53.104 | 34.644 | 24.600 | 1.00 | 41.93 | C |
| ATOM | 1005 | N | GLU | A | 252 | 52.541 | 31.756 | 21.293 | 1.00 | 43.62 | N |
| ATOM | 1006 | CA | GLU | A | 252 | 52.317 | 30.500 | 20.590 | 1.00 | 43.74 | C |
| ATOM | 1007 | C | GLU | A | 252 | 53.332 | 30.314 | 19.465 | 1.00 | 41.50 | C |
| ATOM | 1008 | O | GLU | A | 252 | 53.789 | 29.203 | 19.215 | 1.00 | 41.39 | O |
| ATOM | 1009 | CB | GLU | A | 252 | 50.893 | 30.456 | 20.020 | 1.00 | 46.53 | C |
| ATOM | 1010 | CG | GLU | A | 252 | 49.920 | 29.576 | 20.810 | 1.00 | 51.69 | C |
| ATOM | 1011 | CD | GLU | A | 252 | 49.586 | 30.124 | 22.193 | 1.00 | 54.01 | C |
| ATOM | 1012 | OE1 | GLU | A | 252 | 48.841 | 31.128 | 22.279 | 1.00 | 53.93 | O |
| ATOM | 1013 | OE2 | GLU | A | 252 | 50.070 | 29.545 | 23.194 | 1.00 | 55.79 | O |
| ATOM | 1014 | N | ALA | A | 253 | 53.682 | 31.404 | 18.788 | 1.00 | 38.82 | N |
| ATOM | 1015 | CA | ALA | A | 253 | 54.651 | 31.343 | 17.698 | 1.00 | 36.89 | C |
| ATOM | 1016 | C | ALA | A | 253 | 56.078 | 31.102 | 18.212 | 1.00 | 36.24 | C |
| ATOM | 1017 | O | ALA | A | 253 | 56.968 | 30.739 | 17.441 | 1.00 | 35.13 | O |
| ATOM | 1018 | CB | ALA | A | 253 | 54.596 | 32.622 | 16.881 | 1.00 | 35.91 | C |
| ATOM | 1019 | N | GLY | A | 254 | 56.292 | 31.313 | 19.510 | 1.00 | 35.29 | N |
| ATOM | 1020 | CA | GLY | A | 254 | 57.609 | 31.085 | 20.086 | 1.00 | 35.95 | C |
| ATOM | 1021 | C | GLY | A | 254 | 58.480 | 32.301 | 20.380 | 1.00 | 35.64 | C |
| ATOM | 1022 | O | GLY | A | 254 | 59.684 | 32.159 | 20.578 | 1.00 | 35.66 | O |
| ATOM | 1023 | N | ALA | A | 255 | 57.895 | 33.493 | 20.410 | 1.00 | 35.20 | N |
| ATOM | 1024 | CA | ALA | A | 255 | 58.675 | 34.694 | 20.697 | 1.00 | 33.82 | C |
| ATOM | 1025 | C | ALA | A | 255 | 59.321 | 34.554 | 22.074 | 1.00 | 32.75 | C |
| ATOM | 1026 | O | ALA | A | 255 | 58.653 | 34.196 | 23.045 | 1.00 | 32.02 | O |
| ATOM | 1027 | CB | ALA | A | 255 | 57.779 | 35.922 | 20.657 | 1.00 | 33.94 | C |
| ATOM | 1028 | N | ASP | A | 256 | 60.621 | 34.834 | 22.156 | 1.00 | 31.67 | N |
| ATOM | 1029 | CA | ASP | A | 256 | 61.351 | 34.723 | 23.418 | 1.00 | 32.02 | C |
| ATOM | 1030 | C | ASP | A | 256 | 61.145 | 35.912 | 24.355 | 1.00 | 31.11 | C |
| ATOM | 1031 | O | ASP | A | 256 | 61.234 | 35.777 | 25.574 | 1.00 | 30.14 | O |
| ATOM | 1032 | CB | ASP | A | 256 | 62.841 | 34.541 | 23.139 | 1.00 | 33.02 | C |
| ATOM | 1033 | CG | ASP | A | 256 | 63.129 | 33.275 | 22.362 | 1.00 | 34.81 | C |
| ATOM | 1034 | OD1 | ASP | A | 256 | 63.114 | 32.188 | 22.979 | 1.00 | 36.54 | O |
| ATOM | 1035 | OD2 | ASP | A | 256 | 63.350 | 33.365 | 21.135 | 1.00 | 33.32 | O |
| ATOM | 1036 | N | VAL | A | 257 | 60.871 | 37.077 | 23.784 | 1.00 | 30.39 | N |
| ATOM | 1037 | CA | VAL | A | 257 | 60.660 | 38.271 | 24.589 | 1.00 | 29.66 | C |
| ATOM | 1038 | C | VAL | A | 257 | 59.823 | 39.270 | 23.808 | 1.00 | 29.38 | C |
| ATOM | 1039 | O | VAL | A | 257 | 59.879 | 39.308 | 22.582 | 1.00 | 28.28 | O |
| ATOM | 1040 | CB | VAL | A | 257 | 62.012 | 38.911 | 24.988 | 1.00 | 29.16 | C |
| ATOM | 1041 | CG1 | VAL | A | 257 | 62.829 | 39.194 | 23.747 | 1.00 | 29.29 | C |
| ATOM | 1042 | CG2 | VAL | A | 257 | 61.782 | 40.177 | 25.798 | 1.00 | 28.00 | C |
| ATOM | 1043 | N | LEU | A | 258 | 59.038 | 40.065 | 24.523 | 1.00 | 28.75 | N |
| ATOM | 1044 | CA | LEU | A | 258 | 58.187 | 41.059 | 23.886 | 1.00 | 29.85 | C |
| ATOM | 1045 | C | LEU | A | 258 | 58.608 | 42.453 | 24.344 | 1.00 | 29.91 | C |
| ATOM | 1046 | O | LEU | A | 258 | 59.381 | 42.597 | 25.293 | 1.00 | 30.16 | O |

TABLE 4-continued

| | | | | | | | | | | |
|---|---|---|---|---|---|---|---|---|---|---|
| ATOM | 1047 | CB | LEU | A | 258 | 56.720 | 40.823 | 24.265 | 1.00 | 28.53 | C |
| ATOM | 1048 | CG | LEU | A | 258 | 56.167 | 39.402 | 24.111 | 1.00 | 29.86 | C |
| ATOM | 1049 | CD1 | LEU | A | 258 | 54.713 | 39.397 | 24.543 | 1.00 | 30.36 | C |
| ATOM | 1050 | CD2 | LEU | A | 258 | 56.296 | 38.921 | 22.670 | 1.00 | 28.79 | C |
| ATOM | 1051 | N | CYS | A | 259 | 58.104 | 43.477 | 23.663 | 1.00 | 29.40 | N |
| ATOM | 1052 | CA | CYS | A | 259 | 58.416 | 44.850 | 24.034 | 1.00 | 28.72 | C |
| ATOM | 1053 | C | CYS | A | 259 | 57.344 | 45.795 | 23.530 | 1.00 | 27.77 | C |
| ATOM | 1054 | O | CYS | A | 259 | 57.043 | 45.820 | 22.337 | 1.00 | 27.16 | O |
| ATOM | 1055 | CB | CYS | A | 259 | 59.772 | 45.285 | 23.465 | 1.00 | 28.20 | C |
| ATOM | 1056 | SG | CYS | A | 259 | 60.305 | 46.904 | 24.092 | 1.00 | 28.27 | S |
| ATOM | 1057 | N | ILE | A | 260 | 56.766 | 46.564 | 24.446 | 1.00 | 28.22 | N |
| ATOM | 1058 | CA | ILE | A | 260 | 55.744 | 47.533 | 24.083 | 1.00 | 29.67 | C |
| ATOM | 1059 | C | ILE | A | 260 | 56.463 | 48.683 | 23.373 | 1.00 | 31.98 | C |
| ATOM | 1060 | O | ILE | A | 260 | 57.365 | 49.308 | 23.927 | 1.00 | 31.74 | O |
| ATOM | 1061 | CB | ILE | A | 260 | 55.010 | 48.056 | 25.325 | 1.00 | 28.89 | C |
| ATOM | 1062 | CG1 | ILE | A | 260 | 54.391 | 46.877 | 26.086 | 1.00 | 28.30 | C |
| ATOM | 1063 | CG2 | ILE | A | 260 | 53.926 | 49.045 | 24.912 | 1.00 | 26.45 | C |
| ATOM | 1064 | CD1 | ILE | A | 260 | 53.791 | 47.257 | 27.423 | 1.00 | 26.77 | C |
| ATOM | 1065 | N | ASP | A | 261 | 56.045 | 48.936 | 22.139 | 1.00 | 33.17 | N |
| ATOM | 1066 | CA | ASP | A | 261 | 56.625 | 49.951 | 21.267 | 1.00 | 35.06 | C |
| ATOM | 1067 | C | ASP | A | 261 | 55.836 | 51.272 | 21.315 | 1.00 | 35.12 | C |
| ATOM | 1068 | O | ASP | A | 261 | 54.712 | 51.338 | 20.820 | 1.00 | 36.56 | O |
| ATOM | 1069 | CB | ASP | A | 261 | 56.647 | 49.349 | 19.852 | 1.00 | 36.45 | C |
| ATOM | 1070 | CG | ASP | A | 261 | 57.248 | 50.264 | 18.819 | 1.00 | 38.72 | C |
| ATOM | 1071 | OD1 | ASP | A | 261 | 58.086 | 51.109 | 19.176 | 1.00 | 41.12 | O |
| ATOM | 1072 | OD2 | ASP | A | 261 | 56.892 | 50.118 | 17.630 | 1.00 | 41.11 | O |
| ATOM | 1073 | N | SER | A | 262 | 56.420 | 52.321 | 21.902 | 1.00 | 33.61 | N |
| ATOM | 1074 | CA | SER | A | 262 | 55.729 | 53.610 | 22.003 | 1.00 | 33.31 | C |
| ATOM | 1075 | C | SER | A | 262 | 56.640 | 54.837 | 22.141 | 1.00 | 32.60 | C |
| ATOM | 1076 | O | SER | A | 262 | 57.725 | 54.751 | 22.711 | 1.00 | 32.55 | O |
| ATOM | 1077 | CB | SER | A | 262 | 54.755 | 53.566 | 23.185 | 1.00 | 34.17 | C |
| ATOM | 1078 | OG | SER | A | 262 | 54.108 | 54.811 | 23.367 | 1.00 | 33.91 | O |
| ATOM | 1079 | N | SER | A | 263 | 56.185 | 55.986 | 21.638 | 1.00 | 31.57 | N |
| ATOM | 1080 | CA | SER | A | 263 | 56.976 | 57.216 | 21.715 | 1.00 | 31.90 | C |
| ATOM | 1081 | C | SER | A | 263 | 56.966 | 57.806 | 23.119 | 1.00 | 31.13 | C |
| ATOM | 1082 | O | SER | A | 263 | 57.846 | 58.585 | 23.483 | 1.00 | 32.42 | O |
| ATOM | 1083 | CB | SER | A | 263 | 56.471 | 58.265 | 20.709 | 1.00 | 32.36 | C |
| ATOM | 1084 | OG | SER | A | 263 | 55.175 | 58.741 | 21.027 | 1.00 | 34.74 | O |
| ATOM | 1085 | N | ASP | A | 264 | 55.963 | 57.441 | 23.905 | 1.00 | 29.11 | N |
| ATOM | 1086 | CA | ASP | A | 264 | 55.864 | 57.918 | 25.279 | 1.00 | 27.37 | C |
| ATOM | 1087 | C | ASP | A | 264 | 55.321 | 56.786 | 26.142 | 1.00 | 26.83 | C |
| ATOM | 1088 | O | ASP | A | 264 | 54.107 | 56.594 | 26.249 | 1.00 | 26.56 | O |
| ATOM | 1089 | CB | ASP | A | 264 | 54.960 | 59.156 | 25.351 | 1.00 | 26.62 | C |
| ATOM | 1090 | CG | ASP | A | 264 | 54.591 | 59.538 | 26.778 | 1.00 | 25.32 | C |
| ATOM | 1091 | OD1 | ASP | A | 264 | 55.309 | 59.148 | 27.725 | 1.00 | 23.54 | O |
| ATOM | 1092 | OD2 | ASP | A | 264 | 53.578 | 60.243 | 26.949 | 1.00 | 25.29 | O |
| ATOM | 1093 | N | GLY | A | 265 | 56.239 | 56.036 | 26.744 | 1.00 | 25.91 | N |
| ATOM | 1094 | CA | GLY | A | 265 | 55.868 | 54.908 | 27.581 | 1.00 | 26.10 | C |
| ATOM | 1095 | C | GLY | A | 265 | 55.421 | 55.273 | 28.981 | 1.00 | 26.66 | C |
| ATOM | 1096 | O | GLY | A | 265 | 55.005 | 54.404 | 29.750 | 1.00 | 26.18 | O |
| ATOM | 1097 | N | PHE | A | 266 | 55.514 | 56.551 | 29.328 | 1.00 | 26.34 | N |
| ATOM | 1098 | CA | PHE | A | 266 | 55.082 | 56.982 | 30.650 | 1.00 | 26.68 | C |
| ATOM | 1099 | C | PHE | A | 266 | 53.564 | 57.071 | 30.531 | 1.00 | 27.63 | C |
| ATOM | 1100 | O | PHE | A | 266 | 52.988 | 58.150 | 30.606 | 1.00 | 26.70 | O |
| ATOM | 1101 | CB | PHE | A | 266 | 55.677 | 58.352 | 30.984 | 1.00 | 25.83 | C |
| ATOM | 1102 | CG | PHE | A | 266 | 55.781 | 58.634 | 32.462 | 1.00 | 26.28 | C |
| ATOM | 1103 | CD1 | PHE | A | 266 | 55.018 | 57.915 | 33.386 | 1.00 | 25.02 | C |
| ATOM | 1104 | CD2 | PHE | A | 266 | 56.618 | 59.647 | 32.927 | 1.00 | 25.66 | C |
| ATOM | 1105 | CE1 | PHE | A | 266 | 55.083 | 58.201 | 34.745 | 1.00 | 23.88 | C |
| ATOM | 1106 | CE2 | PHE | A | 266 | 56.694 | 59.946 | 34.290 | 1.00 | 24.67 | C |
| ATOM | 1107 | CZ | PHE | A | 266 | 55.923 | 59.221 | 35.202 | 1.00 | 26.34 | C |
| ATOM | 1108 | N | SER | A | 267 | 52.924 | 55.917 | 30.338 | 1.00 | 29.46 | N |
| ATOM | 1109 | CA | SER | A | 267 | 51.477 | 55.855 | 30.154 | 1.00 | 30.33 | C |
| ATOM | 1110 | C | SER | A | 267 | 50.777 | 54.748 | 30.930 | 1.00 | 31.43 | C |
| ATOM | 1111 | O | SER | A | 267 | 51.302 | 53.642 | 31.087 | 1.00 | 29.64 | O |
| ATOM | 1112 | CB | SER | A | 267 | 51.160 | 55.677 | 28.670 | 1.00 | 30.83 | C |
| ATOM | 1113 | OG | SER | A | 267 | 49.775 | 55.456 | 28.462 | 1.00 | 33.50 | O |
| ATOM | 1114 | N | GLU | A | 268 | 49.572 | 55.053 | 31.394 | 1.00 | 32.18 | N |
| ATOM | 1115 | CA | GLU | A | 268 | 48.783 | 54.087 | 32.135 | 1.00 | 33.83 | C |
| ATOM | 1116 | C | GLU | A | 268 | 48.483 | 52.896 | 31.227 | 1.00 | 33.76 | C |
| ATOM | 1117 | O | GLU | A | 268 | 48.289 | 51.778 | 31.699 | 1.00 | 34.08 | O |
| ATOM | 1118 | CB | GLU | A | 268 | 47.481 | 54.729 | 32.621 | 1.00 | 35.26 | C |
| ATOM | 1119 | CG | GLU | A | 268 | 46.691 | 53.851 | 33.573 | 1.00 | 39.14 | C |
| ATOM | 1120 | CD | GLU | A | 268 | 45.494 | 54.561 | 34.188 | 1.00 | 41.79 | C |
| ATOM | 1121 | OE1 | GLU | A | 268 | 44.761 | 53.901 | 34.961 | 1.00 | 43.08 | O |
| ATOM | 1122 | OE2 | GLU | A | 268 | 45.286 | 55.767 | 33.908 | 1.00 | 41.44 | O |
| ATOM | 1123 | N | TRP | A | 269 | 48.458 | 53.133 | 29.920 | 1.00 | 33.42 | N |
| ATOM | 1124 | CA | TRP | A | 269 | 48.190 | 52.058 | 28.972 | 1.00 | 34.58 | C |
| ATOM | 1125 | C | TRP | A | 269 | 49.255 | 50.963 | 29.027 | 1.00 | 34.05 | C |

TABLE 4-continued

| | | | | | | | | | | |
|---|---|---|---|---|---|---|---|---|---|---|
| ATOM | 1126 | O | TRP | A | 269 | 48.942 | 49.784 | 28.846 | 1.00 | 33.83 | O |
| ATOM | 1127 | CB | TRP | A | 269 | 48.087 | 52.602 | 27.543 | 1.00 | 36.69 | C |
| ATOM | 1128 | CG | TRP | A | 269 | 46.919 | 53.508 | 27.340 | 1.00 | 40.80 | C |
| ATOM | 1129 | CD1 | TRP | A | 269 | 46.944 | 54.869 | 27.236 | 1.00 | 41.67 | C |
| ATOM | 1130 | CD2 | TRP | A | 269 | 45.540 | 53.126 | 27.268 | 1.00 | 42.61 | C |
| ATOM | 1131 | NE1 | TRP | A | 269 | 45.667 | 55.359 | 27.106 | 1.00 | 43.36 | N |
| ATOM | 1132 | CE2 | TRP | A | 269 | 44.785 | 54.311 | 27.123 | 1.00 | 43.31 | C |
| ATOM | 1133 | CE3 | TRP | A | 269 | 44.868 | 51.896 | 27.315 | 1.00 | 43.67 | C |
| ATOM | 1134 | CZ2 | TRP | A | 269 | 43.390 | 54.305 | 27.024 | 1.00 | 44.76 | C |
| ATOM | 1135 | CZ3 | TRP | A | 269 | 43.480 | 51.888 | 27.216 | 1.00 | 44.62 | C |
| ATOM | 1136 | CH2 | TRP | A | 269 | 42.757 | 53.087 | 27.072 | 1.00 | 45.35 | C |
| ATOM | 1137 | N | GLN | A | 270 | 50.510 | 51.344 | 29.257 | 1.00 | 32.55 | N |
| ATOM | 1138 | CA | GLN | A | 270 | 51.582 | 50.354 | 29.343 | 1.00 | 32.29 | C |
| ATOM | 1139 | C | GLN | A | 270 | 51.421 | 49.566 | 30.641 | 1.00 | 31.72 | C |
| ATOM | 1140 | O | GLN | A | 270 | 51.685 | 48.368 | 30.686 | 1.00 | 31.18 | O |
| ATOM | 1141 | CB | GLN | A | 270 | 52.961 | 51.025 | 29.314 | 1.00 | 31.01 | C |
| ATOM | 1142 | CG | GLN | A | 270 | 53.207 | 51.882 | 28.083 | 1.00 | 30.60 | C |
| ATOM | 1143 | CD | GLN | A | 270 | 54.489 | 51.525 | 27.357 | 1.00 | 30.06 | C |
| ATOM | 1144 | OE1 | GLN | A | 270 | 55.390 | 50.904 | 27.923 | 1.00 | 29.84 | O |
| ATOM | 1145 | NE2 | GLN | A | 270 | 54.584 | 51.932 | 26.100 | 1.00 | 28.50 | N |
| ATOM | 1146 | N | LYS | A | 271 | 50.991 | 50.246 | 31.698 | 1.00 | 32.14 | N |
| ATOM | 1147 | CA | LYS | A | 271 | 50.782 | 49.575 | 32.971 | 1.00 | 33.59 | C |
| ATOM | 1148 | C | LYS | A | 271 | 49.694 | 48.514 | 32.793 | 1.00 | 33.87 | C |
| ATOM | 1149 | O | LYS | A | 271 | 49.838 | 47.378 | 33.246 | 1.00 | 33.86 | O |
| ATOM | 1150 | CB | LYS | A | 271 | 50.355 | 50.568 | 34.051 | 1.00 | 33.76 | C |
| ATOM | 1151 | CG | LYS | A | 271 | 50.063 | 49.894 | 35.384 | 1.00 | 35.01 | C |
| ATOM | 1152 | CD | LYS | A | 271 | 49.834 | 50.893 | 36.498 | 1.00 | 36.09 | C |
| ATOM | 1153 | CE | LYS | A | 271 | 49.709 | 50.170 | 37.835 | 1.00 | 38.50 | C |
| ATOM | 1154 | NZ | LYS | A | 271 | 49.561 | 51.103 | 38.991 | 1.00 | 41.38 | N |
| ATOM | 1155 | N | ILE | A | 272 | 48.612 | 48.895 | 32.121 | 1.00 | 33.39 | N |
| ATOM | 1156 | CA | ILE | A | 272 | 47.501 | 47.987 | 31.873 | 1.00 | 34.07 | C |
| ATOM | 1157 | C | ILE | A | 272 | 47.957 | 46.798 | 31.034 | 1.00 | 33.99 | C |
| ATOM | 1158 | O | ILE | A | 272 | 47.635 | 45.653 | 31.345 | 1.00 | 34.22 | O |
| ATOM | 1159 | CB | ILE | A | 272 | 46.341 | 48.713 | 31.145 | 1.00 | 33.73 | C |
| ATOM | 1160 | CG1 | ILE | A | 272 | 45.735 | 49.768 | 32.074 | 1.00 | 34.18 | C |
| ATOM | 1161 | CG2 | ILE | A | 272 | 45.281 | 47.710 | 30.707 | 1.00 | 33.44 | C |
| ATOM | 1162 | CD1 | ILE | A | 272 | 44.704 | 50.668 | 31.413 | 1.00 | 34.51 | C |
| ATOM | 1163 | N | THR | A | 273 | 48.715 | 47.072 | 29.977 | 1.00 | 33.02 | N |
| ATOM | 1164 | CA | THR | A | 273 | 49.205 | 46.013 | 29.104 | 1.00 | 33.58 | C |
| ATOM | 1165 | C | THR | A | 273 | 50.099 | 45.011 | 29.835 | 1.00 | 34.00 | C |
| ATOM | 1166 | O | THR | A | 273 | 49.921 | 43.800 | 29.697 | 1.00 | 33.77 | O |
| ATOM | 1167 | CE | THR | A | 273 | 49.986 | 46.595 | 27.911 | 1.00 | 33.70 | C |
| ATOM | 1168 | OG1 | THR | A | 273 | 49.114 | 47.426 | 27.135 | 1.00 | 35.34 | O |
| ATOM | 1169 | CG2 | THR | A | 273 | 50.521 | 45.480 | 27.025 | 1.00 | 32.30 | C |
| ATOM | 1170 | N | ILE | A | 274 | 51.065 | 45.512 | 30.599 | 1.00 | 33.72 | N |
| ATOM | 1171 | CA | ILE | A | 274 | 51.969 | 44.640 | 31.340 | 1.00 | 33.64 | C |
| ATOM | 1172 | C | ILE | A | 274 | 51.176 | 43.843 | 32.375 | 1.00 | 34.72 | C |
| ATOM | 1173 | O | ILE | A | 274 | 51.414 | 42.650 | 32.571 | 1.00 | 33.85 | O |
| ATOM | 1174 | CB | ILE | A | 274 | 53.060 | 45.451 | 32.071 | 1.00 | 33.60 | C |
| ATOM | 1175 | CG1 | ILE | A | 274 | 53.927 | 46.194 | 31.051 | 1.00 | 33.18 | C |
| ATOM | 1176 | CG2 | ILE | A | 274 | 53.906 | 44.521 | 32.950 | 1.00 | 33.23 | C |
| ATOM | 1177 | CD1 | ILE | A | 274 | 54.987 | 47.089 | 31.674 | 1.00 | 33.18 | C |
| ATOM | 1178 | N | GLY | A | 275 | 50.231 | 44.513 | 33.030 | 1.00 | 34.87 | N |
| ATOM | 1179 | CA | GLY | A | 275 | 49.412 | 43.860 | 34.036 | 1.00 | 36.02 | C |
| ATOM | 1180 | C | GLY | A | 275 | 48.617 | 42.686 | 33.492 | 1.00 | 36.38 | C |
| ATOM | 1181 | O | GLY | A | 275 | 48.494 | 41.655 | 34.147 | 1.00 | 37.56 | O |
| ATOM | 1182 | N | TRP | A | 276 | 48.075 | 42.846 | 32.292 | 1.00 | 36.26 | N |
| ATOM | 1183 | CA | TRP | A | 276 | 47.292 | 41.796 | 31.656 | 1.00 | 36.36 | C |
| ATOM | 1184 | C | TRP | A | 276 | 48.193 | 40.601 | 31.366 | 1.00 | 37.31 | C |
| ATOM | 1185 | O | TRP | A | 276 | 47.788 | 39.448 | 31.531 | 1.00 | 37.11 | O |
| ATOM | 1186 | CB | TRP | A | 276 | 46.701 | 42.307 | 30.344 | 1.00 | 35.76 | C |
| ATOM | 1187 | CG | TRP | A | 276 | 45.824 | 41.316 | 29.656 | 1.00 | 36.30 | C |
| ATOM | 1188 | CD1 | TRP | A | 276 | 44.483 | 41.132 | 29.850 | 1.00 | 35.72 | C |
| ATOM | 1189 | CD2 | TRP | A | 276 | 46.222 | 40.359 | 28.665 | 1.00 | 35.75 | C |
| ATOM | 1190 | NE1 | TRP | A | 276 | 44.023 | 40.121 | 29.038 | 1.00 | 35.15 | N |
| ATOM | 1191 | CE2 | TRP | A | 276 | 45.067 | 39.629 | 28.301 | 1.00 | 35.45 | C |
| ATOM | 1192 | CE3 | TRP | A | 276 | 47.443 | 40.047 | 28.050 | 1.00 | 35.85 | C |
| ATOM | 1193 | CZ2 | TRP | A | 276 | 45.094 | 38.607 | 27.347 | 1.00 | 35.33 | C |
| ATOM | 1194 | CZ3 | TRP | A | 276 | 47.471 | 39.027 | 27.098 | 1.00 | 36.37 | C |
| ATOM | 1195 | CN2 | TRP | A | 276 | 46.300 | 38.320 | 26.758 | 1.00 | 36.25 | C |
| ATOM | 1196 | N | ILE | A | 277 | 49.415 | 40.885 | 30.926 | 1.00 | 36.56 | N |
| ATOM | 1197 | CA | ILE | A | 277 | 50.370 | 39.834 | 30.607 | 1.00 | 36.06 | C |
| ATOM | 1198 | C | ILE | A | 277 | 50.757 | 39.048 | 31.857 | 1.00 | 37.15 | C |
| ATOM | 1199 | O | ILE | A | 277 | 50.865 | 37.824 | 31.821 | 1.00 | 36.69 | O |
| ATOM | 1200 | CE | ILE | A | 277 | 51.636 | 40.424 | 29.942 | 1.00 | 34.92 | C |
| ATOM | 1201 | CG1 | ILE | A | 277 | 51.282 | 40.963 | 28.550 | 1.00 | 34.03 | C |
| ATOM | 1202 | CG2 | ILE | A | 277 | 52.724 | 39.363 | 29.837 | 1.00 | 34.16 | C |
| ATOM | 1203 | CD1 | ILE | A | 277 | 52.412 | 41.698 | 27.863 | 1.00 | 32.67 | C |
| ATOM | 1204 | N | ARG | A | 278 | 50.955 | 39.756 | 32.962 | 1.00 | 38.15 | N |

TABLE 4-continued

| ATOM | 1205 | CA | ARG | A | 278 | 51.328 | 39.124 | 34.220 | 1.00 | 40.72 | C |
| --- | --- | --- | --- | --- | --- | --- | --- | --- | --- | --- | --- |
| ATOM | 1206 | C | ARG | A | 278 | 50.198 | 38.278 | 34.802 | 1.00 | 42.31 | C |
| ATOM | 1207 | O | ARG | A | 278 | 50.445 | 37.273 | 35.468 | 1.00 | 42.76 | O |
| ATOM | 1208 | CB | ARG | A | 278 | 51.743 | 40.189 | 35.234 | 1.00 | 39.40 | C |
| ATOM | 1209 | CG | ARG | A | 278 | 53.054 | 40.864 | 34.911 | 1.00 | 38.26 | C |
| ATOM | 1220 | CD | ARG | A | 278 | 54.240 | 39.956 | 35.206 | 1.00 | 37.49 | C |
| ATOM | 1211 | NE | ARG | A | 278 | 55.493 | 40.590 | 34.802 | 1.00 | 35.79 | N |
| ATOM | 1212 | CZ | ARG | A | 278 | 56.192 | 40.250 | 33.725 | 1.00 | 34.09 | C |
| ATOM | 1213 | NH1 | ARG | A | 278 | 55.774 | 39.267 | 32.938 | 1.00 | 33.23 | N |
| ATOM | 1214 | NH2 | ARG | A | 278 | 57.298 | 40.913 | 33.420 | 1.00 | 33.05 | N |
| ATOM | 1215 | N | GLU | A | 279 | 48.962 | 38.692 | 34.543 | 1.00 | 44.10 | N |
| ATOM | 1216 | CA | GLU | A | 279 | 47.785 | 37.989 | 35.039 | 1.00 | 46.28 | C |
| ATOM | 1217 | C | GLU | A | 279 | 47.513 | 36.691 | 34.282 | 1.00 | 45.72 | C |
| ATOM | 1218 | O | GLU | A | 279 | 46.944 | 35.752 | 34.832 | 1.00 | 46.12 | O |
| ATOM | 1219 | CB | GLU | A | 279 | 46.561 | 38.903 | 34.944 | 1.00 | 48.80 | C |
| ATOM | 1220 | CG | GLU | A | 279 | 45.260 | 38.276 | 35.411 | 1.00 | 54.66 | C |
| ATOM | 1221 | CD | GLU | A | 279 | 44.101 | 39.259 | 35.381 | 1.00 | 58.25 | C |
| ATOM | 1222 | OE1 | GLU | A | 279 | 43.781 | 39.778 | 34.285 | 1.00 | 60.30 | O |
| ATOM | 1223 | OE2 | GLU | A | 279 | 43.511 | 39.515 | 36.455 | 1.00 | 59.99 | O |
| ATOM | 1224 | N | LYS | A | 280 | 47.927 | 36.638 | 33.022 | 1.00 | 44.85 | N |
| ATOM | 1225 | CA | LYS | A | 280 | 47.704 | 35.454 | 32.207 | 1.00 | 44.61 | C |
| ATOM | 1226 | C | LYS | A | 280 | 48.924 | 34.556 | 32.057 | 1.00 | 43.52 | C |
| ATOM | 1227 | O | LYS | A | 280 | 48.787 | 33.361 | 31.808 | 1.00 | 44.19 | O |
| ATOM | 1228 | CB | LYS | A | 280 | 47.212 | 35.867 | 30.817 | 1.00 | 46.41 | C |
| ATOM | 1229 | CG | LYS | A | 280 | 47.082 | 34.709 | 29.834 | 1.00 | 48.70 | C |
| ATOM | 1230 | CD | LYS | A | 280 | 46.383 | 35.138 | 28.550 | 1.00 | 50.95 | C |
| ATOM | 1231 | CE | LYS | A | 280 | 46.292 | 33.987 | 27.556 | 1.00 | 51.64 | C |
| ATOM | 1232 | NZ | LYS | A | 280 | 45.625 | 32.794 | 28.148 | 1.00 | 53.00 | N |
| ATOM | 1233 | N | TYR | A | 281 | 50.115 | 35.122 | 32.217 | 1.00 | 41.82 | N |
| ATOM | 1234 | CA | TYR | A | 281 | 51.338 | 34.353 | 32.050 | 1.00 | 39.15 | C |
| ATOM | 1235 | C | TYR | A | 281 | 52.317 | 34.435 | 33.216 | 1.00 | 38.62 | C |
| ATOM | 1236 | O | TYR | A | 281 | 53.355 | 33.773 | 33.198 | 1.00 | 37.75 | O |
| ATOM | 1237 | CB | TYR | A | 281 | 52.059 | 34.816 | 30.787 | 1.00 | 38.77 | C |
| ATOM | 1238 | CG | TYR | A | 281 | 51.280 | 34.655 | 29.503 | 1.00 | 37.82 | C |
| ATOM | 1239 | CD1 | TYR | A | 281 | 51.167 | 33.409 | 28.882 | 1.00 | 37.09 | C |
| ATOM | 1240 | CD2 | TYR | A | 281 | 50.693 | 35.757 | 28.882 | 1.00 | 36.24 | C |
| ATOM | 1241 | CE1 | TYR | A | 281 | 50.498 | 33.267 | 27.670 | 1.00 | 36.51 | C |
| ATOM | 1242 | CE2 | TYR | A | 281 | 50.019 | 35.625 | 27.674 | 1.00 | 37.22 | C |
| ATOM | 1243 | CZ | TYR | A | 281 | 49.928 | 34.378 | 27.071 | 1.00 | 37.04 | C |
| ATOM | 1244 | OH | TYR | A | 281 | 49.284 | 34.247 | 25.863 | 1.00 | 38.46 | O |
| ATOM | 1245 | N | GLY | A | 282 | 52.002 | 35.236 | 34.225 | 1.00 | 38.46 | N |
| ATOM | 1246 | CA | GLY | A | 282 | 52.926 | 35.370 | 35.337 | 1.00 | 39.34 | C |
| ATOM | 1247 | C | GLY | A | 282 | 54.249 | 35.931 | 34.829 | 1.00 | 40.34 | C |
| ATOM | 1248 | O | GLY | A | 282 | 54.262 | 36.760 | 33.919 | 1.00 | 38.99 | O |
| ATOM | 1249 | N | ASP | A | 283 | 55.360 | 35.479 | 35.402 | 1.00 | 42.07 | N |
| ATOM | 1250 | CA | ASP | A | 283 | 56.682 | 35.945 | 34.990 | 1.00 | 44.04 | C |
| ATOM | 1251 | C | ASP | A | 283 | 57.306 | 35.069 | 33.905 | 1.00 | 44.08 | C |
| ATOM | 1252 | O | ASP | A | 283 | 58.510 | 35.130 | 33.674 | 1.00 | 44.67 | O |
| ATOM | 1253 | CB | ASP | A | 283 | 57.629 | 35.994 | 36.193 | 1.00 | 45.90 | C |
| ATOM | 1254 | CG | ASP | A | 283 | 57.267 | 37.087 | 37.180 | 1.00 | 49.98 | C |
| ATOM | 1255 | OD1 | ASP | A | 283 | 57.233 | 38.274 | 36.777 | 1.00 | 51.56 | O |
| ATOM | 1256 | OD2 | ASP | A | 283 | 57.023 | 36.760 | 38.363 | 1.00 | 52.17 | O |
| ATOM | 1257 | N | LYS | A | 284 | 56.493 | 34.260 | 33.236 | 1.00 | 44.69 | N |
| ATOM | 1258 | CA | LYS | A | 284 | 57.000 | 33.373 | 32.191 | 1.00 | 45.15 | C |
| ATOM | 1259 | C | LYS | A | 284 | 57.172 | 34.086 | 30.854 | 1.00 | 43.68 | C |
| ATOM | 1260 | O | LYS | A | 284 | 57.955 | 33.664 | 30.001 | 1.00 | 44.14 | O |
| ATOM | 1261 | CB | LYS | A | 284 | 56.064 | 32.171 | 32.024 | 1.00 | 48.63 | C |
| ATOM | 1262 | CG | LYS | A | 284 | 56.003 | 31.260 | 33.249 | 1.00 | 53.02 | C |
| ATOM | 1263 | CD | LYS | A | 284 | 57.377 | 30.674 | 33.572 | 1.00 | 56.22 | C |
| ATOM | 1264 | CE | LYS | A | 284 | 57.326 | 29.736 | 34.772 | 1.00 | 58.58 | C |
| ATOM | 1265 | NZ | LYS | A | 284 | 58.679 | 29.181 | 35.089 | 1.00 | 60.63 | N |
| ATOM | 1266 | N | VAL | A | 285 | 56.425 | 35.164 | 30.669 | 1.00 | 40.25 | N |
| ATOM | 1267 | CA | VAL | A | 285 | 56.514 | 35.937 | 29.446 | 1.00 | 37.27 | C |
| ATOM | 1268 | C | VAL | A | 285 | 57.225 | 37.243 | 29.773 | 1.00 | 35.62 | C |
| ATOM | 1269 | O | VAL | A | 285 | 56.792 | 37.997 | 30.641 | 1.00 | 35.11 | O |
| ATOM | 1270 | CB | VAL | A | 285 | 55.114 | 36.213 | 28.874 | 1.00 | 37.07 | C |
| ATOM | 1271 | CG1 | VAL | A | 285 | 55.205 | 37.182 | 27.706 | 1.00 | 35.98 | C |
| ATOM | 1272 | CG2 | VAL | A | 285 | 54.489 | 34.897 | 28.418 | 1.00 | 37.05 | C |
| ATOM | 1273 | N | LYS | A | 286 | 58.331 | 37.494 | 29.084 | 1.00 | 34.12 | N |
| ATOM | 1274 | CA | LYS | A | 286 | 59.117 | 38.699 | 29.311 | 1.00 | 31.70 | C |
| ATOM | 1275 | C | LYS | A | 286 | 58.643 | 39.823 | 28.404 | 1.00 | 30.65 | C |
| ATOM | 1276 | O | LYS | A | 286 | 58.443 | 39.625 | 27.206 | 1.00 | 29.79 | O |
| ATOM | 1277 | CB | LYS | A | 286 | 60.599 | 38.411 | 29.059 | 1.00 | 30.46 | C |
| ATOM | 1278 | CG | LYS | A | 286 | 61.135 | 37.224 | 29.847 | 1.00 | 30.11 | C |
| ATOM | 1279 | CD | LYS | A | 286 | 60.902 | 37.387 | 31.344 | 1.00 | 29.65 | C |
| ATOM | 1280 | CE | LYS | A | 286 | 61.427 | 36.183 | 32.118 | 1.00 | 29.40 | C |
| ATOM | 1281 | NZ | LYS | A | 286 | 61.201 | 36.319 | 33.591 | 1.00 | 30.72 | N |
| ATOM | 1282 | N | VAL | A | 287 | 58.469 | 41.005 | 28.983 | 1.00 | 28.78 | N |
| ATOM | 1283 | CA | VAL | A | 287 | 58.004 | 42.154 | 28.224 | 1.00 | 27.93 | C |

TABLE 4-continued

| ATOM | 1284 | C | VAL | A | 287 | 58.722 | 43.442 | 28.617 | 1.00 | 27.40 | C |
|---|---|---|---|---|---|---|---|---|---|---|---|
| ATOM | 1285 | O | VAL | A | 287 | 58.733 | 43.838 | 29.784 | 1.00 | 26.80 | O |
| ATOM | 1286 | CB | VAL | A | 287 | 56.463 | 42.338 | 28.400 | 1.00 | 27.55 | C |
| ATOM | 1287 | CG1 | VAL | A | 287 | 56.102 | 42.398 | 29.876 | 1.00 | 28.57 | C |
| ATOM | 1288 | CG2 | VAL | A | 287 | 56.002 | 43.603 | 27.704 | 1.00 | 28.04 | C |
| ATOM | 1289 | N | GLY | A | 288 | 59.340 | 44.081 | 27.630 | 1.00 | 28.27 | N |
| ATOM | 1290 | CA | GLY | A | 288 | 60.031 | 45.336 | 27.873 | 1.00 | 27.27 | C |
| ATOM | 1291 | C | GLY | A | 288 | 59.038 | 46.459 | 27.644 | 1.00 | 27.80 | C |
| ATOM | 1292 | O | GLY | A | 288 | 58.042 | 46.263 | 26.944 | 1.00 | 28.16 | O |
| ATOM | 1293 | N | ALA | A | 289 | 59.293 | 47.627 | 28.230 | 1.00 | 27.53 | N |
| ATOM | 1294 | CA | ALA | A | 289 | 58.396 | 48.771 | 28.085 | 1.00 | 28.35 | C |
| ATOM | 1295 | C | ALA | A | 289 | 59.171 | 50.063 | 27.815 | 1.00 | 29.42 | C |
| ATOM | 1296 | O | ALA | A | 289 | 60.386 | 50.120 | 28.021 | 1.00 | 29.84 | O |
| ATOM | 1297 | CB | ALA | A | 289 | 57.543 | 48.923 | 29.346 | 1.00 | 28.05 | C |
| ATOM | 1298 | N | GLY | A | 290 | 58.461 | 51.096 | 27.364 | 1.00 | 28.77 | N |
| ATOM | 1299 | CA | GLY | A | 290 | 59.096 | 52.371 | 27.063 | 1.00 | 28.22 | C |
| ATOM | 1300 | C | GLY | A | 290 | 58.395 | 53.070 | 25.905 | 1.00 | 28.36 | C |
| ATOM | 1301 | O | GLY | A | 290 | 57.369 | 52.588 | 25.433 | 1.00 | 27.76 | O |
| ATOM | 1302 | N | ASN | A | 291 | 58.942 | 54.184 | 25.418 | 1.00 | 26.86 | N |
| ATOM | 1303 | CA | ASN | A | 291 | 60.186 | 54.766 | 25.919 | 1.00 | 25.60 | C |
| ATOM | 1304 | C | ASN | A | 291 | 59.985 | 55.857 | 26.969 | 1.00 | 25.05 | C |
| ATOM | 1305 | O | ASN | A | 291 | 58.963 | 56.536 | 26.987 | 1.00 | 25.04 | O |
| ATOM | 1306 | CB | ASN | A | 291 | 60.973 | 55.357 | 24.748 | 1.00 | 24.30 | C |
| ATOM | 1307 | CG | ASN | A | 291 | 61.485 | 54.298 | 23.793 | 1.00 | 24.09 | C |
| ATOM | 1308 | OD1 | ASN | A | 291 | 60.978 | 53.180 | 23.761 | 1.00 | 25.26 | O |
| ATOM | 1309 | ND2 | ASN | A | 291 | 62.492 | 54.651 | 23.001 | 1.00 | 20.96 | N |
| ATOM | 1310 | N | ILE | A | 292 | 60.965 | 56.010 | 27.852 | 1.00 | 23.64 | N |
| ATOM | 1311 | CA | ILE | A | 292 | 60.923 | 57.054 | 28.867 | 1.00 | 23.62 | C |
| ATOM | 1312 | C | ILE | A | 292 | 62.290 | 57.733 | 28.846 | 1.00 | 24.18 | C |
| ATOM | 1313 | O | ILE | A | 292 | 63.219 | 57.230 | 28.200 | 1.00 | 24.40 | O |
| ATOM | 1314 | CB | ILE | A | 292 | 60.583 | 56.498 | 30.289 | 1.00 | 24.12 | C |
| ATOM | 1315 | CG1 | ILE | A | 292 | 61.395 | 55.238 | 30.599 | 1.00 | 23.86 | C |
| ATOM | 1316 | CG2 | ILE | A | 292 | 59.093 | 56.210 | 30.383 | 1.00 | 24.23 | C |
| ATOM | 1317 | CD1 | ILE | A | 292 | 62.865 | 55.491 | 30.874 | 1.00 | 24.33 | C |
| ATOM | 1318 | N | VAL | A | 293 | 62.420 | 58.870 | 29.528 | 1.00 | 22.80 | N |
| ATOM | 1319 | CA | VAL | A | 293 | 63.686 | 59.597 | 29.526 | 1.00 | 22.92 | C |
| ATOM | 1320 | C | VAL | A | 293 | 64.146 | 60.119 | 30.876 | 1.00 | 23.26 | C |
| ATOM | 1321 | O | VAL | A | 293 | 65.142 | 60.840 | 30.951 | 1.00 | 23.53 | O |
| ATOM | 1322 | CB | VAL | A | 293 | 63.635 | 60.805 | 28.561 | 1.00 | 22.53 | C |
| ATOM | 1323 | CG1 | VAL | A | 293 | 63.492 | 60.330 | 27.122 | 1.00 | 21.53 | C |
| ATOM | 1324 | CG2 | VAL | A | 293 | 62.474 | 61.717 | 28.943 | 1.00 | 21.31 | C |
| ATOM | 1325 | N | ASP | A | 294 | 63.430 | 59.779 | 31.942 | 1.00 | 23.20 | N |
| ATOM | 1326 | CA | ASP | A | 294 | 63.824 | 60.241 | 33.269 | 1.00 | 23.65 | C |
| ATOM | 1327 | C | ASP | A | 294 | 63.528 | 59.203 | 34.352 | 1.00 | 24.09 | C |
| ATOM | 1328 | O | ASP | A | 294 | 62.885 | 58.188 | 34.096 | 1.00 | 24.41 | O |
| ATOM | 1329 | CB | ASP | A | 294 | 63.122 | 61.570 | 33.597 | 1.00 | 23.02 | C |
| ATOM | 1330 | CG | ASP | A | 294 | 61.620 | 61.418 | 33.778 | 1.00 | 24.10 | C |
| ATOM | 1331 | OD1 | ASP | A | 294 | 61.064 | 60.375 | 33.376 | 1.00 | 26.12 | O |
| ATOM | 1332 | OD2 | ASP | A | 294 | 60.990 | 62.354 | 34.312 | 1.00 | 25.00 | O |
| ATOM | 1333 | N | GLY | A | 295 | 64.006 | 59.467 | 35.561 | 1.00 | 25.18 | N |
| ATOM | 1334 | CA | GLY | A | 295 | 63.793 | 58.553 | 36.669 | 1.00 | 25.72 | C |
| ATOM | 1335 | C | GLY | A | 295 | 62.339 | 58.246 | 36.987 | 1.00 | 26.61 | C |
| ATOM | 1336 | O | GLY | A | 295 | 62.016 | 57.105 | 37.326 | 1.00 | 25.47 | O |
| ATOM | 1337 | N | GLU | A | 296 | 61.463 | 59.249 | 36.894 | 1.00 | 27.36 | N |
| ATOM | 1338 | CA | GLU | A | 296 | 60.042 | 59.049 | 37.184 | 1.00 | 28.17 | C |
| ATOM | 1339 | C | GLU | A | 296 | 59.417 | 58.064 | 36.214 | 1.00 | 26.97 | C |
| ATOM | 1340 | O | GLU | A | 296 | 58.684 | 57.166 | 36.620 | 1.00 | 26.88 | O |
| ATOM | 1341 | CB | GLU | A | 296 | 59.261 | 60.367 | 37.103 | 1.00 | 31.11 | C |
| ATOM | 1342 | CG | GLU | A | 296 | 59.579 | 61.376 | 38.182 | 1.00 | 37.71 | C |
| ATOM | 1343 | CD | GLU | A | 296 | 58.622 | 62.567 | 38.160 | 1.00 | 43.64 | C |
| ATOM | 1344 | OE1 | GLU | A | 296 | 58.943 | 63.589 | 38.808 | 1.00 | 45.94 | O |
| ATOM | 1345 | OE2 | GLU | A | 296 | 57.550 | 62.482 | 37.503 | 1.00 | 44.55 | O |
| ATOM | 1346 | N | GLY | A | 297 | 59.695 | 58.251 | 34.928 | 1.00 | 26.28 | N |
| ATOM | 1347 | CA | GLY | A | 297 | 59.151 | 57.363 | 33.917 | 1.00 | 26.08 | C |
| ATOM | 1348 | C | GLY | A | 297 | 59.661 | 55.944 | 34.094 | 1.00 | 25.81 | C |
| ATOM | 1349 | O | GLY | A | 297 | 58.910 | 54.984 | 33.932 | 1.00 | 26.85 | O |
| ATOM | 1350 | N | PHE | A | 298 | 60.945 | 55.813 | 34.415 | 1.00 | 25.29 | N |
| ATOM | 1351 | CA | PHE | A | 298 | 61.554 | 54.506 | 34.639 | 1.00 | 25.86 | C |
| ATOM | 1352 | C | PHE | A | 298 | 60.856 | 53.815 | 35.805 | 1.00 | 26.44 | C |
| ATOM | 1353 | O | PHE | A | 298 | 60.461 | 52.656 | 35.712 | 1.00 | 26.85 | O |
| ATOM | 1354 | CB | PHE | A | 298 | 63.040 | 54.655 | 34.988 | 1.00 | 25.61 | C |
| ATOM | 1355 | CG | PHE | A | 298 | 63.640 | 53.410 | 35.585 | 1.00 | 25.67 | C |
| ATOM | 1356 | CD1 | PHE | A | 298 | 64.139 | 52.398 | 34.771 | 1.00 | 24.15 | C |
| ATOM | 1357 | CD2 | PHE | A | 298 | 63.627 | 53.214 | 36.964 | 1.00 | 24.54 | C |
| ATOM | 1358 | CE1 | PHE | A | 298 | 64.611 | 51.202 | 35.325 | 1.00 | 24.57 | C |
| ATOM | 1359 | CE2 | PHE | A | 298 | 64.093 | 52.025 | 37.524 | 1.00 | 24.83 | C |
| ATOM | 1360 | CZ | PHE | A | 298 | 64.584 | 51.017 | 36.701 | 1.00 | 23.36 | C |
| ATOM | 1361 | N | ARG | A | 299 | 60.733 | 54.553 | 36.905 | 1.00 | 27.12 | N |
| ATOM | 1362 | CA | ARG | A | 299 | 60.110 | 54.089 | 38.143 | 1.00 | 29.07 | C |

TABLE 4-continued

| | | | | | | | | | | |
|---|---|---|---|---|---|---|---|---|---|---|
| ATOM | 1363 | C | ARG | A | 299 | 58.680 | 53.603 | 37.910 | 1.00 | 29.11 | C |
| ATOM | 1364 | O | ARG | A | 299 | 58.275 | 52.554 | 38.420 | 1.00 | 28.93 | O |
| ATOM | 1365 | CB | ARG | A | 299 | 60.136 | 55.235 | 39.162 | 1.00 | 30.82 | C |
| ATOM | 1366 | CG | ARG | A | 299 | 59.233 | 55.085 | 40.370 | 1.00 | 35.20 | C |
| ATOM | 1367 | CD | ARG | A | 299 | 59.914 | 54.374 | 41.518 | 1.00 | 38.25 | C |
| ATOM | 1368 | NE | ARG | A | 299 | 61.166 | 55.010 | 41.934 | 1.00 | 39.66 | N |
| ATOM | 1369 | CZ | ARG | A | 299 | 61.900 | 54.581 | 42.959 | 1.00 | 40.55 | C |
| ATOM | 1370 | NH1 | ARG | A | 299 | 61.497 | 53.533 | 43.662 | 1.00 | 39.93 | N |
| ATOM | 1371 | NH2 | ARG | A | 299 | 63.045 | 55.173 | 43.270 | 1.00 | 40.75 | N |
| ATOM | 1372 | N | TYR | A | 300 | 57.912 | 54.363 | 37.139 | 1.00 | 28.00 | N |
| ATOM | 1373 | CA | TYR | A | 300 | 56.542 | 53.973 | 36.853 | 1.00 | 27.38 | C |
| ATOM | 1374 | C | TYR | A | 300 | 56.486 | 52.639 | 36.113 | 1.00 | 27.60 | C |
| ATOM | 1375 | O | TYR | A | 300 | 55.658 | 51.793 | 36.424 | 1.00 | 27.82 | O |
| ATOM | 1376 | CB | TYR | A | 300 | 55.841 | 55.033 | 36.006 | 1.00 | 25.95 | C |
| ATOM | 1377 | CG | TYR | A | 300 | 54.385 | 54.714 | 35.739 | 1.00 | 25.23 | C |
| ATOM | 1378 | CD1 | TYR | A | 300 | 53.410 | 54.933 | 36.716 | 1.00 | 24.39 | C |
| ATOM | 1379 | CD2 | TYR | A | 300 | 53.984 | 54.183 | 34.516 | 1.00 | 24.30 | C |
| ATOM | 1380 | CE1 | TYR | A | 300 | 52.069 | 54.631 | 36.477 | 1.00 | 23.68 | C |
| ATOM | 1381 | CE2 | TYR | A | 300 | 52.650 | 53.875 | 34.268 | 1.00 | 25.86 | C |
| ATOM | 1382 | CZ | TYR | A | 300 | 51.698 | 54.104 | 35.252 | 1.00 | 24.81 | C |
| ATOM | 1383 | OH | TYR | A | 300 | 50.379 | 53.810 | 34.995 | 1.00 | 24.58 | O |
| ATOM | 1384 | N | LEU | A | 301 | 57.355 | 52.454 | 35.124 | 1.00 | 27.28 | N |
| ATOM | 1385 | CA | LEU | A | 301 | 57.339 | 51.210 | 34.369 | 1.00 | 27.52 | C |
| ATOM | 1386 | C | LEU | A | 301 | 57.922 | 50.044 | 35.168 | 1.00 | 27.98 | C |
| ATOM | 1387 | O | LEU | A | 301 | 57.539 | 48.896 | 34.968 | 1.00 | 28.58 | O |
| ATOM | 1388 | CB | LEU | A | 301 | 58.078 | 51.386 | 33.036 | 1.00 | 25.33 | C |
| ATOM | 1389 | CG | LEU | A | 301 | 57.369 | 52.305 | 32.024 | 1.00 | 25.53 | C |
| ATOM | 1390 | CD1 | LEU | A | 301 | 58.189 | 52.409 | 30.741 | 1.00 | 20.77 | C |
| ATOM | 1391 | CD2 | LEU | A | 301 | 55.979 | 51.756 | 31.714 | 1.00 | 23.64 | C |
| ATOM | 1392 | N | ALA | A | 302 | 58.837 | 50.340 | 36.081 | 1.00 | 28.68 | N |
| ATOM | 1393 | CA | ALA | A | 302 | 59.437 | 49.301 | 36.911 | 1.00 | 29.55 | C |
| ATOM | 1394 | C | ALA | A | 302 | 58.365 | A8.740 | 37.852 | 1.00 | 29.73 | C |
| ATOM | 1395 | O | ALA | A | 302 | 58.159 | 47.528 | 37.925 | 1.00 | 29.99 | O |
| ATOM | 1396 | CB | ALA | A | 302 | 60.607 | 49.877 | 37.714 | 1.00 | 27.04 | C |
| ATOM | 1397 | N | ASP | A | 303 | 57.679 | 49.624 | 38.565 | 1.00 | 30.56 | N |
| ATOM | 1398 | CA | ASP | A | 303 | 56.625 | 49.193 | 39.474 | 1.00 | 31.48 | C |
| ATOM | 1399 | C | ASP | A | 303 | 55.527 | 48.474 | 38.704 | 1.00 | 32.09 | C |
| ATOM | 1400 | O | ASP | A | 303 | 54.836 | 47.620 | 39.256 | 1.00 | 33.91 | O |
| ATOM | 1401 | CB | ASP | A | 303 | 56.013 | 50.381 | 40.218 | 1.00 | 31.91 | C |
| ATOM | 1402 | CG | ASP | A | 303 | 56.947 | 50.968 | 41.254 | 1.00 | 33.42 | C |
| ATOM | 1403 | OD1 | ASP | A | 303 | 57.869 | 50.253 | 41.701 | 1.00 | 34.40 | O |
| ATOM | 1404 | OD2 | ASP | A | 303 | 56.743 | 52.139 | 41.639 | 1.00 | 34.93 | O |
| ATOM | 1405 | N | ALA | A | 304 | 55.358 | 48.828 | 37.434 | 1.00 | 31.62 | N |
| ATOM | 1406 | CA | ALA | A | 304 | 54.336 | 48.198 | 36.605 | 1.00 | 30.73 | C |
| ATOM | 1407 | C | ALA | A | 304 | 54.723 | 46.759 | 36.239 | 1.00 | 30.76 | C |
| ATOM | 1408 | O | ALA | A | 304 | 53.873 | 45.969 | 35.823 | 1.00 | 30.18 | O |
| ATOM | 1409 | CB | ALA | A | 304 | 54.103 | 49.020 | 35.346 | 1.00 | 30.45 | C |
| ATOM | 1410 | N | GLY | A | 305 | 56.007 | 46.425 | 36.379 | 1.00 | 29.89 | N |
| ATOM | 1411 | CA | GLY | A | 305 | 56.452 | 45.069 | 36.086 | 1.00 | 28.06 | C |
| ATOM | 1412 | C | GLY | A | 305 | 57.299 | 44.817 | 34.850 | 1.00 | 28.84 | C |
| ATOM | 1413 | O | GLY | A | 305 | 57.596 | 43.661 | 34.535 | 1.00 | 28.23 | O |
| ATOM | 1414 | N | ALA | A | 306 | 57.695 | 45.873 | 34.144 | 1.00 | 28.22 | N |
| ATOM | 1415 | CA | ALA | A | 306 | 58.510 | 45.719 | 32.937 | 1.00 | 27.85 | C |
| ATOM | 1416 | C | ALA | A | 306 | 59.772 | 44.889 | 33.206 | 1.00 | 27.06 | C |
| ATOM | 1417 | O | ALA | A | 306 | 60.378 | 45.010 | 34.270 | 1.00 | 26.25 | O |
| ATOM | 1418 | CB | ALA | A | 306 | 58.896 | 47.094 | 32.399 | 1.00 | 28.08 | C |
| ATOM | 1419 | N | ASP | A | 307 | 60.157 | 44.049 | 32.244 | 1.00 | 27.17 | N |
| ATOM | 1420 | CA | ASP | A | 307 | 61.350 | 43.201 | 32.374 | 1.00 | 27.07 | C |
| ATOM | 1421 | C | ASP | A | 307 | 62.618 | 43.950 | 31.946 | 1.00 | 27.21 | C |
| ATOM | 1422 | O | ASP | A | 307 | 63.737 | 43.546 | 32.259 | 1.00 | 27.56 | O |
| ATOM | 1423 | CB | ASP | A | 307 | 61.178 | 41.918 | 31.553 | 1.00 | 26.85 | C |
| ATOM | 1424 | CG | ASP | A | 307 | 60.190 | 40.954 | 32.187 | 1.00 | 29.12 | C |
| ATOM | 1425 | OD1 | ASP | A | 307 | 60.488 | 40.450 | 33.290 | 1.00 | 29.15 | O |
| ATOM | 1426 | OD2 | ASP | A | 307 | 59.116 | 40.709 | 31.592 | 1.00 | 29.54 | O |
| ATOM | 1427 | N | PHE | A | 308 | 62.424 | 45.021 | 31.189 | 1.00 | 26.81 | N |
| ATOM | 1428 | CA | PHE | A | 308 | 63.507 | 45.896 | 30.771 | 1.00 | 26.08 | C |
| ATOM | 1429 | C | PHE | A | 308 | 62.823 | 47.180 | 30.314 | 1.00 | 26.24 | C |
| ATOM | 1430 | O | PHE | A | 308 | 61.677 | 47.158 | 29.871 | 1.00 | 25.83 | O |
| ATOM | 1431 | CB | PHE | A | 308 | 64.416 | 45.245 | 29.703 | 1.00 | 25.02 | C |
| ATOM | 1432 | CG | PHE | A | 308 | 63.879 | 45.264 | 28.291 | 1.00 | 24.83 | C |
| ATOM | 1433 | CD1 | PHE | A | 308 | 63.847 | 46.447 | 27.552 | 1.00 | 24.91 | C |
| ATOM | 1434 | CD2 | PHE | A | 308 | 63.492 | 44.076 | 27.671 | 1.00 | 24.33 | C |
| ATOM | 1435 | CE1 | PHE | A | 308 | 63.443 | 46.449 | 26.210 | 1.00 | 24.84 | C |
| ATOM | 1436 | CE2 | PHE | A | 308 | 63.085 | 44.062 | 26.330 | 1.00 | 25.69 | C |
| ATOM | 1437 | CZ | PHE | A | 308 | 63.062 | 45.255 | 25.597 | 1.00 | 25.81 | C |
| ATOM | 1438 | N | ILE | A | 309 | 63.503 | 48.305 | 30.484 | 1.00 | 25.90 | N |
| ATOM | 1439 | CA | ILE | A | 309 | 62.928 | 49.591 | 30.130 | 1.00 | 25.03 | C |
| ATOM | 1440 | C | ILE | A | 309 | 63.754 | 50.294 | 29.053 | 1.00 | 24.57 | C |
| ATOM | 1441 | O | ILE | A | 309 | 64.976 | 50.407 | 29.160 | 1.00 | 24.32 | O |

TABLE 4-continued

| ATOM | 1442 | CB | ILE | A | 309 | 62.784 | 50.445 | 31.414 | 1.00 | 25.42 | C |
|---|---|---|---|---|---|---|---|---|---|---|---|
| ATOM | 1443 | CG1 | ILE | A | 309 | 61.756 | 49.763 | 32.331 | 1.00 | 22.98 | C |
| ATOM | 1444 | CG2 | ILE | A | 309 | 62.390 | 51.891 | 31.072 | 1.00 | 24.21 | C |
| ATOM | 1445 | CD1 | ILE | A | 309 | 61.674 | 50.320 | 33.740 | 1.00 | 22.68 | C |
| ATOM | 1446 | N | LYS | A | 310 | 63.068 | 50.750 | 28.009 | 1.00 | 24.43 | N |
| ATOM | 1447 | CA | LYS | A | 310 | 63.713 | 51.396 | 26.877 | 1.00 | 24.50 | C |
| ATOM | 1448 | C | LYS | A | 310 | 63.785 | 52.921 | 27.042 | 1.00 | 24.35 | C |
| ATOM | 1449 | O | LYS | A | 310 | 62.786 | 53.583 | 27.334 | 1.00 | 23.81 | O |
| ATOM | 1450 | CB | LYS | A | 310 | 62.970 | 51.000 | 25.598 | 1.00 | 24.83 | C |
| ATOM | 1451 | CG | LYS | A | 310 | 63.793 | 51.071 | 24.336 | 1.00 | 24.74 | C |
| ATOM | 1452 | CD | LYS | A | 310 | 63.473 | 49.906 | 23.401 | 1.00 | 24.26 | C |
| ATOM | 1453 | CE | LYS | A | 310 | 62.069 | 49.994 | 22.836 | 1.00 | 24.22 | C |
| ATOM | 1454 | NZ | LYS | A | 310 | 61.904 | 51.272 | 22.092 | 1.00 | 23.28 | N |
| ATOM | 1455 | N | ILE | A | 311 | 64.986 | 53.459 | 26.851 | 1.00 | 23.88 | N |
| ATOM | 1456 | CA | ILE | A | 311 | 65.252 | 54.890 | 27.009 | 1.00 | 23.05 | C |
| ATOM | 1457 | C | ILE | A | 311 | 65.399 | 55.641 | 25.693 | 1.00 | 23.48 | C |
| ATOM | 1458 | O | ILE | A | 311 | 66.113 | 55.194 | 24.792 | 1.00 | 22.99 | O |
| ATOM | 1459 | CB | ILE | A | 311 | 66.562 | 55.118 | 27.804 | 1.00 | 21.85 | C |
| ATOM | 1460 | CG1 | ILE | A | 311 | 66.503 | 54.367 | 29.137 | 1.00 | 19.66 | C |
| ATOM | 1461 | CG2 | ILE | A | 311 | 66.782 | 56.619 | 28.037 | 1.00 | 19.08 | C |
| ATOM | 1462 | CD1 | ILE | A | 311 | 67.858 | 54.239 | 29.821 | 1.00 | 19.70 | C |
| ATOM | 1463 | N | GLY | A | 312 | 64.730 | 56.785 | 25.582 | 1.00 | 23.63 | N |
| ATOM | 1464 | CA | GLY | A | 312 | 64.871 | 57.569 | 24.374 | 1.00 | 24.66 | C |
| ATOM | 1465 | C | GLY | A | 312 | 63.644 | 58.103 | 23.669 | 1.00 | 26.40 | C |
| ATOM | 1466 | O | GLY | A | 312 | 62.771 | 57.350 | 23.240 | 1.00 | 25.18 | O |
| ATOM | 1467 | N | ILE | A | 313 | 63.595 | 59.426 | 23.553 | 1.00 | 28.70 | N |
| ATOM | 1468 | CA | ILE | A | 313 | 62.527 | 60.128 | 22.854 | 1.00 | 31.54 | C |
| ATOM | 1469 | C | ILE | A | 313 | 63.184 | 61.309 | 22.152 | 1.00 | 35.25 | C |
| ATOM | 1470 | O | ILE | A | 313 | 63.698 | 62.216 | 22.811 | 1.00 | 33.97 | O |
| ATOM | 1471 | CB | ILE | A | 313 | 61.450 | 60.678 | 23.812 | 1.00 | 30.50 | C |
| ATOM | 1472 | CG1 | ILE | A | 313 | 60.739 | 59.528 | 24.529 | 1.00 | 29.70 | C |
| ATOM | 1473 | CG2 | ILE | A | 313 | 60.438 | 61.498 | 23.021 | 1.00 | 30.02 | C |
| ATOM | 1474 | CD1 | ILE | A | 313 | 59.794 | 59.984 | 25.624 | 1.00 | 27.55 | C |
| ATOM | 1475 | N | GLY | A | 314 | 63.190 | 61.283 | 20.823 | 1.00 | 40.22 | N |
| ATOM | 1476 | CA | GLY | A | 314 | 63.780 | 62.372 | 20.065 | 1.00 | 47.64 | C |
| ATOM | 1477 | C | GLY | A | 314 | 65.152 | 62.121 | 19.458 | 1.00 | 53.44 | C |
| ATOM | 1478 | O | GLY | A | 314 | 65.474 | 62.660 | 18.392 | 1.00 | 54.62 | O |
| ATOM | 1479 | N | GLY | A | 315 | 65.965 | 61.306 | 20.125 | 1.00 | 57.31 | N |
| ATOM | 1480 | CA | GLY | A | 315 | 67.304 | 61.024 | 19.632 | 1.00 | 62.24 | C |
| ATOM | 1481 | C | GLY | A | 315 | 67.422 | 60.395 | 18.251 | 1.00 | 65.54 | C |
| ATOM | 1482 | O | GLY | A | 315 | 68.347 | 60.724 | 17.509 | 1.00 | 66.23 | O |
| ATOM | 1483 | N | GLY | A | 316 | 66.499 | 59.497 | 17.906 | 1.00 | 68.35 | N |
| ATOM | 1484 | CA | GLY | A | 316 | 66.534 | 58.826 | 16.611 | 1.00 | 71.80 | C |
| ATOM | 1485 | C | GLY | A | 316 | 66.996 | 59.648 | 15.415 | 1.00 | 74.31 | C |
| ATOM | 1486 | O | GLY | A | 316 | 66.889 | 60.875 | 15.413 | 1.00 | 74.26 | O |
| ATOM | 1487 | N | SER | A | 317 | 67.505 | 58.968 | 14.388 | 1.00 | 76.73 | N |
| ATOM | 1488 | CA | SER | A | 317 | 67.989 | 59.635 | 13.178 | 1.00 | 79.34 | C |
| ATOM | 1489 | C | SER | A | 317 | 66.831 | 60.196 | 12.357 | 1.00 | 81.34 | C |
| ATOM | 1490 | O | SER | A | 317 | 66.887 | 61.330 | 11.879 | 1.00 | 81.51 | O |
| ATOM | 1491 | CB | SER | A | 317 | 68.799 | 58.663 | 12.314 | 1.00 | 79.01 | C |
| ATOM | 1492 | OG | SER | A | 317 | 67.969 | 57.683 | 11.719 | 1.00 | 78.20 | O |
| ATOM | 1493 | N | ILE | A | 318 | 65.789 | 59.387 | 12.189 | 1.00 | 83.77 | N |
| ATOM | 1494 | CA | ILE | A | 318 | 64.602 | 59.797 | 11.444 | 1.00 | 86.14 | C |
| ATOM | 1495 | C | ILE | A | 318 | 63.663 | 60.558 | 12.371 | 1.00 | 87.68 | C |
| ATOM | 1496 | O | ILE | A | 318 | 62.441 | 60.481 | 12.236 | 1.00 | 87.87 | O |
| ATOM | 1497 | CS | ILE | A | 318 | 63.845 | 58.575 | 10.866 | 1.00 | 85.84 | C |
| ATOM | 1498 | CG1 | ILE | A | 318 | 64.062 | 57.346 | 11.756 | 1.00 | 85.74 | C |
| ATOM | 1499 | CG2 | ILE | A | 318 | 64.323 | 58.291 | 9.448 | 1.00 | 86.18 | C |
| ATOM | 1500 | CD1 | ILE | A | 318 | 63.713 | 57.544 | 13.210 | 1.00 | 84.97 | C |
| ATOM | 1501 | N | CYS | A | 319 | 64.250 | 61.293 | 13.312 | 1.00 | 89.77 | N |
| ATOM | 1502 | CA | CYS | A | 319 | 63.484 | 62.064 | 14.282 | 1.00 | 91.80 | C |
| ATOM | 1503 | C | CYS | A | 319 | 63.660 | 63.571 | 14.135 | 1.00 | 92.66 | C |
| ATOM | 1504 | O | CYS | A | 319 | 64.776 | 64.090 | 14.207 | 1.00 | 92.78 | O |
| ATOM | 1505 | CS | CYS | A | 319 | 63.878 | 61.660 | 15.703 | 1.00 | 92.28 | C |
| ATOM | 1506 | SG | CYS | A | 319 | 63.009 | 62.593 | 16.985 | 1.00 | 94.56 | S |
| ATOM | 1507 | N | ILE | A | 320 | 62.545 | 64.268 | 13.937 | 1.00 | 93.64 | N |
| ATOM | 1508 | CA | ILE | A | 320 | 62.552 | 65.720 | 13.800 | 1.00 | 94.66 | C |
| ATOM | 1509 | C | ILE | A | 320 | 61.771 | 66.290 | 14.988 | 1.00 | 94.85 | C |
| ATOM | 1510 | O | ILE | A | 320 | 60.809 | 67.041 | 14.814 | 1.00 | 95.16 | O |
| ATOM | 1511 | CB | ILE | A | 320 | 61.876 | 66.165 | 12.473 | 1.00 | 95.15 | C |
| ATOM | 1512 | CG1 | ILE | A | 320 | 62.418 | 65.339 | 11.299 | 1.00 | 95.39 | C |
| ATOM | 1513 | CG2 | ILE | A | 320 | 62.132 | 67.649 | 12.226 | 1.00 | 94.99 | C |
| ATOM | 1514 | CD1 | ILE | A | 320 | 63.920 | 65.452 | 11.086 | 1.00 | 95.47 | C |
| ATOM | 1515 | N | THR | A | 321 | 62.200 | 65.913 | 16.193 | 1.00 | 94.85 | N |
| ATOM | 1516 | CA | THR | A | 321 | 61.572 | 66.338 | 17.446 | 1.00 | 94.56 | C |
| ATOM | 1517 | C | THR | A | 321 | 60.932 | 67.723 | 17.389 | 1.00 | 94.12 | C |
| ATOM | 1518 | O | THR | A | 321 | 59.744 | 67.876 | 17.683 | 1.00 | 93.67 | O |
| ATOM | 1519 | CS | THR | A | 321 | 62.590 | 66.322 | 18.606 | 1.00 | 94.80 | C |
| ATOM | 1520 | OG1 | THR | A | 321 | 63.228 | 65.040 | 18.664 | 1.00 | 94.77 | O |

TABLE 4-continued

| | | | | | | | | | | |
|---|---|---|---|---|---|---|---|---|---|---|
| ATOM | 1521 | CG2 | THR | A | 321 | 61.891 | 66.588 | 19.931 | 1.00 | 94.58 | C |
| ATOM | 1522 | N | ARG | A | 322 | 61.721 | 68.730 | 17.022 | 1.00 | 93.60 | N |
| ATOM | 1523 | CA | ARG | A | 322 | 61.208 | 70.091 | 16.926 | 1.00 | 92.93 | C |
| ATOM | 1524 | C | ARG | A | 322 | 59.929 | 70.126 | 16.098 | 1.00 | 91.61 | C |
| ATOM | 1525 | O | ARG | A | 322 | 58.860 | 70.457 | 16.611 | 1.00 | 91.89 | O |
| ATOM | 1526 | CB | ARG | A | 322 | 62.250 | 71.025 | 16.301 | 1.00 | 93.99 | C |
| ATOM | 1527 | CG | ARG | A | 322 | 63.301 | 71.546 | 17.274 | 1.00 | 95.47 | C |
| ATOM | 1528 | CD | ARG | A | 322 | 64.337 | 70.495 | 17.640 | 1.00 | 96.98 | C |
| ATOM | 1529 | NE | ARG | A | 322 | 65.319 | 71.030 | 18.583 | 1.00 | 98.14 | N |
| ATOM | 1530 | CZ | ARG | A | 322 | 66.530 | 70.517 | 18.784 | 1.00 | 98.80 | C |
| ATOM | 1531 | NH1 | ARG | A | 322 | 66.925 | 69.448 | 18.105 | 1.00 | 98.87 | N |
| ATOM | 1532 | NH2 | ARG | A | 322 | 67.348 | 71.079 | 19.663 | 1.00 | 99.15 | N |
| ATOM | 1533 | N | GLU | A | 323 | 60.036 | 69.778 | 14.820 | 1.00 | 89.52 | N |
| ATOM | 1534 | CA | GLU | A | 323 | 58.871 | 69.778 | 13.946 | 1.00 | 87.37 | C |
| ATOM | 1535 | C | GLU | A | 323 | 57.958 | 68.588 | 14.247 | 1.00 | 84.86 | C |
| ATOM | 1536 | O | GLU | A | 323 | 57.628 | 67.795 | 13.361 | 1.00 | 84.93 | O |
| ATOM | 1537 | CB | GLU | A | 323 | 59.311 | 69.757 | 12.478 | 1.00 | 88.77 | C |
| ATOM | 1538 | CG | GLU | A | 323 | 58.163 | 69.856 | 11.473 | 1.00 | 90.52 | C |
| ATOM | 1539 | CD | GLU | A | 323 | 57.281 | 71.080 | 11.689 | 1.00 | 91.42 | C |
| ATOM | 1540 | OE1 | GLU | A | 323 | 56.303 | 71.245 | 10.927 | 1.00 | 91.57 | O |
| ATOM | 1541 | OE2 | GLU | A | 323 | 57.560 | 71.875 | 12.615 | 1.00 | 91.76 | O |
| ATOM | 1542 | N | GLN | A | 324 | 57.553 | 68.473 | 15.509 | 1.00 | 81.41 | N |
| ATOM | 1543 | CA | GLN | A | 324 | 56.676 | 67.393 | 15.944 | 1.00 | 77.43 | C |
| ATOM | 1544 | C | GLN | A | 324 | 55.848 | 67.831 | 17.153 | 1.00 | 73.46 | C |
| ATOM | 1545 | O | GLN | A | 324 | 54.919 | 68.630 | 17.018 | 1.00 | 73.89 | O |
| ATOM | 1546 | CB | GLN | A | 324 | 57.503 | 66.146 | 16.289 | 1.00 | 79.24 | C |
| ATOM | 1547 | CG | GLN | A | 324 | 56.677 | 64.923 | 16.679 | 1.00 | 81.03 | C |
| ATOM | 1548 | CD | GLN | A | 324 | 55.595 | 64.599 | 15.665 | 1.00 | 82.58 | C |
| ATOM | 1549 | OE1 | GLN | A | 324 | 55.867 | 64.472 | 14.471 | 1.00 | 83.19 | O |
| ATOM | 1550 | NE2 | GLN | A | 324 | 54.359 | 64.463 | 16.137 | 1.00 | 83.06 | N |
| ATOM | 1551 | N | LYS | A | 325 | 56.191 | 67.312 | 18.329 | 1.00 | 67.65 | N |
| ATOM | 1552 | CA | LYS | A | 325 | 55.476 | 67.644 | 19.556 | 1.00 | 61.35 | C |
| ATOM | 1553 | C | LYS | A | 325 | 56.326 | 68.484 | 20.492 | 1.00 | 56.32 | C |
| ATOM | 1554 | O | LYS | A | 325 | 55.807 | 69.147 | 21.391 | 1.00 | 55.43 | O |
| ATOM | 1555 | CB | LYS | A | 325 | 55.056 | 66.375 | 20.299 | 1.00 | 62.67 | C |
| ATOM | 1556 | CG | LYS | A | 325 | 53.889 | 65.612 | 19.697 | 1.00 | 63.57 | C |
| ATOM | 1557 | CD | LYS | A | 325 | 53.512 | 64.469 | 20.624 | 1.00 | 64.06 | C |
| ATOM | 1558 | CE | LYS | A | 325 | 52.278 | 63.738 | 20.158 | 1.00 | 64.95 | C |
| ATOM | 1559 | NZ | LYS | A | 325 | 51.932 | 62.638 | 21.100 | 1.00 | 65.54 | N |
| ATOM | 1560 | N | GLY | A | 326 | 57.636 | 68.444 | 20.292 | 1.00 | 50.41 | N |
| ATOM | 1561 | CA | GLY | A | 326 | 58.515 | 69.204 | 21.152 | 1.00 | 44.73 | C |
| ATOM | 1562 | C | GLY | A | 326 | 58.777 | 68.502 | 22.473 | 1.00 | 41.12 | C |
| ATOM | 1563 | O | GLY | A | 326 | 59.036 | 69.151 | 23.484 | 1.00 | 38.92 | O |
| ATOM | 1564 | N | ILE | A | 327 | 58.684 | 67.174 | 22.474 | 1.00 | 37.83 | N |
| ATOM | 1565 | CA | ILE | A | 327 | 58.954 | 66.403 | 23.680 | 1.00 | 34.93 | C |
| ATOM | 1566 | C | ILE | A | 327 | 60.248 | 65.627 | 23.449 | 1.00 | 32.50 | C |
| ATOM | 1567 | O | ILE | A | 327 | 60.556 | 65.229 | 22.329 | 1.00 | 30.63 | O |
| ATOM | 1568 | CB | ILE | A | 327 | 57.807 | 65.406 | 24.022 | 1.00 | 35.16 | C |
| ATOM | 1569 | CG1 | ILE | A | 327 | 57.684 | 64.340 | 22.936 | 1.00 | 35.16 | C |
| ATOM | 1570 | CG2 | ILE | A | 327 | 56.485 | 66.157 | 24.169 | 1.00 | 36.07 | C |
| ATOM | 1571 | CD1 | ILE | A | 327 | 56.624 | 63.273 | 23.233 | 1.00 | 37.60 | C |
| ATOM | 1572 | N | GLY | A | 328 | 61.018 | 65.429 | 24.507 | 1.00 | 30.83 | N |
| ATOM | 1573 | CA | GLY | A | 328 | 62.257 | 64.695 | 24.351 | 1.00 | 30.46 | C |
| ATOM | 1574 | C | GLY | A | 328 | 63.331 | 65.116 | 25.326 | 1.00 | 28.07 | C |
| ATOM | 1575 | O | GLY | A | 328 | 63.087 | 65.907 | 26.241 | 1.00 | 26.85 | O |
| ATOM | 1576 | N | ARG | A | 329 | 64.531 | 64.587 | 25.121 | 1.00 | 27.11 | N |
| ATOM | 1577 | CA | ARG | A | 329 | 65.650 | 64.897 | 25.991 | 1.00 | 25.00 | C |
| ATOM | 1578 | C | ARG | A | 329 | 66.912 | 64.341 | 25.355 | 1.00 | 24.52 | C |
| ATOM | 1579 | O | ARG | A | 329 | 66.866 | 63.282 | 24.728 | 1.00 | 24.57 | O |
| ATOM | 1580 | CB | ARG | A | 329 | 65.426 | 64.243 | 27.356 | 1.00 | 25.02 | C |
| ATOM | 1581 | CG | ARG | A | 329 | 66.250 | 64.828 | 28.486 | 1.00 | 23.52 | C |
| ATOM | 1582 | CD | ARG | A | 329 | 66.101 | 63.994 | 29.745 | 1.00 | 23.12 | C |
| ATOM | 1583 | NE | ARG | A | 329 | 66.454 | 64.757 | 30.935 | 1.00 | 23.07 | N |
| ATOM | 1584 | CZ | ARG | A | 329 | 66.352 | 64.300 | 32.177 | 1.00 | 24.79 | C |
| ATOM | 1585 | NH1 | ARG | A | 329 | 65.909 | 63.067 | 32.402 | 1.00 | 25.05 | N |
| ATOM | 1586 | NH2 | ARG | A | 329 | 66.670 | 65.086 | 33.198 | 1.00 | 23.95 | N |
| ATOM | 1587 | N | GLY | A | 330 | 68.031 | 65.053 | 25.502 | 1.00 | 22.80 | N |
| ATOM | 1588 | CA | GLY | A | 330 | 69.281 | 64.560 | 24.952 | 1.00 | 21.71 | C |
| ATOM | 1589 | C | GLY | A | 330 | 69.466 | 63.134 | 25.449 | 1.00 | 22.12 | C |
| ATOM | 1590 | O | GLY | A | 330 | 69.269 | 62.856 | 26.635 | 1.00 | 21.20 | O |
| ATOM | 1591 | N | GLN | A | 331 | 69.844 | 62.230 | 24.552 | 1.00 | 22.96 | N |
| ATOM | 1592 | CA | GLN | A | 331 | 70.005 | 60.824 | 24.900 | 1.00 | 23.04 | C |
| ATOM | 1593 | C | GLN | A | 331 | 70.969 | 60.550 | 26.054 | 1.00 | 23.91 | C |
| ATOM | 1594 | O | GLN | A | 331 | 70.689 | 59.699 | 26.901 | 1.00 | 24.69 | O |
| ATOM | 1595 | CB | GLN | A | 331 | 70.440 | 60.023 | 23.670 | 1.00 | 23.45 | C |
| ATOM | 1596 | CG | GLN | A | 331 | 70.322 | 58.504 | 23.848 | 1.00 | 23.57 | C |
| ATOM | 1597 | CD | GLN | A | 331 | 68.876 | 58.025 | 23.890 | 1.00 | 26.07 | C |
| ATOM | 1598 | OE1 | GLN | A | 331 | 68.595 | 56.889 | 24.278 | 1.00 | 28.19 | O |
| ATOM | 1599 | NE2 | GLN | A | 331 | 67.954 | 58.887 | 23.483 | 1.00 | 23.86 | N |

TABLE 4-continued

| | | | | | | | | | | |
|---|---|---|---|---|---|---|---|---|---|---|
| ATOM | 1600 | N | ALA | A | 332 | 72.098 | 61.256 | 26.096 | 1.00 | 22.41 | N |
| ATOM | 1601 | CA | ALA | A | 332 | 73.068 | 61.042 | 27.169 | 1.00 | 22.13 | C |
| ATOM | 1602 | C | ALA | A | 332 | 72.460 | 61.375 | 28.529 | 1.00 | 21.81 | C |
| ATOM | 1603 | O | ALA | A | 332 | 72.528 | 60.581 | 29.472 | 1.00 | 20.89 | O |
| ATOM | 1604 | CB | ALA | A | 332 | 74.326 | 61.886 | 26.928 | 1.00 | 21.50 | C |
| ATOM | 1605 | N | THR | A | 333 | 71.857 | 62.553 | 28.626 | 1.00 | 20.86 | N |
| ATOM | 1606 | CA | THR | A | 333 | 71.239 | 62.979 | 29.867 | 1.00 | 21.05 | C |
| ATOM | 1607 | C | THR | A | 333 | 70.148 | 61.998 | 30.276 | 1.00 | 22.50 | C |
| ATOM | 1608 | O | THR | A | 333 | 70.013 | 61.668 | 31.456 | 1.00 | 22.49 | O |
| ATOM | 1609 | CB | THR | A | 333 | 70.622 | 64.384 | 29.730 | 1.00 | 20.97 | C |
| ATOM | 1610 | CG1 | THR | A | 333 | 71.643 | 65.308 | 29.334 | 1.00 | 19.27 | O |
| ATOM | 1611 | CG2 | THR | A | 333 | 70.023 | 64.839 | 31.069 | 1.00 | 20.51 | C |
| ATOM | 1612 | N | ALA | A | 334 | 69.378 | 61.529 | 29.297 | 1.00 | 21.69 | N |
| ATOM | 1613 | CA | ALA | A | 334 | 68.299 | 60.583 | 29.568 | 1.00 | 22.09 | C |
| ATOM | 1614 | C | ALA | A | 334 | 68.835 | 59.278 | 30.163 | 1.00 | 21.26 | C |
| ATOM | 1615 | O | ALA | A | 334 | 68.314 | 58.780 | 31.160 | 1.00 | 22.26 | O |
| ATOM | 1616 | CB | ALA | A | 334 | 67.521 | 60.290 | 28.281 | 1.00 | 20.13 | C |
| ATOM | 1617 | N | VAL | A | 335 | 69.866 | 58.721 | 29.539 | 1.00 | 22.35 | N |
| ATOM | 1618 | CA | VAL | A | 335 | 70.458 | 57.469 | 30.010 | 1.00 | 22.27 | C |
| ATOM | 1619 | C | VAL | A | 335 | 71.061 | 57.628 | 31.404 | 1.00 | 22.75 | C |
| ATOM | 1620 | O | VAL | A | 335 | 70.810 | 56.814 | 32.298 | 1.00 | 24.25 | O |
| ATOM | 1621 | CB | VAL | A | 335 | 71.561 | 56.965 | 29.041 | 1.00 | 22.72 | C |
| ATOM | 1622 | CG1 | VAL | A | 335 | 72.273 | 55.739 | 29.639 | 1.00 | 23.71 | C |
| ATOM | 1623 | CG2 | VAL | A | 335 | 70.945 | 56.602 | 27.702 | 1.00 | 21.59 | C |
| ATOM | 1624 | N | ILE | A | 336 | 71.848 | 58.680 | 31.590 | 1.00 | 22.45 | N |
| ATOM | 1625 | CA | ILE | A | 336 | 72.489 | 58.930 | 32.876 | 1.00 | 22.52 | C |
| ATOM | 1626 | C | ILE | A | 336 | 71.465 | 59.051 | 34.004 | 1.00 | 23.41 | C |
| ATOM | 1627 | O | ILE | A | 336 | 71.662 | 58.518 | 35.095 | 1.00 | 22.49 | O |
| ATOM | 1628 | CB | ILE | A | 336 | 73.349 | 60.217 | 32.817 | 1.00 | 21.60 | C |
| ATOM | 1629 | CG1 | ILE | A | 336 | 74.548 | 59.985 | 31.890 | 1.00 | 19.73 | C |
| ATOM | 1630 | CG2 | ILE | A | 336 | 73.804 | 60.623 | 34.220 | 1.00 | 18.66 | C |
| ATOM | 1631 | CD1 | ILE | A | 336 | 75.364 | 61.233 | 31.615 | 1.00 | 21.73 | C |
| ATOM | 1632 | N | ASP | A | 337 | 70.364 | 59.742 | 33.730 | 1.00 | 24.43 | N |
| ATOM | 1633 | CA | ASP | A | 337 | 69.319 | 59.938 | 34.729 | 1.00 | 24.42 | C |
| ATOM | 1634 | C | ASP | A | 337 | 68.550 | 58.646 | 35.026 | 1.00 | 24.54 | C |
| ATOM | 1635 | O | ASP | A | 337 | 68.294 | 58.317 | 36.186 | 1.00 | 23.43 | O |
| ATOM | 1636 | CS | ASP | A | 337 | 68.364 | 61.038 | 34.260 | 1.00 | 25.94 | C |
| ATOM | 1637 | CG | ASP | A | 337 | 67.298 | 61.359 | 35.285 | 1.00 | 28.42 | C |
| ATOM | 1638 | OD1 | ASP | A | 337 | 67.631 | 61.405 | 36.483 | 1.00 | 31.45 | O |
| ATOM | 1639 | OD2 | ASP | A | 337 | 66.131 | 61.578 | 34.897 | 1.00 | 29.42 | O |
| ATOM | 1640 | N | VAL | A | 338 | 68.187 | 57.912 | 33.980 | 1.00 | 24.02 | N |
| ATOM | 1641 | CA | VAL | A | 338 | 67.457 | 56.664 | 34.161 | 1.00 | 23.68 | C |
| ATOM | 1642 | C | VAL | A | 338 | 68.326 | 55.622 | 34.868 | 1.00 | 24.05 | C |
| ATOM | 1643 | O | VAL | A | 338 | 67.842 | 54.896 | 35.735 | 1.00 | 23.76 | O |
| ATOM | 1644 | CB | VAL | A | 338 | 66.956 | 56.110 | 32.800 | 1.00 | 24.17 | C |
| ATOM | 1645 | CG1 | VAL | A | 338 | 66.387 | 54.704 | 32.973 | 1.00 | 22.42 | C |
| ATOM | 1646 | CG2 | VAL | A | 338 | 65.882 | 57.046 | 32.228 | 1.00 | 21.26 | C |
| ATOM | 1647 | N | VAL | A | 339 | 69.607 | 55.562 | 34.505 | 1.00 | 23.11 | N |
| ATOM | 1648 | CA | VAL | A | 339 | 70.533 | 54.614 | 35.117 | 1.00 | 23.44 | C |
| ATOM | 1649 | C | VAL | A | 339 | 70.680 | 54.852 | 36.624 | 1.00 | 24.25 | C |
| ATOM | 1650 | O | VAL | A | 339 | 70.759 | 53.898 | 37.397 | 1.00 | 25.77 | O |
| ATOM | 1651 | CB | VAL | A | 339 | 71.930 | 54.683 | 34.444 | 1.00 | 23.37 | C |
| ATOM | 1652 | CG1 | VAL | A | 339 | 72.970 | 53.969 | 35.290 | 1.00 | 21.96 | C |
| ATOM | 1653 | CG2 | VAL | A | 339 | 71.866 | 54.039 | 33.067 | 1.00 | 21.79 | C |
| ATOM | 1654 | N | ALA | A | 340 | 70.719 | 56.114 | 37.043 | 1.00 | 23.85 | N |
| ATOM | 1655 | CA | ALA | A | 340 | 70.844 | 56.428 | 38.464 | 1.00 | 24.36 | C |
| ATOM | 1656 | C | ALA | A | 340 | 69.579 | 55.983 | 39.200 | 1.00 | 24.66 | C |
| ATOM | 1657 | O | ALA | A | 340 | 69.645 | 55.467 | 40.315 | 1.00 | 24.46 | O |
| ATOM | 1658 | CB | ALA | A | 340 | 71.068 | 57.923 | 38.661 | 1.00 | 22.34 | C |
| ATOM | 1659 | N | GLU | A | 341 | 68.426 | 56.179 | 38.571 | 1.00 | 24.16 | N |
| ATOM | 1660 | CA | GLU | A | 341 | 67.170 | 55.784 | 39.188 | 1.00 | 25.70 | C |
| ATOM | 1661 | C | GLU | A | 341 | 67.116 | 54.261 | 39.261 | 1.00 | 25.09 | C |
| ATOM | 1662 | O | GLU | A | 341 | 66.681 | 53.701 | 40.258 | 1.00 | 24.84 | O |
| ATOM | 1663 | CB | GLU | A | 341 | 65.980 | 56.309 | 38.375 | 1.00 | 26.08 | C |
| ATOM | 1664 | CG | GLU | A | 341 | 64.630 | 56.199 | 39.082 | 1.00 | 27.72 | C |
| ATOM | 1665 | CD | GLU | A | 341 | 64.541 | 57.095 | 40.311 | 1.00 | 31.11 | C |
| ATOM | 1666 | OE2 | GLU | A | 341 | 65.068 | 58.227 | 40.269 | 1.00 | 32.05 | O |
| ATOM | 1667 | OE2 | GLU | A | 341 | 63.929 | 56.680 | 41.315 | 1.00 | 31.72 | O |
| ATOM | 1668 | N | ARG | A | 342 | 67.558 | 53.601 | 38.195 | 1.00 | 25.02 | N |
| ATOM | 1669 | CA | ARG | A | 342 | 67.567 | 52.141 | 38.137 | 1.00 | 25.81 | C |
| ATOM | 1670 | C | ARG | A | 342 | 68.459 | 51.563 | 39.241 | 1.00 | 25.77 | C |
| ATOM | 1671 | O | ARG | A | 342 | 68.101 | 50.572 | 39.869 | 1.00 | 25.65 | O |
| ATOM | 1672 | CB | ARG | A | 342 | 68.045 | 51.676 | 36.752 | 1.00 | 24.80 | C |
| ATOM | 1673 | CG | ARG | A | 342 | 67.994 | 50.162 | 36.495 | 1.00 | 24.72 | C |
| ATOM | 1674 | CD | ARG | A | 342 | 69.246 | 49.441 | 37.015 | 1.00 | 23.36 | C |
| ATOM | 1675 | NE | ARG | A | 342 | 70.486 | 49.936 | 36.413 | 1.00 | 22.99 | N |
| ATOM | 1676 | CZ | ARG | A | 342 | 70.856 | 49.729 | 35.149 | 1.00 | 23.14 | C |
| ATOM | 1677 | NH1 | ARG | A | 342 | 70.086 | 49.028 | 34.325 | 1.00 | 23.28 | N |
| ATOM | 1678 | NH2 | ARG | A | 342 | 72.002 | 50.227 | 34.701 | 1.00 | 22.15 | N |

TABLE 4-continued

| ATOM | 1679 | N   | ASN | A | 343 | 69.609 | 52.189 | 39.481 | 1.00 | 25.74 | N |
|------|------|-----|-----|---|-----|--------|--------|--------|------|-------|---|
| ATOM | 1680 | CA  | ASN | A | 343 | 70.524 | 51.722 | 40.519 | 1.00 | 26.49 | C |
| ATOM | 1681 | C   | ASN | A | 343 | 69.928 | 51.972 | 41.899 | 1.00 | 28.14 | C |
| ATOM | 1682 | O   | ASN | A | 343 | 70.119 | 51.191 | 42.826 | 1.00 | 28.20 | O |
| ATOM | 1683 | CB  | ASN | A | 343 | 71.880 | 52.418 | 40.396 | 1.00 | 24.99 | C |
| ATOM | 1684 | CO  | ASN | A | 343 | 72.642 | 51.980 | 39.163 | 1.00 | 26.53 | C |
| ATOM | 1685 | OD1 | ASN | A | 343 | 72.333 | 50.943 | 38.572 | 1.00 | 25.64 | O |
| ATOM | 1686 | ND2 | ASN | A | 343 | 73.650 | 52.756 | 38.774 | 1.00 | 24.62 | N |
| ATOM | 1687 | N   | LYS | A | 344 | 69.198 | 53.071 | 42.026 | 1.00 | 29.38 | N |
| ATOM | 1688 | CA  | LYS | A | 344 | 68.545 | 53.410 | 43.276 | 1.00 | 30.78 | C |
| ATOM | 1689 | C   | LYS | A | 344 | 67.447 | 52.373 | 43.508 | 1.00 | 30.83 | C |
| ATOM | 1690 | O   | LYS | A | 344 | 67.280 | 51.861 | 44.612 | 1.00 | 31.06 | O |
| ATOM | 1691 | CB  | LYS | A | 344 | 67.947 | 54.810 | 43.172 | 1.00 | 33.74 | C |
| ATOM | 1692 | CG  | LYS | A | 344 | 67.298 | 55.335 | 44.437 | 1.00 | 38.78 | C |
| ATOM | 1693 | CD  | LYS | A | 344 | 66.906 | 56.799 | 44.255 | 1.00 | 41.30 | C |
| ATOM | 1694 | CE  | LYS | A | 344 | 66.250 | 57.364 | 45.501 | 1.00 | 43.10 | C |
| ATOM | 1695 | NZ  | LYS | A | 344 | 65.928 | 58.810 | 45.325 | 1.00 | 46.21 | N |
| ATOM | 1696 | N   | TYR | A | 345 | 66.715 | 52.054 | 42.448 | 1.00 | 29.99 | N |
| ATOM | 1697 | CA  | TYR | A | 345 | 65.640 | 51.076 | 42.516 | 1.00 | 30.40 | C |
| ATOM | 1698 | C   | TYR | A | 345 | 66.174 | 49.696 | 42.921 | 1.00 | 31.13 | C |
| ATOM | 1699 | O   | TYR | A | 345 | 65.538 | 48.977 | 43.693 | 1.00 | 31.45 | O |
| ATOM | 1700 | CB  | TYR | A | 345 | 64.950 | 50.968 | 41.162 | 1.00 | 29.11 | C |
| ATOM | 1701 | CG  | TYR | A | 345 | 63.630 | 50.231 | 41.196 | 1.00 | 29.15 | C |
| ATOM | 1702 | CD1 | TYR | A | 345 | 62.465 | 50.880 | 41.597 | 1.00 | 29.67 | C |
| ATOM | 1703 | CD2 | TYR | A | 345 | 63.539 | 48.896 | 40.802 | 1.00 | 28.37 | C |
| ATOM | 1704 | CE1 | TYR | A | 345 | 61.243 | 50.226 | 41.597 | 1.00 | 29.42 | C |
| ATOM | 1705 | CE2 | TYR | A | 345 | 62.318 | 48.230 | 40.800 | 1.00 | 29.73 | C |
| ATOM | 1706 | CZ  | TYR | A | 345 | 61.175 | 48.905 | 41.196 | 1.00 | 30.08 | C |
| ATOM | 1707 | OH  | TYR | A | 345 | 59.954 | 48.279 | 41.163 | 1.00 | 31.23 | O |
| ATOM | 1708 | N   | PHE | A | 346 | 67.334 | 49.328 | 42.387 | 1.00 | 31.61 | N |
| ATOM | 1709 | CA  | PHE | A | 346 | 67.949 | 48.040 | 42.705 | 1.00 | 32.63 | C |
| ATOM | 1710 | C   | PHE | A | 346 | 68.288 | 47.958 | 44.194 | 1.00 | 33.80 | C |
| ATOM | 1711 | O   | PHE | A | 346 | 68.060 | 46.932 | 44.837 | 1.00 | 33.23 | O |
| ATOM | 1712 | CB  | PHE | A | 346 | 69.223 | 47.836 | 41.877 | 1.00 | 32.13 | C |
| ATOM | 1713 | CG  | PHE | A | 346 | 69.961 | 46.567 | 42.204 | 1.00 | 33.47 | C |
| ATOM | 1714 | CD1 | PHE | A | 346 | 69.380 | 45.326 | 41.969 | 1.00 | 33.38 | C |
| ATOM | 1715 | CD2 | PHE | A | 346 | 71.235 | 46.613 | 42.763 | 1.00 | 35.61 | C |
| ATOM | 1716 | CE1 | PHE | A | 346 | 70.050 | 44.151 | 42.284 | 1.00 | 33.75 | C |
| ATOM | 1717 | CE2 | PHE | A | 346 | 71.917 | 45.440 | 43.084 | 1.00 | 36.22 | C |
| ATOM | 1718 | CZ  | PHE | A | 346 | 71.320 | 44.206 | 42.842 | 1.00 | 35.99 | C |
| ATOM | 1719 | N   | GLU | A | 347 | 68.826 | 49.045 | 44.737 | 1.00 | 34.63 | N |
| ATOM | 1720 | CA  | GLU | A | 347 | 69.187 | 49.090 | 46.148 | 1.00 | 37.31 | C |
| ATOM | 1721 | C   | GLU | A | 347 | 67.980 | 48.990 | 47.074 | 1.00 | 37.23 | C |
| ATOM | 1722 | O   | GLU | A | 347 | 68.068 | 48.393 | 48.144 | 1.00 | 38.77 | O |
| ATOM | 1723 | CB  | GLU | A | 347 | 69.953 | 50.377 | 46.468 | 1.00 | 37.91 | C |
| ATOM | 1724 | CG  | GLU | A | 347 | 71.349 | 50.441 | 45.877 | 1.00 | 43.97 | C |
| ATOM | 1725 | CD  | GLU | A | 347 | 72.215 | 49.262 | 46.296 | 1.00 | 47.61 | C |
| ATOM | 1726 | OE1 | GLU | A | 347 | 72.231 | 48.923 | 47.501 | 1.00 | 50.24 | O |
| ATOM | 1727 | OE2 | GLU | A | 347 | 72.889 | 48.675 | 45.420 | 1.00 | 50.39 | O |
| ATOM | 1728 | N   | GLU | A | 348 | 66.858 | 49.571 | 46.664 | 1.00 | 36.75 | N |
| ATOM | 1729 | CA  | GLU | A | 348 | 65.652 | 49.556 | 47.482 | 1.00 | 36.89 | C |
| ATOM | 1730 | C   | GLU | A | 348 | 64.901 | 48.230 | 47.444 | 1.00 | 36.67 | C |
| ATOM | 1731 | O   | GLU | A | 348 | 64.376 | 47.780 | 48.460 | 1.00 | 37.48 | O |
| ATOM | 1732 | CB  | GLU | A | 348 | 64.672 | 50.643 | 47.022 | 1.00 | 37.65 | C |
| ATOM | 1733 | CG  | GLU | A | 348 | 65.295 | 51.969 | 46.635 | 1.00 | 40.22 | C |
| ATOM | 1734 | CD  | GLU | A | 348 | 64.265 | 52.960 | 46.108 | 1.00 | 40.32 | C |
| ATOM | 1735 | OE1 | GLU | A | 348 | 63.309 | 52.526 | 45.434 | 1.00 | 41.11 | O |
| ATOM | 1736 | OE2 | GLU | A | 348 | 64.417 | 54.174 | 46.356 | 1.00 | 41.33 | O |
| ATOM | 1737 | N   | THR | A | 349 | 64.856 | 47.610 | 46.268 | 1.00 | 35.60 | N |
| ATOM | 1738 | CA  | THR | A | 349 | 64.096 | 46.382 | 46.075 | 1.00 | 33.65 | C |
| ATOM | 1739 | C   | THR | A | 349 | 64.859 | 45.094 | 45.759 | 1.00 | 33.57 | C |
| ATOM | 1740 | O   | THR | A | 349 | 64.282 | 44.006 | 45.807 | 1.00 | 33.25 | O |
| ATOM | 1741 | CB  | THR | A | 349 | 63.071 | 46.588 | 44.950 | 1.00 | 33.39 | C |
| ATOM | 1742 | OG1 | THR | A | 349 | 63.763 | 46.710 | 43.700 | 1.00 | 32.24 | O |
| ATOM | 1743 | CG2 | THR | A | 349 | 62.265 | 47.863 | 45.187 | 1.00 | 33.01 | C |
| ATOM | 1744 | N   | GLY | A | 350 | 66.138 | 45.205 | 45.425 | 1.00 | 32.80 | N |
| ATOM | 1745 | CA  | GLY | A | 350 | 66.903 | 44.018 | 45.085 | 1.00 | 31.46 | C |
| ATOM | 1746 | C   | GLY | A | 350 | 66.608 | 43.556 | 43.666 | 1.00 | 29.99 | C |
| ATOM | 1747 | O   | GLY | A | 350 | 67.073 | 42.503 | 43.232 | 1.00 | 30.31 | O |
| ATOM | 1748 | N   | ILE | A | 351 | 65.832 | 44.346 | 42.933 | 1.00 | 28.63 | N |
| ATOM | 1749 | CA  | ILE | A | 351 | 65.482 | 44.001 | 41.557 | 1.00 | 27.69 | C |
| ATOM | 1750 | C   | ILE | A | 351 | 66.327 | 44.807 | 40.575 | 1.00 | 27.05 | C |
| ATOM | 1751 | O   | ILE | A | 351 | 66.315 | 46.036 | 40.612 | 1.00 | 24.50 | O |
| ATOM | 1752 | CB  | ILE | A | 351 | 64.004 | 44.315 | 41.253 | 1.00 | 29.37 | C |
| ATOM | 1753 | CG1 | ILE | A | 351 | 63.092 | 43.640 | 42.281 | 1.00 | 31.00 | C |
| ATOM | 1754 | CG2 | ILE | A | 351 | 63.662 | 43.862 | 39.841 | 1.00 | 28.85 | C |
| ATOM | 1755 | CD1 | ILE | A | 351 | 61.625 | 44.051 | 42.154 | 1.00 | 32.57 | C |
| ATOM | 1756 | N   | TYR | A | 352 | 67.060 | 44.121 | 39.702 | 1.00 | 26.80 | N |
| ATOM | 1757 | CA  | TYR | A | 352 | 67.879 | 44.811 | 38.715 | 1.00 | 26.62 | C |

TABLE 4-continued

| ATOM | 1758 | C | TYR | A | 352 | 67.142 | 44.808 | 37.385 | 1.00 | 26.67 | C |
|---|---|---|---|---|---|---|---|---|---|---|---|
| ATOM | 1759 | O | TYR | A | 352 | 66.899 | 43.751 | 36.804 | 1.00 | 26.28 | O |
| ATOM | 1760 | CB | TYR | A | 352 | 69.240 | 44.130 | 38.527 | 1.00 | 25.22 | C |
| ATOM | 1761 | CG | TYR | A | 352 | 70.153 | 44.886 | 37.578 | 1.00 | 24.08 | C |
| ATOM | 1762 | CD1 | TYR | A | 352 | 70.961 | 45.931 | 38.035 | 1.00 | 22.64 | C |
| ATOM | 1763 | CD2 | TYR | A | 352 | 70.185 | 44.580 | 36.218 | 1.00 | 23.85 | C |
| ATOM | 1764 | CE1 | TYR | A | 352 | 71.780 | 46.647 | 37.161 | 1.00 | 21.59 | C |
| ATOM | 1765 | CE2 | TYR | A | 352 | 70.998 | 45.294 | 35.334 | 1.00 | 22.91 | C |
| ATOM | 1766 | CZ | TYR | A | 352 | 71.793 | 46.321 | 35.814 | 1.00 | 21.43 | C |
| ATOM | 1767 | OH | TYR | A | 352 | 72.621 | 47.001 | 34.951 | 1.00 | 22.44 | O |
| ATOM | 1768 | N | ILE | A | 353 | 66.782 | 45.992 | 36.906 | 1.00 | 26.51 | N |
| ATOM | 1769 | CA | ILE | A | 353 | 66.085 | 46.094 | 35.635 | 1.00 | 26.58 | C |
| ATOM | 1770 | C | ILE | A | 353 | 67.019 | 46.605 | 34.542 | 1.00 | 26.72 | C |
| ATOM | 1771 | O | ILE | A | 353 | 67.517 | 47.730 | 34.612 | 1.00 | 26.19 | O |
| ATOM | 1772 | CB | ILE | A | 353 | 64.882 | 47.042 | 35.735 | 1.00 | 27.79 | C |
| ATOM | 1773 | CG1 | ILE | A | 353 | 63.948 | 46.566 | 36.855 | 1.00 | 28.55 | C |
| ATOM | 1774 | CG2 | ILE | A | 353 | 64.147 | 47.086 | 34.399 | 1.00 | 27.23 | C |
| ATOM | 1775 | CD1 | ILE | A | 353 | 62.751 | 47.446 | 37.089 | 1.00 | 27.39 | C |
| ATOM | 1776 | N | PRO | A | 354 | 67.290 | 45.770 | 33.526 | 1.00 | 25.87 | N |
| ATOM | 1777 | CA | PRO | A | 354 | 68.174 | 46.189 | 32.435 | 1.00 | 24.49 | C |
| ATOM | 1778 | C | PRO | A | 354 | 67.530 | 47.347 | 31.680 | 1.00 | 24.47 | C |
| ATOM | 1779 | O | PRO | A | 354 | 66.312 | 47.368 | 31.503 | 1.00 | 24.18 | O |
| ATOM | 1780 | CB | PRO | A | 354 | 68.273 | 44.935 | 31.568 | 1.00 | 23.91 | C |
| ATOM | 1781 | CG | PRO | A | 354 | 68.077 | 43.813 | 32.561 | 1.00 | 24.60 | C |
| ATOM | 1782 | CD | PRO | A | 354 | 66.947 | 44.341 | 33.409 | 1.00 | 25.26 | C |
| ATOM | 1783 | N | VAL | A | 355 | 68.333 | 48.317 | 31.250 | 1.00 | 23.40 | N |
| ATOM | 1784 | CA | VAL | A | 355 | 67.783 | 49.433 | 30.495 | 1.00 | 22.64 | C |
| ATOM | 1785 | C | VAL | A | 355 | 68.418 | 49.464 | 29.119 | 1.00 | 22.19 | C |
| ATOM | 1786 | O | VAL | A | 355 | 69.576 | 49.090 | 28.944 | 1.00 | 21.72 | O |
| ATOM | 1787 | CB | VAL | A | 355 | 67.989 | 50.805 | 31.211 | 1.00 | 23.23 | C |
| ATOM | 1788 | CG1 | VAL | A | 355 | 67.314 | 50.773 | 32.582 | 1.00 | 20.89 | C |
| ATOM | 1789 | CG2 | VAL | A | 355 | 69.478 | 51.144 | 31.325 | 1.00 | 20.18 | C |
| ATOM | 1790 | N | CYS | A | 356 | 67.640 | 49.905 | 28.141 | 1.00 | 21.94 | N |
| ATOM | 1791 | CA | CYS | A | 356 | 68.100 | 49.965 | 26.769 | 1.00 | 22.63 | C |
| ATOM | 1792 | C | CYS | A | 356 | 68.172 | 51.393 | 26.251 | 1.00 | 23.07 | C |
| ATOM | 1793 | O | CYS | A | 356 | 67.192 | 52.131 | 26.330 | 1.00 | 24.45 | O |
| ATOM | 1794 | CB | CYS | A | 356 | 67.148 | 49.152 | 25.887 | 1.00 | 22.81 | C |
| ATOM | 1795 | SG | CYS | A | 356 | 67.367 | 49.360 | 24.113 | 1.00 | 23.52 | S |
| ATOM | 1796 | N | SER | A | 357 | 69.332 | 51.784 | 25.732 | 1.00 | 23.41 | N |
| ATOM | 1797 | CA | SER | A | 357 | 69.480 | 53.118 | 25.158 | 1.00 | 23.70 | C |
| ATOM | 1798 | C | SER | A | 357 | 69.024 | 52.967 | 23.712 | 1.00 | 23.48 | C |
| ATOM | 1799 | O | SER | A | 357 | 69.703 | 52.339 | 22.902 | 1.00 | 23.03 | O |
| ATOM | 1800 | CB | SER | A | 357 | 70.933 | 53.587 | 25.186 | 1.00 | 23.53 | C |
| ATOM | 1801 | OG | SER | A | 357 | 71.039 | 54.865 | 24.579 | 1.00 | 23.13 | O |
| ATOM | 1802 | N | ASP | A | 358 | 67.871 | 53.550 | 23.406 | 1.00 | 23.76 | N |
| ATOM | 1803 | CA | ASP | A | 358 | 67.269 | 53.465 | 22.080 | 1.00 | 24.67 | C |
| ATOM | 1804 | C | ASP | A | 358 | 67.363 | 54.754 | 21.268 | 1.00 | 25.27 | C |
| ATOM | 1805 | O | ASP | A | 358 | 66.749 | 55.762 | 21.608 | 1.00 | 24.49 | O |
| ATOM | 1806 | CB | ASP | A | 358 | 65.799 | 53.040 | 22.238 | 1.00 | 24.63 | C |
| ATOM | 1807 | CG | ASP | A | 358 | 65.060 | 52.947 | 20.922 | 1.00 | 24.23 | C |
| ATOM | 1808 | OD1 | ASP | A | 358 | 65.706 | 52.780 | 19.869 | 1.00 | 24.31 | O |
| ATOM | 1809 | OD2 | ASP | A | 358 | 63.818 | 53.024 | 20.952 | 1.00 | 23.07 | O |
| ATOM | 1810 | N | GLY | A | 359 | 68.144 | 54.711 | 20.192 | 1.00 | 26.85 | N |
| ATOM | 1811 | CA | GLY | A | 359 | 68.284 | 55.870 | 19.332 | 1.00 | 28.13 | C |
| ATOM | 1812 | C | GLY | A | 359 | 69.370 | 56.852 | 19.717 | 1.00 | 30.06 | C |
| ATOM | 1813 | O | GLY | A | 359 | 69.890 | 56.829 | 20.832 | 1.00 | 30.69 | O |
| ATOM | 1814 | N | GLY | A | 360 | 69.722 | 57.717 | 18.775 | 1.00 | 32.24 | N |
| ATOM | 1815 | CA | GLY | A | 360 | 70.740 | 58.714 | 19.037 | 1.00 | 34.39 | C |
| ATOM | 1816 | C | GLY | A | 360 | 72.159 | 58.243 | 18.804 | 1.00 | 34.76 | C |
| ATOM | 1817 | O | GLY | A | 360 | 73.099 | 58.981 | 19.085 | 1.00 | 37.37 | O |
| ATOM | 1818 | N | ILE | A | 361 | 72.328 | 57.019 | 18.315 | 1.00 | 36.00 | N |
| ATOM | 1819 | CA | ILE | A | 361 | 73.664 | 56.496 | 18.046 | 1.00 | 37.27 | C |
| ATOM | 1820 | C | ILE | A | 361 | 74.052 | 56.893 | 16.627 | 1.00 | 39.44 | C |
| ATOM | 1821 | O | ILE | A | 361 | 73.479 | 56.392 | 15.657 | 1.00 | 39.25 | O |
| ATOM | 1822 | CB | ILE | A | 361 | 73.715 | 54.949 | 18.144 | 1.00 | 36.74 | C |
| ATOM | 1823 | CG1 | ILE | A | 361 | 73.421 | 54.490 | 19.580 | 1.00 | 36.41 | C |
| ATOM | 1824 | CG2 | ILE | A | 361 | 75.081 | 54.442 | 17.679 | 1.00 | 35.82 | C |
| ATOM | 1825 | CD1 | ILE | A | 361 | 74.512 | 54.788 | 20.589 | 1.00 | 33.92 | C |
| ATOM | 1826 | N | VAL | A | 362 | 75.024 | 57.793 | 16.508 | 1.00 | 41.13 | N |
| ATOM | 1827 | CA | VAL | A | 362 | 75.479 | 58.248 | 15.201 | 1.00 | 42.28 | C |
| ATOM | 1828 | C | VAL | A | 362 | 76.807 | 57.608 | 14.801 | 1.00 | 42.57 | C |
| ATOM | 1829 | O | VAL | A | 362 | 76.993 | 57.249 | 13.640 | 1.00 | 44.09 | O |
| ATOM | 1830 | CB | VAL | A | 362 | 75.630 | 59.781 | 15.167 | 1.00 | 43.37 | C |
| ATOM | 1831 | CG1 | VAL | A | 362 | 76.025 | 60.236 | 13.762 | 1.00 | 44.64 | C |
| ATOM | 1832 | CG2 | VAL | A | 362 | 74.324 | 60.438 | 15.592 | 1.00 | 43.73 | C |
| ATOM | 1833 | N | TYR | A | 363 | 77.722 | 57.459 | 15.760 | 1.00 | 41.34 | N |
| ATOM | 1834 | CA | TYR | A | 363 | 79.032 | 56.857 | 15.495 | 1.00 | 39.51 | C |
| ATOM | 1835 | C | TYR | A | 363 | 79.287 | 55.654 | 16.396 | 1.00 | 37.48 | C |
| ATOM | 1836 | O | TYR | A | 363 | 78.654 | 55.512 | 17.440 | 1.00 | 37.25 | O |

TABLE 4-continued

| | | | | | | | | | | |
|---|---|---|---|---|---|---|---|---|---|---|
| ATOM | 1837 | CB | TYR | A | 363 | 80.236 | 57.887 | 15.728 | 1.00 | 42.87 | C |
| ATOM | 1838 | CG | TYR | A | 363 | 79.974 | 59.140 | 14.896 | 1.00 | 45.48 | C |
| ATOM | 1839 | CD1 | TYR | A | 363 | 80.011 | 59.093 | 13.504 | 1.00 | 47.49 | C |
| ATOM | 1840 | CD2 | TYR | A | 363 | 79.779 | 60.374 | 15.509 | 1.00 | 46.57 | C |
| ATOM | 1841 | CE1 | TYR | A | 363 | 79.858 | 60.246 | 12.742 | 1.00 | 49.35 | C |
| ATOM | 1842 | CE2 | TYR | A | 363 | 79.625 | 61.531 | 14.759 | 1.00 | 48.79 | C |
| ATOM | 1843 | CZ | TYR | A | 363 | 79.666 | 61.461 | 13.377 | 2.00 | 49.83 | C |
| ATOM | 1844 | OH | TYR | A | 363 | 79.519 | 62.610 | 12.629 | 1.00 | 52.64 | O |
| ATOM | 1845 | N | ASP | A | 364 | 80.223 | 54.793 | 16.007 | 1.00 | 35.17 | N |
| ATOM | 1846 | CA | ASP | A | 364 | 80.523 | 53.619 | 16.821 | 1.00 | 34.10 | C |
| ATOM | 1847 | C | ASP | A | 364 | 80.846 | 53.973 | 18.271 | 1.00 | 32.20 | C |
| ATOM | 1848 | O | ASP | A | 364 | 80.387 | 53.298 | 19.191 | 1.00 | 33.00 | O |
| ATOM | 1849 | CB | ASP | A | 364 | 81.696 | 52.815 | 16.240 | 1.00 | 36.21 | C |
| ATOM | 1850 | CG | ASP | A | 364 | 81.321 | 52.031 | 14.991 | 1.00 | 36.90 | C |
| ATOM | 1851 | OD1 | ASP | A | 364 | 80.170 | 51.566 | 14.885 | 1.00 | 36.58 | O |
| ATOM | 1852 | OD2 | ASP | A | 364 | 82.194 | 51.860 | 14.118 | 1.00 | 38.57 | O |
| ATOM | 1853 | N | TYR | A | 365 | 81.621 | 55.033 | 18.485 | 1.00 | 30.02 | N |
| ATOM | 1854 | CA | TYR | A | 365 | 81.994 | 55.401 | 19.848 | 1.00 | 28.95 | C |
| ATOM | 1855 | C | TYR | A | 365 | 80.802 | 55.809 | 20.709 | 1.00 | 27.94 | C |
| ATOM | 1856 | O | TYR | A | 365 | 80.899 | 55.825 | 21.931 | 1.00 | 26.36 | O |
| ATOM | 1857 | CB | TYR | A | 365 | 83.081 | 56.489 | 19.843 | 1.00 | 28.15 | C |
| ATOM | 1858 | CG | TYR | A | 365 | 82.607 | 57.921 | 19.696 | 1.00 | 29.09 | C |
| ATOM | 1859 | CD1 | TYR | A | 365 | 82.405 | 58.729 | 20.816 | 1.00 | 28.03 | C |
| ATOM | 1860 | CD2 | TYR | A | 365 | 82.421 | 58.487 | 18.437 | 1.00 | 29.60 | C |
| ATOM | 1861 | CE1 | TYR | A | 365 | 82.039 | 60.073 | 20.681 | 1.00 | 29.32 | C |
| ATOM | 1862 | CE2 | TYR | A | 365 | 82.055 | 59.830 | 18.291 | 1.00 | 30.03 | C |
| ATOM | 1863 | CZ | TYR | A | 365 | 81.868 | 60.613 | 19.414 | 1.00 | 30.20 | C |
| ATOM | 1864 | OH | TYR | A | 365 | 81.519 | 61.936 | 19.259 | 1.00 | 32.66 | O |
| ATOM | 1865 | N | HIS | A | 366 | 79.674 | 56.126 | 20.074 | 1.00 | 28.10 | N |
| ATOM | 1866 | CA | HIS | A | 366 | 78.478 | 56.477 | 20.829 | 1.00 | 27.17 | C |
| ATOM | 1867 | C | HIS | A | 366 | 77.995 | 55.216 | 21.548 | 1.00 | 25.93 | C |
| ATOM | 1868 | O | HIS | A | 366 | 77.380 | 55.301 | 22.609 | 1.00 | 24.73 | O |
| ATOM | 1869 | CB | HIS | A | 366 | 77.371 | 57.003 | 19.909 | 1.00 | 28.22 | C |
| ATOM | 1870 | CG | HIS | A | 366 | 77.616 | 58.387 | 19.394 | 1.00 | 29.65 | C |
| ATOM | 1871 | ND1 | HIS | A | 366 | 78.642 | 59.184 | 19.856 | 1.00 | 31.11 | N |
| ATOM | 1872 | CD2 | HIS | A | 366 | 76.947 | 59.129 | 18.481 | 1.00 | 30.20 | C |
| ATOM | 1873 | CE1 | HIS | A | 366 | 78.593 | 60.357 | 19.252 | 1.00 | 29.57 | C |
| ATOM | 1874 | NE2 | HIS | A | 366 | 77.574 | 60.350 | 18.412 | 1.00 | 31.07 | N |
| ATOM | 1875 | N | MET | A | 367 | 78.275 | 54.051 | 20.960 | 1.00 | 24.23 | N |
| ATOM | 1876 | CA | MET | A | 367 | 77.892 | 52.773 | 21.569 | 1.00 | 24.28 | C |
| ATOM | 1877 | C | MET | A | 367 | 78.634 | 52.627 | 22.892 | 1.00 | 22.96 | C |
| ATOM | 1878 | O | MET | A | 367 | 78.036 | 52.342 | 23.924 | 1.00 | 23.44 | O |
| ATOM | 1879 | CB | MET | A | 367 | 78.273 | 51.595 | 20.666 | 1.00 | 24.50 | C |
| ATOM | 1880 | CG | MET | A | 367 | 77.537 | 51.530 | 19.332 | 1.00 | 26.42 | C |
| ATOM | 1881 | SD | MET | A | 367 | 78.087 | 50.102 | 18.355 | 1.00 | 29.45 | 5 |
| ATOM | 1882 | CE | MET | A | 367 | 77.053 | 50.267 | 16.894 | 1.00 | 28.05 | C |
| ATOM | 1883 | N | THR | A | 368 | 79.947 | 52.827 | 22.853 | 1.00 | 23.22 | N |
| ATOM | 1884 | CA | THR | A | 368 | 80.764 | 52.719 | 24.058 | 1.00 | 23.72 | C |
| ATOM | 1885 | C | THR | A | 368 | 80.266 | 53.711 | 25.110 | 1.00 | 22.92 | C |
| ATOM | 1886 | O | THR | A | 368 | 80.180 | 53.379 | 26.290 | 1.00 | 23.78 | O |
| ATOM | 1887 | CB | THR | A | 368 | 82.249 | 53.005 | 23.748 | 1.00 | 24.12 | C |
| ATOM | 1888 | OG1 | THR | A | 368 | 82.625 | 52.305 | 22.554 | 1.00 | 24.48 | O |
| ATOM | 1889 | CG2 | THR | A | 368 | 83.138 | 52.537 | 24.902 | 1.00 | 23.20 | C |
| ATOM | 1890 | N | LEU | A | 369 | 79.939 | 54.929 | 24.680 | 1.00 | 22.01 | N |
| ATOM | 1891 | CA | LEU | A | 369 | 79.435 | 55.947 | 25.602 | 1.00 | 22.78 | C |
| ATOM | 1892 | C | LEU | A | 369 | 78.125 | 55.525 | 26.253 | 1.00 | 22.41 | C |
| ATOM | 1893 | O | LEU | A | 369 | 77.958 | 55.659 | 27.464 | 1.00 | 23.15 | O |
| ATOM | 1894 | CB | LEU | A | 369 | 79.217 | 57.280 | 24.882 | 1.00 | 21.96 | C |
| ATOM | 1895 | CG | LEU | A | 369 | 80.456 | 58.127 | 24.604 | 1.00 | 23.46 | C |
| ATOM | 1896 | CD1 | LEU | A | 369 | 80.050 | 59.369 | 23.807 | 1.00 | 22.62 | C |
| ATOM | 1897 | CD2 | LEU | A | 369 | 81.114 | 58.520 | 25.929 | 1.00 | 21.25 | C |
| ATOM | 1898 | N | ALA | A | 370 | 77.197 | 55.016 | 25.445 | 1.00 | 21.89 | N |
| ATOM | 1899 | CA | ALA | A | 370 | 75.898 | 54.592 | 25.956 | 1.00 | 22.53 | C |
| ATOM | 1900 | C | ALA | A | 370 | 76.069 | 53.503 | 27.013 | 1.00 | 21.32 | C |
| ATOM | 1901 | O | ALA | A | 370 | 75.411 | 53.524 | 28.047 | 1.00 | 22.46 | O |
| ATOM | 1902 | CB | ALA | A | 370 | 75.018 | 54.087 | 24.805 | 1.00 | 20.75 | C |
| ATOM | 1903 | N | LEU | A | 371 | 76.959 | 52.555 | 26.751 | 1.00 | 21.38 | N |
| ATOM | 1904 | CA | LEU | A | 371 | 77.205 | 51.470 | 27.693 | 1.00 | 21.60 | C |
| ATOM | 1905 | C | LEU | A | 371 | 77.899 | 52.010 | 28.950 | 1.00 | 22.18 | C |
| ATOM | 1906 | O | LEU | A | 371 | 77.494 | 51.700 | 30.063 | 1.00 | 22.86 | O |
| ATOM | 1907 | CB | LEU | A | 371 | 78.062 | 50.384 | 27.029 | 1.00 | 20.20 | C |
| ATOM | 1908 | CG | LEU | A | 371 | 77.444 | 49.692 | 25.806 | 1.00 | 21.57 | C |
| ATOM | 1909 | CD1 | LEU | A | 371 | 78.482 | 48.784 | 25.147 | 1.00 | 23.83 | C |
| ATOM | 1910 | CD2 | LEU | A | 371 | 76.220 | 48.884 | 26.228 | 1.00 | 21.62 | C |
| ATOM | 1911 | N | ALA | A | 372 | 78.932 | 52.835 | 28.763 | 1.00 | 22.30 | N |
| ATOM | 1912 | CA | ALA | A | 372 | 79.675 | 53.407 | 29.883 | 1.00 | 22.28 | C |
| ATOM | 1913 | C | ALA | A | 372 | 78.768 | 54.196 | 30.814 | 1.00 | 23.49 | C |
| ATOM | 1914 | O | ALA | A | 372 | 78.979 | 54.225 | 32.027 | 1.00 | 22.49 | O |
| ATOM | 1915 | CB | ALA | A | 372 | 80.794 | 54.305 | 29.369 | 1.00 | 21.55 | C |

TABLE 4-continued

| | | | | | | | | | | |
|---|---|---|---|---|---|---|---|---|---|---|
| ATOM | 1916 | N | MET | A | 373 | 77.763 | 54.848 | 30.242 | 1.00 | 23.46 | N |
| ATOM | 1917 | CA | MET | A | 373 | 76.837 | 55.631 | 31.043 | 1.00 | 23.37 | C |
| ATOM | 1918 | C | MET | A | 373 | 75.850 | 54.762 | 31.830 | 1.00 | 22.64 | C |
| ATOM | 1919 | O | MET | A | 373 | 75.111 | 55.269 | 32.662 | 1.00 | 22.93 | O |
| ATOM | 1920 | CB | MET | A | 373 | 76.100 | 56.639 | 30.150 | 1.00 | 23.08 | C |
| ATOM | 1921 | CG | MET | A | 373 | 77.007 | 57.763 | 29.640 | 1.00 | 23.17 | C |
| ATOM | 1922 | SD | MET | A | 373 | 76.206 | 58.901 | 28.474 | 1.00 | 23.90 | S |
| ATOM | 1923 | CE | MET | A | 373 | 77.545 | 60.031 | 28.102 | 1.00 | 22.19 | C |
| ATOM | 1924 | N | GLY | A | 374 | 75.842 | 53.457 | 31.577 | 1.00 | 23.01 | N |
| ATOM | 1925 | CA | GLY | A | 374 | 74.952 | 52.579 | 32.322 | 1.00 | 22.40 | C |
| ATOM | 1926 | C | GLY | A | 374 | 73.945 | 51.751 | 31.540 | 1.00 | 23.47 | C |
| ATOM | 1927 | O | GLY | A | 374 | 73.316 | 50.853 | 32.106 | 1.00 | 24.05 | O |
| ATOM | 1928 | N | ALA | A | 375 | 73.764 | 52.041 | 30.257 | 1.00 | 22.06 | N |
| ATOM | 1929 | CA | ALA | A | 375 | 72.826 | 51.264 | 29.460 | 1.00 | 23.47 | C |
| ATOM | 1930 | C | ALA | A | 375 | 73.365 | 49.840 | 29.331 | 1.00 | 23.69 | C |
| ATOM | 1931 | O | ALA | A | 375 | 74.549 | 49.641 | 29.065 | 1.00 | 25.05 | O |
| ATOM | 1932 | CB | ALA | A | 375 | 72.655 | 51.887 | 28.082 | 1.00 | 20.67 | C |
| ATOM | 1933 | N | ASP | A | 376 | 72.497 | 48.854 | 29.528 | 1.00 | 24.20 | N |
| ATOM | 1934 | CA | ASP | A | 376 | 72.895 | 47.453 | 29.431 | 1.00 | 24.16 | C |
| ATOM | 1935 | C | ASP | A | 376 | 73.021 | 47.053 | 27.968 | 1.00 | 23.81 | C |
| ATOM | 1936 | O | ASP | A | 376 | 73.937 | 46.324 | 27.596 | 1.00 | 23.82 | O |
| ATOM | 1937 | CB | ASP | A | 376 | 71.878 | 46.579 | 30.159 | 1.00 | 24.02 | C |
| ATOM | 1938 | CG | ASP | A | 376 | 71.763 | 46.939 | 31.632 | 1.00 | 24.67 | C |
| ATOM | 1939 | OD1 | ASP | A | 376 | 72.561 | 46.418 | 32.444 | 1.00 | 24.99 | O |
| ATOM | 1940 | OD2 | ASP | A | 376 | 70.889 | 47.764 | 31.977 | 1.00 | 24.71 | O |
| ATOM | 1941 | N | PHE | A | 377 | 72.094 | 47.521 | 27.139 | 1.00 | 23.81 | N |
| ATOM | 1942 | CA | PHE | A | 377 | 72.164 | 47.245 | 25.712 | 1.00 | 23.63 | C |
| ATOM | 1943 | C | PHE | A | 377 | 71.667 | 48.440 | 24.905 | 1.00 | 23.27 | C |
| ATOM | 1944 | O | PHE | A | 377 | 71.132 | 49.398 | 25.462 | 1.00 | 22.71 | O |
| ATOM | 1945 | CB | PHE | A | 377 | 71.427 | 45.942 | 25.320 | 1.00 | 22.50 | C |
| ATOM | 1946 | CG | PHE | A | 377 | 70.013 | 45.838 | 25.817 | 1.00 | 23.64 | C |
| ATOM | 1947 | CD1 | PHE | A | 377 | 69.748 | 45.464 | 27.132 | 1.00 | 25.15 | C |
| ATOM | 1948 | CD2 | PHE | A | 377 | 68.941 | 46.055 | 24.953 | 1.00 | 22.89 | C |
| ATOM | 1949 | CE1 | PHE | A | 377 | 68.428 | 45.300 | 27.579 | 1.00 | 25.01 | C |
| ATOM | 1950 | CE2 | PHE | A | 377 | 67.626 | 45.895 | 25.387 | 1.00 | 23.60 | C |
| ATOM | 1951 | CZ | PHE | A | 377 | 67.369 | 45.516 | 26.702 | 1.00 | 24.96 | C |
| ATOM | 1952 | N | ILE | A | 378 | 71.857 | 48.376 | 23.592 | 1.00 | 22.99 | N |
| ATOM | 1953 | CA | ILE | A | 378 | 71.512 | 49.470 | 22.698 | 1.00 | 23.32 | C |
| ATOM | 1954 | C | ILE | A | 378 | 70.573 | 49.043 | 21.573 | 1.00 | 24.13 | C |
| ATOM | 1955 | O | ILE | A | 378 | 70.760 | 47.983 | 20.978 | 1.00 | 24.04 | O |
| ATOM | 1956 | CB | ILE | A | 378 | 72.815 | 50.030 | 22.061 | 1.00 | 24.07 | C |
| ATOM | 1957 | CG1 | ILE | A | 378 | 73.807 | 50.406 | 23.163 | 1.00 | 25.55 | C |
| ATOM | 1958 | CG2 | ILE | A | 378 | 72.521 | 51.232 | 21.176 | 1.00 | 23.97 | C |
| ATOM | 1959 | CD1 | ILE | A | 378 | 75.242 | 50.486 | 22.665 | 1.00 | 25.45 | C |
| ATOM | 1960 | N | MET | A | 379 | 69.565 | 49.866 | 21.285 | 1.00 | 23.06 | N |
| ATOM | 1961 | CA | MET | A | 379 | 68.643 | 49.566 | 20.195 | 1.00 | 23.94 | C |
| ATOM | 1962 | C | MET | A | 379 | 68.968 | 50.516 | 19.045 | 1.00 | 24.07 | C |
| ATOM | 1963 | O | MET | A | 379 | 69.061 | 51.725 | 19.237 | 1.00 | 23.67 | O |
| ATOM | 1964 | CB | MET | A | 379 | 67.179 | 49.746 | 20.621 | 1.00 | 23.89 | C |
| ATOM | 1965 | CG | MET | A | 379 | 66.206 | 49.546 | 19.461 | 1.00 | 23.47 | C |
| ATOM | 1966 | SD | MET | A | 379 | 64.466 | 49.424 | 19.913 | 1.00 | 23.78 | S |
| ATOM | 1967 | CE | MET | A | 379 | 64.375 | 47.682 | 20.458 | 1.00 | 23.21 | C |
| ATOM | 1968 | N | LEU | A | 380 | 69.136 | 49.961 | 17.851 | 1.00 | 24.45 | N |
| ATOM | 1969 | CA | LEU | A | 380 | 69.476 | 50.758 | 16.682 | 1.00 | 25.64 | C |
| ATOM | 1970 | C | LEU | A | 380 | 68.561 | 50.484 | 15.502 | 1.00 | 25.46 | C |
| ATOM | 1971 | O | LEU | A | 380 | 68.162 | 49.346 | 15.265 | 1.00 | 24.86 | O |
| ATOM | 1972 | CB | LEU | A | 380 | 70.922 | 50.477 | 16.259 | 1.00 | 26.84 | C |
| ATOM | 1973 | CG | LEU | A | 380 | 72.033 | 50.818 | 17.255 | 1.00 | 28.40 | C |
| ATOM | 1974 | CD1 | LEU | A | 380 | 73.394 | 50.462 | 16.689 | 1.00 | 28.92 | C |
| ATOM | 1975 | CD2 | LEU | A | 380 | 71.977 | 52.299 | 17.546 | 1.00 | 31.59 | C |
| ATOM | 1976 | N | GLY | A | 381 | 68.238 | 51.539 | 14.764 | 1.00 | 26.35 | N |
| ATOM | 1977 | CA | GLY | A | 381 | 67.398 | 51.397 | 13.587 | 1.00 | 27.38 | C |
| ATOM | 1978 | C | GLY | A | 381 | 68.230 | 51.618 | 12.335 | 1.00 | 27.51 | C |
| ATOM | 1979 | O | GLY | A | 381 | 68.535 | 50.679 | 11.604 | 1.00 | 27.02 | O |
| ATOM | 1980 | N | ARG | A | 382 | 68.611 | 52.870 | 12.108 | 1.00 | 29.52 | N |
| ATOM | 1981 | CA | ARG | A | 382 | 69.412 | 53.264 | 10.947 | 1.00 | 32.19 | C |
| ATOM | 1982 | C | ARG | A | 382 | 70.626 | 52.353 | 10.722 | 1.00 | 30.92 | C |
| ATOM | 1983 | O | ARG | A | 382 | 70.878 | 51.899 | 9.608 | 1.00 | 30.21 | O |
| ATOM | 1984 | CB | ARG | A | 382 | 69.895 | 54.707 | 11.125 | 1.00 | 35.86 | C |
| ATOM | 1985 | CG | ARG | A | 382 | 69.994 | 55.497 | 9.834 | 1.00 | 42.94 | C |
| ATOM | 1986 | CD | ARG | A | 382 | 70.799 | 56.793 | 9.990 | 1.00 | 48.04 | C |
| ATOM | 1987 | NE | ARG | A | 382 | 72.237 | 56.531 | 10.060 | 1.00 | 52.92 | N |
| ATOM | 1988 | CZ | ARG | A | 382 | 72.883 | 56.136 | 11.156 | 1.00 | 55.81 | C |
| ATOM | 1989 | NH1 | ARG | A | 382 | 72.228 | 55.961 | 12.296 | 1.00 | 57.30 | N |
| ATOM | 1990 | NH2 | ARG | A | 382 | 74.187 | 55.896 | 11.106 | 1.00 | 56.34 | N |
| ATOM | 1991 | N | TYR | A | 383 | 71.376 | 52.105 | 11.791 | 1.00 | 29.98 | N |
| ATOM | 1992 | CA | TYR | A | 383 | 72.569 | 51.261 | 11.748 | 1.00 | 28.39 | C |
| ATOM | 1993 | C | TYR | A | 383 | 72.324 | 49.926 | 11.034 | 1.00 | 28.21 | C |
| ATOM | 1994 | O | TYR | A | 383 | 73.084 | 49.543 | 10.143 | 1.00 | 27.77 | O |

TABLE 4-continued

| | | | | | | | | | | | |
|---|---|---|---|---|---|---|---|---|---|---|---|
| ATOM | 1995 | CB | TYR | A | 383 | 73.059 | 51.000 | 13.179 | 1.00 | 26.48 | C |
| ATOM | 1996 | CG | TYR | A | 383 | 74.301 | 50.137 | 13.276 | 1.00 | 25.37 | C |
| ATOM | 1997 | CD1 | TYR | A | 383 | 75.578 | 50.703 | 13.240 | 1.00 | 24.67 | C |
| ATOM | 1998 | CD2 | TYR | A | 383 | 74.196 | 48.752 | 13.397 | 1.00 | 24.26 | C |
| ATOM | 1999 | CE1 | TYR | A | 383 | 76.716 | 49.910 | 13.322 | 1.00 | 24.73 | C |
| ATOM | 2000 | CE2 | TYR | A | 383 | 75.320 | 47.951 | 13.479 | 1.00 | 23.84 | C |
| ATOM | 2001 | CZ | TYR | A | 383 | 76.578 | 48.530 | 13.440 | 1.00 | 25.89 | C |
| ATOM | 2002 | OH | TYR | A | 383 | 77.689 | 47.722 | 13.511 | 1.00 | 25.39 | O |
| ATOM | 2003 | N | PHE | A | 384 | 71.263 | 49.228 | 11.428 | 1.00 | 27.07 | N |
| ATOM | 2004 | CA | PHE | A | 384 | 70.922 | 47.931 | 10.843 | 1.00 | 28.18 | C |
| ATOM | 2005 | C | PHE | A | 384 | 70.200 | 48.007 | 9.493 | 1.00 | 28.50 | C |
| ATOM | 2006 | O | PHE | A | 384 | 70.278 | 47.076 | 8.696 | 1.00 | 29.39 | O |
| ATOM | 2007 | CB | PHE | A | 384 | 70.068 | 47.122 | 11.827 | 1.00 | 25.94 | C |
| ATOM | 2008 | CG | PHE | A | 384 | 70.832 | 46.611 | 13.025 | 1.00 | 26.50 | C |
| ATOM | 2009 | CG | PHE | A | 384 | 71.790 | 45.610 | 12.882 | 1.00 | 25.77 | C |
| ATOM | 2010 | CD2 | PHE | A | 384 | 70.595 | 47.133 | 14.295 | 1.00 | 25.04 | C |
| ATOM | 2011 | CE1 | PHE | A | 384 | 72.502 | 45.135 | 13.983 | 1.00 | 25.85 | C |
| ATOM | 2012 | CE2 | PHE | A | 384 | 71.300 | 46.666 | 15.402 | 1.00 | 26.26 | C |
| ATOM | 2013 | CZ | PHE | A | 384 | 72.258 | 45.663 | 15.246 | 1.00 | 25.10 | C |
| ATOM | 2014 | N | ALA | A | 385 | 69.493 | 49.105 | 9.244 | 1.00 | 29.51 | N |
| ATOM | 2015 | CA | ALA | A | 385 | 68.758 | 49.281 | 7.996 | 1.00 | 29.99 | C |
| ATOM | 2016 | C | ALA | A | 385 | 69.686 | 49.249 | 6.780 | 1.00 | 31.15 | C |
| ATOM | 2017 | O | ALA | A | 385 | 69.275 | 48.868 | 5.685 | 1.00 | 31.07 | O |
| ATOM | 2018 | CB | ALA | A | 385 | 67.993 | 50.600 | 8.033 | 1.00 | 29.53 | C |
| ATOM | 2019 | N | ARG | A | 386 | 70.939 | 49.647 | 6.989 | 1.00 | 32.12 | N |
| ATOM | 2020 | CA | ARG | A | 386 | 71.949 | 49.686 | 5.936 | 1.00 | 32.14 | C |
| ATOM | 2021 | C | ARG | A | 386 | 72.391 | 48.308 | 5.453 | 1.00 | 32.91 | C |
| ATOM | 2022 | O | ARG | A | 386 | 72.983 | 48.180 | 4.380 | 1.00 | 33.24 | O |
| ATOM | 2023 | CB | ARG | A | 386 | 73.204 | 50.405 | 6.434 | 1.00 | 32.61 | C |
| ATOM | 2024 | CG | ARG | A | 386 | 73.039 | 51.825 | 6.908 | 1.00 | 33.83 | C |
| ATOM | 2025 | CD | ARG | A | 386 | 74.356 | 52.269 | 7.538 | 1.00 | 36.13 | C |
| ATOM | 2026 | NE | ARG | A | 386 | 74.740 | 51.371 | 8.628 | 1.00 | 36.98 | N |
| ATOM | 2027 | CZ | ARG | A | 386 | 75.990 | 51.156 | 9.027 | 1.00 | 37.29 | C |
| ATOM | 2028 | NH1 | ARG | A | 386 | 77.004 | 51.772 | 8.429 | 1.00 | 36.98 | N |
| ATOM | 2029 | NH2 | ARG | A | 386 | 76.227 | 50.318 | 10.027 | 1.00 | 36.19 | N |
| ATOM | 2030 | N | PHE | A | 387 | 72.126 | 47.279 | 6.248 | 1.00 | 33.19 | N |
| ATOM | 2031 | CA | PHE | A | 387 | 72.565 | 45.941 | 5.890 | 1.00 | 33.56 | C |
| ATOM | 2032 | C | PHE | A | 387 | 71.710 | 45.194 | 4.872 | 1.00 | 35.13 | C |
| ATOM | 2033 | O | PHE | A | 387 | 70.511 | 45.448 | 4.711 | 1.00 | 34.37 | O |
| ATOM | 2034 | CB | PHE | A | 387 | 72.725 | 45.085 | 7.155 | 1.00 | 32.86 | C |
| ATOM | 2035 | CG | PHE | A | 387 | 73.621 | 45.701 | 8.200 | 1.00 | 32.36 | C |
| ATOM | 2036 | CD1 | PHE | A | 387 | 74.756 | 46.417 | 7.832 | 1.00 | 31.61 | C |
| ATOM | 2037 | CD2 | PHE | A | 387 | 73.331 | 45.563 | 9.553 | 1.00 | 31.75 | C |
| ATOM | 2038 | CE1 | PHE | A | 387 | 75.586 | 46.991 | 8.797 | 1.00 | 32.70 | C |
| ATOM | 2039 | CE2 | PHE | A | 387 | 74.156 | 46.132 | 10.529 | 1.00 | 31.49 | C |
| ATOM | 2040 | CZ | PHE | A | 387 | 75.284 | 46.848 | 10.151 | 1.00 | 30.49 | C |
| ATOM | 2041 | N | GLU | A | 388 | 72.364 | 44.265 | 4.186 | 1.00 | 35.81 | N |
| ATOM | 2042 | CA | GLU | A | 388 | 71.731 | 43.428 | 3.181 | 1.00 | 36.15 | C |
| ATOM | 2043 | C | GLU | A | 388 | 70.509 | 42.735 | 3.770 | 1.00 | 34.62 | C |
| ATOM | 2044 | O | GLU | A | 388 | 69.494 | 42.577 | 3.098 | 1.00 | 33.35 | O |
| ATOM | 2045 | CB | GLU | A | 388 | 72.730 | 42.374 | 2.689 | 1.00 | 38.38 | C |
| ATOM | 2046 | CG | GLU | A | 388 | 72.130 | 41.319 | 1.771 | 1.00 | 42.94 | C |
| ATOM | 2047 | CD | GLU | A | 388 | 71.780 | 41.870 | 0.404 | 1.00 | 45.98 | C |
| ATOM | 2048 | OE1 | GLU | A | 388 | 70.997 | 41.216 | −0.324 | 1.00 | 48.50 | O |
| ATOM | 2049 | OE2 | GLU | A | 388 | 72.297 | 42.954 | 0.054 | 1.00 | 47.51 | O |
| ATOM | 2050 | N | GLU | A | 389 | 70.609 | 42.343 | 5.038 | 1.00 | 33.73 | N |
| ATOM | 2051 | CA | GLU | A | 389 | 69.526 | 41.639 | 5.706 | 1.00 | 33.32 | C |
| ATOM | 2052 | C | GLU | A | 389 | 68.295 | 42.448 | 6.115 | 1.00 | 33.33 | C |
| ATOM | 2053 | O | GLU | A | 389 | 67.313 | 41.864 | 6.563 | 1.00 | 33.97 | O |
| ATOM | 2054 | CB | GLU | A | 389 | 70.067 | 40.883 | 6.924 | 1.00 | 33.42 | C |
| ATOM | 2055 | CG | GLU | A | 389 | 71.099 | 39.827 | 6.575 | 1.00 | 33.24 | C |
| ATOM | 2056 | CD | GLU | A | 389 | 72.525 | 40.343 | 6.656 | 1.00 | 34.22 | C |
| ATOM | 2057 | OE1 | GLU | A | 389 | 72.736 | 41.563 | 6.511 | 1.00 | 33.67 | O |
| ATOM | 2058 | OE2 | GLU | A | 389 | 73.441 | 39.519 | 6.854 | 1.00 | 34.50 | O |
| ATOM | 2059 | N | SER | A | 390 | 68.328 | 43.772 | 5.986 | 1.00 | 33.75 | N |
| ATOM | 2060 | CA | SER | A | 390 | 67.145 | 44.558 | 6.341 | 1.00 | 35.12 | C |
| ATOM | 2061 | C | SER | A | 390 | 66.106 | 44.264 | 5.252 | 1.00 | 36.23 | C |
| ATOM | 2062 | O | SER | A | 390 | 66.462 | 44.028 | 4.097 | 1.00 | 35.59 | O |
| ATOM | 2063 | CB | SER | A | 390 | 67.456 | 46.055 | 6.397 | 1.00 | 33.40 | C |
| ATOM | 2064 | OG | SER | A | 390 | 67.716 | 46.575 | 5.112 | 1.00 | 35.26 | O |
| ATOM | 2065 | N | PRO | A | 391 | 64.811 | 44.290 | 5.608 | 1.00 | 37.69 | N |
| ATOM | 2066 | CA | PRO | A | 391 | 63.704 | 44.012 | 4.686 | 1.00 | 39.43 | C |
| ATOM | 2067 | C | PRO | A | 391 | 63.332 | 45.059 | 3.635 | 1.00 | 40.72 | C |
| ATOM | 2068 | O | PRO | A | 391 | 62.291 | 44.938 | 2.991 | 1.00 | 41.37 | O |
| ATOM | 2069 | CB | PRO | A | 391 | 62.548 | 43.729 | 5.639 | 1.00 | 39.02 | C |
| ATOM | 2070 | CG | PRO | A | 391 | 62.797 | 44.733 | 6.725 | 1.00 | 38.46 | C |
| ATOM | 2071 | CD | PRO | A | 391 | 64.300 | 44.637 | 6.949 | 1.00 | 36.88 | C |
| ATOM | 2072 | N | THR | A | 392 | 64.167 | 46.071 | 3.443 | 1.00 | 41.57 | N |
| ATOM | 2073 | CA | THR | A | 392 | 63.844 | 47.103 | 2.469 | 1.00 | 42.35 | C |

TABLE 4-continued

| ATOM | 2074 | C | THR | A | 392 | 64.520 | 46.929 | 1.114 | 1.00 | 44.91 | C |
|------|------|-----|-----|---|-----|--------|--------|--------|------|-------|---|
| ATOM | 2075 | O | THR | A | 392 | 65.399 | 46.084 | 0.938 | 1.00 | 45.02 | O |
| ATOM | 2076 | CB | THR | A | 392 | 64.178 | 48.502 | 3.011 | 1.00 | 41.05 | C |
| ATOM | 2077 | OG1 | THR | A | 392 | 65.579 | 48.587 | 3.293 | 1.00 | 39.97 | O |
| ATOM | 2078 | CG2 | THR | A | 392 | 63.383 | 48.778 | 4.281 | 1.00 | 39.92 | C |
| ATOM | 2079 | N | ARG | A | 393 | 64.094 | 47.747 | 0.159 | 1.00 | 47.45 | N |
| ATOM | 2080 | CA | ARG | A | 393 | 64.623 | 47.703 | 1.195 | 1.00 | 50.03 | C |
| ATOM | 2081 | C | ARG | A | 393 | 65.990 | 48.355 | 1.317 | 1.00 | 50.45 | C |
| ATOM | 2082 | O | ARG | A | 393 | 66.243 | 49.419 | -0.751 | 1.00 | 50.27 | O |
| ATOM | 2083 | CB | ARG | A | 393 | 63.640 | 48.380 | -2.163 | 1.00 | 51.81 | C |
| ATOM | 2084 | CG | ARG | A | 393 | 62.377 | 47.565 | -2.431 | 1.00 | 54.92 | C |
| ATOM | 2085 | CD | ARG | A | 393 | 61.284 | 48.366 | -3.146 | 1.00 | 57.32 | C |
| ATOM | 2086 | NE | ARG | A | 393 | 61.775 | 49.068 | -4.328 | 1.00 | 59.58 | N |
| ATOM | 2087 | CZ | ARG | A | 393 | 62.024 | 50.375 | -4.370 | 1.00 | 61.26 | C |
| ATOM | 2088 | NH1 | ARG | A | 393 | 61.823 | 51.125 | -3.295 | 1.00 | 61.47 | N |
| ATOM | 2089 | NH2 | ARG | A | 393 | 62.481 | 50.934 | -5.484 | 1.00 | 62.64 | N |
| ATOM | 2090 | N | LYS | A | 394 | 66.872 | 47.690 | -2.053 | 1.00 | 50.90 | N |
| ATOM | 2091 | CA | LYS | A | 394 | 68.213 | 48.191 | -2.299 | 1.00 | 51.87 | C |
| ATOM | 2092 | C | LYS | A | 394 | 68.046 | 49.050 | -3.545 | 1.00 | 53.29 | C |
| ATOM | 2093 | O | LYS | A | 394 | 67.637 | 48.551 | -4.590 | 1.00 | 53.60 | O |
| ATOM | 2094 | CB | LYS | A | 394 | 69.158 | 47.023 | -2.579 | 1.00 | 51.11 | C |
| ATOM | 2095 | CG | LYS | A | 394 | 70.618 | 47.333 | -2.352 | 1.00 | 50.68 | C |
| ATOM | 2096 | CD | LYS | A | 394 | 71.508 | 46.184 | -2.795 | 1.00 | 49.41 | C |
| ATOM | 2097 | CE | LYS | A | 394 | 71.231 | 44.910 | -2.025 | 1.00 | 48.96 | C |
| ATOM | 2098 | NZ | LYS | A | 394 | 72.139 | 43.816 | -2.476 | 1.00 | 47.88 | N |
| ATOM | 2099 | N | VAL | A | 395 | 68.343 | 50.340 | -3.435 | 1.00 | 55.26 | N |
| ATOM | 2100 | CA | VAL | A | 395 | 68.183 | 51.253 | -4.562 | 1.00 | 57.43 | C |
| ATOM | 2101 | C | VAL | A | 395 | 69.475 | 51.939 | -4.979 | 1.00 | 58.81 | C |
| ATOM | 2102 | O | VAL | A | 395 | 70.207 | 52.463 | -4.145 | 1.00 | 59.36 | O |
| ATOM | 2103 | CB | VAL | A | 395 | 67.141 | 52.344 | -4.238 | 1.00 | 57.67 | C |
| ATOM | 2104 | CG1 | VAL | A | 395 | 67.047 | 53.339 | -5.388 | 1.00 | 58.68 | C |
| ATOM | 2105 | CG2 | VAL | A | 395 | 65.789 | 51.703 | -3.974 | 1.00 | 57.82 | C |
| ATOM | 2106 | N | THR | A | 396 | 69.740 | 51.946 | -6.281 | 1.00 | 60.52 | N |
| ATOM | 2107 | CA | THR | A | 396 | 70.942 | 52.577 | -6.813 | 1.00 | 62.17 | C |
| ATOM | 2108 | C | THR | A | 396 | 70.648 | 53.995 | -7.284 | 1.00 | 63.08 | C |
| ATOM | 2109 | O | THR | A | 396 | 69.919 | 54.197 | -8.255 | 1.00 | 63.34 | O |
| ATOM | 2110 | CB | THR | A | 396 | 71.514 | 51.781 | -7.998 | 1.00 | 62.45 | C |
| ATOM | 2111 | OG1 | THR | A | 396 | 71.837 | 50.454 | -7.569 | 1.00 | 63.27 | O |
| ATOM | 2112 | CG2 | THR | A | 396 | 72.772 | 52.452 | -8.529 | 1.00 | 63.24 | C |
| ATOM | 2113 | N | ILE | A | 397 | 71.222 | 54.970 | -6.586 | 1.00 | 64.02 | N |
| ATOM | 2114 | CA | ILE | A | 397 | 71.035 | 56.376 | -6.918 | 1.00 | 65.04 | C |
| ATOM | 2115 | C | ILE | A | 397 | 72.365 | 56.980 | -7.362 | 1.00 | 65.43 | C |
| ATOM | 2116 | O | ILE | A | 397 | 73.287 | 57.134 | -6.559 | 1.00 | 65.88 | O |
| ATOM | 2117 | CB | ILE | A | 397 | 70.509 | 57.168 | -5.701 | 1.00 | 65.43 | C |
| ATOM | 2118 | CG1 | ILE | A | 397 | 69.229 | 56.516 | -5.171 | 1.00 | 65.85 | C |
| ATOM | 2119 | CG2 | ILE | A | 397 | 70.230 | 58.608 | -6.099 | 1.00 | 65.50 | C |
| ATOM | 2120 | CD1 | ILE | A | 397 | 68.688 | 57.167 | -3.914 | 1.00 | 66.46 | C |
| ATOM | 2121 | N | ASN | A | 398 | 72.450 | 57.319 | -8.644 | 1.00 | 65.44 | N |
| ATOM | 2122 | CA | ASN | A | 398 | 73.652 | 57.900 | -9.238 | 1.00 | 65.13 | C |
| ATOM | 2123 | C | ASN | A | 398 | 74.959 | 57.251 | -8.770 | 1.00 | 63.59 | C |
| ATOM | 2124 | O | ASN | A | 398 | 75.819 | 57.911 | -8.186 | 1.00 | 63.13 | O |
| ATOM | 2125 | CB | ASN | A | 398 | 73.703 | 59.417 | -8.988 | 1.00 | 67.26 | C |
| ATOM | 2126 | CG | ASN | A | 398 | 73.838 | 59.773 | -7.515 | 1.00 | 69.20 | C |
| ATOM | 2127 | OD1 | ASN | A | 398 | 72.906 | 59.598 | -6.730 | 1.00 | 70.21 | O |
| ATOM | 2128 | ND2 | ASN | A | 398 | 75.009 | 60.278 | -7.135 | 1.00 | 69.87 | N |
| ATOM | 2129 | N | GLY | A | 399 | 75.097 | 55.954 | -9.031 | 1.00 | 61.70 | N |
| ATOM | 2130 | CA | GLY | A | 399 | 76.306 | 55.242 | -8.653 | 1.00 | 59.47 | C |
| ATOM | 2131 | C | GLY | A | 399 | 76.406 | 54.789 | -7.207 | 1.00 | 57.89 | C |
| ATOM | 2132 | O | GLY | A | 399 | 77.324 | 54.047 | -6.850 | 1.00 | 57.93 | O |
| ATOM | 2133 | N | SER | A | 400 | 75.477 | 55.232 | -6.368 | 1.00 | 55.71 | N |
| ATOM | 2134 | CA | SER | A | 400 | 75.495 | 54.850 | -4.960 | 1.00 | 52.89 | C |
| ATOM | 2135 | C | SER | A | 400 | 74.343 | 53.929 | -4.604 | 1.00 | 50.55 | C |
| ATOM | 2136 | O | SER | A | 400 | 73.182 | 54.249 | -4.841 | 1.00 | 50.80 | O |
| ATOM | 2137 | CB | SER | A | 400 | 75.445 | 56.090 | -4.067 | 1.00 | 52.32 | C |
| ATOM | 2138 | OG | SER | A | 400 | 76.657 | 56.816 | -4.147 | 1.00 | 53.54 | O |
| ATOM | 2139 | N | VAL | A | 401 | 74.672 | 52.778 | -4.033 | 1.00 | 48.12 | N |
| ATOM | 2140 | CA | VAL | A | 401 | 73.655 | 51.824 | -3.629 | 1.00 | 46.03 | C |
| ATOM | 2141 | C | VAL | A | 401 | 73.166 | 52.225 | -2.237 | 1.00 | 45.54 | C |
| ATOM | 2142 | O | VAL | A | 401 | 73.959 | 52.368 | -1.302 | 1.00 | 44.42 | O |
| ATOM | 2143 | CB | VAL | A | 401 | 74.224 | 50.397 | -3.605 | 1.00 | 45.67 | C |
| ATOM | 2144 | CG1 | VAL | A | 401 | 73.149 | 49.412 | -3.178 | 1.00 | 44.59 | C |
| ATOM | 2145 | CG2 | VAL | A | 401 | 74.768 | 50.041 | -4.985 | 1.00 | 44.66 | C |
| ATOM | 2146 | N | MET | A | 402 | 71.856 | 52.418 | -2.118 | 1.00 | 44.66 | N |
| ATOM | 2147 | CA | MET | A | 402 | 71.236 | 52.829 | -0.863 | 1.00 | 43.40 | C |
| ATOM | 2148 | C | MET | A | 402 | 70.154 | 51.846 | -0.434 | 1.00 | 42.35 | C |
| ATOM | 2149 | O | MET | A | 402 | 69.786 | 50.933 | -1.175 | 1.00 | 41.19 | O |
| ATOM | 2150 | CB | MET | A | 402 | 70.580 | 54.208 | -1.020 | 1.00 | 45.15 | C |
| ATOM | 2151 | CG | MET | A | 402 | 71.414 | 55.261 | -1.728 | 1.00 | 45.44 | C |
| ATOM | 2152 | SD | MET | A | 402 | 72.814 | 55.813 | -0.761 | 1.00 | 50.48 | S |

TABLE 4-continued

| | | | | | | | | | | |
|---|---|---|---|---|---|---|---|---|---|---|
| ATOM | 2153 | CE | MET | A | 402 | 72.042 | 57.060 | 0.274 | 1.00 | 47.04 | C |
| ATOM | 2154 | N | LYS | A | 403 | 69.646 | 52.045 | 0.776 | 1.00 | 40.23 | N |
| ATOM | 2155 | CA | LYS | A | 403 | 68.575 | 51.217 | 1.297 | 1.00 | 38.93 | C |
| ATOM | 2156 | C | LYS | A | 403 | 67.506 | 52.157 | 1.827 | 1.00 | 38.85 | C |
| ATOM | 2157 | O | LYS | A | 403 | 67.805 | 53.246 | 2.325 | 1.00 | 37.82 | O |
| ATOM | 2158 | CB | LYS | A | 403 | 69.071 | 50.295 | 2.414 | 1.00 | 38.52 | C |
| ATOM | 2159 | CG | LYS | A | 403 | 70.049 | 49.234 | 1.944 | 1.00 | 38.14 | C |
| ATOM | 2160 | CD | LYS | A | 403 | 69.733 | 47.871 | 2.535 | 1.00 | 38.41 | C |
| ATOM | 2161 | CE | LYS | A | 403 | 68.425 | 47.321 | 1.989 | 1.00 | 38.28 | C |
| ATOM | 2162 | NZ | LYS | A | 403 | 68.123 | 45.957 | 2.514 | 1.00 | 36.94 | N |
| ATOM | 2163 | N | GLU | A | 404 | 66.255 | 51.746 | 1.697 | 1.00 | 39.27 | N |
| ATOM | 2164 | CA | GLU | A | 404 | 65.159 | 52.567 | 2.169 | 1.00 | 39.45 | C |
| ATOM | 2165 | C | GLU | A | 404 | 65.108 | 52.518 | 3.682 | 1.00 | 38.83 | C |
| ATOM | 2166 | O | GLU | A | 404 | 65.459 | 51.509 | 4.297 | 1.00 | 37.69 | O |
| ATOM | 2167 | CB | GLU | A | 404 | 63.840 | 52.060 | 1.609 | 1.00 | 41.56 | C |
| ATOM | 2168 | CG | GLU | A | 404 | 63.763 | 52.059 | 0.103 | 1.00 | 45.30 | C |
| ATOM | 2169 | CD | GLU | A | 404 | 62.435 | 51.539 | −0.384 | 1.00 | 46.12 | C |
| ATOM | 2170 | OE1 | GLU | A | 404 | 62.155 | 50.338 | −0.167 | 1.00 | 47.85 | O |
| ATOM | 2171 | OE2 | GLU | A | 404 | 61.673 | 52.334 | −0.971 | 1.00 | 47.62 | O |
| ATOM | 2172 | N | TYR | A | 405 | 64.665 | 53.616 | 4.275 | 1.00 | 38.06 | N |
| ATOM | 2173 | CA | TYR | A | 405 | 64.550 | 53.700 | 5.717 | 1.00 | 37.61 | C |
| ATOM | 2174 | C | TYR | A | 405 | 63.512 | 54.746 | 6.066 | 1.00 | 36.92 | C |
| ATOM | 2175 | O | TYR | A | 405 | 63.619 | 55.899 | 5.658 | 1.00 | 37.99 | O |
| ATOM | 2176 | CB | TYR | A | 405 | 65.892 | 54.078 | 6.335 | 1.00 | 37.41 | C |
| ATOM | 2177 | CG | TYR | A | 405 | 65.857 | 54.147 | 7.842 | 1.00 | 37.40 | C |
| ATOM | 2178 | CD1 | TYR | A | 405 | 65.593 | 53.013 | 8.603 | 1.00 | 36.23 | C |
| ATOM | 2179 | CD2 | TYR | A | 405 | 66.084 | 55.349 | 8.507 | 1.00 | 38.07 | C |
| ATOM | 2180 | CE1 | TYR | A | 405 | 65.557 | 53.072 | 9.990 | 1.00 | 36.68 | C |
| ATOM | 2181 | CE2 | TYR | A | 405 | 66.049 | 55.417 | 9.892 | 1.00 | 38.81 | C |
| ATOM | 2182 | CZ | TYR | A | 405 | 65.784 | 54.274 | 10.627 | 1.00 | 36.81 | C |
| ATOM | 2183 | OH | TYR | A | 405 | 65.736 | 54.345 | 11.999 | 1.00 | 37.95 | O |
| ATOM | 2184 | N | TRP | A | 406 | 62.498 | 54.336 | 6.813 | 1.00 | 35.74 | N |
| ATOM | 2185 | CA | TRP | A | 406 | 61.450 | 55.256 | 7.214 | 1.00 | 34.25 | C |
| ATOM | 2186 | C | TRP | A | 406 | 61.075 | 54.979 | 8.661 | 1.00 | 34.05 | C |
| ATOM | 2187 | O | TRP | A | 406 | 61.165 | 53.841 | 9.126 | 1.00 | 33.82 | O |
| ATOM | 2188 | CB | TRP | A | 406 | 60.232 | 55.113 | 6.281 | 1.00 | 32.23 | C |
| ATOM | 2189 | CG | TRP | A | 406 | 59.577 | 53.763 | 6.285 | 1.00 | 29.53 | C |
| ATOM | 2190 | CD1 | TRP | A | 406 | 58.605 | 53.327 | 7.138 | 1.00 | 29.14 | C |
| ATOM | 2191 | CD2 | TRP | A | 406 | 59.874 | 52.659 | 5.419 | 1.00 | 29.51 | C |
| ATOM | 2192 | NE1 | TRP | A | 406 | 58.280 | 52.023 | 6.860 | 1.00 | 28.25 | N |
| ATOM | 2193 | CE2 | TRP | A | 406 | 59.045 | 51.586 | 5.811 | 1.00 | 28.80 | C |
| ATOM | 2194 | CE3 | TRP | A | 406 | 60.764 | 52.472 | 4.350 | 1.00 | 30.06 | C |
| ATOM | 2195 | CZ2 | TRP | A | 406 | 59.077 | 50.337 | 5.173 | 1.00 | 29.23 | C |
| ATOM | 2196 | CZ3 | TRP | A | 406 | 60.797 | 51.230 | 3.713 | 1.00 | 30.49 | C |
| ATOM | 2197 | CH2 | TRP | A | 406 | 59.956 | 50.178 | 4.131 | 1.00 | 30.09 | C |
| ATOM | 2198 | N | GLY | A | 407 | 60.682 | 56.030 | 9.372 | 1.00 | 33.97 | N |
| ATOM | 2199 | CA | GLY | A | 407 | 60.300 | 55.883 | 10.763 | 1.00 | 35.09 | C |
| ATOM | 2200 | C | GLY | A | 407 | 58.921 | 55.270 | 10.912 | 1.00 | 35.29 | C |
| ATOM | 2201 | O | GLY | A | 407 | 58.124 | 55.281 | 9.978 | 1.00 | 34.78 | O |
| ATOM | 2202 | N | GLU | A | 408 | 58.640 | 54.723 | 12.090 | 1.00 | 35.40 | N |
| ATOM | 2203 | CA | GLU | A | 408 | 57.347 | 54.112 | 12.356 | 1.00 | 35.13 | C |
| ATOM | 2204 | C | GLU | A | 408 | 56.273 | 55.189 | 12.468 | 1.00 | 36.19 | C |
| ATOM | 2205 | O | GLU | A | 408 | 55.081 | 54.899 | 12.408 | 1.00 | 35.83 | O |
| ATOM | 2206 | CB | GLU | A | 408 | 57.414 | 53.295 | 13.647 | 1.00 | 33.46 | C |
| ATOM | 2207 | CG | GLU | A | 408 | 58.193 | 51.999 | 13.498 | 1.00 | 32.80 | C |
| ATOM | 2208 | CD | GLU | A | 408 | 57.499 | 51.006 | 12.569 | 1.00 | 31.60 | C |
| ATOM | 2209 | OE1 | GLU | A | 408 | 56.402 | 50.534 | 12.918 | 1.00 | 29.78 | O |
| ATOM | 2210 | OE2 | GLU | A | 408 | 58.047 | 50.701 | 11.490 | 1.00 | 31.44 | O |
| ATOM | 2211 | N | GLY | A | 409 | 56.709 | 56.436 | 12.619 | 1.00 | 37.77 | N |
| ATOM | 2212 | CA | GLY | A | 409 | 55.773 | 57.539 | 12.734 | 1.00 | 39.49 | C |
| ATOM | 2213 | C | GLY | A | 409 | 55.400 | 58.156 | 11.397 | 1.00 | 40.71 | C |
| ATOM | 2214 | O | GLY | A | 409 | 54.482 | 58.970 | 11.323 | 1.00 | 40.61 | O |
| ATOM | 2215 | N | SER | A | 410 | 56.109 | 57.782 | 10.338 | 1.00 | 42.27 | N |
| ATOM | 2216 | CA | SER | A | 410 | 55.813 | 58.318 | 9.013 | 1.00 | 44.24 | C |
| ATOM | 2217 | C | SER | A | 410 | 54.485 | 57.742 | 8.526 | 1.00 | 45.74 | C |
| ATOM | 2218 | O | SER | A | 410 | 54.065 | 56.672 | 8.968 | 1.00 | 44.79 | O |
| ATOM | 2219 | CB | SER | A | 410 | 56.917 | 57.952 | 8.017 | 1.00 | 43.45 | C |
| ATOM | 2220 | OG | SER | A | 410 | 56.832 | 56.587 | 7.641 | 1.00 | 44.08 | O |
| ATOM | 2221 | N | SER | A | 411 | 53.828 | 58.457 | 7.618 | 1.00 | 48.17 | N |
| ATOM | 2222 | CA | SER | A | 411 | 52.556 | 57.998 | 7.081 | 1.00 | 50.72 | C |
| ATOM | 2223 | C | SER | A | 411 | 52.777 | 56.708 | 6.301 | 1.00 | 51.98 | C |
| ATOM | 2224 | O | SER | A | 411 | 51.885 | 55.865 | 6.205 | 1.00 | 51.95 | O |
| ATOM | 2225 | CB | SER | A | 411 | 51.947 | 59.064 | 6.170 | 1.00 | 51.02 | C |
| ATOM | 2226 | OG | SER | A | 411 | 52.832 | 59.393 | 5.116 | 1.00 | 52.23 | O |
| ATOM | 2227 | N | ARG | A | 412 | 53.978 | 56.555 | 5.754 | 1.00 | 53.68 | N |
| ATOM | 2228 | CA | ARG | A | 412 | 54.323 | 55.363 | 4.989 | 1.00 | 55.96 | C |
| ATOM | 2229 | C | ARG | A | 412 | 54.226 | 54.083 | 5.819 | 1.00 | 58.17 | C |
| ATOM | 2230 | O | ARG | A | 412 | 54.018 | 53.000 | 5.275 | 1.00 | 57.86 | O |
| ATOM | 2231 | CB | ARG | A | 412 | 55.741 | 55.491 | 4.419 | 1.00 | 54.66 | C |

TABLE 4-continued

| ATOM | 2232 | CG  | ARG | A | 412 | 56.208 | 54.242 | 3.687  | 1.00 | 53.34 | C |
| ATOM | 2233 | CD  | ARG | A | 412 | 57.550 | 54.426 | 3.003  | 1.00 | 51.73 | C |
| ATOM | 2234 | NE  | ARG | A | 412 | 57.933 | 53.211 | 2.288  | 1.00 | 50.66 | N |
| ATOM | 2235 | CZ  | ARG | A | 412 | 59.023 | 53.086 | 1.539  | 1.00 | 51.11 | C |
| ATOM | 2236 | NH1 | ARG | A | 412 | 59.860 | 54.108 | 1.396  | 1.00 | 50.38 | N |
| ATOM | 2237 | NH2 | ARG | A | 412 | 59.276 | 51.935 | 0.929  | 1.00 | 51.44 | N |
| ATOM | 2238 | N   | ALA | A | 413 | 54.374 | 54.212 | 7.134  | 1.00 | 61.58 | N |
| ATOM | 2239 | CA  | ALA | A | 413 | 54.321 | 53.057 | 8.031  | 1.00 | 64.71 | C |
| ATOM | 2240 | C   | ALA | A | 413 | 52.976 | 52.880 | 8.733  | 1.00 | 67.35 | C |
| ATOM | 2241 | O   | ALA | A | 413 | 52.495 | 51.757 | 8.877  | 1.00 | 66.86 | O |
| ATOM | 2242 | CB  | ALA | A | 413 | 55.436 | 53.165 | 9.067  | 1.00 | 63.82 | C |
| ATOM | 2243 | N   | ARG | A | 414 | 52.386 | 53.987 | 9.179  | 1.00 | 71.43 | N |
| ATOM | 2244 | CA  | ARG | A | 414 | 51.102 | 53.948 | 9.874  | 1.00 | 75.31 | C |
| ATOM | 2245 | C   | ARG | A | 414 | 49.999 | 53.373 | 8.991  | 1.00 | 77.02 | C |
| ATOM | 2246 | O   | ARG | A | 414 | 49.031 | 52.789 | 9.485  | 1.00 | 77.08 | O |
| ATOM | 2247 | CB  | ARG | A | 414 | 50.683 | 55.353 | 10.322 | 1.00 | 76.52 | C |
| ATOM | 2248 | CG  | ARG | A | 414 | 51.456 | 55.939 | 11.491 | 1.00 | 78.03 | C |
| ATOM | 2249 | CD  | ARG | A | 414 | 50.703 | 57.153 | 12.026 | 1.00 | 80.11 | C |
| ATOM | 2250 | NE  | ARG | A | 414 | 51.381 | 57.807 | 13.142 | 1.00 | 81.88 | N |
| ATOM | 2251 | CZ  | ARG | A | 414 | 50.844 | 58.779 | 13.874 | 1.00 | 82.61 | C |
| ATOM | 2252 | NH1 | ARG | A | 414 | 49.617 | 59.210 | 13.612 | 1.00 | 83.27 | N |
| ATOM | 2253 | NH2 | ARG | A | 414 | 51.532 | 59.325 | 14.867 | 1.00 | 83.16 | N |
| ATOM | 2254 | N   | ASN | A | 415 | 50.154 | 53.546 | 7.683  | 1.00 | 78.97 | N |
| ATOM | 2255 | CA  | ASN | A | 415 | 49.170 | 53.058 | 6.725  | 1.00 | 81.09 | C |
| ATOM | 2256 | C   | ASN | A | 415 | 49.252 | 51.540 | 6.520  | 1.00 | 81.85 | C |
| ATOM | 2257 | O   | ASN | A | 415 | 49.489 | 51.069 | 5.403  | 1.00 | 81.77 | O |
| ATOM | 2258 | CB  | ASN | A | 415 | 49.356 | 53.774 | 5.380  | 1.00 | 82.25 | C |
| ATOM | 2259 | CG  | ASN | A | 415 | 48.070 | 53.845 | 4.568  | 1.00 | 83.78 | C |
| ATOM | 2260 | OD1 | ASN | A | 415 | 47.434 | 52.825 | 4.295  | 1.00 | 84.64 | O |
| ATOM | 2261 | ND2 | ASN | A | 415 | 47.681 | 55.055 | 4.181  | 1.00 | 84.44 | N |
| ATOM | 2262 | N   | TRP | A | 416 | 49.055 | 50.778 | 7.598  | 1.00 | 82.26 | N |
| ATOM | 2263 | CA  | TRP | A | 416 | 49.095 | 49.316 | 7.519  | 1.00 | 82.50 | C |
| ATOM | 2264 | C   | TRP | A | 416 | 47.758 | 48.722 | 7.927  | 1.00 | 82.72 | C |
| ATOM | 2265 | O   | TRP | A | 416 | 47.554 | 47.515 | 7.823  | 1.00 | 83.08 | O |
| ATOM | 2266 | CE  | TRP | A | 416 | 50.209 | 48.732 | 8.412  | 1.00 | 82.13 | C |
| ATOM | 2267 | CG  | TRP | A | 416 | 49.928 | 48.742 | 9.894  | 1.00 | 81.82 | C |
| ATOM | 2268 | CD1 | TRP | A | 416 | 50.244 | 49.730 | 10.781 | 1.00 | 82.00 | C |
| ATOM | 2269 | CD2 | TRP | A | 416 | 49.273 | 47.714 | 10.659 | 1.00 | 81.56 | C |
| ATOM | 2270 | NE1 | TRP | A | 416 | 49.830 | 49.385 | 12.048 | 1.00 | 81.96 | N |
| ATOM | 2271 | CE2 | TRP | A | 416 | 49.230 | 48.154 | 12.001 | 1.00 | 81.69 | C |
| ATOM | 2272 | CE3 | TRP | A | 416 | 48.716 | 46.467 | 10.339 | 1.00 | 81.07 | C |
| ATOM | 2273 | CZ2 | TRP | A | 416 | 48.652 | 47.390 | 13.026 | 1.00 | 81.58 | C |
| ATOM | 2274 | CZ3 | TRP | A | 416 | 48.140 | 45.706 | 11.359 | 1.00 | 80.88 | C |
| ATOM | 2275 | CH2 | TRP | A | 416 | 48.113 | 46.173 | 12.685 | 1.00 | 81.28 | C |
| ATOM | 2276 | N   | SER | A | 428 | 47.786 | 65.086 | 7.718  | 1.00 | 95.79 | N |
| ATOM | 2277 | CA  | SER | A | 428 | 48.357 | 66.353 | 7.278  | 1.00 | 95.93 | C |
| ATOM | 2278 | C   | SER | A | 428 | 49.676 | 66.643 | 7.988  | 1.00 | 96.13 | C |
| ATOM | 2279 | O   | SER | A | 428 | 50.268 | 67.709 | 7.812  | 1.00 | 96.06 | O |
| ATOM | 2280 | CE  | SER | A | 428 | 47.367 | 67.497 | 7.532  | 1.00 | 95.59 | C |
| ATOM | 2281 | OG  | SER | A | 428 | 47.047 | 67.610 | 8.907  | 1.00 | 95.03 | O |
| ATOM | 2282 | N   | PHE | A | 429 | 50.134 | 65.687 | 8.789  | 1.00 | 96.33 | N |
| ATOM | 2283 | CA  | PHE | A | 429 | 51.384 | 65.837 | 9.525  | 1.00 | 96.45 | C |
| ATOM | 2284 | C   | PHE | A | 429 | 52.185 | 64.541 | 9.412  | 1.00 | 95.70 | C |
| ATOM | 2285 | O   | PHE | A | 429 | 51.867 | 63.685 | 8.586  | 1.00 | 95.85 | O |
| ATOM | 2286 | CB  | PHE | A | 429 | 51.091 | 66.156 | 10.995 | 1.00 | 97.56 | C |
| ATOM | 2287 | CG  | PHE | A | 429 | 52.269 | 66.717 | 11.741 | 1.00 | 98.75 | C |
| ATOM | 2288 | CD1 | PHE | A | 429 | 52.886 | 67.889 | 11.311 | 1.00 | 99.16 | C |
| ATOM | 2289 | CD2 | PHE | A | 429 | 52.771 | 66.069 | 12.866 | 1.00 | 99.35 | C |
| ATOM | 2290 | CE1 | PHE | A | 429 | 53.987 | 68.410 | 11.989 | 1.00 | 99.58 | C |
| ATOM | 2291 | CE2 | PHE | A | 429 | 53.872 | 66.581 | 13.553 | 1.00 | 99.81 | C |
| ATOM | 2292 | CZ  | PHE | A | 429 | 54.481 | 67.754 | 13.113 | 1.00 | 99.76 | C |
| ATOM | 2293 | N   | GLU | A | 430 | 53.222 | 64.395 | 10.235 | 1.00 | 94.58 | N |
| ATOM | 2294 | CA  | GLU | A | 430 | 54.047 | 63.191 | 10.205 | 1.00 | 93.27 | C |
| ATOM | 2295 | C   | GLU | A | 430 | 55.093 | 63.181 | 11.320 | 1.00 | 91.79 | C |
| ATOM | 2296 | O   | GLU | A | 430 | 55.884 | 64.115 | 11.453 | 1.00 | 91.62 | O |
| ATOM | 2297 | CB  | GLU | A | 430 | 54.728 | 63.065 | 8.841  | 1.00 | 94.00 | C |
| ATOM | 2298 | CG  | GLU | A | 430 | 55.300 | 61.691 | 8.559  | 1.00 | 94.70 | C |
| ATOM | 2299 | CD  | GLU | A | 430 | 55.471 | 61.436 | 7.076  | 1.00 | 95.05 | C |
| ATOM | 2300 | OE1 | GLU | A | 430 | 54.459 | 61.503 | 6.346  | 1.00 | 95.03 | O |
| ATOM | 2301 | OE2 | GLU | A | 430 | 56.612 | 61.168 | 6.642  | 1.00 | 95.48 | O |
| ATOM | 2302 | N   | GLU | A | 431 | 55.092 | 62.110 | 12.110 | 1.00 | 89.87 | N |
| ATOM | 2303 | CA  | GLU | A | 431 | 56.014 | 61.960 | 13.234 | 1.00 | 87.81 | C |
| ATOM | 2304 | C   | GLU | A | 431 | 57.423 | 61.519 | 12.843 | 1.00 | 85.39 | C |
| ATOM | 2305 | O   | GLU | A | 431 | 58.356 | 61.618 | 13.643 | 1.00 | 85.00 | O |
| ATOM | 2306 | CB  | GLU | A | 43L | 55.437 | 60.973 | 14.257 | 1.00 | 89.03 | C |
| ATOM | 2307 | CG  | GLU | A | 431 | 54.235 | 61.494 | 15.044 | 1.00 | 90.63 | C |
| ATOM | 2308 | CD  | GLU | A | 431 | 53.091 | 61.955 | 14.153 | 1.00 | 91.93 | C |
| ATOM | 2309 | OE1 | GLU | A | 431 | 52.602 | 61.144 | 13.336 | 1.00 | 92.15 | O |
| ATOM | 2310 | OE2 | GLU | A | 431 | 52.678 | 63.130 | 14.274 | 1.00 | 92.38 | O |

TABLE 4-continued

| | | | | | | | | | | |
|---|---|---|---|---|---|---|---|---|---|---|
| ATOM | 2311 | N | GLY | A | 432 | 57.577 | 61.031 | 11.618 | 1.00 | 82.69 | N |
| ATOM | 2312 | CA | GLY | A | 432 | 58.885 | 60.587 | 11.170 | 1.00 | 79.01 | C |
| ATOM | 2313 | C | GLY | A | 432 | 59.146 | 60.936 | 9.720 | 1.00 | 76.48 | C |
| ATOM | 2314 | O | GLY | A | 432 | 58.345 | 61.623 | 9.087 | 1.00 | 76.66 | O |
| ATOM | 2315 | N | VAL | A | 433 | 60.269 | 60.464 | 9.190 | 1.00 | 73.56 | N |
| ATOM | 2316 | CA | VAL | A | 433 | 60.615 | 60.739 | 7.803 | 1.00 | 70.14 | C |
| ATOM | 2317 | C | VAL | A | 433 | 60.915 | 59.466 | 7.014 | 1.00 | 67.42 | C |
| ATOM | 2318 | O | VAL | A | 433 | 61.128 | 58.399 | 7.588 | 1.00 | 67.04 | O |
| ATOM | 2319 | CE | VAL | A | 433 | 61.827 | 61.699 | 7.710 | 1.00 | 70.47 | C |
| ATOM | 2320 | CG1 | VAL | A | 433 | 61.451 | 63.062 | 8.272 | 1.00 | 70.12 | C |
| ATOM | 2321 | CG2 | VAL | A | 433 | 63.010 | 61.124 | 8.465 | 1.00 | 70.31 | C |
| ATOM | 2322 | N | ASP | A | 434 | 60.913 | 59.598 | 5.691 | 1.00 | 63.84 | N |
| ATOM | 2323 | CA | ASP | A | 434 | 61.173 | 58.491 | 4.778 | 1.00 | 60.33 | C |
| ATOM | 2324 | C | ASP | A | 434 | 62.386 | 58.864 | 3.930 | 1.00 | 58.07 | C |
| ATOM | 2325 | O | ASP | A | 434 | 62.300 | 59.737 | 3.066 | 1.00 | 57.72 | O |
| ATOM | 2326 | CB | ASP | A | 434 | 59.937 | 58.261 | 3.899 | 1.00 | 60.27 | C |
| ATOM | 2327 | CG | ASP | A | 434 | 60.115 | 57.123 | 2.914 | 1.00 | 60.71 | C |
| ATOM | 2328 | OD1 | ASP | A | 434 | 60.683 | 56.081 | 3.297 | 1.00 | 61.60 | O |
| ATOM | 2329 | OD2 | ASP | A | 434 | 59.669 | 57.261 | 1.756 | 1.00 | 60.76 | O |
| ATOM | 2330 | N | SER | A | 435 | 63.516 | 58.207 | 4.181 | 1.00 | 55.22 | N |
| ATOM | 2331 | CA | SER | A | 435 | 64.741 | 58.509 | 3.448 | 1.00 | 52.53 | C |
| ATOM | 2332 | C | SER | A | 435 | 65.566 | 57.297 | 3.028 | 1.00 | 49.99 | C |
| ATOM | 2333 | O | SER | A | 435 | 65.072 | 56.172 | 2.970 | 1.00 | 49.04 | O |
| ATOM | 2334 | CB | SER | A | 435 | 65.620 | 59.437 | 4.284 | 1.00 | 53.18 | C |
| ATOM | 2335 | OG | SER | A | 435 | 65.947 | 58.820 | 5.515 | 1.00 | 54.44 | O |
| ATOM | 2336 | N | TYR | A | 436 | 66.838 | 57.550 | 2.740 | 1.00 | 47.61 | N |
| ATOM | 2337 | CA | TYR | A | 436 | 67.765 | 56.513 | 2.307 | 1.00 | 45.82 | C |
| ATOM | 2338 | C | TYR | A | 436 | 69.026 | 56.466 | 3.168 | 1.00 | 44.39 | C |
| ATOM | 2339 | O | TYR | A | 436 | 69.481 | 57.490 | 3.685 | 1.00 | 44.28 | O |
| ATOM | 2340 | CB | TYR | A | 436 | 68.184 | 56.764 | 0.858 | 1.00 | 46.81 | C |
| ATOM | 2341 | CG | TYR | A | 436 | 67.075 | 56.643 | −0.159 | 1.00 | 47.16 | C |
| ATOM | 2342 | CD1 | TYR | A | 436 | 66.584 | 55.396 | −0.537 | 1.00 | 47.36 | C |
| ATOM | 2343 | CD2 | TYR | A | 436 | 66.527 | 57.778 | −0.754 | 1.00 | 48.36 | C |
| ATOM | 2344 | CE1 | TYR | A | 436 | 65.575 | 55.279 | −1.485 | 1.00 | 49.05 | C |
| ATOM | 2345 | CE2 | TYR | A | 436 | 65.515 | 57.674 | −1.706 | 1.00 | 49.53 | C |
| ATOM | 2346 | CZ | TYR | A | 436 | 65.046 | 56.422 | −2.066 | 1.00 | 49.47 | C |
| ATOM | 2347 | OH | TYR | A | 436 | 64.050 | 56.312 | −3.007 | 1.00 | 51.33 | O |
| ATOM | 2348 | N | VAL | A | 437 | 69.585 | 55.269 | 3.318 | 1.00 | 41.45 | N |
| ATOM | 2349 | CA | VAL | A | 437 | 70.817 | 55.089 | 4.072 | 1.00 | 38.90 | C |
| ATOM | 2350 | C | VAL | A | 437 | 71.765 | 54.336 | 3.151 | 1.00 | 38.06 | C |
| ATOM | 2351 | O | VAL | A | 437 | 71.334 | 53.496 | 2.366 | 1.00 | 37.46 | O |
| ATOM | 2352 | CB | VAL | A | 437 | 70.600 | 54.275 | 5.370 | 1.00 | 38.21 | C |
| ATOM | 2353 | CG1 | VAL | A | 437 | 69.639 | 55.014 | 6.286 | 1.00 | 38.54 | C |
| ATOM | 2354 | CG2 | VAL | A | 437 | 70.086 | 52.884 | 5.042 | 1.00 | 36.53 | C |
| ATOM | 2355 | N | PRO | A | 438 | 73.071 | 54.635 | 3.226 | 1.00 | 37.64 | N |
| ATOM | 2356 | CA | PRO | A | 438 | 74.049 | 53.958 | 2.371 | 1.00 | 36.86 | C |
| ATOM | 2357 | C | PRO | A | 438 | 74.220 | 52.474 | 2.674 | 1.00 | 36.29 | C |
| ATOM | 2358 | O | PRO | A | 438 | 74.336 | 52.069 | 3.834 | 1.00 | 36.41 | O |
| ATOM | 2359 | CB | PRO | A | 438 | 75.327 | 54.764 | 2.608 | 1.00 | 36.76 | C |
| ATOM | 2360 | CG | PRO | A | 438 | 75.175 | 55.210 | 4.026 | 1.00 | 37.68 | C |
| ATOM | 2361 | CD | PRO | A | 438 | 73.725 | 55.641 | 4.080 | 1.00 | 37.02 | C |
| ATOM | 2362 | N | TYR | A | 439 | 74.223 | 51.671 | 1.613 | 1.00 | 35.21 | N |
| ATOM | 2363 | CA | TYR | A | 439 | 74.381 | 50.227 | 1.717 | 1.00 | 34.92 | C |
| ATOM | 2364 | C | TYR | A | 439 | 75.744 | 49.913 | 2.328 | 1.00 | 34.83 | C |
| ATOM | 2365 | O | TYR | A | 439 | 76.768 | 50.436 | 1.888 | 1.00 | 35.17 | O |
| ATOM | 2366 | CB | TYR | A | 439 | 74.267 | 49.599 | 0.325 | 1.00 | 34.07 | C |
| ATOM | 2367 | CG | TYR | A | 439 | 74.418 | 48.098 | 0.299 | 1.00 | 33.14 | C |
| ATOM | 2368 | CD1 | TYR | A | 439 | 73.561 | 47.279 | 1.029 | 1.00 | 32.78 | C |
| ATOM | 2369 | CD2 | TYR | A | 439 | 75.407 | 47.494 | −0.478 | 1.00 | 34.43 | C |
| ATOM | 2370 | CE1 | TYR | A | 439 | 73.682 | 45.892 | 0.984 | 1.00 | 34.47 | C |
| ATOM | 2371 | CE2 | TYR | A | 439 | 75.536 | 46.110 | −0.529 | 1.00 | 34.40 | C |
| ATOM | 2372 | CZ | TYR | A | 439 | 74.670 | 45.317 | 0.202 | 1.00 | 34.68 | C |
| ATOM | 2373 | OH | TYR | A | 439 | 74.791 | 43.949 | 0.148 | 1.00 | 36.73 | O |
| ATOM | 2374 | N | ALA | A | 440 | 75.752 | 49.051 | 3.337 | 1.00 | 34.57 | N |
| ATOM | 2375 | CA | ALA | A | 440 | 76.990 | 48.696 | 4.019 | 1.00 | 34.81 | C |
| ATOM | 2376 | C | ALA | A | 440 | 77.361 | 47.225 | 3.860 | 1.00 | 34.72 | C |
| ATOM | 2377 | O | ALA | A | 440 | 78.375 | 46.776 | 4.390 | 1.00 | 34.93 | O |
| ATOM | 2378 | CE | ALA | A | 440 | 76.874 | 49.047 | 5.502 | 1.00 | 33.67 | C |
| ATOM | 2379 | N | GLY | A | 441 | 76.542 | 46.474 | 3.134 | 1.00 | 34.47 | N |
| ATOM | 2380 | CA | GLY | A | 441 | 76.833 | 45.066 | 2.945 | 1.00 | 34.40 | C |
| ATOM | 2381 | C | GLY | A | 441 | 76.172 | 44.203 | 4.003 | 1.00 | 34.97 | C |
| ATOM | 2382 | O | GLY | A | 441 | 75.144 | 44.581 | 4.567 | 1.00 | 35.10 | O |
| ATOM | 2383 | N | LYS | A | 442 | 76.763 | 43.043 | 4.276 | 1.00 | 35.43 | N |
| ATOM | 2384 | CA | LYS | A | 442 | 76.226 | 42.110 | 5.265 | 1.00 | 35.71 | C |
| ATOM | 2385 | C | LYS | A | 442 | 76.421 | 42.615 | 6.694 | 1.00 | 34.74 | C |
| ATOM | 2386 | O | LYS | A | 442 | 77.415 | 43.272 | 7.005 | 1.00 | 33.81 | O |
| ATOM | 2387 | CB | LYS | A | 442 | 76.909 | 40.745 | 5.132 | 1.00 | 37.45 | C |
| ATOM | 2388 | CG | LYS | A | 442 | 76.860 | 40.138 | 3.739 | 1.00 | 41.47 | C |
| ATOM | 2389 | CD | LYS | A | 442 | 75.891 | 38.966 | 3.666 | 1.00 | 44.08 | C |

TABLE 4-continued

| ATOM | 2390 | CE  | LYS | A | 442 | 74.461 | 39.409 | 3.914  | 1.00 | 47.03 | C |
|------|------|-----|-----|---|-----|--------|--------|--------|------|-------|---|
| ATOM | 2391 | NZ  | LYS | A | 442 | 73.508 | 38.265 | 3.826  | 1.00 | 49.47 | N |
| ATOM | 2392 | N   | LEU | A | 443 | 75.466 | 42.282 | 7.555  | 1.00 | 33.84 | N |
| ATOM | 2393 | CA  | LEU | A | 443 | 75.497 | 42.663 | 8.962  | 1.00 | 33.05 | C |
| ATOM | 2394 | C   | LEU | A | 443 | 76.769 | 42.197 | 9.681  | 1.00 | 33.87 | C |
| ATOM | 2395 | O   | LEU | A | 443 | 77.401 | 42.968 | 10.398 | 1.00 | 32.69 | O |
| ATOM | 2396 | CB  | LEU | A | 443 | 74.265 | 42.084 | 9.672  | 1.00 | 31.90 | C |
| ATOM | 2397 | CG  | LEU | A | 443 | 74.104 | 42.252 | 11.190 | 1.00 | 31.99 | C |
| ATOM | 2398 | CD1 | LEU | A | 443 | 72.651 | 42.031 | 11.568 | 1.00 | 31.10 | C |
| ATOM | 2399 | CD2 | LEU | A | 443 | 75.001 | 41.274 | 11.935 | 1.00 | 31.47 | C |
| ATOM | 2400 | N   | LYS | A | 444 | 77.135 | 40.934 | 9.481  | 1.00 | 34.24 | N |
| ATOM | 2401 | CA  | LYS | A | 444 | 78.304 | 40.344 | 10.134 | 1.00 | 36.18 | C |
| ATOM | 2402 | C   | LYS | A | 444 | 79.587 | 41.182 | 10.174 | 1.00 | 35.95 | C |
| ATOM | 2403 | O   | LYS | A | 444 | 80.089 | 41.499 | 11.252 | 1.00 | 36.11 | O |
| ATOM | 2404 | CB  | LYS | A | 444 | 78.621 | 38.981 | 9.510  | 1.00 | 37.74 | C |
| ATOM | 2405 | CG  | LYS | A | 444 | 79.746 | 38.236 | 10.219 | 1.00 | 41.26 | C |
| ATOM | 2406 | CD  | LYS | A | 444 | 79.871 | 36.804 | 9.720  | 1.00 | 44.01 | C |
| ATOM | 2407 | CE  | LYS | A | 444 | 80.857 | 36.013 | 10.560 | 1.00 | 44.57 | C |
| ATOM | 2408 | NZ  | LYS | A | 444 | 82.223 | 36.599 | 10.490 | 1.00 | 46.17 | N |
| ATOM | 2409 | N   | ASP | A | 445 | 80.113 | 41.530 | 9.005  | 1.00 | 35.90 | N |
| ATOM | 2410 | CA  | ASP | A | 445 | 81.347 | 42.301 | 8.904  | 1.00 | 36.42 | C |
| ATOM | 2411 | C   | ASP | A | 445 | 81.273 | 43.666 | 9.569  | 1.00 | 35.53 | C |
| ATOM | 2412 | O   | ASP | A | 445 | 82.241 | 44.125 | 10.172 | 1.00 | 35.05 | O |
| ATOM | 2413 | CB  | ASP | A | 445 | 81.733 | 42.490 | 7.433  | 1.00 | 39.61 | C |
| ATOM | 2414 | CG  | ASP | A | 445 | 81.951 | 41.172 | 6.713  | 1.00 | 42.27 | C |
| ATOM | 2415 | OD1 | ASP | A | 445 | 82.810 | 40.383 | 7.163  | 1.00 | 43.65 | O |
| ATOM | 2416 | OD2 | ASP | A | 445 | 81.262 | 40.927 | 5.700  | 1.00 | 45.22 | O |
| ATOM | 2417 | N   | ASN | A | 446 | 80.126 | 44.317 | 9.447  | 1.00 | 34.05 | N |
| ATOM | 2418 | CA  | ASN | A | 446 | 79.945 | 45.639 | 10.027 | 1.00 | 33.14 | C |
| ATOM | 2419 | C   | ASN | A | 446 | 79.862 | 45.596 | 11.547 | 1.00 | 32.11 | C |
| ATOM | 2420 | O   | ASN | A | 446 | 80.506 | 46.394 | 12.227 | 1.00 | 31.82 | O |
| ATOM | 2421 | CB  | ASN | A | 446 | 78.693 | 46.281 | 9.439  | 1.00 | 34.11 | C |
| ATOM | 2422 | CG  | ASN | A | 446 | 78.853 | 46.608 | 7.969  | 1.00 | 35.94 | C |
| ATOM | 2423 | OD1 | ASN | A | 446 | 79.391 | 47.659 | 7.612  | 1.00 | 37.15 | O |
| ATOM | 2424 | ND2 | ASN | A | 446 | 78.406 | 45.698 | 7.104  | 1.00 | 33.70 | N |
| ATOM | 2425 | N   | VAL | A | 447 | 79.071 | 44.669 | 12.078 | 1.00 | 31.18 | N |
| ATOM | 2426 | CA  | VAL | A | 447 | 78.929 | 44.533 | 13.523 | 1.00 | 30.87 | C |
| ATOM | 2427 | C   | VAL | A | 447 | 80.273 | 44.161 | 14.154 | 1.00 | 31.57 | C |
| ATOM | 2428 | O   | VAL | A | 447 | 80.621 | 44.637 | 15.233 | 1.00 | 31.53 | O |
| ATOM | 2429 | CB  | VAL | A | 447 | 77.883 | 43.454 | 13.882 | 1.00 | 30.26 | C |
| ATOM | 2430 | CG1 | VAL | A | 447 | 77.995 | 43.087 | 15.354 | 1.00 | 29.78 | C |
| ATOM | 2431 | CG2 | VAL | A | 447 | 76.490 | 43.969 | 13.581 | 1.00 | 29.08 | C |
| ATOM | 2432 | N   | GLU | A | 448 | 81.030 | 43.313 | 13.468 | 1.00 | 31.62 | N |
| ATOM | 2433 | CA  | GLU | A | 448 | 82.326 | 42.887 | 13.971 | 1.00 | 33.06 | C |
| ATOM | 2434 | C   | GLU | A | 448 | 83.279 | 44.082 | 14.049 | 1.00 | 31.22 | C |
| ATOM | 2435 | O   | GLU | A | 448 | 83.975 | 44.257 | 15.042 | 1.00 | 29.89 | O |
| ATOM | 2436 | CB  | GLU | A | 448 | 82.900 | 41.790 | 13.066 | 1.00 | 35.76 | C |
| ATOM | 2437 | CG  | GLU | A | 448 | 84.250 | 41.240 | 13.503 | 1.00 | 41.89 | C |
| ATOM | 2438 | CD  | GLU | A | 448 | 84.719 | 40.085 | 12.623 | 1.00 | 46.86 | C |
| ATOM | 2439 | OE1 | GLU | A | 448 | 84.030 | 39.037 | 12.596 | 1.00 | 49.61 | O |
| ATOM | 2440 | OE2 | GLU | A | 448 | 85.770 | 40.228 | 11.957 | 1.00 | 47.95 | O |
| ATOM | 2441 | N   | ALA | A | 449 | 83.302 | 44.904 | 13.004 | 1.00 | 29.89 | N |
| ATOM | 2442 | CA  | ALA | A | 449 | 84.167 | 46.083 | 12.982 | 1.00 | 29.27 | C |
| ATOM | 2443 | C   | ALA | A | 449 | 83.764 | 47.074 | 14.075 | 1.00 | 28.76 | C |
| ATOM | 2444 | O   | ALA | A | 449 | 84.619 | 47.677 | 14.725 | 1.00 | 28.88 | O |
| ATOM | 2445 | CB  | ALA | A | 449 | 84.099 | 46.764 | 11.616 | 1.00 | 28.30 | C |
| ATOM | 2446 | N   | SER | A | 450 | 82.460 | 47.243 | 14.267 | 1.00 | 27.76 | N |
| ATOM | 2447 | CA  | SER | A | 450 | 81.947 | 48.157 | 15.282 | 1.00 | 27.63 | C |
| ATOM | 2448 | C   | SER | A | 450 | 82.321 | 47.712 | 16.691 | 1.00 | 27.22 | C |
| ATOM | 2449 | O   | SER | A | 450 | 82.815 | 48.507 | 17.490 | 1.00 | 26.61 | O |
| ATOM | 2450 | CB  | SER | A | 450 | 80.421 | 48.272 | 15.182 | 1.00 | 27.03 | C |
| ATOM | 2451 | OG  | SER | A | 450 | 80.037 | 49.038 | 14.053 | 1.00 | 28.56 | O |
| ATOM | 2452 | N   | LEU | A | 451 | 82.086 | 46.437 | 16.989 | 1.00 | 26.98 | N |
| ATOM | 2453 | CA  | LEU | A | 451 | 82.378 | 45.906 | 18.310 | 1.00 | 27.66 | C |
| ATOM | 2454 | C   | LEU | A | 451 | 83.870 | 45.755 | 18.598 | 1.00 | 29.12 | C |
| ATOM | 2455 | O   | LEU | A | 451 | 84.270 | 45.719 | 19.758 | 1.00 | 28.46 | O |
| ATOM | 2456 | CB  | LEU | A | 451 | 81.638 | 44.580 | 18.522 | 1.00 | 26.68 | C |
| ATOM | 2457 | CG  | LEU | A | 451 | 80.112 | 44.754 | 18.493 | 1.00 | 26.86 | C |
| ATOM | 2458 | CD1 | LEU | A | 451 | 79.422 | 43.455 | 18.852 | 1.00 | 24.50 | C |
| ATOM | 2459 | CD2 | LEU | A | 451 | 79.704 | 45.860 | 19.461 | 1.00 | 26.58 | C |
| ATOM | 2460 | N   | ASN | A | 452 | 84.697 | 45.671 | 17.559 | 1.00 | 30.10 | N |
| ATOM | 2461 | CA  | ASN | A | 452 | 86.132 | 45.577 | 17.795 | 1.00 | 31.68 | C |
| ATOM | 2462 | C   | ASN | A | 452 | 86.595 | 46.926 | 18.323 | 1.00 | 31.06 | C |
| ATOM | 2463 | O   | ASN | A | 452 | 87.470 | 46.999 | 19.187 | 1.00 | 30.69 | O |
| ATOM | 2464 | CB  | ASN | A | 452 | 86.907 | 45.230 | 16.519 | 1.00 | 33.39 | C |
| ATOM | 2465 | CG  | ASN | A | 452 | 86.881 | 43.747 | 16.208 | 1.00 | 37.58 | C |
| ATOM | 2466 | OD1 | ASN | A | 452 | 86.800 | 42.908 | 17.113 | 1.00 | 40.20 | O |
| ATOM | 2467 | ND2 | ASN | A | 452 | 86.969 | 43.411 | 14.925 | 1.00 | 39.30 | N |
| ATOM | 2468 | N   | LYS | A | 453 | 86.000 | 47.996 | 17.805 | 1.00 | 30.67 | N |

TABLE 4-continued

| ATOM | 2469 | CA | LYS | A | 453 | 86.358 | 49.334 | 18.256 | 1.00 | 31.02 | C |
|------|------|-----|-----|---|-----|--------|--------|--------|------|-------|---|
| ATOM | 2470 | C | LYS | A | 453 | 85.863 | 49.550 | 19.680 | 1.00 | 28.53 | C |
| ATOM | 2471 | O | LYS | A | 453 | 86.549 | 50.170 | 20.489 | 1.00 | 28.63 | O |
| ATOM | 2472 | CB | LYS | A | 453 | 85.779 | 50.407 | 17.326 | 1.00 | 32.56 | C |
| ATOM | 2473 | CG | LYS | A | 453 | 86.475 | 50.454 | 15.974 | 1.00 | 38.18 | C |
| ATOM | 2474 | CD | LYS | A | 453 | 86.326 | 51.813 | 15.290 | 1.00 | 40.85 | C |
| ATOM | 2475 | CE | LYS | A | 453 | 84.888 | 52.108 | 14.928 | 1.00 | 43.86 | C |
| ATOM | 2476 | NZ | LYS | A | 453 | 84.745 | 53.424 | 14.236 | 1.00 | 45.10 | N |
| ATOM | 2477 | N | VAL | A | 454 | 84.674 | 49.041 | 19.982 | 1.00 | 26.35 | N |
| ATOM | 2478 | CA | VAL | A | 454 | 84.121 | 49.168 | 21.321 | 1.00 | 25.14 | C |
| ATOM | 2479 | C | VAL | A | 454 | 85.037 | 48.436 | 22.305 | 1.00 | 25.64 | C |
| ATOM | 2480 | O | VAL | A | 454 | 85.395 | 48.980 | 23.352 | 1.00 | 24.53 | O |
| ATOM | 2481 | CB | VAL | A | 454 | 82.700 | 48.566 | 21.409 | 1.00 | 25.38 | C |
| ATOM | 2482 | CG1 | VAL | A | 454 | 82.241 | 48.504 | 22.869 | 1.00 | 24.56 | C |
| ATOM | 2483 | CG2 | VAL | A | 454 | 81.725 | 49.413 | 20.589 | 1.00 | 24.60 | C |
| ATOM | 2484 | N | LYS | A | 455 | 85.419 | 47.208 | 21.956 | 1.00 | 25.47 | N |
| ATOM | 2485 | CA | LYS | A | 455 | 86.290 | 46.393 | 22.805 | 1.00 | 26.49 | C |
| ATOM | 2486 | C | LYS | A | 455 | 87.634 | 47.073 | 23.053 | 1.00 | 27.06 | C |
| ATOM | 2487 | O | LYS | A | 455 | 88.162 | 47.051 | 24.165 | 1.00 | 26.76 | O |
| ATOM | 2488 | CB | LYS | A | 455 | 86.534 | 45.030 | 22.157 | 1.00 | 26.81 | C |
| ATOM | 2489 | CG | LYS | A | 455 | 85.335 | 44.099 | 22.139 | 1.00 | 27.88 | C |
| ATOM | 2490 | CD | LYS | A | 455 | 85.653 | 42.889 | 21.279 | 1.00 | 29.25 | C |
| ATOM | 2491 | CE | LYS | A | 455 | 84.558 | 41.857 | 21.344 | 1.00 | 32.72 | C |
| ATOM | 2492 | NZ | LYS | A | 455 | 84.871 | 40.695 | 20.464 | 1.00 | 33.72 | N |
| ATOM | 2493 | N | SER | A | 456 | 88.185 | 47.664 | 22.000 | 1.00 | 26.88 | N |
| ATOM | 2494 | CA | SER | A | 456 | 89.463 | 48.355 | 22.084 | 1.00 | 28.22 | C |
| ATOM | 2495 | C | SER | A | 456 | 89.356 | 49.563 | 23.021 | 1.00 | 27.71 | C |
| ATOM | 2496 | O | SER | A | 456 | 90.221 | 49.788 | 23.868 | 1.00 | 27.11 | O |
| ATOM | 2497 | CB | SER | A | 456 | 89.896 | 48.801 | 20.684 | 1.00 | 29.36 | C |
| ATOM | 2498 | OG | SER | A | 456 | 91.173 | 49.401 | 20.715 | 1.00 | 32.57 | O |
| ATOM | 2499 | N | THR | A | 457 | 88.289 | 50.339 | 22.866 | 1.00 | 26.02 | N |
| ATOM | 2500 | CA | THR | A | 457 | 88.083 | 51.502 | 23.713 | 1.00 | 25.29 | C |
| ATOM | 2501 | C | THR | A | 457 | 87.905 | 51.052 | 25.159 | 1.00 | 24.88 | C |
| ATOM | 2502 | O | THR | A | 457 | 88.407 | 51.692 | 26.083 | 1.00 | 25.60 | O |
| ATOM | 2503 | CB | THR | A | 457 | 86.847 | 52.297 | 23.269 | 1.00 | 24.46 | C |
| ATOM | 2504 | OG1 | THR | A | 457 | 87.013 | 52.689 | 21.904 | 1.00 | 26.98 | O |
| ATOM | 2505 | CG2 | THR | A | 457 | 86.677 | 53.541 | 24.113 | 1.00 | 21.68 | C |
| ATOM | 2506 | N | MET | A | 458 | 87.192 | 49.948 | 25.355 | 1.00 | 24.86 | N |
| ATOM | 2507 | CA | MET | A | 458 | 86.977 | 49.430 | 26.697 | 1.00 | 23.62 | C |
| ATOM | 2508 | C | MET | A | 458 | 88.314 | 49.140 | 27.363 | 1.00 | 24.86 | C |
| ATOM | 2509 | O | MET | A | 458 | 88.496 | 49.424 | 28.545 | 1.00 | 25.51 | O |
| ATOM | 2510 | CB | MET | A | 458 | 86.097 | 48.179 | 26.653 | 1.00 | 23.91 | C |
| ATOM | 2511 | CG | MET | A | 458 | 84.603 | 48.501 | 26.525 | 1.00 | 23.56 | C |
| ATOM | 2512 | SD | MET | A | 458 | 83.557 | 47.082 | 26.176 | 1.00 | 24.90 | S |
| ATOM | 2513 | CE | MET | A | 458 | 83.569 | 46.235 | 27.743 | 1.00 | 23.81 | C |
| ATOM | 2514 | N | CYS | A | 459 | 89.268 | 48.599 | 26.613 | 1.00 | 26.31 | N |
| ATOM | 2515 | CA | CYS | A | 459 | 90.567 | 48.321 | 27.213 | 1.00 | 27.49 | C |
| ATOM | 2516 | C | GYS | A | 459 | 91.294 | 49.613 | 27.561 | 1.00 | 27.38 | C |
| ATOM | 2517 | O | CYS | A | 459 | 92.055 | 49.655 | 28.528 | 1.00 | 27.52 | O |
| ATOM | 2518 | CB | CYS | A | 459 | 91.418 | 47.440 | 26.300 | 1.00 | 29.11 | C |
| ATOM | 2519 | SG | CYS | A | 459 | 90.985 | 45.676 | 26.452 | 1.00 | 33.31 | S |
| ATOM | 2520 | N | ASN | A | 460 | 91.052 | 50.665 | 26.780 | 1.00 | 26.76 | N |
| ATOM | 2521 | CA | ASN | A | 460 | 91.659 | 51.966 | 27.053 | 1.00 | 26.30 | C |
| ATOM | 2522 | C | ASN | A | 460 | 91.112 | 52.452 | 28.387 | 1.00 | 25.18 | C |
| ATOM | 2523 | O | ASN | A | 460 | 91.780 | 53.177 | 29.110 | 1.00 | 25.85 | O |
| ATOM | 2524 | CB | ASN | A | 460 | 91.284 | 52.996 | 25.983 | 1.00 | 26.49 | C |
| ATOM | 2525 | CG | ASN | A | 460 | 91.974 | 52.753 | 24.662 | 1.00 | 27.93 | C |
| ATOM | 2526 | OD1 | ASN | A | 460 | 91.321 | 52.628 | 23.629 | 1.00 | 30.37 | O |
| ATOM | 2527 | ND2 | ASN | A | 460 | 93.301 | 52.698 | 24.683 | 1.00 | 27.47 | N |
| ATOM | 2528 | N | CYS | A | 461 | 89.886 | 52.049 | 28.704 | 1.00 | 24.75 | N |
| ATOM | 2529 | CA | CYS | A | 461 | 89.245 | 52.468 | 29.946 | 1.00 | 24.35 | C |
| ATOM | 2530 | C | GYS | A | 461 | 89.471 | 51.485 | 31.093 | 1.00 | 24.59 | C |
| ATOM | 2531 | O | CYS | A | 461 | 88.929 | 51.663 | 32.179 | 1.00 | 24.19 | O |
| ATOM | 2532 | CB | CYS | A | 461 | 87.738 | 52.665 | 29.716 | 1.00 | 25.37 | C |
| ATOM | 2533 | SG | CYS | A | 461 | 87.342 | 53.931 | 28.465 | 1.00 | 26.44 | S |
| ATOM | 2534 | N | GLY | A | 462 | 90.266 | 50.449 | 30.839 | 1.00 | 25.17 | N |
| ATOM | 2535 | CA | GLY | A | 462 | 90.562 | 49.454 | 31.857 | 1.00 | 24.26 | C |
| ATOM | 2536 | C | GLY | A | 462 | 89.424 | 48.490 | 32.136 | 1.00 | 25.01 | C |
| ATOM | 2537 | O | GLY | A | 462 | 89.300 | 47.970 | 33.250 | 1.00 | 25.14 | O |
| ATOM | 2538 | N | ALA | A | 463 | 88.601 | 48.228 | 31.127 | 1.00 | 23.44 | N |
| ATOM | 2539 | CA | ALA | A | 463 | 87.462 | 47.339 | 31.302 | 1.00 | 23.93 | C |
| ATOM | 2540 | C | ALA | A | 463 | 87.479 | 46.110 | 30.397 | 1.00 | 24.29 | C |
| ATOM | 2541 | O | ALA | A | 463 | 87.688 | 46.216 | 29.185 | 1.00 | 23.39 | O |
| ATOM | 2542 | CB | ALA | A | 463 | 86.169 | 48.122 | 31.085 | 1.00 | 21.46 | C |
| ATOM | 2543 | N | LEU | A | 464 | 87.245 | 44.950 | 31.002 | 1.00 | 24.49 | N |
| ATOM | 2544 | CA | LEU | A | 464 | 87.195 | 43.686 | 30.275 | 1.00 | 26.40 | C |
| ATOM | 2545 | C | LEU | A | 464 | 85.749 | 43.260 | 30.066 | 1.00 | 25.77 | C |
| ATOM | 2546 | O | LEU | A | 464 | 85.476 | 42.351 | 29.287 | 1.00 | 27.45 | O |
| ATOM | 2547 | CB | LEU | A | 464 | 87.936 | 42.582 | 31.039 | 1.00 | 27.85 | C |

TABLE 4-continued

| | | | | | | | | | | |
|---|---|---|---|---|---|---|---|---|---|---|
| ATOM | 2548 | CG | LEU | A | 464 | 89.448 | 42.499 | 30.823 | 1.00 | 29.66 | C |
| ATOM | 2549 | CD1 | LEU | A | 464 | 90.024 | 41.335 | 31.630 | 1.00 | 31.06 | C |
| ATOM | 2550 | CD2 | LEU | A | 464 | 89.730 | 42.304 | 29.349 | 1.00 | 30.29 | C |
| ATOM | 2551 | N | THR | A | 465 | 84.829 | 43.909 | 30.775 | 1.00 | 25.23 | N |
| ATOM | 2552 | CA | THR | A | 465 | 83.406 | 43.603 | 30.656 | 1.00 | 24.98 | C |
| ATOM | 2553 | C | THR | A | 465 | 82.589 | 44.893 | 30.684 | 1.00 | 25.79 | C |
| ATOM | 2554 | O | THR | A | 465 | 83.096 | 45.955 | 31.057 | 1.00 | 24.88 | O |
| ATOM | 2555 | CB | THR | A | 465 | 82.913 | 42.719 | 31.812 | 1.00 | 25.00 | C |
| ATOM | 2556 | OG1 | THR | A | 465 | 82.998 | 43.458 | 33.035 | 1.00 | 24.92 | O |
| ATOM | 2557 | CG2 | THR | A | 465 | 83.757 | 41.447 | 31.921 | 1.00 | 24.20 | C |
| ATOM | 2558 | N | ILE | A | 466 | 81.323 | 44.801 | 30.293 | 1.00 | 24.73 | N |
| ATOM | 2559 | CA | ILE | A | 466 | 80.470 | 45.977 | 30.294 | 1.00 | 24.59 | C |
| ATOM | 2560 | C | ILE | A | 466 | 80.269 | 46.503 | 31.717 | 1.00 | 24.91 | C |
| ATOM | 2561 | O | ILE | A | 466 | 80.359 | 47.702 | 31.952 | 1.00 | 26.03 | O |
| ATOM | 2562 | CB | ILE | A | 466 | 79.117 | 45.672 | 29.616 | 1.00 | 24.22 | C |
| ATOM | 2563 | CG1 | ILE | A | 466 | 79.340 | 45.548 | 28.104 | 1.00 | 22.81 | C |
| ATOM | 2564 | CG2 | ILE | A | 466 | 78.095 | 46.761 | 29.931 | 1.00 | 20.91 | C |
| ATOM | 2565 | CD1 | ILE | A | 466 | 78.132 | 45.051 | 27.344 | 1.00 | 23.02 | C |
| ATOM | 2566 | N | PRO | A | 467 | 79.997 | 45.614 | 32.688 | 1.00 | 25.66 | N |
| ATOM | 2567 | CA | PRO | A | 467 | 79.811 | 46.107 | 34.058 | 1.00 | 25.52 | C |
| ATOM | 2568 | C | PRO | A | 467 | 81.057 | 46.840 | 34.566 | 1.00 | 26.38 | C |
| ATOM | 2569 | O | PRO | A | 467 | 80.967 | 47.837 | 35.284 | 1.00 | 25.66 | O |
| ATOM | 2570 | CB | PRO | A | 467 | 79.525 | 44.829 | 34.846 | 1.00 | 25.82 | C |
| ATOM | 2571 | CG | PRO | A | 467 | 78.798 | 43.980 | 33.829 | 1.00 | 25.19 | C |
| ATOM | 2572 | CD | PRO | A | 467 | 79.658 | 44.181 | 32.596 | 1.00 | 24.50 | C |
| ATOM | 2573 | N | GLN | A | 468 | 82.225 | 46.346 | 34.183 | 1.00 | 26.53 | N |
| ATOM | 2574 | CA | GLN | A | 468 | 83.464 | 46.968 | 34.609 | 1.00 | 27.70 | C |
| ATOM | 2575 | C | GLN | A | 468 | 83.626 | 48.344 | 33.954 | 1.00 | 28.31 | C |
| ATOM | 2576 | O | GLN | A | 468 | 84.153 | 49.279 | 34.567 | 1.00 | 27.56 | O |
| ATOM | 2577 | CB | GLN | A | 468 | 84.631 | 46.052 | 34.265 | 1.00 | 29.61 | C |
| ATOM | 2578 | CG | GLN | A | 468 | 85.932 | 46.460 | 34.882 | 1.00 | 32.72 | C |
| ATOM | 2579 | CD | GLN | A | 468 | 86.925 | 45.320 | 34.922 | 1.00 | 32.87 | C |
| ATOM | 2580 | OE2 | GLN | A | 468 | 87.034 | 44.540 | 33.977 | 1.00 | 30.31 | O |
| ATOM | 2581 | NE2 | GLN | A | 468 | 87.670 | 45.231 | 36.015 | 1.00 | 35.10 | N |
| ATOM | 2582 | N | LEU | A | 469 | 83.156 | 48.468 | 32.713 | 1.00 | 27.10 | N |
| ATOM | 2583 | CA | LEU | A | 469 | 83.222 | 49.734 | 31.994 | 1.00 | 26.38 | C |
| ATOM | 2584 | C | LEU | A | 469 | 82.286 | 50.742 | 32.656 | 1.00 | 25.76 | C |
| ATOM | 2585 | O | LEU | A | 469 | 82.641 | 51.904 | 32.840 | 1.00 | 24.62 | O |
| ATOM | 2586 | CE | LEU | A | 469 | 82.809 | 49.547 | 30.530 | 1.00 | 26.12 | C |
| ATOM | 2587 | CG | LEU | A | 469 | 82.606 | 50.848 | 29.742 | 1.00 | 26.70 | C |
| ATOM | 2588 | CD1 | LEU | A | 469 | 83.947 | 51.530 | 29.499 | 1.00 | 24.80 | C |
| ATOM | 2589 | CD2 | LEU | A | 469 | 81.920 | 50.538 | 28.421 | 1.00 | 26.30 | C |
| ATOM | 2590 | N | GLN | A | 470 | 81.092 | 50.285 | 33.018 | 1.00 | 24.81 | N |
| ATOM | 2591 | CA | GLN | A | 470 | 80.101 | 51.148 | 33.652 | 1.00 | 26.06 | C |
| ATOM | 2592 | C | GLN | A | 470 | 80.595 | 51.643 | 35.004 | 1.00 | 27.46 | C |
| ATOM | 2593 | O | GLN | A | 470 | 80.229 | 52.723 | 35.473 | 1.00 | 27.35 | O |
| ATOM | 2594 | CB | GLN | A | 470 | 78.779 | 50.383 | 33.798 | 1.00 | 25.66 | C |
| ATOM | 2595 | CG | GLN | A | 470 | 78.145 | 50.108 | 32.437 | 1.00 | 26.19 | C |
| ATOM | 2596 | CD | GLN | A | 470 | 76.907 | 49.240 | 32.484 | 1.00 | 27.08 | C |
| ATOM | 2597 | OE1 | GLN | A | 470 | 76.089 | 49.270 | 31.561 | 1.00 | 28.25 | O |
| ATOM | 2598 | NE2 | GLN | A | 470 | 76.768 | 48.452 | 33.537 | 1.00 | 24.83 | N |
| ATOM | 2599 | N | SER | A | 471 | 81.464 | 50.855 | 35.611 | 1.00 | 27.91 | N |
| ATOM | 2600 | CA | SER | A | 471 | 82.008 | 51.194 | 36.909 | 1.00 | 29.16 | C |
| ATOM | 2601 | C | SER | A | 471 | 83.245 | 52.094 | 36.831 | 1.00 | 28.62 | C |
| ATOM | 2602 | O | SER | A | 471 | 83.387 | 53.028 | 37.618 | 1.00 | 29.46 | O |
| ATOM | 2603 | CB | SER | A | 471 | 82.346 | 49.901 | 37.660 | 1.00 | 28.43 | C |
| ATOM | 2604 | OG | SER | A | 471 | 82.917 | 50.183 | 38.920 | 1.00 | 33.24 | O |
| ATOM | 2605 | N | LYS | A | 472 | 84.116 | 51.832 | 35.863 | 1.00 | 28.60 | N |
| ATOM | 2606 | CA | LYS | A | 472 | 85.368 | 52.578 | 35.732 | 1.00 | 28.32 | C |
| ATOM | 2607 | C | LYS | A | 472 | 85.459 | 53.725 | 34.728 | 1.00 | 27.50 | C |
| ATOM | 2608 | O | LYS | A | 472 | 86.386 | 54.526 | 34.803 | 1.00 | 26.62 | O |
| ATOM | 2609 | CE | LYS | A | 472 | 86.499 | 51.591 | 35.437 | 1.00 | 28.80 | C |
| ATOM | 2610 | CG | LYS | A | 472 | 86.598 | 50.469 | 36.445 | 1.00 | 29.70 | C |
| ATOM | 2611 | CD | LYS | A | 472 | 87.547 | 49.371 | 35.990 | 1.00 | 32.26 | C |
| ATOM | 2612 | CE | LYS | A | 472 | 88.992 | 49.826 | 35.994 | 1.00 | 33.68 | C |
| ATOM | 2613 | NZ | LYS | A | 472 | 89.910 | 48.692 | 35.671 | 1.00 | 34.81 | N |
| ATOM | 2614 | N | ALA | A | 473 | 84.523 | 53.811 | 33.789 | 1.00 | 26.86 | N |
| ATOM | 2615 | CA | ALA | A | 473 | 84.586 | 54.866 | 32.784 | 1.00 | 26.51 | C |
| ATOM | 2616 | C | ALA | A | 473 | 84.672 | 56.284 | 33.351 | 1.00 | 26.27 | C |
| ATOM | 2617 | O | ALA | A | 473 | 83.986 | 56.637 | 34.313 | 1.00 | 26.64 | O |
| ATOM | 2618 | CE | ALA | A | 473 | 83.394 | 54.760 | 31.831 | 1.00 | 26.47 | C |
| ATOM | 2619 | N | LYS | A | 474 | 85.544 | 57.080 | 32.742 | 1.00 | 25.53 | N |
| ATOM | 2620 | CA | LYS | A | 474 | 85.746 | 58.476 | 33.110 | 1.00 | 25.18 | C |
| ATOM | 2621 | C | LYS | A | 474 | 85.178 | 59.222 | 31.911 | 1.00 | 25.48 | C |
| ATOM | 2622 | O | LYS | A | 474 | 85.742 | 59.190 | 30.816 | 1.00 | 25.05 | O |
| ATOM | 2623 | CE | LYS | A | 474 | 87.237 | 58.749 | 33.293 | 1.00 | 23.52 | C |
| ATOM | 2624 | CG | LYS | A | 474 | 87.842 | 57.916 | 34.425 | 1.00 | 25.87 | C |
| ATOM | 2625 | CD | LYS | A | 474 | 89.333 | 57.657 | 34.217 | 1.00 | 24.85 | C |
| ATOM | 2626 | CE | LYS | A | 474 | 90.152 | 58.924 | 34.356 | 1.00 | 25.06 | C |

TABLE 4-continued

| | | | | | | | | | | |
|---|---|---|---|---|---|---|---|---|---|---|
| ATOM | 2627 | NZ | LYS | A | 474 | 91.582 | 58.631 | 34.061 | 1.00 | 25.87 | N |
| ATOM | 2628 | N | ILE | A | 475 | 84.044 | 59.881 | 32.118 | 1.00 | 25.73 | N |
| ATOM | 2629 | CA | ILE | A | 475 | 83.361 | 60.558 | 31.025 | 1.00 | 25.74 | C |
| ATOM | 2630 | C | ILE | A | 475 | 83.328 | 62.069 | 31.166 | 1.00 | 25.52 | C |
| ATOM | 2631 | O | ILE | A | 475 | 82.858 | 62.598 | 32.173 | 1.00 | 25.22 | O |
| ATOM | 2632 | CE | ILE | A | 475 | 81.912 | 60.020 | 30.906 | 1.00 | 26.10 | C |
| ATOM | 2633 | CG1 | ILE | A | 475 | 81.934 | 58.482 | 30.888 | 1.00 | 25.99 | C |
| ATOM | 2634 | CG2 | ILE | A | 475 | 81.254 | 60.550 | 29.639 | 1.00 | 27.00 | C |
| ATOM | 2635 | CD1 | ILE | A | 475 | 80.559 | 57.819 | 30.973 | 1.00 | 22.84 | C |
| ATOM | 2636 | N | THR | A | 476 | 83.833 | 62.766 | 30.154 | 1.00 | 25.28 | N |
| ATOM | 2637 | CA | THR | A | 476 | 83.839 | 64.220 | 30.199 | 1.00 | 24.69 | C |
| ATOM | 2638 | C | THR | A | 476 | 82.968 | 64.853 | 29.137 | 1.00 | 24.58 | C |
| ATOM | 2639 | O | THR | A | 476 | 82.822 | 64.340 | 28.026 | 1.00 | 23.13 | O |
| ATOM | 2640 | CB | THR | A | 476 | 85.254 | 64.819 | 30.029 | 1.00 | 24.42 | C |
| ATOM | 2641 | OG1 | THR | A | 476 | 85.179 | 66.245 | 30.177 | 1.00 | 24.64 | O |
| ATOM | 2642 | CG2 | THR | A | 476 | 85.817 | 64.506 | 28.641 | 1.00 | 21.62 | C |
| ATOM | 2643 | N | LEU | A | 477 | 82.392 | 65.985 | 29.504 | 1.00 | 25.11 | N |
| ATOM | 2644 | CA | LEU | A | 477 | 81.568 | 66.751 | 28.599 | 1.00 | 26.78 | C |
| ATOM | 2645 | C | LEU | A | 477 | 82.580 | 67.571 | 27.798 | 1.00 | 26.72 | C |
| ATOM | 2646 | O | LEU | A | 477 | 83.672 | 67.855 | 28.290 | 1.00 | 26.01 | O |
| ATOM | 2647 | CB | LEU | A | 477 | 80.645 | 67.668 | 29.405 | 1.00 | 27.13 | C |
| ATOM | 2648 | CG | LEU | A | 477 | 79.566 | 68.443 | 28.661 | 1.00 | 28.34 | C |
| ATOM | 2649 | CD1 | LEU | A | 477 | 78.598 | 67.476 | 27.985 | 1.00 | 27.41 | C |
| ATOM | 2650 | CD2 | LEU | A | 477 | 78.838 | 69.331 | 29.653 | 1.00 | 29.11 | C |
| ATOM | 2651 | N | VAL | A | 478 | 82.221 | 67.924 | 26.569 | 1.00 | 27.82 | N |
| ATOM | 2652 | CA | VAL | A | 478 | 83.075 | 68.708 | 25.678 | 1.00 | 28.66 | C |
| ATOM | 2653 | C | VAL | A | 478 | 82.407 | 70.062 | 25.415 | 1.00 | 29.15 | C |
| ATOM | 2654 | O | VAL | A | 478 | 81.186 | 70.143 | 25.327 | 1.00 | 28.79 | O |
| ATOM | 2655 | CB | VAL | A | 478 | 83.275 | 67.964 | 24.342 | 1.00 | 30.20 | C |
| ATOM | 2656 | CG1 | VAL | A | 478 | 83.918 | 68.870 | 23.326 | 1.00 | 33.41 | C |
| ATOM | 2657 | CG2 | VAL | A | 478 | 84.133 | 66.731 | 24.563 | 1.00 | 30.57 | C |
| ATOM | 2658 | N | SER | A | 479 | 83.200 | 71.121 | 25.288 | 1.00 | 29.64 | N |
| ATOM | 2659 | CA | SER | A | 479 | 82.645 | 72.455 | 25.054 | 1.00 | 31.24 | C |
| ATOM | 2660 | C | SER | A | 479 | 82.016 | 72.595 | 23.675 | 1.00 | 32.88 | C |
| ATOM | 2661 | O | SER | A | 479 | 82.376 | 71.878 | 22.745 | 1.00 | 32.90 | O |
| ATOM | 2662 | CB | SER | A | 479 | 83.731 | 73.523 | 25.208 | 1.00 | 28.66 | C |
| ATOM | 2663 | OG | SER | A | 479 | 84.669 | 73.432 | 24.151 | 1.00 | 29.51 | O |
| ATOM | 2664 | N | SER | A | 480 | 81.075 | 73.528 | 23.556 | 1.00 | 36.21 | N |
| ATOM | 2665 | CA | SER | A | 480 | 80.389 | 73.798 | 22.290 | 1.00 | 40.17 | C |
| ATOM | 2666 | C | SER | A | 480 | 81.393 | 74.060 | 21.172 | 1.00 | 41.93 | C |
| ATOM | 2667 | O | SER | A | 480 | 81.303 | 73.479 | 20.091 | 1.00 | 42.38 | O |
| ATOM | 2668 | CB | SER | A | 480 | 79.487 | 75.026 | 22.429 | 1.00 | 40.09 | C |
| ATOM | 2669 | OG | SER | A | 480 | 78.558 | 74.864 | 23.482 | 1.00 | 42.83 | O |
| ATOM | 2670 | N | VAL | A | 481 | 82.346 | 74.948 | 21.447 | 1.00 | 44.79 | N |
| ATOM | 2671 | CA | VAL | A | 481 | 83.377 | 75.316 | 20.483 | 1.00 | 47.03 | C |
| ATOM | 2672 | C | VAL | A | 481 | 84.169 | 74.125 | 19.958 | 1.00 | 48.55 | C |
| ATOM | 2673 | O | VAL | A | 481 | 84.514 | 74.083 | 18.778 | 1.00 | 49.15 | O |
| ATOM | 2674 | CB | VAL | A | 481 | 84.368 | 76.327 | 21.091 | 1.00 | 46.95 | C |
| ATOM | 2675 | CG1 | VAL | A | 481 | 85.504 | 76.593 | 20.111 | 1.00 | 47.91 | C |
| ATOM | 2676 | CG2 | VAL | A | 481 | 83.646 | 77.625 | 21.420 | 1.00 | 47.48 | C |
| ATOM | 2677 | N | SER | A | 482 | 84.466 | 73.168 | 20.832 | 1.00 | 50.46 | N |
| ATOM | 2678 | CA | SER | A | 482 | 85.219 | 71.982 | 20.438 | 1.00 | 52.74 | C |
| ATOM | 2679 | C | SER | A | 482 | 84.505 | 71.250 | 19.312 | 1.00 | 54.09 | C |
| ATOM | 2680 | O | SER | A | 482 | 85.131 | 70.520 | 18.543 | 1.00 | 54.30 | O |
| ATOM | 2681 | CB | SER | A | 482 | 85.381 | 71.022 | 21.620 | 1.00 | 52.72 | C |
| ATOM | 2682 | OG | SER | A | 482 | 86.013 | 71.650 | 22.718 | 1.00 | 55.18 | O |
| ATOM | 2683 | N | ILE | A | 483 | 83.193 | 71.446 | 19.222 | 1.00 | 55.12 | N |
| ATOM | 2684 | CA | ILE | A | 483 | 82.391 | 70.791 | 18.194 | 1.00 | 56.51 | C |
| ATOM | 2685 | C | ILE | A | 483 | 82.101 | 71.737 | 17.026 | 1.00 | 56.96 | C |
| ATOM | 2686 | O | ILE | A | 483 | 82.516 | 71.404 | 15.895 | 1.00 | 58.03 | O |
| ATOM | 2687 | CB | ILE | A | 483 | 81.063 | 70.276 | 18.792 | 1.00 | 56.37 | C |
| ATOM | 2688 | CG1 | ILE | A | 483 | 81.355 | 69.431 | 20.037 | 1.00 | 56.23 | C |
| ATOM | 2689 | CG2 | ILE | A | 483 | 80.304 | 69.450 | 17.763 | 1.00 | 56.35 | C |
| ATOM | 2690 | CD1 | ILE | A | 483 | 80.121 | 69.014 | 20.813 | 1.00 | 56.41 | C |
| TER | 2691 | | ILE | A | 483 | | | | | | |
| HETATM | 2692 | K | K | A | 900 | 94.574 | 53.191 | 29.387 | 0.75 | 33.20 | K |
| HETATM | 2693 | P | XMP | | 602 | 68.081 | 55.369 | 14.890 | 1.00 | 29.26 | P |
| HETATM | 2694 | O1P | XMP | | 602 | 67.684 | 55.295 | 13.481 | 1.00 | 30.18 | O |
| HETATM | 2695 | O2P | XMP | | 602 | 68.902 | 54.234 | 15.354 | 1.00 | 31.70 | O |
| HETATM | 2696 | O5' | XMP | | 602 | 66.787 | 55.392 | 15.717 | 1.00 | 28.83 | O |
| HETATM | 2697 | O3P | XMP | | 602 | 68.651 | 56.672 | 15.275 | 1.00 | 30.39 | O |
| HETATM | 2698 | C5' | XMP | | 602 | 65.796 | 54.347 | 15.863 | 1.00 | 26.57 | C |
| HETATM | 2699 | C4' | XMP | | 602 | 64.756 | 54.593 | 16.960 | 1.00 | 26.90 | C |
| HETATM | 2700 | O4' | XMP | | 602 | 63.943 | 55.732 | 16.688 | 1.00 | 27.02 | O |
| HETATM | 2701 | C1' | XMP | | 602 | 62.618 | 55.681 | 17.180 | 1.00 | 27.81 | C |
| HETATM | 2702 | W9 | XMP | | 602 | 61.690 | 55.9S3 | 16.031 | 1.00 | 28.12 | N |
| HETATM | 2703 | C4 | XMP | | 602 | 61.248 | 57.183 | 15.601 | 1.00 | 28.78 | C |
| HETATM | 2704 | N3 | XMP | | 602 | 61.556 | 58.444 | 16.121 | 1.00 | 29.01 | N |
| HETATM | 2705 | N1 | XMP | | 602 | 60.086 | 59.258 | 14.353 | 1.00 | 29.05 | N |

TABLE 4-continued

| | | | | | | | | | |
|---|---|---|---|---|---|---|---|---|---|
| HETATM | 2706 | C2 | XMP | 602 | 60.942 | 59.481 | 15.459 | 1.00 | 30.77 | C |
| HETATM | 2707 | O2 | XMP | 602 | 61.128 | 60.639 | 15.829 | 1.00 | 31.42 | O |
| HETATM | 2708 | C6 | XMP | 602 | 59.764 | 57.989 | 13.811 | 1.00 | 27.88 | C |
| HETATM | 2709 | O6 | XMP | 602 | 59.015 | 57.875 | 12.853 | 1.00 | 28.97 | O |
| HETATM | 2710 | C5 | XMP | 602 | 60.406 | 56.909 | 14.506 | 1.00 | 28.31 | C |
| HETATM | 2711 | N7 | XMP | 602 | 60.325 | 55.573 | 14.268 | 1.00 | 27.77 | N |
| HETATM | 2712 | C8 | XMP | 602 | 61.076 | 55.082 | 15.166 | 1.00 | 27.54 | C |
| HETATM | 2713 | C2' | XMP | 602 | 62.604 | 54.298 | 17.878 | 1.00 | 26.62 | C |
| HETATM | 2714 | O2' | XMP | 602 | 62.808 | 54.554 | 19.261 | 1.00 | 26.73 | O |
| HETATM | 2715 | C3' | XMP | 602 | 63.705 | 53.537 | 17.141 | 1.00 | 26.75 | C |
| HETATM | 2716 | O3' | XMP | 602 | 64.161 | 52.438 | 17.926 | 1.00 | 26.88 | O |
| HETATM | 2717 | C1 | MOA | 600 | 60.161 | 58.910 | 19.598 | 1.00 | 39.69 | C |
| HETATM | 2718 | C2 | MOA | 600 | 55.659 | 56.950 | 16.499 | 1.00 | 41.87 | C |
| HETATM | 2719 | C3 | MOA | 600 | 54.526 | 56.264 | 16.209 | 1.00 | 42.80 | C |
| HETATM | 2720 | C4 | MOA | 600 | 53.214 | 56.947 | 16.563 | 1.00 | 43.33 | C |
| HETATM | 2721 | C5 | MOA | 600 | 52.615 | 56.311 | 17.824 | 1.00 | 44.46 | C |
| HETATM | 2722 | C6 | MOA | 600 | 53.260 | 56.803 | 19.110 | 1.00 | 45.19 | C |
| HETATM | 2723 | C7 | MOA | 600 | 59.586 | 54.022 | 20.007 | 1.00 | 38.55 | C |
| HETATM | 2724 | C8 | MOA | 600 | 56.536 | 53.702 | 18.367 | 1.00 | 39.77 | C |
| HETATM | 272S | C9 | MOA | 600 | 54.498 | 54.877 | 15.549 | 1.00 | 42.56 | C |
| HETATM | 2726 | C10 | MOA | 600 | 60.713 | 56.925 | 20.765 | 1.00 | 38.97 | C |
| HETATM | 2727 | C11 | MOA | 600 | 59.765 | 56.576 | 19.638 | 1.00 | 38.97 | C |
| HETATM | 2728 | C12 | MOA | 600 | 59.227 | 55.285 | 19.257 | 1.00 | 38.94 | C |
| HETATM | 2729 | C13 | MOA | 600 | 58.328 | 55.252 | 18.116 | 1.00 | 38.60 | C |
| HETATM | 2730 | C14 | MOA | 600 | 58.002 | 56.474 | 17.412 | 1.00 | 39.76 | C |
| HETATM | 2731 | C15 | MOA | 600 | 58.558 | 57.736 | 17.831 | 1.00 | 39.72 | C |
| HETATM | 2732 | C16 | MOA | 600 | 59.443 | 57.754 | 18.951 | 1.00 | 39.74 | C |
| HETATM | 2733 | C17 | MOA | 600 | 57.066 | 56.441 | 16.206 | 1.00 | 41.19 | C |
| HETATM | 2734 | O1 | MOA | 600 | 60.164 | 60.070 | 19.326 | 1.00 | 40.10 | O |
| HETATM | 2735 | O2 | MOA | 600 | 60.857 | 58.377 | 20.607 | 1.00 | 39.52 | O |
| HETATM | 2736 | O3 | MOA | 600 | 57.806 | 54.039 | 17.729 | 1.00 | 38.84 | O |
| HETATM | 2737 | O4 | MOA | 600 | 58.226 | 58.894 | 17.131 | 1.00 | 41.40 | O |
| HETATM | 2738 | O5 | MOA | 600 | 53.221 | 58.031 | 19.364 | 1.00 | 46.62 | O |
| HETATM | 2739 | O6 | MOA | 600 | 53.815 | 55.961 | 19.854 | 1.00 | 44.12 | O |
| HETATM | 2740 | O | HOH | 1 | 61.376 | 37.927 | 37.348 | 1.00 | 48.46 | O |
| HETATM | 2741 | O | HOH | 2 | 66.118 | 60.676 | 24.768 | 1.00 | 20.39 | O |
| NETATM | 2742 | O | HOH | 3 | 57.906 | 58.970 | 28.360 | 1.00 | 26.84 | O |
| HETATM | 2743 | O | HOH | 4 | 66.772 | 48.007 | 38.757 | 1.00 | 2S.49 | O |
| HETATM | 2744 | O | HOH | 5 | 87.612 | 55.755 | 31.226 | 1.00 | 23.33 | O |
| NETATM | 2745 | O | HOH | 6 | 79.992 | 42.156 | 29.537 | 1.00 | 21.25 | O |
| HETATM | 2746 | O | HOH | 7 | 59.636 | 45.401 | 36.922 | 1.00 | 29.33 | O |
| NETATM | 2747 | O | HOH | 8 | 71.079 | 54.650 | 21.993 | 1.00 | 25.95 | O |
| HETATM | 2748 | O | HOH | 9 | 75.154 | 45.933 | 32.815 | 1.00 | 29.51 | O |
| HETATM | 2749 | O | HOH | 10 | 84.715 | 43.023 | 9.513 | 1.00 | 52.28 | O |
| NETATM | 2750 | O | HOH | 11 | 78.040 | 54.255 | 34.365 | 1.00 | 26.73 | O |
| HETATM | 2751 | O | HOH | 12 | 56.541 | 77.341 | 37.146 | 1.00 | 29.92 | O |
| NETATM | 2752 | O | HOH | 13 | 71.260 | 53.575 | 14.099 | 1.00 | 27.29 | O |
| HETATM | 2753 | O | HOH | 14 | 76.501 | 44.082 | 31.079 | 1.00 | 23.02 | O |
| HETATM | 2754 | O | HOH | 15 | 56.998 | 79.001 | 34.463 | 1.00 | 24.15 | O |
| HETATM | 2755 | O | HOH | 16 | 73.891 | 57.573 | 36.189 | 1.00 | 25.33 | O |
| HETATM | 2756 | O | HOH | 17 | 79.049 | 48.291 | 37.245 | 1.00 | 34.20 | O |
| HETATM | 2757 | O | HOH | 18 | 84.628 | 53.459 | 21.080 | 1.00 | 24.55 | O |
| HETATM | 2758 | O | HOH | 19 | 60.274 | 50.551 | 20.190 | 1.00 | 29.66 | O |
| HETATM | 2759 | O | HOH | 20 | 88.720 | 54.039 | 33.349 | 1.00 | 25.23 | O |
| HETATM | 2760 | O | HOH | 21 | 72.841 | 38.348 | 33.765 | 1.00 | 30.16 | O |
| HETATM | 2761 | O | HOH | 22 | 66.292 | 58.791 | 21.349 | 1.00 | 29.06 | O |
| HETATM | 2762 | O | HOH | 23 | 67.212 | 67.480 | 30.959 | 1.00 | 23.37 | O |
| HETATM | 2763 | O | HOH | 24 | 64.926 | 73.569 | 32.978 | 1.00 | 27.92 | O |
| HETATM | 2764 | O | HOH | 25 | 74.543 | 60.063 | 37.886 | 1.00 | 37.97 | O |
| HETATM | 2765 | O | HOH | 26 | 70.536 | 33.662 | 27.436 | 1.00 | 32.78 | O |
| HETATM | 2766 | O | HOH | 27 | 49.672 | 44.473 | 20.960 | 1.00 | 32.61 | O |
| HETATM | 2767 | O | HOH | 28 | 82.525 | 67.407 | 31.912 | 1.00 | 36.84 | O |
| HETATM | 2768 | O | HOH | 29 | 62.576 | 38.739 | 33.869 | 1.00 | 27.93 | O |
| HETATM | 2769 | O | HOH | 30 | 65.657 | 36.916 | 34.650 | 1.00 | 31.90 | O |
| HETATM | 2770 | O | HOH | 31 | 77.268 | 36.846 | 6.578 | 1.00 | 54.28 | O |
| HETATM | 2771 | O | HOH | 32 | 53.069 | 53.133 | 19.199 | 1.00 | 50.49 | O |
| HETATM | 2772 | O | HOH | 33 | 76.732 | 41.427 | 32.285 | 1.00 | 26.63 | O |
| HETATM | 2773 | O | HOH | 34 | 59.082 | 42.334 | 5.797 | 1.00 | 52.93 | O |
| HETATM | 2774 | O | HOH | 35 | 75.506 | 39.010 | 8.246 | 1.00 | 30.82 | O |
| HETATM | 2775 | O | HOH | 36 | 69.343 | 68.054 | 32.924 | 1.00 | 32.47 | O |
| HETATM | 2776 | O | HOH | 37 | 64.457 | 56.749 | 20.210 | 1.00 | 32.67 | O |
| HETATM | 2777 | O | HOH | 38 | 62.747 | 61.776 | 37.438 | 1.00 | 35.12 | O |
| HETATM | 2778 | O | HOH | 39 | 73.816 | 64.979 | 30.707 | 1.00 | 34.05 | O |
| HETATM | 2779 | O | HOH | 40 | 64.885 | 41.594 | 7.798 | 1.00 | 30.67 | O |
| HETATM | 2780 | O | HOH | 41 | 87.291 | 69.760 | 24.178 | 1.00 | 33.68 | O |
| HETATM | 2781 | O | HOH | 42 | 63.521 | 39.537 | 6.109 | 1.00 | 44.37 | O |
| HETATM | 2782 | O | HOH | 43 | 65.271 | 63.920 | 35.809 | 1.00 | 34.06 | O |
| HETATM | 2783 | O | HOH | 44 | 56.965 | 57.545 | 38.806 | 1.00 | 37.58 | O |
| HETATM | 2784 | O | HOH | 45 | 79.547 | 40.499 | 32.022 | 1.00 | 37.32 | O |

TABLE 4-continued

| | | | | | | | | | |
|---|---|---|---|---|---|---|---|---|---|
| HETATM | 2785 | O | HOH | 46 | 60.019 | 51.355 | 9.831 | 1.00 | 30.80 | O |
| HETATM | 2786 | O | HOH | 47 | 61.960 | 50.701 | 17.845 | 1.00 | 28.12 | O |
| HETATM | 2787 | O | HOH | 48 | 74.307 | 50.935 | 36.302 | 1.00 | 32.12 | O |
| HETATM | 2788 | O | HOH | 49 | 48.640 | 54.380 | 36.947 | 1.00 | 38.70 | O |
| HETATM | 2789 | O | HOH | 50 | 53.284 | 51.835 | 37.998 | 1.00 | 35.47 | O |
| HETATM | 2790 | O | HOH | 51 | 51.464 | 58.781 | 25.814 | 1.00 | 42.15 | O |
| HETATM | 2791 | O | HOH | 52 | 66.312 | 31.378 | 26.604 | 1.00 | 42.30 | O |
| HETATM | 2792 | O | HOH | 53 | 51.114 | 46.450 | 35.768 | 1.00 | 39.78 | O |
| HETATM | 2793 | O | HOH | 54 | 72.161 | 53.847 | 44.046 | 1.00 | 49.25 | O |
| HETATM | 2794 | O | HOH | 55 | 68.174 | 38.435 | 46.467 | 1.00 | 39.10 | O |
| HETATM | 2795 | O | HOH | 56 | 62.329 | 64.325 | 35.245 | 1.00 | 31.82 | O |
| HETATM | 2796 | O | HOH | 57 | 56.533 | 41.432 | 37.289 | 1.00 | 42.75 | O |
| HETATM | 2797 | O | HOH | 58 | 60.631 | 39.846 | 6.689 | 1.00 | 42.47 | O |
| HETATM | 2798 | O | HOH | 59 | 54.566 | 73.818 | 39.035 | 1.00 | 35.31 | O |
| HETATM | 2799 | O | HOH | 60 | 60.006 | 59.911 | 30.562 | 1.00 | 39.12 | O |
| HETATM | 2800 | O | HOH | 61 | 93.037 | 49.413 | 23.367 | 1.00 | 39.58 | O |
| HETATM | 2801 | O | HOH | 62 | 78.413 | 51.159 | 38.006 | 1.00 | 44.41 | O |
| HETATM | 2802 | O | HOH | 63 | 66.743 | 37.946 | 16.658 | 1.00 | 31.22 | O |
| HETATM | 2803 | O | HOH | 64 | 61.454 | 73.868 | 39.323 | 1.00 | 45.74 | O |
| HETATM | 2804 | O | HOH | 65 | 52.424 | 53.998 | 25.927 | 1.00 | 36.17 | O |
| HETATM | 2805 | O | HOH | 66 | 59.056 | 45.472 | 5.839 | 1.00 | 44.80 | O |
| HETATM | 2806 | O | HOH | 67 | 71.714 | 56.136 | 41.913 | 1.00 | 33.23 | O |
| HETATM | 2807 | O | HOH | 68 | 92.961 | 54.326 | 36.232 | 1.00 | 47.69 | O |
| HETATM | 2808 | O | HOH | 69 | 82.193 | 63.483 | 21.263 | 1.00 | 31.53 | O |
| HETATM | 2809 | O | HOH | 70 | 80.771 | 49.496 | 10.878 | 1.00 | 59.85 | O |
| HETATM | 2810 | O | HOH | 71 | 50.884 | 32.054 | 16.328 | 1.00 | 46.83 | O |
| HETATM | 2811 | O | HOH | 72 | 43.572 | 44.049 | 23.478 | 1.00 | 40.54 | O |
| HETATM | 2812 | O | HOH | 73 | 79.532 | 38.613 | 17.574 | 1.00 | 40.24 | O |
| HETATM | 2813 | O | HOH | 74 | 94.403 | 49.046 | 26.001 | 1.00 | 45.47 | O |
| HETATM | 2814 | O | HOH | 75 | 59.694 | 51.808 | 16.401 | 1.00 | 31.05 | O |
| HETATM | 2815 | O | HOH | 76 | 72.250 | 67.511 | 32.157 | 1.00 | 37.70 | O |
| HETATM | 2816 | O | HOH | 77 | 62.657 | 53.868 | −3.472 | 1.00 | 54.27 | O |
| HETATM | 2817 | O | HOH | 78 | 51.622 | 50.791 | 21.993 | 1.00 | 42.86 | O |
| HETATM | 2818 | O | HOH | 79 | 92.002 | 50.835 | 35.387 | 1.00 | 48.05 | O |
| HETATM | 2819 | O | HOH | 80 | 59.267 | 38.498 | 34.638 | 1.00 | 33.40 | O |
| HETATM | 2820 | O | HOH | 81 | 90.144 | 53.498 | 35.941 | 1.00 | 39.87 | O |
| HETATM | 2821 | O | HOH | 82 | 78.700 | 70.970 | 25.462 | 1.00 | 45.50 | O |
| HETATM | 2822 | O | HOH | 83 | 75.528 | 70.617 | 31.893 | 1.00 | 36.82 | O |
| HETATM | 2823 | O | HOH | 84 | 58.864 | 51.527 | 22.923 | 1.00 | 41.16 | O |
| HETATM | 2824 | O | HOH | 85 | 85.509 | 49.375 | 39.516 | 1.00 | 46.27 | O |
| HETATM | 2825 | O | HOH | 86 | 75.401 | 39.056 | 31.150 | 1.00 | 35.14 | O |
| HETATM | 2826 | O | HOH | 87 | 75.010 | 37.307 | 10.676 | 1.00 | 38.37 | O |
| HETATM | 2827 | O | HOH | 88 | 91.471 | 42.227 | 35.142 | 1.00 | 46.93 | O |
| HETATM | 2828 | O | HOH | 89 | 49.032 | 57.262 | 26.680 | 1.00 | 45.04 | O |
| HETATM | 2829 | O | HOH | 90 | 58.819 | 35.855 | 26.787 | 1.00 | 33.51 | O |
| HETATM | 2830 | O | HOH | 91 | 66.610 | 35.147 | 36.987 | 1.00 | 41.70 | O |
| HETATM | 2831 | O | HOH | 92 | 66.423 | 29.073 | 14.771 | 1.00 | 36.38 | O |
| HETATM | 2832 | O | HOH | 93 | 50.205 | 43.386 | 7.840 | 1.00 | 48.37 | O |
| HETATM | 2833 | O | HOH | 94 | 69.770 | 36.084 | 7.610 | 1.00 | 43.71 | O |
| HETATM | 2834 | O | HOH | 95 | 56.434 | 31.334 | 8.824 | 1.00 | 51.14 | O |
| HETATM | 2835 | O | HOH | 96 | 68.525 | 59.191 | 7.595 | 1.00 | 57.38 | O |
| HETATM | 2836 | O | HOH | 97 | 68.856 | 74.797 | 33.274 | 1.00 | 45.02 | O |
| HETATM | 2837 | O | HOH | 98 | 45.466 | 44.918 | 32.864 | 1.00 | 44.79 | O |
| HETATM | 2838 | O | HOH | 99 | 73.439 | 40.590 | 41.918 | 1.00 | 43.45 | O |
| HETATM | 2839 | O | HOH | 100 | 82.331 | 76.466 | 24.096 | 1.00 | 49.31 | O |
| HETATM | 2840 | O | HOH | 101 | 63.989 | 58.544 | 43.317 | 1.00 | 49.06 | O |
| HETATM | 2841 | O | HOH | 102 | 52.822 | 30.334 | 14.629 | 1.00 | 50.72 | O |
| HETATM | 2842 | O | HOH | 103 | 69.162 | 44.078 | 0.587 | 1.00 | 44.93 | O |
| HETATM | 2843 | O | HOH | 104 | 57.966 | 65.984 | 38.109 | 1.00 | 50.45 | O |
| HETATM | 2844 | O | HOH | 105 | 61.009 | 30.223 | 22.762 | 1.00 | 54.86 | O |
| HETATM | 2845 | O | HOH | 106 | 92.696 | 40.912 | 20.325 | 1.00 | 51.59 | O |
| HETATM | 2846 | O | HOH | 107 | 83.364 | 55.951 | 16.129 | 1.00 | 38.90 | O |
| HETATM | 2847 | O | HOH | 108 | 80.747 | 50.654 | 40.836 | 1.00 | 49.94 | O |
| HETATM | 2848 | O | HOH | 109 | 55.067 | 32.734 | 36.953 | 1.00 | 52.02 | O |
| HETATM | 2849 | O | HOH | 110 | 61.338 | 24.112 | 16.927 | 1.00 | 75.61 | O |
| HETATM | 2850 | O | HOH | 111 | 55.363 | 51.236 | 15.584 | 1.00 | 50.23 | O |
| HETATM | 2851 | O | HOH | 112 | 86.105 | 39.380 | 22.608 | 1.00 | 43.92 | O |
| HETATM | 2852 | O | HOH | 113 | 65.590 | 61.745 | 38.398 | 1.00 | 44.21 | O |
| HETATM | 2853 | O | HOH | 114 | 76.005 | 54.691 | −0.953 | 1.00 | 60.80 | O |
| HETATM | 2854 | O | HOH | 115 | 63.472 | 78.599 | 34.826 | 1.00 | 49.03 | O |
| HETATM | 2855 | O | HOH | 116 | 56.584 | 48.288 | 14.849 | 1.00 | 40.92 | O |
| HETATM | 2856 | O | HOH | 117 | 74.848 | 29.487 | 24.069 | 1.00 | 48.29 | O |
| HETATM | 2857 | O | HOH | 118 | 60.786 | 51.033 | 45.907 | 1.00 | 58.58 | O |
| HETATM | 2858 | O | HOH | 119 | 63.463 | 59.191 | 18.549 | 1.00 | 40.51 | O |
| HETATM | 2859 | O | HOH | 120 | 64.003 | 26.220 | 24.484 | 1.00 | 50.15 | O |
| HETATM | 2860 | O | HOH | 121 | 58.655 | 37.671 | 5.381 | 1.00 | 53.24 | O |
| HETATM | 2861 | O | HOH | 122 | 63.615 | 31.933 | 25.497 | 1.00 | 40.97 | O |
| HETATM | 2862 | O | HOH | 123 | 65.616 | 76.381 | 33.672 | 1.00 | 46.89 | O |
| HETATM | 2863 | O | HOH | 124 | 55.158 | 44.415 | 39.591 | 1.00 | 56.77 | O |

TABLE 4-continued

| | | | | | | | | | | |
|---|---|---|---|---|---|---|---|---|---|---|
| HETATM | 2864 | O | HOH | | 125 | 75.132 | 48.039 | 35.838 | 1.00 | 43.66 | O |
| HETATM | 2865 | O | HOH | | 126 | 65.816 | 28.316 | 26.676 | 1.00 | 42.04 | O |
| HETATM | 2866 | O | HOH | | 127 | 54.208 | 52.470 | 12.608 | 1.00 | 47.30 | O |
| HETATM | 2867 | O | HOH | | 128 | 53.242 | 30.460 | 11.276 | 1.00 | 68.84 | O |
| HETATM | 2868 | O | HOH | | 129 | 60.726 | 33.090 | 34.181 | 1.00 | 47.71 | O |
| HETATM | 2869 | O | HOH | | 130 | 64.010 | 40.397 | 3.202 | 1.00 | 52.21 | O |
| HETATM | 2870 | O | HOH | | 131 | 77.504 | 52.228 | 0.017 | 1.00 | 50.80 | O |
| HETATM | 2871 | O | HOH | | 132 | 69.804 | 61.883 | 38.293 | 1.00 | 46.95 | O |
| HETATM | 2872 | O | HOH | | 133 | 45.792 | 41.736 | 13.068 | 1.00 | 47.40 | O |
| HETATM | 2873 | O | HOH | | 134 | 50.939 | 33.262 | 11.744 | 1.00 | 43.38 | O |
| HETATM | 2874 | O | HOH | | 135 | 76.312 | 35.442 | 27.267 | 1.00 | 53.79 | O |
| HETATM | 2875 | O | HOH | | 136 | 62.510 | 56.249 | 46.266 | 1.00 | 55.19 | O |
| HETATM | 2876 | O | HOH | | 137 | 73.706 | 35.590 | 8.247 | 1.00 | 48.59 | O |
| HETATM | 2877 | O | HOH | | 138 | 66.547 | 78.277 | 31.624 | 1.00 | 74.03 | O |
| HETATM | 2878 | O | HOH | | 139 | 64.392 | 81.457 | 33.669 | 1.00 | 49.54 | O |
| HETATM | 2879 | O | HOH | | 140 | 61.558 | 64.657 | 38.228 | 1.00 | 56.05 | O |
| HETATM | 2880 | O | HOH | | 141 | 96.215 | 46.485 | 27.601 | 1.00 | 49.93 | O |
| HETATM | 2881 | O | HOH | | 142 | 61.787 | 33.565 | 27.109 | 1.00 | 49.84 | O |
| HETATM | 2882 | O | HOH | | 143 | 52.202 | 49.654 | 40.025 | 1.00 | 57.52 | O |
| HETATM | 2883 | O | HOH | | 144 | 65.216 | 31.604 | 29.511 | 1.00 | 59.80 | O |
| HETATM | 2884 | O | HOH | | 145 | 69.153 | 31.657 | 25.777 | 1.00 | 57.79 | O |
| HETATM | 2885 | O | HOH | | 146 | 60.092 | 41.511 | 39.950 | 1.00 | 50.45 | O |
| HETATM | 2886 | O | HOH | | 147 | 74.800 | 33.112 | 28.850 | 1.00 | 67.42 | O |
| HETATM | 2887 | O | HOH | | 148 | 62.654 | 33.516 | 30.073 | 1.00 | 62.16 | O |
| HETATM | 2888 | O | HOH | | 149 | 71.897 | 32.924 | 29.976 | 1.00 | 50.48 | O |
| HETATM | 2889 | O | HOH | | 150 | 56.804 | 34.357 | 25.133 | 1.00 | 46.97 | O |
| HETATM | 2890 | O | HOH | | 151 | 73.224 | 33.332 | 26.044 | 1.00 | 49.98 | O |
| HETATM | 2891 | O | HOH | | 152 | 62.549 | 28.935 | 25.883 | 1.00 | 63.89 | O |
| HETATM | 2892 | O | HOH | | 153 | 72.526 | 31.533 | 23.597 | 1.00 | 46.02 | O |
| HETATM | 2893 | O | HOH | | 154 | 55.400 | 54.063 | 40.193 | 1.00 | 51.55 | O |
| HETATM | 2894 | O | HOH | | 155 | 56.260 | 50.851 | 2.415 | 1.00 | 59.29 | O |
| HETATM | 2895 | O | HOH | | 156 | 59.029 | 24.830 | 22.198 | 1.00 | 60.82 | O |
| HETATM | 2896 | O | HOH | | 157 | 65.228 | 26.246 | 14.456 | 1.00 | 42.42 | O |
| HETATM | 2897 | O | HOH | | 158 | 74.086 | 29.603 | 13.669 | 1.00 | 44.88 | O |
| HETATM | 2898 | O | HOH | | 159 | 71.012 | 57.900 | 14.425 | 1.00 | 49.16 | O |
| HETATM | 2899 | O | HOH | | 160 | 76.443 | 52.766 | 36.176 | 1.00 | 32.86 | O |
| HETATM | 2900 | O | HOH | | 161 | 74.501 | 55.579 | 38.525 | 1.00 | 43.80 | O |
| HETATM | 2901 | O | HOH | | 162 | 68.390 | 53.333 | 47.198 | 1.00 | 57.30 | O |
| HETATM | 2902 | O | HOH | | 163 | 66.068 | 54.957 | 48.273 | 1.00 | 52.03 | O |
| HETATM | 2903 | O | HOH | | 164 | 90.274 | 44.981 | 34.515 | 1.00 | 42.74 | O |
| HETATM | 2904 | O | HOH | | 165 | 92.357 | 46.800 | 32.648 | 1.00 | 50.13 | O |
| HETATM | 2905 | O | HOH | | 166 | 87.411 | 55.494 | 37.249 | 1.00 | 49.75 | O |
| HETATM | 2906 | O | HOH | | 167 | 65.234 | 66.995 | 39.283 | 1.00 | 56.66 | O |
| HETATM | 2907 | O | HOH | | 168 | 75.023 | 62.880 | 19.374 | 1.00 | 43.60 | O |
| HETATM | 2908 | O | HOH | | 169 | 49.785 | 54.078 | 24.384 | 1.00 | 56.06 | O |
| HETATM | 2909 | O | HOH | | 170 | 93.198 | 47.611 | 19.693 | 1.00 | 57.65 | O |
| HETATM | 2910 | O | HOH | | 171 | 69.700 | 45.410 | 46.557 | 1.00 | 42.35 | O |
| HETATM | 2911 | O | HOH | | 172 | 66.820 | 41.422 | 2.567 | 1.00 | 50.29 | O |
| HETATM | 2912 | O | HOH | | 173 | 87.119 | 47.913 | 13.662 | 1.00 | 52.23 | O |
| HETATM | 2913 | O | HOH | | 174 | 72.571 | 61.611 | 21.232 | 1.00 | 34.11 | O |
| HETATM | 2914 | O | HOH | | 175 | 81.561 | 38.698 | 24.061 | 1.00 | 46.29 | O |
| HETATM | 2915 | O | HOH | | 176 | 70.615 | 32.679 | 38.298 | 1.00 | 45.72 | O |
| HETATM | 2916 | O | HOH | | 177 | 53.945 | 58.607 | 38.141 | 1.00 | 50.80 | O |
| HETATM | 2917 | O | HOH | | 178 | 69.562 | 62.885 | 21.604 | 1.00 | 28.51 | O |
| HETATM | 2918 | O | HOH | | 179 | 69.716 | 68.855 | 36.042 | 1.00 | 48.11 | O |
| HETATM | 2919 | O | HOH | | 180 | 67.633 | 69.270 | 38.272 | 1.00 | 45.15 | O |
| CONECT | 202 | 2519 | | | | | | | | | |
| CONECT | 2519 | 202 | | | | | | | | | |
| CONECT | 2693 | 2694 | 2695 | 2696 | 2697 | | | | | | |
| CONECT | 2694 | 2693 | | | | | | | | | |
| CONECT | 2695 | 2693 | | | | | | | | | |
| CONECT | 2696 | 2693 | 2698 | | | | | | | | |
| CONECT | 2697 | 2693 | | | | | | | | | |
| CONECT | 2698 | 2696 | 2699 | | | | | | | | |
| CONECT | 2699 | 2698 | 2700 | 2715 | | | | | | | |
| CONECT | 2700 | 2699 | 2701 | | | | | | | | |
| CONECT | 2701 | 2700 | 2702 | 2713 | | | | | | | |
| CONECT | 2702 | 2701 | 2703 | 2712 | | | | | | | |
| CONECT | 2703 | 2702 | 2704 | 2710 | | | | | | | |
| CONECT | 2704 | 2703 | 2706 | | | | | | | | |
| CONECT | 2705 | 2706 | 2708 | | | | | | | | |
| CONECT | 2706 | 2704 | 2705 | 2707 | | | | | | | |
| CONECT | 2707 | 2706 | | | | | | | | | |
| CONECT | 2708 | 2705 | 2709 | 2710 | | | | | | | |
| CONECT | 2709 | 2708 | | | | | | | | | |
| CONECT | 2710 | 2703 | 2708 | 2711 | | | | | | | |
| CONECT | 2711 | 2710 | 2712 | | | | | | | | |
| CONECT | 2712 | 2702 | 2711 | | | | | | | | |
| CONECT | 2713 | 2701 | 2714 | 2715 | | | | | | | |

TABLE 4-continued

| | | | | |
|---|---|---|---|---|
| CONECT | 2714 | 2713 | | |
| CONECT | 2715 | 2699 | 2713 | 2716 |
| CONECT | 2716 | 2715 | | |
| CONECT | 2717 | 2732 | 2734 | 2735 |
| CONECT | 2718 | 2719 | 2733 | |
| CONECT | 2719 | 2718 | 2720 | 2725 |
| CONECT | 2720 | 2719 | 2721 | |
| CONECT | 2721 | 2720 | 2722 | |
| CONECT | 2722 | 2721 | 2738 | 2739 |
| CONECT | 2723 | 2728 | | |
| CONECT | 2724 | 2736 | | |
| CONECT | 2725 | 2719 | | |
| CONECT | 2726 | 2727 | 2735 | |
| CONECT | 2727 | 2726 | 2728 | 2732 |
| CONECT | 2728 | 2723 | 2727 | 2729 |
| CONECT | 2729 | 2728 | 2730 | 2736 |
| CONECT | 2730 | 2729 | 2731 | 2733 |
| CONECT | 2731 | 2730 | 2732 | 2737 |
| CONECT | 2732 | 2717 | 2727 | 2731 |
| CONECT | 2733 | 2718 | 2730 | |
| CONECT | 2734 | 2717 | | |
| CONECT | 2735 | 2717 | 2726 | |
| CONECT | 2736 | 2724 | 2729 | |
| CONECT | 2737 | 2731 | | |
| CONECT | 2738 | 2722 | | |
| CONECT | 2739 | 2722 | | |
| MASTER | | 550  0  3  14  18  0  0  6  2918  1  49  39 | | |
| END | | | | |

FIG. 13
P-UC 5440
Page 21

TABLE 5

| | | |
|---|---|---|
| HEADER | | OXIDOREDUCTASE                08-AUG-02  1MEW |
| TITLE | | INOSINE MONOPHOSPHATE DEHYDROGENASE (IMPDH) FROM |
| TITLE | 2 | TRITRICHOMONAS FOETUS WITH XMP AND NAD BOUND |
| COMPND | | MOL_ID: 1; |
| COMPND | 2 | MOLECULE: INOSINE-5'-MONOPHOSPHATE DEHYDROGENASE; |
| COMPND | 3 | CHAIN: A; |
| COMPND | 4 | SYNONYM: IMP DEHYDROGENASE, IMPDH; |
| COMPND | 5 | EC: 1.1.1.205; |
| COMPND | 6 | ENGINEERED: YES |
| SOURCE | | MOL_ID: 1; |
| SOURCE | 2 | ORGANISM_SCIENTIFIC: TRITRICHOMONAS FOETUS; |
| SOURCE | 3 | GENE: IMPDH; |
| SOURCE | 4 | EXPRESSION_SYSTEM: *ESCHERICHIA COLI*; |
| SOURCE | 5 | EXPRESSION_SYSTEM_COMMON: BACTERIA; |
| SOURCE | 6 | EXPRESSION_SYSTEM_STRAIN: H712; |
| SOURCE | 7 | EXPRESSION_SYSTEM_VECTOR_TYPE: PLASMID; |
| SOURCE | 8 | EXPRESSION_SYSTEM_PLASMID: PEACE |
| KEYWDS | | ALPHA BETA BARREL |
| EXPDTA | | X-RAY DIFFRACTION |
| AUTHOR | | G.L. PROSISE, H. LUECKE |
| JRNL | | AUTH        G.L. PROSISE, H. LUECKE |
| JRNL | | TITL         CRYSTAL STRUCTURE OF T. FOETUS INOSINE |
| JRNL | | TITL       2 MONOPHOSPHATE DEHYDROGENASE IN COMPLEX WITH |
| JRNL | | TITL       3 SUBSTRATE, COFACTOR, AND ANALOGS: STRUCTURAL BASIS |
| JRNL | | TITL       4 FOR THE RANDOM-IN ORDERED-OUT KINETIC MECHANISM |
| JRNL | | REF          TO BE PUBLISHED |
| JRNL | | REFN |
| REMARK | 1 | |
| REMARK | 2 | |
| REMARK | 2 | RESOLUTION. 2.15 ANGSTROMS. |
| REMARK | 3 | |
| REMARK | 3 | REFINEMENT. |
| REMARK | 3 | PROGRAM   : CNS 1.1 |
| REMARK | 3 | AUTHORS   : BRUNGER, ADAMS, CLORE, DELANO, GROS, GROSSE- |
| REMARK | 3 |             : KUNSTLEVE, JIANG, KUSZEWSKI, NILGES, PANNU, |
| REMARK | 3 |             : READ, RICE, SIMONSON, WARREN |
| REMARK | 3 | |
| REMARK | 3 | REFINEMENT TARGET : ENGH & HUBER |
| REMARK | 3 | |
| REMARK | 3 | DATA USED IN REFINEMENT. |
| REMARK | 3 | RESOLUTION RANGE HIGH (ANGSTROMS)      : 2.15 |
| REMARK | 3 | RESOLUTION RANGE LOW  (ANGSTROMS)      : 29.61 |

TABLE 5-continued

| | | | |
|---|---|---|---|
| REMARK | 3 | DATA CUTOFF (SIGMA(F)) | : 0.000 |
| REMARK | 3 | OUTLIER CUTOFF HIGH (RMS(ABS(F))) | : NULL |
| REMARK | 3 | COMPLETENESS (WORKING+TEST) (%) | : 98.3 |
| REMARK | 3 | NUMBER OF REFLECTIONS | : 33857 |
| REMARK | 3 | | |
| REMARK | 3 | FIT TO DATA USED IN REFINEMENT. | |
| REMARK | 3 | CROSS-VALIDATION METHOD | : THROUGHOUT |
| REMARK | 3 | FREE R VALUE TEST SET SELECTION | : RANDOM |
| REMARK | 3 | R VALUE (WORKING SET) | : 0.224 |
| REMARK | 3 | FREE R VALUE | : 0.246 |
| REMARK | 3 | FREE R VALUE TEST SET SIZE (%) | : 5.200 |
| REMARK | 3 | FREE R VALUE TEST SET COUNT | : 1768 |
| REMARK | 3 | ESTIMATED ERROR OF FREE R VALUE | : 0.006 |
| REMARK | 3 | | |
| REMARK | 3 | FIT IN THE HIGHEST RESOLUTION BIN. | |
| REMARK | 3 | TOTAL NUMBER OF BINS USED | : 6 |
| REMARK | 3 | BIN RESOLUTION RANGE HIGH (A) | : 2.15 |
| REMARK | 3 | BIN RESOLUTION RANGE LOW (A) | : 2.28 |
| REMARK | 3 | BIN COMPLETENESS (WORKING+TEST) (%) | : 95.80 |
| REMARK | 3 | REFLECTIONS IN BIN (WORKING SET) | : 5092 |
| REMARK | 3 | BIN R VALUE (WORKING SET) | : 0.2580 |
| REMARK | 3 | BIN FREE R VALUE | : 0.2840 |
| REMARK | 3 | BIN FREE R VALUE TEST SET SIZE (%) | : 5.00 |
| REMARK | 3 | BIN FREE R VALUE TEST SET COUNT | : 270 |
| REMARK | 3 | ESTIMATED ERROR OF BIN FREE R VALUE | : 0.017 |
| REMARK | 3 | | |
| REMARK | 3 | NUMBER OF NON-HYDROGEN ATOMS USED IN REFINEMENT. | |
| REMARK | 3 | PROTEIN ATOMS | : 2635 |
| REMARK | 3 | NUCLEIC ACID ATOMS | : 0 |
| REMARK | 3 | HETEROGEN ATOMS | : 69 |
| REMARK | 3 | SOLVENT ATOMS | : 164 |
| REMARK | 3 | | |
| REMARK | 3 | B VALUES. | |
| REMARK | 3 | FROM WILSON PLOT (A**2) | : 28.80 |
| REMARK | 3 | MEAN B VALUE (OVERALL, A**2) | : 36.10 |
| REMARK | 3 | OVERALL ANISOTROPIC B VALUE. | |
| REMARK | 3 | B11 (A**2)    : 0.00000 | |
| REMARK | 3 | B22 (A**2)    : 0.00000 | |
| REMARK | 3 | B33 (A**2)    : 0.00000 | |
| REMARK | 3 | B12 (A**2)    : 0.00000 | |
| REMARK | 3 | B13 (A**2)    : 0.00000 | |
| REMARK | 3 | B23 (A**2)    : 0.00000 | |
| REMARK | 3 | | |
| REMARK | 3 | ESTIMATED COORDINATE ERROR. | |
| REMARK | 3 | ESD FROM LUZZATI PLOT | (A) : 0.26 |
| REMARK | 3 | ESD FROM SIGMAA | (A) : 0.22 |
| REMARK | 3 | LOW RESOLUTION CUTOFF | (A) : 5.00 |
| REMARK | 3 | | |
| REMARK | 3 | CROSS-VALIDATED ESTIMATED COORDINATE ERROR. | |
| REMARK | 3 | ESO FROM C-V LUZZATI PLOT | (A) : 0.30 |
| REMARK | 3 | ESD FROM C-V SIGMAA | (A) : 0.28 |
| REMARK | 3 | | |
| REMARK | 3 | RMS DEVIATIONS FROM IDEAL VALUES. | |
| REMARK | 3 | BOND LENGTHS | (A) : 0.006 |
| REMARK | 3 | BOND ANGLES | (DEGREES) : 1.20 |
| REMARK | 3 | DIHEDRAL ANGLES | (DEGREES) : 22.90 |
| REMARK | 3 | IMPROPER ANGLES | (DEGREES) : 0.77 |
| REMARK | 3 | | |
| REMARK | 3 | ISOTROPIC THERMAL MODEL : RESTRAINED | |
| REMARK | 3 | | |
| REMARK | 3 | ISOTROPIC THERMAL FACTOR RESTRAINTS. RMS | SIGMA |
| REMARK | 3 | MAIN-CHAIN BOND | (A**2) : 0.780 ;    1.500 |
| REMARK | 3 | MAIN-CHAIN ANGLE | (A**2) : 1.410 ;    2.000 |
| REMARK | 3 | SIDE-CHAIN BOND | (A**2) : 0.900 ;    2.000 |
| REMARK | 3 | SIDE-CHAIN ANGLE | (A**2) : 1.480 ;    2.500 |
| REMARK | 3 | | |
| REMARK | 3 | BULK SOLVENT MODELING. | |
| REMARK | 3 | METHOD USED | : FLAT MODEL |
| REMARK | 3 | KSOL | : 0.38 |
| REMARK | 3 | ESOL | : 41.94 |
| REMARK | 3 | | |
| REMARK | 3 | NCS MODEL | : NULL |
| REMARK | 3 | | |
| REMARK | 3 | NCS RESTRAINTS.    RMS    SIGMA/WEIGHT | |
| REMARK | 3 | GROUP 1 POSITIONAL    : NULL ;    NULL (A) | |
| REMARK | 3 | GROUP 1 B-FACTOR    : NULL ;    NULL (A**2) | |
| REMARK | 3 | | |

TABLE 5-continued

| REMARK | 3 | PARAMETER FILE 1 | : PROTEIN_REP.PARAM |
|---|---|---|---|
| REMARK | 3 | PARAMETER FILE 2 | : PARAM.GNSOL |
| REMARK | 3 | PARAMETER FILE 3 | : CIS_PEPTIDE.PARAM |
| REMARK | 3 | PARAMETER FILE 4 | : XMPG.PAR |
| REMARK | 3 | PARAMETER FILE 5 | : NAD_PROD.PAR |
| REMARK | 3 | PARAMETER FILE 6 | : NULL |
| REMARK | 3 | TOPOLOGY FILE 1 | : PROTEIN.TOP |
| REMARK | 3 | TOPOLOGY FILE 2 | : XMPG.TOP |
| REMARK | 3 | TOPOLOGY FILE 3 | : NAD_PROD.TOP |
| REMARK | 3 | TOPOLOGY FILE 4 | : ION.TOP |
| REMARK | 3 | TOPOLOGY FILE 5 | : TOPH.GNSOL |
| REMARK | 3 | TOPOLOGY FILE 6 | : NULL |
| REMARK | 3 | | |
| REMARK | 3 | OTHER REFINEMENT REMARKS: NULL | |
| REMARK | 4 | | |
| REMARK | 4 | 1MEW COMPLIES WITH FORMAT V. 2.3, 09-JULY-1998 | |
| REMARK | 100 | | |
| REMARK | 100 | THIS ENTRY HAS BEEN PROCESSED BY RCSB ON 16-AUG-2002. | |
| REMARK | 100 | THE RCSB ID CODE IS RCSB016859. | |
| REMARK | 200 | | |
| REMARK | 200 | EXPERIMENTAL DETAILS | |
| REMARK | 200 | EXPERIMENT TYPE | : X-RAY DIFFRACTION |
| REMARK | 200 | DATE OF DATA COLLECTION | : 01-NOV-2000 |
| REMARK | 200 | TEMPERATURE (KELVIN) | : 100.0 |
| REMARK | 200 | PH | : 7.50 |
| REMARK | 200 | NUMBER OF CRYSTALS USED | : 1 |
| REMARK | 200 | | |
| REMARK | 200 | SYNCHROTRON (Y/N) | : Y |
| REMARK | 200 | RADIATION SOURCE | : ALS |
| REMARK | 200 | BEAMLINE | : 5.0.2 |
| REMARK | 200 | X-RAY GENERATOR MODEL | : NULL |
| REMARK | 200 | MONOCHROMATIC OR LAUE (M/L) | : M |
| REMARK | 200 | WAVELENGTH OR RANGE (A) | : 1.00 |
| REMARK | 200 | MONOCHROMATOR | : NULL |
| REMARK | 200 | OPTICS | : NULL |
| REMARK | 200 | | |
| REMARK | 200 | DETECTOR TYPE | : CCD |
| REMARK | 200 | DETECTOR MANUFACTURER | : ADSC QUANTUM 4 |
| REMARK | 200 | INTENSITY-INTEGRATION SOFTWARE | : DENZO |
| REMARK | 200 | DATA SCALING SOFTWARE | : SCALEPACK |
| REMARK | 200 | | |
| REMARK | 200 | NUMBER OF UNIQUE REFLECTIONS | : 33857 |
| REMARK | 200 | RESOLUTION RANGE HIGH (A) | : 2.150 |
| REMARK | 200 | RESOLUTION RANGE LOW (A) | : 50.000 |
| REMARK | 200 | REJECTION CRITERIA (SIGMA(I)) | : 0.000 |
| REMARK | 200 | | |
| REMARK | 200 | OVERALL. | |
| REMARK | 200 | COMPLETENESS FOR RANGE (%) | : 98.4 |
| REMARK | 200 | DATA REDUNDANCY | : 5.400 |
| REMARK | 200 | R MERGE (I) | : 0.08000 |
| REMARK | 200 | R SYM (I) | : NULL |
| REMARK | 200 | <I/SIGMA(I)> FOR THE DATA SET | : 19.0000 |
| REMARK | 200 | | |
| REMARK | 200 | IN THE HIGHEST RESOLUTION SHELL. | |
| REMARK | 200 | HIGHEST RESOLUTION SHELL, RANGE HIGH | (A) : 2.15 |
| REMARK | 200 | HIGHEST RESOLUTION SHELL, RANGE LOW | (A) : 2.19 |
| REMARK | 200 | COMPLETENESS FOR SHELL (%) | : 95.9 |
| REMARK | 200 | DATA REDUNDANCY IN SHELL | : NULL |
| REMARK | 200 | R MERGE FOR SHELL (I) | : 0.58000 |
| REMARK | 200 | R SYM FOR SHELL (I) | : NULL |
| REMARK | 200 | <I/SIGMA(I)> FOR SHELL | : 2.200 |
| REMARK | 200 | | |
| REMARK | 200 | DIFFRACTION PROTOCOL: SINGLE WAVELENGTH | |
| REMARK | 200 | METHOD USED TO DETERMINE THE STRUCTURE: FOURIER SYNTHESIS | |
| REMARK | 200 | SOFTWARE USED: CNS | |
| REMARK | 200 | STARTING MODEL: PDB ENTRY 1AK5 | |
| REMARK | 200 | | |
| REMARK | 200 | REMARK: NULL | |
| REMARK | 280 | | |
| REMARK | 280 | CRYSTAL | |
| REMARK | 280 | SOLVENT CONTENT, VS (%) : NULL | |
| REMARK | 280 | MATTHEWS COEFFICIENT, VM (ANGSTROMS**3/DA) : NULL | |
| REMARK | 280 | | |
| REMARK | 280 | CRYSTALLIZATION CONDITIONS: SODIUM MALONATE, TRIS, 2- | |
| REMARK | 280 | MERCAPTOETHANOL, EDTA, GLYCEROL | |
| REMARK | 290 | | |
| REMARK | 290 | CRYSTALLOGRAPHIC SYMMETRY | |
| REMARK | 290 | SYMMETRY OPERATORS FOR SPACE GROUP: P 4 3 2 | |
| REMARK | 290 | | |

TABLE 5-continued

| | | | | | | | |
|---|---|---|---|---|---|---|---|
| REMARK | 290 | SYMOP | SYMMETRY | | | | |
| REMARK | 290 | NNNMMM | OPERATOR | | | | |
| REMARK | 290 | 1555 | X, Y, Z | | | | |
| REMARK | 290 | 2555 | X, −Y, Z | | | | |
| REMARK | 290 | 3555 | −X, Y, −Z | | | | |
| REMARK | 290 | 4555 | X, −Y, −Z | | | | |
| REMARK | 290 | 5555 | Z, X, Y | | | | |
| REMARK | 290 | 6555 | Z, −X, −Y | | | | |
| REMARK | 290 | 7555 | −Z, −X, Y | | | | |
| REMARK | 290 | 8555 | −Z, X, −Y | | | | |
| REMARK | 290 | 9555 | Y, Z, X | | | | |
| REMARK | 290 | 10555 | −Y, Z, −X | | | | |
| REMARK | 290 | 11555 | Y, −Z, −X | | | | |
| REMARK | 290 | 12555 | −Y, −Z, X | | | | |
| REMARK | 290 | 13555 | Y, X, −Z | | | | |
| REMARK | 290 | 14555 | −Y, −X, −Z | | | | |
| REMARK | 290 | 15555 | Y, −X, Z | | | | |
| REMARK | 290 | 16555 | −Y, X, Z | | | | |
| REMARK | 290 | 17555 | X, Z, −Y | | | | |
| REMARK | 290 | 18555 | −X, Z, Y | | | | |
| REMARK | 290 | 19555 | −X, −Z, −Y | | | | |
| REMARK | 290 | 20555 | X, −Z, Y | | | | |
| REMARK | 290 | 21555 | Z, Y, −X | | | | |
| REMARK | 290 | 22555 | Z, −Y, X | | | | |
| REMARK | 290 | 23555 | −Z, Y, X | | | | |
| REMARK | 290 | 24555 | −Z, −Y, −X | | | | |
| REMARK | 290 | | | | | | |
| REMARK | 290 | WHERE | NNN -> OPERATOR NUMBER | | | | |
| REMARK | 290 | | MMM -> TRANSLATION VECTOR | | | | |
| REMARK | 290 | | | | | | |
| REMARK | 290 | CRYSTALLOGRAPHIC SYMMETRY TRANSFORMATIONS | | | | | |
| REMARK | 290 | THE FOLLOWING TRANSFORMATIONS OPERATE ON THE ATOM/HETATM | | | | | |
| REMARK | 290 | RECORDS IN THIS ENTRY TO PRODUCE CRYSTALLOGRAPHICALLY | | | | | |
| REMARK | 290 | RELATED MOLECULES. | | | | | |
| REMARK | 290 | SMTRY1 | 1 | 1.000000 | 0.000000 | 0.000000 | 0.00000 |
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | −1.000000 | 0.000000 | 0.000000 | 0.00000 |
| REMARK | 290 | SMTRY2 | 2 | 0.000000 | −1.000000 | 0.000000 | 0.00000 |
| REMARK | 290 | SMTRY3 | 2 | 0.000000 | 0.000000 | 1.000000 | 0.00000 |
| REMARK | 290 | SMTRY1 | 3 | −1.000000 | 0.000000 | 0.000000 | 0.00000 |
| REMARK | 290 | SMTRY2 | 3 | 0.000000 | 1.000000 | 0.000000 | 0.00000 |
| REMARK | 290 | SMTRY3 | 3 | 0.000000 | 0.000000 | −1.000000 | 0.00000 |
| REMARK | 290 | SMTRY1 | 4 | 1.000000 | 0.000000 | 0.000000 | 0.00000 |
| REMARK | 290 | SMTRY2 | 4 | 0.000000 | −1.000000 | 0.000000 | 0.00000 |
| REMARK | 290 | SMTRY3 | 4 | 0.000000 | 0.000000 | −1.000000 | 0.00000 |
| REMARK | 290 | SMTRY1 | 5 | 0.000000 | 0.000000 | 1.000000 | 0.00000 |
| REMARK | 290 | SMTRY2 | 5 | 1.000000 | 0.000000 | 0.000000 | 0.00000 |
| REMARK | 290 | SMTRY3 | 5 | 0.000000 | 1.000000 | 0.000000 | 0.00000 |
| REMARK | 290 | SMTRY1 | 6 | 0.000000 | 0.000000 | 1.000000 | 0.00000 |
| REMARK | 290 | SMTRY2 | 6 | −1.000000 | 0.000000 | 0.000000 | 0.00000 |
| REMARK | 290 | SMTRY3 | 6 | 0.000000 | −1.000000 | 0.000000 | 0.00000 |
| REMARK | 290 | SMTRY1 | 7 | 0.000000 | 0.000000 | −1.000000 | 0.00000 |
| REMARK | 290 | SMTRY2 | 7 | −1.000000 | 0.000000 | 0.000000 | 0.00000 |
| REMARK | 290 | SMTRY3 | 7 | 0.000000 | 1.000000 | 0.000000 | 0.00000 |
| REMARK | 290 | SMTRY1 | 8 | 0.000000 | 0.000000 | −1.000000 | 0.00000 |
| REMARK | 290 | SMTRY2 | 8 | 1.000000 | 0.000000 | 0.000000 | 0.00000 |
| REMARK | 290 | SMTRY3 | 8 | 0.000000 | −1.000000 | 0.000000 | 0.00000 |
| REMARK | 290 | SMTRY1 | 9 | 0.000000 | 1.000000 | 0.000000 | 0.00000 |
| REMARK | 290 | SMTRY2 | 9 | 0.000000 | 0.000000 | 1.000000 | 0.00000 |
| REMARK | 290 | SMTRY3 | 9 | 1.000000 | 0.000000 | 0.000000 | 0.00000 |
| REMARK | 290 | SMTRY1 | 10 | 0.000000 | −1.000000 | 0.000000 | 0.00000 |
| REMARK | 290 | SMTRY2 | 10 | 0.000000 | 0.000000 | 1.000000 | 0.00000 |
| REMARK | 290 | SMTRY3 | 10 | −1.000000 | 0.000000 | 0.000000 | 0.00000 |
| REMARK | 290 | SMTRY1 | 11 | 0.000000 | 1.000000 | 0.000000 | 0.00000 |
| REMARK | 290 | SMTRY2 | 11 | 0.000000 | 0.000000 | −1.000000 | 0.00000 |
| REMARK | 290 | SMTRY3 | 11 | −1.000000 | 0.000000 | 0.000000 | 0.00000 |
| REMARK | 290 | SMTRY1 | 12 | 0.000000 | −1.000000 | 0.000000 | 0.00000 |
| REMARK | 290 | SMTRY2 | 12 | 0.000000 | 0.000000 | −1.000000 | 0.00000 |
| REMARK | 290 | SMTRY3 | 12 | 1.000000 | 0.000000 | 0.000000 | 0.00000 |
| REMARK | 290 | SMTRY1 | 13 | 0.000000 | 1.000000 | 0.000000 | 0.00000 |
| REMARK | 290 | SMTRY2 | 13 | 1.000000 | 0.000000 | 0.000000 | 0.00000 |
| REMARK | 290 | SMTRY3 | 13 | 0.000000 | 0.000000 | −1.000000 | 0.00000 |
| REMARK | 290 | SMTRY1 | 14 | 0.000000 | −1.000000 | 0.000000 | 0.00000 |
| REMARK | 290 | SMTRY2 | 14 | −1.000000 | 0.000000 | 0.000000 | 0.00000 |
| REMARK | 290 | SMTRY3 | 14 | 0.000000 | 0.000000 | −1.000000 | 0.00000 |
| REMARK | 290 | SMTRY1 | 15 | 0.000000 | 1.000000 | 0.000000 | 0.00000 |
| REMARK | 290 | SMTRY2 | 15 | −1.000000 | 0.000000 | 0.000000 | 0.00000 |
| REMARK | 290 | SMTRY3 | 15 | 0.000000 | 0.000000 | 1.000000 | 0.00000 |

TABLE 5-continued

| | | | | | | | |
|---|---|---|---|---|---|---|---|
| REMARK | 290 | SMTRY1 | 16 | 0.000000 | −1.000000 | 0.000000 | 0.00000 |
| REMARK | 290 | SMTRY2 | 16 | 1.000000 | 0.000000 | 0.000000 | 0.00000 |
| REMARK | 290 | SMTRY3 | 16 | 0.000000 | 0.000000 | 1.000000 | 0.00000 |
| REMARK | 290 | SMTRY1 | 17 | 1.000000 | 0.000000 | 0.000000 | 0.00000 |
| REMARK | 290 | SMTRY2 | 17 | 0.000000 | 0.000000 | 1.000000 | 0.00000 |
| REMARK | 290 | SMTRY3 | 17 | 0.000000 | −1.000000 | 0.000000 | 0.00000 |
| REMARK | 290 | SMTRY1 | 18 | −1.000000 | 0.000000 | 0.000000 | 0.00000 |
| REMARK | 290 | SMTRY2 | 18 | 0.000000 | 0.000000 | 1.000000 | 0.00000 |
| REMARK | 290 | SMTRY3 | 18 | 0.000000 | 1.000000 | 0.000000 | 0.00000 |
| REMARK | 290 | SMTRY1 | 19 | −1.000000 | 0.000000 | 0.000000 | 0.00000 |
| REMARK | 290 | SMTRY2 | 19 | 0.000000 | 0.000000 | −1.000000 | 0.00000 |
| REMARK | 290 | SMTRY3 | 19 | 0.000000 | −1.000000 | 0.000000 | 0.00000 |
| REMARK | 290 | SMTRY1 | 20 | 1.000000 | 0.000000 | 0.000000 | 0.00000 |
| REMARK | 290 | SMTRY2 | 20 | 0.000000 | 0.000000 | −1.000000 | 0.00000 |
| REMARK | 290 | SMTRY3 | 20 | 0.000000 | 1.000000 | 0.000000 | 0.00000 |
| REMARK | 290 | SMTRY1 | 21 | 0.000000 | 0.000000 | 1.000000 | 0.00000 |
| REMARK | 290 | SMTRY2 | 21 | 0.000000 | 1.000000 | 0.000000 | 0.00000 |
| REMARK | 290 | SMTRY3 | 21 | −1.000000 | 0.000000 | 0.000000 | 0.00000 |
| REMARK | 290 | SMTRY1 | 22 | 0.000000 | 0.000000 | 1.000000 | 0.00000 |
| REMARK | 290 | SMTRY2 | 22 | 0.000000 | −1.000000 | 0.000000 | 0.00000 |
| REMARK | 290 | SMTRY3 | 22 | 1.000000 | 0.000000 | 0.000000 | 0.00000 |
| REMARK | 290 | SMTRY1 | 23 | 0.000000 | 0.000000 | −1.000000 | 0.00000 |
| REMARK | 290 | SMTRY2 | 23 | 0.000000 | 1.000000 | 0.000000 | 0.00000 |
| REMARK | 290 | SMTRY3 | 23 | 1.000000 | 0.000000 | 0.000000 | 0.00000 |
| REMARK | 290 | SMTRY1 | 24 | 0.000000 | 0.000000 | −1.000000 | 0.00000 |
| REMARK | 290 | SMTRY2 | 24 | 0.000000 | −1.000000 | 0.000000 | 0.00000 |
| REMARK | 290 | SMTRY3 | 24 | −1.000000 | 0.000000 | 0.000000 | 0.00000 |
| REMARK | 290 | | | | | | |
| REMARK | 290 | REMARK: NULL | | | | | |
| REMARK | 300 | | | | | | |
| REMARK | 300 | BIOMOLECULE: 1 | | | | | |
| REMARK | 300 | THIS ENTRY CONTAINS THE CRYSTALLOGRAPHIC ASYMMETRIC UNIT | | | | | |
| REMARK | 300 | WHICH CONSISTS OF 1 CHAIN(S). SEE REMARK 350 FOR | | | | | |
| REMARK | 300 | INFORMATION ON GENERATING THE BIOLOGICAL MOLECULE(S). | | | | | |
| REMARK | 350 | | | | | | |
| REMARK | 350 | GENERATING THE BIOMOLECULE | | | | | |
| REMARK | 350 | COORDINATES FOR A COMPLETE MULTIMER REPRESENTING THE KNOWN | | | | | |
| REMARK | 350 | BIOLOGICALLY SIGNIFICANT OLIGOMERIZATION STATE OF THE | | | | | |
| REMARK | 350 | MOLECULE CAN BE GENERATED BY APPLYING BIOMT TRANSFORMATIONS | | | | | |
| REMARK | 350 | GIVEN BELOW. BOTH NON-CRYSTALLOGRAPHIC AND | | | | | |
| REMARK | 350 | CRYSTALLOGRAPHIC OPERATIONS ARE GIVEN. | | | | | |
| REMARK | 350 | | | | | | |
| REMARK | 350 | BIOMOLECULE: 1 | | | | | |
| REMARK | 350 | APPLY THE FOLLOWING TO CHAINS: A | | | | | |
| REMARK | 350 | BIOMT1 | 1 | 1.000000 | 0.000000 | 0.000000 | 0.00000 |
| REMARK | 350 | BIOMT2 | 1 | 0.000000 | 1.000000 | 0.000000 | 0.00000 |
| REMARK | 350 | BIOMT3 | 1 | 0.000000 | 0.000000 | 1.000000 | 0.00000 |
| REMARK | 350 | BIOMT1 | 2 | −1.000000 | 0.000000 | 0.000000 | 153.82700 |
| REMARK | 350 | BIOMT2 | 2 | 0.000000 | −1.000000 | 0.000000 | 153.82700 |
| REMARK | 350 | BIOMT3 | 2 | 0.000000 | 0.000000 | 1.000000 | 0.00000 |
| REMARK | 350 | BIOMT1 | 3 | 0.000000 | 1.000000 | 0.000000 | 0.00000 |
| REMARK | 350 | BIOMT2 | 3 | −1.000000 | 0.000000 | 0.000000 | 153.82700 |
| REMARK | 350 | BIOMT3 | 3 | 0.000000 | 0.000000 | 1.000000 | 0.00000 |
| REMARK | 350 | BIOMT1 | 4 | 0.000000 | −1.000000 | 0.000000 | 153.82700 |
| REMARK | 350 | BIOMT2 4 | 1.000000 | 0.000000 | 0.000000 | 0.00000 | |
| REMARK | 350 | BIOMT3 4 | 0.000000 | 0.000000 | 1.000000 | 0.00000 | |
| REMARK | 465 | | | | | | |
| REMARK | 465 | MISSING RESIDUES | | | | | |
| REMARK | 465 | THE FOLLOWING RESIDUES WERE NOT LOCATED IN THE | | | | | |
| REMARK | 465 | EXPERIMENT. (M=MODEL NUMBER; RES=RESIDUE NAME; C=CHAIN | | | | | |
| REMARK | 465 | IDENTIFIER; SSSEQ=SEQUENCE NUMBER; I=INSERTION CODE.) | | | | | |
| REMARK | 465 | | | | | | |
| REMARK | 465 | M RES C SSSEQI | | | | | |
| REMARK | 465 | MET A | | | | | |
| REMARK | 465 | GLY A | | 102 | | | |
| REMARK | 465 | PHE A | | 103 | | | |
| REMARK | 465 | VAL A | | 104 | | | |
| REMARK | 465 | VAL A | | 105 | | | |
| REMARK | 465 | SER A | | 106 | | | |
| REMARK | 465 | ASP A | | 107 | | | |
| REMARK | 465 | SER A | | 108 | | | |
| REMARK | 465 | ASN A | | 109 | | | |
| REMARK | 465 | VAL A | | 110 | | | |
| REMARK | 465 | LYS A | | 111 | | | |
| REMARK | 465 | PRO A | | 112 | | | |
| REMARK | 465 | ASP A | | 113 | | | |
| REMARK | 465 | GLN A | | 114 | | | |
| REMARK | 465 | THR A | | 115 | | | |
| REMARK | 465 | PHE A | | 116 | | | |

TABLE 5-continued

| | | | |
|---|---|---|---|
| REMARK | 465 | ALA A | 117 |
| REMARK | 465 | ASP A | 118 |
| REMARK | 465 | VAL A | 119 |
| REMARK | 465 | LEU A | 120 |
| REMARK | 465 | ALA A | 121 |
| REMARK | 465 | ILE A | 122 |
| REMARK | 465 | SER A | 123 |
| REMARK | 465 | GLN A | 124 |
| REMARK | 465 | ARG A | 125 |
| REMARK | 465 | THR A | 126 |
| REMARK | 465 | THR A | 127 |
| REMARK | 465 | HIS A | 128 |
| REMARK | 465 | ASN A | 129 |
| REMARK | 465 | THR A | 130 |
| REMARK | 465 | VAL A | 131 |
| REMARK | 465 | ALA A | 132 |
| REMARK | 465 | VAL A | 133 |
| REMARK | 465 | THR A | 134 |
| REMARK | 465 | ASP A | 135 |
| REMARK | 465 | ASP A | 136 |
| REMARK | 465 | GLY A | 137 |
| REMARK | 465 | THR A | 138 |
| REMARK | 465 | PRO A | 139 |
| REMARK | 465 | HIS A | 140 |
| REMARK | 465 | GLY A | 141 |
| REMARK | 465 | VAL A | 142 |
| REMARK | 465 | LEU A | 143 |
| REMARK | 465 | LEU A | 144 |
| REMARK | 46S | GLY A | 145 |
| REMARK | 465 | LEU A | 146 |
| REMARK | 465 | VAL A | 147 |
| REMARK | 465 | THR A | 148 |
| REMARK | 465 | GLN A | 149 |
| REMARK | 465 | ARG A | 150 |
| REMARK | 465 | ASP A | 151 |
| REMARK | 465 | TYR A | 152 |
| REMARK | 465 | PRO A | 153 |
| REMARK | 465 | ILE A | 154 |
| REMARK | 465 | ASP A | 155 |
| REMARK | 465 | LEU A | 156 |
| REMARK | 465 | THR A | 157 |
| REMARK | 465 | GLN A | 158 |
| REMARK | 465 | THR A | 159 |
| REMARK | 465 | GLU A | 160 |
| REMARK | 465 | THR A | 161 |
| REMARK | 465 | LYS A | 162 |
| REMARK | 465 | VAL A | 163 |
| REMARK | 465 | SER A | 164 |
| REMARK | 465 | ASP A | 165 |
| REMARK | 465 | MET A | 166 |
| REMARK | 465 | MET A | 167 |
| REMARK | 465 | THR A | 168 |
| REMARK | 465 | PRO A | 169 |
| REMARK | 465 | PHE A | 170 |
| REMARK | 465 | SER A | 171 |
| REMARK | 465 | LYS A | 172 |
| REMARK | 465 | LEU A | 173 |
| REMARK | 465 | VAL A | 174 |
| REMARK | 465 | THR A | 175 |
| REMARK | 465 | ALA A | 176 |
| REMARK | 465 | HIS A | 177 |
| REMARK | 465 | GLN A | 178 |
| REMARK | 465 | ASP A | 179 |
| REMARK | 465 | THR A | 180 |
| REMARK | 465 | LYS A | 181 |
| REMARK | 465 | LEU A | 182 |
| REMARK | 465 | SER A | 183 |
| REMARK | 465 | GLU A | 184 |
| REMARK | 465 | ALA A | 185 |
| REMARK | 465 | ASN A | 186 |
| REMARK | 465 | LYS A | 187 |
| REMARK | 465 | ILE A | 188 |
| REMARK | 465 | ILE A | 189 |
| REMARK | 465 | TRP A | 190 |
| REMARK | 465 | GLU A | 191 |
| REMARK | 465 | LYS A | 192 |
| REMARK | 465 | LYS A | 193 |
| REMARK | 465 | LEU A | 194 |
| REMARK | 465 | ASM A | 195 |

TABLE 5-continued

| | | | |
|---|---|---|---|
| REMARK | 465 | ALA A | 196 |
| REMARK | 465 | LEU A | 197 |
| REMARK | 465 | PRO A | 198 |
| REMARK | 465 | ILE A | 199 |
| REMARK | 465 | ILE A | 200 |
| REMARK | 465 | ASP A | 201 |
| REMARK | 465 | ASP A | 202 |
| REMARK | 465 | ASP A | 203 |
| REMARK | 465 | GLN A | 204 |
| REMARK | 465 | HIS A | 205 |
| REMARK | 465 | LEU A | 206 |
| REMARK | 465 | ARG A | 207 |
| REMARK | 465 | TYR A | 208 |
| REMARK | 465 | ILE A | 209 |
| REMARK | 465 | VAL A | 210 |
| REMARK | 465 | PHE A | 211 |
| REMARK | 465 | ARG A | 212 |
| REMARK | 465 | LYS A | 213 |
| REMARK | 465 | ASP A | 214 |
| REMARK | 465 | TYR A | 215 |
| REMARK | 465 | ASP A | 216 |
| REMARK | 465 | ARG A | 217 |
| REMARK | 465 | SER A | 218 |
| REMARK | 465 | GLN A | 219 |
| REMARK | 465 | VAL A | 220 |
| REMARK | 465 | CYS A | 221 |
| REMARK | 465 | ILE A | 318 |
| REMARK | 465 | CYS A | 319 |
| REMARK | 465 | ILE A | 320 |
| REMARK | 465 | THR A | 321 |
| REMARK | 465 | GLN A | 417 |
| REMARK | 465 | ARG A | 418 |
| REMARK | 465 | TYR A | 419 |
| REMARK | 465 | ASP A | 420 |
| REMARK | 465 | LEU A | 421 |
| REMARK | 465 | GLY A | 422 |
| REMARK | 465 | GLY A | 423 |
| REMARK | 465 | LYS A | 424 |
| REMARK | 465 | GLN A | 425 |
| REMARK | 465 | LYS A | 426 |
| REMARK | 465 | LEU A | 427 |
| REMARK | 465 | SER A | 428 |
| REMARK | 465 | PHE A | 429 |
| REMARK | 465 | GLU A | 430 |
| REMARK | 465 | VAL A | 484 |
| REMARK | 465 | GLU A | 485 |
| REMARK | 465 | GLY A | 486 |
| REMARK | 465 | GLY A | 487 |
| REMARK | 465 | ALA A | 488 |
| REMARK | 465 | HIS A | 489 |
| REMARK | 465 | ASP A | 490 |
| REMARK | 465 | VAL A | 491 |
| REMARK | 465 | ILE A | 492 |
| REMARK | 465 | VAL A | 493 |
| REMARK | 465 | LYS A | 494 |
| REMARK | 465 | ASP A | 495 |
| REMARK | 465 | ARG A | 496 |
| REMARK | 465 | ILE A | 497 |
| REMARK | 465 | ASN A | 498 |
| REMARK | 465 | ASP A | 499 |
| REMARK | 465 | TYR A | 500 |
| REMARK | 465 | HIS A | 501 |
| REMARK | 465 | PRO A | 502 |
| REMARK | 465 | LYS A | 503 |
| REMARK | 500 | | |
| REMARK | 500 | GEOMETRY AND STEREOCHEMISTRY | |
| REMARK | 500 | SUBTOPIC: COVALENT BOND LENGTHS | |
| REMARK | 500 | | |
| REMARK | 500 | THE STEREOCHEMICAL PARAMETERS OF THE FOLLOWIMG RESIDUES | |
| REMARK | 500 | HAVE VALUES WHICH DEVIATE FROM EXPECTED VALUES BY MORE | |
| REMARK | 500 | THAN 6*RMSD (M=MODEL NUMBER; RES=RESIDUE NAME; C=CHAIN | |
| REMARK | 500 | IDENTIFIER; SSEQ=SEQUENCE NUMBER; I=INSERTION CODE). | |
| REMARK | 500 | | |
| REMARK | 500 | STANDARD TABLE: | |
| REMARK | 500 | FORMAT: (10X, I3, 1X, 2 (A3, 1X, A1, I4, A1, 1X, A4, 3X), F6.3) | |
| REMARK | 500 | | |
| REMARK | 500 | EXPECTED VALUES: ENGH AND HUBER, 1991 | |
| REMARK | 500 | | |

TABLE 5-continued

| | | | | | | | | |
|---|---|---|---|---|---|---|---|---|
| REMARK | 500 | M RES | CSSEQI | ATM1 | RES | CSSEQI | ATM2 | DEVIATION |
| REMARK | 500 | VAL A | 62 | CB | VAL A | 62 | CA | 0.036 |
| REMARK | 500 | MET A | 92 | CE | MET A | 92 | SD | −0.071 |
| REMARK | 500 | MET A | 458 | CE | MET A | 458 SD | 0.037 | |
| REMARK | 500 | | | | | | | |
| REMARK | 500 | GEOMETRY AND STEREOCHEMISTRY | | | | | | |
| REMARK | 500 | SUBTOPIC: COVALENT BOND ANGLES | | | | | | |
| REMARK | 500 | | | | | | | |
| REMARK | 500 | THE STEREOCHEMICAL PARAMETERS OF THE FOLLOWING RESIDUES | | | | | | |
| REMARK | 500 | HAVE VALUES WHICH DEVIATE FROM EXPECTED VALUES BY MORE | | | | | | |
| REMARK | 500 | THAN 6*RMSD (M=MODEL NUMBER; RES=RESIDUE NAME; C=CHAIN | | | | | | |
| REMARK | 500 | IDENTIFIER; SSEQ=SEQUENCE NUMBER; I=INSERTION CODE). | | | | | | |
| REMARK | 500 | | | | | | | |
| REMARK | 500 | STANDARD TABLE: | | | | | | |
| REMARK | 500 | FORMAT: (10X, I3, 1X, A3, 1X, A1, I4, A1, 3(1X, A4, 2X), 12X, F5.1). | | | | | | |
| REMARK | 500 | | | | | | | |
| REMARK | 500 | EXPECTED VALUES: ENGH AND HUBER, 1991 | | | | | | |
| REMARK | 500 | | | | | | | |
| REMARK | 500 | M RES | CSSEQI | ATM1 | ATM2 | ATM3 | | |
| REMARK | 500 | GLY A | 20 | N - CA - C | | | ANGL. DEV. = −7.9 DEGREES | |
| REMARK | 500 | ILE A | 27 | N - CA - C | | | ANGL. DEV. = −9.5 DEGREES | |
| REMARK | 500 | PHE A | 266 | N - CA - C | | | ANGL. DEV. = −7.5 DEGREES | |
| REMARK | 500 | GLY A | 312 | N - CA - C | | | ANGL. DEV. = 7.8 DEGREES | |
| REMARK | 500 | LYS A | 472 | N - CA - C | | | ANGL. DEV. = 8.0 DEGREES | |
| REMARK | 500 | LYS A | 474 | N - CA - C | | | ANGL. DEV. = −8.4 DEGREES | |
| REMARK | 500 | LEU A | 477 | N - CA - C | | | ANGL. DEV. = −8.5 DEGREES | |
| REMARK | 900 | | | | | | | |
| REMARK | 900 | RELATED ENTRIES | | | | | | |
| REMARK | 900 | RELATED ID: 1AK5 RELATED DB: PDB | | | | | | |
| REMARK | 900 | INOSINE MONOPHOSPHATE DEHYDROGENASE (IMPDH) FROM. | | | | | | |
| REMARK | 900 | TRITRICHOMONAS FOETUS | | | | | | |
| REMARK | 900 | RELATED ID: 1ME7 RELATED DB: PDB | | | | | | |
| REMARK | 900 | 1ME7 CONTAINS THE SAME PROTEIN WITH RVP AND MOA BOUND | | | | | | |
| REMARK | 900 | RELATED ID: 1ME8 RELATED DB: PDB | | | | | | |
| REMARK | 900 | 1ME8 CONTAINS THE SAME PROTEIN WITH RVP BOUND | | | | | | |
| REMARK | 900 | RELATED ID: 1ME9 RELATED DB: PDB | | | | | | |
| REMARK | 900 | 1ME9 CONTAINS THE SAME PROTEIN WITH IMP BOUND | | | | | | |
| REMARK | 900 | RELATED ID: 1MEH RELATED DB: PDB | | | | | | |
| REMARK | 900 | 1MEH CONTAINS THE SAME PROTEIN WITH IMP AND MOA BOUND | | | | | | |
| REMARK | 900 | RELATED ID: 1MEI RELATED DB: PDB | | | | | | |
| REMARK | 900 | 1MEI CONTAINS THE SAME PROTEIN WITH XMP AND MYCOPHENOLIC | | | | | | |
| REMARK | 900 | ACID BOUND | | | | | | |
| DBREF | | 1MEW A | 1 503 | SWS | P50097 | IMDH_TRIFO | 1 503 | |
| SEQRES | 1 A | 503 | MET ALA LYS TYR TYR ASN GLU PRO CYS HIS THR PHE ASN | | | | | |
| SEQRES | 2 A | 503 | GLU TYR LEU LEU ILE PRO GLY LEU SER THR VAL ASP CYS | | | | | |
| SEQRES | 3 A | 503 | ILE PRO SER ASN VAL ASN LEU SER THR PRO LEU VAL LYS | | | | | |
| SEQRES | 4 A | 503 | PHE GLN LYS GLY GLN GLN SER GLU ILE ASN LEU LYS ILE | | | | | |
| SEQRES | 5 A | 503 | PRO LEU VAL SER ALA ILE MET GLN SER VAL SER GLY GLU | | | | | |
| SEQRES | 6 A | 503 | LYS MET ALA ILE ALA LEU ALA ARG GLU GLY GLY ILE SER | | | | | |
| SEQRES | 7 A | 503 | PHE ILE PHE GLY SER GLN SER ILE GLU SER GLN ALA ALA | | | | | |
| SEQRES | 8 A | 503 | MET VAL HIS ALA VAL LYS ASN PHE LYS ALA GLY PHE VAL | | | | | |
| SEQRES | 9 A | 503 | VAL SER ASP SER ASN VAL LYS PRO ASP GLN THR PHE ALA | | | | | |
| SEQRES | 10 A | 503 | ASP VAL LEU ALA ILE SER GLN ARG THR THR HIS ASN THR | | | | | |
| SEQRES | 11 A | 503 | VAL ALA VAL THR ASP ASP GLY THR PRO HIS GLY VAL LEU | | | | | |
| SEQRES | 12 A | 503 | LEU GLY LEU VAL THR GLN ARG ASP TYR PRO ILE ASP LEU | | | | | |
| SEQRES | 13 A | 503 | THR GLN THR GLU THR LYS VAL SER ASP MET MET THR PRO | | | | | |
| SEQRES | 14 A | 503 | PHE SER LYS LEU VAL THR ALA HIS GLN ASP THR LYS LEU | | | | | |
| SEQRES | 15 A | 503 | SER GLU ALA ASN LYS ILE ILE TRP GLN LYS LYS LEU ASN | | | | | |
| SEQRES | 16 A | 503 | ALA LEU PRO ILE ILE ASP ASP ASP GLN HIS LEU ARG TYR | | | | | |
| SEQRES | 17 A | 503 | ILE VAL PHE ARG LYS ASP TYR ASP ARG SER GLN VAL CYS | | | | | |
| SEQRES | 18 A | 503 | HIS ASN GLU LEU VAL ASP SER GLN LYS ARO TYR LEU VAL | | | | | |
| SEQRES | 19 A | 503 | GLY ALA GLY ILE ASN THR ARG ASP PHE ARG GLU ARO VAL | | | | | |
| SEQRES | 20 A | 503 | PRO ALA LEU VAL GLU ALA GLY ALA ASP VAL LEU CYS ILE | | | | | |
| SEQRES | 21 A | 503 | ASP SER SER ASP GLY PHE SER GLU TRP GLN LYS ILE THR | | | | | |
| SEQRES | 22 A | 503 | ILE GLY TRP ILE ARG GLU LYS TYR GLY ASP LYS VAL LYS | | | | | |
| SEQRES | 23 A | 503 | VAL GLY ALA GLY ASN ILE VAL ASP GLY GLU GLY PHE ARG | | | | | |
| SEQRES | 24 A | 503 | TYR LEU ALA ASP ALA GLY ALA ASP PHE ILE LYS ILE GLY | | | | | |
| SEQRES | 25 A | 503 | ILE GLY GLY GLY SER ILE CYS ILE THR ARG GLU GLN LYS | | | | | |
| SEQRES | 26 A | 503 | GLY ILE GLY ARG GLY GLN ALA THR ALA VAL ILE ASP VAL | | | | | |
| SEQRES | 27 A | 503 | VAL ALA GLU ARG ASN LYS TYR PHE GLU GLU THR GLY ILE | | | | | |
| SEQRES | 28 A | 503 | TYR ILE PRO VAL CYS SER ASP GLY GLY ILE VAL TYR ASP | | | | | |
| SEQRES | 29 A | 503 | TYR HIS MET THR LEU ALA LEU ALA MET GLY ALA ASP PHE | | | | | |
| SEQRES | 30 A | 503 | ILE MET LEU GLY ARG TYR PHE ALA ARG PHE GLU GLU SER | | | | | |
| SEQRES | 31 A | 503 | PRO THR ARG LYS VAL THR ILE ASN GLY SER VAL MET LYS | | | | | |
| SEQRES | 32 A | 503 | GLU TYR TRP GLY GLU GLY SER SER ARG ALA ARG ASN TRP | | | | | |
| SEQRES | 33 A | 503 | GLN ARG TYR ASP LEU GLY GLY LYS GLN LYS LEU SER PHE | | | | | |
| SEQRES | 34 A | 503 | GLU GLU GLY VAL ASP SER TYR VAL PRO TYR ALA GLY LYS | | | | | |
| SEQRES | 35 A | 503 | LEU LYS ASP ASN VAL GLU ALA SER LEU ASN LYS VAL LYS | | | | | |
| SEQRES | 36 A | 503 | SER THR MET CYS ASN CYS GLY ALA LEU THR ILE PRO GLN |

TABLE 5-continued

```
SEQRES   37  A  503   LEU GLN SER LYS ALA LYS ILE THR LEU VAL SER SER VAL
SEQRES   38  A  503   SER ILE VAL GLU GLY GLY ALA HIS ASP VAL ILE VAL LYS
SEQRES   39  A  503   ASP ARG ILE ASN ASP TYR HIS PRO LYS
HET          K     A   900       1
HET          XMP       602      24
HET          NAD       987      44
HETNAM       K   POTASSIUM ION
HETNAM       XMP XANTHOSINE-5'-MONOPHOSPHATE
HETNAM       NAD NICOTINAMIDE-ADENINE-DINUCLEOTIDE
HETSYN       XMP 5--MONOPHOSPHATE-9-BETA-D-RIBOFURANOSYL XANTHINE
FORMUL    2  K       K1 1+
FORMUL    3  XMP     C10 H14 N4 O9 P1 1+
FORMUL    4  NAD     C21 H27 N7 O14 P2
FORMUL    5  HOH     *164 (H2 O1)
HELIX     1   1  THR A    11  ASN A    13  5                              3
HELIX     2   2  ILE A    27  VAL A    31  5                              5
HELIX     3   3  GLY A    64  GLU A    74  1                             11
HELIX     4   4  SER A    85  ASN A    98  1                             14
HELIX     5   5  ASP A   242  GLY A   254  1                             13
HELIX     6   6  SER A   267  GLY A   282  1                             16
HELIX     7   7  ASP A   283  VAL A   285  5                              3
HELIX     8   8  ASP A   294  GLY A   305  1                             12
HELIX     9   9  GLY A   330  GLY A   350  1                             21
HELIX    10  10  TYR A   363  MET A   373  1                             11
HELIX    11  11  GLY A   381  ARG A   386  1                              6
HELIX    12  12  LYS A   442  CYS A   461  1                             20
HELIX    13  13  THR A   465  ALA A   473  1                              9
SHEET     1  A 2  TYR A    15  LEU A    17  0
SHEET     2  A 2  ILE A   475  LEU A   477 -1  O THR A   476   N LEU A    16
SHEET     1  B 2  THR A    35  PRO A    36  0
SHEET     2  B 2  ASN A    49  LEU A    50 -1  O LEU A    50   N THR A    35
SHEET     1  C 2  PHE A    40  GLN A    41  0
SHEET     2  C 2  ILE A   351  TYR A   352 -1  O TYR A   352   N PHE A    40
SHEET     1  D 9  LEU A    54  SER A    56  0
SHEET     2  D 9  ILE A    77  ILE A    80  1  O ILE A    77   N SER A    56
SHEET     3  D 9  GLY A   235  ILE A   238  1  O GLY A   237   N ILE A    80
SHEET     4  D 9  VAL A   257  ILE A   260  1  O CYS A   259   N ILE A   238
SHEET     5  D 9  VAL A   287  ILE A   292  1  O GLY A   288   N LEU A   258
SHEET     6  D 9  PHE A   308  ILE A   311  1  O LYS A   310   N ALA A   289
SHEET     7  D 9  VAL A   355  ASP A   358  1  O CYS A   356   N ILE A   311
SHEET     8  D 9  PHE A   377  LEU A   380  1  O MET A   379   N SER A   357
SHEET     9  D 9  LEU A    54  SER A    56  1  N VAL A    55   O ILE A   378
SHEET     1  E 3  LYS A   394  ILE A   397  0
SHEET     2  E 3  SER A   400  TRP A   406 -1  O MET A   402   N VAL A   395
SHEET     3  E 3  ASP A   434  PRO A   438 -1  O SER A   435   N TYR A   405
SSBOND    1  CYS A    26     CYS A   459
CISPEP    1  GLY A   290     ASN A   291     0        1.02
CRYST1       153.827 153.827 153.827 90.00 90.00 90.00 P 4 3 2    24
ORIGX1       1.000000    0.000000    0.000000     0.00000
ORIGX2       0.000000    1.000000    0.000000     0.00000
ORIGX3       0.000000    0.000000    1.000000     0.00000
SCALE1       0.006501    0.000000    0.000000     0.00000
SCALE2       0.000000    0.006501    0.000000     0.00000
SCALE3       0.000000    0.000000    0.006501     0.00000
ATOM      1   N    ALA A    2      54.794  74.512  36.618  1.00  30.12   N
ATOM      2   CA   ALA A    2      55.518  73.408  35.927  1.00  29.62   C
ATOM      3   C    ALA A    2      56.825  73.048  36.643  1.00  30.02   C
ATOM      4   O    ALA A    2      57.295  73.782  37.518  1.00  28.78   O
ATOM      5   CE   ALA A    2      55.807  73.811  34.492  1.00  29.41   C
ATOM      6   N    LYS A    3      57.397  71.908  36.261  1.00  29.90   N
ATOM      7   CA   LYS A    3      58.649  71.435  36.834  1.00  30.45   C
ATOM      8   C    LYS A    3      59.766  71.663  35.818  1.00  30.17   C
ATOM      9   O    LYS A    3      59.626  71.311  34.648  1.00  29.92   O
ATOM     10   CB   LYS A    3      58.564  69.938  37.150  1.00  31.27   C
ATOM     11   CG   LYS A    3      59.840  69.374  37.767  1.00  33.74   C
ATOM     12   CD   LYS A    3      59.988  67.882  37.515  1.00  35.82   C
ATOM     13   CE   LYS A    3      61.209  67.325  38.235  1.00  37.03   C
ATOM     14   NZ   LYS A    3      62.422  68.153  38.000  1.00  37.77   N
ATOM     15   N    TYR A    4      60.868  72.249  36.273  1.00  30.13   N
ATOM     16   CA   TYR A    4      62.022  72.523  35.421  1.00  30.22   C
ATOM     17   C    TYR A    4      63.218  71.738  35.939  1.00  30.80   C
ATOM     18   O    TYR A    4      63.151  71.131  37.003  1.00  31.54   O
ATOM     19   CB   TYR A    4      62.333  74.023  35.429  1.00  29.07   C
ATOM     20   CG   TYR A    4      61.238  74.845  34.800  1.00  28.39   C
ATOM     21   CD1  TYR A    4      61.148  74.974  33.417  1.00  27.65   C
ATOM     22   CD2  TYR A    4      60.260  75.464  35.588  1.00  28.22   C
ATOM     23   CE1  TYR A    4      60.106  75.701  32.827  1.00  27.89   C
ATOM     24   CE2  TYR A    4      59.213  76.192  35.007  1.00  27.42   C
ATOM     25   CZ   TYR A    4      59.145  76.304  33.629  1.00  27.38   C
```

TABLE 5-continued

| ATOM | 26 | OH | TYR A | 4 | 58.116 | 77.005 | 33.045 | 1.00 | 27.02 | O |
|---|---|---|---|---|---|---|---|---|---|---|
| ATOM | 27 | N | TYR A | 5 | 64.313 | 71.749 | 35.190 | 1.00 | 31.44 | N |
| ATOM | 28 | CA | TYR A | 5 | 65.508 | 71.016 | 35.597 | 1.00 | 32.16 | C |
| ATOM | 29 | C | TYR A | 5 | 66.719 | 71.930 | 35.741 | 1.00 | 32.66 | C |
| ATOM | 30 | O | TYR A | 5 | 66.779 | 73.005 | 35.142 | 1.00 | 32.67 | O |
| ATOM | 31 | CB | TYR A | 5 | 65.806 | 69.894 | 34.594 | 1.00 | 31.56 | C |
| ATOM | 32 | CG | TYR A | 5 | 64.679 | 68.891 | 34.466 | 1.00 | 31.13 | C |
| ATOM | 33 | CD1 | TYR A | 5 | 63.511 | 69.212 | 33.777 | 1.00 | 30.96 | C |
| ATOM | 34 | CD2 | TYR A | 5 | 64.763 | 67.634 | 35.073 | 1.00 | 31.04 | C |
| ATOM | 35 | CE1 | TYR A | 5 | 62.453 | 68.311 | 33.694 | 1.00 | 30.92 | C |
| ATOM | 36 | CE2 | TYR A | 5 | 63.713 | 66.726 | 34.997 | 1.00 | 30.33 | C |
| ATOM | 37 | CZ | TYR A | 5 | 62.559 | 67.071 | 34.307 | 1.00 | 31.08 | C |
| ATOM | 38 | OH | TYR A | 5 | 61.504 | 66.189 | 34.242 | 1.00 | 30.49 | O |
| ATOM | 39 | N | ASN A | 6 | 67.681 | 71.495 | 36.545 | 1.00 | 33.45 | N |
| ATOM | 40 | CA | ASN A | 6 | 68.889 | 72.271 | 36.796 | 1.00 | 34.17 | C |
| ATOM | 41 | C | ASN A | 6 | 69.829 | 72.350 | 35.596 | 1.00 | 33.77 | C |
| ATOM | 42 | O | ASN A | 6 | 70.505 | 73.357 | 35.404 | 1.00 | 34.57 | O |
| ATOM | 43 | CB | ASN A | 6 | 69.635 | 71.684 | 37.997 | 1.00 | 36.09 | C |
| ATOM | 44 | CG | ASN A | 6 | 68.893 | 71.902 | 39.311 | 1.00 | 38.01 | C |
| ATOM | 45 | OD1 | ASN A | 6 | 69.083 | 71.156 | 40.276 | 1.00 | 39.34 | O |
| ATOM | 46 | ND2 | ASN A | 6 | 68.054 | 72.936 | 39.356 | 1.00 | 38.72 | N |
| ATOM | 47 | N | GLU A | 7 | 69.868 | 71.296 | 34.786 | 1.00 | 32.81 | N |
| ATOM | 48 | CA | GLU A | 7 | 70.752 | 71.262 | 33.623 | 1.00 | 31.44 | C |
| ATOM | 49 | C | GLU A | 7 | 70.016 | 70.880 | 32.351 | 1.00 | 30.04 | C |
| ATOM | 50 | O | GLU A | 7 | 69.016 | 70.166 | 32.393 | 1.00 | 29.37 | O |
| ATOM | 51 | CB | GLU A | 7 | 71.870 | 70.238 | 33.840 | 1.00 | 32.95 | C |
| ATOM | 52 | CG | GLU A | 7 | 72.811 | 70.511 | 35.009 | 1.00 | 34.80 | C |
| ATOM | 53 | CD | GLU A | 7 | 73.665 | 71.758 | 34.814 | 1.00 | 36.26 | C |
| ATOM | 54 | OE1 | GLU A | 7 | 74.098 | 72.025 | 33.667 | 1.00 | 37.11 | O |
| ATOM | 55 | OE2 | GLU A | 7 | 73.919 | 72.463 | 35.816 | 1.00 | 37.12 | O |
| ATOM | 56 | N | PRO A | 8 | 70.505 | 71.353 | 31.193 | 1.00 | 28.73 | N |
| ATOM | 57 | CA | PRO A | 8 | 69.854 | 71.015 | 29.925 | 1.00 | 27.94 | C |
| ATOM | 58 | C | PRO A | 8 | 70.216 | 69.567 | 29.597 | 1.00 | 27.17 | C |
| ATOM | 59 | O | PRO A | 8 | 71.198 | 69.043 | 30.127 | 1.00 | 26.26 | O |
| ATOM | 60 | CB | PRO A | 8 | 70.481 | 72.004 | 28.945 | 1.00 | 27.85 | C |
| ATOM | 61 | CG | PRO A | 8 | 71.873 | 72.153 | 29.484 | 1.00 | 27.96 | C |
| ATOM | 62 | CD | PRO A | 8 | 71.641 | 72.268 | 30.975 | 1.00 | 28.51 | C |
| ATOM | 63 | N | CYS A | 9 | 69.432 | 68.918 | 28.742 | 1.00 | 26.44 | N |
| ATOM | 64 | CA | CYS A | 9 | 69.730 | 67.539 | 28.375 | 1.00 | 26.06 | C |
| ATOM | 65 | C | CYS A | 9 | 70.788 | 67.503 | 27.266 | 1.00 | 25.59 | C |
| ATOM | 66 | O | CYS A | 9 | 70.978 | 68.484 | 26.546 | 1.00 | 25.32 | O |
| ATOM | 67 | CB | CYS A | 9 | 68.452 | 66.801 | 27.950 | 1.00 | 26.04 | C |
| ATOM | 68 | SG | CYS A | 9 | 67.458 | 67.585 | 26.659 | 1.00 | 27.03 | S |
| ATOM | 69 | N | HIS A | 10 | 71.478 | 66.373 | 27.146 | 1.00 | 25.08 | N |
| ATOM | 70 | CA | HIS A | 10 | 72.545 | 66.203 | 26.163 | 1.00 | 24.94 | C |
| ATOM | 71 | C | HIS A | 10 | 72.398 | 64.914 | 25.351 | 1.00 | 25.14 | C |
| ATOM | 72 | O | HIS A | 10 | 71.761 | 63.957 | 25.789 | 1.00 | 24.67 | O |
| ATOM | 73 | CB | HIS A | 10 | 73.900 | 66.172 | 26.875 | 1.00 | 25.17 | C |
| ATOM | 74 | CG | HIS A | 10 | 74.154 | 67.356 | 27.755 | 1.00 | 25.33 | C |
| ATOM | 75 | ND1 | HIS A | 10 | 74.603 | 68.565 | 27.269 | 1.00 | 25.05 | N |
| ATOM | 76 | CD2 | HIS A | 10 | 74.016 | 67.517 | 29.092 | 1.00 | 25.00 | C |
| ATOM | 77 | CE1 | HIS A | 10 | 74.731 | 69.419 | 28.267 | 1.00 | 24.83 | C |
| ATOM | 78 | NE2 | HIS A | 10 | 74.381 | 68.807 | 29.385 | 1.00 | 25.63 | N |
| ATOM | 79 | N | THR A | 11 | 73.012 | 64.905 | 24.174 | 1.00 | 25.28 | N |
| ATOM | 80 | CA | THR A | 11 | 72.988 | 63.760 | 23.268 | 1.00 | 26.09 | C |
| ATOM | 81 | C | THR A | 11 | 74.336 | 63.045 | 23.334 | 1.00 | 25.82 | C |
| ATOM | 82 | O | THR A | 11 | 75.309 | 63.600 | 23.852 | 1.00 | 25.75 | O |
| ATOM | 83 | CB | THR A | 11 | 72.759 | 64.210 | 21.814 | 1.00 | 26.08 | C |
| ATOM | 84 | OG1 | THR A | 11 | 73.768 | 65.160 | 21.456 | 1.00 | 27.99 | O |
| ATOM | 85 | CG2 | THR A | 11 | 71.401 | 64.859 | 21.655 | 1.00 | 26.96 | C |
| ATOM | 86 | N | PHE A | 12 | 74.391 | 61.825 | 22.803 | 1.00 | 26.03 | N |
| ATOM | 87 | CA | PHE A | 12 | 75.618 | 61.028 | 22.798 | 1.00 | 26.92 | C |
| ATOM | 88 | C | PHE A | 12 | 76.820 | 61.750 | 22.185 | 1.00 | 27.61 | C |
| ATOM | 89 | O | PHE A | 12 | 77.957 | 61.556 | 22.625 | 1.00 | 27.79 | O |
| ATOM | 90 | CB | PHE A | 12 | 75.400 | 59.710 | 22.050 | 1.00 | 26.64 | C |
| ATOM | 91 | CG | PHE A | 12 | 74.493 | 58.740 | 22.763 | 1.00 | 26.79 | C |
| ATOM | 92 | CD1 | PHE A | 12 | 74.631 | 58.510 | 24.131 | 1.00 | 26.53 | C |
| ATOM | 93 | CD2 | PHE A | 12 | 73.533 | 58.023 | 22.056 | 1.00 | 26.50 | C |
| ATOM | 94 | CE1 | PHE A | 12 | 73.826 | 57.577 | 24.787 | 1.00 | 26.96 | C |
| ATOM | 95 | CE2 | PHE A | 12 | 72.723 | 57.085 | 22.700 | 1.00 | 27.06 | C |
| ATOM | 96 | CZ | PHE A | 12 | 72.870 | 56.861 | 24.072 | 1.00 | 26.55 | C |
| ATOM | 97 | N | ASN A | 13 | 76.567 | 62.569 | 21.167 | 1.00 | 28.01 | N |
| ATOM | 98 | CA | ASN A | 13 | 77.614 | 63.330 | 20.484 | 1.00 | 28.79 | C |
| ATOM | 99 | C | ASN A | 13 | 78.353 | 64.309 | 21.392 | 1.00 | 28.20 | C |
| ATOM | 100 | O | ASN A | 13 | 79.409 | 64.822 | 21.027 | 1.00 | 28.50 | O |
| ATOM | 101 | CB | ASN A | 13 | 77.013 | 64.115 | 19.316 | 1.00 | 30.83 | C |
| ATOM | 102 | CG | ASN A | 13 | 76.925 | 63.299 | 18.041 | 1.00 | 33.42 | C |
| ATOM | 103 | OD1 | ASN A | 13 | 76.014 | 63.490 | 17.235 | 1.00 | 35.66 | O |
| ATOM | 104 | ND2 | ASN A | 13 | 77.883 | 62.400 | 17.838 | 1.00 | 34.84 | N |

TABLE 5-continued

| ATOM | 105 | N | GLU A | 14 | 77.799 | 64.580 | 22.568 | 1.00 | 27.32 | N |
|---|---|---|---|---|---|---|---|---|---|---|
| ATOM | 106 | CA | GLU A | 14 | 78.422 | 65.520 | 23.494 | 1.00 | 26.81 | C |
| ATOM | 107 | C | GLU A | 14 | 79.333 | 64.863 | 24.528 | 1.00 | 26.48 | C |
| ATOM | 108 | O | GLU A | 14 | 79.794 | 65.524 | 25.462 | 1.00 | 26.71 | O |
| ATOM | 109 | CB | GLU A | 14 | 77.342 | 66.330 | 24.215 | 1.00 | 26.50 | C |
| ATOM | 110 | CG | GLU A | 14 | 76.448 | 67.124 | 23.283 | 1.00 | 26.18 | C |
| ATOM | 111 | CD | GLU A | 14 | 75.339 | 67.860 | 24.014 | 1.00 | 25.91 | C |
| ATOM | 112 | OE1 | GLU A | 14 | 75.643 | 68.736 | 24.848 | 1.00 | 25.89 | O |
| ATOM | 113 | OE2 | GLU A | 14 | 74.158 | 67.559 | 23.750 | 1.00 | 25.85 | O |
| ATOM | 114 | N | TYR A | 15 | 79.610 | 63.576 | 24.363 | 1.00 | 25.89 | N |
| ATOM | 115 | CA | TYR A | 15 | 80.454 | 62.880 | 25.325 | 1.00 | 25.89 | C |
| ATOM | 116 | C | TYR A | 15 | 81.647 | 62.145 | 24.733 | 1.00 | 25.92 | C |
| ATOM | 117 | O | TYR A | 15 | 81.652 | 61.758 | 23.562 | 1.00 | 25.82 | O |
| ATOM | 118 | CB | TYR A | 15 | 79.616 | 61.876 | 26.122 | 1.00 | 25.79 | C |
| ATOM | 119 | CG | TYR A | 15 | 78.551 | 62.505 | 26.986 | 1.00 | 26.02 | C |
| ATOM | 120 | CD1 | TYR A | 15 | 78.814 | 62.856 | 28.310 | 1.00 | 25.94 | C |
| ATOM | 121 | CD2 | TYR A | 15 | 77.276 | 62.757 | 26.475 | 1.00 | 25.51 | C |
| ATOM | 122 | CE1 | TYR A | 15 | 77.831 | 63.440 | 29.107 | 1.00 | 26.32 | C |
| ATOM | 123 | CE2 | TYR A | 15 | 76.296 | 63.339 | 27.256 | 1.00 | 25.69 | C |
| ATOM | 124 | CZ | TYR A | 15 | 76.574 | 63.678 | 28.567 | 1.00 | 26.16 | C |
| ATOM | 125 | OH | TYR A | 15 | 75.595 | 64.268 | 29.328 | 1.00 | 27.92 | O |
| ATOM | 126 | N | LEU A | 16 | 82.659 | 61.958 | 25.571 | 1.00 | 25.68 | N |
| ATOM | 127 | CA | LEU A | 16 | 83.857 | 61.221 | 25.201 | 1.00 | 25.59 | C |
| ATOM | 128 | C | LEU A | 16 | 84.240 | 60.398 | 26.421 | 1.00 | 25.18 | C |
| ATOM | 129 | O | LEU A | 16 | 83.879 | 60.741 | 27.545 | 1.00 | 23.99 | O |
| ATOM | 130 | CB | LEU A | 16 | 85.011 | 62.163 | 24.835 | 1.00 | 25.74 | C |
| ATOM | 131 | CG | LEU A | 16 | 84.924 | 62.928 | 23.513 | 1.00 | 26.58 | C |
| ATOM | 132 | CD1 | LEU A | 16 | 86.164 | 63.782 | 23.349 | 1.00 | 26.64 | C |
| ATOM | 133 | CD2 | LEU A | 16 | 84.802 | 61.955 | 22.355 | 1.00 | 26.82 | C |
| ATOM | 134 | N | LEU A | 17 | 84.955 | 59.304 | 26.193 | 1.00 | 25.52 | N |
| ATOM | 135 | CA | LEU A | 17 | 85.403 | 58.444 | 27.281 | 1.00 | 25.75 | C |
| ATOM | 136 | C | LEU A | 17 | 86.873 | 58.726 | 27.569 | 1.00 | 25.91 | C |
| ATOM | 137 | O | LEU A | 17 | 87.685 | 58.859 | 26.649 | 1.00 | 26.05 | O |
| ATOM | 138 | CB | LEU A | 17 | 85.236 | 56.973 | 26.898 | 1.00 | 25.70 | C |
| ATOM | 139 | CG | LEU A | 17 | 83.811 | 56.418 | 26.904 | 1.00 | 25.75 | C |
| ATOM | 140 | CD1 | LEU A | 17 | 83.715 | 55.203 | 25.988 | 1.00 | 25.70 | C |
| ATOM | 141 | CD2 | LEU A | 17 | 83.422 | 56.062 | 28.330 | 1.00 | 24.96 | C |
| ATOM | 142 | N | ILE A | 18 | 87.207 | 58.841 | 28.848 | 1.00 | 26.13 | N |
| ATOM | 143 | CA | ILE A | 18 | 88.584 | 59.070 | 29.247 | 1.00 | 26.23 | C |
| ATOM | 144 | C | ILE A | 18 | 89.125 | 57.707 | 29.665 | 1.00 | 26.76 | C |
| ATOM | 145 | O | ILE A | 18 | 88.568 | 57.054 | 30.547 | 1.00 | 26.89 | O |
| ATOM | 146 | CB | ILE A | 18 | 88.657 | 60.077 | 30.408 | 1.00 | 26.10 | C |
| ATOM | 147 | CG1 | ILE A | 18 | 88.213 | 61.457 | 29.896 | 1.00 | 25.77 | C |
| ATOM | 148 | CG2 | ILE A | 18 | 90.078 | 60.122 | 30.983 | 1.00 | 25.02 | C |
| ATOM | 149 | CD1 | ILE A | 18 | 88.079 | 62.511 | 30.963 | 1.00 | 27.03 | C |
| ATOM | 150 | N | PRO A | 19 | 90.209 | 57.251 | 29.016 | 1.00 | 27.09 | N |
| ATOM | 151 | CA | PRO A | 19 | 90.821 | 55.949 | 29.319 | 1.00 | 27.41 | C |
| ATOM | 152 | C | PRO A | 19 | 91.121 | 55.680 | 30.792 | 1.00 | 27.03 | C |
| ATOM | 153 | O | PRO A | 19 | 91.403 | 56.595 | 31.562 | 1.00 | 27.37 | O |
| ATOM | 154 | CB | PRO A | 19 | 92.098 | 55.960 | 28.477 | 1.00 | 27.80 | C |
| ATOM | 155 | CG | PRO A | 19 | 91.703 | 56.803 | 27.280 | 1.00 | 27.76 | C |
| ATOM | 156 | CD | PRO A | 19 | 90.949 | 57.944 | 27.944 | 1.00 | 27.42 | C |
| ATOM | 157 | N | GLY A | 20 | 91.040 | 54.410 | 31.169 | 1.00 | 26.77 | N |
| ATOM | 158 | CA | GLY A | 20 | 91.346 | 54.000 | 32.528 | 1.00 | 26.84 | C |
| ATOM | 159 | C | GLY A | 20 | 92.544 | 53.079 | 32.388 | 1.00 | 27.02 | C |
| ATOM | 160 | O | GLY A | 20 | 93.130 | 53.018 | 31.314 | 1.00 | 26.32 | O |
| ATOM | 161 | N | LEU A | 21 | 92.919 | 52.360 | 33.437 | 1.00 | 27.85 | N |
| ATOM | 162 | CA | LEU A | 21 | 94.070 | 51.468 | 33.333 | 1.00 | 28.67 | C |
| ATOM | 163 | C | LEU A | 21 | 93.765 | 50.236 | 32.500 | 1.00 | 29.29 | C |
| ATOM | 164 | O | LEU A | 21 | 92.834 | 49.491 | 32.795 | 1.00 | 29.57 | O |
| ATOM | 165 | CB | LEU A | 21 | 94.549 | 51.022 | 34.724 | 1.00 | 28.50 | C |
| ATOM | 166 | CG | LEU A | 21 | 95.732 | 50.038 | 34.732 | 1.00 | 28.54 | C |
| ATOM | 167 | CD1 | LEU A | 21 | 96.928 | 50.654 | 34.003 | 1.00 | 27.17 | C |
| ATOM | 168 | CD2 | LEU A | 21 | 96.101 | 49.681 | 36.175 | 1.00 | 28.26 | C |
| ATOM | 169 | N | SER A | 22 | 94.552 | 50.032 | 31.449 | 1.00 | 30.33 | N |
| ATOM | 170 | CA | SER A | 22 | 94.392 | 48.867 | 30.592 | 1.00 | 31.39 | C |
| ATOM | 171 | C | SER A | 22 | 95.419 | 47.829 | 31.039 | 1.00 | 32.61 | C |
| ATOM | 172 | O | SER A | 22 | 96.626 | 48.063 | 30.930 | 1.00 | 32.22 | O |
| ATOM | 173 | CB | SER A | 22 | 94.650 | 49.233 | 29.131 | 1.00 | 31.24 | C |
| ATOM | 174 | OG | SER A | 22 | 93.690 | 50.152 | 28.652 | 1.00 | 31.78 | O |
| ATOM | 175 | N | THR A | 23 | 94.941 | 46.693 | 31.547 | 1.00 | 33.62 | N |
| ATOM | 176 | CA | THR A | 23 | 95.821 | 45.620 | 32.007 | 1.00 | 34.86 | C |
| ATOM | 177 | C | THR A | 23 | 96.222 | 44.737 | 30.834 | 1.00 | 35.59 | C |
| ATOM | 178 | O | THR A | 23 | 95.573 | 44.757 | 29.786 | 1.00 | 35.63 | O |
| ATOM | 179 | CB | THR A | 23 | 95.132 | 44.727 | 33.059 | 1.00 | 35.00 | C |
| ATOM | 180 | OG1 | THR A | 23 | 93.945 | 44.160 | 32.493 | 1.00 | 36.07 | O |
| ATOM | 181 | CG2 | THR A | 23 | 94.766 | 45.533 | 34.295 | 1.00 | 35.01 | C |
| ATOM | 182 | N | VAL A | 24 | 97.287 | 43.958 | 31.015 | 1.00 | 36.20 | N |
| ATOM | 183 | CA | VAL A | 24 | 97.767 | 43.070 | 29.962 | 1.00 | 37.31 | C |

TABLE 5-continued

| | | | | | | | | | | |
|---|---|---|---|---|---|---|---|---|---|---|
| ATOM | 184 | C | VAL A | 24 | 96.717 | 42.041 | 29.553 | 1.00 | 38.42 | C |
| ATOM | 185 | O | VAL A | 24 | 96.757 | 41.520 | 28.439 | 1.00 | 38.33 | O |
| ATOM | 186 | CB | VAL A | 24 | 99.053 | 42.308 | 30.388 | 1.00 | 37.05 | C |
| ATOM | 187 | CG1 | VAL A | 24 | 100.194 | 43.295 | 30.612 | 1.00 | 36.36 | C |
| ATOM | 188 | CG2 | VAL A | 24 | 98.786 | 41.485 | 31.642 | 1.00 | 36.49 | C |
| ATOM | 189 | N | ASP A | 25 | 95.773 | 41.749 | 30.441 | 1.00 | 39.90 | N |
| ATOM | 190 | CA | ASP A | 25 | 94.753 | 40.772 | 30.101 | 1.00 | 41.78 | C |
| ATOM | 191 | C | ASP A | 25 | 93.581 | 41.335 | 29.298 | 1.00 | 41.86 | C |
| ATOM | 192 | O | ASP A | 25 | 92.762 | 40.570 | 28.794 | 1.00 | 42.34 | O |
| ATOM | 193 | CB | ASP A | 25 | 94.251 | 40.050 | 31.362 | 1.00 | 43.81 | C |
| ATOM | 194 | CG | ASP A | 25 | 93.534 | 40.968 | 32.323 | 1.00 | 45.75 | C |
| ATOM | 195 | OD1 | ASP A | 25 | 92.406 | 41.397 | 32.011 | 1.00 | 47.52 | O |
| ATOM | 196 | OD2 | ASP A | 25 | 94.099 | 41.261 | 33.400 | 1.00 | 48.02 | O |
| ATOM | 197 | N | CYS A | 26 | 93.485 | 42.656 | 29.151 | 1.00 | 41.52 | N |
| ATOM | 198 | CA | CYS A | 26 | 92.374 | 43.173 | 28.363 | 1.00 | 41.49 | C |
| ATOM | 199 | C | CYS A | 26 | 92.701 | 43.323 | 26.898 | 1.00 | 41.58 | C |
| ATOM | 200 | O | CYS A | 26 | 93.229 | 44.343 | 26.456 | 1.00 | 41.10 | O |
| ATOM | 201 | CB | CYS A | 26 | 91.854 | 44.522 | 28.856 | 1.00 | 40.64 | C |
| ATOM | 202 | SG | CYS A | 26 | 90.147 | 44.844 | 28.259 | 1.00 | 40.94 | S |
| ATOM | 203 | N | ILE A | 27 | 92.379 | 42.281 | 26.151 | 1.00 | 42.19 | N |
| ATOM | 204 | CA | ILE A | 27 | 92.563 | 42.280 | 24.721 | 1.00 | 42.85 | C |
| ATOM | 205 | C | ILE A | 27 | 91.140 | 42.075 | 24.226 | 1.00 | 43.07 | C |
| ATOM | 206 | O | ILE A | 27 | 90.327 | 41.450 | 24.911 | 1.00 | 42.66 | O |
| ATOM | 207 | CB | ILE A | 27 | 93.491 | 41.125 | 24.265 | 1.00 | 43.47 | C |
| ATOM | 208 | CG1 | ILE A | 27 | 93.134 | 39.831 | 25.002 | 1.00 | 43.91 | C |
| ATOM | 209 | CG2 | ILE A | 27 | 94.940 | 41.501 | 24.523 | 1.00 | 43.28 | C |
| ATOM | 210 | CD1 | ILE A | 27 | 94.064 | 38.662 | 24.686 | 1.00 | 44.36 | C |
| ATOM | 211 | N | PRO A | 28 | 90.809 | 42.628 | 23.052 | 1.00 | 43.47 | N |
| ATOM | 212 | CA | PRO A | 28 | 89.476 | 42.516 | 22.456 | 1.00 | 43.48 | C |
| ATOM | 213 | C | PRO A | 28 | 88.861 | 41.117 | 22.465 | 1.00 | 43.56 | C |
| ATOM | 214 | O | PRO A | 28 | 87.685 | 40.956 | 22.797 | 1.00 | 43.47 | O |
| ATOM | 215 | CB | PRO A | 28 | 89.696 | 43.049 | 21.044 | 1.00 | 44.02 | C |
| ATOM | 216 | CG | PRO A | 28 | 90.692 | 44.142 | 21.277 | 1.00 | 43.69 | C |
| ATOM | 217 | CD | PRO A | 28 | 91.680 | 43.481 | 22.220 | 1.00 | 43.81 | C |
| ATOM | 218 | N | SER A | 29 | 89.654 | 40.109 | 22.116 | 1.00 | 43.37 | N |
| ATOM | 219 | CA | SER A | 29 | 89.152 | 38.739 | 22.065 | 1.00 | 43.09 | C |
| ATOM | 220 | C | SER A | 29 | 88.731 | 38.182 | 23.422 | 1.00 | 42.29 | C |
| ATOM | 221 | O | SER A | 29 | 88.027 | 37.176 | 23.493 | 1.00 | 42.98 | O |
| ATOM | 222 | CB | SER A | 29 | 90.192 | 37.810 | 21.414 | 1.00 | 43.86 | C |
| ATOM | 223 | OG | SER A | 29 | 91.393 | 37.743 | 22.165 | 1.00 | 45.20 | O |
| ATOM | 224 | N | ASN A | 30 | 89.154 | 38.828 | 24.500 | 1.00 | 41.03 | N |
| ATOM | 225 | CA | ASN A | 30 | 88.780 | 38.362 | 25.829 | 1.00 | 39.63 | C |
| ATOM | 226 | C | ASN A | 30 | 87.608 | 39.158 | 26.410 | 1.00 | 37.78 | C |
| ATOM | 227 | O | ASN A | 30 | 87.194 | 38.931 | 27.545 | 1.00 | 37.59 | O |
| ATOM | 228 | CB | ASN A | 30 | 89.986 | 38.429 | 26.765 | 1.00 | 41.20 | C |
| ATOM | 229 | CG | ASN A | 30 | 90.922 | 37.244 | 26.591 | 1.00 | 42.75 | C |
| ATOM | 230 | OD1 | ASN A | 30 | 91.261 | 36.864 | 25.468 | 1.00 | 43.71 | O |
| ATOM | 231 | ND2 | ASN A | 30 | 91.345 | 36.656 | 27.704 | 1.00 | 43.38 | N |
| ATOM | 232 | N | VAL A | 31 | 87.072 | 40.088 | 25.627 | 1.00 | 35.31 | N |
| ATOM | 233 | CA | VAL A | 31 | 85.948 | 40.894 | 26.087 | 1.00 | 33.17 | C |
| ATOM | 234 | C | VAL A | 31 | 84.636 | 40.127 | 25.953 | 1.00 | 32.15. | C |
| ATOM | 235 | O | VAL A | 31 | 84.319 | 39.593 | 24.892 | 1.00 | 31.40 | O |
| ATOM | 236 | CB | VAL A | 31 | 85.847 | 42.227 | 25.302 | 1.00 | 32.76 | C |
| ATOM | 237 | CG1 | VAL A | 31 | 84.590 | 42.989 | 25.715 | 1.00 | 31.80 | C |
| ATOM | 238 | CG2 | VAL A | 31 | 87.088 | 43.074 | 25.570 | 1.00 | 32.13 | C |
| ATOM | 239 | N | ASN A | 32 | 83.887 | 40.075 | 27.047 | 1.00 | 30.94 | N |
| ATOM | 240 | CA | ASN A | 32 | 82.604 | 39.383 | 27.088 | 1.00 | 30.49 | C |
| ATOM | 241 | C | ASN A | 32 | 81.503 | 40.434 | 26.951 | 1.00 | 29.50 | C |
| ATOM | 242 | O | ASN A | 32 | 81.363 | 41.307 | 27.804 | 1.00 | 29.55 | O |
| ATOM | 243 | CB | ASN A | 32 | 82.474 | 38.633 | 28.421 | 1.00 | 30.56 | C |
| ATOM | 244 | CG | ASN A | 32 | 81.174 | 37.862 | 28.542 | 1.00 | 31.78 | C |
| ATOM | 245 | OD1 | ASN A | 32 | 80.279 | 37.978 | 27.705 | 1.00 | 31.47 | O |
| ATOM | 246 | ND2 | ASN A | 32 | 81.062 | 37.068 | 29.604 | 1.00 | 32.67 | N |
| ATOM | 247 | N | LEU A | 33 | 80.728 | 40.343 | 25.875 | 1.00 | 28.85 | N |
| ATOM | 248 | CA | LEU A | 33 | 79.647 | 41.290 | 25.591 | 1.00 | 28.13 | C |
| ATOM | 249 | C | LEU A | 33 | 78.259 | 40.780 | 25.983 | 1.00 | 27.84 | C |
| ATOM | 250 | O | LEU A | 33 | 77.240 | 41.298 | 25.524 | 1.00 | 28.25 | O |
| ATOM | 251 | CB | LEU A | 33 | 79.662 | 41.637 | 24.101 | 1.00 | 27.87 | C |
| ATOM | 252 | CG | LEU A | 33 | 80.228 | 42.982 | 23.621 | 1.00 | 28.18 | C |
| ATOM | 253 | CD1 | LEU A | 33 | 81.299 | 43.515 | 24.546 | 1.00 | 27.71 | C |
| ATOM | 254 | CD2 | LEU A | 33 | 80.757 | 42.799 | 22.215 | 1.00 | 27.10 | C |
| ATOM | 255 | N | SER A | 34 | 78.223 | 39.762 | 26.828 | 1.00 | 27.39 | N |
| ATOM | 256 | CA | SER A | 34 | 76.963 | 39.183 | 27.291 | 1.00 | 27.16 | C |
| ATOM | 257 | C | SER A | 34 | 76.204 | 40.218 | 28.129 | 1.00 | 26.24 | C |
| ATOM | 258 | O | SER A | 34 | 76.814 | 41.063 | 28.774 | 1.00 | 25.91 | O |
| ATOM | 259 | CB | SER A | 34 | 77.263 | 37.930 | 28.124 | 1.00 | 27.60 | C |
| ATOM | 260 | OG | SER A | 34 | 76.102 | 37.434 | 28.756 | 1.00 | 30.45 | O |
| ATOM | 261 | N | THR A | 35 | 74.877 | 40.157 | 28.124 | 1.00 | 25.86 | N |
| ATOM | 262 | CA | THR A | 35 | 74.095 | 41.125 | 28.885 | 1.00 | 24.92 | C |

TABLE 5-continued

| | | | | | | | | | | |
|---|---|---|---|---|---|---|---|---|---|---|
| ATOM | 263 | C | THR A | 35 | 72.687 | 40.592 | 29.158 | 1.00 | 24.89 | C |
| ATOM | 264 | O | THR A | 35 | 72.115 | 39.865 | 28.344 | 1.00 | 25.03 | O |
| ATOM | 265 | CB | THR A | 35 | 74.021 | 42.485 | 28.121 | 1.00 | 25.02 | C |
| ATOM | 266 | OG1 | THR A | 35 | 73.744 | 43.549 | 29.040 | 1.00 | 25.25 | O |
| ATOM | 267 | CG2 | THR A | 35 | 72.931 | 42.456 | 27.070 | 1.00 | 24.69 | C |
| ATOM | 268 | N | PRO A | 36 | 72.109 | 40.948 | 30.314 | 1.00 | 24.52 | N |
| ATOM | 269 | CA | PRO A | 36 | 70.761 | 40.485 | 30.665 | 1.00 | 24.57 | C |
| ATOM | 270 | C | PRO A | 36 | 69.651 | 41.167 | 29.867 | 1.00 | 25.00 | C |
| ATOM | 271 | O | PRO A | 36 | 69.697 | 42.375 | 29.631 | 1.00 | 25.19 | O |
| ATOM | 272 | CB | PRO A | 36 | 70.672 | 40.797 | 32.155 | 1.00 | 24.46 | C |
| ATOM | 273 | CG | PRO A | 36 | 71.479 | 42.072 | 32.264 | 1.00 | 24.23 | C |
| ATOM | 274 | CD | PRO A | 36 | 72.684 | 41.786 | 31.383 | 1.00 | 24.01 | C |
| ATOM | 275 | N | LEU A | 37 | 68.651 | 40.393 | 29.456 | 1.00 | 24.96 | N |
| ATOM | 276 | CA | LEU A | 37 | 67.535 | 40.946 | 28.705 | 1.00 | 25.21 | C |
| ATOM | 277 | C | LEU A | 37 | 66.308 | 41.179 | 29.593 | 1.00 | 25.43 | C |
| ATOM | 278 | O | LEU A | 37 | 65.599 | 42.175 | 29.426 | 1.00 | 25.20 | O |
| ATOM | 279 | CB | LEU A | 37 | 67.156 | 40.017 | 27.546 | 1.00 | 24.90 | C |
| ATOM | 280 | CG | LEU A | 37 | 66.049 | 40.506 | 26.599 | 1.00 | 25.00 | C |
| ATOM | 281 | CD1 | LEU A | 37 | 66.593 | 41.629 | 25.709 | 1.00 | 24.59 | C |
| ATOM | 282 | CD2 | LEU A | 37 | 65.550 | 39.351 | 25.729 | 1.00 | 24.58 | C |
| ATOM | 283 | N | VAL A | 38 | 66.061 | 40.274 | 30.539 | 1.00 | 25.54 | N |
| ATOM | 284 | CA | VAL A | 38 | 64.896 | 40.397 | 31.415 | 1.00 | 25.63 | C |
| ATOM | 285 | C | VAL A | 38 | 65.241 | 40.442 | 32.904 | 1.00 | 26.35 | C |
| ATOM | 286 | O | VAL A | 38 | 66.268 | 39.919 | 33.335 | 1.00 | 26.41 | O |
| ATOM | 287 | CB | VAL A | 38 | 63.885 | 39.262 | 31.136 | 1.00 | 25.83 | C |
| ATOM | 288 | CG1 | VAL A | 38 | 63.410 | 39.357 | 29.679 | 1.00 | 25.31 | C |
| ATOM | 289 | CG2 | VAL A | 38 | 64.523 | 37.895 | 31.398 | 1.00 | 24.98 | C |
| ATOM | 290 | N | LYS A | 39 | 64.368 | 41.074 | 33.682 | 1.00 | 26.62 | N |
| ATOM | 291 | CA | LYS A | 39 | 64.588 | 41.251 | 35.113 | 1.00 | 27.40 | C |
| ATOM | 292 | C | LYS A | 39 | 64.768 | 39.986 | 35.943 | 1.00 | 27.98 | C |
| ATOM | 293 | O | LYS A | 39 | 64.220 | 38.926 | 35.625 | 1.00 | 28.34 | O |
| ATOM | 294 | CB | LYS A | 39 | 63.453 | 42.085 | 35.722 | 1.00 | 27.32 | C |
| ATOM | 295 | CG | LYS A | 39 | 62.098 | 41.400 | 35.710 | 1.00 | 27.27 | C |
| ATOM | 296 | CD | LYS A | 39 | 61.075 | 42.203 | 36.491 | 1.00 | 27.48 | C |
| ATOM | 297 | CE | LYS A | 39 | 59.703 | 41.538 | 36.465 | 1.00 | 27.05 | C |
| ATOM | 298 | NZ | LYS A | 39 | 58.735 | 42.262 | 37.335 | 1.00 | 26.75 | N |
| ATOM | 299 | N | PHE A | 40 | 65.539 | 40.133 | 37.017 | 1.00 | 28.20 | N |
| ATOM | 300 | CA | PHE A | 40 | 65.828 | 39.057 | 37.958 | 1.00 | 29.34 | C |
| ATOM | 301 | C | PHE A | 40 | 66.082 | 39.682 | 39.337 | 1.00 | 30.13 | C |
| ATOM | 302 | O | PHE A | 40 | 66.226 | 40.899 | 39.447 | 1.00 | 30.16 | O |
| ATOM | 303 | CB | PHE A | 40 | 67.058 | 38.258 | 37.501 | 1.00 | 28.35 | C |
| ATOM | 304 | CG | PHE A | 40 | 68.264 | 39.110 | 37.197 | 1.00 | 27.78 | C |
| ATOM | 305 | CD1 | PHE A | 40 | 68.448 | 39.650 | 35.924 | 1.00 | 26.96 | C |
| ATOM | 306 | CD2 | PHE A | 40 | 69.209 | 39.379 | 38.183 | 1.00 | 27.28 | C |
| ATOM | 307 | CE1 | PHE A | 40 | 69.553 | 40.442 | 35.635 | 1.00 | 26.45 | C |
| ATOM | 308 | CE2 | PHE A | 40 | 70.325 | 40.174 | 37.907 | 1.00 | 27.06 | C |
| ATOM | 309 | CZ | PHE A | 40 | 70.497 | 40.706 | 36.628 | 1.00 | 27.14 | C |
| ATOM | 310 | N | GLN A | 41 | 66.130 | 38.851 | 40.379 | 1.00 | 31.29 | N |
| ATOM | 311 | CA | GLN A | 41 | 66.358 | 39.317 | 41.754 | 1.00 | 32.59 | C |
| ATOM | 312 | C | GLN A | 41 | 67.851 | 39.354 | 42.054 | 1.00 | 32.23 | C |
| ATOM | 313 | O | GLN A | 41 | 68.637 | 38.714 | 41.362 | 1.00 | 31.49 | O |
| ATOM | 314 | CB | GLN A | 41 | 65.698 | 38.365 | 42.759 | 1.00 | 34.28 | C |
| ATOM | 315 | CG | GLN A | 41 | 64.249 | 38.045 | 42.486 | 1.00 | 37.74 | C |
| ATOM | 316 | CD | GLN A | 41 | 63.310 | 39.092 | 43.041 | 1.00 | 40.33 | C |
| ATOM | 317 | OE1 | GLN A | 41 | 63.397 | 40.277 | 42.694 | 1.00 | 41.23 | O |
| ATOM | 318 | NE2 | GLN A | 41 | 62.397 | 38.662 | 43.916 | 1.00 | 41.92 | N |
| ATOM | 319 | N | LYS A | 42 | 68.245 | 40.084 | 43.095 | 1.00 | 32.61 | N |
| ATOM | 320 | CA | LYS A | 42 | 69.659 | 40.152 | 43.442 | 1.00 | 33.23 | C |
| ATOM | 321 | C | LYS A | 42 | 70.235 | 38.768 | 43.716 | 1.00 | 33.05 | C |
| ATOM | 322 | O | LYS A | 42 | 69.609 | 37.943 | 44.384 | 1.00 | 32.65 | O |
| ATOM | 323 | CB | LYS A | 42 | 69.898 | 41.024 | 44.672 | 1.00 | 34.37 | |
| ATOM | 324 | CG | LYS A | 42 | 71.380 | 41.106 | 45.002 | 1.00 | 36.49 | C |
| ATOM | 325 | CD | LYS A | 42 | 71.712 | 42.108 | 46.093 | 1.00 | 38.56 | C |
| ATOM | 326 | CE | LYS A | 42 | 71.361 | 41.595 | 47.463 | 1.00 | 38.86 | C |
| ATOM | 327 | NZ | LYS A | 42 | 71.973 | 42.474 | 48.502 | 1.00 | 40.12 | N |
| ATOM | 328 | N | GLY A | 43 | 71.432 | 38.518 | 43.198 | 1.00 | 32.94 | N |
| ATOM | 329 | CA | GLY A | 43 | 72.064 | 37.231 | 43.414 | 1.00 | 32.98 | C |
| ATOM | 330 | C | GLY A | 43 | 71.847 | 36.234 | 42.297 | 1.00 | 32.97 | C |
| ATOM | 331 | O | GLY A | 43 | 72.611 | 35.279 | 42.170 | 1.00 | 32.75 | O |
| ATOM | 332 | N | GLN A | 44 | 70.815 | 36.430 | 41.483 | 1.00 | 33.23 | N |
| ATOM | 333 | CA | GLN A | 44 | 70.580 | 35.498 | 40.388 | 1.00 | 33.79 | C |
| ATOM | 334 | C | GLN A | 44 | 70.996 | 36.029 | 39.023 | 1.00 | 33.69 | C |
| ATOM | 335 | O | GLN A | 44 | 71.505 | 37.139 | 38.906 | 1.00 | 33.63 | O |
| ATOM | 336 | CB | GLN A | 44 | 69.113 | 35.039 | 40.362 | 1.00 | 34.55 | C |
| ATOM | 337 | CG | GLN A | 44 | 68.093 | 36.090 | 40.695 | 1.00 | 35.61 | C |
| ATOM | 338 | CD | GLN A | 44 | 66.677 | 35.538 | 40.781 | 1.00 | 35.93 | C |
| ATOM | 339 | OE1 | GLN A | 44 | 66.382 | 34.665 | 41.599 | 1.00 | 37.13 | O |
| ATOM | 340 | NE2 | GLN A | 44 | 65.793 | 36.051 | 39.938 | 1.00 | 35.37 | N |
| ATOM | 341 | N | GLN A | 45 | 70.803 | 35.204 | 37.999 | 1.00 | 33.77 | N |

TABLE 5-continued

| | | | | | | | | | | |
|---|---|---|---|---|---|---|---|---|---|---|
| ATOM | 342 | CA | GLN A | 45 | 71.135 | 35.560 | 36.623 | 1.00 | 33.60 | C |
| ATOM | 343 | C | GLN A | 45 | 69.832 | 35.752 | 35.874 | 1.00 | 32.34 | C |
| ATOM | 344 | O | GLN A | 45 | 68.794 | 35.245 | 36.287 | 1.00 | 31.56 | O |
| ATOM | 345 | CB | GLN A | 45 | 71.921 | 34.432 | 35.938 | 1.00 | 35.04 | C |
| ATOM | 346 | CG | GLN A | 45 | 73.297 | 34.165 | 36.516 | 1.00 | 37.78 | C |
| ATOM | 347 | CD | GLN A | 45 | 74.285 | 35.267 | 36.191 | 1.00 | 39.44 | C |
| ATOM | 348 | OE1 | GLN A | 45 | 74.613 | 35.497 | 35.022 | 1.00 | 40.59 | O |
| ATOM | 349 | NE2 | GLN A | 45 | 74.767 | 35.959 | 37.225 | 1.00 | 39.68 | N |
| ATOM | 350 | N | SER A | 46 | 69.889 | 36.483 | 34.771 | 1.00 | 31.43 | N |
| ATOM | 351 | CA | SER A | 46 | 68.701 | 36.703 | 33.969 | 1.00 | 31.01 | C |
| ATOM | 352 | C | SER A | 46 | 68.396 | 35.419 | 33.211 | 1.00 | 30.99 | C |
| ATOM | 353 | O | SER A | 46 | 69.312 | 34.730 | 32.766 | 1.00 | 31.11 | O |
| ATOM | 354 | CB | SER A | 46 | 68.931 | 37.833 | 32.964 | 1.00 | 30.11 | C |
| ATOM | 355 | OG | SER A | 46 | 67.752 | 38.074 | 32.219 | 1.00 | 28.77 | O |
| ATOM | 356 | N | GLU A | 47 | 67.113 | 35.100 | 33.068 | 1.00 | 31.10 | N |
| ATOM | 357 | CA | GLU A | 47 | 66.708 | 33.905 | 32.337 | 1.00 | 31.53 | C |
| ATOM | 358 | C | GLU A | 47 | 67.119 | 34.002 | 30.877 | 1.00 | 31.11 | C |
| ATOM | 359 | O | GLU A | 47 | 67.311 | 32.985 | 30.215 | 1.00 | 31.30 | O |
| ATOM | 360 | CB | GLU A | 47 | 65.198 | 33.710 | 32.427 | 1.00 | 32.16 | C |
| ATOM | 361 | CG | GLU A | 47 | 64.717 | 33.337 | 33.814 | 1.00 | 34.70 | C |
| ATOM | 362 | CD | GLU A | 47 | 63.211 | 33.402 | 33.933 | 1.00 | 36.22 | C |
| ATOM | 363 | OE1 | GLU A | 47 | 62.524 | 32.650 | 33.208 | 1.00 | 37.59 | O |
| ATOM | 364 | OE2 | GLU A | 47 | 62.715 | 34.211 | 34.747 | 1.00 | 37.82 | O |
| ATOM | 365 | N | ILE A | 48 | 67.233 | 35.226 | 30.367 | 1.00 | 30.49 | N |
| ATOM | 366 | CA | ILE A | 48 | 67.643 | 35.431 | 28.981 | 1.00 | 29.71 | C |
| ATOM | 367 | C | ILE A | 48 | 68.791 | 36.432 | 28.911 | 1.00 | 29.44 | C |
| ATOM | 368 | O | ILE A | 48 | 68.670 | 37.575 | 29.356 | 1.00 | 29.08 | O |
| ATOM | 369 | CB | ILE A | 48 | 66.488 | 35.962 | 28.099 | 1.00 | 30.08 | C |
| ATOM | 370 | CG1 | ILE A | 48 | 65.281 | 35.021 | 28.171 | 1.00 | 30.16 | C |
| ATOM | 371 | CG2 | ILE A | 48 | 66.967 | 36.091 | 26.653 | 1.00 | 29.55 | C |
| ATOM | 372 | CD1 | ILE A | 48 | 64.082 | 35.489 | 27.348 | 1.00 | 29.84 | C |
| ATOM | 373 | N | ASN A | 49 | 69.905 | 35.988 | 28.347 | 1.00 | 28.86 | N |
| ATOM | 374 | CA | ASN A | 49 | 71.085 | 36.820 | 28.198 | 1.00 | 29.07 | C |
| ATOM | 375 | C | ASN A | 49 | 71.483 | 36.882 | 26.730 | 1.00 | 28.95 | C |
| ATOM | 376 | O | ASN A | 49 | 71.609 | 35.852 | 26.067 | 1.00 | 29.13 | O |
| ATOM | 377 | CB | ASN A | 49 | 72.245 | 36.245 | 29.021 | 1.00 | 28.75 | C |
| ATOM | 378 | CG | ASN A | 49 | 72.023 | 36.385 | 30.515 | 1.00 | 28.90 | C |
| ATOM | 379 | OD1 | ASN A | 49 | 72.210 | 37.459 | 31.084 | 1.00 | 28.55 | O |
| ATOM | 380 | ND2 | ASN A | 49 | 71.609 | 35.302 | 31.155 | 1.00 | 29.52 | N |
| ATOM | 381 | N | LEU A | 50 | 71.658 | 38.094 | 26.220 | 1.00 | 28.25 | N |
| ATOM | 382 | CA | LEU A | 50 | 72.071 | 38.273 | 24.834 | 1.00 | 27.70 | C |
| ATOM | 383 | C | LEU A | 50 | 73.568 | 37.994 | 24.791 | 1.00 | 27.62 | C |
| ATOM | 384 | O | LEU A | 50 | 74.252 | 38.178 | 25.793 | 1.00 | 27.10 | O |
| ATOM | 385 | CB | LEU A | 50 | 71.814 | 39.718 | 24.389 | 1.00 | 26.87 | C |
| ATOM | 386 | CG | LEU A | 50 | 70.381 | 40.241 | 24.527 | 1.00 | 27.52 | C |
| ATOM | 387 | CD1 | LEU A | 50 | 70.339 | 41.740 | 24.227 | 1.00 | 27.19 | C |
| ATOM | 388 | CD2 | LEU A | 50 | 69.467 | 39.465 | 23.588 | 1.00 | 27.05 | C |
| ATOM | 389 | N | LYS A | 51 | 74.073 | 37.541 | 23.646 | 1.00 | 28.04 | N |
| ATOM | 390 | CA | LYS A | 51 | 75.507 | 37.286 | 23.493 | 1.00 | 28.80 | C |
| ATOM | 391 | C | LYS A | 51 | 76.182 | 38.622 | 23.166 | 1.00 | 27.80 | C |
| ATOM | 392 | O | LYS A | 51 | 77.351 | 38.834 | 23.481 | 1.00 | 28.10 | O |
| ATOM | 393 | CB | LYS A | 51 | 75.772 | 36.277 | 22.364 | 1.00 | 30.63 | C |
| ATOM | 394 | CG | LYS A | 51 | 76.038 | 34.848 | 22.827 | 1.00 | 32.96 | C |
| ATOM | 395 | CD | LYS A | 51 | 74.829 | 34.217 | 23.460 | 1.00 | 34.61 | C |
| ATOM | 396 | CE | LYS A | 51 | 75.131 | 32.788 | 23.913 | 1.00 | 35.94 | C |
| ATOM | 397 | NZ | LYS A | 51 | 75.513 | 31.887 | 22.788 | 1.00 | 36.84 | N |
| ATOM | 398 | N | ILE A | 52 | 75.431 | 39.508 | 22.518 | 1.00 | 26.90 | N |
| ATOM | 399 | CA | ILE A | 52 | 75.899 | 40.848 | 22.177 | 1.00 | 26.16 | C |
| ATOM | 400 | C | ILE A | 52 | 74.759 | 41.798 | 22.556 | 1.00 | 26.14 | C |
| ATOM | 401 | O | ILE A | 52 | 73.583 | 41.452 | 22.430 | 1.00 | 26.42 | O |
| ATOM | 402 | CB | ILE A | 52 | 76.247 | 40.989 | 20.671 | 1.00 | 25.90 | C |
| ATOM | 403 | CG1 | ILE A | 52 | 75.041 | 40.634 | 19.803 | 1.00 | 25.37 | C |
| ATOM | 404 | CG2 | ILE A | 52 | 77.443 | 40.086 | 20.329 | 1.00 | 25.95 | C |
| ATOM | 405 | CD1 | ILE A | 52 | 75.244 | 40.975 | 18.331 | 1.00 | 24.51 | C |
| ATOM | 406 | N | PRO A | 53 | 75.093 | 43.011 | 23.016 | 1.00 | 25.79 | N |
| ATOM | 407 | CA | PRO A | 53 | 74.090 | 43.999 | 23.431 | 1.00 | 25.66 | C |
| ATOM | 408 | C | PRO A | 53 | 73.334 | 44.765 | 22.345 | 1.00 | 25.90 | C |
| ATOM | 409 | O | PRO A | 53 | 73.041 | 45.947 | 22.521 | 1.00 | 26.17 | O |
| ATOM | 410 | CB | PRO A | 53 | 74.900 | 44.929 | 24.319 | 1.00 | 24.87 | C |
| ATOM | 411 | CG | PRO A | 53 | 76.207 | 44.999 | 23.568 | 1.00 | 25.16 | C |
| ATOM | 412 | CD | PRO A | 53 | 76.459 | 43.553 | 23.167 | 1.00 | 25.11 | C |
| ATOM | 413 | N | LEU A | 54 | 73.002 | 44.101 | 21.241 | 1.00 | 25.97 | N |
| ATOM | 414 | CA | LEU A | 54 | 72.285 | 44.767 | 20.157 | 1.00 | 25.81 | C |
| ATOM | 415 | C | LEU A | 54 | 70.975 | 44.072 | 19.799 | 1.00 | 26.02 | C |
| ATOM | 416 | O | LEU A | 54 | 70.931 | 42.847 | 19.653 | 1.00 | 26.13 | O |
| ATOM | 417 | CB | LEU A | 54 | 73.160 | 44.839 | 18.897 | 1.00 | 25.47 | C |
| ATOM | 418 | CG | LEU A | 54 | 74.556 | 45.459 | 19.009 | 1.00 | 26.34 | C |
| ATOM | 419 | CD1 | LEU A | 54 | 75.216 | 45.494 | 17.627 | 1.00 | 26.06 | C |
| ATOM | 420 | CD2 | LEU A | 54 | 74.458 | 46.863 | 19.591 | 1.00 | 26.01 | C |

TABLE 5-continued

| ATOM | 421 | N | VAL A | 55 | 69.911 | 44.858 | 19.668 | 1.00 | 25.53 | N |
|---|---|---|---|---|---|---|---|---|---|---|
| ATOM | 422 | CA | VAL A | 55 | 68.614 | 44.325 | 19.277 | 1.00 | 25.73 | C |
| ATOM | 423 | C | VAL A | 55 | 68.078 | 45.236 | 18.172 | 1.00 | 26.28 | C |
| ATOM | 424 | O | VAL A | 55 | 68.287 | 46.455 | 18.207 | 1.00 | 26.42 | O |
| ATOM | 425 | CB | VAL A | 55 | 67.612 | 44.265 | 20.477 | 1.00 | 25.52 | C |
| ATOM | 426 | CG1 | VAL A | 55 | 68.262 | 43.550 | 21.654 | 1.00 | 24.72 | C |
| ATOM | 427 | CG2 | VAL A | 55 | 67.139 | 45.656 | 20.868 | 1.00 | 24.62 | C |
| ATOM | 428 | N | SER A | 56 | 67.418 | 44.652 | 17.174 | 1.00 | 26.19 | N |
| ATOM | 429 | CA | SER A | 56 | 66.884 | 45.447 | 16.073 | 1.00 | 25.97 | C |
| ATOM | 430 | C | SER A | 56 | 65.508 | 46.017 | 16.417 | 1.00 | 25.83 | C |
| ATOM | 431 | O | SER A | 56 | 64.700 | 45.373 | 17.089 | 1.00 | 25.99 | O |
| ATOM | 432 | CB | SER A | 56 | 66.831 | 44.610 | 14.788 | 1.00 | 25.77 | C |
| ATOM | 433 | OG | SER A | 56 | 66.050 | 43.446 | 14.965 | 1.00 | 26.05 | O |
| ATOM | 434 | N | ALA A | 57 | 65.264 | 47.238 | 15.957 | 1.00 | 25.89 | N |
| ATOM | 435 | CA | ALA A | 57 | 64.024 | 47.966 | 16.218 | 1.00 | 26.47 | C |
| ATOM | 436 | C | ALA A | 57 | 62.721 | 47.300 | 15.756 | 1.00 | 27.16 | C |
| ATOM | 437 | O | ALA A | 57 | 62.692 | 46.554 | 14.779 | 1.00 | 27.22 | O |
| ATOM | 438 | CB | ALA A | 57 | 64.133 | 49.358 | 15.619 | 1.00 | 25.66 | C |
| ATOM | 439 | N | ILE A | 58 | 61.643 | 47.594 | 16.478 | 1.00 | 27.68 | N |
| ATOM | 440 | CA | ILE A | 58 | 60.316 | 47.056 | 16.184 | 1.00 | 28.41 | C |
| ATOM | 441 | C | ILE A | 58 | 59.737 | 47.863 | 15.021 | 1.00 | 28.86 | C |
| ATOM | 442 | O | ILE A | 58 | 58.795 | 48.644 | 15.194 | 1.00 | 29.04 | O |
| ATOM | 443 | CB | ILE A | 58 | 59.388 | 47.204 | 17.414 | 1.00 | 27.86 | C |
| ATOM | 444 | CG1 | ILE A | 58 | 60.156 | 46.808 | 18.683 | 1.00 | 27.40 | C |
| ATOM | 445 | CG2 | ILE A | 58 | 58.145 | 46.335 | 17.239 | 1.00 | 27.81 | C |
| ATOM | 446 | CD1 | ILE A | 58 | 59.338 | 46.846 | 19.959 | 1.00 | 26.01 | C |
| ATOM | 447 | N | MET A | 59 | 60.304 | 47.659 | 13.836 | 1.00 | 29.07 | N |
| ATOM | 448 | CA | MET A | 59 | 59.896 | 48.407 | 12.652 | 1.00 | 29.93 | C |
| ATOM | 449 | C | MET A | 59 | 59.747 | 47.546 | 11.400 | 1.00 | 30.41 | C |
| ATOM | 450 | O | MET A | 59 | 60.510 | 46.605 | 11.185 | 1.00 | 29.96 | O |
| ATOM | 451 | CB | MET A | 59 | 60.922 | 49.507 | 12.379 | 1.00 | 29.62 | C |
| ATOM | 452 | CG | MET A | 59 | 61.172 | 50.439 | 13.556 | 1.00 | 29.09 | C |
| ATOM | 453 | SD | MET A | 59 | 62.564 | 51.543 | 13.248 | 1.00 | 29.35 | S |
| ATOM | 454 | CE | MET A | 59 | 61.850 | 52.630 | 12.008 | 1.00 | 28.25 | C |
| ATOM | 455 | N | GLN A | 60 | 58.766 | 47.901 | 10.575 | 1.00 | 31.54 | N |
| ATOM | 456 | CA | GLN A | 60 | 58.476 | 47.186 | 9.331 | 1.00 | 32.53 | C |
| ATOM | 457 | C | GLN A | 60 | 59.685 | 47.152 | 8.411 | 1.00 | 32.76 | C |
| ATOM | 458 | O | GLN A | 60 | 59.904 | 46.173 | 7.707 | 1.00 | 32.70 | O |
| ATOM | 459 | CB | GLN A | 60 | 57.334 | 47.862 | 8.565 | 1.00 | 32.88 | C |
| ATOM | 460 | CG | GLN A | 60 | 56.084 | 48.176 | 9.362 | 1.00 | 34.01 | C |
| ATOM | 461 | CD | GLN A | 60 | 55.010 | 48.821 | 8.497 | 1.00 | 34.77 | C |
| ATOM | 462 | OE1 | GLN A | 60 | 55.313 | 49.611 | 7.603 | 1.00 | 35.73 | O |
| ATOM | 463 | NE2 | GLN A | 60 | 53.749 | 48.497 | 8.767 | 1.00 | 35.22 | N |
| ATOM | 464 | N | SER A | 61 | 60.463 | 48.232 | 8.418 | 1.00 | 33.31 | N |
| ATOM | 465 | CA | SER A | 61 | 61.629 | 48.334 | 7.552 | 1.00 | 33.30 | C |
| ATOM | 466 | C | SER A | 61 | 62.931 | 47.752 | 8.099 | 1.00 | 33.20 | C |
| ATOM | 467 | O | SER A | 61 | 63.988 | 47.933 | 7.492 | 1.00 | 33.61 | O |
| ATOM | 468 | CB | SER A | 61 | 61.853 | 49.799 | 7.143 | 1.00 | 33.43 | C |
| ATOM | 469 | OG | SER A | 61 | 62.047 | 50.635 | 8.271 | 1.00 | 35.07 | O |
| ATOM | 470 | N | VAL A | 62 | 62.875 | 47.052 | 9.227 | 1.00 | 32.70 | N |
| ATOM | 471 | CA | VAL A | 62 | 64.101 | 46.475 | 9.764 | 1.00 | 32.55 | C |
| ATOM | 472 | C | VAL A | 62 | 63.999 | 45.079 | 10.358 | 1.00 | 32.60 | C |
| ATOM | 473 | O | VAL A | 62 | 64.800 | 44.213 | 10.026 | 1.00 | 33.59 | O |
| ATOM | 474 | CB | VAL A | 62 | 64.789 | 47.432 | 10.810 | 1.00 | 32.46 | C |
| ATOM | 475 | CG1 | VAL A | 62 | 63.860 | 48.545 | 11.206 | 1.00 | 32.31 | C |
| ATOM | 476 | CG2 | VAL A | 62 | 65.245 | 46.655 | 12.041 | 1.00 | 31.54 | C |
| ATOM | 477 | N | SER A | 63 | 63.017 | 44.838 | 11.215 | 1.00 | 33.04 | N |
| ATOM | 478 | CA | SER A | 63 | 62.924 | 43.531 | 11.845 | 1.00 | 32.74 | C |
| ATOM | 479 | C | SER A | 63 | 61.986 | 42.510 | 11.214 | 1.00 | 33.02 | C |
| ATOM | 480 | O | SER A | 63 | 60.871 | 42.283 | 11.692 | 1.00 | 32.02 | O |
| ATOM | 481 | CB | SER A | 63 | 62.600 | 43.700 | 13.331 | 1.00 | 32.70 | C |
| ATOM | 482 | OG | SER A | 63 | 63.666 | 44.356 | 14.005 | 1.00 | 31.78 | O |
| ATOM | 483 | N | GLY A | 64 | 62.467 | 41.894 | 10.138 | 1.00 | 33.46 | N |
| ATOM | 484 | CA | GLY A | 64 | 61.717 | 40.857 | 9.454 | 1.00 | 33.96 | C |
| ATOM | 485 | C | GLY A | 64 | 62.338 | 39.518 | 9.829 | 1.00 | 34.68 | C |
| ATOM | 486 | O | GLY A | 64 | 63.160 | 39.455 | 10.749 | 1.00 | 33.86 | O |
| ATOM | 487 | N | GLU A | 65 | 61.961 | 38.453 | 9.123 | 1.00 | 35.46 | N |
| ATOM | 488 | CA | GLU A | 65 | 62.482 | 37.113 | 9.394 | 1.00 | 36.69 | C |
| ATOM | 489 | C | GLU A | 65 | 63.987 | 36.993 | 9.207 | 1.00 | 36.64 | C |
| ATOM | 490 | O | GLU A | 65 | 64.694 | 36.532 | 10.101 | 1.00 | 36.51 | O |
| ATOM | 491 | CB | GLU A | 65 | 61.809 | 36.077 | 8.489 | 1.00 | 38.32 | C |
| ATOM | 492 | CG | GLU A | 65 | 60.441 | 35.608 | 8.946 | 1.00 | 41.08 | C |
| ATOM | 493 | CD | GLU A | 65 | 59.808 | 34.623 | 7.964 | 1.00 | 42.59 | C |
| ATOM | 494 | OE1 | GLU A | 65 | 60.483 | 33.631 | 7.595 | 1.00 | 43.43 | O |
| ATOM | 495 | OE2 | GLU A | 65 | 58.639 | 34.844 | 7.568 | 1.00 | 42.90 | O |
| ATOM | 496 | N | LYS A | 66 | 64.470 | 37.386 | 8.033 | 1.00 | 36.50 | N |
| ATOM | 497 | CA | LYS A | 66 | 65.891 | 37.293 | 7.734 | 1.00 | 36.67 | C |
| ATOM | 498 | C | LYS A | 66 | 66.729 | 38.082 | 8.734 | 1.00 | 35.70 | C |
| ATOM | 499 | O | LYS A | 66 | 67.803 | 37.639 | 9.137 | 1.00 | 35.10 | O |

TABLE 5-continued

| ATOM | 500 | CB | LYS A | 66 | 66.164 | 37.775 | 6.304 | 1.00 | 37.83 | C |
|---|---|---|---|---|---|---|---|---|---|---|
| ATOM | 501 | CG | LYS A | 66 | 65.512 | 36.899 | 5.242 | 1.00 | 40.02 | C |
| ATOM | 502 | CD | LYS A | 66 | 65.935 | 37.299 | 3.828 | 1.00 | 42.33 | C |
| ATOM | 503 | CE | LYS A | 66 | 65.202 | 36.465 | 2.776 | 1.00 | 43.21 | C |
| ATOM | 504 | NZ | LYS A | 66 | 65.582 | 36.849 | 1.381 | 1.00 | 44.57 | N |
| ATOM | 505 | N | MET A | 67 | 66.231 | 39.247 | 9.134 | 1.00 | 34.61 | N |
| ATOM | 506 | CA | MET A | 67 | 66.938 | 40.068 | 10.105 | 1.00 | 33.55 | C |
| ATOM | 507 | C | MET A | 67 | 67.023 | 39.306 | 11.427 | 1.00 | 32.84 | C |
| ATOM | 508 | O | MET A | 67 | 68.104 | 39.148 | 11.995 | 1.00 | 32.24 | O |
| ATOM | 509 | CB | MET A | 67 | 66.204 | 41.394 | 10.322 | 1.00 | 33.32 | C |
| ATOM | 510 | CG | MET A | 67 | 66.868 | 42.316 | 11.338 | 1.00 | 32.81 | C |
| ATOM | 511 | SD | MET A | 67 | 68.526 | 42.816 | 10.844 | 1.00 | 32.40 | S |
| ATOM | 512 | CE | MET A | 67 | 68.141 | 43.942 | 9.476 | 1.00 | 31.53 | C |
| ATOM | 513 | N | ALA A | 68 | 65.877 | 38.825 | 11.899 | 1.00 | 31.91 | N |
| ATOM | 514 | CA | ALA A | 68 | 65.811 | 38.093 | 13.156 | 1.00 | 31.69 | C |
| ATOM | 515 | C | ALA A | 68 | 66.789 | 36.928 | 13.183 | 1.00 | 31.70 | C |
| ATOM | 516 | O | ALA A | 68 | 67.459 | 36.686 | 14.190 | 1.00 | 31.79 | O |
| ATOM | 517 | CB | ALA A | 68 | 64.389 | 37.592 | 13.394 | 1.00 | 31.52 | C |
| ATOM | 518 | N | ILE A | 69 | 66.866 | 36.203 | 12.073 | 1.00 | 31.40 | N |
| ATOM | 519 | CA | ILE A | 69 | 67.766 | 35.061 | 11.969 | 1.00 | 31.19 | C |
| ATOM | 520 | C | ILE A | 69 | 69.226 | 35.511 | 11.942 | 1.00 | 30.56 | C |
| ATOM | 521 | O | ILE A | 69 | 70.059 | 34.992 | 12.686 | 1.00 | 30.98 | O |
| ATOM | 522 | CB | ILE A | 69 | 67.452 | 34.234 | 10.691 | 1.00 | 31.73 | C |
| ATOM | 523 | CG1 | ILE A | 69 | 66.083 | 33.563 | 10.836 | 1.00 | 32.13 | C |
| ATOM | 524 | CG2 | ILE A | 69 | 68.529 | 33.184 | 10.459 | 1.00 | 32.02 | C |
| ATOM | 525 | CD1 | ILE A | 69 | 65.529 | 33.009 | 9.536 | 1.00 | 32.48 | C |
| ATOM | 526 | N | ALA A | 70 | 69.526 | 36.484 | 11.088 | 1.00 | 29.80 | N |
| ATOM | 527 | CA | ALA A | 70 | 70.882 | 36.998 | 10.953 | 1.00 | 29.27 | C |
| ATOM | 528 | C | ALA A | 70 | 71.425 | 37.592 | 12.249 | 1.00 | 28.89 | C |
| ATOM | 529 | O | ALA A | 70 | 72.589 | 37.391 | 12.583 | 1.00 | 28.35 | O |
| ATOM | 530 | CB | ALA A | 70 | 70.932 | 38.041 | 9.847 | 1.00 | 29.17 | C |
| ATOM | 531 | N | LEU A | 71 | 70.585 | 38.324 | 12.979 | 1.00 | 28.72 | N |
| ATOM | 532 | CA | LEU A | 71 | 71.027 | 38.937 | 14.224 | 1.00 | 28.35 | C |
| ATOM | 533 | C | LEU A | 71 | 71.187 | 37.890 | 15.316 | 1.00 | 28.41 | C |
| ATOM | 534 | O | LEU A | 71 | 72.158 | 37.913 | 16.064 | 1.00 | 27.56 | O |
| ATOM | 535 | CE | LEU A | 71 | 70.044 | 40.021 | 14.669 | 1.00 | 27.97 | C |
| ATOM | 536 | CG | LEU A | 71 | 70.409 | 40.792 | 15.945 | 1.00 | 27.65 | C |
| ATOM | 537 | CD1 | LEU A | 71 | 71.861 | 41.254 | 15.890 | 1.00 | 26.83 | C |
| ATOM | 538 | CD2 | LEU A | 71 | 69.476 | 41.990 | 16.092 | 1.00 | 27.34 | C |
| ATOM | 539 | N | ALA A | 72 | 70.235 | 36.967 | 15.398 | 1.00 | 29.11 | N |
| ATOM | 540 | CA | ALA A | 72 | 70.302 | 35.911 | 16.400 | 1.00 | 30.05 | C |
| ATOM | 541 | C | ALA A | 72 | 71.587 | 35.109 | 16.211 | 1.00 | 30.73 | C |
| ATOM | 542 | O | ALA A | 72 | 72.212 | 34.688 | 17.187 | 1.00 | 30.22 | O |
| ATOM | 543 | CB | ALA A | 72 | 69.081 | 34.992 | 16.288 | 1.00 | 29.99 | C |
| ATOM | 544 | N | ARG A | 73 | 71.980 | 34.900 | 14.955 | 1.00 | 31.51 | N |
| ATOM | 545 | CA | ARG A | 73 | 73.203 | 34.152 | 14.659 | 1.00 | 32.60 | C |
| ATOM | 546 | C | ARG A | 73 | 74.432 | 34.827 | 15.253 | 1.00 | 32.59 | C |
| ATOM | 547 | O | ARG A | 73 | 75.402 | 34.161 | 15.602 | 1.00 | 32.71 | O |
| ATOM | 548 | CB | ARG A | 73 | 73.392 | 34.000 | 13.147 | 1.00 | 33.56 | C |
| ATOM | 549 | CG | ARG A | 73 | 72.540 | 32.910 | 12.528 | 1.00 | 35.32 | C |
| ATOM | 550 | CD | ARG A | 73 | 72.697 | 32.866 | 11.022 | 1.00 | 36.95 | C |
| ATOM | 551 | NE | ARG A | 73 | 71.978 | 31.732 | 10.448 | 1.00 | 39.16 | N |
| ATOM | 552 | CZ | ARG A | 73 | 71.740 | 31.572 | 9.149 | 1.00 | 39.97 | C |
| ATOM | 553 | NH1 | ARG A | 73 | 72.161 | 32.476 | 8.274 | 1.00 | 39.65 | N |
| ATOM | 554 | NH2 | ARG A | 73 | 71.075 | 30.505 | 8.726 | 1.00 | 40.71 | N |
| ATOM | 555 | N | GLU A | 74 | 74.384 | 36.151 | 15.368 | 1.00 | 32.40 | N |
| ATOM | 556 | CA | GLU A | 74 | 75.498 | 36.908 | 15.920 | 1.00 | 32.28 | C |
| ATOM | 557 | C | GLU A | 74 | 75.397 | 37.091 | 17.430 | 1.00 | 31.45 | C |
| ATOM | 558 | O | GLU A | 74 | 76.299 | 37.642 | 18.047 | 1.00 | 31.66 | O |
| ATOM | 559 | CE | GLU A | 74 | 75.595 | 38.274 | 15.235 | 1.00 | 33.47 | C |
| ATOM | 560 | CG | GLU A | 74 | 75.967 | 38.197 | 13.759 | 1.00 | 35.41 | C |
| ATOM | 561 | CD | GLU A | 74 | 77.306 | 37.510 | 13.524 | 1.00 | 37.04 | C |
| ATOM | 562 | OE1 | GLU A | 74 | 78.337 | 38.018 | 14.017 | 1.00 | 37.82 | O |
| ATOM | 563 | OE2 | GLU A | 74 | 77.325 | 36.458 | 12.846 | 1.00 | 38.54 | O |
| ATOM | 564 | N | GLY A | 75 | 74.295 | 36.646 | 18.026 | 1.00 | 30.81 | N |
| ATOM | 565 | CA | GLY A | 75 | 74.152 | 36.774 | 19.467 | 1.00 | 30.19 | C |
| ATOM | 566 | C | GLY A | 75 | 73.133 | 37.780 | 19.966 | 1.00 | 29.59 | C |
| ATOM | 567 | O | GLY A | 75 | 72.909 | 37.888 | 21.176 | 1.00 | 28.90 | O |
| ATOM | 568 | N | GLY A | 76 | 72.524 | 38.522 | 19.044 | 1.00 | 29.15 | N |
| ATOM | 569 | CA | GLY A | 76 | 71.526 | 39.504 | 19.427 | 1.00 | 28.52 | C |
| ATOM | 570 | C | GLY A | 76 | 70.124 | 38.968 | 19.194 | 1.00 | 28.42 | C |
| ATOM | 571 | O | GLY A | 76 | 69.949 | 37.769 | 18.970 | 1.00 | 28.19 | O |
| ATOM | 572 | N | ILE A | 77 | 69.124 | 39.846 | 19.250 | 1.00 | 27.85 | N |
| ATOM | 573 | CA | ILE A | 77 | 67.744 | 39.435 | 19.026 | 1.00 | 27.34 | C |
| ATOM | 574 | C | ILE A | 77 | 66.963 | 40.538 | 18.315 | 1.00 | 27.73 | C |
| ATOM | 575 | O | ILE A | 77 | 67.228 | 41.730 | 18.507 | 1.00 | 27.71 | O |
| ATOM | 576 | CB | ILE A | 77 | 67.043 | 39.089 | 20.363 | 1.00 | 26.95 | C |
| ATOM | 577 | CG1 | ILE A | 77 | 65.811 | 38.217 | 20.097 | 1.00 | 26.86 | C |
| ATOM | 578 | CG2 | ILE A | 77 | 66.642 | 40.370 | 21.099 | 1.00 | 26.54 | C |

TABLE 5-continued

| | | | | | | | | | | |
|---|---|---|---|---|---|---|---|---|---|---|
| ATOM | 579 | CD1 | ILE A | 77 | 65.128 | 37.709 | 21.362 | 1.00 | 25.58 | C |
| ATOM | 580 | N | SER A | 78 | 66.010 | 40.135 | 17.481 | 1.00 | 27.61 | N |
| ATOM | 581 | CA | SER A | 78 | 65.176 | 41.083 | 16.752 | 1.00 | 27.42 | C |
| ATOM | 582 | C | SER A | 78 | 63.763 | 41.054 | 17.313 | 1.00 | 27.91 | C |
| ATOM | 583 | O | SER A | 78 | 63.317 | 40.045 | 17.858 | 1.00 | 27.91 | O |
| ATOM | 584 | CE | SER A | 78 | 65.104 | 40.721 | 15.264 | 1.00 | 26.86 | C |
| ATOM | 585 | OG | SER A | 78 | 66.353 | 40.859 | 14.618 | 1.00 | 26.59 | O |
| ATOM | 586 | N | PHE A | 79 | 63.056 | 42.166 | 17.180 | 1.00 | 28.37 | N |
| ATOM | 587 | CA | PHE A | 79 | 61.681 | 42.228 | 17.634 | 1.00 | 28.70 | C |
| ATOM | 588 | C | PHE A | 79 | 60.796 | 42.394 | 16.403 | 1.00 | 29.22 | C |
| ATOM | 589 | O | PHE A | 79 | 60.599 | 43.505 | 15.920 | 1.00 | 29.28 | O |
| ATOM | 590 | CB | PHE A | 79 | 61.489 | 43.389 | 18.620 | 1.00 | 28.26 | C |
| ATOM | 591 | CG | PHE A | 79 | 62.076 | 43.121 | 19.980 | 1.00 | 28.13 | C |
| ATOM | 592 | CD1 | PHE A | 79 | 63.421 | 43.363 | 20.234 | 1.00 | 28.01 | C |
| ATOM | 593 | CD2 | PHE A | 79 | 61.291 | 42.574 | 20.995 | 1.00 | 28.23 | C |
| ATOM | 594 | CE1 | PHE A | 79 | 63.981 | 43.063 | 21.479 | 1.00 | 28.23 | C |
| ATOM | 595 | CE2 | PHE A | 79 | 61.840 | 42.270 | 22.244 | 1.00 | 27.87 | C |
| ATOM | 596 | CZ | PHE A | 79 | 63.185 | 42.514 | 22.485 | 1.00 | 27.96 | C |
| ATOM | 597 | N | ILE A | 80 | 60.286 | 41.279 | 15.880 | 1.00 | 30.20 | N |
| ATOM | 598 | CA | ILE A | 80 | 59.426 | 41.316 | 14.697 | 1.00 | 30.73 | C |
| ATOM | 599 | C | ILE A | 80 | 58.372 | 42.393 | 14.884 | 1.00 | 31.00 | C |
| ATOM | 600 | O | ILE A | 80 | 57.661 | 42.407 | 15.892 | 1.00 | 30.84 | O |
| ATOM | 601 | CE | ILE A | 80 | 58.730 | 39.948 | 14.441 | 1.00 | 31.03 | C |
| ATOM | 602 | CG1 | ILE A | 80 | 59.673 | 39.001 | 13.696 | 1.00 | 31.69 | C |
| ATOM | 603 | CG2 | ILE A | 80 | 57.508 | 40.137 | 13.549 | 1.00 | 30.82 | C |
| ATOM | 604 | CD1 | ILE A | 80 | 60.976 | 38.770 | 14.361 | 1.00 | 32.86 | C |
| ATOM | 605 | N | PHE A | 81 | 58.277 | 43.299 | 13.914 | 1.00 | 31.46 | N |
| ATOM | 606 | CA | PHE A | 81 | 57.318 | 44.387 | 14.010 | 1.00 | 32.33 | C |
| ATOM | 607 | C | PHE A | 81 | 55.884 | 43.903 | 14.193 | 1.00 | 32.76 | C |
| ATOM | 608 | O | PHE A | 81 | 55.464 | 42.908 | 13.595 | 1.00 | 32.74 | O |
| ATOM | 609 | CB | PHE A | 81 | 57.417 | 45.316 | 12.788 | 1.00 | 32.73 | C |
| ATOM | 610 | CG | PHE A | 81 | 57.167 | 44.635 | 11.470 | 1.00 | 33.07 | C |
| ATOM | 611 | CD1 | PHE A | 81 | 58.155 | 43.859 | 10.872 | 1.00 | 33.23 | C |
| ATOM | 612 | CD2 | PHE A | 81 | 55.949 | 44.796 | 10.812 | 1.00 | 33.18 | C |
| ATOM | 613 | CE1 | PHE A | 81 | 57.937 | 43.251 | 9.629 | 1.00 | 33.42 | C |
| ATOM | 614 | CE2 | PHE A | 81 | 55.717 | 44.194 | 9.571 | 1.00 | 33.24 | C |
| ATOM | 615 | CZ | PHE A | 81 | 56.716 | 43.420 | 8.979 | 1.00 | 33.26 | C |
| ATOM | 616 | N | GLY A | 82 | 55.143 | 44.615 | 15.035 | 1.00 | 33.07 | N |
| ATOM | 617 | CA | GLY A | 82 | 53.763 | 44.260 | 15.303 | 1.00 | 34.00 | C |
| ATOM | 618 | C | GLY A | 82 | 52.780 | 45.069 | 14.481 | 1.00 | 34.67 | C |
| ATOM | 619 | O | GLY A | 82 | 51.567 | 44.884 | 14.600 | 1.00 | 34.70 | O |
| ATOM | 620 | N | SER A | 83 | 53.300 | 45.971 | 13.651 | 1.00 | 35.05 | N |
| ATOM | 621 | CA | SER A | 83 | 52.459 | 46.795 | 12.791 | 1.00 | 35.41 | C |
| ATOM | 622 | C | SER A | 83 | 52.095 | 45.999 | 11.538 | 1.00 | 36.15 | C |
| ATOM | 623 | O | SER A | 83 | 52.438 | 46.367 | 10.411 | 1.00 | 36.11 | O |
| ATOM | 624 | CB | SER A | 83 | 53.185 | 48.085 | 12.409 | 1.00 | 35.00 | C |
| ATOM | 625 | OG | SER A | 83 | 54.407 | 47.807 | 11.755 | 1.00 | 34.80 | O |
| ATOM | 626 | N | GLN A | 84 | 51.411 | 44.884 | 11.766 | 1.00 | 36.71 | N |
| ATOM | 627 | CA | GLN A | 84 | 50.952 | 43.993 | 10.714 | 1.00 | 37.15 | C |
| ATOM | 628 | C | GLN A | 84 | 49.907 | 43.107 | 11.386 | 1.00 | 37.55 | C |
| ATOM | 629 | O | GLN A | 84 | 49.734 | 43.173 | 12.605 | 1.00 | 37.38 | O |
| ATOM | 630 | CB | GLN A | 84 | 52.115 | 43.157 | 10.165 | 1.00 | 37.55 | C |
| ATOM | 631 | CG | GLN A | 84 | 52.783 | 42.238 | 11.179 | 1.00 | 37.88 | C |
| ATOM | 632 | CD | GLN A | 84 | 53.907 | 41.426 | 10.569 | 1.00 | 38.47 | C |
| ATOM | 633 | OE1 | GLN A | 84 | 53.730 | 40.791 | 9.530 | 1.00 | 39.45 | O |
| ATOM | 634 | NE2 | GLN A | 84 | 55.072 | 41.435 | 11.214 | 1.00 | 38.16 | N |
| ATOM | 635 | N | SER A | 85 | 49.208 | 42.286 | 10.610 | 1.00 | 37.98 | N |
| ATOM | 636 | CA | SER A | 85 | 48.177 | 41.427 | 11.183 | 1.00 | 38.63 | C |
| ATOM | 637 | C | SER A | 85 | 48.755 | 40.456 | 12.205 | 1.00 | 39.17 | C |
| ATOM | 638 | O | SER A | 85 | 49.922 | 40.068 | 12.119 | 1.00 | 39.21 | O |
| ATOM | 639 | CB | SER A | 85 | 47.471 | 40.625 | 10.089 | 1.00 | 38.43 | C |
| ATOM | 640 | OG | SER A | 85 | 48.237 | 39.491 | 9.726 | 1.00 | 38.74 | O |
| ATOM | 641 | N | ILE A | 86 | 47.928 | 40.059 | 13.167 | 1.00 | 39.52 | N |
| ATOM | 642 | CA | ILE A | 86 | 48.348 | 39.116 | 14.192 | 1.00 | 40.46 | C |
| ATOM | 643 | C | ILE A | 86 | 48.837 | 37.827 | 13.533 | 1.00 | 41.43 | C |
| ATOM | 644 | O | ILE A | 86 | 49.832 | 37.239 | 13.959 | 1.00 | 41.37 | O |
| ATOM | 645 | CB | ILE A | 86 | 47.179 | 38.792 | 15.155 | 1.00 | 40.12 | C |
| ATOM | 646 | CG1 | ILE A | 86 | 46.847 | 40.034 | 15.993 | 1.00 | 40.13 | C |
| ATOM | 647 | CG2 | ILE A | 86 | 47.533 | 37.605 | 16.043 | 1.00 | 39.47 | C |
| ATOM | 648 | CD1 | ILE A | 86 | 45.631 | 39.878 | 16.891 | 1.00 | 39.39 | C |
| ATOM | 649 | N | GLU A | 87 | 48.139 | 37.403 | 12.480 | 1.00 | 42.20 | N |
| ATOM | 650 | CA | GLU A | 87 | 48.497 | 36.182 | 11.768 | 1.00 | 42.84 | C |
| ATOM | 651 | C | GLU A | 87 | 49.845 | 36.280 | 11.057 | 1.00 | 42.23 | C |
| ATOM | 652 | O | GLU A | 87 | 50.633 | 35.337 | 11.089 | 1.00 | 42.25 | O |
| ATOM | 653 | CB | GLU A | 87 | 47.405 | 35.809 | 10.755 | 1.00 | 44.28 | C |
| ATOM | 654 | CG | GLU A | 87 | 46.291 | 36.848 | 10.587 | 1.00 | 46.83 | C |
| ATOM | 655 | CD | GLU A | 87 | 45.454 | 37.041 | 11.847 | 1.00 | 47.87 | C |
| ATOM | 656 | OE1 | GLU A | 87 | 44.982 | 36.030 | 12.416 | 1.00 | 48.85 | O |
| ATOM | 657 | OE2 | GLU A | 87 | 45.261 | 38.206 | 12.264 | 1.00 | 48.52 | O |

TABLE 5-continued

| | | | | | | | | | | |
|---|---|---|---|---|---|---|---|---|---|---|
| ATOM | 658 | N | SER A | 88 | 50.108 | 37.415 | 10.416 | 1.00 | 41.90 | N |
| ATOM | 659 | CA | SER A | 88 | 51.372 | 37.617 | 9.710 | 1.00 | 41.64 | C |
| ATOM | 660 | C | SER A | 88 | 52.563 | 37.665 | 10.665 | 1.00 | 40.67 | C |
| ATOM | 661 | O | SER A | 88 | 53.596 | 37.048 | 10.409 | 1.00 | 40.52 | O |
| ATOM | 662 | CB | SER A | 88 | 51.337 | 38.916 | 8.902 | 1.00 | 42.19 | C |
| ATOM | 663 | OG | SER A | 88 | 50.359 | 38.853 | 7.882 | 1.00 | 44.49 | O |
| ATOM | 664 | N | GLN A | 89 | 52.423 | 38.405 | 11.759 | 1.00 | 39.75 | N |
| ATOM | 665 | CA | GLN A | 89 | 53.507 | 38.518 | 12.729 | 1.00 | 39.13 | C |
| ATOM | 666 | C | GLN A | 89 | 53.805 | 37.160 | 13.353 | 1.00 | 38.91 | C |
| ATOM | 667 | O | GLN A | 89 | 54.964 | 36.754 | 13.453 | 1.00 | 38.76 | O |
| ATOM | 668 | CB | GLN A | 89 | 53.151 | 39.534 | 13.821 | 1.00 | 38.26 | C |
| ATOM | 669 | CG | GLN A | 89 | 54.226 | 39.689 | 14.888 | 1.00 | 37.37 | C |
| ATOM | 670 | CD | GLN A | 89 | 53.860 | 40.714 | 15.946 | 1.00 | 36.90 | C |
| ATOM | 671 | OE1 | GLN A | 89 | 52.692 | 40.870 | 16.299 | 1.00 | 36.35 | O |
| ATOM | 672 | NE2 | GLN A | 89 | 54.863 | 41.407 | 16.470 | 1.00 | 36.22 | N |
| ATOM | 673 | N | ALA A | 90 | 52.753 | 36.457 | 13.762 | 1.00 | 39.14 | N |
| ATOM | 674 | CA | ALA A | 90 | 52.902 | 35.140 | 14.370 | 1.00 | 39.24 | C |
| ATOM | 675 | C | ALA A | 90 | 53.587 | 34.185 | 13.395 | 1.00 | 39.46 | C |
| ATOM | 676 | O | ALA A | 90 | 54.404 | 33.354 | 13.798 | 1.00 | 39.52 | O |
| ATOM | 677 | CB | ALA A | 90 | 51.537 | 34.593 | 14.774 | 1.00 | 39.44 | C |
| ATOM | 678 | N | ALA A | 91 | 53.260 | 34.312 | 12.112 | 1.00 | 39.32 | N |
| ATOM | 679 | CA | ALA A | 91 | 53.856 | 33.456 | 11.093 | 1.00 | 39.50 | C |
| ATOM | 680 | C | ALA A | 91 | 55.357 | 33.724 | 10.984 | 1.00 | 39.72 | C |
| ATOM | 681 | O | ALA A | 91 | 56.154 | 32.793 | 10.840 | 1.00 | 39.86 | O |
| ATOM | 682 | CB | ALA A | 91 | 53.177 | 33.689 | 9.745 | 1.00 | 39.16 | C |
| ATOM | 683 | N | MET A | 92 | 55.741 | 34.995 | 11.045 | 1.00 | 39.61 | N |
| ATOM | 684 | CA | MET A | 92 | 57.151 | 35.352 | 10.967 | 1.00 | 39.71 | C |
| ATOM | 685 | C | MET A | 92 | 57.889 | 34.791 | 12.173 | 1.00 | 39.19 | C |
| ATOM | 686 | O | MET A | 92 | 58.990 | 34.258 | 12.041 | 1.00 | 39.13 | O |
| ATOM | 687 | CB | MET A | 92 | 57.326 | 36.871 | 10.918 | 1.00 | 40.44 | C |
| ATOM | 688 | CG | MET A | 92 | 56.931 | 37.495 | 9.598 | 1.00 | 41.57 | C |
| ATOM | 689 | SD | MET A | 92 | 57.352 | 39.245 | 9.523 | 1.00 | 42.86 | S |
| ATOM | 690 | CE | MET A | 92 | 59.055 | 39.148 | 9.746 | 1.00 | 43.00 | C |
| ATOM | 691 | N | VAL A | 93 | 57.277 | 34.917 | 13.348 | 1.00 | 38.70 | N |
| ATOM | 692 | CA | VAL A | 93 | 57.871 | 34.413 | 14.581 | 1.00 | 38.24 | C |
| ATOM | 693 | C | VAL A | 93 | 58.066 | 32.909 | 14.452 | 1.00 | 38.82 | C |
| ATOM | 694 | O | VAL A | 93 | 59.139 | 32.381 | 14.744 | 1.00 | 38.41 | O |
| ATOM | 695 | CB | VAL A | 93 | 56.962 | 34.708 | 15.800 | 1.00 | 37.90 | C |
| ATOM | 696 | CG1 | VAL A | 93 | 57.400 | 33.883 | 17.003 | 1.00 | 37.53 | C |
| ATOM | 697 | CG2 | VAL A | 93 | 57.011 | 36.185 | 16.133 | 1.00 | 37.21 | C |
| ATOM | 698 | N | HIS A | 94 | 57.018 | 32.226 | 14.001 | 1.00 | 39.48 | N |
| ATOM | 699 | CA | HIS A | 94 | 57.061 | 30.778 | 13.828 | 1.00 | 40.12 | C |
| ATOM | 700 | C | HIS A | 94 | 58.181 | 30.377 | 12.866 | 1.00 | 39.88 | C |
| ATOM | 701 | O | HIS A | 94 | 58.927 | 29.434 | 13.127 | 1.00 | 39.95 | O |
| ATOM | 702 | CB | HIS A | 94 | 55.722 | 30.274 | 13.288 | 1.00 | 41.19 | C |
| ATOM | 703 | CG | HIS A | 94 | 55.595 | 28.785 | 13.294 | 1.00 | 42.21 | C |
| ATOM | 704 | ND1 | HIS A | 94 | 55.385 | 28.062 | 14.448 | 1.00 | 42.90 | N |
| ATOM | 705 | CD2 | HIS A | 94 | 55.676 | 27.879 | 12.291 | 1.00 | 42.67 | C |
| ATOM | 706 | CE1 | HIS A | 94 | 55.340 | 26.775 | 14.156 | 1.00 | 42.91 | C |
| ATOM | 707 | NE2 | HIS A | 94 | 55.515 | 26.637 | 12.854 | 1.00 | 43.21 | N |
| ATOM | 708 | N | ALA A | 95 | 58.294 | 31.104 | 11.759 | 1.00 | 39.52 | N |
| ATOM | 709 | CA | ALA A | 95 | 59.318 | 30.828 | 10.757 | 1.00 | 39.41 | C |
| ATOM | 710 | C | ALA A | 95 | 60.732 | 30.903 | 11.336 | 1.00 | 39.70 | C |
| ATOM | 711 | O | ALA A | 95 | 61.600 | 30.104 | 10.979 | 1.00 | 39.80 | O |
| ATOM | 712 | CB | ALA A | 95 | 59.181 | 31.800 | 9.599 | 1.00 | 39.04 | C |
| ATOM | 713 | N | VAL A | 96 | 60.968 | 31.868 | 12.221 | 1.00 | 39.80. | N |
| ATOM | 714 | CA | VAL A | 96 | 62.280 | 32.022 | 12.834 | 1.00 | 39.46 | C |
| ATOM | 715 | C | VAL A | 96 | 62.540 | 30.876 | 13.807 | 1.00 | 40.06 | C |
| ATOM | 716 | O | VAL A | 96 | 63.640 | 30.322 | 13.851 | 1.00 | 40.00 | O |
| ATOM | 717 | CB | VAL A | 96 | 62.392 | 33.367 | 13.593 | 1.00 | 39.16 | C |
| ATOM | 718 | CG1 | VAL A | 96 | 63.723 | 33.449 | 14.326 | 1.00 | 38.41 | C |
| ATOM | 719 | CG2 | VAL A | 96 | 62.264 | 34.522 | 12.617 | 1.00 | 38.80 | C |
| ATOM | 720 | N | LYS A | 97 | 61.518 | 30.516 | 14.574 | 1.00 | 40.40 | N |
| ATOM | 721 | CA | LYS A | 97 | 61.641 | 29.442 | 15.550 | 1.00 | 41.60 | C |
| ATOM | 722 | C | LYS A | 97 | 61.861 | 28.063 | 14.927 | 1.00 | 42.73 | C |
| ATOM | 723 | O | LYS A | 97 | 62.472 | 27.193 | 15.548 | 1.00 | 42.73 | O |
| ATOM | 724 | CB | LYS A | 97 | 60.398 | 29.405 | 16.448 | 1.00 | 40.87 | C |
| ATOM | 725 | CG | LYS A | 97 | 60.165 | 30.681 | 17.242 | 1.00 | 39.77 | C |
| ATOM | 726 | CD | LYS A | 97 | 61.374 | 31.020 | 18.112 | 1.00 | 38.88 | C |
| ATOM | 727 | CE | LYS A | 97 | 61.645 | 29.938 | 19.146 | 1.00 | 38.08 | C |
| ATOM | 728 | NZ | LYS A | 97 | 62.859 | 30.238 | 19.957 | 1.00 | 37.01 | N |
| ATOM | 729 | N | ASN A | 98 | 61.373 | 27.867 | 13.705 | 1.00 | 44.37 | N |
| ATOM | 730 | CA | ASN A | 98 | 61.509 | 26.579 | 13.024 | 1.00 | 46.53 | C |
| ATOM | 731 | C | ASN A | 98 | 62.485 | 26.602 | 11.854 | 1.00 | 47.31 | C |
| ATOM | 732 | O | ASN A | 98 | 62.519 | 25.664 | 11.056 | 1.00 | 47.58 | O |
| ATOM | 733 | CB | ASN A | 98 | 60.146 | 26.112 | 12.506 | 1.00 | 47.72 | C |
| ATOM | 734 | CG | ASN A | 98 | 59.160 | 25.828 | 13.621 | 1.00 | 49.35 | C |
| ATOM | 735 | OD1 | ASN A | 98 | 57.953 | 25.977 | 13.439 | 1.00 | 50.61 | O |
| ATOM | 736 | ND2 | ASN A | 98 | 59.664 | 25.403 | 14.778 | 1.00 | 49.87 | N |

TABLE 5-continued

| | | | | | | | | | | |
|---|---|---|---|---|---|---|---|---|---|---|
| ATOM | 737 | N | PHE A | 99 | 63.284 | 27.659 | 11.751 | 1.00 | 48.16 | N |
| ATOM | 738 | CA | PHE A | 99 | 64.227 | 27.782 | 10.644 | 1.00 | 48.79 | C |
| ATOM | 739 | C | PHE A | 99 | 65.234 | 26.636 | 10.519 | 1.00 | 49.62 | C |
| ATOM | 740 | O | PHE A | 99 | 65.528 | 26.189 | 9.412 | 1.00 | 49.73 | O |
| ATOM | 741 | CB | PHE A | 99 | 64.988 | 29.107 | 10.741 | 1.00 | 48.15 | C |
| ATOM | 742 | CG | PHE A | 99 | 65.802 | 29.425 | 9.518 | 1.00 | 47.62 | C |
| ATOM | 743 | CD1 | PHE A | 99 | 65.179 | 29.755 | 8.319 | 1.00 | 47.45 | C |
| ATOM | 744 | CD2 | PHE A | 99 | 67.192 | 29.383 | 9.559 | 1.00 | 47.46 | C |
| ATOM | 745 | CE1 | PHE A | 99 | 65.928 | 30.038 | 7.177 | 1.00 | 47.25 | C |
| ATOM | 746 | CE2 | PHE A | 99 | 67.950 | 29.663 | 8.425 | 1.00 | 47.37 | C |
| ATOM | 747 | CZ | PHE A | 99 | 67.317 | 29.992 | 7.231 | 1.00 | 47.38 | C |
| ATOM | 748 | N | LYS A | 100 | 65.752 | 26.160 | 11.648 | 1.00 | 50.63 | N |
| ATOM | 749 | CA | LYS A | 100 | 66.751 | 25.092 | 11.644 | 1.00 | 51.74 | C |
| ATOM | 750 | C | LYS A | 100 | 66.180 | 23.677 | 11.537 | 1.00 | 52.59 | C |
| ATOM | 751 | O | LYS A | 100 | 66.768 | 22.722 | 12.045 | 1.00 | 53.01 | O |
| ATOM | 752 | CB | LYS A | 100 | 67.625 | 25.215 | 12.896 | 1.00 | 51.65 | C |
| ATOM | 753 | CG | LYS A | 100 | 68.234 | 26.604 | 13.048 | 1.00 | 51.70 | C |
| ATOM | 754 | CD | LYS A | 100 | 68.860 | 26.837 | 14.417 | 1.00 | 51.72 | C |
| ATOM | 755 | CE | LYS A | 100 | 70.214 | 26.175 | 14.552 | 1.00 | 51.52 | C |
| ATOM | 756 | NZ | LYS A | 100 | 70.846 | 26.548 | 15.844 | 1.00 | 51.13 | N |
| ATOM | 757 | N | ALA A | 101 | 65.041 | 23.543 | 10.864 | 1.00 | 53.24 | N |
| ATOM | 758 | CA | ALA A | 101 | 64.402 | 22.241 | 10.691 | 1.00 | 53.65 | C |
| ATOM | 759 | C | ALA A | 101 | 64.609 | 21.717 | 9.270 | 1.00 | 53.86 | C |
| ATOM | 760 | O | ALA A | 101 | 64.007 | 22.218 | 8.317 | 1.00 | 53.99 | O |
| ATOM | 761 | CB | ALA A | 101 | 62.908 | 22.347 | 10.997 | 1.00 | 53.63 | C |
| ATOM | 762 | N | HIS A | 222 | 79.084 | 30.118 | 16.803 | 1.00 | 56.10 | N |
| ATOM | 763 | CA | HIS A | 222 | 79.441 | 29.875 | 18.198 | 1.00 | 56.03 | C |
| ATOM | 764 | C | HIS A | 222 | 78.777 | 30.884 | 19.132 | 1.00 | 54.99 | C |
| ATOM | 765 | O | HIS A | 222 | 78.609 | 30.624 | 20.326 | 1.00 | 54.92 | O |
| ATOM | 766 | CB | HIS A | 222 | 80.964 | 29.929 | 18.373 | 1.00 | 57.63 | C |
| ATOM | 767 | CG | HIS A | 222 | 81.692 | 28.829 | 17.662 | 1.00 | 59.44 | C |
| ATOM | 768 | ND1 | HIS A | 222 | 81.472 | 27.495 | 17.935 | 1.00 | 60.05 | N |
| ATOM | 769 | CD2 | HIS A | 222 | 82.619 | 28.863 | 16.675 | 1.00 | 60.20 | C |
| ATOM | 770 | CE1 | HIS A | 222 | 82.231 | 26.755 | 17.145 | 1.00 | 60.69 | C |
| ATOM | 771 | NE2 | HIS A | 222 | 82.937 | 27.560 | 16.370 | 1.00 | 60.70 | N |
| ATOM | 772 | N | ASN A | 223 | 78.399 | 32.036 | 18.588 | 1.00 | 53.33 | N |
| ATOM | 773 | CA | ASN A | 223 | 77.749 | 33.058 | 19.391 | 1.00 | 51.76 | C |
| ATOM | 774 | C | ASN A | 223 | 76.279 | 33.236 | 19.049 | 1.00 | 49.93 | C |
| ATOM | 775 | O | ASN A | 223 | 75.713 | 34.298 | 19.289 | 1.00 | 49.49 | O |
| ATOM | 776 | CB | ASN A | 223 | 78.473 | 34.399 | 19.249 | 1.00 | 52.87 | C |
| ATOM | 777 | CO | ASN A | 223 | 79.779 | 34.438 | 20.020 | 1.00 | 53.79 | C |
| ATOM | 778 | OD1 | ASN A | 223 | 80.743 | 33.748 | 19.676 | 1.00 | 54.29 | O |
| ATOM | 779 | ND2 | ASN A | 223 | 79.815 | 35.244 | 21.078 | 1.00 | 54.20 | N |
| ATOM | 780 | N | GLU A | 224 | 75.657 | 32.201 | 18.490 | 1.00 | 47.90 | N |
| ATOM | 781 | CA | GLU A | 224 | 74.243 | 32.288 | 18.148 | 1.00 | 46.08 | C |
| ATOM | 782 | C | GLU A | 224 | 73.406 | 32.282 | 19.418 | 1.00 | 43.99 | C |
| ATOM | 783 | O | GLU A | 224 | 73.720 | 31.581 | 20.379 | 1.00 | 42.95 | O |
| ATOM | 784 | CB | GLU A | 224 | 73.816 | 31.127 | 17.239 | 1.00 | 46.94 | C |
| ATOM | 785 | CG | GLU A | 224 | 74.134 | 29.736 | 17.778 | 1.00 | 48.84 | C |
| ATOM | 786 | CD | GLU A | 224 | 73.590 | 28.616 | 16.896 | 1.00 | 49.60 | C |
| ATOM | 787 | OE1 | GLU A | 224 | 73.641 | 28.749 | 15.651 | 1.00 | 50.06 | O |
| ATOM | 788 | OE2 | GLU A | 224 | 73.126 | 27.594 | 17.452 | 1.00 | 49.95 | O |
| ATOM | 789 | N | LEU A | 225 | 72.350 | 33.086 | 19.418 | 1.00 | 42.15 | N |
| ATOM | 790 | CA | LEU A | 225 | 71.453 | 33.175 | 20.558 | 1.00 | 40.63 | C |
| ATOM | 791 | C | LEU A | 225 | 70.303 | 32.200 | 20.332 | 1.00 | 39.80 | C |
| ATOM | 792 | O | LEU A | 225 | 69.475 | 32.407 | 19.445 | 1.00 | 39.10 | O |
| ATOM | 793 | CB | LEU A | 225 | 70.915 | 34.600 | 20.692 | 1.00 | 39.95 | C |
| ATOM | 794 | CG | LEU A | 225 | 70.043 | 34.870 | 21.920 | 1.00 | 39.53 | C |
| ATOM | 795 | CD1 | LEU A | 225 | 70.866 | 34.649 | 23.180 | 1.00 | 39.09 | C |
| ATOM | 796 | CD2 | LEU A | 225 | 69.509 | 36.292 | 21.871 | 1.00 | 38.92 | C |
| ATOM | 797 | N | VAL A | 226 | 70.255 | 31.143 | 21.138 | 1.00 | 39.41 | N |
| ATOM | 798 | CA | VAL A | 226 | 69.216 | 30.121 | 21.005 | 1.00 | 39.48 | C |
| ATOM | 799 | C | VAL A | 226 | 68.609 | 29.668 | 22.334 | 1.00 | 39.55 | C |
| ATOM | 800 | O | VAL A | 226 | 69.121 | 29.985 | 23.409 | 1.00 | 39.03 | O |
| ATOM | 801 | CE | VAL A | 226 | 69.772 | 28.859 | 20.301 | 1.00 | 39.18 | C |
| ATOM | 802 | CG1 | VAL A | 226 | 70.195 | 29.185 | 18.873 | 1.00 | 38.53 | C |
| ATOM | 803 | CG2 | VAL A | 226 | 70.951 | 28.313 | 21.092 | 1.00 | 39.07 | C |
| ATOM | 804 | N | ASP A | 227 | 67.506 | 28.926 | 22.245 | 1.00 | 40.09 | N |
| ATOM | 805 | CA | ASP A | 227 | 66.848 | 28.399 | 23.431 | 1.00 | 40.34 | C |
| ATOM | 806 | C | ASP A | 227 | 67.377 | 26.996 | 23.720 | 1.00 | 41.22 | C |
| ATOM | 807 | O | ASP A | 227 | 68.309 | 26.530 | 23.058 | 1.00 | 40.82 | O |
| ATOM | 808 | CB | ASP A | 227 | 65.324 | 28.359 | 23.253 | 1.00 | 40.17 | C |
| ATOM | 809 | CG | ASP A | 227 | 64.883 | 27.591 | 22.013 | 1.00 | 39.66 | C |
| ATOM | 810 | OD1 | ASP A | 227 | 65.540 | 26.598 | 21.635 | 1.00 | 39.52 | O |
| ATOM | 811 | OD2 | ASP A | 227 | 63.851 | 27.975 | 21.424 | 1.00 | 39.07 | O |
| ATOM | 812 | N | SER A | 228 | 66.778 | 26.328 | 24.705 | 1.00 | 42.36 | N |
| ATOM | 813 | CA | SER A | 228 | 67.190 | 24.979 | 25.098 | 1.00 | 43.39 | C |
| ATOM | 814 | C | SER A | 228 | 67.033 | 23.945 | 23.981 | 1.00 | 44.03 | C |
| ATOM | 815 | O | SER A | 228 | 67.660 | 22.884 | 24.022 | 1.00 | 44.51 | O |

TABLE 5-continued

| ATOM | 816 | CE | SER A | 228 | 66.398 | 24.526 | 26.328 | 1.00 | 43.24 | C |
|---|---|---|---|---|---|---|---|---|---|---|
| ATOM | 817 | OG | SER A | 228 | 65.008 | 24.504 | 26.053 | 1.00 | 43.57 | O |
| ATOM | 818 | N | GLN A | 229 | 66.199 | 24.255 | 22.993 | 1.00 | 44.53 | N |
| ATOM | 819 | CA | GLN A | 229 | 65.970 | 23.361 | 21.861 | 1.00 | 45.10 | C |
| ATOM | 820 | C | GLN A | 229 | 66.852 | 23.748 | 20.676 | 1.00 | 44.98 | C |
| ATOM | 821 | O | GLN A | 229 | 66.675 | 23.241 | 19.568 | 1.00 | 44.97 | O |
| ATOM | 822 | CB | GLN A | 229 | 64.497 | 23.407 | 21.431 | 1.00 | 45.98 | C |
| ATOM | 823 | CG | GLN A | 229 | 63.517 | 22.870 | 22.464 | 1.00 | 47.38 | C |
| ATOM | 824 | CD | GLN A | 229 | 62.069 | 22.994 | 22.014 | 1.00 | 48.68 | C |
| ATOM | 825 | OE1 | GLN A | 229 | 61.684 | 22.476 | 20.962 | 1.00 | 49.59 | O |
| ATOM | 826 | NE2 | GLN A | 229 | 61.259 | 23.683 | 22.810 | 1.00 | 49.07 | N |
| ATOM | 827 | N | LYS A | 230 | 67.793 | 24.657 | 20.919 | 1.00 | 44.98 | N |
| ATOM | 828 | CA | LYS A | 230 | 68.717 | 25.136 | 19.893 | 1.00 | 44.38 | C |
| ATOM | 829 | C | LYS A | 230 | 68.072 | 25.967 | 18.788 | 1.00 | 43.28 | C |
| ATOM | 830 | O | LYS A | 230 | 68.639 | 26.116 | 17.708 | 1.00 | 43.52 | O |
| ATOM | 831 | CB | LYS A | 230 | 69.486 | 23.961 | 19.274 | 1.00 | 45.73 | C |
| ATOM | 832 | CG | LYS A | 230 | 70.609 | 23.431 | 20.158 | 1.00 | 47.31 | C |
| ATOM | 833 | CD | LYS A | 230 | 71.619 | 24.538 | 20.461 | 1.00 | 49.00 | C |
| ATOM | 834 | CE | LYS A | 230 | 72.772 | 24.046 | 21.334 | 1.00 | 50.10 | C |
| ATOM | 835 | NZ | LYS A | 230 | 73.732 | 25.151 | 21.659 | 1.00 | 50.80 | N |
| ATOM | 836 | N | ARG A | 231 | 66.891 | 26.512 | 19.054 | 1.00 | 42.16 | N |
| ATOM | 837 | CA | ARG A | 231 | 66.206 | 27.344 | 18.068 | 1.00 | 41.22 | C |
| ATOM | 838 | C | ARG A | 231 | 66.596 | 28.797 | 18.324 | 1.00 | 40.06 | C |
| ATOM | 839 | O | ARG A | 231 | 66.782 | 29.199 | 19.474 | 1.00 | 39.86 | O |
| ATOM | 840 | CB | ARG A | 231 | 64.687 | 27.189 | 18.194 | 1.00 | 42.00 | C |
| ATOM | 841 | CG | ARG A | 231 | 64.195 | 25.742 | 18.119 | 1.00 | 43.23 | C |
| ATOM | 842 | CD | ARG A | 231 | 62.693 | 25.651 | 18.341 | 1.00 | 44.06 | C |
| ATOM | 843 | NE | ARG A | 231 | 62.304 | 26.202 | 19.636 | 1.00 | 45.39 | N |
| ATOM | 844 | CZ | ARG A | 231 | 61.047 | 26.309 | 20.058 | 1.00 | 46.06 | C |
| ATOM | 845 | NH1 | ARG A | 231 | 60.047 | 25.900 | 19.287 | 1.00 | 46.08 | N |
| ATOM | 846 | NH2 | ARG A | 231 | 60.787 | 26.833 | 21.251 | 1.00 | 46.43 | N |
| ATOM | 847 | N | TYR A | 232 | 66.730 | 29.578 | 17.256 | 1.00 | 38.48 | N |
| ATOM | 848 | CA | TYR A | 232 | 67.093 | 30.985 | 17.390 | 1.00 | 37.00 | C |
| ATOM | 849 | C | TYR A | 232 | 66.068 | 31.733 | 18.236 | 1.00 | 35.83 | C |
| ATOM | 850 | O | TYR A | 232 | 64.867 | 31.475 | 18.154 | 1.00 | 35.57 | O |
| ATOM | 851 | CB | TYR A | 232 | 67.183 | 31.656 | 16.015 | 1.00 | 37.19 | C |
| ATOM | 852 | CG | TYR A | 232 | 68.311 | 31.153 | 15.143 | 1.00 | 37.51 | C |
| ATOM | 853 | CD1 | TYR A | 232 | 69.633 | 31.195 | 15.585 | 1.00 | 37.61 | C |
| ATOM | 854 | CD2 | TYR A | 232 | 68.058 | 30.636 | 13.872 | 1.00 | 37.62 | C |
| ATOM | 855 | CE1 | TYR A | 232 | 70.679 | 30.730 | 14.782 | 1.00 | 37.95 | C |
| ATOM | 856 | CE2 | TYR A | 232 | 69.097 | 30.171 | 13.060 | 1.00 | 37.82 | C |
| ATOM | 857 | CZ | TYR A | 232 | 70.400 | 30.219 | 13.521 | 1.00 | 38.06 | C |
| ATOM | 858 | OH | TYR A | 232 | 71.422 | 29.752 | 12.729 | 1.00 | 38.65 | O |
| ATOM | 859 | N | LEU A | 233 | 66.547 | 32.654 | 19.061 | 1.00 | 34.40 | N |
| ATOM | 860 | CA | LEU A | 233 | 65.653 | 33.447 | 19.887 | 1.00 | 33.28 | C |
| ATOM | 861 | C | LEU A | 233 | 65.058 | 34.541 | 19.015 | 1.00 | 32.48 | C |
| ATOM | 862 | O | LEU A | 233 | 65.681 | 34.992 | 18.053 | 1.00 | 32.36 | O |
| ATOM | 863 | CB | LEU A | 233 | 66.418 | 34.080 | 21.057 | 1.00 | 33.73 | C |
| ATOM | 864 | CG | LEU A | 233 | 66.128 | 33.504 | 22.449 | 1.00 | 34.07 | C |
| ATOM | 865 | CD1 | LEU A | 233 | 66.374 | 32.010 | 22.441 | 1.00 | 33.66 | C |
| ATOM | 866 | CD2 | LEU A | 233 | 66.994 | 34.190 | 23.496 | 1.00 | 34.12 | C |
| ATOM | 867 | N | VAL A | 234 | 63.842 | 34.958 | 19.335 | 1.00 | 31.40 | N |
| ATOM | 868 | CA | VAL A | 234 | 63.210 | 36.020 | 18.574 | 1.00 | 30.69 | C |
| ATOM | 869 | C | VAL A | 234 | 62.213 | 36.752 | 19.447 | 1.00 | 30.26 | C |
| ATOM | 870 | O | VAL A | 234 | 61.584 | 36.156 | 20.319 | 1.00 | 30.27 | O |
| ATOM | 871 | CB | VAL A | 234 | 62.488 | 35.479 | 17.321 | 1.00 | 30.52 | C |
| ATOM | 872 | CG1 | VAL A | 234 | 61.272 | 34.654 | 17.719 | 1.00 | 30.18 | C |
| ATOM | 873 | CG2 | VAL A | 234 | 62.083 | 36.636 | 16.434 | 1.00 | 30.21 | C |
| ATOM | 874 | N | GLY A | 235 | 62.087 | 38.052 | 19.218 | 1.00 | 30.07 | N |
| ATOM | 875 | CA | GLY A | 235 | 61.158 | 38.851 | 19.987 | 1.00 | 29.43 | C |
| ATOM | 876 | C | GLY A | 235 | 60.039 | 39.341 | 19.095 | 1.00 | 29.31 | C |
| ATOM | 877 | O | GLY A | 235 | 60.105 | 39.201 | 17.874 | 1.00 | 29.17 | O |
| ATOM | 878 | N | ALA A | 236 | 59.011 | 39.922 | 19.699 | 1.00 | 28.71 | N |
| ATOM | 879 | CA | ALA A | 236 | 57.888 | 40.420 | 18.929 | 1.00 | 28.71 | C |
| ATOM | 880 | C | ALA A | 236 | 57.267 | 41.637 | 19.600 | 1.00 | 28.78 | C |
| ATOM | 881 | O | ALA A | 236 | 57.035 | 41.643 | 20.809 | 1.00 | 28.79 | O |
| ATOM | 882 | CB | ALA A | 236 | 56.846 | 39.320 | 18.768 | 1.00 | 28.81 | C |
| ATOM | 883 | N | GLY A | 237 | 57.007 | 42.670 | 18.809 | 1.00 | 28.64 | N |
| ATOM | 884 | CA | GLY A | 237 | 56.405 | 43.866 | 19.355 | 1.00 | 28.99 | C |
| ATOM | 885 | C | GLY A | 237 | 54.902 | 43.715 | 19.462 | 1.00 | 29.51 | C |
| ATOM | 886 | O | GLY A | 237 | 54.284 | 43.014 | 18.657 | 1.00 | 29.85 | O |
| ATOM | 887 | N | ILE A | 238 | 54.311 | 44.352 | 20.467 | 1.00 | 29.44 | N |
| ATOM | 888 | CA | ILE A | 238 | 52.866 | 44.301 | 20.649 | 1.00 | 29.75 | C |
| ATOM | 889 | C | ILE A | 238 | 52.370 | 45.707 | 20.959 | 1.00 | 30.10 | C |
| ATOM | 890 | O | ILE A | 238 | 53.150 | 46.580 | 21.332 | 1.00 | 29.88 | O |
| ATOM | 891 | CE | ILE A | 238 | 52.449 | 43.359 | 21.814 | 1.00 | 29.59 | C |
| ATOM | 892 | CG1 | ILE A | 238 | 52.950 | 43.912 | 23.151 | 1.00 | 29.43 | C |
| ATOM | 893 | CG2 | ILE A | 238 | 53.001 | 41.964 | 21.578 | 1.00 | 29.87 | C |
| ATOM | 894 | CD1 | ILE A | 238 | 52.438 | 43.149 | 24.376 | 1.00 | 28.69 | C |

TABLE 5-continued

| ATOM | 895 | N | ASN A | 239 | 51.072 | 45.925 | 20.789 | 1.00 | 30.32 | N |
|---|---|---|---|---|---|---|---|---|---|---|
| ATOM | 896 | CA | ASN A | 239 | 50.488 | 47.224 | 21.067 | 1.00 | 30.41 | C |
| ATOM | 897 | C | ASN A | 239 | 49.515 | 47.095 | 22.233 | 1.00 | 30.69 | C |
| ATOM | 898 | O | ASN A | 239 | 49.107 | 45.992 | 22.599 | 1.00 | 30.13 | O |
| ATOM | 899 | CB | ASN A | 239 | 49.774 | 47.760 | 19.822 | 1.00 | 30.86 | C |
| ATOM | 900 | CG | ASN A | 239 | 48.606 | 46.892 | 19.397 | 1.00 | 30.89 | C |
| ATOM | 901 | OD1 | ASN A | 239 | 47.610 | 46.785 | 20.108 | 1.00 | 30.90 | O |
| ATOM | 902 | ND2 | ASN A | 239 | 48.724 | 46.269 | 18.231 | 1.00 | 31.26 | N |
| ATOM | 903 | N | THR A | 240 | 49.144 | 48.226 | 22.816 | 1.00 | 31.46 | N |
| ATOM | 904 | CA | THR A | 240 | 48.236 | 48.229 | 23.953 | 1.00 | 32.48 | C |
| ATOM | 905 | C | THR A | 240 | 46.760 | 48.143 | 23.557 | 1.00 | 33.71 | C |
| ATOM | 906 | O | THR A | 240 | 45.885 | 48.393 | 24.383 | 1.00 | 33.65 | O |
| ATOM | 907 | CB | THR A | 240 | 48.448 | 49.491 | 24.792 | 1.00 | 32.03 | C |
| ATOM | 908 | OG1 | THR A | 240 | 48.264 | 50.635 | 23.957 | 1.00 | 31.61 | O |
| ATOM | 909 | CG2 | THR A | 240 | 49.862 | 49.526 | 25.366 | 1.00 | 31.27 | C |
| ATOM | 910 | N | ARG A | 241 | 46.484 | 47.782 | 22.305 | 1.00 | 34.92 | N |
| ATOM | 911 | CA | ARG A | 241 | 45.100 | 47.680 | 21.837 | 1.00 | 36.67 | C |
| ATOM | 912 | C | ARG A | 241 | 44.578 | 46.259 | 21.614 | 1.00 | 36.73 | C |
| ATOM | 913 | O | ARG A | 241 | 43.619 | 45.848 | 22.262 | 1.00 | 36.77 | O |
| ATOM | 914 | CB | ARG A | 241 | 44.909 | 48.494 | 20.552 | 1.00 | 37.87 | C |
| ATOM | 915 | CG | ARG A | 241 | 44.891 | 50.010 | 20.755 | 1.00 | 40.48 | C |
| ATOM | 916 | CD | ARG A | 241 | 44.875 | 50.729 | 19.409 | 1.00 | 42.72 | C |
| ATOM | 917 | NE | ARG A | 241 | 44.876 | 52.188 | 19.522 | 1.00 | 44.49 | N |
| ATOM | 918 | CZ | ARG A | 241 | 43.818 | 52.916 | 19.866 | 1.00 | 45.58 | C |
| ATOM | 919 | NE1 | ARG A | 241 | 42.661 | 52.325 | 20.140 | 1.00 | 46.47 | N |
| ATOM | 920 | NH2 | ARG A | 241 | 43.909 | 54.239 | 19.912 | 1.00 | 45.69 | N |
| ATOM | 921 | N | ASP A | 242 | 45.202 | 45.505 | 20.713 | 1.00 | 36.96 | N |
| ATOM | 922 | CA | ASP A | 242 | 44.732 | 44.148 | 20.424 | 1.00 | 37.70 | C |
| ATOM | 923 | C | ASP A | 242 | 45.537 | 43.008 | 21.051 | 1.00 | 37.72 | C |
| ATOM | 924 | O | ASP A | 242 | 45.525 | 41.888 | 20.540 | 1.00 | 38.14 | O |
| ATOM | 925 | CB | ASP A | 242 | 44.663 | 43.927 | 18.904 | 1.00 | 37.89 | C |
| ATOM | 926 | CG | ASP A | 242 | 46.025 | 44.024 | 18.225 | 1.00 | 38.50 | C |
| ATOM | 927 | OD1 | ASP A | 242 | 47.055 | 43.712 | 18.866 | 1.00 | 38.41 | O |
| ATOM | 928 | OD2 | ASP A | 242 | 46.066 | 44.394 | 17.029 | 1.00 | 38.58 | O |
| ATOM | 929 | N | PHE A | 243 | 46.210 | 43.287 | 22.163 | 1.00 | 37.60 | N |
| ATOM | 930 | CA | PHE A | 243 | 47.043 | 42.293 | 22.838 | 1.00 | 37.44 | C |
| ATOM | 931 | C | PHE A | 243 | 46.355 | 41.022 | 23.339 | 1.00 | 37.84 | C |
| ATOM | 932 | O | PHE A | 243 | 46.992 | 39.970 | 23.425 | 1.00 | 37.47 | O |
| ATOM | 933 | CB | PHE A | 243 | 47.796 | 42.957 | 23.996 | 1.00 | 36.54 | C |
| ATOM | 934 | CG | PHE A | 243 | 46.903 | 43.587 | 25.022 | 1.00 | 35.45 | C |
| ATOM | 935 | CD1 | PHE A | 243 | 46.382 | 42.833 | 26.066 | 1.00 | 35.41 | C |
| ATOM | 936 | CD2 | PHE A | 243 | 46.594 | 44.940 | 24.955 | 1.00 | 35.12 | C |
| ATOM | 937 | CE1 | PHE A | 243 | 45.566 | 43.416 | 27.033 | 1.00 | 34.98 | C |
| ATOM | 938 | CE2 | PHE A | 243 | 45.780 | 45.534 | 25.916 | 1.00 | 35.22 | C |
| ATOM | 939 | CZ | PHE A | 243 | 45.265 | 44.769 | 26.959 | 1.00 | 35.05 | C |
| ATOM | 940 | N | ARG A | 244 | 45.072 | 41.114 | 23.675 | 1.00 | 38.36 | N |
| ATOM | 941 | CA | ARG A | 244 | 44.337 | 39.949 | 24.163 | 1.00 | 38.96 | C |
| ATOM | 942 | C | ARG A | 244 | 44.291 | 38.857 | 23.099 | 1.00 | 39.31 | C |
| ATOM | 943 | O | ARG A | 244 | 44.140 | 37.676 | 23.413 | 1.00 | 39.37 | O |
| ATOM | 944 | CB | ARG A | 244 | 42.913 | 40.340 | 24.579 | 1.00 | 38.87 | C |
| ATOM | 945 | CG | ARG A | 244 | 42.863 | 41.345 | 25.722 | 1.00 | 38.92 | C |
| ATOM | 946 | CD | ARG A | 244 | 41.440 | 41.607 | 26.189 | 1.00 | 38.85 | C |
| ATOM | 947 | NE | ARG A | 244 | 41.389 | 42.595 | 27.267 | 1.00 | 39.27 | N |
| ATOM | 948 | CZ | ARG A | 244 | 41.572 | 43.902 | 27.095 | 1.00 | 39.54 | C |
| ATOM | 949 | NH1 | ARG A | 244 | 41.816 | 44.388 | 25.885 | 1.00 | 39.23 | N |
| ATOM | 950 | NH2 | ARG A | 244 | 41.510 | 44.725 | 28.135 | 1.00 | 39.60 | N |
| ATOM | 951 | N | GLU A | 245 | 44.422 | 39.257 | 21.839 | 1.00 | 39.62 | N |
| ATOM | 952 | CA | GLU A | 245 | 44.413 | 38.300 | 20.742 | 1.00 | 39.94 | C |
| ATOM | 953 | C | GLU A | 245 | 45.822 | 38.091 | 20.183 | 1.00 | 39.41 | C |
| ATOM | 954 | O | GLU A | 245 | 46.214 | 36.965 | 19.873 | 1.00 | 39.17 | O |
| ATOM | 955 | CB | GLU.A | 245 | 43.477 | 38.772 | 19.618 | 1.00 | 41.18 | C |
| ATOM | 956 | CG | GLU A | 245 | 41.987 | 38.670 | 19.955 | 1.00 | 43.82 | C |
| ATOM | 957 | CD | GLU A | 245 | 41.479 | 39.800 | 20.848 | 1.00 | 45.62 | C |
| ATOM | 958 | OE1 | GLU A | 245 | 40.433 | 39.604 | 21.510 | 1.00 | 46.25 | O |
| ATOM | 959 | OE2 | GLU A | 245 | 42.105 | 40.889 | 20.881 | 1.00 | 46.89 | O |
| ATOM | 960 | N | ARG A | 246 | 46.584 | 39.177 | 20.067 | 1.00 | 38.53 | N |
| ATOM | 961 | CA | ARG A | 246 | 47.940 | 39.103 | 19.528 | 1.00 | 37.66 | C |
| ATOM | 962 | C | ARG A | 246 | 48.908 | 38.320 | 20.415 | 1.00 | 37.14 | C |
| ATOM | 963 | O | ARG A | 246 | 49.651 | 37.469 | 19.931 | 1.00 | 37.14 | O |
| ATOM | 964 | CB | ARG A | 246 | 48.490 | 40.516 | 19.287 | 1.00 | 36.94 | C |
| ATOM | 965 | CG | ARG A | 246 | 49.819 | 40.546 | 18.536 | 1.00 | 36.46 | C |
| ATOM | 966 | CD | ARG A | 246 | 50.278 | 41.970 | 18.276 | 1.00 | 35.96 | C |
| ATOM | 967 | NE | ARG A | 246 | 49.341 | 42.724 | 17.441 | 1.00 | 35.46 | N |
| ATOM | 968 | CZ | ARG A | 246 | 49.311 | 42.687 | 16.111 | 1.00 | 35.16 | C |
| ATOM | 969 | NH1 | ARG A | 246 | 50.170 | 41.932 | 15.441 | 1.00 | 34.77 | N |
| ATOM | 970 | NH2 | ARG A | 246 | 48.421 | 43.417 | 15.448 | 1.00 | 35.59 | N |
| ATOM | 971 | N | VAL A | 247 | 48.896 | 38.599 | 21.714 | 1.00 | 36.70 | N |
| ATOM | 972 | CA | VAL A | 247 | 49.802 | 37.919 | 22.630 | 1.00 | 36.48 | C |
| ATOM | 973 | C | VAL A | 247 | 49.701 | 36.389 | 22.572 | 1.00 | 36.82 | C |

TABLE 5-continued

| ATOM | 974 | O | VAL A | 247 | 50.702 | 35.710 | 22.328 | 1.00 | 36.60 | O |
|---|---|---|---|---|---|---|---|---|---|---|
| ATOM | 975 | CB | VAL A | 247 | 49.589 | 38.404 | 24.087 | 1.00 | 35.99 | C |
| ATOM | 976 | CG1 | VAL A | 247 | 50.425 | 37.578 | 25.042 | 1.00 | 35.65 | C |
| ATOM | 977 | CG2 | VAL A | 247 | 49.969 | 39.877 | 24.202 | 1.00 | 35.85 | C |
| ATOM | 978 | N | PRO A | 248 | 48.497 | 35.824 | 22.800 | 1.00 | 36.88 | N |
| ATOM | 979 | CA | PRO A | 248 | 48.355 | 34.363 | 22.756 | 1.00 | 36.60 | C |
| ATOM | 980 | C | PRO A | 248 | 48.891 | 33.775 | 21.453 | 1.00 | 36.20 | C |
| ATOM | 981 | O | PRO A | 248 | 49.538 | 32.729 | 21.450 | 1.00 | 36.15 | O |
| ATOM | 982 | CB | PRO A | 248 | 46.850 | 34.163 | 22.920 | 1.00 | 36.98 | C |
| ATOM | 983 | CG | PRO A | 248 | 46.469 | 35.306 | 23.823 | 1.00 | 36.81 | C |
| ATOM | 984 | CD | PRO A | 248 | 47.223 | 36.459 | 23.192 | 1.00 | 36.48 | C |
| ATOM | 985 | N | ALA A | 249 | 48.626 | 34.465 | 20.349 | 1.00 | 36.16 | N |
| ATOM | 986 | CA | ALA A | 249 | 49.087 | 34.025 | 19.042 | 1.00 | 36.32 | C |
| ATOM | 987 | C | ALA A | 249 | 50.613 | 34.043 | 19.000 | 1.00 | 36.64 | C |
| ATOM | 988 | O | ALA A | 249 | 51.242 | 33.137 | 18.444 | 1.00 | 36.51 | O |
| ATOM | 989 | CB | ALA A | 249 | 48.517 | 34.931 | 17.959 | 1.00 | 36.44 | C |
| ATOM | 990 | N | LEU A | 250 | 51.206 | 35.076 | 19.596 | 1.00 | 36.66 | N |
| ATOM | 991 | CA | LEU A | 250 | 52.660 | 35.202 | 19.629 | 1.00 | 36.66 | C |
| ATOM | 992 | C | LEU A | 250 | 53.284 | 34.148 | 20.540 | 1.00 | 36.79 | C |
| ATOM | 993 | O | LEU A | 250 | 54.328 | 33.586 | 20.222 | 1.00 | 36.30 | O |
| ATOM | 994 | CB | LEU A | 250 | 53.062 | 36.610 | 20.090 | 1.00 | 36.33 | C |
| ATOM | 995 | CG | LEU A | 250 | 53.366 | 37.679 | 19.026 | 1.00 | 36.54 | C |
| ATOM | 996 | CD1 | LEU A | 250 | 52.849 | 37.266 | 17.658 | 1.00 | 36.13 | C |
| ATOM | 997 | CD2 | LEU A | 250 | 52.757 | 39.002 | 19.461 | 1.00 | 35.88 | C |
| ATOM | 998 | N | VAL A | 251 | 52.644 | 33.878 | 21.671 | 1.00 | 37.78 | N |
| ATOM | 999 | CA | VAL A | 251 | 53.166 | 32.875 | 22.593 | 1.00 | 39.09 | C |
| ATOM | 1000 | C | VAL A | 251 | 53.103 | 31.507 | 21.928 | 1.00 | 39.91 | C |
| ATOM | 1001 | O | VAL A | 251 | 54.069 | 30.745 | 21.961 | 1.00 | 40.18 | O |
| ATOM | 1002 | CB | VAL A | 251 | 52.358 | 32.829 | 23.907 | 1.00 | 38.94 | C |
| ATOM | 1003 | CG1 | VAL A | 251 | 52.815 | 31.651 | 24.761 | 1.00 | 39.25 | C |
| ATOM | 1004 | CG2 | VAL A | 251 | 52.545 | 34.126 | 24.674 | 1.00 | 39.03 | C |
| ATOM | 1005 | N | GLU A | 252 | 51.963 | 31.200 | 21.317 | 1.00 | 40.90 | N |
| ATOM | 1006 | CA | GLU A | 252 | 51.794 | 29.918 | 20.642 | 1.00 | 41.65 | C |
| ATOM | 1007 | C | GLU A | 252 | 52.801 | 29.762 | 19.504 | 1.00 | 40.64 | C |
| ATOM | 1008 | O | GLU A | 252 | 53.293 | 28.666 | 19.251 | 1.00 | 40.83 | O |
| ATOM | 1009 | CB | GLU A | 252 | 50.370 | 29.784 | 20.095 | 1.00 | 43.45 | C |
| ATOM | 1010 | CG | GLU A | 252 | 49.477 | 28.839 | 20.889 | 1.00 | 46.51 | C |
| ATOM | 1011 | CD | GLU A | 252 | 49.239 | 29.298 | 22.318 | 1.00 | 48.31 | C |
| ATOM | 1012 | OE1 | GLU A | 252 | 48.600 | 30.359 | 22.512 | 1.00 | 49.25 | O |
| ATOM | 1013 | OE2 | GLU A | 252 | 49.691 | 28.589 | 23.249 | 1.00 | 49.10 | O |
| ATOM | 1014 | N | ALA A | 253 | 53.103 | 30.864 | 18.822 | 1.00 | 39.42 | N |
| ATOM | 1015 | CA | ALA A | 253 | 54.051 | 30.844 | 17.714 | 1.00 | 38.09 | C |
| ATOM | 1016 | C | ALA A | 253 | 55.488 | 30.617 | 18.189 | 1.00 | 37.51 | C |
| ATOM | 1017 | O | ALA A | 253 | 56.377 | 30.344 | 17.380 | 1.00 | 37.32 | O |
| ATOM | 1018 | CB | ALA A | 253 | 53.961 | 32.137 | 16.931 | 1.00 | 37.90 | C |
| ATOM | 1019 | N | GLY A | 254 | 55.715 | 30.740 | 19.495 | 1.00 | 36.62 | N |
| ATOM | 1020 | CA | GLY A | 254 | 57.048 | 30.521 | 20.033 | 1.00 | 35.88 | C |
| ATOM | 1021 | C | GLY A | 254 | 57.879 | 31.754 | 20.366 | 1.00 | 35.36 | C |
| ATOM | 1022 | O | GLY A | 254 | 59.072 | 31.632 | 20.651 | 1.00 | 34.95 | O |
| ATOM | 1023 | N | ALA A | 255 | 57.270 | 32.938 | 20.330 | 1.00 | 34.50 | N |
| ATOM | 1024 | CA | ALA A | 255 | 57.994 | 34.166 | 20.649 | 1.00 | 33.48 | C |
| ATOM | 1025 | C | ALA A | 255 | 58.659 | 34.025 | 22.019 | 1.00 | 32.88 | C |
| ATOM | 1026 | O | ALA A | 255 | 58.016 | 33.663 | 23.000 | 1.00 | 32.47 | O |
| ATOM | 1027 | CB | ALA A | 255 | 57.039 | 35.352 | 20.644 | 1.00 | 33.55 | C |
| ATOM | 1028 | N | ASP A | 256 | 59.954 | 34.309 | 22.079 | 1.00 | 32.31 | N |
| ATOM | 1029 | CA | ASP A | 256 | 60.703 | 34.185 | 23.323 | 1.00 | 31.81 | C |
| ATOM | 1030 | C | ASP A | 256 | 60.518 | 35.367 | 24.266 | 1.00 | 31.12 | C |
| ATOM | 1031 | O | ASP A | 256 | 60.649 | 35.232 | 25.481 | 1.00 | 30.65 | O |
| ATOM | 1032 | CB | ASP A | 256 | 62.181 | 33.994 | 22.999 | 1.00 | 31.98 | C |
| ATOM | 1033 | CG | ASP A | 256 | 62.425 | 32.745 | 22.182 | 1.00 | 32.65 | C |
| ATOM | 1034 | OD1 | ASP A | 256 | 62.295 | 31.643 | 22.749 | 1.00 | 33.20 | O |
| ATOM | 1035 | OD2 | ASP A | 256 | 62.725 | 32.860 | 20.975 | 1.00 | 32.82 | O |
| ATOM | 1036 | N | VAL A | 257 | 60.211 | 36.526 | 23.700 | 1.00 | 30.48 | N |
| ATOM | 1037 | CA | VAL A | 257 | 60.007 | 37.722 | 24.500 | 1.00 | 29.85 | C |
| ATOM | 1038 | C | VAL A | 257 | 59.153 | 38.696 | 23.708 | 1.00 | 29.52 | C |
| ATOM | 1039 | O | VAL A | 257 | 59.158 | 38.683 | 22.477 | 1.00 | 29.18 | O |
| ATOM | 1040 | CB | VAL A | 257 | 61.359 | 38.398 | 24.867 | 1.00 | 29.74 | C |
| ATOM | 1041 | CG1 | VAL A | 257 | 62.118 | 38.768 | 23.603 | 1.00 | 29.96 | C |
| ATOM | 1042 | CG2 | VAL A | 257 | 61.116 | 39.636 | 25.721 | 1.00 | 29.25 | C |
| ATOM | 1043 | N | LEU A | 258 | 58.410 | 39.530 | 24.422 | 1.00 | 28.83 | N |
| ATOM | 1044 | CA | LEU A | 258 | 57.556 | 40.513 | 23.785 | 1.00 | 28.70 | C |
| ATOM | 1045 | C | LEU A | 258 | 57.993 | 41.899 | 24.238 | 1.00 | 28.49 | C |
| ATOM | 1046 | O | LEU A | 258 | 58.752 | 42.041 | 25.198 | 1.00 | 28.65 | O |
| ATOM | 1047 | CB | LEU A | 258 | 56.094 | 40.289 | 24.189 | 1.00 | 28.62 | C |
| ATOM | 1048 | CG | LEU A | 258 | 55.534 | 38.871 | 24.065 | 1.00 | 29.10 | C |
| ATOM | 1049 | CD1 | LEU A | 258 | 54.122 | 38.855 | 24.605 | 1.00 | 29.34 | C |
| ATOM | 1050 | CD2 | LEU A | 258 | 55.573 | 38.407 | 22.610 | 1.00 | 29.01 | C |
| ATOM | 1051 | N | CYS A | 259 | 57.527 | 42.920 | 23.535 | 1.00 | 27.96 | N |
| ATOM | 1052 | CA | CYS A | 259 | 57.840 | 44.286 | 23.914 | 1.00 | 27.94 | C |

TABLE 5-continued

| | | | | | | | | | | |
|---|---|---|---|---|---|---|---|---|---|---|
| ATOM | 1053 | C | CYS A | 259 | 56.759 | 45.216 | 23.403 | 1.00 | 27.70 | C |
| ATOM | 1054 | O | CYS A | 259 | 56.475 | 45.257 | 22.209 | 1.00 | 27.35 | O |
| ATOM | 1055 | CB | CYS A | 259 | 59.198 | 44.730 | 23.358 | 1.00 | 27.38 | C |
| ATOM | 1056 | SG | CYS A | 259 | 59.725 | 46.331 | 24.021 | 1.00 | 26.82 | S |
| ATOM | 1057 | N | ILE A | 260 | 56.143 | 45.950 | 24.320 | 1.00 | 28.21 | N |
| ATOM | 1058 | CA | ILE A | 260 | 55.108 | 46.898 | 23.943 | 1.00 | 28.49 | C |
| ATOM | 1059 | C | ILE A | 260 | 55.815 | 48.001 | 23.168 | 1.00 | 29.26 | C |
| ATOM | 1060 | O | ILE A | 260 | 56.769 | 48.615 | 23.657 | 1.00 | 28.86 | O |
| ATOM | 1061 | CB | ILE A | 260 | 54.421 | 47.483 | 25.182 | 1.00 | 28.21 | C |
| ATOM | 1062 | CG1 | ILE A | 260 | 53.792 | 46.346 | 25.994 | 1.00 | 27.85 | C |
| ATOM | 1063 | CG2 | ILE A | 260 | 53.373 | 48.510 | 24.761 | 1.00 | 27.76 | C |
| ATOM | 1064 | CD1 | ILE A | 260 | 53.275 | 46.763 | 27.351 | 1.00 | 27.51 | C |
| ATOM | 1065 | N | ASP A | 261 | 55.344 | 48.233 | 21.951 | 1.00 | 29.87 | N |
| ATOM | 1066 | CA | ASP A | 261 | 55.920 | 49.224 | 21.062 | 1.00 | 30.69 | C |
| ATOM | 1067 | C | ASP A | 261 | 55.160 | 50.552 | 21.108 | 1.00 | 31.35 | C |
| ATOM | 1068 | O | ASP A | 261 | 54.046 | 50.659 | 20.597 | 1.00 | 31.90 | O |
| ATOM | 1069 | CB | ASP A | 261 | 55.934 | 48.632 | 19.651 | 1.00 | 31.21 | C |
| ATOM | 1070 | CG | ASP A | 261 | 56.417 | 49.603 | 18.599 | 1.00 | 31.62 | C |
| ATOM | 1071 | OD1 | ASP A | 261 | 57.220 | 50.508 | 18.913 | 1.00 | 31.79 | O |
| ATOM | 1072 | OD2 | ASP A | 261 | 55.997 | 49.438 | 17.437 | 1.00 | 32.40 | O |
| ATOM | 1073 | N | SER A | 262 | 55.767 | 51.562 | 21.727 | 1.00 | 31.57 | N |
| ATOM | 1074 | CA | SER A | 262 | 55.136 | 52.876 | 21.843 | 1.00 | 32.25 | C |
| ATOM | 1075 | C | SER A | 262 | 56.162 | 53.984 | 22.056 | 1.00 | 32.15 | C |
| ATOM | 1076 | O | SER A | 262 | 57.250 | 53.730 | 22.574 | 1.00 | 32.40 | O |
| ATOM | 1077 | CB | SER A | 262 | 54.146 | 52.871 | 23.012 | 1.00 | 32.42 | C |
| ATOM | 1078 | OG | SER A | 262 | 53.637 | 54.171 | 23.261 | 1.00 | 33.43 | O |
| ATOM | 1079 | N | SER A | 263 | 55.818 | 55.212 | 21.665 | 1.00 | 31.88 | N |
| ATOM | 1080 | CA | SER A | 263 | 56.734 | 56.331 | 21.847 | 1.00 | 31.98 | C |
| ATOM | 1081 | C | SER A | 263 | 56.658 | 56.839 | 23.280 | 1.00 | 31.45 | C |
| ATOM | 1082 | O | SER A | 263 | 57.683 | 57.118 | 23.898 | 1.00 | 32.24 | O |
| ATOM | 1083 | CB | SER A | 263 | 56.433 | 57.465 | 20.859 | 1.00 | 32.64 | C |
| ATOM | 1084 | OG | SER A | 263 | 55.121 | 57.971 | 20.999 | 1.00 | 35.89 | O |
| ATOM | 1085 | N | ASP A | 264 | 55.447 | 56.941 | 23.814 | 1.00 | 30.33 | N |
| ATOM | 1086 | CA | ASP A | 264 | 55.253 | 57.394 | 25.189 | 1.00 | 29.38 | C |
| ATOM | 1087 | C | ASP A | 264 | 54.694 | 56.241 | 26.026 | 1.00 | 28.76 | C |
| ATOM | 1088 | O | ASP A | 264 | 53.481 | 56.036 | 26.093 | 1.00 | 28.66 | O |
| ATOM | 1089 | CB | ASP A | 264 | 54.298 | 58.597 | 25.215 | 1.00 | 29.24 | C |
| ATOM | 1090 | CG | ASP A | 264 | 53.927 | 59.037 | 26.632 | 1.00 | 29.06 | C |
| ATOM | 1091 | OD1 | ASP A | 264 | 54.618 | 58.666 | 27.606 | 1.00 | 28.24 | O |
| ATOM | 1092 | OD2 | ASP A | 264 | 52.935 | 59.780 | 26.763 | 1.00 | 28.61 | O |
| ATOM | 1093 | N | GLY A | 265 | 55.594 | 55.497 | 26.664 | 1.00 | 27.72 | N |
| ATOM | 1094 | CA | GLY A | 265 | 55.194 | 54.358 | 27.474 | 1.00 | 26.80 | C |
| ATOM | 1095 | C | GLY A | 265 | 54.724 | 54.700 | 28.874 | 1.00 | 26.32 | C |
| ATOM | 1096 | O | GLY A | 265 | 54.304 | 53.815 | 29.622 | 1.00 | 25.26 | O |
| ATOM | 1097 | N | PHE A | 266 | 54.800 | 55.978 | 29.238 | 1.00 | 26.32 | N |
| ATOM | 1098 | CA | PHE A | 266 | 54.358 | 56.418 | 30.555 | 1.00 | 26.48 | C |
| ATOM | 1099 | C | PHE A | 266 | 52.841 | 56.551 | 30.402 | 1.00 | 27.26 | C |
| ATOM | 1100 | O | PHE A | 266 | 52.277 | 57.642 | 30.427 | 1.00 | 26.89 | O |
| ATOM | 1101 | CB | PHE A | 266 | 55.000 | 57.764 | 30.903 | 1.00 | 26.26 | C |
| ATOM | 1102 | CG | PHE A | 266 | 55.074 | 58.045 | 32.388 | 1.00 | 26.33 | C |
| ATOM | 1103 | CD1 | PHE A | 266 | 54.336 | 57.289 | 33.301 | 1.00 | 25.12 | C |
| ATOM | 1104 | CD2 | PHE A | 266 | 55.866 | 59.089 | 32.867 | 1.00 | 25.66 | C |
| ATOM | 1105 | CE1 | PHE A | 266 | 54.385 | 57.569 | 34.664 | 1.00 | 25.49 | C |
| ATOM | 1106 | CE2 | PHE A | 266 | 55.922 | 59.378 | 34.228 | 1.00 | 24.95 | C |
| ATOM | 1107 | CZ | PHE A | 266 | 55.179 | 58.617 | 35.131 | 1.00 | 25.18 | C |
| ATOM | 1108 | N | SER A | 267 | 52.195 | 55.403 | 30.239 | 1.00 | 28.41 | N |
| ATOM | 1109 | CA | SER A | 267 | 50.764 | 55.334 | 30.010 | 1.00 | 29.17 | C |
| ATOM | 1110 | C | SER A | 267 | 50.084 | 54.224 | 30.791 | 1.00 | 29.72 | C |
| ATOM | 1111 | O | SER A | 267 | 50.659 | 53.155 | 31.012 | 1.00 | 29.22 | O |
| ATOM | 1112 | CB | SER A | 267 | 50.515 | 55.112 | 28.521 | 1.00 | 29.55 | C |
| ATOM | 1113 | OG | SER A | 267 | 49.162 | 54.792 | 28.269 | 1.00 | 31.97 | O |
| ATOM | 1114 | N | GLU A | 268 | 48.844 | 54.482 | 31.188 | 1.00 | 30.02 | N |
| ATOM | 1115 | CA | GLU A | 268 | 48.072 | 53.506 | 31.927 | 1.00 | 31.13 | C |
| ATOM | 1116 | C | GLU A | 268 | 47.767 | 52.325 | 31.005 | 1.00 | 31.03 | C |
| ATOM | 1117 | O | GLU A | 268 | 47.618 | 51.195 | 31.462 | 1.00 | 30.56 | O |
| ATOM | 1118 | CE | GLU A | 268 | 46.775 | 54.139 | 32.437 | 1.00 | 32.14 | C |
| ATOM | 1119 | CG | GLU A | 268 | 45.961 | 53.213 | 33.322 | 1.00 | 34.23 | C |
| ATOM | 1120 | CD | GLU A | 268 | 44.724 | 53.872 | 33.902 | 1.00 | 35.72 | C |
| ATOM | 1121 | OE1 | GLU A | 268 | 43.933 | 53.148 | 34.551 | 1.00 | 36.93 | O |
| ATOM | 1122 | OE2 | GLU A | 268 | 44.542 | 55.099 | 33.717 | 1.00 | 35.59 | O |
| ATOM | 1123 | N | TRP A | 269 | 47.688 | 52.592 | 29.703 | 1.00 | 31.57 | N |
| ATOM | 1124 | CA | TRP A | 269 | 47.414 | 51.539 | 28.730 | 1.00 | 32.18 | C |
| ATOM | 1125 | C | TRP A | 269 | 48.488 | 50.453 | 28.800 | 1.00 | 32.07 | C |
| ATOM | 1126 | O | TRP A | 269 | 48.194 | 49.266 | 28.661 | 1.00 | 32.37 | O |
| ATOM | 1127 | CB | TRP A | 269 | 47.347 | 52.109 | 27.309 | 1.00 | 32.84 | C |
| ATOM | 1128 | CG | TRP A | 269 | 46.211 | 53.064 | 27.085 | 1.00 | 34.12 | C |
| ATOM | 1129 | CD1 | TRP A | 269 | 46.306 | 54.401 | 26.827 | 1.00 | 34.63 | C |
| ATOM | 1130 | CD2 | TRP A | 269 | 44.807 | 52.761 | 27.114 | 1.00 | 34.88 | C |
| ATOM | 1132 | NE1 | TRP A | 269 | 45.051 | 54.950 | 26.694 | 1.00 | 35.25 | N |

TABLE 5-continued

| | | | | | | | | | | |
|---|---|---|---|---|---|---|---|---|---|---|
| ATOM | 1132 | CE2 | TRP A | 269 | 44.114 | 53.966 | 26.866 | 1.00 | 34.78 | C |
| ATOM | 1133 | CE3 | TRP A | 269 | 44.068 | 51.587 | 27.325 | 1.00 | 35.27 | C |
| ATOM | 1134 | CZ2 | TRP A | 269 | 42.717 | 54.035 | 26.823 | 1.00 | 35.56 | C |
| ATOM | 1135 | CZ3 | TRP A | 269 | 42.675 | 51.655 | 27.284 | 1.00 | 35.55 | C |
| ATOM | 1136 | CH2 | TRP A | 269 | 42.017 | 52.872 | 27.035 | 1.00 | 35.57 | C |
| ATOM | 1137 | N | GLN A | 270 | 49.736 | 50.855 | 29.013 | 1.00 | 31.69 | N |
| ATOM | 1138 | CA | GLN A | 270 | 50.808 | 49.875 | 29.114 | 1.00 | 31.74 | C |
| ATOM | 1139 | C | GLN A | 270 | 50.720 | 49.115 | 30.430 | 1.00 | 31.80 | C |
| ATOM | 1140 | O | GLN A | 270 | 51.002 | 47.916 | 30.480 | 1.00 | 32.05 | O |
| ATOM | 1141 | CB | GLN A | 270 | 52.179 | 50.544 | 28.965 | 1.00 | 30.95 | C |
| ATOM | 1142 | CG | GLN A | 270 | 52.461 | 50.929 | 27.526 | 1.00 | 30.42 | C |
| ATOM | 1143 | CD | GLN A | 270 | 53.936 | 50.960 | 27.191 | 1.00 | 29.71 | C |
| ATOM | 1144 | OE1 | GLN A | 270 | 54.755 | 50.317 | 27.851 | 1.00 | 28.19 | O |
| ATOM | 1145 | NE2 | GLN A | 270 | 54.278 | 51.691 | 26.141 | 1.00 | 28.75 | N |
| ATOM | 1146 | N | LYS A | 271 | 50.325 | 49.803 | 31.495 | 1.00 | 31.92 | N |
| ATOM | 1147 | CA | LYS A | 271 | 50.192 | 49.138 | 32.781 | 1.00 | 32.22 | C |
| ATOM | 1148 | C | LYS A | 271 | 49.114 | 48.065 | 32.643 | 1.00 | 31.72 | C |
| ATOM | 1149 | O | LYS A | 271 | 49.265 | 46.949 | 33.135 | 1.00 | 31.50 | O |
| ATOM | 1150 | CB | LYS A | 271 | 49.795 | 50.131 | 33.872 | 1.00 | 32.96 | C |
| ATOM | 1151 | CG | LYS A | 271 | 49.476 | 49.448 | 35.190 | 1.00 | 34.60 | C |
| ATOM | 1152 | CD | LYS A | 271 | 49.184 | 50.433 | 36.301 | 1.00 | 36.08 | C |
| ATOM | 1153 | CE | LYS A | 271 | 48.928 | 49.688 | 37.605 | 1.00 | 37.48 | C |
| ATOM | 1154 | NZ | LYS A | 271 | 48.792 | 50.615 | 38.769 | 1.00 | 39.24 | N |
| ATOM | 1155 | N | ILE A | 272 | 48.031 | 48.421 | 31.959 | 1.00 | 31.65 | N |
| ATOM | 1156 | CA | ILE A | 272 | 46.919 | 47.511 | 31.733 | 1.00 | 31.59 | C |
| ATOM | 1157 | C | ILE A | 272 | 47.351 | 46.309 | 30.904 | 1.00 | 31.68 | C |
| ATOM | 1158 | O | ILE A | 272 | 46.967 | 45.182 | 31.203 | 1.00 | 31.84 | O |
| ATOM | 1159 | CB | ThE A | 272 | 45.751 | 48.232 | 31.025 | 1.00 | 31.59 | C |
| ATOM | 1160 | CG1 | ILE A | 272 | 45.058 | 49.167 | 32.018 | 1.00 | 30.96 | C |
| ATOM | 1161 | CG2 | ILE A | 272 | 44.761 | 47.214 | 30.452 | 1.00 | 31.15 | C |
| ATOM | 1162 | CD1 | ILE A | 272 | 44.109 | 50.157 | 31.367 | 1.00 | 30.73 | C |
| ATOM | 1163 | N | THR A | 273 | 48.151 | 46.548 | 29.869 | 1.00 | 31.76 | N |
| ATOM | 1164 | CA | THR A | 273 | 48.634 | 45.465 | 29.015 | 1.00 | 31.96 | C |
| ATOM | 1165 | C | THR A | 273 | 49.536 | 44.497 | 29.788 | 1.00 | 32.26 | C |
| ATOM | 1166 | O | THR A | 273 | 49.374 | 43.280 | 29.695 | 1.00 | 32.32 | O |
| ATOM | 1167 | CB | THR A | 273 | 49.406 | 46.020 | 27.806 | 1.00 | 32.10 | C |
| ATOM | 1168 | OG1 | THR A | 273 | 48.522 | 46.813 | 27.004 | 1.00 | 32.10 | O |
| ATOM | 1169 | CG2 | THR A | 273 | 49.970 | 44.890 | 26.960 | 1.00 | 32.28 | C |
| ATOM | 1170 | N | ILE A | 274 | 50.487 | 45.030 | 30.548 | 1.00 | 32.22 | N |
| ATOM | 1171 | CA | ILE A | 274 | 51.377 | 44.176 | 31.328 | 1.00 | 32.21 | C |
| ATOM | 1172 | C | ILE A | 274 | 50.558 | 43.401 | 32.366 | 1.00 | 32.57 | C |
| ATOM | 1173 | O | ILE A | 274 | 50.783 | 42.212 | 32.590 | 1.00 | 32.28 | O |
| ATOM | 1174 | CB | ILE A | 274 | 52.445 | 44.999 | 32.071 | 1.00 | 31.88 | C |
| ATOM | 1175 | CG1 | ILE A | 274 | 53.279 | 45.802 | 31.070 | 1.00 | 31.35 | C |
| ATOM | 1176 | CG2 | ILE A | 274 | 53.332 | 44.068 | 32.899 | 1.00 | 31.40 | C |
| ATOM | 1177 | CD1 | ILE A | 274 | 54.276 | 46.749 | 31.724 | 1.00 | 31.35 | C |
| ATOM | 1178 | N | GLY A | 275 | 49.610 | 44.089 | 32.994 | 1.00 | 32.79 | N |
| ATOM | 1179 | CA | GLY A | 275 | 48.772 | 43.454 | 33.994 | 1.00 | 33.65 | C |
| ATOM | 1180 | C | GLY A | 275 | 47.998 | 42.274 | 33.438 | 1.00 | 33.76 | C |
| ATOM | 1181 | O | GLY A | 275 | 47.845 | 41.251 | 34.103 | 1.00 | 34.32 | O |
| ATOM | 1182 | N | TRP A | 276 | 47.505 | 42.412 | 32.214 | 1.00 | 33.77 | N |
| ATOM | 1183 | CA | TRP A | 276 | 46.752 | 41.341 | 31.580 | 1.00 | 34.23 | C |
| ATOM | 1184 | C | TRP A | 276 | 47.677 | 40.152 | 31.331 | 1.00 | 34.65 | C |
| ATOM | 1185 | O | TRP A | 276 | 47.293 | 39.001 | 31.536 | 1.00 | 34.89 | O |
| ATOM | 1186 | CB | TRP A | 276 | 46.163 | 41.821 | 30.253 | 1.00 | 34.33 | C |
| ATOM | 1187 | CG | TRP A | 276 | 45.278 | 40.809 | 29.591 | 1.00 | 34.90 | C |
| ATOM | 1188 | CD1 | TRP A | 276 | 43.932 | 40.639 | 29.784 | 1.00 | 34.76 | C |
| ATOM | 1189 | CD2 | TRP A | 276 | 45.675 | 39.817 | 28.635 | 1.00 | 34.98 | C |
| ATOM | 1190 | NE1 | TRP A | 276 | 43.469 | 39.604 | 29.003 | 1.00 | 34.35 | N |
| ATOM | 1191 | CE2 | TRP A | 276 | 44.516 | 39.082 | 28.289 | 1.00 | 34.87 | C |
| ATOM | 1192 | CE3 | TRP A | 276 | 46.898 | 39.476 | 28.038 | 1.00 | 35.16 | C |
| ATOM | 1193 | CZ2 | TRP A | 276 | 44.545 | 38.026 | 27.368 | 1.00 | 35.33 | C |
| ATOM | 1194 | CZ3 | TRP A | 276 | 46.927 | 38.425 | 27.122 | 1.00 | 35.14 | C |
| ATOM | 1195 | CH2 | TRP A | 276 | 45.755 | 37.713 | 26.797 | 1.00 | 35.58 | C |
| ATOM | 1196 | N | ILE A | 277 | 48.900 | 40.435 | 30.890 | 1.00 | 34.66 | N |
| ATOM | 1197 | CA | ILE A | 277 | 49.868 | 39.381 | 30.620 | 1.00 | 34.37 | C |
| ATOM | 1198 | C | ILE A | 277 | 50.227 | 38.622 | 31.900 | 1.00 | 35.02 | C |
| ATOM | 1199 | O | ILE A | 277 | 50.350 | 37.399 | 31.891 | 1.00 | 34.44 | O |
| ATOM | 1200 | CE | ILE A | 277 | 51.146 | 39.961 | 29.972 | 1.00 | 33.65 | C |
| ATOM | 1201 | CG1 | ILE A | 277 | 50.802 | 40.550 | 28.604 | 1.00 | 33.07 | C |
| ATOM | 1202 | CG2 | ILE A | 277 | 52.206 | 38.877 | 29.823 | 1.00 | 32.69 | C |
| ATOM | 1203 | CD1 | ILE A | 277 | 51.952 | 41.268 | 27.926 | 1.00 | 32.85 | C |
| ATOM | 1204 | N | ARG A | 278 | 50.390 | 39.346 | 33.001 | 1.00 | 36.08 | N |
| ATOM | 1205 | CA | ARG A | 278 | 50.722 | 38.713 | 34.275 | 1.00 | 37.93 | C |
| ATOM | 1206 | C | ARG A | 278 | 49.570 | 37.835 | 34.757 | 1.00 | 39.10 | C |
| ATOM | 1207 | O | ARG A | 278 | 49.778 | 36.704 | 35.192 | 1.00 | 39.55 | O |
| ATOM | 1208 | CB | ARG A | 278 | 51.037 | 39.774 | 35.334 | 1.00 | 37.11 | C |
| ATOM | 1209 | CG | ARG A | 278 | 52.342 | 40.499 | 35.106 | 1.00 | 36.58 | C |
| ATOM | 1210 | CD | ARG A | 278 | 53.533 | 39.574 | 35.306 | 1.00 | 36.31 | C |

TABLE 5-continued

| | | | | | | | | | | |
|---|---|---|---|---|---|---|---|---|---|---|
| ATOM | 1211 | NE | ARG A | 278 | 54.770 | 40.224 | 34.883 | 1.00 | 35.73 | N |
| ATOM | 1212 | CZ | ARG A | 278 | 55.478 | 39.861 | 33.819 | 1.00 | 35.12 | C |
| ATOM | 1213 | NH1 | ARG A | 278 | 55.079 | 38.840 | 33.072 | 1.00 | 33.98 | N |
| ATOM | 1214 | NH2 | ARG A | 278 | 56.569 | 40.539 | 33.487 | 1.00 | 34.31 | N |
| ATOM | 1215 | N | GLU A | 279 | 48.356 | 38.367 | 34.669 | 1.00 | 40.86 | N |
| ATOM | 1216 | CA | GLU A | 279 | 47.157 | 37.654 | 35.089 | 1.00 | 42.25 | C |
| ATOM | 1217 | C | GLU A | 279 | 46.961 | 36.339 | 34.331 | 1.00 | 42.65 | C |
| ATOM | 1218 | O | GLU A | 279 | 46.500 | 35.352 | 34.900 | 1.00 | 42.50 | O |
| ATOM | 1219 | CB | GLU A | 279 | 45.931 | 38.556 | 34.894 | 1.00 | 43.71 | C |
| ATOM | 1220 | CG | GLU A | 279 | 44.582 | 37.864 | 35.074 | 1.00 | 46.30 | C |
| ATOM | 1221 | CD | GLU A | 279 | 43.398 | 38.825 | 34.946 | 1.00 | 48.03 | C |
| ATOM | 1222 | OE1 | GLU A | 279 | 43.314 | 39.555 | 33.928 | 1.00 | 48.89 | O |
| ATOM | 1223 | OE2 | GLU A | 279 | 42.544 | 38.844 | 35.863 | 1.00 | 48.40 | O |
| ATOM | 1224 | N | LYS A | 280 | 47.324 | 36.319 | 33.055 | 1.00 | 42.53 | N |
| ATOM | 1225 | CA | LYS A | 280 | 47.144 | 35.116 | 32.255 | 1.00 | 42.83 | C |
| ATOM | 1226 | C | LYS A | 280 | 48.356 | 34.188 | 32.182 | 1.00 | 42.50 | C |
| ATOM | 1227 | O | LYS A | 280 | 48.201 | 32.975 | 32.047 | 1.00 | 42.55 | O |
| ATOM | 1228 | CB | LYS A | 280 | 46.723 | 35.499 | 30.834 | 1.00 | 43.85 | C |
| ATOM | 1229 | CG | LYS A | 280 | 46.229 | 34.321 | 30.008 | 1.00 | 45.53 | C |
| ATOM | 1230 | CD | LYS A | 280 | 45.821 | 34.743 | 28.602 | 1.00 | 46.52 | C |
| ATOM | 1231 | CE | LYS A | 280 | 45.103 | 33.612 | 27.871 | 1.00 | 46.76 | C |
| ATOM | 1232 | NZ | LYS A | 280 | 45.916 | 32.367 | 27.837 | 1.00 | 47.35 | N |
| ATOM | 1233 | N | TYR A | 281 | 49.557 | 34.749 | 32.287 | 1.00 | 41.56 | N |
| ATOM | 1234 | CA | TYR A | 281 | 50.771 | 33.949 | 32.172 | 1.00 | 40.39 | C |
| ATOM | 1235 | C | TYR A | 281 | 51.738 | 34.039 | 33.341 | 1.00 | 40.00 | C |
| ATOM | 1236 | O | TYR A | 281 | 52.746 | 33.335 | 33.360 | 1.00 | 39.98 | O |
| ATOM | 1237 | CB | TYR A | 281 | 51.530 | 34.355 | 30.910 | 1.00 | 40.02 | C |
| ATOM | 1238 | CG | TYR A | 281 | 50.757 | 34.204 | 29.625 | 1.00 | 39.56 | C |
| ATOM | 1239 | CD1 | TYR A | 281 | 50.552 | 32.949 | 29.056 | 1.00 | 39.41 | C |
| ATOM | 1240 | CD2 | TYR A | 281 | 50.255 | 35.322 | 28.957 | 1.00 | 39.51 | C |
| ATOM | 1241 | CE1 | TYR A | 281 | 49.873 | 32.809 | 27.853 | 1.00 | 39.24 | C |
| ATOM | 1242 | CE2 | TYR A | 281 | 49.571 | 35.193 | 27.752 | 1.00 | 39.30 | C |
| ATOM | 1243 | CZ | TYR A | 281 | 49.386 | 33.933 | 27.206 | 1.00 | 39.40 | C |
| ATOM | 1244 | OH | TYR A | 281 | 48.722 | 33.794 | 26.012 | 1.00 | 39.81 | O |
| ATOM | 1245 | N | GLY A | 282 | 51.444 | 34.892 | 34.313 | 1.00 | 39.64 | N |
| ATOM | 1246 | CA | GLY A | 282 | 52.365 | 35.045 | 35.422 | 1.00 | 39.49 | C |
| ATOM | 1247 | C | GLY A | 282 | 53.673 | 35.588 | 34.863 | 1.00 | 39.77 | C |
| ATOM | 1248 | O | GLY A | 282 | 53.665 | 36.379 | 33.916 | 1.00 | 39.23 | O |
| ATOM | 1249 | N | ASP A | 283 | 54.796 | 35.156 | 35.427 | 1.00 | 39.96 | N |
| ATOM | 1250 | CA | ASP A | 283 | 56.105 | 35.611 | 34.968 | 1.00 | 40.22 | C |
| ATOM | 1251 | C | ASP A | 283 | 56.709 | 34.682 | 33.916 | 1.00 | 39.77 | C |
| ATOM | 1252 | O | ASP A | 283 | 57.905 | 34.745 | 33.638 | 1.00 | 40.01 | O |
| ATOM | 1253 | CB | ASP A | 283 | 57.063 | 35.737 | 36.157 | 1.00 | 41.08 | C |
| ATOM | 1254 | CG | ASP A | 283 | 56.660 | 36.845 | 37.118 | 1.00 | 42.76 | C |
| ATOM | 1255 | OD1 | ASP A | 283 | 56.621 | 38.024 | 36.696 | 1.00 | 43.36 | O |
| ATOM | 1256 | OD2 | ASP A | 283 | 56.381 | 36.541 | 38.300 | 1.00 | 43.92 | O |
| ATOM | 1257 | N | LYS A | 284 | 55.882 | 33.825 | 33.328 | 1.00 | 39.38 | N |
| ATOM | 1258 | CA | LYS A | 284 | 56.354 | 32.887 | 32.314 | 1.00 | 39.05 | C |
| ATOM | 1259 | C | LYS A | 284 | 56.482 | 33.538 | 30.937 | 1.00 | 37.99 | C |
| ATOM | 1260 | O | LYS A | 284 | 57.178 | 33.026 | 30.061 | 1.00 | 38.55 | O |
| ATOM | 1261 | CB | LYS A | 284 | 55.416 | 31.678 | 32.234 | 1.00 | 40.57 | C |
| ATOM | 1262 | CG | LYS A | 284 | 55.327 | 30.866 | 33.526 | 1.00 | 42.45 | C |
| ATOM | 1263 | CD | LYS A | 284 | 56.686 | 30.300 | 33.930 | 1.00 | 44.18 | C |
| ATOM | 1264 | CE | LYS A | 284 | 56.559 | 29.340 | 35.112 | 1.00 | 45.45 | C |
| ATOM | 1265 | NZ | LYS A | 284 | 57.886 | 28.778 | 35.524 | 1.00 | 46.66 | N |
| ATOM | 1266 | N | VAL A | 285 | 55.793 | 34.655 | 30.741 | 1.00 | 36.07 | N |
| ATOM | 1267 | CA | VAL A | 285 | 55.863 | 35.383 | 29.482 | 1.00 | 34.18 | C |
| ATOM | 1268 | C | VAL A | 285 | 56.556 | 36.709 | 29.781 | 1.00 | 33.12 | C |
| ATOM | 1269 | O | VAL A | 285 | 56.094 | 37.486 | 30.619 | 1.00 | 32.87 | O |
| ATOM | 1270 | CB | VAL A | 285 | 54.453 | 35.630 | 28.899 | 1.00 | 33.89 | C |
| ATOM | 1271 | CG1 | VAL A | 285 | 54.520 | 36.625 | 27.749 | 1.00 | 33.39 | C |
| ATOM | 1272 | CG2 | VAL A | 285 | 53.868 | 34.311 | 28.408 | 1.00 | 33.56 | C |
| ATOM | 1273 | N | LYS A | 286 | 57.676 | 36.951 | 29.108 | 1.00 | 32.14 | N |
| ATOM | 1274 | CA | LYSA | 286 | 58.457 | 38.171 | 29.313 | 1.00 | 31.09 | C |
| ATOM | 1275 | C | LYS A | 286 | 57.988 | 39.305 | 28.407 | 1.00 | 30.39 | C |
| ATOM | 1276 | O | LYS A | 286 | 57.751 | 39.107 | 27.216 | 1.00 | 29.75 | O |
| ATOM | 1277 | CB | LYS A | 286 | 59.943 | 37.885 | 29.067 | 1.00 | 31.10 | C |
| ATOM | 1278 | CG | LYS A | 286 | 60.484 | 36.696 | 29.857 | 1.00 | 31.07 | C |
| ATOM | 1279 | CD | LYS A | 286 | 60.260 | 36.865 | 31.357 | 1.00 | 31.03 | C |
| ATOM | 1280 | CE | LYS A | 286 | 60.845 | 35.697 | 32.145 | 1.00 | 31.38 | C |
| ATOM | 1281 | NZ | LYS A | 286 | 60.578 | 35.811 | 33.619 | 1.00 | 31.84 | N |
| ATOM | 1282 | N | VAL A | 287 | 57.858 | 40.498 | 28.980 | 1.00 | 29.67 | N |
| ATOM | 1283 | CA | VAL A | 287 | 57.402 | 41.649 | 28.218 | 1.00 | 28.82 | C |
| ATOM | 1284 | C | VAL A | 287 | 58.123 | 42.952 | 28.571 | 1.00 | 28.35 | C |
| ATOM | 1285 | O | VAL A | 287 | 58.116 | 43.395 | 29.723 | 1.00 | 28.33 | O |
| ATOM | 1286 | CB | VAL A | 287 | 55.870 | 41.843 | 28.397 | 1.00 | 29.01 | C |
| ATOM | 1287 | CG1 | VAL A | 287 | 55.514 | 41.886 | 29.873 | 1.00 | 29.59 | C |
| ATOM | 1288 | CG2 | VAL A | 287 | 55.417 | 43.120 | 27.721 | 1.00 | 28.72 | C |
| ATOM | 1289 | N | GLY A | 288 | 58.754 | 43.555 | 27.568 | 1.00 | 27.62 | N |

TABLE 5-continued

| ATOM | 1290 | CA | GLY A | 288 | 59.441 | 44.817 | 27.771 | 1.00 | 26.79 | C |
|------|------|------|------|-----|--------|--------|--------|------|-------|---|
| ATOM | 1291 | C | GLY A | 288 | 58.434 | 45.938 | 27.573 | 1.00 | 26.65 | C |
| ATOM | 1292 | O | GLY A | 288 | 57.403 | 45.737 | 26.922 | 1.00 | 26.44 | O |
| ATOM | 1293 | N | ALA A | 289 | 58.721 | 47.112 | 28.128 | 1.00 | 26.17 | N |
| ATOM | 1294 | CA | ALA A | 289 | 57.820 | 48.255 | 28.012 | 1.00 | 26.19 | C |
| ATOM | 1295 | C | ALA A | 289 | 58.591 | 49.543 | 27.741 | 1.00 | 26.50 | C |
| ATOM | 1296 | O | ALA A | 289 | 59.810 | 49.593 | 27.900 | 1.00 | 26.69 | O |
| ATOM | 1297 | CB | ALA A | 289 | 56.994 | 48.401 | 29.291 | 1.00 | 26.59 | C |
| ATOM | 1298 | N | GLY A | 290 | 57.871 | 50.584 | 27.331 | 1.00 | 26.15 | N |
| ATOM | 1299 | CA | GLY A | 290 | 58.502 | 51.856 | 27.037 | 1.00 | 25.55 | C |
| ATOM | 1300 | C | GLY A | 290 | 57.745 | 52.567 | 25.930 | 1.00 | 25.64 | C |
| ATOM | 1301 | O | GLY A | 290 | 56.726 | 52.059 | 25.470 | 1.00 | 25.93 | O |
| ATOM | 1302 | N | ASN A | 291 | 58.246 | 53.712 | 25.468 | 1.00 | 24.68 | N |
| ATOM | 1303 | CA | ASN A | 291 | 59.491 | 54.295 | 25.961 | 1.00 | 24.17 | C |
| ATOM | 1304 | C | ASN A | 291 | 59.309 | 55.373 | 27.022 | 1.00 | 23.88 | C |
| ATOM | 1305 | O | ASN A | 291 | 58.278 | 56.041 | 27.078 | 1.00 | 24.05 | O |
| ATOM | 1306 | CB | ASN A | 291 | 60.279 | 54.883 | 24.788 | 1.00 | 23.44 | C |
| ATOM | 1307 | CG | ASN A | 291 | 60.771 | 53.819 | 23.840 | 1.00 | 24.01 | C |
| ATOM | 1308 | OD1 | ASN A | 291 | 60.266 | 52.695 | 23.849 | 1.00 | 24.09 | O |
| ATOM | 1309 | ND2 | ASN A | 291 | 61.756 | 54.162 | 23.012 | 1.00 | 22.58 | N |
| ATOM | 1310 | N | ILE A | 292 | 60.323 | 55.522 | 27.867 | 1.00 | 23.43 | N |
| ATOM | 1311 | CA | ILE A | 292 | 60.329 | 56.541 | 28.906 | 1.00 | 23.67 | C |
| ATOM | 1312 | C | ILE A | 292 | 61.706 | 57.220 | 28.861 | 1.00 | 23.76 | C |
| ATOM | 1313 | O | ILE A | 292 | 62.642 | 56.688 | 28.247 | 1.00 | 23.31 | O |
| ATOM | 1314 | CB | ILE A | 292 | 60.033 | 55.936 | 30.324 | 1.00 | 23.51 | C |
| ATOM | 1315 | CG1 | ILE A | 292 | 60.898 | 54.703 | 30.594 | 1.00 | 23.67 | C |
| ATOM | 1316 | CG2 | ILE A | 292 | 58.561 | 55.563 | 30.426 | 1.00 | 23.40 | C |
| ATOM | 1317 | CD1 | ILE A | 292 | 62.342 | 55.009 | 30.958 | 1.00 | 23.64 | C |
| ATOM | 1318 | N | VAL A | 293 | 61.823 | 58.393 | 29.481 | 1.00 | 23.36 | N |
| ATOM | 1319 | CA | VAL A | 293 | 63.084 | 59.137 | 29.478 | 1.00 | 23.68 | C |
| ATOM | 1320 | C | VAL A | 293 | 63.490 | 59.686 | 30.844 | 1.00 | 24.18 | C |
| ATOM | 1321 | O | VAL A | 293 | 64.459 | 60.439 | 30.946 | 1.00 | 24.31 | O |
| ATOM | 1322 | CB | VAL A | 293 | 63.033 | 60.329 | 28.480 | 1.00 | 23.27 | C |
| ATOM | 1323 | CG1 | VAL A | 293 | 62.966 | 59.815 | 27.047 | 1.00 | 22.91 | C |
| ATOM | 1324 | CG2 | VAL A | 293 | 61.823 | 61.209 | 28.776 | 1.00 | 22.79 | C |
| ATOM | 1325 | N | ASP A | 294 | 62.750 | 59.328 | 31.889 | 1.00 | 24.54 | N |
| ATOM | 1326 | CA | ASP A | 294 | 63.095 | 59.794 | 33.227 | 1.00 | 25.28 | C |
| ATOM | 1327 | C | ASP A | 294 | 62.808 | 58.743 | 34.300 | 1.00 | 25.54 | C |
| ATOM | 1328 | O | ASP A | 294 | 62.245 | 57.688 | 34.013 | 1.00 | 25.69 | O |
| ATOM | 1329 | CB | ASP A | 294 | 62.372 | 61.120 | 33.544 | 1.00 | 24.98 | C |
| ATOM | 1330 | CG | ASP A | 294 | 60.862 | 60.962 | 33.726 | 1.00 | 25.49 | C |
| ATOM | 1331 | OD1 | ASP A | 294 | 60.290 | 59.921 | 33.347 | 1.00 | 26.22 | O |
| ATOM | 1332 | OD2 | ASP A | 294 | 60.238 | 61.911 | 34.244 | 1.00 | 25.60 | O |
| ATOM | 1333 | N | GLY A | 295 | 63.221 | 59.031 | 35.531 | 1.00 | 26.27 | N |
| ATOM | 1334 | CA | GLY A | 295 | 63.008 | 58.106 | 36.628 | 1.00 | 26.98 | C |
| ATOM | 1335 | C | GLY A | 295 | 61.553 | 57.787 | 36.914 | 1.00 | 27.45 | C |
| ATOM | 1336 | O | GLY A | 295 | 61.216 | 56.643 | 37.216 | 1.00 | 27.19 | O |
| ATOM | 1337 | N | GLU A | 296 | 60.686 | 58.793 | 36.829 | 1.00 | 28.15 | N |
| ATOM | 1338 | CA | GLU A | 296 | 59.263 | 58.582 | 37.084 | 1.00 | 29.28 | C |
| ATOM | 1339 | C | GLU A | 296 | 58.669 | 57.578 | 36.110 | 1.00 | 28.28 | C |
| ATOM | 1340 | O | GLU A | 296 | 57.908 | 56.705 | 36.508 | 1.00 | 28.87 | O |
| ATOM | 1341 | CB | GLU A | 296 | 58.477 | 59.889 | 36.959 | 1.00 | 31.29 | C |
| ATOM | 1342 | CG | GLU A | 296 | 58.771 | 60.920 | 38.014 | 1.00 | 35.34 | C |
| ATOM | 1343 | CD | GLU A | 296 | 57.900 | 62.166 | 37.866 | 1.00 | 38.57 | C |
| ATOM | 1344 | OE1 | GLU A | 296 | 58.213 | 63.169 | 38.544 | 1.00 | 40.66 | O |
| ATOM | 1345 | OE2 | GLU A | 296 | 56.910 | 62.148 | 37.081 | 1.00 | 39.48 | O |
| ATOM | 1346 | N | GLY A | 297 | 58.996 | 57.728 | 34.830 | 1.00 | 27.39 | N |
| ATOM | 1347 | CA | GLY A | 297 | 58.482 | 56.819 | 33.821 | 1.00 | 26.83 | C |
| ATOM | 1348 | C | GLY A | 297 | 58.997 | 55.406 | 34.032 | 1.00 | 26.40 | C |
| ATOM | 1349 | O | GLY A | 297 | 58.261 | 54.436 | 33.850 | 1.00 | 26.39 | O |
| ATOM | 1350 | N | PHE A | 298 | 60.270 | 55.292 | 34.399 | 1.00 | 25.90 | N |
| ATOM | 1351 | CA | PHE A | 298 | 60.886 | 53.992 | 34.667 | 1.00 | 25.89 | C |
| ATOM | 1352 | C | PHE A | 298 | 60.156 | 53.324 | 35.825 | 1.00 | 26.26 | C |
| ATOM | 1353 | O | PHE A | 298 | 59.741 | 52.173 | 35.736 | 1.00 | 26.46 | O |
| ATOM | 1354 | CB | PHE A | 298 | 62.356 | 54.158 | 35.073 | 1.00 | 24.63 | C |
| ATOM | 1355 | CG | PHE A | 298 | 62.973 | 52.900 | 35.625 | 1.00 | 24.52 | C |
| ATOM | 1356 | CD1 | PHE A | 298 | 63.510 | 51.935 | 34.774 | 1.00 | 24.45 | C |
| ATOM | 1357 | CD2 | PHE A | 298 | 62.948 | 52.642 | 36.993 | 1.00 | 24.69 | C |
| ATOM | 1358 | CE1 | PHE A | 298 | 64.004 | 50.729 | 35.283 | 1.00 | 24.11 | C |
| ATOM | 1359 | CE2 | PHE A | 298 | 63.438 | 51.441 | 37.506 | 1.00 | 24.45 | C |
| ATOM | 1360 | CZ | PHE A | 298 | 63.965 | 50.485 | 36.648 | 1.00 | 24.01 | C |
| ATOM | 1361 | N | ARG A | 299 | 60.038 | 54.071 | 36.917 | 1.00 | 26.97 | N |
| ATOM | 1362 | CA | ARG A | 299 | 59.392 | 53.627 | 38.148 | 1.00 | 27.76 | C |
| ATOM | 1363 | C | ARG A | 299 | 57.979 | 53.112 | 37.896 | 1.00 | 27.50 | C |
| ATOM | 1364 | O | ARG A | 299 | 57.575 | 52.073 | 38.432 | 1.00 | 27.02 | O |
| ATOM | 1365 | CB | ARG A | 299 | 59.368 | 54.798 | 39.134 | 1.00 | 29.28 | C |
| ATOM | 1366 | CG | ARG A | 299 | 58.488 | 54.625 | 40.354 | 1.00 | 32.58 | C |
| ATOM | 1367 | CD | ARG A | 299 | 59.185 | 53.881 | 41.472 | 1.00 | 34.72 | C |
| ATOM | 1368 | NE | ARG A | 299 | 60.450 | 54.500 | 41.869 | 1.00 | 36.94 | N |

TABLE 5-continued

| | | | | | | | | | | |
|---|---|---|---|---|---|---|---|---|---|---|
| ATOM | 1369 | CZ | ARG A | 299 | 61.175 | 54.093 | 42.911 | 1.00 | 37.49 | C |
| ATOM | 1370 | NH1 | ARG A | 299 | 60.748 | 53.081 | 43.656 | 1.00 | 37.79 | N |
| ATOM | 1371 | NH2 | ARG A | 299 | 62.336 | 54.671 | 43.191 | 1.00 | 37.51 | N |
| ATOM | 1372 | N | TYR A | 300 | 57.228 | 53.840 | 37.076 | 1.00 | 26.42 | N |
| ATOM | 1373 | CA | TYR A | 300 | 55.867 | 53.448 | 36.764 | 1.00 | 26.07 | C |
| ATOM | 1374 | C | TYR A | 300 | 55.807 | 52.106 | 36.028 | 1.00 | 25.82 | C |
| ATOM | 1375 | O | TYR A | 300 | 54.967 | 51.263 | 36.332 | 1.00 | 25.66 | O |
| ATOM | 1376 | CB | TYR A | 300 | 55.194 | 54.517 | 35.905 | 1.00 | 26.47 | C |
| ATOM | 1377 | CG | TYR A | 300 | 53.740 | 54.220 | 35.612 | 1.00 | 26.10 | C |
| ATOM | 1378 | CD1 | TYR A | 300 | 52.755 | 54.430 | 36.583 | 1.00 | 25.70 | C |
| ATOM | 1379 | CD2 | TYR A | 300 | 53.349 | 53.726 | 34.367 | 1.00 | 25.87 | C |
| ATOM | 1380 | CE1 | TYR A | 300 | 51.413 | 54.157 | 36.318 | 1.00 | 25.69 | C |
| ATOM | 1381 | CE2 | TYR A | 300 | 52.013 | 53.450 | 34.092 | 1.00 | 26.08 | C |
| ATOM | 1382 | CZ | TYR A | 300 | 51.052 | 53.671 | 35.069 | 1.00 | 26.05 | C |
| ATOM | 1383 | OH | TYR A | 300 | 49.729 | 53.428 | 34.780 | 1.00 | 26.67 | O |
| ATOM | 1384 | N | LEU A | 301 | 56.687 | 51.912 | 35.054 | 1.00 | 24.94 | N |
| ATOM | 1385 | CA | LEU A | 301 | 56.686 | 50.667 | 34.297 | 1.00 | 24.79 | C |
| ATOM | 1386 | C | LEU A | 301 | 57.290 | 49.516 | 35.104 | 1.00 | 25.13 | C |
| ATOM | 1387 | O | LEU A | 301 | 56.933 | 48.356 | 34.910 | 1.00 | 24.72 | O |
| ATOM | 1388 | CD | LEU A | 301 | 57.422 | 50.860 | 32.965 | 1.00 | 23.46 | C |
| ATOM | 1389 | CG | LEU A | 301 | 56.676 | 51.797 | 31.998 | 1.00 | 22.90 | C |
| ATOM | 1390 | CD1 | LEU A | 301 | 57.460 | 51.938 | 30.687 | 1.00 | 21.27 | C |
| ATOM | 1391 | CD2 | LEU A | 301 | 55.273 | 51.237 | 31.726 | 1.00 | 22.01 | C |
| ATOM | 1392 | N | ALA A | 302 | 58.194 | 49.844 | 36.020 | 1.00 | 25.45 | N |
| ATOM | 1393 | CA | ALA A | 302 | 58.803 | 48.828 | 36.867 | 1.00 | 26.43 | C |
| ATOM | 1394 | C | ALA A | 302 | 57.718 | 48.269 | 37.802 | 1.00 | 27.00 | C |
| ATOM | 1395 | O | ALA A | 302 | 57.551 | 47.053 | 37.912 | 1.00 | 26.60 | O |
| ATOM | 1396 | CD | ALA A | 302 | 59.944 | 49.433 | 37.676 | 1.00 | 25.79 | C |
| ATOM | 1397 | N | ASP A | 303 | 56.976 | 49.163 | 38.456 | 1.00 | 27.78 | N |
| ATOM | 1398 | CA | ASP A | 303 | 55.911 | 48.748 | 39.366 | 1.00 | 28.82 | C |
| ATOM | 1399 | C | ASP A | 303 | 54.817 | 48.007 | 38.606 | 1.00 | 29.16 | C |
| ATOM | 1400 | O | ASP A | 303 | 54.177 | 47.115 | 39.157 | 1.00 | 30.06 | O |
| ATOM | 1401 | CD | ASP A | 303 | 55.287 | 49.948 | 40.100 | 1.00 | 29.58 | C |
| ATOM | 1402 | CG | ASP A | 303 | 56.218 | 50.565 | 41.138 | 1.00 | 31.14 | C |
| ATOM | 1403 | OD1 | ASP A | 303 | 57.081 | 49.848 | 41.693 | 1.00 | 31.95 | O |
| ATOM | 1404 | OD2 | ASP A | 303 | 56.070 | 51.774 | 41.417 | 1.00 | 32.16 | O |
| ATOM | 1405 | N | ALA A | 304 | 54.594 | 48.382 | 37.348 | 1.00 | 28.83 | N |
| ATOM | 1406 | CA | ALA A | 304 | 53.581 | 47.721 | 36.531 | 1.00 | 28.20 | C |
| ATOM | 1407 | C | ALA A | 304 | 54.008 | 46.288 | 36.197 | 1.00 | 28.33 | C |
| ATOM | 1408 | O | ALA A | 304 | 53.179 | 45.461 | 35.818 | 1.00 | 28.02 | O |
| ATOM | 1409 | CD | ALA A | 304 | 53.343 | 48.499 | 35.260 | 1.00 | 27.85 | C |
| ATOM | 1410 | N | GLY A | 305 | 55.303 | 46.001 | 36.316 | 1.00 | 28.12 | N |
| ATOM | 1411 | CA | GLY A | 305 | 55.777 | 44.649 | 36.051 | 1.00 | 27.69 | C |
| ATOM | 1412 | C | GLY A | 305 | 56.626 | 44.386 | 34.820 | 1.00 | 27.36 | C |
| ATOM | 1413 | O | GLY A | 305 | 56.891 | 43.228 | 34.486 | 1.00 | 27.45 | O |
| ATOM | 1414 | N | ALA A | 306 | 57.064 | 45.439 | 34.141 | 1.00 | 26.93 | N |
| ATOM | 1415 | CA | ALA A | 306 | 57.884 | 45.268 | 32.945 | 1.00 | 26.72 | C |
| ATOM | 1416 | C | ALA A | 306 | 59.144 | 44.438 | 33.220 | 1.00 | 26.12 | C |
| ATOM | 1417 | O | ALA A | 306 | 59.759 | 44.557 | 34.277 | 1.00 | 26.19 | O |
| ATOM | 1418 | CB | ALA A | 306 | 58.271 | 46.642 | 32.382 | 1.00 | 26.69 | C |
| ATOM | 1419 | N | ASP A | 307 | 59.521 | 43.595 | 32.263 | 1.00 | 26.12 | N |
| ATOM | 1420 | CA | ASP A | 307 | 60.716 | 42.763 | 32.392 | 1.00 | 25.75 | C |
| ATOM | 1421 | C | ASP A | 307 | 61.976 | 43.541 | 31.989 | 1.00 | 25.56 | C |
| ATOM | 1422 | O | ASP A | 307 | 63.084 | 43.221 | 32.414 | 1.00 | 25.02 | O |
| ATOM | 1423 | CD | ASP A | 307 | 60.550 | 41.494 | 31.556 | 1.00 | 25.88 | C |
| ATOM | 1424 | CG | ASP A | 307 | 59.605 | 40.503 | 32.210 | 1.00 | 26.34 | C |
| ATOM | 1425 | OD1 | ASP A | 307 | 59.941 | 40.031 | 33.316 | 1.00 | 25.65 | O |
| ATOM | 1426 | OD2 | ASP A | 307 | 58.532 | 40.208 | 31.639 | 1.00 | 26.39 | O |
| ATOM | 1427 | N | PHE A | 308 | 61.791 | 44.553 | 31.148 | 1.00 | 25.21 | N |
| ATOM | 1428 | CA | PHE A | 308 | 62.872 | 45.435 | 30.739 | 1.00 | 25.37 | C |
| ATOM | 1429 | C | PHE A | 308 | 62.207 | 46.715 | 30.251 | 1.00 | 25.54 | C |
| ATOM | 1430 | O | PHE A | 308 | 61.096 | 46.689 | 29.718 | 1.00 | 26.05 | O |
| ATOM | 1431 | CD | PHE A | 308 | 63.803 | 44.781 | 29.692 | 1.00 | 24.85 | C |
| ATOM | 1432 | CG | PHE A | 308 | 63.254 | 44.722 | 28.286 | 1.00 | 25.59 | C |
| ATOM | 1433 | CD1 | PHE A | 308 | 63.202 | 45.866 | 27.488 | 1.00 | 25.36 | C |
| ATOM | 1434 | CD2 | PHE A | 308 | 62.863 | 43.499 | 27.730 | 1.00 | 25.52 | C |
| ATOM | 1435 | CE1 | PHE A | 308 | 62.776 | 45.789 | 26.158 | 1.00 | 25.87 | C |
| ATOM | 1436 | CE2 | PHE A | 308 | 62.435 | 43.413 | 26.397 | 1.00 | 25.33 | C |
| ATOM | 1437 | CZ | PHE A | 308 | 62.393 | 44.558 | 25.611 | 1.00 | 25.03 | C |
| ATOM | 1438 | N | ILE A | 309 | 62.860 | 47.844 | 30.490 | 1.00 | 25.29 | N |
| ATOM | 1439 | CA | ILE A | 309 | 62.293 | 49.126 | 30.118 | 1.00 | 25.21 | C |
| ATOM | 1440 | C | ILE A | 309 | 63.119 | 49.820 | 29.041 | 1.00 | 24.80 | C |
| ATOM | 1441 | O | ILE A | 309 | 64.338 | 49.945 | 29.152 | 1.00 | 24.39 | O |
| ATOM | 1442 | CD | ILE A | 309 | 62.124 | 50.001 | 31.390 | 1.00 | 25.06 | C |
| ATOM | 1443 | CG1 | ILE A | 309 | 61.045 | 49.356 | 32.280 | 1.00 | 24.71 | C |
| ATOM | 1444 | CG2 | ILE A | 309 | 61.743 | 51.429 | 31.018 | 1.00 | 24.45 | C |
| ATOM | 1445 | CD1 | ILE A | 309 | 60.990 | 49.849 | 33.715 | 1.00 | 23.70 | C |
| ATOM | 1446 | N | LYS A | 310 | 62.430 | 50.249 | 27.988 | 1.00 | 24.64 | N |
| ATOM | 1447 | CA | LYS A | 310 | 63.066 | 50.895 | 26.850 | 1.00 | 24.86 | C |

TABLE 5-continued

| | | | | | | | | | | |
|---|---|---|---|---|---|---|---|---|---|---|
| ATOM | 1448 | C | LYS A | 310 | 63.134 | 52.416 | 27.024 | 1.00 | 24.46 | C |
| ATOM | 1449 | O | LYS A | 310 | 62.146 | 53.060 | 27.373 | 1.00 | 24.21 | O |
| ATOM | 1450 | CD | LYS A | 310 | 62.311 | 50.509 | 25.574 | 1.00 | 25.07 | C |
| ATOM | 1451 | CG | LYS A | 310 | 63.177 | 50.404 | 24.340 | 1.00 | 25.07 | C |
| ATOM | 1452 | CD | LYS A | 310 | 62.769 | 49.218 | 23.461 | 1.00 | 25.06 | C |
| ATOM | 1453 | CE | LYS A | 310 | 61.376 | 49.398 | 22.850 | 1.00 | 25.52 | C |
| ATOM | 1454 | NZ | LYS A | 310 | 61.267 | 50.678 | 22.090 | 1.00 | 25.01 | N |
| ATOM | 1455 | N | ILE A | 311 | 64.316 | 52.971 | 26.768 | 1.00 | 24.00 | N |
| ATOM | 1456 | CA | ILE A | 311 | 64.571 | 54.401 | 26.925 | 1.00 | 23.52 | C |
| ATOM | 1457 | C | ILE A | 311 | 64.715 | 55.166 | 25.613 | 1.00 | 23.91 | C |
| ATOM | 1458 | O | ILE A | 311 | 65.486 | 54.776 | 24.737 | 1.00 | 23.10 | O |
| ATOM | 1459 | CB | ILE A | 311 | 65.883 | 54.643 | 27.715 | 1.00 | 22.79 | C |
| ATOM | 1460 | CG1 | ILE A | 311 | 65.828 | 53.933 | 29.070 | 1.00 | 22.26 | C |
| ATOM | 1461 | CG2 | ILE A | 311 | 66.121 | 56.146 | 27.878 | 1.00 | 21.49 | C |
| ATOM | 1462 | CD1 | ILE A | 311 | 67.200 | 53.802 | 29.751 | 1.00 | 21.78 | C |
| ATOM | 1463 | N | GLY A | 312 | 63.991 | 56.270 | 25.484 | 1.00 | 24.94 | N |
| ATOM | 1464 | CA | GLY A | 312 | 64.137 | 57.058 | 24.280 | 1.00 | 26.52 | C |
| ATOM | 1465 | C | GLY A | 312 | 62.921 | 57.644 | 23.599 | 1.00 | 28.07 | C |
| ATOM | 1466 | O | GLY A | 312 | 62.052 | 56.925 | 23.108 | 1.00 | 27.43 | O |
| ATOM | 1467 | N | ILE A | 313 | 62.876 | 58.971 | 23.575 | 1.00 | 30.06 | N |
| ATOM | 1468 | CA | ILE A | 313 | 61.819 | 59.715 | 22.907 | 1.00 | 32.43 | C |
| ATOM | 1469 | C | ILE A | 313 | 62.497 | 60.917 | 22.262 | 1.00 | 34.74 | C |
| ATOM | 1470 | O | ILE A | 313 | 63.031 | 61.788 | 22.954 | 1.00 | 33.88 | O |
| ATOM | 1471 | CB | ILE A | 313 | 60.745 | 60.229 | 23.881 | 1.00 | 32.08 | C |
| ATOM | 1472 | CG1 | ILE A | 313 | 60.029 | 59.055 | 24.554 | 1.00 | 31.93 | C |
| ATOM | 1473 | CG2 | ILE A | 313 | 59.735 | 61.071 | 23.117 | 1.00 | 32.14 | C |
| ATOM | 1474 | CD1 | ILE A | 313 | 58.970 | 59.481 | 25.560 | 1.00 | 31.83 | C |
| ATOM | 1475 | N | GLY A | 314 | 62.484 | 60.959 | 20.935 | 1.00 | 37.68 | N |
| ATOM | 1476 | CA | GLY A | 314 | 63.115 | 62.065 | 20.241 | 1.00 | 41.68 | C |
| ATOM | 1477 | C | GLY A | 314 | 64.614 | 61.848 | 20.205 | 1.00 | 44.77 | C |
| ATOM | 1478 | O | GLY A | 314 | 65.380 | 62.540 | 20.898 | 1.00 | 45.22 | O |
| ATOM | 1479 | N | GLY A | 315 | 65.025 | 60.864 | 19.406 | 1.00 | 46.78 | N |
| ATOM | 1480 | CA | GLY A | 315 | 66.432 | 60.539 | 19.265 | 1.00 | 49.14 | C |
| ATOM | 1481 | C | GLY A | 315 | 66.702 | 59.826 | 17.952 | 1.00 | 50.80 | C |
| ATOM | 1482 | O | GLY A | 315 | 67.732 | 60.057 | 17.310 | 1.00 | 51.20 | O |
| ATOM | 1483 | N | GLY A | 316 | 65.774 | 58.962 | 17.547 | 1.00 | 52.08 | N |
| ATOM | 1484 | CA | GLY A | 316 | 65.934 | 58.224 | 16.304 | 1.00 | 53.45 | C |
| ATOM | 1485 | C | GLY A | 316 | 66.265 | 59.085 | 15.092 | 1.00 | 54.43 | C |
| ATOM | 1486 | O | GLY A | 316 | 66.109 | 60.310 | 15.124 | 1.00 | 54.52 | O |
| ATOM | 1487 | N | SER A | 317 | 66.718 | 58.437 | 14.019 | 1.00 | 55.17 | N |
| ATOM | 1488 | CA | SER A | 317 | 67.086 | 59.120 | 12.776 | 1.00 | 55.85 | C |
| ATOM | 1489 | C | SER A | 317 | 66.116 | 60.238 | 12.410 | 1.00 | 56.05 | C |
| ATOM | 1490 | O | SER A | 317 | 66.224 | 60.838 | 11.338 | 1.00 | 56.24 | O |
| ATOM | 1491 | CB | SER A | 317 | 67.152 | 58.117 | 11.618 | 1.00 | 56.06 | C |
| ATOM | 1492 | OG | SER A | 317 | 68.116 | 57.109 | 11.864 | 1.00 | 56.47 | O |
| ATOM | 1493 | N | ARG A | 322 | 60.666 | 65.002 | 18.046 | 1.00 | 69.94 | N |
| ATOM | 1494 | CA | ARG A | 322 | 60.632 | 66.036 | 19.075 | 1.00 | 69.88 | C |
| ATOM | 1495 | C | ARG A | 322 | 60.442 | 67.421 | 18.458 | 1.00 | 69.25 | C |
| ATOM | 1496 | O | ARG A | 322 | 59.992 | 68.357 | 19.123 | 1.00 | 69.33 | O |
| ATOM | 1497 | CB | ARG A | 322 | 61.922 | 65.990 | 19.904 | 1.00 | 70.76 | C |
| ATOM | 1498 | CG | ARG A | 322 | 63.200 | 66.013 | 19.077 | 1.00 | 72.26 | C |
| ATOM | 1499 | CD | ARG A | 322 | 64.412 | 65.622 | 19.916 | 1.00 | 73.59 | C |
| ATOM | 1500 | NE | ARG A | 322 | 65.616 | 65.472 | 19.098 | 1.00 | 75.09 | N |
| ATOM | 1501 | CZ | ARG A | 322 | 66.295 | 66.483 | 18.561 | 1.00 | 75.74 | C |
| ATOM | 1502 | NH1 | ARG A | 322 | 65.893 | 67.733 | 18.757 | 1.00 | 75.89 | N |
| ATOM | 1503 | NH2 | ARG A | 322 | 67.372 | 66.241 | 17.818 | 1.00 | 75.84 | N |
| ATOM | 1504 | N | GLU A | 323 | 60.786 | 67.544 | 17.180 | 1.00 | 68.34 | N |
| ATOM | 1505 | CA | GLU A | 323 | 60.638 | 68.805 | 16.466 | 1.00 | 66.98 | C |
| ATOM | 1506 | C | GLU A | 323 | 59.314 | 68.796 | 15.706 | 1.00 | 65.40 | C |
| ATOM | 1507 | O | GLU A | 323 | 59.205 | 69.339 | 14.603 | 1.00 | 65.33 | O |
| ATOM | 1508 | CB | GLU A | 323 | 61.805 | 69.003 | 15.495 | 1.00 | 68.07 | C |
| ATOM | 1509 | CG | GLU A | 323 | 63.168 | 69.072 | 16.178 | 1.00 | 69.20 | C |
| ATOM | 1510 | CD | GLU A | 323 | 64.322 | 69.148 | 15.188 | 1.00 | 70.01 | C |
| ATOM | 1511 | OE1 | GLU A | 323 | 64.371 | 70.116 | 14.393 | 1.00 | 70.24 | O |
| ATOM | 1512 | OE2 | GLU A | 323 | 65.181 | 68.238 | 15.209 | 1.00 | 70.24 | O |
| ATOM | 1513 | N | GLN A | 324 | 58.311 | 68.163 | 16.311 | 1.00 | 63.21 | N |
| ATOM | 1514 | CA | GLN A | 324 | 56.982 | 68.075 | 15.722 | 1.00 | 60.76 | C |
| ATOM | 1515 | C | GLN A | 324 | 55.916 | 68.047 | 16.814 | 1.00 | 58.40 | C |
| ATOM | 1516 | O | GLN A | 324 | 54.859 | 68.662 | 16.679 | 1.00 | 58.63 | O |
| ATOM | 1517 | CB | GLN A | 324 | 56.861 | 66.821 | 14.852 | 1.00 | 61.63 | C |
| ATOM | 1518 | CG | GLN A | 324 | 55.533 | 66.714 | 14.120 | 1.00 | 62.44 | C |
| ATOM | 1519 | CD | GLN A | 324 | 55.341 | 67.814 | 13.085 | 1.00 | 63.06 | C |
| ATOM | 1520 | OE1 | GLN A | 324 | 55.567 | 68.996 | 13.363 | 1.00 | 63.40 | O |
| ATOM | 1521 | NE2 | GLN A | 324 | 54.910 | 67.431 | 11.887 | 1.00 | 63.02 | N |
| ATOM | 1522 | N | LYS A | 325 | 56.193 | 67.329 | 17.897 | 1.00 | 55.16 | N |
| ATOM | 1523 | CA | LYS A | 325 | 55.246 | 67.250 | 19.001 | 1.00 | 51.62 | C |
| ATOM | 1524 | C | LYS A | 325 | 55.822 | 67.983 | 20.207 | 1.00 | 48.73 | C |
| ATOM | 1525 | O | LYS A | 325 | 55.092 | 68.412 | 21.099 | 1.00 | 48.29 | O |
| ATOM | 1526 | CB | LYS A | 325 | 54.962 | 65.789 | 19.347 | 1.00 | 52.41 | C |

TABLE 5-continued

| ATOM | 1527 | CG | LYS A | 325 | 53.645 | 65.576 | 20.063 | 1.00 | 52.70 | C |
| --- | --- | --- | --- | --- | --- | --- | --- | --- | --- | --- |
| ATOM | 1528 | CD | LYS A | 325 | 53.291 | 64.104 | 20.115 | 1.00 | 53.01 | C |
| ATOM | 1529 | CE | LYS A | 325 | 51.906 | 63.905 | 20.678 | 1.00 | 53.28 | C |
| ATOM | 1530 | NZ | LYS A | 325 | 51.527 | 62.469 | 20.681 | 1.00 | 54.05 | N |
| ATOM | 1531 | N | GLY A | 326 | 57.141 | 68.124 | 20.225 | 1.00 | 45.49 | N |
| ATOM | 1532 | CA | GLY A | 326 | 57.789 | 68.832 | 21.311 | 1.00 | 42.06 | C |
| ATOM | 1533 | C | GLY A | 326 | 58.097 | 68.028 | 22.558 | 1.00 | 39.58 | C |
| ATOM | 1534 | O | GLY A | 326 | 58.407 | 68.613 | 23.591 | 1.00 | 38.74 | O |
| ATOM | 1535 | N | ILE A | 327 | 58.002 | 66.703 | 22.478 | 1.00 | 37.33 | N |
| ATOM | 1536 | CA | ILE A | 327 | 58.302 | 65.861 | 23.629 | 1.00 | 35.54 | C |
| ATOM | 1537 | C | ILE A | 327 | 59.598 | 65.096 | 23.385 | 1.00 | 34.11 | C |
| ATOM | 1538 | O | ILE A | 327 | 59.911 | 64.723 | 22.256 | 1.00 | 33.94 | O |
| ATOM | 1539 | CB | ILE A | 327 | 57.165 | 64.836 | 23.936 | 1.00 | 35.64 | C |
| ATOM | 1540 | CG1 | ILE A | 327 | 57.042 | 63.815 | 22.807 | 1.00 | 35.72 | C |
| ATOM | 1541 | CG2 | ILE A | 327 | 55.837 | 65.563 | 24.130 | 1.00 | 35.90 | C |
| ATOM | 1542 | CD1 | ILE A | 327 | 56.106 | 62.650 | 23.131 | 1.00 | 36.15 | C |
| ATOM | 1543 | N | GLY A | 328 | 60.357 | 64.869 | 24.447 | 1.00 | 32.52 | N |
| ATOM | 1544 | CA | GLY A | 328 | 61.599 | 64.142 | 24.295 | 1.00 | 30.76 | C |
| ATOM | 1545 | C | GLY A | 328 | 62.680 | 64.581 | 25.260 | 1.00 | 29.34 | C |
| ATOM | 1546 | O | GLY A | 328 | 62.447 | 65.403 | 26.153 | 1.00 | 27.81 | O |
| ATOM | 1547 | N | ARG A | 329 | 63.874 | 64.030 | 25.066 | 1.00 | 27.97 | N |
| ATOM | 1548 | CA | ARG A | 329 | 65.008 | 64.343 | 25.919 | 1.00 | 27.02 | C |
| ATOM | 1549 | C | ARG A | 329 | 66.265 | 63.793 | 25.272 | 1.00 | 26.17 | C |
| ATOM | 1550 | O | ARG A | 329 | 66.222 | 62.730 | 24.657 | 1.00 | 26.57 | O |
| ATOM | 1551 | CB | ARG A | 329 | 64.813 | 63.691 | 27.295 | 1.00 | 26.66 | C |
| ATOM | 1552 | CG | ARG A | 329 | 65.752 | 64.198 | 28.374 | 1.00 | 25.97 | C |
| ATOM | 1553 | CD | ARG A | 329 | 65.514 | 63.470 | 29.688 | 1.00 | 26.09 | C |
| ATOM | 1554 | NE | ARG A | 329 | 65.797 | 64.324 | 30.835 | 1.00 | 26.17 | N |
| ATOM | 1555 | CZ | ARG A | 329 | 65.626 | 63.964 | 32.103 | 1.00 | 27.08 | C |
| ATOM | 1556 | NH1 | ARG A | 329 | 65.177 | 62.752 | 32.408 | 1.00 | 26.65 | N |
| ATOM | 1557 | NH2 | ARG A | 329 | 65.884 | 64.829 | 33.072 | 1.00 | 27.28 | N |
| ATOM | 1558 | N | GLY A | 330 | 67.377 | 64.513 | 25.396 | 1.00 | 25.55 | N |
| ATOM | 1559 | CA | GLY A | 330 | 68.625 | 64.021 | 24.837 | 1.00 | 24.59 | C |
| ATOM | 1560 | C | GLY A | 330 | 68.797 | 62.587 | 25.311 | 1.00 | 24.12 | C |
| ATOM | 1561 | O | GLY A | 330 | 68.580 | 62.287 | 26.482 | 1.00 | 23.28 | O |
| ATOM | 1562 | N | GLN A | 331 | 69.180 | 61.698 | 24.404 | 1.00 | 24.45 | N |
| ATOM | 1563 | CA | GLN A | 331 | 69.332 | 60.286 | 24.729 | 1.00 | 24.31 | C |
| ATOM | 1564 | C | GLN A | 331 | 70.295 | 60.017 | 25.883 | 1.00 | 24.63 | C |
| ATOM | 1565 | O | GLN A | 331 | 70.000 | 59.191 | 26.751 | 1.00 | 24.51 | O |
| ATOM | 1566 | CB | GLN A | 331 | 69.772 | 59.505 | 23.486 | 1.00 | 24.66 | C |
| ATOM | 1567 | CG | GLN A | 331 | 69.635 | 57.989 | 23.627 | 1.00 | 25.35 | C |
| ATOM | 1568 | CD | GLN A | 331 | 68.181 | 57.536 | 23.753 | 1.00 | 26.40 | C |
| ATOM | 1569 | OE1 | GLN A | 331 | 67.905 | 56.422 | 24.197 | 1.00 | 27.18 | O |
| ATOM | 1570 | NE2 | GLN A | 331 | 67.251 | 58.395 | 23.351 | 1.00 | 25.73 | N |
| ATOM | 1571 | N | ALA A | 332 | 71.435 | 60.713 | 25.904 | 1.00 | 23.94 | N |
| ATOM | 1572 | CA | ALA A | 332 | 72.420 | 60.515 | 26.964 | 1.00 | 23.57 | C |
| ATOM | 1573 | C | ALA A | 332 | 71.833 | 60.835 | 28.338 | 1.00 | 23.62 | C |
| ATOM | 1574 | O | ALA A | 332 | 71.955 | 60.044 | 29.278 | 1.00 | 23.57 | O |
| ATOM | 1575 | CB | ALA A | 332 | 73.669 | 61.375 | 26.702 | 1.00 | 23.41 | C |
| ATOM | 1576 | N | THR A | 333 | 71.192 | 61.993 | 28.451 | 1.00 | 23.21 | N |
| ATOM | 1577 | CA | THR A | 333 | 70.584 | 62.403 | 29.707 | 1.00 | 22.90 | C |
| ATOM | 1578 | C | THR A | 333 | 69.500 | 61.408 | 30.105 | 1.00 | 23.18 | C |
| ATOM | 1579 | O | THR A | 333 | 69.380 | 61.031 | 31.273 | 1.00 | 22.90 | O |
| ATOM | 1580 | CB | THR A | 333 | 69.967 | 63.814 | 29.590 | 1.00 | 22.97 | C |
| ATOM | 1581 | OG1 | THR A | 333 | 70.992 | 64.751 | 29.222 | 1.00 | 22.52 | O |
| ATOM | 1582 | CG2 | THR A | 333 | 69.349 | 64.240 | 30.922 | 1.00 | 21.69 | C |
| ATOM | 1583 | N | ALA A | 334 | 68.717 | 60.977 | 29.123 | 1.00 | 23.07 | N |
| ATOM | 1584 | CA | ALA A | 334 | 67.648 | 60.018 | 29.373 | 1.00 | 23.70 | C |
| ATOM | 1585 | C | ALA A | 334 | 68.206 | 58.718 | 29.963 | 1.00 | 23.40 | C |
| ATOM | 1586 | O | ALA A | 334 | 67.717 | 58.223 | 30.977 | 1.00 | 23.84 | O |
| ATOM | 1587 | CB | ALA A | 334 | 66.890 | 59.731 | 28.070 | 1.00 | 23.17 | C |
| ATOM | 1588 | N | VAL A | 335 | 69.231 | 58.168 | 29.324 | 1.00 | 23.69 | N |
| ATOM | 1589 | CA | VAL A | 335 | 69.842 | 56.933 | 29.797 | 1.00 | 24.02 | C |
| ATOM | 1590 | C | VAL A | 335 | 70.430 | 57.107 | 31.194 | 1.00 | 24.09 | C |
| ATOM | 1591 | O | VAL A | 335 | 70.147 | 56.316 | 32.100 | 1.00 | 24.31 | O |
| ATOM | 1592 | CB | VAL A | 335 | 70.955 | 56.459 | 28.837 | 1.00 | 24.63 | C |
| ATOM | 1593 | CG1 | VAL A | 335 | 71.682 | 55.254 | 29.431 | 1.00 | 25.02 | C |
| ATOM | 1594 | CG2 | VAL A | 335 | 70.348 | 56.090 | 27.487 | 1.00 | 24.84 | C |
| ATOM | 1595 | N | ILE A | 336 | 71.240 | 58.147 | 31.371 | 1.00 | 24.11 | N |
| ATOM | 1596 | CA | ILE A | 336 | 71.867 | 58.416 | 32.661 | 1.00 | 23.87 | C |
| ATOM | 1597 | C | ILE A | 336 | 70.851 | 58.544 | 33.801 | 1.00 | 24.46 | C |
| ATOM | 1598 | O | ILE A | 336 | 71.039 | 57.963 | 34.874 | 1.00 | 23.73 | O |
| ATOM | 1599 | CB | ILE A | 336 | 72.725 | 59.701 | 32.607 | 1.00 | 23.25 | C |
| ATOM | 1600 | CG1 | ILE A | 336 | 73.913 | 59.495 | 31.660 | 1.00 | 22.68 | C |
| ATOM | 1601 | CG2 | ILE A | 336 | 73.234 | 60.055 | 34.008 | 1.00 | 22.89 | C |
| ATOM | 1602 | CD1 | ILE A | 336 | 74.743 | 60.756 | 31.431 | 1.00 | 22.49 | C |
| ATOM | 1603 | N | ASP A | 337 | 69.775 | 59.296 | 33.572 | 1.00 | 24.98 | N |
| ATOM | 1604 | CA | ASP A | 337 | 68.759 | 59.479 | 34.606 | 1.00 | 25.52 | C |
| ATOM | 1605 | C | ASP A | 337 | 67.938 | 58.219 | 34.875 | 1.00 | 24.84 | C |

TABLE 5-continued

| ATOM | 1606 | O | ASP A | 337 | 67.629 | 57.907 | 36.024 | 1.00 | 24.56 | O |
|---|---|---|---|---|---|---|---|---|---|---|
| ATOM | 1607 | CB | ASP A | 337 | 67.818 | 60.637 | 34.245 | 1.00 | 27.31 | C |
| ATOM | 1608 | CG | ASP A | 337 | 68.502 | 62.000 | 34.327 | 1.00 | 30.71 | C |
| ATOM | 1609 | OD1 | ASP A | 337 | 69.614 | 62.096 | 34.913 | 1.00 | 32.05 | O |
| ATOM | 1610 | OD2 | ASP A | 337 | 67.918 | 62.983 | 33.815 | 1.00 | 31.24 | O |
| ATOM | 1611 | N | VAL A | 338 | 67.569 | 57.501 | 33.822 | 1.00 | 24.57 | N |
| ATOM | 1612 | CA | VAL A | 338 | 66.787 | 56.280 | 34.006 | 1.00 | 23.99 | C |
| ATOM | 1613 | C | VAL A | 338 | 67.631 | 55.230 | 34.735 | 1.00 | 23.85 | C |
| ATOM | 1614 | O | VAL A | 338 | 67.139 | 54.547 | 35.627 | 1.00 | 23.32 | O |
| ATOM | 1615 | CB | VAL A | 338 | 66.288 | 55.716 | 32.646 | 1.00 | 23.60 | C |
| ATOM | 1616 | CG1 | VAL A | 338 | 65.631 | 54.347 | 32.848 | 1.00 | 23.15 | C |
| ATOM | 1617 | CG2 | VAL A | 338 | 65.280 | 56.690 | 32.019 | 1.00 | 22.47 | C |
| ATOM | 1618 | N | VAL A | 339 | 68.906 | 55.126 | 34.362 | 1.00 | 23.84. | N |
| ATOM | 1619 | CA | VAL A | 339 | 69.816 | 54.165 | 34.981 | 1.00 | 24.21 | C |
| ATOM | 1620 | C | VAL A | 339 | 69.980 | 54.429 | 36.480 | 1.00 | 25.13 | C |
| ATOM | 1621 | O | VAL A | 339 | 70.043 | 53.493 | 37.278 | 1.00 | 25.49 | O |
| ATOM | 1622 | CB | VAL A | 339 | 71.215 | 54.195 | 34.289 | 1.00 | 23.92 | C |
| ATOM | 1623 | CG1 | VAL A | 339 | 72.270 | 53.502 | 35.158 | 1.00 | 23.40 | C |
| ATOM | 1624 | CG2 | VAL A | 339 | 71.134 | 53.503 | 32.940 | 1.00 | 23.43 | C |
| ATOM | 1625 | N | ALA A | 340 | 70.053 | 55.700 | 36.866 | 1.00 | 25.88 | N |
| ATOM | 1626 | CA | ALA A | 340 | 70.202 | 56.042 | 38.278 | 1.00 | 26.36 | C |
| ATOM | 1627 | C | ALA A | 340 | 68.959 | 55.600 | 39.051 | 1.00 | 26.83 | C |
| ATOM | 1628 | O | ALA A | 340 | 69.053 | 55.132 | 40.185 | 1.00 | 26.86 | O |
| ATOM | 1629 | CB | ALA A | 340 | 70.419 | 57.540 | 38.437 | 1.00 | 26.17 | C |
| ATOM | 1630 | N | GLU A | 341 | 67.796 | 55.750 | 38.429 | 1.00 | 27.07 | N |
| ATOM | 1631 | CA | GLU A | 341 | 66.542 | 55.358 | 39.061 | 1.00 | 27.92 | C |
| ATOM | 1632 | C | GLU A | 341 | 66.472 | 53.834 | 39.131 | 1.00 | 27.70 | C |
| ATOM | 1633 | O | GLU A | 341 | 66.016 | 53.273 | 40.124 | 1.00 | 27.73 | O |
| ATOM | 1634 | CB | GLU A | 341 | 65.358 | 55.898 | 38.256 | 1.00 | 28.93 | C |
| ATOM | 1635 | CG | GLU A | 341 | 64.004 | 55.796 | 38.960 | 1.00 | 30.89 | C |
| ATOM | 1636 | CD | GLU A | 341 | 63.955 | 56.592 | 40.258 | 1.00 | 32.66 | C |
| ATOM | 1637 | OE1 | GLU A | 341 | 64.480 | 57.727 | 40.299 | 1.00 | 34.48 | O |
| ATOM | 1638 | OE2 | GLU A | 341 | 63.380 | 56.090 | 41.240 | 1.00 | 34.06 | O |
| ATOM | 1639 | N | ARG A | 342 | 66.926 | 53.173 | 38.067 | 1.00 | 27.14 | N |
| ATOM | 1640 | CA | ARG A | 342 | 66.928 | 51.714 | 37.999 | 1.00 | 26.71 | C |
| ATOM | 1641 | C | ARG A | 342 | 67.821 | 51.149 | 39.103 | 1.00 | 26.54 | C |
| ATOM | 1642 | O | ARG A | 342 | 67.497 | 50.130 | 39.716 | 1.00 | 26.18 | O |
| ATOM | 1643 | CB | ARG A | 342 | 67.426 | 51.254 | 36.618 | 1.00 | 25.95 | C |
| ATOM | 1644 | CG | ARG A | 342 | 67.409 | 49.739 | 36.373 | 1.00 | 24.78 | C |
| ATOM | 1645 | CD | ARG A | 342 | 68.642 | 49.033 | 36.940 | 1.00 | 23.69 | C |
| ATOM | 1646 | NE | ARG A | 342 | 69.905 | 49.458 | 36.335 | 1.00 | 23.29 | N |
| ATOM | 1647 | CZ | ARG A | 342 | 70.262 | 49.229 | 35.070 | 1.00 | 23.19 | C |
| ATOM | 1648 | NH1 | ARG A | 342 | 69.453 | 48.574 | 34.247 | 1.00 | 22.48 | N |
| ATOM | 1649 | NH2 | ARG A | 342 | 71.442 | 49.648 | 34.626 | 1.00 | 22.80 | N |
| ATOM | 1650 | N | ASN A | 343 | 68.943 | 51.815 | 39.354 | 1.00 | 26.63 | N |
| ATOM | 1651 | CA | ASN A | 343 | 69.866 | 51.363 | 40.389 | 1.00 | 27.25 | C |
| ATOM | 1652 | C | ASN A | 343 | 69.271 | 51.619 | 41.770 | 1.00 | 28.00 | C |
| ATOM | 1653 | O | ASN A | 343 | 69.415 | 50.804 | 42.680 | 1.00 | 27.55 | O |
| ATOM | 1654 | CB | ASN A | 343 | 71.222 | 52.055 | 40.238 | 1.00 | 26.44 | C |
| ATOM | 1655 | CG | ASN A | 343 | 71.979 | 51.575 | 39.008 | 1.00 | 26.67 | C |
| ATOM | 1656 | OD1 | ASN A | 343 | 71.660 | 50.523 | 38.445 | 1.00 | 26.42 | O |
| ATOM | 1657 | ND2 | ASN A | 343 | 72.995 | 52.330 | 38.595 | 1.00 | 25.68 | N |
| ATOM | 1658 | N | LYS A | 344 | 68.585 | 52.748 | 41.913 | 1.00 | 28.63 | N |
| ATOM | 1659 | CA | LYS A | 344 | 67.937 | 53.089 | 43.168 | 1.00 | 30.19 | C |
| ATOM | 1660 | C | LYS A | 344 | 66.852 | 52.044 | 43.419 | 1.00 | 30.06 | C |
| ATOM | 1661 | O | LYS A | 344 | 66.702 | 51.536 | 44.530 | 1.00 | 30.48 | O |
| ATOM | 1662 | CB | LYS A | 344 | 67.308 | 54.481 | 43.073 | 1.00 | 31.64 | C |
| ATOM | 1663 | CG | LYS A | 344 | 66.560 | 54.917 | 44.323 | 1.00 | 34.82 | C |
| ATOM | 1664 | CD | LYS A | 344 | 65.887 | 56.276 | 44.143 | 1.00 | 36.84 | C |
| ATOM | 1665 | CE | LYS A | 344 | 66.890 | 57.354 | 43.756 | 1.00 | 38.89 | C |
| ATOM | 1666 | NZ | LYS A | 344 | 66.248 | 58.707 | 43.638 | 1.00 | 41.17 | N |
| ATOM | 1667 | N | TYR A | 345 | 66.107 | 51.723 | 42.367 | 1.00 | 29.84 | N |
| ATOM | 1668 | CA | TYR A | 345 | 65.032 | 50.743 | 42.443 | 1.00 | 30.10 | C |
| ATOM | 1669 | C | TYR A | 345 | 65.576 | 49.370 | 42.854 | 1.00 | 30.60 | C |
| ATOM | 1670 | O | TYR A | 345 | 64.960 | 48.665 | 43.654 | 1.00 | 30.17 | O |
| ATOM | 1671 | CB | TYR A | 345 | 64.334 | 50.635 | 41.088 | 1.00 | 29.60 | C |
| ATOM | 1672 | CG | TYR A | 345 | 63.051 | 49.828 | 41.103 | 1.00 | 30.01 | C |
| ATOM | 1673 | CD1 | TYR A | 345 | 61.847 | 50.407 | 41.508 | 1.00 | 29.92 | C |
| ATOM | 1674 | CD2 | TYR A | 345 | 63.032 | 48.499 | 40.675 | 1.00 | 29.79 | C |
| ATOM | 1675 | CE1 | TYR A | 345 | 60.658 | 49.690 | 41.476 | 1.00 | 30.21 | C |
| ATOM | 1676 | CE2 | TYR A | 345 | 61.843 | 47.770 | 40.641 | 1.00 | 30.08 | C |
| ATOM | 1677 | CZ | TYR A | 345 | 60.662 | 48.376 | 41.040 | 1.00 | 30.51 | C |
| ATOM | 1678 | OH | TYR A | 345 | 59.479 | 47.685 | 40.978 | 1.00 | 31.68 | O |
| ATOM | 1679 | N | PHE A | 346 | 66.726 | 48.996 | 42.298 | 1.00 | 31.26 | N |
| ATOM | 1680 | CA | PHE A | 346 | 67.351 | 47.717 | 42.619 | 1.00 | 32.37 | C |
| ATOM | 1681 | C | PHE A | 346 | 67.722 | 47.651 | 44.102 | 1.00 | 33.09 | C |
| ATOM | 1682 | O | PHE A | 346 | 67.528 | 46.630 | 44.754 | 1.00 | 32.99 | O |
| ATOM | 1683 | CB | PHE A | 346 | 68.613 | 47.509 | 41.781 | 1.00 | 32.81 | C |
| ATOM | 1684 | CG | PHE A | 346 | 69.374 | 46.269 | 42.141 | 1.00 | 33.53 | C |

TABLE 5-continued

| | | | | | | | | | | |
|---|---|---|---|---|---|---|---|---|---|---|
| ATOM | 1685 | CD1 | PHE A | 346 | 68.841 | 45.011 | 41.881 | 1.00 | 33.63 | C |
| ATOM | 1686 | CD2 | PHE A | 346 | 70.608 | 46.357 | 42.777 | 1.00 | 34.62 | C |
| ATOM | 1687 | CE1 | PHE A | 346 | 69.519 | 43.858 | 42.246 | 1.00 | 34.10 | C |
| ATOM | 1688 | CE2 | PHE A | 346 | 71.301 | 45.206 | 43.152 | 1.00 | 35.41 | C |
| ATOM | 1689 | CZ | PHE A | 346 | 70.750 | 43.950 | 42.883 | 1.00 | 35.25 | C |
| ATOM | 1690 | N | GLU A | 347 | 68.260 | 48.745 | 44.626 | 1.00 | 33.99 | N |
| ATOM | 1691 | CA | GLU A | 347 | 68.646 | 48.803 | 46.026 | 1.00 | 35.45 | C |
| ATOM | 1692 | C | GLU A | 347 | 67.435 | 48.732 | 46.958 | 1.00 | 35.29 | C |
| ATOM | 1693 | O | GLU A | 347 | 67.540 | 48.231 | 48.075 | 1.00 | 35.27 | O |
| ATOM | 1694 | CB | GLU A | 347 | 69.429 | 50.088 | 46.312 | 1.00 | 36.72 | C |
| ATOM | 1695 | CG | GLU A | 347 | 70.769 | 50.204 | 45.594 | 1.00 | 40.50 | C |
| ATOM | 1696 | CD | GLU A | 347 | 71.714 | 49.039 | 45.888 | 1.00 | 42.72 | C |
| ATOM | 1697 | OE1 | GLU A | 347 | 71.826 | 48.625 | 47.069 | 1.00 | 44.09 | O |
| ATOM | 1698 | OE2 | GLU A | 347 | 72.360 | 48.544 | 44.935 | 1.00 | 44.09 | O |
| ATOM | 1699 | N | GLU A | 348 | 66.287 | 49.225 | 46.504 | 1.00 | 35.07 | N |
| ATOM | 1700 | CA | GLU A | 348 | 65.089 | 49.221 | 47.337 | 1.00 | 35.42 | C |
| ATOM | 1701 | C | GLU A | 348 | 64.306 | 47.914 | 47.303 | 1.00 | 34.55 | C |
| ATOM | 1702 | O | GLU A | 348 | 63.739 | 47.502 | 48.309 | 1.00 | 34.49 | O |
| ATOM | 1703 | CB | GLU A | 348 | 64.127 | 50.339 | 46.915 | 1.00 | 37.00 | C |
| ATOM | 1704 | CG | GLU A | 348 | 64.759 | 51.699 | 46.683 | 1.00 | 39.47 | C |
| ATOM | 1705 | CD | GLU A | 348 | 63.750 | 52.738 | 46.194 | 1.00 | 40.68 | C |
| ATOM | 1706 | OE1 | GLU A | 348 | 62.928 | 52.416 | 45.308 | 1.00 | 41.24 | O |
| ATOM | 1707 | OE2 | GLU A | 348 | 63.788 | 53.883 | 46.690 | 1.00 | 41.95 | O |
| ATOM | 1708 | N | THR A | 349 | 64.281 | 47.266 | 46.143 | 1.00 | 33.77 | N |
| ATOM | 1709 | CA | THR A | 349 | 63.501 | 46.049 | 45.957 | 1.00 | 32.68 | C |
| ATOM | 1710 | C | THR A | 349 | 64.277 | 44.756 | 45.706 | 1.00 | 32.25 | C |
| ATOM | 1711 | O | THR A | 349 | 63.717 | 43.670 | 45.813 | 1.00 | 32.24 | O |
| ATOM | 1712 | CB | THR A | 349 | 62.534 | 46.231 | 44.770 | 1.00 | 32.69 | C |
| ATOM | 1713 | OG1 | THR A | 349 | 63.296 | 46.372 | 43.562 | 1.00 | 32.06 | O |
| ATOM | 1714 | CG2 | THR A | 349 | 61.678 | 47.481 | 44.959 | 1.00 | 32.19 | C |
| ATOM | 1715 | N | GLY A | 350 | 65.554 | 44.867 | 45.363 | 1.00 | 31.82 | N |
| ATOM | 1716 | CA | GLY A | 350 | 66.335 | 43.678 | 45.072 | 1.00 | 30.66 | C |
| ATOM | 1717 | C | GLY A | 350 | 66.068 | 43.202 | 43.648 | 1.00 | 29.93 | C |
| ATOM | 1718 | O | GLY A | 350 | 66.557 | 42.157 | 43.220 | 1.00 | 30.20 | O |
| ATOM | 1719 | N | ILE A | 351 | 65.287 | 43.978 | 42.906 | 1.00 | 28.99 | N |
| ATOM | 1720 | CA | ILE A | 351 | 64.950 | 43.633 | 41.529 | 1.00 | 27.61 | C |
| ATOM | 1721 | C | ILE A | 351 | 65.773 | 44.447 | 40.538 | 1.00 | 26.84 | C |
| ATOM | 1722 | O | ILE A | 351 | 65.744 | 45.675 | 40.558 | 1.00 | 26.06 | O |
| ATOM | 1723 | CB | ILE A | 351 | 63.459 | 43.901 | 41.239 | 1.00 | 27.81 | C |
| ATOM | 1724 | CG1 | ILE A | 351 | 62.588 | 43.128 | 42.233 | 1.00 | 27.74 | C |
| ATOM | 1725 | CG2 | ILE A | 351 | 63.123 | 43.498 | 39.802 | 1.00 | 27.06 | C |
| ATOM | 1726 | CD1 | ILE A | 351 | 61.150 | 43.611 | 42.277 | 1.00 | 27.83 | C |
| ATOM | 1727 | N | TYR A | 352 | 66.518 | 43.757 | 39.681 | 1.00 | 26.12 | N |
| ATOM | 1728 | CA | TYR A | 352 | 67.323 | 44.431 | 38.675 | 1.00 | 25.65 | C |
| ATOM | 1729 | C | TYR A | 352 | 66.570 | 44.364 | 37.358 | 1.00 | 25.14 | C |
| ATOM | 1730 | O | TYR A | 352 | 66.344 | 43.279 | 36.829 | 1.00 | 25.00 | O |
| ATOM | 1731 | CB | TYR A | 352 | 68.682 | 43.754 | 38.490 | 1.00 | 24.90 | C |
| ATOM | 1732 | CG | TYR A | 352 | 69.562 | 44.497 | 37.502 | 1.00 | 24.91 | C |
| ATOM | 1733 | CD1 | TYR A | 352 | 70.365 | 45.561 | 37.915 | 1.00 | 24.55 | C |
| ATOM | 1734 | CD2 | TYR A | 352 | 69.574 | 44.150 | 36.152 | 1.00 | 24.86 | C |
| ATOM | 1735 | CE1 | TYR A | 352 | 71.161 | 46.258 | 37.010 | 1.00 | 25.05 | C |
| ATOM | 1736 | CE2 | TYR A | 352 | 70.371 | 44.843 | 35.234 | 1.00 | 24.70 | C |
| ATOM | 1737 | CZ | TYR A | 352 | 71.161 | 45.892 | 35.670 | 1.00 | 24.84 | C |
| ATOM | 1738 | OH | TYR A | 352 | 71.976 | 46.555 | 34.783 | 1.00 | 24.66 | O |
| ATOM | 1739 | N | ILE A | 353 | 66.181 | 45.522 | 36.835 | 1.00 | 25.14 | N |
| ATOM | 1740 | CA | ILE A | 353 | 65.455 | 45.581 | 35.574 | 1.00 | 24.39 | C |
| ATOM | 1741 | C | ILE A | 353 | 66.364 | 46.094 | 34.467 | 1.00 | 24.46 | C |
| ATOM | 1742 | O | ILE A | 353 | 66.838 | 47.229 | 34.519 | 1.00 | 24.61 | O |
| ATOM | 1743 | CB | ILE A | 353 | 64.234 | 46.515 | 35.678 | 1.00 | 25.03 | C |
| ATOM | 1744 | CG1 | ILE A | 353 | 63.298 | 46.017 | 36.786 | 1.00 | 24.96 | C |
| ATOM | 1745 | CG2 | ILE A | 353 | 63.499 | 46.567 | 34.336 | 1.00 | 24.60 | C |
| ATOM | 1746 | CD1 | ILE A | 353 | 62.097 | 46.889 | 37.009 | 1.00 | 25.74 | C |
| ATOM | 1747 | N | PRO A | 354 | 66.635 | 45.256 | 33.453 | 1.00 | 24.02 | N |
| ATOM | 1748 | CA | PRO A | 354 | 67.504 | 45.700 | 32.356 | 1.00 | 23.55 | C |
| ATOM | 1749 | C | PRO A | 354 | 66.849 | 46.858 | 31.617 | 1.00 | 23.06 | C |
| ATOM | 1750 | O | PRO A | 354 | 65.627 | 46.896 | 31.491 | 1.00 | 23.02 | O |
| ATOM | 1751 | CB | PRO A | 354 | 67.619 | 44.454 | 31.470 | 1.00 | 23.02 | C |
| ATOM | 1752 | CG | PRO A | 354 | 67.455 | 43.318 | 32.455 | 1.00 | 23.37 | C |
| ATOM | 1753 | CD | PRO A | 354 | 66.323 | 43.819 | 33.334 | 1.00 | 23.29 | C |
| ATOM | 1754 | N | VAL A | 355 | 67.652 | 47.807 | 31.142 | 1.00 | 22.63 | N |
| ATOM | 1755 | CA | VAL A | 355 | 67.107 | 48.929 | 30.398 | 1.00 | 22.20 | C |
| ATOM | 1756 | C | VAL A | 355 | 67.732 | 48.959 | 29.011 | 1.00 | 22.50 | C |
| ATOM | 1757 | O | VAL A | 355 | 68.885 | 48.573 | 28.817 | 1.00 | 22.33 | O |
| ATOM | 1758 | CB | VAL A | 355 | 67.318 | 50.296 | 31.134 | 1.00 | 21.96 | C |
| ATOM | 1759 | CG1 | VAL A | 355 | 66.618 | 50.258 | 32.483 | 1.00 | 20.76 | C |
| ATOM | 1760 | CG2 | VAL A | 355 | 68.806 | 50.617 | 31.293 | 1.00 | 20.60 | C |
| ATOM | 1761 | N | CYS A | 356 | 66.950 | 49.408 | 28.044 | 1.00 | 23.02 | N |
| ATOM | 1762 | CA | CYS A | 356 | 67.394 | 49.457 | 26.667 | 1.00 | 23.36 | C |
| ATOM | 1763 | C | CYS A | 356 | 67.484 | 50.882 | 26.130 | 1.00 | 23.39 | C |

TABLE 5-continued

| | | | | | | | | | | |
|---|---|---|---|---|---|---|---|---|---|---|
| ATOM | 1764 | O | CYS A | 356 | 66.510 | 51.633 | 26.191 | 1.00 | 22.96 | O |
| ATOM | 1765 | CB | CYS A | 356 | 66.422 | 48.643 | 25.801 | 1.00 | 23.63 | C |
| ATOM | 1766 | SG | CYS A | 356 | 66.671 | 48.801 | 24.017 | 1.00 | 24.61 | S |
| ATOM | 1767 | N | SER A | 357 | 68.657 | 51.255 | 25.621 | 1.00 | 23.18 | N |
| ATOM | 1768 | CA | SER A | 357 | 68.819 | 52.577 | 25.033 | 1.00 | 23.61 | C |
| ATOM | 1769 | C | SER A | 357 | 68.312 | 52.425 | 23.601 | 1.00 | 23.62 | C |
| ATOM | 1770 | O | SER A | 357 | 68.930 | 51.746 | 22.783 | 1.00 | 23.43 | O |
| ATOM | 1771 | CB | SER A | 357 | 70.283 | 53.013 | 25.027 | 1.00 | 23.25 | C |
| ATOM | 1772 | OG | SER A | 357 | 70.387 | 54.322 | 24.490 | 1.00 | 23.60 | O |
| ATOM | 1773 | N | ASP A | 358 | 67.177 | 53.051 | 23.315 | 1.00 | 24.07 | N |
| ATOM | 1774 | CA | ASP A | 358 | 66.554 | 52.951 | 21.998 | 1.00 | 25.02 | C |
| ATOM | 1775 | C | ASP A | 358 | 66.654 | 54.226 | 21.164 | 1.00 | 25.69 | C |
| ATOM | 1776 | O | ASP A | 358 | 66.047 | 55.244 | 21.494 | 1.00 | 24.92 | O |
| ATOM | 1777 | CB | ASP A | 358 | 65.081 | 52.549 | 22.182 | 1.00 | 24.37 | C |
| ATOM | 1778 | CG | ASP A | 358 | 64.336 | 52.369 | 20.867 | 1.00 | 24.57 | C |
| ATOM | 1779 | OD1 | ASP A | 358 | 64.978 | 52.209 | 19.804 | 1.00 | 24.40 | O |
| ATOM | 1780 | OD2 | ASP A | 358 | 63.088 | 52.369 | 20.909 | 1.00 | 24.16 | O |
| ATOM | 1781 | N | GLY A | 359 | 67.427 | 54.151 | 20.083 | 1.00 | 27.42 | N |
| ATOM | 1782 | CA | GLY A | 359 | 67.585 | 55.281 | 19.186 | 1.00 | 29.54 | C |
| ATOM | 1783 | C | GLY A | 359 | 68.670 | 56.272 | 19.559 | 1.00 | 31.70 | C |
| ATOM | 1784 | O | GLY A | 359 | 69.235 | 56.224 | 20.652 | 1.00 | 32.10 | O |
| ATOM | 1785 | N | GLY A | 360 | 68.975 | 57.171 | 18.631 | 1.00 | 33.51 | N |
| ATOM | 1786 | CA | GLY A | 360 | 69.983 | 58.183 | 18.883 | 1.00 | 35.62 | C |
| ATOM | 1787 | C | GLY A | 360 | 71.415 | 57.733 | 18.679 | 1.00 | 36.94 | C |
| ATOM | 1788 | O | GLY A | 360 | 72.343 | 58.451 | 19.049 | 1.00 | 37.99 | O |
| ATOM | 1789 | N | ILE A | 361 | 71.611 | 56.552 | 18.105 | 1.00 | 38.04 | N |
| ATOM | 1790 | CA | ILE A | 361 | 72.962 | 56.069 | 17.871 | 1.00 | 39.16 | C |
| ATOM | 1791 | C | ILE A | 361 | 73.376 | 56.307 | 16.426 | 1.00 | 40.31 | C |
| ATOM | 1792 | O | ILE A | 361 | 72.908 | 55.631 | 15.502 | 1.00 | 40.46 | O |
| ATOM | 1793 | CB | ILE A | 361 | 73.100 | 54.572 | 18.249 | 1.00 | 39.05 | C |
| ATOM | 1794 | CG1 | ILE A | 361 | 73.124 | 54.459 | 19.783 | 1.00 | 39.14 | C |
| ATOM | 1795 | CG2 | ILE A | 361 | 74.344 | 53.961 | 17.601 | 1.00 | 38.66 | C |
| ATOM | 1796 | CD1 | ILE A | 361 | 73.769 | 53.223 | 20.332 | 1.00 | 38.76 | C |
| ATOM | 1797 | N | VAL A | 362 | 74.257 | 57.288 | 16.244 | 1.00 | 41.02 | N |
| ATOM | 1798 | CA | VAL A | 362 | 74.746 | 57.655 | 14.924 | 1.00 | 41.61 | C |
| ATOM | 1799 | C | VAL A | 362 | 76.048 | 56.942 | 14.566 | 1.00 | 41.66 | C |
| ATOM | 1800 | O | VAL A | 362 | 76.193 | 56.430 | 13.455 | 1.00 | 42.31 | O |
| ATOM | 1801 | CB | VAL A | 362 | 74.973 | 59.179 | 14.829 | 1.00 | 42.09 | C |
| ATOM | 1802 | CG1 | VAL A | 362 | 75.272 | 59.577 | 13.386 | 1.00 | 42.28 | C |
| ATOM | 1803 | CG2 | VAL A | 362 | 73.751 | 59.916 | 15.347 | 1.00 | 42.45 | C |
| ATOM | 1804 | N | TYR A | 363 | 76.987 | 56.902 | 15.510 | 1.00 | 41.20 | N |
| ATOM | 1805 | CA | TYR A | 363 | 78.282 | 56.260 | 15.283 | 1.00 | 40.38 | C |
| ATOM | 1806 | C | TYR A | 363 | 78.523 | 55.080 | 16.219 | 1.00 | 39.29 | C |
| ATOM | 1807 | O | TYR A | 363 | 77.904 | 54.985 | 17.278 | 1.00 | 38.90 | O |
| ATOM | 1808 | CB | TYR A | 363 | 79.396 | 57.293 | 15.454 | 1.00 | 41.48 | C |
| ATOM | 1809 | CG | TYR A | 363 | 79.233 | 58.478 | 14.535 | 1.00 | 43.32 | C |
| ATOM | 1810 | CD1 | TYR A | 363 | 79.265 | 58.315 | 13.150 | 1.00 | 44.27 | C |
| ATOM | 1811 | CD2 | TYR A | 363 | 79.001 | 59.755 | 15.045 | 1.00 | 44.05 | C |
| ATOM | 1812 | CE1 | TYR A | 363 | 79.067 | 59.392 | 12.293 | 1.00 | 45.45 | C |
| ATOM | 1813 | CE2 | TYR A | 363 | 78.801 | 60.841 | 14.197 | 1.00 | 45.25 | C |
| ATOM | 1814 | CZ | TYR A | 363 | 78.836 | 60.652 | 12.822 | 1.00 | 45.68 | C |
| ATOM | 1815 | OH | TYR A | 363 | 78.647 | 61.719 | 11.972 | 1.00 | 47.00 | O |
| ATOM | 1816 | N | ASP A | 364 | 79.425 | 54.182 | 15.828 | 1.00 | 37.99 | N |
| ATOM | 1817 | CA | ASP A | 364 | 79.731 | 53.016 | 16.649 | 1.00 | 36.91 | C |
| ATOM | 1818 | C | ASP A | 364 | 80.088 | 53.368 | 18.089 | 1.00 | 35.76 | C |
| ATOM | 1819 | O | ASP A | 364 | 79.629 | 52.701 | 19.018 | 1.00 | 35.85 | O |
| ATOM | 1820 | CB | ASP A | 364 | 80.892 | 52.202 | 16.062 | 1.00 | 37.35 | C |
| ATOM | 1821 | CG | ASP A | 364 | 80.504 | 51.412 | 14.824 | 1.00 | 37.70 | C |
| ATOM | 1822 | OD1 | ASP A | 364 | 79.312 | 51.080 | 14.647 | 1.00 | 37.53 | O |
| ATOM | 1823 | OD2 | ASP A | 364 | 81.417 | 51.102 | 14.033 | 1.00 | 38.32 | O |
| ATOM | 1824 | N | TYR A | 365 | 80.898 | 54.407 | 18.283 | 1.00 | 34.01 | N |
| ATOM | 1825 | CA | TYR A | 365 | 81.304 | 54.771 | 19.638 | 1.00 | 33.07 | C |
| ATOM | 1826 | C | TYR A | 365 | 80.131 | 55.199 | 20.524 | 1.00 | 31.99 | C |
| ATOM | 1827 | O | TYR A | 365 | 80.255 | 55.228 | 21.745 | 1.00 | 31.66 | O |
| ATOM | 1828 | CB | TYR A | 365 | 82.413 | 55.840 | 19.609 | 1.00 | 32.88 | C |
| ATOM | 1829 | CG | TYR A | 365 | 81.962 | 57.282 | 19.513 | 1.00 | 33.91 | C |
| ATOM | 1830 | CD1 | TYR A | 365 | 81.650 | 58.015 | 20.660 | 1.00 | 33.73 | C |
| ATOM | 1831 | CD2 | TYR A | 365 | 81.883 | 57.927 | 18.278 | 1.00 | 34.01 | C |
| ATOM | 1832 | CE1 | TYR A | 365 | 81.275 | 59.357 | 20.578 | 1.00 | 34.76 | C |
| ATOM | 1833 | CE2 | TYR A | 365 | 81.507 | 59.268 | 18.184 | 1.00 | 34.68 | C |
| ATOM | 1834 | CZ | TYR A | 365 | 81.206 | 59.977 | 19.335 | 1.00 | 34.89 | C |
| ATOM | 1835 | OH | TYR A | 365 | 80.841 | 61.302 | 19.239 | 1.00 | 35.48 | O |
| ATOM | 1836 | N | HIS A | 366 | 78.995 | 55.519 | 19.912 | 1.00 | 31.15 | N |
| ATOM | 1837 | CA | HIS A | 366 | 77.807 | 55.886 | 20.680 | 1.00 | 30.50 | C |
| ATOM | 1838 | C | HIS A | 366 | 77.305 | 54.640 | 21.411 | 1.00 | 29.58 | C |
| ATOM | 1839 | O | HIS A | 366 | 76.639 | 54.742 | 22.439 | 1.00 | 28.57 | O |
| ATOM | 1840 | CB | HIS A | 366 | 76.694 | 56.411 | 19.767 | 1.00 | 31.15 | C |
| ATOM | 1841 | CG | HIS A | 366 | 76.918 | 57.806 | 19.275 | 1.00 | 32.03 | C |
| ATOM | 1842 | ND1 | HIS A | 366 | 77.928 | 58.613 | 19.753 | 1.00 | 32.57 | N |

TABLE 5-continued

| ATOM | 1843 | CD2 | HIS A | 366 | 76.227 | 58.557 | 18.383 | 1.00 | 32.25 | C |
| ATOM | 1844 | CE1 | HIS A | 366 | 77.848 | 59.800 | 19.179 | 1.00 | 32.26 | C |
| ATOM | 1845 | NE2 | HIS A | 366 | 76.824 | 59.793 | 18.346 | 1.00 | 32.44 | N |
| ATOM | 1846 | N | MET A | 367 | 77.618 | 53.466 | 20.861 | 1.00 | 28.34 | N |
| ATOM | 1847 | CA | MET A | 367 | 77.215 | 52.201 | 21.475 | 1.00 | 27.90 | C |
| ATOM | 1848 | C | MET A | 367 | 77.951 | 52.050 | 22.801 | 1.00 | 26.79 | C |
| ATOM | 1849 | O | MET A | 367 | 77.350 | 51.752 | 23.829 | 1.00 | 26.19 | O |
| ATOM | 1850 | CB | MET A | 367 | 77.573 | 51.008 | 20.577 | 1.00 | 27.81 | C |
| ATOM | 1851 | CG | MET A | 367 | 76.771 | 50.894 | 19.285 | 1.00 | 28.28 | C |
| ATOM | 1852 | SD | MET A | 367 | 77.371 | 49.505 | 18.270 | 1.00 | 29.89 | S |
| ATOM | 1853 | CE | MET A | 367 | 76.390 | 49.722 | 16.782 | 1.00 | 29.69 | C |
| ATOM | 1854 | N | THR A | 368 | 79.262 | 52.256 | 22.758 | 1.00 | 26.73 | N |
| ATOM | 1855 | CA | THR A | 368 | 80.095 | 52.142 | 23.945 | 1.00 | 26.43 | C |
| ATOM | 1856 | C | THR A | 368 | 79.609 | 53.141 | 24.993 | 1.00 | 26.11 | C |
| ATOM | 1857 | O | THR A | 368 | 79.501 | 52.804 | 26.168 | 1.00 | 26.83 | O |
| ATOM | 1858 | CB | THR A | 368 | 81.572 | 52.399 | 23.592 | 1.00 | 26.81 | C |
| ATOM | 1859 | OG1 | THR A | 368 | 81.911 | 51.638 | 22.424 | 1.00 | 26.87 | O |
| ATOM | 1860 | CG2 | THR A | 368 | 82.480 | 51.975 | 24.738 | 1.00 | 26.28 | C |
| ATOM | 1861 | N | LEU A | 369 | 79.302 | 54.362 | 24.565 | 1.00 | 25.06 | N |
| ATOM | 1862 | CA | LEU A | 369 | 78.801 | 55.380 | 25.482 | 1.00 | 24.58 | C |
| ATOM | 1863 | C | LEU A | 369 | 77.494 | 54.938 | 26.142 | 1.00 | 23.99 | C |
| ATOM | 1864 | O | LEU A | 369 | 77.352 | 55.015 | 27.360 | 1.00 | 23.70 | O |
| ATOM | 1865 | CB | LEU A | 369 | 78.567 | 56.706 | 24.744 | 1.00 | 24.31 | C |
| ATOM | 1866 | CG | LEU A | 369 | 79.799 | 57.572 | 24.453 | 1.00 | 25.45 | C |
| ATOM | 1867 | CD1 | LEU A | 369 | 79.369 | 58.829 | 23.700 | 1.00 | 24.63 | C |
| ATOM | 1868 | CD2 | LEU A | 369 | 80.494 | 57.952 | 25.770 | 1.00 | 24.55 | C |
| ATOM | 1869 | N | ALA A | 370 | 76.544 | 54.478 | 25.330 | 1.00 | 23.02 | N |
| ATOM | 1870 | CA | ALA A | 370 | 75.250 | 54.031 | 25.833 | 1.00 | 22.95 | C |
| ATOM | 1871 | C | ALA A | 370 | 75.427 | 52.936 | 26.885 | 1.00 | 22.49 | C |
| ATOM | 1872 | O | ALA A | 370 | 74.777 | 52.951 | 27.930 | 1.00 | 22.45 | O |
| ATOM | 1873 | CB | ALA A | 370 | 74.380 | 53.519 | 24.674 | 1.00 | 21.80 | C |
| ATOM | 1874 | N | LEU A | 371 | 76.311 | 51.987 | 26.604 | 1.00 | 22.45 | N |
| ATOM | 1875 | CA | LEU A | 371 | 76.561 | 50.902 | 27.539 | 1.00 | 22.46 | C |
| ATOM | 1876 | C | LEU A | 371 | 77.268 | 51.435 | 28.793 | 1.00 | 22.58 | C |
| ATOM | 1877 | O | LEU A | 371 | 76.910 | 51.071 | 29.912 | 1.00 | 22.70 | O |
| ATOM | 1878 | CB | LEU A | 371 | 77.407 | 49.810 | 26.863 | 1.00 | 22.22 | C |
| ATOM | 1879 | CG | LEU A | 371 | 76.777 | 49.111 | 25.644 | 1.00 | 23.05 | C |
| ATOM | 1880 | CD1 | LEU A | 371 | 77.821 | 48.224 | 24.960 | 1.00 | 23.28 | C |
| ATOM | 1881 | CD2 | LEU A | 371 | 75.570 | 48.278 | 26.074 | 1.00 | 22.74 | C |
| ATOM | 1882 | N | ALA A | 372 | 78.259 | 52.306 | 28.607 | 1.00 | 22.30 | N |
| ATOM | 1883 | CA | ALA A | 372 | 79.001 | 52.863 | 29.736 | 1.00 | 22.69 | C |
| ATOM | 1884 | C | ALA A | 372 | 78.100 | 53..669 | 30.663 | 1.00 | 23.09 | C |
| ATOM | 1885 | O | ALA A | 372 | 78.320 | 53.705 | 31.874 | 1.00 | 22.83 | O |
| ATOM | 1886 | CB | ALA A | 372 | 80.140 | 53.738 | 29.236 | 1.00 | 22.43 | C |
| ATOM | 1887 | N | MET A | 373 | 77.087 | 54.316 | 30.091 | 1.00 | 23.19 | N |
| ATOM | 1888 | CA | MET A | 373 | 76.159 | 55.113 | 30.883 | 1.00 | 23.33 | C |
| ATOM | 1889 | C | MET A | 373 | 75.140 | 54.272 | 31.654 | 1.00 | 23.50 | C |
| ATOM | 1890 | O | MET A | 373 | 74.361 | 54.813 | 32.431 | 1.00 | 23.61 | O |
| ATOM | 1891 | CB | MET A | 373 | 75.437 | 56.127 | 29.992 | 1.00 | 23.33 | C |
| ATOM | 1892 | CG | MET A | 373 | 76.355 | 57.212 | 29.437 | 1.00 | 23.20 | C |
| ATOM | 1893 | SD | MET A | 373 | 75.548 | 58.296 | 28.242 | 1.00 | 24.70 | S |
| ATOM | 1894 | CE | MET A | 373 | 76.895 | 59.426 | 27.833 | 1.00 | 23.13 | C |
| ATOM | 1895 | N | GLY A | 374 | 75.135 | 52.956 | 31.437 | 1.00 | 23.73 | N |
| ATOM | 1896 | CA | GLY A | 374 | 74.210 | 52.108 | 32.174 | 1.00 | 23.47 | C |
| ATOM | 1897 | C | GLY A | 374 | 73.258 | 51.222 | 31.386 | 1.00 | 23.98 | C |
| ATOM | 1898 | O | GLY A | 374 | 72.709 | 50.266 | 31.941 | 1.00 | 24.30 | O |
| ATOM | 1899 | N | ALA A | 375 | 73.034 | 51.533 | 30.113 | 1.00 | 23.43 | N |
| ATOM | 1900 | CA | ALA A | 375 | 72.147 | 50.713 | 29.296 | 1.00 | 24.14 | C |
| ATOM | 1901 | C | ALA A | 375 | 72.716 | 49.298 | 29.212 | 1.00 | 24.24 | C |
| ATOM | 1902 | O | ALA A | 375 | 73.916 | 49.118 | 29.022 | 1.00 | 24.62 | O |
| ATOM | 1903 | CB | ALA A | 375 | 72.010 | 51.302 | 27.898 | 1.00 | 22.91 | C |
| ATOM | 1904 | N | ASP A | 376 | 71.848 | 48.304 | 29.369 | 1.00 | 24.28 | N |
| ATOM | 1905 | CA | ASP A | 376 | 72.248 | 46.905 | 29.301 | 1.00 | 24.39 | C |
| ATOM | 1906 | C | ASP A | 376 | 72.343 | 46.495 | 27.839 | 1.00 | 24.24 | C |
| ATOM | 1907 | O | ASP A | 376 | 73.206 | 45.708 | 27.455 | 1.00 | 24.28 | O |
| ATOM | 1908 | CB | ASP A | 376 | 71.227 | 46.042 | 30.040 | 1.00 | 24.71 | C |
| ATOM | 1909 | CG | ASP A | 376 | 71.144 | 46.385 | 31.518 | 1.00 | 25.23 | C |
| ATOM | 1910 | OD1 | ASP A | 376 | 71.931 | 45.821 | 32.307 | 1.00 | 25.91 | O |
| ATOM | 1911 | OD2 | ASP A | 376 | 70.304 | 47.234 | 31.890 | 1.00 | 25.50 | O |
| ATOM | 1912 | N | PHE A | 377 | 71.432 | 47.011 | 27.025 | 1.00 | 24.62 | N |
| ATOM | 1913 | CA | PHE A | 377 | 71.472 | 46.728 | 25.604 | 1.00 | 25.19 | C |
| ATOM | 1914 | C | PHE A | 377 | 70.944 | 47.899 | 24.795 | 1.00 | 25.15 | C |
| ATOM | 1915 | O | PHE A | 377 | 70.363 | 48.838 | 25.341 | 1.00 | 25.14 | O |
| ATOM | 1916 | CB | PHE A | 377 | 70.754 | 45.413 | 25.240 | 1.00 | 24.88 | C |
| ATOM | 1917 | CG | PHE A | 377 | 69.354 | 45.301 | 25.750 | 1.00 | 25.68 | C |
| ATOM | 1918 | CD1 | PHE A | 377 | 69.105 | 44.892 | 27.056 | 1.00 | 25.76 | C |
| ATOM | 1919 | CD2 | PHE A | 377 | 68.274 | 45.533 | 24.901 | 1.00 | 25.64 | C |
| ATOM | 1920 | CE1 | PHE A | 377 | 67.795 | 44.709 | 27.512 | 1.00 | 25.70 | C |
| ATOM | 1921 | CE2 | PHE A | 377 | 66.961 | 45.353 | 25.346 | 1.00 | 25.63 | C |

TABLE 5-continued

| ATOM | 1922 | CZ | PHE A | 377 | 66.724 | 44.939 | 26.653 | 1.00 | 26.08 | C |
| ATOM | 1923 | N | ILE A | 378 | 71.159 | 47.827 | 23.488 | 1.00 | 25.27 | N |
| ATOM | 1924 | CA | ILE A | 378 | 70.802 | 48.895 | 22.575 | 1.00 | 25.00 | C |
| ATOM | 1925 | C | ILE A | 378 | 69.858 | 48.454 | 21.466 | 1.00 | 25.29 | C |
| ATOM | 1926 | O | ILE A | 378 | 70.023 | 47.379 | 20.895 | 1.00 | 25.10 | O |
| ATOM | 1927 | CB | ILE A | 378 | 72.099 | 49.445 | 21.936 | 1.00 | 25.25 | C |
| ATOM | 1928 | CG1 | ILE A | 378 | 73.083 | 49.820 | 23.043 | 1.00 | 24.86 | C |
| ATOM | 1929 | CG2 | ILE A | 378 | 71.802 | 50.659 | 21.052 | 1.00 | 25.15 | C |
| ATOM | 1930 | CD1 | ILE A | 378 | 74.499 | 49.981 | 22.560 | 1.00 | 26.24 | C |
| ATOM | 1931 | N | MET A | 379 | 68.859 | 49.285 | 21.177 | 1.00 | 25.26 | N |
| ATOM | 1932 | CA | MET A | 379 | 67.922 | 48.996 | 20.101 | 1.00 | 25.45 | C |
| ATOM | 1933 | C | MET A | 379 | 68.271 | 49.957 | 18.968 | 1.00 | 25.68 | C |
| ATOM | 1934 | O | MET A | 379 | 68.464 | 51.147 | 19.199 | 1.00 | 25.94 | O |
| ATOM | 1935 | CB | MET A | 379 | 66.467 | 49.208 | 20.546 | 1.00 | 25.00 | C |
| ATOM | 1936 | CG | MET A | 379 | 65.466 | 48.982 | 19.413 | 1.00 | 24.97 | C |
| ATOM | 1937 | SD | MET A | 379 | 63.735 | 48.885 | 19.881 | 1.00 | 24.78 | S |
| ATOM | 1938 | CE | MET A | 379 | 63.630 | 47.182 | 20.459 | 1.00 | 24.64 | C |
| ATOM | 1939 | N | LEU A | 380 | 68.367 | 49.443 | 17.747 | 1.00 | 26.01 | N |
| ATOM | 1940 | CA | LEU A | 380 | 68.712 | 50.287 | 16.606 | 1.00 | 26.36 | C |
| ATOM | 1941 | C | LEU A | 380 | 67.836 | 49.997 | 15.398 | 1.00 | 26.33 | C |
| ATOM | 1942 | O | LEU A | 380 | 67.452 | 48.852 | 15.160 | 1.00 | 25.51 | O |
| ATOM | 1943 | CB | LEU A | 380 | 70.183 | 50.090 | 16.208 | 1.00 | 26.63 | C |
| ATOM | 1944 | CG | LEU A | 380 | 71.270 | 50.303 | 17.268 | 1.00 | 27.60 | C |
| ATOM | 1945 | CD1 | LEU A | 380 | 71.391 | 49.039 | 18.110 | 1.00 | 28.42 | C |
| ATOM | 1946 | CD2 | LED A | 380 | 72.609 | 50.595 | 16.608 | 1.00 | 27.51 | C |
| ATOM | 1947 | N | GLY A | 381 | 67.529 | 51.048 | 14.644 | 1.00 | 26.78 | N |
| ATOM | 1948 | CA | GLY A | 381 | 66.720 | 50.907 | 13.446 | 1.00 | 27.90 | C |
| ATOM | 1949 | C | GLY A | 381 | 67.566 | 51.146 | 12.206 | 1.00 | 28.83 | C |
| ATOM | 1950 | O | GLY A | 381 | 67.879 | 50.215 | 11.465 | 1.00 | 28.61 | O |
| ATOM | 1951 | N | ARG A | 382 | 67.950 | 52.399 | 11.991 | 1.00 | 30.04 | N |
| ATOM | 1952 | CA | ARG A | 382 | 68.766 | 52.775 | 10.837 | 1.00 | 31.91 | C |
| ATOM | 1953 | C | ARG A | 382 | 69.988 | 51.873 | 10.639 | 1.00 | 31.42 | C |
| ATOM | 1954 | O | ARG A | 382 | 70.278 | 51.442 | 9.522 | 1.00 | 31.49 | O |
| ATOM | 1955 | CB | ARG A | 382 | 69.220 | 54.232 | 10.971 | 1.00 | 34.20 | C |
| ATOM | 1956 | CG | ARG A | 382 | 70.290 | 54.630 | 9.964 | 1.00 | 38.29 | C |
| ATOM | 1957 | CD | ARG A | 382 | 70.947 | 55.962 | 10.312 | 1.00 | 41.29 | C |
| ATOM | 1958 | NE | ARG A | 382 | 72.287 | 56.062 | 9.729 | 1.00 | 44.45 | N |
| ATOM | 1959 | CZ | ARG A | 382 | 72.542 | 56.128 | 8.423 | 1.00 | 45.83 | C |
| ATOM | 1960 | NH1 | ARG A | 382 | 71.545 | 56.111 | 7.544 | 1.00 | 46.63 | N |
| ATOM | 1961 | NH2 | ARG A | 382 | 73.796 | 56.202 | 7.994 | 1.00 | 46.53 | N |
| ATOM | 1962 | N | TYR A | 383 | 70.700 | 51.596 | 11.727 | 1.00 | 30.70 | N |
| ATOM | 1963 | CA | TYR A | 383 | 71.892 | 50.753 | 11.692 | 1.00 | 29.42 | C |
| ATOM | 1964 | C | TYR A | 383 | 71.652 | 49.421 | 10.978 | 1.00 | 29.27 | C |
| ATOM | 1965 | O | TYR A | 383 | 72.448 | 49.013 | 10.128 | 1.00 | 29.04 | O |
| ATOM | 1966 | CB | TYR A | 383 | 72.380 | 50.487 | 13.124 | 1.00 | 28.61 | C |
| ATOM | 1967 | CG | TYR A | 383 | 73.607 | 49.602 | 13.223 | 1.00 | 27.85 | C |
| ATOM | 1968 | CD1 | TYR A | 383 | 74.894 | 50.134 | 13.107 | 1.00 | 27.60 | C |
| ATOM | 1969 | CD2 | TYR A | 383 | 73.479 | 48.228 | 13.419 | 1.00 | 27.75 | C |
| ATOM | 1970 | CE1 | TYR A | 383 | 76.020 | 49.317 | 13.185 | 1.00 | 27.67 | C |
| ATOM | 1971 | CE2 | TYR A | 383 | 74.592 | 47.403 | 13.495 | 1.00 | 27.39 | C |
| ATOM | 1972 | CZ | TYR A | 383 | 75.859 | 47.948 | 13.377 | 1.00 | 27.90 | C |
| ATOM | 1973 | OH | TYR A | 383 | 76.958 | 47.118 | 13.438 | 1.00 | 27.45 | O |
| ATOM | 1974 | N | PHE A | 384 | 70.560 | 48.747 | 11.327 | 1.00 | 28.44 | N |
| ATOM | 1975 | CA | PHE A | 384 | 70.232 | 47.454 | 10.733 | 1.00 | 28.47 | C |
| ATOM | 1976 | C | PHE A | 384 | 69.521 | 47.555 | 9.381 | 1.00 | 28.91 | C |
| ATOM | 1977 | O | PHE A | 384 | 69.627 | 46.650 | 8.555 | 1.00 | 28.72 | O |
| ATOM | 1978 | CB | PHE A | 384 | 69.375 | 46.636 | 11.705 | 1.00 | 27.39 | C |
| ATOM | 1979 | CG | PHE A | 384 | 70.132 | 46.130 | 12.906 | 1.00 | 26.72 | C |
| ATOM | 1980 | CD1 | PHE A | 384 | 71.098 | 45.132 | 12.768 | 1.00 | 25.87 | C |
| ATOM | 1981 | CD2 | PHE A | 384 | 69.886 | 46.656 | 14.173 | 1.00 | 25.64 | C |
| ATOM | 1982 | CE1 | PHE A | 384 | 71.807 | 44.664 | 13.868 | 1.00 | 25.34 | C |
| ATOM | 1983 | CE2 | PHE A | 384 | 70.591 | 46.193 | 15.285 | 1.00 | 25.24 | C |
| ATOM | 1984 | CZ | PHE A | 384 | 71.554 | 45.195 | 15.134 | 1.00 | 24.96 | C |
| ATOM | 1985 | N | ALA A | 385 | 68.804 | 48.653 | 9.158 | 1.00 | 29.46 | N |
| ATOM | 1986 | CA | ALA A | 385 | 68.081 | 48.852 | 7.905 | 1.00 | 30.43 | C |
| ATOM | 1987 | C | ALA A | 385 | 69.024 | 48.849 | 6.701 | 1.00 | 31.20 | C |
| ATOM | 1988 | O | ALA A | 385 | 68.626 | 48.506 | 5.592 | 1.00 | 31.54 | O |
| ATOM | 1989 | CB | ALA A | 385 | 67.299 | 50.166 | 7.958 | 1.00 | 29.86 | C |
| ATOM | 1990 | N | ARG A | 386 | 70.278 | 49.226 | 6.934 | 1.00 | 32.25 | N |
| ATOM | 1991 | CA | ARG A | 386 | 71.291 | 49.281 | 5.883 | 1.00 | 32.76 | C |
| ATOM | 1992 | C | ARG A | 386 | 71.725 | 47.907 | 5.381 | 1.00 | 33.11 | C |
| ATOM | 1993 | O | ARG A | 386 | 72.310 | 47.794 | 4.305 | 1.00 | 32.93 | O |
| ATOM | 1994 | CB | ARG A | 386 | 72.542 | 49.995 | 6.392 | 1.00 | 33.15 | C |
| ATOM | 1995 | CG | ARG A | 386 | 72.363 | 51.434 | 6.832 | 1.00 | 34.37 | C |
| ATOM | 1996 | CD | ARG A | 386 | 73.645 | 51.881 | 7.510 | 1.00 | 34.93 | C |
| ATOM | 1997 | NE | ARG A | 386 | 74.002 | 50.939 | 8.567 | 1.00 | 36.03 | N |
| ATOM | 1998 | CZ | ARG A | 386 | 75.245 | 50.652 | 8.938 | 1.00 | 36.05 | C |
| ATOM | 1999 | NH1 | ARG A | 386 | 76.278 | 51.233 | 8.338 | 1.00 | 35.62 | N |
| ATOM | 2000 | NH2 | ARG A | 386 | 75.451 | 49.774 | 9.910 | 1.00 | 35.65 | N |

TABLE 5-continued

| | | | | | | | | | | |
|---|---|---|---|---|---|---|---|---|---|---|
| ATOM | 2001 | N | PHE A | 387 | 71.447 | 46.867 | 6.158 | 1.00 | 33.64 | N |
| ATOM | 2002 | CA | PHE A | 387 | 71.875 | 45.525 | 5.787 | 1.00 | 34.50 | C |
| ATOM | 2003 | C | PHE A | 387 | 71.012 | 44.785 | 4.768 | 1.00 | 35.58 | C |
| ATOM | 2004 | O | PHE A | 387 | 69.818 | 45.037 | 4.623 | 1.00 | 35.41 | O |
| ATOM | 2005 | CB | PHE A | 387 | 72.040 | 44.665 | 7.046 | 1.00 | 33.89 | C |
| ATOM | 2006 | CG | PHE A | 387 | 72.940 | 45.276 | 8.091 | 1.00 | 33.56 | C |
| ATOM | 2007 | CD1 | PHE A | 387 | 74.033 | 46.058 | 7.722 | 1.00 | 33.59 | C |
| ATOM | 2008 | CD2 | PHE A | 387 | 72.707 | 45.050 | 9.444 | 1.00 | 33.20 | C |
| ATOM | 2009 | CE1 | PHE A | 387 | 74.881 | 46.607 | 8.689 | 1.00 | 33.28 | C |
| ATOM | 2010 | CE2 | PHE A | 387 | 73.547 | 45.592 | 10.417 | 1.00 | 32.86 | C |
| ATOM | 2011 | CZ | PHE A | 387 | 74.636 | 46.372 | 10.040 | 1.00 | 33.10 | C |
| ATOM | 2012 | N | GLU A | 388 | 71.647 | 43.859 | 4.064 | 1.00 | 37.23 | N |
| ATOM | 2013 | CA | GLU A | 388 | 70.979 | 43.061 | 3.048 | 1.00 | 38.92 | C |
| ATOM | 2014 | C | GLU A | 388 | 69.769 | 42.341 | 3.632 | 1.00 | 38.75 | C |
| ATOM | 2015 | O | GLU A | 388 | 68.737 | 42.209 | 2.972 | 1.00 | 38.22 | O |
| ATOM | 2016 | CB | GLU A | 388 | 71.957 | 42.034 | 2.473 | 1.00 | 40.97 | C |
| ATOM | 2Q17 | CG | GLU A | 388 | 71.424 | 41.264 | 1.272 | 1.00 | 44.75 | C |
| ATOM | 2018 | CD | GLU A | 388 | 72.279 | 40.056 | 0.934 | 1.00 | 47.13 | C |
| ATOM | 2019 | OE1 | GLU A | 388 | 72.425 | 39.172 | 1.808 | 1.00 | 48.77 | O |
| ATOM | 2020 | OE2 | GLU A | 388 | 72.803 | 39.985 | −0.202 | 1.00 | 48.96 | O |
| ATOM | 2021 | N | GLU A | 389 | 69.899 | 41.886 | 4.876 | 1.00 | 38.62 | N |
| ATOM | 2022 | CA | GLU A | 389 | 68.823 | 41.159 | 5.534 | 1.00 | 38.62 | C |
| ATOM | 2023 | C | GLU A | 389 | 67.615 | 41.987 | 5.964 | 1.00 | 38.96 | C |
| ATOM | 2024 | O | GLU A | 389 | 66.621 | 41.424 | 6.413 | 1.00 | 39.16 | O |
| ATOM | 2025 | CB | GLU A | 389 | 69.369 | 40.375 | 6.732 | 1.00 | 37.80 | C |
| ATOM | 2026 | CG | GLU A | 389 | 70.398 | 39.320 | 6.347 | 1.00 | 36.96 | C |
| ATOM | 2027 | CD | GLU A | 389 | 71.834 | 39.798 | 6.504 | 1.00 | 36.79 | C |
| ATOM | 2028 | OE1 | GLU A | 389 | 72.100 | 41.004 | 6.310 | 1.00 | 36.41 | O |
| ATOM | 2029 | OE2 | GLU A | 389 | 72.704 | 38.958 | 6.808 | 1.00 | 35.78 | O |
| ATOM | 2030 | N | SER A | 390 | 67.679 | 43.310 | 5.843 | 1.00 | 39.56 | N |
| ATOM | 2031 | CA | SER A | 390 | 66.515 | 44.105 | 6.216 | 1.00 | 40.72 | C |
| ATOM | 2032 | C | SER A | 390 | 65.467 | 43.815 | 5.138 | 1.00 | 41.70 | C |
| ATOM | 2033 | O | SER A | 390 | 65.807 | 43.599 | 3.973 | 1.00 | 41.48 | O |
| ATOM | 2034 | CB | SER A | 390 | 66.844 | 45.598 | 6.278 | 1.00 | 40.08 | C |
| ATOM | 2035 | OG | SER A | 390 | 67.105 | 46.130 | 5.000 | 1.00 | 40.77 | O |
| ATOM | 2036 | N | PRO A | 391 | 64.181 | 43.804 | 5.515 | 1.00 | 42.67 | N |
| ATOM | 2037 | CA | PRO A | 391 | 63.073 | 43.523 | 4.595 | 1.00 | 43.86 | C |
| ATOM | 2038 | C | PRO A | 391 | 62.716 | 44.593 | 3.567 | 1.00 | 44.88 | C |
| ATOM | 2039 | O | PRO A | 391 | 61.651 | 44.530 | 2.959 | 1.00 | 45.36 | O |
| ATOM | 2040 | CB | PRO A | 391 | 61.917 | 43.245 | 5.550 | 1.00 | 43.53 | C |
| ATOM | 2041 | CG | PRO A | 391 | 62.172 | 44.253 | 6.634 | 1.00 | 42.86 | C |
| ATOM | 2042 | CD | PRO A | 391 | 63.672 | 44.149 | 6.858 | 1.00 | 42.43 | C |
| ATOM | 2043 | N | THR A | 392 | 63.588 | 45.570 | 3.361 | 1.00 | 46.16 | N |
| ATOM | 2044 | CA | THR A | 392 | 63.280 | 46.619 | 2.402 | 1.00 | 47.44 | C |
| ATOM | 2045 | C | THR A | 392 | 63.962 | 46.419 | 1.057 | 1.00 | 48.73 | C |
| ATOM | 2046 | O | THR A | 392 | 64.940 | 45.680 | 0.939 | 1.00 | 48.53 | O |
| ATOM | 2047 | CB | THR A | 392 | 63.646 | 48.010 | 2.955 | 1.00 | 47.37 | C |
| ATOM | 2048 | OG1 | THR A | 392 | 65.056 | 48.081 | 3.190 | 1.00 | 47.28 | O |
| ATOM | 2049 | CG2 | THR A | 392 | 62.901 | 48.266 | 4.264 | 1.00 | 47.46 | C |
| ATOM | 2050 | N | ARG A | 393 | 63.430 | 47.085 | 0.041 | 1.00 | 50.37 | N |
| ATOM | 2051 | CA | ARG A | 393 | 63.966 | 46.980 | −1.305 | 1.00 | 52.41 | C |
| ATOM | 2052 | C | ARG A | 393 | 65.285 | 47.716 | −1.481 | 1.00 | 52.98 | C |
| ATOM | 2053 | O | ARG A | 393 | 65.459 | 48.846 | −1.020 | 1.00 | 52.98 | O |
| ATOM | 2054 | CB | ARG A | 393 | 62.936 | 47.494 | −2.318 | 1.00 | 53.44 | C |
| ATOM | 2055 | CG | ARG A | 393 | 61.734 | 46.567 | −2.475 | 1.00 | 54.94 | C |
| ATOM | 2056 | CD | ARG A | 393 | 60.591 | 47.199 | −3.269 | 1.00 | 56.14 | C |
| ATOM | 2057 | NE | ARG A | 393 | 61.022 | 47.742 | −4.554 | 1.00 | 57.05 | N |
| ATOM | 2058 | CZ | ARG A | 393 | 61.422 | 48.997 | −4.739 | 1.00 | 57.73 | C |
| ATOM | 2059 | NH1 | ARG A | 393 | 61.444 | 49.848 | −3.720 | 1.00 | 58.03 | N |
| ATOM | 2060 | NH2 | ARG A | 393 | 61.803 | 49.402 | −5.943 | 1.00 | 58.01 | N |
| ATOM | 2061 | N | LYS A | 394 | 66.220 | 47.046 | −2.141 | 1.00 | 53.68 | N |
| ATOM | 2062 | CA | LYS A | 394 | 67.526 | 47.616 | −2.417 | 1.00 | 54.28 | C |
| ATOM | 2063 | C | LYS A | 394 | 67.338 | 48.454 | −3.674 | 1.00 | 54.83 | C |
| ATOM | 2064 | O | LYS A | 394 | 66.910 | 47.943 | −4.704 | 1.00 | 54.68 | O |
| ATOM | 2065 | CB | LYS A | 394 | 68.532 | 46.495 | −2.670 | 1.00 | 53.95 | C |
| ATOM | 2066 | CG | LYS A | 394 | 69.979 | 46.924 | −2.607 | 1.00 | 53.65 | C |
| ATOM | 2067 | CD | LYS A | 394 | 70.900 | 45.769 | −2.961 | 1.00 | 53.38 | C |
| ATOM | 2068 | CE | LYS A | 394 | 70.731 | 44.601 | −2.009 | 1.00 | 52.92 | C |
| ATOM | 2069 | NZ | LYS A | 394 | 71.581 | 43.452 | −2.415 | 1.00 | 52.51 | N |
| ATOM | 2070 | N | VAL A | 395 | 67.640 | 49.742 | −3.585 | 1.00 | 55.84 | N |
| ATOM | 2071 | CA | VAL A | 395 | 67.471 | 50.629 | −4.724 | 1.00 | 57.03 | C |
| ATOM | 2072 | C | VAL A | 395 | 68.749 | 51.379 | −5.052 | 1.00 | 57.77 | C |
| ATOM | 2073 | O | VAL A | 395 | 69.439 | 51.859 | −4.159 | 1.00 | 58.06 | O |
| ATOM | 2074 | CB | VAL A | 395 | 66.352 | 51.653 | −4.457 | 1.00 | 57.18 | C |
| ATOM | 2075 | CG1 | VAL A | 395 | 66.227 | 52.612 | −5.632 | 1.00 | 57.63 | C |
| ATOM | 2076 | CG2 | VAL A | 395 | 65.036 | 50.926 | −4.220 | 1.00 | 57.44 | C |
| ATOM | 2077 | N | THR A | 396 | 69.055 | 51.480 | −6.340 | 1.00 | 58.78 | N |
| ATOM | 2078 | CA | THR A | 396 | 70.255 | 52.176 | −6.786 | 1.00 | 59.74 | C |
| ATOM | 2079 | C | THR A | 396 | 69.940 | 53.611 | −7.189 | 1.00 | 60.37 | C |

TABLE 5-continued

| ATOM | 2080 | O | THR A | 396 | 69.146 | 53.851 | −8.096 | 1.00 | 60.74 | O |
|---|---|---|---|---|---|---|---|---|---|---|
| ATOM | 2081 | CB | THR A | 396 | 70.900 | 51.466 | −7.989 | 1.00 | 59.62 | C |
| ATOM | 2082 | OG1 | THR A | 396 | 71.197 | 50.110 | −7.639 | 1.00 | 59.68 | O |
| ATOM | 2083 | CG2 | THR A | 396 | 72.184 | 52.173 | −8.394 | 1.00 | 59.73 | C |
| ATOM | 2084 | N | ILE A | 397 | 70.565 | 54.559 | −6.502 | 1.00 | 61.02 | N |
| ATOM | 2085 | CA | ILE A | 397 | 70.366 | 55.974 | −6.783 | 1.00 | 61.57 | C |
| ATOM | 2086 | C | ILE A | 397 | 71.659 | 56.562 | −7.342 | 1.00 | 61.67 | C |
| ATOM | 2087 | O | ILE A | 397 | 72.589 | 56.872 | −6.595 | 1.00 | 61.90 | O |
| ATOM | 2088 | CB | ILE A | 397 | 69.962 | 56.744 | −5.506 | 1.00 | 61.92 | C |
| ATOM | 2089 | CG1 | ILE A | 397 | 68.655 | 56.173 | −4.950 | 1.00 | 62.18 | C |
| ATOM | 2090 | CG2 | ILE A | 397 | 69.792 | 58.223 | −5.817 | 1.00 | 62.12 | C |
| ATOM | 2091 | CD1 | ILE A | 397 | 68.171 | 56.858 | −3.689 | 1.00 | 62.37 | C |
| ATOM | 2092 | N | ASN A | 398 | 71.700 | 56.708 | −8.663 | 1.00 | 61.56 | N |
| ATOM | 2093 | CA | ASN A | 398 | 72.856 | 57.247 | −9.375 | 1.00 | 61.04 | C |
| ATOM | 2094 | C | ASN A | 398 | 74.211 | 56.789 | −8.831 | 1.00 | 60.11 | C |
| ATOM | 2095 | O | ASN A | 398 | 74.960 | 57.570 | −8.239 | 1.00 | 60.00 | O |
| ATOM | 2096 | CB | ASN A | 398 | 72.795 | 58.784 | −9.415 | 1.00 | 62.12 | C |
| ATOM | 2097 | CG | ASN A | 398 | 72.965 | 59.425 | −8.047 | 1.00 | 62.95 | C |
| ATOM | 2098 | OD1 | ASN A | 398 | 72.154 | 59.222 | −7.145 | 1.00 | 63.58 | O |
| ATOM | 2099 | ND2 | ASN A | 398 | 74.026 | 60.216 | −7.892 | 1.00 | 63.27 | N |
| ATOM | 2100 | N | GLY A | 399 | 74.516 | 55.512 | −9.039 | 1.00 | 58.84 | N |
| ATOM | 2101 | CA | GLY A | 399 | 75.786 | 54.965 | −8.593 | 1.00 | 57.27 | C |
| ATOM | 2102 | C | GLY A | 399 | 75.861 | 54.494 | −7.153 | 1.00 | 56.12 | C |
| ATOM | 2103 | O | GLY A | 399 | 76.847 | 53.867 | −6.761 | 1.00 | 56.17 | O |
| ATOM | 2104 | N | SER A | 400 | 74.835 | 54.788 | −6.359 | 1.00 | 54.73 | N |
| ATOM | 2105 | CA | SER A | 400 | 74.832 | 54.379 | −4.957 | 1.00 | 52.89 | C |
| ATOM | 2106 | C | SER A | 400 | 73.686 | 53.444 | −4.603 | 1.00 | 51.55 | C |
| ATOM | 2107 | O | SER A | 400 | 72.517 | 53.775 | −4.785 | 1.00 | 51.45 | O |
| ATOM | 2108 | CB | SER A | 400 | 74.779 | 55.608 | −4.047 | 1.00 | 52.78 | C |
| ATOM | 2109 | OG | SER A | 400 | 75.979 | 56.353 | −4.134 | 1.00 | 52.96 | O |
| ATOM | 2110 | N | VAL A | 401 | 74.030 | 52.268 | −4.094 | 1.00 | 50.01 | N |
| ATOM | 2111 | CA | VAL A | 401 | 73.025 | 51.298 | −3.697 | 1.00 | 48.59 | C |
| ATOM | 2112 | C | VAL A | 401 | 72.507 | 51.704 | −2.320 | 1.00 | 48.17 | C |
| ATOM | 2113 | O | VAL A | 401 | 73.275 | 51.816 | −1.360 | 1.00 | 47.91 | O |
| ATOM | 2114 | CB | VAL A | 401 | 73.620 | 49.883 | −3.637 | 1.00 | 48.31 | C |
| ATOM | 2115 | CG1 | VAL A | 401 | 72.563 | 48.892 | −3.182 | 1.00 | 47.71 | C |
| ATOM | 2116 | CG2 | VAL A | 401 | 74.167 | 49.499 | −5.007 | 1.00 | 47.95 | C |
| ATOM | 2117 | N | MET A | 402 | 71.202 | 51.941 | −2.238 | 1.00 | 47.38 | N |
| ATOM | 2118 | CA | MET A | 402 | 70.566 | 52.360 | −0.998 | 1.00 | 46.51 | C |
| ATOM | 2119 | C | MET A | 402 | 69.492 | 51.365 | −0.589 | 1.00 | 45.72 | C |
| ATOM | 2120 | O | MET A | 402 | 69.161 | 50.440 | −1.333 | 1.00 | 45.52 | O |
| ATOM | 2121 | CB | MET A | 402 | 69.893 | 53.724 | −1.179 | 1.00 | 47.39 | C |
| ATOM | 2122 | CG | MET A | 402 | 70.722 | 54.785 | −1.882 | 1.00 | 47.80 | C |
| ATOM | 2123 | SD | MET A | 402 | 72.046 | 55.436 | −0.875 | 1.00 | 49.53 | S |
| ATOM | 2124 | CE | MET A | 402 | 71.130 | 56.502 | 0.246 | 1.00 | 48.12 | C |
| ATOM | 2125 | N | LYS A | 403 | 68.953 | 51.568 | 0.606 | 1.00 | 44.48 | N |
| ATOM | 2126 | CA | LYS A | 403 | 67.879 | 50.735 | 1.118 | 1.00 | 43.18 | C |
| ATOM | 2127 | C | LYS A | 403 | 66.843 | 51.671 | 1.713 | 1.00 | 42.91 | C |
| ATOM | 2128 | O | LYS A | 403 | 67.178 | 52.736 | 2.232 | 1.00 | 42.51 | O |
| ATOM | 2129 | CB | LYS A | 403 | 68.387 | 49.759 | 2.180 | 1.00 | 42.62 | C |
| ATOM | 2130 | CG | LYS A | 403 | 69.316 | 48.691 | 1.632 | 1.00 | 41.97 | C |
| ATOM | 2131 | CD | LYS A | 403 | 69.087 | 47.352 | 2.306 | 1.00 | 41.27 | C |
| ATOM | 2132 | CE | LYS A | 403 | 67.729 | 46.777 | 1.941 | 1.00 | 40.54 | C |
| ATOM | 2133 | NZ | LYS A | 403 | 67.534 | 45.407 | 2.492 | 1.00 | 39.50 | N |
| ATOM | 2134 | N | GLU A | 404 | 65.580 | 51.280 | 1.622 | 1.00 | 42.89 | N |
| ATOM | 2135 | CA | GLU A | 404 | 64.500 | 52.097 | 2.146 | 1.00 | 42.99 | C |
| ATOM | 2136 | C | GLU A | 404 | 64.451 | 52.019 | 3.661 | 1.00 | 42.20 | C |
| ATOM | 2137 | O | GLU A | 404 | 64.760 | 50.987 | 4.254 | 1.00 | 41.68 | O |
| ATOM | 2138 | CB | GLU A | 404 | 63.166 | 51.623 | 1.580 | 1.00 | 44.40 | C |
| ATOM | 2139 | CG | GLU A | 404 | 63.131 | 51.559 | 0.071 | 1.00 | 46.68 | C |
| ATOM | 2140 | CD | GLU A | 404 | 61.810 | 51.042 | −0.446 | 1.00 | 48.00 | C |
| ATOM | 2141 | OE1 | GLU A | 404 | 61.485 | 49.856 | −0.191 | 1.00 | 49.02 | O |
| ATOM | 2142 | OE2 | GLU A | 404 | 61.095 | 51.827 | −1.101 | 1.00 | 49.09 | O |
| ATOM | 2143 | N | TYR A | 405 | 64.061 | 53.124 | 4.284 | 1.00 | 41.51 | N |
| ATOM | 2144 | CA | TYR A | 405 | 63.949 | 53.180 | 5.729 | 1.00 | 40.50 | C |
| ATOM | 2145 | C | TYR A | 405 | 62.918 | 54.221 | 6.123 | 1.00 | 40.07 | C |
| ATOM | 2146 | O | TYR A | 405 | 63.100 | 55.416 | 5.882 | 1.00 | 40.71 | O |
| ATOM | 2147 | CB | TYR A | 405 | 65.294 | 53.524 | 6.365 | 1.00 | 40.22 | C |
| ATOM | 2148 | CG | TYR A | 405 | 65.231 | 53.579 | 7.872 | 1.00 | 40.08 | C |
| ATOM | 2149 | CD1 | TYR A | 405 | 64.847 | 52.463 | 8.611 | 1.00 | 39.84 | C |
| ATOM | 2150 | CD2 | TYR A | 405 | 65.539 | 54.750 | 8.561 | 1.00 | 40.31 | C |
| ATOM | 2151 | CE1 | TYR A | 405 | 64.771 | 52.508 | 9.998 | 1.00 | 39.70 | C |
| ATOM | 2152 | CE2 | TYR A | 405 | 65.466 | 54.807 | 9.949 | 1.00 | 40.16 | C |
| ATOM | 2153 | CZ | TYR A | 405 | 65.080 | 53.681 | 10.659 | 1.00 | 39.81 | C |
| ATOM | 2154 | OH | TYR A | 405 | 64.990 | 53.734 | 12.027 | 1.00 | 39.77 | O |
| ATOM | 2155 | N | TRP A | 406 | 61.830 | 53.764 | 6.729 | 1.00 | 38.92 | N |
| ATOM | 2156 | CA | TRP A | 406 | 60.773 | 54.666 | 7.153 | 1.00 | 38.11 | C |
| ATOM | 2157 | C | TRP A | 406 | 60.373 | 54.354 | 8.588 | 1.00 | 38.26 | C |
| ATOM | 2158 | O | TRP A | 406 | 60.439 | 53.202 | 9.026 | 1.00 | 37.61 | O |

TABLE 5-continued

| ATOM | 2159 | CB | TRP A | 406 | 59.565 | 54.545 | 6.212 | 1.00 | 36.65 | C |
| ATOM | 2160 | CG | TRP A | 406 | 58.932 | 53.186 | 6.184 | 1.00 | 35.15 | C |
| ATOM | 2161 | CD1 | TRP A | 406 | 57.972 | 52.715 | 7.028 | 1.00 | 34.75 | C |
| ATOM | 2162 | CD2 | TRP A | 406 | 59.246 | 52.111 | 5.293 | 1.00 | 34.82 | C |
| ATOM | 2163 | NE1 | TRP A | 406 | 57.667 | 51.414 | 6.722 | 1.00 | 34.33 | N |
| ATOM | 2164 | CE2 | TRP A | 406 | 58.437 | 51.015 | 5.661 | 1.00 | 34.71 | C |
| ATOM | 2165 | CE3 | TRP A | 406 | 60.135 | 51.965 | 4.218 | 1.00 | 34.73 | C |
| ATOM | 2166 | CZ2 | TRP A | 406 | 58.488 | 49.784 | 4.994 | 1.00 | 34.60 | C |
| ATOM | 2167 | CZ3 | TRP A | 406 | 60.186 | 50.740 | 3.551 | 1.00 | 34.68 | C |
| ATOM | 2168 | CH2 | TRP A | 406 | 59.366 | 49.666 | 3.946 | 1.00 | 34.70 | C |
| ATOM | 2169 | N | GLY A | 407 | 59.978 | 55.392 | 9.316 | 1.00 | 38.58 | N |
| ATOM | 2170 | CA | GLY A | 407 | 59.571 | 55.221 | 10.695 | 1.00 | 39.46 | C |
| ATOM | 2171 | C | GLY A | 407 | 58.182 | 54.625 | 10.820 | 1.00 | 40.35 | C |
| ATOM | 2172 | O | GLY A | 407 | 57.402 | 54.627 | 9.867 | 1.00 | 40.02 | O |
| ATOM | 2173 | N | GLU A | 408 | 57.878 | 54.102 | 12.003 | 1.00 | 41.35 | N |
| ATOM | 2174 | CA | GLU A | 408 | 56.578 | 53.506 | 12.271 | 1.00 | 42.48 | C |
| ATOM | 2175 | C | GLU A | 408 | 55.513 | 54.585 | 12.394 | 1.00 | 43.53 | C |
| ATOM | 2176 | O | GLU A | 408 | 54.320 | 54.302 | 12.334 | 1.00 | 43.54 | O |
| ATOM | 2177 | CB | GLU A | 408 | 56.641 | 52.682 | 13.555 | 1.00 | 42.13 | C |
| ATOM | 2178 | CG | GLU A | 408 | 57.446 | 51.408 | 13.410 | 1.00 | 41.70 | C |
| ATOM | 2179 | CD | GLU A | 408 | 56.789 | 50.416 | 12.464 | 1.00 | 41.39 | C |
| ATOM | 2180 | OE1 | GLU A | 408 | 55.688 | 49.927 | 12.785 | 1.00 | 41.50 | O |
| ATOM | 2181 | OE2 | GLU A | 408 | 57.370 | 50.126 | 11.401 | 1.00 | 40.96 | O |
| ATOM | 2182 | N | GLY A | 409 | 55.954 | 55.827 | 12.562 | 1.00 | 45.08 | N |
| ATOM | 2183 | CA | GLY A | 409 | 55.022 | 56.932 | 12.681 | 1.00 | 47.32 | C |
| ATOM | 2184 | C | GLY A | 409 | 54.711 | 57.588 | 11.345 | 1.00 | 48.91 | C |
| ATOM | 2185 | O | GLY A | 409 | 53.891 | 58.502 | 11.274 | 1.00 | 48.67 | O |
| ATOM | 2186 | N | SER A | 410 | 55.365 | 57.130 | 10.281 | 1.00 | 50.68 | N |
| ATOM | 2187 | CA | SER A | 410 | 55.132 | 57.699 | 8.958 | 1.00 | 52.76 | C |
| ATOM | 2188 | C | SER A | 410 | 53.849 | 57.131 | 8.373 | 1.00 | 54.23 | C |
| ATOM | 2189 | O | SER A | 410 | 53.454 | 56.008 | 8.689 | 1.00 | 53.75 | O |
| ATOM | 2190 | CB | SER A | 410 | 56.301 | 57.394 | 8.015 | 1.00 | 52.65 | C |
| ATOM | 2191 | OG | SER A | 410 | 56.325 | 56.026 | 7.646 | 1.00 | 53.09 | O |
| ATOM | 2192 | N | SER A | 411 | 53.200 | 57.918 | 7.520 | 1.00 | 56.27 | N |
| ATOM | 2193 | CA | SER A | 411 | 51.960 | 57.493 | 6.889 | 1.00 | 58.56 | C |
| ATOM | 2194 | C | SER A | 411 | 52.188 | 56.213 | 6.088 | 1.00 | 60.08 | C |
| ATOM | 2195 | O | SER A | 411 | 51.270 | 55.406 | 5.916 | 1.00 | 60.54 | O |
| ATOM | 2196 | CB | SER A | 411 | 51.430 | 58.600 | 5.973 | 1.00 | 58.70 | C |
| ATOM | 2197 | OG | SER A | 411 | 52.376 | 58.934 | 4.974 | 1.00 | 59.09 | O |
| ATOM | 2198 | N | ARG A | 412 | 53.418 | 56.027 | 5.612 | 1.00 | 61.61 | N |
| ATOM | 2199 | CA | ARG A | 412 | 53.770 | 54.844 | 4.831 | 1.00 | 63.31 | C |
| ATOM | 2200 | C | ARG A | 412 | 53.527 | 53.549 | 5.609 | 1.00 | 64.68 | C |
| ATOM | 2201 | O | ARG A | 412 | 53.565 | 52.457 | 5.043 | 1.00 | 64.66 | O |
| ATOM | 2202 | CB | ARG A | 412 | 55.236 | 54.921 | 4.385 | 1.00 | 62.76 | C |
| ATOM | 2203 | CG | ARG A | 412 | 55.694 | 53.712 | 3.581 | 1.00 | 62.41 | C |
| ATOM | 2204 | CD | ARG A | 412 | 57.020 | 53.948 | 2.877 | 1.00 | 61.98 | C |
| ATOM | 2205 | NE | ARG A | 412 | 57.408 | 52.776 | 2.097 | 1.00 | 61.77 | N |
| ATOM | 2206 | CZ | ARG A | 412 | 58.493 | 52.701 | 1.332 | 1.00 | 62.01 | C |
| ATOM | 2207 | NH1 | ARG A | 412 | 59.321 | 53.736 | 1.229 | 1.00 | 61.70 | N |
| ATOM | 2208 | NH2 | ARG A | 412 | 58.751 | 51.581 | 0.669 | 1.00 | 62.05 | N |
| ATOM | 2209 | N | ALA A | 413 | 53.273 | 53.681 | 6.908 | 1.00 | 66.59 | N |
| ATOM | 2210 | CA | ALA A | 413 | 53.016 | 52.532 | 7.770 | 1.00 | 68.37 | C |
| ATOM | 2211 | C | ALA A | 413 | 51.774 | 52.795 | 8.617 | 1.00 | 69.80 | C |
| ATOM | 2212 | O | ALA A | 413 | 50.907 | 53.587 | 8.232 | 1.00 | 70.13 | O |
| ATOM | 2213 | CB | ALA A | 413 | 54.222 | 52.279 | 8.672 | 1.00 | 68.21 | C |
| ATOM | 2214 | N | ARG A | 414 | 51.697 | 52.124 | 9.767 | 1.00 | 71.35 | N |
| ATOM | 2215 | CA | ARG A | 414 | 50.586 | 52.267 | 10.715 | 1.00 | 72.93 | C |
| ATOM | 2216 | C | ARG A | 414 | 49.190 | 52.288 | 10.097 | 1.00 | 73.77 | C |
| ATOM | 2217 | O | ARG A | 414 | 48.213 | 52.609 | 10.774 | 1.00 | 73.88 | O |
| ATOM | 2218 | CB | ARG A | 414 | 50.783 | 53.530 | 11.570 | 1.00 | 73.43 | C |
| ATOM | 2219 | CG | ARG A | 414 | 51.031 | 54.815 | 10.779 | 1.00 | 74.17 | C |
| ATOM | 2220 | CD | ARG A | 414 | 51.446 | 55.967 | 11.688 | 1.00 | 74.85 | C |
| ATOM | 2221 | NE | ARG A | 414 | 50.307 | 56.638 | 12.308 | 1.00 | 75.54 | N |
| ATOM | 2222 | CZ | ARG A | 414 | 49.508 | 57.492 | 11.675 | 1.00 | 75.93 | C |
| ATOM | 2223 | NH1 | ARG A | 414 | 49.724 | 57.784 | 10.398 | 1.00 | 76.05 | N |
| ATOM | 2224 | NH2 | ARG A | 414 | 48.495 | 58.059 | 12.319 | 1.00 | 76.11 | N |
| ATOM | 2225 | N | ASN A | 415 | 49.098 | 51.936 | 8.819 | 1.00 | 74.50 | N |
| ATOM | 2226 | CA | ASN A | 415 | 47.818 | 51.923 | 8.124 | 1.00 | 75.19 | C |
| ATOM | 2227 | C | ASN A | 415 | 47.577 | 50.540 | 7.515 | 1.00 | 75.37 | C |
| ATOM | 2228 | O | ASN A | 415 | 47.344 | 50.406 | 6.311 | 1.00 | 75.45 | O |
| ATOM | 2229 | CB | ASN A | 415 | 47.809 | 52.996 | 7.028 | 1.00 | 75.72 | C |
| ATOM | 2230 | CG | ASN A | 415 | 46.402 | 53.424 | 6.634 | 1.00 | 76.17 | C |
| ATOM | 2231 | OD1 | ASN A | 415 | 46.214 | 54.171 | 5.671 | 1.00 | 76.40 | O |
| ATOM | 2232 | ND2 | ASN A | 415 | 45.406 | 52.958 | 7.385 | 1.00 | 76.16 | N |
| ATOM | 2233 | N | TRP A | 416 | 47.644 | 49.516 | 8.361 | 1.00 | 75.41 | N |
| ATOM | 2234 | CA | TRP A | 416 | 47.437 | 48.136 | 7.931 | 1.00 | 75.40 | C |
| ATOM | 2235 | C | TRP A | 416 | 46.062 | 47.625 | 8.366 | 1.00 | 75.38 | C |
| ATOM | 2236 | O | TRP A | 416 | 45.571 | 47.959 | 9.448 | 1.00 | 75.34 | O |
| ATOM | 2237 | CB | TRP A | 416 | 48.532 | 47.232 | 8.515 | 1.00 | 75.24 | C |

TABLE 5-continued

| | | | | | | | | | | |
|---|---|---|---|---|---|---|---|---|---|---|
| ATOM | 2238 | CG | TRP A | 416 | 48.733 | 47.426 | 9.990 | 1.00 | 74.99 | C |
| ATOM | 2239 | CD1 | TRP A | 416 | 49.406 | 48.449 | 10.599 | 1.00 | 74.96 | C |
| ATOM | 2240 | CD2 | TRP A | 416 | 48.190 | 46.620 | 11.044 | 1.00 | 74.76 | C |
| ATOM | 2241 | NE1 | TRP A | 416 | 49.311 | 48.333 | 11.966 | 1.00 | 74.83 | N |
| ATOM | 2242 | CE2 | TRP A | 416 | 48.570 | 47.220 | 12.267 | 1.00 | 74.77 | C |
| ATOM | 2243 | CE3 | TRP A | 416 | 47.415 | 45.453 | 11.075 | 1.00 | 74.57 | C |
| ATOM | 2244 | CZ2 | TRP A | 416 | 48.200 | 46.691 | 13.510 | 1.00 | 74.66 | C |
| ATOM | 2245 | CZ3 | TRP A | 416 | 47.047 | 44.927 | 12.313 | 1.00 | 74.66 | C |
| ATOM | 2246 | CH2 | TRP A | 416 | 47.442 | 45.549 | 13.513 | 1.00 | 74.65 | C |
| ATOM | 2247 | N | GLU A | 431 | 54.518 | 61.394 | 12.341 | 1.00 | 65.44 | N |
| ATOM | 2248 | CA | GLU A | 431 | 55.528 | 61.368 | 13.394 | 1.00 | 65.56 | C |
| ATOM | 2249 | C | GLU A | 431 | 56.862 | 60.844 | 12.879 | 1.00 | 64.74 | C |
| ATOM | 2250 | O | GLU A | 431 | 57.864 | 60.865 | 13.595 | 1.00 | 64.65 | O |
| ATOM | 2251 | CB | GLU A | 431 | 55.072 | 60.484 | 14.557 | 1.00 | 66.48 | C |
| ATOM | 2252 | CG | GLU A | 431 | 53.806 | 60.944 | 15.256 | 1.00 | 68.09 | C |
| ATOM | 2253 | CD | GLU A | 431 | 53.483 | 60.087 | 16.469 | 1.00 | 69.15 | C |
| ATOM | 2254 | OE1 | GLU A | 431 | 53.319 | 58.854 | 16.306 | 1.00 | 69.66 | O |
| ATOM | 2255 | OE2 | GLU A | 431 | 53.397 | 60.647 | 17.586 | 1.00 | 69.60 | O |
| ATOM | 2256 | N | GLY A | 432 | 56.873 | 60.368 | 11.641 | 1.00 | 63.84 | N |
| ATOM | 2257 | CA | GLY A | 432 | 58.100 | 59.842 | 11.080 | 1.00 | 62.59 | C |
| ATOM | 2258 | C | GLY A | 432 | 58.315 | 60.225 | 9.633 | 1.00 | 61.80 | C |
| ATOM | 2259 | O | GLY A | 432 | 57.421 | 60.765 | 8.977 | 1.00 | 61.75 | O |
| ATOM | 2260 | N | VAL A | 433 | 59.513 | 59.938 | 9.135 | 1.00 | 60.79 | N |
| ATOM | 2261 | CA | VAL A | 433 | 59.867 | 60.246 | 7.758 | 1.00 | 59.34 | C |
| ATOM | 2262 | C | VAL A | 433 | 60.128 | 58.968 | 6.964 | 1.00 | 58.28 | C |
| ATOM | 2263 | O | VAL A | 433 | 60.193 | 57.874 | 7.527 | 1.00 | 58.02 | O |
| ATOM | 2264 | CB | VAL A | 433 | 61.124 | 61.149 | 7.700 | 1.00 | 59.34 | C |
| ATOM | 2265 | CG1 | VAL A | 433 | 60.851 | 62.462 | 8.413 | 1.00 | 59.24 | C |
| ATOM | 2266 | CG2 | VAL A | 433 | 62.309 | 60.442 | 8.336 | 1.00 | 59.25 | C |
| ATOM | 2267 | N | ASP A | 434 | 60.263 | 59.122 | 5.651 | 1.00 | 56.94 | N |
| ATOM | 2268 | CA | ASP A | 434 | 60.528 | 58.010 | 4.747 | 1.00 | 55.49 | C |
| ATOM | 2269 | C | ASP A | 434 | 61.778 | 58.380 | 3.957 | 1.00 | 54.43 | C |
| ATOM | 2270 | O | ASP A | 434 | 61.777 | 59.359 | 3.210 | 1.00 | 54.60 | O |
| ATOM | 2271 | CB | ASP A | 434 | 59.333 | 57.808 | 3.809 | 1.00 | 55.70 | C |
| ATOM | 2272 | CG | ASP A | 434 | 59.529 | 56.653 | 2.849 | 1.00 | 55.96 | C |
| ATOM | 2273 | OD1 | ASP A | 434 | 59.987 | 55.578 | 3.288 | 1.00 | 56.51 | O |
| ATOM | 2274 | OD2 | ASP A | 434 | 59.212 | 56.812 | 1.652 | 1.00 | 56.42 | O |
| ATOM | 2275 | N | SER A | 435 | 62.845 | 57.602 | 4.119 | 1.00 | 52.71 | N |
| ATOM | 2276 | CA | SER A | 435 | 64.099 | 57.908 | 3.440 | 1.00 | 50.99 | C |
| ATOM | 2277 | C | SER A | 435 | 64.910 | 56.705 | 2.962 | 1.00 | 49.63 | C |
| ATOM | 2278 | O | SER A | 435 | 64.416 | 55.581 | 2.891 | 1.00 | 48.99 | O |
| ATOM | 2279 | CB | SER A | 435 | 64.971 | 58.757 | 4.366 | 1.00 | 51.10 | C |
| ATOM | 2280 | OG | SER A | 435 | 65.160 | 58.097 | 5.608 | 1.00 | 50.72 | O |
| ATOM | 2281 | N | TYR A | 436 | 66.172 | 56.970 | 2.640 | 1.00 | 48.33 | N |
| ATOM | 2282 | CA | TYR A | 436 | 67.091 | 55.947 | 2.163 | 1.00 | 47.20 | C |
| ATOM | 2283 | C | TYR A | 436 | 68.375 | 55.936 | 2.984 | 1.00 | 45.70 | C |
| ATOM | 2284 | O | TYR A | 436 | 68.863 | 56.987 | 3.400 | 1.00 | 45.68 | O |
| ATOM | 2285 | CB | TYR A | 436 | 67.452 | 56.211 | 0.699 | 1.00 | 48.21 | C |
| ATOM | 2286 | CG | TYR A | 436 | 66.289 | 56.130 | −0.260 | 1.00 | 49.01 | C |
| ATOM | 2287 | CD1 | TYR A | 436 | 65.771 | 54.895 | −0.656 | 1.00 | 49.13 | C |
| ATOM | 2288 | CD2 | TYR A | 436 | 65.701 | 57.288 | −0.769 | 1.00 | 49.35 | C |
| ATOM | 2289 | CE1 | TYR A | 436 | 64.694 | 54.816 | −1.538 | 1.00 | 49.77 | C |
| ATOM | 2290 | CE2 | TYR A | 436 | 64.622 | 57.221 | −1.650 | 1.00 | 49.98 | C |
| ATOM | 2291 | CZ | TYR A | 436 | 64.125 | 55.982 | −2.029 | 1.00 | 49.99 | C |
| ATOM | 2292 | OH | TYR A | 436 | 63.054 | 55.911 | −2.891 | 1.00 | 50.64 | O |
| ATOM | 2293 | N | VAL A | 437 | 68.913 | 54.743 | 3.214 | 1.00 | 43.68 | N |
| ATOM | 2294 | CA | VAL A | 437 | 70.164 | 54.591 | 3.944 | 1.00 | 41.96 | C |
| ATOM | 2295 | C | VAL A | 437 | 71.139 | 53.869 | 3.025 | 1.00 | 40.88 | C |
| ATOM | 2296 | O | VAL A | 437 | 70.741 | 53.013 | 2.238 | 1.00 | 40.43 | O |
| ATOM | 2297 | CB | VAL A | 437 | 69.992 | 53.765 | 5.245 | 1.00 | 41.57 | C |
| ATOM | 2298 | CG1 | VAL A | 437 | 69.165 | 54.547 | 6.252 | 1.00 | 41.59 | C |
| ATOM | 2299 | CG2 | VAL A | 437 | 69.341 | 52.433 | 4.936 | 1.00 | 41.15 | C |
| ATOM | 2300 | N | PRO A | 438 | 72.431 | 54.210 | 3.107 | 1.00 | 40.34 | N |
| ATOM | 2301 | CA | PRO A | 438 | 73.428 | 53.559 | 2.252 | 1.00 | 39.68 | C |
| ATOM | 2302 | C | PRO A | 438 | 73.553 | 52.068 | 2.546 | 1.00 | 39.03 | C |
| ATOM | 2303 | O | PRO A | 438 | 73.591 | 51.656 | 3.708 | 1.00 | 38.81 | O |
| ATOM | 2304 | CB | PRO A | 438 | 74.706 | 54.329 | 2.570 | 1.00 | 39.92 | C |
| ATOM | 2305 | CG | PRO A | 438 | 74.512 | 54.693 | 4.014 | 1.00 | 40.33 | C |
| ATOM | 2306 | CD | PRO A | 438 | 73.072 | 55.149 | 4.043 | 1.00 | 40.10 | C |
| ATOM | 2307 | N | TYR A | 439 | 73.606 | 51.267 | 1.486 | 1.00 | 38.09 | N |
| ATOM | 2308 | CA | TYR A | 439 | 73.736 | 49.821 | 1.614 | 1.00 | 37.58 | C |
| ATOM | 2309 | C | TYR A | 439 | 75.059 | 49.499 | 2.299 | 1.00 | 37.43 | C |
| ATOM | 2310 | O | TYR A | 439 | 76.098 | 50.048 | 1.948 | 1.00 | 37.52 | O |
| ATOM | 2311 | CB | TYR A | 439 | 73.688 | 49.170 | 0.229 | 1.00 | 36.98 | C |
| ATOM | 2312 | CG | TYR A | 439 | 73.817 | 47.666 | 0.237 | 1.00 | 36.27 | C |
| ATOM | 2313 | CD1 | TYR A | 439 | 72.869 | 46.871 | 0.870 | 1.00 | 36.31 | C |
| ATOM | 2314 | CD2 | TYR A | 439 | 74.879 | 47.034 | −0.414 | 1.00 | 36.64 | C |
| ATOM | 2315 | CE1 | TYR A | 439 | 72.970 | 45.479 | 0.856 | 1.00 | 36.58 | C |
| ATOM | 2316 | CE2 | TYR A | 439 | 74.989 | 45.646 | −0.434 | 1.00 | 36.33 | C |

TABLE 5-continued

| | | | | | | | | | | |
|---|---|---|---|---|---|---|---|---|---|---|
| ATOM | 2317 | CZ | TYR A | 439 | 74.030 | 44.877 | 0.202 | 1.00 | 36.46 | C |
| ATOM | 2318 | OH | TYR A | 439 | 74.134 | 43.506 | 0.187 | 1.00 | 37.16 | O |
| ATOM | 2319 | N | ALA A | 440 | 75.024 | 48.598 | 3.272 | 1.00 | 37.46 | N |
| ATOM | 2320 | CA | ALA A | 440 | 76.236 | 48.251 | 4.002 | 1.00 | 37.42 | C |
| ATOM | 2321 | C | ALA A | 440 | 76.672 | 46.809 | 3.794 | 1.00 | 37.20 | C |
| ATOM | 2322 | O | ALA A | 440 | 77.760 | 46.424 | 4.213 | 1.00 | 37.15 | O |
| ATOM | 2323 | CB | ALA A | 440 | 76.033 | 48.523 | 5.494 | 1.00 | 37.18 | C |
| ATOM | 2324 | N | GLY A | 441 | 75.828 | 46.016 | 3.145 | 1.00 | 37.04 | N |
| ATOM | 2325 | CA | GLY A | 441 | 76.169 | 44.624 | 2.926 | 1.00 | 37.04 | C |
| ATOM | 2326 | C | GLY A | 441 | 75.475 | 43.746 | 3.950 | 1.00 | 37.28 | C |
| ATOM | 2327 | O | GLY A | 441 | 74.415 | 44.107 | 4.456 | 1.00 | 37.10 | O |
| ATOM | 2328 | N | LYS A | 442 | 76.067 | 42.598 | 4.265 | 1.00 | 37.56 | N |
| ATOM | 2329 | CA | LYS A | 442 | 75.469 | 41.687 | 5.232 | 1.00 | 37.84 | C |
| ATOM | 2330 | C | LYS A | 442 | 75.707 | 42.113 | 6.677 | 1.00 | 37.14 | C |
| ATOM | 2331 | O | LYS A | 442 | 76.746 | 42.683 | 7.013 | 1.00 | 36.64 | O |
| ATOM | 2332 | CB | LYS A | 442 | 75.995 | 40.266 | 5.017 | 1.00 | 39.16 | C |
| ATOM | 2333 | CG | LYS A | 442 | 75.839 | 39.789 | 3.584 | 1.00 | 41.53 | C |
| ATOM | 2334 | CD | LYS A | 442 | 75.692 | 38.280 | 3.495 | 1.00 | 43.26 | C |
| ATOM | 2335 | CE | LYS A | 442 | 74.316 | 37.842 | 3.976 | 1.00 | 44.48 | C |
| ATOM | 2336 | NZ | LYS A | 442 | 74.126 | 36.365 | 3.858 | 1.00 | 45.91 | N |
| ATOM | 2337 | N | LEU A | 443 | 74.724 | 41.823 | 7.524 | 1.00 | 36.39 | N |
| ATOM | 2338 | CA | LEU A | 443 | 74.774 | 42.161 | 8.940 | 1.00 | 35.72 | C |
| ATOM | 2339 | C | LEU A | 443 | 76.055 | 41.701 | 9.645 | 1.00 | 35.73 | C |
| ATOM | 2340 | O | LEU A | 443 | 76.723 | 42.493 | 10.314 | 1.00 | 35.02 | O |
| ATOM | 2341 | CB | LEU A | 443 | 73.545 | 41.571 | 9.640 | 1.00 | 34.56 | C |
| ATOM | 2342 | CG | LEU A | 443 | 73.386 | 41.723 | 11.157 | 1.00 | 34.09 | C |
| ATOM | 2343 | CD1 | LEU A | 443 | 71.921 | 41.572 | 11.526 | 1.00 | 33.35 | C |
| ATOM | 2344 | CD2 | LEU A | 443 | 74.234 | 40.685 | 11.883 | 1.00 | 33.47 | C |
| ATOM | 2345 | N | LYS A | 444 | 76.396 | 40.428 | 9.479 | 1.00 | 35.89 | N |
| ATOM | 2346 | CA | LYS A | 444 | 77.572 | 39.840 | 10.116 | 1.00 | 36.54 | C |
| ATOM | 2347 | C | LYS A | 444 | 78.837 | 40.702 | 10.158 | 1.00 | 36.30 | C |
| ATOM | 2348 | O | LYS A | 444 | 79.285 | 41.100 | 11.232 | 1.00 | 36.27 | O |
| ATOM | 2349 | CB | LYS A | 444 | 77.910 | 38.500 | 9.455 | 1.00 | 37.62 | C |
| ATOM | 2350 | CG | LYS A | 444 | 78.998 | 37.715 | 10.180 | 1.00 | 39.34 | C |
| ATOM | 2351 | CD | LYS A | 444 | 79.322 | 36.415 | 9.452 | 1.00 | 40.97 | C |
| ATOM | 2352 | CE | LYS A | 444 | 80.227 | 35.523 | 10.285 | 1.00 | 41.64 | C |
| ATOM | 2353 | NZ | LYS A | 444 | 81.483 | 36.221 | 10.689 | 1.00 | 42.46 | N |
| ATOM | 2354 | N | ASP A | 445 | 79.406 | 40.985 | 8.991 | 1.00 | 35.80 | N |
| ATOM | 2355 | CA | ASP A | 445 | 80.638 | 41.762 | 8.892 | 1.00 | 35.72 | C |
| ATOM | 2356 | C | ASP A | 445 | 80.567 | 43.135 | 9.546 | 1.00 | 34.60 | C |
| ATOM | 2357 | O | ASP A | 445 | 81.541 | 43.593 | 10.148 | 1.00 | 34.07 | O |
| ATOM | 2358 | CB | ASP A | 445 | 81.033 | 41.918 | 7.421 | 1.00 | 37.61 | C |
| ATOM | 2359 | CG | ASP A | 445 | 81.167 | 40.580 | 6.711 | 1.00 | 39.41 | C |
| ATOM | 2360 | OD1 | ASP A | 445 | 82.084 | 39.804 | 7.066 | 1.00 | 39.74 | O |
| ATOM | 2361 | OD2 | ASP A | 445 | 80.343 | 40.301 | 5.810 | 1.00 | 40.68 | O |
| ATOM | 2362 | N | ASN A | 446 | 79.420 | 43.792 | 9.415 | 1.00 | 33.16 | N |
| ATOM | 2363 | CA | ASN A | 446 | 79.231 | 45.117 | 9.991 | 1.00 | 32.29 | C |
| ATOM | 2364 | C | ASN A | 446 | 79.121 | 45.054 | 11.508 | 1.00 | 31.85 | C |
| ATOM | 2365 | O | ASN A | 446 | 79.757 | 45.833 | 12.217 | 1.00 | 31.32 | O |
| ATOM | 2366 | CB | ASN A | 446 | 77.983 | 45.759 | 9.398 | 1.00 | 32.15 | C |
| ATOM | 2367 | CG | ASN A | 446 | 78.181 | 46.173 | 7.956 | 1.00 | 32.29 | C |
| ATOM | 2368 | OD1 | ASN A | 446 | 78.690 | 47.264 | 7.678 | 1.00 | 32.36 | O |
| ATOM | 2369 | ND2 | ASN A | 446 | 77.797 | 45.300 | 7.029 | 1.00 | 30.94 | N |
| ATOM | 2370 | N | VAL A | 447 | 78.318 | 44.120 | 12.004 | 1.00 | 31.23 | N |
| ATOM | 2371 | CA | VAL A | 447 | 78.151 | 43.965 | 13.436 | 1.00 | 31.20 | C |
| ATOM | 2372 | C | VAL A | 447 | 79.477 | 43.588 | 14.104 | 1.00 | 31.65 | C |
| ATOM | 2373 | O | VAL A | 447 | 79.819 | 44.124 | 15.156 | 1.00 | 31.22 | O |
| ATOM | 2374 | CB | VAL A | 447 | 77.088 | 42.889 | 13.763 | 1.00 | 30.72 | C |
| ATOM | 2375 | CG1 | VAL A | 447 | 77.151 | 42.519 | 15.235 | 1.00 | 30.21 | C |
| ATOM | 2376 | CG2 | VAL A | 447 | 75.705 | 43.416 | 13.424 | 1.00 | 30.13 | C |
| ATOM | 2377 | N | GLU A | 448 | 80.228 | 42.679 | 13.490 | 1.00 | 31.79 | N |
| ATOM | 2378 | CA | GLU A | 448 | 81.493 | 42.260 | 14.071 | 1.00 | 32.87 | C |
| ATOM | 2379 | C | GLU A | 448 | 82.509 | 43.398 | 14.062 | 1.00 | 32.19 | C |
| ATOM | 2380 | O | GLU A | 448 | 83.329 | 43.506 | 14.970 | 1.00 | 31.93 | O |
| ATOM | 2381 | CB | GLU A | 448 | 82.037 | 41.021 | 13.339 | 1.00 | 34.51 | C |
| ATOM | 2382 | CG | GLU A | 448 | 81.008 | 39.886 | 13.264 | 1.00 | 37.38 | C |
| ATOM | 2383 | CD | GLU A | 448 | 81.609 | 38.522 | 12.933 | 1.00 | 39.91 | C |
| ATOM | 2384 | OE1 | GLU A | 448 | 82.543 | 38.447 | 12.098 | 1.00 | 41.39 | O |
| ATOM | 2385 | OE2 | GLU A | 448 | 81.129 | 37.514 | 13.501 | 1.00 | 40.50 | O |
| ATOM | 2386 | N | ALA A | 449 | 82.448 | 44.254 | 13.049 | 1.00 | 31.62 | N |
| ATOM | 2387 | CA | ALA A | 449 | 83.366 | 45.385 | 12.978 | 1.00 | 30.96 | C |
| ATOM | 2388 | C | ALA A | 449 | 82.995 | 46.398 | 14.063 | 1.00 | 30.59 | C |
| ATOM | 2389 | O | ALA A | 449 | 83.866 | 46.907 | 14.775 | 1.00 | 29.96 | O |
| ATOM | 2390 | CB | ALA A | 449 | 83.304 | 46.040 | 11.600 | 1.00 | 31.10 | C |
| ATOM | 2391 | N | SER A | 450 | 81.701 | 46.686 | 14.187 | 1.00 | 30.07 | N |
| ATOM | 2392 | CA | SER A | 450 | 81.222 | 47.625 | 15.197 | 1.00 | 29.77 | C |
| ATOM | 2393 | C | SER A | 450 | 81.589 | 47.160 | 16.606 | 1.00 | 29.70 | C |
| ATOM | 2394 | O | SER A | 450 | 82.085 | 47.943 | 17.419 | 1.00 | 29.34 | O |
| ATOM | 2395 | CB | SER A | 450 | 79.699 | 47.779 | 15.117 | 1.00 | 29.51 | C |

TABLE 5-continued

| | | | | | | | | | | |
|---|---|---|---|---|---|---|---|---|---|---|
| ATOM | 2396 | OG | SER A | 450 | 79.306 | 48.434 | 13.931 | 1.00 | 29.55 | O |
| ATOM | 2397 | N | LEU A | 451 | 81.341 | 45.884 | 16.886 | 1.00 | 29.59 | N |
| ATOM | 2398 | CA | LEU A | 451 | 81.624 | 45.321 | 18.202 | 1.00 | 29.99 | C |
| ATOM | 2399 | C | LEU A | 451 | 83.111 | 45.175 | 18.505 | 1.00 | 30.55 | C |
| ATOM | 2400 | O | LEU A | 451 | 83.509 | 45.213 | 19.670 | 1.00 | 30.21 | O |
| ATOM | 2401 | CB | LEU A | 451 | 80.902 | 43.981 | 18.372 | 1.00 | 28.74 | C |
| ATOM | 2402 | CG | LEU A | 451 | 79.374 | 44.128 | 18.335 | 1.00 | 28.52 | C |
| ATOM | 2403 | CD1 | LEU A | 451 | 78.726 | 42.808 | 18.674 | 1.00 | 27.60 | C |
| ATOM | 2404 | CD2 | LEU A | 451 | 78.924 | 45.215 | 19.319 | 1.00 | 27.59 | C |
| ATOM | 2405 | N | ASN A | 452 | 83.933 | 45.012 | 17.471 | 1.00 | 31.38 | N |
| ATOM | 2406 | CA | ASN A | 452 | 85.372 | 44.923 | 17.694 | 1.00 | 32.50 | C |
| ATOM | 2407 | C | ASN A | 452 | 85.838 | 46.287 | 18.185 | 1.00 | 32.25 | C |
| ATOM | 2408 | O | ASN A | 452 | 86.751 | 46.390 | 19.005 | 1.00 | 32.13 | O |
| ATOM | 2409 | CB | ASN A | 452 | 86.130 | 44.568 | 16.411 | 1.00 | 33.77 | C |
| ATOM | 2410 | CG | ASN A | 452 | 86.149 | 43.079 | 16.140 | 1.00 | 36.12 | C |
| ATOM | 2411 | OD1 | ASN A | 452 | 86.254 | 42.263 | 17.066 | 1.00 | 37.33 | O |
| ATOM | 2412 | ND2 | ASN A | 452 | 86.069 | 42.712 | 14.866 | 1.00 | 37.13 | N |
| ATOM | 2413 | N | LYS A | 453 | 85.203 | 47.335 | 17.674 | 1.00 | 31.85 | N |
| ATOM | 2414 | CA | LYS A | 453 | 85.547 | 48.693 | 18.067 | 1.00 | 32.30 | C |
| ATOM | 2415 | C | LYS A | 453 | 85.137 | 48.922 | 19.519 | 1.00 | 31.23 | C |
| ATOM | 2416 | O | LYS A | 453 | 85.888 | 49.497 | 20.303 | 1.00 | 30.82 | O |
| ATOM | 2417 | CB | LYS A | 453 | 84.838 | 49.694 | 17.157 | 1.00 | 33.75 | C |
| ATOM | 2418 | CG | LYS A | 453 | 85.166 | 51.143 | 17.450 | 1.00 | 36.50 | C |
| ATOM | 2419 | CD | LYS A | 453 | 84.539 | 52.063 | 16.406 | 1.00 | 39.06 | C |
| ATOM | 2420 | CE | LYS A | 453 | 85.055 | 51.754 | 14.999 | 1.00 | 39.28 | C |
| ATOM | 2421 | NZ | LYS A | 453 | 84.355 | 52.589 | 13.978 | 1.00 | 40.79 | N |
| ATOM | 2422 | N | VAL A | 454 | 83.937 | 48.462 | 19.864 | 1.00 | 30.16 | N |
| ATOM | 2423 | CA | VAL A | 454 | 83.418 | 48.591 | 21.215 | 1.00 | 29.31 | C |
| ATOM | 2424 | C | VAL A | 454 | 84.334 | 47.848 | 22.189 | 1.00 | 29.13 | C |
| ATOM | 2425 | O | VAL A | 454 | 84.696 | 48.372 | 23.243 | 1.00 | 28.31 | O |
| ATOM | 2426 | CB | VAL A | 454 | 81.984 | 48.012 | 21.314 | 1.00 | 29.18 | C |
| ATOM | 2427 | CG1 | VAL A | 454 | 81.506 | 48.019 | 22.765 | 1.00 | 28.54 | C |
| ATOM | 2428 | CG2 | VAL A | 454 | 81.038 | 48.830 | 20.444 | 1.00 | 28.30 | C |
| ATOM | 2429 | N | LYS A | 455 | 84.705 | 46.623 | 21.824 | 1.00 | 28.92 | N |
| ATOM | 2430 | CA | LYS A | 455 | 85.581 | 45.804 | 22.656 | 1.00 | 28.73 | C |
| ATOM | 2431 | C | LYS A | 455 | 86.919 | 46.498 | 22.855 | 1.00 | 28.34 | C |
| ATOM | 2432 | O | LYS A | 455 | 87.462 | 46.522 | 23.954 | 1.00 | 28.12 | O |
| ATOM | 2433 | CB | LYS A | 455 | 85.822 | 44.440 | 22.006 | 1.00 | 28.84 | C |
| ATOM | 2434 | CG | LYS A | 455 | 84.620 | 43.517 | 21.976 | 1.00 | 29.31 | C |
| ATOM | 2435 | CD | LYS A | 455 | 84.971 | 42.252 | 21.200 | 1.00 | 29.86 | C |
| ATOM | 2436 | CE | LYS A | 455 | 83.802 | 41.296 | 21.114 | 1.00 | 31.18 | C |
| ATOM | 2437 | NZ | LYS A | 455 | 84.174 | 40.040 | 20.399 | 1.00 | 31.56 | N |
| ATOM | 2438 | N | SER A | 456 | 87.448 | 47.057 | 21.774 | 1.00 | 28.04 | N |
| ATOM | 2439 | CA | SER A | 456 | 88.720 | 47.754 | 21.834 | 1.00 | 28.45 | C |
| ATOM | 2440 | C | SER A | 456 | 88.631 | 48.936 | 22.802 | 1.00 | 27.62 | C |
| ATOM | 2441 | O | SER A | 456 | 89.497 | 49.121 | 23.658 | 1.00 | 27.05 | O |
| ATOM | 2442 | CB | SER A | 456 | 89.114 | 48.237 | 20.434 | 1.00 | 28.94 | C |
| ATOM | 2443 | OG | SER A | 456 | 90.336 | 48.950 | 20.475 | 1.00 | 31.01 | O |
| ATOM | 2444 | N | THR A | 457 | 87.578 | 49.733 | 22.662 | 1.00 | 26.61 | N |
| ATOM | 2445 | CA | THR A | 457 | 87.377 | 50.885 | 23.528 | 1.00 | 26.30 | C |
| ATOM | 2446 | C | THR A | 457 | 87.186 | 50.444 | 24.978 | 1.00 | 25.88 | C |
| ATOM | 2447 | O | THR A | 457 | 87.697 | 51.080 | 25.896 | 1.00 | 25.21 | O |
| ATOM | 2448 | CE | THR A | 457 | 86.157 | 51.706 | 23.070 | 1.00 | 26.38 | C |
| ATOM | 2449 | OG1 | THR A | 457 | 86.378 | 52.139 | 21.727 | 1.00 | 27.27 | O |
| ATOM | 2450 | CG2 | THR A | 457 | 85.949 | 52.926 | 23.961 | 1.00 | 25.15 | C |
| ATOM | 2451 | N | MET A | 458 | 86.456 | 49.353 | 25.184 | 1.00 | 25.53 | N |
| ATOM | 2452 | CA | MET A | 458 | 86.244 | 48.857 | 26.535 | 1.00 | 26.03 | C |
| ATOM | 2453 | C | MET A | 458 | 87.578 | 48.547 | 27.201 | 1.00 | 26.68 | C |
| ATOM | 2454 | O | MET A | 458 | 87.768 | 48.826 | 28.383 | 1.00 | 26.93 | O |
| ATOM | 2455 | CE | MET A | 458 | 85.340 | 47.623 | 26.521 | 1.00 | 25.33 | C |
| ATOM | 2456 | CG | MET A | 458 | 83.876 | 47.976 | 26.285 | 1.00 | 24.43 | C |
| ATOM | 2457 | SD | MET A | 458 | 82.816 | 46.551 | 26.067 | 1.00 | 25.53 | S |
| ATOM | 2458 | CE | MET A | 458 | 82.942 | 45.769 | 27.715 | 1.00 | 24.14 | C |
| ATOM | 2459 | N | CYS A | 459 | 88.507 | 47.977 | 26.445 | 1.00 | 27.44 | N |
| ATOM | 2460 | CA | CYS A | 459 | 89.819 | 47.682 | 27.000 | 1.00 | 28.79 | C |
| ATOM | 2461 | C | CYS A | 459 | 90.578 | 48.968 | 27.351 | 1.00 | 28.24 | C |
| ATOM | 2462 | O | CYS A | 459 | 91.338 | 48.996 | 28.322 | 1.00 | 27.71 | O |
| ATOM | 2463 | CE | CYS A | 459 | 90.628 | 46.819 | 26.030 | 1.00 | 31.37 | C |
| ATOM | 2464 | SG | CYS A | 459 | 90.257 | 45.047 | 26.230 | 1.00 | 35.38 | S |
| ATOM | 2465 | N | ASN A | 460 | 90.375 | 50.030 | 26.569 | 1.00 | 27.55 | N |
| ATOM | 2466 | CA | ASN A | 460 | 91.028 | 51.309 | 26.855 | 1.00 | 27.53 | C |
| ATOM | 2467 | C | ASN A | 460 | 90.504 | 51.804 | 28.202 | 1.00 | 27.21 | C |
| ATOM | 2468 | O | ASN A | 460 | 91.202 | 52.496 | 28.938 | 1.00 | 26.69 | O |
| ATOM | 2469 | CB | ASN A | 460 | 90.696 | 52.362 | 25.787 | 1.00 | 27.94 | C |
| ATOM | 2470 | CG | ASN A | 460 | 91.419 | 52.122 | 24.471 | 1.00 | 29.27 | C |
| ATOM | 2471 | OD1 | ASN A | 460 | 90.796 | 52.061 | 23.409 | 1.00 | 29.42 | O |
| ATOM | 2472 | ND2 | ASN A | 460 | 92.741 | 51.998 | 24.533 | 1.00 | 29.31 | N |
| ATOM | 2473 | N | CYS A | 461 | 89.261 | 51.441 | 28.512 | 1.00 | 26.99 | N |
| ATOM | 2474 | CA | CYS A | 461 | 88.632 | 51.855 | 29.755 | 1.00 | 26.90 | C |

TABLE 5-continued

| | | | | | | | | | | |
|---|---|---|---|---|---|---|---|---|---|---|
| ATOM | 2475 | C | CYS A | 461 | 88.865 | 50.838 | 30.871 | 1.00 | 26.66 | C |
| ATOM | 2476 | O | CYS A | 461 | 88.367 | 51.003 | 31.976 | 1.00 | 26.77 | O |
| ATOM | 2477 | CE | CYS A | 461 | 87.126 | 52.063 | 29.538 | 1.00 | 27.30 | C |
| ATOM | 2478 | SG | CYS A | 461 | 86.714 | 53.341 | 28.304 | 1.00 | 27.83 | S |
| ATOM | 2479 | N | GLY A | 462 | 89.627 | 49.793 | 30.570 | 1.00 | 26.92 | N |
| ATOM | 2480 | CA | GLY A | 462 | 89.919 | 48.768 | 31.557 | 1.00 | 26.65 | C |
| ATOM | 2481 | C | GLY A | 462 | 88.758 | 47.842 | 31.881 | 1.00 | 26.78 | C |
| ATOM | 2482 | O | GLY A | 462 | 88.659 | 47.347 | 33.001 | 1.00 | 26.85 | O |
| ATOM | 2483 | N | ALA A | 463 | 87.882 | 47.592 | 30.913 | 1.00 | 26.47 | N |
| ATOM | 2484 | CA | ALA A | 463 | 86.731 | 46.725 | 31.155 | 1.00 | 26.74 | C |
| ATOM | 2485 | C | ALA A | 463 | 86.700 | 45.507 | 30.249 | 1.00 | 26.80 | C |
| ATOM | 2486 | O | ALA A | 463 | 86.898 | 45.616 | 29.034 | 1.00 | 26.39 | O |
| ATOM | 2487 | CB | ALA A | 463 | 85.433 | 47.515 | 30.991 | 1.00 | 26.14 | C |
| ATOM | 2488 | N | LEU A | 464 | 86.444 | 44.349 | 30.850 | 1.00 | 27.16 | N |
| ATOM | 2489 | CA | LEU A | 464 | 86.356 | 43.101 | 30.105 | 1.00 | 27.87 | C |
| ATOM | 2490 | C | LEU A | 464 | 84.901 | 42.683 | 29.943 | 1.00 | 27.47 | C |
| ATOM | 2491 | O | LEU A | 464 | 84.604 | 41.722 | 29.239 | 1.00 | 28.26 | O |
| ATOM | 2492 | CB | LEU A | 464 | 87.138 | 41.984 | 30.806 | 1.00 | 28.54 | C |
| ATOM | 2493 | CG | LEU A | 464 | 88.634 | 41.869 | 30.492 | 1.00 | 29.79 | C |
| ATOM | 2494 | CD1 | LEU A | 464 | 88.827 | 41.779 | 28.983 | 1.00 | 29.98 | C |
| ATOM | 2495 | CD2 | LEU A | 464 | 89.388 | 43.078 | 31.039 | 1.00 | 31.57 | C |
| ATOM | 2496 | N | THR A | 465 | 83.997 | 43.398 | 30.606 | 1.00 | 26.65 | N |
| ATOM | 2497 | CA | THR A | 465 | 82.573 | 43.096 | 30.515 | 1.00 | 25.99 | C |
| ATOM | 2498 | C | THR A | 465 | 81.786 | 44.391 | 30.567 | 1.00 | 25.84 | C |
| ATOM | 2499 | O | THR A | 465 | 82.318 | 45.435 | 30.945 | 1.00 | 25.20 | O |
| ATOM | 2500 | CB | THR A | 465 | 82.077 | 42.229 | 31.688 | 1.00 | 25.98 | C |
| ATOM | 2501 | OG1 | THR A | 465 | 82.139 | 42.991 | 32.899 | 1.00 | 25.86 | O |
| ATOM | 2502 | CG2 | THR A | 465 | 82.921 | 40.975 | 31.827 | 1.00 | 26.08 | C |
| ATOM | 2503 | N | ILE A | 466 | 80.514 | 44.316 | 30.197 | 1.00 | 25.29 | N |
| ATOM | 2504 | CA | ILE A | 466 | 79.666 | 45.495 | 30.229 | 1.00 | 25.21 | C |
| ATOM | 2505 | C | ILE A | 466 | 79.470 | 45.999 | 31.650 | 1.00 | 25.01 | C |
| ATOM | 2506 | O | ILE A | 466 | 79.569 | 47.197 | 31.902 | 1.00 | 25.19 | O |
| ATOM | 2507 | CB | ILE A | 466 | 78.316 | 45.208 | 29.531 | 1.00 | 25.13 | C |
| ATOM | 2508 | CG1 | ILE A | 466 | 78.565 | 45.033 | 28.025 | 1.00 | 25.57 | C |
| ATOM | 2509 | CG2 | ILE A | 466 | 77.323 | 46.336 | 29.809 | 1.00 | 24.41 | C |
| ATOM | 2510 | CD1 | ILE A | 466 | 77.351 | 44.586 | 27.223 | 1.00 | 26.34 | C |
| ATOM | 2511 | N | PRO A | 467 | 79.197 | 45.095 | 32.610 | 1.00 | 25.04 | N |
| ATOM | 2512 | CA | PRO A | 467 | 79.023 | 45.598 | 33.975 | 1.00 | 24.53 | C |
| ATOM | 2513 | C | PRO A | 467 | 80.303 | 46.274 | 34.464 | 1.00 | 24.42 | C |
| ATOM | 2514 | O | PRO A | 467 | 80.256 | 47.287 | 35.155 | 1.00 | 24.23 | O |
| ATOM | 2515 | CB | PRO A | 467 | 78.686 | 44.333 | 34.767 | 1.00 | 24.74 | C |
| ATOM | 2516 | CG | PRO A | 467 | 77.936 | 43.508 | 33.754 | 1.00 | 24.43 | C |
| ATOM | 2517 | CD | PRO A | 467 | 78.817 | 43.672 | 32.527 | 1.00 | 24.58 | C |
| ATOM | 2518 | N | GLN A | 468 | 81.455 | 45.723 | 34.105 | 1.00 | 24.65 | N |
| ATOM | 2519 | CA | GLN A | 468 | 82.702 | 46.335 | 34.536 | 1.00 | 25.05 | C |
| ATOM | 2520 | C | GLN A | 468 | 82.883 | 47.705 | 33.873 | 1.00 | 25.35 | C |
| ATOM | 2521 | O | GLN A | 468 | 83.447 | 48.621 | 34.471 | 1.00 | 25.30 | O |
| ATOM | 2522 | CB | GLN A | 468 | 83.890 | 45.430 | 34.219 | 1.00 | 24.93 | C |
| ATOM | 2523 | CG | GLN A | 468 | 85.207 | 46.019 | 34.668 | 1.00 | 25.22 | C |
| ATOM | 2524 | CD | GLN A | 468 | 86.347 | 45.017 | 34.648 | 1.00 | 25.10 | C |
| ATOM | 2525 | OE1 | GLN A | 468 | 86.493 | 44.234 | 33.707 | 1.00 | 24.05 | O |
| ATOM | 2526 | NE2 | GLN A | 468 | 87.176 | 45.054 | 35.686 | 1.00 | 25.09 | N |
| ATOM | 2527 | N | LEU A | 469 | 82.400 | 47.840 | 32.639 | 1.00 | 25.06 | N |
| ATOM | 2528 | CA | LEU A | 469 | 82.488 | 49.108 | 31.919 | 1.00 | 24.83 | C |
| ATOM | 2529 | C | LEU A | 469 | 81.609 | 50.150 | 32.617 | 1.00 | 25.01 | C |
| ATOM | 2530 | O | LEU A | 469 | 82.023 | 51.292 | 32.838 | 1.00 | 24.50 | O |
| ATOM | 2531 | CB | LEU A | 469 | 82.010 | 48.932 | 30.476 | 1.00 | 24.41 | C |
| ATOM | 2532 | CG | LEU A | 469 | 81.852 | 50.214 | 29.655 | 1.00 | 24.56 | C |
| ATOM | 2533 | CD1 | LEU A | 469 | 83.223 | 50.807 | 29.360 | 1.00 | 24.30 | C |
| ATOM | 2534 | CD2 | LEU A | 469 | 81.112 | 49.906 | 28.358 | 1.00 | 24.10 | C |
| ATOM | 2535 | N | GLN A | 470 | 80.395 | 49.741 | 32.966 | 1.00 | 25.06. | N |
| ATOM | 2536 | CA | GLN A | 470 | 79.441 | 50.622 | 33.629 | 1.00 | 25.82 | C |
| ATOM | 2537 | C | GLN A | 470 | 79.966 | 51.100 | 34.981 | 1.00 | 26.53 | C |
| ATOM | 2538 | O | GLN A | 470 | 79.627 | 52.184 | 35.467 | 1.00 | 26.74 | O |
| ATOM | 2539 | CB | GLN A | 470 | 78.102 | 49.886 | 33.775 | 1.00 | 25.24 | C |
| ATOM | 2540 | CG | GLN A | 470 | 77.455 | 49.646 | 32.406 | 1.00 | 25.04 | C |
| ATOM | 2541 | CD | GLN A | 470 | 76.245 | 48.731 | 32.421 | 1.00 | 25.22 | C |
| ATOM | 2542 | OE1 | GLN A | 470 | 75.453 | 48.722 | 31.469 | 1.00 | 25.47 | O |
| ATOM | 2543 | NE2 | GLN A | 470 | 76.099 | 47.948 | 33.479 | 1.00 | 24.84 | N |
| ATOM | 2544 | N | SER A | 471 | 80.829 | 50.291 | 35.572 | 1.00 | 27.02 | N |
| ATOM | 2545 | CA | SER A | 471 | 81.404 | 50.617 | 36.860 | 1.00 | 27.70 | C |
| ATOM | 2546 | C | SER A | 471 | 82.654 | 51.505 | 36.756 | 1.00 | 27.93 | C |
| ATOM | 2547 | O | SER A | 471 | 82.805 | 52.458 | 37.517 | 1.00 | 28.18 | O |
| ATOM | 2548 | CB | SER A | 471 | 81.741 | 49.316 | 37.596 | 1.00 | 27.39 | C |
| ATOM | 2549 | OG | SER A | 471 | 82.515 | 49.569 | 38.748 | 1.00 | 29.07 | O |
| ATOM | 2550 | N | LYS A | 472 | 83.522 | 51.208 | 35.794 | 1.00 | 28.02 | N |
| ATOM | 2551 | CA | LYS A | 472 | 84.785 | 51.935 | 35.630 | 1.00 | 28.71 | C |
| ATOM | 2552 | C | LYS A | 472 | 84.851 | 53.106 | 34.647 | 1.00 | 28.19 | C |
| ATOM | 2553 | O | LYS A | 472 | 85.796 | 53.891 | 34.696 | 1.00 | 28.07 | O |

TABLE 5-continued

| | | | | | | | | | | |
|---|---|---|---|---|---|---|---|---|---|---|
| ATOM | 2554 | CB | LYS A | 472 | 85.883 | 50.938 | 35.257 | 1.00 | 29.32 | C |
| ATOM | 2555 | CG | LYS A | 472 | 86.050 | 49.816 | 36.267 | 1.00 | 31.72 | C |
| ATOM | 2556 | CD | LYS A | 472 | 87.050 | 48.764 | 35.805 | 1.00 | 32.09 | C |
| ATOM | 2557 | CE | LYS A | 472 | 88.459 | 49.308 | 35.753 | 1.00 | 32.85 | C |
| ATOM | 2558 | NZ | LYS A | 472 | 89.418 | 48.212 | 35.419 | 1.00 | 33.48 | N |
| ATOM | 2559 | N | ALA A | 473 | 83.868 | 53.223 | 33.760 | 1.00 | 27.53 | N |
| ATOM | 2560 | CA | ALA A | 473 | 83.875 | 54.283 | 32.758 | 1.00 | 27.01 | C |
| ATOM | 2561 | C | ALA A | 473 | 83.977 | 55.698 | 33.313 | 1.00 | 26.91 | C |
| ATOM | 2562 | O | ALA A | 473 | 83.341 | 56.049 | 34.309 | 1.00 | 26.92 | O |
| ATOM | 2563 | CB | ALA A | 473 | 82.635 | 54.169 | 31.859 | 1.00 | 27.23 | C |
| ATOM | 2564 | N | LYS A | 474 | 84.803 | 56.499 | 32.649 | 1.00 | 26.59 | N |
| ATOM | 2565 | CA | LYS A | 474 | 85.012 | 57.898 | 32.999 | 1.00 | 26.15 | C |
| ATOM | 2566 | C | LYS A | 474 | 84.444 | 58.636 | 31.791 | 1.00 | 26.08 | C |
| ATOM | 2567 | O | LYS A | 474 | 84.973 | 58.545 | 30.684 | 1.00 | 25.63 | O |
| ATOM | 2568 | CB | LYS A | 474 | 86.504 | 58.161 | 33.190 | 1.00 | 25.22 | C |
| ATOM | 2569 | CG | LYS A | 474 | 87.062 | 57.433 | 34.414 | 1.00 | 25.03 | C |
| ATOM | 2570 | CD | LYS A | 474 | 88.530 | 57.064 | 34.245 | 1.00 | 24.53 | C |
| ATOM | 2571 | CE | LYS A | 474 | 89.433 | 58.274 | 34.298 | 1.00 | 24.54 | C |
| ATOM | 2572 | NZ | LYS A | 474 | 90.837 | 57.870 | 33.996 | 1.00 | 23.96 | N |
| ATOM | 2573 | N | ILE A | 475 | 83.348 | 59.350 | 32.011 | 1.00 | 26.24 | N |
| ATOM | 2574 | CA | ILE A | 475 | 82.652 | 60.025 | 30.926 | 1.00 | 26.16 | C |
| ATOM | 2575 | C | ILE A | 475 | 82.601 | 61.527 | 31.073 | 1.00 | 26.07 | C |
| ATOM | 2576 | O | ILE A | 475 | 82.064 | 62.045 | 32.049 | 1.00 | 26.61 | O |
| ATOM | 2577 | CB | ILE A | 475 | 81.206 | 59.489 | 30.821 | 1.00 | 26.31 | C |
| ATOM | 2578 | CG1 | ILE A | 475 | 81.230 | 57.954 | 30.784 | 1.00 | 26.16 | C |
| ATOM | 2579 | CG2 | ILE A | 475 | 80.526 | 60.042 | 29.572 | 1.00 | 26.65 | C |
| ATOM | 2580 | CD1 | ILE A | 475 | 79.853 | 57.299 | 30.764 | 1.00 | 24.83 | C |
| ATOM | 2581 | N | THR A | 476 | 83.156 | 62.228 | 30.093 | 1.00 | 25.67 | N |
| ATOM | 2582 | CA | THR A | 476 | 83.158 | 63.677 | 30.136 | 1.00 | 25.52 | C |
| ATOM | 2583 | C | THR A | 476 | 82.290 | 64.288 | 29.056 | 1.00 | 25.76 | C |
| ATOM | 2584 | O | THR A | 476 | 82.160 | 63.752 | 27.951 | 1.00 | 25.51 | O |
| ATOM | 2585 | CB | THR A | 476 | 84.581 | 64.261 | 29.977 | 1.00 | 25.15 | C |
| ATOM | 2586 | OG1 | THR A | 476 | 84.519 | 65.689 | 30.093 | 1.00 | 24.81 | O |
| ATOM | 2587 | CG2 | THR A | 476 | 85.168 | 63.897 | 28.616 | 1.00 | 24.56 | C |
| ATOM | 2588 | N | LEU A | 477 | 81.686 | 65.414 | 29.401 | 1.00 | 26.07 | N |
| ATOM | 2589 | CA | LEU A | 477 | 80.869 | 66.159 | 28.467 | 1.00 | 27.01 | C |
| ATOM | 2590 | C | LEU A | 477 | 81.908 | 66.963 | 27.677 | 1.00 | 27.30 | C |
| ATOM | 2591 | O | LEU A | 477 | 82.996 | 67.239 | 28.183 | 1.00 | 26.31 | O |
| ATOM | 2592 | CB | LEU A | 477 | 79.929 | 67.103 | 29.225 | 1.00 | 27.31 | C |
| ATOM | 2593 | CG | LEU A | 477 | 78.834 | 67.808 | 28.421 | 1.00 | 28.63 | C |
| ATOM | 2594 | CD1 | LEU A | 477 | 77.822 | 66.782 | 27.915 | 1.00 | 28.11 | C |
| ATOM | 2595 | CD2 | LEU A | 477 | 78.148 | 68.842 | 29.303 | 1.00 | 28.70 | C |
| ATOM | 2596 | N | VAL A | 478 | 81.577 | 67.317 | 26.443 | 1.00 | 27.88 | N |
| ATOM | 2597 | CA | VAL A | 478 | 82.472 | 68.085 | 25.590 | 1.00 | 29.05 | C |
| ATOM | 2598 | C | VAL A | 478 | 81.802 | 69.428 | 25.295 | 1.00 | 29.61 | C |
| ATOM | 2599 | O | VAL A | 478 | 80.581 | 69.504 | 25.177 | 1.00 | 29.56 | O |
| ATOM | 2600 | CB | VAL A | 478 | 82.737 | 67.322 | 24.269 | 1.00 | 29.48 | C |
| ATOM | 2601 | CG1 | VAL A | 478 | 83.643 | 68.125 | 23.368 | 1.00 | 30.38 | C |
| ATOM | 2602 | CG2 | VAL A | 478 | 83.370 | 65.970 | 24.579 | 1.00 | 29.54 | C |
| ATOM | 2603 | N | SER A | 479 | 82.596 | 70.484 | 25.183 | 1.00 | 30.34 | N |
| ATOM | 2604 | CA | SER A | 479 | 82.058 | 71.819 | 24.916 | 1.00 | 31.62 | C |
| ATOM | 2605 | C | SER A | 479 | 81.402 | 71.940 | 23.545 | 1.00 | 32.67 | C |
| ATOM | 2606 | O | SER A | 479 | 81.770 | 71.232 | 22.609 | 1.00 | 31.95 | O |
| ATOM | 2607 | CB | SER A | 479 | 83.168 | 72.866 | 25.021 | 1.00 | 30.68 | C |
| ATOM | 2608 | OG | SER A | 479 | 84.085 | 72.730 | 23.949 | 1.00 | 30.46 | O |
| ATOM | 2609 | N | SER A | 480 | 80.442 | 72.858 | 23.437 | 1.00 | 34.86 | N |
| ATOM | 2610 | CA | SER A | 480 | 79.729 | 73.110 | 22.183 | 1.00 | 37.33 | C |
| ATOM | 2611 | C | SER A | 480 | 80.703 | 73.371 | 21.041 | 1.00 | 38.47 | C |
| ATOM | 2612 | O | SER A | 480 | 80.561 | 72.816 | 19.951 | 1.00 | 38.60 | O |
| ATOM | 2613 | CB | SER A | 480 | 78.813 | 74.331 | 22.317 | 1.00 | 37.61 | C |
| ATOM | 2614 | OG | SER A | 480 | 77.888 | 74.175 | 23.373 | 1.00 | 39.26 | O |
| ATOM | 2615 | N | VAL A | 481 | 81.685 | 74.229 | 21.302 | 1.00 | 40.19 | N |
| ATOM | 2616 | CA | VAL A | 481 | 82.694 | 74.592 | 20.311 | 1.00 | 42.19 | C |
| ATOM | 2617 | C | VAL A | 481 | 83.561 | 73.422 | 19.843 | 1.00 | 43.43 | C |
| ATOM | 2618 | O | VAL A | 481 | 83.944 | 73.364 | 18.676 | 1.00 | 43.73 | O |
| ATOM | 2619 | CB | VAL A | 481 | 83.617 | 75.716 | 20.848 | 1.00 | 42.42 | C |
| ATOM | 2620 | CG1 | VAL A | 481 | 84.833 | 75.879 | 19.941 | 1.00 | 42.66 | C |
| ATOM | 2621 | CG2 | VAL A | 481 | 82.844 | 77.029 | 20.917 | 1.00 | 42.27 | C |
| ATOM | 2622 | N | SER A | 482 | 83.879 | 72.499 | 20.744 | 1.00 | 44.59 | N |
| ATOM | 2623 | CA | SER A | 482 | 84.697 | 71.346 | 20.378 | 1.00 | 46.25 | C |
| ATOM | 2624 | C | SER A | 482 | 84.013 | 70.517 | 19.293 | 1.00 | 47.04 | C |
| ATOM | 2625 | O | SER A | 482 | 84.670 | 69.773 | 18.556 | 1.00 | 47.14 | O |
| ATOM | 2626 | CB | SER A | 482 | 84.943 | 70.448 | 21.594 | 1.00 | 46.49 | C |
| ATOM | 2627 | OG | SER A | 482 | 85.710 | 71.107 | 22.583 | 1.00 | 48.50 | O |
| ATOM | 2628 | N | ILE A | 483 | 82.693 | 70.638 | 19.204 | 1.00 | 47.71 | N |
| ATOM | 2629 | CA | ILE A | 483 | 81.934 | 69.876 | 18.219 | 1.00 | 48.77 | C |
| ATOM | 2630 | C | ILE A | 483 | 81.656 | 70.687 | 16.952 | 1.00 | 49.17 | C |
| ATOM | 2631 | O | ILE A | 483 | 81.552 | 71.931 | 17.042 | 1.00 | 49.53 | O |
| ATOM | 2632 | CB | ILE A | 483 | 80.597 | 69.387 | 18.833 | 1.00 | 48.86 | C |

TABLE 5-continued

| | | | | | | | | | | |
|---|---|---|---|---|---|---|---|---|---|---|
| ATOM | 2633 | CG1 | ILE A | 483 | 80.886 | 68.549 | 20.081 | 1.00 | 48.85 | C |
| ATOM | 2634 | CG2 | ILE A | 483 | 79.818 | 68.552 | 17.822 | 1.00 | 49.17 | C |
| ATOM | 2635 | CD1 | ILE A | 483 | 79.650 | 68.141 | 20.845 | 1.00 | 49.07 | C |
| TER | 2636 | | ILE A | 483 | | | | | | |
| HETATM | 2637 | K | K A | 900 | 52.558 | 59.979 | 29.204 | 0.75 | 33.19 | K |
| HETATM | 2638 | P | XMP | 602 | 67.402 | 54.842 | 14.904 | 1.00 | 30.34 | P |
| HETATM | 2639 | O1P | XMP | 602 | 67.002 | 54.789 | 13.486 | 1.00 | 30.72 | O |
| HETATM | 2640 | O2P | XMP | 602 | 68.190 | 53.690 | 15.379 | 1.00 | 30.78 | O |
| HETATM | 2641 | O5' | XMP | 602 | 66.075 | 54.823 | 15.699 | 1.00 | 29.65 | O |
| HETATM | 2642 | O3P | XMP | 602 | 67.954 | 56.140 | 15.323 | 1.00 | 30.68 | O |
| HETATM | 2643 | C5' | XMP | 602 | 65.078 | 53.767 | 15.814 | 1.00 | 29.12 | C |
| HETATM | 2644 | C4' | XMP | 602 | 63.985 | 54.002 | 16.886 | 1.00 | 29.15 | C |
| HETATM | 2645 | O4' | XMP | 602 | 63.144 | 55.124 | 16.601 | 1.00 | 29.44 | O |
| HETATM | 2646 | C1' | XMP | 602 | 61.803 | 55.041 | 17.060 | 1.00 | 29.86 | C |
| HETATM | 2647 | N9 | XMP | 602 | 60.863 | 55.346 | 15.925 | 1.00 | 30.85 | N |
| HETATM | 2648 | C4 | XMP | 602 | 60.396 | 56.585 | 15.533 | 1.00 | 31.77 | C |
| HETATM | 2649 | N3 | XMP | 602 | 60.681 | 57.809 | 16.083 | 1.00 | 32.09 | N |
| HETATM | 2650 | N1 | XMP | 602 | 59.202 | 58.646 | 14.358 | 1.00 | 32.72 | N |
| HETATM | 2651 | C2 | XMP | 602 | 60.053 | 58.836 | 15.454 | 1.00 | 33.14 | C |
| HETATM | 2652 | O2 | XMP | 602 | 60.229 | 59.983 | 15.858 | 1.00 | 33.63 | O |
| HETATM | 2653 | C6 | XMP | 602 | 58.897 | 57.407 | 13.781 | 1.00 | 32.30 | C |
| HETATM | 2654 | O6 | XMP | 602 | 58.148 | 57.308 | 12.825 | 1.00 | 33.30 | O |
| HETATM | 2655 | C5 | XMP | 602 | 59.556 | 56.336 | 14.439 | 1.00 | 32.02 | C |
| HETATM | 2656 | N7 | XMP | 602 | 59.498 | 55.005 | 14.154 | 1.00 | 31.42 | N |
| HETATM | 2657 | C8 | XMP | 602 | 60.263 | 54.494 | 15.036 | 1.00 | 31.18 | C |
| HETATM | 2658 | C2' | XMP | 602 | 61.788 | 53.653 | 17.733 | 1.00 | 29.10 | C |
| HETATM | 2659 | O2' | XMP | 602 | 61.947 | 53.880 | 19.132 | 1.00 | 29.07 | O |
| HETATM | 2660 | C3' | XMP | 602 | 62.943 | 52.927 | 17.024 | 1.00 | 28.77 | C |
| HETATM | 2661 | O3' | XMP | 602 | 63.388 | 51.798 | 17.768 | 1.00 | 28.12 | O |
| HETATM | 2662 | AP | NAD | 987 | 50.634 | 53.888 | 20.452 | 1.00 | 70.18 | P |
| HETATM | 2663 | AO1 | NAD | 987 | 49.686 | 52.811 | 20.084 | 1.00 | 70.10 | O |
| HETATM | 2664 | AO2 | NAD | 987 | 51.622 | 53.619 | 21.519 | 1.00 | 70.18 | O |
| HETATM | 2665 | AO5* | NAD | 987 | 49.807 | 55.222 | 20.825 | 1.00 | 70.73 | O |
| HETATM | 2666 | AC5* | NAD | 987 | 48.836 | 55.190 | 21.879 | 1.00 | 71.96 | C |
| HETATM | 2667 | AC4* | NAD | 987 | 48.158 | 56.575 | 22.018 | 1.00 | 72.40 | C |
| HETATM | 2668 | AO4* | NAD | 987 | 47.053 | 56.406 | 22.993 | 1.00 | 72.62 | O |
| HETATM | 2669 | AC3* | NAD | 987 | 47.458 | 56.986 | 20.719 | 1.00 | 72.81 | C |
| HETATM | 2670 | AO3* | NAD | 987 | 48.185 | 56.491 | 19.587 | 1.00 | 73.24 | O |
| HETATM | 2671 | AC2* | NAD | 987 | 46.117 | 56.309 | 20.794 | 1.00 | 72.87 | C |
| HETATM | 2672 | AO2* | NAD | 987 | 46.258 | 54.925 | 20.444 | 1.00 | 72.72 | O |
| HETATM | 2673 | AC1* | NAD | 987 | 45.766 | 56.439 | 22.272 | 1.00 | 72.67 | C |
| HETATM | 2674 | AN9 | NAD | 987 | 44.784 | 55.412 | 22.731 | 1.00 | 72.51 | N |
| HETATM | 2675 | AC8 | NAD | 987 | 43.460 | 55.583 | 22.865 | 1.00 | 72.46 | C |
| HETATM | 2676 | AN7 | NAD | 987 | 42.908 | 54.431 | 23.274 | 1.00 | 72.16 | N |
| HETATM | 2677 | AC5 | NAD | 987 | 43.880 | 53.538 | 23.399 | 1.00 | 72.08 | C |
| HETATM | 2678 | AC6 | NAD | 987 | 43.920 | 52.200 | 23.781 | 1.00 | 72.01 | C |
| HETATM | 2679 | AN6 | NAD | 987 | 42.803 | 51.558 | 24.105 | 1.00 | 72.25 | N |
| HETATM | 2680 | AN1 | NAD | 987 | 45.108 | 51.553 | 23.810 | 1.00 | 71.86 | N |
| HETATM | 2681 | AC2 | NAD | 987 | 46.241 | 52.179 | 23.476 | 1.00 | 71.78 | C |
| HETATM | 2682 | AN3 | NAD | 987 | 46.228 | 53.462 | 23.105 | 1.00 | 71.90 | N |
| HETATM | 2683 | AC4 | NAD | 987 | 45.069 | 54.157 | 23.059 | 1.00 | 72.20 | C |
| HETATM | 2684 | O3 | NAD | 987 | 51.412 | 54.316 | 19.101 | 1.00 | 69.74 | O |
| HETATM | 2685 | NP | NAD | 987 | 52.634 | 55.383 | 19.126 | 1.00 | 69.12 | P |
| HETATM | 2686 | NO1 | NAD | 987 | 53.103 | 55.572 | 20.519 | 1.00 | 68.69 | O |
| HETATM | 2687 | NO2 | NAD | 987 | 52.250 | 56.578 | 18.341 | 1.00 | 69.23 | O |
| HETATM | 2688 | NO5* | NAD | 987 | 53.807 | 54.613 | 18.343 | 1.00 | 69.13 | O |
| HETATM | 2689 | NC5* | NAD | 987 | 53.538 | 53.954 | 17.101 | 1.00 | 68.98 | C |
| HETATM | 2690 | NC4* | NAD | 987 | 54.844 | 53.577 | 16.381 | 1.00 | 68.78 | C |
| HETATM | 2691 | NO4* | NAD | 987 | 55.536 | 54.846 | 16.049 | 1.00 | 68.83 | O |
| HETATM | 2692 | NC3* | NAD | 987 | 55.787 | 52.849 | 17.333 | 1.00 | 68.59 | C |
| HETATM | 2693 | NO3* | NAD | 987 | 56.629 | 51.948 | 16.611 | 1.00 | 68.69 | O |
| HETATM | 2694 | NC2* | NAD | 987 | 56.615 | 53.936 | 17.951 | 1.00 | 68.50 | C |
| HETATM | 2695 | NO2* | NAD | 987 | 57.896 | 53.435 | 18.333 | 1.00 | 68.13 | O |
| HETATM | 2696 | NC1* | NAD | 987 | 56.784 | 54.933 | 16.818 | 1.00 | 68.70 | C |
| HETATM | 2697 | NN1 | NAD | 987 | 57.133 | 56.318 | 17.254 | 1.00 | 69.08 | N |
| HETATM | 2698 | NC2 | NAD | 987 | 58.217 | 56.537 | 18.152 | 1.00 | 69.28 | C |
| HETATM | 2699 | NC3 | NAD | 987 | 58.549 | 57.847 | 18.538 | 1.00 | 69.57 | C |
| HETATM | 2700 | NC7 | NAD | 987 | 59.715 | 58.103 | 19.514 | 1.00 | 69.91 | C |
| HETATM | 2701 | NO7 | NAD | 987 | 60.134 | 59.245 | 19.712 | 1.00 | 70.20 | O |
| HETATM | 2702 | NN7 | NAD | 987 | 60.220 | 57.016 | 20.103 | 1.00 | 69.78 | N |
| HETATM | 2703 | NC4 | NAD | 987 | 57.806 | 58.929 | 18.030 | 1.00 | 69.34 | C |
| HETATM | 2704 | NC5 | NAD | 987 | 56.734 | 58.723 | 17.144 | 1.00 | 69.28 | C |
| HETATM | 2705 | NC6 | NAD | 987 | 56.393 | 57.421 | 16.753 | 1.00 | 69.10 | C |
| HETATM | 2706 | O | HOH | 1 | 80.159 | 44.885 | 4.169 | 1.00 | 45.58 | O |
| HETATM | 2707 | O | HOH | 2 | 70.459 | 54.183 | 21.914 | 1.00 | 24.31 | O |
| HETATM | 2708 | O | HOH | 3 | 57.313 | 58.461 | 28.306 | 1.00 | 24.50 | O |
| HETATM | 2709 | O | NOH | 4 | 65.571 | 60.118 | 24.639 | 1.00 | 23.07 | O |
| HETATM | 2710 | O | HOH | 5 | 40.291 | 38.852 | 28.760 | 1.00 | 49.15 | O |
| HETATM | 2711 | O | HOH | 6 | 66.287 | 47.668 | 38.747 | 1.00 | 21.93 | O |

TABLE 5-continued

| | | | | | | | | | | |
|---|---|---|---|---|---|---|---|---|---|---|
| HETATM | 2712 | O | HOH | 7 | 86.808 | 55.200 | 31.125 | 1.00 | 27.24 | O |
| HETATM | 2713 | O | HOH | 8 | 79.324 | 41.691 | 29.401 | 1.00 | 21.83 | O |
| HETATM | 2714 | O | HOH | 9 | 69.419 | 61.415 | 38.396 | 1.00 | 44.68 | O |
| HETATM | 2715 | O | HOH | 10 | 58.291 | 50.786 | 22.925 | 1.00 | 24.55 | O |
| HETATM | 2716 | O | HOH | 11 | 70.499 | 53.076 | 14.172 | 1.00 | 25.36 | O |
| HETATM | 2717 | O | HOH | 12 | 75.758 | 43.567 | 30.918 | 1.00 | 21.79 | O |
| HETATH | 2718 | O | HOH | 13 | 88.069 | 53.459 | 33.173 | 1.00 | 26.13 | O |
| HETATM | 2719 | O | HOH | 14 | 67.647 | 38.078 | 46.052 | 1.00 | 35.25 | O |
| HETATM | 2720 | O | HOH | 15 | 72.291 | 37.808 | 33.719 | 1.00 | 27.23 | O |
| HETATM | 2721 | O | HOH | 16 | 56.445 | 78.452 | 34.278 | 1.00 | 24.45 | O |
| HETATM | 2722 | O | HOH | 17 | 58.982 | 44.997 | 36.851 | 1.00 | 25.40 | O |
| HETATM | 2723 | O | HOH | 18 | 51.923 | 53.605 | 25.905 | 1.00 | 30.95 | O |
| HETATM | 2724 | O | HOH | 19 | 58.261 | 35.282 | 26.925 | 1.00 | 32.59 | O |
| HETATM | 2725 | O | NON | 20 | 78.214 | 47.801 | 37.366 | 1.00 | 36.04 | O |
| HETATM | 2726 | O | HOH | 21 | 77.272 | 53.707 | 34.316 | 1.00 | 27.76 | O |
| HETATM | 2727 | O | HOH | 22 | 47.841 | 54.106 | 36.571 | 1.00 | 37.78 | O |
| HETATM | 2728 | O | HOH | 23 | 64.271 | 41.030 | 7.745 | 1.00 | 31.98 | O |
| HETATM | 2729 | O | HOH | 24 | 73.286 | 57.144 | 36.094 | 1.00 | 24.02 | O |
| HETATM | 2730 | O | HOH | 25 | 67.036 | 59.452 | 38.278 | 1.00 | 48.34 | O |
| HETATM | 2731 | O | HOH | 26 | 56.058 | 41.046 | 37.332 | 1.00 | 41.47 | O |
| HETATM | 2732 | O | HOH | 27 | 59.588 | 50.684 | 20.017 | 1.00 | 32.62 | O |
| HETATM | 2733 | O | HOH | 28 | 68.814 | 67.431 | 32.848 | 1.00 | 28.56 | O |
| HETATM | 2734 | O | HOH | 29 | 81.923 | 66.876 | 31.746 | 1.00 | 32.25 | O |
| HETATM | 2735 | O | HOH | 30 | 61.989 | 38.331 | 33.948 | 1.00 | 24.11 | O |
| HETATM | 2736 | O | HOH | 31 | 69.891 | 33.131 | 27.256 | 1.00 | 33.89 | O |
| HETATM | 2737 | O | HOH | 32 | 60.032 | 39.147 | 6.730 | 1.00 | 39.28 | O |
| HETATM | 2738 | O | HOH | 33 | 61.745 | 63.891 | 35.416 | 1.00 | 31.28 | O |
| HETATM | 2739 | O | HOH | 34 | 48.981 | 43.802 | 20.915 | 1.00 | 29.86 | O |
| HETATM | 2740 | O | HOH | 35 | 69.168 | 35.704 | 7.655 | 1.00 | 35.67 | O |
| HETATM | 2741 | O | NOH | 36 | 76.202 | 65.130 | 31.664 | 1.00 | 44.93 | O |
| HETATM | 2742 | O | HOH | 37 | 69.263 | 32.519 | 38.368 | 1.00 | 38.37 | O |
| HETATM | 2743 | O | HOH | 38 | 65.179 | 36.434 | 34.852 | 1.00 | 29.61 | O |
| HETATM | 2744 | O | HOH | 39 | 59.293 | 59.263 | 30.587 | 1.00 | 36.96 | O |
| HETATM | 2745 | O | NOH | 40 | 49.423 | 42.410 | 7.845 | 1.00 | 53.80 | O |
| HETATM | 2746 | O | HOH | 41 | 64.358 | 73.055 | 32.790 | 1.00 | 26.48 | O |
| HETATM | 2747 | O | HOH | 42 | 71.857 | 63.707 | 34.068 | 1.00 | 60.77 | O |
| HETATM | 2748 | O | HOH | 43 | 56.071 | 57.344 | 38.813 | 1.00 | 42.44 | O |
| HETATM | 2749 | O | HOH | 44 | 63.542 | 56.163 | 20.268 | 1.00 | 36.97 | O |
| HETATM | 2750 | O | HOH | 45 | 61.356 | 50.051 | 17.813 | 1.00 | 26.22 | O |
| HETATM | 2751 | O | HOH | 46 | 92.220 | 40.526 | 20.299 | 1.00 | 49.10 | O |
| HETATM | 2752 | O | HOH | 47 | 71.972 | 61.198 | 21.121 | 1.00 | 35.90 | O |
| HETATM | 2753 | O | HOH | 48 | 83.870 | 52.797 | 20.905 | 1.00 | 29.24 | O |
| HETATM | 2754 | O | HOH | 49 | 56.116 | 76.920 | 37.019 | 1.00 | 36.67 | O |
| HETATM | 2755 | O | HOH | 50 | 50.418 | 45.939 | 35.861 | 1.00 | 36.94 | O |
| HETATM | 2756 | O | HOH | 51 | 81.571 | 63.014 | 21.227 | 1.00 | 32.08 | O |
| HETATM | 2757 | O | HOH | 52 | 66.576 | 33.997 | 36.818 | 1.00 | 42.85 | O |
| HETATM | 2758 | O | HOH | 53 | 59.306 | 51.362 | 16.242 | 1.00 | 31.71 | O |
| HETATM | 2759 | O | HOH | 54 | 58.726 | 37.969 | 34.720 | 1.00 | 37.12 | O |
| HETATM | 2760 | O | HOH | 55 | 59.306 | 53.739 | 20.688 | 1.00 | 31.48 | O |
| HETATM | 2761 | O | HOH | 56 | 52.755 | 51.235 | 37.729 | 1.00 | 38.98 | O |
| HETATM | 2762 | O | HOH | 57 | 77.948 | 70.194 | 25.195 | 1.00 | 40.94 | O |
| HETATM | 2763 | O | HOH | 58 | 42.877 | 43.465 | 23.430 | 1.00 | 37.12 | O |
| HETATM | 2764 | O | HOH | 59 | 74.941 | 70.159 | 31.554 | 1.00 | 37.95 | O |
| HETATM | 2765 | O | HOH | 60 | 62.836 | 39.227 | 5.777 | 1.00 | 41.89 | O |
| HETATM | 2766 | O | HOH | 61 | 63.043 | 31.312 | 25.273 | 1.00 | 42.37 | O |
| HETATM | 2767 | O | HOH | 62 | 73.944 | 59.700 | 37.703 | 1.00 | 39.09 | O |
| HETATM | 2768 | O | HOH | 63 | 45.718 | 48.708 | 27.281 | 1.00 | 38.46 | O |
| HETATM | 2769 | O | HOH | 64 | 65.979 | 37.356 | 16.650 | 1.00 | 29.39 | O |
| HETATM | 2770 | O | HOH | 65 | 74.924 | 38.483 | 8.198 | 1.00 | 36.88 | O |
| HETATM | 2771 | O | HOH | 66 | 72.792 | 32.939 | 26.042 | 1.00 | 49.82 | O |
| HETATM | 2772 | O | HOH | 67 | 71.174 | 32.495 | 29.960 | 1.00 | 43.86 | O |
| HETATM | 2773 | O | HOH | 68 | 86.835 | 69.123 | 23.909 | 1.00 | 40.67 | O |
| HETATM | 2774 | O | HOH | 69 | 51.919 | 29.585 | 14.737 | 1.00 | 50.08 | O |
| HETATM | 2775 | O | HOH | 70 | 74.502 | 36.683 | 10.729 | 1.00 | 38.28 | O |
| HETATM | 2776 | O | HOH | 71 | 74.398 | 47.611 | 35.605 | 1.00 | 39.16 | O |
| HETATM | 2777 | O | HOH | 72 | 73.613 | 50.462 | 36.144 | 1.00 | 32.41 | O |
| HETATM | 2778 | O | HOH | 73 | 54.489 | 46.459 | 17.581 | 1.00 | 46.38 | O |
| HETATM | 2779 | O | HOH | 74 | 73.145 | 64.449 | 30.898 | 1.00 | 37.64 | O |
| HETATM | 2780 | O | HOH | 75 | 69.890 | 53.682 | 17.707 | 1.00 | 40.51 | O |
| HETATM | 2781 | O | HOH | 76 | 44.394 | 42.781 | 15.412 | 1.00 | 49.08 | O |
| HETATM | 2782 | O | HOH | 77 | 59.413 | 50.782 | 9.634 | 1.00 | 33.53 | O |
| HETATM | 2783 | O | HOH | 78 | 68.121 | 74.231 | 33.089 | 1.00 | 42.30 | O |
| HETATM | 2784 | O | HOH | 79 | 58.561 | 44.690 | 5.902 | 1.00 | 40.98 | O |
| HETATM | 2785 | O | HOH | 80 | 65.000 | 31.161 | 29.173 | 1.00 | 52.37 | O |
| HETATM | 2786 | O | HOH | 81 | 74.095 | 34.670 | 40.190 | 1.00 | 36.19 | O |
| HETATM | 2787 | O | HOH | 82 | 78.806 | 36.429 | 24.680 | 1.00 | 48.73 | O |
| HETATM | 2788 | O | HOH | 83 | 72.866 | 40.403 | 41.762 | 1.00 | 43.72 | O |
| HETATM | 2789 | O | HOH | 84 | 71.162 | 55.709 | 41.847 | 1.00 | 30.47 | O |
| HETATM | 2790 | O | HOH | 85 | 50.170 | 31.463 | 16.442 | 1.00 | 46.81 | O |

TABLE 5-continued

| | | | | | | | | | | |
|---|---|---|---|---|---|---|---|---|---|---|
| HETATM | 2791 | O | HOH | 86 | 55.811 | 30.709 | 8.794 | 1.00 | 49.33 | O |
| HETATM | 2792 | O | HOH | 87 | 61.016 | 73.187 | 39.258 | 1.00 | 46.28 | O |
| HETATM | 2793 | O | HOH | 88 | 83.287 | 41.191 | 17.129 | 1.00 | 48.85 | O |
| HETATM | 2794 | O | HOH | 89 | 85.733 | 38.892 | 22.703 | 1.00 | 43.02 | O |
| HETATM | 2795 | O | HOH | 90 | 67.617 | 53.275 | 46.890 | 1.00 | 44.36 | O |
| HETATM | 2796 | O | HOH | 91 | 76.440 | 36.363 | 6.407 | 1.00 | 60.32 | O |
| HETATM | 2797 | O | HOH | 92 | 74.688 | 38.584 | 30.945 | 1.00 | 34.79 | O |
| HETATM | 2798 | O | HOH | 93 | 57.076 | 65.531 | 38.139 | 1.00 | 47.34 | O |
| HETATM | 2799 | O | HOH | 94 | 78.761 | 38.342 | 17.426 | 1.00 | 41.15 | O |
| HETATM | 2800 | O | HOH | 95 | 61.259 | 33.096 | 26.930 | 1.00 | 44.33 | O |
| HETATM | 2801 | O | HOH | 96 | 65.482 | 28.592 | 14.900 | 1.00 | 41.37 | O |
| HETATM | 2802 | O | HOH | 97 | 93.557 | 52.441 | 21.951 | 1.00 | 58.36 | O |
| HETATM | 2803 | O | HOH | 98 | 52.048 | 50.238 | 18.507 | 1.00 | 50.58 | O |
| HETATM | 2804 | O | HOH | 99 | 69.144 | 44.907 | 46.298 | 1.00 | 41.41 | O |
| HETATM | 2805 | O | HOH | 100 | 92.572 | 46.733 | 19.480 | 1.00 | 53.29 | O |
| HETATM | 2806 | O | HOH | 101 | 60.394 | 50.886 | 46.427 | 1.00 | 58.13 | O |
| HETATM | 2807 | O | HOH | 102 | 60.206 | 29.776 | 22.560 | 1.00 | 51.85 | O |
| HETATM | 2808 | O | HOH | 103 | 55.550 | 45.667 | 5.832 | 1.00 | 54.36 | O |
| HETATM | 2809 | O | HOH | 104 | 66.124 | 45.356 | 49.309 | 1.00 | 55.34 | O |
| HETATM | 2810 | O | HOH | 105 | 42.594 | 47.628 | 27.697 | 1.00 | 57.72 | O |
| HETATM | 2811 | O | HOH | 106 | 78.097 | 71.838 | 27.740 | 1.00 | 51.84 | O |
| HETATM | 2812 | O | HOH | 107 | 74.276 | 62.445 | 19.161 | 1.00 | 40.85 | O |
| HETATM | 2813 | O | HOH | 108 | 47.828 | 41.389 | 36.858 | 1.00 | 50.41 | O |
| HETATM | 2814 | O | HOH | 109 | 71.642 | 67.017 | 32.073 | 1.00 | 37.86 | O |
| HETATM | 2815 | O | HOH | 110 | 74.696 | 67.506 | 33.229 | 1.00 | 57.41 | O |
| HETATM | 2816 | O | HOH | 111 | 75.703 | 52.363 | 36.244 | 1.00 | 30.66 | O |
| HETATM | 2817 | O | HOH | 112 | 73.719 | 66.099 | 18.701 | 1.00 | 56.53 | O |
| HETATM | 2818 | O | HOH | 113 | 51.821 | 45.822 | 7.467 | 1.00 | 52.27 | O |
| HETATM | 2819 | O | HOH | 114 | 81.307 | 38.594 | 20.656 | 1.00 | 70.73 | O |
| HETATM | 2820 | O | HOH | 115 | 81.169 | 38.251 | 23.961 | 1.00 | 41.30 | O |
| HETATM | 2821 | O | NOH | 116 | 45.113 | 41.184 | 12.778 | 1.00 | 63.00 | O |
| HETATM | 2822 | O | HOH | 117 | 68.809 | 39.136 | 48.780 | 1.00 | 38.97 | O |
| HETATM | 2823 | O | HOH | 118 | 62.055 | 33.092 | 29.952 | 1.00 | 52.24 | O |
| HETATM | 2824 | O | HOH | 119 | 51.760 | 31.011 | 12.019 | 1.00 | 58.64 | O |
| HETATM | 2825 | O | HOH | 120 | 59.767 | 32.566 | 33.591 | 1.00 | 52.66 | O |
| HETATM | 2826 | O | HOH | 121 | 56.985 | 32.023 | 26.849 | 1.00 | 57.15 | O |
| HETATM | 2827 | O | HOH | 122 | 60.737 | 40.820 | 44.361 | 1.00 | 56.30 | O |
| HETATM | 2828 | O | HOH | 123 | 64.564 | 25.631 | 14.455 | 1.00 | 43.27 | O |
| HETATM | 2829 | O | HOH | 124 | 49.818 | 53.007 | 23.891 | 1.00 | 49.86 | O |
| HETATM | 2830 | O | HOH | 125 | 50.978 | 50.308 | 21.539 | 1.00 | 35.65 | O |
| HETATM | 2831 | O | HOH | 126 | 67.755 | 31.430 | 25.861 | 1.00 | 55.46 | O |
| HETATM | 2832 | O | HOH | 127 | 48.199 | 31.294 | 25.210 | 1.00 | 54.24 | O |
| HETATM | 2833 | O | HOH | 128 | 73.604 | 54.433 | 12.696 | 1.00 | 61.45 | O |
| HETATM | 2834 | O | HOH | 129 | 70.275 | 57.346 | 14.361 | 1.00 | 41.07 | O |
| HETATM | 2835 | O | HOH | 130 | 74.635 | 45.539 | 32.754 | 1.00 | 32.00 | O |
| HETATM | 2836 | O | HOH | 131 | 75.089 | 72.613 | 28.286 | 1.00 | 49.39 | O |
| HETATM | 2837 | O | HOH | 132 | 86.853 | 66.678 | 30.930 | 1.00 | 25.20 | O |
| HETATM | 2838 | O | HOH | 133 | 78.835 | 40.047 | 31.875 | 1.00 | 31.20 | O |
| HETATM | 2839 | O | HOH | 134 | 62.167 | 61.367 | 37.551 | 1.00 | 30.60 | O |
| HETATM | 2840 | O | HOH | 135 | 65.184 | 28.026 | 26.437 | 1.00 | 48.57 | O |
| HETATM | 2841 | O | HOH | 136 | 76.047 | 40.918 | 32.141 | 1.00 | 34.64 | O |
| HETATM | 2842 | O | HOH | 137 | 59.729 | 41.105 | 39.908 | 1.00 | 47.69 | O |
| HETATM | 2843 | O | HOH | 138 | 70.728 | 75.819 | 32.304 | 1.00 | 53.80 | O |
| HETATM | 2844 | O | HOH | 139 | 81.807 | 75.821 | 23.632 | 1.00 | 51.16 | O |
| HETATM | 2845 | O | HOH | 140 | 79.607 | 73.914 | 25.874 | 1.00 | 49.38 | O |
| HETATM | 2846 | O | HOH | 141 | 44.883 | 44.348 | 32.806 | 1.00 | 49.33 | O |
| HETATM | 2847 | O | HOH | 142 | 74.170 | 42.608 | 43.856 | 1.00 | 52.82 | O |
| HETATM | 2848 | O | HOH | 143 | 53.514 | 41.420 | 6.894 | 1.00 | 48.12 | O |
| HETATM | 2849 | O | HOH | 144 | 76.967 | 51.935 | 3.952 | 1.00 | 54.45 | O |
| HETATM | 2850 | O | HOH | 145 | 82.602 | 55.478 | 15.958 | 1.00 | 37.47 | O |
| HETATM | 2851 | O | HOH | 146 | 58.199 | 49.374 | 44.387 | 1.00 | 54.43 | O |
| HETATM | 2852 | O | HOH | 147 | 53.891 | 73.194 | 38.807 | 1.00 | 45.80 | O |
| HETATM | 2853 | O | HOH | 148 | 48.842 | 61.463 | 23.357 | 1.00 | 44.65 | O |
| HETATM | 2854 | O | HOH | 149 | 49.731 | 59.561 | 25.854 | 1.00 | 55.20 | O |
| HETATM | 2855 | O | HOH | 150 | 51.048 | 56.764 | 24.880 | 1.00 | 58.92 | O |
| HETATM | 2856 | O | HOH | 151 | 52.529 | 57.301 | 22.316 | 1.00 | 49.02 | O |
| HETATM | 2857 | O | HOH | 152 | 46.169 | 58.096 | 27.292 | 1.00 | 44.50 | O |
| HETATM | 2858 | O | HOH | 153 | 40.023 | 51.519 | 24.080 | 1.00 | 57.09 | O |
| HETATM | 2859 | O | HOH | 154 | 70.783 | 28.023 | 10.528 | 1.00 | 65.20 | O |
| HETATM | 2860 | O | HOH | 155 | 55.358 | 44.178 | 39.610 | 1.00 | 55.31 | O |
| HETATM | 2861 | O | HOH | 156 | 50.499 | 52.835 | 39.274 | 1.00 | 56.09 | O |
| HETATM | 2862 | O | HOH | 157 | 51.427 | 49.112 | 39.630 | 1.00 | 50.88 | O |
| HETATM | 2863 | O | HOH | 158 | 54.238 | 33.150 | 37.602 | 1.00 | 49.72 | O |
| HETATM | 2864 | O | HOH | 159 | 62.155 | 53.228 | 3.383 | 1.00 | 55.20 | O |
| HETATM | 2865 | O | HOH | 160 | 65.352 | 58.405 | 21.237 | 1.00 | 40.73 | O |
| HETATM | 2866 | O | HOH | 161 | 55.476 | 50.398 | 2.549 | 1.00 | 58.50 | O |
| HETATM | 2867 | O | HOH | 162 | 73.645 | 34.699 | 8.566 | 1.00 | 52.83 | O |
| HETATM | 2868 | O | HOH | 163 | 71.990 | 36.204 | 6.534 | 1.00 | 56.54 | O |
| HETATM | 2869 | O | HOH | 164 | 70.553 | 26.585 | 7.610 | 1.00 | 59.27 | O |

TABLE 5-continued

| | |
|---|---|
| CONECT | 202 2464 |
| CONECT | 2464 202 |
| CONECT | 2638 2639 2640 2641 2642 |
| CONECT | 2639 2638 |
| CONECT | 2640 2638 |
| CONECT | 2641 2638 2643 |
| CONECT | 2642 2638 |
| CONECT | 2643 2641 2644 |
| CONECT | 2644 2643 2645 2660 |
| CONECT | 2645 2644 2646 |
| CONECT | 2646 2645 2647 2658 |
| CONECT | 2647 2646 2648 2657 |
| CONECT | 2648 2647 2649 2655 |
| CONECT | 2649 2648 2651 |
| CONECT | 2650 2651 2653 |
| CONECT | 2651 2649 2650 2652 |
| CONECT | 2652 2651 |
| CONECT | 2653 2650 2654 2655 |
| CONECT | 2654 2653 |
| CONECT | 2655 2648 2653 2656 |
| CONECT | 2656 2655 2657 |
| CONECT | 2657 2647 2656 |
| CONECT | 2658 2646 2659 2660 |
| CONECT | 2659 2658 |
| CONECT | 2660 2644 2658 2661 |
| CONECT | 2661 2660 |
| CONECT | 2662 2663 2664 2665 2684 |
| CONECT | 2663 2662 |
| CONECT | 2664 2662 |
| CONECT | 2665 2662 2666 |
| CONECT | 2666 2665 2667 |
| CONECT | 2667 2666 2668 2669 |
| CONECT | 2668 2667 2673 |
| CONECT | 2669 2667 2670 2671 |
| CONECT | 2670 2669 |
| CONECT | 2671 2669 2672 2673 |
| CONECT | 2672 2671 |
| CONECT | 2673 2668 2671 2674 |
| CONECT | 2674 2673 2675 2683 |
| CONECT | 2675 2674 2676 |
| CONECT | 2676 2675 2677 |
| CONECT | 2677 2676 2678 2683 |
| CONECT | 2678 2677 2679 2680 |
| CONECT | 2679 2678 |
| CONECT | 2680 2678 2681 |
| CONECT | 2681 2680 2682 |
| CONECT | 2682 2681 2683 |
| CONECT | 2683 2674 2677 2682 |
| CONECT | 2684 2662 2685 |
| CONECT | 2685 2684 2686 2687 2688 |
| CONECT | 2686 2685 |
| CONECT | 2687 2685 |
| CONECT | 2688 2685 2689 |
| CONECT | 2689 2688 2690 |
| CONECT | 2690 2689 2691 2692 |
| CONECT | 2691 2690 2696 |
| CONECT | 2692 2690 2693 2694 |
| CONECT | 2693 2692 |
| CONECT | 2694 2692 2695 2696 |
| CONECT | 2695 2694 |
| CONECT | 2696 2691 2694 2697 |
| CONECT | 2697 2696 2698 2705 |
| CONECT | 2698 2697 2699 |
| CONECT | 2699 2698 2700 2703 |
| CONECT | 2700 2699 2701 2702 |
| CONECT | 2701 2700 |
| CONECT | 2702 2700 |
| CONECT | 2703 2699 2704 |
| CONECT | 2704 2703 2705 |
| CONECT | 2705 2697 2704 |
| MASTER | 527   0   3   13   18   0   0   6   2868   1   70   39 |
| END | |

FIG. 14

TABLE 6

| | | | |
|---|---|---|---|
| HEADER | | OXIDOREDUCTASE | 08-AUG-02 1ME7 |
| TITLE | | INOSINE MONOPHOSPHATE DEHYDROGENASE (IMPDH) FROM | |
| TITLE | 2 | TRITRICHOMONAS FOETUS WITH RVP AND MOA BOUND | |
| COMPND | | MOL_ID: 1; | |
| COMPND | 2 | MOLECULE: INOSINE-5'-MONOPHOSPHATE DEHYDROGENASE; | |
| COMPND | 3 | CHAIN: A; | |
| COMPND | 4 | SYNONYM: IMP DEHYDROGENASE, IMPDH; | |
| COMPND | 5 | EC: 1.1.1.205; | |
| COMPND | 6 | ENGINEERED: YES | |
| SOURCE | | MOL_ID: 1; | |
| SOURCE | 2 | ORGANISM_SCIENTIFIC: TRITRICHOMONAS FOETUS; | |
| SOURCE | 3 | GENE: IMPDH; | |
| SOURCE | 4 | EXPRESSION_SYSTEM: ESCHERICHIA COLI; | |
| SOURCE | 5 | EXPRESSION_SYSTEM_COMMON: BACTERIA; | |
| SOURCE | 6 | EXPRESSION_SYSTEM_STRAIN: H712; | |
| SOURCE | 7 | EXPRESSION_SYSTEM_VECTOR_TYPE: PLASMID; | |
| SOURCE | 8 | EXPRESSION_SYSTEM_PLASMID: PBACE | |
| KEYWDS | | ALPHA BETA BARREL | |
| EXPDTA | | X-RAY DIFFRACTION | |
| AUTHOR | | G.L.PROSISE,J.WU,H.LUECKE | |
| JRNL | | AUTH G.L.PROSISE,J.WU,H.LUECKE | |
| JRNL | | TITL CRYSTAL STRUCTURE OF T. FOETUS INOSINE | |
| JRNL | | TITL 2 MONOPHOSPHATE DEHYDROGENASE IN COMPLEX WITH THE | |
| JRNL | | TITL 3 INHIBITOR RIBAVIRIN REVEALS A CATALYSIS-DEPENDENT | |
| JRNL | | TITL 4 ION BINDING SITE | |
| JRNL | | REF TO BE PUBLISHED | |
| JRNL | | REFN | |
| REMARK | 1 | | |
| REMARK | 2 | | |
| REMARK | 2 | RESOLUTION. 2.15 ANGSTROMS. | |
| REMARK | 3 | | |
| REMARK | 3 | REFINEMENT. | |
| REMARK | 3 | PROGRAM   : CNS 1.1 | |
| REMARK | 3 | AUTHORS   : BRUNGER,ADAMS,CLORE,DELANO,GROS,GROSSE- | |
| REMARK | 3 |             : KUNSTLEVE,JIANG,KUSZEWSKI,NILGES, PANNU, | |
| REMARK | 3 |             : READ,RICE,SIMONSON,WARREN | |
| REMARK | 3 | | |
| REMARK | 3 | REFINEMENT TARGET : ENGH & HUBER | |
| REMARK | 3 | | |
| REMARK | 3 | DATA USED IN REFINEMENT. | |
| REMARK | 3 | RESOLUTION RANGE HIGH (ANGSTROMS) | : 2.15 |
| REMARK | 3 | RESOLUTION RANGE LOW (ANGSTROMS) | : 49.04 |
| REMARK | 3 | DATA CUTOFF (SIGMA(F)) | : 0.000 |
| REMARK | 3 | OUTLIER CUTOFF HIGH (RMS(ABS(F))) | : NULL |
| REMARK | 3 | COMPLETENESS (WORKING+TEST) (%) | : 94.0 |
| REMARK | 3 | NUMBER OF REFLECTIONS | : 32980 |
| REMARK | 3 | | |
| REMARK | 3 | FIT TO DATA USED IN REFINEMENT. | |
| REMARK | 3 | CROSS-VALIDATION METHOD | : THROUGHOUT |
| REMARK | 3 | FREE R VALUE TEST SET SELECTION | : RANDOM |
| REMARK | 3 | R VALUE (WORKING SET) | : 0.233 |
| REMARK | 3 | FREE R VALUE | : 0.264 |
| REMARK | 3 | FREE R VALUE TEST SET SIZE (%) | : 5.200 |
| REMARK | 3 | FREE R VALUE TEST SET COUNT | : 1712 |
| REMARK | 3 | ESTIMATED ERROR OF FREE R VALUE | : 0.006 |
| REMARK | 3 | | |
| REMARK | 3 | FIT IN THE HIGHEST RESOLUTION BIN. | |
| REMARK | 3 | TOTAL NUMBER OF BINS USED | : 6 |
| REMARK | 3 | BIN RESOLUTION RANGE HIGH (A) | : 2.15 |
| REMARK | 3 | BIN RESOLUTION RANGE LOW (A) | : 2.28 |
| REMARK | 3 | BIN COMPLETENESS (WORKING+TEST) (%) | : 77.30 |
| REMARK | 3 | REFLECTIONS IN BIN (WORKING SET) | : 4218 |
| REMARK | 3 | BIN R VALUE (WORKING SET) | : 0.2880 |
| REMARK | 3 | BIN FREE R VALUE | : 0.3290 |
| REMARK | 3 | BIN FREE R VALUE TEST SET SIZE (%) | : 4.80 |
| REMARK | 3 | BIN FREE R VALUE TEST SET COUNT | : 215 |
| REMARK | 3 | ESTIMATED ERROR OF BIN FREE R VALUE | : 0.023 |
| REMARK | 3 | | |
| REMARK | 3 | NUMBER OF NON-HYDROGEN ATOMS USED IN REFINEMENT. | |
| REMARK | 3 | PROTEIN ATOMS       : 2782 | |
| REMARK | 3 | NUCLEIC ACID ATOMS  : 0 | |
| REMARK | 3 | HETEROGEN ATOMS     : 46 | |
| REMARK | 3 | SOLVENT ATOMS       : 120 | |
| REMARK | 3 | | |
| REMARK | 3 | B VALUES. | |
| REMARK | 3 | FROM WILSON PLOT (A**2)      : 33.10 | |
| REMARK | 3 | MEAN B VALUE (OVERALL, A**2) : 44.70 | |

TABLE 6-continued

| REMARK | 3 | OVERALL ANISOTROPIC B VALUE. | | | |
|---|---|---|---|---|---|
| REMARK | 3 | B11 (A**2) : 0.00000 | | | |
| REMARK | 3 | B22 (A**2) : 0.00000 | | | |
| REMARK | 3 | B33 (A**2) : 0.00000 | | | |
| REMARK | 3 | B12 (A**2) : 0.00000 | | | |
| REMARK | 3 | B13 (A**2) : 0.00000 | | | |
| REMARK | 3 | B23 (A**2) : 0.00000 | | | |
| REMARK | 3 | | | | |
| REMARK | 3 | ESTIMATED COORDINATE ERROR. | | | |
| REMARK | 3 | ESD FROM LUZZATI PLOT | (A) : 0.29 | | |
| REMARK | 3 | ESD FROM SIGMAA | (A) : 0.25 | | |
| REMARK | 3 | LOW RESOLUTION CUTOFF | (A) : 5.00 | | |
| REMARK | 3 | | | | |
| REMARK | 3 | CROSS-VALIDATED ESTIMATED COORDINATE ERROR. | | | |
| REMARK | 3 | ESD FROM C-V LUZZATI PLOT | (A) : 0.35 | | |
| REMARK | 3 | ESD FROM C-V SIGMAA | (A) : 0.28 | | |
| REMARK | 3 | | | | |
| REMARK | 3 | RMS DEVIATIONS FROM IDEAL VALUES. | | | |
| REMARK | 3 | BOND LENGTHS (A) | : 0.006 | | |
| REMARK | 3 | BOND ANGLES (DEGREES) | : 1.20 | | |
| REMARK | 3 | DIHEDRAL ANGLES (DEGREES) | : 22.50 | | |
| REMARK | 3 | IMPROPER ANGLES (DEGREES) | : 0.71 | | |
| REMARK | 3 | | | | |
| REMARK | 3 | ISOTROPIC THERMAL MODEL : RESTRAINED | | | |
| REMARK | 3 | | | | |
| REMARK | 3 | ISOTROPIC THERMAL FACTOR RESTRAINTS. | | RMS | SIGMA |
| REMARK | 3 | MAIN-CHAIN BOND | (A**2) | : 1.190 | ; 1.500 |
| REMARK | 3 | MAIN-CHAIN ANGLE | (A**2) | : 2.070 | ; 2.000 |
| REMARK | 3 | SIDE-CHAIN BOND | (A**2) | : 1.630 | ; 2.000 |
| REMARK | 3 | SIDE-CHAIN ANGLE | (A**2) | : 2.500 | ; 2.500 |
| REMARK | 3 | | | | |
| REMARK | 3 | BULK SOLVENT MODELING. | | | |
| REMARK | 3 | METHOD USED | : FLAT MODEL | | |
| REMARK | 3 | KSOL | : 0.36 | | |
| REMARK | 3 | BSOL | : 41.54 | | |
| REMARK | 3 | | | | |
| REMARK | 3 | NCS MODEL : NULL | | | |
| REMARK | 3 | | | | |
| REMARK | 3 | NCS RESTRAINTS. | | RMS | SIGMA/WEIGHT |
| REMARK | 3 | GROUP 1 POSITIONAL | (A) | : NULL | ; NULL |
| REMARK | 3 | GROUP 1 B-FACTOR | (A**2) | : NULL | ; NULL |
| REMARK | 3 | | | | |
| REMARK | 3 | PARAMETER FILE 1 : PROTEIN_REP.PARAM | | | |
| REMARK | 3 | PARAMETER FILE 2 : PARAM.GNSOL | | | |
| REMARK | 3 | PARAMETER FILE 3 : CIS_PEPTIDE.PARAM | | | |
| REMARK | 3 | PARAMETER FILE 4 : RMP_MPA.PAR | | | |
| REMARK | 3 | PARAMETER FILE 5 : ION.PARAM | | | |
| REMARK | 3 | PARAMETER FILE 6 : NULL | | | |
| REMARK | 3 | TOPOLOGY FILE 1 : PROTEIN.TOP | | | |
| REMARK | 3 | TOPOLOGY FILE 2 : RMP.TOP | | | |
| REMARK | 3 | TOPOLOGY FILE 3 : MPA.TOP | | | |
| REMARK | 3 | TOPOLOGY FILE 4 : ION.TOP | | | |
| REMARK | 3 | TOPOLOGY FILE 5 : TOPH.GNSOL | | | |
| REMARK | 3 | TOPOLOGY FILE 6 : NULL | | | |
| REMARK | 3 | | | | |
| REMARK | 3 | OTHER REFINEMENT REMARKS: NULL | | | |
| REMARK | 4 | | | | |
| REMARK | 4 | 1ME7 COMPLIES WITH FORMAT V. 2.3, 09-JULY-1998 | | | |
| REMARK | 100 | | | | |
| REMARK | 100 | THIS ENTRY HAS BEEN PROCESSED BY RCSB ON 16-AUG-2002. | | | |
| REMARK | 100 | THE RCSB ID CODE IS RCSB016849. | | | |
| REMARK | 200 | | | | |
| REMARK | 200 | EXPERIMENTAL DETAILS | | | |
| REMARK | 200 | EXPERIMENT TYPE | : X-RAY DIFFRACTION | | |
| REMARK | 200 | DATE OF DATA COLLECTION | : 12-JUN-2001 | | |
| REMARK | 200 | TEMPERATURE (KELVIN) | : 100.0 | | |
| REMARK | 200 | PH | : 7.50 | | |
| REMARK | 200 | NUMBER OF CRYSTALS USED | : 1 | | |
| REMARK | 200 | | | | |
| REMARK | 200 | SYNCHROTRON (Y/N) | : Y | | |
| REMARK | 200 | RADIATION SOURCE | : SSRL | | |
| REMARK | 200 | BEAMLINE | : 9-1 | | |
| REMARK | 200 | X-RAY GENERATOR MODEL | : NULL | | |
| REMARK | 200 | MONOCHROMATIC OR LAUE (M/L) | : M | | |
| REMARK | 200 | WAVELENGTH OR RANGE (A) | : 0.97 | | |

TABLE 6-continued

| | | | |
|---|---|---|---|
| REMARK | 200 | MONOCHROMATOR | : NULL |
| REMARK | 200 | OPTICS | : NULL |
| REMARK | 200 | | |
| REMARK | 200 | DETECTOR TYPE | : IMAGE PLATE |
| REMARK | 200 | DETECTOR MANUFACTURER | : MARRESEARCH |
| REMARK | 200 | INTENSITY-INTEGRATION SOFTWARE | : DENZO |
| REMARK | 200 | DATA SCALING SOFTWARE | : SCALEPACK |
| REMARK | 200 | | |
| REMARK | 200 | NUMBER OF UNIQUE REFLECTIONS | : 33143 |
| REMARK | 200 | RESOLUTION RANGE HIGH (A) | : 2.150 |
| REMARK | 200 | RESOLUTION RANGE LOW (A) | : 50.000 |
| REMARK | 200 | REJECTION CRITERIA (SIGMA(I)) | : 0.000 |
| REMARK | 200 | | |
| REMARK | 200 | OVERALL. | |
| REMARK | 200 | COMPLETENESS FOR RANGE (%) | : 94.0 |
| REMARK | 200 | DATA REDUNDANCY | : 5.300 |
| REMARK | 200 | R MERGE (I) | : 0.07200 |
| REMARK | 200 | R SYM (I) | : NULL |
| REMARK | 200 | <I/SIGMA(I)> FOR THE DATA SET | : 2.0500 |
| REMARK | 200 | | |
| REMARK | 200 | IN THE HIGHEST RESOLUTION SHELL. | |
| REMARK | 200 | HIGHEST RESOLUTION SHELL, RANGE HIGH (A) | : 2.2.5 |
| REMARK | 200 | HIGHEST RESOLUTION SHELL, RANGE LOW (A) | : 2.19 |
| REMARK | 200 | COMPLETENESS FOR SHELL (%) | : 79.5 |
| REMARK | 200 | DATA REDUNDANCY IN SHELL | : NULL |
| REMARK | 200 | R MERGE FOR SHELL (I) | : 0.49100 |
| REMARK | 200 | R SYM FOR SHELL (I) | : NULL |
| REMARK | 200 | <I/SIGMA(I)> FOR SHELL | : 2.050 |
| REMARK | 200 | | |
| REMARK | 200 | DIFFRACTION PROTOCOL: SINGLE WAVELENGTH | |
| REMARK | 200 | METHOD USED TO DETERMINE THE STRUCTURE: FOURIER SYNTHESIS | |
| REMARK | 200 | SOFTWARE USED: CNS | |
| REMARK | 200 | STARTING MODEL: PDB ENTRY 1AK5 | |
| REMARK | 200 | | |
| REMARK | 200 | REMARK: NULL | |
| REMARK | 280 | | |
| REMARK | 280 | CRYSTAL | |
| REMARK | 280 | SOLVENT CONTENT, VS (%): NULL | |
| REMARK | 280 | MATTHEWS COEFFICIENT, VM (ANGSTROMS**3/DA): NULL | |
| REMARK | 280 | | |
| REMARK | 280 | CRYSTALLIZATION CONDITIONS: SODIUM MALONATE, TRIS, 2- | |
| REMARK | 280 | MERCAPTOETHANOL, EDTA, GLYCEROL | |
| REMARK | 290 | | |
| REMARK | 290 | CRYSTALLOGRAPHIC SYMMETRY | |
| REMARK | 290 | SYMMETRY OPERATORS FOR SPACE GROUP: P 4 3 2 | |
| REMARK | 290 | | |
| REMARK | 290 | SYMOP | SYMMETRY |
| REMARK | 290 | NNNMMM | OPERATOR |
| REMARK | 290 | 1555 | X,Y,Z |
| REMARK | 290 | 2555 | –X,–Y,Z |
| REMARK | 290 | 3555 | –X,Y,–Z |
| REMARK | 290 | 4555 | X,–Y,–Z |
| REMARK | 290 | 5555 | Z,X,Y |
| REMARK | 290 | 6555 | Z,–X,–Y |
| REMARK | 290 | 7555 | –Z,–X,Y |
| REMARK | 290 | 8555 | –Z,X,–Y |
| REMARK | 290 | 9555 | Y,Z,X |
| REMARK | 290 | 10555 | –Y,Z,–X |
| REMARK | 290 | 11555 | Y,Z,–X |
| REMARK | 290 | 12555 | –Y,–Z,X |
| REMARK | 290 | 13555 | Y,X,Z |
| REMARK | 290 | 14555 | –Y,–X,–Z |
| REMARK | 290 | 15555 | Y,–X,Z |
| REMARK | 290 | 16555 | –Y,X,Z |
| REMARK | 290 | 17555 | X,Z,–Y |
| REMARK | 290 | 18555 | –X,Z,Y |
| REMARK | 290 | 19555 | –X,–Z,–Y |
| REMARK | 290 | 20555 | X,–Z,Y |
| REMARK | 290 | 21555 | Z,Y,–X |
| REMARK | 290 | 22555 | Z,–Y,X |
| REMARK | 290 | 23555 | –Z,Y,X |
| REMARK | 290 | 24555 | –Z,–Y,–X |
| REMARK | 290 | | |
| REMARK | 290 | WHERE NNN –> OPERATOR NUMBER | |
| REMARK | 290 | MMM –> TRANSLATION VECTOR | |
| REMARK | 290 | | |

TABLE 6-continued

| | | | | | | | |
|---|---|---|---|---|---|---|---|
| REMARK | 290 | CRYSTALLOGRAPHIC SYMMETRY TRANSFORMATIONS | | | | | |
| REMARK | 290 | THE FOLLOWING TRANSFORMATIONS OPERATE ON THE ATOM/HETATM | | | | | |
| REMARK | 290 | RECORDS IN THIS ENTRY TO PRODUCE CRYSTALLOGRAPHICALLY | | | | | |
| REMARK | 290 | RELATED MOLECULES. | | | | | |
| REMARK | 290 | SMTRY1 | 1 | 1.000000 | 0.000000 | 0.000000 | 0.00000 |
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | −1.000000 | 0.000000 | 0.000000 | 0.00000 |
| REMARK | 290 | SMTRY2 | 2 | 0.000000 | −1.000000 | 0.000000 | 0.00000 |
| REMARK | 290 | SMTRY3 | 2 | 0.000000 | 0.000000 | 1.000000 | 0.00000 |
| REMARK | 290 | SMTRY1 | 3 | −1.000000 | 0.000000 | 0.000000 | 0.00000 |
| REMARK | 290 | SMTRY2 | 3 | 0.000000 | 1.000000 | 0.000000 | 0.00000 |
| REMARK | 290 | SMTRY3 | 3 | 0.000000 | 0.000000 | −1.000000 | 0.00000 |
| REMARK | 290 | SMTRY1 | 4 | 1.000000 | 0.000000 | 0.000000 | 0.00000 |
| REMARK | 290 | SMTRY2 | 4 | 0.000000 | −1.000000 | 0.000000 | 0.00000 |
| REMARK | 290 | SMTRY3 | 4 | 0.000000 | 0.000000 | −1.000000 | 0.00000 |
| REMARK | 290 | SMTRY1 | 5 | 0.000000 | 0.000000 | 1.000000 | 0.00000 |
| REMARK | 290 | SMTRY2 | 5 | 1.000000 | 0.000000 | 0.000000 | 0.00000 |
| REMARK | 290 | SMTRY3 | 5 | 0.000000 | 1.000000 | 0.000000 | 0.00000 |
| REMARK | 290 | SMTRY1 | 6 | 0.000000 | 0.000000 | 1.000000 | 0.00000 |
| REMARK | 290 | SMTRY2 | 6 | −1.000000 | 0.000000 | 0.000000 | 0.00000 |
| REMARK | 290 | SMTRY3 | 6 | 0.000000 | −1.000000 | 0.000000 | 0.00000 |
| REMARK | 290 | SMTRY1 | 7 | 0.000000 | 0.000000 | −1.000000 | 0.00000 |
| REMARK | 290 | SMTRY2 | 7 | −1.000000 | 0.000000 | 0.000000 | 0.00000 |
| REMARK | 290 | SMTRY3 | 7 | 0.000000 | 1.000000 | 0.000000 | 0.00000 |
| REMARK | 290 | SMTRY1 | 8 | 0.000000 | 0.000000 | −1.000000 | 0.00000 |
| REMARK | 290 | SMTRY2 | 8 | 1.000000 | 0.000000 | 0.000000 | 0.00000 |
| REMARK | 290 | SMTRY3 | 8 | 0.000000 | −1.000000 | 0.000000 | 0.00000 |
| REMARK | 290 | SMTRY1 | 9 | 0.000000 | 1.000000 | 0.000000 | 0.00000 |
| REMARK | 290 | SMTRY2 | 9 | 0.000000 | 0.000000 | 1.000000 | 0.00000 |
| REMARK | 290 | SMTRY3 | 9 | 1.000000 | 0.000000 | 0.000000 | 0.00000 |
| REMARK | 290 | SMTRY1 | 10 | 0.000000 | −1.000000 | 0.000000 | 0.00000 |
| REMARK | 290 | SMTRY2 | 10 | 0.000000 | 0.000000 | 1.000000 | 0.00000 |
| REMARK | 290 | SMTRY3 | 10 | −1.000000 | 0.000000 | 0.000000 | 0.00000 |
| REMARK | 290 | SMTRY1 | 11 | 0.000000 | 1.000000 | 0.000000 | 0.00000 |
| REMARK | 290 | SMTRY2 | 11 | 0.000000 | 0.000000 | −1.000000 | 0.00000 |
| REMARK | 290 | SMTRY3 | 11 | −1.000000 | 0.000000 | 0.000000 | 0.00000 |
| REMARK | 290 | SMTRY1 | 12 | 0.000000 | −1.000000 | 0.000000 | 0.00000 |
| REMARK | 290 | SMTRY2 | 12 | 0.000000 | 0.000000 | −1.000000 | 0.00000 |
| REMARK | 290 | SMTRY3 | 12 | 1.000000 | 0.000000 | 0.000000 | 0.00000 |
| REMARK | 290 | SMTRY1 | 13 | 0.000000 | 1.000000 | 0.000000 | 0.00000 |
| REMARK | 290 | SMTRY2 | 13 | 1.000000 | 0.000000 | 0.000000 | 0.00000 |
| REMARK | 290 | SMTRY3 | 13 | 0.000000 | 0.000000 | −1.000000 | 0.00000 |
| REMARK | 290 | SMTRY1 | 14 | 0.000000 | −1.000000 | 0.000000 | 0.00000 |
| REMARK | 290 | SMTRY2 | 14 | −1.000000 | 0.000000 | 0.000000 | 0.00000 |
| REMARK | 290 | SMTRY3 | 14 | 0.000000 | 0.000000 | −1.000000 | 0.00000 |
| REMARK | 290 | SMTRY1 | 15 | 0.000000 | 1.000000 | 0.000000 | 0.00000 |
| REMARK | 290 | SMTRY2 | 15 | −1.000000 | 0.000000 | 0.000000 | 0.00000 |
| REMARK | 290 | SMTRY3 | 15 | 0.000000 | 0.000000 | 1.000000 | 0.00000 |
| REMARK | 290 | SMTRY1 | 16 | 0.000000 | −1.000000 | 0.000000 | 0.00000 |
| REMARK | 290 | SMTRY2 | 16 | 1.000000 | 0.000000 | 0.000000 | 0.00000 |
| REMARK | 290 | SMTRY3 | 16 | 0.000000 | 0.000000 | 1.000000 | 0.00000 |
| REMARK | 290 | SMTRY1 | 17 | 1.000000 | 0.000000 | 0.000000 | 0.00000 |
| REMARK | 290 | SMTRY2 | 17 | 0.000000 | 0.000000 | 1.000000 | 0.00000 |
| REMARK | 290 | SMTRY3 | 17 | 0.000000 | −1.000000. | 0.000000 | 0.00000 |
| REMARK | 290 | SMTRY1 | 18 | −1.000000 | 0.000000 | 0.000000 | 0.00000 |
| REMARK | 290 | SMTRY2 | 18 | 0.000000 | 0.000000 | 1.000000 | 0.00000 |
| REMARK | 290 | SMTRY3 | 18 | 0.000000 | 1.000000 | 0.000000 | 0.00000 |
| REMARK | 290 | SMTRY1 | 19 | −1.000000 | 0.000000 | 0.000000 | 0.00000 |
| REMARK | 290 | SMTRY2 | 19 | 0.000000 | 0.000000 | −1.000000 | 0.00000 |
| REMARK | 290 | SMTRY3 | 19 | 0.000000 | −2.000000 | 0.000000 | 0.00000 |
| REMARK | 290 | SMTRY1 | 20 | 1.000000 | 0.000000 | 0.000000 | 0.00000 |
| REMARK | 290 | SMTRY2 | 20 | 0.000000 | 0.000000 | −1.000000 | 0.00000 |
| REMARK | 290 | SMTRY3 | 20 | 0.000000 | 1.000000 | 0.000000 | 0.00000 |
| REMARK | 290 | SMTRY1 | 21 | 0.000000 | 0.000000 | 1.000000 | 0.00000 |
| REMARK | 290 | SMTRY2 | 21 | 0.000000 | 1.000000 | 0.000000 | 0.00000 |
| REMARK | 290 | SMTRY3 | 21 | −1.000000 | 0.000000 | 0.000000 | 0.00000 |
| REMARK | 290 | SMTRY1 | 22 | 0.000000 | 0.000000 | 1.000000 | 0.00000 |
| REMARK | 290 | SMTRY2 | 22 | 0.000000 | −1.000000 | 0.000000 | 0.00000 |
| REMARK | 290 | SMTRY3 | 22 | 1.000000 | 0.000000 | 0.000000 | 0.00000 |
| REMARK | 290 | SMTRY1 | 23 | 0.000000 | 0.000000 | −1.000000 | 0.00000 |
| REMARK | 290 | SMTRY2 | 23 | 0.000000 | 1.000000 | 0.000000 | 0.00000 |
| REMARK | 290 | SMTRY3 | 23 | 1.000000 | 0.000000 | 0.000000 | 0.00000 |
| REMARK | 290 | SMTRY1 | 24 | 0.000000 | 0.000000 | −1.000000 | 0.00000 |
| REMARK | 290 | SMTRY2 | 24 | 0.000000 | −1.000000 | 0.000000 | 0.00000 |
| REMARK | 290 | SMTRY3 | 24 | −1.000000 | 0.000000 | 0.000000 | 0.00000 |
| REMARK | 290 | | | | | | |
| REMARK | 290 | REMARK: NULL | | | | | |
| REMARK | 300 | | | | | | |

TABLE 6-continued

```
REMARK  300  BIOMOLECULE: 1
REMARK  300  THIS ENTRY CONTAINS THE CRYSTALLOGRAPHIC ASYMMETRIC UNIT
REMARK  300  WHICH CONSISTS OF 1 CHAIN(S). SEE REMARK 350 FOR
REMARK  300  INFORMATION ON GENERATING THE BIOLOGICAL MOLECULE(S).
REMARK  350
REMARK  350  GENERATING THE BIOMOLECULE
REMARK  350  COORDINATES FOR A COMPLETE MULTIMER REPRESENTING THE KNOWN
REMARK  350  BIOLOGICALLY SIGNIFICANT OLIGOMERIZATION STATE OF THE
REMARK  350  MOLECULE CAN BE GENERATED BY APPLYING BIOMT TRANSFORMATIONS
REMARK  350  GIVEN BELOW. BOTH NON-CRYSTALLOGRAPHIC AND
REMARK  350  CRYSTALLOGRAPHIC OPERATIONS ARE GIVEN.
REMARK  350
REMARK  350  BIOMOLECULE: 1
REMARK  350  APPLY THE FOLLOWING TO CHAINS: A
REMARK  350  BIOMT1   1   1.000000   0.000000   0.000000         0.00000
REMARK  350  BIOMT2   1   0.000000   1.000000   0.000000         0.00000
REMARK  350  BIOMT3   1   0.000000   0.000000   1.000000         0.00000
REMARK  350  BIOMT1   2  -1.000000   0.000000   0.000000       155.06800
REMARK  350  BIOMT2   2   0.000000  -1.000000   0.000000       155.06800
REMARK  350  BIOMT3   2   0.000000   0.000000   1.000000         0.00000
REMARK  350  BIOMT1   3   0.000000   1.000000   0.000000         0.00000
REMARK  350  BIOMT2   3  -1.000000   0.000000   0.000000       155.06800
REMARK  350  BIOMT3   3   0.000000   0.000000   1.000000         0.00000
REMARK  350  BIOMT1   4   0.000000  -1.000000   0.000000       155.06800
REMARK  350  BIOMT2   4   1.000000   0.000000   0.000000         0.00000
REMARK  350  BIOMT3   4   0.000000   0.000000   1.000000         0.00000
REMARK  465
REMARK  465  MISSING RESIDUES
REMARK  465  THE FOLLOWING RESIDUES WERE NOT LOCATED IN THE
REMARK  465  EXPERIMENT. (M = MODEL NUMBER; RES = RESIDUE NAME; C = CHAIN
REMARK  465  IDENTIFIER; SSSEQ = SEQUENCE NUMBER; I = INSERTION CODE.)
REMARK  465
REMARK  465    M RES C SSSEQI
REMARK  465      MET A      1
REMARK  465      SER A    108
REMARK  465      ASN A    109
REMARK  465      VAL A    110
REMARK  465      LYS A    111
REMARK  465      PRO A    112
REMARK  465      ASP A    113
REMARK  465      GLN A    114
REMARK  465      THR A    115
REMARK  465      PHE A    116
REMARK  465      ALA A    117
REMARK  465      ASP A    118
REMARK  465      VAL A    119
REMARK  465      LEU A    120
REMARK  465      ALA A    121
REMARK  465      ILE A    122
REMARK  465      SER A    123
REMARK  465      GLN A    124
REMARK  465      ARG A    125
REMARK  465      THR A    126
REMARK  465      THR A    127
REMARK  465      HIS A    128
REMARK  465      ASN A    129
REMARK  465      THR A    130
REMARK  465      VAL A    131
REMARK  465      ALA A    132
REMARK  465      VAL A    133
REMARK  465      THR A    134
REMARK  465      ASP A    135
REMARK  465      ASP A    136
REMARK  465      GLY A    137
REMARK  465      THR A    138
REMARK  465      PRO A    139
REMARK  465      HIS A    140
REMARK  465      GLY A    141
REMARK  465      VAL A    142
REMARK  465      LEU A    143
REMARK  465      LEU A    144
REMARK  465      GLY A    145
REMARK  465      LEU A    146
REMARK  465      VAL A    147
REMARK  465      THR A    148
REMARK  465      GLN A    149
REMARK  465      ARG A    150
REMARK  465      ASP A    151
REMARK  465      TYR A    152
```

TABLE 6-continued

| REMARK | 465 | PRO | A | 153 |
|---|---|---|---|---|
| REMARK | 465 | ILE | A | 154 |
| REMARK | 465 | ASP | A | 155 |
| REMARK | 465 | LEU | A | 156 |
| REMARK | 465 | THR | A | 157 |
| REMARK | 465 | GLN | A | 158 |
| REMARK | 465 | THR | A | 159 |
| REMARK | 465 | GLU | A | 160 |
| REMARK | 465 | THR | A | 161 |
| REMARK | 465 | LYS | A | 162 |
| REMARK | 465 | VAL | A | 163 |
| REMARK | 465 | SER | A | 164 |
| REMARK | 465 | ASP | A | 165 |
| REMARK | 465 | MET | A | 166 |
| REMARK | 465 | MET | A | 167 |
| REMARK | 465 | THR | A | 168 |
| REMARK | 465 | PRO | A | 169 |
| REMARK | 465 | PHE | A | 170 |
| REMARK | 465 | SER | A | 171 |
| REMARK | 465 | LYS | A | 172 |
| REMARK | 465 | LEU | A | 173 |
| REMARK | 465 | VAL | A | 174 |
| REMARK | 465 | THR | A | 175 |
| REMARK | 465 | ALA | A | 176 |
| REMARK | 465 | HIS | A | 177 |
| REMARK | 465 | GLN | A | 178 |
| REMARK | 465 | ASP | A | 179 |
| REMARK | 465 | THR | A | 180 |
| REMARK | 465 | LYS | A | 181 |
| REMARK | 465 | LEU | A | 182 |
| REMARK | 465 | SER | A | 183 |
| REMARK | 465 | GLU | A | 184 |
| REMARK | 465 | ALA | A | 185 |
| REMARK | 465 | ASN | A | 186 |
| REMARK | 465 | LYS | A | 187 |
| REMARK | 465 | ILE | A | 188 |
| REMARK | 465 | ILE | A | 189 |
| REMARK | 465 | TRP | A | 190 |
| REMARK | 465 | GLU | A | 191 |
| REMARK | 465 | LYS | A | 192 |
| REMARK | 465 | LYS | A | 193 |
| REMARK | 465 | LEU | A | 194 |
| REMARK | 465 | ASN | A | 195 |
| REMARK | 465 | ALA | A | 196 |
| REMARK | 465 | LEU | A | 197 |
| REMARK | 465 | PRO | A | 198 |
| REMARK | 465 | ILE | A | 199 |
| REMARK | 465 | ILE | A | 200 |
| REMARK | 465 | ASP | A | 201 |
| REMARK | 465 | ASP | A | 202 |
| REMARK | 465 | ASP | A | 203 |
| REMARK | 465 | GLN | A | 204 |
| REMARK | 465 | HIS | A | 205 |
| REMARK | 465 | LEU | A | 206 |
| REMARK | 465 | ARG | A | 207 |
| REMARK | 465 | TYR | A | 208 |
| REMARK | 465 | ILE | A | 209 |
| REMARK | 465 | VAL | A | 210 |
| REMARK | 465 | PHE | A | 211 |
| REMARK | 465 | ARG | A | 212 |
| REMARK | 465 | LYS | A | 213 |
| REMARK | 465 | ASP | A | 214 |
| REMARK | 465 | TYR | A | 215 |
| REMARK | 465 | ASP | A | 216 |
| REMARK | 465 | ARG | A | 217 |
| REMARK | 465 | SER | A | 218 |
| REMARK | 465 | GLN | A | 219 |
| REMARK | 465 | GLN | A | 417 |
| REMARK | 465 | ARG | A | 418 |
| REMARK | 465 | TYR | A | 419 |
| REMARK | 465 | ASP | A | 420 |
| REMARK | 465 | LEU | A | 421 |
| REMARK | 465 | GLY | A | 422 |
| REMARK | 465 | GLY | A | 423 |
| REMARK | 465 | LYS | A | 424 |
| REMARK | 465 | GLN | A | 425 |
| REMARK | 465 | LYS | A | 426 |
| REMARK | 465 | LEU | A | 427 |
| REMARK | 465 | SER | A | 428 |

TABLE 6-continued

```
REMARK  465  PHE  A      429
REMARK  465  GLU  A      430
REMARK  465  VAL  A      493
REMARK  465  LYS  A      494
REMARK  465  ASP  A      495
REMARK  465  ARG  A      496
REMARK  465  ILE  A      497
REMARK  465  ASN  A      498
REMARK  465  ASP  A      499
REMARK  465  TYR  A      500
REMARK  465  HIS  A      502
REMARK  465  PRO  A      502
REMARK  465  LYS  A      503
REMARK  500
REMARK  500  GEOMETRY AND STEREOCHEMISTRY
REMARK  500  SUBTOPIC: COVALENT BOND LENGTHS
REMARK  500
REMARK  500  THE STEREOCHEMICAL PARAMETERS OF THE FOLLOWING RESIDUES
REMARK  500  HAVE VALUES WHICH DEVIATE FROM EXPECTED VALUES BY MORE
REMARK  500  THAN 6*RMSD (M = MODEL NUMBER; RES = RESIDUE NAME; C = CHAIN
REMARK  500  IDENTIFIER; SSEQ = SEQUENCE NUMBER; I = INSERTION CODE).
REMARK  500
REMARK  500  STANDARD TABLE:
REMARK  500  FORMAT: (10X,I3,1X,2(A3,1X,A1,I4,A1,1X,A4,3X),F6.3)
REMARK  500
REMARK  500  EXPECTED VALUES: ENGH AND HUBER, 1991
REMARK  500
REMARK  500  M RES CSSEQI    ATM1    RES CSSEQI    ATM2    DEVIATION
REMARK  500    ASP A 107     OD2     ASP A 107     CG      0.080
REMARK  500    MET A 373     CE      MET A 373     SD      0.038
REMARK  500
REMARK  500  GEOMETRY AND STEREOCHEMISTRY.
REMARK  500  SUBTOPIC: COVALENT BOND ANGLES
REMARK  500
REMARK  500  THE STEREOCHEMICAL PARAMETERS OF THE FOLLOWING RESIDUES
REMARK  500  HAVE VALUES WHICH DEVIATE FROM EXPECTED VALUES BY MORE
REMARK  500  THAN 6*RMSD (M = MODEL NUMBER; RES = RESIDUE NAME; C = CHAIN
REMARK  500  IDENTIFIER; SSEQ = SEQUENCE NUMBER; I = INSERTION CODE).
REMARK  500
REMARK  500  STANDARD TABLE:
REMARK  500  FORMAT: (10X,I3,1X,A3,1X,A1,I4,A1,3(1X,A4,2X),12X,F5.1)
REMARK  500
REMARK  500  EXPECTED VALUES: ENGH AND HUBER, 1991
REMARK  500
REMARK  500  M RES CSSEQI    ATM1    ATM2    ATM3
REMARK  500    GLY A 20      N -     CA -    C ANGL. DEV. = -7.6 DEGREES
REMARK  500    ILE A 27      N -     CA -    C ANGL. DEV. = -7.8 DEGREES
REMARK  500    ILE A 52      N -     CA -    C ANGL. DEV. = -7.9 DEGREES
REMARK  500    SER A 63      N -     CA -    C ANGL. DEV. = 8.1 DEGREES
REMARK  500    GLY A 64      N -     CA -    C ANGL. DEV. = -7.5 DEGREES
REMARK  500    GLY A 305     N -     CA -    C ANGL. DEV. = 7.5 DEGREES
REMARK  500    SER A 357     N -     CA -    C ANGL. DEV. = -7.4 DEGREES
REMARK  500    LYS A 444     N -     CA -    C ANGL. DEV. = 7.7 DEGREES
```

TABLE 6-continued

| REMARK | 500 LYS A 472 | N – | CA – | C ANGL. DEV. = 7.6 DEGREES |
|---|---|---|---|---|
| REMARK | 500 LYS A 474 | N – | CA – | C ANGL. DEV. = –9.1 DEGREES |
| REMARK | 500 LEU A 477 | N – | CA – | C ANGL. DEV. = –8.2 DEGREES |
| REMARK | 900 | | | |
| REMARK | 900 RELATED ENTRIES | | | |
| REMARK | 900 RELATED ID: 1AK5   RELATED DB: PDB | | | |
| REMARK | 900 INOSINE MONOPHOSPHATE DEHYDROGENASE (IMPDH) FROM | | | |
| REMARK | 900 TRITRICHOMONAS FOETUS | | | |
| REMARK | 900 RELATED ID: 1ME8   RELATED DB: PDB | | | |
| REMARK | 900 1ME8 CONTAINS THE SAME PROTEIN WITH RVP BOUND | | | |
| REMARK | 900 RELATED ID: 1ME9   RELATED DB: PDB | | | |
| REMARK | 900 1ME9 CONTAINS THE SAME PROTEIN WITH IMP BOUND | | | |
| REMARK | 900 RELATED ID: 1MEH   RELATED DB: PDB | | | |
| REMARK | 900 1MEH CONTAINS THE SAME PROTEIN WITH IMP AND MOA BOUND | | | |
| REMARK | 900 RELATED ID: 1MEI   RELATED DB: PDB | | | |
| REMARK | 900 1MEI CONTAINS THE SAME PROTEIN WITH XMP AND MYCOPHENOLIC | | | |
| REMARK | 900 ACID BOUND | | | |
| REMARK | 900 RELATED ID: 1MEW   RELATED DB: PDB | | | |
| REMARK | 900 1MEW CONTAINS THE SAME PROTEIN WITH XMP AND NAD BOUND | | | |
| DBREF | 1ME7 A   1   503   SWS   P50097   IMDH_TRIFO   1   503 | | | |
| SEQRES | 1 A   503  MET ALA LYS TYR TYR ASN GLU PRO CYS HIS THR PHE ASN | | | |
| SEQRES | 2 A   503  GLU TYR LEU LEU ILE PRO GLY LEU SER THR VAL ASP CYS | | | |
| SEQRES | 3 A   503  ILE PRO SER ASN VAL ASN LEU SER THR PRO LEU VAL LYS | | | |
| SEQRES | 4 A   503  PHE GLN LYS GLY GLN GLN SER GLU ILE ASN LEU LYS ILE | | | |
| SEQRES | 5 A   503  PRO LEU VAL SER ALA ILE MET GLN SER VAL SER GLY GLU | | | |
| SEQRES | 6 A   503  LYS MET ALA ILE ALA LEU ALA ARG GLU GLY GLY ILE SER | | | |
| SEQRES | 7 A   503  PHE ILE PHE GLY SER GLN SER ILE GLU SER GLN ALA ALA | | | |
| SEQRES | 8 A   503  MET VAL HIS ALA VAL LYS ASN PHE LYS ALA GLY PHE VAL | | | |
| SEQRES | 9 A   503  VAL SER ASP SER ASN VAL LYS PRO ASP GLN THR PHE ALA | | | |
| SEQRES | 10 A   503  ASP VAL LEU ALA ILE SER GLN ARG THR THR HIS ASN THR | | | |
| SEQRES | 11 A   503  VAL ALA VAL THR ASP ASP GLY THR PRO HIS GLY VAL LEU | | | |
| SEQRES | 12 A   503  LEU GLY LEU VAL THR GLN ARG ASP TYR PRO ILE ASP LEU | | | |
| SEQRES | 13 A   503  THR GLN THR GLU THR LYS VAL SER ASP MET MET THR PRO | | | |
| SEQRES | 14 A   503  PHE SER LYS LEU VAL THR ALA HIS GLN ASP THR LYS LEU | | | |
| SEQRES | 15 A   503  SER GLU ALA ASN LYS ILE ILE TRP GLU LYS LYS LEU ASN | | | |
| SEQRES | 16 A   503  ALA LEU PRO ILE ILE ASP ASP ASP GLN HIS LEU ARG TYR | | | |
| SEQRES | 17 A   503  ILE VAL PHE ARG LYS ASP TYR ASP ARG SER GLN VAL CYS | | | |
| SEQRES | 18 A   503  HIS ASN GLU LEU VAL ASP SER GLN LYS ARG TYR LEU VAL | | | |
| SEQRES | 19 A   503  GLY ALA GLY ILE ASN THR ARG ASP PHE ARG GLU ARG VAL | | | |
| SEQRES | 20 A   503  PRO ALA LEU VAL GLU ALA GLY ALA ASP VAL LEU CYS ILE | | | |
| SEQRES | 21 A   503  ASP SER SER ASP GLY PHE SER GLU TRP GLN LYS ILE THR | | | |
| SEQRES | 22 A   503  ILE GLY TRP ILE ARG GLU LYS TYR GLY ASP LYS VAL LYS | | | |
| SEQRES | 23 A   503  VAL GLY ALA GLY ASN ILE VAL GLY GLU GLY LYS PHE ARG | | | |
| SEQRES | 24 A   503  TYR LEU ALA ASP ALA GLY ALA ASP PHE ILE LYS ILE GLY | | | |
| SEQRES | 25 A   503  ILE GLY GLY GLY SER ILE CYS ILE THR ARG GLU GLN LYS | | | |
| SEQRES | 26 A   503  GLY ILE GLY ARG GLY GLN ALA THR ALA VAL ILE ASP VAL | | | |
| SEQRES | 27 A   503  VAL ALA GLU ARG ASN LYS TYR PHE GLU GLU THR GLY ILE | | | |
| SEQRES | 28 A   503  SER TYR ILE PRO VAL CYS SER ASP GLY GLY ILE VAL TYR ASP | | | |
| SEQRES | 29 A   503  TYR HIS MET THR LEU ALA LEU ALA MET GLY ALA ASP PHE | | | |
| SEQRES | 30 A   503  ILE MET LEU GLY ARG TYR PHE ALA ARG PHE GLU GLU SER | | | |
| SEQRES | 31 A   503  PRO THR ARG LYS VAL THR ILE ASN GLY SER VAL MET LYS | | | |
| SEQRES | 32 A   503  GLU TYR TRP GLY GLU GLY SER SER ARG ALA ARG ASN TRP | | | |
| SEQRES | 33 A   503  GLN ARG TYR ASP LEU GLY GLY LYS GLN LYS LEU SER PHE | | | |
| SEQRES | 34 A   503  GLU GLU GLY VAL ASP SER TYR VAL PRO TYR ALA GLY LYS | | | |
| SEQRES | 35 A   503  LEU LYS ASP ASN VAL GLU ALA SER LEU ASN LYS VAL LYS | | | |
| SEQRES | 36 A   503  SER THR MET CYS ASN CYS GLY ALA LEU THR ILE PRO GLN | | | |
| SEQRES | 37 A   503  LEU GLN SER LYS ALA LYS ILE THR LEU VAL SER SER VAL | | | |
| SEQRES | 38 A   503  SER ILE VAL GLU GLY GLY ALA HIS ASP VAL ILE VAL LYS | | | |
| SEQRES | 39 A   503  ASP ARG ILE ASN ASP TYR HIS PRO LYS | | | |
| HET | NA   901   1 | | | |
| HET | K A   900   1 | | | |
| HET | RVP   602   21 | | | |
| RET | MOA   600   23 | | | |
| HETNAM | NA SODIUM ION | | | |
| HETNAM | K POTASSIUM ION | | | |
| HETNAN | RVP RIBAVIRIN MONOPHOSPHATE | | | |
| HETNAN | MOA MYCOPHENOLIC ACID | | | |
| HETSYN | MOA 6-(1,3-DIHYDRO-7-HYDROXY-5-METHOXY-4-METHYL-1- | | | |
| HETSYN | 2 MOA OXOISOBENZOFURAN-6-YL)-4-METHYL-4-HEXANOIC ACID | | | |

TABLE 6-continued

| | | | | | | | | | | | | | |
|---|---|---|---|---|---|---|---|---|---|---|---|---|---|
| FORMUL | 2 | NA | NA1 1+ | | | | | | | | | | |
| FORMUL | 3 | K | K1 1+ | | | | | | | | | | |
| FORMUL | 4 | RVP | C8 H13 N4 O8 P1 | | | | | | | | | | |
| FORMUL | 5 | MOA | C17 H20 O6 | | | | | | | | | | |
| FORMUL | 6 | HON | *120 (H2 O1) | | | | | | | | | | |
| HELIX | 1 1 | THR | A | 11 ASN | A | 135 | | | | | | | 3 |
| HELIX | 2 2 | ILE | A | 27 VAL | A | 315 | | | | | | | 5 |
| HELIX | 3 3 | GLY | A | 64 GLU | A | 741 | | | | | | | 11 |
| HELIX | 4 4 | SER | A | 85 ASN | A | 981 | | | | | | | 14 |
| HELIX | 5 5 | ASP | A | 242 ALA | A | 2531 | | | | | | | 12 |
| HELIX | 6 6 | SER | A | 267 GLY | A | 2821 | | | | | | | 16 |
| HELIX | 7 7 | ASP | A | 283 VAL | A | 2855 | | | | | | | 3 |
| HELIX | 8 8 | ASP | A | 294 ALA | A | 3041 | | | | | | | 11 |
| HELIX | 9 9 | GLY | A | 330 GLY | A | 3501 | | | | | | | 21 |
| HELIX | 10 0 | TYR | A | 363 MET | A | 3731 | | | | | | | 11 |
| HELIX | 11 1 | GLY | A | 381 ARG | A | 3861 | | | | | | | 6 |
| HELIX | 12 2 | LYS | A | 442 CYS | A | 4611 | | | | | | | 20 |
| HELIX | 13 3 | THR | A | 465 ALA | A | 4731 | | | | | | | 9 |
| SHEET | 1A | 2 | TYR | A 15 | ILE | A 8 | 0 | | | | | | |
| SHEET | 2A | 2 | LYS | A 474 | LEU | 477 | −1 | O | LYS A | 474 | N | ILE A | 18 |
| SHEET | 1B | 2 | THR | A 35 | PRO | A 6 | 0 | | | | | | |
| SHEET | 2B | 2 | ASN | A 49 | LEU | A 0 | −1 | O | LEU A | 50 | N | THR A | 35 |
| SHEET | 1C | 2 | PHE | A 40 | GLN | A 1 | 0 | | | | | | |
| SHEET | 2C | 2 | ILE | A 351 | TYR | A 52 | −1 | O | TYR A | 352 | N | PHE A | 40 |
| SHEET | 1D | 9 | LEU | A 54 | SER | A 6 | 0 | | | | | | |
| SHEET | 2D | 9 | ILE | A 77 | ILE | A 0 | 1 | O | ILE A | 77 | N | SER A | 56 |
| SHEET | 3D | 9 | GLY | A 235 | ILE | 2 8 | 1 | O | GLY A | 237 | N | ILE A | 80 |
| SHEET | 4D | 9 | VAL | A 257 | ILE | 2 0 | 1 | O | CYS A | 259 | N | ILE A | 238 |
| SHEET | 5D | 9 | VAL | A 287 | ILE | 2 2 | 1 | O | GLY A | 288 | N | LEU A | 258 |
| SHEET | 6D | 9 | PHE | A 308 | ILE | 3 1 | 1 | O | LYS A | 310 | N | ALA A | 289 |
| SHEET | 7D | 9 | VAL | A 355 | ASP | 3 8 | 1 | O | CYS A | 356 | N | ILE A | 311 |
| SHEET | 8D | 9 | PHE | A 377 | LEU | 3 0 | 1 | O | MET A | 379 | N | SER A | 357 |
| SHEET | 9D | 9 | LEU | A 54 | SER | A 6 | 1 | N | VAL A | 55 | O | ILE A | 378 |
| SHEET | 1E | 3 | LYS | A 394 | ILE | 3 7 | 0 | | | | | | |
| SHEET | 2E | 3 | SER | A 400 | TRP | 4 6 | −1 | O | MET A | 402 | N | VAL A | 395 |
| SHEET | 3E | 3 | ASP | A 434 | PRO | 4 8 | −1 | O | SER A | 435 | N | TYR A | 405 |
| SSBOND | 1 | CYS | A26 | CYS | A | 459 | | | | | | | |
| CISPEP | 1 | GLY | A90 | ASN | A | 291 | 0 | 1.08 | | | | | |
| CRYST1 | 155.068 | 155.068 | 55.068 | 90.00 | 90.00 | 90.00 | P 4 3 2 | | 24 | | | | |
| ORIGX1 | | 1.000000 | 0.000000 | 0.000000 | 0.00000 | | | | | | | | |
| ORIGX2 | | 0.000000 | 1.000000 | 0.000000 | 0.00000 | | | | | | | | |
| ORIGX3 | | 0.000000 | 0.000000 | 1.000000 | 0.00000 | | | | | | | | |
| SCALE1 | | 0.006449 | 0.000000 | 0.000000 | 0.00000 | | | | | | | | |
| SCALE2 | | 0.000000 | 0.006449 | 0.000000 | 0.00000 | | | | | | | | |
| SCALE3 | | 0.000000 | 0.000000 | 0.006449 | 0.00000 | | | | | | | | |
| ATOM | 1 | N | ALA | A | 2 | 55.337 | 75.180 | 36.704 | 1.00 | 34.41 | N | | |
| ATOM | 2 | CA | ALA | A | 2 | 56.037 | 74.068 | 35.999 | 1.00 | 33.40 | C | | |
| ATOM | 3 | C | ALA | A | 2 | 57.330 | 73.693 | 36.728 | 1.00 | 33.89 | C | | |
| ATOM | 4 | O | ALA | A | 2 | 57.769 | 74.397 | 37.640 | 1.00 | 32.06 | O | | |
| ATOM | 5 | CB | ALA | A | 2 | 56.344 | 74.482 | 34.569 | 1.00 | 33.59 | C | | |
| ATOM | 6 | N | LYS | A | 3 | 57.931 | 72.578 | 36.328 | 1.00 | 33.85 | N | | |
| ATOM | 7 | CA | LYS | A | 3 | 59.175 | 72.132 | 36.943 | 1.00 | 35.52 | C | | |
| ATOM | 8 | C | LYS | A | 3 | 60.319 | 72.311 | 35.953 | 1.00 | 34.41 | C | | |
| ATOM | 9 | O | LYS | A | 3 | 60.214 | 71.899 | 34.800 | 1.00 | 34.80 | O | | |
| ATOM | 10 | CB | LYS | A | 3 | 59.086 | 70.654 | 37.343 | 1.00 | 38.16 | C | | |
| ATOM | 11 | CG | LYS | A | 3 | 60.364 | 70.140 | 38.018 | 1.00 | 42.91 | C | | |
| ATOM | 12 | CD | LYS | A | 3 | 60.512 | 68.625 | 37.892 | 1.00 | 46.63 | C | | |
| ATOM | 13 | CE | LYS | A | 3 | 61.851 | 68.159 | 38.443 | 1.00 | 48.14 | C | | |
| ATOM | 14 | NZ | LYS | A | 3 | 62.983 | 68.796 | 37.717 | 1.00 | 49.64 | N | | |
| ATOM | 15 | N | TYR | A | 4 | 61.410 | 72.915 | 36.413 | 1.00 | 33.82 | N | | |
| ATOM | 16 | CA | TYR | A | 4 | 62.582 | 73.157 | 35.576 | 1.00 | 34.00 | C | | |
| ATOM | 17 | C | TYR | A | 4 | 63.792 | 72.378 | 36.094 | 1.00 | 35.31 | C | | |
| ATOM | 18 | O | TYR | A | 4 | 63.748 | 71.806 | 37.179 | 1.00 | 35.23 | O | | |
| ATOM | 19 | CB | TYR | A | 4 | 62.886 | 74.661 | 35.548 | 1.00 | 32.00 | C | | |
| ATOM | 20 | CG | TYR | A | 4 | 61.771 | 75.471 | 34.930 | 1.00 | 31.34 | C | | |
| ATOM | 21 | CD1 | TYR | A | 4 | 61.659 | 75.598 | 33.546 | 1.00 | 30.66 | C | | |
| ATOM | 22 | CD2 | TYR | A | 4 | 60.793 | 76.070 | 35.726 | 1.00 | 32.52 | C | | |
| ATOM | 23 | CE1 | TYR | A | 4 | 60.593 | 76.303 | 32.969 | 1.00 | 29.90 | C | | |
| ATOM | 24 | CE2 | TYR | A | 4 | 59.726 | 76.776 | 35.158 | 1.00 | 30.38 | C | | |
| ATOM | 25 | CZ | TYR | A | 4 | 59.635 | 76.884 | 33.784 | 1.00 | 29.87 | C | | |
| ATOM | 26 | OH | TYR | A | 4 | 58.582 | 77.565 | 33.222 | 1.00 | 31.29 | O | | |
| ATOM | 27 | N | TYR | A | 5 | 64.867 | 72.351 | 35.314 | 1.00 | 36.84 | N | | |
| ATOM | 28 | CA | TYR | A | 5 | 66.072 | 71.630 | 35.708 | 1.00 | 38.47 | C | | |
| ATOM | 29 | C | TYR | A | 5 | 67.273 | 72.559 | 35.843 | 1.00 | 39.48 | C | | |
| ATOM | 30 | O | TYR | A | 5 | 67.312 | 73.636 | 35.243 | 1.00 | 39.29 | O | | |
| ATOM | 31 | CB | TYR | A | 5 | 66.377 | 70.519 | 34.698 | 1.00 | 37.98 | C | | |
| ATOM | 32 | CG | TYR | A | 5 | 65.243 | 69.530 | 34.551 | 1.00 | 38.25 | C | | |
| ATOM | 33 | CD1 | TYR | A | 5 | 64.068 | 69.884 | 33.884 | 1.00 | 38.19 | C | | |
| ATOM | 34 | CD2 | TYR | A | 5 | 65.320 | 68.258 | 35.128 | 1.00 | 37.95 | C | | |

TABLE 6-continued

| | | | | | | | | | | |
|---|---|---|---|---|---|---|---|---|---|---|
| ATOM | 35 | CE1 | TYR | A | 5 | 62.995 | 69.002 | 33.796 | 1.00 | 38.93 C |
| ATOM | 36 | CE2 | TYR | A | 5 | 64.251 | 67.363 | 35.050 | 1.00 | 38.15 C |
| ATOM | 37 | CZ | TYR | A | 5 | 63.091 | 67.744 | 34.383 | 1.00 | 39.68 C |
| ATOM | 38 | OH | TYR | A | 5 | 62.028 | 66.879 | 34.309 | 1.00 | 38.51 O |
| ATOM | 39 | N | ASN | A | 6 | 68.249 | 72.136 | 36.641 | 1.00 | 40.42 N |
| ATOM | 40 | CA | ASN | A | 6 | 69.450 | 72.931 | 36.876 | 1.00 | 41.21 C |
| ATOM | 41 | C | ASN | A | 6 | 70.427 | 72.917 | 35.706 | 1.00 | 40.26 C |
| ATOM | 42 | O | ASN | A | 6 | 71.205 | 73.851 | 35.543 | 1.00 | 40.88 O |
| ATOM | 43 | CB | ASN | A | 6 | 70.164 | 72.432 | 38.134 | 1.00 | 44.17 C |
| ATOM | 44 | CG | ASN | A | 6 | 69.365 | 72.682 | 39.400 | 1.00 | 48.00 C |
| ATOM | 45 | OD1 | ASN | A | 6 | 69.468 | 71.926 | 40.371 | 1.00 | 49.62 O |
| ATOM | 46 | ND2 | ASN | A | 6 | 68.574 | 73.757 | 39.405 | 1.00 | 49.76 N |
| ATOM | 47 | N | GLU | A | 7 | 70.388 | 71.868 | 34.892 | 1.00 | 38.65 N |
| ATOM | 48 | CA | GLU | A | 7 | 71.304 | 71.760 | 33.754 | 1.00 | 37.25 C |
| ATOM | 49 | C | GLU | A | 7 | 70.606 | 71.443 | 32.441 | 1.00 | 34.73 C |
| ATOM | 50 | O | GLU | A | 7 | 69.592 | 70.750 | 32.417 | 1.00 | 34.20 O |
| ATOM | 51 | CB | GLU | A | 7 | 72.340 | 70.656 | 34.004 | 1.00 | 38.95 C |
| ATOM | 52 | CG | GLU | A | 7 | 73.284 | 70.878 | 35.186 | 1.00 | 43.43 C |
| ATOM | 53 | CD | GLU | A | 7 | 74.155 | 72.110 | 35.020 | 1.00 | 45.61 C |
| ATOM | 54 | OE1 | GLU | A | 7 | 74.568 | 72.401 | 33.874 | 1.00 | 45.97 O |
| ATOM | 55 | OE2 | GLU | A | 7 | 74.438 | 72.779 | 36.040 | 1.00 | 49.17 O |
| ATOM | 56 | N | PRO | A | 8 | 71.140 | 71.952 | 31.326 | 1.00 | 32.47 N |
| ATOM | 57 | CA | PRO | A | 8 | 70.498 | 71.644 | 30.048 | 1.00 | 31.28 C |
| ATOM | 58 | C | PRO | A | 8 | 70.855 | 70.188 | 29.731 | 1.00 | 31.10 C |
| ATOM | 59 | O | PRO | A | 8 | 71.830 | 69.667 | 30.271 | 1.00 | 30.11 O |
| ATOM | 60 | CB | PRO | A | 8 | 71.160 | 72.627 | 29.089 | 1.00 | 31.56 C |
| ATOM | 61 | CG | PRO | A | 8 | 72.558 | 72.782 | 29.675 | 1.00 | 30.51 C |
| ATOM | 62 | CD | PRO | A | 8 | 72.273 | 72.883 | 31.153 | 1.00 | 32.79 C |
| ATOM | 63 | N | CYS | A | 9 | 70.077 | 69.522 | 28.882 | 1.00 | 30.22 N |
| ATOM | 64 | CA | CYS | A | 9 | 70.389 | 68.137 | 28.531 | 1.00 | 29.58 C |
| ATOM | 65 | C | CYS | A | 9 | 71.493 | 68.098 | 27.462 | 1.00 | 28.36 C |
| ATOM | 66 | O | CYS | A | 9 | 71.727 | 69.096 | 26.772 | 1.00 | 26.35 O |
| ATOM | 67 | CB | CYS | A | 9 | 69.124 | 67.414 | 28.046 | 1.00 | 31.88 C |
| ATOM | 68 | SG | CYS | A | 9 | 68.260 | 68.177 | 26.653 | 1.00 | 38.35 S |
| ATOM | 69 | N | HIS | A | 10 | 72.169 | 66.955 | 27.343 | 1.00 | 27.89 N |
| ATOM | 70 | CA | HIS | A | 10 | 73.271 | 66.765 | 26.391 | 1.00 | 27.84 C |
| ATOM | 71 | C | HIS | A | 10 | 73.107 | 65.471 | 25.593 | 1.00 | 28.16 C |
| ATOM | 72 | O | HIS | A | 10 | 72.470 | 64.524 | 26.066 | 1.00 | 27.35 O |
| ATOM | 73 | CB | HIS | A | 10 | 74.610 | 66.693 | 27.142 | 1.00 | 29.04 C |
| ATOM | 74 | CG | HIS | A | 10 | 74.871 | 67.865 | 28.034 | 1.00 | 30.87 C |
| ATOM | 75 | ND1 | HIS | A | 10 | 75.329 | 69.075 | 27.560 | 1.00 | 30.98 N |
| ATOM | 76 | CD2 | HIS | A | 10 | 74.695 | 68.025 | 29.368 | 1.00 | 31.03 C |
| ATOM | 77 | CE1 | HIS | A | 10 | 75.423 | 69.931 | 28.563 | 1.00 | 30.39 C |
| ATOM | 78 | NE2 | HIS | A | 10 | 75.045 | 69.318 | 29.670 | 1.00 | 31.86 N |
| ATOM | 79 | N | THR | A | 11 | 73.690 | 65.440 | 24.393 | 1.00 | 28.34 N |
| ATOM | 80 | CA | THR | A | 11 | 73.642 | 64.268 | 23.505 | 1.00 | 30.45 C |
| ATOM | 81 | C | THR | A | 11 | 75.019 | 63.582 | 23.511 | 1.00 | 29.54 C |
| ATOM | 82 | O | THR | A | 11 | 75.994 | 64.158 | 23.987 | 1.00 | 29.40 O |
| ATOM | 83 | CE | THR | A | 11 | 73.324 | 64.667 | 22.038 | 1.00 | 31.33 C |
| ATOM | 84 | OG1 | THR | A | 11 | 74.374 | 65.507 | 21.537 | 1.00 | 35.21 O |
| ATOM | 85 | CG2 | THR | A | 11 | 72.016 | 65.425 | 21.947 | 1.00 | 32.48 C |
| ATOM | 86 | N | PHE | A | 12 | 75.095 | 62.368 | 22.964 | 1.00 | 30.67 N |
| ATOM | 87 | CA | PHE | A | 12 | 76.349 | 61.606 | 22.916 | 1.00 | 32.58 C |
| ATOM | 88 | C | PHE | A | 12 | 77.534 | 62.334 | 22.291 | 1.00 | 32.84 C |
| ATOM | 89 | O | PHE | A | 12 | 78.664 | 62.178 | 22.745 | 1.00 | 32.45 O |
| ATOM | 90 | CB | PHE | A | 12 | 76.155 | 60.280 | 22.167 | 1.00 | 32.22 C |
| ATOM | 91 | CG | PHE | A | 12 | 75.231 | 59.318 | 22.859 | 1.00 | 32.84 C |
| ATOM | 92 | CD1 | PHE | A | 12 | 75.383 | 59.038 | 24.213 | 1.00 | 32.67 C |
| ATOM | 93 | CD2 | PHE | A | 12 | 74.217 | 58.682 | 22.152 | 1.00 | 32.52 C |
| ATOM | 94 | CE1 | PHE | A | 12 | 74.535 | 58.137 | 24.854 | 1.00 | 33.67 C |
| ATOM | 95 | CE2 | PHE | A | 12 | 73.364 | 57.777 | 22.783 | 1.00 | 32.40 C |
| ATOM | 96 | CZ | PHE | A | 12 | 73.522 | 57.505 | 24.133 | 1.00 | 32.01 C |
| ATOM | 97 | N | ASN | A | 13 | 77.280 | 63.111 | 21.242 | 1.00 | 34.83 N |
| ATOM | 98 | CA | ASN | A | 13 | 78.341 | 63.850 | 20.564 | 1.00 | 35.40 C |
| ATOM | 99 | C | ASN | A | 13 | 79.075 | 64.842 | 21.460 | 1.00 | 34.57 C |
| ATOM | 100 | O | ASN | A | 13 | 80.147 | 65.319 | 21.096 | 1.00 | 34.83 O |
| ATOM | 101 | CE | ASN | A | 13 | 77.783 | 64.602 | 19.349 | 1.00 | 39.42 C |
| ATOM | 102 | CG | ASN | A | 13 | 77.635 | 63.714 | 18.130 | 1.00 | 44.49 C |
| ATOM | 103 | OD1 | ASN | A | 13 | 78.553 | 62.970 | 17.773 | 1.00 | 47.75 O |
| ATOM | 104 | ND2 | ASN | A | 13 | 76.482 | 63.796 | 17.473 | 1.00 | 48.05 N |
| ATOM | 105 | N | GLU | A | 14 | 78.501 | 65.153 | 22.621 | 1.00 | 33.44 N |
| ATOM | 106 | CA | GLU | A | 14 | 79.108 | 66.100 | 23.553 | 1.00 | 33.47 C |
| ATOM | 107 | C | GLU | A | 14 | 80.050 | 65.462 | 24.572 | 1.00 | 33.77 C |
| ATOM | 108 | O | GLU | A | 14 | 80.608 | 66.157 | 25.418 | 1.00 | 34.50 O |
| ATOM | 109 | CE | GLU | A | 14 | 78.018 | 66.868 | 24.307 | 1.00 | 32.95 C |
| ATOM | 110 | CG | GLU | A | 14 | 77.087 | 67.648 | 23.406 | 1.00 | 33.19 C |
| ATOM | 111 | CD | GLU | A | 14 | 76.050 | 68.434 | 24.175 | 1.00 | 32.32 C |
| ATOM | 112 | OE1 | GLU | A | 14 | 76.433 | 69.350 | 24.936 | 1.00 | 32.77 O |
| ATOM | 113 | OE2 | GLU | A | 14 | 74.852 | 68.131 | 24.016 | 1.00 | 31.82 O |

TABLE 6-continued

| | | | | | | | | | | |
|---|---|---|---|---|---|---|---|---|---|---|
| ATOM | 114 | N | TYR | A | 15 | 80.230 | 64.148 | 24.496 | 1.00 | 32.50 | N |
| ATOM | 115 | CA | TYR | A | 15 | 81.093 | 63.463 | 25.444 | 1.00 | 31.35 | C |
| ATOM | 116 | C | TYR | A | 15 | 82.280 | 62.747 | 24.829 | 1.00 | 32.01 | C |
| ATOM | 117 | O | TYR | A | 15 | 82.283 | 62.403 | 23.649 | 1.00 | 32.05 | O |
| ATOM | 118 | CB | TYR | A | 15 | 80.286 | 62.435 | 26.236 | 1.00 | 30.88 | C |
| ATOM | 119 | CG | TYR | A | 15 | 79.251 | 63.028 | 27.153 | 1.00 | 31.45 | C |
| ATOM | 120 | CD1 | TYR | A | 15 | 79.571 | 63.380 | 28.462 | 1.00 | 31.97 | C |
| ATOM | 121 | CD2 | TYR | A | 15 | 77.947 | 63.241 | 26.710 | 1.00 | 31.39 | C |
| ATOM | 122 | CE1 | TYR | A | 15 | 78.614 | 63.928 | 29.314 | 1.00 | 33.72 | C |
| ATOM | 123 | CE2 | TYR | A | 15 | 76.986 | 63.790 | 27.549 | 1.00 | 33.18 | C |
| ATOM | 124 | CZ | TYR | A | 15 | 77.321 | 64.129 | 28.846 | 1.00 | 32.92 | C |
| ATOM | 125 | ON | TYR | A | 15 | 76.363 | 64.677 | 29.669 | 1.00 | 36.12 | O |
| ATOM | 126 | N | LEU | A | 16 | 83.290 | 62.523 | 25.661 | 1.00 | 32.48 | N |
| ATOM | 127 | CA | LEU | A | 16 | 84.479 | 61.779 | 25.263 | 1.00 | 31.96 | C |
| ATOM | 128 | C | LEU | A | 16 | 84.859 | 60.959 | 26.486 | 1.00 | 30.88 | C |
| ATOM | 129 | O | LEU | A | 16 | 84.541 | 61.336 | 27.609 | 1.00 | 29.12 | O |
| ATOM | 130 | CB | LEU | A | 16 | 85.641 | 62.711 | 24.888 | 1.00 | 31.45 | C |
| ATOM | 131 | CG | LEU | A | 16 | 85.562 | 63.515 | 23.583 | 1.00 | 33.88 | C |
| ATOM | 132 | CD1 | LEU | A | 16 | 86.829 | 64.331 | 23.436 | 1.00 | 34.99 | C |
| ATOM | 133 | CD2 | LEU | A | 16 | 85.406 | 62.591 | 22.383 | 1.00 | 33.78 | C |
| ATOM | 134 | N | LEU | A17 | 85.521 | 59.830 | 26.261 | 1.00 | 31.45 | N | |
| ATOM | 135 | CA | LEU | A | 17 | 85.977 | 58.966 | 27.347 | 1.00 | 32.43 | C |
| ATOM | 136 | C | LEU | A | 17 | 87.454 | 59.276 | 27.617 | 1.00 | 32.04 | C |
| ATOM | 137 | O | LEU | A | 17 | 88.245 | 59.410 | 26.678 | 1.00 | 32.62 | O |
| ATOM | 138 | CB | LEU | A | 17 | 85.840 | 57.489 | 26.944 | 1.00 | 31.23 | C |
| ATOM | 139 | CG | LEU | A | 17 | 84.423 | 56.919 | 26.852 | 1.00 | 32.03 | C |
| ATOM | 140 | CD1 | LEU | A | 17 | 84.389 | 55.730 | 25.898 | 1.00 | 30.72 | C |
| ATOM | 141 | CD2 | LEU | A | 17 | 83.943 | 56.532 | 28.243 | 1.00 | 29.59 | C |
| ATOM | 142 | N | ILE | A | 18 | 87.809 | 59.410 | 28.893 | 1.00 | 31.01 | N |
| ATOM | 143 | CA | ILE | A | 18 | 89.190 | 59.664 | 29.287 | 1.00 | 30.55 | C |
| ATOM | 144 | C | ILE | A | 18 | 89.743 | 58.306 | 29.717 | 1.00 | 30.47 | C |
| ATOM | 145 | O | ILE | A | 18 | 89.188 | 57.659 | 30.598 | 1.00 | 30.46 | O |
| ATOM | 146 | CB | ILE | A | 18 | 89.273 | 60.651 | 30.471 | 1.00 | 30.96 | C |
| ATOM | 147 | CG1 | ILE | A | 18 | 88.794 | 62.035 | 30.026 | 1.00 | 31.21 | C |
| ATOM | 148 | CG2 | ILE | A | 18 | 90.712 | 60.731 | 30.989 | 1.00 | 29.69 | C |
| ATOM | 149 | CD1 | ILE | A | 18 | 88.792 | 63.066 | 31.139 | 1.00 | 32.55 | C |
| ATOM | 150 | N | PRO | A | 19 | 90.842 | 57.857 | 29.095 | 1.00 | 30.24 | N |
| ATOM | 151 | CA | PRO | A | 19 | 91.439 | 56.562 | 29.428 | 1.00 | 32.18 | C |
| ATOM | 152 | C | PRO | A | 19 | 91.766 | 56.336 | 30.903 | 1.00 | 31.60 | C |
| ATOM | 153 | O | PRO | A | 19 | 91.999 | 57.282 | 31.662 | 1.00 | 31.91 | O |
| ATOM | 154 | CB | PRO | A | 19 | 92.697 | 56.517 | 28.552 | 1.00 | 31.40 | C |
| ATOM | 155 | CG | PRO | A | 19 | 92.326 | 57.403 | 27.384 | 1.00 | 31.65 | C |
| ATOM | 156 | CD | PRO | A | 19 | 91.634 | 58.550 | 28.065 | 1.00 | 30.73 | C |
| ATOM | 157 | N | GLY | A | 20 | 91.757 | 55.062 | 31.285 | 1.00 | 31.52 | N |
| ATOM | 158 | CA | GLY | A | 20 | 92.092 | 54.655 | 32.638 | 1.00 | 31.25 | C |
| ATOM | 159 | C | GLY | A | 20 | 93.307 | 53.755 | 32.485 | 1.00 | 31.86 | C |
| ATOM | 160 | O | GLY | A | 20 | 93.903 | 53.696 | 31.403 | 1.00 | 30.12 | O |
| ATOM | 161 | N | LEU | A | 21 | 93.677 | 53.040 | 33.539 | 1.00 | 32.96 | N |
| ATOM | 162 | CA | LEU | A | 21 | 94.840 | 52.163 | 33.458 | 1.00 | 34.19 | C |
| ATOM | 163 | C | LEU | A | 21 | 94.525 | 50.904 | 32.669 | 1.00 | 33.97 | C |
| ATOM | 164 | O | LEU | A | 21 | 93.619 | 50.151 | 33.020 | 1.00 | 34.45 | O |
| ATOM | 165 | CB | LEU | A | 21 | 95.330 | 51.770 | 34.863 | 1.00 | 34.37 | C |
| ATOM | 166 | CG | LEU | A | 21 | 96.489 | 50.759 | 34.904 | 1.00 | 34.20 | C |
| ATOM | 167 | CD1 | LEU | A | 21 | 97.700 | 51.336 | 34.182 | 1.00 | 30.55 | C |
| ATOM | 168 | CD2 | LEU | A | 21 | 96.838 | 50.420 | 36.355 | 1.00 | 34.84 | C |
| ATOM | 169 | N | SER | A | 22 | 95.269 | 50.688 | 31.592 | 1.00 | 34.75 | N |
| ATOM | 170 | CA | SER | A | 22 | 95.079 | 49.502 | 30.774 | 1.00 | 36.74 | C |
| ATOM | 171 | C | SER | A | 22 | 96.083 | 48.451 | 31.233 | 1.00 | 38.35 | C |
| ATOM | 172 | O | SER | A | 22 | 97.294 | 48.668 | 31.165 | 1.00 | 36.70 | O |
| ATOM | 173 | CB | SER | A | 22 | 95.313 | 49.827 | 29.300 | 1.00 | 36.32 | C |
| ATOM | 174 | OG | SER | A | 22 | 94.402 | 50.807 | 28.845 | 1.00 | 37.15 | O |
| ATOM | 175 | N | THR | A | 23 | 95.575 | 47.318 | 31.706 | 1.00 | 40.20 | N |
| ATOM | 176 | CA | THR | A | 23 | 96.429 | 46.235 | 32.183 | 1.00 | 42.51 | C |
| ATOM | 177 | C | THR | A | 23 | 96.838 | 45.318 | 31.036 | 1.00 | 43.43 | C |
| ATOM | 178 | O | THR | A | 23 | 96.204 | 45.321 | 29.980 | 1.00 | 44.38 | O |
| ATOM | 179 | CB | THR | A | 23 | 95.711 | 45.414 | 33.258 | 1.00 | 42.79 | C |
| ATOM | 180 | OG1 | THR | A | 23 | 94.456 | 44.957 | 32.744 | 1.00 | 45.13 | O |
| ATOM | 181 | CG2 | THR | A | 23 | 95.461 | 46.263 | 34.492 | 1.00 | 43.22 | C |
| ATOM | 182 | N | VAL | A | 24 | 97.897 | 44.535 | 31.241 | 1.00 | 43.96 | N |
| ATOM | 183 | CA | VAL | A | 24 | 98.383 | 43.632 | 30.198 | 1.00 | 45.09 | C |
| ATOM | 184 | C | VAL | A | 24 | 97.369 | 42.587 | 29.737 | 1.00 | 45.87. | C |
| ATOM | 185 | O | VAL | A | 24 | 97.391 | 42.175 | 28.576 | 1.00 | 45.20 | O |
| ATOM | 186 | CB | VAL | A | 24 | 99.678 | 42.894 | 30.632 | 1.00 | 45.95 | C |
| ATOM | 187 | CG1 | VAL | A | 24 | 100.823 | 43.893 | 30.783 | 1.00 | 45.49 | C |
| ATOM | 188 | CG2 | VAL | A | 24 | 99.442 | 42.134 | 31.933 | 1.00 | 45.36 | C |
| ATOM | 189 | N | ASP | A | 25 | 96.479 | 42.159 | 30.628 | 1.00 | 47.13 | N |
| ATOM | 190 | CA | ASP | A | 25 | 95.489 | 41.159 | 30.244 | 1.00 | 50.41 | C |
| ATOM | 191 | C | ASP | A | 25 | 94.326 | 41.710 | 29.421 | 1.00 | 50.20 | C |
| ATOM | 192 | O | ASP | A | 25 | 93.519 | 40.940 | 28.909 | 1.00 | 50.81 | O |

TABLE 6-continued

| ATOM | 193 | CB | ASP | A | 25 | 94.936 | 40.430 | 31.479 | 1.00 | 52.89 | C |
| ATOM | 194 | CG | ASP | A | 25 | 94.232 | 41.361 | 32.446 | 1.00 | 56.19 | C |
| ATOM | 195 | OD1 | ASP | A | 25 | 93.566 | 40.864 | 33.381 | 1.00 | 58.03 | O |
| ATOM | 196 | OD2 | ASP | A | 25 | 94.345 | 42.590 | 32.281 | 1.00 | 59.03 | O |
| ATOM | 197 | N | CYS | A | 26 | 94.234 | 43.030 | 29.270 | 1.00 | 49.99 | N |
| ATOM | 198 | CA | CYS | A | 26 | 93.124 | 43.581 | 28.497 | 1.00 | 48.97 | C |
| ATOM | 199 | C | CYS | A | 26 | 93.408 | 43.743 | 27.018 | 1.00 | 49.15 | C |
| ATOM | 200 | O | CYS | A | 26 | 93.939 | 44.764 | 26.581 | 1.00 | 48.97 | O |
| ATOM | 201 | CB | CYS | A | 26 | 92.660 | 44.937 | 29.047 | 1.00 | 47.43 | C |
| ATOM | 202 | SG | CYS | A | 26 | 90.937 | 45.377 | 28.585 | 1.00 | 43.74 | S |
| ATOM | 203 | N | ILE | A | 27 | 93.054 | 42.722 | 26.250 | 1.00 | 49.92 | N |
| ATOM | 204 | CA | ILE | A | 27 | 93.204 | 42.774 | 24.810 | 1.00 | 50.73 | C |
| ATOM | 205 | C | ILE | A | 27 | 91.781 | 42.593 | 24.300 | 1.00 | 50.66 | C |
| ATOM | 206 | O | ILE | A | 27 | 90.960 | 41.941 | 24.953 | 1.00 | 50.24 | O |
| ATOM | 207 | CB | ILE | A | 27 | 94.111 | 41.644 | 24.271 | 1.00 | 52.78 | C |
| ATOM | 208 | CG1 | ILE | A | 27 | 93.547 | 40.280 | 24.661 | 1.00 | 53.35 | C |
| ATOM | 209 | CG2 | ILE | A | 27 | 95.530 | 41.814 | 24.810 | 1.00 | 52.47 | C |
| ATOM | 210 | CD1 | ILE | A | 27 | 94.339 | 39.120 | 24.094 | 1.00 | 56.96 | C |
| ATOM | 211 | N | PRO | A | 28 | 91.460 | 43.188 | 23.145 | 1.00 | 50.63 | N |
| ATOM | 212 | CA | PRO | A | 28 | 90.126 | 43.096 | 22.548 | 1.00 | 50.44 | C |
| ATOM | 213 | C | PRO | A | 28 | 89.496 | 41.705 | 22.535 | 1.00 | 50.71 | C |
| ATOM | 214 | O | PRO | A | 28 | 88.329 | 41.545 | 22.895 | 1.00 | 50.80 | O |
| ATOM | 215 | CB | PRO | A | 28 | 90.349 | 43.653 | 21.148 | 1.00 | 50.84 | C |
| ATOM | 216 | CG | PRO | A | 28 | 91.336 | 44.746 | 21.407 | 1.00 | 50.51 | C |
| ATOM | 217 | CD | PRO | A | 28 | 92.325 | 44.085 | 22.356 | 1.00 | 50.67 | C |
| ATOM | 218 | N | SER | A | 29 | 90.265 | 40.700 | 22.131 | 1.00 | 50.62 | N |
| ATOM | 219 | CA | SER | A | 29 | 89.745 | 39.340 | 22.060 | 1.00 | 49.43 | C |
| ATOM | 220 | C | SER | A | 29 | 89.327 | 38.758 | 23.409 | 1.00 | 48.35 | C |
| ATOM | 221 | O | SER | A | 29 | 88.575 | 37.786 | 23.456 | 1.00 | 49.06 | O |
| ATOM | 222 | CB | SER | A | 29 | 90.767 | 38.416 | 21.383 | 1.00 | 51.07 | C |
| ATOM | 223 | OG | SER | A | 29 | 91.969 | 38.322 | 22.126 | 1.00 | 53.31 | O |
| ATOM | 224 | N | ASN | A | 30 | 89.801 | 39.335 | 24.508 | 1.00 | 45.87 | N |
| ATOM | 225 | CA | ASN | A | 30 | 89.414 | 38.824 | 25.819 | 1.00 | 44.49 | C |
| ATOM | 226 | C | ASN | A | 30 | 88.238 | 39.593 | 26.433 | 1.00 | 42.49 | C |
| ATOM | 227 | O | ASN | A | 30 | 87.765 | 39.248 | 27.518 | 1.00 | 42.16 | O |
| ATOM | 228 | CB | ASN | A | 30 | 90.594 | 38.854 | 26.793 | 1.00 | 46.85 | C |
| ATOM | 229 | CG | ASN | A | 30 | 91.698 | 37.892 | 26.404 | 1.00 | 50.18 | C |
| ATOM | 230 | OD1 | ASN | A | 30 | 91.443 | 36.831 | 25.828 | 1.00 | 52.17 | O |
| ATOM | 231 | ND2 | ASN | A | 30 | 92.936 | 38.250 | 26.734 | 1.00 | 51.10 | N |
| ATOM | 232 | N | VAL | A | 31 | 87.768 | 40.632 | 25.746 | 1.00 | 38.75 | N |
| ATOM | 233 | CA | VAL | A | 31 | 86.651 | 41.422 | 26.258 | 1.00 | 36.68 | C |
| ATOM | 234 | C | VAL | A | 31 | 85.333 | 40.660 | 26.097 | 1.00 | 35.73 | C |
| ATOM | 235 | O | VAL | A | 31 | 85.033 | 40.127 | 25.034 | 1.00 | 33.64 | O |
| ATOM | 236 | CB | VAL | A | 31 | 86.558 | 42.802 | 25.538 | 1.00 | 36.09 | C |
| ATOM | 237 | CG1 | VAL | A | 31 | 85.357 | 43.593 | 26.053 | 1.00 | 34.31 | C |
| ATOM | 238 | CG2 | VAL | A | 31 | 87.839 | 43.598 | 25.782 | 1.00 | 35.58 | C |
| ATOM | 239 | N | ASN | A | 32 | 84.564 | 40.589 | 27.174 | 1.00 | 35.18 | N |
| ATOM | 240 | CA | ASN | A | 32 | 83.284 | 39.894 | 27.152 | 1.00 | 35.95 | C |
| ATOM | 241 | C | ASN | A | 32 | 82.173 | 40.938 | 27.055 | 1.00 | 35.44 | C |
| ATOM | 242 | O | ASN | A | 32 | 82.050 | 41.802 | 27.918 | 1.00 | 36.50 | O |
| ATOM | 243 | CB | ASN | A | 32 | 83.150 | 39.041 | 28.423 | 1.00 | 36.77 | C |
| ATOM | 244 | CG | ASN | A | 32 | 81.740 | 38.509 | 28.644 | 1.00 | 38.35 | C |
| ATOM | 245 | OD1 | ASN | A | 32 | 80.908 | 38.499 | 27.739 | 1.00 | 37.24 | O |
| ATOM | 246 | ND2 | ASN | A | 32 | 81.475 | 38.050 | 29.863 | 1.00 | 40.73 | N |
| ATOM | 247 | N | LEU | A | 33 | 81.373 | 40.863 | 25.995 | 1.00 | 34.92 | N |
| ATOM | 248 | CA | LEU | A | 33 | 80.291 | 41.822 | 25.799 | 1.00 | 34.68 | C |
| ATOM | 249 | C | LEU | A | 33 | 78.908 | 41.292 | 26.161 | 1.00 | 34.77 | C |
| ATOM | 250 | O | LEU | A | 33 | 77.900 | 41.799 | 25.663 | 1.00 | 35.47 | O |
| ATOM | 251 | CB | LEU | A | 33 | 80.282 | 42.329 | 24.348 | 1.00 | 34.75 | C |
| ATOM | 252 | CG | LEU | A | 33 | 81.474 | 43.173 | 23.894 | 1.00 | 35.98 | C |
| ATOM | 253 | CD1 | LEU | A | 33 | 81.283 | 43.601 | 22.451 | 1.00 | 35.27 | C |
| ATOM | 254 | CD2 | LEU | A | 33 | 81.621 | 44.392 | 24.799 | 1.00 | 35.37 | C |
| ATOM | 255 | N | SER | A | 34 | 78.851 | 40.275 | 27.016 | 1.00 | 33.98 | N |
| ATOM | 256 | CA | SER | A | 34 | 77.566 | 39.724 | 27.449 | 1.00 | 34.88 | C |
| ATOM | 257 | C | SER | A | 34 | 76.841 | 40.762 | 28.301 | 1.00 | 34.25 | C |
| ATOM | 258 | O | SER | A | 34 | 77.472 | 41.554 | 28.998 | 1.00 | 33.82 | O |
| ATOM | 259 | CB | SER | A | 34 | 77.770 | 38.456 | 28.284 | 1.00 | 35.12 | C |
| ATOM | 260 | OG | SER | A | 34 | 78.323 | 37.420 | 27.491 | 1.00 | 42.00 | O |
| ATOM | 261 | N | THR | A | 35 | 75.516 | 40.748 | 28.263 | 1.00 | 32.80 | N |
| ATOM | 262 | CA | THR | A | 35 | 74.754 | 41.708 | 29.034 | 1.00 | 31.26 | C |
| ATOM | 263 | C | THR | A | 35 | 73.342 | 41.170 | 29.282 | 1.00 | 31.11 | C |
| ATOM | 264 | O | THR | A | 35 | 72.798 | 40.424 | 28.466 | 1.00 | 31.76 | O |
| ATOM | 265 | CB | THR | A | 35 | 74.706 | 43.068 | 28.280 | 1.00 | 31.41 | C |
| ATOM | 266 | OG1 | THR | A | 35 | 74.416 | 44.123 | 29.202 | 1.00 | 30.49 | O |
| ATOM | 267 | CG2 | THR | A | 35 | 73.644 | 43.043 | 27.184 | 1.00 | 30.33 | C |
| ATOM | 268 | N | PRO | A | 36 | 72.736 | 41.530 | 30.422 | 1.00 | 29.74 | N |
| ATOM | 269 | CA | PRO | A | 36 | 71.385 | 41.070 | 30.758 | 1.00 | 30.21 | C |
| ATOM | 270 | C | PRO | A | 36 | 70.264 | 41.741 | 29.958 | 1.00 | 31.22 | C |
| ATOM | 271 | O | PRO | A | 36 | 70.291 | 42.953 | 29.713 | 1.00 | 31.11 | O |

TABLE 6-continued

| ATOM | 272 | CB  | PRO | A | 36 | 71.284 | 41.366 | 32.253 | 1.00 | 30.05 | C |
| ATOM | 273 | CG  | PRO | A | 36 | 72.114 | 42.613 | 32.397 | 1.00 | 27.96 | C |
| ATOM | 274 | CD  | PRO | A | 36 | 73.322 | 42.310 | 31.529 | 1.00 | 28.83 | C |
| ATOM | 275 | N   | LEU | A | 37 | 69.276 | 40.943 | 29.566 | 1.00 | 30.99 | N |
| ATOM | 276 | CA  | LEU | A | 37 | 68.142 | 41.438 | 28.805 | 1.00 | 31.62 | C |
| ATOM | 277 | C   | LEU | A | 37 | 66.910 | 41.656 | 29.683 | 1.00 | 32.81 | C |
| ATOM | 278 | O   | LEU | A | 37 | 66.165 | 42.618 | 29.485 | 1.00 | 34.25 | O |
| ATOM | 279 | CB  | LEU | A | 37 | 67.788 | 40.459 | 27.681 | 1.00 | 31.89 | C |
| ATOM | 280 | CG  | LEU | A | 37 | 66.642 | 40.913 | 26.764 | 1.00 | 32.36 | C |
| ATOM | 281 | CD1 | LEU | A | 37 | 67.124 | 42.073 | 25.888 | 1.00 | 31.95 | C |
| ATOM | 282 | CD2 | LEU | A | 37 | 66.175 | 39.757 | 25.892 | 1.00 | 31.83 | C |
| ATOM | 283 | N   | VAL | A | 38 | 66.691 | 40.774 | 30.655 | 1.00 | 32.12 | N |
| ATOM | 284 | CA  | VAL | A | 38 | 65.521 | 40.901 | 31.517 | 1.00 | 31.54 | C |
| ATOM | 285 | C   | VAL | A | 38 | 65.869 | 40.922 | 33.004 | 1.00 | 32.49 | C |
| ATOM | 286 | O   | VAL | A | 38 | 66.867 | 40.344 | 33.427 | 1.00 | 33.79 | O |
| ATOM | 287 | CE  | VAL | A | 38 | 64.486 | 39.772 | 31.219 | 1.00 | 31.66 | C |
| ATOM | 288 | CG1 | VAL | A | 38 | 64.026 | 39.872 | 29.765 | 1.00 | 28.94 | C |
| ATOM | 289 | CG2 | VAL | A | 38 | 65.093 | 38.398 | 31.482 | 1.00 | 29.49 | C |
| ATOM | 290 | N   | LYE | A | 39 | 65.025 | 41.584 | 33.789 | 1.00 | 31.86 | N |
| ATOM | 291 | CA  | LYS | A | 39 | 65.246 | 41.742 | 35.219 | 1.00 | 33.55 | C |
| ATOM | 292 | C   | LYE | A | 39 | 65.423 | 40.464 | 36.025 | 1.00 | 34.23 | C |
| ATOM | 293 | O   | LYE | A | 39 | 64.893 | 39.415 | 35.678 | 1.00 | 34.30 | O |
| ATOM | 294 | CB  | LYS | A | 39 | 64.112 | 42.560 | 35.842 | 1.00 | 34.12 | C |
| ATOM | 295 | CG  | LYS | A | 39 | 62.743 | 41.886 | 35.791 | 1.00 | 34.26 | C |
| ATOM | 296 | CD  | LYS | A | 39 | 61.727 | 42.681 | 36.588 | 1.00 | 34.93 | C |
| ATOM | 297 | CE  | LYS | A | 39 | 60.368 | 41.981 | 36.614 | 1.00 | 35.16 | C |
| ATOM | 298 | NZ  | LYS | A | 39 | 59.412 | 42.684 | 37.515 | 1.00 | 34.58 | N |
| ATOM | 299 | N   | PHE | A | 40 | 66.175 | 40.592 | 37.114 | 1.00 | 34.89 | N |
| ATOM | 300 | CA  | PHE | A | 40 | 66.454 | 39.499 | 38.032 | 1.00 | 36.02 | C |
| ATOM | 301 | C   | PHE | A | 40 | 66.698 | 40.089 | 39.416 | 1.00 | 37.46 | C |
| ATOM | 302 | O   | PHE | A | 40 | 66.849 | 41.303 | 39.562 | 1.00 | 38.06 | O |
| ATOM | 303 | CB  | PHE | A | 40 | 67.687 | 38.699 | 37.582 | 1.00 | 34.23 | C |
| ATOM | 304 | CG  | PHE | A | 40 | 68.926 | 39.535 | 37.376 | 1.00 | 33.77 | C |
| ATOM | 305 | CD1 | PHE | A | 40 | 69.178 | 40.142 | 36.145 | 1.00 | 32.47 | C |
| ATOM | 306 | CD2 | PHE | A | 40 | 69.844 | 39.704 | 38.405 | 1.00 | 31.36 | C |
| ATOM | 307 | CE1 | PHE | A | 40 | 70.326 | 40.899 | 35.945 | 1.00 | 31.93 | C |
| ATOM | 308 | CE2 | PHE | A | 40 | 70.998 | 40.460 | 38.218 | 1.00 | 31.43 | C |
| ATOM | 309 | CZ  | PHE | A | 40 | 71.241 | 41.060 | 36.984 | 1.00 | 31.40 | C |
| ATOM | 310 | N   | GLN | A | 41 | 66.728 | 39.227 | 40.427 | 1.00 | 38.80 | N |
| ATOM | 311 | CA  | GLN | A | 41 | 66.954 | 39.653 | 41.800 | 1.00 | 40.40 | C |
| ATOM | 312 | C   | GLN | A | 41 | 68.439 | 39.656 | 42.110 | 1.00 | 39.88 | C |
| ATOM | 313 | O   | GLN | A | 41 | 69.238 | 39.044 | 41.402 | 1.00 | 39.75 | O |
| ATOM | 314 | CB  | GLN | A | 41 | 66.256 | 38.705 | 42.790 | 1.00 | 44.12 | C |
| ATOM | 315 | CG  | GLN | A | 41 | 64.735 | 38.752 | 42.795 | 1.00 | 49.04 | C |
| ATOM | 316 | CD  | GLN | A | 41 | 64.188 | 40.059 | 43.352 | 1.00 | 51.98 | C |
| ATOM | 317 | OE1 | GLN | A | 41 | 64.464 | 40.433 | 44.501 | 1.00 | 54.77 | O |
| ATOM | 318 | NE2 | GLN | A | 41 | 63.406 | 40.761 | 42.541 | 1.00 | 52.25 | N |
| ATOM | 319 | N   | LYS | A | 42 | 68.798 | 40.353 | 43.179 | 1.00 | 39.91 | N |
| ATOM | 320 | CA  | LYS | A | 42 | 70.178 | 40.423 | 43.627 | 1.00 | 41.35 | C |
| ATOM | 321 | C   | LYS | A | 42 | 70.701 | 38.997 | 43.872 | 1.00 | 41.68 | C |
| ATOM | 322 | O   | LYE | A | 42 | 69.993 | 38.157 | 44.428 | 1.00 | 40.20 | O |
| ATOM | 323 | CE  | LYS | A | 42 | 70.236 | 41.226 | 44.921 | 1.00 | 42.49 | C |
| ATOM | 324 | CG  | LYS | A | 42 | 71.606 | 41.323 | 45.551 | 1.00 | 45.67 | C |
| ATOM | 325 | CD  | LYE | A | 42 | 71.501 | 42.014 | 46.902 | 1.00 | 47.42 | C |
| ATOM | 326 | CE  | LYS | A | 42 | 72.844 | 42.067 | 47.605 | 1.00 | 48.87 | C |
| ATOM | 327 | NZ  | LYS | A | 42 | 72.721 | 42.779 | 48.906 | 1.00 | 52.09 | N |
| ATOM | 328 | N   | GLY | A | 43 | 71.929 | 38.728 | 43.442 | 1.00 | 41.55 | N |
| ATOM | 329 | CA  | GLY | A | 43 | 72.511 | 37.412 | 43.644 | 1.00 | 40.73 | C |
| ATOM | 330 | C   | GLY | A | 43 | 72.226 | 36.425 | 42.532 | 1.00 | 40.52 | C |
| ATOM | 331 | O   | GLY | A | 43 | 72.807 | 35.341 | 42.496 | 1.00 | 40.95 | O |
| ATOM | 332 | N   | GLN | A | 44 | 71.330 | 36.788 | 41.625 | 1.00 | 40.46 | N |
| ATOM | 333 | CA  | GLN | A | 44 | 70.992 | 35.912 | 40.511 | 1.00 | 41.27 | C |
| ATOM | 334 | C   | GLN | A | 44 | 71.591 | 36.440 | 39.211 | 1.00 | 41.60 | C |
| ATOM | 335 | O   | GLN | A | 44 | 72.292 | 37.450 | 39.196 | 1.00 | 40.78 | O |
| ATOM | 336 | CE  | GLN | A | 44 | 69.471 | 35.822 | 40.342 | 1.00 | 42.42 | C |
| ATOM | 337 | CG  | GLN | A | 44 | 68.688 | 35.691 | 41.637 | 1.00 | 45.60 | C |
| ATOM | 338 | CD  | GLN | A | 44 | 67.186 | 35.582 | 41.402 | 1.00 | 47.33 | C |
| ATOM | 339 | OE1 | GLN | A | 44 | 66.621 | 36.293 | 40.565 | 1.00 | 48.58 | O |
| ATOM | 340 | NE2 | GLN | A | 44 | 66.533 | 34.703 | 42.149 | 1.00 | 46.68 | N |
| ATOM | 341 | N   | GLN | A | 45 | 71.308 | 35.726 | 38.127 | 1.00 | 42.62 | N |
| ATOM | 342 | CA  | GLN | A | 45 | 71.741 | 36.089 | 36.784 | 1.00 | 43.67 | C |
| ATOM | 343 | C   | GLN | A | 45 | 70.443 | 36.216 | 35.999 | 1.00 | 41.83 | C |
| ATOM | 344 | O   | GLN | A | 45 | 69.439 | 35.611 | 36.367 | 1.00 | 40.98 | O |
| ATOM | 345 | CB  | GLN | A | 45 | 72.593 | 34.981 | 36.153 | 1.00 | 46.80 | C |
| ATOM | 346 | CG  | GLN | A | 45 | 73.929 | 34.741 | 36.833 | 1.00 | 52.13 | C |
| ATOM | 347 | CD  | GLN | A | 45 | 74.909 | 35.872 | 36.601 | 1.00 | 54.67 | C |
| ATOM | 348 | OE1 | GLN | A | 45 | 75.420 | 36.047 | 35.489 | 1.00 | 57.71 | O |
| ATOM | 349 | NE2 | GLN | A | 45 | 75.175 | 36.653 | 37.647 | 1.00 | 54.39 | N |
| ATOM | 350 | N   | SER | A | 46 | 70.458 | 36.999 | 34.928 | 1.00 | 39.93 | N |

TABLE 6-continued

| | | | | | | | | | | |
|---|---|---|---|---|---|---|---|---|---|---|
| ATOM | 351 | CA | SER | A | 46 | 69.268 | 37.162 | 34.110 | 1.00 | 38.73 | C |
| ATOM | 352 | C | SER | A | 46 | 69.005 | 35.868 | 33.347 | 1.00 | 39.01 | C |
| ATOM | 353 | O | SER | A | 46 | 69.942 | 35.211 | 32.906 | 1.00 | 39.13 | O |
| ATOM | 354 | CB | SER | A | 46 | 69.464 | 38.304 | 33.113 | 1.00 | 36.60 | C |
| ATOM | 355 | OG | SER | A | 46 | 68.330 | 38.437 | 32.280 | 1.00 | 35.88 | O |
| ATOM | 356 | N | GLU | A | 47 | 67.733 | 35.511 | 33.190 | 1.00 | 39.22 | N |
| ATOM | 357 | CA | GLU | A | 47 | 67.363 | 34.297 | 32.463 | 1.00 | 39.59 | C |
| ATOM | 358 | C | GLU | A | 47 | 67.762 | 34.400 | 31.000 | 1.00 | 38.86 | C |
| ATOM | 359 | O | GLU | A | 47 | 67.904 | 33.385 | 30.316 | 1.00 | 38.01 | O |
| ATOM | 360 | CB | GLU | A | 47 | 65.857 | 34.057 | 32.563 | 1.00 | 41.44 | C |
| ATOM | 361 | CG | GLU | A | 47 | 65.365 | 33.806 | 33.978 | 1.00 | 44.53 | C |
| ATOM | 362 | CD | GLU | A | 47 | 63.853 | 33.843 | 34.073 | 1.00 | 47.63 | C |
| ATOM | 363 | OE1 | GLU | A | 47 | 63.197 | 32.987 | 33.436 | 1.00 | 49.95 | O |
| ATOM | 364 | OE2 | GLU | A | 47 | 63.321 | 34.732 | 34.777 | 1.00 | 49.50 | O |
| ATOM | 365 | N | ILE | A | 48 | 67.920 | 35.631 | 30.514 | 1.00 | 37.02 | N |
| ATOM | 366 | CA | ILE | A | 48 | 68.318 | 35.856 | 29.126 | 1.00 | 35.30 | C |
| ATOM | 367 | C | ILE | A | 48 | 69.474 | 36.854 | 29.055 | 1.00 | 34.82 | C |
| ATOM | 368 | O | ILE | A | 48 | 69.372 | 37.982 | 29.538 | 1.00 | 34.21 | O |
| ATOM | 369 | CB | ILE | A | 48 | 67.144 | 36.400 | 28.273 | 1.00 | 35.95 | C |
| ATOM | 370 | CG1 | ILE | A | 48 | 65.958 | 35.434 | 28.328 | 1.00 | 37.12 | C |
| ATOM | 371 | CG2 | ILE | A | 48 | 67.595 | 36.583 | 26.836 | 1.00 | 34.56 | C |
| ATOM | 372 | CD1 | ILE | A | 48 | 64.768 | 35.879 | 27.509 | 1.00 | 37.86 | C |
| ATOM | 373 | N | ASN | A | 49 | 70.579 | 36.426 | 28.462 | 1.00 | 34.10 | N |
| ATOM | 374 | CA | ASN | A | 49 | 71.739 | 37.285 | 28.323 | 1.00 | 34.92 | C |
| ATOM | 375 | C | ASN | A | 49 | 72.160 | 37.365 | 26.866 | 1.00 | 35.76 | C |
| ATOM | 376 | O | ASN | A | 49 | 72.383 | 36.341 | 26.218 | 1.00 | 36.32 | O |
| ATOM | 377 | CB | ASN | A | 49 | 72.903 | 36.752 | 29.169 | 1.00 | 35.35 | C |
| ATOM | 378 | CG | ASN | A | 49 | 72.634 | 36.856 | 30.660 | 1.00 | 37.43 | C |
| ATOM | 379 | OD1 | ASN | A | 49 | 72.802 | 37.917 | 31.263 | 1.00 | 34.90 | O |
| ATOM | 380 | ND2 | ASN | A | 49 | 72.193 | 35.755 | 31.258 | 1.00 | 36.59 | N |
| ATOM | 381 | N | LEU | A | 50 | 72.242 | 38.582 | 26.342 | 1.00 | 34.27 | N |
| ATOM | 382 | CA | LEU | A | 50 | 72.682 | 38.770 | 24.965 | 1.00 | 33.47 | C |
| ATOM | 383 | C | LEU | A | 50 | 74.184 | 38.504 | 24.991 | 1.00 | 33.03 | C |
| ATOM | 384 | O | LEU | A | 50 | 74.809 | 38.633 | 26.040 | 1.00 | 31.70 | O |
| ATOM | 385 | CE | LEU | A | 50 | 72.444 | 40.213 | 24.522 | 1.00 | 33.25 | C |
| ATOM | 386 | CG | LEU | A | 50 | 71.041 | 40.784 | 24.715 | 1.00 | 33.75 | C |
| ATOM | 387 | CD1 | LEU | A | 50 | 71.050 | 42.270 | 24.362 | 1.00 | 33.97 | C |
| ATOM | 388 | CD2 | LEU | A | 50 | 70.054 | 40.019 | 23.846 | 1.00 | 35.15 | C |
| ATOM | 389 | N | LYS | A | 51 | 74.766 | 38.132 | 23.855 | 1.00 | 33.34 | N |
| ATOM | 390 | CA | LYS | A | 51 | 76.208 | 37.902 | 23.815 | 1.00 | 33.66 | C |
| ATOM | 391 | C | LYS | A | 51 | 76.902 | 39.177 | 23.335 | 1.00 | 32.95 | C |
| ATOM | 392 | O | LYS | A | 51 | 78.109 | 39.359 | 23.532 | 1.00 | 32.77 | O |
| ATOM | 393 | CE | LYS | A | 51 | 76.531 | 36.680 | 22.946 | 1.00 | 34.82 | C |
| ATOM | 394 | CG | LYS | A | 51 | 75.984 | 35.408 | 23.593 | 1.00 | 37.49 | C |
| ATOM | 395 | CD | LYE | A | 51 | 76.413 | 34.136 | 22.897 | 1.00 | 39.84 | C |
| ATOM | 396 | CE | LYS | A | 51 | 75.893 | 32.920 | 23.663 | 1.00 | 40.88 | C |
| ATOM | 397 | NZ | LYE | A | 51 | 76.295 | 31.643 | 22.997 | 1.00 | 43.33 | N |
| ATOM | 398 | N | ILE | A | 52 | 76.119 | 40.054 | 22.708 | 1.00 | 31.66 | N |
| ATOM | 399 | CA | ILE | A | 52 | 76.585 | 41.370 | 22.274 | 1.00 | 31.00 | C |
| ATOM | 400 | C | ILE | A | 52 | 75.425 | 42.297 | 22.651 | 1.00 | 31.49 | C |
| ATOM | 401 | O | ILE | A | 52 | 74.257 | 41.937 | 22.498 | 1.00 | 31.89 | O |
| ATOM | 402 | CB | ILE | A | 52 | 76.912 | 41.454 | 20.750 | 1.00 | 31.40 | C |
| ATOM | 403 | CG1 | ILE | A | 52 | 75.685 | 41.121 | 19.892 | 1.00 | 31.59 | C |
| ATOM | 404 | CG2 | ILE | A | 52 | 78.089 | 40.538 | 20.432 | 1.00 | 31.15 | C |
| ATOM | 405 | CD1 | ILE | A | 52 | 75.900 | 41.415 | 18.400 | 1.00 | 29.50 | C |
| ATOM | 406 | N | PRO | A | 53 | 75.733 | 43.499 | 23.1.54 | 1.00 | 31.49 | N |
| ATOM | 407 | CA | PRO | A | 53 | 74.731 | 44.482 | 23.579 | 1.00 | 31.87 | C |
| ATOM | 408 | C | PRO | A | 53 | 73.958 | 45.252 | 22.506 | 1.00 | 32.48 | C |
| ATOM | 409 | O | PRO | A | 53 | 73.645 | 46.428 | 22.698 | 1.00 | 33.45 | O |
| ATOM | 410 | CB | PRO | A | 53 | 75.544 | 45.412 | 24.468 | 1.00 | 31.07 | C |
| ATOM | 411 | CG | PRO | A | 53 | 76.853 | 45.479 | 23.713 | 1.00 | 31.12 | C |
| ATOM | 412 | CD | PRO | A | 53 | 77.101 | 44.034 | 23.325 | 1.00 | 30.40 | C |
| ATOM | 413 | N | LEU | A | 54 | 73.630 | 44.602 | 21.395 | 1.00 | 31.62 | N |
| ATOM | 414 | CA | LEU | A | 54 | 72.901 | 45.279 | 20.331 | 1.00 | 30.89 | C |
| ATOM | 415 | C | LEU | A | 54 | 71.582 | 44.592 | 19.986 | 1.00 | 31.85 | C |
| ATOM | 416 | O | LEU | A | 54 | 71.524 | 43.365 | 19.872 | 1.00 | 32.82 | O |
| ATOM | 417 | CB | LEU | A | 54 | 73.767 | 45.347 | 19.069 | 1.00 | 29.66 | C |
| ATOM | 418 | CG | LEU | A | 54 | 75.192 | 45.900 | 19.182 | 1.00 | 30.68 | C |
| ATOM | 419 | CD1 | LEU | A | 54 | 75.876 | 45.810 | 17.824 | 1.00 | 29.65 | C |
| ATOM | 420 | CD2 | LEU | A | 54 | 75.162 | 47.347 | 19.678 | 1.00 | 30.19 | C |
| ATOM | 421 | N | VAL | A | 55 | 70.519 | 45.377 | 19.840 | 1.00 | 31.15 | N |
| ATOM | 422 | CA | VAL | A | 55 | 69.230 | 44.830 | 19.441 | 1.00 | 30.86 | C |
| ATOM | 423 | C | VAL | A | 55 | 68.692 | 45.737 | 18.333 | 1.00 | 32.57 | C |
| ATOM | 424 | O | VAL | A | 55 | 68.876 | 46.956 | 18.385 | 1.00 | 33.70 | O |
| ATOM | 425 | CB | VAL | A | 55 | 68.214 | 44.757 | 20.618 | 1.00 | 29.59 | C |
| ATOM | 426 | CG1 | VAL | A | 55 | 68.833 | 44.009 | 21.786 | 1.00 | 28.25 | C |
| ATOM | 427 | CG2 | VAL | A | 55 | 67.750 | 46.146 | 21.025 | 1.00 | 29.12 | C |
| ATOM | 428 | N | SER | A | 56 | 68.058 | 45.144 | 17.322 | 1.00 | 32.00 | N |
| ATOM | 429 | CA | SER | A | 56 | 67.511 | 45.914 | 16.207 | 1.00 | 31.93 | C |

TABLE 6-continued

| | | | | | | | | | | |
|---|---|---|---|---|---|---|---|---|---|---|
| ATOM | 430 | C | SER | A | 56 | 66.134 | 46.469 | 16.556 | 1.00 | 31.63 C |
| ATOM | 431 | O | SER | A | 56 | 65.324 | 45.812 | 17.214 | 1.00 | 31.90 O |
| ATOM | 432 | CB | SER | A | 56 | 67.459 | 45.056 | 14.929 | 1.00 | 31.63 C |
| ATOM | 433 | OG | SER | A | 56 | 66.668 | 43.895 | 15.102 | 1.00 | 31.84 O |
| ATOM | 434 | N | ALA | A | 57 | 65.891 | 47.697 | 16.115 | 1.00 | 31.38 N |
| ATOM | 435 | CA | ALA | A | 57 | 64.654 | 48.419 | 16.395 | 1.00 | 31.55 C |
| ATOM | 436 | C | ALA | A | 57 | 63.361 | 47.756 | 15.907 | 1.00 | 32.70 C |
| ATOM | 437 | O | ALA | A | 57 | 63.351 | 47.012 | 14.922 | 1.00 | 33.02 O |
| ATOM | 438 | CB | ALA | A | 57 | 64.764 | 49.833 | 15.836 | 1.00 | 29.58 C |
| ATOM | 439 | N | ILE | A | 58 | 62.277 | 48.047 | 16.620 | 1.00 | 32.44 N |
| ATOM | 440 | CA | ILE | A | 58 | 60.950 | 47.511 | 16.328 | 1.00 | 33.86 C |
| ATOM | 441 | C | ILE | A | 58 | 60.380 | 48.325 | 15.173 | 1.00 | 34.14 C |
| ATOM | 442 | O | ILE | A | 58 | 59.463 | 49.129 | 15.359 | 1.00 | 34.72 O |
| ATOM | 443 | CB | ILE | A | 58 | 60.032 | 47.654 | 17.578 | 1.00 | 32.65 C |
| ATOM | 444 | CG1 | ILE | A | 58 | 60.827 | 47.277 | 18.835 | 1.00 | 33.43 C |
| ATOM | 445 | CG2 | ILE | A | 58 | 58.800 | 46.759 | 17.444 | 1.00 | 30.11 C |
| ATOM | 446 | CD1 | ILE | A | 58 | 60.068 | 47.428 | 20.135 | 1.00 | 31.89 C |
| ATOM | 447 | N | MET | A | 59 | 60.931 | 48.111 | 13.982 | 1.00 | 34.79 N |
| ATOM | 448 | CA | MET | A | 59 | 60.523 | 48.870 | 12.803 | 1.00 | 35.21 C |
| ATOM | 449 | C | MET | A | 59 | 60.363 | 48.024 | 11.545 | 1.00 | 36.00 C |
| ATOM | 450 | O | MET | A | 59 | 61.151 | 47.107 | 11.287 | 1.00 | 34.61 O |
| ATOM | 451 | CB | MET | A | 59 | 61.554 | 49.971 | 12.525 | 1.00 | 35.03 C |
| ATOM | 452 | CG | MET | A | 59 | 61.851 | 50.887 | 13.706 | 1.00 | 34.37 C |
| ATOM | 453 | SD | MET | A | 59 | 63.181 | 52.051 | 13.323 | 1.00 | 35.17 S |
| ATOM | 454 | CE | MET | A | 59 | 62.401 | 53.057 | 12.081 | 1.00 | 35.07 C |
| ATOM | 455 | N | GLN | A | 60 | 59.353 | 48.366 | 10.748 | 1.00 | 37.49 N |
| ATOM | 456 | CA | GLN | A | 60 | 59.063 | 47.649 | 9.509 | 1.00 | 39.05 C |
| ATOM | 457 | C | GLN | A | 60 | 60.275 | 47.600 | 8.594 | 1.00 | 38.95 C |
| ATOM | 458 | O | GLN | A | 60 | 60.506 | 46.603 | 7.915 | 1.00 | 39.70 O |
| ATOM | 459 | CB | GLN | A | 60 | 57.927 | 48.329 | 8.738 | 1.00 | 39.93 C |
| ATOM | 460 | CG | GLN | A | 60 | 56.671 | 48.629 | 9.532 | 1.00 | 41.07 C |
| ATOM | 461 | CD | GLN | A | 60 | 55.609 | 49.290 | 8.665 | 1.00 | 42.66 C |
| ATOM | 462 | OE1 | GLN | A | 60 | 55.930 | 50.010 | 7.717 | 1.00 | 42.94 O |
| ATOM | 463 | NE2 | GLN | A | 60 | 54.342 | 49.058 | 8.992 | 1.00 | 42.62 N |
| ATOM | 464 | N | SER | A | 61 | 61.046 | 48.683 | 8.578 | 1.00 | 39.09 N |
| ATOM | 465 | CA | SER | A | 61 | 62.215 | 48.770 | 7.705 | 1.00 | 38.98 C |
| ATOM | 466 | C | SER | A | 61 | 63.506 | 48.217 | 8.296 | 1.00 | 38.63 C |
| ATOM | 467 | O | SER | A | 61 | 64.577 | 48.352 | 7.694 | 1.00 | 38.93 O |
| ATOM | 468 | CB | SER | A | 61 | 62.436 | 50.228 | 7.280 | 1.00 | 39.27 C |
| ATOM | 469 | OG | SER | A | 61 | 62.568 | 51.078 | 8.409 | 1.00 | 42.11 O |
| ATOM | 470 | N | VAL | A | 62 | 63.407 | 47.578 | 9.457 | 1.00 | 37.45 N |
| ATOM | 471 | CA | VAL | A | 62 | 64.593 | 47.048 | 10.112 | 1.00 | 36.30 C |
| ATOM | 472 | C | VAL | A | 62 | 64.535 | 45.590 | 10.53.6 | 1.00 | 37.04 C |
| ATOM | 473 | O | VAL | A | 62 | 65.304 | 44.765 | 10.050 | 1.00 | 38.38 O |
| ATOM | 474 | CB | VAL | A | 62 | 64.939 | 47.869 | 11.382 | 1.00 | 36.10 C |
| ATOM | 475 | CG1 | VAL | A | 62 | 66.168 | 47.274 | 12.069 | 1.00 | 34.59 C |
| ATOM | 476 | CG2 | VAL | A | 62 | 65.175 | 49.330 | 11.016 | 1.00 | 35.17 C |
| ATOM | 477 | N | SER | A | 63 | 63.621 | 45.275 | 11.444 | 1.00 | 37.88 N |
| ATOM | 478 | CA | SER | A | 63 | 63.540 | 43.929 | 11.982 | 1.00 | 38.55 C |
| ATOM | 479 | C | SER | A | 63 | 62.557 | 42.938 | 11.368 | 1.00 | 39.50 C |
| ATOM | 480 | O | SER | A | 63 | 61.454 | 42.727 | 11.879 | 1.00 | 37.63 O |
| ATOM | 481 | CB | SER | A | 63 | 63.319 | 44.013 | 13.495 | 1.00 | 38.61 C |
| ATOM | 482 | OG | SER | A | 63 | 64.401 | 44.694 | 14.120 | 1.00 | 36.71 O |
| ATOM | 483 | N | GLY | A | 64 | 62.991 | 42.329 | 10.268 | 1.00 | 39.83 N |
| ATOM | 484 | CA | GLY | A | 64 | 62.201 | 41.317 | 9.597 | 1.00 | 41.35 C |
| ATOM | 485 | C | GLY | A | 64 | 62.814 | 39.992 | 10.023 | 1.00 | 43.17 C |
| ATOM | 486 | O | GLY | A | 64 | 63.710 | 39.973 | 10.874 | 1.00 | 39.88 O |
| ATOM | 487 | N | GLU | A | 65 | 62.373 | 38.884 | 9.432 | 1.00 | 44.98 N |
| ATOM | 488 | CA | GLU | A | 65 | 62.913 | 37.593 | 9.832 | 1.00 | 47.09 C |
| ATOM | 489 | C | GLU | A | 65 | 64.384 | 37.401 | 9.484 | 1.00 | 45.97 C |
| ATOM | 490 | O | GLU | A | 65 | 65.129 | 36.825 | 10.274 | 1.00 | 45.63 O |
| ATOM | 491 | CB | GLU | A | 65 | 62.069 | 36.447 | 9.259 | 1.00 | 50.39 C |
| ATOM | 492 | CG | GLU | A | 65 | 62.087 | 36.305 | 7.758 | 1.00 | 56.03 C |
| ATOM | 493 | CD | GLU | A | 65 | 61.206 | 35.158 | 7.297 | 1.00 | 60.65 C |
| ATOM | 494 | OE1 | GLU | A | 65 | 59.968 | 35.256 | 7.478 | 1.00 | 62.24 O |
| ATOM | 495 | OE2 | GLU | A | 65 | 61.752 | 34.158 | 6.768 | 1.00 | 61.62 O |
| ATOM | 496 | N | LYS | A | 66 | 64.814 | 37.885 | 8.322 | 1.00 | 45.39 N |
| ATOM | 497 | CA | LYS | A | 66 | 66.216 | 37.740 | 7.941 | 1.00 | 45.57 C |
| ATOM | 498 | C | LYS | A | 66 | 67.118 | 38.490 | 8.917 | 1.00 | 43.76 C |
| ATOM | 499 | O | LYS | A | 66 | 68.197 | 38.014 | 9.275 | 1.00 | 43.26 O |
| ATOM | 500 | CB | LYS | A | 66 | 66.452 | 38.255 | 6.518 | 1.00 | 48.10 C |
| ATOM | 501 | CG | LYS | A | 66 | 66.051 | 37.272 | 5.426 | 1.00 | 53.08 C |
| ATOM | 502 | CD | LYS | A | 66 | 66.353 | 37.827 | 4.032 | 1.00 | 56.63 C |
| ATOM | 503 | CE | LYS | A | 66 | 65.933 | 36.847 | 2.937 | 1.00 | 58.88 C |
| ATOM | 504 | NZ | LYS | A | 66 | 66.138 | 37.403 | 1.561 | 1.00 | 59.62 N |
| ATOM | 505 | N | MET | A | 67 | 66.671 | 39.665 | 9.347 | 1.00 | 41.61 N |
| ATOM | 506 | CA | MET | A | 67 | 67.440 | 40.468 | 10.290 | 1.00 | 40.17 C |
| ATOM | 507 | C | MET | A | 67 | 67.552 | 39.730 | 11.625 | 1.00 | 39.71 C |
| ATOM | 508 | O | MET | A | 67 | 68.638 | 39.619 | 12.199 | 1.00 | 38.59 O |

TABLE 6-continued

| | | | | | | | | | | | |
|---|---|---|---|---|---|---|---|---|---|---|---|
| ATOM | 509 | CB | MET | A | 67 | 66.761 | 41.822 | 10.507 | 1.00 | 39.65 | C |
| ATOM | 510 | CG | MET | A | 67 | 67.451 | 42.722 | 11.525 | 1.00 | 38.90 | C |
| ATOM | 511 | SD | MET | A | 67 | 69.110 | 43.219 | 11.014 | 1.00 | 38.59 | S |
| ATOM | 512 | CE | MET | A | 67 | 68.730 | 44.370 | 9.680 | 1.00 | 37.11 | C |
| ATOM | 513 | N | ALA | A | 68 | 66.422 | 39.217 | 12.102 | 1.00 | 38.12 | N |
| ATOM | 514 | CA | ALA | A | 68 | 66.370 | 38.505 | 13.371 | 1.00 | 38.12 | C |
| ATOM | 515 | C | ALA | A | 68 | 67.314 | 37.306 | 13.407 | 1.00 | 38.48 | C |
| ATOM | 516 | O | ALA | A | 68 | 67.919 | 37.009 | 14.437 | 1.00 | 38.33 | O |
| ATOM | 517 | CB | ALA | A | 68 | 64.947 | 38.064 | 13.652 | 1.00 | 37.40 | C |
| ATOM | 518 | N | ILE | A | 69 | 67.435 | 36.622 | 12.275 | 1.00 | 38.50 | N |
| ATOM | 519 | CA | ILE | A | 69 | 68.308 | 35.461 | 12.163 | 1.00 | 38.32 | C |
| ATOM | 520 | C | ILE | A | 69 | 69.774 | 35.896 | 12.129 | 1.00 | 37.75 | C |
| ATOM | 521 | O | ILE | A | 69 | 70.601 | 35.383 | 12.883 | 1.00 | 38.40 | O |
| ATOM | 522 | CB | ILE | A | 69 | 67.981 | 34.656 | 10.874 | 1.00 | 40.02 | C |
| ATOM | 523 | CG1 | ILE | A | 69 | 66.603 | 33.998 | 11.006 | 1.00 | 40.60 | C |
| ATOM | 524 | CG2 | ILE | A | 69 | 69.042 | 33.599 | 10.625 | 1.00 | 38.98 | C |
| ATOM | 525 | CD1 | ILE | A | 69 | 66.013 | 33.545 | 9.678 | 1.00 | 41.31 | C |
| ATOM | 526 | N | ALA | A | 70 | 70.084 | 36.847 | 11.254 | 1.00 | 37.08 | N |
| ATOM | 527 | CA | ALA | A | 70 | 71.442 | 37.348 | 11.109 | 1.00 | 36.18 | C |
| ATOM | 528 | C | ALA | A | 70 | 72.000 | 37.959 | 12.392 | 1.00 | 36.22 | C |
| ATOM | 529 | O | ALA | A | 70 | 73.182 | 37.796 | 12.695 | 1.00 | 36.51 | O |
| ATOM | 530 | CB | ALA | A | 70 | 71.499 | 38.366 | 9.987 | 1.00 | 36.62 | C |
| ATOM | 531 | N | LEU | A | 71 | 71.155 | 38.661 | 13.142 | 1.00 | 35.64 | N |
| ATOM | 532 | CA | LEU | A | 71 | 71.593 | 39.293 | 14.381 | 1.00 | 35.41 | C |
| ATOM | 533 | C | LEU | A | 71 | 71.752 | 38.281 | 15.511 | 1.00 | 35.81 | C |
| ATOM | 534 | O | LEU | A | 71 | 72.707 | 38.353 | 16.282 | 1.00 | 34.47 | O |
| ATOM | 535 | CB | LEU | A | 71 | 70.617 | 40.400 | 14.792 | 1.00 | 33.24 | C |
| ATOM | 536 | CG | LEU | A | 71 | 70.921 | 41.215 | 16.061 | 1.00 | 33.66 | C |
| ATOM | 537 | CD1 | LEU | A | 71 | 72.391 | 41.629 | 16.110 | 1.00 | 31.27 | C |
| ATOM | 538 | CD2 | LEU | A | 71 | 70.021 | 42.451 | 16.083 | 1.00 | 31.14 | C |
| ATOM | 539 | N | ALA | A | 72 | 70.822 | 37.337 | 15.608 | 1.00 | 37.05 | N |
| ATOM | 540 | CA | ALA | A | 72 | 70.906 | 36.317 | 16.648 | 1.00 | 38.69 | C |
| ATOM | 541 | C | ALA | A | 72 | 72.166 | 35.476 | 16.445 | 1.00 | 40.01 | C |
| ATOM | 542 | O | ALA | A | 72 | 72.756 | 34.988 | 17.411 | 1.00 | 39.86 | O |
| ATOM | 543 | CB | ALA | A | 72 | 69.665 | 35.422 | 16.620 | 1.00 | 37.80 | C |
| ATOM | 544 | N | ARG | A | 73 | 72.570 | 35.304 | 15.188 | 1.00 | 40.95 | N |
| ATOM | 545 | CA | ARG | A | 73 | 73.761 | 34.525 | 14.874 | 1.00 | 43.10 | C |
| ATOM | 546 | C | ARG | A | 73 | 75.004 | 35.169 | 15.464 | 1.00 | 43.29 | C |
| ATOM | 547 | O | ARG | A | 73 | 75.963 | 34.477 | 15.807 | 1.00 | 42.95 | O |
| ATOM | 548 | CB | ARG | A | 73 | 73.940 | 34.384 | 13.359 | 1.00 | 45.58 | C |
| ATOM | 549 | CG | ARG | A | 73 | 73.014 | 33.367 | 12.707 | 1.00 | 49.18 | C |
| ATOM | 550 | CD | ARG | A | 73 | 73.285 | 33.246 | 11.210 | 1.00 | 52.08 | C |
| ATOM | 551 | NE | ARG | A | 73 | 72.430 | 32.238 | 10.591 | 1.00 | 55.80 | N |
| ATOM | 552 | CZ | ARG | A | 73 | 72.264 | 32.093 | 9.278 | 1.00 | 58.09 | C |
| ATOM | 553 | NH1 | ARG | A | 73 | 72.897 | 32.895 | 8.427 | 1.00 | 58.20 | N |
| ATOM | 554 | NH2 | ARG | A | 73 | 71.460 | 31.144 | 8.813 | 1.00 | 58.98 | N |
| ATOM | 555 | N | GLU | A | 74 | 74.976 | 36.495 | 15.585 | 1.00 | 42.49 | N |
| ATOM | 556 | CA | GLU | A | 74 | 76.103 | 37.239 | 16.129 | 1.00 | 41.53 | C |
| ATOM | 557 | C | GLU | A | 74 | 75.987 | 37.478 | 17.631 | 1.00 | 39.63 | C |
| ATOM | 558 | O | GLU | A | 74 | 76.896 | 38.031 | 18.242 | 1.00 | 40.05 | O |
| ATOM | 559 | CB | GLU | A | 74 | 76.255 | 38.577 | 15.401 | 1.00 | 42.87 | C |
| ATOM | 560 | CG | GLU | A | 74 | 76.467 | 38.458 | 13.892 | 1.00 | 45.91 | C |
| ATOM | 561 | CD | GLU | A | 74 | 77.673 | 37.595 | 13.522 | 1.00 | 49.55 | C |
| ATOM | 562 | OE1 | GLU | A | 74 | 78.768 | 37.813 | 14.094 | 1.00 | 50.07 | O |
| ATOM | 563 | OE2 | GLU | A | 74 | 77.524 | 36.704 | 12.653 | 1.00 | 50.61 | O |
| ATOM | 564 | N | GLY | A | 75 | 74.869 | 37.074 | 18.229 | 1.00 | 38.37 | N |
| ATOM | 565 | CA | GLY | A | 75 | 74.716 | 37.250 | 19.664 | 1.00 | 38.10 | C |
| ATOM | 566 | C | GLY | A | 75 | 73.715 | 38.287 | 20.132 | 1.00 | 38.30 | C |
| ATOM | 567 | O | GLY | A | 75 | 73.517 | 38.458 | 21.337 | 1.00 | 39.24 | O |
| ATOM | 568 | N | GLY | A | 76 | 73.092 | 38.987 | 19.192 | 1.00 | 37.09 | N |
| ATOM | 569 | CA | GLY | A | 76 | 72.107 | 39.990 | 19.549 | 1.00 | 36.51 | C |
| ATOM | 570 | C | GLY | A | 76 | 70.708 | 39.449 | 19.312 | 1.00 | 36.82 | C |
| ATOM | 571 | O | GLY | A | 76 | 70.546 | 38.266 | 18.989 | 1.00 | 36.23 | O |
| ATOM | 572 | N | ILE | A | 77 | 69.698 | 40.298 | 19.477 | 1.00 | 35.24 | N |
| ATOM | 573 | CA | ILE | A | 77 | 68.316 | 39.875 | 19.259 | 1.00 | 34.74 | C |
| ATOM | 574 | C | ILE | A | 77 | 67.536 | 40.962 | 18.518 | 1.00 | 35.14 | C |
| ATOM | 575 | O | ILE | A | 77 | 67.837 | 42.159 | 18.634 | 1.00 | 34.83 | O |
| ATOM | 576 | CB | ILE | A | 77 | 67.609 | 39.552 | 20.602 | 1.00 | 33.95 | C |
| ATOM | 577 | CG1 | ILE | A | 77 | 66.389 | 38.655 | 20.350 | 1.00 | 34.82 | C |
| ATOM | 578 | CG2 | ILE | A | 77 | 67.179 | 40.850 | 21.305 | 1.00 | 33.35 | C |
| ATOM | 579 | CD1 | ILE | A | 77 | 65.636 | 38.255 | 21.619 | 1.00 | 31.17 | C |
| ATOM | 580 | N | SER | A | 78 | 66.543 | 40.539 | 17.744 | 1.00 | 34.83 | N |
| ATOM | 581 | CA | SER | A | 78 | 65.711 | 41.467 | 16.993 | 1.00 | 33.97 | C |
| ATOM | 582 | C | SER | A | 78 | 64.300 | 41.484 | 17.547 | 1.00 | 34.42 | C |
| ATOM | 583 | O | SER | A | 78 | 63.817 | 40.484 | 18.074 | 1.00 | 35.04 | 0 |
| ATOM | 584 | CB | SER | A | 78 | 65.645 | 41.068 | 15.513 | 1.00 | 32.74 | C |
| ATOM | 585 | OG | SER | A | 78 | 66.870 | 41.295 | 14.848 | 1.00 | 30.88 | O |
| ATOM | 586 | N | PHE | A | 79 | 63.641 | 42.629 | 17.439 | 1.00 | 34.58 | N |
| ATOM | 587 | CA | PHE | A | 79 | 62.270 | 42.740 | 17.891 | 1.00 | 35.16 | C |

TABLE 6-continued

| ATOM | 588 | C | PHE | A | 79 | 61.405 | 42.906 | 16.646 | 1.00 | 35.89 | C |
|---|---|---|---|---|---|---|---|---|---|---|---|
| ATOM | 589 | O | PHE | A | 79 | 61.253 | 44.011 | 16.126 | 1.00 | 36.16 | O |
| ATOM | 590 | CB | PHE | A | 79 | 62.094 | 43.929 | 18.846 | 1.00 | 33.75 | C |
| ATOM | 591 | CG | PHE | A | 79 | 62.664 | 43.688 | 20.219 | 1.00 | 34.30 | C |
| ATOM | 592 | CD1 | PHE | A | 79 | 64.016 | 43.911 | 20.481 | 1.00 | 35.61 | C |
| ATOM | 593 | CD2 | PHE | A | 79 | 61.862 | 43.182 | 21.238 | 1.00 | 33.96 | C |
| ATOM | 594 | CE1 | PHE | A | 79 | 64.559 | 43.626 | 21.745 | 1.00 | 35.47 | C |
| ATOM | 595 | CE2 | PHE | A | 79 | 62.395 | 42.893 | 22.503 | 1.00 | 33.04 | C |
| ATOM | 596 | CZ | PHE | A | 79 | 63.741 | 43.115 | 22.755 | 1.00 | 33.81 | C |
| ATOM | 597 | N | ILE | A | 80 | 60.869 | 41.790 | 16.158 | 1.00 | 35.40 | N |
| ATOM | 598 | CA | ILE | A | 80 | 60.011 | 41.791 | 14.977 | 1.00 | 35.16 | C |
| ATOM | 599 | C | ILE | A | 80 | 58.951 | 42.878 | 15.136 | 1.00 | 35.68 | C |
| ATOM | 600 | O | ILE | A | 80 | 58.241 | 42.916 | 16.149 | 1.00 | 35.60 | O |
| ATOM | 601 | CB | ILE | A | 80 | 59.317 | 40.417 | 14.802 | 1.00 | 35.87 | C |
| ATOM | 602 | CG1 | ILE | A | 80 | 60.373 | 39.319 | 14.621 | 1.00 | 35.71 | C |
| ATOM | 603 | CG2 | ILE | A | 80 | 58.381 | 40.446 | 13.592 | 1.00 | 35.14 | C |
| ATOM | 604 | CD1 | ILE | A | 80 | 61.235 | 39.494 | 13.386 | 1.00 | 34.65 | C |
| ATOM | 605 | N | PHE | A | 81 | 58.838 | 43.754 | 14.140 | 1.00 | 35.48 | N |
| ATOM | 606 | CA | PHE | A | 81 | 57.879 | 44.848 | 14.221 | 1.00 | 37.39 | C |
| ATOM | 607 | C | PHE | A | 81 | 56.427 | 44.423 | 14.437 | 1.00 | 37.98 | C |
| ATOM | 608 | O | PHE | A | 81 | 55.953 | 43.440 | 13.863 | 1.00 | 38.21 | O |
| ATOM | 609 | CB | PHE | A | 81 | 57.989 | 45.773 | 12.990 | 1.00 | 38.37 | C |
| ATOM | 610 | CG | PHE | A | 81 | 57.733 | 45.093 | 11.666 | 1.00 | 39.29 | C |
| ATOM | 611 | CD1 | PHE | A | 81 | 58.693 | 44.272 | 11.089 | 1.00 | 39.25 | C |
| ATOM | 612 | CD2 | PHE | A | 81 | 56.543 | 45.315 | 10.978 | 1.00 | 39.78 | C |
| ATOM | 613 | CE1 | PHE | A | 81 | 58.476 | 43.681 | 9.838 | 1.00 | 39.50 | C |
| ATOM | 614 | CE2 | PHE | A | 81 | 56.313 | 44.731 | 9.729 | 1.00 | 40.29 | C |
| ATOM | 615 | CZ | PHE | A | 81 | 57.284 | 43.911 | 9.158 | 1.00 | 39.87 | C |
| ATOM | 616 | N | GLY | A | 82 | 55.730 | 45.178 | 15.281 | 1.00 | 38.14 | N |
| ATOM | 617 | CA | GLY | A | 82 | 54.341 | 44.878 | 15.570 | 1.00 | 39.76 | C |
| ATOM | 618 | C | GLY | A | 82 | 53.374 | 45.678 | 14.720 | 1.00 | 40.57 | C |
| ATOM | 619 | O | GLY | A | 82 | 52.158 | 45.550 | 14.869 | 1.00 | 41.33 | O |
| ATOM | 620 | N | SER | A | 83 | 53.909 | 46.504 | 13.826 | 1.00 | 40.23 | N |
| ATOM | 621 | CA | SER | A | 83 | 53.076 | 47.313 | 12.945 | 1.00 | 41.14 | C |
| ATOM | 622 | C | SER | A | 83 | 52.678 | 46.522 | 11.698 | 1.00 | 41.79 | C |
| ATOM | 623 | O | SER | A | 83 | 52.958 | 46.920 | 10.566 | 1.00 | 40.82 | O |
| ATOM | 624 | CB | SER | A | 83 | 53.816 | 48.590 | 12.549 | 1.00 | 40.01 | C |
| ATOM | 625 | OG | SER | A | 83 | 55.077 | 48.281 | 11.989 | 1.00 | 42.73 | O |
| ATOM | 626 | N | GLN | A | 84 | 52.034 | 45.385 | 11.934 | 1.00 | 42.84 | N |
| ATOM | 627 | CA | GLN | A | 84 | 51.552 | 44.502 | 10.879 | 1.00 | 43.52 | C |
| ATOM | 628 | C | GLN | A | 84 | 50.500 | 43.599 | 11.524 | 1.00 | 44.66 | C |
| ATOM | 629 | O | GLN | A | 84 | 50.323 | 43.632 | 12.742 | 1.00 | 44.23 | O |
| ATOM | 630 | CB | GLN | A | 84 | 52.699 | 43.665 | 10.310 | 1.00 | 43.55 | C |
| ATOM | 631 | CG | GLN | A | 84 | 53.361 | 42.741 | 11.318 | 1.00 | 43.62 | C |
| ATOM | 632 | CD | GLN | A | 84 | 54.467 | 41.917 | 10.694 | 1.00 | 45.55 | C |
| ATOM | 633 | OE1 | GLN | A | 84 | 54.266 | 41.275 | 9.662 | 1.00 | 46.16 | O |
| ATOM | 634 | NE2 | GLN | A | 84 | 55.646 | 41.926 | 11.319 | 1.00 | 44.86 | N |
| ATOM | 635 | N | SER | A | 85 | 49.807 | 42.798 | 10.720 | 1.00 | 46.26 | N |
| ATOM | 636 | CA | SER | A | 85 | 48.774 | 41.912 | 11.249 | 1.00 | 47.95 | C |
| ATOM | 637 | C | SER | A | 85 | 49.364 | 40.964 | 12.283 | 1.00 | 48.90 | C |
| ATOM | 638 | O | SER | A | 85 | 50.554 | 40.648 | 12.239 | 1.00 | 48.83 | O |
| ATOM | 639 | CB | SER | A | 85 | 48.135 | 41.087 | 10.128 | 1.00 | 47.83 | C |
| ATOM | 640 | OG | SER | A | 85 | 48.937 | 39.965 | 9.804 | 1.00 | 48.77 | O |
| ATOM | 641 | N | ILE | A | 86 | 48.520 | 40.517 | 13.209 | 1.00 | 49.03 | N |
| ATOM | 642 | CA | ILE | A | 86 | 48.934 | 39.593 | 14.256 | 1.00 | 50.14 | C |
| ATOM | 643 | C | ILE | A | 86 | 49.416 | 38.281 | 13.636 | 1.00 | 51.13 | C |
| ATOM | 644 | O | ILE | A | 86 | 50.425 | 37.715 | 14.059 | 1.00 | 50.51 | O |
| ATOM | 645 | CB | ILE | A | 86 | 47.764 | 39.305 | 15.222 | 1.00 | 49.46 | C |
| ATOM | 646 | CG1 | ILE | A | 86 | 47.346 | 40.605 | 15.919 | 1.00 | 49.50 | C |
| ATOM | 647 | CG2 | ILE | A | 86 | 48.162 | 38.236 | 16.227 | 1.00 | 48.57 | C |
| ATOM | 648 | CD1 | ILE | A | 86 | 46.160 | 40.463 | 16.864 | 1.00 | 49.15 | C |
| ATOM | 649 | N | GLU | A | 87 | 48.689 | 37.811 | 12.626 | 1.00 | 52.14 | N |
| ATOM | 650 | CA | GLU | A | 87 | 49.028 | 36.573 | 11.930 | 1.00 | 53.33 | C |
| ATOM | 651 | C | GLU | A | 87 | 50.377 | 36.714 | 11.227 | 1.00 | 52.06 | C |
| ATOM | 652 | O | GLU | A | 87 | 51.197 | 35.795 | 11.228 | 1.00 | 51.76 | O |
| ATOM | 653 | CB | GLU | A | 87 | 47.956 | 36.237 | 10.881 | 1.00 | 55.49 | C |
| ATOM | 654 | CG | GLU | A | 87 | 46.545 | 35.978 | 11.430 | 1.00 | 59.83 | C |
| ATOM | 655 | CD | GLU | A | 87 | 45.948 | 37.179 | 12.164 | 1.00 | 62.66 | C |
| ATOM | 656 | OE1 | GLU | A | 87 | 45.934 | 38.298 | 11.594 | 1.00 | 63.16 | O |
| ATOM | 657 | OE2 | GLU | A | 87 | 45.484 | 36.998 | 13.314 | 1.00 | 64.49 | O |
| ATOM | 658 | N | SER | A | 88 | 50.594 | 37.876 | 10.623 | 1.00 | 51.42 | N |
| ATOM | 659 | CA | SER | A | 88 | 51.828 | 38.149 | 9.895 | 1.00 | 51.37 | C |
| ATOM | 660 | C | SER | A | 88 | 53.048 | 38.223 | 10.818 | 1.00 | 49.76 | C |
| ATOM | 661 | O | SER | A | 88 | 54.098 | 37.651 | 10.522 | 1.00 | 48.93 | O |
| ATOM | 662 | CB | SER | A | 88 | 51.683 | 39.459 | 9.116 | 1.00 | 52.05 | C |
| ATOM | 663 | OG | SER | A | 88 | 52.784 | 39.661 | 8.253 | 1.00 | 54.78 | O |
| ATOM | 664 | N | GLN | A | 89 | 52.909 | 38.927 | 11.935 | 1.00 | 48.17 | N |
| ATOM | 665 | CA | GLN | A | 89 | 54.010 | 39.051 | 12.878 | 1.00 | 47.23 | C |
| ATOM | 666 | C | GLN | A | 89 | 54.338 | 37.692 | 13.493 | 1.00 | 47.15 | C |

TABLE 6-continued

| | | | | | | | | | | | |
|---|---|---|---|---|---|---|---|---|---|---|---|
| ATOM | 667 | O | GLN | A | 89 | 55.507 | 37.333 | 13.636 | 1.00 | 47.13 | O |
| ATOM | 668 | CB | GLN | A | 89 | 53.663 | 40.060 | 13.980 | 1.00 | 45.26 | C |
| ATOM | 669 | CG | GLN | A | 89 | 54.718 | 40.149 | 15.081 | 1.00 | 43.42 | C |
| ATOM | 670 | CD | GLN | A | 89 | 54.405 | 41.207 | 16.127 | 1.00 | 42.17 | C |
| ATOM | 671 | OE1 | GLN | A | 89 | 53.243 | 41.438 | 16.470 | 1.00 | 40.51 | O |
| ATOM | 672 | NE2 | GLN | A | 89 | 55.447 | 41.840 | 16.658 | 1.00 | 40.16 | N |
| ATOM | 673 | N | ALA | A | 90 | 53.305 | 36.934 | 13.848 | 1.00 | 47.23 | N |
| ATOM | 674 | CA | ALA | A | 90 | 53.498 | 35.616 | 14.445 | 1.00 | 47.19 | C |
| ATOM | 675 | C | ALA | A | 90 | 54.224 | 34.678 | 13.486 | 1.00 | 47.12 | C |
| ATOM | 676 | O | ALA | A | 90 | 55.065 | 33.881 | 13.903 | 1.00 | 48.12 | O |
| ATOM | 677 | CB | ALA | A | 90 | 52.154 | 35.022 | 14.848 | 1.00 | 47.65 | C |
| ATOM | 678 | N | ALA | A | 91 | 53.909 | 34.774 | 12.199 | 1.00 | 46.68 | N |
| ATOM | 679 | CA | ALA | A | 91 | 54.560 | 33.924 | 11.211 | 1.00 | 47.00 | C |
| ATOM | 680 | C | ALA | A | 92 | 56.064 | 34.212 | 11.175 | 1.00 | 47.22 | C |
| ATOM | 681 | O | ALA | A | 91 | 56.877 | 33.291 | 11.081 | 1.00 | 47.71 | O |
| ATOM | 682 | CB | ALA | A | 91 | 53.940 | 34.142 | 9.828 | 1.00 | 46.18 | C |
| ATOM | 683 | N | MET | A | 92 | 56.439 | 35.486 | 11.249 | 1.00 | 47.06 | N |
| ATOM | 684 | CA | MET | A | 92 | 57.856 | 35.840 | 11.237 | 1.00 | 46.89 | C |
| ATOM | 685 | C | MET | A | 92 | 58.568 | 35.257 | 12.451 | 1.00 | 46.53 | C |
| ATOM | 686 | O | MET | A | 92 | 59.684 | 34.753 | 12.340 | 1.00 | 47.29 | O |
| ATOM | 687 | CB | MET | A | 92 | 58.041 | 37.357 | 11.222 | 1.00 | 46.77 | C |
| ATOM | 688 | CG | MET | A | 92 | 57.871 | 37.987 | 9.863 | 1.00 | 46.28 | C |
| ATOM | 689 | SD | MET | A | 92 | 58.254 | 39.733 | 9.915 | 1.00 | 45.24 | S |
| ATOM | 690 | CE | MET | A | 92 | 56.986 | 40.381 | 8.852 | 1.00 | 46.35 | C |
| ATOM | 691 | N | VAL | A | 93 | 57.925 | 35.333 | 13.611 | 1.00 | 46.27 | N |
| ATOM | 692 | CA | VAL | A | 93 | 58.511 | 34.796 | 14.829 | 1.00 | 46.01 | C |
| ATOM | 693 | C | VAL | A | 93 | 58.675 | 33.290 | 14.682 | 1.00 | 47.76 | C |
| ATOM | 694 | O | VAL | A | 93 | 59.715 | 32.733 | 15.037 | 1.00 | 48.37 | O |
| ATOM | 695 | CB | VAL | A | 93 | 57.624 | 35.090 | 16.057 | 1.00 | 44.88 | C |
| ATOM | 696 | CG1 | VAL | A | 93 | 58.080 | 34.254 | 17.251 | 1.00 | 43.31 | C |
| ATOM | 697 | CG2 | VAL | A | 93 | 57.692 | 36.568 | 16.394 | 1.00 | 43.70 | C |
| ATOM | 698 | N | HIS | A | 94 | 57.642 | 32.637 | 14.153 | 1.00 | 49.11 | N |
| ATOM | 699 | CA | HIS | A | 94 | 57.668 | 31.189 | 13.955 | 1.00 | 49.55 | C |
| ATOM | 700 | C | HIS | A | 94 | 58.818 | 30.791 | 13.035 | 1.00 | 48.88 | C |
| ATOM | 701 | O | HIS | A | 94 | 59.572 | 29.862 | 13.330 | 1.00 | 49.22 | O |
| ATOM | 702 | CB | HIS | A | 94 | 56.344 | 30.703 | 13.349 | 1.00 | 51.41 | C |
| ATOM | 703 | CG | HIS | A | 94 | 56.256 | 29.213 | 13.221 | 1.00 | 53.19 | C |
| ATOM | 704 | ND1 | HIS | A | 94 | 55.924 | 28.394 | 14.278 | 1.00 | 53.72 | N |
| ATOM | 705 | CD2 | HIS | A | 94 | 56.520 | 28.391 | 12.176 | 1.00 | 54.01 | C |
| ATOM | 706 | CE1 | HIS | A | 94 | 55.989 | 27.131 | 13.893 | 1.00 | 53.86 | C |
| ATOM | 707 | NE2 | HIS | A | 94 | 56.351 | 27.102 | 12.622 | 1.00 | 54.56 | N |
| ATOM | 708 | N | ALA | A | 95 | 58.952 | 31.502 | 11.921 | 1.00 | 48.06 | N |
| ATOM | 709 | CA | ALA | A | 95 | 60.006 | 31.219 | 10.956 | 1.00 | 47.57 | C |
| ATOM | 710 | C | ALA | A | 95 | 61.405 | 31.321 | 11.567 | 1.00 | 48.34 | C |
| ATOM | 711 | O | ALA | A | 95 | 62.294 | 30.538 | 11.233 | 1.00 | 48.18 | O |
| ATOM | 712 | CB | ALA | A | 95 | 59.887 | 32.162 | 9.770 | 1.00 | 46.85 | C |
| ATOM | 713 | N | VAL | A | 96 | 61.604 | 32.289 | 12.458 | 1.00 | 48.08 | N |
| ATOM | 714 | CA | VAL | A | 96 | 62.906 | 32.463 | 13.087 | 1.00 | 47.54 | C |
| ATOM | 715 | C | VAL | A | 96 | 63.165 | 31.344 | 14.086 | 1.00 | 48.02 | C |
| ATOM | 716 | O | VAL | A | 96 | 64.276 | 30.815 | 14.164 | 1.00 | 47.17 | O |
| ATOM | 717 | CB | VAL | A | 96 | 63.003 | 33.826 | 13.815 | 1.00 | 47.26 | C |
| ATOM | 718 | CG1 | VAL | A | 96 | 64.336 | 33.945 | 14.537 | 1.00 | 46.34 | C |
| ATOM | 719 | CG2 | VAL | A | 96 | 62.856 | 34.952 | 12.813 | 1.00 | 47.02 | C |
| ATOM | 720 | N | LYS | A | 97 | 62.133 | 30.979 | 14.840 | 1.00 | 48.62 | N |
| ATOM | 721 | CA | LYS | A | 97 | 62.252 | 29.924 | 15.837 | 1.00 | 50.60 | C |
| ATOM | 722 | C | LYS | A | 97 | 62.459 | 28.546 | 15.209 | 1.00 | 52.32 | C |
| ATOM | 723 | O | LYS | A | 97 | 63.068 | 27.670 | 15.823 | 1.00 | 52.87 | O |
| ATOM | 724 | CB | LYS | A | 97 | 61.010 | 29.899 | 16.742 | 1.00 | 49.44 | C |
| ATOM | 725 | CG | LYS | A | 97 | 60.791 | 31.169 | 17.564 | 1.00 | 47.42 | C |
| ATOM | 726 | CD | LYS | A | 97 | 61.988 | 31.489 | 18.467 | 1.00 | 45.88 | C |
| ATOM | 727 | CE | LYS | A | 97 | 62.191 | 30.440 | 19.557 | 1.00 | 44.36 | C |
| ATOM | 728 | NZ | LYS | A | 97 | 63.433 | 30.692 | 20.354 | 1.00 | 42.11 | N |
| ATOM | 729 | N | ASN | A | 98 | 61.962 | 28.354 | 13.991 | 1.00 | 54.75 | N |
| ATOM | 730 | CA | ASN | A | 98 | 62.108 | 27.066 | 13.315 | 1.00 | 58.07 | C |
| ATOM | 731 | C | ASN | A | 98 | 63.004 | 27.120 | 12.085 | 1.00 | 59.49 | C |
| ATOM | 732 | O | ASN | A | 98 | 62.799 | 26.361 | 11.138 | 1.00 | 60.40 | O |
| ATOM | 733 | CB | ASN | A | 98 | 60.738 | 26.515 | 12.899 | 1.00 | 58.95 | C |
| ATOM | 734 | CG | ASN | A | 98 | 59.882 | 26.119 | 14.082 | 1.00 | 61.39 | C |
| ATOM | 735 | OD1 | ASN | A | 98 | 59.420 | 26.970 | 14.845 | 1.00 | 62.44 | O |
| ATOM | 736 | ND2 | ASN | A | 98 | 59.668 | 24.816 | 14.248 | 1.00 | 62.55 | N |
| ATOM | 737 | N | PHE | A | 99 | 64.000 | 27.999 | 12.092 | 1.00 | 61.00 | N |
| ATOM | 738 | CA | PHE | A | 99 | 64.889 | 28.117 | 10.942 | 1.00 | 62.73 | C |
| ATOM | 739 | C | PHE | A | 99 | 65.827 | 26.926 | 10.774 | 1.00 | 64.62 | C |
| ATOM | 740 | O | PHE | A | 99 | 66.150 | 26.544 | 9.650 | 1.00 | 64.73 | O |
| ATOM | 741 | CB | PHE | A | 99 | 65.719 | 29.398 | 11.028 | 1.00 | 61.76 | C |
| ATOM | 742 | CG | PHE | A | 99 | 66.492 | 29.703 | 9.772 | 1.00 | 61.06 | C |
| ATOM | 743 | CD1 | PHE | A | 99 | 65.827 | 29.971 | 8.579 | 1.00 | 60.96 | C |
| ATOM | 744 | CD2 | PHE | A | 99 | 67.881 | 29.727 | 9.780 | 1.00 | 60.81 | C |
| ATOM | 745 | CE1 | PHE | A | 99 | 66.537 | 30.258 | 7.412 | 1.00 | 60.52 | C |

TABLE 6-continued

| ATOM | 746 | CE2 | PHE | A | 99 | 68.599 | 30.012 | 8.620 | 1.00 | 60.86 | C |
| --- | --- | --- | --- | --- | --- | --- | --- | --- | --- | --- | --- |
| ATOM | 747 | CZ | PHE | A | 99 | 67.924 | 30.279 | 7.434 | 1.00 | 60.69 | C |
| ATOM | 748 | N | LYS | A | 100 | 66.267 | 26.340 | 11.883 | 1.00 | 67.08 | N |
| ATOM | 749 | CA | LYS | A | 100 | 67.178 | 25.199 | 11.820 | 1.00 | 70.33 | C |
| ATOM | 750 | C | LYS | A | 100 | 66.462 | 23.871 | 11.582 | 1.00 | 72.95 | C |
| ATOM | 751 | O | LYS | A | 100 | 66.988 | 22.809 | 11.914 | 1.00 | 72.97 | O |
| ATOM | 752 | CB | LYS | A | 100 | 68.006 | 25.108 | 13.104 | 1.00 | 69.54 | C |
| ATOM | 753 | CG | LYS | A | 100 | 68.932 | 26.288 | 13.333 | 1.00 | 68.73 | C |
| ATOM | 754 | CD | LYS | A | 100 | 69.765 | 26.088 | 14.586 | 1.00 | 68.36 | C |
| ATOM | 755 | CE | LYS | A | 100 | 70.750 | 27.227 | 14.791 | 1.00 | 67.27 | C |
| ATOM | 756 | NZ | LYS | A | 100 | 71.581 | 27.006 | 16.000 | 1.00 | 66.23 | N |
| ATOM | 757 | N | ALA | A | 101 | 65.269 | 23.937 | 10.999 | 1.00 | 76.17 | N |
| ATOM | 758 | CA | ALA | A | 101 | 64.486 | 22.739 | 10.717 | 1.00 | 79.28 | C |
| ATOM | 759 | C | ALA | A | 101 | 64.671 | 22.262 | 9.275 | 1.00 | 81.72 | C |
| ATOM | 760 | O | ALA | A | 101 | 65.159 | 21.154 | 9.043 | 1.00 | 81.99 | O |
| ATOM | 761 | CB | ALA | A | 101 | 63.011 | 23.002 | 10.996 | 1.00 | 79.19 | C |
| ATOM | 762 | N | GLY | A | 102 | 64.280 | 23.092 | 8.310 | 1.00 | 84.33 | N |
| ATOM | 763 | CA | GLY | A | 102 | 64.420 | 22.707 | 6.915 | 1.00 | 87.56 | C |
| ATOM | 764 | C | GLY | A | 102 | 63.773 | 23.645 | 5.910 | 1.00 | 89.81 | C |
| ATOM | 765 | O | GLY | A | 102 | 62.728 | 24.243 | 6.179 | 1.00 | 90.05 | O |
| ATOM | 766 | N | PHE | A | 103 | 64.402 | 23.760 | 4.741 | 1.00 | 91.88 | N |
| ATOM | 767 | CA | PHE | A | 103 | 63.930 | 24.618 | 3.653 | 1.00 | 93.97 | C |
| ATOM | 768 | C | PHE | A | 103 | 62.785 | 23.976 | 2.864 | 1.00 | 95.19 | C |
| ATOM | 769 | O | PHE | A | 103 | 61.854 | 24.661 | 2.427 | 1.00 | 95.10 | O |
| ATOM | 770 | CB | PHE | A | 103 | 65.107 | 24.933 | 2.714 | 1.00 | 94.40 | C |
| ATOM | 771 | CG | PHE | A | 103 | 64.716 | 25.637 | 1.439 | 1.00 | 95.36 | C |
| ATOM | 772 | CD1 | PHE | A | 103 | 64.030 | 24.961 | 0.430 | 1.00 | 95.96 | C |
| ATOM | 773 | CD2 | PHE | A | 103 | 65.052 | 26.973 | 1.238 | 1.00 | 95.68 | C |
| ATOM | 774 | CE1 | PHE | A | 103 | 63.682 | 25.603 | 0.758 | 1.00 | 96.63 | C |
| ATOM | 775 | CE2 | PHE | A | 103 | 64.710 | 27.627 | 0.054 | 1.00 | 96.41 | C |
| ATOM | 776 | CZ | PHE | A | 103 | 64.024 | 26.940 | 0.947 | 1.00 | 96.90 | C |
| ATOM | 777 | N | VAL | A | 104 | 62.867 | 22.660 | 2.685 | 1.00 | 96.51 | N |
| ATOM | 778 | CA | VAL | A | 104 | 61.864 | 21.904 | 1.941 | 1.00 | 97.40 | C |
| ATOM | 779 | C | VAL | A | 104 | 60.668 | 21.484 | 2.796 | 1.00 | 98.06 | C |
| ATOM | 780 | O | VAL | A | 104 | 60.475 | 21.986 | 3.905 | 1.00 | 98.29 | O |
| ATOM | 781 | CB | VAL | A | 104 | 62.494 | 20.639 | 1.318 | 1.00 | 97.53 | C |
| ATOM | 782 | CG1 | VAL | A | 104 | 63.604 | 21.035 | 0.358 | 1.00 | 97.83 | C |
| ATOM | 783 | CG2 | VAL | A | 104 | 63.043 | 19.733 | 2.415 | 1.00 | 97.17 | C |
| ATOM | 784 | N | VAL | A | 105 | 59.869 | 20.562 | 2.265 | 1.00 | 98.68 | N |
| ATOM | 785 | CA | VAL | A | 105 | 58.690 | 20.055 | 2.960 | 1.00 | 99.19 | C |
| ATOM | 786 | C | VAL | A | 105 | 58.840 | 18.556 | 3.223 | 1.00 | 99.69 | C |
| ATOM | 787 | O | VAL | A | 105 | 59.955 | 18.034 | 3.251 | 1.00 | 99.86 | O |
| ATOM | 788 | CB | VAL | A | 105 | 57.408 | 20.294 | 2.130 | 1.00 | 99.21 | C |
| ATOM | 789 | CG1 | VAL | A | 105 | 57.207 | 21.786 | 1.904 | 1.00 | 98.66 | C |
| ATOM | 790 | CG2 | VAL | A | 105 | 57.505 | 19.562 | 0.798 | 1.00 | 99.13 | C |
| ATOM | 791 | N | SER | A | 106 | 57.720 | 17.864 | 3.411 | 1.00 | 100.19 | N |
| ATOM | 792 | CA | SER | A | 106 | 57.748 | 16.427 | 3.674 | 1.00 | 100.80 | C |
| ATOM | 793 | C | SER | A | 106 | 57.538 | 15.604 | 2.401 | 1.00 | 101.31 | C |
| ATOM | 794 | O | SER | A | 106 | 56.616 | 14.788 | 2.323 | 1.00 | 101.42 | O |
| ATOM | 795 | CB | SER | A | 106 | 56.678 | 16.063 | 4.707 | 1.00 | 100.69 | C |
| ATOM | 796 | OG | SER | A | 106 | 55.384 | 16.412 | 4.245 | 1.00 | 100.34 | O |
| ATOM | 797 | N | ASP | A | 107 | 58.402 | 15.816 | 1.412 | 1.00 | 101.66 | N |
| ATOM | 798 | CA | ASP | A | 107 | 58.312 | 15.101 | 0.142 | 1.00 | 101.66 | C |
| ATOM | 799 | C | ASP | A | 107 | 59.084 | 13.785 | 0.184 | 1.00 | 101.55 | C |
| ATOM | 800 | O | ASP | A | 107 | 59.050 | 13.003 | 0.767 | 1.00 | 101.37 | O |
| ATOM | 801 | CB | ASP | A | 107 | 58.848 | 15.976 | 0.997 | 1.00 | 101.95 | C |
| ATOM | 802 | CG | ASP | A | 107 | 60.326 | 16.302 | 0.843 | 1.00 | 102.22 | C |
| ATOM | 803 | OD1 | ASP | A | 107 | 60.742 | 16.916 | 0.140 | 1.00 | 102.16 | O |
| ATOM | 804 | OD2 | ASP | A | 107 | 61.126 | 15.891 | 1.821 | 1.00 | 102.12 | O |
| ATOM | 805 | N | VAL | A | 220 | 77.129 | 27.310 | 12.363 | 1.00 | 82.99 | N |
| ATOM | 806 | CA | VAL | A | 220 | 78.036 | 26.953 | 13.450 | 1.00 | 82.93 | C |
| ATOM | 807 | C | VAL | A | 220 | 78.735 | 28.199 | 13.998 | 1.00 | 82.11 | C |
| ATOM | 808 | O | VAL | A | 220 | 79.965 | 28.283 | 14.018 | 1.00 | 82.35 | O |
| ATOM | 809 | CB | VAL | A | 220 | 79.103 | 25.942 | 12.967 | 1.00 | 83.59 | C |
| ATOM | 810 | CG1 | VAL | A | 220 | 79.931 | 25.443 | 14.152 | 1.00 | 83.61 | C |
| ATOM | 811 | CG2 | VAL | A | 220 | 78.424 | 24.777 | 12.252 | 1.00 | 84.13 | C |
| ATOM | 812 | N | CYS | A | 221 | 77.936 | 29.165 | 14.439 | 1.00 | 80.94 | N |
| ATOM | 813 | CA | CYS | A | 221 | 78.454 | 30.414 | 14.989 | 1.00 | 79.61 | C |
| ATOM | 814 | C | CYS | A | 221 | 78.548 | 30.290 | 16.509 | 1.00 | 78.38 | C |
| ATOM | 815 | O | CYS | A | 221 | 77.557 | 29.996 | 17.176 | 1.00 | 78.27 | O |
| ATOM | 816 | CB | CYS | A | 221 | 77.526 | 31.568 | 14.602 | 1.00 | 80.09 | C |
| ATOM | 817 | SG | CYS | A | 221 | 77.159 | 31.648 | 12.823 | 1.00 | 80.23 | S |
| ATOM | 818 | N | HIS | A | 222 | 79.739 | 30.518 | 17.054 | 1.00 | 76.79 | N |
| ATOM | 819 | CA | HIS | A | 222 | 79.949 | 30.395 | 18.493 | 1.00 | 74.99 | C |
| ATOM | 820 | C | HIS | A | 222 | 79.364 | 31.496 | 19.366 | 1.00 | 72.24 | C |
| ATOM | 821 | O | HIS | A | 222 | 79.359 | 31.376 | 20.592 | 1.00 | 72.13 | O |
| ATOM | 822 | CB | HIS | A | 222 | 81.442 | 30.238 | 18.799 | 1.00 | 77.56 | C |
| ATOM | 823 | CG | HIS | A | 222 | 81.952 | 28.846 | 18.586 | 1.00 | 80.75 | C |
| ATOM | 824 | ND1 | HIS | A | 222 | 81.352 | 27.741 | 19.155 | 1.00 | 81.58 | N |

TABLE 6-continued

| ATOM | 825 | CD2 | HIS | A | 222 | 83.003 | 28.377 | 17.872 | 1.00 | 81.49 | C |
| --- | --- | --- | --- | --- | --- | --- | --- | --- | --- | --- | --- |
| ATOM | 826 | CE1 | HIS | A | 222 | 82.011 | 26.653 | 18.799 | 1.00 | 82.43 | C |
| ATOM | 827 | NE2 | HIS | A | 222 | 83.017 | 27.011 | 18.021 | 1.00 | 82.72 | N |
| ATOM | 828 | N | ASN | A | 223 | 78.875 | 32.565 | 18.751 | 1.00 | 68.37 | N |
| ATOM | 829 | CA | ASN | A | 223 | 78.282 | 33.643 | 19.526 | 1.00 | 64.96 | C |
| ATOM | 830 | C | ASN | A | 223 | 76.793 | 33.775 | 19.261 | 1.00 | 61.91 | C |
| ATOM | 831 | O | ASN | A | 223 | 76.185 | 34.788 | 19.599 | 1.00 | 60.48 | O |
| ATOM | 832 | CB | ASN | A | 223 | 78.984 | 34.968 | 19.237 | 1.00 | 65.81 | C |
| ATOM | 833 | CG | ASN | A | 223 | 80.285 | 35.107 | 19.998 | 1.00 | 66.63 | C |
| ATOM | 834 | OD1 | ASN | A | 223 | 80.302 | 35.069 | 21.229 | 1.00 | 65.69 | O |
| ATOM | 835 | ND2 | ASN | A | 223 | 81.385 | 35.266 | 19.270 | 1.00 | 67.36 | N |
| ATOM | 836 | N | GLU | A | 224 | 76.206 | 32.746 | 18.660 | 1.00 | 58.19 | N |
| ATOM | 837 | CA | GLU | A | 224 | 74.780 | 32.774 | 18.371 | 1.00 | 55.64 | C |
| ATOM | 838 | C | GLU | A | 224 | 73.972 | 32.796 | 19.657 | 1.00 | 51.83 | C |
| ATOM | 839 | O | GLU | A | 224 | 74.341 | 32.166 | 20.646 | 1.00 | 50.93 | O |
| ATOM | 840 | CB | GLU | A | 224 | 74.367 | 31.560 | 17.534 | 1.00 | 56.74 | C |
| ATOM | 841 | CG | GLU | A | 224 | 74.747 | 30.220 | 18.136 | 1.00 | 59.42 | C |
| ATOM | 842 | CD | GLU | A | 224 | 74.114 | 29.053 | 17.398 | 1.00 | 60.69 | C |
| ATOM | 843 | OE1 | GLU | A | 224 | 74.019 | 29.115 | 16.149 | 1.00 | 61.36 | O |
| ATOM | 844 | OE2 | GLU | A | 224 | 73.722 | 28.073 | 18.069 | 1.00 | 60.59 | O |
| ATOM | 845 | N | LEU | A | 225 | 72.871 | 33.536 | 19.634 | 1.00 | 48.65 | N |
| ATOM | 846 | CA | LEU | A | 225 | 71.991 | 33.641 | 20.785 | 1.00 | 46.12 | C |
| ATOM | 847 | C | LEU | A | 225 | 70.843 | 32.660 | 20.571 | 1.00 | 44.98 | C |
| ATOM | 848 | O | LEU | A | 225 | 70.031 | 32.832 | 19.660 | 1.00 | 42.50 | O |
| ATOM | 849 | CB | LEU | A | 225 | 71.456 | 35.071 | 20.904 | 1.00 | 45.35 | C |
| ATOM | 850 | CG | LEU | A | 225 | 70.635 | 35.402 | 22.151 | 1.00 | 46.02 | C |
| ATOM | 851 | CD1 | LEU | A | 225 | 71.483 | 35.146 | 23.389 | 1.00 | 46.56 | C |
| ATOM | 852 | CD2 | LEU | A | 225 | 70.174 | 36.851 | 22.107 | 1.00 | 45.65 | C |
| ATOM | 853 | N | VAL | A | 226 | 70.778 | 31.634 | 21.415 | 1.00 | 45.11 | N |
| ATOM | 854 | CA | VAL | A | 226 | 69.740 | 30.612 | 21.293 | 1.00 | 45.18 | C |
| ATOM | 855 | C | VAL | A | 226 | 69.138 | 30.162 | 22.623 | 1.00 | 46.10 | C |
| ATOM | 856 | O | VAL | A | 226 | 69.664 | 30.461 | 23.698 | 1.00 | 46.22 | O |
| ATOM | 857 | CB | VAL | A | 226 | 70.294 | 29.355 | 20.598 | 1.00 | 44.37 | C |
| ATOM | 858 | CG1 | VAL | A | 226 | 70.698 | 29.674 | 19.170 | 1.00 | 42.78 | C |
| ATOM | 859 | CG2 | VAL | A | 226 | 71.478 | 28.826 | 21.383 | 1.00 | 43.24 | C |
| ATOM | 860 | N | ASP | A | 227 | 68.026 | 29.435 | 22.535 | 1.00 | 46.56 | N |
| ATOM | 861 | CA | ASP | A | 227 | 67.366 | 28.912 | 23.721 | 1.00 | 47.21 | C |
| ATOM | 862 | C | ASP | A | 227 | 67.910 | 27.516 | 24.017 | 1.00 | 48.24 | C |
| ATOM | 863 | O | ASP | A | 227 | 68.808 | 27.034 | 23.325 | 1.00 | 47.45 | O |
| ATOM | 864 | CB | ASP | A | 227 | 65.848 | 28.854 | 23.523 | 1.00 | 46.83 | C |
| ATOM | 865 | CG | ASP | A | 227 | 65.445 | 28.110 | 22.264 | 1.00 | 46.84 | C |
| ATOM | 866 | OD1 | ASP | A | 227 | 66.094 | 27.099 | 21.924 | 1.00 | 47.01 | O |
| ATOM | 867 | OD2 | ASP | A | 227 | 64.460 | 28.529 | 21.620 | 1.00 | 46.98 | O |
| ATOM | 868 | N | SER | A | 228 | 67.357 | 26.875 | 25.043 | 1.00 | 50.32 | N |
| ATOM | 869 | CA | SER | A | 228 | 67.782 | 25.541 | 25.456 | 1.00 | 52.29 | C |
| ATOM | 870 | C | SER | A | 228 | 67.580 | 24.487 | 24.366 | 1.00 | 53.54 | C |
| ATOM | 871 | O | SER | A | 228 | 68.129 | 23.386 | 24.448 | 1.00 | 54.15 | O |
| ATOM | 872 | CB | SER | A | 228 | 67.031 | 25.127 | 26.723 | 1.00 | 51.85 | C |
| ATOM | 873 | OG | SER | A | 228 | 65.636 | 25.099 | 26.492 | 1.00 | 52.33 | O |
| ATOM | 874 | N | GLN | A | 229 | 66.793 | 24.832 | 23.352 | 1.00 | 54.18 | N |
| ATOM | 875 | CA | GLN | A | 229 | 66.526 | 23.934 | 22.237 | 1.00 | 54.92 | C |
| ATOM | 876 | C | GLN | A | 229 | 67.418 | 24.282 | 21.049 | 1.00 | 55.01 | C |
| ATOM | 877 | O | GLN | A | 229 | 67.224 | 23.772 | 19.942 | 1.00 | 55.05 | O |
| ATOM | 878 | CB | GLN | A | 229 | 65.058 | 24.038 | 21.818 | 1.00 | 56.21 | C |
| ATOM | 879 | CG | GLN | A | 229 | 64.088 | 23.265 | 22.691 | 1.00 | 58.02 | C |
| ATOM | 880 | CD | GLN | A | 229 | 62.641 | 23.613 | 22.386 | 1.00 | 60.19 | C |
| ATOM | 881 | OE1 | GLN | A | 229 | 62.130 | 24.637 | 22.845 | 1.00 | 60.85 | O |
| ATOM | 882 | NE2 | GLN | A | 229 | 61.976 | 22.770 | 21.597 | 1.00 | 61.03 | N |
| ATOM | 883 | N | LYS | A | 230 | 68.392 | 25.157 | 21.287 | 1.00 | 54.58 | N |
| ATOM | 884 | CA | LYS | A | 230 | 69.328 | 25.596 | 20.255 | 1.00 | 53.47 | C |
| ATOM | 885 | C | LYS | A | 230 | 68.684 | 26.418 | 19.137 | 1.00 | 51.87 | C |
| ATOM | 886 | O | LYS | A | 230 | 69.257 | 26.554 | 18.055 | 1.00 | 51.62 | O |
| ATOM | 887 | CB | LYS | A | 230 | 70.057 | 24.390 | 19.652 | 1.00 | 55.91 | C |
| ATOM | 888 | CG | LYS | A | 230 | 70.846 | 23.572 | 20.669 | 1.00 | 58.78 | C |
| ATOM | 889 | CD | LYS | A | 230 | 71.977 | 24.381 | 21.305 | 1.00 | 61.46 | C |
| ATOM | 890 | CE | LYS | A | 230 | 73.062 | 24.738 | 20.290 | 1.00 | 62.75 | C |
| ATOM | 891 | NZ | LYS | A | 230 | 74.211 | 25.454 | 20.926 | 1.00 | 63.92 | N |
| ATOM | 892 | N | ARG | A | 231 | 67.501 | 26.970 | 19.395 | 1.00 | 50.44 | N |
| ATOM | 893 | CA | ARG | A | 231 | 66.816 | 27.796 | 18.400 | 1.00 | 48.86 | C |
| ATOM | 894 | C | ARG | A | 231 | 67.179 | 29.261 | 18.644 | 1.00 | 47.36 | C |
| ATOM | 895 | O | ARG | A | 231 | 67.351 | 29.679 | 19.789 | 1.00 | 45.45 | O |
| ATOM | 896 | CB | ARG | A | 231 | 65.296 | 27.637 | 18.512 | 1.00 | 50.40 | C |
| ATOM | 897 | CG | ARG | A | 231 | 64.794 | 26.199 | 18.451 | 1.00 | 51.58 | C |
| ATOM | 898 | CD | ARG | A | 231 | 63.779 | 25.952 | 19.553 | 1.00 | 53.03 | C |
| ATOM | 899 | NE | ARG | A | 231 | 62.461 | 26.504 | 19.257 | 1.00 | 55.50 | N |
| ATOM | 900 | CZ | ARG | A | 231 | 61.573 | 26.852 | 20.186 | 1.00 | 56.77 | C |
| ATOM | 901 | NH1 | ARG | A | 231 | 61.869 | 26.716 | 21.471 | 1.00 | 57.45 | N |
| ATOM | 902 | NH2 | ARG | A | 231 | 60.379 | 27.317 | 19.833 | 1.00 | 57.86 | N |
| ATOM | 903 | N | TYR | A | 232 | 67.294 | 30.034 | 17.567 | 1.00 | 45.64 | N |

TABLE 6-continued

| | | | | | | | | | | |
|---|---|---|---|---|---|---|---|---|---|---|
| ATOM | 904 | CA | TYR | A | 232 | 67.623 | 31.450 | 17.671 | 1.00 | 43.85 C |
| ATOM | 905 | C | TYR | A | 232 | 66.581 | 32.200 | 18.497 | 1.00 | 42.80 C |
| ATOM | 906 | O | TYR | A | 232 | 65.376 | 31.965 | 18.361 | 1.00 | 41.87 O |
| ATOM | 907 | CB | TYR | A | 232 | 67.692 | 32.093 | 16.286 | 1.00 | 43.80 C |
| ATOM | 908 | CG | TYR | A | 232 | 68.821 | 31.603 | 15.423 | 1.00 | 44.82 C |
| ATOM | 909 | CD1 | TYR | A | 232 | 70.142 | 31.650 | 15.871 | 1.00 | 45.02 C |
| ATOM | 910 | CD2 | TYR | A | 232 | 68.573 | 31.094 | 14.151 | 1.00 | 45.58 C |
| ATOM | 911 | CE1 | TYR | A | 232 | 71.193 | 31.197 | 15.066 | 1.00 | 46.46 C |
| ATOM | 912 | CE2 | TYR | A | 232 | 69.610 | 30.642 | 13.341 | 1.00 | 46.70 C |
| ATOM | 913 | CZ | TYR | A | 232 | 70.915 | 30.694 | 13.803 | 1.00 | 46.56 C |
| ATOM | 914 | OH | TYR | A | 232 | 71.932 | 30.237 | 12.998 | 1.00 | 47.52 O |
| ATOM | 915 | N | LEU | A | 233 | 67.044 | 33.097 | 19.358 | 1.00 | 41.20 N |
| ATOM | 916 | CA | LEU | A | 233 | 66.119 | 33.882 | 20.160 | 1.00 | 40.26 C |
| ATOM | 917 | C | LEU | A | 233 | 65.573 | 34.990 | 19.275 | 1.00 | 39.17 C |
| ATOM | 918 | O | LEU | A | 233 | 66.231 | 35.428 | 18.328 | 1.00 | 39.41 O |
| ATOM | 919 | CB | LEU | A | 233 | 66.816 | 34.493 | 21.380 | 1.00 | 39.71 C |
| ATOM | 920 | CG | LEU | A | 233 | 67.335 | 33.532 | 22.453 | 1.00 | 40.47 C |
| ATOM | 921 | CD1 | LEU | A | 233 | 67.794 | 34.339 | 23.661 | 1.00 | 40.88 C |
| ATOM | 922 | CD2 | LEU | A | 233 | 66.243 | 32.562 | 22.870 | 1.00 | 39.44 C |
| ATOM | 923 | N | VAL | A | 234 | 64.360 | 35.432 | 19.572 | 1.00 | 37.75 N |
| ATOM | 924 | CA | VAL | A | 234 | 63.756 | 36.498 | 18.799 | 1.00 | 37.14 C |
| ATOM | 925 | C | VAL | A | 234 | 62.766 | 37.241 | 19.681 | 1.00 | 37.43 C |
| ATOM | 926 | O | VAL | A | 234 | 62.157 | 36.653 | 20.575 | 1.00 | 37.88 O |
| ATOM | 927 | CB | VAL | A | 234 | 63.032 | 35.946 | 17.544 | 1.00 | 36.92 C |
| ATOM | 928 | CG1 | VAL | A | 234 | 61.826 | 35.102 | 17.954 | 1.00 | 34.91 C |
| ATOM | 929 | CG2 | VAL | A | 234 | 62.619 | 37.096 | 16.638 | 1.00 | 35.20 C |
| ATOM | 930 | N | GLY | A | 235 | 62.631 | 38.540 | 19.444 | 1.00 | 36.87 N |
| ATOM | 931 | CA | GLY | A | 235 | 61.703 | 39.335 | 20.223 | 1.00 | 36.91 C |
| ATOM | 932 | C | GLY | A | 235 | 60.596 | 39.828 | 19.318 | 1.00 | 36.80 C |
| ATOM | 933 | O | GLY | A | 235 | 60.670 | 39.654 | 18.098 | 1.00 | 37.13 O |
| ATOM | 934 | N | ALA | A | 236 | 59.572 | 40.440 | 19.903 | 1.00 | 35.88 N |
| ATOM | 935 | CA | ALA | A | 236 | 58.465 | 40.958 | 19.116 | 1.00 | 35.95 C |
| ATOM | 936 | C | ALA | A | 236 | 57.824 | 42.165 | 19.791 | 1.00 | 35.70 C |
| ATOM | 937 | O | ALA | A | 236 | 57.559 | 42.153 | 20.995 | 1.00 | 37.71 O |
| ATOM | 938 | CB | ALA | A | 236 | 57.423 | 39.860 | 18.893 | 1.00 | 36.04 C |
| ATOM | 939 | N | GLY | A | 237 | 57.578 | 43.212 | 19.012 | 1.00 | 35.37 N |
| ATOM | 940 | CA | GLY | A | 237 | 56.961 | 44.401 | 19.564 | 1.00 | 36.75 C |
| ATOM | 941 | C | GLY | A | 237 | 55.459 | 44.243 | 19.696 | 1.00 | 38.21 C |
| ATOM | 942 | O | GLY | A | 237 | 54.837 | 43.542 | 18.895 | 1.00 | 39.76 O |
| ATOM | 943 | N | ILE | A | 238 | 54.876 | 44.870 | 20.715 | 1.00 | 36.81 N |
| ATOM | 944 | CA | ILE | A | 238 | 53.437 | 44.818 | 20.926 | 1.00 | 37.17 C |
| ATOM | 945 | C | ILE | A | 238 | 52.933 | 46.227 | 21.232 | 1.00 | 37.51 C |
| ATOM | 946 | O | ILE | A | 238 | 53.713 | 47.111 | 21.591 | 1.00 | 36.78 O |
| ATOM | 947 | CB | ILE | A | 238 | 53.043 | 43.883 | 22.107 | 1.00 | 38.27 C |
| ATOM | 948 | CG1 | ILE | A | 238 | 53.568 | 44.449 | 23.432 | 1.00 | 38.61 C |
| ATOM | 949 | CG2 | ILE | A | 238 | 53.588 | 42.485 | 21.872 | 1.00 | 36.69 C |
| ATOM | 950 | CD1 | ILE | A | 238 | 53.046 | 43.710 | 24.665 | 1.00 | 38.14 C |
| ATOM | 951 | N | ASN | A | 239 | 51.631 | 46.442 | 21.074 | 1.00 | 37.56 N |
| ATOM | 952 | CA | ASN | A | 239 | 51.048 | 47.746 | 21.351 | 1.00 | 37.15 C |
| ATOM | 953 | C | ASN | A | 239 | 50.037 | 47.630 | 22.484 | 1.00 | 38.42 C |
| ATOM | 954 | O | ASN | A | 239 | 49.644 | 46.526 | 22.873 | 1.00 | 37.39 O |
| ATOM | 955 | CB | ASN | A | 239 | 50.388 | 48.312 | 20.090 | 1.00 | 37.73 C |
| ATOM | 956 | CG | ASN | A | 239 | 49.255 | 47.439 | 19.575 | 1.00 | 38.01 C |
| ATOM | 957 | OD1 | ASN | A | 239 | 48.224 | 47.300 | 20.228 | 1.00 | 37.30 O |
| ATOM | 958 | ND2 | ASN | A | 239 | 49.446 | 46.846 | 18.402 | 1.00 | 37.32 N |
| ATOM | 959 | N | THR | A | 240 | 49.629 | 48.776 | 23.018 | 1.00 | 39.33 N |
| ATOM | 960 | CA | THR | A | 240 | 48.678 | 48.832 | 24.121 | 1.00 | 40.33 C |
| ATOM | 961 | C | THR | A | 240 | 47.219 | 48.678 | 23.672 | 1.00 | 42.53 C |
| ATOM | 962 | O | THR | A | 240 | 46.299 | 48.869 | 24.468 | 1.00 | 41.92 O |
| ATOM | 963 | CB | THR | A | 240 | 48.812 | 50.168 | 24.870 | 1.00 | 39.24 C |
| ATOM | 964 | OG1 | THR | A | 240 | 48.634 | 51.242 | 23.940 | 1.00 | 39.26 O |
| ATOM | 965 | CG2 | THR | A | 240 | 50.192 | 50.293 | 25.514 | 1.00 | 37.80 C |
| ATOM | 966 | N | ARG | A | 241 | 47.010 | 48.319 | 22.409 | 1.00 | 44.79 N |
| ATOM | 967 | CA | ARG | A | 241 | 45.659 | 48.177 | 21.876 | 1.00 | 48.48 C |
| ATOM | 968 | C | ARG | A | 241 | 45.165 | 46.738 | 21.739 | 1.00 | 48.69 C |
| ATOM | 969 | O | ARG | A | 241 | 44.291 | 46.305 | 22.487 | 1.00 | 48.51 O |
| ATOM | 970 | CB | ARG | A | 241 | 45.565 | 48.862 | 20.509 | 1.00 | 51.38 C |
| ATOM | 971 | CG | ARG | A | 241 | 45.987 | 50.327 | 20.508 | 1.00 | 56.77 C |
| ATOM | 972 | CD | ARG | A | 241 | 44.854 | 51.258 | 20.917 | 1.00 | 60.32 C |
| ATOM | 973 | NE | ARG | A | 241 | 43.743 | 51.209 | 19.965 | 1.00 | 63.77 N |
| ATOM | 974 | CZ | ARG | A | 241 | 42.827 | 52.166 | 19.829 | 1.00 | 65.29 C |
| ATOM | 975 | NH1 | ARG | A | 241 | 42.885 | 53.260 | 20.583 | 1.00 | 65.45 N |
| ATOM | 976 | NH2 | ARG | A | 241 | 41.850 | 52.030 | 18.939 | 1.00 | 65.16 N |
| ATOM | 977 | N | ASP | A | 242 | 45.724 | 46.006 | 20.781 | 1.00 | 48.65 N |
| ATOM | 978 | CA | ASP | A | 242 | 45.304 | 44.632 | 20.523 | 1.00 | 50.20 C |
| ATOM | 979 | C | ASP | A | 242 | 46.142 | 43.558 | 21.206 | 1.00 | 50.06 C |
| ATOM | 980 | O | ASP | A | 242 | 46.237 | 42.442 | 20.702 | 1.00 | 51.04 O |
| ATOM | 981 | CB | ASP | A | 242 | 45.306 | 44.362 | 19.013 | 1.00 | 49.94 C |
| ATOM | 982 | CG | ASP | A | 242 | 46.696 | 44.458 | 18.404 | 1.00 | 51.08 C |

TABLE 6-continued

| ATOM | 983 | OD1 | ASP | A | 242 | 47.683 | 44.268 | 19.146 | 1.00 | 50.09 | O |
|---|---|---|---|---|---|---|---|---|---|---|---|
| ATOM | 984 | 0D2 | ASP | A | 242 | 46.804 | 44.708 | 17.181 | 1.00 | 51.20 | O |
| ATOM | 985 | N | PHE | A | 243 | 46.732 | 43.879 | 22.353 | 1.00 | 49.77 | N |
| ATOM | 986 | CA | PHE | A | 243 | 47.579 | 42.924 | 23.065 | 1.00 | 49.06 | C |
| ATOM | 987 | C | PHE | A | 243 | 46.889 | 41.647 | 23.549 | 1.00 | 49.87 | C |
| ATOM | 988 | O | PHE | A | 243 | 47.539 | 40.609 | 23.694 | 1.00 | 49.78 | O |
| ATOM | 989 | CB | PHE | A | 243 | 48.274 | 43.617 | 24.242 | 1.00 | 45.99 | C |
| ATOM | 990 | CG | PHE | A | 243 | 47.334 | 44.151 | 25.279 | 1.00 | 44.15 | C |
| ATOM | 991 | CD1 | PHE | A | 243 | 46.841 | 43.323 | 26.283 | 1.00 | 43.69 | C |
| ATOM | 992 | CD2 | PHE | A | 243 | 46.956 | 45.490 | 25.268 | 1.00 | 43.83 | C |
| ATOM | 993 | CE1 | PHE | A | 243 | 45.989 | 43.821 | 27.266 | 1.00 | 42.27 | C |
| ATOM | 994 | CE2 | PHE | A | 243 | 46.103 | 46.001 | 26.247 | 1.00 | 43.52 | C |
| ATOM | 995 | CZ | PHE | A | 243 | 45.619 | 45.163 | 27.249 | 1.00 | 43.49 | C |
| ATOM | 996 | N | ARG | A | 244 | 45.583 | 41.714 | 23.796 | 1.00 | 50.68 | N |
| ATOM | 997 | CA | ARG | A | 244 | 44.852 | 40.537 | 24.260 | 1.00 | 51.51 | C |
| ATOM | 998 | C | ARG | A | 244 | 44.820 | 39.453 | 23.187 | 1.00 | 51.28 | C |
| ATOM | 999 | O | ARG | A | 244 | 44.697 | 38.268 | 23.494 | 1.00 | 51.51 | O |
| ATOM | 1000 | CB | ARG | A | 244 | 43.423 | 40.915 | 24.682 | 1.00 | 52.01 | C |
| ATOM | 1001 | CG | ARG | A | 244 | 43.368 | 41.841 | 25.899 | 1.00 | 52.37 | C |
| ATOM | 1002 | CD | ARG | A | 244 | 41.939 | 42.089 | 26.374 | 1.00 | 53.17 | C |
| ATOM | 1003 | NE | ARG | A | 244 | 41.895 | 43.054 | 27.473 | 1.00 | 54.20 | N |
| ATOM | 1004 | CZ | ARG | A | 244 | 42.125 | 44.359 | 27.337 | 1.00 | 55.49 | C |
| ATOM | 1005 | NH1 | ARG | A | 244 | 42.408 | 44.870 | 26.144 | 1.00 | 54.46 | N |
| ATOM | 1006 | NH2 | ARG | A | 244 | 42.089 | 45.154 | 28.399 | 1.00 | 55.06 | N |
| ATOM | 1007 | N | GLU | A | 245 | 44.935 | 39.859 | 21.928 | 1.00 | 50.95 | N |
| ATOM | 1008 | CA | GLU | A | 245 | 44.940 | 38.906 | 20.826 | 1.00 | 51.31 | C |
| ATOM | 1009 | C | GLU | A | 245 | 46.362 | 38.666 | 20.335 | 1.00 | 50.29 | C |
| ATOM | 1010 | O | GLU | A | 245 | 46.770 | 37.526 | 20.107 | 1.00 | 50.46 | O |
| ATOM | 1011 | CB | GLU | A | 245 | 44.095 | 39.415 | 19.653 | 1.00 | 53.93 | C |
| ATOM | 1012 | CG | GLU | A | 245 | 42.588 | 39.248 | 19.813 | 1.00 | 58.44 | C |
| ATOM | 1013 | CD | GLU | A | 245 | 42.012 | 40.073 | 20.950 | 1.00 | 61.81 | C |
| ATOM | 1014 | OE1 | GLU | A | 245 | 42.234 | 41.309 | 20.972 | 1.00 | 63.52 | O |
| ATOM | 1015 | OE2 | GLU | A | 245 | 41.329 | 39.484 | 21.818 | 1.00 | 63.32 | O |
| ATOM | 1016 | N | ARG | A | 246 | 47.117 | 39.749 | 20.181 | 1.00 | 48.30 | N |
| ATOM | 1017 | CA | ARG | A | 246 | 48.489 | 39.671 | 19.689 | 1.00 | 46.47 | C |
| ATOM | 1018 | C | ARG | A | 246 | 49.447 | 38.897 | 20.599 | 1.00 | 45.04 | C |
| ATOM | 1019 | O | ARG | A | 246 | 50.187 | 38.036 | 20.132 | 1.00 | 44.61 | O |
| ATOM | 1020 | CB | ARG | A | 246 | 49.029 | 41.085 | 19.442 | 1.00 | 45.89 | C |
| ATOM | 1021 | CG | ARG | A | 246 | 50.345 | 41.127 | 18.681 | 1.00 | 45.20 | C |
| ATOM | 1022 | CD | ARG | A | 246 | 50.833 | 42.556 | 18.513 | 1.00 | 44.73 | C |
| ATOM | 1023 | NE | ARG | A | 246 | 49.950 | 43.359 | 17.671 | 1.00 | 43.18 | N |
| ATOM | 1024 | CZ | ARG | A | 246 | 49.880 | 43.265 | 16.347 | 1.00 | 42.54 | C |
| ATOM | 1025 | NH1 | ARG | A | 246 | 50.644 | 42.402 | 15.694 | 1.00 | 41.20 | N |
| ATOM | 1026 | NH2 | ARG | A | 246 | 49.042 | 44.040 | 15.673 | 1.00 | 44.27 | N |
| ATOM | 1027 | N | VAL | A | 247 | 49.435 | 39.193 | 21.894 | 1.00 | 44.31 | N |
| ATOM | 1028 | CA | VAL | A | 247 | 50.335 | 38.509 | 22.819 | 1.00 | 44.71 | C |
| ATOM | 1029 | C | VAL | A | 247 | 50.238 | 36.976 | 22.757 | 1.00 | 45.57 | C |
| ATOM | 1030 | O | VAL | A | 247 | 51.245 | 36.296 | 22.530 | 1.00 | 45.24 | O |
| ATOM | 1031 | CB | VAL | A | 247 | 50.101 | 38.984 | 24.274 | 1.00 | 43.46 | C |
| ATOM | 1032 | CG1 | VAL | A | 247 | 50.894 | 38.123 | 25.244 | 1.00 | 43.08 | C |
| ATOM | 1033 | CG2 | VAL | A | 247 | 50.512 | 40.444 | 24.410 | 1.00 | 43.85 | C |
| ATOM | 1034 | N | PRO | A | 248 | 49.027 | 36.411 | 22.959 | 1.00 | 45.51 | N |
| ATOM | 1035 | CA | PRO | A | 248 | 48.879 | 34.952 | 22.912 | 1.00 | 44.41 | C |
| ATOM | 1036 | C | PRO | A | 248 | 49.439 | 34.367 | 21.624 | 1.00 | 44.05 | C |
| ATOM | 1037 | O | PRO | A | 248 | 50.118 | 33.348 | 21.641 | 1.00 | 44.00 | O |
| ATOM | 1038 | CB | PRO | A | 248 | 47.369 | 34.755 | 23.030 | 1.00 | 45.34 | C |
| ATOM | 1039 | CG | PRO | A | 248 | 46.956 | 35.899 | 23.898 | 1.00 | 45.42 | C |
| ATOM | 1040 | CD | PRO | A | 248 | 47.741 | 37.052 | 23.297 | 1.00 | 44.89 | C |
| ATOM | 1041 | N | ALA | A | 249 | 49.162 | 35.028 | 20.508 | 1.00 | 43.48 | N |
| ATOM | 1042 | CA | ALA | A | 249 | 49.639 | 34.565 | 19.215 | 1.00 | 43.34 | C |
| ATOM | 1043 | C | ALA | A | 249 | 51.167 | 34.583 | 19.129 | 1.00 | 44.16 | C |
| ATOM | 1044 | O | ALA | A | 249 | 51.774 | 33.705 | 18.504 | 1.00 | 43.00 | O |
| ATOM | 1045 | CB | ALA | A | 249 | 49.040 | 35.421 | 18.111 | 1.00 | 42.95 | C |
| ATOM | 1046 | N | LEU | A | 250 | 51.786 | 35.582 | 19.755 | 1.00 | 43.64 | N |
| ATOM | 1047 | CA | LEU | A | 250 | 53.238 | 35.692 | 19.729 | 1.00 | 43.74 | C |
| ATOM | 1048 | C | LEU | A | 250 | 53.862 | 34.647 | 20.643 | 1.00 | 43.57 | C |
| ATOM | 1049 | O | LEU | A | 250 | 54.897 | 34.069 | 20.322 | 1.00 | 41.77 | O |
| ATOM | 1050 | CB | LEU | A | 250 | 53.677 | 37.110 | 20.125 | 1.00 | 43.33 | C |
| ATOM | 1051 | CG | LEU | A | 250 | 53.303 | 38.171 | 19.078 | 1.00 | 43.68 | C |
| ATOM | 1052 | CD1 | LEU | A | 250 | 53.687 | 39.554 | 19.563 | 1.00 | 43.65 | C |
| ATOM | 1053 | CD2 | LEU | A | 250 | 54.001 | 37.858 | 17.761 | 1.00 | 42.84 | C |
| ATOM | 1054 | N | VAL | A | 251 | 53.223 | 34.398 | 21.778 | 1.00 | 44.52 | N |
| ATOM | 1055 | CA | VAL | A | 251 | 53.721 | 33.398 | 22.708 | 1.00 | 47.01 | C |
| ATOM | 1056 | C | VAL | A | 251 | 53.668 | 32.020 | 22.049 | 1.00 | 48.22 | C |
| ATOM | 1057 | O | VAL | A | 251 | 54.659 | 31.289 | 22.047 | 1.00 | 48.12 | O |
| ATOM | 1058 | CB | VAL | A | 251 | 52.883 | 33.364 | 23.993 | 1.00 | 47.37 | C |
| ATOM | 1059 | CG1 | VAL | A | 251 | 53.327 | 32.206 | 24.870 | 1.00 | 48.76 | C |
| ATOM | 1060 | CG2 | VAL | A | 251 | 53.031 | 34.678 | 24.739 | 1.00 | 48.75 | C |
| ATOM | 1061 | N | GLU | A | 252 | 52.512 | 31.676 | 21.483 | 1.00 | 49.02 | N |

TABLE 6-continued

| ATOM | 1062 | CA | GLU | A | 252 | 52.341 | 30.383 | 20.821 | 1.00 | 50.45 | C |
| --- | --- | --- | --- | --- | --- | --- | --- | --- | --- | --- | --- |
| ATOM | 1063 | C | GLU | A | 252 | 53.372 | 30.211 | 19.712 | 1.00 | 48.80 | C |
| ATOM | 1064 | O | GLU | A | 252 | 53.859 | 29.109 | 19.476 | 1.00 | 48.65 | O |
| ATOM | 1065 | CB | GLU | A | 252 | 50.945 | 30.253 | 20.195 | 1.00 | 53.26 | C |
| ATOM | 1066 | CG | GLU | A | 252 | 49.795 | 30.809 | 21.010 | 1.00 | 58.83 | C |
| ATOM | 1067 | CD | GLU | A | 252 | 49.648 | 30.175 | 22.379 | 1.00 | 62.50 | C |
| ATOM | 1068 | OE1 | GLU | A | 252 | 48.721 | 30.596 | 23.108 | 1.00 | 64.11 | O |
| ATOM | 1069 | OE2 | GLU | A | 252 | 50.444 | 29.267 | 22.727 | 1.00 | 64.32 | O |
| ATOM | 1070 | N | ALA | A | 253 | 53.688 | 31.303 | 19.022 | 1.00 | 47.24 | N |
| ATOM | 1071 | CA | ALA | A | 253 | 54.658 | 31.270 | 17.933 | 1.00 | 45.47 | C |
| ATOM | 1072 | C | ALA | A | 253 | 56.075 | 31.044 | 18.457 | 1.00 | 44.43 | C |
| ATOM | 1073 | O | ALA | A | 253 | 56.988 | 30.749 | 17.686 | 1.00 | 43.74 | O |
| ATOM | 1074 | CB | ALA | A | 253 | 54.591 | 32.563 | 17.131 | 1.00 | 45.15 | C |
| ATOM | 1075 | N | GLY | A | 254 | 56.253 | 31.184 | 19.769 | 1.00 | 43.76 | N |
| ATOM | 1076 | CA | GLY | A | 254 | 57.562 | 30.968 | 20.366 | 1.00 | 43.81 | C |
| ATOM | 1077 | C | GLY | A | 254 | 58.415 | 32.207 | 20.610 | 1.00 | 43.78 | C |
| ATOM | 1078 | O | GLY | A | 254 | 59.635 | 32.103 | 20.751 | 1.00 | 43.49 | O |
| ATOM | 1079 | N | ALA | A | 255 | 57.793 | 33.381 | 20.658 | 1.00 | 42.53 | N |
| ATOM | 1080 | CA | ALA | A | 255 | 58.540 | 34.611 | 20.902 | 1.00 | 40.96 | C |
| ATOM | 1081 | C | ALA | A | 255 | 59.227 | 34.506 | 22.263 | 1.00 | 39.56 | C |
| ATOM | 1082 | O | ALA | A | 255 | 58.595 | 34.154 | 23.260 | 1.00 | 40.08 | O |
| ATOM | 1083 | CB | ALA | A | 255 | 57.603 | 35.805 | 20.871 | 1.00 | 40.32 | C |
| ATOM | 1084 | N | ASP | A | 256 | 60.520 | 34.812 | 22.307 | 1.00 | 38.45 | N |
| ATOM | 1085 | CA | ASP | A | 256 | 61.274 | 34.723 | 23.557 | 1.00 | 38.35 | C |
| ATOM | 1086 | C | ASP | A | 256 | 61.088 | 35.928 | 24.478 | 1.00 | 37.56 | C |
| ATOM | 1087 | O | ASP | A | 256 | 61.159 | 35.802 | 25.700 | 1.00 | 36.65 | O |
| ATOM | 1088 | CB | ASP | A | 256 | 62.752 | 34.522 | 23.247 | 1.00 | 38.22 | C |
| ATOM | 1089 | CG | ASP | A | 256 | 63.007 | 33.235 | 22.497 | 1.00 | 40.05 | C |
| ATOM | 1090 | OD1 | ASP | A | 256 | 62.884 | 32.161 | 23.123 | 1.00 | 42.66 | O |
| ATOM | 1091 | OD2 | ASP | A | 256 | 63.313 | 33.292 | 21.286 | 1.00 | 37.79 | O |
| ATOM | 1092 | N | VAL | A | 257 | 60.847 | 37.093 | 23.890 | 1.00 | 36.57 | N |
| ATOM | 1093 | CA | VAL | A | 257 | 60.647 | 38.302 | 24.676 | 1.00 | 35.73 | C |
| ATOM | 1094 | C | VAL | A | 257 | 59.773 | 39.278 | 23.903 | 1.00 | 35.41 | C |
| ATOM | 1095 | O | VAL | A | 257 | 59.755 | 39.265 | 22.678 | 1.00 | 36.12 | O |
| ATOM | 1096 | CB | VAL | A | 257 | 61.999 | 38.979 | 25.019 | 1.00 | 34.09 | C |
| ATOM | 1097 | CG1 | VAL | A | 257 | 62.725 | 39.352 | 23.746 | 1.00 | 33.95 | C |
| ATOM | 1098 | CG2 | VAL | A | 257 | 61.771 | 40.206 | 25.889 | 1.00 | 33.54 | C |
| ATOM | 1099 | N | LEU | A | 258 | 59.040 | 40.113 | 24.626 | 1.00 | 34.36 | N |
| ATOM | 1100 | CA | LEU | A | 258 | 58.173 | 41.095 | 23.993 | 1.00 | 35.77 | C |
| ATOM | 1101 | C | LEU | A | 258 | 58.597 | 42.498 | 24.423 | 1.00 | 35.65 | C |
| ATOM | 1102 | O | LEU | A | 258 | 59.376 | 42.661 | 25.359 | 1.00 | 36.03 | O |
| ATOM | 1103 | CB | LEU | A | 258 | 56.713 | 40.857 | 24.402 | 1.00 | 34.23 | C |
| ATOM | 1104 | CG | LEU | A | 258 | 56.155 | 39.441 | 24.206 | 1.00 | 35.31 | C |
| ATOM | 1105 | CD1 | LEU | A | 258 | 54.719 | 39.402 | 24.682 | 1.00 | 38.42 | C |
| ATOM | 1106 | CD2 | LEU | A | 258 | 56.245 | 39.027 | 22.747 | 1.00 | 34.36 | C |
| ATOM | 1107 | N | CYS | A | 259 | 58.100 | 43.509 | 23.721 | 1.00 | 36.29 | N |
| ATOM | 1108 | CA | CYS | A | 259 | 58.403 | 44.886 | 24.080 | 1.00 | 34.94 | C |
| ATOM | 1109 | C | CYS | A | 259 | 57.318 | 45.825 | 23.576 | 1.00 | 34.40 | C |
| ATOM | 1110 | O | CYS | A | 259 | 57.033 | 45.867 | 22.377 | 1.00 | 33.93 | O |
| ATOM | 1111 | CB | CYS | A | 259 | 59.756 | 45.329 | 23.512 | 1.00 | 34.49 | C |
| ATOM | 1112 | SG | CYS | A | 259 | 60.296 | 46.925 | 24.191 | 1.00 | 34.45 | S |
| ATOM | 1113 | N | ILE | A | 260 | 56.712 | 46.568 | 24.496 | 1.00 | 34.72 | N |
| ATOM | 1114 | CA | ILE | A | 260 | 55.682 | 47.526 | 24.126 | 1.00 | 36.19 | C |
| ATOM | 1115 | C | ILE | A | 260 | 56.391 | 48.632 | 23.350 | 1.00 | 37.93 | C |
| ATOM | 1116 | O | ILE | A | 260 | 57.355 | 49.223 | 23.829 | 1.00 | 37.54 | O |
| ATOM | 1117 | CB | ILE | A | 260 | 55.003 | 48.122 | 25.364 | 1.00 | 35.39 | C |
| ATOM | 1118 | CG1 | ILE | A | 260 | 54.471 | 46.988 | 26.247 | 1.00 | 34.45 | C |
| ATOM | 1119 | CG2 | ILE | A | 260 | 53.868 | 49.052 | 24.937 | 1.00 | 34.98 | C |
| ATOM | 1120 | CD1 | ILE | A | 260 | 53.866 | 47.456 | 27.556 | 1.00 | 32.91 | C |
| ATOM | 1121 | N | ASP | A | 261 | 55.905 | 48.886 | 22.143 | 1.00 | 39.60 | N |
| ATOM | 1122 | CA | ASP | A | 261 | 56.472 | 49.873 | 21.236 | 1.00 | 40.88 | C |
| ATOM | 1123 | C | ASP | A | 261 | 55.700 | 51.197 | 21.318 | 1.00 | 41.39 | C |
| ATOM | 1124 | O | ASP | A | 261 | 54.549 | 51.275 | 20.887 | 1.00 | 42.16 | O |
| ATOM | 1125 | CB | ASP | A | 261 | 56.422 | 49.266 | 19.826 | 1.00 | 42.12 | C |
| ATOM | 1126 | CG | ASP | A | 261 | 56.977 | 50.179 | 18.756 | 1.00 | 43.34 | C |
| ATOM | 1127 | OD1 | ASP | A | 261 | 57.842 | 51.025 | 19.061 | 1.00 | 43.64 | O |
| ATOM | 1128 | OD2 | ASP | A | 261 | 56.553 | 50.025 | 17.591 | 1.00 | 42.92 | O |
| ATOM | 1129 | N | SER | A | 262 | 56.328 | 52.232 | 21.881 | 1.00 | 40.43 | N |
| ATOM | 1130 | CA | SER | A | 262 | 55.673 | 53.535 | 22.030 | 1.00 | 39.93 | C |
| ATOM | 1131 | C | SER | A | 262 | 56.679 | 54.678 | 22.197 | 1.00 | 39.85 | C |
| ATOM | 1132 | O | SER | A | 262 | 57.777 | 54.464 | 22.711 | 1.00 | 40.98 | O |
| ATOM | 1133 | CB | SER | A | 262 | 54.733 | 53.492 | 23.242 | 1.00 | 40.30 | C |
| ATOM | 1134 | OG | SER | A | 262 | 54.167 | 54.761 | 23.518 | 1.00 | 40.02 | O |
| ATOM | 1135 | N | SER | A | 263 | 56.305 | 55.888 | 21.778 | 1.00 | 38.66 | N |
| ATOM | 2136 | CA | SER | A | 263 | 57.202 | 57.040 | 22.904 | 1.00 | 39.38 | C |
| ATOM | 1137 | C | SER | A | 263 | 57.161 | 57.641 | 23.302 | 1.00 | 38.48 | C |
| ATOM | 1138 | O | SER | A | 263 | 58.107 | 58.300 | 23.733 | 1.00 | 40.33 | O |
| ATOM | 1139 | CE | SER | A | 263 | 56.867 | 58.121 | 20.869 | 1.00 | 38.57 | C |
| ATOM | 1140 | OG | SER | A | 263 | 55.566 | 58.644 | 21.047 | 1.00 | 45.09 | O |

TABLE 6-continued

| | | | | | | | | | | |
|---|---|---|---|---|---|---|---|---|---|---|
| ATOM | 1141 | N | ASP | A | 264 | 56.057 | 57.425 | 24.005 | 1.00 | 35.74 N |
| ATOM | 1142 | CA | ASP | A | 264 | 55.913 | 57.920 | 25.366 | 1.00 | 33.57 C |
| ATOM | 1143 | C | ASP | A | 264 | 55.358 | 56.776 | 26.217 | 1.00 | 33.27 C |
| ATOM | 1144 | O | ASP | A | 264 | 54.144 | 56.587 | 26.313 | 1.00 | 32.17 O |
| ATOM | 1145 | CB | ASP | A | 264 | 54.975 | 59.136 | 25.399 | 1.00 | 32.37 C |
| ATOM | 1146 | CG | ASP | A | 264 | 54.581 | 59.537 | 26.812 | 1.00 | 32.47 C |
| ATOM | 1147 | OD1 | ASP | A | 264 | 55.252 | 59.113 | 27.781 | 1.00 | 30.31 O |
| ATOM | 1148 | OD2 | ASP | A | 264 | 53.598 | 60.287 | 26.957 | 1.00 | 32.93 O |
| ATOM | 1149 | N | GLY | A | 265 | 56.265 | 56.014 | 26.822 | 1.00 | 32.50 N |
| ATOM | 1150 | CA | GLY | A | 265 | 55.872 | 54.888 | 27.649 | 1.00 | 32.54 C |
| ATOM | 1151 | C | GLY | A | 265 | 55.400 | 55.262 | 29.039 | 1.00 | 32.72 C |
| ATOM | 1152 | O | GLY | A | 265 | 54.959 | 54.397 | 29.799 | 1.00 | 33.52 O |
| ATOM | 1153 | N | PHE | A | 266 | 55.502 | 56.539 | 29.390 | 1.00 | 31.81 N |
| ATOM | 1154 | CA | PHE | A | 266 | 55.057 | 56.985 | 30.705 | 1.00 | 32.42 C |
| ATOM | 1155 | C | PHE | A | 266 | 53.540 | 57.082 | 30.577 | 1.00 | 33.52 C |
| ATOM | 1156 | O | PHE | A | 266 | 52.967 | 58.166 | 30.582 | 1.00 | 31.71 O |
| ATOM | 1157 | CS | PHE | A | 266 | 55.664 | 58.352 | 31.043 | 1.00 | 30.79 C |
| ATOM | 1158 | CG | PHE | A | 266 | 55.742 | 58.641 | 32.525 | 1.00 | 32.48 C |
| ATOM | 1159 | CD1 | PHE | A | 266 | 55.019 | 57.877 | 33.450 | 1.00 | 31.15 C |
| ATOM | 1160 | CD2 | PHE | A | 266 | 56.534 | 59.690 | 32.997 | 1.00 | 31.72 C |
| ATOM | 1161 | CE1 | PHE | A | 266 | 55.085 | 58.153 | 34.823 | 1.00 | 31.90 C |
| ATOM | 1162 | CE2 | PHE | A | 266 | 56.611 | 59.976 | 34.361 | 1.00 | 31.70 C |
| ATOM | 1163 | CZ | PHE | A | 266 | 55.883 | 59.206 | 35.281 | 1.00 | 32.01 C |
| ATOM | 1164 | N | SER | A | 267 | 52.896 | 55.922 | 30.468 | 1.00 | 35.51 N |
| ATOM | 1165 | CA | SER | A | 267 | 51.455 | 55.859 | 30.272 | 1.00 | 35.95 C |
| ATOM | 1166 | C | SER | A | 267 | 50.735 | 54.762 | 31.045 | 1.00 | 36.73 C |
| ATOM | 1167 | O | SER | A | 267 | 51.233 | 53.644 | 31.187 | 1.00 | 34.99 O |
| ATOM | 1168 | CE | SER | A | 267 | 51.169 | 55.671 | 28.785 | 1.00 | 36.57 C |
| ATOM | 1169 | OG | SER | A | 267 | 49.795 | 55.428 | 28.553 | 1.00 | 40.30 O |
| ATOM | 1170 | N | GLU | A | 268 | 49.543 | 55.089 | 31.523 | 1.00 | 37.27 N |
| ATOM | 1171 | CA | GLU | A | 268 | 48.736 | 54.133 | 32.252 | 1.00 | 38.55 C |
| ATOM | 1172 | C | GLU | A | 268 | 48.437 | 52.945 | 31.331 | 1.00 | 38.48 C |
| ATOM | 1173 | O | GLU | A | 268 | 48.204 | 51.830 | 31.797 | 1.00 | 38.40 O |
| ATOM | 1174 | CB | GLU | A | 268 | 47.436 | 54.793 | 32.719 | 1.00 | 39.99 C |
| ATOM | 1175 | CG | GLU | A | 268 | 46.601 | 53.903 | 33.614 | 1.00 | 44.01 C |
| ATOM | 1176 | CD | GLU | A | 268 | 45.427 | 54.627 | 34.254 | 1.00 | 46.54 C |
| ATOM | 1177 | OE1 | GLU | A | 268 | 44.703 | 53.969 | 35.037 | 1.00 | 48.88 O |
| ATOM | 1178 | OE2 | GLU | A | 268 | 45.230 | 55.836 | 33.983 | 1.00 | 44.63 O |
| ATOM | 1179 | N | TRP | A | 269 | 48.453 | 53.184 | 30.022 | 1.00 | 38.21 N |
| ATOM | 1180 | CA | TRP | A | 269 | 48.198 | 52.114 | 29.061 | 1.00 | 39.86 C |
| ATOM | 1181 | C | TRP | A | 269 | 49.267 | 51.024 | 29.131 | 1.00 | 39.35 C |
| ATOM | 1182 | O | TRP | A | 269 | 48.967 | 49.849 | 28.917 | 1.00 | 40.08 O |
| ATOM | 1183 | CE | TRP | A | 269 | 48.129 | 52.657 | 27.630 | 1.00 | 41.72 C |
| ATOM | 1184 | CG | TRP | A | 269 | 46.968 | 53.561 | 27.393 | 1.00 | 46.52 C |
| ATOM | 1185 | CD1 | TRP | A | 269 | 47.004 | 54.914 | 27.207 | 1.00 | 46.39 C |
| ATOM | 1186 | CD2 | TRP | A | 269 | 45.585 | 53.186 | 27.347 | 1.00 | 47.71 C |
| ATOM | 1187 | NE1 | TRP | A | 269 | 45.731 | 55.404 | 27.049 | 1.00 | 47.84 N |
| ATOM | 1188 | CE2 | TRP | A | 269 | 44.841 | 54.366 | 27.130 | 1.00 | 48.66 C |
| ATOM | 1189 | CE3 | TRP | A | 269 | 44.903 | 51.969 | 27.470 | 1.00 | 49.25 C |
| ATOM | 1190 | CZ2 | TRP | A | 269 | 43.445 | 54.364 | 27.032 | 1.00 | 49.71 C |
| ATOM | 1191 | CZ3 | TRP | A | 269 | 43.513 | 51.966 | 27.373 | 1.00 | 49.48 C |
| ATOM | 1192 | CH2 | TRP | A | 269 | 42.802 | 53.158 | 27.156 | 1.00 | 50.26 C |
| ATOM | 1193 | N | GLN | A | 270 | 50.512 | 51.401 | 29.411 | 1.00 | 37.64 N |
| ATOM | 1194 | CA | GLN | A | 270 | 51.575 | 50.401 | 29.506 | 1.00 | 37.63 C |
| ATOM | 1195 | C | GLN | A | 270 | 51.402 | 49.609 | 30.803 | 1.00 | 37.10 C |
| ATOM | 1196 | O | GLN | A | 270 | 51.661 | 48.410 | 30.838 | 1.00 | 37.39 O |
| ATOM | 1197 | CB | GLN | A | 270 | 52.972 | 51.053 | 29.461 | 1.00 | 35.59 C |
| ATOM | 1198 | CG | GLN | A | 270 | 53.233 | 51.888 | 28.205 | 1.00 | 34.03 C |
| ATOM | 1199 | CD | GLN | A | 270 | 54.518 | 51.520 | 27.470 | 1.00 | 33.74 C |
| ATOM | 1200 | OE1 | GLN | A | 270 | 55.417 | 50.883 | 28.024 | 1.00 | 31.90 O |
| ATOM | 1201 | NE2 | GLN | A | 270 | 54.615 | 51.943 | 26.217 | 1.00 | 31.81 N |
| ATOM | 1202 | N | LYS | A | 271 | 50.955 | 50.276 | 31.864 | 1.00 | 37.76 N |
| ATOM | 1203 | CA | LYS | A | 271 | 50.737 | 49.592 | 33.135 | 1.00 | 39.58 C |
| ATOM | 1204 | C | LYS | A | 271 | 49.646 | 48.532 | 32.968 | 1.00 | 39.28 C |
| ATOM | 1205 | O | LYS | A | 271 | 49.780 | 47.412 | 33.455 | 1.00 | 39.33 O |
| ATOM | 1206 | CB | LYS | A | 271 | 50.320 | 50.574 | 34.228 | 1.00 | 41.44 C |
| ATOM | 1207 | CG | LYS | A | 271 | 50.086 | 49.901 | 35.578 | 1.00 | 43.95 C |
| ATOM | 1208 | CD | LYS | A | 271 | 49.844 | 50.909 | 36.688 | 1.00 | 46.05 C |
| ATOM | 1209 | CE | LYS | A | 271 | 49.756 | 50.209 | 38.044 | 1.00 | 48.90 C |
| ATOM | 1210 | NZ | LYS | A | 271 | 49.762 | 51.161 | 39.201 | 1.00 | 50.93 N |
| ATOM | 1211 | N | ILE | A | 272 | 48.574 | 48.896 | 32.269 | 1.00 | 38.91 N |
| ATOM | 1212 | CA | ILE | A | 272 | 47.462 | 47.984 | 32.029 | 1.00 | 39.12 C |
| ATOM | 1213 | C | ILE | A | 272 | 47.926 | 46.793 | 31.198 | 1.00 | 39.33 C |
| ATOM | 1214 | O | ILE | A | 272 | 47.616 | 45.654 | 31.517 | 1.00 | 40.20 O |
| ATOM | 1215 | CB | ILE | A | 272 | 46.297 | 48.701 | 31.300 | 1.00 | 38.48 C |
| ATOM | 1216 | CG1 | ILE | A | 272 | 45.626 | 49.687 | 32.257 | 1.00 | 38.00 C |
| ATOM | 1217 | CG2 | ILE | A | 272 | 45.286 | 47.682 | 30.781 | 1.00 | 38.67 C |
| ATOM | 1218 | CD1 | ILE | A | 272 | 44.609 | 50.606 | 31.596 | 1.00 | 39.18 C |
| ATOM | 1219 | N | THR | A | 273 | 48.685 | 47.061 | 30.143 | 1.00 | 38.73 N |

TABLE 6-continued

| ATOM | 1220 | CA  | THR | A | 273 | 49.184 | 45.999 | 29.287 | 1.00 | 38.01 | C |
| ATOM | 1221 | C   | THR | A | 273 | 50.089 | 45.016 | 30.030 | 1.00 | 39.07 | C |
| ATOM | 1222 | O   | THR | A | 273 | 49.935 | 43.802 | 29.896 | 1.00 | 38.49 | O |
| ATOM | 1223 | CB  | THR | A | 273 | 49.959 | 46.577 | 28.091 | 1.00 | 37.70 | C |
| ATOM | 1224 | OG1 | THR | A | 273 | 49.086 | 47.409 | 27.316 | 1.00 | 37.99 | O |
| ATOM | 1225 | CG2 | THR | A | 273 | 50.494 | 45.458 | 27.212 | 1.00 | 36.21 | C |
| ATOM | 1226 | N   | ILE | A | 274 | 51.045 | 45.537 | 30.797 | 1.00 | 38.89 | N |
| ATOM | 1227 | CA  | ILE | A | 274 | 51.958 | 44.681 | 31.547 | 1.00 | 38.36 | C |
| ATOM | 1228 | C   | ILE | A | 274 | 51.168 | 43.894 | 32.586 | 1.00 | 39.27 | C |
| ATOM | 1229 | O   | ILE | A | 274 | 51.452 | 42.726 | 32.847 | 1.00 | 37.60 | O |
| ATOM | 1230 | CB  | ILE | A | 274 | 53.040 | 45.507 | 32.277 | 1.00 | 38.10 | C |
| ATOM | 1231 | CG1 | ILE | A | 274 | 53.911 | 46.250 | 31.259 | 1.00 | 38.10 | C |
| ATOM | 1232 | CG2 | ILE | A | 274 | 53.887 | 44.588 | 33.163 | 1.00 | 37.28 | C |
| ATOM | 1233 | CD1 | ILE | A | 274 | 54.879 | 47.247 | 31.888 | 1.00 | 37.22 | C |
| ATOM | 1234 | N   | GLY | A | 275 | 50.177 | 44.547 | 33.182 | 1.00 | 39.95 | N |
| ATOM | 1235 | CA  | GLY | A | 275 | 49.361 | 43.884 | 34.183 | 1.00 | 41.68 | C |
| ATOM | 1236 | C   | GLY | A | 275 | 48.607 | 42.702 | 33.600 | 1.00 | 41.85 | C |
| ATOM | 1237 | O   | GLY | A | 275 | 48.576 | 41.622 | 34.187 | 1.00 | 42.65 | O |
| ATOM | 1238 | N   | TRP | A | 276 | 48.002 | 42.904 | 32.437 | 1.00 | 41.82 | N |
| ATOM | 1239 | CA  | TRP | A | 276 | 47.242 | 41.847 | 31.785 | 1.00 | 42.57 | C |
| ATOM | 1240 | C   | TRP | A | 276 | 48.144 | 40.658 | 31.487 | 1.00 | 43.64 | C |
| ATOM | 1241 | O   | TRP | A | 276 | 47.707 | 39.505 | 31.545 | 1.00 | 42.42 | O |
| ATOM | 1242 | CB  | TRP | A | 276 | 46.641 | 42.356 | 30.479 | 1.00 | 42.84 | C |
| ATOM | 1243 | CG  | TRP | A | 276 | 45.770 | 41.356 | 29.809 | 1.00 | 43.77 | C |
| ATOM | 1244 | CD1 | TRP | A | 276 | 44.431 | 41.168 | 30.008 | 1.00 | 44.10 | C |
| ATOM | 1245 | CD2 | TRP | A | 276 | 46.170 | 40.390 | 28.829 | 1.00 | 44.12 | C |
| ATOM | 1246 | NE1 | TRP | A | 276 | 43.972 | 40.146 | 29.209 | 1.00 | 43.95 | N |
| ATOM | 1247 | CE2 | TRP | A | 276 | 45.018 | 39.651 | 28.475 | 1.00 | 44.37 | C |
| ATOM | 1248 | CE3 | TRP | A | 276 | 47.391 | 40.077 | 28.216 | 1.00 | 44.62 | C |
| ATOM | 1249 | CZ2 | TRP | A | 276 | 45.049 | 38.620 | 27.533 | 1.00 | 44.03 | C |
| ATOM | 1250 | CZ3 | TRP | A | 276 | 47.424 | 39.049 | 27.278 | 1.00 | 44.60 | C |
| ATOM | 1251 | CH2 | TRP | A | 276 | 46.256 | 38.333 | 26.946 | 1.00 | 44.88 | C |
| ATOM | 1252 | N   | ILE | A | 277 | 49.401 | 40.945 | 31.159 | 1.00 | 43.10 | N |
| ATOM | 1253 | CA  | ILE | A | 277 | 50.366 | 39.899 | 30.849 | 1.00 | 43.16 | C |
| ATOM | 1254 | C   | ILE | A | 277 | 50.781 | 39.127 | 32.101 | 1.00 | 44.32 | C |
| ATOM | 1255 | O   | ILE | A | 277 | 50.872 | 37.901 | 32.079 | 1.00 | 43.89 | O |
| ATOM | 1256 | CB  | ILE | A | 277 | 51.619 | 40.490 | 30.160 | 1.00 | 42.16 | C |
| ATOM | 1257 | CG1 | ILE | A | 277 | 51.249 | 40.985 | 28.759 | 1.00 | 40.86 | C |
| ATOM | 1258 | CG2 | ILE | A | 277 | 52.724 | 39.444 | 30.084 | 1.00 | 41.70 | C |
| ATOM | 1259 | CD1 | ILE | A | 277 | 52.370 | 41.677 | 28.027 | 1.00 | 39.92 | C |
| ATOM | 1260 | N   | ARG | A | 278 | 51.029 | 39.845 | 33.190 | 1.00 | 45.51 | N |
| ATOM | 1261 | CA  | ARG | A | 278 | 51.427 | 39.217 | 34.445 | 1.00 | 47.63 | C |
| ATOM | 1262 | C   | ARG | A | 278 | 50.313 | 38.350 | 35.026 | 1.00 | 49.58 | C |
| ATOM | 1263 | O   | ARG | A | 278 | 50.570 | 37.299 | 35.617 | 1.00 | 49.82 | O |
| ATOM | 1264 | CB  | ARG | A | 278 | 51.815 | 40.287 | 35.466 | 1.00 | 46.39 | C |
| ATOM | 1265 | CG  | ARG | A | 278 | 53.125 | 40.967 | 35.172 | 1.00 | 44.78 | C |
| ATOM | 1266 | CD  | ARG | A | 278 | 54.320 | 40.087 | 35.522 | 1.00 | 43.71 | C |
| ATOM | 1267 | NE  | ARG | A | 278 | 55.551 | 40.701 | 35.032 | 1.00 | 42.04 | N |
| ATOM | 1268 | CZ  | ARG | A | 278 | 56.199 | 40.311 | 33.942 | 1.00 | 40.35 | C |
| ATOM | 1269 | NH1 | ARG | A | 278 | 55.751 | 39.287 | 33.229 | 1.00 | 38.71 | N |
| ATOM | 1270 | NH2 | ARG | A | 278 | 57.272 | 40.976 | 33.536 | 1.00 | 39.83 | N |
| ATOM | 1271 | N   | GLU | A | 279 | 49.077 | 38.801 | 34.853 | 1.00 | 51.53 | N |
| ATOM | 1272 | CA  | GLU | A | 279 | 47.908 | 38.094 | 35.359 | 1.00 | 53.86 | C |
| ATOM | 1273 | C   | GLU | A | 279 | 47.596 | 36.819 | 34.575 | 1.00 | 53.60 | C |
| ATOM | 1274 | O   | GLU | A | 279 | 47.070 | 35.854 | 35.127 | 1.00 | 53.73 | O |
| ATOM | 1275 | CB  | GLU | A | 279 | 46.703 | 39.048 | 35.343 | 1.00 | 56.33 | C |
| ATOM | 1276 | CG  | GLU | A | 279 | 45.337 | 38.391 | 35.440 | 1.00 | 61.52 | C |
| ATOM | 1277 | CD  | GLU | A | 279 | 44.917 | 37.730 | 34.137 | 1.00 | 64.89 | C |
| ATOM | 1278 | OE1 | GLU | A | 279 | 44.882 | 38.429 | 33.096 | 1.00 | 66.72 | O |
| ATOM | 1279 | OE2 | GLU | A | 279 | 44.623 | 36.512 | 34.154 | 1.00 | 66.94 | O |
| ATOM | 1280 | N   | LYS | A | 280 | 47.942 | 36.813 | 33.294 | 1.00 | 53.24 | N |
| ATOM | 1281 | CA  | LYS | A | 280 | 47.672 | 35.671 | 32.432 | 1.00 | 53.14 | C |
| ATOM | 1282 | C   | LYS | A | 280 | 48.863 | 34.724 | 32.294 | 1.00 | 52.81 | C |
| ATOM | 1283 | O   | LYE | A | 280 | 48.685 | 33.537 | 32.029 | 1.00 | 52.92 | O |
| ATOM | 1284 | CE  | LYS | A | 280 | 47.250 | 36.182 | 31.049 | 1.00 | 55.15 | C |
| ATOM | 1285 | CG  | LYS | A | 280 | 46.435 | 35.209 | 30.199 | 1.00 | 57.74 | C |
| ATOM | 1286 | CD  | LYS | A | 280 | 47.296 | 34.157 | 29.519 | 1.00 | 59.91 | C |
| ATOM | 1287 | CE  | LYS | A | 280 | 46.441 | 33.170 | 28.715 | 1.00 | 61.61 | C |
| ATOM | 1288 | NZ  | LYS | A | 280 | 45.645 | 33.828 | 27.634 | 1.00 | 61.74 | N |
| ATOM | 1289 | N   | TYR | A | 281 | 50.074 | 35.241 | 32.490 | 1.00 | 51.29 | N |
| ATOM | 1290 | CA  | TYR | A | 281 | 51.273 | 34.426 | 32.338 | 1.00 | 47.99 | C |
| ATOM | 1291 | C   | TYR | A | 281 | 52.260 | 34.496 | 33.494 | 1.00 | 46.98 | C |
| ATOM | 1292 | O   | TYR | A | 281 | 53.268 | 33.794 | 33.485 | 1.00 | 46.65 | O |
| ATOM | 1293 | CB  | TYR | A | 281 | 52.016 | 34.835 | 31.066 | 1.00 | 47.79 | C |
| ATOM | 1294 | CG  | TYR | A | 281 | 51.239 | 34.703 | 29.778 | 1.00 | 46.17 | C |
| ATOM | 1295 | CD1 | TYR | A | 281 | 51.086 | 33.465 | 29.154 | 1.00 | 46.76 | C |
| ATOM | 1296 | CD2 | TYR | A | 281 | 50.699 | 35.828 | 29.153 | 1.00 | 45.95 | C |
| ATOM | 1297 | CE1 | TYR | A | 281 | 50.420 | 33.353 | 27.930 | 1.00 | 46.42 | C |
| ATOM | 1298 | CE2 | TYR | A | 281 | 50.032 | 35.729 | 27.939 | 1.00 | 45.43 | C |

TABLE 6-continued

| ATOM | 1299 | CZ | TYR | A | 281 | 49.897 | 34.492 | 27.330 | 1.00 | 46.84 | C |
| ATOM | 1300 | OH | TYR | A | 281 | 49.255 | 34.401 | 26.118 | 1.00 | 47.66 | O |
| ATOM | 1301 | N | GLY | A | 282 | 51.990 | 35.336 | 34.484 | 1.00 | 46.78 | N |
| ATOM | 1302 | CA | GLY | A | 282 | 52.926 | 35.458 | 35.588 | 1.00 | 46.99 | C |
| ATOM | 1303 | C | GLY | A | 282 | 54.252 | 35.993 | 35.064 | 1.00 | 48.06 | C |
| ATOM | 1304 | O | GLY | A | 282 | 54.270 | 36.784 | 34.122 | 1.00 | 45.90 | O |
| ATOM | 1305 | N | ASP | A | 283 | 55.362 | 35.566 | 35.660 | 1.00 | 49.43 | N |
| ATOM | 1306 | CA | ASP | A | 283 | 56.682 | 36.019 | 35.223 | 1.00 | 50.90 | C |
| ATOM | 1307 | C | ASP | A | 283 | 57.290 | 35.115 | 34.146 | 1.00 | 50.49 | C |
| ATOM | 1308 | O | ASP | A | 283 | 58.501 | 35.117 | 33.940 | 1.00 | 51.46 | O |
| ATOM | 1309 | CB | ASP | A | 283 | 57.637 | 36.099 | 36.418 | 1.00 | 52.54 | C |
| ATOM | 1310 | CG | ASP | A | 283 | 57.266 | 37.208 | 37.395 | 1.00 | 56.76 | C |
| ATOM | 1311 | OD1 | ASP | A | 283 | 57.213 | 38.387 | 36.974 | 1.00 | 57.47 | O |
| ATOM | 1312 | OD2 | ASP | A | 283 | 57.034 | 36.903 | 38.587 | 1.00 | 57.67 | O |
| ATOM | 1313 | N | LYS | A | 284 | 56.452 | 34.354 | 33.450 | 1.00 | 50.15 | N |
| ATOM | 1314 | CA | LYS | A | 284 | 56.935 | 33.443 | 32.412 | 1.00 | 50.38 | C |
| ATOM | 1315 | C | LYS | A | 284 | 57.073 | 34.116 | 31.052 | 1.00 | 48.98 | C |
| ATOM | 1316 | O | LYS | A | 284 | 57.780 | 33.632 | 30.168 | 1.00 | 48.72 | O |
| ATOM | 1317 | CB | LYS | A | 284 | 56.003 | 32.229 | 32.297 | 1.00 | 53.78 | C |
| ATOM | 1318 | CG | LYS | A | 284 | 56.138 | 31.226 | 33.449 | 1.00 | 58.18 | C |
| ATOM | 1319 | CD | LYS | A | 284 | 55.845 | 31.868 | 34.802 | 1.00 | 60.71 | C |
| ATOM | 1320 | CE | LYS | A | 284 | 56.104 | 30.899 | 35.950 | 1.00 | 63.62 | C |
| ATOM | 1321 | NZ | LYS | A | 284 | 55.874 | 31.551 | 37.276 | 1.00 | 64.97 | N |
| ATOM | 1322 | N | VAL | A | 285 | 56.374 | 35.227 | 30.880 | 1.00 | 46.54 | N |
| ATOM | 1323 | CA | VAL | A | 285 | 56.445 | 35.969 | 29.634 | 1.00 | 43.33 | C |
| ATOM | 1324 | C | VAL | A | 285 | 57.170 | 37.270 | 29.950 | 1.00 | 41.39 | C |
| ATOM | 1325 | O | VAL | A | 285 | 56.759 | 38.019 | 30.840 | 1.00 | 40.81 | O |
| ATOM | 1326 | CB | VAL | A | 285 | 55.039 | 36.252 | 29.086 | 1.00 | 43.01 | C |
| ATOM | 1327 | CG1 | VAL | A | 285 | 55.122 | 37.183 | 27.887 | 1.00 | 42.67 | C |
| ATOM | 1328 | CG2 | VAL | A | 285 | 54.380 | 34.936 | 28.690 | 1.00 | 42.46 | C |
| ATOM | 1329 | N | LYS | A | 286 | 58.261 | 37.520 | 29.234 | 1.00 | 38.50 | N |
| ATOM | 1330 | CA | LYS | A | 286 | 59.060 | 38.720 | 29.451 | 1.00 | 36.37 | C |
| ATOM | 1331 | C | LYS | A | 286 | 58.594 | 39.861 | 28.556 | 1.00 | 34.87 | C |
| ATOM | 1332 | O | LYS | A | 286 | 58.383 | 39.680 | 27.359 | 1.00 | 34.64 | O |
| ATOM | 1333 | CB | LYS | A | 286 | 60.541 | 38.417 | 29.193 | 1.00 | 34.83 | C |
| ATOM | 1334 | CG | LYS | A | 286 | 61.077 | 37.232 | 29.993 | 1.00 | 35.06 | C |
| ATOM | 1335 | CD | LYS | A | 286 | 60.840 | 37.401 | 31.495 | 1.00 | 34.44 | C |
| ATOM | 1336 | CE | LYS | A | 286 | 61.373 | 36.207 | 32.282 | 1.00 | 35.15 | C |
| ATOM | 1337 | NZ | LYS | A | 286 | 61.155 | 36.341 | 33.759 | 1.00 | 35.87 | N |
| ATOM | 1338 | N | VAL | A | 287 | 58.437 | 41.042 | 29.139 | 1.00 | 33.15 | N |
| ATOM | 1339 | CA | VAL | A | 287 | 57.979 | 42.185 | 28.367 | 1.00 | 33.28 | C |
| ATOM | 1340 | C | VAL | A | 287 | 58.706 | 43.480 | 28.730 | 1.00 | 32.69 | C |
| ATOM | 1341 | O | VAL | A | 287 | 58.745 | 43.886 | 29.892 | 1.00 | 32.80 | O |
| ATOM | 1342 | CB | VAL | A | 287 | 56.437 | 42.379 | 28.543 | 1.00 | 32.82 | C |
| ATOM | 1343 | CG1 | VAL | A | 287 | 56.083 | 42.447 | 30.020 | 1.00 | 32.50 | C |
| ATOM | 1344 | CG2 | VAL | A | 287 | 55.978 | 43.644 | 27.843 | 1.00 | 34.03 | C |
| ATOM | 1345 | N | GLY | A | 288 | 59.295 | 44.113 | 27.722 | 1.00 | 33.35 | N |
| ATOM | 1346 | CA | GLY | A | 288 | 59.983 | 45.373 | 27.935 | 1.00 | 32.17 | C |
| ATOM | 1347 | C | GLY | A | 288 | 58.966 | 46.477 | 27.731 | 1.00 | 32.40 | C |
| ATOM | 1348 | O | GLY | A | 288 | 57.953 | 46.263 | 27.056 | 1.00 | 33.04 | O |
| ATOM | 1349 | N | ALA | A | 289 | 59.221 | 47.646 | 28.309 | 1.00 | 31.58 | N |
| ATOM | 1350 | CA | ALA | A | 289 | 58.309 | 48.783 | 28.190 | 1.00 | 32.03 | C |
| ATOM | 1351 | C | ALA | A | 289 | 59.088 | 50.084 | 27.944 | 1.00 | 33.08 | C |
| ATOM | 1352 | O | ALA | A | 289 | 60.304 | 50.126 | 28.138 | 1.00 | 32.71 | O |
| ATOM | 1353 | CB | ALA | A | 289 | 57.463 | 48.899 | 29.464 | 1.00 | 31.09 | C |
| ATOM | 1354 | N | GLY | A | 290 | 58.384 | 51.135 | 27.519 | 1.00 | 32.95 | N |
| ATOM | 1355 | CA | GLY | A | 290 | 59.027 | 52.415 | 27.242 | 1.00 | 33.02 | C |
| ATOM | 1356 | C | GLY | A | 290 | 58.397 | 53.107 | 26.039 | 1.00 | 33.75 | C |
| ATOM | 1357 | O | GLY | A | 290 | 57.396 | 52.622 | 25.517 | 1.00 | 34.16 | O |
| ATOM | 1358 | N | ASN | A | 291 | 58.975 | 54.210 | 25.560 | 1.00 | 32.53 | N |
| ATOM | 1359 | CA | ASN | A | 291 | 60.199 | 54.804 | 26.095 | 1.00 | 31.60 | C |
| ATOM | 1360 | C | ASN | A | 291 | 59.964 | 55.899 | 27.134 | 1.00 | 31.33 | C |
| ATOM | 1361 | O | ASN | A | 291 | 58.936 | 56.577 | 27.123 | 1.00 | 30.56 | O |
| ATOM | 1362 | CB | ASN | A | 291 | 61.019 | 55.405 | 24.943 | 1.00 | 30.32 | C |
| ATOM | 1363 | CG | ASN | A | 291 | 61.501 | 54.354 | 23.958 | 1.00 | 31.30 | C |
| ATOM | 1364 | OD1 | ASN | A | 291 | 60.981 | 53.240 | 23.923 | 1.00 | 31.67 | O |
| ATOM | 1365 | ND2 | ASN | A | 291 | 62.495 | 54.708 | 23.147 | 1.00 | 28.26 | N |
| ATOM | 1366 | N | ILE | A | 292 | 60.933 | 56.052 | 28.033 | 1.00 | 30.09 | N |
| ATOM | 1367 | CA | ILE | A | 292 | 60.904 | 57.090 | 29.053 | 1.00 | 30.04 | C |
| ATOM | 1368 | C | ILE | A | 292 | 62.276 | 57.774 | 29.013 | 1.00 | 30.43 | C |
| ATOM | 1369 | O | ILE | A | 292 | 63.205 | 57.266 | 28.375 | 1.00 | 30.27 | O |
| ATOM | 1370 | CB | ILE | A | 292 | 60.583 | 56.526 | 30.484 | 1.00 | 29.76 | C |
| ATOM | 1371 | CG1 | ILE | A | 292 | 61.381 | 55.253 | 30.787 | 1.00 | 30.31 | C |
| ATOM | 1372 | CG2 | ILE | A | 292 | 59.105 | 56.229 | 30.588 | 1.00 | 30.24 | C |
| ATOM | 1373 | CD1 | ILE | A | 292 | 62.856 | 55.473 | 31.028 | 1.00 | 29.06 | C |
| ATOM | 1374 | N | VAL | A | 293 | 62.409 | 58.924 | 29.668 | 1.00 | 30.29 | N |
| ATOM | 1375 | CA | VAL | A | 293 | 63.680 | 59.640 | 29.641 | 1.00 | 29.96 | C |
| ATOM | 1376 | C | VAL | A | 293 | 64.153 | 60.149 | 30.991 | 1.00 | 30.54 | C |
| ATOM | 1377 | O | VAL | A | 293 | 65.175 | 60.829 | 31.068 | 1.00 | 30.92 | O |

TABLE 6-continued

| | | | | | | | | | | | |
|---|---|---|---|---|---|---|---|---|---|---|---|
| ATOM | 1378 | CB | VAL | A | 293 | 63.612 | 60.839 | 28.680 | 1.00 | 29.70 | C |
| ATOM | 1379 | CG1 | VAL | A | 293 | 63.492 | 60.351 | 27.238 | 1.00 | 27.77 | C |
| ATOM | 1380 | CG2 | VAL | A | 293 | 62.418 | 61.717 | 29.045 | 1.00 | 28.93 | C |
| ATOM | 1381 | N | ASP | A | 294 | 63.414 | 59.841 | 32.053 | 1.00 | 29.98 | N |
| ATOM | 1382 | CA | ASP | A | 294 | 63.822 | 60.282 | 33.384 | 1.00 | 30.26 | C |
| ATOM | 1383 | C | ASP | A | 294 | 63.503 | 59.249 | 34.465 | 1.00 | 29.51 | C |
| ATOM | 1384 | O | ASP | A | 294 | 62.859 | 58.237 | 34.201 | 1.00 | 28.45 | O |
| ATOM | 1385 | CB | ASP | A | 294 | 63.184 | 61.645 | 33.733 | 1.00 | 29.22 | C |
| ATOM | 1386 | CG | ASP | A | 294 | 61.667 | 61.579 | 33.893 | 1.00 | 30.83 | C |
| ATOM | 1387 | OD1 | ASP | A | 294 | 61.069 | 60.517 | 33.634 | 1.00 | 30.38 | O |
| ATOM | 1388 | OD2 | ASP | A | 294 | 61.065 | 62.609 | 34.277 | 1.00 | 31.14 | O |
| ATOM | 1389 | N | GLY | A | 295 | 63.970 | 59.516 | 35.680 | 1.00 | 30.57 | N |
| ATOM | 1390 | CA | GLY | A | 295 | 63.739 | 58.613 | 36.793 | 1.00 | 32.07 | C |
| ATOM | 1391 | C | GLY | A | 295 | 62.278 | 58.313 | 37.065 | 1.00 | 33.84 | C |
| ATOM | 1392 | O | GLY | A | 295 | 61.928 | 57.165 | 37.359 | 1.00 | 33.24 | O |
| ATOM | 1393 | N | GLU | A | 296 | 61.426 | 59.337 | 36.986 | 1.00 | 35.06 | N |
| ATOM | 1394 | CA | GLU | A | 296 | 59.986 | 59.172 | 37.221 | 1.00 | 36.02 | C |
| ATOM | 1395 | C | GLU | A | 296 | 59.400 | 58.100 | 36.315 | 1.00 | 34.20 | C |
| ATOM | 1396 | O | GLU | A | 296 | 58.739 | 57.179 | 36.775 | 1.00 | 34.47 | O |
| ATOM | 1397 | CB | GLU | A | 296 | 59.222 | 60.473 | 36.938 | 1.00 | 39.08 | C |
| ATOM | 1398 | CG | GLU | A | 296 | 59.026 | 61.420 | 38.101 | 1.00 | 44.63 | C |
| ATOM | 1399 | CD | GLU | A | 296 | 57.731 | 62.229 | 37.955 | 1.00 | 49.36 | C |
| ATOM | 1400 | OE1 | GLU | A | 296 | 57.490 | 62.820 | 36.868 | 1.00 | 49.76 | O |
| ATOM | 1401 | OE2 | GLU | A | 296 | 56.946 | 62.266 | 38.930 | 1.00 | 52.97 | O |
| ATOM | 1402 | N | GLY | A | 297 | 59.634 | 58.251 | 35.015 | 1.00 | 34.02 | N |
| ATOM | 1403 | CA | GLY | A | 297 | 59.120 | 57.307 | 34.040 | 1.00 | 32.68 | C |
| ATOM | 1404 | C | GLY | A | 297 | 59.651 | 55.901 | 34.239 | 1.00 | 32.72 | C |
| ATOM | 1405 | O | GLY | A | 297 | 58.912 | 54.930 | 34.091 | 1.00 | 33.28 | O |
| ATOM | 1406 | N | PHE | A | 298 | 60.937 | 55.791 | 34.558 | 1.00 | 31.86 | N |
| ATOM | 1407 | CA | PHE | A | 298 | 61.557 | 54.490 | 34.793 | 1.00 | 32.60 | C |
| ATOM | 1408 | C | PHE | A | 298 | 60.832 | 53.804 | 35.946 | 1.00 | 33.15 | C |
| ATOM | 1409 | O | PHE | A | 298 | 60.382 | 52.668 | 35.829 | 1.00 | 33.25 | O |
| ATOM | 1410 | CB | PHE | A | 298 | 63.029 | 54.656 | 35.183 | 1.00 | 30.95 | C |
| ATOM | 1411 | CG | PHE | A | 298 | 63.635 | 53.414 | 35.773 | 1.00 | 31.63 | C |
| ATOM | 1412 | CD1 | PHE | A | 298 | 64.151 | 52.414 | 34.953 | 1.00 | 31.00 | C |
| ATOM | 1413 | CD2 | PHE | A | 298 | 63.622 | 53.209 | 37.149 | 1.00 | 31.36 | C |
| ATOM | 1414 | CE1 | PHE | A | 298 | 64.641 | 51.221 | 35.498 | 1.00 | 30.09 | C |
| ATOM | 1415 | CE2 | PHE | A | 298 | 64.108 | 52.023 | 37.701 | 1.00 | 30.73 | C |
| ATOM | 1416 | CZ | PHE | A | 298 | 64.616 | 51.028 | 36.871 | 1.00 | 30.06 | C |
| ATOM | 1417 | N | ARG | A | 299 | 60.743 | 54.528 | 37.057 | 1.00 | 33.22 | N |
| ATOM | 1418 | CA | ARG | A | 299 | 60.111 | 54.074 | 38.291 | 1.00 | 34.33 | C |
| ATOM | 1419 | C | ARG | A | 299 | 58.671 | 53.593 | 38.074 | 1.00 | 34.12 | C |
| ATOM | 1420 | O | ARG | A | 299 | 58.252 | 52.577 | 38.635 | 1.00 | 32.73 | O |
| ATOM | 1421 | CB | ARG | A | 299 | 60.161 | 55.228 | 39.300 | 1.00 | 35.94 | C |
| ATOM | 1422 | CG | ARG | A | 299 | 59.224 | 55.130 | 40.491 | 1.00 | 41.25 | C |
| ATOM | 1423 | CD | ARG | A | 299 | 59.892 | 54.483 | 41.682 | 1.00 | 42.59 | C |
| ATOM | 1424 | NE | ARG | A | 299 | 61.160 | 55.121 | 42.041 | 1.00 | 44.25 | N |
| ATOM | 1425 | CZ | ARG | A | 299 | 61.927 | 54.709 | 43.050 | 1.00 | 44.43 | C |
| ATOM | 1426 | NH1 | ARG | A | 299 | 61.544 | 53.677 | 43.791 | 1.00 | 42.61 | N |
| ATOM | 1427 | NH2 | ARG | A | 299 | 63.085 | 55.304 | 43.304 | 1.00 | 44.39 | N |
| ATOM | 1428 | N | TYR | A | 300 | 57.920 | 54.318 | 37.255 | 1.00 | 32.22 | N |
| ATOM | 1429 | CA | TYR | A | 300 | 56.540 | 53.948 | 36.981 | 1.00 | 32.60 | C |
| ATOM | 1430 | C | TYR | A | 300 | 56.453 | 52.607 | 36.251 | 1.00 | 33.71 | C |
| ATOM | 1431 | O | TYR | A | 300 | 55.643 | 51.750 | 36.606 | 1.00 | 34.20 | O |
| ATOM | 1432 | CB | TYR | A | 300 | 55.855 | 55.027 | 36.143 | 1.00 | 32.42 | C |
| ATOM | 1433 | CG | TYR | A | 300 | 54.398 | 54.736 | 35.864 | 1.00 | 32.17 | C |
| ATOM | 1434 | CD1 | TYR | A | 300 | 53.418 | 54.973 | 36.828 | 1.00 | 31.34 | C |
| ATOM | 1435 | CD2 | TYR | A | 300 | 54.002 | 54.216 | 34.637 | 1.00 | 30.83 | C |
| ATOM | 1436 | CE1 | TYR | A | 300 | 52.073 | 54.700 | 36.568 | 1.00 | 30.71 | C |
| ATOM | 1437 | CE2 | TYR | A | 300 | 52.670 | 53.942 | 34.369 | 1.00 | 32.95 | C |
| ATOM | 1438 | CZ | TYR | A | 300 | 51.712 | 54.186 | 35.334 | 1.00 | 31.71 | C |
| ATOM | 1439 | OH | TYR | A | 300 | 50.396 | 53.929 | 35.041 | 1.00 | 31.68 | O |
| ATOM | 1440 | N | LEU | A | 301 | 57.275 | 52.429 | 35.222 | 1.00 | 32.89 | N |
| ATOM | 1441 | CA | LEU | A | 301 | 57.257 | 51.180 | 34.477 | 1.00 | 32.98 | C |
| ATOM | 1442 | C | LEU | A | 301 | 57.881 | 50.045 | 35.304 | 1.00 | 33.13 | C |
| ATOM | 1443 | O | LEU | A | 301 | 57.547 | 48.878 | 35.114 | 1.00 | 33.27 | O |
| ATOM | 1444 | CB | LEU | A | 301 | 57.992 | 51.349 | 33.140 | 1.00 | 31.76 | C |
| ATOM | 1445 | CG | LEU | A | 301 | 57.342 | 52.341 | 32.160 | 1.00 | 31.64 | C |
| ATOM | 1446 | CD1 | LEU | A | 301 | 58.174 | 52.459 | 30.891 | 1.00 | 29.55 | C |
| ATOM | 1447 | CD2 | LEU | A | 301 | 55.928 | 51.870 | 31.823 | 1.00 | 30.86 | C |
| ATOM | 1448 | N | ALA | A | 302 | 58.780 | 50.390 | 36.220 | 1.00 | 32.34 | N |
| ATOM | 1449 | CA | ALA | A | 302 | 59.418 | 49.385 | 37.066 | 1.00 | 34.28 | C |
| ATOM | 1450 | C | ALA | A | 302 | 58.355 | 48.806 | 38.008 | 1.00 | 34.11 | C |
| ATOM | 1451 | O | ALA | A | 302 | 58.169 | 47.590 | 38.082 | 1.00 | 34.00 | O |
| ATOM | 1452 | CB | ALA | A | 302 | 60.563 | 50.012 | 37.866 | 1.00 | 31.06 | C |
| ATOM | 1453 | N | ASP | A | 303 | 57.652 | 49.686 | 38.711 | 1.0.0 | 34.91 | N |
| ATOM | 1454 | CA | ASP | A | 303 | 56.595 | 49.262 | 39.618 | 1.00 | 35.64 | C |
| ATOM | 1455 | C | ASP | A | 303 | 55.485 | 48.552 | 38.846 | 1.00 | 36.85 | C |
| ATOM | 1456 | O | ASP | A | 303 | 54.761 | 47.737 | 39.408 | 1.00 | 37.85 | O |

TABLE 6-continued

| ATOM | 1457 | CB | ASP | A | 303 | 56.008 | 50.458 | 40.365 | 1.00 | 35.88 | C |
| ATOM | 1458 | CG | ASP | A | 303 | 56.956 | 51.022 | 41.398 | 1.00 | 38.13 | C |
| ATOM | 1459 | OD1 | ASP | A | 303 | 57.843 | 50.276 | 41.863 | 1.00 | 40.12 | O |
| ATOM | 1460 | OD2 | ASP | A | 303 | 56.800 | 52.205 | 41.764 | 1.00 | 40.53 | O |
| ATOM | 1461 | N | ALA | A | 304 | 55.356 | 48.859 | 37.557 | 1.00 | 36.62 | N |
| ATOM | 1462 | CA | ALA | A | 304 | 54.331 | 48.233 | 36.725 | 1.00 | 36.26 | C |
| ATOM | 1463 | C | ALA | A | 304 | 54.719 | 46.802 | 36.343 | 1.00 | 36.18 | C |
| ATOM | 1464 | O | ALA | A | 304 | 53.876 | 46.035 | 35.868 | 1.00 | 35.97 | O |
| ATOM | 1465 | CB | ALA | A | 304 | 54.095 | 49.063 | 35.466 | 1.00 | 35.66 | C |
| ATOM | 1466 | N | GLY | A | 305 | 55.994 | 46.454 | 36.519 | 1.00 | 35.62 | N |
| ATOM | 1467 | CA | GLY | A | 305 | 56.440 | 45.102 | 36.212 | 1.00 | 33.54 | C |
| ATOM | 1468 | C | GLY | A | 305 | 57.266 | 44.840 | 34.964 | 1.00 | 34.83 | C |
| ATOM | 1469 | O | GLY | A | 305 | 57.559 | 43.678 | 34.654 | 1.00 | 34.47 | O |
| ATOM | 1470 | N | ALA | A | 306 | 57.648 | 45.890 | 34.239 | 1.00 | 34.51 | N |
| ATOM | 1471 | CA | ALA | A | 306 | 58.448 | 45.718 | 33.022 | 1.00 | 34.01 | C |
| ATOM | 1472 | C | ALA | A | 306 | 59.718 | 44.902 | 33.304 | 1.00 | 33.98 | C |
| ATOM | 1473 | O | ALA | A | 306 | 60.302 | 45.017 | 34.378 | 1.00 | 33.26 | O |
| ATOM | 1474 | CB | ALA | A | 306 | 58.825 | 47.084 | 32.450 | 1.00 | 33.19 | C |
| ATOM | 1475 | N | ASP | A | 307 | 60.137 | 44.085 | 32.339 | 1.00 | 34.27 | N |
| ATOM | 1476 | CA | ASP | A | 307 | 61.341 | 43.257 | 32.489 | 1.00 | 35.04 | C |
| ATOM | 1477 | C | ASP | A | 307 | 62.605 | 44.014 | 32.075 | 1.00 | 34.78 | C |
| ATOM | 1478 | O | ASP | A | 307 | 63.716 | 43.658 | 32.462 | 1.00 | 35.12 | O |
| ATOM | 1479 | CE | ASP | A | 307 | 61.191 | 41.967 | 31.684 | 1.00 | 34.06 | C |
| ATOM | 1480 | CG | ASP | A | 307 | 60.205 | 41.010 | 32.322 | 1.00 | 35.84 | C |
| ATOM | 1481 | OD1 | ASP | A | 307 | 60.511 | 40.519 | 33.429 | 1.00 | 33.94 | O |
| ATOM | 1482 | OD2 | ASP | A | 307 | 59.127 | 40.764 | 31.733 | 1.00 | 35.52 | O |
| ATOM | 1483 | N | PHE | A | 308 | 62.418 | 45.042 | 31.255 | 1.00 | 33.72 | N |
| ATOM | 1484 | CA | PHE | A | 308 | 63.499 | 45.920 | 30.838 | 1.00 | 32.62 | C |
| ATOM | 1485 | C | PHE | A | 308 | 62.811 | 47.210 | 30.396 | 1.00 | 32.76 | C |
| ATOM | 1486 | O | PHE | A | 308 | 61.660 | 47.194 | 29.961 | 1.00 | 32.31 | O |
| ATOM | 1487 | CE | PHE | A | 308 | 64.389 | 45.282 | 29.751 | 1.00 | 30.88 | C |
| ATOM | 1488 | CG | PHE | A | 308 | 63.833 | 45.325 | 28.351 | 1.00 | 31.29 | C |
| ATOM | 1489 | CD1 | PHE | A | 308 | 63.823 | 46.514 | 27.622 | 1.00 | 30.95 | C |
| ATOM | 1490 | CD2 | PHE | A | 308 | 63.399 | 44.152 | 27.729 | 1.00 | 31.69 | C |
| ATOM | 1491 | CE1 | PHE | A | 308 | 63.396 | 46.536 | 26.289 | 1.00 | 31.24 | C |
| ATOM | 1492 | CE2 | PHE | A | 308 | 62.968 | 44.158 | 26.393 | 1.00 | 32.80 | C |
| ATOM | 1493 | CZ | PHE | A | 308 | 62.968 | 45.356 | 25.671 | 1.00 | 33.19 | C |
| ATOM | 1494 | N | ILE | A | 309 | 63.499 | 48.330 | 30.558 | 1.00 | 32.53 | N |
| ATOM | 1495 | CA | ILE | A | 309 | 62.919 | 49.618 | 30.221 | 1.00 | 31.47 | C |
| ATOM | 1496 | C | ILE | A | 309 | 63.723 | 50.323 | 29.138 | 1.00 | 31.48 | C |
| ATOM | 1497 | O | ILE | A | 309 | 64.952 | 50.428 | 29.228 | 1.00 | 29.64 | O |
| ATOM | 1498 | CB | ILE | A | 309 | 62.809 | 50.477 | 31.502 | 1.00 | 31.63 | C |
| ATOM | 1499 | CG1 | ILE | A | 309 | 61.767 | 49.835 | 32.431 | 1.00 | 29.83 | C |
| ATOM | 1500 | CG2 | ILE | A | 309 | 62.467 | 51.924 | 31.160 | 1.00 | 30.76 | C |
| ATOM | 1501 | CD1 | ILE | A | 309 | 61.696 | 50.434 | 33.823 | 1.00 | 30.01 | C |
| ATOM | 1502 | N | LYS | A | 310 | 63.016 | 50.794 | 28.109 | 1.00 | 30.52 | N |
| ATOM | 1503 | CA | LYS | A | 310 | 63.649 | 51.456 | 26.977 | 1.00 | 30.74 | C |
| ATOM | 1504 | C | LYS | A | 310 | 63.730 | 52.975 | 27.166 | 1.00 | 30.46 | C |
| ATOM | 1505 | O | LYS | A | 310 | 62.746 | 53.630 | 27.515 | 1.00 | 30.84 | O |
| ATOM | 1506 | CE | LYS | A | 310 | 62.899 | 51.092 | 25.693 | 1.00 | 30.85 | C |
| ATOM | 1507 | CG | LYS | A | 310 | 63.787 | 50.985 | 24.461 | 1.00 | 30.94 | C |
| ATOM | 1508 | CD | LYS | A | 310 | 63.396 | 49.797 | 23.572 | 1.00 | 29.84 | C |
| ATOM | 1509 | CE | LYS | A | 310 | 62.017 | 49.979 | 22.964 | 1.00 | 28.94 | C |
| ATOM | 1510 | NZ | LYS | A | 310 | 61.928 | 51.268 | 22.219 | 1.00 | 28.29 | N |
| ATOM | 1511 | N | ILE | A | 311 | 64.917 | 53.517 | 26.920 | 1.00 | 29.41 | N |
| ATOM | 1512 | CA | ILE | A | 311 | 65.197 | 54.943 | 27.097 | 1.00 | 29.44 | C |
| ATOM | 1513 | C | ILE | A | 311 | 65.362 | 55.711 | 25.796 | 1.00 | 29.18 | C |
| ATOM | 1514 | O | ILE | A | 311 | 66.100 | 55.288 | 24.908 | 1.00 | 28.56 | O |
| ATOM | 1515 | CB | ILE | A | 311 | 66.517 | 55.158 | 27.887 | 1.00 | 28.45 | C |
| ATOM | 1516 | CG1 | ILE | A | 311 | 66.498 | 54.353 | 29.186 | 1.00 | 27.16 | C |
| ATOM | 1517 | CG2 | ILE | A | 311 | 66.721 | 56.653 | 28.178 | 1.00 | 25.82 | C |
| ATOM | 1518 | CD1 | ILE | A | 311 | 67.864 | 54.280 | 29.857 | 1.00 | 27.18 | C |
| ATOM | 1519 | N | GLY | A | 312 | 64.690 | 56.852 | 25.692 | 1.00 | 30.57 | N |
| ATOM | 1520 | CA | GLY | A | 312 | 64.856 | 57.660 | 24.502 | 1.00 | 30.97 | C |
| ATOM | 1521 | C | GLY | A | 312 | 63.637 | 58.202 | 23.798 | 1.00 | 33.02 | C |
| ATOM | 1522 | O | GLY | A | 312 | 62.739 | 57.460 | 23.412 | 1.00 | 32.51 | O |
| ATOM | 1523 | N | ILE | A | 313 | 63.622 | 59.519 | 23.631 | 1.00 | 35.45 | N |
| ATOM | 1524 | CA | ILE | A | 313 | 62.558 | 60.210 | 22.920 | 1.00 | 37.38 | C |
| ATOM | 1525 | C | ILE | A | 313 | 63.194 | 61.380 | 22.181 | 1.00 | 40.19 | C |
| ATOM | 1526 | O | ILE | A | 313 | 63.759 | 62.280 | 22.807 | 1.00 | 39.32 | O |
| ATOM | 1527 | CE | ILE | A | 313 | 61.484 | 60.766 | 23.865 | 1.00 | 36.69 | C |
| ATOM | 1528 | CG1 | ILE | A | 313 | 60.825 | 59.625 | 24.646 | 1.00 | 37.09 | C |
| ATOM | 1529 | CG2 | ILE | A | 313 | 60.437 | 61.517 | 23.053 | 1.00 | 36.17 | C |
| ATOM | 1530 | CD1 | ILE | A | 313 | 59.810 | 60.097 | 25.666 | 1.00 | 34.32 | C |
| ATOM | 1531 | N | GLY | A | 314 | 63.121 | 61.350 | 20.853 | 1.00 | 43.35 | N |
| ATOM | 1532 | CA | GLY | A | 314 | 63.682 | 62.424 | 20.055 | 1.00 | 47.92 | C |
| ATOM | 1533 | C | GLY | A | 314 | 65.013 | 62.127 | 19.386 | 1.00 | 51.41 | C |
| ATOM | 1534 | O | GLY | A | 314 | 65.318 | 62.690 | 18.333 | 1.00 | 52.28 | O |
| ATOM | 1535 | N | GLY | A | 315 | 65.804 | 61.244 | 19.990 | 1.00 | 53.66 | N |

TABLE 6-continued

| | | | | | | | | | | |
|---|---|---|---|---|---|---|---|---|---|---|
| ATOM | 1536 | CA | GLY | A | 315 | 67.109 | 60.902 | 19.443 | 1.00 | 55.96 | C |
| ATOM | 1537 | C | GLY | A | 315 | 67.151 | 60.218 | 18.085 | 1.00 | 57.72 | C |
| ATOM | 1538 | O | GLY | A | 315 | 68.050 | 60.499 | 17.288 | 1.00 | 58.05 | O |
| ATOM | 1539 | N | GLY | A | 316 | 66.202 | 59.320 | 17.818 | 1.00 | 58.68 | N |
| ATOM | 1540 | CA | GLY | A | 316 | 66.174 | 58.615 | 16.542 | 1.00 | 60.38 | C |
| ATOM | 1541 | C | GLY | A | 316 | 66.578 | 59.446 | 15.330 | 1.00 | 61.63 | C |
| ATOM | 1542 | O | GLY | A | 316 | 66.212 | 60.617 | 15.216 | 1.00 | 61.39 | O |
| ATOM | 1543 | N | SER | A | 317 | 67.328 | 58.838 | 14.415 | 1.00 | 63.21 | N |
| ATOM | 1544 | CA | SER | A | 317 | 67.786 | 59.529 | 13.211 | 1.00 | 64.85 | C |
| ATOM | 1545 | C | SER | A | 317 | 66.626 | 59.987 | 12.331 | 1.00 | 66.57 | C |
| ATOM | 1546 | O | SER | A | 317 | 66.711 | 61.022 | 11.667 | 1.00 | 66.58 | O |
| ATOM | 1547 | CB | SER | A | 317 | 68.714 | 58.621 | 12.395 | 1.00 | 64.42 | C |
| ATOM | 1548 | OG | SER | A | 317 | 68.001 | 57.556 | 11.787 | 1.00 | 62.55 | O |
| ATOM | 1549 | N | ILE | A | 318 | 65.547 | 59.212 | 12.324 | 1.00 | 68.56 | N |
| ATOM | 1550 | CA | ILE | A | 318 | 64.376 | 59.542 | 11.517 | 1.00 | 71.22 | C |
| ATOM | 1551 | C | ILE | A | 318 | 63.259 | 60.192 | 12.327 | 1.00 | 72.91 | C |
| ATOM | 1552 | O | ILE | A | 318 | 62.098 | 60.185 | 11.913 | 1.00 | 73.31 | O |
| ATOM | 1553 | CB | ILE | A | 318 | 63.815 | 58.286 | 10.805 | 1.00 | 71.18 | C |
| ATOM | 1554 | CG1 | ILE | A | 318 | 63.983 | 57.051 | 11.698 | 1.00 | 71.48 | C |
| ATOM | 1555 | CG2 | ILE | A | 318 | 64.529 | 58.080 | 9.475 | 1.00 | 70.96 | C |
| ATOM | 1556 | CD1 | ILE | A | 318 | 63.326 | 57.162 | 13.049 | 1.00 | 70.32 | C |
| ATOM | 1557 | N | CYS | A | 319 | 63.617 | 60.755 | 13.478 | 1.00 | 75.09 | N |
| ATOM | 1558 | CA | CYS | A | 319 | 62.651 | 61.417 | 14.350 | 1.00 | 77.73 | C |
| ATOM | 1559 | C | CYS | A | 319 | 62.958 | 62.911 | 14.448 | 1.00 | 78.61 | C |
| ATOM | 1560 | O | CYS | A | 319 | 64.091 | 63.300 | 14.731 | 1.00 | 78.56 | O |
| ATOM | 1561 | CB | CYS | A | 319 | 62.686 | 60.789 | 15.746 | 1.00 | 78.48 | C |
| ATOM | 1562 | SG | CYS | A | 319 | 61.465 | 61.464 | 16.899 | 1.00 | 81.82 | S |
| ATOM | 1563 | N | ILE | A | 320 | 61.947 | 63.743 | 14.214 | 1.00 | 79.90 | N |
| ATOM | 1564 | CA | ILE | A | 320 | 62.123 | 65.194 | 14.271 | 1.00 | 81.47 | C |
| ATOM | 1565 | C | ILE | A | 320 | 61.255 | 65.828 | 15.362 | 1.00 | 82.10 | C |
| ATOM | 1566 | O | ILE | A | 320 | 60.147 | 66.298 | 15.096 | 1.00 | 82.35 | O |
| ATOM | 1567 | CB | ILE | A | 320 | 61.776 | 65.850 | 12.911 | 1.00 | 81.84 | C |
| ATOM | 1568 | CG1 | ILE | A | 320 | 62.556 | 65.162 | 11.787 | 1.00 | 82.02 | C |
| ATOM | 1569 | CG2 | ILE | A | 320 | 62.121 | 67.340 | 12.946 | 1.00 | 82.15 | C |
| ATOM | 1570 | CD1 | ILE | A | 320 | 62.212 | 65.669 | 10.396 | 1.00 | 82.11 | C |
| ATOM | 1571 | N | THR | A | 321 | 61.775 | 65.841 | 16.587 | 1.00 | 82.35 | N |
| ATOM | 1572 | CA | THR | A | 321 | 61.072 | 66.403 | 17.738 | 1.00 | 82.60 | C |
| ATOM | 1573 | C | THR | A | 321 | 60.461 | 67.782 | 17.469 | 1.00 | 82.30 | C |
| ATOM | 1574 | O | THR | A | 321 | 59.253 | 67.975 | 17.619 | 1.00 | 81.76 | O |
| ATOM | 1575 | CB | THR | A | 321 | 62.019 | 66.527 | 18.949 | 1.00 | 82.94 | C |
| ATOM | 1576 | OG1 | THR | A | 321 | 62.607 | 65.250 | 19.232 | 1.00 | 83.54 | O |
| ATOM | 1577 | CG2 | THR | A | 321 | 61.257 | 67.016 | 20.167 | 1.00 | 82.53 | C |
| ATOM | 1578 | N | ARG | A | 322 | 61.306 | 68.735 | 17.083 | 1.00 | 82.27 | N |
| ATOM | 1579 | CA | ARG | A | 322 | 60.863 | 70.099 | 16.800 | 1.00 | 82.39 | C |
| ATOM | 1580 | C | ARG | A | 322 | 59.651 | 70.172 | 15.878 | 1.00 | 81.93 | C |
| ATOM | 1581 | O | ARG | A | 322 | 58.611 | 70.714 | 16.254 | 1.00 | 81.88 | O |
| ATOM | 1582 | CB | ARG | A | 322 | 62.005 | 70.915 | 16.191 | 1.00 | 83.09 | C |
| ATOM | 1583 | CG | ARG | A | 322 | 63.009 | 71.456 | 17.199 | 1.00 | 83.95 | C |
| ATOM | 1584 | CD | ARG | A | 322 | 63.963 | 72.423 | 16.516 | 1.00 | 84.72 | C |
| ATOM | 1585 | NE | ARG | A | 322 | 64.729 | 73.227 | 17.464 | 1.00 | 85.49 | N |
| ATOM | 1586 | CZ | ARG | A | 322 | 65.543 | 74.218 | 17.108 | 1.00 | 85.83 | C |
| ATOM | 1587 | NH1 | ARG | A | 322 | 65.696 | 74.526 | 15.824 | 1.00 | 85.76 | N |
| ATOM | 1588 | NH2 | ARG | A | 322 | 66.203 | 74.903 | 18.032 | 1.00 | 85.80 | N |
| ATOM | 1589 | N | GLU | A | 323 | 59.791 | 69.634 | 14.668 | 1.00 | 81.06 | N |
| ATOM | 1590 | CA | GLU | A | 323 | 58.699 | 69.643 | 13.697 | 1.00 | 80.15 | C |
| ATOM | 1591 | C | GLU | A | 323 | 57.547 | 68.739 | 14.131 | 1.00 | 78.66 | C |
| ATOM | 1592 | O | GLU | A | 323 | 56.713 | 68.343 | 13.313 | 1.00 | 78.92 | O |
| ATOM | 1593 | CB | GLU | A | 323 | 59.205 | 69.192 | 12.324 | 1.00 | 81.16 | C |
| ATOM | 1594 | CG | GLU | A | 323 | 60.194 | 70.145 | 11.677 | 1.00 | 83.13 | C |
| ATOM | 1595 | CD | GLU | A | 323 | 60.632 | 69.676 | 10.302 | 1.00 | 84.05 | C |
| ATOM | 1596 | OE1 | GLU | A | 323 | 61.266 | 68.602 | 10.212 | 1.00 | 84.52 | O |
| ATOM | 1597 | OE2 | GLU | A | 323 | 60.337 | 70.381 | 9.312 | 1.00 | 84.85 | O |
| ATOM | 1598 | N | GLN | A | 324 | 57.500 | 68.420 | 15.421 | 1.00 | 76.17 | N |
| ATOM | 1599 | CA | GLN | A | 324 | 56.451 | 67.559 | 15.947 | 1.00 | 73.65 | C |
| ATOM | 1600 | C | GLN | A | 324 | 55.768 | 68.105 | 17.202 | 1.00 | 70.58 | C |
| ATOM | 1601 | O | GLN | A | 324 | 55.066 | 69.117 | 17.147 | 1.00 | 70.75 | O |
| ATOM | 1602 | CB | GLN | A | 324 | 57.019 | 66.160 | 16.218 | 1.00 | 76.03 | C |
| ATOM | 1603 | CG | GLN | A | 324 | 57.091 | 65.267 | 14.980 | 1.00 | 78.70 | C |
| ATOM | 1604 | CD | GLN | A | 324 | 58.247 | 64.274 | 15.029 | 1.00 | 80.71 | C |
| ATOM | 1605 | OE1 | GLN | A | 324 | 58.488 | 63.623 | 16.050 | 1.00 | 81.60 | O |
| ATOM | 1606 | NE2 | GLN | A | 324 | 58.964 | 64.150 | 13.913 | 1.00 | 81.50 | N |
| ATOM | 1607 | N | LYS | A | 325 | 55.987 | 67.439 | 18.331 | 1.00 | 66.07 | N |
| ATOM | 1608 | CA | LYS | A | 325 | 55.358 | 67.823 | 19.588 | 1.00 | 61.45 | C |
| ATOM | 1609 | C | LYS | A | 325 | 56.260 | 68.589 | 20.549 | 1.00 | 57.60 | C |
| ATOM | 1610 | O | LYS | A | 325 | 55.778 | 69.239 | 21.479 | 1.00 | 56.87 | O |
| ATOM | 1611 | CB | LYS | A | 325 | 54.817 | 66.566 | 20.274 | 1.00 | 62.25 | C |
| ATOM | 1612 | CG | LYS | A | 325 | 53.832 | 65.795 | 19.402 | 1.00 | 63.17 | C |
| ATOM | 1613 | CD | LYS | A | 325 | 53.889 | 64.295 | 19.660 | 1.00 | 63.20 | C |
| ATOM | 1614 | CE | LYS | A | 325 | 53.295 | 63.928 | 20.999 | 1.00 | 62.14 | C |

TABLE 6-continued

| | | | | | | | | | | |
|---|---|---|---|---|---|---|---|---|---|---|
| ATOM | 1615 | NZ | LYS | A | 325 | 51.844 | 64.232 | 21.055 | 1.00 | 62.08 N |
| ATOM | 1616 | N | GLY | A | 326 | 57.566 | 68.515 | 20.335 | 1.00 | 52.89 N |
| ATOM | 1617 | CA | GLY | A | 326 | 58.468 | 69.220 | 21.222 | 1.00 | 48.72 C |
| ATOM | 1618 | C | GLY | A | 326 | 58.716 | 68.493 | 22.534 | 1.00 | 45.75 C |
| ATOM | 1619 | O | GLY | A | 326 | 58.952 | 69.129 | 23.557 | 1.00 | 44.02 O |
| ATOM | 1620 | N | ILE | A | 327 | 58.639 | 67.164 | 22.510 | 1.00 | 42.92 N |
| ATOM | 1621 | CA | ILE | A | 327 | 58.901 | 66.362 | 23.698 | 1.00 | 41.83 C |
| ATOM | 1622 | C | ILE | A | 327 | 60.222 | 65.632 | 23.463 | 1.00 | 40.05 C |
| ATOM | 1623 | O | ILE | A | 327 | 60.573 | 65.316 | 22.329 | 1.00 | 39.48 O |
| ATOM | 1624 | CB | ILE | A | 327 | 57.777 | 65.310 | 23.974 | 1.00 | 42.64 C |
| ATOM | 1625 | CG1 | ILE | A | 327 | 57.577 | 64.408 | 22.754 | 1.00 | 44.04 C |
| ATOM | 1626 | CG2 | ILE | A | 327 | 56.470 | 66.012 | 24.333 | 1.00 | 42.95 C |
| ATOM | 1627 | CD1 | ILE | A | 327 | 56.582 | 63.261 | 22.982 | 1.00 | 46.03 C |
| ATOM | 1628 | N | GLY | A | 328 | 60.964 | 65.374 | 24.528 | 1.00 | 38.80 N |
| ATOM | 1629 | CA | GLY | A | 328 | 62.223 | 64.681 | 24.360 | 1.00 | 37.90 C |
| ATOM | 1630 | C | GLY | A | 328 | 63.289 | 65.133 | 25.334 | 1.00 | 36.87 C |
| ATOM | 1631 | O | GLY | A | 328 | 63.041 | 65.973 | 26.206 | 1.00 | 35.37 O |
| ATOM | 1632 | N | ARG | A | 329 | 64.484 | 64.573 | 25.175 | 1.00 | 34.44 N |
| ATOM | 1633 | CA | ARG | A | 329 | 65.602 | 64.901 | 26.042 | 1.00 | 32.91 C |
| ATOM | 1634 | C | ARG | A | 329 | 66.872 | 64.373 | 25.389 | 1.00 | 32.38 C |
| ATOM | 1635 | O | ARG | A | 329 | 66.826 | 63.365 | 24.689 | 1.00 | 32.32 O |
| ATOM | 1636 | CS | ARG | A | 329 | 65.395 | 64.239 | 27.410 | 1.00 | 32.23 C |
| ATOM | 1637 | CG | ARG | A | 329 | 66.233 | 64.822 | 28.530 | 1.00 | 31.22 C |
| ATOM | 1638 | CD | ARG | A | 329 | 66.062 | 64.023 | 29.813 | 1.00 | 31.90 C |
| ATOM | 1639 | NE | ARG | A | 329 | 66.413 | 64.807 | 30.991 | 1.00 | 30.70 N |
| ATOM | 1640 | CZ | ARG | A | 329 | 66.373 | 64.344 | 32.235 | 1.00 | 33.01 C |
| ATOM | 1641 | NH1 | ARG | A | 329 | 66.002 | 63.093 | 32.469 | 1.00 | 32.08 N |
| ATOM | 1642 | NH2 | ARG | A | 329 | 66.692 | 65.139 | 33.249 | 1.00 | 32.28 N |
| ATOM | 1643 | N | GLY | A | 330 | 67.999 | 65.058 | 25.592 | 1.00 | 31.61 N |
| ATOM | 1644 | CA | GLY | A | 330 | 69.245 | 64.582 | 25.012 | 1.00 | 29.56 C |
| ATOM | 1645 | C | GLY | A | 330 | 69.431 | 63.148 | 25.481 | 1.00 | 29.63 C |
| ATOM | 1646 | O | GLY | A | 330 | 69.267 | 62.861 | 26.666 | 1.00 | 29.00 O |
| ATOM | 1647 | N | GLN | A | 331 | 69.775 | 62.253 | 24.563 | 1.00 | 29.35 N |
| ATOM | 1648 | CA | GLN | A | 331 | 69.936 | 60.839 | 24.880 | 1.00 | 29.79 C |
| ATOM | 1649 | C | GLN | A | 331 | 70.913 | 60.538 | 26.021 | 1.00 | 30.69 C |
| ATOM | 1650 | O | GLN | A | 331 | 70.644 | 59.654 | 26.840 | 1.00 | 30.62 O |
| ATOM | 1651 | CB | GLN | A | 331 | 70.348 | 60.057 | 23.625 | 1.00 | 29.75 C |
| ATOM | 1652 | CG | GLN | A | 331 | 70.254 | 58.531 | 23.781 | 1.00 | 31.50 C |
| ATOM | 1653 | CD | GLN | A | 331 | 68.822 | 58.039 | 23.959 | 1.00 | 33.75 C |
| ATOM | 1654 | OE1 | GLN | A | 331 | 68.590 | 56.903 | 24.387 | 1.00 | 35.72 O |
| ATOM | 1655 | NE2 | GLN | A | 331 | 67.858 | 58.885 | 23.623 | 1.00 | 30.84 N |
| ATOM | 1656 | N | ALA | A | 332 | 72.039 | 61.254 | 26.078 | 1.00 | 28.60 N |
| ATOM | 1657 | CA | ALA | A | 332 | 73.017 | 61.020 | 27.142 | 1.00 | 29.13 C |
| ATOM | 1658 | C | ALA | A | 332 | 72.422 | 61.330 | 28.513 | 1.00 | 28.73 C |
| ATOM | 1659 | O | ALA | A | 332 | 72.495 | 60.513 | 29.437 | 1.00 | 28.92 O |
| ATOM | 1660 | CB | ALA | A | 332 | 74.281 | 61.873 | 26.912 | 1.00 | 29.21 C |
| ATOM | 1661 | N | THR | A | 333 | 71.833 | 62.513 | 28.639 | 1.00 | 26.69 N |
| ATOM | 1662 | CA | THR | A | 333 | 71.229 | 62.933 | 29.893 | 1.00 | 27.66 C |
| ATOM | 1663 | C | THR | A | 333 | 70.126 | 61.968 | 30.321 | 1.00 | 27.96 C |
| ATOM | 1664 | O | THR | A | 333 | 70.017 | 61.619 | 31.496 | 1.00 | 27.38 O |
| ATOM | 1665 | CB | THR | A | 333 | 70.643 | 64.347 | 29.770 | 1.00 | 28.02 C |
| ATOM | 1666 | 0G1 | THR | A | 333 | 71.681 | 65.249 | 29.359 | 1.00 | 27.47 O |
| ATOM | 1667 | CG2 | THR | A | 333 | 70.066 | 64.804 | 31.121 | 1.00 | 28.00 C |
| ATOM | 1668 | N | ALA | A | 334 | 69.317 | 61.534 | 29.361 | 1.00 | 27.55 N |
| ATOM | 1669 | CA | ALA | A | 334 | 68.236 | 60.596 | 29.642 | 1.00 | 27.85 C |
| ATOM | 1670 | C | ALA | A | 334 | 68.795 | 59.294 | 30.219 | 1.00 | 27.98 C |
| ATOM | 1671 | O | ALA | A | 334 | 68.318 | 58.792 | 31.238 | 1.00 | 28.76 O |
| ATOM | 1672 | CB | ALA | A | 334 | 67.448 | 60.309 | 28.362 | 1.00 | 26.67 C |
| ATOM | 1673 | N | VAL | A | 335 | 69.809 | 58.745 | 29.562 | 1.00 | 29.11 N |
| ATOM | 1674 | CA | VAL | A | 335 | 70.416 | 57.499 | 30.011 | 1.00 | 29.37 C |
| ATOM | 1675 | C | VAL | A | 335 | 71.009 | 57.652 | 31.411 | 1.00 | 29.55 C |
| ATOM | 1676 | O | VAL | A | 335 | 70.721 | 56.856 | 32.311 | 1.00 | 28.49 O |
| ATOM | 1677 | CB | VAL | A | 335 | 71.524 | 57.039 | 29.033 | 1.00 | 30.52 C |
| ATOM | 1678 | CG1 | VAL | A | 335 | 72.291 | 55.859 | 29.622 | 1.00 | 31.70 C |
| ATOM | 1679 | CG2 | VAL | A | 335 | 70.904 | 56.644 | 27.701 | 1.00 | 30.54 C |
| ATOM | 1680 | N | ILE | A | 336 | 71.823 | 58.686 | 31.592 | 1.00 | 29.23 N |
| ATOM | 1681 | CA | ILE | A | 336 | 72.464 | 58.938 | 32.878 | 1.00 | 28.94 C |
| ATOM | 1682 | C | ILE | A | 336 | 71.450 | 59.063 | 34.013 | 1.00 | 30.36 C |
| ATOM | 1683 | O | ILE | A | 336 | 71.652 | 58.525 | 35.109 | 1.00 | 28.57 O |
| ATOM | 1684 | CS | ILE | A | 336 | 73.325 | 60.216 | 32.813 | 1.00 | 28.69 C |
| ATOM | 1685 | CG1 | ILE | A | 336 | 74.531 | 59.974 | 31.898 | 1.00 | 27.72 C |
| ATOM | 1686 | CG2 | ILE | A | 336 | 73.768 | 60.630 | 34.211 | 1.00 | 24.85 C |
| ATOM | 1687 | CD1 | ILE | A | 336 | 75.352 | 61.229 | 31.609 | 1.00 | 29.74 C |
| ATOM | 1688 | N | ASP | A | 337 | 70.351 | 59.761 | 33.743 | 1.00 | 30.78 N |
| ATOM | 1689 | CA | ASP | A | 337 | 69.312 | 59.964 | 34.746 | 1.00 | 30.67 C |
| ATOM | 1690 | C | ASP | A | 337 | 68.563 | 58.662 | 35.065 | 1.00 | 30.77 C |
| ATOM | 1691 | O | ASP | A | 337 | 68.358 | 58.320 | 36.229 | 1.00 | 29.22 O |
| ATOM | 1692 | CB | ASP | A | 337 | 68.325 | 61.018 | 34.250 | 1.00 | 33.77 C |
| ATOM | 1693 | CG | ASP | A | 337 | 67.287 | 61.373 | 35.285 | 1.00 | 35.46 C |

TABLE 6-continued

| ATOM | 1694 | OD1 | ASP | A | 337 | 66.180 | 61.806 | 34.897 | 1.00 | 36.96 | O |
|------|------|-----|-----|---|-----|--------|--------|--------|------|-------|---|
| ATOM | 1695 | OD2 | ASP | A | 337 | 67.581 | 61.228 | 36.488 | 1.00 | 38.65 | O |
| ATOM | 1696 | N | VAL | A | 338 | 68.152 | 57.941 | 34.027 | 1.00 | 30.12 | N |
| ATOM | 1697 | CA | VAL | A | 338 | 67.427 | 56.693 | 34.217 | 1.00 | 29.17 | C |
| ATOM | 1698 | C | VAL | A | 338 | 68.289 | 55.663 | 34.935 | 1.00 | 30.19 | C |
| ATOM | 1699 | O | VAL | A | 338 | 67.808 | 54.963 | 35.829 | 1.00 | 29.30 | O |
| ATOM | 1700 | CB | VAL | A | 338 | 66.947 | 56.103 | 32.865 | 1.00 | 29.20 | C |
| ATOM | 1701 | CG1 | VAL | A | 338 | 66.423 | 54.683 | 33.068 | 1.00 | 26.29 | C |
| ATOM | 1702 | CG2 | VAL | A | 338 | 65.845 | 56.986 | 32.277 | 1.00 | 27.28 | C |
| ATOM | 1703 | N | VAL | A | 339 | 69.556 | 55.572 | 34.535 | 1.00 | 28.08 | N |
| ATOM | 1704 | CA | VAL | A | 339 | 70.489 | 54.636 | 35.147 | 1.00 | 29.13 | C |
| ATOM | 1705 | C | VAL | A | 339 | 70.653 | 54.889 | 36.648 | 1.00 | 30.51 | C |
| ATOM | 1706 | O | VAL | A | 339 | 70.731 | 53.943 | 37.432 | 1.00 | 31.60 | O |
| ATOM | 1707 | CB | VAL | A | 339 | 71.874 | 54.710 | 34.457 | 1.00 | 29.06 | C |
| ATOM | 1708 | CG1 | VAL | A | 339 | 72.931 | 54.010 | 35.302 | 1.00 | 27.64 | C |
| ATOM | 1709 | CG2 | VAL | A | 339 | 71.789 | 54.062 | 33.070 | 1.00 | 27.50 | C |
| ATOM | 1710 | N | ALA | A | 340 | 70.708 | 56.158 | 37.048 | 1.00 | 30.84 | N |
| ATOM | 1711 | CA | ALA | A | 340 | 70.851 | 56.490 | 38.463 | 1.00 | 31.17 | C |
| ATOM | 1712 | C | ALA | A | 340 | 69.610 | 56.014 | 39.211 | 1.00 | 31.63 | C |
| ATOM | 1713 | O | ALA | A | 340 | 69.701 | 55.469 | 40.313 | 1.00 | 32.08 | O |
| ATOM | 1714 | CB | ALA | A | 340 | 71.028 | 57.999 | 38.644 | 1.00 | 30.25 | C |
| ATOM | 1715 | N | GLU | A | 341 | 68.448 | 56.215 | 38.601 | 1.00 | 31.19 | N |
| ATOM | 1716 | CA | GLU | A | 341 | 67.196 | 55.810 | 39.225 | 1.00 | 31.45 | C |
| ATOM | 1717 | C | GLU | A | 341 | 67.138 | 54.290 | 39.301 | 1.00 | 31.09 | C |
| ATOM | 1718 | O | GLU | A | 341 | 66.702 | 53.730 | 40.305 | 1.00 | 30.16 | O |
| ATOM | 1719 | CB | GLU | A | 341 | 66.006 | 56.334 | 38.419 | 1.00 | 31.78 | C |
| ATOM | 1720 | CG | GLU | A | 341 | 64.668 | 56.257 | 39.149 | 1.00 | 34.04 | C |
| ATOM | 1721 | CD | GLU | A | 341 | 64.611 | 57.177 | 40.362 | 1.00 | 37.16 | C |
| ATOM | 1722 | OE1 | GLU | A | 341 | 65.211 | 58.273 | 40.313 | 1.00 | 38.31 | O |
| ATOM | 1723 | OE2 | GLU | A | 341 | 63.954 | 56.816 | 41.358 | 1.00 | 37.63 | O |
| ATOM | 1724 | N | ARG | A | 342 | 67.578 | 53.634 | 38.232 | 1.00 | 30.40 | N |
| ATOM | 1725 | CA | ARG | A | 342 | 67.585 | 52.177 | 38.170 | 1.00 | 31.42 | C |
| ATOM | 1726 | C | ARG | A | 342 | 68.469 | 51.616 | 39.286 | 1.00 | 31.57 | C |
| ATOM | 1727 | O | ARG | A | 342 | 68.099 | 50.646 | 39.937 | 1.00 | 32.09 | O |
| ATOM | 1728 | CB | ARG | A | 342 | 68.086 | 51.709 | 36.791 | 1.00 | 31.10 | C |
| ATOM | 1729 | CG | ARG | A | 342 | 68.037 | 50.192 | 36.542 | 1.00 | 28.82 | C |
| ATOM | 1730 | CD | ARG | A | 342 | 69.284 | 49.477 | 37.069 | 1.00 | 28.26 | C |
| ATOM | 1731 | NE | ARG | A | 342 | 70.531 | 49.919 | 36.441 | 1.00 | 26.03 | N |
| ATOM | 1732 | CZ | ARG | A | 342 | 70.871 | 49.696 | 35.172 | 1.00 | 26.57 | C |
| ATOM | 1733 | NH1 | ARG | A | 342 | 70.060 | 49.035 | 34.360 | 1.00 | 25.10 | N |
| ATOM | 1734 | NH2 | ARG | A | 342 | 72.043 | 50.120 | 34.714 | 1.00 | 26.92 | N |
| ATOM | 1735 | N | ASN | A | 343 | 69.626 | 52.236 | 39.508 | 1.00 | 31.96 | N |
| ATOM | 1736 | CA | ASN | A | 343 | 70.537 | 51.788 | 40.557 | 1.00 | 33.03 | C |
| ATOM | 1737 | C | ASN | A | 343 | 69.943 | 52.031 | 41.946 | 1.00 | 34.72 | C |
| ATOM | 1738 | O | ASN | A | 343 | 70.122 | 51.220 | 42.854 | 1.00 | 35.11 | O |
| ATOM | 1739 | CB | ASN | A | 343 | 71.898 | 52.478 | 40.418 | 1.00 | 31.35 | C |
| ATOM | 1740 | CG | ASN | A | 343 | 72.651 | 52.020 | 39.176 | 1.00 | 32.01 | C |
| ATOM | 1741 | OD1 | ASN | A | 343 | 72.335 | 50.976 | 38.604 | 1.00 | 31.68 | O |
| ATOM | 1742 | ND2 | ASN | A | 343 | 73.657 | 52.786 | 38.765 | 1.00 | 29.30 | N |
| ATOM | 1743 | N | LYS | A | 344 | 69.229 | 53.141 | 42.107 | 1.00 | 36.02 | N |
| ATOM | 1744 | CA | LYS | A | 344 | 68.587 | 53.446 | 43.378 | 1.00 | 38.22 | C |
| ATOM | 1745 | C | LYS | A | 344 | 67.512 | 52.384 | 43.615 | 1.00 | 37.85 | C |
| ATOM | 1746 | O | LYS | A | 344 | 67.392 | 51.834 | 44.709 | 1.00 | 39.02 | O |
| ATOM | 1747 | CB | LYS | A | 344 | 67.942 | 54.837 | 43.338 | 1.00 | 40.96 | C |
| ATOM | 1748 | CG | LYS | A | 344 | 67.139 | 55.177 | 44.589 | 1.00 | 46.89 | C |
| ATOM | 1749 | CD | LYS | A | 344 | 66.252 | 56.412 | 44.393 | 1.00 | 51.33 | C |
| ATOM | 1750 | CE | LYS | A | 344 | 67.040 | 57.709 | 44.454 | 1.00 | 54.56 | C |
| ATOM | 1751 | NZ | LYS | A | 344 | 67.416 | 58.052 | 45.862 | 1.00 | 58.14 | N |
| ATOM | 1752 | N | TYR | A | 345 | 66.744 | 52.092 | 42.573 | 1.00 | 37.18 | N |
| ATOM | 1753 | CA | TYR | A | 345 | 65.679 | 51.098 | 42.639 | 1.00 | 36.37 | C |
| ATOM | 1754 | C | TYR | A | 345 | 66.223 | 49.722 | 43.031 | 1.00 | 37.15 | C |
| ATOM | 1755 | O | TYR | A | 345 | 65.615 | 49.009 | 43.827 | 1.00 | 36.61 | O |
| ATOM | 1756 | CB | TYR | A | 345 | 64.987 | 50.991 | 41.287 | 1.00 | 35.78 | C |
| ATOM | 1757 | CG | TYR | A | 345 | 63.677 | 50.235 | 41.321 | 1.00 | 37.12 | C |
| ATOM | 1758 | CD1 | TYR | A | 345 | 62.506 | 50.863 | 41.736 | 1.00 | 36.58 | C |
| ATOM | 1759 | CD2 | TYR | A | 345 | 63.600 | 48.905 | 40.906 | 1.00 | 35.92 | C |
| ATOM | 1760 | CE1 | TYR | A | 345 | 61.294 | 50.196 | 41.731 | 1.00 | 37.36 | C |
| ATOM | 1761 | CE2 | TYR | A | 345 | 62.385 | 48.223 | 40.897 | 1.00 | 37.19 | C |
| ATOM | 1762 | CZ | TYR | A | 345 | 61.238 | 48.880 | 41.309 | 1.00 | 37.67 | C |
| ATOM | 1763 | OH | TYR | A | 345 | 60.025 | 48.240 | 41.280 | 1.00 | 39.76 | O |
| ATOM | 1764 | N | PHE | A | 346 | 67.359 | 49.346 | 42.452 | 1.00 | 37.41 | N |
| ATOM | 1765 | CA | PHE | A | 346 | 67.986 | 48.064 | 42.759 | 1.00 | 38.71 | C |
| ATOM | 1766 | C | PHE | A | 346 | 68.354 | 47.996 | 44.244 | 1.00 | 39.07 | C |
| ATOM | 1767 | O | PHE | A | 346 | 68.162 | 46.969 | 44.889 | 1.00 | 38.25 | O |
| ATOM | 1768 | CB | PHE | A | 346 | 69.251 | 47.869 | 41.915 | 1.00 | 37.92 | C |
| ATOM | 1769 | CG | PHE | A | 346 | 70.018 | 46.621 | 42.252 | 1.00 | 39.35 | C |
| ATOM | 1770 | CD1 | PHE | A | 346 | 69.484 | 45.362 | 41.984 | 1.00 | 38.94 | C |
| ATOM | 1771 | CD2 | PHE | A | 346 | 71.277 | 46.703 | 42.841 | 1.00 | 41.21 | C |
| ATOM | 1772 | CE1 | PHE | A | 346 | 70.190 | 44.203 | 42.294 | 1.00 | 39.83 | C |

TABLE 6-continued

| | | | | | | | | | | |
|---|---|---|---|---|---|---|---|---|---|---|
| ATOM | 1773 | CE2 | PHE | A | 346 | 71.997 | 45.545 | 43.159 | 1.00 | 41.80 C |
| ATOM | 1774 | CZ | PHE | A | 346 | 71.449 | 44.292 | 42.883 | 1.00 | 41.67 C |
| ATOM | 1775 | N | GLU | A | 347 | 68.877 | 49.096 | 44.778 | 1.00 | 40.05 N |
| ATOM | 1776 | CA | GLU | A | 347 | 69.269 | 49.150 | 46.183 | 1.00 | 42.73 C |
| ATOM | 1777 | C | GLU | A | 347 | 68.091 | 49.066 | 47.147 | 1.00 | 42.82 C |
| ATOM | 1778 | O | GLU | A | 347 | 68.227 | 48.534 | 48.249 | 1.00 | 43.20 O |
| ATOM | 1779 | CB | GLU | A | 347 | 70.061 | 50.429 | 46.472 | 1.00 | 43.65 C |
| ATOM | 1780 | CG | GLU | A | 347 | 71.410 | 50.480 | 45.778 | 1.00 | 50.82 C |
| ATOM | 1781 | CD | GLU | A | 347 | 72.321 | 49.322 | 46.176 | 1.00 | 54.96 C |
| ATOM | 1782 | OE1 | GLU | A | 347 | 73.405 | 49.177 | 45.565 | 1.00 | 57.64 O |
| ATOM | 1783 | OE2 | GLU | A | 347 | 71.961 | 48.556 | 47.101 | 1.00 | 57.77 O |
| ATOM | 1784 | N | GLU | A | 348 | 66.940 | 49.582 | 46.731 | 1.00 | 41.38 N |
| ATOM | 1785 | CA | GLU | A | 348 | 65.760 | 49.574 | 47.580 | 1.00 | 42.21 C |
| ATOM | 1786 | C | GLU | A | 348 | 64.987 | 48.265 | 47.522 | 1.00 | 41.45 C |
| ATOM | 1787 | O | GLU | A | 348 | 64.437 | 47.821 | 48.526 | 1.00 | 41.84 O |
| ATOM | 1788 | CB | GLU | A | 348 | 64.800 | 50.705 | 47.178 | 1.00 | 43.87 C |
| ATOM | 1789 | CG | GLU | A | 348 | 65.481 | 52.020 | 46.833 | 1.00 | 47.35 C |
| ATOM | 1790 | CD | GLU | A | 348 | 64.505 | 53.097 | 46.375 | 1.00 | 49.04 C |
| ATOM | 1791 | OE1 | GLU | A | 348 | 63.565 | 52.781 | 45.611 | 1.00 | 47.83 O |
| ATOM | 1792 | OE2 | GLU | A | 348 | 64.694 | 54.268 | 46.773 | 1.00 | 51.17 O |
| ATOM | 1793 | N | THR | A | 349 | 64.954 | 47.645 | 46.349 | 1.00 | 40.08 N |
| ATOM | 1794 | CA | THR | A | 349 | 64.171 | 46.432 | 46.159 | 1.00 | 37.91 C |
| ATOM | 1795 | C | THR | A | 349 | 64.910 | 45.133 | 45.859 | 1.00 | 37.79 C |
| ATOM | 1796 | O | THR | A | 349 | 64.306 | 44.062 | 45.895 | 1.00 | 37.84 O |
| ATOM | 1797 | CB | THR | A | 349 | 63.173 | 46.639 | 45.020 | 1.00 | 37.46 C |
| ATOM | 1798 | OG1 | THR | A | 349 | 63.894 | 46.724 | 43.784 | 1.00 | 37.27 O |
| ATOM | 1799 | CG2 | THR | A | 349 | 62.387 | 47.933 | 45.223 | 1.00 | 36.70 C |
| ATOM | 1800 | N | GLY | A | 350 | 66.197 | 45.216 | 45.550 | 1.00 | 37.03 N |
| ATOM | 1801 | CA | GLY | A | 350 | 66.940 | 44.014 | 45.215 | 1.00 | 36.78 C |
| ATOM | 1802 | C | GLY | A | 350 | 66.646 | 43.568 | 43.787 | 1.00 | 36.94 C |
| ATOM | 1803 | O | GLY | A | 350 | 67.115 | 42.520 | 43.340 | 1.00 | 37.38 O |
| ATOM | 1804 | N | ILE | A | 351 | 65.863 | 44.362 | 43.061 | 1.00 | 34.88 N |
| ATOM | 1805 | CA | ILE | A | 351 | 65.515 | 44.027 | 41.683 | 1.00 | 33.79 C |
| ATOM | 1806 | C | ILE | A | 351 | 66.368 | 44.835 | 40.708 | 1.00 | 32.41 C |
| ATOM | 1807 | O | ILE | A | 351 | 66.378 | 46.061 | 40.765 | 1.00 | 31.22 O |
| ATOM | 1808 | CB | ILE | A | 351 | 64.043 | 44.357 | 41.381 | 1.00 | 36.04 C |
| ATOM | 1809 | CG1 | ILE | A | 351 | 63.125 | 43.668 | 42.391 | 1.00 | 36.61 C |
| ATOM | 1810 | CG2 | ILE | A | 351 | 63.706 | 43.948 | 39.948 | 1.00 | 35.73 C |
| ATOM | 1811 | CD1 | ILE | A | 351 | 61.686 | 44.165 | 42.331 | 1.00 | 37.65 C |
| ATOM | 1812 | N | TYR | A | 352 | 67.078 | 44.153 | 39.817 | 1.00 | 32.08 N |
| ATOM | 1813 | CA | TYR | A | 352 | 67.904 | 44.843 | 38.835 | 1.00 | 32.62 C |
| ATOM | 1814 | C | TYR | A | 352 | 67.177 | 44.844 | 37.493 | 1.00 | 33.29 C |
| ATOM | 1815 | O | TYR | A | 352 | 66.953 | 43.791 | 36.904 | 1.00 | 33.54 O |
| ATOM | 1816 | CB | TYR | A | 352 | 69.264 | 44.158 | 38.666 | 1.00 | 31.31 C |
| ATOM | 1817 | CG | TYR | A | 352 | 70.174 | 44.889 | 37.695 | 1.00 | 30.97 C |
| ATOM | 1818 | CD1 | TYR | A | 352 | 70.998 | 45.930 | 38.128 | 1.00 | 29.66 C |
| ATOM | 1819 | CD2 | TYR | A | 352 | 70.171 | 44.575 | 36.336 | 1.00 | 30.63 C |
| ATOM | 1820 | CE1 | TYR | A | 352 | 71.794 | 46.638 | 37.237 | 1.00 | 28.10 C |
| ATOM | 1821 | CE2 | TYR | A | 352 | 70.966 | 45.280 | 35.434 | 1.00 | 30.54 C |
| ATOM | 1822 | CZ | TYR | A | 352 | 71.775 | 46.309 | 35.895 | 1.00 | 29.18 C |
| ATOM | 1823 | OH | TYR | A | 352 | 72.580 | 46.996 | 35.019 | 1.00 | 31.65 O |
| ATOM | 1824 | N | ILE | A | 353 | 66.811 | 46.027 | 37.010 | 1.00 | 32.84 N |
| ATOM | 1825 | CA | ILE | A | 353 | 66.113 | 46.119 | 35.735 | 1.00 | 31.85 C |
| ATOM | 1826 | C | ILE | A | 353 | 67.028 | 46.626 | 34.634 | 1.00 | 31.84 C |
| ATOM | 1827 | O | ILE | A | 353 | 67.506 | 47.760 | 34.679 | 1.00 | 32.46 O |
| ATOM | 1828 | CB | ILE | A | 353 | 64.900 | 47.048 | 35.835 | 1.00 | 32.61 C |
| ATOM | 1829 | CG1 | ILE | A | 353 | 63.962 | 46.536 | 36.936 | 1.00 | 34.08 C |
| ATOM | 1830 | CG2 | ILE | A | 353 | 64.181 | 47.105 | 34.487 | 1.00 | 33.22 C |
| ATOM | 1831 | CD1 | ILE | A | 353 | 62.793 | 47.431 | 37.244 | 1.00 | 32.45 C |
| ATOM | 1832 | N | PRO | A | 354 | 67.303 | 45.779 | 33.634 | 1.00 | 30.90 N |
| ATOM | 1833 | CA | PRO | A | 354 | 68.177 | 46.197 | 32.533 | 1.00 | 29.68 C |
| ATOM | 1834 | C | PRO | A | 354 | 67.528 | 47.344 | 31.763 | 1.00 | 29.05 C |
| ATOM | 1835 | O | PRO | A | 354 | 66.308 | 47.368 | 31.600 | 1.00 | 28.14 O |
| ATOM | 1836 | CB | PRO | A | 354 | 68.293 | 44.934 | 31.679 | 1.00 | 28.34 C |
| ATOM | 1837 | CG | PRO | A | 354 | 68.051 | 43.808 | 32.680 | 1.00 | 29.10 C |
| ATOM | 1838 | CD | PRO | A | 354 | 66.921 | 44.360 | 33.506 | 1.00 | 29.33 C |
| ATOM | 1839 | N | VAL | A | 355 | 68.330 | 48.302 | 31.301 | 1.00 | 28.33 N |
| ATOM | 1840 | CA | VAL | A | 355 | 67.771 | 49.404 | 30.529 | 1.00 | 27.79 C |
| ATOM | 1841 | C | VAL | A | 355 | 68.406 | 49.446 | 29.151 | 1.00 | 27.36 C |
| ATOM | 1842 | O | VAL | A | 355 | 69.552 | 49.044 | 28.958 | 1.00 | 26.70 O |
| ATOM | 1843 | CB | VAL | A | 355 | 67.931 | 50.788 | 31.246 | 1.00 | 28.56 C |
| ATOM | 1844 | CG1 | VAL | A | 355 | 67.191 | 50.759 | 32.584 | 1.00 | 27.11 C |
| ATOM | 1845 | CG2 | VAL | A | 355 | 69.406 | 51.147 | 31.427 | 1.00 | 24.91 C |
| ATOM | 1846 | N | CYS | A | 356 | 67.640 | 49.941 | 28.193 | 1.00 | 26.85 N |
| ATOM | 1847 | CA | CYS | A | 356 | 68.075 | 50.008 | 26.813 | 1.00 | 27.44 C |
| ATOM | 1848 | C | CYS | A | 356 | 68.148 | 51.436 | 26.298 | 1.00 | 27.62 C |
| ATOM | 1849 | O | CYS | A | 356 | 67.170 | 52.177 | 26.385 | 1.00 | 28.60 O |
| ATOM | 1850 | CB | CYS | A | 356 | 67.099 | 49.198 | 25.945 | 1.00 | 28.37 C |
| ATOM | 1851 | SG | CYS | A | 356 | 67.313 | 49.376 | 24.155 | 1.00 | 31.02 S |

TABLE 6-continued

| ATOM | 1852 | N   | SER | A | 357 | 69.305  | 51.826 | 25.770 | 1.00 | 27.52 | N |
|------|------|-----|-----|---|-----|---------|--------|--------|------|-------|---|
| ATOM | 1853 | CA  | SER | A | 357 | 69.455  | 53.160 | 25.196 | 1.00 | 28.11 | C |
| ATOM | 1854 | C   | SER | A | 357 | 68.975  | 52.992 | 23.756 | 1.00 | 28.62 | C |
| ATOM | 1855 | O   | SEP | A | 357 | 69.628  | 52.323 | 22.948 | 1.00 | 28.65 | O |
| ATOM | 1856 | CB  | SER | A | 357 | 70.916  | 53.610 | 25.210 | 1.00 | 27.16 | C |
| ATOM | 1857 | OG  | SER | A | 357 | 71.045  | 54.894 | 24.615 | 1.00 | 28.40 | O |
| ATOM | 1858 | N   | ASP | A | 358 | 67.831  | 53.594 | 23.451 | 1.00 | 29.11 | N |
| ATOM | 1859 | CA  | ASP | A | 358 | 67.215  | 53.487 | 22.124 | 1.00 | 30.39 | C |
| ATOM | 1860 | C   | ASP | A | 358 | 67.269  | 54.773 | 21.294 | 1.00 | 30.74 | C |
| ATOM | 1861 | O   | ASP | A | 358 | 66.604  | 55.758 | 21.608 | 1.00 | 29.70 | O |
| ATOM | 1862 | CB  | ASP | A | 358 | 65.762  | 53.019 | 22.305 | 1.00 | 29.62 | C |
| ATOM | 1863 | CG  | ASP | A | 358 | 64.978  | 52.960 | 21.007 | 1.00 | 30.36 | C |
| ATOM | 1864 | OD1 | ASP | A | 358 | 65.580  | 52.835 | 19.920 | 1.00 | 31.20 | O |
| ATOM | 1865 | OD2 | ASP | A | 358 | 63.734  | 53.022 | 21.086 | 1.00 | 30.14 | O |
| ATOM | 1866 | N   | GLY | A | 359 | 68.081  | 54.751 | 20.240 | 1.00 | 33.56 | N |
| ATOM | 1867 | CA  | GLY | A | 359 | 68.193  | 55.899 | 19.357 | 1.00 | 35.42 | C |
| ATOM | 1868 | C   | GLY | A | 359 | 69.310  | 56.878 | 19.659 | 1.00 | 38.10 | C |
| ATOM | 1869 | O   | GLY | A | 359 | 69.854  | 56.901 | 20.761 | 1.00 | 39.07 | O |
| ATOM | 1870 | N   | GLY | A | 360 | 69.662  | 57.681 | 18.659 | 1.00 | 40.00 | N |
| ATOM | 1871 | CA  | GLY | A | 360 | 70.706  | 58.673 | 18.831 | 1.00 | 41.21 | C |
| ATOM | 1872 | C   | GLY | A | 360 | 72.123  | 58.198 | 18.581 | 1.00 | 41.96 | C |
| ATOM | 1873 | O   | GLY | A | 360 | 73.055  | 58.987 | 18.695 | 1.00 | 44.15 | O |
| ATOM | 1874 | N   | ILE | A | 361 | 72.305  | 56.923 | 18.256 | 1.00 | 42.76 | N |
| ATOM | 1875 | CA  | ILE | A | 361 | 73.646  | 56.410 | 17.996 | 1.00 | 43.52 | C |
| ATOM | 1876 | C   | ILE | A | 361 | 74.052  | 56.802 | 16.581 | 1.00 | 44.42 | C |
| ATOM | 1877 | O   | ILE | A | 361 | 73.470  | 56.322 | 15.609 | 1.00 | 44.27 | O |
| ATOM | 1878 | CB  | ILE | A | 361 | 73.714  | 54.862 | 18.107 | 1.00 | 43.69 | C |
| ATOM | 1879 | CG1 | ILE | A | 361 | 73.392  | 54.412 | 19.538 | 1.00 | 43.46 | C |
| ATOM | 1880 | CG2 | ILE | A | 361 | 75.095  | 54.366 | 17.685 | 1.00 | 42.46 | C |
| ATOM | 1881 | CD1 | ILE | A | 361 | 74.429  | 54.792 | 20.565 | 1.00 | 42.32 | C |
| ATOM | 1882 | N   | VAL | A | 362 | 75.049  | 57.675 | 16.469 | 1.00 | 45.42 | N |
| ATOM | 1883 | CA  | VAL | A | 362 | 75.529  | 58.118 | 15.166 | 1.00 | 45.68 | C |
| ATOM | 1884 | C   | VAL | A | 362 | 76.851  | 57.440 | 14.820 | 1.00 | 45.91 | C |
| ATOM | 1885 | O   | VAL | A | 362 | 77.035  | 56.969 | 13.696 | 1.00 | 46.38 | O |
| ATOM | 1886 | CB  | VAL | A | 362 | 75.723  | 59.643 | 15.135 | 1.00 | 46.35 | C |
| ATOM | 1887 | CG1 | VAL | A | 362 | 76.105  | 60.091 | 13.727 | 1.00 | 48.19 | C |
| ATOM | 1888 | CG2 | VAL | A | 362 | 74.444  | 60.333 | 15.572 | 1.00 | 46.73 | C |
| ATOM | 1889 | N   | TYR | A | 363 | 77.761  | 57.379 | 15.792 | 1.00 | 44.38 | N |
| ATOM | 1890 | CA  | TYR | A | 363 | 79.067  | 56.759 | 15.589 | 1.00 | 43.12 | C |
| ATOM | 1891 | C   | TYR | A | 363 | 79.278  | 55.547 | 16.491 | 1.00 | 41.17 | C |
| ATOM | 1892 | O   | TYR | A | 363 | 78.599  | 55.387 | 17.501 | 1.00 | 40.86 | O |
| ATOM | 1893 | CB  | TYR | A | 363 | 80.176  | 57.771 | 15.862 | 1.00 | 46.18 | C |
| ATOM | 1894 | CG  | TYR | A | 363 | 80.072  | 59.040 | 15.052 | 1.00 | 49.95 | C |
| ATOM | 1895 | CD1 | TYR | A | 363 | 80.052  | 59.001 | 13.659 | 1.00 | 52.89 | C |
| ATOM | 1896 | CD2 | TYR | A | 363 | 80.012  | 60.283 | 15.677 | 1.00 | 51.68 | C |
| ATOM | 1897 | CE1 | TYR | A | 363 | 79.978  | 60.171 | 12.905 | 1.00 | 55.23 | C |
| ATOM | 1898 | CE2 | TYR | A | 363 | 79.938  | 61.462 | 14.934 | 1.00 | 54.25 | C |
| ATOM | 1899 | CZ  | TYR | A | 363 | 79.924  | 61.397 | 13.549 | 1.00 | 55.42 | C |
| ATOM | 1900 | OH  | TYR | A | 363 | 79-.872 | 62.556 | 12.803 | 1.00 | 58.12 | O |
| ATOM | 1901 | N   | ASP | A | 364 | 80.231  | 54.695 | 16.134 | 1.00 | 39.35 | N |
| ATOM | 1902 | CA  | ASP | A | 364 | 80.507  | 53.523 | 16.953 | 1.00 | 38.37 | C |
| ATOM | 1903 | C   | ASP | A | 364 | 80.828  | 53.907 | 18.396 | 1.00 | 36.34 | C |
| ATOM | 1904 | O   | ASP | A | 364 | 80.378  | 53.245 | 19.331 | 1.00 | 37.10 | O |
| ATOM | 1905 | CB  | ASP | A | 364 | 81.681  | 52.712 | 16.386 | 1.00 | 40.35 | C |
| ATOM | 1906 | CG  | ASP | A | 364 | 81.347  | 52.031 | 15.068 | 1.00 | 41.28 | C |
| ATOM | 1907 | OD1 | ASP | A | 364 | 80.207  | 51.547 | 14.912 | 1.00 | 39.82 | O |
| ATOM | 1908 | OD2 | ASP | A | 364 | 82.236  | 51.964 | 14.197 | 1.00 | 42.22 | O |
| ATOM | 1909 | N   | TYR | A | 365 | 81.594  | 54.978 | 18.587 | 1.00 | 33.88 | N |
| ATOM | 1910 | CA  | TYR | A | 365 | 81.959  | 55.375 | 19.945 | 1.00 | 33.29 | C |
| ATOM | 1911 | C   | TYR | A | 365 | 80.754  | 55.781 | 20.792 | 1.00 | 31.98 | C |
| ATOM | 1912 | O   | TYR | A | 365 | 80.827  | 55.776 | 22.016 | 1.00 | 30.93 | O |
| ATOM | 1913 | CB  | TYR | A | 365 | 83.031  | 56.477 | 19.926 | 1.00 | 32.04 | C |
| ATOM | 1914 | CG  | TYR | A | 365 | 82.536  | 57.903 | 19.814 | 1.00 | 35.20 | C |
| ATOM | 1915 | CD1 | TYR | A | 365 | 82.298  | 58.677 | 20.954 | 1.00 | 34.49 | C |
| ATOM | 1916 | CD2 | TYR | A | 365 | 82.362  | 58.501 | 18.567 | 1.00 | 35.46 | C |
| ATOM | 1917 | CE1 | TYR | A | 365 | 81.905  | 60.016 | 20.849 | 1.00 | 36.12 | C |
| ATOM | 1918 | CE2 | TYR | A | 365 | 81.971  | 59.837 | 18.452 | 1.00 | 37.53 | C |
| ATOM | 1919 | CZ  | TYR | A | 365 | 81.744  | 60.586 | 19.594 | 1.00 | 37.51 | C |
| ATOM | 1920 | OH  | TYR | A | 365 | 81.351  | 61.901 | 19.461 | 1.00 | 40.00 | O |
| ATOM | 1921 | N   | HIS | A | 366 | 79.641  | 56.119 | 20.143 | 1.00 | 31.70 | N |
| ATOM | 1922 | CA  | HIS | A | 366 | 78.434  | 56.467 | 20.882 | 1.00 | 32.08 | C |
| ATOM | 1923 | C   | HIS | A | 366 | 77.938  | 55.198 | 21.591 | 1.00 | 30.99 | C |
| ATOM | 1924 | O   | HIS | A | 366 | 77.289  | 55.278 | 22.635 | 1.00 | 30.53 | O |
| ATOM | 1925 | CB  | HIS | A | 366 | 77.336  | 57.002 | 19.947 | 1.00 | 32.20 | C |
| ATOM | 1926 | CG  | HIS | A | 366 | 77.597  | 58.378 | 19.422 | 1.00 | 33.31 | C |
| ATOM | 1927 | ND1 | HIS | A | 366 | 78.598  | 59.190 | 19.914 | 1.00 | 34.60 | N |
| ATOM | 1928 | CD2 | HIS | A | 366 | 76.948  | 59.110 | 18.485 | 1.00 | 33.99 | C |
| ATOM | 1929 | CE1 | HIS | A | 366 | 78.552  | 60.362 | 19.305 | 1.00 | 32.63 | C |
| ATOM | 1930 | NE2 | HIS | A | 366 | 77.560  | 60.339 | 18.434 | 1.00 | 35.91 | N |

TABLE 6-continued

| ATOM | 1931 | N   | MET | A | 367 | 78.244 | 54.031 | 21.017 | 1.00 | 30.17 | N |
| ATOM | 1932 | CA  | MET | A | 367 | 77.853 | 52.748 | 21.619 | 1.00 | 30.37 | C |
| ATOM | 1933 | C   | MET | A | 367 | 78.588 | 52.573 | 22.953 | 1.00 | 29.75 | C |
| ATOM | 1934 | O   | MET | A | 367 | 77.997 | 52.214 | 23.967 | 1.00 | 31.07 | O |
| ATOM | 1935 | CE  | MET | A | 367 | 78.232 | 51.567 | 20.711 | 1.00 | 30.58 | C |
| ATOM | 1936 | CG  | MET | A | 367 | 77.477 | 51.457 | 19.385 | 1.00 | 31.52 | C |
| ATOM | 1937 | SD  | MET | A | 367 | 78.053 | 50.007 | 18.447 | 1.00 | 35.95 | S |
| ATOM | 1938 | CE  | MET | A | 367 | 77.121 | 50.189 | 16.917 | 1.00 | 34.32 | C |
| ATOM | 1939 | N   | THR | A | 368 | 79.894 | 52.810 | 22.928 | 1.00 | 29.18 | N |
| ATOM | 1940 | CA  | THR | A | 368 | 80.726 | 52.688 | 24.118 | 1.00 | 29.61 | C |
| ATOM | 1941 | C   | THR | A | 368 | 80.241 | 53.682 | 25.165 | 1.00 | 28.28 | C |
| ATOM | 1942 | O   | THR | A | 368 | 80.163 | 53.354 | 26.343 | 1.00 | 29.90 | O |
| ATOM | 1943 | CB  | THR | A | 368 | 82.196 | 52.974 | 23.775 | 1.00 | 29.95 | C |
| ATOM | 1944 | OG1 | THR | A | 368 | 82.548 | 52.222 | 22.606 | 1.00 | 31.91 | O |
| ATOM | 1945 | CG2 | THR | A | 368 | 83.113 | 52.574 | 24.928 | 1.00 | 28.50 | C |
| ATOM | 1946 | N   | LEU | A | 369 | 79.916 | 54.895 | 24.729 | 1.00 | 28.13 | N |
| ATOM | 1947 | CA  | LEU | A | 369 | 79.418 | 55.925 | 25.639 | 1.00 | 29.19 | C |
| ATOM | 1948 | C   | LEU | A | 369 | 78.117 | 55.493 | 26.321 | 1.00 | 28.58 | C |
| ATOM | 1949 | O   | LEU | A | 369 | 77.978 | 55.619 | 27.535 | 1.00 | 28.56 | O |
| ATOM | 1950 | CB  | LEU | A | 369 | 79.165 | 57.245 | 24.890 | 1.00 | 29.00 | C |
| ATOM | 1951 | CG  | LEU | A | 369 | 80.362 | 58.150 | 24.593 | 1.00 | 30.35 | C |
| ATOM | 1952 | CD1 | LEU | A | 369 | 79.877 | 59.404 | 23.866 | 1.00 | 30.34 | C |
| ATOM | 1953 | CD2 | LEU | A | 369 | 81.064 | 58.528 | 25.898 | 1.00 | 28.91 | C |
| ATOM | 1954 | N   | ALA | A | 370 | 77.172 | 54.990 | 25.529 | 1.00 | 28.37 | N |
| ATOM | 1955 | CA  | ALA | A | 370 | 75.880 | 54.560 | 26.052 | 1.00 | 28.93 | C |
| ATOM | 1956 | C   | ALA | A | 370 | 76.052 | 53.464 | 27.103 | 1.00 | 27.87 | C |
| ATOM | 1957 | O   | ALA | A | 370 | 75.424 | 53.500 | 28.152 | 1.00 | 28.49 | O |
| ATOM | 1958 | CB  | ALA | A | 370 | 74.987 | 54.064 | 24.911 | 1.00 | 26.15 | C |
| ATOM | 1959 | N   | LEU | A | 371 | 76.905 | 52.491 | 26.813 | 1.00 | 27.99 | N |
| ATOM | 1960 | CA  | LEU | A | 371 | 77.146 | 51.401 | 27.746 | 1.00 | 28.20 | C |
| ATOM | 1961 | C   | LEU | A | 371 | 77.852 | 51.935 | 28.995 | 1.00 | 28.01 | C |
| ATOM | 1962 | O   | LEU | A | 371 | 77.475 | 51.599 | 30.111 | 1.00 | 27.43 | O |
| ATOM | 1963 | CE  | LEU | A | 371 | 77.992 | 50.309 | 27.069 | 1.00 | 27.75 | C |
| ATOM | 1964 | CG  | LEU | A | 371 | 77.347 | 49.632 | 25.844 | 1.00 | 29.75 | C |
| ATOM | 1965 | CD1 | LEU | A | 371 | 78.370 | 48.736 | 25.140 | 1.00 | 31.88 | C |
| ATOM | 1966 | CD2 | LEU | A | 371 | 76.140 | 48.815 | 26.272 | 1.00 | 29.40 | C |
| ATOM | 1967 | N   | ALA | A | 372 | 78.863 | 52.783 | 28.803 | 1.00 | 27.59 | N |
| ATOM | 1968 | CA  | ALA | A | 372 | 79.608 | 53.346 | 29.923 | 1.00 | 27.55 | C |
| ATOM | 1969 | C   | ALA | A | 372 | 78.710 | 54.146 | 30.845 | 1.00 | 28.89 | C |
| ATOM | 1970 | O   | ALA | A | 372 | 78.913 | 54.158 | 32.063 | 1.00 | 28.91 | O |
| ATOM | 1971 | CB  | ALA | A | 372 | 80.746 | 54.226 | 29.423 | 1.00 | 25.48 | C |
| ATOM | 1972 | N   | MET | A | 373 | 77.723 | 54.828 | 30.271 | 1.00 | 28.54 | N |
| ATOM | 1973 | CA  | MET | A | 373 | 76.813 | 55.616 | 31.090 | 1.00 | 28.48 | C |
| ATOM | 1974 | C   | MET | A | 373 | 75.815 | 54.738 | 31.853 | 1.00 | 28.37 | C |
| ATOM | 1975 | O   | MET | A | 373 | 75.048 | 55.238 | 32.665 | 1.00 | 28.46 | O |
| ATOM | 1976 | CE  | MET | A | 373 | 76.084 | 56.655 | 30.229 | 1.00 | 26.76 | C |
| ATOM | 1977 | CG  | MET | A | 373 | 76.992 | 57.775 | 29.722 | 1.00 | 26.55 | C |
| ATOM | 1978 | SD  | MET | A | 373 | 76.204 | 58.784 | 28.435 | 1.00 | 29.55 | S |
| ATOM | 1979 | CE  | MET | A | 373 | 77.549 | 59.940 | 27.986 | 1.00 | 27.96 | C |
| ATOM | 1980 | N   | GLY | A | 374 | 75.825 | 53.430 | 31.606 | 1.00 | 28.86 | N |
| ATOM | 1981 | CA  | GLY | A | 374 | 74.917 | 52.563 | 32.344 | 1.00 | 27.32 | C |
| ATOM | 1982 | C   | GLY | A | 374 | 73.906 | 51.744 | 31.563 | 1.00 | 28.78 | C |
| ATOM | 1983 | O   | GLY | A | 374 | 73.257 | 50.862 | 32.133 | 1.00 | 29.86 | O |
| ATOM | 1984 | N   | ALA | A | 375 | 73.746 | 52.023 | 30.274 | 1.00 | 27.82 | N |
| ATOM | 1985 | CA  | ALA | A | 375 | 72.812 | 51.249 | 29.472 | 1.00 | 28.98 | C |
| ATOM | 1986 | C   | ALA | A | 375 | 73.363 | 49.829 | 29.355 | 1.00 | 29.41 | C |
| ATOM | 1987 | O   | ALA | A | 375 | 74.552 | 49.641 | 29.099 | 1.00 | 30.88 | O |
| ATOM | 1988 | CB  | ALA | A | 375 | 72.657 | 51.866 | 28.086 | 1.00 | 26.18 | C |
| ATOM | 1989 | N   | ASP | A | 376 | 72.500 | 48.837 | 29.545 | 1.00 | 29.72 | N |
| ATOM | 1990 | CA  | ASP | A | 376 | 72.900 | 47.435 | 29.457 | 1.00 | 30.17 | C |
| ATOM | 1992 | C   | ASP | A | 376 | 72.997 | 47.034 | 27.994 | 1.00 | 30.68 | C |
| ATOM | 1992 | O   | ASP | A | 376 | 73.896 | 46.293 | 27.597 | 1.00 | 30.02 | O |
| ATOM | 1993 | CB  | ASP | A | 376 | 71.882 | 46.568 | 30.187 | 1.00 | 30.75 | C |
| ATOM | 1994 | CG  | ASP | A | 376 | 71.780 | 46.924 | 31.658 | 1.00 | 31.02 | C |
| ATOM | 1995 | OD1 | ASP | A | 376 | 72.596 | 46.409 | 32.455 | 1.00 | 29.99 | O |
| ATOM | 1996 | OD2 | ASP | A | 376 | 70.895 | 47.733 | 32.013 | 1.00 | 31.49 | O |
| ATOM | 1997 | N   | PHE | A | 377 | 72.058 | 47.513 | 27.189 | 1.00 | 30.61 | N |
| ATOM | 1998 | CA  | PHE | A | 377 | 72.106 | 47.236 | 25.767 | 1.00 | 30.87 | C |
| ATOM | 1999 | C   | PHE | A | 377 | 71.603 | 48.425 | 24.954 | 1.00 | 30.14 | C |
| ATOM | 2000 | O   | PHE | A | 377 | 71.047 | 49.388 | 25.498 | 1.00 | 29.61 | O |
| ATOM | 2001 | CB  | PHE | A | 377 | 71.374 | 45.922 | 25.396 | 1.00 | 29.78 | C |
| ATOM | 2002 | CG  | PHE | A | 377 | 69.955 | 45.827 | 25.881 | 1.00 | 31.57 | C |
| ATOM | 2003 | CD1 | PHE | A | 377 | 69.673 | 45.401 | 27.178 | 1.00 | 31.78 | C |
| ATOM | 2004 | CD2 | PHE | A | 377 | 68.894 | 46.099 | 25.020 | 1.00 | 31.27 | C |
| ATOM | 2005 | CE1 | PHE | A | 377 | 68.349 | 45.242 | 27.610 | 1.00 | 32.32 | C |
| ATOM | 2006 | CE2 | PHE | A | 377 | 67.569 | 45.945 | 25.436 | 1.00 | 32.45 | C |
| ATOM | 2007 | CZ  | PHE | A | 377 | 67.295 | 45.514 | 26.735 | 1.00 | 32.96 | C |
| ATOM | 2008 | N   | ILE | A | 378 | 71.820 | 48.354 | 23.648 | 1.00 | 30.17 | N |
| ATOM | 2009 | CA  | ILE | A | 378 | 71.473 | 49.436 | 22.742 | 1.00 | 30.04 | C |

TABLE 6-continued

| | | | | | | | | | | |
|---|---|---|---|---|---|---|---|---|---|---|
| ATOM | 2010 | C | ILE | A | 378 | 70.520 | 49.007 | 21.627 | 1.00 | 30.86 | C |
| ATOM | 2011 | O | ILE | A | 378 | 70.693 | 47.939 | 21.038 | 1.00 | 31.49 | O |
| ATOM | 2012 | CB | ILE | A | 378 | 72.772 | 49.974 | 22.099 | 1.00 | 31.01 | C |
| ATOM | 2013 | CG1 | ILE | A | 378 | 73.760 | 50.360 | 23.201 | 1.00 | 32.35 | C |
| ATOM | 2014 | CG2 | ILE | A | 378 | 72.482 | 51.174 | 21.191 | 1.00 | 31.58 | C |
| ATOM | 2015 | CD1 | ILE | A | 378 | 75.178 | 50.566 | 22.694 | 1.00 | 34.75 | C |
| ATOM | 2016 | N | MET | A | 379 | 69.511 | 49.829 | 21.349 | 1.00 | 29.83 | N |
| ATOM | 2017 | CA | MET | A | 379 | 68.581 | 49.531 | 20.265 | 1.00 | 30.54 | C |
| ATOM | 2018 | C | MET | A | 379 | 68.913 | 50.461 | 19.095 | 1.00 | 30.14 | C |
| ATOM | 2019 | O | MET | A | 379 | 69.010 | 51.669 | 19.268 | 1.00 | 29.93 | O |
| ATOM | 2020 | CS | MET | A | 379 | 67.122 | 49.749 | 20.694 | 1.00 | 30.89 | C |
| ATOM | 2021 | CG | MET | A | 379 | 66.139 | 49.547 | 19.538 | 1.00 | 31.32 | C |
| ATOM | 2022 | SD | MET | A | 379 | 64.386 | 49.460 | 19.961 | 1.00 | 31.78 | S |
| ATOM | 2023 | CE | MET | A | 379 | 64.246 | 47.743 | 20.461 | 1.00 | 30.99 | C |
| ATOM | 2024 | N | LEU | A | 380 | 69.090 | 49.901 | 17.906 | 1.00 | 30.34 | N |
| ATOM | 2025 | CA | LEU | A | 380 | 69.416 | 50.720 | 16.746 | 1.00 | 31.69 | C |
| ATOM | 2026 | C | LEU | A | 380 | 68.521 | 50.429 | 15.553 | 1.00 | 31.86 | C |
| ATOM | 2027 | O | LEU | A | 380 | 68.100 | 49.293 | 15.343 | 1.00 | 31.20 | O |
| ATOM | 2028 | CB | LEU | A | 380 | 70.879 | 50.514 | 16.331 | 1.00 | 31.86 | C |
| ATOM | 2029 | CG | LEU | A | 380 | 71.975 | 50.752 | 17.373 | 1.00 | 33.23 | C |
| ATOM | 2030 | CD1 | LEU | A | 380 | 72.067 | 49.532 | 18.2821 | 1.00 | 34.47 | C |
| ATOM | 2031 | CD2 | LEU | A | 380 | 73.319 | 50.966 | 16.679 | 1.00 | 33.89 | C |
| ATOM | 2032 | N | GLY | A | 381 | 68.241 | 51.469 | 14.775 | 1.00 | 32.46 | N |
| ATOM | 2033 | CA | GLY | A | 381 | 67.414 | 51.321 | 13.589 | 1.00 | 33.27 | C |
| ATOM | 2034 | C | GLY | A | 381 | 68.237 | 51.561 | 12.338 | 1.00 | 34.20 | C |
| ATOM | 2035 | O | GLY | A | 381 | 68.519 | 50.635 | 11.580 | 1.00 | 34.83 | O |
| ATOM | 2036 | N | ARG | A | 382 | 68.630 | 52.813 | 12.132 | 1.00 | 35.93 | N |
| ATOM | 2037 | CA | ARG | A | 382 | 69.431 | 53.220 | 10.978 | 1.00 | 37.19 | C |
| ATOM | 2038 | C | ARG | A | 382 | 70.643 | 52.297 | 10.765 | 1.00 | 36.78 | C |
| ATOM | 2039 | O | ARG | A | 382 | 70.879 | 51.801 | 9.660 | 1.00 | 35.86 | O |
| ATOM | 2040 | CB | ARG | A | 382 | 69.905 | 54.666 | 11.181 | 1.00 | 39.94 | C |
| ATOM | 2041 | CG | ARG | A | 382 | 70.739 | 55.238 | 10.039 | 1.00 | 45.52 | C |
| ATOM | 2042 | CD | ARG | A | 382 | 71.468 | 56.513 | 10.466 | 1.00 | 49.66 | C |
| ATOM | 2043 | NE | ARG | A | 382 | 72.418 | 56.259 | 11.552 | 1.00 | 53.52 | N |
| ATOM | 2044 | CZ | ARG | A | 382 | 73.540 | 55.552 | 11.423 | 1.00 | 54.96 | C |
| ATOM | 2045 | NH1 | ARG | A | 382 | 73.871 | 55.023 | 10.249 | 1.00 | 54.91 | N |
| ATOM | 2046 | NH2 | ARG | A | 382 | 74.327 | 55.359 | 12.478 | 1.00 | 54.92 | N |
| ATOM | 2047 | N | TYR | A | 383 | 71.405 | 52.080 | 11.834 | 1.00 | 35.43 | N |
| ATOM | 2048 | CA | TYR | A | 383 | 72.595 | 51.230 | 11.798 | 1.00 | 34.40 | C |
| ATOM | 2049 | C | TYR | A | 383 | 72.324 | 49.893 | 11.108 | 1.00 | 34.58 | C |
| ATOM | 2050 | O | TYR | A | 383 | 73.082 | 49.480 | 10.229 | 1.00 | 35.55 | O |
| ATOM | 2051 | CB | TYR | A | 383 | 73.091 | 50.975 | 13.230 | 1.00 | 32.13 | C |
| ATOM | 2052 | CG | TYR | A | 383 | 74.315 | 50.090 | 13.328 | 1.00 | 32.06 | C |
| ATOM | 2053 | CD1 | TYR | A | 383 | 75.603 | 50.628 | 13.275 | 1.00 | 31.61 | C |
| ATOM | 2054 | CD2 | TYR | A | 383 | 74.185 | 48.711 | 13.476 | 1.00 | 31.52 | C |
| ATOM | 2055 | CE1 | TYR | A | 383 | 76.728 | 49.811 | 13.370 | 1.00 | 32.15 | C |
| ATOM | 2056 | CE2 | TYR | A | 383 | 75.293 | 47.889 | 13.569 | 1.00 | 30.67 | C |
| ATOM | 2057 | CZ | TYR | A | 383 | 76.564 | 48.440 | 13.516 | 1.00 | 33.10 | C |
| ATOM | 2058 | OH | TYR | A | 383 | 77.662 | 47.610 | 13.604 | 1.00 | 30.90 | O |
| ATOM | 2059 | N | PHE | A | 384 | 71.242 | 49.227 | 11.505 | 1.00 | 32.76 | N |
| ATOM | 2060 | CA | PHE | A | 384 | 70.877 | 47.929 | 10.936 | 1.00 | 34.01 | C |
| ATOM | 2061 | C | PHE | A | 384 | 70.164 | 47.997 | 9.574 | 1.00 | 34.71 | C |
| ATOM | 2062 | O | PHE | A | 384 | 70.249 | 47.058 | 8.782 | 1.00 | 35.23 | O |
| ATOM | 2063 | CB | PHE | A | 384 | 70.004 | 47.150 | 11.930 | 1.00 | 32.49 | C |
| ATOM | 2064 | CG | PHE | A | 384 | 70.764 | 46.603 | 13.115 | 1.00 | 33.56 | C |
| ATOM | 2065 | CD1 | PHE | A | 384 | 71.737 | 45.618 | 12.944 | 1.00 | 32.15 | C |
| ATOM | 2066 | CD2 | PHE | A | 384 | 70.510 | 47.076 | 14.401 | 1.00 | 31.87 | C |
| ATOM | 2067 | CE1 | PHE | A | 384 | 72.447 | 45.113 | 14.037 | 1.00 | 32.91 | C |
| ATOM | 2068 | CE2 | PHE | A | 384 | 71.211 | 46.579 | 15.497 | 1.00 | 32.18 | C |
| ATOM | 2069 | CZ | PHE | A | 384 | 72.181 | 45.596 | 15.317 | 1.00 | 31.64 | C |
| ATOM | 2070 | N | ALA | A | 385 | 69.465 | 49.096 | 9.305 | 1.00 | 35.43 | N |
| ATOM | 2071 | CA | ALA | A | 385 | 68.750 | 49.250 | 8.036 | 2.00 | 36.93 | C |
| ATOM | 2072 | C | ALA | A | 385 | 69.702 | 49.171 | 6.842 | 1.00 | 37.68 | C |
| ATOM | 2073 | O | ALA | A | 385 | 69.335 | 48.678 | 5.776 | 1.00 | 37.47 | O |
| ATOM | 2074 | CB | ALA | A | 385 | 67.999 | 50.585 | 8.014 | 1.00 | 35.75 | C |
| ATOM | 2075 | N | ARG | A | 386 | 70.926 | 49.658 | 7.038 | 1.00 | 38.60 | N |
| ATOM | 2076 | CA | ARG | A | 386 | 71.956 | 49.672 | 6.001 | 1.00 | 38.80 | C |
| ATOM | 2077 | C | ARG | A | 386 | 72.388 | 48.285 | 5.532 | 1.00 | 39.38 | C |
| ATOM | 2078 | O | ARG | A | 386 | 73.027 | 48.151 | 4.482 | 1.00 | 39.24 | O |
| ATOM | 2079 | CB | ARG | A | 386 | 73.213 | 50.392 | 6.506 | 1.00 | 38.96 | C |
| ATOM | 2080 | CG | ARG | A | 386 | 73.057 | 51.842 | 6.915 | 1.00 | 41.08 | C |
| ATOM | 2081 | CD | ARG | A | 386 | 74.373 | 52.314 | 7.530 | 1.00 | 43.49 | C |
| ATOM | 2082 | NE | ARG | A | 386 | 74.784 | 51.422 | 8.616 | 1.00 | 45.03 | N |
| ATOM | 2083 | CZ | ARG | A | 386 | 76.045 | 51.162 | 8.950 | 1.00 | 45.42 | C |
| ATOM | 2084 | NH1 | ARG | A | 386 | 77.049 | 51.724 | 8.284 | 1.00 | 44.14 | N |
| ATOM | 2085 | NH2 | ARG | A | 386 | 76.301 | 50.330 | 9.954 | 1.00 | 44.38 | N |
| ATOM | 2086 | N | PHE | A | 387 | 72.057 | 47.256 | 6.302 | 1.00 | 40.14 | N |
| ATOM | 2087 | CA | PHE | A | 387 | 72.483 | 45.911 | 5.950 | 1.00 | 41.48 | C |
| ATOM | 2088 | C | PHE | A | 387 | 71.620 | 45.137 | 4.954 | 1.00 | 43.09 | C |

TABLE 6-continued

| ATOM | 2089 | O   | PHE | A | 387 | 70.412 | 45.350 | 4.827  | 1.00 | 43.30 | O |
|------|------|-----|-----|---|-----|--------|--------|--------|------|-------|---|
| ATOM | 2090 | CB  | PHE | A | 387 | 72.658 | 45.066 | 7.218  | 1.00 | 41.15 | C |
| ATOM | 2091 | CG  | PHE | A | 387 | 73.559 | 45.690 | 8.255  | 1.00 | 41.44 | C |
| ATOM | 2092 | CD1 | PHE | A | 387 | 74.665 | 46.450 | 7.878  | 1.00 | 40.93 | C |
| ATOM | 2093 | CD2 | PHE | A | 387 | 73.312 | 45.496 | 9.614  | 1.00 | 40.05 | C |
| ATOM | 2094 | CE1 | PHE | A | 387 | 75.512 | 47.007 | 8.837  | 1.00 | 40.83 | C |
| ATOM | 2095 | CE2 | PHE | A | 387 | 74.154 | 46.048 | 10.583 | 1.00 | 39.34 | C |
| ATOM | 2096 | CZ  | PHE | A | 387 | 75.254 | 46.804 | 10.196 | 1.00 | 39.79 | C |
| ATOM | 2097 | N   | GLU | A | 388 | 72.284 | 44.222 | 4.261  | 1.00 | 44.03 | N |
| ATOM | 2098 | CA  | GLU | A | 388 | 71.673 | 43.348 | 3.274  | 1.00 | 45.03 | C |
| ATOM | 2099 | C   | GLU | A | 388 | 70.445 | 42.655 | 3.850  | 1.00 | 44.35 | C |
| ATOM | 2100 | O   | GLU | A | 388 | 69.431 | 42.507 | 3.171  | 1.00 | 43.66 | O |
| ATOM | 2101 | CB  | GLU | A | 388 | 72.700 | 42.297 | 2.846  | 1.00 | 46.61 | C |
| ATOM | 2102 | CG  | GLU | A | 388 | 72.210 | 41.252 | 1.853  | 1.00 | 50.47 | C |
| ATOM | 2103 | CD  | GLU | A | 388 | 71.843 | 41.854 | 0.516  | 1.00 | 52.73 | C |
| ATOM | 2104 | OE1 | GLU | A | 388 | 72.569 | 42.769 | 0.063  | 1.00 | 54.19 | O |
| ATOM | 2105 | OE2 | GLU | A | 388 | 70.842 | 41.407 | −0.089 | 1.00 | 54.15 | O |
| ATOM | 2106 | N   | GLU | A | 389 | 70.535 | 42.250 | 5.114  | 1.00 | 43.43 | N |
| ATOM | 2107 | CA  | GLU | A | 389 | 69.442 | 41.540 | 5.762  | 1.00 | 42.71 | C |
| ATOM | 2108 | C   | GLU | A | 389 | 68.218 | 42.345 | 6.187  | 1.00 | 42.10 | C |
| ATOM | 2109 | O   | GLU | A | 389 | 67.249 | 41.765 | 6.663  | 1.00 | 41.97 | O |
| ATOM | 2110 | CB  | GLU | A | 389 | 69.973 | 40.738 | 6.955  | 1.00 | 41.76 | C |
| ATOM | 2111 | CG  | GLU | A | 389 | 71.002 | 39.695 | 6.563  | 1.00 | 42.42 | C |
| ATOM | 2112 | CD  | GLU | A | 389 | 72.429 | 40.180 | 6.750  | 1.00 | 43.40 | C |
| ATOM | 2113 | OE1 | GLU | A | 389 | 72.688 | 41.387 | 6.567  | 1.00 | 42.57 | O |
| ATOM | 2114 | OE2 | GLU | A | 389 | 73.297 | 39.344 | 7.074  | 1.00 | 43.26 | O |
| ATOM | 2115 | N   | SER | A | 390 | 68.245 | 43.666 | 6.041  | 1.00 | 43.01 | N |
| ATOM | 2116 | CA  | SER | A | 390 | 67.065 | 44.446 | 6.399  | 1.00 | 45.54 | C |
| ATOM | 2117 | C   | SER | A | 390 | 66.047 | 44.174 | 5.280  | 1.00 | 47.27 | C |
| ATOM | 2118 | O   | SER | A | 390 | 66.422 | 44.044 | 4.112  | 1.00 | 46.75 | O |
| ATOM | 2119 | CB  | SER | A | 390 | 67.387 | 45.938 | 6.492  | 1.00 | 44.44 | C |
| ATOM | 2120 | OG  | SER | A | 390 | 67.730 | 46.469 | 5.230  | 1.00 | 47.93 | O |
| ATOM | 2121 | N   | PRO | A | 391 | 64.750 | 44.096 | 5.625  | 1.00 | 48.64 | N |
| ATOM | 2122 | CA  | PRO | A | 391 | 63.649 | 43.825 | 4.690  | 1.00 | 50.18 | C |
| ATOM | 2123 | C   | PRO | A | 391 | 63.348 | 44.842 | 3.587  | 1.00 | 51.58 | C |
| ATOM | 2124 | O   | PRO | A | 391 | 62.530 | 44.575 | 2.707  | 1.00 | 53.10 | O |
| ATOM | 2125 | CB  | PRO | A | 391 | 62.459 | 43.632 | 5.626  | 1.00 | 49.90 | C |
| ATOM | 2126 | CG  | PRO | A | 391 | 62.741 | 44.643 | 6.698  | 1.00 | 48.60 | C |
| ATOM | 2127 | CD  | PRO | A | 391 | 64.223 | 44.439 | 6.962  | 1.00 | 47.30 | C |
| ATOM | 2128 | N   | THR | A | 392 | 63.996 | 45.998 | 3.623  | 1.00 | 52.18 | N |
| ATOM | 2129 | CA  | THR | A | 392 | 63.737 | 47.020 | 2.620  | 1.00 | 52.69 | C |
| ATOM | 2130 | C   | THR | A | 392 | 64.409 | 46.724 | 1.287  | 1.00 | 54.68 | C |
| ATOM | 2131 | O   | THR | A | 392 | 65.163 | 45.759 | 1.158  | 1.00 | 54.94 | O |
| ATOM | 2132 | CB  | THR | A | 392 | 64.186 | 48.403 | 3.114  | 1.00 | 51.72 | C |
| ATOM | 2133 | OG1 | THR | A | 392 | 65.610 | 48.421 | 3.263  | 1.00 | 50.10 | O |
| ATOM | 2134 | CG2 | THR | A | 392 | 63.528 | 48.719 | 4.455  | 1.00 | 50.74 | C |
| ATOM | 2135 | N   | ARG | A | 393 | 64.132 | 47.565 | 0.295  | 1.00 | 56.32 | N |
| ATOM | 2136 | CA  | ARG | A | 393 | 64.699 | 47.376 | −1.032 | 1.00 | 58.34 | C |
| ATOM | 2137 | C   | ARG | A | 393 | 66.023 | 48.088 | −1.244 | 1.00 | 58.35 | C |
| ATOM | 2138 | O   | ARG | A | 393 | 66.223 | 49.219 | −0.800 | 1.00 | 57.31 | O |
| ATOM | 2139 | CB  | ARG | A | 393 | 63.701 | 47.818 | −2.112 | 1.00 | 60.27 | C |
| ATOM | 2140 | CG  | ARG | A | 393 | 62.463 | 46.928 | −2.205 | 1.00 | 63.46 | C |
| ATOM | 2141 | CD  | ARG | A | 393 | 61.561 | 47.293 | −3.386 | 1.00 | 65.10 | C |
| ATOM | 2142 | NE  | ARG | A | 393 | 61.125 | 48.684 | −3.338 | 1.00 | 66.35 | N |
| ATOM | 2143 | CZ  | ARG | A | 393 | 61.584 | 49.639 | −4.139 | 1.00 | 67.03 | C |
| ATOM | 2144 | NH1 | ARG | A | 393 | 62.495 | 49.355 | −5.063 | 1.00 | 67.37 | N |
| ATOM | 2145 | NH2 | ARG | A | 393 | 61.144 | 50.883 | −4.006 | 1.00 | 67.53 | N |
| ATOM | 2146 | N   | LYS | A | 394 | 66.927 | 47.394 | −1.925 | 1.00 | 59.11 | N |
| ATOM | 2147 | CA  | LYS | A | 394 | 68.241 | 47.922 | −2.248 | 1.00 | 59.88 | C |
| ATOM | 2148 | C   | LYS | A | 394 | 68.034 | 48.693 | −3.542 | 1.00 | 60.73 | C |
| ATOM | 2149 | O   | LYS | A | 394 | 67.680 | 48.106 | −4.562 | 1.00 | 61.24 | O |
| ATOM | 2150 | CB  | LYS | A | 394 | 69.218 | 46.768 | −2.479 | 1.00 | 59.07 | C |
| ATOM | 2151 | CG  | LYS | A | 394 | 70.646 | 47.055 | −2.060 | 1.00 | 58.59 | C |
| ATOM | 2152 | CD  | LYS | A | 394 | 71.590 | 45.945 | −2.504 | 1.00 | 58.08 | C |
| ATOM | 2153 | CE  | LYS | A | 394 | 71.164 | 44.582 | −1.990 | 1.00 | 57.63 | C |
| ATOM | 2154 | NZ  | LYS | A | 394 | 72.088 | 43.519 | −2.476 | 1.00 | 57.79 | N |
| ATOM | 2155 | N   | VAL | A | 395 | 68.234 | 50.005 | −3.503 | 1.00 | 62.13 | N |
| ATOM | 2156 | CA  | VAL | A | 395 | 68.048 | 50.827 | −4.692 | 1.00 | 63.84 | C |
| ATOM | 2157 | C   | VAL | A | 395 | 69.326 | 51.564 | −5.069 | 1.00 | 65.15 | C |
| ATOM | 2158 | O   | VAL | A | 395 | 69.995 | 52.143 | −4.215 | 1.00 | 65.50 | O |
| ATOM | 2159 | CB  | VAL | A | 395 | 66.917 | 51.859 | −4.483 | 1.00 | 63.69 | C |
| ATOM | 2160 | CG1 | VAL | A | 395 | 65.642 | 51.147 | −4.064 | 1.00 | 63.82 | C |
| ATOM | 2161 | CG2 | VAL | A | 395 | 67.323 | 52.884 | −3.438 | 1.00 | 63.76 | C |
| ATOM | 2162 | N   | THR | A | 396 | 69.666 | 51.537 | −6.354 | 1.00 | 66.43 | N |
| ATOM | 2163 | CA  | THR | A | 396 | 70.869 | 52.209 | −6.829 | 1.00 | 67.58 | C |
| ATOM | 2164 | C   | THR | A | 396 | 70.552 | 53.613 | −7.319 | 1.00 | 68.48 | C |
| ATOM | 2165 | O   | THR | A | 396 | 69.742 | 53.799 | −8.227 | 1.00 | 68.56 | O |
| ATOM | 2166 | CB  | THR | A | 396 | 71.535 | 51.427 | −7.971 | 1.00 | 67.68 | C |
| ATOM | 2167 | OG1 | THR | A | 396 | 71.919 | 50.130 | −7.500 | 1.00 | 68.09 | O |

TABLE 6-continued

| | | | | | | | | | | |
|---|---|---|---|---|---|---|---|---|---|---|
| ATOM | 2168 | CG2 | THR | A | 396 | 72.773 | 52.162 | −8.464 | 1.00 | 68.17 | C |
| ATOM | 2169 | N | ILE | A | 397 | 71.198 | 54.599 | −6.707 | 1.00 | 69.55 | N |
| ATOM | 2170 | CA | ILE | A | 397 | 70.999 | 55.996 | −7.066 | 1.00 | 70.46 | C |
| ATOM | 2171 | C | ILE | A | 397 | 72.322 | 56.609 | −7.518 | 1.00 | 71.03 | C |
| ATOM | 2172 | O | ILE | A | 397 | 73.224 | 56.826 | −6.708 | 1.00 | 71.53 | O |
| ATOM | 2173 | CB | ILE | A | 397 | 70.453 | 56.791 | −5.867 | 1.00 | 70.76 | C |
| ATOM | 2174 | CG1 | ILE | A | 397 | 69.148 | 56.154 | −5.384 | 1.00 | 71.18 | C |
| ATOM | 2175 | CG2 | ILE | A | 397 | 70.231 | 58.246 | −6.259 | 1.00 | 70.80 | C |
| ATOM | 2176 | CD1 | ILE | A | 397 | 68.542 | 56.832 | −4.175 | 1.00 | 71.99 | C |
| ATOM | 2177 | N | ASN | A | 398 | 72.425 | 56.879 | −8.817 | 1.00 | 71.45 | N |
| ATOM | 2178 | CA | ASN | A | 398 | 73.624 | 57.464 | −9.417 | 1.00 | 71.04 | C |
| ATOM | 2179 | C | ASN | A | 398 | 74.940 | 56.865 | −8.914 | 1.00 | 69.90 | C |
| ATOM | 2180 | O | ASN | A | 398 | 75.802 | 57.574 | −8.389 | 1.00 | 69.77 | O |
| ATOM | 2181 | CB | ASN | A | 398 | 73.630 | 58.989 | −9.218 | 1.00 | 72.89 | C |
| ATOM | 2182 | CG | ASN | A | 398 | 73.544 | 59.397 | −7.755 | 1.00 | 74.87 | C |
| ATOM | 2183 | OD1 | ASN | A | 398 | 74.421 | 59.071 | −6.949 | 1.00 | 76.25 | O |
| ATOM | 2184 | ND2 | ASN | A | 398 | 72.483 | 60.119 | −7.406 | 1.00 | 75.32 | N |
| ATOM | 2185 | N | GLY | A | 399 | 75.088 | 55.554 | −9.082 | 1.00 | 68.28 | N |
| ATOM | 2186 | CA | GLY | A | 399 | 76.307 | 54.885 | −8.659 | 1.00 | 66.71 | C |
| ATOM | 2187 | C | GLY | A | 399 | 76.392 | 54.549 | −7.181 | 1.00 | 65.56 | C |
| ATOM | 2188 | O | GLY | A | 399 | 77.351 | 53.912 | −6.739 | 1.00 | 65.55 | O |
| ATOM | 2189 | N | SER | A | 400 | 75.398 | 54.976 | −6.410 | 1.00 | 63.82 | N |
| ATOM | 2190 | CA | SER | A | 400 | 75.391 | 54.697 | −4.980 | 1.00 | 61.70 | C |
| ATOM | 2191 | C | SER | A | 400 | 74.256 | 53.761 | −4.602 | 1.00 | 59.98 | C |
| ATOM | 2192 | O | SER | A | 400 | 73.086 | 54.095 | −4.768 | 1.00 | 60.36 | O |
| ATOM | 2193 | CS | SER | A | 400 | 75.267 | 55.997 | −4.185 | 1.00 | 61.29 | C |
| ATOM | 2194 | OG | SER | A | 400 | 76.440 | 56.778 | −4.317 | 1.00 | 62.16 | O |
| ATOM | 2195 | N | VAL | A | 401 | 74.606 | 52.583 | −4.101 | 1.00 | 58.09 | N |
| ATOM | 2196 | CA | VAL | A | 401 | 73.602 | 51.617 | −3.685 | 1.00 | 56.62 | C |
| ATOM | 2197 | C | VAL | A | 401 | 73.099 | 52.029 | −2.303 | 1.00 | 56.96 | C |
| ATOM | 2198 | O | VAL | A | 401 | 73.886 | 52.176 | −1.361 | 1.00 | 57.55 | O |
| ATOM | 2199 | CS | VAL | A | 401 | 74.190 | 50.198 | −3.621 | 1.00 | 56.19 | C |
| ATOM | 2200 | CG1 | VAL | A | 401 | 73.129 | 49.214 | −3.161 | 1.00 | 54.63 | C |
| ATOM | 2201 | CG2 | VAL | A | 401 | 74.729 | 49.805 | −4.992 | 1.00 | 55.02 | C |
| ATOM | 2202 | N | MET | A | 402 | 71.789 | 52.226 | −2.190 | 1.00 | 55.36 | N |
| ATOM | 2203 | CA | MET | A | 402 | 71.181 | 52.648 | −0.935 | 1.00 | 53.84 | C |
| ATOM | 2204 | C | MET | A | 402 | 70.113 | 51.661 | −0.482 | 1.00 | 52.61 | C |
| ATOM | 2205 | O | MET | A | 402 | 69.789 | 50.707 | −1.188 | 1.00 | 51.84 | O |
| ATOM | 2206 | CS | MET | A | 402 | 70.521 | 54.022 | −1.109 | 1.00 | 55.25 | C |
| ATOM | 2207 | CG | MET | A | 402 | 71.356 | 55.062 | −1.837 | 1.00 | 55.38 | C |
| ATOM | 2208 | SD | MET | A | 402 | 72.760 | 55.653 | −0.884 | 1.00 | 59.37 | S |
| ATOM | 2209 | CE | MET | A | 402 | 71.959 | 56.904 | 0.134 | 1.00 | 56.83 | C |
| ATOM | 2210 | N | LYS | A | 403 | 69.579 | 51.900 | 0.713 | 1.00 | 50.16 | N |
| ATOM | 2211 | CA | LYS | A | 403 | 68.506 | 51.082 | 1.258 | 1.00 | 48.17 | C |
| ATOM | 2212 | C | LYS | A | 403 | 67.452 | 52.043 | 1.791 | 1.00 | 47.24 | C |
| ATOM | 2213 | O | LYS | A | 403 | 67.776 | 53.124 | 2.285 | 1.00 | 46.17 | O |
| ATOM | 2214 | CS | LYS | A | 403 | 69.007 | 50.168 | 2.382 | 1.00 | 48.44 | C |
| ATOM | 2215 | CG | LYS | A | 403 | 69.976 | 49.093 | 1.921 | 1.00 | 48.79 | C |
| ATOM | 2216 | CD | LYS | A | 403 | 69.677 | 47.739 | 2.552 | 1.00 | 48.91 | C |
| ATOM | 2217 | CE | LYS | A | 403 | 68.415 | 47.121 | 1.972 | 1.00 | 48.79 | C |
| ATOM | 2218 | NZ | LYS | A | 403 | 68.133 | 45.771 | 2.538 | 1.00 | 47.65 | N |
| ATOM | 2219 | N | GLU | A | 404 | 66.189 | 51.660 | 1.674 | 1.00 | 46.83 | N |
| ATOM | 2220 | CA | GLU | A | 404 | 65.115 | 52.514 | 2.147 | 1.00 | 46.62 | C |
| ATOM | 2221 | C | GLU | A | 404 | 65.046 | 52.448 | 3.661 | 1.00 | 45.53 | C |
| ATOM | 2222 | O | GLU | A | 404 | 65.329 | 51.412 | 4.269 | 1.00 | 43.78 | O |
| ATOM | 2223 | CB | GLU | A | 404 | 63.776 | 52.064 | 1.582 | 1.00 | 49.02 | C |
| ATOM | 2224 | CG | GLU | A | 404 | 63.846 | 51.421 | 0.222 | 1.00 | 53.76 | C |
| ATOM | 2225 | CD | GLU | A | 404 | 62.473 | 51.056 | −0.291 | 1.00 | 55.98 | C |
| ATOM | 2226 | OE1 | GLU | A | 404 | 61.767 | 51.971 | −0.772 | 1.00 | 56.94 | O |
| ATOM | 2227 | OE2 | GLU | A | 404 | 62.100 | 49.863 | −0.193 | 1.00 | 57.61 | O |
| ATOM | 2228 | N | TYR | A | 405 | 64.661 | 53.560 | 4.268 | 1.00 | 44.22 | N |
| ATOM | 2229 | CA | TYR | A | 405 | 64.543 | 53.615 | 5.708 | 1.00 | 43.49 | C |
| ATOM | 2230 | C | TYR | A | 405 | 63.488 | 54.634 | 6.071 | 1.00 | 42.96 | C |
| ATOM | 2231 | O | TYR | A | 405 | 63.612 | 55.811 | 5.744 | 1.00 | 43.26 | O |
| ATOM | 2232 | CB | TYR | A | 405 | 65.883 | 53.992 | 6.341 | 1.00 | 43.62 | C |
| ATOM | 2233 | CG | TYR | A | 405 | 65.853 | 54.018 | 7.851 | 1.00 | 43.93 | C |
| ATOM | 2234 | CD1 | TYR | A | 405 | 65.416 | 52.913 | 8.579 | 1.00 | 42.98 | C |
| ATOM | 2235 | CD2 | TYR | A | 405 | 66.258 | 55.150 | 8.554 | 1.00 | 44.65 | C |
| ATOM | 2236 | CE1 | TYR | A | 405 | 65.380 | 52.938 | 9.972 | 1.00 | 44.02 | C |
| ATOM | 2237 | CE2 | TYR | A | 405 | 66.227 | 55.184 | 9.946 | 1.00 | 44.86 | C |
| ATOM | 2238 | CZ | TYR | A | 405 | 65.786 | 54.077 | 10.646 | 1.00 | 43.66 | C |
| ATOM | 2239 | OH | TYR | A | 405 | 65.736 | 54.126 | 12.018 | 1.00 | 43.77 | O |
| ATOM | 2240 | N | TRP | A | 406 | 62.438 | 54.171 | 6.738 | 1.00 | 41.92 | N |
| ATOM | 2241 | CA | TRP | A | 406 | 61.361 | 55.052 | 7.149 | 1.00 | 40.82 | C |
| ATOM | 2242 | C | TRP | A | 406 | 60.985 | 54.760 | 8.594 | 1.00 | 40.62 | C |
| ATOM | 2243 | O | TRP | A | 406 | 61.088 | 53.622 | 9.056 | 1.00 | 40.00 | O |
| ATOM | 2244 | CB | TRP | A | 406 | 60.147 | 54.878 | 6.214 | 1.00 | 38.27 | C |
| ATOM | 2245 | CG | TRP | A | 406 | 59.520 | 53.510 | 6.228 | 1.00 | 35.96 | C |
| ATOM | 2246 | CD1 | TRP | A | 406 | 58.543 | 53.065 | 7.074 | 1.00 | 35.09 | C |

TABLE 6-continued

| ATOM | 2247 | CD2 | TRP | A | 406 | 59.845 | 52.405 | 5.373 | 1.00 | 35.52 | C |
| --- | --- | --- | --- | --- | --- | --- | --- | --- | --- | --- | --- |
| ATOM | 2248 | NE1 | TRP | A | 406 | 58.239 | 51.752 | 6.800 | 1.00 | 36.00 | N |
| ATOM | 2249 | CE2 | TRP | A | 406 | 59.024 | 51.320 | 5.762 | 1.00 | 36.30 | C |
| ATOM | 2250 | CE3 | TRP | A | 406 | 60.750 | 52.225 | 4.315 | 1.00 | 36.42 | C |
| ATOM | 2251 | CZ2 | TRP | A | 406 | 59.079 | 50.068 | 5.130 | 1.00 | 35.10 | C |
| ATOM | 2252 | CZ3 | TRP | A | 406 | 60.806 | 50.979 | 3.683 | 1.00 | 35.93 | C |
| ATOM | 2253 | CH2 | TRP | A | 406 | 59.972 | 49.918 | 4.096 | 1.00 | 35.80 | C |
| ATOM | 2254 | N | GLY | A | 407 | 60.568 | 55.800 | 9.307 | 1.00 | 41.39 | N |
| ATOM | 2255 | CA | GLY | A | 407 | 60.178 | 55.640 | 10.693 | 1.00 | 42.59 | C |
| ATOM | 2256 | C | GLY | A | 407 | 58.772 | 55.085 | 10.825 | 1.00 | 43.19 | C |
| ATOM | 2257 | O | GLY | A | 407 | 57.991 | 55.101 | 9.874 | 1.00 | 43.52 | O |
| ATOM | 2258 | N | GLU | A | 408 | 58.452 | 54.589 | 12.013 | 1.00 | 43.79 | N |
| ATOM | 2259 | CA | GLU | A | 408 | 57.138 | 54.029 | 12.287 | 1.00 | 43.77 | C |
| ATOM | 2260 | C | GLU | A | 408 | 56.100 | 55.139 | 12.370 | 1.00 | 45.22 | C |
| ATOM | 2261 | O | GLU | A | 408 | 54.899 | 54.891 | 12.292 | 1.00 | 45.34 | O |
| ATOM | 2262 | CB | GLU | A | 408 | 57.181 | 53.252 | 13.599 | 1.00 | 42.61 | C |
| ATOM | 2263 | CG | GLU | A | 408 | 58.025 | 51.997 | 13.524 | 1.00 | 41.23 | C |
| ATOM | 2264 | CD | GLU | A | 408 | 57.372 | 50.920 | 12.674 | 1.00 | 39.91 | C |
| ATOM | 2265 | OE1 | GLU | A | 408 | 56.280 | 50.456 | 13.056 | 1.00 | 39.37 | O |
| ATOM | 2266 | OE2 | GLU | A | 408 | 57.944 | 50.540 | 11.632 | 1.00 | 39.32 | O |
| ATOM | 2267 | N | GLY | A | 409 | 56.576 | 56.368 | 12.529 | 1.00 | 46.42 | N |
| ATOM | 2268 | CA | GLY | A | 409 | 55.676 | 57.500 | 12.619 | 1.00 | 48.58 | C |
| ATOM | 2269 | C | GLY | A | 409 | 55.339 | 58.095 | 11.265 | 1.00 | 49.72 | C |
| ATOM | 2270 | O | GLY | A | 409 | 54.491 | 58.977 | 11.174 | 1.00 | 49.49 | O |
| ATOM | 2271 | N | SER | A | 410 | 56.001 | 57.628 | 10.210 | 1.00 | 51.57 | N |
| ATOM | 2272 | CA | SER | A | 410 | 55.725 | 58.151 | 8.876 | 1.00 | 53.58 | C |
| ATOM | 2273 | C | SER | A | 410 | 54.411 | 57.566 | 8.385 | 1.00 | 55.64 | C |
| ATOM | 2274 | O | SER | A | 410 | 54.006 | 56.486 | 8.816 | 1.00 | 54.76 | O |
| ATOM | 2275 | CB | SER | A | 410 | 56.849 | 57.791 | 7.899 | 1.00 | 53.27 | C |
| ATOM | 2276 | OG | SER | A | 410 | 56.837 | 56.411 | 7.578 | 1.00 | 54.06 | O |
| ATOM | 2277 | N | SER | A | 411 | 53.740 | 58.285 | 7.490 | 1.00 | 58.45 | N |
| ATOM | 2278 | CA | SER | A | 411 | 52.472 | 57.816 | 6.951 | 1.00 | 61.28 | C |
| ATOM | 2279 | C | SER | A | 411 | 52.689 | 56.508 | 6.199 | 1.00 | 62.71 | C |
| ATOM | 2280 | O | SER | A | 411 | 51.794 | 55.662 | 6.123 | 1.00 | 62.97 | O |
| ATOM | 2281 | CB | SER | A | 411 | 51.875 | 58.873 | 6.020 | 1.00 | 62.05 | C |
| ATOM | 2282 | OG | SER | A | 411 | 52.807 | 59.264 | 5.028 | 1.00 | 63.19 | O |
| ATOM | 2283 | N | ARG | A | 412 | 53.892 | 56.343 | 5.658 | 1.00 | 64.06 | N |
| ATOM | 2284 | CA | ARG | A | 412 | 54.241 | 55.141 | 4.910 | 1.00 | 65.82 | C |
| ATOM | 2285 | C | ARG | A | 412 | 54.229 | 53.882 | 5.776 | 1.00 | 67.23 | C |
| ATOM | 2286 | O | ARG | A | 412 | 54.157 | 52.768 | 5.259 | 1.00 | 66.85 | O |
| ATOM | 2287 | CB | ARG | A | 412 | 55.626 | 55.306 | 4.273 | 1.00 | 64.77 | C |
| ATOM | 2288 | CG | ARG | A | 412 | 56.114 | 54.068 | 3.544 | 1.00 | 63.53 | C |
| ATOM | 2289 | CD | ARG | A | 412 | 57.441 | 54.298 | 2.845 | 1.00 | 62.50 | C |
| ATOM | 2290 | NE | ARG | A | 412 | 57.882 | 53.089 | 2.155 | 1.00 | 61.94 | N |
| ATOM | 2291 | CZ | ARG | A | 412 | 58.990 | 52.996 | 1.429 | 1.00 | 62.83 | C |
| ATOM | 2292 | NH1 | ARG | A | 412 | 59.791 | 54.047 | 1.286 | 1.00 | 62.91 | N |
| ATOM | 2293 | NH2 | ARG | A | 412 | 59.298 | 51.846 | 0.842 | 1.00 | 62.91 | N |
| ATOM | 2294 | N | ALA | A | 413 | 54.285 | 54.065 | 7.093 | 1.00 | 69.94 | N |
| ATOM | 2295 | CA | ALA | A | 413 | 54.315 | 52.940 | 8.022 | 1.00 | 72.61 | C |
| ATOM | 2296 | C | ALA | A | 413 | 52.973 | 52.554 | 8.631 | 1.00 | 74.53 | C |
| ATOM | 2297 | O | ALA | A | 413 | 52.439 | 51.485 | 8.337 | 1.00 | 74.51 | O |
| ATOM | 2298 | CB | ALA | A | 413 | 55.323 | 53.221 | 9.138 | 1.00 | 71.60 | C |
| ATOM | 2299 | N | ARG | A | 414 | 52.434 | 53.419 | 9.487 | 1.00 | 77.76 | N |
| ATOM | 2300 | CA | ARG | A | 414 | 51.167 | 53.137 | 10.155 | 1.00 | 80.61 | C |
| ATOM | 2301 | C | ARG | A | 414 | 49.963 | 53.024 | 9.213 | 1.00 | 81.50 | C |
| ATOM | 2302 | O | ARG | A | 414 | 48.815 | 53.073 | 9.661 | 1.00 | 81.79 | O |
| ATOM | 2303 | CB | ARG | A | 414 | 50.893 | 54.184 | 11.247 | 1.00 | 81.68 | C |
| ATOM | 2304 | CG | ARG | A | 414 | 50.556 | 55.589 | 10.755 | 1.00 | 83.90 | C |
| ATOM | 2305 | CD | ARG | A | 414 | 50.207 | 56.490 | 11.941 | 1.00 | 85.67 | C |
| ATOM | 2306 | NE | ARG | A | 414 | 49.470 | 57.693 | 11.558 | 1.00 | 87.41 | N |
| ATOM | 2307 | CZ | ARG | A | 414 | 48.918 | 58.537 | 12.426 | 1.00 | 88.02 | C |
| ATOM | 2308 | NH1 | ARG | A | 414 | 49.021 | 58.312 | 13.731 | 1.00 | 87.96 | N |
| ATOM | 2309 | NH2 | ARG | A | 414 | 48.253 | 59.602 | 11.994 | 1.00 | 88.30 | N |
| ATOM | 2310 | N | ASN | A | 415 | 50.226 | 52.867 | 7.916 | 1.00 | 82.42 | N |
| ATOM | 2311 | CA | ASN | A | 415 | 49.152 | 52.714 | 6.932 | 1.00 | 82.74 | C |
| ATOM | 2312 | C | ASN | A | 415 | 48.897 | 51.218 | 6.722 | 1.00 | 83.26 | C |
| ATOM | 2313 | O | ASN | A | 415 | 48.846 | 50.745 | 5.583 | 1.00 | 82.62 | O |
| ATOM | 2314 | CB | ASN | A | 415 | 49.535 | 53.345 | 5.581 | 1.00 | 83.10 | C |
| ATOM | 2315 | CG | ASN | A | 415 | 48.309 | 53.763 | 4.757 | 1.00 | 83.44 | C |
| ATOM | 2316 | OD1 | ASN | A | 415 | 48.403 | 53.990 | 3.538 | 1.00 | 81.84 | O |
| ATOM | 2317 | ND2 | ASN | A | 415 | 47.148 | 53.894 | 5.426 | 1.00 | 83.48 | N |
| ATOM | 2318 | N | TRP | A | 416 | 48.751 | 50.476 | 7.819 | 1.00 | 83.43 | N |
| ATOM | 2319 | CA | TRP | A | 416 | 48.504 | 49.039 | 7.734 | 1.00 | 83.29 | C |
| ATOM | 2320 | C | TRP | A | 416 | 47.153 | 48.658 | 8.340 | 1.00 | 83.50 | C |
| ATOM | 2321 | O | TRP | A | 416 | 46.650 | 49.328 | 9.246 | 1.00 | 83.70 | O |
| ATOM | 2322 | CB | TRP | A | 416 | 49.622 | 48.251 | 8.435 | 1.00 | 83.05 | C |
| ATOM | 2323 | CG | TRP | A | 416 | 49.577 | 48.306 | 9.936 | 1.00 | 83.22 | C |
| ATOM | 2324 | CD1 | TRP | A | 416 | 50.081 | 49.288 | 10.742 | 1.00 | 83.70 | C |
| ATOM | 2325 | CD2 | TRP | A | 416 | 48.957 | 47.350 | 10.807 | 1.00 | 83.09 | C |

TABLE 6-continued

| | | | | | | | | | | |
|---|---|---|---|---|---|---|---|---|---|---|
| ATOM | 2326 | NE1 | TRP | A | 416 | 49.812 | 49.003 | 12.062 | 1.00 | 83.83 N |
| ATOM | 2327 | CE2 | TRP | A | 416 | 49.122 | 47.820 | 12.130 | 1.00 | 83.53 C |
| ATOM | 2328 | CE3 | TRP | A | 416 | 48.274 | 46.143 | 10.597 | 1.00 | 82.77 C |
| ATOM | 2329 | CZ2 | TRP | A | 416 | 48.629 | 47.123 | 13.240 | 1.00 | 83.40 C |
| ATOM | 2330 | CZ3 | TRP | A | 416 | 47.784 | 45.452 | 11.699 | 1.00 | 82.88 C |
| ATOM | 2331 | CH2 | TRP | A | 416 | 47.965 | 45.945 | 13.005 | 1.00 | 83.24 C |
| ATOM | 2332 | N | GLU | A | 431 | 55.027 | 62.893 | 11.346 | 1.00 | 77.68 N |
| ATOM | 2333 | CA | GLU | A | 431 | 55.426 | 62.297 | 12.617 | 1.00 | 77.79 C |
| ATOM | 2334 | C | GLU | A | 431 | 56.719 | 61.495 | 12.439 | 1.00 | 76.90 C |
| ATOM | 2335 | O | GLU | A | 431 | 57.500 | 61.317 | 13.379 | 1.00 | 77.08 O |
| ATOM | 2336 | CB | GLU | A | 431 | 54.302 | 61.396 | 13.140 | 1.00 | 79.27 C |
| ATOM | 2337 | CG | GLU | A | 431 | 52.947 | 62.100 | 13.227 | 1.00 | 81.73 C |
| ATOM | 2338 | CD | GLU | A | 431 | 51.852 | 61.222 | 13.817 | 1.00 | 83.20 C |
| ATOM | 2339 | OE1 | GLU | A | 431 | 51.961 | 60.841 | 15.004 | 1.00 | 83.92 O |
| ATOM | 2340 | OE2 | GLU | A | 431 | 50.881 | 60.914 | 13.093 | 1.00 | 83.75 O |
| ATOM | 2341 | N | GLY | A | 432 | 56.936 | 61.018 | 11.218 | 1.00 | 75.40 N |
| ATOM | 2342 | CA | GLY | A | 432 | 58.133 | 60.258 | 10.909 | 1.00 | 73.03 C |
| ATOM | 2343 | C | GLY | A | 432 | 58.611 | 60.653 | 9.525 | 1.00 | 71.34 C |
| ATOM | 2344 | O | GLY | A | 432 | 57.915 | 61.386 | 8.818 | 1.00 | 71.32 O |
| ATOM | 2345 | N | VAL | A | 433 | 59.789 | 60.179 | 9.130 | 1.00 | 69.14 N |
| ATOM | 2346 | CA | VAL | A | 433 | 60.319 | 60.512 | 7.813 | 1.00 | 66.51 C |
| ATOM | 2347 | C | VAL | A | 433 | 60.700 | 59.280 | 6.994 | 1.00 | 64.72 C |
| ATOM | 2348 | O | VAL | A | 433 | 60.990 | 58.216 | 7.543 | 1.00 | 64.04 O |
| ATOM | 2349 | CB | VAL | A | 433 | 61.551 | 61.445 | 7.924 | 1.00 | 66.56 C |
| ATOM | 2350 | CG1 | VAL | A | 433 | 61.165 | 62.728 | 8.642 | 1.00 | 66.22 C |
| ATOM | 2351 | CG2 | VAL | A | 433 | 62.676 | 60.743 | 8.658 | 1.00 | 66.90 C |
| ATOM | 2352 | N | ASP | A | 434 | 60.683 | 59.446 | 5.675 | 1.00 | 62.15 N |
| ATOM | 2353 | CA | ASP | A | 434 | 61.019 | 58.387 | 4.732 | 1.00 | 59.84 C |
| ATOM | 2354 | C | ASP | A | 434 | 62.320 | 58.807 | 4.046 | 1.00 | 58.55 C |
| ATOM | 2355 | O | ASP | A | 434 | 62.383 | 59.876 | 3.441 | 1.00 | 58.58 O |
| ATOM | 2356 | CB | ASP | A | 434 | 59.894 | 58.247 | 3.699 | 1.00 | 59.57 C |
| ATOM | 2357 | CG | ASP | A | 434 | 60.072 | 57.047 | 2.795 | 1.00 | 59.49 C |
| ATOM | 2358 | OD1 | ASP | A | 434 | 59.322 | 56.927 | 1.804 | 1.00 | 59.07 O |
| ATOM | 2359 | OD2 | ASP | A | 434 | 60.959 | 56.217 | 3.079 | 1.00 | 60.22 O |
| ATOM | 2360 | N | SER | A | 435 | 63.355 | 57.976 | 4.136 | 1.00 | 56.49 N |
| ATOM | 2361 | CA | SER | A | 435 | 64.641 | 58.320 | 3.537 | 1.00 | 54.56 C |
| ATOM | 2362 | C | SER | A | 435 | 65.459 | 57.138 | 3.031 | 1.00 | 52.57 C |
| ATOM | 2363 | O | SER | A | 435 | 64.954 | 56.028 | 2.890 | 1.00 | 51.40 O |
| ATOM | 2364 | CB | SER | A | 435 | 65.480 | 59.107 | 4.546 | 1.00 | 55.14 C |
| ATOM | 2365 | OG | SER | A | 435 | 65.660 | 58.357 | 5.736 | 1.00 | 56.74 O |
| ATOM | 2366 | N | TYR | A | 436 | 66.735 | 57.401 | 2.764 | 1.00 | 51.28 N |
| ATOM | 2367 | CA | TYR | A | 436 | 67.664 | 56.391 | 2.269 | 1.00 | 50.73 C |
| ATOM | 2368 | C | TYR | A | 436 | 68.936 | 56.359 | 3.114 | 1.00 | 50.04 C |
| ATOM | 2369 | O | TYR | A | 436 | 69.356 | 57.382 | 3.657 | 1.00 | 50.12 O |
| ATOM | 2370 | CB | TYR | A | 436 | 68.057 | 56.704 | 0.824 | 1.00 | 52.87 C |
| ATOM | 2371 | CG | TYR | A | 436 | 66.940 | 56.591 | −0.185 | 1.00 | 53.47 C |
| ATOM | 2372 | CD1 | TYR | A | 436 | 66.475 | 55.344 | −0.603 | 1.00 | 53.78 C |
| ATOM | 2373 | CD2 | TYR | A | 436 | 66.356 | 57.733 | −0.733 | 1.00 | 54.90 C |
| ATOM | 2374 | CE1 | TYR | A | 436 | 65.457 | 55.237 | −1.545 | 1.00 | 54.59 C |
| ATOM | 2375 | CE2 | TYR | A | 436 | 65.333 | 57.637 | −1.679 | 1.00 | 55.49 C |
| ATOM | 2376 | CZ | TYR | A | 436 | 64.891 | 56.386 | −2.077 | 1.00 | 55.11 C |
| ATOM | 2377 | OH | TYR | A | 436 | 63.876 | 56.285 | −2.999 | 1.00 | 56.28 O |
| ATOM | 2378 | N | VAL | A | 437 | 69.541 | 55.180 | 3.227 | 1.00 | 47.66 N |
| ATOM | 2379 | CA | VAL | A | 437 | 70.785 | 55.022 | 3.969 | 1.00 | 46.24 C |
| ATOM | 2380 | C | VAL | A | 437 | 71.743 | 54.236 | 3.089 | 1.00 | 46.02 C |
| ATOM | 2381 | O | VAL | A | 437 | 71.343 | 53.283 | 2.421 | 1.00 | 45.29 O |
| ATOM | 2382 | CB | VAL | A | 437 | 70.592 | 54.260 | 5.314 | 1.00 | 46.00 C |
| ATOM | 2383 | CG1 | VAL | A | 437 | 69.654 | 55.037 | 6.227 | 1.00 | 45.51 C |
| ATOM | 2384 | CG2 | VAL | A | 437 | 70.071 | 52.853 | 5.058 | 1.00 | 44.32 C |
| ATOM | 2385 | N | PRO | A | 438 | 73.026 | 54.628 | 3.073 | 1.00 | 46.55 N |
| ATOM | 2386 | CA | PRO | A | 438 | 74.024 | 53.935 | 2.252 | 1.00 | 45.89 C |
| ATOM | 2387 | C | PRO | A | 438 | 74.178 | 52.463 | 2.600 | 1.00 | 45.71 C |
| ATOM | 2388 | O | PRO | A | 438 | 74.268 | 52.095 | 3.773 | 1.00 | 45.41 O |
| ATOM | 2389 | CE | PRO | A | 438 | 75.301 | 54.738 | 2.506 | 1.00 | 46.50 C |
| ATOM | 2390 | CG | PRO | A | 438 | 75.099 | 55.254 | 3.901 | 1.00 | 47.81 C |
| ATOM | 2391 | CD | PRO | A | 438 | 73.652 | 55.688 | 3.881 | 1.00 | 46.25 C |
| ATOM | 2392 | N | TYR | A | 439 | 74.191 | 51.629 | 1.564 | 1.00 | 44.94 N |
| ATOM | 2393 | CA | TYR | A | 439 | 74.340 | 50.187 | 1.712 | 1.00 | 44.07 C |
| ATOM | 2394 | C | TYR | A | 439 | 75.686 | 49.898 | 2.371 | 1.00 | 44.51 C |
| ATOM | 2395 | O | TYR | A | 439 | 76.711 | 50.459 | 1.985 | 1.00 | 44.53 O |
| ATOM | 2396 | CB | TYR | A | 439 | 74.273 | 49.521 | 0.334 | 1.00 | 42.82 C |
| ATOM | 2397 | CG | TYR | A | 439 | 74.442 | 48.019 | 0.340 | 1.00 | 41.12 C |
| ATOM | 2398 | CD1 | TYR | A | 439 | 73.561 | 47.201 | 1.041 | 1.00 | 41.19 C |
| ATOM | 2399 | CD2 | TYR | A | 439 | 75.464 | 47.412 | −0.388 | 1.00 | 42.23 C |
| ATOM | 2400 | CE1 | TYR | A | 439 | 73.690 | 45.811 | 1.014 | 1.00 | 41.86 C |
| ATOM | 2401 | CE2 | TYR | A | 439 | 75.603 | 46.025 | −0.420 | 1.00 | 42.30 C |
| ATOM | 2402 | CZ | TYR | A | 439 | 74.712 | 45.232 | 0.281 | 1.00 | 42.80 C |
| ATOM | 2403 | OH | TYR | A | 439 | 74.834 | 43.861 | 0.242 | 1.00 | 44.53 O |
| ATOM | 2404 | N | ALA | A | 440 | 75.684 | 49.014 | 3.361 | 1.00 | 44.65 N |

TABLE 6-continued

| | | | | | | | | | | | |
|---|---|---|---|---|---|---|---|---|---|---|---|
| ATOM | 2405 | CA | ALA | A | 440 | 76.914 | 48.689 | 4.067 | 1.00 | 44.96 | C |
| ATOM | 2406 | C | ALA | A | 440 | 77.335 | 47.239 | 3.880 | 1.00 | 44.76 | C |
| ATOM | 2407 | O | ALA | A | 440 | 78.424 | 46.847 | 4.294 | 1.00 | 45.32 | O |
| ATOM | 2408 | CB | ALA | A | 440 | 76.751 | 49.001 | 5.549 | 1.00 | 44.41 | C |
| ATOM | 2409 | N | GLY | A | 441 | 76.479 | 46.447 | 3.248 | 1.00 | 44.13 | N |
| ATOM | 2410 | CA | GLY | A | 441 | 76.803 | 45.049 | 3.041 | 1.00 | 43.90 | C |
| ATOM | 2411 | C | GLY | A | 441 | 76.135 | 44.176 | 4.087 | 1.00 | 43.49 | C |
| ATOM | 2412 | O | GLY | A | 441 | 75.115 | 44.559 | 4.660 | 1.00 | 43.21 | O |
| ATOM | 2413 | N | LYS | A | 442 | 76.713 | 43.005 | 4.341 | 1.00 | 44.00 | N |
| ATOM | 2414 | CA | LYS | A | 442 | 76.171 | 42.064 | 5.318 | 1.00 | 44.24 | C |
| ATOM | 2415 | C | LYS | A | 442 | 76.360 | 42.533 | 6.757 | 1.00 | 43.92 | C |
| ATOM | 2416 | O | LYS | A | 442 | 77.363 | 43.171 | 7.091 | 1.00 | 44.02 | O |
| ATOM | 2417 | CB | LYS | A | 442 | 76.834 | 40.697 | 5.142 | 1.00 | 46.18 | C |
| ATOM | 2418 | CG | LYS | A | 442 | 76.608 | 40.085 | 3.766 | 1.00 | 50.07 | C |
| ATOM | 2419 | CD | LYS | A | 442 | 75.542 | 38.992 | 3.794 | 1.00 | 51.33 | C |
| ATOM | 2420 | CE | LYS | A | 442 | 76.086 | 37.716 | 4.431 | 1.00 | 54.42 | C |
| ATOM | 2421 | NZ | LYS | A | 442 | 75.115 | 36.573 | 4.373 | 1.00 | 55.91 | N |
| ATOM | 2422 | N | LEU | A | 443 | 75.393 | 42.200 | 7.605 | 1.00 | 42.94 | N |
| ATOM | 2423 | CA | LEU | A | 443 | 75.421 | 42.568 | 9.018 | 1.00 | 41.75 | C |
| ATOM | 2424 | C | LEU | A | 443 | 76.697 | 42.133 | 9.746 | 1.00 | 42.03 | C |
| ATOM | 2425 | O | LEU | A | 443 | 77.295 | 42.912 | 10.485 | 1.00 | 40.47 | O |
| ATOM | 2426 | CB | LEU | A | 443 | 74.201 | 41.968 | 9.726 | 1.00 | 40.09 | C |
| ATOM | 2427 | CG | LEU | A | 443 | 74.055 | 42.185 | 11.238 | 1.00 | 39.89 | C |
| ATOM | 2428 | CD1 | LEU | A | 443 | 72.596 | 42.020 | 11.640 | 1.00 | 38.06 | C |
| ATOM | 2429 | CD2 | LEU | A | 443 | 74.937 | 41.200 | 11.997 | 1.00 | 38.79 | C |
| ATOM | 2430 | N | LYS | A | 444 | 77.108 | 40.890 | 9.522 | 1.00 | 42.70 | N |
| ATOM | 2431 | CA | LYS | A | 444 | 78.281 | 40.315 | 10.178 | 1.00 | 44.85 | C |
| ATOM | 2432 | C | LYS | A | 444 | 79.577 | 41.134 | 10.229 | 1.00 | 45.18 | C |
| ATOM | 2433 | O | LYS | A | 444 | 80.073 | 41.445 | 11.314 | 1.00 | 44.50 | O |
| ATOM | 2434 | CB | LYS | A | 444 | 78.595 | 38.945 | 9.571 | 1.00 | 46.48 | C |
| ATOM | 2435 | CG | LYS | A | 444 | 79.616 | 38.150 | 10.374 | 1.00 | 50.45 | C |
| ATOM | 2436 | CD | LYS | A | 444 | 79.867 | 36.779 | 9.768 | 1.00 | 53.23 | C |
| ATOM | 2437 | CE | LYS | A | 444 | 80.731 | 35.935 | 10.688 | 1.00 | 54.88 | C |
| ATOM | 2438 | NZ | LYS | A | 444 | 82.030 | 36.605 | 10.975 | 1.00 | 55.49 | N |
| ATOM | 2439 | N | ASP | A | 445 | 80.134 | 41.466 | 9.068 | 1.00 | 45.06 | N |
| ATOM | 2440 | CA | ASP | A | 445 | 81.388 | 42.212 | 9.017 | 1.00 | 45.21 | C |
| ATOM | 2441 | C | ASP | A | 445 | 81.284 | 43.592 | 9.636 | 1.00 | 43.85 | C |
| ATOM | 2442 | O | ASP | A | 445 | 82.255 | 44.105 | 10.192 | 1.00 | 43.92 | O |
| ATOM | 2443 | CB | ASP | A | 445 | 81.880 | 42.349 | 7.573 | 1.00 | 48.38 | C |
| ATOM | 2444 | CG | ASP | A | 445 | 82.108 | 41.005 | 6.902 | 1.00 | 51.51 | C |
| ATOM | 2445 | OD1 | ASP | A | 445 | 82.776 | 40.133 | 7.507 | 1.00 | 52.73 | O |
| ATOM | 2446 | OD2 | ASP | A | 445 | 81.620 | 40.825 | 5.766 | 1.00 | 53.93 | O |
| ATOM | 2447 | N | ASN | A | 446 | 80.110 | 44.195 | 9.533 | 1.00 | 41.34 | N |
| ATOM | 2448 | CA | ASN | A | 446 | 79.900 | 45.522 | 10.086 | 1.00 | 40.70 | C |
| ATOM | 2449 | C | ASN | A | 446 | 79.815 | 45.501 | 11.605 | 1.00 | 39.56 | C |
| ATOM | 2450 | O | ASN | A | 446 | 80.439 | 46.318 | 12.273 | 1.00 | 40.02 | O |
| ATOM | 2451 | CB | ASN | A | 446 | 78.637 | 46.126 | 9.491 | 1.00 | 40.72 | C |
| ATOM | 2452 | CG | ASN | A | 446 | 78.823 | 46.520 | 8.046 | 1.00 | 41.93 | C |
| ATOM | 2453 | OD1 | ASN | A | 446 | 79.347 | 47.601 | 7.748 | 1.00 | 42.76 | O |
| ATOM | 2454 | ND2 | ASN | A | 446 | 78.416 | 45.640 | 7.134 | 1.00 | 39.05 | N |
| ATOM | 2455 | N | VAL | A | 447 | 79.039 | 44.571 | 12.146 | 1.00 | 38.14 | N |
| ATOM | 2456 | CA | VAL | A | 447 | 78.901 | 44.450 | 13.590 | 1.00 | 38.14 | C |
| ATOM | 2457 | C | VAL | A | 447 | 80.251 | 44.071 | 14.215 | 1.00 | 38.90 | C |
| ATOM | 2458 | O | VAL | A | 447 | 80.594 | 44.534 | 15.295 | 1.00 | 38.04 | O |
| ATOM | 2459 | CB | VAL | A | 447 | 77.837 | 43.386 | 13.952 | 1.00 | 37.40 | C |
| ATOM | 2460 | CG1 | VAL | A | 447 | 77.891 | 43.065 | 15.437 | 1.00 | 37.24 | C |
| ATOM | 2461 | CG2 | VAL | A | 447 | 76.454 | 43.899 | 13.579 | 1.00 | 36.23 | C |
| ATOM | 2462 | N | GLU | A | 448 | 81.018 | 43.235 | 13.524 | 1.00 | 39.10 | N |
| ATOM | 2463 | CA | GLU | A | 448 | 82.313 | 42.826 | 14.039 | 1.00 | 39.82 | C |
| ATOM | 2464 | C | GLU | A | 448 | 83.247 | 44.036 | 14.100 | 1.00 | 37.84 | C |
| ATOM | 2465 | O | GLU | A | 448 | 83.963 | 44.222 | 15.078 | 1.00 | 36.51 | O |
| ATOM | 2466 | CB | GLU | A | 448 | 82.917 | 41.728 | 13.153 | 1.00 | 42.41 | C |
| ATOM | 2467 | CG | GLU | A | 448 | 84.226 | 41.149 | 13.677 | 1.00 | 48.39 | C |
| ATOM | 2468 | CD | GLU | A | 448 | 84.802 | 40.073 | 12.760 | 1.00 | 53.42 | C |
| ATOM | 2469 | OE1 | GLU | A | 448 | 85.409 | 40.422 | 11.718 | 1.00 | 53.76 | O |
| ATOM | 2470 | OE2 | GLU | A | 448 | 84.634 | 38.871 | 13.078 | 1.00 | 56.37 | O |
| ATOM | 2471 | N | ALA | A | 449 | 83.235 | 44.854 | 13.053 | 1.00 | 36.52 | N |
| ATOM | 2472 | CA | ALA | A | 449 | 84.081 | 46.045 | 13.006 | 1.00 | 36.71 | C |
| ATOM | 2473 | C | ALA | A | 449 | 83.704 | 47.016 | 14.122 | 1.00 | 36.23 | C |
| ATOM | 2474 | O | ALA | A | 449 | 84.572 | 47.530 | 14.823 | 1.00 | 36.73 | O |
| ATOM | 2475 | CB | ALA | A | 449 | 83.951 | 46.741 | 11.646 | 1.00 | 34.97 | C |
| ATOM | 2476 | N | SER | A | 450 | 82.406 | 47.262 | 14.277 | 1.00 | 34.72 | N |
| ATOM | 2477 | CA | SER | A | 450 | 81.914 | 48.166 | 15.310 | 1.00 | 34.31 | C |
| ATOM | 2478 | C | SER | A | 450 | 82.313 | 47.717 | 16.714 | 1.00 | 34.50 | C |
| ATOM | 2479 | O | SER | A | 450 | 82.868 | 48.501 | 17.493 | 1.00 | 31.24 | O |
| ATOM | 2480 | CB | SER | A | 450 | 80.387 | 48.279 | 15.235 | 1.00 | 33.37 | C |
| ATOM | 2481 | OG | SER | A | 450 | 79.991 | 49.068 | 14.130 | 1.00 | 33.43 | O |
| ATOM | 2482 | N | LEU | A | 451 | 82.043 | 46.450 | 17.026 | 1.00 | 34.30 | N |
| ATOM | 2483 | CA | LEU | A | 451 | 82.348 | 45.923 | 18.346 | 1.00 | 35.10 | C |

TABLE 6-continued

| ATOM | 2484 | C | LEU | A | 451 | 83.838 | 45.784 | 18.631 | 1.00 | 36.71 | C |
| ATOM | 2485 | O | LEU | A | 451 | 84.245 | 45.789 | 19.791 | 1.00 | 36.58 | O |
| ATOM | 2486 | CB | LEU | A | 451 | 81.6.21 | 44.596 | 18.565 | 1.00 | 34.20 | C |
| ATOM | 2487 | CG | LEU | A | 451 | 80.095 | 44.766 | 18.562 | 1.00 | 34.08 | C |
| ATOM | 2488 | CD1 | LEU | A | 451 | 79.423 | 43.457 | 18.926 | 1.00 | 32.06 | C |
| ATOM | 2489 | CD2 | LEU | A | 451 | 79.693 | 45.861 | 19.543 | 1.00 | 32.22 | C |
| ATOM | 2490 | N | ASN | A | 452 | 84.655 | 45.665 | 17.588 | 1.00 | 37.71 | N |
| ATOM | 2491 | CA | ASN | A | 452 | 86.089 | 45.579 | 17.811 | 1.00 | 39.20 | C |
| ATOM | 2492 | C | ASN | A | 452 | 86.536 | 46.934 | 18.347 | 1.00 | 38.74 | C |
| ATOM | 2493 | O | ASN | A | 452 | 87.394 | 47.009 | 19.231 | 1.00 | 38.71 | O |
| ATOM | 2494 | CB | ASN | A | 452 | 86.853 | 45.263 | 16.523 | 1.00 | 40.36 | C |
| ATOM | 2495 | CG | ASN | A | 452 | 86.888 | 43.781 | 16.215 | 1.00 | 44.54 | C |
| ATOM | 2496 | OD1 | ASN | A | 452 | 86.761 | 42.940 | 17.113 | 1.00 | 46.29 | O |
| ATOM | 2497 | ND2 | ASN | A | 452 | 87.085 | 43.447 | 14.941 | 1.00 | 46.83 | N |
| ATOM | 2498 | N | LYS | A | 453 | 85.949 | 48.001 | 17.812 | 1.00 | 37.17 | N |
| ATOM | 2499 | CA | LYS | A | 453 | 86.292 | 49.347 | 18.256 | 1.00 | 37.39 | C |
| ATOM | 2500 | C | LYS | A | 453 | 85.809 | 49.571 | 19.685 | 1.00 | 35.35 | C |
| ATOM | 2501 | O | LYS | A | 453 | 86.501 | 50.197 | 20.481 | 1.00 | 35.05 | O |
| ATOM | 2502 | CB | LYS | A | 453 | 85.700 | 50.395 | 17.303 | 1.00 | 38.34 | C |
| ATOM | 2503 | CG | LYS | A | 453 | 86.488 | 50.492 | 15.995 | 1.00 | 42.57 | C |
| ATOM | 2504 | CD | LYS | A | 453 | 85.717 | 51.157 | 14.858 | 1.00 | 44.00 | C |
| ATOM | 2505 | CE | LYS | A | 453 | 85.478 | 52.635 | 15.094 | 1.00 | 45.69 | C |
| ATOM | 2506 | NZ | LYS | A | 453 | 84.699 | 53.222 | 13.962 | 1.00 | 46.71 | N |
| ATOM | 2507 | N | VAL | A | 454 | 84.631 | 49.048 | 20.008 | 1.00 | 32.74 | N |
| ATOM | 2508 | CA | VAL | A | 454 | 84.093 | 49.188 | 21.352 | 1.00 | 31.66 | C |
| ATOM | 2509 | C | VAL | A | 454 | 85.019 | 48.455 | 22.328 | 1.00 | 32.27 | C |
| ATOM | 2510 | O | VAL | A | 454 | 85.418 | 49.007 | 23.358 | 1.00 | 30.47 | O |
| ATOM | 2511 | CB | VAL | A | 454 | 82.663 | 48.597 | 21.455 | 1.00 | 31.71 | C |
| ATOM | 2512 | CG1 | VAL | A | 454 | 82.225 | 48.527 | 22.920 | 1.00 | 30.29 | C |
| ATOM | 2513 | CG2 | VAL | A | 454 | 81.680 | 49.459 | 20.651 | 1.00 | 30.64 | C |
| ATOM | 2514 | N | LYS | A | 455 | 85.365 | 47.216 | 21.989 | 1.00 | 32.48 | N |
| ATOM | 2515 | CA | LYS | A | 455 | 86.245 | 46.402 | 22.828 | 1.00 | 34.26 | C |
| ATOM | 2516 | C | LYS | A | 455 | 87.589 | 47.081 | 23.053 | 1.00 | 34.74 | C |
| ATOM | 2517 | O | LYS | A | 455 | 88.123 | 47.081 | 24.162 | 1.00 | 34.39 | O |
| ATOM | 2518 | CB | LYS | A | 455 | 86.483 | 45.035 | 22.182 | 1.00 | 34.75 | C |
| ATOM | 2519 | CG | LYS | A | 455 | 85.336 | 44.055 | 22.297 | 1.00 | 35.60 | C |
| ATOM | 2520 | CD | LYS | A | 455 | 85.607 | 42.860 | 21.395 | 1.00 | 38.09 | C |
| ATOM | 2521 | CE | LYS | A | 455 | 84.529 | 41.811 | 21.508 | 1.00 | 41.48 | C |
| ATOM | 2522 | NZ | LYS | A | 455 | 84.809 | 40.638 | 20.627 | 1.00 | 41.09 | N |
| ATOM | 2523 | N | SER | A | 456 | 88.140 | 47.652 | 21.989 | 1.00 | 35.13 | N |
| ATOM | 2524 | CA | SER | A | 456 | 89.421 | 48.327 | 22.090 | 1.00 | 36.02 | C |
| ATOM | 2525 | C | SER | A | 456 | 89.313 | 49.533 | 23.031 | 1.00 | 35.16 | C |
| ATOM | 2526 | O | SER | A | 456 | 90.171 | 49.744 | 23.890 | 1.00 | 33.17 | O |
| ATOM | 2527 | CB | SER | A | 456 | 89.888 | 48.764 | 20.702 | 1.00 | 36.46 | C |
| ATOM | 2528 | OG | SER | A | 456 | 91.172 | 49.341 | 20.779 | 1.00 | 39.49 | O |
| ATOM | 2529 | N | THR | A | 457 | 88.254 | 50.320 | 22.875 | 1.00 | 33.64 | N |
| ATOM | 2530 | CA | THR | A | 457 | 88.056 | 51.478 | 23.734 | 1.00 | 33.01 | C |
| ATOM | 2531 | C | THR | A | 457 | 87.863 | 51.029 | 25.182 | 1.00 | 32.03 | C |
| ATOM | 2532 | O | THR | A | 457 | 88.352 | 51.672 | 26.108 | 1.00 | 32.59 | O |
| ATOM | 2533 | CB | THR | A | 457 | 86.835 | 52.297 | 23.286 | 1.00 | 32.27 | C |
| ATOM | 2534 | OG1 | THR | A | 457 | 87.050 | 52.756 | 21.949 | 1.00 | 34.93 | O |
| ATOM | 2535 | CG2 | THR | A | 457 | 86.624 | 53.497 | 24.193 | 1.00 | 29.23 | C |
| ATOM | 2536 | N | MET | A | 458 | 87.150 | 49.926 | 25.379 | 1.00 | 31.95 | N |
| ATOM | 2537 | CA | MET | A | 458 | 86.925 | 49.419 | 26.723 | 1.00 | 30.89 | C |
| ATOM | 2538 | C | MET | A | 458 | 88.256 | 49.114 | 27.407 | 1.00 | 32.55 | C |
| ATOM | 2539 | O | MET | A | 458 | 88.426 | 49.391 | 28.598 | 1.00 | 31.39 | O |
| ATOM | 2540 | CB | MET | A | 458 | 86.031 | 48.179 | 26.683 | 1.00 | 30.61 | C |
| ATOM | 2541 | CG | MET | A | 458 | 84.548 | 48.518 | 26.564 | 1.00 | 28.50 | C |
| ATOM | 2542 | SD | MET | A | 458 | 83.488 | 47.100 | 26.262 | 1.00 | 29.80 | S |
| ATOM | 2543 | CE | MET | A | 458 | 83.570 | 46.223 | 27.839 | 1.00 | 27.13 | C |
| ATOM | 2544 | N | CYS | A | 459 | 89.211 | 48.568 | 26.660 | 1.00 | 32.81 | N |
| ATOM | 2545 | CA | CYS | A | 459 | 90.508 | 48.281 | 27.257 | 1.00 | 34.73 | C |
| ATOM | 2546 | C | CYS | A | 459 | 91.260 | 49.572 | 27.583 | 1.00 | 34.20 | C |
| ATOM | 2547 | O | CYS | A | 459 | 91.998 | 49.620 | 28.566 | 1.00 | 33.88 | O |
| ATOM | 2548 | CB | CYS | A | 459 | 91.347 | 47.380 | 26.350 | 1.00 | 36.62 | C |
| ATOM | 2549 | SG | CYS | A | 459 | 90.944 | 45.616 | 26.569 | 1.00 | 40.92 | S |
| ATOM | 2550 | N | ASN | A | 460 | 91.075 | 50.610 | 26.766 | 1.00 | 32.61 | N |
| ATOM | 2551 | CA | ASN | A | 460 | 91.721 | 51.892 | 27.034 | 1.00 | 32.54 | C |
| ATOM | 2552 | C | ASN | A | 460 | 91.176 | 52.381 | 28.368 | 1.00 | 31.81 | C |
| ATOM | 2553 | O | ASN | A | 460 | 91.853 | 53.091 | 29.098 | 1.00 | 32.53 | O |
| ATOM | 2554 | CB | ASN | A | 460 | 91.371 | 52.947 | 25.976 | 1.00 | 33.21 | C |
| ATOM | 2555 | CG | ASN | A | 460 | 92.034 | 52.693 | 24.646 | 1.00 | 35.78 | C |
| ATOM | 2556 | OD1 | ASN | A | 460 | 91.356 | 52.543 | 23.633 | 1.00 | 36.50 | O |
| ATOM | 2557 | ND2 | ASN | A | 460 | 93.365 | 52.648 | 24.634 | 1.00 | 34.40 | N |
| ATOM | 2558 | N | CYS | A | 461 | 89.932 | 52.010 | 28.668 | 1.00 | 31.68 | N |
| ATOM | 2559 | CA | CYS | A | 461 | 89.285 | 52.423 | 29.907 | 1.00 | 31.03 | C |
| ATOM | 2560 | C | CYS | A | 461 | 89.515 | 51.437 | 31.053 | 1.00 | 31.06 | C |
| ATOM | 2561 | O | CYS | A | 461 | 89.005 | 51.630 | 32.146 | 1.00 | 32.13 | O |
| ATOM | 2562 | CB | CYS | A | 461 | 87.777 | 52.617 | 29.675 | 1.00 | 32.30 | C |

TABLE 6-continued

| ATOM | 2563 | SG | CYS | A | 461 | 87.364 | 53.913 | 28.455 | 1.00 | 34.10 | S |
| --- | --- | --- | --- | --- | --- | --- | --- | --- | --- | --- | --- |
| ATOM | 2564 | N | GLY | A | 462 | 90.281 | 50.381 | 30.795 | 1.00 | 31.97 | N |
| ATOM | 2565 | CA | GLY | A | 462 | 90.569 | 49.393 | 31.822 | 1.00 | 31.72 | C |
| ATOM | 2566 | C | GLY | A | 462 | 89.412 | 48.464 | 32.149 | 1.00 | 32.82 | C |
| ATOM | 2567 | O | GLY | A | 462 | 89.277 | 47.995 | 33.282 | 1.00 | 32.24 | O |
| ATOM | 2568 | N | ALA | A | 463 | 88.588 | 48.171 | 31.151 | 1.00 | 31.78 | N |
| ATOM | 2569 | CA | ALA | A | 463 | 87.427 | 47.320 | 31.362 | 1.00 | 31.54 | C |
| ATOM | 2570 | C | ALA | A | 463 | 87.420 | 46.075 | 30.484 | 1.00 | 32.00 | C |
| ATOM | 2571 | O | ALA | A | 463 | 87.657 | 46.150 | 29.278 | 1.00 | 31.09 | O |
| ATOM | 2572 | CB | ALA | A | 463 | 86.160 | 48.132 | 31.126 | 1.00 | 30.25 | C |
| ATOM | 2573 | N | LEU | A | 464 | 87.152 | 44.928 | 31.102 | 1.00 | 32.25 | N |
| ATOM | 2574 | CA | LEU | A | 464 | 87.095 | 43.661 | 30.377 | 1.00 | 33.90 | C |
| ATOM | 2575 | C | LEU | A | 464 | 85.652 | 43.241 | 30.158 | 1.00 | 32.84 | C |
| ATOM | 2576 | O | LEU | A | 464 | 85.380 | 42.324 | 29.386 | 1.00 | 34.74 | O |
| ATOM | 2577 | CB | LEU | A | 464 | 87.829 | 42.550 | 31.144 | 1.00 | 34.92 | C |
| ATOM | 2578 | CG | LEU | A | 464 | 89.345 | 42.457 | 30.945 | 1.00 | 36.98 | C |
| ATOM | 2579 | CD1 | LEU | A | 464 | 89.906 | 41.276 | 31.739 | 1.00 | 38.71 | C |
| ATOM | 2580 | CD2 | LEU | A | 464 | 89.647 | 42.278 | 29.470 | 1.00 | 37.33 | C |
| ATOM | 2581 | N | THR | A | 465 | 84.732 | 43.906 | 30.850 | 1.00 | 31.76 | N |
| ATOM | 2582 | CA | THR | A | 465 | 83.312 | 43.602 | 30.734 | 1.00 | 30.63 | C |
| ATOM | 2583 | C | THR | A | 465 | 82.499 | 44.887 | 30.760 | 1.00 | 31.08 | C |
| ATOM | 2584 | O | THR | A | 465 | 83.005 | 45.953 | 31.122 | 1.00 | 29.95 | O |
| ATOM | 2585 | CB | THR | A | 465 | 82.835 | 42.718 | 31.891 | 1.00 | 31.43 | C |
| ATOM | 2586 | OG1 | THR | A | 465 | 82.906 | 43.464 | 33.110 | 1.00 | 32.51 | O |
| ATOM | 2587 | CG2 | THR | A | 465 | 83.710 | 41.464 | 32.010 | 1.00 | 30.28 | C |
| ATOM | 2588 | N | ILE | A | 466 | 81.234 | 44.791 | 30.377 | 1.00 | 29.59 | N |
| ATOM | 2589 | CA | ILE | A | 466 | 80.386 | 45.965 | 30.376 | 1.00 | 28.97 | C |
| ATOM | 2590 | C | ILE | A | 466 | 80.180 | 46.491 | 31.797 | 1.00 | 28.90 | C |
| ATOM | 2591 | O | ILE | A | 466 | 80.254 | 47.696 | 32.034 | 1.00 | 29.22 | O |
| ATOM | 2592 | CB | ILE | A | 466 | 79.035 | 45.662 | 29.695 | 1.00 | 29.12 | C |
| ATOM | 2593 | CG1 | ILE | A | 466 | 79.270 | 45.502 | 28.187 | 1.00 | 27.85 | C |
| ATOM | 2594 | CG2 | ILE | A | 466 | 78.028 | 46.770 | 29.985 | 1.00 | 26.21 | C |
| ATOM | 2595 | CD1 | ILE | A | 466 | 78.052 | 45.094 | 27.404 | 1.00 | 27.38 | C |
| ATOM | 2596 | N | PRO | A | 467 | 79.923 | 45.597 | 32.765 | 1.00 | 28.55 | N |
| ATOM | 2597 | CA | PRO | A | 467 | 79.733 | 46.105 | 34.125 | 1.00 | 28.14 | C |
| ATOM | 2598 | C | PRO | A | 467 | 80.986 | 46.813 | 34.642 | 1.00 | 29.41 | C |
| ATOM | 2599 | O | PRO | A | 467 | 80.905 | 47.805 | 35.373 | 1.00 | 28.53 | O |
| ATOM | 2600 | CB | PRO | A | 467 | 79.405 | 44.842 | 34.919 | 1.00 | 29.15 | C |
| ATOM | 2601 | CG | PRO | A | 467 | 78.676 | 43.992 | 33.890 | 1.00 | 28.98 | C |
| ATOM | 2602 | CD | PRO | A | 467 | 79.588 | 44.163 | 32.688 | 1.00 | 27.09 | C |
| ATOM | 2603 | N | GLN | A | 468 | 82.151 | 46.314 | 34.253 | 1.00 | 30.32 | N |
| ATOM | 2604 | CA | GLN | A | 468 | 83.386 | 46.929 | 34.705 | 1.00 | 32.43 | C |
| ATOM | 2605 | C | GLN | A | 468 | 83.566 | 48.299 | 34.049 | 1.00 | 32.77 | C |
| ATOM | 2606 | O | GLN | A | 468 | 84.100 | 49.233 | 34.657 | 1.00 | 32.94 | O |
| ATOM | 2607 | CB | GLN | A | 468 | 84.561 | 46.006 | 34.390 | 1.00 | 34.93 | C |
| ATOM | 2608 | CG | GLN | A | 468 | 85.869 | 46.461 | 34.969 | 1.00 | 36.80 | C |
| ATOM | 2609 | CD | GLN | A | 468 | 86.912 | 45.364 | 34.940 | 1.00 | 37.36 | C |
| ATOM | 2610 | OE1 | GLN | A | 468 | 87.016 | 44.611 | 33.971 | 1.00 | 33.81 | O |
| ATOM | 2611 | NE2 | GLN | A | 468 | 87.703 | 45.281 | 36.000 | 1.00 | 38.34 | N |
| ATOM | 2612 | N | LEU | A | 469 | 83.106 | 48.418 | 32.808 | 1.00 | 31.40 | N |
| ATOM | 2613 | CA | LEU | A | 469 | 83.191 | 49.672 | 32.082 | 1.00 | 30.05 | C |
| ATOM | 2614 | C | LEU | A | 469 | 82.263 | 50.700 | 32.729 | 1.00 | 29.95 | C |
| ATOM | 2615 | O | LEU | A | 469 | 82.628 | 51.862 | 32.899 | 1.00 | 29.45 | O |
| ATOM | 2616 | CB | LEU | A | 469 | 82.780 | 49.471 | 30.620 | 1.00 | 30.63 | C |
| ATOM | 2617 | CG | LEU | A | 469 | 82.579 | 50.765 | 29.819 | 1.00 | 32.08 | C |
| ATOM | 2618 | CD1 | LEU | A | 469 | 83.925 | 51.423 | 29.568 | 1.00 | 29.55 | C |
| ATOM | 2619 | CD2 | LEU | A | 469 | 81.882 | 50.454 | 28.493 | 1.00 | 32.46 | C |
| ATOM | 2620 | N | GLN | A | 470 | 81.062 | 50.267 | 33.092 | 1.00 | 29.40 | N |
| ATOM | 2621 | CA | GLN | A | 470 | 80.089 | 51.169 | 33.697 | 1.00 | 31.46 | C |
| ATOM | 2622 | C | GLN | A | 470 | 80.599 | 51.680 | 35.039 | 1.00 | 33.28 | C |
| ATOM | 2623 | O | GLN | A | 470 | 80.275 | 52.790 | 35.479 | 1.00 | 32.37 | O |
| ATOM | 2624 | CB | GLN | A | 470 | 78.748 | 50.444 | 33.859 | 1.00 | 31.66 | C |
| ATOM | 2625 | CG | GLN | A | 470 | 78.209 | 49.929 | 32.515 | 1.00 | 32.34 | C |
| ATOM | 2626 | CD | GLN | A | 470 | 76.891 | 49.192 | 32.633 | 1.00 | 33.38 | C |
| ATOM | 2627 | OE1 | GLN | A | 470 | 76.671 | 48.454 | 33.585 | 1.00 | 34.59 | O |
| ATOM | 2628 | NE2 | GLN | A | 470 | 76.017 | 49.375 | 31.652 | 1.00 | 31.58 | N |
| ATOM | 2629 | N | SER | A | 471 | 81.435 | 50.870 | 35.668 | 1.00 | 33.02 | N |
| ATOM | 2630 | CA | SER | A | 471 | 81.997 | 51.222 | 36.955 | 1.00 | 34.85 | C |
| ATOM | 2631 | C | SER | A | 471 | 83.239 | 52.119 | 36.863 | 1.00 | 33.52 | C |
| ATOM | 2632 | O | SER | A | 471 | 83.374 | 53.070 | 37.625 | 1.00 | 34.04 | O |
| ATOM | 2633 | CB | SER | A | 471 | 82.329 | 49.934 | 37.722 | 1.00 | 34.20 | C |
| ATOM | 2634 | OG | SER | A | 471 | 82.985 | 50.221 | 38.940 | 1.00 | 40.00 | O |
| ATOM | 2635 | N | LYS | A | 472 | 84.121 | 51.837 | 35.910 | 1.00 | 33.54 | N |
| ATOM | 2636 | CA | LYS | A | 472 | 8.5.375 | 52.582 | 35.774 | 1.00 | 33.02 | C |
| ATOM | 2637 | C | LYS | A | 472 | 85.437 | 53.746 | 34.784 | 1.00 | 32.17 | C |
| ATOM | 2638 | O | LYS | A | 472 | 86.312 | 54.599 | 34.904 | 1.00 | 32.35 | O |
| ATOM | 2639 | CB | LYS | A | 472 | 86.505 | 51.605 | 35.431 | 1.00 | 33.39 | C |
| ATOM | 2640 | CG | LYS | A | 472 | 86.599 | 50.420 | 36.374 | 1.00 | 35.66 | C |
| ATOM | 2641 | CD | LYS | A | 472 | 87.597 | 49.369 | 35.885 | 1.00 | 37.76 | C |

TABLE 6-continued

| ATOM | 2642 | CE  | LYS | A | 472 | 89.036 | 49.761 | 36.185 | 1.00 | 40.51 | C |
| ATOM | 2643 | NZ  | LYS | A | 472 | 90.004 | 48.705 | 35.750 | 1.00 | 41.85 | N |
| ATOM | 2644 | N   | ALA | A | 473 | 84.538 | 53.782 | 33.804 | 1.00 | 30.79 | N |
| ATOM | 2645 | CA  | ALA | A | 473 | 84.563 | 54.849 | 32.806 | 1.00 | 30.86 | C |
| ATOM | 2646 | C   | ALA | A | 473 | 84.644 | 56.263 | 33.382 | 1.00 | 30.77 | C |
| ATOM | 2647 | O   | ALA | A | 473 | 83.971 | 56.599 | 34.358 | 1.00 | 31.90 | O |
| ATOM | 2648 | CB  | ALA | A | 473 | 83.343 | 54.738 | 31.882 | 1.00 | 30.21 | C |
| ATOM | 2649 | N   | LYS | A | 474 | 85.491 | 57.077 | 32.762 | 1.00 | 31.21 | N |
| ATOM | 2650 | CA  | LYS | A | 474 | 85.685 | 58.476 | 33.136 | 1.00 | 31.60 | C |
| ATOM | 2651 | C   | LYS | A | 474 | 85.118 | 59.211 | 31.930 | 1.00 | 32.45 | C |
| ATOM | 2652 | O   | LYS | A | 474 | 85.681 | 59.165 | 30.829 | 1.00 | 30.42 | O |
| ATOM | 2653 | CB  | LYS | A | 474 | 87.175 | 58.769 | 33.326 | 1.00 | 30.92 | C |
| ATOM | 2654 | CG  | LYS | A | 474 | 87.773 | 58.010 | 34.520 | 1.00 | 31.60 | C |
| ATOM | 2655 | CD  | LYS | A | 474 | 89.251 | 57.668 | 34.302 | 1.00 | 32.08 | C |
| ATOM | 2656 | CE  | LYS | A | 474 | 90.125 | 58.906 | 34.302 | 1.00 | 32.99 | C |
| ATOM | 2657 | NZ  | LYS | A | 474 | 91.550 | 58.543 | 34.039 | 1.00 | 33.32 | N |
| ATOM | 2658 | N   | ILE | A | 475 | 83.990 | 59.875 | 32.146 | 1.00 | 32.69 | N |
| ATOM | 2659 | CA  | ILE | A | 475 | 83.285 | 60.546 | 31.066 | 1.00 | 33.22 | C |
| ATOM | 2660 | C   | ILE | A | 475 | 83.237 | 62.056 | 31.203 | 1.00 | 32.93 | C |
| ATOM | 2661 | O   | ILE | A | 475 | 82.713 | 62.581 | 32.183 | 1.00 | 33.43 | O |
| ATOM | 2662 | CB  | ILE | A | 475 | 81.848 | 59.991 | 30.977 | 1.00 | 33.86 | C |
| ATOM | 2663 | CG1 | ILE | A | 475 | 81.907 | 58.456 | 30.907 | 1.00 | 34.55 | C |
| ATOM | 2664 | CG2 | ILE | A | 475 | 81.128 | 60.569 | 29.758 | 1.00 | 34.88 | C |
| ATOM | 2665 | CD1 | ILE | A | 475 | 80.562 | 57.756 | 31.036 | 1.00 | 33.21 | C |
| ATOM | 2666 | N   | THR | A | 476 | 83.786 | 62.751 | 30.212 | 1.00 | 32.44 | N |
| ATOM | 2667 | CA  | THR | A | 476 | 83.792 | 64.206 | 30.239 | 1.00 | 31.82 | C |
| ATOM | 2668 | C   | THR | A | 476 | 82.921 | 64.803 | 29.154 | 1.00 | 31.41 | C |
| ATOM | 2669 | O   | THR | A | 476 | 82.734 | 64.225 | 28.084 | 1.00 | 29.60 | O |
| ATOM | 2670 | CB  | THR | A | 476 | 85.212 | 64.803 | 30.054 | 1.00 | 31.71 | C |
| ATOM | 2671 | OG1 | THR | A | 476 | 85.143 | 66.233 | 30.185 | 1.00 | 32.39 | O |
| ATOM | 2672 | CG2 | THR | A | 476 | 85.770 | 64.464 | 28.665 | 1.00 | 28.14 | C |
| ATOM | 2673 | N   | LEU | A | 477 | 82.391 | 65.977 | 29.461 | 1.00 | 32.16 | N |
| ATOM | 2674 | CA  | LEU | A | 477 | 81.569 | 66.737 | 28.542 | 1.00 | 34.25 | C |
| ATOM | 2675 | C   | LEU | A | 477 | 82.595 | 67.593 | 27.787 | 1.00 | 34.56 | C |
| ATOM | 2676 | O   | LEU | A | 477 | 83.646 | 67.907 | 28.345 | 1.00 | 32.54 | O |
| ATOM | 2677 | CB  | LEU | A | 477 | 80.622 | 67.621 | 29.357 | 1.00 | 35.42 | C |
| ATOM | 2678 | CG  | LEU | A | 477 | 79.408 | 68.279 | 28.719 | 1.00 | 37.43 | C |
| ATOM | 2679 | CD1 | LEU | A | 477 | 78.496 | 67.223 | 28.120 | 1.00 | 34.96 | C |
| ATOM | 2680 | CD2 | LEU | A | 477 | 78.667 | 69.082 | 29.798 | 1.00 | 39.05 | C |
| ATOM | 2681 | N   | VAL | A | 478 | 82.320 | 67.941 | 26.531 | 1.00 | 35.71 | N |
| ATOM | 2682 | CA  | VAL | A | 478 | 83.242 | 68.778 | 25.761 | 1.00 | 38.92 | C |
| ATOM | 2683 | C   | VAL | A | 478 | 82.573 | 70.119 | 25.463 | 1.00 | 41.05 | C |
| ATOM | 2684 | O   | VAL | A | 478 | 81.359 | 70.187 | 25.298 | 1.00 | 40.84 | O |
| ATOM | 2685 | CB  | VAL | A | 478 | 83.659 | 68.111 | 24.428 | 1.00 | 39.90 | C |
| ATOM | 2686 | CG1 | VAL | A | 478 | 84.015 | 66.662 | 24.672 | 1.00 | 40.76 | C |
| ATOM | 2687 | CG2 | VAL | A | 478 | 82.551 | 68.237 | 23.400 | 1.00 | 41.86 | C |
| ATOM | 2688 | N   | SER | A | 479 | 83.370 | 71.181 | 25.386 | 1.00 | 43.62 | N |
| ATOM | 2689 | CA  | SER | A | 479 | 82.849 | 72.525 | 25.147 | 1.00 | 47.07 | C |
| ATOM | 2690 | C   | SER | A | 479 | 82.082 | 72.745 | 23.854 | 1.00 | 50.19 | C |
| ATOM | 2691 | O   | SER | A | 479 | 82.356 | 72.129 | 22.821 | 1.00 | 49.40 | O |
| ATOM | 2692 | CB  | SER | A | 479 | 83.979 | 73.553 | 25.207 | 1.00 | 46.48 | C |
| ATOM | 2693 | OG  | SER | A | 479 | 84.904 | 73.327 | 24.160 | 1.00 | 46.18 | O |
| ATOM | 2694 | N   | SER | A | 480 | 81.124 | 73.662 | 23.933 | 1.00 | 54.55 | N |
| ATOM | 2695 | CA  | SER | A | 480 | 80.297 | 74.036 | 22.799 | 1.00 | 59.07 | C |
| ATOM | 2696 | C   | SER | A | 480 | 81.192 | 74.534 | 21.668 | 1.00 | 61.48 | C |
| ATOM | 2697 | O   | SER | A | 480 | 81.036 | 74.146 | 20.505 | 1.00 | 61.36 | O |
| ATOM | 2698 | CB  | SER | A | 480 | 79.327 | 75.143 | 23.224 | 1.00 | 59.36 | C |
| ATOM | 2699 | OG  | SER | A | 480 | 78.625 | 75.669 | 22.113 | 1.00 | 62.01 | O |
| ATOM | 2700 | N   | VAL | A | 481 | 82.145 | 75.382 | 22.040 | 1.00 | 64.75 | N |
| ATOM | 2701 | CA  | VAL | A | 481 | 83.088 | 75.982 | 21.104 | 1.00 | 67.50 | C |
| ATOM | 2702 | C   | VAL | A | 481 | 84.162 | 75.015 | 20.611 | 1.00 | 69.03 | C |
| ATOM | 2703 | O   | VAL | A | 481 | 85.113 | 75.432 | 19.949 | 1.00 | 69.98 | O |
| ATOM | 2704 | CB  | VAL | A | 481 | 83.804 | 77.179 | 21.753 | 1.00 | 67.66 | C |
| ATOM | 2705 | CG1 | VAL | A | 481 | 84.155 | 78.211 | 20.693 | 1.00 | 68.62 | C |
| ATOM | 2706 | CG2 | VAL | A | 481 | 82.935 | 77.775 | 22.841 | 1.00 | 67.94 | C |
| ATOM | 2707 | N   | SER | A | 482 | 84.016 | 73.731 | 20.922 | 1.00 | 70.23 | N |
| ATOM | 2708 | CA  | SER | A | 482 | 85.010 | 72.749 | 20.504 | 1.00 | 71.93 | C |
| ATOM | 2709 | C   | SER | A | 482 | 84.445 | 71.675 | 19.590 | 1.00 | 73.15 | C |
| ATOM | 2710 | O   | SER | A | 482 | 83.495 | 71.916 | 18.841 | 1.00 | 73.05 | O |
| ATOM | 2711 | CB  | SER | A | 482 | 85.636 | 72.068 | 21.724 | 1.00 | 72.51 | C |
| ATOM | 2712 | OG  | SER | A | 482 | 84.711 | 71.185 | 22.344 | 1.00 | 72.87 | O |
| ATOM | 2713 | N   | ILE | A | 483 | 85.048 | 70.487 | 19.686 | 1.00 | 74.34 | N |
| ATOM | 2714 | CA  | ILE | A | 483 | 84.698 | 69.305 | 18.899 | 1.00 | 75.21 | C |
| ATOM | 2715 | C   | ILE | A | 483 | 85.510 | 69.316 | 17.609 | 1.00 | 75.65 | C |
| ATOM | 2716 | O   | ILE | A | 483 | 85.821 | 68.263 | 17.049 | 1.00 | 75.17 | O |
| ATOM | 2717 | CB  | ILE | A | 483 | 83.189 | 69.254 | 18.536 | 1.00 | 75.76 | C |
| ATOM | 2718 | CG1 | ILE | A | 483 | 82.338 | 69.219 | 19.809 | 1.00 | 75.65 | C |
| ATOM | 2719 | CG2 | ILE | A | 483 | 82.903 | 68.025 | 17.680 | 1.00 | 75.47 | C |
| ATOM | 2720 | CD1 | ILE | A | 483 | 80.852 | 69.350 | 19.554 | 1.00 | 74.79 | C |

TABLE 6-continued

| | | | | | | | | | | |
|---|---|---|---|---|---|---|---|---|---|---|
| ATOM | 2721 | N | VAL | A | 484 | 85.854 | 70.517 | 17.150 | 1.00 | 76.42 | N |
| ATOM | 2722 | CA | VAL | A | 484 | 86.630 | 70.686 | 15.924 | 1.00 | 77.07 | C |
| ATOM | 2723 | C | VAL | A | 484 | 88.022 | 70.077 | 16.085 | 1.00 | 77.20 | C |
| ATOM | 2724 | O | VAL | A | 484 | 88.540 | 69.442 | 15.163 | 1.00 | 77.05 | O |
| ATOM | 2725 | CB | VAL | A | 484 | 86.773 | 72.186 | 15.549 | 1.00 | 77.33 | C |
| ATOM | 2726 | CG1 | VAL | A | 484 | 87.463 | 72.322 | 14.193 | 1.00 | 77.06 | C |
| ATOM | 2727 | CG2 | VAL | A | 484 | 85.401 | 72.853 | 15.521 | 1.00 | 76.24 | C |
| ATOM | 2728 | N | GLU | A | 485 | 88.620 | 70.272 | 17.259 | 1.00 | 77.14 | N |
| ATOM | 2729 | CA | GLU | A | 485 | 89.948 | 69.733 | 17.545 | 1.00 | 77.36 | C |
| ATOM | 2730 | C | GLU | A | 485 | 89.935 | 68.210 | 17.439 | 1.00 | 77.78 | C |
| ATOM | 2731 | O | GLU | A | 485 | 90.907 | 67.599 | 16.991 | 1.00 | 77.16 | O |
| ATOM | 2732 | CB | GLU | A | 485 | 90.398 | 70.127 | 18.957 | 1.00 | 76.63 | C |
| ATOM | 2733 | CG | GLU | A | 485 | 91.730 | 69.499 | 19.372 | 1.00 | 76.08 | C |
| ATOM | 2734 | CD | GLU | A | 485 | 92.030 | 69.654 | 20.854 | 1.00 | 75.36 | C |
| ATOM | 2735 | OE1 | GLU | A | 485 | 91.261 | 69.135 | 21.687 | 1.00 | 75.07 | O |
| ATOM | 2736 | OE2 | GLU | A | 485 | 93.041 | 70.294 | 21.190 | 1.00 | 75.66 | O |
| ATOM | 2737 | N | GLY | A | 486 | 88.824 | 67.610 | 17.861 | 1.00 | 78.37 | N |
| ATOM | 2738 | CA | GLY | A | 486 | 88.682 | 66.165 | 17.831 | 1.00 | 79.06 | C |
| ATOM | 2739 | C | GLY | A | 486 | 88.873 | 65.533 | 16.466 | 1.00 | 79.40 | C |
| ATOM | 2740 | O | GLY | A | 486 | 89.530 | 64.499 | 16.348 | 1.00 | 79.68 | O |
| ATOM | 2741 | N | GLY | A | 487 | 88.295 | 66.145 | 15.435 | 1.00 | 79.72 | N |
| ATOM | 2742 | CA | GLY | A | 487 | 88.428 | 65.611 | 14.091 | 1.00 | 79.91 | C |
| ATOM | 2743 | C | GLY | A | 487 | 89.646 | 66.164 | 13.376 | 1.00 | 80.25 | C |
| ATOM | 2744 | O | GLY | A | 487 | 90.467 | 66.857 | 13.982 | 1.00 | 80.14 | O |
| ATOM | 2745 | N | ALA | A | 488 | 89.773 | 65.854 | 12.088 | 1.00 | 80.34 | N |
| ATOM | 2746 | CA | ALA | A | 488 | 90.896 | 66.341 | 11.292 | 1.00 | 80.30 | C |
| ATOM | 2747 | C | ALA | A | 488 | 90.694 | 67.833 | 11.037 | 1.00 | 80.42 | C |
| ATOM | 2748 | O | ALA | A | 488 | 89.584 | 68.272 | 10.730 | 1.00 | 79.93 | O |
| ATOM | 2749 | CB | ALA | A | 488 | 90.972 | 65.584 | 9.969 | 1.00 | 79.95 | C |
| ATOM | 2750 | N | HIS | A | 489 | 91.763 | 68.612 | 11.165 | 1.00 | 80.61 | N |
| ATOM | 2751 | CA | HIS | A | 489 | 91.661 | 70.052 | 10.957 | 1.00 | 81.04 | C |
| ATOM | 2752 | C | HIS | A | 489 | 92.937 | 70.687 | 10.424 | 1.00 | 81.07 | C |
| ATOM | 2753 | O | HIS | A | 489 | 94.046 | 70.253 | 10.742 | 1.00 | 80.28 | O |
| ATOM | 2754 | CB | HIS | A | 489 | 91.271 | 70.743 | 12.266 | 1.00 | 81.48 | C |
| ATOM | 2755 | CG | HIS | A | 489 | 92.196 | 70.442 | 13.405 | 1.00 | 81.91 | C |
| ATOM | 2756 | ND1 | HIS | A | 489 | 92.241 | 69.210 | 14.020 | 1.00 | 81.93 | N |
| ATOM | 2757 | CD2 | HIS | A | 489 | 93.121 | 71.209 | 14.030 | 1.00 | 81.89 | C |
| ATOM | 2758 | CE1 | HIS | A | 489 | 93.153 | 69.231 | 14.976 | 1.00 | 81.92 | C |
| ATOM | 2759 | NE2 | HIS | A | 489 | 93.702 | 70.432 | 15.002 | 1.00 | 81.66 | N |
| ATOM | 2760 | N | ASP | A | 490 | 92.758 | 71.727 | 9.614 | 1.00 | 81.38 | N |
| ATOM | 2761 | CA | ASP | A | 490 | 93.870 | 72.467 | 9.027 | 1.00 | 81.57 | C |
| ATOM | 2762 | C | ASP | A | 490 | 94.730 | 71.605 | 8.111 | 1.00 | 81.88 | C |
| ATOM | 2763 | O | ASP | A | 490 | 95.940 | 71.810 | 7.997 | 1.00 | 81.99 | O |
| ATOM | 2764 | CB | ASP | A | 490 | 94.721 | 73.079 | 10.141 | 1.00 | 81.37 | C |
| ATOM | 2765 | CG | ASP | A | 490 | 93.915 | 73.990 | 11.046 | 1.00 | 81.51 | C |
| ATOM | 2766 | OD1 | ASP | A | 490 | 93.484 | 75.069 | 10.579 | 1.00 | 81.11 | O |
| ATOM | 2767 | OD2 | ASP | A | 490 | 93.701 | 73.622 | 12.220 | 1.00 | 81.49 | O |
| ATOM | 2768 | N | VAL | A | 491 | 94.093 | 70.638 | 7.462 | 1.00 | 81.98 | N |
| ATOM | 2769 | CA | VAL | A | 491 | 94.779 | 69.748 | 6.537 | 1.00 | 82.24 | C |
| ATOM | 2770 | C | VAL | A | 491 | 93.841 | 69.392 | 5.390 | 1.00 | 82.41 | C |
| ATOM | 2771 | O | VAL | A | 491 | 92.621 | 69.331 | 5.566 | 1.00 | 81.92 | O |
| ATOM | 2772 | CB | VAL | A | 491 | 95.252 | 68.440 | 7.231 | 1.00 | 82.15. | C |
| ATOM | 2773 | CG1 | VAL | A | 491 | 96.314 | 68.755 | 8.273 | 1.00 | 82.08 | C |
| ATOM | 2774 | CG2 | VAL | A | 491 | 94.069 | 67.727 | 7.873 | 1.00 | 82.18 | C |
| ATOM | 2775 | N | ILE | A | 492 | 94.419 | 69.169 | 4.215 | 1.00 | 82.73 | N |
| ATOM | 2776 | CA | ILE | A | 492 | 93.651 | 68.816 | 3.029 | 1.00 | 83.15 | C |
| ATOM | 2777 | C | ILE | A | 492 | 93.731 | 67.309 | 2.792 | 1.00 | 83.71 | C |
| ATOM | 2778 | O | ILE | A | 492 | 94.558 | 66.887 | 1.954 | 1.00 | 84.19 | O |
| ATOM | 2779 | CB | ILE | A | 492 | 94.180 | 69.565 | 1.782 | 1.00 | 83.08 | C |
| ATOM | 2780 | CG1 | ILE | A | 492 | 94.136 | 71.075 | 2.032 | 1.00 | 82.87 | C |
| ATOM | 2781 | CG2 | ILE | A | 492 | 93.342 | 69.211 | 0.560 | 1.00 | 82.77 | C |
| ATOM | 2782 | CD1 | ILE | A | 492 | 94.640 | 71.911 | 0.874 | 1.00 | 83.43 | C |
| TER | 2783 | | ILE | A | 492 | | | | | | |
| HETATM | 2784 | NA | NA | | 901 | 65.965 | 62.918 | 15.945 | 1.00 | 69.25 | NA |
| HETATM | 2785 | K | K | A | 900 | 94.585 | 53.172 | 29.328 | 0.75 | 36.10 | K |
| HETATM | 2786 | P | RVP | | 602 | 67.957 | 55.327 | 15.029 | 1.00 | 40.98 | P |
| HETATM | 2787 | O1P | RVP | | 602 | 67.605 | 55.290 | 13.581 | 1.00 | 40.82 | O |
| HETATM | 2788 | O2P | RVP | | 602 | 68.778 | 54.118 | 15.349 | 1.00 | 40.06 | O |
| HETATM | 2789 | O3P | RVP | | 602 | 68.738 | 56.618 | 15.412 | 1.00 | 40.73 | O |
| HETATM | 2790 | O5* | RVP | | 602 | 66.712 | 55.356 | 16.019 | 1.00 | 39.48 | O |
| HETATM | 2791 | C5* | RVP | | 602 | 65.743 | 54.315 | 15.953 | 1.00 | 38.43 | C |
| HETATM | 2792 | C4* | RVP | | 602 | 64.678 | 54.509 | 16.989 | 1.00 | 38.00 | C |
| HETATM | 2793 | O4* | RVP | | 602 | 63.938 | 55.721 | 16.576 | 1.00 | 38.49 | O |
| HETATM | 2794 | C3* | RVP | | 602 | 63.577 | 53.475 | 17.169 | 1.00 | 36.61 | C |
| HETATM | 2795 | O3* | RVP | | 602 | 63.978 | 52.319 | 17.881 | 1.00 | 35.40 | O |
| HETATM | 2796 | C2* | RVP | | 602 | 62.504 | 54.269 | 17.841 | 1.00 | 36.75 | C |
| HETATM | 2797 | O2* | RVP | | 602 | 62.653 | 54.352 | 19.240 | 1.00 | 36.68 | O |
| HETATM | 2798 | C1* | RVP | | 602 | 62.606 | 55.609 | 17.106 | 1.00 | 38.31 | C |
| HETATM | 2799 | N9 | RVP | | 602 | 61.637 | 55.746 | 15.950 | 1.00 | 40.51 | N |

TABLE 6-continued

| | | | | | | | | | |
|---|---|---|---|---|---|---|---|---|---|
| HETATM | 2800 | C8 | RVP | 602 | 61.076 | 54.833 | 15.070 | 1.00 | 40.32 | C |
| HETATM | 2801 | N7 | RVP | 602 | 60.285 | 55.383 | 14.214 | 1.00 | 40.61 | N |
| HETATM | 2802 | C5 | RVP | 602 | 60.285 | 56.713 | 14.493 | 1.00 | 41.77 | C |
| HETATM | 2803 | C6 | RVP | 602 | 59.586 | 57.820 | 13.858 | 1.00 | 41.63 | C |
| HETATM | 2804 | O6 | RVP | 602 | 58.824 | 57.752 | 12.898 | 1.00 | 40.85 | O |
| HETATM | 2805 | N1 | RVP | 602 | 59.848 | 59.109 | 14.451 | 1.00 | 42.44 | N |
| HETATM | 2806 | N4 | RVP | 602 | 61.119 | 56.976 | 15.575 | 1.00 | 41.17 | N |
| HETATM | 2807 | C1 | MOA | 600 | 60.515 | 58.824 | 19.697 | 0.50 | 46.30 | C |
| HETATM | 2808 | C2 | MOA | 600 | 55.761 | 57.322 | 16.893 | 0.50 | 49.27 | C |
| HETATM | 2809 | C3 | MOA | 600 | 54.536 | 56.866 | 16.570 | 0.50 | 50.25 | C |
| HETATM | 2810 | C4 | MOA | 600 | 53.366 | 57.590 | 17.224 | 0.50 | 51.18 | C |
| HETATM | 2811 | C5 | MOA | 600 | 52.702 | 56.677 | 18.266 | 0.50 | 52.05 | C |
| HETATM | 2812 | C6 | MOA | 600 | 53.320 | 56.768 | 19.656 | 0.50 | 52.48 | C |
| HETATM | 2813 | C7 | MOA | 600 | 59.541 | 53.995 | 20.040 | 0.50 | 45.22 | C |
| HETATM | 2814 | C8 | MOA | 600 | 56.392 | 53.973 | 18.496 | 0.50 | 45.61 | C |
| HETATM | 2815 | C9 | MOA | 600 | 54.279 | 55.668 | 15.641 | 0.50 | 50.49 | C |
| HETATM | 2816 | C10 | MOA | 600 | 60.943 | 56.779 | 20.807 | 0.50 | 45.42 | C |
| HETATM | 2817 | C11 | MOA | 600 | 59.925 | 56.532 | 19.711 | 0.50 | 45.86 | C |
| HETATM | 2818 | C12 | MOA | 600 | 59.265 | 55.296 | 19.328 | 0.50 | 45.51 | C |
| HETATM | 2819 | C13 | MOA | 600 | 58.321 | 55.359 | 18.230 | 0.50 | 45.35 | C |
| HETATM | 2820 | C14 | MOA | 600 | 58.073 | 56.626 | 17.563 | 0.50 | 46.27 | C |
| HETATM | 2821 | C15 | MOA | 600 | 58.756 | 57.824 | 17.978 | 0.50 | 45.96 | C |
| HETATM | 2822 | C16 | MOA | 600 | 59.679 | 57.745 | 19.060 | 0.50 | 46.34 | C |
| HETATM | 2823 | C17 | MOA | 600 | 57.082 | 56.722 | 16.411 | 0.50 | 47.60 | C |
| HETATM | 2824 | O1 | MOA | 600 | 60.600 | 59.983 | 19.446 | 0.50 | 47.39 | O |
| HETATM | 2825 | O2 | MOA | 600 | 61.200 | 58.218 | 20.669 | 0.50 | 46.12 | O |
| HETATM | 2826 | O3 | MOA | 600 | 57.682 | 54.195 | 17.849 | 0.50 | 44.59 | O |
| HETATM | 2827 | O4 | MOA | 600 | 58.494 | 59.017 | 17.318 | 0.50 | 45.53 | O |
| HETATM | 2828 | O5 | MOA | 600 | 53.045 | 57.763 | 20.364 | 0.50 | 53.35 | O |
| HETATM | 2829 | O6 | MOA | 600 | 54.072 | 55.841 | 20.036 | 0.50 | 50.72 | O |
| HETATM | 2830 | O | HOH | 1 | 86.937 | 48.115 | 13.619 | 1.00 | 53.10 | O |
| HETATM | 2831 | O | HOH | 2 | 66.156 | 60.715 | 24.787 | 1.00 | 30.04 | O |
| HETATM | 2832 | O | HOH | 3 | 57.859 | 59.028 | 28.431 | 1.00 | 32.40 | O |
| HETATM | 2833 | O | HOH | 4 | 71.017 | 54.648 | 22.049 | 1.00 | 29.86 | O |
| HETATM | 2834 | O | HOH | 5 | 59.607 | 45.471 | 36.968 | 1.00 | 31.13 | O |
| HETATM | 2835 | O | HOH | 6 | 66.879 | 48.121 | 38.970 | 1.00 | 31.37 | O |
| HETATM | 2836 | O | HOH | 7 | 79.892 | 42.101 | 29.537 | 1.00 | 28.27 | O |
| HETATM | 2837 | O | HOH | 8 | 75.265 | 45.936 | 32.827 | 1.00 | 34.43 | O |
| HETATM | 2838 | O | HOH | 9 | 56.912 | 79.011 | 34.524 | 1.00 | 32.22 | O |
| NETATM | 2839 | O | HOH | 10 | 71.224 | 53.547 | 14.238 | 1.00 | 33.27 | O |
| HETATM | 2840 | O | HOH | 11 | 87.551 | 55.794 | 31.268 | 1.00 | 29.17 | O |
| HETATM | 2841 | O | HOH | 12 | 78.951 | 48.244 | 37.321 | 1.00 | 38.69 | O |
| HETATM | 2842 | O | HOH | 13 | 76.535 | 44.032 | 31.071 | 1.00 | 33.29 | O |
| HETATM | 2843 | O | NOH | 14 | 77.984 | 54.327 | 34.370 | 1.00 | 35.16 | O |
| HETATM | 2844 | O | HOH | 15 | 84.500 | 53.321 | 21.118 | 1.00 | 31.74 | O |
| HETATM | 2845 | O | HOH | 16 | 74.544 | 60.085 | 37.904 | 1.00 | 44.09 | O |
| HETATM | 2846 | O | HOH | 17 | 88.665 | 54.024 | 33.427 | 1.00 | 31.82 | O |
| HETATM | 2847 | O | HOH | 18 | 64.790 | 41.466 | 7.903 | 1.00 | 37.49 | O |
| HETATN | 2848 | O | HOH | 19 | 73.871 | 57.655 | 36.239 | 1.00 | 31.87 | O |
| HETATM | 2849 | O | HOH | 20 | 58.900 | 51.481 | 22.980 | 1.00 | 34.30 | O |
| HETATM | 2850 | O | HOH | 21 | 64.317 | 56.651 | 20.399 | 1.00 | 39.92 | O |
| HETATM | 2851 | O | HOH | 22 | 65.490 | 36.877 | 34.840 | 1.00 | 40.17 | O |
| HETATM | 2852 | O | HOH | 23 | 60.085 | 50.861 | 20.174 | 1.00 | 43.72 | O |
| HETATM | 2853 | O | HOH | 24 | 76.358 | 52.869 | 36.274 | 1.00 | 39.41 | O |
| HETATM | 2854 | O | HOH | 25 | 64.918 | 73.696 | 32.920 | 1.00 | 32.12 | O |
| HETATM | 2855 | O | HOH | 26 | 56.665 | 77.507 | 37.267 | 1.00 | 37.89 | O |
| HETATM | 2856 | O | HOH | 27 | 72.867 | 38.426 | 33.907 | 1.00 | 35.88 | O |
| HETATM | 2857 | O | HOH | 28 | 72.686 | 61.731 | 21.624 | 1.00 | 43.41 | O |
| HETATM | 2858 | O | HOH | 29 | 67.317 | 67.438 | 30.698 | 1.00 | 36.92 | O |
| HETATM | 2859 | O | HOH | 30 | 49.555 | 44.437 | 21.119 | 1.00 | 42.21 | O |
| HETATM | 2860 | O | HOH | 31 | 70.551 | 33.609 | 27.633 | 1.00 | 41.14 | O |
| HETATM | 2861 | O | HOH | 32 | 76.699 | 41.425 | 32.331 | 1.00 | 34.07 | O |
| HETATM | 2862 | O | HOH | 33 | 61.925 | 50.659 | 17.855 | 1.00 | 31.53 | O |
| HETATM | 2863 | O | HOH | 34 | 62.610 | 38.767 | 34.074 | 1.00 | 31.70 | O |
| HETATM | 2864 | O | HOH | 35 | 56.933 | 57.813 | 38.879 | 1.00 | 41.65 | O |
| HETATM | 2865 | O | HOH | 36 | 66.624 | 37.892 | 16.896 | 1.00 | 37.69 | O |
| HETATM | 2866 | O | HOH | 37 | 69.286 | 68.051 | 32.916 | 1.00 | 43.83 | O |
| HETATM | 2867 | O | HOH | 38 | 53.353 | 51.944 | 38.099 | 1.00 | 36.77 | O |
| HETATM | 2868 | O | HOH | 39 | 82.373 | 67.465 | 31.922 | 1.00 | 39.48 | O |
| HETATM | 2869 | O | HOH | 40 | 62.969 | 61.940 | 37.710 | 1.00 | 45.75 | O |
| HETATM | 2870 | O | HOH | 41 | 60.077 | 59.723 | 30.997 | 1.00 | 46.18 | O |
| HETATM | 2871 | O | HOH | 42 | 51.139 | 46.321 | 36.000 | 1.00 | 41.32 | O |
| HETATM | 2872 | O | HOH | 43 | 59.604 | 51.735 | 16.489 | 1.00 | 35.27 | O |
| HETATM | 2873 | O | HOH | 44 | 61.183 | 37.811 | 37.337 | 1.00 | 47.18 | O |
| HETATM | 2874 | O | HOH | 45 | 66.082 | 58.886 | 21.454 | 1.00 | 35.99 | O |
| HETATM | 2875 | O | HOH | 46 | 66.187 | 63.971 | 21.615 | 1.00 | 43.24 | O |
| HETATM | 2876 | O | HOH | 47 | 68.276 | 38.487 | 46.493 | 1.00 | 41.00 | O |
| HETATM | 2877 | O | HOH | 48 | 73.810 | 65.033 | 30.854 | 1.00 | 44.46 | O |
| HETATM | 2878 | O | HOH | 49 | 59.036 | 45.342 | 5.912 | 1.00 | 45.26 | O |

TABLE 6-continued

| | | | | | | | | | |
|---|---|---|---|---|---|---|---|---|---|
| HETATM | 2879 | O | HOH | 50 | 58.693 | 35.801 | 27.026 | 1.00 | 42.44 | O |
| HETATM | 2880 | O | HOH | 51 | 54.551 | 73.802 | 39.044 | 1.00 | 44.81 | O |
| HETATM | 2881 | O | HOH | 52 | 59.942 | 51.276 | 9.798 | 1.00 | 38.47 | O |
| HETATM | 2882 | O | HOH | 53 | 75.437 | 38.984 | 31.295 | 1.00 | 41.54 | O |
| HETATM | 2883 | O | HOH | 54 | 56.511 | 41.592 | 37.450 | 1.00 | 50.73 | O |
| HETATM | 2884 | O | HOH | 55 | 55.967 | 71.689 | 16.393 | 1.00 | 42.82 | O |
| HETATM | 2885 | O | HOH | 56 | 79.457 | 38.647 | 17.552 | 1.00 | 40.99 | O |
| HETATM | 2886 | O | HOH | 57 | 61.441 | 73.979 | 39.270 | 1.00 | 51.02 | O |
| HETATM | 2887 | O | HOH | 58 | 74.980 | 37.209 | 10.810 | 1.00 | 44.24 | O |
| HETATM | 2888 | O | HOH | 59 | 87.106 | 70.131 | 23.910 | 1.00 | 48.62 | O |
| HETATM | 2889 | O | HOH | 60 | 78.921 | 72.296 | 28.132 | 1.00 | 44.83. | O |
| HETATM | 2890 | O | HOH | 61 | 59.217 | 38.449 | 34.738 | 1.00 | 41.72 | O |
| HETATM | 2891 | O | HOH | 62 | 62.392 | 64.439 | 35.307 | 1.00 | 38.87 | O |
| HETATM | 2892 | O | HOH | 63 | 52.186 | 54.149 | 25.895 | 1.00 | 39.43 | O |
| HETATM | 2893 | O | HOH | 64 | 91.884 | 51.151 | 35.362 | 1.00 | 47.95 | O |
| HETATM | 2894 | O | HOH | 65 | 74.410 | 50.817 | 36.320 | 1.00 | 40.80 | O |
| HETATM | 2895 | O | HOH | 66 | 75.694 | 70.804 | 31.847 | 1.00 | 45.76 | O |
| HETATM | 2896 | O | HOH | 67 | 85.562 | 49.382 | 39.692 | 1.00 | 44.65 | O |
| HETATM | 2897 | O | HOH | 68 | 50.848 | 31.856 | 16.493 | 1.00 | 47.42 | O |
| HETATM | 2898 | O | HOH | 69 | 75.545 | 38.878 | 8.328 | 1.00 | 39.75 | O |
| HETATM | 2899 | O | HOH | 70 | 72.184 | 67.522 | 32.127 | 1.00 | 41.79 | O |
| HETATM | 2900 | O | HOH | 71 | 81.557 | 38.617 | 24.306 | 1.00 | 45.21 | O |
| HETATM | 2901 | O | HOH | 72 | 82.150 | 63.522 | 21.264 | 1.00 | 45.28 | O |
| HETATM | 2902 | O | HOH | 73 | 43.465 | 44.041 | 23.652 | 1.00 | 49.13 | O |
| HETATM | 2903 | O | NOH | 74 | 65.282 | 64.106 | 36.024 | 1.00 | 42.80 | O |
| HETATM | 2904 | O | HOH | 75 | 71.791 | 56.052 | 42.026 | 1.00 | 43.68 | O |
| HETATM | 2905 | O | HOH | 76 | 70.611 | 32.750 | 38.320 | 1.00 | 50.18 | O |
| HETATM | 2906 | O | HOH | 77 | 65.746 | 28.372 | 26.829 | 1.00 | 51.32 | O |
| HETATM | 2907 | O | HOH | 78 | 46.316 | 49.216 | 27.478 | 1.00 | 49.98 | O |
| HETATM | 2908 | O | HOH | 79 | 66.218 | 28.865 | 15.007 | 1.00 | 49.39 | O |
| HETATM | 2909 | O | HOH | 80 | 45.899 | 41.751 | 13.150 | 1.00 | 50.35 | O |
| HETATM | 2910 | O | HOH | 81 | 67.812 | 59.668 | 38.963 | 1.00 | 53.98 | O |
| HETATM | 2911 | O | HOH | 82 | 67.783 | 69.548 | 38.244 | 1.00 | 50.77 | O |
| HETATM | 2912 | O | HOH | 83 | 90.501 | 38.801 | 36.127 | 1.00 | 59.97 | O |
| HETATM | 2913 | O | HOH | 84 | 57.960 | 65.710 | 38.116 | 1.00 | 51.75 | O |
| HETATM | 2914 | O | HOH | 85 | 48.770 | 54.414 | 37.079 | 1.00 | 51.59 | O |
| HETATM | 2915 | O | HOH | 86 | 54.375 | 62.285 | 36.120 | 1.00 | 46.20 | O |
| HETATM | 2916 | O | HOH | 87 | 60.479 | 39.480 | 6.892 | 1.00 | 48.39 | O |
| HETATM | 2917 | O | HOH | 88 | 63.400 | 39.497 | 6.092 | 1.00 | 47.12 | O |
| HETATM | 2918 | O | HOH | 89 | 49.881 | 43.115 | 8.014 | 1.00 | 55.16 | O |
| NETATM | 2919 | O | HOH | 90 | 48.799 | 31.869 | 25.511 | 1.00 | 54.96 | O |
| HETATM | 2920 | O | HOH | 91 | 55.226 | 53.883 | 40.277 | 1.00 | 57.13 | O |
| HETATM | 2921 | O | HOH | 92 | 84.876 | 42.783 | 10.201 | 1.00 | 60.19 | O |
| HETATM | 2922 | O | HOH | 93 | 71.104 | 57.754 | 14.563 | 1.00 | 50.88 | O |
| HETATM | 2923 | O | HOH | 94 | 81.517 | 55.070 | 13.507 | 1.00 | 56.55 | O |
| HETATM | 2924 | O | HOH | 95 | 69.719 | 68.895 | 35.986 | 1.00 | 50.06 | O |
| HETATM | 2925 | O | HOH | 96 | 48.667 | 81.714 | 40.322 | 1.00 | 56.66 | O |
| HETATM | 2926 | O | HOH | 97 | 79.523 | 40.573 | 32.112 | 1.00 | 41.26 | O |
| HETATM | 2927 | O | HOH | 98 | 50.394 | 78.735 | 40.269 | 1.00 | 61.03 | O |
| HETATM | 2928 | O | HOH | 99 | 51.083 | 76.617 | 38.073 | 1.00 | 50.99 | O |
| HETATM | 2929 | O | HOH | 100 | 55.631 | 67.730 | 37.228 | 1.00 | 53.07 | O |
| HETATM | 2930 | O | HOH | 101 | 63.222 | 78.551 | 34.890 | 1.00 | 55.30 | O |
| HETATM | 2931 | O | HOH | 102 | 64.387 | 81.230 | 33.819 | 1.00 | 60.32 | O |
| HETATM | 2932 | O | HOH | 103 | 63.693 | 84.119 | 34.865 | 1.00 | 68.07 | O |
| HETATM | 2933 | O | HOH | 104 | 75.769 | 73.295 | 28.310 | 1.00 | 58.02 | O |
| HETATM | 2934 | O | HOH | 105 | 86.092 | 39.258 | 22.649 | 1.00 | 56.63 | O |
| HETATM | 2935 | O | HOH | 106 | 62.744 | 55.138 | 1.577 | 1.00 | 43.51 | O |
| HETATM | 2936 | O | HOH | 107 | 74.933 | 63.024 | 19.409 | 1.00 | 54.22 | O |
| HETATM | 2937 | O | HOH | 108 | 69.789 | 45.377 | 46.398 | 1.00 | 46.18 | O |
| HETATM | 2938 | O | HOH | 109 | 74.595 | 39.323 | 37.886 | 1.00 | 62.46 | O |
| HETATM | 2939 | O | HOH | 110 | 73.747 | 39.642 | 41.004 | 1.00 | 58.85 | O |
| HETATM | 2940 | O | HOH | 111 | 72.104 | 32.691 | 30.025 | 1.00 | 49.56 | O |
| HETATM | 2941 | O | HOH | 112 | 78.793 | 70.848 | 25.397 | 1.00 | 58.19 | O |
| HETATM | 2942 | O | HOH | 113 | 73.215 | 33.284 | 26.151 | 1.00 | 58.62 | O |
| HETATM | 2943 | O | HOH | 114 | 68.965 | 43.819 | 0.725 | 1.00 | 52.71 | O |
| HETATM | 2944 | O | HOH | 115 | 96.151 | 46.659 | 27.632 | 1.00 | 52.09 | O |
| HETATM | 2945 | O | HOH | 116 | 97.574 | 43.766 | 26.583 | 1.00 | 57.72 | O |
| HETATM | 2946 | O | HOH | 117 | 63.372 | 31.897 | 25.790 | 1.00 | 49.36 | O |
| HETATM | 2947 | O | HOH | 118 | 66.211 | 31.555 | 26.744 | 1.00 | 58.36 | O |
| HETATM | 2948 | O | HOH | 119 | 63.520 | 35.235 | 42.203 | 1.00 | 53.59 | O |
| HETATM | 2949 | O | HOH | 120 | 88.222 | 37.020 | 34.672 | 1.00 | 51.97 | O |
| CONECT | 202 | 2549 | | | | | | | | |
| CONECT | 2549 | 202 | | | | | | | | |
| CONECT | 2786 | 2787 | 2788 | 2789 | 2790 | | | | | |
| CONECT | 2787 | 2786 | | | | | | | | |
| CONECT | 2788 | 2786 | | | | | | | | |
| CONECT | 2789 | 2786 | | | | | | | | |

TABLE 6-continued

| | | | | |
|---|---|---|---|---|
| CONECT | 2790 | 2786 | 2791 | |
| CONECT | 2791 | 2790 | 2792 | |
| CONECT | 2792 | 2791 | 2793 | 2794 |
| CONECT | 2793 | 2792 | 2798 | |
| CONECT | 2794 | 2792 | 2795 | 2796 |
| CONECT | 2795 | 2794 | | |
| CONECT | 2796 | 2794 | 2797 | 2798 |
| CONECT | 2797 | 2796 | | |
| CONECT | 2798 | 2793 | 2796 | 2799 |
| CONECT | 2799 | 2798 | 2800 | 2806 |
| CONECT | 2800 | 2799 | 2801 | |
| CONECT | 2801 | 2800 | 2802 | |
| CONECT | 2802 | 2801 | 2803 | 2806 |
| CONECT | 2803 | 2802 | 2804 | 2805 |
| CONECT | 2804 | 2803 | | |
| CONECT | 2805 | 2803 | | |
| CONECT | 2806 | 2799 | 2802 | |
| CONECT | 2807 | 2822 | 2824 | 2825 |
| CONECT | 2808 | 2809 | 2823 | |
| CONECT | 2809 | 2808 | 2810 | 2815 |
| CONECT | 2810 | 2809 | 2811 | |
| CONECT | 2811 | 2810 | 2812 | |
| CONECT | 2812 | 2811 | 2828 | 2829 |
| CONECT | 2813 | 2818 | | |
| CONECT | 2814 | 2826 | | |
| CONECT | 2815 | 2809 | | |
| CONECT | 2816 | 2817 | 2825 | |
| CONECT | 2817 | 2816 | 2818 | 2822 |
| CONECT | 2818 | 2813 | 2817 | 2819 |
| CONECT | 2819 | 2818 | 2820 | 2826 |
| CONECT | 2820 | 2819 | 2821 | 2823 |
| CONECT | 2821 | 2820 | 2822 | 2827 |
| CONECT | 2822 | 2807 | 2817 | 2821 |
| CONECT | 2823 | 2808 | 2820 | |
| CONECT | 2824 | 2807 | | |
| CONECT | 2825 | 2807 | 2816 | |
| CONECT | 2826 | 2814 | 2819 | |
| CONECT | 2827 | 2821 | | |
| CONECT | 2828 | 2812 | | |
| CONECT | 2829 | 2812 | | |
| MASTER | | 509 | 0 | 4 | 13 | 18 | 0 | 0 | 6 | 2948 | 1 | 46 | | 39 |
| END | | | | |
| FIG. 8 | | | | |
| P-UC 5430 | | | | |
| Page 1 | | | | |

TABLE 7

| | | |
|---|---|---|
| HEADER | OXIDOREDUCTASE 08-AUG-02 1ME8 | |
| TITLE | INOSINE MONOPHOSPHATE DEHYDROGENASE (IMPDH) FROM | |
| TITLE | 2 | *TRITRICHOMONAS FOETUS* WITH RVP BOUND |
| COMPND | MOL_ID: 1; | |
| COMPND | 2 | MOLECULE: INOSINE-5'-MONOPHOSPHATE DEHYDROGENASE; |
| COMPND | 3 | CHAIN: A; |
| COMPND | 4 | SYNONYM: IMP DEHYDROGENASE, IMPDH; |
| COMPND | 5 | EC: 1.1.1.205; |
| COMPND | 6 | ENGINEERED: YES |
| SOURCE | MOL_ID: 1; | |
| SOURCE | 2 | ORGANISM_SCIENTIFIC: *TRITRICHOMONAS FOETUS*; |
| SOURCE | 3 | GENE: IMPDH; |
| SOURCE | 4 | EXPRESSION_SYSTEM: *ESCHERICHIA COLI*; |
| SOURCE | 5 | EXPRESSION_SYSTEM_COMMON: BACTERIA; |
| SOURCE | 6 | EXPRESSION_SYSTEM_STRAIN: H712; |
| SOURCE | 7 | EXPRESSION_SYSTEM_VECTOR_TYPE: PLASMID; |
| SOURCE | 8 | EXPRESSION_SYSTEM_PLASMID: PBACE |
| KEYWDS | ALPHA BETA BARREL | |
| EXPDTA | X-RAY DIFFRACTION | |
| AUTHOR | G. L. PROSISE, J. WU, H. LUECKE | |
| JRNL | AUTH | G. L. PROSISE, J. WU, H. LUECKE |
| JRNL | TITL | CRYSTAL STRUCTURE OF *T. FOETUS* INOSINE |
| JRNL | TITL | 2 MONOPHOSPHATE DEHYDROGENASE IN COMPLEX WITH THE |
| JRNL | TITL | 3 INHIBITOR RIBAVIRIN REVEALS A CATALYSIS-DEPENDENT |

TABLE 7-continued

```
JRNL              TITL    4 ION BINDING SITE
JRNL              REF       TO BE PUBLISHED
JRNL              REFN
REMARK   1
REMARK   2
REMARK   2   RESOLUTION. 1.90 ANGSTROMS.
REMARK   3
REMARK   3   REFINEMENT.
REMARK   3      PROGRAM    :   CNS 1.1
REMARK   3      AUTHORS    :   BRUNGER, ADAMS, CLORE, DELANO, GROS, GROSSE-
REMARK   3                 :   KUNSTLEVE, JIANG, KUSZEWSKI, NILGES, PANNU,
REMARK   3                 :   READ, RICE, SIMONSON, WARREN
REMARK   3
REMARK   3   REFINEMENT TARGET   :   ENGH & HUBER
REMARK   3
REMARK   3   DATA USED IN REFINEMENT.
REMARK   3      RESOLUTION RANGE HIGH           (ANGSTROMS) :   1.90
REMARK   3      RESOLUTION RANGE LOW            (ANGSTROMS) :   48.94
REMARK   3      DATA CUTOFF                       (SIGMA(F)) :   0.000
REMARK   3      OUTLIER CUTOFF HIGH             (RMS(ABS(F))) :  NULL
REMARK   3      COMPLETENESS             (WORKING + TEST) (%) :  99.4
REMARK   3      NUMBER OF REFLECTIONS                        :   50121
REMARK   3
REMARK   3   FIT TO DATA USED IN REFINEMENT.
REMARK   3      CROSS-VALIDATION METHOD                  :   THROUGHOUT
REMARK   3      FREE R VALUE TEST SET SELECTION          :   RANDOM
REMARK   3      R VALUE                     (WORKING SET) :   0.243
REMARK   3      FREE R VALUE                             :   0.258
REMARK   3      FREE R VALUE TEST SET SIZE          (%)  :   5.000
REMARK   3      FREE R VALUE TEST SET COUNT              :   2523
REMARK   3      ESTIMATED ERROR OF FREE R VALUE          :   0.005
REMARK   3
REMARK   3   FIT IN THE HIGHEST RESOLUTION BIN.
REMARK   3      TOTAL NUMBER OF BINS USED                :   6
REMARK   3      BIN RESOLUTION RANGE HIGH           (A)  :   1.90
REMARK   3      BIN RESOLUTION RANGE LOW            (A)  :   2.02
REMARK   3      BIN COMPLETENESS    (WORKING + TEST) (%) :   99.90
REMARK   3      REFLECTIONS IN BIN       (WORKING SET)   :   7832
REMARK   3      BIN R VALUE              (WORKING SET)   :   0.2820
REMARK   3      BIN FREE R VALUE                         :   0.2950
REMARK   3      BIN FREE R VALUE TEST SET SIZE      (%)  :   4.60
REMARK   3      BIN FREE R VALUE TEST SET COUNT          :   378
REMARK   3      ESTIMATED ERROR OF BIN FREE R VALUE      :   0.015
REMARK   3
REMARK   3   NUMBER OF NON-HYDROGEN ATOMS USED IN REFINEMENT.
REMARK   3      PROTEIN ATOMS          :   2727
REMARK   3      NUCLEIC ACID ATOMS     :   0
REMARK   3      HETEROGEN ATOMS        :   23
REMARK   3      SOLVENT ATOMS          :   201
REMARK   3
REMARK   3   B VALUES.
REMARK   3      FROM WILSON PLOT           (A**2) :   23.40
REMARK   3      MEAN B VALUE      (OVERALL, A**2) :   36.90
REMARK   3      OVERALL ANISOTROPIC B VALUE.
REMARK   3      B11    (A**2) :   0.00000
REMARK   3      B22    (A**2) :   0.00000
REMARK   3      B33    (A**2) :   0.00000
REMARK   3      B12    (A**2) :   0.00000
REMARK   3      B13    (A**2) :   0.00000
REMARK   3      B23    (A**2) :   0.00000
REMARK   3
REMARK   3   ESTIMATED COORDINATE ERROR.
REMARK   3      ESD FROM LUZZATI PLOT          (A) :   0.26
REMARK   3      ESD FROM SIGMAA                (A) :   0.18
REMARK   3      LOW RESOLUTION CUTOFF          (A) :   5.00
REMARK   3
REMARK   3   CROSS-VALIDATED ESTIMATED COORDINATE ERROR.
REMARK   3      ESD FROM C-V LUZZATI PLOT      (A) :   0.28
REMARK   3      ESD FROM C-V SIGMAA            (A) :   0.18
REMARK   3
REMARK   3   RMS DEVIATIONS FROM IDEAL VALUES.
REMARK   3      BOND LENGTHS                   (A) :   0.005
REMARK   3      BOND ANGLES              (DEGREES) :   1.20
REMARK   3      DIHEDRAL ANGLES          (DEGREES) :   22.70
REMARK   3      IMPROPER ANGLES          (DEGREES) :   0.71
REMARK   3
REMARK   3   ISOTROPIC THERMAL MODEL   :   RESTRAINED
REMARK   3
```

TABLE 7-continued

```
REMARK   3 ISOTROPIC THERMAL FACTOR RESTRAINTS.   RMS       SIGMA
REMARK   3      MAIN-CHAIN BOND        (A**2) :   0.990 ;   1.500
REMARK   3      MAIN-CHAIN ANGLE       (A**2) :   1.660 ;   2.000
REMARK   3      SIDE-CHAIN BOND        (A**2) :   1.450 ;   2.000
REMARK   3      SIDE-CHAIN ANGLE       (A**2) :   2.260 ;   2.500
REMARK   3
REMARK   3 BULK SOLVENT MODELING.
REMARK   3      METHOD USED :    FLAT MODEL
REMARK   3      KSOL        :    0.36
REMARK   3      BSOL        :    44.08
REMARK   3
REMARK   3 NCS MODEL  :    NULL
REMARK   3
REMARK   3      NCS RESTRAINTS.                          RMS        SIGMA/WEIGHT
REMARK   3          GROUP  1  POSITIONAL     (A) :    NULL ;         NULL
REMARK   3          GROUP  1  B-FACTOR     (A**2) :    NULL ;         NULL
REMARK   3
REMARK   3      PARAMETER FILE   1 :   PROTEIN_REP.PARAM
REMARK   3      PARAMETER FILE   2 :   PARAM.GNSOL
REMARK   3      PARAMETER FILE   3 :   CIS_PEPTIDE.PARAM
REMARK   3      PARAMETER FILE   4 :   RMP_MPA.PAR
REMARK   3      PARAMETER FILE   5 :   ION.PARAM
REMARK   3      PARAMETER FILE   6 :   NULL
REMARK   3      TOPOLOGY FILE    1 :   PROTEIN.TOP
REMARK   3      TOPOLOGY FILE    2 :   RMP.TOP
REMARK   3      TOPOLOGY FILE    3 :   MPA.TOP
REMARK   3      TOPOLOGY FILE    4 :   ION.TOP
REMARK   3      TOPOLOGY FILE    5 :   TOPH.GNSOL
REMARK   3      TOPOLOGY FILE    6 :   NULL
REMARK   3
REMARK   3      OTHER REFINEMENT REMARKS: NULL
REMARK   4
REMARK   4 1ME8 COMPLIES WITH FORMAT V. 2.3, 09-JULY-1998
REMARK 100
REMARK 100 THIS ENTRY HAS BEEN PROCESSED BY RCSB ON 16-AUG-2002.
REMARK 100 THE RCSB ID CODE IS RCSB016850.
REMARK 200
REMARK 200 EXPERIMENTAL DETAILS
REMARK 200      EXPERIMENT TYPE                 :   X-RAY DIFFRACTION
REMARK 200      DATE OF DATA COLLECTION         :   12-JUN-2001
REMARK 200      TEMPERATURE         (KELVIN) :   100.0
REMARK 200      PH                              :   7.50
REMARK 200      NUMBER OF CRYSTALS USED         :   1
REMARK 200
REMARK 200      SYNCHROTRON              (Y/N) :   Y
REMARK 200      RADIATION SOURCE                :   SSRL
REMARK 200      BEAMLINE                        :   9-1
REMARK 200      X-RAY GENERATOR MODEL           :   NULL
REMARK 200      MONOCHROMATIC OR LAUE    (M/L) :   M
REMARK 200      WAVELENGTH OR RANGE        (A) :   0.07
REMARK 200      MONOCHROMATOR                   :   NULL
REMARK 200      OPTICS                          :   NULL
REMARK 200
REMARK 200      DETECTOR TYPE                   :   IMAGE PLATE
REMARK 200      DETECTOR MANUFACTURER           :   MARRESEARCH
REMARK 200      INTENSITY-INTEGRATION SOFTWARE  :   DENZO
REMARK 200      DATA SCALING SOFTWARE           :   SCALEPACK
REMARK 200
REMARK 200      NUMBER OF UNIQUE REFLECTIONS    :   50290
REMARK 200      RESOLUTION RANGE HIGH      (A) :   1.900
REMARK 200      RESOLUTION RANGE LOW       (A) :   50.000
REMARK 200      REJECTION CRITERIA   (SIGMA(I)) :   0.000
REMARK 200
REMARK 200 OVERALL.
REMARK 200      COMPLETENESS FOR RANGE     (%) :   99.9
REMARK 200      DATA REDUNDANCY                 :   10.000
REMARK 200      R MERGE                    (I) :   0.08000
REMARK 200      R SYM                      (I) :   NULL
REMARK 200      <I/SIGMA(I)> FOR THE DATA SET   :   33.8000
REMARK 200
REMARK 200 IN THE HIGHEST RESOLUTION SHELL.
REMARK 200      HIGHEST RESOLUTION SHELL, RANGE HIGH  (A) :   1.90
REMARK 200      HIGHEST RESOLUTION SHELL, RANGE LOW   (A) :   1.93
REMARK 200      COMPLETENESS FOR SHELL     (%) :   100.0
REMARK 200      DATA REDUNDANCY IN SHELL        :   NULL
REMARK 200      R MERGE FOR SHELL          (I) :   0.60000
REMARK 200      R SYM FOR SHELL            (I) :   NULL
REMARK 200      <I/SIGMA(I)> FOR SHELL          :   2.400
REMARK 200
```

TABLE 7-continued

```
REMARK  200  DIFFRACTION PROTOCOL: SINGLE WAVELENGTH
REMARK  200  METHOD USED TO DETERMINE THE STRUCTURE: FOURIER SYNTHESIS
REMARK  200  SOFTWARE USED: CNS
REMARK  200  STARTING MODEL: NULL
REMARK  200
REMARK  200  REMARK: NULL
REMARK  280
REMARK  280  CRYSTAL
REMARK  280  SOLVENT CONTENT, VS (%): NULL
REMARK  280  MATTHEWS COEFFICIENT, VM (ANGSTROMS**3/DA): NULL
REMARK  280
REMARK  280  CRYSTALLIZATION CONDITIONS: SODIUM MALONATE, TRIS, 2-
REMARK  280      MERCAPTOETHANOL, EDTA, GLYCEROL
REMARK  290
REMARK  290  CRYSTALLOGRAPHIC SYMMETRY
REMARK  290  SYMMETRY OPERATORS FOR SPACE GROUP: P 4 3 2
REMARK  290
REMARK  290            SYMOP    SYMMETRY
REMARK  290            NNNMMM   OPERATOR
REMARK  290             1555    X, Y, Z
REMARK  290             2555    —X, —Y, Z
REMARK  290             3555    —X, Y, —Z
REMARK  290             4555    X, —Y, —Z
REMARK  290             5555    Z, X, Y
REMARK  290             6555    Z, —X, —Y
REMARK  290             7555    —Z, —X, Y
REMARK  290             8555    —Z, X, —Y
REMARK  290             9555    Y, Z, X
REMARK  290            10555    —Y, Z, —X
REMARK  290            11555    Y, —Z, —X
REMARK  290            12555    —Y, —Z, X
REMARK  290            13555    Y, X, —Z
REMARK  290            14555    —Y, —X, —Z
REMARK  290            15555    Y, —X, Z
REMARK  290            16555    —Y, X, Z
REMARK  290            17555    X, Z, —Y
REMARK  290            18555    —X, Z, Y
REMARK  290            19555    —X, —Z, —Y
REMARK  290            20555    X, —Z, Y
REMARK  290            21555    Z, Y, —X
REMARK  290            22555    Z, —Y, X
REMARK  290            23555    —Z, Y, X
REMARK  290            24555    —Z, —Y, —X
REMARK  290
REMARK  290        WHERE   NNN ->   OPERATOR NUMBER
REMARK  290                MMM ->   TRANSLATION VECTOR
REMARK  290
REMARK  290  CRYSTALLOGRAPHIC SYMMETRY TRANSFORMATIONS
REMARK  290  THE FOLLOWING TRANSFORMATIONS OPERATE ON THE ATOM/HETATM
REMARK  290  RECORDS IN THIS ENTRY TO PRODUCE CRYSTALLOGRAPHICALLY
REMARK  290  RELATED MOLECULES.
REMARK  290      SMTRY1    1    1.000000   0.000000   0.000000  0.00000
REMARK  290      SMTRY2    1    0.000000   1.000000   0.000000  0.00000
REMARK  290      SMTRY3    1    0.000000   0.000000   1.000000  0.00000
REMARK  290      SMTRY1    2   -1.000000   0.000000   0.000000  0.00000
REMARK  290      SMTRY2    2    0.000000  -1.000000   0.000000  0.00000
REMARK  290      SMTRY3    2    0.000000   0.000000   1.000000  0.00000
REMARK  290      SMTRY1    3   -1.000000   0.000000   0.000000  0.00000
REMARK  290      SMTRY2    3    0.000000   1.000000   0.000000  0.00000
REMARK  290      SMTRY3    3    0.000000   0.000000  -1.000000  0.00000
REMARK  290      SMTRY1    4    1.000000   0.000000   0.000000  0.00000
REMARK  290      SMTRY2    4    0.000000  -1.000000   0.000000  0.00000
REMARK  290      SMTRY3    4    0.000000   0.000000  -1.000000  0.00000
REMARK  290      SMTRY1    5    0.000000   0.000000   1.000000  0.00000
REMARK  290      SMTRY2    5    1.000000   0.000000   0.000000  0.00000
REMARK  290      SMTRY3    5    0.000000   1.000000   0.000000  0.00000
REMARK  290      SMTRY1    6    0.000000   0.000000   1.000000  0.00000
REMARK  290      SMTRY2    6   -1.000000   0.000000   0.000000  0.00000
REMARK  290      SMTRY3    6    0.000000  -1.000000   0.000000  0.00000
REMARK  290      SMTRY1    7    0.000000   0.000000  -1.000000  0.00000
REMARK  290      SMTRY2    7   -1.000000   0.000000   0.000000  0.00000
REMARK  290      SMTRY3    7    0.000000   1.000000   0.000000  0.00000
REMARK  290      SMTRY1    8    0.000000   0.000000  -1.000000  0.00000
REMARK  290      SMTRY2    8    1.000000   0.000000   0.000000  0.00000
REMARK  290      SMTRY3    8    0.000000  -1.000000   0.000000  0.00000
REMARK  290      SMTRY1    9    0.000000   1.000000   0.000000  0.00000
REMARK  290      SMTRY2    9    0.000000   0.000000   1.000000  0.00000
REMARK  290      SMTRY3    9    1.000000   0.000000   0.000000  0.00000
REMARK  290      SMTRY1   10    0.000000  -1.000000   0.000000  0.00000
```

TABLE 7-continued

```
REMARK   290       SMTRY2   10    0.000000   0.000000   1.000000   0.00000
REMARK   290       SMTRY3   10   -1.000000   0.000000   0.000000   0.00000
REMARK   290       SMTRY1   11    0.000000   1.000000   0.000000   0.00000
REMARK   290       SMTRY2   11    0.000000   0.000000  -1.000000   0.00000
REMARK   290       SMTRY3   11   -1.000000   0.000000   0.000000   0.00000
REMARK   290       SMTRY1   12    0.000000  -1.000000   0.000000   0.00000
REMARK   290       SMTRY2   12    0.000000   0.000000  -1.000000   0.00000
REMARK   290       SMTRY3   12    1.000000   0.000000   0.000000   0.00000
REMARK   290       SMTRY1   13    0.000000   1.000000   0.000000   0.00000
REMARK   290       SMTRY2   13    1.000000   0.000000   0.000000   0.00000
REMARK   290       SMTRY3   13    0.000000   0.000000  -1.000000   0.00000
REMARK   290       SMTRY1   14    0.000000  -1.000000   0.000000   0.00000
REMARK   290       SMTRY2   14   -1.000000   0.000000   0.000000   0.00000
REMARK   290       SMTRY3   14    0.000000   0.000000  -1.000000   0.00000
REMARK   290       SMTRY1   15    0.000000   1.000000   0.000000   0.00000
REMARK   290       SMTRY2   15   -1.000000   0.000000   0.000000   0.00000
REMARK   290       SMTRY3   15    0.000000   0.000000   1.000000   0.00000
REMARK   290       SMTRY1   16    0.000000  -1.000000   0.000000   0.00000
REMARK   290       SMTRY2   16    1.000000   0.000000   0.000000   0.00000
REMARK   290       SMTRY3   16    0.000000   0.000000   1.000000   0.00000
REMARK   290       SMTRY1   17    1.000000   0.000000   0.000000   0.00000
REMARK   290       SMTRY2   17    0.000000   0.000000   1.000000   0.00000
REMARK   290       SMTRY3   17    0.000000  -1.000000   0.000000   0.00000
REMARK   290       SMTRY1   18   -1.000000   0.000000   0.000000   0.00000
REMARK   290       SMTRY2   18    0.000000   0.000000   1.000000   0.00000
REMARK   290       SMTRY3   18    0.000000   1.000000   0.000000   0.00000
REMARK   290       SMTRY1   19   -1.000000   0.000000   0.000000   0.00000
REMARK   290       SMTRY2   19    0.000000   0.000000  -1.000000   0.00000
REMARK   290       SMTRY3   19    0.000000  -1.000000   0.000000   0.00000
REMARK   290       SMTRY1   20    1.000000   0.000000   0.000000   0.00000
REMARK   290       SMTRY2   20    0.000000   0.000000  -1.000000   0.00000
REMARK   290       SMTRY3   20    0.000000   1.000000   0.000000   0.00000
REMARK   290       SMTRY1   21    0.000000   0.000000   1.000000   0.00000
REMARK   290       SMTRY2   21    0.000000   1.000000   0.000000   0.00000
REMARK   290       SMTRY3   21   -1.000000   0.000000   0.000000   0.00000
REMARK   290       SMTRY1   22    0.000000   0.000000   1.000000   0.00000
REMARK   290       SMTRY2   22    0.000000  -1.000000   0.000000   0.00000
REMARK   290       SMTRY3   22    1.000000   0.000000   0.000000   0.00000
REMARK   290       SMTRY1   23    0.000000   0.000000  -1.000000   0.00000
REMARK   290       SMTRY2   23    0.000000   1.000000   0.000000   0.00000
REMARK   290       SMTRY3   23    1.000000   0.000000   0.000000   0.00000
REMARK   290       SMTRY1   24    0.000000   0.000000  -1.000000   0.00000
REMARK   290       SMTRY2   24    0.000000  -1.000000   0.000000   0.00000
REMARK   290       SMTRY3   24   -1.000000   0.000000   0.000000   0.00000
REMARK   290
REMARK   290   REMARK: NULL
REMARK   300
REMARK   300   BIOMOLECULE: 1
REMARK   300   THIS ENTRY CONTAINS THE CRYSTALLOGRAPHIC ASYMMETRIC UNIT
REMARK   300   WHICH CONSISTS OF 1 CHAIN(S). SEE REMARK 350 FOR
REMARK   300   INFORMATION ON GENERATING THE BIOLOGICAL MOLECULE(S).
REMARK   350
REMARK   350   GENERATING THE BIOMOLECULE
REMARK   350   COORDINATES FOR A COMPLETE MULTIMER REPRESENTING THE KNOWN
REMARK   350   BIOLOGICALLY SIGNIFICANT OLIGOMERIZATION STATE OF THE
REMARK   350   MOLECULE CAN BE GENERATED BY APPLYING BIOMT TRANSFORMATIONS
REMARK   350   GIVEN BELOW. BOTH NON-CRYSTALLOGRAPHIC AND
REMARK   350   CRYSTALLOGRAPHIC OPERATIONS ARE GIVEN.
REMARK   350
REMARK   350   BIOMOLECULE: 1
REMARK   350   APPLY THE FOLLOWING TO CHAINS: A
REMARK   350       BIOMT1    1    1.000000   0.000000   0.000000     0.00000
REMARK   350       BIOMT2    1    0.000000   1.000000   0.000000     0.00000
REMARK   350       BIOMT3    1    0.000000   0.000000   1.000000     0.00000
REMARK   350       BIOMT1    2   -1.000000   0.000000   0.000000   154.74500
REMARK   350       BIOMT2    2    0.000000  -1.000000   0.000000   154.74500
REMARK   350       BIOMT3    2    0.000000   0.000000   1.000000     0.00000
REMARK   350       BIOMT1    3    0.000000   1.000000   0.000000     0.00000
REMARK   350       BIOMT2    3   -1.000000   0.000000   0.000000   154.74500
REMARK   350       BIOMT3    3    0.000000   0.000000   1.000000     0.00000
REMARK   350       BIOMT1    4    0.000000  -1.000000   0.000000   154.74500
REMARK   350       BIOMT2    4    1.000000   0.000000   0.000000     0.00000
REMARK   350       BIOMT3    4    0.000000   0.000000   1.000000     0.00000
REMARK   465
REMARK   465   MISSING RESIDUES
REMARK   465   THE FOLLOWING, RESIDUES WERE NOT LOCATED IN THE
REMARK   465   EXPERIMENT. (M = MODEL NUMBER; RES = RESIDUE NAME; C = CHAIN
REMARK   465   IDENTIFIER; SSSEQ = SEQUENCE NUMBER; I = INSERTION CODE.)
REMARK   465
```

TABLE 7-continued

| | | | | | |
|---|---|---|---|---|---|
| REMARK | 465 | M | RES | C | SSSEQI |
| REMARK | 465 | | MET | A | 1 |
| REMARK | 465 | | GLY | A | 102 |
| REMARK | 465 | | PHE | A | 103 |
| REMARK | 465 | | VAL | A | 104 |
| REMARK | 465 | | VAL | A | 105 |
| REMARK | 465 | | SER | A | 106 |
| REMARK | 465 | | ASP | A | 107 |
| REMARK | 465 | | SER | A | 108 |
| REMARK | 465 | | ASN | A | 109 |
| REMARK | 465 | | VAL | A | 110 |
| REMARK | 465 | | LYS | A | 111 |
| REMARK | 465 | | PRO | A | 112 |
| REMARK | 465 | | ASP | A | 113 |
| REMARK | 465 | | GLN | A | 114 |
| REMARK | 465 | | THR | A | 115 |
| REMARK | 465 | | PHE | A | 116 |
| REMARK | 465 | | ALA | A | 117 |
| REMARK | 465 | | ASP | A | 118 |
| REMARK | 465 | | VAL | A | 119 |
| REMARK | 465 | | LEU | A | 120 |
| REMARK | 465 | | ALA | A | 121 |
| REMARK | 465 | | ILE | A | 122 |
| REMARK | 465 | | SER | A | 123 |
| REMARK | 465 | | GLN | A | 124 |
| REMARK | 465 | | ARG | A | 125 |
| REMARK | 465 | | THR | A | 126 |
| REMARK | 465 | | THR | A | 127 |
| REMARK | 465 | | HIS | A | 128 |
| REMARK | 465 | | ASN | A | 129 |
| REMARK | 465 | | THR | A | 130 |
| REMARK | 465 | | VAL | A | 131 |
| REMARK | 465 | | ALA | A | 132 |
| REMARK | 465 | | VAL | A | 133 |
| REMARK | 465 | | THR | A | 134 |
| REMARK | 465 | | ASP | A | 135 |
| REMARK | 465 | | ASP | A | 136 |
| REMARK | 465 | | GLY | A | 137 |
| REMARK | 465 | | THR | A | 138 |
| REMARK | 465 | | PRO | A | 139 |
| REMARK | 465 | | HIS | A | 140 |
| REMARK | 465 | | GLY | A | 141 |
| REMARK | 465 | | VAL | A | 142 |
| REMARK | 465 | | LEU | A | 143 |
| REMARK | 465 | | LEU | A | 144 |
| REMARK | 465 | | GLY | A | 145 |
| REMARK | 465 | | LEU | A | 146 |
| REMARK | 465 | | VAL | A | 147 |
| REMARK | 465 | | THR | A | 148 |
| REMARK | 465 | | GLN | A | 149 |
| REMARK | 465 | | ARG | A | 150 |
| REMARK | 465 | | ASP | A | 151 |
| REMARK | 465 | | TYR | A | 152 |
| REMARK | 465 | | PRO | A | 153 |
| REMARK | 465 | | ILE | A | 154 |
| REMARK | 465 | | ASP | A | 155 |
| REMARK | 465 | | LEU | A | 156 |
| REMARK | 465 | | THR | A | 157 |
| REMARK | 465 | | GLN | A | 158 |
| REMARK | 465 | | THR | A | 159 |
| REMARK | 465 | | GLU | A | 160 |
| REMARK | 465 | | THR | A | 161 |
| REMARK | 465 | | LYS | A | 162 |
| REMARK | 465 | | VAL | A | 163 |
| REMARK | 465 | | SER | A | 164 |
| REMARK | 465 | | ASP | A | 165 |
| REMARK | 465 | | MET | A | 166 |
| REMARK | 465 | | MET | A | 167 |
| REMARK | 465 | | THR | A | 168 |
| REMARK | 465 | | PRO | A | 169 |
| REMARK | 465 | | PHE | A | 170 |
| REMARK | 465 | | SER | A | 171 |
| REMARK | 465 | | LYS | A | 172 |
| REMARK | 465 | | LEU | A | 173 |
| REMARK | 465 | | VAL | A | 174 |
| REMARK | 465 | | THR | A | 175 |
| REMARK | 465 | | ALA | A | 176 |
| REMARK | 465 | | HIS | A | 177 |
| REMARK | 465 | | GLN | A | 178 |

TABLE 7-continued

```
REMARK   465        ASP   A   179
REMARK   465        THR   A   180
REMARK   465        LYS   A   181
REMARK   465        LEU   A   182
REMARK   465        SER   A   183
REMARK   465        GLU   A   184
REMARK   465        ALA   A   185
REMARK   465        ASN   A   186
REMARK   465        LYS   A   187
REMARK   465        ILE   A   188
REMARK   465        ILE   A   189
REMARK   465        TRP   A   190
REMARK   465        GLU   A   191
REMARK   465        LYS   A   192
REMARK   465        LYS   A   193
REMARK   465        LEU   A   194
REMARK   465        ASN   A   195
REMARK   465        ALA   A   196
REMARK   465        LEU   A   197
REMARK   465        PRO   A   198
REMARK   465        ILE   A   199
REMARK   465        ILE   A   200
REMARK   465        ASP   A   201
REMARK   465        ASP   A   202
REMARK   465        ASP   A   203
REMARK   465        GLN   A   204
REMARK   465        HIS   A   205
REMARK   465        LEU   A   206
REMARK   465        ARG   A   207
REMARK   465        TYR   A   208
REMARK   465        ILE   A   209
REMARK   465        VAL   A   210
REMARK   465        PHE   A   211
REMARK   465        ARG   A   212
REMARK   465        LYS   A   213
REMARK   465        ASP   A   214
REMARK   465        TYR   A   215
REMARK   465        ASP   A   216
REMARK   465        ARG   A   217
REMARK   465        SER   A   218
REMARK   465        GLN   A   219
REMARK   465        VAL   A   220
REMARK   465        CYS   A   221
REMARK   465        GLN   A   417
REMARK   465        ARG   A   418
REMARK   465        TYR   A   419
REMARK   465        ASP   A   420
REMARK   465        LEU   A   421
REMARK   465        GLY   A   422
REMARK   465        GLY   A   423
REMARK   465        LYS   A   424
REMARK   465        GLN   A   425
REMARK   465        LYS   A   426
REMARK   465        LEU   A   427
REMARK   465        SER   A   428
REMARK   465        PHE   A   429
REMARK   465        GLU   A   430
REMARK   465        VAL   A   493
REMARK   465        LYS   A   494
REMARK   465        ASP   A   495
REMARK   465        ARG   A   496
REMARK   465        ILE   A   497
REMARK   465        ASN   A   498
REMARK   465        ASP   A   499
REMARK   465        TYR   A   500
REMARK   465        HIS   A   501
REMARK   465        PRO   A   502
REMARK   465        LYS   A   503
REMARK   500
REMARK   500  GEOMETRY AND STHREOCHEMISTRY
REMARK   500  SUBTOPIC: COVALENT BOND ANGLES
REMARK   500
REMARK   500  THE STEREOCHEMICAL PARAMETERS OF THE FOLLOWING RESIDUES
REMARK   500  HAVE VALUES WHICH DEVIATE FROM EXPECTED VALUES BY MORE
REMARK   500  THAN 6*RMSD (M = MODEL NUMBER; RES = RESIDUE NAME; C = CHAIN
REMARK   500  IDENTIFIER; SSEQ = SEQUENCE NUMBER; I = INSERTION CODE).
REMARK   500
```

TABLE 7-continued

```
REMARK   500  STANDARD TABLE:
REMARK   500  FORMAT: (10X, I3, 1X, A3, 1X, A1, I4, A1, 3 (1X, A4, 2X), 12X, F5.1)
REMARK   500
REMARK   500  EXPECTED VALUES: ENGH AND HUBER, 1991
REMARK   500
REMARK   500      M  RES    CSSEQI    ATM1        ATM2       ATM3
REMARK   500         GLY   A    20    N    -    CA   -    C    ANGL. DEV. =  -7.5 DEGREES
REMARK   500         ILE   A    27    N    -    CA   -    C    ANGL. DEV. =  -9.2 DEGREES
REMARK   500         PRO   A    53    N    -    CA   -    C    ANGL. DEV. =   7.4 DEGREES
REMARK   500         SER   A    63    N    -    CA   -    C    ANGL. DEV. =   8.5 DEGREES
REMARK   500         SER   A   357    N    -    CA   -    C    ANGL. DEV. =  -7.3 DEGREES
REMARK   500         LYS   A   472    N    -    CA   -    C    ANGL. DEV. =   8.2 DEGREES
REMARK   500         LYS   A   474    N    -    CA   -    C    ANGL. DEV. =  -8.8 DEGREES
REMARK   500         LEU   A   477    N    -    CA   -    C    ANGL. DEV. =  -8.6 DEGREES
REMARK   900
REMARK   900  RELATED ENTRIES
REMARK   900  RELATED ID: 1AK5   RELATED DB: PDB
REMARK   900  INOSINE MONOPHOSPHATE DEHYDROGENASE (IMPDH) FROM
REMARK   900  TRITRICHOMONAS FOETUS
REMARK   900  RELATED ID: 1ME7   RELATED DB: PDB
REMARK   900  1ME7 CONTAINS THE SAME PROTEIN WITH RRP AND MOA BOUND
REMARK   900  RELATED ID: 1ME9   RELATED DB: PDB
REMARK   900  1ME9 CONTAINS THE SAME PROTEIN WITH IMP BOUND
REMARK   900  RELATED ID: 1MEH   RELATED DB: PDB
REMARK   900  1MEH CONTAINS THE SAME PROTEIN WITH IMP AND MOA BOUND
REMARK   900  RELATED ID: 1MEI   RELATED DB: PDB
REMARK   900  1MEI CONTAINS THE SAME PROTEIN WITH XMP AND MYCOPHENOLIC
REMARK   900  ACID BOUND
REMARK   900  RELATED ID: 1MEW   RELATED DB: PDB
REMARK   900  1MEW CONTAINS THE SAME PROTEIN WITH XMP AND NAD BOUND
DBREF    1ME8  A    1   503   SWS     P50097     IMDH_TRIFO         1    503
SEQADV   1ME8  CSO  A  319   SWS  P50097    CYS    319 MODIFIED RESIDUE
SEQRES    1 A   503  MET  ALA  LYS  TYR  TYR  ASN  GLU  PRO  CYS  HIS  THR  PHE  ASN
SEQRES    2 A   503  GLU  TYR  LEU  LEU  ILE  PRO  GLY  LEU  SER  THR  VAL  ASP  CYS
SEQRES    3 A   503  ILE  PRO  SER  ASN  VAL  ASN  LEU  SER  THR  PRO  LEU  VAL  LYS
SEQRES    4 A   503  PHE  GLN  LYS  GLY  GLN  GLN  SER  GLU  ILE  ASN  LEU  LYS  ILE
SEQRES    5 A   503  PRO  LEU  VAL  SER  ALA  ILE  MET  GLN  SER  VAL  SER  GLY  GLU
SEQRES    6 A   503  LYS  MET  ALA  ILE  ALA  LEU  ALA  ARG  GLU  GLY  GLY  ILE  SER
SEQRES    7 A   503  PHE  ILE  PHE  GLY  SER  GLN  SER  ILE  GLU  SER  GLN  ALA  ALA
SEQRES    8 A   503  MET  VAL  HIS  ALA  VAL  LYS  ASN  PHE  LYS  ALA  GLY  PHE  VAL
SEQRES    9 A   503  VAL  SER  ASP  SER  ASN  VAL  LYS  PRO  ASP  GLN  THR  PHE  ALA
SEQRES   10 A   503  ASP  VAL  LEU  ALA  ILE  SER  GLN  ARG  THR  THR  HIS  ASN  THR
SEQRES   11 A   503  VAL  ALA  VAL  THR  ASP  ASP  GLY  THR  PRO  HIS  GLY  VAL  LEU
SEQRES   12 A   503  LEU  GLY  LEU  VAL  THR  GLN  ARG  ASP  TYR  PRO  ILE  ASP  LEU
SEQRES   13 A   503  THR  GLN  THR  GLU  THR  LYS  VAL  SER  ASP  MET  MET  THR  PRO
SEQRES   14 A   503  PHE  SER  LYS  LEU  VAL  THR  ALA  HIS  GLN  ASP  THR  LYS  LEU
SEQRES   15 A   503  SER  GLU  ALA  ASN  LYS  ILE  ILE  TRP  GLU  LYS  LYS  LEU  ASN
SEQRES   16 A   503  ALA  LEU  PRO  ILE  ILE  ASP  ASP  ASP  GLN  HIS  LEU  ARG  TYR
SEQRES   17 A   503  ILE  VAL  PHE  ARG  LYS  ASP  TYR  ASP  ARG  SER  GLN  VAL  CYS
SEQRES   18 A   503  HIS  ASN  GLU  LEU  VAL  ASP  SER  GLN  LYS  ARG  TYR  LEU  VAL
SEQRES   19 A   503  GLY  ALA  GLY  ILE  ASN  THR  ARG  ASP  PHE  ARG  GLU  ARG  VAL
SEQRES   20 A   503  PRO  ALA  LEU  VAL  GLU  ALA  GLY  ALA  ASP  VAL  LEU  CYS  ILE
SEQRES   21 A   503  ASP  SER  SER  ASP  GLY  PHE  SER  GLU  TRP  GLN  LYS  ILE  THR
SEQRES   22 A   503  ILE  GLY  TRP  ILE  ARG  GLU  LYS  TYR  GLY  ASP  LYS  VAL  LYS
SEQRES   23 A   503  VAL  GLY  ALA  GLY  ASN  ILE  VAL  ASP  GLY  GLU  GLY  PHE  ARG
SEQRES   24 A   503  TYR  LEU  ALA  ASP  ALA  GLY  ALA  ASP  PHE  ILE  LYS  ILE  GLY
SEQRES   25 A   503  ILE  GLY  GLY  GLY  SER  ILE  CSO  ILE  THR  ARG  GLU  GLN  LYS
SEQRES   26 A   503  GLY  ILE  GLY  ARG  GLY  GLN  ALA  THR  ALA  VAL  ILE  ASP  VAL
SEQRES   27 A   503  VAL  ALA  GLU  ARG  ASN  LYS  TYR  PHE  GLU  GLU  THR  GLY  ILE
SEQRES   28 A   503  TYR  ILE  PRO  VAL  CYS  SER  ASP  GLY  GLY  ILE  VAL  TYR  ASP
SEQRES   29 A   503  TYR  HIS  MET  THR  LEU  ALA  LEU  ALA  MET  GLY  ALA  ASP  PHE
SEQRES   30 A   503  ILE  MET  LEU  GLY  ARG  TYR  PHE  ALA  ARG  PHE  GLU  GLU  SER
SEQRES   31 A   503  PRO  THR  ARG  LYS  VAL  THR  ILE  ASN  GLY  SER  VAL  MET  LYS
SEQRES   32 A   503  GLU  TYR  TRP  GLY  GLU  GLY  SER  SER  ARG  ALA  ARG  ASN  TRP
SEQRES   33 A   503  GLN  ARG  TYR  ASP  LEU  GLY  GLY  GLY  LYS  LEU  SER  PHE
SEQRES   34 A   503  GLU  GLU  GLY  VAL  ASP  SER  TYR  VAL  PRO  TYR  ALA  GLY  LYS
SEQRES   35 A   503  LEU  LYS  ASP  ASN  VAL  GLU  ALA  SER  LEU  ASN  LYS  VAL  LYS
SEQRES   36 A   503  SER  THR  MET  CYS  ASN  CYS  GLY  ALA  LEU  THR  ILE  PRO  GLN
SEQRES   37 A   503  LEU  GLN  SER  LYS  ALA  LYS  ILE  THR  LEU  VAL  SER  SER  VAL
SEQRES   38 A   503  SER  SER  ILE  VAL  GLU  GLY  GLY  ALA  HIS  ASP  VAL  ILE  VAL  LYS
SEQRES   39 A   503  ASP  ARG  ILE  ASN  ASP  TYR  HIS  PRO  LYS
MODRES   1ME8  CSO  A   319  CYS   5-HYDROXYCYSTEINE
HET           CSO  A  319          7
HET             K     900          1
HET            NA     901          1
HET           RVP     602         21
```

TABLE 7-continued

| HETNAM | | CSO | S-HYDROXYCYSTEINE | | | | | | | | | | | |
|---|---|---|---|---|---|---|---|---|---|---|---|---|---|---|
| HETNAM | | K | POTASSIUM ION | | | | | | | | | | | |
| HETNAM | | NA | SODIUM ION | | | | | | | | | | | |
| HETNAM | | RVP | RIBAVIRIN MONOPHOSPHATE | | | | | | | | | | | |
| FORMUL1 | | CSO | C3 H7 N1 O3 S1 | | | | | | | | | | | |
| FORMUL2 | | K | K1 1+ | | | | | | | | | | | |
| FORMUL3 | | NA | NA1 1+ | | | | | | | | | | | |
| FORMUL4 | | RVP | C8 H13 | N4 | O8 | P1 | | | | | | | | |
| FORMUL5 | | HOH | *201 (H2 O1) | | | | | | | | | | | |
| HELIX 1 3 | | 1 THR | A11 | ASN | A | 13 | 5 | | | | | | | |
| HELIX 2 5 | | 2 ILE | A27 | VAL | A | 31 | 5 | | | | | | | |
| HELIX 3 11 | | 3 GLY | A64 | GLU | A | 74 | 1 | | | | | | | |
| HELIX 4 14 | | 4 SER | A85 | ASN | A | 98 | 1 | | | | | | | |
| HELIX 5 13 | | 5 ASP | A242 | GLY | A | 254 | 1 | | | | | | | |
| HELIX 6 16 | | 6 SER | A267 | GLY | A | 282 | 1 | | | | | | | |
| HELIX 7 3 | | 7 ASP | A283 | VAL | A | 285 | 5 | | | | | | | |
| HELIX 8 12 | | 8 ASP | A294 | GLY | A | 305 | 1 | | | | | | | |
| HELIX 9 21 | | 9 GLY | A330 | GLY | A | 350 | 1 | | | | | | | |
| HELIX 10 11 | | 10 TYR | A363 | MET | A | 373 | 1 | | | | | | | |
| HELIX 11 6 | | 11 GLY | A381 | ARG | A | 386 | 1 | | | | | | | |
| HELIX 12 6 | | 12 SER | A410 | ASN | A | 415 | 1 | | | | | | | |
| HELIX 13 20 | | 13 LYS | A442 | CYS | A | 461 | 1 | | | | | | | |
| HELIX 14 9 | | 14 THR | A465 | ALA | A | 473 | 1 | | | | | | | |
| SHEET | 1 | A | 2 TYR | A | 15 | LEU | A | 17 | 0 | | | | | |
| SHEET | 2 | A | 2 ILE | A | 475 | LEU | A | 477 | -1 | O | THR A | 476 | N | LEU A | 16 |
| SHEET | 1 | B | 2 THR | A | 35 | PRO | A | 36 | 0 | | | | | |
| SHEET | 2 | B | 2 ASN | A | 49 | LEU | A | 50 | -1 | O | LEU A | 50 | N | THR A | 35 |
| SHEET | 1 | C | 2 PHE | A | 40 | GLN | A | 41 | 0 | | | | | |
| SHEET | 2 | C | 2 ILE | A | 351 | TYR | A | 352 | -1 | O | TYR A | 352 | N | PHE A | 40 |
| SHEET | 1 | D | 9 LEU | A | 54 | SER | A | 56 | 0 | | | | | |
| SHEET | 2 | D | 9 ILE | A | 77 | ILE | A | 80 | 1 | O | ILE A | 77 | N | SER A | 56 |
| SHEET | 3 | D | 9 GLY | A | 235 | ILE | A | 238 | 1 | O | GLY A | 237 | N | ILE A | 80 |
| SHEET | 4 | D | 9 VAL | A | 257 | ILE | A | 260 | 1 | O | CYS A | 259 | N | ILE A | 238 |
| SHEET | 5 | D | 9 VAL | A | 287 | ILE | A | 292 | 1 | O | GLY A | 288 | N | LEU A | 258 |
| SHEET | 6 | D | 9 PHE | A | 308 | ILE | A | 311 | 1 | O | LYS A | 310 | N | ALA A | 289 |
| SHEET | 7 | D | 9 VAL | A | 355 | ASP | A | 358 | 1 | O | CYS A | 356 | N | ILE A | 311 |
| SHEET | 8 | D | 9 PHE | A | 377 | LEU | A | 380 | 1 | O | MET A | 379 | N | SER A | 357 |
| SHEET | 9 | D | 9 LEU | A | 54 | SER | A | 56 | 1 | N | VAL A | 55 | O | ILE A | 378 |
| SHEET | 1 | E | 3 LYS | A | 394 | ILE | A | 397 | 0 | | | | | |
| SHEET | 2 | E | 3 SER | A | 400 | TRP | A | 406 | -1 | O | MET A | 402 | N | VAL A | 395 |
| SHEET | 3 | E | 3 ASP | A | 434 | PRO | A | 438 | -1 | O | SER A | 435 | N | TYR A | 405 |
| SSBOND 1 | | CYS A | 26 | CYS | A | 459 | | | | | | | | |
| CISPEP 1 | | GLY A | 290 | ASN | A | 291 | | 0 | 0.82 | | | | | |
| CRYST1 154.745 | | 154.745 | 154.745 | 90.00 | | 90.00 | | 90.00 | P 4 3 2 | | 24 | | | |
| ORIGX1 | 1.000000 | 0.000000 | 0.000000 | 0.00000 | | | | | | | | | | |
| ORIGX2 | 0.000000 | 1.000000 | 0.000000 | 0.00000 | | | | | | | | | | |
| ORIGX3 | 0.000000 | 0.000000 | 1.000000 | 0.00000 | | | | | | | | | | |
| SCALE1 | 0.006462 | 0.000000 | 0.000000 | 0.00000 | | | | | | | | | | |
| SCALE2 | 0.000000 | 0.006462 | 0.000000 | 0.00000 | | | | | | | | | | |
| SCALE3 | 0.000000 | 0.000000 | 0.006462 | 0.00000 | | | | | | | | | | |
| ATOM 1 N | | N | ALA A | 2 | 55.144 | 74.892 | 36.640 | 1.00 | 29.93 | | | | | |
| ATOM 2 C | | CA | ALA A | 2 | 55.885 | 73.830 | 35.910 | 1.00 | 29.54 | | | | | |
| ATOM 3 C | | C | ALA A | 2 | 57.177 | 73.489 | 36.647 | 1.00 | 30.30 | | | | | |
| ATOM 4 O | | O | ALA A | 2 | 57.618 | 74.234 | 37.525 | 1.00 | 29.88 | | | | | |
| ATOM 5 C | | CB | ALA A | 2 | 56.201 | 74.301 | 34.491 | 1.00 | 29.72 | | | | | |
| ATOM 6 N | | N | LYS A | 3 | 57.771 | 72.357 | 36.289 | 1.00 | 29.86 | | | | | |
| ATOM 7 C | | CA | LYS A | 3 | 59.015 | 71.919 | 36.904 | 1.00 | 30.69 | | | | | |

TABLE 7-continued

| ATOM | 8 | C | LYS | A | 3 | 60.155 | 72.132 | 35.922 | 1.00 | 29.48 |
|---|---|---|---|---|---|---|---|---|---|---|
| C | | | | | | | | | | |
| ATOM | 9 | O | LYS | A | 3 | 60.040 | 71.777 | 34.753 | 1.00 | 28.89 |
| O | | | | | | | | | | |
| ATOM | 10 | CB | LYS | A | 3 | 58.943 | 70.434 | 37.275 | 1.00 | 33.07 |
| C | | | | | | | | | | |
| ATOM | 11 | CG | LYS | A | 3 | 60.304 | 69.840 | 37.628 | 1.00 | 37.75 |
| C | | | | | | | | | | |
| ATOM | 12 | CD | LYS | A | 3 | 60.240 | 68.344 | 37.872 | 1.00 | 41.04 |
| C | | | | | | | | | | |
| ATOM | 13 | CE | LYS | A | 3 | 61.628 | 67.728 | 37.773 | 1.00 | 42.33 |
| C | | | | | | | | | | |
| ATOM | 14 | NZ | LYS | A | 3 | 62.601 | 68.424 | 38.656 | 1.00 | 43.20 |
| N | | | | | | | | | | |
| ATOM | 15 | N | TYR | A | 4 | 61.252 | 72.704 | 36.407 | 1.00 | 28.93 |
| N | | | | | | | | | | |
| ATOM | 16 | CA | TYR | A | 4 | 62.425 | 72.961 | 35.581 | 1.00 | 28.85 |
| C | | | | | | | | | | |
| ATOM | 17 | C | TYR | A | 4 | 63.620 | 72.167 | 36.109 | 1.00 | 29.60 |
| C | | | | | | | | | | |
| ATOM | 18 | O | TYR | A | 4 | 63.545 | 71.551 | 37.172 | 1.00 | 28.77 |
| O | | | | | | | | | | |
| ATOM | 19 | CB | TYR | A | 4 | 62.732 | 74.463 | 35.571 | 1.00 | 28.38 |
| C | | | | | | | | | | |
| ATOM | 20 | CG | TYR | A | 4 | 61.634 | 75.274 | 34.917 | 1.00 | 27.99 |
| C | | | | | | | | | | |
| ATOM | 21 | CD1 | TYR | A | 4 | 61.519 | 75.336 | 33.527 | 1.00 | 27.06 |
| C | | | | | | | | | | |
| ATOM | 22 | CD2 | TYR | A | 4 | 60.684 | 75.946 | 35.686 | 1.00 | 28.17 |
| C | | | | | | | | | | |
| ATOM | 23 | CE1 | TYR | A | 4 | 60.479 | 76.050 | 32.919 | 1.00 | 27.85 |
| C | | | | | | | | | | |
| ATOM | 24 | CE2 | TYR | A | 4 | 59.643 | 76.662 | 35.087 | 1.00 | 27.52 |
| C | | | | | | | | | | |
| ATOM | 25 | CZ | TYR | A | 4 | 59.547 | 76.708 | 33.707 | 1.00 | 27.20 |
| C | | | | | | | | | | |
| ATOM | 26 | OH | TYR | A | 4 | 58.512 | 77.400 | 33.115 | 1.00 | 27.38 |
| O | | | | | | | | | | |
| ATOM | 27 | N | TYR | A | 5 | 64.714 | 72.173 | 35.359 | 1.00 | 30.38 |
| N | | | | | | | | | | |
| ATOM | 28 | CA | TYR | A | 5 | 65.909 | 71.436 | 35.756 | 1.00 | 31.23 |
| C | | | | | | | | | | |
| ATOM | 29 | C | TYR | A | 5 | 67.109 | 72.364 | 35.895 | 1.00 | 32.36 |
| C | | | | | | | | | | |
| ATOM | 30 | O | TYR | A | 5 | 67.143 | 73.440 | 35.300 | 1.00 | 31.65 |
| O | | | | | | | | | | |
| ATOM | 31 | CB | TYR | A | 5 | 66.204 | 70.330 | 34.739 | 1.00 | 31.26 |
| C | | | | | | | | | | |
| ATOM | 32 | CG | TYR | A | 5 | 65.063 | 69.349 | 34.584 | 1.00 | 31.28 |
| C | | | | | | | | | | |
| ATOM | 33 | CD1 | TYR | A | 5 | 63.906 | 69.702 | 33.891 | 1.00 | 30.79 |
| C | | | | | | | | | | |
| ATOM | 34 | CD2 | TYR | A | 5 | 65.116 | 68.085 | 35.179 | 1.00 | 31.65 |
| C | | | | | | | | | | |
| ATOM | 35 | CE1 | TYR | A | 5 | 62.824 | 68.826 | 33.794 | 1.00 | 30.64 |
| C | | | | | | | | | | |
| ATOM | 36 | CE2 | TYR | A | 5 | 64.039 | 67.199 | 35.088 | 1.00 | 30.49 |
| C | | | | | | | | | | |
| ATOM | 37 | CZ | TYR | A | 5 | 62.897 | 67.579 | 34.395 | 1.00 | 31.03 |
| C | | | | | | | | | | |
| ATOM | 38 | OH | TYR | A | 5 | 61.817 | 66.725 | 34.313 | 1.00 | 29.28 |
| O | | | | | | | | | | |
| ATOM | 39 | N | ASN | A | 6 | 68.090 | 71.942 | 36.687 | 1.00 | 33.08 |
| N | | | | | | | | | | |
| ATOM | 40 | CA | ASN | A | 6 | 69.285 | 72.744 | 36.925 | 1.00 | 34.41 |
| C | | | | | | | | | | |
| ATOM | 41 | C | ASN | A | 6 | 70.250 | 72.779 | 35.744 | 1.00 | 34.13 |
| C | | | | | | | | | | |
| ATOM | 42 | O | ASN | A | 6 | 70.971 | 73.758 | 35.556 | 1.00 | 34.71 |
| O | | | | | | | | | | |
| ATOM | 43 | CB | ASN | A | 6 | 70.009 | 72.226 | 38.171 | 1.00 | 37.70 |
| C | | | | | | | | | | |
| ATOM | 44 | CG | ASN | A | 6 | 69.207 | 72.440 | 39.444 | 1.00 | 39.54 |
| C | | | | | | | | | | |
| ATOM | 45 | OD1 | ASN | A | 6 | 69.407 | 71.747 | 40.441 | 1.00 | 42.37 |
| O | | | | | | | | | | |
| ATOM | 46 | ND2 | ASN | A | 6 | 68.303 | 73.414 | 39.420 | 1.00 | 42.40 |
| N | | | | | | | | | | |

TABLE 7-continued

| | | | | | | | | | |
|---|---|---|---|---|---|---|---|---|---|
| ATOM | 47 | N | GLU | A | 7 | 70.263 | 71.716 | 34.946 | 1.00 32.89 |
| N | | | | | | | | | |
| ATOM | 48 | CA | GLU | A | 7 | 71.158 | 71.648 | 33.795 | 1.00 32.05 |
| C | | | | | | | | | |
| ATOM | 49 | C | GLU | A | 7 | 70.419 | 71.313 | 32.505 | 1.00 30.13 |
| C | | | | | | | | | |
| ATOM | 50 | O | GLU | A | 7 | 69.369 | 70.675 | 32.528 | 1.00 30.64 |
| O | | | | | | | | | |
| ATOM | 51 | CB | GLU | A | 7 | 72.224 | 70.567 | 34.012 | 1.00 34.45 |
| C | | | | | | | | | |
| ATOM | 52 | CG | GLU | A | 7 | 73.156 | 70.770 | 35.200 | 1.00 38.35 |
| C | | | | | | | | | |
| ATOM | 53 | CD | GLU | A | 7 | 74.057 | 71.981 | 35.049 | 1.00 40.20 |
| C | | | | | | | | | |
| ATOM | 54 | OE1 | GLU | A | 7 | 74.484 | 72.278 | 33.912 | 1.00 41.55 |
| O | | | | | | | | | |
| ATOM | 55 | OE2 | GLU | A | 7 | 74.351 | 72.631 | 36.075 | 1.00 42.84 |
| O | | | | | | | | | |
| ATOM | 56 | N | PRO | A | 8 | 70.962 | 71.745 | 31.359 | 1.00 28.48 |
| N | | | | | | | | | |
| ATOM | 57 | CA | PRO | A | 8 | 70.318 | 71.446 | 30.079 | 1.00 27.48 |
| C | | | | | | | | | |
| ATOM | 58 | C | PRO | A | 8 | 70.655 | 69.995 | 29.755 | 1.00 26.53 |
| C | | | | | | | | | |
| ATOM | 59 | O | PRO | A | 8 | 71.595 | 69.448 | 30.326 | 1.00 24.18 |
| O | | | | | | | | | |
| ATOM | 60 | CB | PRO | A | 8 | 70.992 | 72.423 | 29.121 | 1.00 27.72 |
| C | | | | | | | | | |
| ATOM | 61 | CG | PRO | A | 8 | 72.380 | 72.532 | 29.688 | 1.00 28.52 |
| C | | | | | | | | | |
| ATOM | 62 | CD | PRO | A | 8 | 72.113 | 72.649 | 31.172 | 1.00 28.72 |
| C | | | | | | | | | |
| ATOM | 63 | N | CYS | A | 9 | 69.894 | 69.359 | 28.869 | 1.00 26.18 |
| N | | | | | | | | | |
| ATOM | 64 | CA | CYS | A | 9 | 70.202 | 67.979 | 28.518 | 1.00 25.70 |
| C | | | | | | | | | |
| ATOM | 65 | C | CYS | A | 9 | 71.285 | 67.935 | 27.435 | 1.00 25.71 |
| C | | | | | | | | | |
| ATOM | 66 | O | CYS | A | 9 | 71.474 | 68.905 | 26.685 | 1.00 24.82 |
| O | | | | | | | | | |
| ATOM | 67 | CB | CYS | A | 9 | 68.936 | 67.239 | 28.065 | 1.00 27.09 |
| C | | | | | | | | | |
| ATOM | 68 | SG | CYS | A | 9 | 68.004 | 68.021 | 26.742 | 1.00 29.97 |
| S | | | | | | | | | |
| ATOM | 69 | N | HIS | A | 10 | 72.003 | 66.816 | 27.370 | 1.00 24.60 |
| N | | | | | | | | | |
| ATOM | 70 | CA | HIS | A | 10 | 73.095 | 66.632 | 26.414 | 1.00 24.16 |
| C | | | | | | | | | |
| ATOM | 71 | C | HIS | A | 10 | 72.932 | 65.349 | 25.612 | 1.00 24.05 |
| C | | | | | | | | | |
| ATOM | 72 | O | HIS | A | 10 | 72.269 | 64.415 | 26.058 | 1.00 22.94 |
| O | | | | | | | | | |
| ATOM | 73 | CB | HIS | A | 10 | 74.433 | 66.580 | 27.160 | 1.00 24.38 |
| C | | | | | | | | | |
| ATOM | 74 | CG | HIS | A | 10 | 74.693 | 67.779 | 28.015 | 1.00 25.68 |
| C | | | | | | | | | |
| ATOM | 75 | ND1 | HIS | A | 10 | 75.121 | 68.981 | 27.498 | 1.00 26.11 |
| N | | | | | | | | | |
| ATOM | 76 | CD2 | HIS | A | 10 | 74.544 | 67.973 | 29.347 | 1.00 26.09 |
| C | | | | | | | | | |
| ATOM | 77 | CE1 | HIS | A | 10 | 75.225 | 69.866 | 28.474 | 1.00 26.14 |
| C | | | | | | | | | |
| ATOM | 78 | NE2 | HIS | A | 10 | 74.879 | 69.278 | 29.606 | 1.00 27.18 |
| N | | | | | | | | | |
| ATOM | 79 | N | THR | A | 11 | 73.549 | 65.311 | 24.432 | 1.00 25.34 |
| N | | | | | | | | | |
| ATOM | 80 | CA | THR | A | 11 | 73.494 | 64.139 | 23.550 | 1.00 26.59 |
| C | | | | | | | | | |
| ATOM | 81 | C | THR | A | 11 | 74.857 | 63.439 | 23.539 | 1.00 25.78 |
| C | | | | | | | | | |
| ATOM | 82 | O | THR | A | 11 | 75.843 | 63.990 | 24.021 | 1.00 25.20 |
| O | | | | | | | | | |
| ATOM | 83 | CB | THR | A | 11 | 73.175 | 64.536 | 22.095 | 1.00 28.50 |
| C | | | | | | | | | |
| ATOM | 84 | OG1 | THR | A | 11 | 74.190 | 65.429 | 21.620 | 1.00 31.80 |
| O | | | | | | | | | |
| ATOM | 85 | CG2 | THR | A | 11 | 71.824 | 65.223 | 22.000 | 1.00 31.57 |
| C | | | | | | | | | |

TABLE 7-continued

| ATOM | 86 | N | PHE | A | 12 | 74.909 | 62.240 | 22.964 | 1.00 | 25.57 |
| --- | --- | --- | --- | --- | --- | --- | --- | --- | --- | --- |
| ATOM | 87 | CA | PHE | A | 12 | 76.154 | 61.469 | 22.890 | 1.00 | 26.57 |
| ATOM | 88 | C | PHE | A | 12 | 77.334 | 62.201 | 22.244 | 1.00 | 26.75 |
| ATOM | 89 | O | PHE | A | 12 | 78.477 | 62.029 | 22.666 | 1.00 | 26.43 |
| ATOM | 90 | CB | PHE | A | 12 | 75.923 | 60.150 | 22.139 | 1.00 | 26.43 |
| ATOM | 91 | CG | PHE | A | 12 | 75.034 | 59.180 | 22.869 | 1.00 | 27.74 |
| ATOM | 92 | CD1 | PHE | A | 12 | 75.212 | 58.940 | 24.226 | 1.00 | 28.25 |
| ATOM | 93 | CD2 | PHE | A | 12 | 74.034 | 58.490 | 22.191 | 1.00 | 28.95 |
| ATOM | 94 | CE1 | PHE | A | 12 | 74.405 | 58.024 | 24.905 | 1.00 | 29.61 |
| ATOM | 95 | CE2 | PHE | A | 12 | 73.223 | 57.572 | 22.858 | 1.00 | 29.31 |
| ATOM | 96 | CZ | PHE | A | 12 | 73.408 | 57.339 | 24.215 | 1.00 | 29.14 |
| ATOM | 97 | N | ASN | A | 13 | 77.071 | 63.003 | 21.216 | 1.00 | 27.42 |
| ATOM | 98 | CA | ASN | A | 13 | 78.149 | 63.726 | 20.544 | 1.00 | 28.91 |
| ATOM | 99 | C | ASN | A | 13 | 78.892 | 64.718 | 21.437 | 1.00 | 27.96 |
| ATOM | 100 | O | ASN | A | 13 | 79.972 | 65.193 | 21.076 | 1.00 | 28.99 |
| ATOM | 101 | CB | ASN | A | 13 | 77.621 | 64.471 | 19.314 | 1.00 | 31.81 |
| ATOM | 102 | CG | ASN | A | 13 | 77.584 | 63.600 | 18.079 | 1.00 | 34.70 |
| ATOM | 103 | OD1 | ASN | A | 13 | 78.485 | 62.787 | 17.852 | 1.00 | 36.51 |
| ATOM | 104 | ND2 | ASN | A | 13 | 76.554 | 63.775 | 17.261 | 1.00 | 37.26 |
| ATOM | 105 | N | GLU | A | 14 | 78.323 | 65.027 | 22.596 | 1.00 | 26.74 |
| ATOM | 106 | CA | GLU | A | 14 | 78.948 | 65.975 | 23.517 | 1.00 | 26.62 |
| ATOM | 107 | C | GLU | A | 14 | 79.867 | 65.316 | 24.541 | 1.00 | 26.27 |
| ATOM | 108 | O | GLU | A | 14 | 80.414 | 65.992 | 25.408 | 1.00 | 25.62 |
| ATOM | 109 | CB | GLU | A | 14 | 77.873 | 66.763 | 24.263 | 1.00 | 26.66 |
| ATOM | 110 | CG | GLU | A | 14 | 76.939 | 67.529 | 23.347 | 1.00 | 28.65 |
| ATOM | 111 | CD | GLU | A | 14 | 75.890 | 68.293 | 24.114 | 1.00 | 29.22 |
| ATOM | 112 | OE1 | GLU | A | 14 | 76.260 | 69.212 | 24.878 | 1.00 | 31.67 |
| ATOM | 113 | OE2 | GLU | A | 14 | 74.696 | 67.973 | 23.957 | 1.00 | 29.46 |
| ATOM | 114 | N | TYR | A | 15 | 80.045 | 64.003 | 24.439 | 1.00 | 25.33 |
| ATOM | 115 | CA | TYR | A | 15 | 80.886 | 63.289 | 25.391 | 1.00 | 25.77 |
| ATOM | 116 | C | TYR | A | 15 | 82.069 | 62.544 | 24.788 | 1.00 | 25.99 |
| ATOM | 117 | O | TYR | A | 15 | 82.059 | 62.152 | 23.619 | 1.00 | 26.38 |
| ATOM | 118 | CB | TYR | A | 15 | 80.041 | 62.279 | 26.168 | 1.00 | 26.71 |
| ATOM | 119 | CG | TYR | A | 15 | 79.025 | 62.889 | 27.099 | 1.00 | 28.01 |
| ATOM | 120 | CD1 | TYR | A | 15 | 79.377 | 63.262 | 28.397 | 1.00 | 28.23 |
| ATOM | 121 | CD2 | TYR | A | 15 | 77.711 | 63.100 | 26.683 | 1.00 | 29.05 |
| ATOM | 122 | CE1 | TYR | A | 15 | 78.442 | 63.828 | 29.260 | 1.00 | 30.46 |
| ATOM | 123 | CE2 | TYR | A | 15 | 76.771 | 63.668 | 27.537 | 1.00 | 30.27 |
| ATOM | 124 | CZ | TYR | A | 15 | 77.144 | 64.028 | 28.820 | 1.00 | 30.91 |

TABLE 7-continued

| ATOM | 125 | OH | TYR | A | 15 | 76.219 | 64.604 | 29.659 | 1.00 | 34.07 |
|---|---|---|---|---|---|---|---|---|---|---|
| O | | | | | | | | | | |
| ATOM | 126 | N | LEU | A | 16 | 83.089 | 62.350 | 25.616 | 1.00 | 26.06 |
| N | | | | | | | | | | |
| ATOM | 127 | CA | LEU | A | 16 | 84.273 | 61.593 | 25.233 | 1.00 | 25.76 |
| C | | | | | | | | | | |
| ATOM | 128 | C | LEU | A | 16 | 84.672 | 60.785 | 26.457 | 1.00 | 24.62 |
| C | | | | | | | | | | |
| ATOM | 129 | O | LEU | A | 16 | 84.331 | 61.143 | 27.589 | 1.00 | 23.13 |
| O | | | | | | | | | | |
| ATOM | 130 | CB | LEU | A | 16 | 85.427 | 62.518 | 24.820 | 1.00 | 28.13 |
| C | | | | | | | | | | |
| ATOM | 131 | CG | LEU | A | 16 | 85.291 | 63.282 | 23.495 | 1.00 | 29.82 |
| C | | | | | | | | | | |
| ATOM | 132 | CD1 | LEU | A | 16 | 86.523 | 64.136 | 23.285 | 1.00 | 30.80 |
| C | | | | | | | | | | |
| ATOM | 133 | CD2 | LEU | A | 16 | 85.123 | 62.313 | 22.332 | 1.00 | 30.29 |
| C | | | | | | | | | | |
| ATOM | 134 | N | LEU | A | 17 | 85.374 | 59.683 | 26.230 | 1.00 | 24.43 |
| N | | | | | | | | | | |
| ATOM | 135 | CA | LEU | A | 17 | 85.841 | 58.835 | 27.321 | 1.00 | 25.14 |
| C | | | | | | | | | | |
| ATOM | 136 | C | LEU | A | 17 | 87.311 | 59.147 | 27.608 | 1.00 | 25.20 |
| C | | | | | | | | | | |
| ATOM | 137 | O | LEU | A | 17 | 88.097 | 59.336 | 26.682 | 1.00 | 25.84 |
| O | | | | | | | | | | |
| ATOM | 138 | CB | LEU | A | 17 | 85.706 | 57.359 | 26.933 | 1.00 | 25.29 |
| C | | | | | | | | | | |
| ATOM | 139 | CG | LEU | A | 17 | 84.288 | 56.777 | 26.938 | 1.00 | 25.32 |
| C | | | | | | | | | | |
| ATOM | 140 | CD1 | LEU | A | 17 | 84.233 | 55.534 | 26.077 | 1.00 | 26.22 |
| C | | | | | | | | | | |
| ATOM | 141 | CD2 | LEU | A | 17 | 83.876 | 56.466 | 28.366 | 1.00 | 25.45 |
| C | | | | | | | | | | |
| ATOM | 142 | N | ILE | A | 18 | 87.667 | 59.210 | 28.889 | 1.00 | 25.46 |
| N | | | | | | | | | | |
| ATOM | 143 | CA | ILE | A | 18 | 89.047 | 59.460 | 29.294 | 1.00 | 25.22 |
| C | | | | | | | | | | |
| ATOM | 144 | C | ILE | A | 18 | 89.608 | 58.101 | 29.718 | 1.00 | 25.38 |
| C | | | | | | | | | | |
| ATOM | 145 | O | ILE | A | 18 | 89.062 | 57.446 | 30.598 | 1.00 | 25.99 |
| O | | | | | | | | | | |
| ATOM | 146 | CB | ILE | A | 18 | 89.112 | 60.460 | 30.467 | 1.00 | 25.47 |
| C | | | | | | | | | | |
| ATOM | 147 | CG1 | ILE | A | 18 | 88.653 | 61.843 | 29.979 | 1.00 | 25.88 |
| C | | | | | | | | | | |
| ATOM | 148 | CG2 | ILE | A | 18 | 90.538 | 60.531 | 31.027 | 1.00 | 24.00 |
| C | | | | | | | | | | |
| ATOM | 149 | CD1 | ILE | A | 18 | 88.620 | 62.909 | 31.057 | 1.00 | 28.70 |
| C | | | | | | | | | | |
| ATOM | 150 | N | PRO | A | 19 | 90.701 | 57.657 | 29.080 | 1.00 | 26.62 |
| N | | | | | | | | | | |
| ATOM | 151 | CA | PRO | A | 19 | 91.306 | 56.360 | 29.408 | 1.00 | 26.83 |
| C | | | | | | | | | | |
| ATOM | 152 | C | PRO | A | 19 | 91.605 | 56.116 | 30.889 | 1.00 | 26.38 |
| C | | | | | | | | | | |
| ATOM | 153 | O | PRO | A | 19 | 91.853 | 57.048 | 31.656 | 1.00 | 26.07 |
| O | | | | | | | | | | |
| ATOM | 154 | CB | PRO | A | 19 | 92.584 | 56.350 | 28.564 | 1.00 | 27.54 |
| C | | | | | | | | | | |
| ATOM | 155 | CG | PRO | A | 19 | 92.204 | 57.182 | 27.371 | 1.00 | 28.01 |
| C | | | | | | | | | | |
| ATOM | 156 | CD | PRO | A | 19 | 91.463 | 58.336 | 28.018 | 1.00 | 27.10 |
| C | | | | | | | | | | |
| ATOM | 157 | N | GLY | A | 20 | 91.566 | 54.845 | 31.271 | 1.00 | 25.38 |
| N | | | | | | | | | | |
| ATOM | 158 | CA | GLY | A | 20 | 91.877 | 54.453 | 32.632 | 1.00 | 26.31 |
| C | | | | | | | | | | |
| ATOM | 159 | C | GLY | A | 20 | 93.077 | 53.528 | 32.511 | 1.00 | 26.29 |
| C | | | | | | | | | | |
| ATOM | 160 | O | GLY | A | 20 | 93.662 | 53.423 | 31.437 | 1.00 | 23.85 |
| O | | | | | | | | | | |
| ATOM | 161 | N | LEU | A | 21 | 93.451 | 52.846 | 33.585 | 1.00 | 26.59 |
| N | | | | | | | | | | |
| ATOM | 162 | CA | LEU | A | 21 | 94.601 | 51.948 | 33.506 | 1.00 | 27.89 |
| C | | | | | | | | | | |
| ATOM | 163 | C | LEU | A | 21 | 94.291 | 50.701 | 32.690 | 1.00 | 28.10 |
| C | | | | | | | | | | |

TABLE 7-continued

| | | | | | | | | | |
|---|---|---|---|---|---|---|---|---|---|
| ATOM | 164 | O | LEU | A | 21 | 93.361 | 49.959 | 33.002 | 1.00 28.93 |
| ATOM | 165 | CB | LEU | A | 21 | 95.064 | 51.536 | 34.910 | 1.00 27.80 |
| ATOM | 166 | CG | LEU | A | 21 | 96.225 | 50.531 | 34.941 | 1.00 28.27 |
| ATOM | 167 | CD1 | LEU | A | 21 | 97.431 | 51.084 | 34.182 | 1.00 27.34 |
| ATOM | 168 | CD2 | LEU | A | 21 | 96.583 | 50.230 | 36.390 | 1.00 29.80 |
| ATOM | 169 | N | SER | A | 22 | 95.068 | 50.483 | 31.634 | 1.00 29.02 |
| ATOM | 170 | CA | SER | A | 22 | 94.900 | 49.310 | 30.788 | 1.00 31.01 |
| ATOM | 171 | C | SER | A | 22 | 95.917 | 48.270 | 31.238 | 1.00 32.77 |
| ATOM | 172 | O | SER | A | 22 | 97.118 | 48.530 | 31.234 | 1.00 31.01 |
| ATOM | 173 | CB | SER | A | 22 | 95.149 | 49.663 | 29.321 | 1.00 31.45 |
| ATOM | 174 | OG | SER | A | 22 | 94.206 | 50.608 | 28.855 | 1.00 30.59 |
| ATOM | 175 | N | THR | A | 23 | 95.435 | 47.096 | 31.632 | 1.00 34.58 |
| ATOM | 176 | CA | THR | A | 23 | 96.322 | 46.033 | 32.092 | 1.00 36.68 |
| ATOM | 177 | C | THR | A | 23 | 96.716 | 45.114 | 30.944 | 1.00 37.08 |
| ATOM | 178 | O | THR | A | 23 | 96.105 | 45.144 | 29.875 | 1.00 37.57 |
| ATOM | 179 | CB | THR | A | 23 | 95.658 | 45.207 | 33.202 | 1.00 37.62 |
| ATOM | 180 | OG1 | THR | A | 23 | 94.335 | 44.851 | 32.797 | 1.00 40.83 |
| ATOM | 181 | CG2 | THR | A | 23 | 95.581 | 46.011 | 34.492 | 1.00 39.51 |
| ATOM | 182 | N | VAL | A | 24 | 97.742 | 44.298 | 31.163 | 1.00 37.49 |
| ATOM | 183 | CA | VAL | A | 24 | 98.217 | 43.390 | 30.128 | 1.00 38.46 |
| ATOM | 184 | C | VAL | A | 24 | 97.187 | 42.348 | 29.697 | 1.00 39.49 |
| ATOM | 185 | O | VAL | A | 24 | 97.256 | 41.832 | 28.583 | 1.00 39.42 |
| ATOM | 186 | CB | VAL | A | 24 | 99.508 | 42.660 | 30.575 | 1.00 38.44 |
| ATOM | 187 | CG1 | VAL | A | 24 | 100.651 | 43.662 | 30.713 | 1.00 37.27 |
| ATOM | 188 | CG2 | VAL | A | 24 | 99.272 | 41.940 | 31.894 | 1.00 38.19 |
| ATOM | 189 | N | ASP | A | 25 | 96.224 | 42.045 | 30.562 | 1.00 41.42 |
| ATOM | 190 | CA | ASP | A | 25 | 95.219 | 41.047 | 30.210 | 1.00 44.00 |
| ATOM | 191 | C | ASP | A | 25 | 94.070 | 41.590 | 29.362 | 1.00 44.29 |
| ATOM | 192 | O | ASP | A | 25 | 93.220 | 40.826 | 28.908 | 1.00 44.12 |
| ATOM | 193 | CB | ASP | A | 25 | 94.653 | 40.380 | 31.473 | 1.00 46.46 |
| ATOM | 194 | CG | ASP | A | 25 | 93.826 | 41.329 | 32.327 | 1.00 49.04 |
| ATOM | 195 | OD1 | ASP | A | 25 | 93.177 | 40.852 | 33.280 | 1.00 51.13 |
| ATOM | 196 | OD2 | ASP | A | 25 | 93.819 | 42.545 | 32.058 | 1.00 51.46 |
| ATOM | 197 | N | CYS | A | 26 | 94.032 | 42.898 | 29.132 | 1.00 44.45 |
| ATOM | 198 | CA | CYS | A | 26 | 92.937 | 43.434 | 28.333 | 1.00 44.38 |
| ATOM | 199 | C | CYS | A | 26 | 93.245 | 43.623 | 26.866 | 1.00 44.52 |
| ATOM | 200 | O | CYS | A | 26 | 93.840 | 44.623 | 26.465 | 1.00 44.45 |
| ATOM | 201 | CB | CYS | A | 26 | 92.432 | 44.767 | 28.879 | 1.00 43.39 |
| ATOM | 202 | SG | CYS | A | 26 | 90.722 | 45.164 | 28.351 | 1.00 43.27 |

TABLE 7-continued

| ATOM | 203 | N | ILE | A | 27 | 92.835 | 42.646 | 26.071 | 1.00 | 44.85 | N |
|---|---|---|---|---|---|---|---|---|---|---|---|
| ATOM | 204 | CA | ILE | A | 27 | 92.984 | 42.712 | 24.631 | 1.00 | 45.31 | C |
| ATOM | 205 | C | ILE | A | 27 | 91.559 | 42.482 | 24.155 | 1.00 | 45.02 | C |
| ATOM | 206 | O | ILE | A | 27 | 90.791 | 41.782 | 24.815 | 1.00 | 44.66 | O |
| ATOM | 207 | CB | ILE | A | 27 | 93.924 | 41.612 | 24.084 | 1.00 | 46.44 | C |
| ATOM | 208 | CG1 | ILE | A | 27 | 93.461 | 40.234 | 24.555 | 1.00 | 46.68 | C |
| ATOM | 209 | CG2 | ILE | A | 27 | 95.358 | 41.893 | 24.524 | 1.00 | 46.86 | C |
| ATOM | 210 | CD1 | ILE | A | 27 | 94.354 | 39.098 | 24.083 | 1.00 | 48.06 | C |
| ATOM | 211 | N | PRO | A | 28 | 91.179 | 43.089 | 23.024 | 1.00 | 45.29 | N |
| ATOM | 212 | CA | PRO | A | 28 | 89.836 | 42.959 | 22.453 | 1.00 | 44.96 | C |
| ATOM | 213 | C | PRO | A | 28 | 89.231 | 41.557 | 22.486 | 1.00 | 44.81 | C |
| ATOM | 214 | O | PRO | A | 28 | 88.051 | 41.393 | 22.800 | 1.00 | 44.44 | O |
| ATOM | 215 | CB | PRO | A | 28 | 90.027 | 43.474 | 21.031 | 1.00 | 45.44 | C |
| ATOM | 216 | CG | PRO | A | 28 | 91.024 | 44.565 | 21.223 | 1.00 | 45.66 | C |
| ATOM | 217 | CD | PRO | A | 28 | 92.031 | 43.934 | 22.166 | 1.00 | 45.97 | C |
| ATOM | 218 | N | SER | A | 29 | 90.035 | 40.549 | 22.167 | 1.00 | 44.03 | N |
| ATOM | 219 | CA | SER | A | 29 | 89.547 | 39.174 | 22.134 | 1.00 | 43.07 | C |
| ATOM | 220 | C | SER | A | 29 | 89.168 | 38.597 | 23.495 | 1.00 | 42.20 | C |
| ATOM | 221 | O | SER | A | 29 | 88.477 | 37.582 | 23.567 | 1.00 | 42.12 | O |
| ATOM | 222 | CB | SER | A | 29 | 90.576 | 38.261 | 21.455 | 1.00 | 43.90 | C |
| ATOM | 223 | OG | SER | A | 29 | 91.766 | 38.166 | 22.214 | 1.00 | 45.30 | O |
| ATOM | 224 | N | ASN | A | 30 | 89.615 | 39.227 | 24.575 | 1.00 | 40.59 | N |
| ATOM | 225 | CA | ASN | A | 30 | 89.271 | 38.735 | 25.902 | 1.00 | 39.15 | C |
| ATOM | 226 | C | ASN | A | 30 | 88.079 | 39.489 | 26.491 | 1.00 | 37.08 | C |
| ATOM | 227 | O | ASN | A | 30 | 87.606 | 39.159 | 27.577 | 1.00 | 36.93 | O |
| ATOM | 228 | CB | ASN | A | 30 | 90.463 | 38.844 | 26.858 | 1.00 | 41.71 | C |
| ATOM | 229 | CG | ASN | A | 30 | 91.564 | 37.851 | 26.538 | 1.00 | 44.46 | C |
| ATOM | 230 | OD1 | ASN | A | 30 | 91.296 | 36.703 | 26.186 | 1.00 | 45.63 | O |
| ATOM | 231 | ND2 | ASN | A | 30 | 92.811 | 38.283 | 26.677 | 1.00 | 46.20 | N |
| ATOM | 232 | N | VAL | A | 31 | 87.595 | 40.497 | 25.774 | 1.00 | 33.45 | N |
| ATOM | 233 | CA | VAL | A | 31 | 86.461 | 41.279 | 26.252 | 1.00 | 31.88 | C |
| ATOM | 234 | C | VAL | A | 31 | 85.150 | 40.513 | 26.093 | 1.00 | 30.75 | C |
| ATOM | 235 | O | VAL | A | 31 | 84.858 | 39.981 | 25.025 | 1.00 | 30.55 | O |
| ATOM | 236 | CB | VAL | A | 31 | 86.353 | 42.628 | 25.503 | 1.00 | 30.76 | C |
| ATOM | 237 | CG1 | VAL | A | 31 | 85.074 | 43.355 | 25.914 | 1.00 | 30.99 | C |
| ATOM | 238 | CG2 | VAL | A | 31 | 87.568 | 43.491 | 25.817 | 1.00 | 31.39 | C |
| ATOM | 239 | N | ASN | A | 32 | 84.372 | 40.463 | 27.168 | 1.00 | 30.39 | N |
| ATOM | 240 | CA | ASN | A | 32 | 83.085 | 39.771 | 27.175 | 1.00 | 30.35 | C |
| ATOM | 241 | C | ASN | A | 32 | 81.968 | 40.802 | 27.058 | 1.00 | 29.35 | C |

TABLE 7-continued

| ATOM | 242 | O | ASN | A | 32 | 81.837 | 41.675 | 27.916 | 1.00 | 29.27 |
| --- | --- | --- | --- | --- | --- | --- | --- | --- | --- | --- |
| O | | | | | | | | | | |
| ATOM | 243 | CB | ASN | A | 32 | 82.929 | 38.965 | 28.474 | 1.00 | 32.17 |
| C | | | | | | | | | | |
| ATOM | 244 | CG | ASN | A | 32 | 81.509 | 38.449 | 28.685 | 1.00 | 34.34 |
| C | | | | | | | | | | |
| ATOM | 245 | OD1 | ASN | A | 32 | 80.751 | 38.273 | 27.736 | 1.00 | 34.02 |
| O | | | | | | | | | | |
| ATOM | 246 | ND2 | ASN | A | 32 | 81.153 | 38.193 | 29.941 | 1.00 | 38.74 |
| N | | | | | | | | | | |
| ATOM | 247 | N | LEU | A | 33 | 81.166 | 40.705 | 26.001 | 1.00 | 28.15 |
| N | | | | | | | | | | |
| ATOM | 248 | CA | LEU | A | 33 | 80.077 | 41.661 | 25.803 | 1.00 | 27.70 |
| C | | | | | | | | | | |
| ATOM | 249 | C | LEU | A | 33 | 78.693 | 41.128 | 26.178 | 1.00 | 27.94 |
| C | | | | | | | | | | |
| ATOM | 250 | O | LEU | A | 33 | 77.676 | 41.639 | 25.711 | 1.00 | 27.44 |
| O | | | | | | | | | | |
| ATOM | 251 | CB | LEU | A | 33 | 80.071 | 42.160 | 24.351 | 1.00 | 27.83 |
| C | | | | | | | | | | |
| ATOM | 252 | CG | LEU | A | 33 | 81.288 | 42.979 | 23.906 | 1.00 | 28.65 |
| C | | | | | | | | | | |
| ATOM | 253 | CD1 | LEU | A | 33 | 81.127 | 43.403 | 22.448 | 1.00 | 27.96 |
| C | | | | | | | | | | |
| ATOM | 254 | CD2 | LEU | A | 33 | 81.443 | 44.202 | 24.800 | 1.00 | 28.65 |
| C | | | | | | | | | | |
| ATOM | 255 | N | SER | A | 34 | 78.646 | 40.109 | 27.028 | 1.00 | 28.06 |
| N | | | | | | | | | | |
| ATOM | 256 | CA | SER | A | 34 | 77.361 | 39.559 | 27.457 | 1.00 | 29.26 |
| C | | | | | | | | | | |
| ATOM | 257 | C | SER | A | 34 | 76.628 | 40.593 | 28.310 | 1.00 | 28.04 |
| C | | | | | | | | | | |
| ATOM | 258 | O | SER | A | 34 | 77.255 | 41.406 | 28.987 | 1.00 | 27.93 |
| O | | | | | | | | | | |
| ATOM | 259 | CB | SER | A | 34 | 77.574 | 38.283 | 28.268 | 1.00 | 30.15 |
| C | | | | | | | | | | |
| ATOM | 260 | OG | SER | A | 34 | 78.220 | 37.308 | 27.471 | 1.00 | 35.29 |
| O | | | | | | | | | | |
| ATOM | 261 | N | THR | A | 35 | 75.301 | 40.565 | 28.283 | 1.00 | 27.47 |
| N | | | | | | | | | | |
| ATOM | 262 | CA | THR | A | 35 | 74.533 | 41.528 | 29.058 | 1.00 | 26.66 |
| C | | | | | | | | | | |
| ATOM | 263 | C | THR | A | 35 | 73.113 | 41.009 | 29.299 | 1.00 | 26.85 |
| C | | | | | | | | | | |
| ATOM | 264 | O | THR | A | 35 | 72.540 | 40.317 | 28.455 | 1.00 | 27.02 |
| O | | | | | | | | | | |
| ATOM | 265 | CB | THR | A | 35 | 74.497 | 42.896 | 28.320 | 1.00 | 27.50 |
| C | | | | | | | | | | |
| ATOM | 266 | OG1 | THR | A | 35 | 74.222 | 43.949 | 29.252 | 1.00 | 27.27 |
| O | | | | | | | | | | |
| ATOM | 267 | CG2 | THR | A | 35 | 73.425 | 42.894 | 27.234 | 1.00 | 26.76 |
| C | | | | | | | | | | |
| ATOM | 268 | N | PRO | A | 36 | 72.529 | 41.334 | 30.462 | 1.00 | 26.24 |
| N | | | | | | | | | | |
| ATOM | 269 | CA | PRO | A | 36 | 71.175 | 40.887 | 30.795 | 1.00 | 26.48 |
| C | | | | | | | | | | |
| ATOM | 270 | C | PRO | A | 36 | 70.082 | 41.574 | 29.979 | 1.00 | 26.94 |
| C | | | | | | | | | | |
| ATOM | 271 | O | PRO | A | 36 | 70.166 | 42.769 | 29.683 | 1.00 | 26.63 |
| O | | | | | | | | | | |
| ATOM | 272 | CB | PRO | A | 36 | 71.067 | 41.205 | 32.282 | 1.00 | 25.88 |
| C | | | | | | | | | | |
| ATOM | 273 | CG | PRO | A | 36 | 71.883 | 42.446 | 32.402 | 1.00 | 25.82 |
| C | | | | | | | | | | |
| ATOM | 274 | CD | PRO | A | 36 | 73.098 | 42.144 | 31.554 | 1.00 | 25.46 |
| C | | | | | | | | | | |
| ATOM | 275 | N | LEU | A | 37 | 69.054 | 40.810 | 29.627 | 1.00 | 26.53 |
| N | | | | | | | | | | |
| ATOM | 276 | CA | LEU | A | 37 | 67.942 | 41.344 | 28.857 | 1.00 | 26.66 |
| C | | | | | | | | | | |
| ATOM | 277 | C | LEU | A | 37 | 66.705 | 41.564 | 29.724 | 1.00 | 26.63 |
| C | | | | | | | | | | |
| ATOM | 278 | O | LEU | A | 37 | 65.960 | 42.526 | 29.516 | 1.00 | 26.36 |
| O | | | | | | | | | | |
| ATOM | 279 | CB | LEU | A | 37 | 67.588 | 40.396 | 27.706 | 1.00 | 27.85 |
| C | | | | | | | | | | |
| ATOM | 280 | CG | LEU | A | 37 | 66.499 | 40.910 | 26.759 | 1.00 | 27.81 |
| C | | | | | | | | | | |

TABLE 7-continued

| | | | | | | | | | | |
|---|---|---|---|---|---|---|---|---|---|---|
| ATOM | 281 | CD1 | LEU | A | 37 | 67.061 | 42.044 | 25.911 | 1.00 | 28.43 |
| C | | | | | | | | | | |
| ATOM | 282 | CD2 | LEU | A | 37 | 66.006 | 39.780 | 25.869 | 1.00 | 28.49 |
| C | | | | | | | | | | |
| ATOM | 283 | N | VAL | A | 38 | 66.483 | 40.684 | 30.699 | 1.00 | 26.11 |
| N | | | | | | | | | | |
| ATOM | 284 | CA | VAL | A | 38 | 65.305 | 40.807 | 31.556 | 1.00 | 26.61 |
| C | | | | | | | | | | |
| ATOM | 285 | C | VAL | A | 38 | 65.651 | 40.829 | 33.040 | 1.00 | 27.13 |
| C | | | | | | | | | | |
| ATOM | 286 | O | VAL | A | 38 | 66.667 | 40.279 | 33.461 | 1.00 | 27.11 |
| O | | | | | | | | | | |
| ATOM | 287 | CB | VAL | A | 38 | 64.288 | 39.674 | 31.264 | 1.00 | 26.52 |
| C | | | | | | | | | | |
| ATOM | 288 | CG1 | VAL | A | 38 | 63.862 | 39.748 | 29.803 | 1.00 | 27.45 |
| C | | | | | | | | | | |
| ATOM | 289 | CG2 | VAL | A | 38 | 64.902 | 38.310 | 31.562 | 1.00 | 26.40 |
| C | | | | | | | | | | |
| ATOM | 290 | N | LYS | A | 39 | 64.790 | 41.468 | 33.825 | 1.00 | 27.15 |
| N | | | | | | | | | | |
| ATOM | 291 | CA | LYS | A | 39 | 65.011 | 41.625 | 35.256 | 1.00 | 27.73 |
| C | | | | | | | | | | |
| ATOM | 292 | C | LYS | A | 39 | 65.216 | 40.348 | 36.058 | 1.00 | 28.72 |
| C | | | | | | | | | | |
| ATOM | 293 | O | LYS | A | 39 | 64.724 | 39.274 | 35.695 | 1.00 | 28.88 |
| O | | | | | | | | | | |
| ATOM | 294 | CB | LYS | A | 39 | 63.865 | 42.425 | 35.885 | 1.00 | 28.20 |
| C | | | | | | | | | | |
| ATOM | 295 | CG | LYS | A | 39 | 62.508 | 41.718 | 35.873 | 1.00 | 28.09 |
| C | | | | | | | | | | |
| ATOM | 296 | CD | LYS | A | 39 | 61.492 | 42.510 | 36.690 | 1.00 | 29.72 |
| C | | | | | | | | | | |
| ATOM | 297 | CE | LYS | A | 39 | 60.107 | 41.877 | 36.642 | 1.00 | 30.35 |
| C | | | | | | | | | | |
| ATOM | 298 | NZ | LYS | A | 39 | 59.162 | 42.618 | 37.526 | 1.00 | 31.05 |
| N | | | | | | | | | | |
| ATOM | 299 | N | PHE | A | 40 | 65.947 | 40.502 | 37.159 | 1.00 | 28.59 |
| N | | | | | | | | | | |
| ATOM | 300 | CA | PHE | A | 40 | 66.254 | 39.424 | 38.089 | 1.00 | 29.38 |
| C | | | | | | | | | | |
| ATOM | 301 | C | PHE | A | 40 | 66.508 | 40.026 | 39.469 | 1.00 | 30.67 |
| C | | | | | | | | | | |
| ATOM | 302 | O | PHE | A | 40 | 66.605 | 41.250 | 39.611 | 1.00 | 31.06 |
| O | | | | | | | | | | |
| ATOM | 303 | CB | PHE | A | 40 | 67.485 | 38.633 | 37.627 | 1.00 | 29.02 |
| C | | | | | | | | | | |
| ATOM | 304 | CG | PHE | A | 40 | 68.706 | 39.481 | 37.379 | 1.00 | 28.39 |
| C | | | | | | | | | | |
| ATOM | 305 | CD1 | PHE | A | 40 | 68.920 | 40.074 | 36.136 | 1.00 | 29.01 |
| C | | | | | | | | | | |
| ATOM | 306 | CD2 | PHE | A | 40 | 69.649 | 39.671 | 38.381 | 1.00 | 28.07 |
| C | | | | | | | | | | |
| ATOM | 307 | CE1 | PHE | A | 40 | 70.059 | 40.843 | 35.897 | 1.00 | 28.63 |
| C | | | | | | | | | | |
| ATOM | 308 | CE2 | PHE | A | 40 | 70.790 | 40.435 | 38.157 | 1.00 | 28.51 |
| C | | | | | | | | | | |
| ATOM | 309 | CZ | PHE | A | 40 | 70.997 | 41.022 | 36.912 | 1.00 | 28.67 |
| C | | | | | | | | | | |
| ATOM | 310 | N | GLN | A | 41 | 66.609 | 39.168 | 40.482 | 1.00 | 30.52 |
| N | | | | | | | | | | |
| ATOM | 311 | CA | GLN | A | 41 | 66.843 | 39.608 | 41.857 | 1.00 | 32.51 |
| C | | | | | | | | | | |
| ATOM | 312 | C | GLN | A | 41 | 68.324 | 39.615 | 42.199 | 1.00 | 31.08 |
| C | | | | | | | | | | |
| ATOM | 313 | O | GLN | A | 41 | 69.120 | 38.950 | 41.544 | 1.00 | 32.21 |
| O | | | | | | | | | | |
| ATOM | 314 | CB | GLN | A | 41 | 66.131 | 38.677 | 42.852 | 1.00 | 34.57 |
| C | | | | | | | | | | |
| ATOM | 315 | CG | GLN | A | 41 | 64.623 | 38.683 | 42.769 | 1.00 | 40.18 |
| C | | | | | | | | | | |
| ATOM | 316 | CD | GLN | A | 41 | 64.029 | 40.014 | 43.189 | 1.00 | 42.08 |
| C | | | | | | | | | | |
| ATOM | 317 | OE1 | GLN | A | 41 | 64.187 | 40.451 | 44.333 | 1.00 | 45.71 |
| O | | | | | | | | | | |
| ATOM | 318 | NE2 | GLN | A | 41 | 63.345 | 40.667 | 42.263 | 1.00 | 44.39 |
| N | | | | | | | | | | |
| ATOM | 319 | N | LYS | A | 42 | 68.678 | 40.364 | 43.238 | 1.00 | 30.91 |
| N | | | | | | | | | | |

TABLE 7-continued

| | | | | | | | | | |
|---|---|---|---|---|---|---|---|---|---|
| ATOM | 320 | CA | LYS | A | 42 | 70.057 | 40.444 | 43.705 | 1.00 31.44 |
| C | | | | | | | | | |
| ATOM | 321 | C | LYS | A | 42 | 70.606 | 39.028 | 43.937 | 1.00 31.78 |
| C | | | | | | | | | |
| ATOM | 322 | O | LYS | A | 42 | 69.945 | 38.190 | 44.556 | 1.00 30.49 |
| O | | | | | | | | | |
| ATOM | 323 | CB | LYS | A | 42 | 70.106 | 41.241 | 45.009 | 1.00 33.17 |
| C | | | | | | | | | |
| ATOM | 324 | CG | LYS | A | 42 | 71.456 | 41.242 | 45.701 | 1.00 35.83 |
| C | | | | | | | | | |
| ATOM | 325 | CD | LYS | A | 42 | 71.399 | 42.043 | 46.994 | 1.00 38.92 |
| C | | | | | | | | | |
| ATOM | 326 | CE | LYS | A | 42 | 72.740 | 42.029 | 47.706 | 1.00 40.30 |
| C | | | | | | | | | |
| ATOM | 327 | NZ | LYS | A | 42 | 72.711 | 42.865 | 48.938 | 1.00 43.53 |
| N | | | | | | | | | |
| ATOM | 328 | N | GLY | A | 43 | 71.805 | 38.768 | 43.426 | 1.00 31.76 |
| N | | | | | | | | | |
| ATOM | 329 | CA | GLY | A | 43 | 72.420 | 37.463 | 43.593 | 1.00 31.06 |
| C | | | | | | | | | |
| ATOM | 330 | C | GLY | A | 43 | 72.125 | 36.484 | 42.473 | 1.00 30.81 |
| C | | | | | | | | | |
| ATOM | 331 | O | GLY | A | 43 | 72.751 | 35.426 | 42.384 | 1.00 30.33 |
| O | | | | | | | | | |
| ATOM | 332 | N | GLN | A | 44 | 71.170 | 36.822 | 41.615 | 1.00 30.18 |
| N | | | | | | | | | |
| ATOM | 333 | CA | GLN | A | 44 | 70.817 | 35.946 | 40.507 | 1.00 30.45 |
| C | | | | | | | | | |
| ATOM | 334 | C | GLN | A | 44 | 71.410 | 36.461 | 39.203 | 1.00 31.41 |
| C | | | | | | | | | |
| ATOM | 335 | O | GLN | A | 44 | 72.075 | 37.494 | 39.172 | 1.00 30.58 |
| O | | | | | | | | | |
| ATOM | 336 | CB | GLN | A | 44 | 69.295 | 35.870 | 40.345 | 1.00 31.54 |
| C | | | | | | | | | |
| ATOM | 337 | CG | GLN | A | 44 | 68.521 | 35.673 | 41.637 | 1.00 32.79 |
| C | | | | | | | | | |
| ATOM | 338 | CD | GLN | A | 44 | 67.016 | 35.631 | 41.407 | 1.00 34.29 |
| C | | | | | | | | | |
| ATOM | 339 | OE1 | GLN | A | 44 | 66.492 | 36.327 | 40.537 | 1.00 32.47 |
| O | | | | | | | | | |
| ATOM | 340 | NE2 | GLN | A | 44 | 66.316 | 34.827 | 42.299 | 1.00 32.10 |
| N | | | | | | | | | |
| ATOM | 341 | N | GLN | A | 45 | 71.161 | 35.710 | 38.136 | 1.00 32.01 |
| N | | | | | | | | | |
| ATOM | 342 | CA | GLN | A | 45 | 71.593 | 36.058 | 36.791 | 1.00 33.43 |
| C | | | | | | | | | |
| ATOM | 343 | C | GLN | A | 45 | 70.299 | 36.153 | 35.992 | 1.00 32.33 |
| C | | | | | | | | | |
| ATOM | 344 | O | GLN | A | 45 | 69.310 | 35.516 | 36.345 | 1.00 31.57 |
| O | | | | | | | | | |
| ATOM | 345 | CB | GLN | A | 45 | 72.476 | 34.957 | 36.196 | 1.00 37.06 |
| C | | | | | | | | | |
| ATOM | 346 | CG | GLN | A | 45 | 73.829 | 34.819 | 36.864 | 1.00 42.03 |
| C | | | | | | | | | |
| ATOM | 347 | CD | GLN | A | 45 | 74.634 | 36.097 | 36.781 | 1.00 44.70 |
| C | | | | | | | | | |
| ATOM | 348 | OE1 | GLN | A | 45 | 74.911 | 36.596 | 35.689 | 1.00 47.34 |
| O | | | | | | | | | |
| ATOM | 349 | NE2 | GLN | A | 45 | 75.010 | 36.641 | 37.936 | 1.00 45.66 |
| N | | | | | | | | | |
| ATOM | 350 | N | SER | A | 46 | 70.299 | 36.945 | 34.926 | 1.00 30.96 |
| N | | | | | | | | | |
| ATOM | 351 | CA | SER | A | 46 | 69.103 | 37.082 | 34.107 | 1.00 30.90 |
| C | | | | | | | | | |
| ATOM | 352 | C | SER | A | 46 | 68.791 | 35.762 | 33.407 | 1.00 31.56 |
| C | | | | | | | | | |
| ATOM | 353 | O | SER | A | 46 | 69.700 | 35.004 | 33.078 | 1.00 30.43 |
| O | | | | | | | | | |
| ATOM | 354 | CB | SER | A | 46 | 69.300 | 38.171 | 33.053 | 1.00 29.48 |
| C | | | | | | | | | |
| ATOM | 355 | OG | SER | A | 46 | 68.130 | 38.324 | 32.276 | 1.00 28.63 |
| O | | | | | | | | | |
| ATOM | 356 | N | GLU | A | 47 | 67.507 | 35.495 | 33.180 | 1.00 32.24 |
| N | | | | | | | | | |
| ATOM | 357 | CA | GLU | A | 47 | 67.097 | 34.271 | 32.498 | 1.00 33.72 |
| C | | | | | | | | | |
| ATOM | 358 | C | GLU | A | 47 | 67.495 | 34.336 | 31.033 | 1.00 32.95 |
| C | | | | | | | | | |

TABLE 7-continued

| ATOM | 359 | O | GLU | A | 47 | 67.601 | 33.311 | 30.363 | 1.00 | 32.68 | O |
| ATOM | 360 | CB | GLU | A | 47 | 65.587 | 34.078 | 32.614 | 1.00 | 35.36 | C |
| ATOM | 361 | CG | GLU | A | 47 | 65.118 | 33.791 | 34.027 | 1.00 | 39.32 | C |
| ATOM | 362 | CD | GLU | A | 47 | 63.613 | 33.865 | 34.159 | 1.00 | 41.79 | C |
| ATOM | 363 | OE1 | GLU | A | 47 | 62.918 | 33.052 | 33.513 | 1.00 | 44.11 | O |
| ATOM | 364 | OE2 | GLU | A | 47 | 63.124 | 34.743 | 34.904 | 1.00 | 43.26 | O |
| ATOM | 365 | N | ILE | A | 48 | 67.701 | 35.551 | 30.531 | 1.00 | 31.57 | N |
| ATOM | 366 | CA | ILE | A | 48 | 68.114 | 35.736 | 29.143 | 1.00 | 30.16 | C |
| ATOM | 367 | C | ILE | A | 48 | 69.271 | 36.727 | 29.080 | 1.00 | 29.80 | C |
| ATOM | 368 | O | ILE | A | 48 | 69.148 | 37.869 | 29.521 | 1.00 | 29.23 | O |
| ATOM | 369 | CB | ILE | A | 48 | 66.962 | 36.280 | 28.258 | 1.00 | 31.15 | C |
| ATOM | 370 | CG1 | ILE | A | 48 | 65.780 | 35.308 | 28.267 | 1.00 | 31.70 | C |
| ATOM | 371 | CG2 | ILE | A | 48 | 67.461 | 36.479 | 26.835 | 1.00 | 30.35 | C |
| ATOM | 372 | CD1 | ILE | A | 48 | 64.578 | 35.800 | 27.487 | 1.00 | 33.88 | C |
| ATOM | 373 | N | ASN | A | 49 | 70.396 | 36.280 | 28.536 | 1.00 | 28.20 | N |
| ATOM | 374 | CA | ASN | A | 49 | 71.567 | 37.129 | 28.403 | 1.00 | 28.79 | C |
| ATOM | 375 | C | ASN | A | 49 | 71.982 | 37.194 | 26.947 | 1.00 | 28.45 | C |
| ATOM | 376 | O | ASN | A | 49 | 72.204 | 36.160 | 26.309 | 1.00 | 28.24 | O |
| ATOM | 377 | CB | ASN | A | 49 | 72.728 | 36.579 | 29.238 | 1.00 | 29.15 | C |
| ATOM | 378 | CG | ASN | A | 49 | 72.459 | 36.656 | 30.726 | 1.00 | 30.85 | C |
| ATOM | 379 | OD1 | ASN | A | 49 | 72.610 | 37.712 | 31.343 | 1.00 | 29.61 | O |
| ATOM | 380 | ND2 | ASN | A | 49 | 72.041 | 35.538 | 31.310 | 1.00 | 30.46 | N |
| ATOM | 381 | N | LEU | A | 50 | 72.061 | 38.407 | 26.412 | 1.00 | 27.38 | N |
| ATOM | 382 | CA | LEU | A | 50 | 72.488 | 38.585 | 25.030 | 1.00 | 27.41 | C |
| ATOM | 383 | C | LEU | A | 50 | 73.990 | 38.324 | 25.035 | 1.00 | 27.31 | C |
| ATOM | 384 | O | LEU | A | 50 | 74.635 | 38.498 | 26.069 | 1.00 | 26.24 | O |
| ATOM | 385 | CB | LEU | A | 50 | 72.233 | 40.026 | 24.573 | 1.00 | 27.05 | C |
| ATOM | 386 | CG | LEU | A | 50 | 70.818 | 40.596 | 24.686 | 1.00 | 28.18 | C |
| ATOM | 387 | CD1 | LEU | A | 50 | 70.838 | 42.092 | 24.356 | 1.00 | 28.26 | C |
| ATOM | 388 | CD2 | LEU | A | 50 | 69.887 | 39.849 | 23.745 | 1.00 | 29.22 | C |
| ATOM | 389 | N | LYS | A | 51 | 74.542 | 37.898 | 23.901 | 1.00 | 28.23 | N |
| ATOM | 390 | CA | LYS | A | 51 | 75.978 | 37.666 | 23.804 | 1.00 | 28.76 | C |
| ATOM | 391 | C | LYS | A | 51 | 76.661 | 38.946 | 23.313 | 1.00 | 28.00 | C |
| ATOM | 392 | O | LYS | A | 51 | 77.867 | 39.118 | 23.478 | 1.00 | 27.68 | O |
| ATOM | 393 | CB | LYS | A | 51 | 76.275 | 36.463 | 22.897 | 1.00 | 31.27 | C |
| ATOM | 394 | CG | LYS | A | 51 | 75.819 | 35.155 | 23.546 | 1.00 | 32.77 | C |
| ATOM | 395 | CD | LYS | A | 51 | 76.238 | 33.915 | 22.771 | 1.00 | 35.29 | C |
| ATOM | 396 | CE | LYS | A | 51 | 75.732 | 32.661 | 23.486 | 1.00 | 36.18 | C |
| ATOM | 397 | NZ | LYS | A | 51 | 76.082 | 31.402 | 22.757 | 1.00 | 38.13 | N |

TABLE 7-continued

| ATOM | 398 | N | ILE | A | 52 | 75.877 | 39.834 | 22.700 | 1.00 | 26.71 | N |
| ATOM | 399 | CA | ILE | A | 52 | 76.359 | 41.150 | 22.277 | 1.00 | 26.00 | C |
| ATOM | 400 | C | ILE | A | 52 | 75.227 | 42.109 | 22.668 | 1.00 | 26.56 | C |
| ATOM | 401 | O | ILE | A | 52 | 74.049 | 41.764 | 22.566 | 1.00 | 26.00 | O |
| ATOM | 402 | CB | ILE | A | 52 | 76.689 | 41.247 | 20.756 | 1.00 | 26.91 | C |
| ATOM | 403 | CG1 | ILE | A | 52 | 75.458 | 40.947 | 19.899 | 1.00 | 27.54 | C |
| ATOM | 404 | CG2 | ILE | A | 52 | 77.856 | 40.303 | 20.421 | 1.00 | 27.36 | C |
| ATOM | 405 | CD1 | ILE | A | 52 | 75.675 | 41.287 | 18.423 | 1.00 | 27.06 | C |
| ATOM | 406 | N | PRO | A | 53 | 75.570 | 43.322 | 23.124 | 1.00 | 25.59 | N |
| ATOM | 407 | CA | PRO | A | 53 | 74.590 | 44.326 | 23.556 | 1.00 | 26.47 | C |
| ATOM | 408 | C | PRO | A | 53 | 73.782 | 45.080 | 22.501 | 1.00 | 27.16 | C |
| ATOM | 409 | O | PRO | A | 53 | 73.395 | 46.228 | 22.730 | 1.00 | 26.78 | O |
| ATOM | 410 | CB | PRO | A | 53 | 75.439 | 45.269 | 24.400 | 1.00 | 25.56 | C |
| ATOM | 411 | CG | PRO | A | 53 | 76.720 | 45.315 | 23.605 | 1.00 | 25.49 | C |
| ATOM | 412 | CD | PRO | A | 53 | 76.945 | 43.853 | 23.222 | 1.00 | 25.76 | C |
| ATOM | 413 | N | LEU | A | 54 | 73.502 | 44.443 | 21.368 | 1.00 | 26.87 | N |
| ATOM | 414 | CA | LEU | A | 54 | 72.745 | 45.106 | 20.314 | 1.00 | 27.02 | C |
| ATOM | 415 | C | LEU | A | 54 | 71.426 | 44.404 | 19.979 | 1.00 | 26.78 | C |
| ATOM | 416 | O | LEU | A | 54 | 71.376 | 43.177 | 19.861 | 1.00 | 27.27 | O |
| ATOM | 417 | CB | LEU | A | 54 | 73.588 | 45.201 | 19.038 | 1.00 | 26.49 | C |
| ATOM | 418 | CG | LEU | A | 54 | 75.010 | 45.771 | 19.104 | 1.00 | 26.90 | C |
| ATOM | 419 | CD1 | LEU | A | 54 | 75.588 | 45.807 | 17.692 | 1.00 | 28.33 | C |
| ATOM | 420 | CD2 | LEU | A | 54 | 75.000 | 47.168 | 19.716 | 1.00 | 26.89 | C |
| ATOM | 421 | N | VAL | A | 55 | 70.359 | 45.186 | 19.847 | 1.00 | 26.28 | N |
| ATOM | 422 | CA | VAL | A | 55 | 69.061 | 44.641 | 19.461 | 1.00 | 26.52 | C |
| ATOM | 423 | C | VAL | A | 55 | 68.516 | 45.542 | 18.349 | 1.00 | 26.85 | C |
| ATOM | 424 | O | VAL | A | 55 | 68.753 | 46.751 | 18.353 | 1.00 | 27.05 | O |
| ATOM | 425 | CB | VAL | A | 55 | 68.066 | 44.574 | 20.655 | 1.00 | 26.19 | C |
| ATOM | 426 | CG1 | VAL | A | 55 | 68.718 | 43.837 | 21.823 | 1.00 | 25.91 | C |
| ATOM | 427 | CG2 | VAL | A | 55 | 67.614 | 45.963 | 21.064 | 1.00 | 26.54 | C |
| ATOM | 428 | N | SER | A | 56 | 67.812 | 44.958 | 17.381 | 1.00 | 26.45 | N |
| ATOM | 429 | CA | SER | A | 56 | 67.281 | 45.750 | 16.279 | 1.00 | 26.33 | C |
| ATOM | 430 | C | SER | A | 56 | 65.909 | 46.329 | 16.613 | 1.00 | 26.47 | C |
| ATOM | 431 | O | SER | A | 56 | 65.091 | 45.694 | 17.286 | 1.00 | 26.78 | O |
| ATOM | 432 | CB | SER | A | 56 | 67.239 | 44.916 | 14.985 | 1.00 | 27.61 | C |
| ATOM | 433 | OG | SER | A | 56 | 66.504 | 43.720 | 15.149 | 1.00 | 27.08 | O |
| ATOM | 434 | N | ALA | A | 57 | 65.687 | 47.556 | 16.152 | 1.00 | 26.29 | N |
| ATOM | 435 | CA | ALA | A | 57 | 64.462 | 48.307 | 16.400 | 1.00 | 26.64 | C |
| ATOM | 436 | C | ALA | A | 57 | 63.167 | 47.618 | 15.963 | 1.00 | 27.43 | C |

TABLE 7-continued

| | | | | | | | | | |
|---|---|---|---|---|---|---|---|---|---|
| ATOM | 437 | O | ALA | A | 57 | 63.161 | 46.798 | 15.045 | 1.00 27.98 |
| ATOM | 438 | CB | ALA | A | 57 | 64.572 | 49.672 | 15.739 | 1.00 25.98 |
| ATOM | 439 | N | ILE | A | 58 | 62.076 | 47.968 | 16.638 | 1.00 27.92 |
| ATOM | 440 | CA | ILE | A | 58 | 60.753 | 47.413 | 16.354 | 1.00 28.86 |
| ATOM | 441 | C | ILE | A | 58 | 60.196 | 48.224 | 15.191 | 1.00 29.07 |
| ATOM | 442 | O | ILE | A | 58 | 59.308 | 49.064 | 15.371 | 1.00 29.42 |
| ATOM | 443 | CB | ILE | A | 58 | 59.823 | 47.572 | 17.576 | 1.00 28.92 |
| ATOM | 444 | CG1 | ILE | A | 58 | 60.574 | 47.170 | 18.852 | 1.00 28.75 |
| ATOM | 445 | CG2 | ILE | A | 58 | 58.578 | 46.718 | 17.397 | 1.00 27.62 |
| ATOM | 446 | CD1 | ILE | A | 58 | 59.752 | 47.286 | 20.126 | 1.00 29.63 |
| ATOM | 447 | N | MET | A | 59 | 60.731 | 47.969 | 14.003 | 1.00 29.21 |
| ATOM | 448 | CA | MET | A | 59 | 60.344 | 48.714 | 12.811 | 1.00 29.85 |
| ATOM | 449 | C | MET | A | 59 | 60.187 | 47.851 | 11.565 | 1.00 30.08 |
| ATOM | 450 | O | MET | A | 59 | 60.970 | 46.929 | 11.330 | 1.00 29.39 |
| ATOM | 451 | CB | MET | A | 59 | 61.395 | 49.793 | 12.537 | 1.00 29.69 |
| ATOM | 452 | CG | MET | A | 59 | 61.639 | 50.736 | 13.710 | 1.00 29.89 |
| ATOM | 453 | SD | MET | A | 59 | 63.017 | 51.863 | 13.414 | 1.00 30.04 |
| ATOM | 454 | CE | MET | A | 59 | 62.383 | 52.830 | 12.049 | 1.00 28.55 |
| ATOM | 455 | N | GLN | A | 60 | 59.182 | 48.181 | 10.756 | 1.00 30.89 |
| ATOM | 456 | CA | GLN | A | 60 | 58.906 | 47.452 | 9.520 | 1.00 31.91 |
| ATOM | 457 | C | GLN | A | 60 | 60.127 | 47.431 | 8.606 | 1.00 32.39 |
| ATOM | 458 | O | GLN | A | 60 | 60.374 | 46.447 | 7.916 | 1.00 32.51 |
| ATOM | 459 | CB | GLN | A | 60 | 57.759 | 48.110 | 8.741 | 1.00 32.69 |
| ATOM | 460 | CG | GLN | A | 60 | 56.508 | 48.441 | 9.532 | 1.00 33.24 |
| ATOM | 461 | CD | GLN | A | 60 | 55.445 | 49.085 | 8.656 | 1.00 35.53 |
| ATOM | 462 | OE1 | GLN | A | 60 | 55.761 | 49.829 | 7.723 | 1.00 35.53 |
| ATOM | 463 | NE2 | GLN | A | 60 | 54.178 | 48.813 | 8.957 | 1.00 35.36 |
| ATOM | 464 | N | SER | A | 61 | 60.879 | 48.528 | 8.590 | 1.00 32.34 |
| ATOM | 465 | CA | SER | A | 61 | 62.051 | 48.629 | 7.727 | 1.00 32.96 |
| ATOM | 466 | C | SER | A | 61 | 63.333 | 48.085 | 8.344 | 1.00 32.88 |
| ATOM | 467 | O | SER | A | 61 | 64.415 | 48.273 | 7.790 | 1.00 34.10 |
| ATOM | 468 | CB | SER | A | 61 | 62.273 | 50.089 | 7.312 | 1.00 33.69 |
| ATOM | 469 | OG | SER | A | 61 | 62.544 | 50.910 | 8.437 | 1.00 35.94 |
| ATOM | 470 | N | VAL | A | 62 | 63.218 | 47.394 | 9.472 | 1.00 32.07 |
| ATOM | 471 | CA | VAL | A | 62 | 64.404 | 46.867 | 10.130 | 1.00 31.11 |
| ATOM | 472 | C | VAL | A | 62 | 64.348 | 45.411 | 10.572 | 1.00 31.10 |
| ATOM | 473 | O | VAL | A | 62 | 65.145 | 44.590 | 10.126 | 1.00 31.19 |
| ATOM | 474 | CB | VAL | A | 62 | 64.764 | 47.713 | 11.383 | 1.00 31.46 |
| ATOM | 475 | CG1 | VAL | A | 62 | 65.992 | 47.128 | 12.070 | 1.00 30.28 |

TABLE 7-continued

| | | | | | | | | | |
|---|---|---|---|---|---|---|---|---|---|
| ATOM | 476 | CG2 | VAL | A | 62 | 65.018 | 49.160 | 10.988 | 1.00 30.77 |
| ATOM | 477 | N | SER | A | 63 | 63.399 | 45.091 | 11.444 | 1.00 31.39 |
| ATOM | 478 | CA | SER | A | 63 | 63.312 | 43.752 | 12.000 | 1.00 31.57 |
| ATOM | 479 | C | SER | A | 63 | 62.341 | 42.743 | 11.393 | 1.00 32.24 |
| ATOM | 480 | O | SER | A | 63 | 61.242 | 42.535 | 11.907 | 1.00 31.09 |
| ATOM | 481 | CB | SER | A | 63 | 63.064 | 43.863 | 13.508 | 1.00 31.83 |
| ATOM | 482 | OG | SER | A | 63 | 64.118 | 44.590 | 14.129 | 1.00 31.09 |
| ATOM | 483 | N | GLY | A | 64 | 62.778 | 42.112 | 10.307 | 1.00 32.50 |
| ATOM | 484 | CA | GLY | A | 64 | 61.986 | 41.087 | 9.651 | 1.00 34.07 |
| ATOM | 485 | C | GLY | A | 64 | 62.598 | 39.756 | 10.051 | 1.00 35.58 |
| ATOM | 486 | O | GLY | A | 64 | 63.493 | 39.729 | 10.903 | 1.00 33.57 |
| ATOM | 487 | N | GLU | A | 65 | 62.155 | 38.652 | 9.450 | 1.00 36.69 |
| ATOM | 488 | CA | GLU | A | 65 | 62.704 | 37.350 | 9.821 | 1.00 38.49 |
| ATOM | 489 | C | GLU | A | 65 | 64.187 | 37.205 | 9.494 | 1.00 38.04 |
| ATOM | 490 | O | GLU | A | 65 | 64.942 | 36.652 | 10.292 | 1.00 37.92 |
| ATOM | 491 | CB | GLU | A | 65 | 61.913 | 36.202 | 9.171 | 1.00 41.36 |
| ATOM | 492 | CG | GLU | A | 65 | 61.881 | 36.201 | 7.652 | 1.00 46.27 |
| ATOM | 493 | CD | GLU | A | 65 | 60.758 | 37.049 | 7.076 | 1.00 49.42 |
| ATOM | 494 | OE1 | GLU | A | 65 | 60.603 | 37.055 | 5.835 | 1.00 51.56 |
| ATOM | 495 | OE2 | GLU | A | 65 | 60.028 | 37.706 | 7.852 | 1.00 51.36 |
| ATOM | 496 | N | LYS | A | 66 | 64.606 | 37.700 | 8.333 | 1.00 37.76 |
| ATOM | 497 | CA | LYS | A | 66 | 66.006 | 37.612 | 7.934 | 1.00 38.96 |
| ATOM | 498 | C | LYS | A | 66 | 66.909 | 38.345 | 8.924 | 1.00 37.51 |
| ATOM | 499 | O | LYS | A | 66 | 67.975 | 37.848 | 9.290 | 1.00 36.95 |
| ATOM | 500 | CB | LYS | A | 66 | 66.208 | 38.193 | 6.531 | 1.00 40.79 |
| ATOM | 501 | CG | LYS | A | 66 | 65.594 | 37.358 | 5.415 | 1.00 45.49 |
| ATOM | 502 | CD | LYS | A | 66 | 65.912 | 37.944 | 4.042 | 1.00 48.08 |
| ATOM | 503 | CE | LYS | A | 66 | 65.320 | 37.094 | 2.925 | 1.00 49.82 |
| ATOM | 504 | NZ | LYS | A | 66 | 65.647 | 37.631 | 1.571 | 1.00 51.36 |
| ATOM | 505 | N | MET | A | 67 | 66.480 | 39.527 | 9.351 | 1.00 35.99 |
| ATOM | 506 | CA | MET | A | 67 | 67.254 | 40.314 | 10.304 | 1.00 34.82 |
| ATOM | 507 | C | MET | A | 67 | 67.378 | 39.563 | 11.624 | 1.00 34.24 |
| ATOM | 508 | O | MET | A | 67 | 68.468 | 39.447 | 12.182 | 1.00 33.61 |
| ATOM | 509 | CB | MET | A | 67 | 66.579 | 41.666 | 10.545 | 1.00 34.96 |
| ATOM | 510 | CG | MET | A | 67 | 67.298 | 42.561 | 11.546 | 1.00 34.38 |
| ATOM | 511 | SD | MET | A | 67 | 68.955 | 43.020 | 11.010 | 1.00 35.01 |
| ATOM | 512 | CE | MET | A | 67 | 68.573 | 44.146 | 9.657 | 1.00 33.42 |
| ATOM | 513 | N | ALA | A | 68 | 66.252 | 39.046 | 12.110 | 1.00 33.39 |
| ATOM | 514 | CA | ALA | A | 68 | 66.215 | 38.315 | 13.369 | 1.00 33.20 |

TABLE 7-continued

| ATOM | 515 | C | ALA | A | 68 | 67.165 | 37.123 | 13.387 | 1.00 | 33.51 |
| --- | --- | --- | --- | --- | --- | --- | --- | --- | --- | --- |
| ATOM | 516 | O | ALA | A | 68 | 67.798 | 36.841 | 14.403 | 1.00 | 33.13 |
| ATOM | 517 | CB | ALA | A | 68 | 64.787 | 37.854 | 13.661 | 1.00 | 33.11 |
| ATOM | 518 | N | ILE | A | 69 | 67.262 | 36.419 | 12.265 | 1.00 | 33.68 |
| ATOM | 519 | CA | ILE | A | 69 | 68.147 | 35.265 | 12.182 | 1.00 | 33.04 |
| ATOM | 520 | C | ILE | A | 69 | 69.603 | 35.712 | 12.131 | 1.00 | 32.05 |
| ATOM | 521 | O | ILE | A | 69 | 70.452 | 35.174 | 12.841 | 1.00 | 33.24 |
| ATOM | 522 | CB | ILE | A | 69 | 67.827 | 34.409 | 10.933 | 1.00 | 34.02 |
| ATOM | 523 | CG1 | ILE | A | 69 | 66.463 | 33.736 | 11.104 | 1.00 | 34.34 |
| ATOM | 524 | CG2 | ILE | A | 69 | 68.911 | 33.365 | 10.719 | 1.00 | 33.54 |
| ATOM | 525 | CD1 | ILE | A | 69 | 65.913 | 33.127 | 9.819 | 1.00 | 37.29 |
| ATOM | 526 | N | ALA | A | 70 | 69.884 | 36.709 | 11.300 | 1.00 | 31.48 |
| ATOM | 527 | CA | ALA | A | 70 | 71.236 | 37.225 | 11.149 | 1.00 | 30.65 |
| ATOM | 528 | C | ALA | A | 70 | 71.799 | 37.799 | 12.445 | 1.00 | 30.57 |
| ATOM | 529 | O | ALA | A | 70 | 72.969 | 37.593 | 12.763 | 1.00 | 29.93 |
| ATOM | 530 | CB | ALA | A | 70 | 71.264 | 38.284 | 10.063 | 1.00 | 30.23 |
| ATOM | 531 | N | LEU | A | 71 | 70.967 | 38.523 | 13.188 | 1.00 | 29.53 |
| ATOM | 532 | CA | LEU | A | 71 | 71.409 | 39.129 | 14.438 | 1.00 | 29.98 |
| ATOM | 533 | C | LEU | A | 71 | 71.553 | 38.098 | 15.552 | 1.00 | 30.25 |
| ATOM | 534 | O | LEU | A | 71 | 72.517 | 38.141 | 16.314 | 1.00 | 30.96 |
| ATOM | 535 | CB | LEU | A | 71 | 70.442 | 40.242 | 14.859 | 1.00 | 28.55 |
| ATOM | 536 | CG | LEU | A | 71 | 70.809 | 41.061 | 16.103 | 1.00 | 28.68 |
| ATOM | 537 | CD1 | LEU | A | 71 | 72.271 | 41.482 | 16.041 | 1.00 | 27.67 |
| ATOM | 538 | CD2 | LEU | A | 71 | 69.898 | 42.287 | 16.192 | 1.00 | 28.74 |
| ATOM | 539 | N | ALA | A | 72 | 70.607 | 37.166 | 15.645 | 1.00 | 31.21 |
| ATOM | 540 | CA | ALA | A | 72 | 70.683 | 36.131 | 16.672 | 1.00 | 31.98 |
| ATOM | 541 | C | ALA | A | 72 | 71.953 | 35.308 | 16.468 | 1.00 | 32.78 |
| ATOM | 542 | O | ALA | A | 72 | 72.569 | 34.847 | 17.434 | 1.00 | 31.74 |
| ATOM | 543 | CB | ALA | A | 72 | 69.452 | 35.222 | 16.608 | 1.00 | 31.69 |
| ATOM | 544 | N | ARG | A | 73 | 72.335 | 35.121 | 15.206 | 1.00 | 33.82 |
| ATOM | 545 | CA | ARG | A | 73 | 73.533 | 34.354 | 14.876 | 1.00 | 35.76 |
| ATOM | 546 | C | ARG | A | 73 | 74.786 | 35.010 | 15.435 | 1.00 | 35.30 |
| ATOM | 547 | O | ARG | A | 73 | 75.760 | 34.328 | 15.745 | 1.00 | 34.89 |
| ATOM | 548 | CB | ARG | A | 73 | 73.680 | 34.200 | 13.358 | 1.00 | 37.37 |
| ATOM | 549 | CG | ARG | A | 73 | 72.809 | 33.109 | 12.747 | 1.00 | 39.96 |
| ATOM | 550 | CD | ARG | A | 73 | 72.927 | 33.093 | 11.228 | 1.00 | 42.81 |
| ATOM | 551 | NE | ARG | A | 73 | 72.204 | 31.970 | 10.636 | 1.00 | 45.35 |
| ATOM | 552 | CZ | ARG | A | 73 | 71.945 | 31.844 | 9.337 | 1.00 | 47.16 |
| ATOM | 553 | NH1 | ARG | A | 73 | 72.344 | 32.773 | 8.479 | 1.00 | 47.06 |

TABLE 7-continued

| ATOM | 554 | NH2 | ARG | A | 73 | 71.289 | 30.778 | 8.894 | 1.00 | 48.38 |
|---|---|---|---|---|---|---|---|---|---|---|
| ATOM | 555 | N | GLU | A | 74 | 74.755 | 36.335 | 15.565 | 1.00 | 35.55 |
| ATOM | 556 | CA | GLU | A | 74 | 75.899 | 37.069 | 16.088 | 1.00 | 34.99 |
| ATOM | 557 | C | GLU | A | 74 | 75.796 | 37.327 | 17.591 | 1.00 | 33.84 |
| ATOM | 558 | O | GLU | A | 74 | 76.693 | 37.923 | 18.181 | 1.00 | 33.27 |
| ATOM | 559 | CB | GLU | A | 74 | 76.065 | 38.396 | 15.342 | 1.00 | 37.11 |
| ATOM | 560 | CG | GLU | A | 74 | 76.218 | 38.254 | 13.826 | 1.00 | 39.97 |
| ATOM | 561 | CD | GLU | A | 74 | 77.309 | 37.270 | 13.418 | 1.00 | 43.26 |
| ATOM | 562 | OE1 | GLU | A | 74 | 78.448 | 37.383 | 13.924 | 1.00 | 44.46 |
| ATOM | 563 | OE2 | GLU | A | 74 | 77.027 | 36.384 | 12.580 | 1.00 | 44.73 |
| ATOM | 564 | N | GLY | A | 75 | 74.702 | 36.893 | 18.209 | 1.00 | 32.10 |
| ATOM | 565 | CA | GLY | A | 75 | 74.562 | 37.081 | 19.645 | 1.00 | 31.13 |
| ATOM | 566 | C | GLY | A | 75 | 73.553 | 38.107 | 20.123 | 1.00 | 30.09 |
| ATOM | 567 | O | GLY | A | 75 | 73.352 | 38.256 | 21.330 | 1.00 | 29.67 |
| ATOM | 568 | N | GLY | A | 76 | 72.926 | 38.815 | 19.190 | 1.00 | 28.66 |
| ATOM | 569 | CA | GLY | A | 76 | 71.937 | 39.814 | 19.559 | 1.00 | 28.32 |
| ATOM | 570 | C | GLY | A | 76 | 70.526 | 39.294 | 19.342 | 1.00 | 28.09 |
| ATOM | 571 | O | GLY | A | 76 | 70.325 | 38.101 | 19.089 | 1.00 | 27.76 |
| ATOM | 572 | N | ILE | A | 77 | 69.541 | 40.181 | 19.436 | 1.00 | 27.98 |
| ATOM | 573 | CA | ILE | A | 77 | 68.157 | 39.774 | 19.239 | 1.00 | 27.37 |
| ATOM | 574 | C | ILE | A | 77 | 67.363 | 40.857 | 18.497 | 1.00 | 28.41 |
| ATOM | 575 | O | ILE | A | 77 | 67.632 | 42.053 | 18.638 | 1.00 | 26.87 |
| ATOM | 576 | CB | ILE | A | 77 | 67.491 | 39.456 | 20.603 | 1.00 | 27.78 |
| ATOM | 577 | CG1 | ILE | A | 77 | 66.246 | 38.592 | 20.392 | 1.00 | 27.09 |
| ATOM | 578 | CG2 | ILE | A | 77 | 67.128 | 40.757 | 21.337 | 1.00 | 26.59 |
| ATOM | 579 | CD1 | ILE | A | 77 | 65.560 | 38.187 | 21.679 | 1.00 | 25.93 |
| ATOM | 580 | N | SER | A | 78 | 66.404 | 40.430 | 17.682 | 1.00 | 28.44 |
| ATOM | 581 | CA | SER | A | 78 | 65.570 | 41.364 | 16.936 | 1.00 | 28.97 |
| ATOM | 582 | C | SER | A | 78 | 64.167 | 41.354 | 17.512 | 1.00 | 28.83 |
| ATOM | 583 | O | SER | A | 78 | 63.714 | 40.342 | 18.041 | 1.00 | 28.85 |
| ATOM | 584 | CB | SER | A | 78 | 65.487 | 40.971 | 15.457 | 1.00 | 27.56 |
| ATOM | 585 | OG | SER | A | 78 | 66.716 | 41.168 | 14.790 | 1.00 | 28.48 |
| ATOM | 586 | N | PHE | A | 79 | 63.487 | 42.490 | 17.418 | 1.00 | 29.16 |
| ATOM | 587 | CA | PHE | A | 79 | 62.117 | 42.591 | 17.893 | 1.00 | 29.89 |
| ATOM | 588 | C | PHE | A | 79 | 61.237 | 42.769 | 16.668 | 1.00 | 30.19 |
| ATOM | 589 | O | PHE | A | 79 | 61.060 | 43.879 | 16.176 | 1.00 | 30.27 |
| ATOM | 590 | CB | PHE | A | 79 | 61.941 | 43.779 | 18.847 | 1.00 | 29.28 |
| ATOM | 591 | CG | PHE | A | 79 | 62.503 | 43.536 | 20.216 | 1.00 | 29.03 |
| ATOM | 592 | CD1 | PHE | A | 79 | 63.855 | 43.737 | 20.477 | 1.00 | 30.34 |

TABLE 7-continued

| ATOM | 593 | CD2 | PHE | A | 79 | 61.687 | 43.061 | 21.237 | 1.00 | 29.64 |
| --- | --- | --- | --- | --- | --- | --- | --- | --- | --- | --- |
| C | | | | | | | | | | |
| ATOM | 594 | CE1 | PHE | A | 79 | 64.387 | 43.467 | 21.741 | 1.00 | 30.52 |
| C | | | | | | | | | | |
| ATOM | 595 | CE2 | PHE | A | 79 | 62.207 | 42.786 | 22.502 | 1.00 | 30.51 |
| C | | | | | | | | | | |
| ATOM | 596 | CZ | PHE | A | 79 | 63.561 | 42.990 | 22.753 | 1.00 | 29.61 |
| C | | | | | | | | | | |
| ATOM | 597 | N | ILE | A | 80 | 60.708 | 41.656 | 16.170 | 1.00 | 31.21 |
| N | | | | | | | | | | |
| ATOM | 598 | CA | ILE | A | 80 | 59.844 | 41.659 | 14.993 | 1.00 | 30.53 |
| C | | | | | | | | | | |
| ATOM | 599 | C | ILE | A | 80 | 58.766 | 42.728 | 15.137 | 1.00 | 30.49 |
| C | | | | | | | | | | |
| ATOM | 600 | O | ILE | A | 80 | 58.047 | 42.761 | 16.143 | 1.00 | 30.23 |
| O | | | | | | | | | | |
| ATOM | 601 | CB | ILE | A | 80 | 59.172 | 40.282 | 14.809 | 1.00 | 30.87 |
| C | | | | | | | | | | |
| ATOM | 602 | CD1 | ILE | A | 80 | 60.240 | 39.187 | 14.721 | 1.00 | 30.68 |
| C | | | | | | | | | | |
| ATOM | 603 | CG2 | ILE | A | 80 | 58.303 | 40.288 | 13.561 | 1.00 | 31.61 |
| C | | | | | | | | | | |
| ATOM | 604 | CD1 | ILE | A | 80 | 61.174 | 39.319 | 13.536 | 1.00 | 30.88 |
| C | | | | | | | | | | |
| ATOM | 605 | N | PHE | A | 81 | 58.640 | 43.591 | 14.131 | 1.00 | 30.29 |
| N | | | | | | | | | | |
| ATOM | 606 | CA | PHE | A | 81 | 57.660 | 44.666 | 14.195 | 1.00 | 31.74 |
| C | | | | | | | | | | |
| ATOM | 607 | C | PHE | A | 81 | 56.216 | 44.205 | 14.385 | 1.00 | 32.15 |
| C | | | | | | | | | | |
| ATOM | 608 | O | PHE | A | 81 | 55.799 | 43.178 | 13.851 | 1.00 | 32.55 |
| O | | | | | | | | | | |
| ATOM | 609 | CB | PHE | A | 81 | 57.775 | 45.593 | 12.967 | 1.00 | 31.76 |
| C | | | | | | | | | | |
| ATOM | 610 | CG | PHE | A | 81 | 57.565 | 44.914 | 11.638 | 1.00 | 31.76 |
| C | | | | | | | | | | |
| ATOM | 611 | CD1 | PHE | A | 81 | 58.575 | 44.152 | 11.055 | 1.00 | 31.23 |
| C | | | | | | | | | | |
| ATOM | 612 | CD2 | PHE | A | 81 | 56.370 | 45.084 | 10.942 | 1.00 | 31.53 |
| C | | | | | | | | | | |
| ATOM | 613 | CE1 | PHE | A | 81 | 58.401 | 43.574 | 9.793 | 1.00 | 31.24 |
| C | | | | | | | | | | |
| ATOM | 614 | CE2 | PHE | A | 81 | 56.184 | 44.510 | 9.681 | 1.00 | 31.41 |
| C | | | | | | | | | | |
| ATOM | 615 | CZ | PHE | A | 81 | 57.202 | 43.755 | 9.106 | 1.00 | 32.04 |
| C | | | | | | | | | | |
| ATOM | 616 | N | GLY | A | 82 | 55.467 | 44.976 | 15.168 | 1.00 | 32.45 |
| N | | | | | | | | | | |
| ATOM | 617 | CA | GLY | A | 82 | 54.080 | 44.652 | 15.443 | 1.00 | 33.29 |
| C | | | | | | | | | | |
| ATOM | 618 | C | GLY | A | 82 | 53.117 | 45.479 | 14.616 | 1.00 | 34.37 |
| C | | | | | | | | | | |
| ATOM | 619 | O | GLY | A | 82 | 51.899 | 45.351 | 14.761 | 1.00 | 34.23 |
| O | | | | | | | | | | |
| ATOM | 620 | N | SER | A | 83 | 53.661 | 46.335 | 13.756 | 1.00 | 34.06 |
| N | | | | | | | | | | |
| ATOM | 621 | CA | SER | A | 83 | 52.844 | 47.173 | 12.886 | 1.00 | 34.88 |
| C | | | | | | | | | | |
| ATOM | 622 | C | SER | A | 83 | 52.470 | 46.370 | 11.645 | 1.00 | 35.53 |
| C | | | | | | | | | | |
| ATOM | 623 | O | SER | A | 83 | 52.775 | 46.745 | 10.513 | 1.00 | 34.34 |
| O | | | | | | | | | | |
| ATOM | 624 | CB | SER | A | 83 | 53.607 | 48.440 | 12.491 | 1.00 | 34.13 |
| C | | | | | | | | | | |
| ATOM | 625 | OG | SER | A | 83 | 54.875 | 48.115 | 11.961 | 1.00 | 35.16 |
| O | | | | | | | | | | |
| ATOM | 626 | N | GLN | A | 84 | 51.823 | 45.238 | 11.893 | 1.00 | 36.05 |
| N | | | | | | | | | | |
| ATOM | 627 | CA | GLN | A | 84 | 51.359 | 44.337 | 10.851 | 1.00 | 36.48 |
| C | | | | | | | | | | |
| ATOM | 628 | C | GLN | A | 84 | 50.308 | 43.459 | 11.520 | 1.00 | 36.44 |
| C | | | | | | | | | | |
| ATOM | 629 | O | GLN | A | 84 | 50.125 | 43.532 | 12.737 | 1.00 | 35.78 |
| O | | | | | | | | | | |
| ATOM | 630 | CB | GLN | A | 84 | 52.515 | 43.488 | 10.317 | 1.00 | 36.59 |
| C | | | | | | | | | | |
| ATOM | 631 | CG | GLN | A | 84 | 53.156 | 42.571 | 11.342 | 1.00 | 37.16 |
| C | | | | | | | | | | |

TABLE 7-continued

| | | | | | | | | | |
|---|---|---|---|---|---|---|---|---|---|
| ATOM | 632 | CD | GLN | A | 84 | 54.277 | 41.745 | 10.747 | 1.00 37.80 |
| C | | | | | | | | | |
| ATOM | 633 | OE1 | GLN | A | 84 | 54.114 | 41.137 | 9.689 | 1.00 38.49 |
| O | | | | | | | | | |
| ATOM | 634 | NE2 | GLN | A | 84 | 55.422 | 41.710 | 11.428 | 1.00 36.72 |
| N | | | | | | | | | |
| ATOM | 635 | N | SER | A | 85 | 49.617 | 42.634 | 10.742 | 1.00 37.40 |
| N | | | | | | | | | |
| ATOM | 636 | CA | SER | A | 85 | 48.582 | 41.775 | 11.307 | 1.00 37.95 |
| C | | | | | | | | | |
| ATOM | 637 | C | SER | A | 85 | 49.166 | 40.812 | 12.333 | 1.00 38.81 |
| C | | | | | | | | | |
| ATOM | 638 | O | SER | A | 85 | 50.351 | 40.479 | 12.283 | 1.00 39.00 |
| O | | | | | | | | | |
| ATOM | 639 | CB | SER | A | 85 | 47.886 | 40.974 | 10.205 | 1.00 37.33 |
| C | | | | | | | | | |
| ATOM | 640 | OG | SER | A | 85 | 48.700 | 39.902 | 9.768 | 1.00 38.10 |
| O | | | | | | | | | |
| ATOM | 641 | N | ILE | A | 86 | 48.325 | 40.372 | 13.262 | 1.00 38.89 |
| N | | | | | | | | | |
| ATOM | 642 | CA | ILE | A | 86 | 48.742 | 39.439 | 14.301 | 1.00 40.23 |
| C | | | | | | | | | |
| ATOM | 643 | C | ILE | A | 86 | 49.236 | 38.140 | 13.665 | 1.00 41.35 |
| C | | | | | | | | | |
| ATOM | 644 | O | ILE | A | 86 | 50.240 | 37.569 | 14.090 | 1.00 41.06 |
| O | | | | | | | | | |
| ATOM | 645 | CB | ILE | A | 86 | 47.569 | 39.127 | 15.261 | 1.00 40.08 |
| C | | | | | | | | | |
| ATOM | 646 | CG1 | ILE | A | 86 | 47.192 | 40.391 | 16.041 | 1.00 40.14 |
| C | | | | | | | | | |
| ATOM | 647 | CG2 | ILE | A | 86 | 47.945 | 37.992 | 16.203 | 1.00 39.43 |
| C | | | | | | | | | |
| ATOM | 648 | CD1 | ILE | A | 86 | 46.003 | 40.226 | 16.973 | 1.00 39.32 |
| C | | | | | | | | | |
| ATOM | 649 | N | GLU | A | 87 | 48.525 | 37.687 | 12.638 | 1.00 41.92 |
| N | | | | | | | | | |
| ATOM | 650 | CA | GLU | A | 87 | 48.877 | 36.460 | 11.932 | 1.00 42.93 |
| C | | | | | | | | | |
| ATOM | 651 | C | GLU | A | 87 | 50.228 | 36.595 | 11.230 | 1.00 41.66 |
| C | | | | | | | | | |
| ATOM | 652 | O | GLU | A | 87 | 51.057 | 35.687 | 11.272 | 1.00 41.43 |
| O | | | | | | | | | |
| ATOM | 653 | CB | GLU | A | 87 | 47.800 | 36.122 | 10.893 | 1.00 45.26 |
| C | | | | | | | | | |
| ATOM | 654 | CG | GLU | A | 87 | 46.395 | 35.876 | 11.460 | 1.00 48.53 |
| C | | | | | | | | | |
| ATOM | 655 | CD | GLU | A | 87 | 45.798 | 37.088 | 12.173 | 1.00 50.40 |
| C | | | | | | | | | |
| ATOM | 656 | OE1 | GLU | A | 87 | 45.867 | 38.211 | 11.625 | 1.00 50.61 |
| O | | | | | | | | | |
| ATOM | 657 | OE2 | GLU | A | 87 | 45.243 | 36.910 | 13.282 | 1.00 52.40 |
| O | | | | | | | | | |
| ATOM | 658 | N | SER | A | 88 | 50.439 | 37.736 | 10.585 | 1.00 40.93 |
| N | | | | | | | | | |
| ATOM | 659 | CA | SER | A | 88 | 51.677 | 37.993 | 9.857 | 1.00 41.02 |
| C | | | | | | | | | |
| ATOM | 660 | C | SER | A | 88 | 52.898 | 38.079 | 10.777 | 1.00 39.71 |
| C | | | | | | | | | |
| ATOM | 661 | O | SER | A | 88 | 53.979 | 37.595 | 10.438 | 1.00 39.05 |
| O | | | | | | | | | |
| ATOM | 662 | CB | SER | A | 88 | 51.540 | 39.292 | 9.058 | 1.00 41.43 |
| C | | | | | | | | | |
| ATOM | 663 | OG | SER | A | 88 | 52.675 | 39.507 | 8.242 | 1.00 44.62 |
| O | | | | | | | | | |
| ATOM | 664 | N | GLN | A | 89 | 52.726 | 38.701 | 11.938 | 1.00 38.95 |
| N | | | | | | | | | |
| ATOM | 665 | CA | GLN | A | 89 | 53.827 | 38.837 | 12.886 | 1.00 38.02 |
| C | | | | | | | | | |
| ATOM | 666 | C | GLN | A | 89 | 54.165 | 37.484 | 13.506 | 1.00 38.23 |
| C | | | | | | | | | |
| ATOM | 667 | O | GLN | A | 89 | 55.333 | 37.121 | 13.625 | 1.00 38.13 |
| O | | | | | | | | | |
| ATOM | 668 | CB | GLN | A | 89 | 53.465 | 39.847 | 13.984 | 1.00 36.71 |
| C | | | | | | | | | |
| ATOM | 669 | CG | GLN | A | 89 | 54.536 | 40.002 | 15.067 | 1.00 34.83 |
| C | | | | | | | | | |
| ATOM | 670 | CD | GLN | A | 89 | 54.169 | 41.044 | 16.110 | 1.00 33.42 |
| C | | | | | | | | | |

TABLE 7-continued

| ATOM | 671 | OE1 | GLN | A | 89 | 52.998 | 41.217 | 16.443 | 1.00 | 32.85 |
| --- | --- | --- | --- | --- | --- | --- | --- | --- | --- | --- |
| O | | | | | | | | | | |
| ATOM | 672 | NE2 | GLN | A | 89 | 55.175 | 41.732 | 16.644 | 1.00 | 31.51 |
| N | | | | | | | | | | |
| ATOM | 673 | N | ALA | A | 90 | 53.137 | 36.734 | 13.890 | 1.00 | 38.39 |
| N | | | | | | | | | | |
| ATOM | 674 | CA | ALA | A | 90 | 53.343 | 35.419 | 14.487 | 1.00 | 38.40 |
| C | | | | | | | | | | |
| ATOM | 675 | C | ALA | A | 90 | 54.050 | 34.494 | 13.500 | 1.00 | 38.83 |
| C | | | | | | | | | | |
| ATOM | 676 | O | ALA | A | 90 | 54.847 | 33.639 | 13.894 | 1.00 | 38.82 |
| O | | | | | | | | | | |
| ATOM | 677 | CB | ALA | A | 90 | 52.006 | 34.822 | 14.908 | 1.00 | 38.88 |
| C | | | | | | | | | | |
| ATOM | 678 | N | ALA | A | 91 | 53.762 | 34.670 | 12.215 | 1.00 | 39.13 |
| N | | | | | | | | | | |
| ATOM | 679 | CA | ALA | A | 91 | 54.383 | 33.849 | 11.186 | 1.00 | 39.02 |
| C | | | | | | | | | | |
| ATOM | 680 | C | ALA | A | 91 | 55.893 | 34.091 | 11.157 | 1.00 | 39.29 |
| C | | | | | | | | | | |
| ATOM | 681 | O | ALA | A | 91 | 56.673 | 33.150 | 11.035 | 1.00 | 38.36 |
| O | | | | | | | | | | |
| ATOM | 682 | CB | ALA | A | 91 | 53.767 | 34.157 | 9.820 | 1.00 | 39.60 |
| C | | | | | | | | | | |
| ATOM | 683 | N | MET | A | 92 | 56.306 | 35.351 | 11.272 | 1.00 | 38.81 |
| N | | | | | | | | | | |
| ATOM | 684 | CA | MET | A | 92 | 57.733 | 35.670 | 11.263 | 1.00 | 38.78 |
| C | | | | | | | | | | |
| ATOM | 685 | C | MET | A | 92 | 58.426 | 35.071 | 12.480 | 1.00 | 37.97 |
| C | | | | | | | | | | |
| ATOM | 686 | O | MET | A | 92 | 59.518 | 34.516 | 12.369 | 1.00 | 38.17 |
| O | | | | | | | | | | |
| ATOM | 687 | CB | MET | A | 92 | 57.959 | 37.184 | 11.251 | 1.00 | 38.46 |
| C | | | | | | | | | | |
| ATOM | 688 | CG | MET | A | 92 | 57.461 | 37.876 | 10.009 | 1.00 | 39.51 |
| C | | | | | | | | | | |
| ATOM | 689 | SD | MET | A | 92 | 57.978 | 39.598 | 9.950 | 1.00 | 38.93 |
| S | | | | | | | | | | |
| ATOM | 690 | CE | MET | A | 92 | 57.344 | 40.065 | 8.337 | 1.00 | 39.38 |
| C | | | | | | | | | | |
| ATOM | 691 | N | VAL | A | 93 | 57.789 | 35.193 | 13.641 | 1.00 | 37.66 |
| N | | | | | | | | | | |
| ATOM | 692 | CA | VAL | A | 93 | 58.348 | 34.649 | 14.872 | 1.00 | 37.49 |
| C | | | | | | | | | | |
| ATOM | 693 | C | VAL | A | 93 | 58.501 | 33.136 | 14.725 | 1.00 | 38.78 |
| C | | | | | | | | | | |
| ATOM | 694 | O | VAL | A | 93 | 59.547 | 32.572 | 15.042 | 1.00 | 37.88 |
| O | | | | | | | | | | |
| ATOM | 695 | CB | VAL | A | 93 | 57.434 | 34.951 | 16.082 | 1.00 | 37.04 |
| C | | | | | | | | | | |
| ATOM | 696 | CG1 | VAL | A | 93 | 57.888 | 34.152 | 17.294 | 1.00 | 36.02 |
| C | | | | | | | | | | |
| ATOM | 697 | CG2 | VAL | A | 93 | 57.460 | 36.443 | 16.394 | 1.00 | 36.04 |
| C | | | | | | | | | | |
| ATOM | 698 | N | HIS | A | 94 | 57.451 | 32.486 | 14.231 | 1.00 | 39.37 |
| N | | | | | | | | | | |
| ATOM | 699 | CA | HIS | A | 94 | 57.474 | 31.039 | 14.040 | 1.00 | 39.99 |
| C | | | | | | | | | | |
| ATOM | 700 | C | HIS | A | 94 | 58.616 | 30.632 | 13.110 | 1.00 | 39.10 |
| C | | | | | | | | | | |
| ATOM | 701 | O | HIS | A | 94 | 59.331 | 29.663 | 13.378 | 1.00 | 39.42 |
| O | | | | | | | | | | |
| ATOM | 702 | CB | HIS | A | 94 | 56.144 | 30.560 | 13.449 | 1.00 | 41.81 |
| C | | | | | | | | | | |
| ATOM | 703 | CG | HIS | A | 94 | 56.048 | 29.072 | 13.312 | 1.00 | 43.35 |
| C | | | | | | | | | | |
| ATOM | 704 | ND1 | HIS | A | 94 | 55.746 | 28.244 | 14.372 | 1.00 | 44.55 |
| N | | | | | | | | | | |
| ATOM | 705 | CD2 | HIS | A | 94 | 56.249 | 28.261 | 12.247 | 1.00 | 44.14 |
| C | | | | | | | | | | |
| ATOM | 706 | CE1 | HIS | A | 94 | 55.765 | 26.987 | 13.966 | 1.00 | 44.38 |
| C | | | | | | | | | | |
| ATOM | 707 | NE2 | HIS | A | 94 | 56.069 | 26.970 | 12.681 | 1.00 | 44.90 |
| N | | | | | | | | | | |
| ATOM | 708 | N | ALA | A | 95 | 58.784 | 31.377 | 12.022 | 1.00 | 38.67 |
| N | | | | | | | | | | |
| ATOM | 709 | CA | ALA | A | 95 | 59.828 | 31.093 | 11.043 | 1.00 | 38.33 |
| C | | | | | | | | | | |

TABLE 7-continued

| | | | | | | | | | |
|---|---|---|---|---|---|---|---|---|---|
| ATOM C | 710 | C | ALA | A | 95 | 61.224 | 31.175 | 11.648 | 1.00 38.74 |
| ATOM O | 711 | O | ALA | A | 95 | 62.107 | 30.393 | 11.299 | 1.00 37.70 |
| ATOM C | 712 | CB | ALA | A | 95 | 59.717 | 32.055 | 9.866 | 1.00 38.60 |
| ATOM N | 713 | N | VAL | A | 96 | 61.429 | 32.126 | 12.554 | 1.00 38.74 |
| ATOM C | 714 | CA | VAL | A | 96 | 62.732 | 32.279 | 13.186 | 1.00 38.66 |
| ATOM C | 715 | C | VAL | A | 96 | 62.972 | 31.145 | 14.179 | 1.00 38.92 |
| ATOM O | 716 | O | VAL | A | 96 | 64.054 | 30.558 | 14.212 | 1.00 39.96 |
| ATOM C | 717 | CB | VAL | A | 96 | 62.843 | 33.640 | 13.920 | 1.00 38.15 |
| ATOM C | 718 | CG1 | VAL | A | 96 | 64.174 | 33.738 | 14.642 | 1.00 37.72 |
| ATOM C | 719 | CG2 | VAL | A | 96 | 62.709 | 34.776 | 12.919 | 1.00 38.27 |
| ATOM N | 720 | N | LYS | A | 97 | 61.958 | 30.828 | 14.976 | 1.00 39.73 |
| ATOM C | 721 | CA | LYS | A | 97 | 62.081 | 29.767 | 15.969 | 1.00 40.96 |
| ATOM C | 722 | C | LYS | A | 97 | 62.273 | 28.383 | 15.351 | 1.00 42.44 |
| ATOM O | 723 | O | LYS | A | 97 | 62.860 | 27.502 | 15.977 | 1.00 42.21 |
| ATOM C | 724 | CB | LYS | A | 97 | 60.856 | 29.750 | 16.892 | 1.00 40.24 |
| ATOM C | 725 | CG | LYS | A | 97 | 60.659 | 31.021 | 17.716 | 1.00 39.72 |
| ATOM C | 726 | CD | LYS | A | 97 | 61.884 | 31.343 | 18.578 | 1.00 38.30 |
| ATOM C | 727 | CE | LYS | A | 97 | 62.148 | 30.271 | 19.627 | 1.00 37.68 |
| ATOM N | 728 | NZ | LYS | A | 97 | 63.372 | 30.567 | 20.429 | 1.00 37.01 |
| ATOM N | 729 | N | ASN | A | 98 | 61.783 | 28.187 | 14.129 | 1.00 44.02 |
| ATOM C | 730 | CA | ASN | A | 98 | 61.917 | 26.886 | 13.474 | 1.00 46.56 |
| ATOM C | 731 | C | ASN | A | 98 | 62.802 | 26.915 | 12.232 | 1.00 47.43 |
| ATOM O | 732 | O | ASN | A | 98 | 62.605 | 26.126 | 11.307 | 1.00 47.95 |
| ATOM C | 733 | CB | ASN | A | 98 | 60.537 | 26.336 | 13.096 | 1.00 47.77 |
| ATOM C | 734 | CG | ASN | A | 98 | 59.630 | 26.158 | 14.297 | 1.00 49.18 |
| ATOM O | 735 | OD1 | ASN | A | 98 | 59.106 | 27.127 | 14.843 | 1.00 50.44 |
| ATOM N | 736 | ND2 | ASN | A | 98 | 59.447 | 24.912 | 14.721 | 1.00 50.23 |
| ATOM N | 737 | N | PHE | A | 99 | 63.784 | 27.811 | 12.215 | 1.00 48.01 |
| ATOM C | 738 | CA | PHE | A | 99 | 64.676 | 27.927 | 11.068 | 1.00 48.77 |
| ATOM C | 739 | C | PHE | A | 99 | 65.630 | 26.745 | 10.914 | 1.00 49.32 |
| ATOM O | 740 | O | PHE | A | 99 | 66.000 | 26.386 | 9.798 | 1.00 49.30 |
| ATOM C | 741 | CB | PHE | A | 99 | 65.496 | 29.214 | 11.161 | 1.00 48.62 |
| ATOM C | 742 | CG | PHE | A | 99 | 66.281 | 29.521 | 9.916 | 1.00 48.84 |
| ATOM C | 743 | CD1 | PHE | A | 99 | 65.631 | 29.895 | 8.745 | 1.00 48.95 |
| ATOM C | 744 | CD2 | PHE | A | 99 | 67.669 | 29.439 | 9.914 | 1.00 49.12 |
| ATOM C | 745 | CE1 | PHE | A | 99 | 66.353 | 30.184 | 7.590 | 1.00 49.40 |
| ATOM C | 746 | CE2 | PHE | A | 99 | 68.399 | 29.726 | 8.765 | 1.00 48.92 |
| ATOM C | 747 | CZ | PHE | A | 99 | 67.741 | 30.100 | 7.602 | 1.00 49.64 |
| ATOM N | 748 | N | LYS | A | 100 | 66.032 | 26.147 | 12.031 | 1.00 49.95 |

TABLE 7-continued

| ATOM | 749 | CA | LYS | A | 100 | 66.957 | 25.017 | 11.992 | 1.00 | 51.02 |
| --- | --- | --- | --- | --- | --- | --- | --- | --- | --- | --- |
| C | | | | | | | | | | |
| ATOM | 750 | C | LYS | A | 100 | 66.268 | 23.675 | 11.766 | 1.00 | 51.54 |
| C | | | | | | | | | | |
| ATOM | 751 | O | LYS | A | 100 | 66.911 | 22.628 | 11.824 | 1.00 | 51.71 |
| O | | | | | | | | | | |
| ATOM | 752 | CB | LYS | A | 100 | 67.771 | 24.953 | 13.287 | 1.00 | 51.20 |
| C | | | | | | | | | | |
| ATOM | 753 | CG | LYS | A | 100 | 68.664 | 26.160 | 13.528 | 1.00 | 51.10 |
| C | | | | | | | | | | |
| ATOM | 754 | CD | LYS | A | 100 | 69.464 | 25.986 | 14.808 | 1.00 | 51.19 |
| C | | | | | | | | | | |
| ATOM | 755 | CE | LYS | A | 100 | 70.428 | 27.136 | 15.032 | 1.00 | 50.48 |
| C | | | | | | | | | | |
| ATOM | 756 | NZ | LYS | A | 100 | 71.198 | 26.947 | 16.290 | 1.00 | 50.06 |
| N | | | | | | | | | | |
| ATOM | 757 | N | ALA | A | 101 | 64.965 | 23.708 | 11.508 | 1.00 | 52.15 |
| N | | | | | | | | | | |
| ATOM | 758 | CA | ALA | A | 101 | 64.201 | 22.486 | 11.272 | 1.00 | 52.52 |
| C | | | | | | | | | | |
| ATOM | 759 | C | ALA | A | 101 | 64.673 | 21.777 | 10.003 | 1.00 | 52.76 |
| C | | | | | | | | | | |
| ATOM | 760 | O | ALA | A | 101 | 64.913 | 22.413 | 8.975 | 1.00 | 52.56 |
| O | | | | | | | | | | |
| ATOM | 761 | CB | ALA | A | 101 | 62.717 | 22.811 | 11.168 | 1.00 | 52.86 |
| C | | | | | | | | | | |
| ATOM | 762 | N | HIS | A | 222 | 79.141 | 30.211 | 17.140 | 1.00 | 53.16 |
| N | | | | | | | | | | |
| ATOM | 763 | CA | HIS | A | 222 | 79.966 | 30.550 | 18.294 | 1.00 | 53.11 |
| C | | | | | | | | | | |
| ATOM | 764 | C | HIS | A | 222 | 79.233 | 31.452 | 19.280 | 1.00 | 51.53 |
| C | | | | | | | | | | |
| ATOM | 765 | O | HIS | A | 222 | 79.099 | 31.117 | 20.458 | 1.00 | 51.93 |
| O | | | | | | | | | | |
| ATOM | 766 | CB | HIS | A | 222 | 81.257 | 31.242 | 17.844 | 1.00 | 55.36 |
| C | | | | | | | | | | |
| ATOM | 767 | CG | HIS | A | 222 | 82.390 | 30.299 | 17.582 | 1.00 | 57.46 |
| C | | | | | | | | | | |
| ATOM | 768 | ND1 | HIS | A | 222 | 82.940 | 29.508 | 18.568 | 1.00 | 58.71 |
| N | | | | | | | | | | |
| ATOM | 769 | CD2 | HIS | A | 222 | 83.087 | 30.032 | 16.452 | 1.00 | 58.36 |
| C | | | | | | | | | | |
| ATOM | 770 | CE1 | HIS | A | 222 | 83.928 | 28.794 | 18.056 | 1.00 | 59.17 |
| C | | | | | | | | | | |
| ATOM | 771 | NE2 | HIS | A | 222 | 84.038 | 29.093 | 16.774 | 1.00 | 59.10 |
| N | | | | | | | | | | |
| ATOM | 772 | N | ASN | A | 223 | 78.766 | 32.597 | 18.799 | 1.00 | 49.32 |
| N | | | | | | | | | | |
| ATOM | 773 | CA | ASN | A | 223 | 78.056 | 33.540 | 19.653 | 1.00 | 47.79 |
| C | | | | | | | | | | |
| ATOM | 774 | C | ASN | A | 223 | 76.565 | 33.582 | 19.357 | 1.00 | 45.63 |
| C | | | | | | | | | | |
| ATOM | 775 | O | ASN | A | 223 | 75.905 | 34.587 | 19.624 | 1.00 | 44.59 |
| O | | | | | | | | | | |
| ATOM | 776 | CB | ASN | A | 223 | 78.643 | 34.945 | 19.496 | 1.00 | 49.26 |
| C | | | | | | | | | | |
| ATOM | 777 | CG | ASN | A | 223 | 80.075 | 35.035 | 19.981 | 1.00 | 50.67 |
| C | | | | | | | | | | |
| ATOM | 778 | OD1 | ASN | A | 223 | 80.360 | 34.793 | 21.154 | 1.00 | 51.68 |
| O | | | | | | | | | | |
| ATOM | 779 | ND2 | ASN | A | 223 | 80.986 | 35.387 | 19.079 | 1.00 | 52.28 |
| N | | | | | | | | | | |
| ATOM | 780 | N | GLU | A | 224 | 76.029 | 32.498 | 18.807 | 1.00 | 43.13 |
| N | | | | | | | | | | |
| ATOM | 781 | CA | GLU | A | 224 | 74.606 | 32.467 | 18.503 | 1.00 | 41.15 |
| C | | | | | | | | | | |
| ATOM | 782 | C | GLU | A | 224 | 73.799 | 32.540 | 19.786 | 1.00 | 38.97 |
| C | | | | | | | | | | |
| ATOM | 783 | O | GLU | A | 224 | 74.153 | 31.927 | 20.792 | 1.00 | 38.56 |
| O | | | | | | | | | | |
| ATOM | 784 | CB | GLU | A | 224 | 74.227 | 31.193 | 17.739 | 1.00 | 42.39 |
| C | | | | | | | | | | |
| ATOM | 785 | CG | GLU | A | 224 | 74.553 | 29.893 | 18.462 | 1.00 | 44.37 |
| C | | | | | | | | | | |
| ATOM | 786 | CD | GLU | A | 224 | 73.820 | 28.693 | 17.876 | 1.00 | 45.22 |
| C | | | | | | | | | | |
| ATOM | 787 | OE1 | GLU | A | 224 | 73.539 | 28.698 | 16.658 | 1.00 | 45.16 |
| O | | | | | | | | | | |

TABLE 7-continued

| | | | | | | | | | |
|---|---|---|---|---|---|---|---|---|---|
| ATOM | 788 | OE2 | GLU | A | 224 | 73.535 | 27.741 | 18.632 | 1.00 45.27 |
| O | | | | | | | | | |
| ATOM | 789 | N | LEU | A | 225 | 72.718 | 33.309 | 19.747 | 1.00 37.03 |
| N | | | | | | | | | |
| ATOM | 790 | CA | LEU | A | 225 | 71.842 | 33.454 | 20.897 | 1.00 36.33 |
| C | | | | | | | | | |
| ATOM | 791 | C | LEU | A | 225 | 70.674 | 32.500 | 20.682 | 1.00 36.34 |
| C | | | | | | | | | |
| ATOM | 792 | O | LEU | A | 225 | 69.849 | 32.710 | 19.792 | 1.00 34.87 |
| O | | | | | | | | | |
| ATOM | 793 | CB | LEU | A | 225 | 71.333 | 34.891 | 20.999 | 1.00 35.11 |
| C | | | | | | | | | |
| ATOM | 794 | CG | LEU | A | 225 | 70.432 | 35.181 | 22.200 | 1.00 34.22 |
| C | | | | | | | | | |
| ATOM | 795 | CD1 | LEU | A | 225 | 71.185 | 34.882 | 23.490 | 1.00 34.98 |
| C | | | | | | | | | |
| ATOM | 796 | CD2 | LEU | A | 225 | 69.981 | 36.633 | 22.161 | 1.00 33.29 |
| C | | | | | | | | | |
| ATOM | 797 | N | VAL | A | 226 | 70.608 | 31.453 | 21.500 | 1.00 36.84 |
| N | | | | | | | | | |
| ATOM | 798 | CA | VAL | A | 226 | 69.557 | 30.450 | 21.369 | 1.00 37.69 |
| C | | | | | | | | | |
| ATOM | 799 | C | VAL | A | 226 | 68.924 | 30.035 | 22.693 | 1.00 38.39 |
| C | | | | | | | | | |
| ATOM | 800 | O | VAL | A | 226 | 69.410 | 30.390 | 23.769 | 1.00 38.54 |
| O | | | | | | | | | |
| ATOM | 801 | CB | VAL | A | 226 | 70.108 | 29.174 | 20.702 | 1.00 37.69 |
| C | | | | | | | | | |
| ATOM | 802 | CG1 | VAL | A | 226 | 70.616 | 29.486 | 19.306 | 1.00 36.12 |
| C | | | | | | | | | |
| ATOM | 803 | CG2 | VAL | A | 226 | 71.221 | 28.589 | 21.560 | 1.00 38.03 |
| C | | | | | | | | | |
| ATOM | 804 | N | ASP | A | 227 | 67.832 | 29.280 | 22.600 | 1.00 39.17 |
| N | | | | | | | | | |
| ATOM | 805 | CA | ASP | A | 227 | 67.143 | 28.782 | 23.780 | 1.00 39.84 |
| C | | | | | | | | | |
| ATOM | 806 | C | ASP | A | 227 | 67.697 | 27.398 | 24.129 | 1.00 41.46 |
| C | | | | | | | | | |
| ATOM | 807 | O | ASP | A | 227 | 68.671 | 26.944 | 23.526 | 1.00 41.37 |
| O | | | | | | | | | |
| ATOM | 808 | CB | ASP | A | 227 | 65.625 | 28.702 | 23.543 | 1.00 39.27 |
| C | | | | | | | | | |
| ATOM | 809 | CG | ASP | A | 227 | 65.253 | 27.900 | 22.299 | 1.00 38.93 |
| C | | | | | | | | | |
| ATOM | 810 | OD1 | ASP | A | 227 | 65.938 | 26.903 | 21.987 | 1.00 38.27 |
| O | | | | | | | | | |
| ATOM | 811 | OD2 | ASP | A | 227 | 64.253 | 28.259 | 21.639 | 1.00 38.73 |
| O | | | | | | | | | |
| ATOM | 812 | N | SER | A | 228 | 67.073 | 26.733 | 25.096 | 1.00 42.85 |
| N | | | | | | | | | |
| ATOM | 813 | CA | SER | A | 228 | 67.510 | 25.408 | 25.535 | 1.00 44.79 |
| C | | | | | | | | | |
| ATOM | 814 | C | SER | A | 228 | 67.415 | 24.358 | 24.428 | 1.00 45.78 |
| C | | | | | | | | | |
| ATOM | 815 | O | SER | A | 228 | 68.052 | 23.305 | 24.502 | 1.00 46.20 |
| O | | | | | | | | | |
| ATOM | 816 | CB | SER | A | 228 | 66.680 | 24.961 | 26.740 | 1.00 44.77 |
| C | | | | | | | | | |
| ATOM | 817 | OG | SER | A | 228 | 65.301 | 24.915 | 26.413 | 1.00 45.35 |
| O | | | | | | | | | |
| ATOM | 818 | N | GLN | A | 229 | 66.618 | 24.653 | 23.405 | 1.00 46.62 |
| N | | | | | | | | | |
| ATOM | 819 | CA | GLN | A | 229 | 66.433 | 23.748 | 22.278 | 1.00 47.22 |
| C | | | | | | | | | |
| ATOM | 820 | C | GLN | A | 229 | 67.327 | 24.128 | 21.102 | 1.00 46.93 |
| C | | | | | | | | | |
| ATOM | 821 | O | GLN | A | 229 | 67.181 | 23.595 | 20.000 | 1.00 46.64 |
| O | | | | | | | | | |
| ATOM | 822 | CB | GLN | A | 229 | 64.967 | 23.756 | 21.841 | 1.00 48.67 |
| C | | | | | | | | | |
| ATOM | 823 | CG | GLN | A | 229 | 64.029 | 23.082 | 22.828 | 1.00 51.08 |
| C | | | | | | | | | |
| ATOM | 824 | CD | GLN | A | 229 | 62.568 | 23.334 | 22.512 | 1.00 52.25 |
| C | | | | | | | | | |
| ATOM | 825 | OE1 | GLN | A | 229 | 62.036 | 24.405 | 22.800 | 1.00 53.70 |
| O | | | | | | | | | |
| ATOM | 826 | NE2 | GLN | A | 229 | 61.913 | 22.349 | 21.907 | 1.00 53.63 |
| N | | | | | | | | | |

TABLE 7-continued

| | | | | | | | | | |
|---|---|---|---|---|---|---|---|---|---|
| ATOM | 827 | N | LYS | A | 230 | 68.249 | 25.055 | 21.346 | 1.00 46.17 |
| ATOM | 828 | CA | LYS | A | 230 | 69.188 | 25.512 | 20.324 | 1.00 45.18 |
| ATOM | 829 | C | LYS | A | 230 | 68.553 | 26.317 | 19.195 | 1.00 43.43 |
| ATOM | 830 | O | LYS | A | 230 | 69.146 | 26.471 | 18.126 | 1.00 44.02 |
| ATOM | 831 | CB | LYS | A | 230 | 69.950 | 24.318 | 19.742 | 1.00 46.95 |
| ATOM | 832 | CG | LYS | A | 230 | 70.781 | 23.563 | 20.771 | 1.00 48.94 |
| ATOM | 833 | CD | LYS | A | 230 | 71.905 | 24.431 | 21.332 | 1.00 51.11 |
| ATOM | 834 | CB | LYS | A | 230 | 72.929 | 24.788 | 20.257 | 1.00 52.17 |
| ATOM | 835 | NZ | LYS | A | 230 | 74.049 | 25.620 | 20.790 | 1.00 53.38 |
| ATOM | 836 | N | ARG | A | 231 | 67.353 | 26.836 | 19.429 | 1.00 41.91 |
| ATOM | 837 | CA | ARG | A | 231 | 66.671 | 27.648 | 18.424 | 1.00 40.32 |
| ATOM | 838 | C | ARG | A | 231 | 66.997 | 29.116 | 18.691 | 1.00 38.38 |
| ATOM | 839 | O | ARG | A | 231 | 67.125 | 29.528 | 19.843 | 1.00 36.84 |
| ATOM | 840 | CB | ARG | A | 231 | 65.159 | 27.435 | 18.504 | 1.00 42.41 |
| ATOM | 841 | CG | ARG | A | 231 | 64.729 | 25.994 | 18.290 | 1.00 45.13 |
| ATOM | 842 | CD | ARG | A | 231 | 63.663 | 25.608 | 19.290 | 1.00 47.63 |
| ATOM | 843 | NE | ARG | A | 231 | 62.397 | 26.291 | 19.050 | 1.00 50.64 |
| ATOM | 844 | CZ | ARG | A | 231 | 61.549 | 26.636 | 20.013 | 1.00 51.82 |
| ATOM | 845 | NH1 | ARG | A | 231 | 61.842 | 26.371 | 21.277 | 1.00 53.05 |
| ATOM | 846 | NH2 | ARG | A | 231 | 60.401 | 27.230 | 19.712 | 1.00 52.91 |
| ATOM | 847 | N | TYR | A | 232 | 67.140 | 29.896 | 17.627 | 1.00 36.74 |
| ATOM | 848 | CA | TYR | A | 232 | 67.451 | 31.313 | 17.763 | 1.00 35.61 |
| ATOM | 849 | C | TYR | A | 232 | 66.388 | 32.035 | 18.579 | 1.00 34.70 |
| ATOM | 850 | O | TYR | A | 232 | 65.193 | 31.755 | 18.453 | 1.00 33.91 |
| ATOM | 851 | CB | TYR | A | 232 | 67.538 | 31.976 | 16.390 | 1.00 36.14 |
| ATOM | 852 | CG | TYR | A | 232 | 68.648 | 31.455 | 15.517 | 1.00 37.40 |
| ATOM | 853 | CD1 | TYR | A | 232 | 69.973 | 31.464 | 15.955 | 1.00 37.55 |
| ATOM | 854 | CD2 | TYR | A | 232 | 68.377 | 30.966 | 14.241 | 1.00 38.07 |
| ATOM | 855 | CE1 | TYR | A | 232 | 71.003 | 30.996 | 15.136 | 1.00 39.02 |
| ATOM | 856 | CE2 | TYR | A | 232 | 69.396 | 30.498 | 13.419 | 1.00 39.05 |
| ATOM | 857 | CZ | TYR | A | 232 | 70.703 | 30.516 | 13.870 | 1.00 39.19 |
| ATOM | 858 | OH | TYR | A | 232 | 71.704 | 30.060 | 13.045 | 1.00 40.49 |
| ATOM | 859 | N | LEU | A | 233 | 66.823 | 32.964 | 19.420 | 1.00 33.09 |
| ATOM | 860 | CA | LEU | A | 233 | 65.877 | 33.726 | 20.214 | 1.00 32.70 |
| ATOM | 861 | C | LEU | A | 233 | 65.359 | 34.854 | 19.338 | 1.00 31.76 |
| ATOM | 862 | O | LEU | A | 233 | 66.051 | 35.321 | 18.431 | 1.00 32.09 |
| ATOM | 863 | CB | LEU | A | 233 | 66.541 | 34.310 | 21.467 | 1.00 32.69 |
| ATOM | 864 | CG | LEU | A | 233 | 67.114 | 33.357 | 22.522 | 1.00 33.44 |
| ATOM | 865 | CD1 | LEU | A | 233 | 67.532 | 34.178 | 23.738 | 1.00 33.23 |

TABLE 7-continued

| ATOM | 866 | CD2 | LEU | A | 233 | 66.084 | 32.316 | 22.936 | 1.00 | 33.22 | C |
| --- | --- | --- | --- | --- | --- | --- | --- | --- | --- | --- | --- |
| ATOM | 867 | N | VAL | A | 234 | 64.132 | 35.281 | 19.598 | 1.00 | 32.10 | N |
| ATOM | 868 | CA | VAL | A | 234 | 63.539 | 36.365 | 18.839 | 1.00 | 31.38 | C |
| ATOM | 869 | C | VAL | A | 234 | 62.535 | 37.088 | 19.723 | 1.00 | 30.84 | C |
| ATOM | 870 | O | VAL | A | 234 | 61.919 | 36.487 | 20.601 | 1.00 | 30.80 | O |
| ATOM | 871 | CB | VAL | A | 234 | 62.832 | 35.845 | 17.560 | 1.00 | 31.94 | C |
| ATOM | 872 | CG1 | VAL | A | 234 | 61.608 | 35.011 | 17.930 | 1.00 | 31.25 | C |
| ATOM | 873 | CG2 | VAL | A | 234 | 62.448 | 37.013 | 16.672 | 1.00 | 30.99 | C |
| ATOM | 874 | N | GLY | A | 235 | 62.400 | 38.391 | 19.508 | 1.00 | 30.91 | N |
| ATOM | 875 | CA | GLY | A | 235 | 61.456 | 39.164 | 20.286 | 1.00 | 30.22 | C |
| ATOM | 876 | C | GLY | A | 235 | 60.382 | 39.673 | 19.349 | 1.00 | 29.78 | C |
| ATOM | 877 | O | GLY | A | 235 | 60.501 | 39.517 | 18.136 | 1.00 | 29.75 | O |
| ATOM | 878 | N | ALA | A | 236 | 59.336 | 40.276 | 19.904 | 1.00 | 29.91 | N |
| ATOM | 879 | CA | ALA | A | 236 | 58.255 | 40.811 | 19.093 | 1.00 | 29.86 | C |
| ATOM | 880 | C | ALA | A | 236 | 57.639 | 42.027 | 19.774 | 1.00 | 29.27 | C |
| ATOM | 881 | O | ALA | A | 236 | 57.439 | 42.037 | 20.986 | 1.00 | 29.23 | O |
| ATOM | 882 | CB | ALA | A | 236 | 57.192 | 39.741 | 18.868 | 1.00 | 30.79 | C |
| ATOM | 883 | N | GLY | A | 237 | 57.345 | 43.054 | 18.987 | 1.00 | 29.87 | N |
| ATOM | 884 | CA | GLY | A | 237 | 56.745 | 44.249 | 19.544 | 1.00 | 29.77 | C |
| ATOM | 885 | C | GLY | A | 237 | 55.242 | 44.109 | 19.649 | 1.00 | 30.45 | C |
| ATOM | 886 | O | GLY | A | 237 | 54.626 | 43.420 | 18.839 | 1.00 | 30.39 | O |
| ATOM | 887 | N | ILE | A | 238 | 54.650 | 44.744 | 20.656 | 1.00 | 29.85 | N |
| ATOM | 888 | CA | ILE | A | 238 | 53.206 | 44.703 | 20.835 | 1.00 | 30.46 | C |
| ATOM | 889 | C | ILE | A | 238 | 52.708 | 46.115 | 21.130 | 1.00 | 31.10 | C |
| ATOM | 890 | O | ILE | A | 238 | 53.493 | 47.003 | 21.470 | 1.00 | 30.41 | O |
| ATOM | 891 | CB | ILE | A | 238 | 52.788 | 43.767 | 22.001 | 1.00 | 29.94 | C |
| ATOM | 892 | CG1 | ILE | A | 238 | 53.310 | 44.313 | 23.333 | 1.00 | 30.64 | C |
| ATOM | 893 | CG2 | ILE | A | 238 | 53.322 | 42.357 | 21.758 | 1.00 | 29.80 | C |
| ATOM | 894 | CD1 | ILE | A | 238 | 52.808 | 43.550 | 24.556 | 1.00 | 31.03 | C |
| ATOM | 895 | N | ASN | A | 239 | 51.406 | 46.328 | 20.980 | 1.00 | 31.30 | N |
| ATOM | 896 | CA | ASN | A | 239 | 50.825 | 47.632 | 21.249 | 1.00 | 30.86 | C |
| ATOM | 897 | C | ASN | A | 239 | 49.859 | 47.518 | 22.419 | 1.00 | 31.81 | C |
| ATOM | 898 | O | ASN | A | 239 | 49.535 | 46.416 | 22.862 | 1.00 | 30.42 | O |
| ATOM | 899 | CB | ASN | A | 239 | 50.108 | 48.171 | 20.006 | 1.00 | 31.76 | C |
| ATOM | 900 | CG | ASN | A | 239 | 49.028 | 47.231 | 19.495 | 1.00 | 31.45 | C |
| ATOM | 901 | OD1 | ASN | A | 239 | 48.019 | 47.004 | 20.160 | 1.00 | 32.62 | O |
| ATOM | 902 | ND2 | ASN | A | 239 | 49.240 | 46.678 | 18.309 | 1.00 | 32.41 | N |
| ATOM | 903 | N | THR | A | 240 | 49.406 | 48.660 | 22.921 | 1.00 | 32.10 | N |
| ATOM | 904 | CA | THR | A | 240 | 48.494 | 48.686 | 24.054 | 1.00 | 32.56 | C |

TABLE 7-continued

| ATOM | 905 | C | THR | A | 240 | 47.025 | 48.523 | 23.648 | 1.00 | 34.33 |
| --- | --- | --- | --- | --- | --- | --- | --- | --- | --- | --- |
| ATOM | 906 | O | THR | A | 240 | 46.130 | 48.681 | 24.477 | 1.00 | 33.93 |
| ATOM | 907 | CB | THR | A | 240 | 48.653 | 50.004 | 24.831 | 1.00 | 32.45 |
| ATOM | 908 | OG1 | THR | A | 240 | 48.432 | 51.107 | 23.941 | 1.00 | 31.46 |
| ATOM | 909 | CG2 | THR | A | 240 | 50.065 | 50.112 | 25.418 | 1.00 | 31.19 |
| ATOM | 910 | N | ARG | A | 241 | 46.787 | 48.179 | 22.385 | 1.00 | 35.96 |
| ATOM | 911 | CA | ARG | A | 241 | 45.426 | 48.032 | 21.873 | 1.00 | 39.04 |
| ATOM | 912 | C | ARG | A | 241 | 44.919 | 46.596 | 21.719 | 1.00 | 39.35 |
| ATOM | 913 | O | ARG | A | 241 | 43.981 | 46.188 | 22.406 | 1.00 | 40.01 |
| ATOM | 914 | CB | ARG | A | 241 | 45.313 | 48.743 | 20.522 | 1.00 | 41.18 |
| ATOM | 915 | CG | ARG | A | 241 | 45.852 | 50.167 | 20.516 | 1.00 | 45.22 |
| ATOM | 916 | CD | ARG | A | 241 | 44.809 | 51.195 | 20.920 | 1.00 | 48.22 |
| ATOM | 917 | NE | ARG | A | 241 | 43.702 | 51.247 | 19.968 | 1.00 | 50.77 |
| ATOM | 918 | CZ | ARG | A | 241 | 42.962 | 52.329 | 19.735 | 1.00 | 52.50 |
| ATOM | 919 | NH1 | ARG | A | 241 | 43.211 | 53.461 | 20.383 | 1.00 | 52.88 |
| ATOM | 920 | NH2 | ARG | A | 241 | 41.971 | 52.279 | 18.853 | 1.00 | 52.52 |
| ATOM | 921 | N | ASP | A | 242 | 45.532 | 45.836 | 20.816 | 1.00 | 39.54 |
| ATOM | 922 | CA | ASP | A | 242 | 45.105 | 44.459 | 20.557 | 1.00 | 40.21 |
| ATOM | 923 | C | ASP | A | 242 | 45.938 | 43.371 | 21.230 | 1.00 | 39.85 |
| ATOM | 924 | O | ASP | A | 242 | 46.016 | 42.253 | 20.723 | 1.00 | 40.56 |
| ATOM | 925 | CB | ASP | A | 242 | 45.087 | 44.192 | 19.045 | 1.00 | 40.36 |
| ATOM | 926 | CG | ASP | A | 242 | 46.461 | 44.345 | 18.399 | 1.00 | 40.93 |
| ATOM | 927 | OD1 | ASP | A | 242 | 47.480 | 44.013 | 19.045 | 1.00 | 41.17 |
| ATOM | 928 | OD2 | ASP | A | 242 | 46.526 | 44.781 | 17.230 | 1.00 | 41.45 |
| ATOM | 929 | N | PHE | A | 243 | 46.537 | 43.681 | 22.373 | 1.00 | 39.48 |
| ATOM | 930 | CA | PHE | A | 243 | 47.381 | 42.712 | 23.066 | 1.00 | 39.13 |
| ATOM | 931 | C | PHE | A | 243 | 46.677 | 41.442 | 23.547 | 1.00 | 39.39 |
| ATOM | 932 | O | PHE | A | 243 | 47.293 | 40.380 | 23.604 | 1.00 | 38.77 |
| ATOM | 933 | CB | PHE | A | 243 | 48.108 | 43.392 | 24.235 | 1.00 | 37.88 |
| ATOM | 934 | CG | PHE | A | 243 | 47.198 | 43.915 | 25.305 | 1.00 | 37.59 |
| ATOM | 935 | CD1 | PHE | A | 243 | 46.746 | 43.082 | 26.323 | 1.00 | 37.35 |
| ATOM | 936 | CD2 | PHE | A | 243 | 46.797 | 45.248 | 25.301 | 1.00 | 37.10 |
| ATOM | 937 | CE1 | PHE | A | 243 | 45.908 | 43.569 | 27.326 | 1.00 | 37.14 |
| ATOM | 938 | CE2 | PHE | A | 243 | 45.959 | 45.744 | 26.299 | 1.00 | 37.25 |
| ATOM | 939 | CZ | PHE | A | 243 | 45.515 | 44.901 | 27.313 | 1.00 | 37.29 |
| ATOM | 940 | N | ARG | A | 244 | 45.395 | 41.543 | 23.887 | 1.00 | 40.11 |
| ATOM | 941 | CA | ARG | A | 244 | 44.653 | 40.375 | 24.354 | 1.00 | 40.93 |
| ATOM | 942 | C | ARG | A | 244 | 44.619 | 39.281 | 23.289 | 1.00 | 40.69 |
| ATOM | 943 | O | ARG | A | 244 | 44.502 | 38.099 | 23.609 | 1.00 | 41.20 |

TABLE 7-continued

| ATOM | 944 | CB | ARG | A | 244 | 43.229 | 40.773 | 24.760 | 1.00 | 41.45 |
| --- | --- | --- | --- | --- | --- | --- | --- | --- | --- | --- |
| C |
| ATOM | 945 | CG | ARG | A | 244 | 43.188 | 41.719 | 25.952 | 1.00 | 42.10 |
| C |
| ATOM | 946 | CD | ARG | A | 244 | 41.766 | 42.050 | 26.382 | 1.00 | 43.32 |
| C |
| ATOM | 947 | NE | ARG | A | 244 | 41.749 | 43.039 | 27.456 | 1.00 | 44.43 |
| N |
| ATOM | 948 | CZ | ARG | A | 244 | 42.035 | 44.328 | 27.291 | 1.00 | 45.14 |
| C |
| ATOM | 949 | NH1 | ARG | A | 244 | 42.357 | 44.793 | 26.090 | 1.00 | 44.75 |
| N |
| ATOM | 950 | NH2 | ARG | A | 244 | 42.010 | 45.153 | 28.329 | 1.00 | 45.44 |
| N |
| ATOM | 951 | N | GLU | A | 245 | 44.726 | 39.677 | 22.026 | 1.00 | 40.84 |
| N |
| ATOM | 952 | CA | GLU | A | 245 | 44.732 | 38.718 | 20.928 | 1.00 | 40.87 |
| C |
| ATOM | 953 | C | GLU | A | 245 | 46.147 | 38.501 | 20.393 | 1.00 | 40.07 |
| C |
| ATOM | 954 | O | GLU | A | 245 | 46.537 | 37.374 | 20.083 | 1.00 | 39.45 |
| O |
| ATOM | 955 | CB | GLU | A | 245 | 43.838 | 39.197 | 19.781 | 1.00 | 43.54 |
| C |
| ATOM | 956 | CG | GLU | A | 245 | 42.334 | 39.160 | 20.061 | 1.00 | 47.70 |
| C |
| ATOM | 957 | CD | GLU | A | 245 | 41.900 | 40.111 | 21.164 | 1.00 | 50.68 |
| C |
| ATOM | 958 | OE1 | GLU | A | 245 | 42.282 | 41.305 | 21.121 | 1.00 | 52.80 |
| O |
| ATOM | 959 | OE2 | GLU | A | 245 | 41.162 | 39.665 | 22.072 | 1.00 | 52.45 |
| O |
| ATOM | 960 | N | ARG | A | 246 | 46.915 | 39.581 | 20.291 | 1.00 | 38.14 |
| N |
| ATOM | 961 | CA | ARG | A | 246 | 48.277 | 39.501 | 19.764 | 1.00 | 36.50 |
| C |
| ATOM | 962 | C | ARG | A | 246 | 49.259 | 38.743 | 20.660 | 1.00 | 36.05 |
| C |
| ATOM | 963 | O | ARG | A | 246 | 50.051 | 37.943 | 20.170 | 1.00 | 36.35 |
| O |
| ATOM | 964 | CB | ARG | A | 246 | 48.814 | 40.913 | 19.489 | 1.00 | 35.90 |
| C |
| ATOM | 965 | CG | ARG | A | 246 | 50.130 | 40.945 | 18.713 | 1.00 | 35.45 |
| C |
| ATOM | 966 | CD | ARG | A | 246 | 50.611 | 42.375 | 18.505 | 1.00 | 34.86 |
| C |
| ATOM | 967 | NE | ARG | A | 246 | 49.743 | 43.147 | 17.619 | 1.00 | 34.95 |
| N |
| ATOM | 968 | CZ | ARG | A | 246 | 49.766 | 43.077 | 16.291 | 1.00 | 34.35 |
| C |
| ATOM | 969 | NH1 | ARG | A | 246 | 50.616 | 42.267 | 15.676 | 1.00 | 35.15 |
| N |
| ATOM | 970 | NH2 | ARG | A | 246 | 48.939 | 43.827 | 15.574 | 1.00 | 35.50 |
| N |
| ATOM | 971 | N | VAL | A | 247 | 49.212 | 38.986 | 21.967 | 1.00 | 35.97 |
| N |
| ATOM | 972 | CA | VAL | A | 247 | 50.129 | 38.315 | 22.886 | 1.00 | 36.75 |
| C |
| ATOM | 973 | C | VAL | A | 247 | 50.020 | 36.788 | 22.837 | 1.00 | 37.56 |
| C |
| ATOM | 974 | O | VAL | A | 247 | 51.033 | 36.096 | 22.706 | 1.00 | 37.16 |
| O |
| ATOM | 975 | CB | VAL | A | 247 | 49.927 | 38.806 | 24.340 | 1.00 | 36.31 |
| C |
| ATOM | 976 | CG1 | VAL | A | 247 | 50.775 | 37.987 | 25.296 | 1.00 | 35.75 |
| C |
| ATOM | 977 | CG2 | VAL | A | 247 | 50.314 | 40.282 | 24.444 | 1.00 | 36.50 |
| C |
| ATOM | 978 | N | PRO | A | 248 | 48.794 | 36.241 | 22.946 | 1.00 | 37.33 |
| N |
| ATOM | 979 | CA | PRO | A | 248 | 48.638 | 34.783 | 22.901 | 1.00 | 36.95 |
| C |
| ATOM | 980 | C | PRO | A | 248 | 49.231 | 34.184 | 21.629 | 1.00 | 36.36 |
| C |
| ATOM | 981 | O | PRO | A | 248 | 49.897 | 33.155 | 21.677 | 1.00 | 37.14 |
| O |
| ATOM | 982 | CB | PRO | A | 248 | 47.125 | 34.598 | 22.979 | 1.00 | 37.52 |
| C |

TABLE 7-continued

| ATOM | 983 | CG | PRO | A | 248 | 46.709 | 35.735 | 23.858 | 1.00 | 37.69 |
|---|---|---|---|---|---|---|---|---|---|---|
| C | | | | | | | | | | |
| ATOM | 984 | CD | PRO | A | 248 | 47.515 | 36.890 | 23.290 | 1.00 | 36.69 |
| C | | | | | | | | | | |
| ATOM | 985 | N | ALA | A | 249 | 48.997 | 34.840 | 20.497 | 1.00 | 35.60 |
| N | | | | | | | | | | |
| ATOM | 986 | CA | ALA | A | 249 | 49.507 | 34.367 | 19.217 | 1.00 | 35.36 |
| C | | | | | | | | | | |
| ATOM | 987 | C | ALA | A | 249 | 51.034 | 34.354 | 19.183 | 1.00 | 35.63 |
| C | | | | | | | | | | |
| ATOM | 988 | O | ALA | A | 249 | 51.646 | 33.411 | 18.669 | 1.00 | 33.65 |
| O | | | | | | | | | | |
| ATOM | 989 | CB | ALA | A | 249 | 48.968 | 35.236 | 18.090 | 1.00 | 36.03 |
| C | | | | | | | | | | |
| ATOM | 990 | N | LEU | A | 250 | 51.646 | 35.403 | 19.728 | 1.00 | 35.24 |
| N | | | | | | | | | | |
| ATOM | 991 | CA | LEU | A | 250 | 53.099 | 35.505 | 19.754 | 1.00 | 35.85 |
| C | | | | | | | | | | |
| ATOM | 992 | C | LEU | A | 250 | 53.701 | 34.458 | 20.681 | 1.00 | 36.48 |
| C | | | | | | | | | | |
| ATOM | 993 | O | LEU | A | 250 | 54.758 | 33.899 | 20.395 | 1.00 | 36.97 |
| O | | | | | | | | | | |
| ATOM | 994 | CB | LEU | A | 250 | 53.520 | 36.915 | 20.189 | 1.00 | 34.62 |
| C | | | | | | | | | | |
| ATOM | 995 | CG | LEU | A | 250 | 53.067 | 38.010 | 19.215 | 1.00 | 34.74 |
| C | | | | | | | | | | |
| ATOM | 996 | CD1 | LEU | A | 250 | 53.473 | 39.384 | 19.731 | 1.00 | 34.92 |
| C | | | | | | | | | | |
| ATOM | 997 | CD2 | LEU | A | 250 | 53.678 | 37.749 | 17.847 | 1.00 | 34.43 |
| C | | | | | | | | | | |
| ATOM | 998 | N | VAL | A | 251 | 53.025 | 34.191 | 21.790 | 1.00 | 38.25 |
| N | | | | | | | | | | |
| ATOM | 999 | CA | VAL | A | 251 | 53.501 | 33.193 | 22.738 | 1.00 | 40.28 |
| C | | | | | | | | | | |
| ATOM | 1000 | C | VAL | A | 251 | 53.471 | 31.810 | 22.087 | 1.00 | 41.33 |
| C | | | | | | | | | | |
| ATOM | 1001 | O | VAL | A | 251 | 54.447 | 31.062 | 22.159 | 1.00 | 41.27 |
| O | | | | | | | | | | |
| ATOM | 1002 | CB | VAL | A | 251 | 52.632 | 33.173 | 24.013 | 1.00 | 40.67 |
| C | | | | | | | | | | |
| ATOM | 1003 | CG1 | VAL | A | 251 | 53.018 | 31.986 | 24.895 | 1.00 | 42.14 |
| C | | | | | | | | | | |
| ATOM | 1004 | CG2 | VAL | A | 251 | 52.813 | 34.474 | 24.780 | 1.00 | 40.95 |
| C | | | | | | | | | | |
| ATOM | 1005 | N | GLU | A | 252 | 52.355 | 31.480 | 21.439 | 1.00 | 41.97 |
| N | | | | | | | | | | |
| ATOM | 1006 | CA | GLU | A | 252 | 52.217 | 30.182 | 20.783 | 1.00 | 43.27 |
| C | | | | | | | | | | |
| ATOM | 1007 | C | GLU | A | 252 | 53.252 | 30.030 | 19.679 | 1.00 | 42.06 |
| C | | | | | | | | | | |
| ATOM | 1008 | O | GLU | A | 252 | 53.804 | 28.949 | 19.484 | 1.00 | 42.29 |
| O | | | | | | | | | | |
| ATOM | 1009 | CB | GLU | A | 252 | 50.822 | 30.019 | 20.172 | 1.00 | 45.54 |
| C | | | | | | | | | | |
| ATOM | 1010 | CG | GLU | A | 252 | 49.688 | 30.558 | 21.016 | 1.00 | 49.93 |
| C | | | | | | | | | | |
| ATOM | 1011 | CD | GLU | A | 252 | 49.586 | 29.929 | 22.392 | 1.00 | 52.52 |
| C | | | | | | | | | | |
| ATOM | 1012 | OE1 | GLU | A | 252 | 48.789 | 30.449 | 23.201 | 1.00 | 54.25 |
| O | | | | | | | | | | |
| ATOM | 1013 | OE2 | GLU | A | 252 | 50.280 | 28.924 | 22.670 | 1.00 | 55.02 |
| O | | | | | | | | | | |
| ATOM | 1014 | N | ALA | A | 253 | 53.503 | 31.116 | 18.953 | 1.00 | 40.26 |
| N | | | | | | | | | | |
| ATOM | 1015 | CA | ALA | A | 253 | 54.472 | 31.103 | 17.865 | 1.00 | 38.87 |
| C | | | | | | | | | | |
| ATOM | 1016 | C | ALA | A | 253 | 55.889 | 30.880 | 18.390 | 1.00 | 38.28 |
| C | | | | | | | | | | |
| ATOM | 1017 | O | ALA | A | 253 | 56.788 | 30.523 | 17.628 | 1.00 | 38.29 |
| O | | | | | | | | | | |
| ATOM | 1018 | CB | ALA | A | 253 | 54.398 | 32.406 | 17.082 | 1.00 | 39.08 |
| C | | | | | | | | | | |
| ATOM | 1019 | N | GLY | A | 254 | 56.088 | 31.103 | 19.686 | 1.00 | 37.14 |
| N | | | | | | | | | | |
| ATOM | 1020 | CA | GLY | A | 254 | 57.399 | 30.885 | 20.275 | 1.00 | 36.67 |
| C | | | | | | | | | | |
| ATOM | 1021 | C | GLY | A | 254 | 58.226 | 32.111 | 20.631 | 1.00 | 35.76 |
| C | | | | | | | | | | |

TABLE 7-continued

| ATOM | 1022 | O | GLY | A | 254 | 59.433 | 31.995 | 20.845 | 1.00 | 35.05 |
| --- | --- | --- | --- | --- | --- | --- | --- | --- | --- | --- |
| ATOM | 1023 | N | ALA | A | 255 | 57.596 | 33.282 | 20.701 | 1.00 | 35.10 |
| ATOM | 1024 | CA | ALA | A | 255 | 58.321 | 34.502 | 21.045 | 1.00 | 34.05 |
| ATOM | 1025 | C | ALA | A | 255 | 59.011 | 34.342 | 22.399 | 1.00 | 33.03 |
| ATOM | 1026 | O | ALA | A | 255 | 58.402 | 33.902 | 23.372 | 1.00 | 32.76 |
| ATOM | 1027 | CB | ALA | A | 255 | 57.369 | 35.692 | 21.078 | 1.00 | 34.00 |
| ATOM | 1028 | N | ASP | A | 256 | 60.285 | 34.710 | 22.454 | 1.00 | 32.35 |
| ATOM | 1029 | CA | ASP | A | 256 | 61.061 | 34.601 | 23.682 | 1.00 | 32.05 |
| ATOM | 1030 | C | ASP | A | 256 | 60.886 | 35.807 | 24.597 | 1.00 | 31.18 |
| ATOM | 1031 | O | ASP | A | 256 | 61.004 | 35.699 | 25.817 | 1.00 | 30.47 |
| ATOM | 1032 | CB | ASP | A | 256 | 62.531 | 34.409 | 23.329 | 1.00 | 32.35 |
| ATOM | 1033 | CG | ASP | A | 256 | 62.770 | 33.118 | 22.575 | 1.00 | 34.08 |
| ATOM | 1034 | OD1 | ASP | A | 256 | 62.639 | 32.044 | 23.199 | 1.00 | 34.90 |
| ATOM | 1035 | OD2 | ASP | A | 256 | 63.068 | 33.172 | 21.365 | 1.00 | 33.17 |
| ATOM | 1036 | N | VAL | A | 257 | 60.602 | 36.957 | 24.002 | 1.00 | 30.50 |
| ATOM | 1037 | CA | VAL | A | 257 | 60.402 | 38.173 | 24.778 | 1.00 | 29.68 |
| ATOM | 1038 | C | VAL | A | 257 | 59.555 | 39.139 | 23.961 | 1.00 | 29.30 |
| ATOM | 1039 | O | VAL | A | 257 | 59.584 | 39.111 | 22.733 | 1.00 | 29.73 |
| ATOM | 1040 | CB | VAL | A | 257 | 61.756 | 38.844 | 25.125 | 1.00 | 29.48 |
| ATOM | 1041 | CG1 | VAL | A | 257 | 62.462 | 39.273 | 23.848 | 1.00 | 29.83 |
| ATOM | 1042 | CG2 | VAL | A | 257 | 61.531 | 40.040 | 26.044 | 1.00 | 29.61 |
| ATOM | 1043 | N | LEU | A | 258 | 58.800 | 39.982 | 24.654 | 1.00 | 28.19 |
| ATOM | 1044 | CA | LEU | A | 258 | 57.942 | 40.961 | 24.007 | 1.00 | 28.90 |
| ATOM | 1045 | C | LEU | A | 258 | 58.369 | 42.354 | 24.457 | 1.00 | 28.21 |
| ATOM | 1046 | O | LEU | A | 258 | 59.113 | 42.503 | 25.419 | 1.00 | 28.37 |
| ATOM | 1047 | CB | LEU | A | 258 | 56.485 | 40.746 | 24.425 | 1.00 | 27.71 |
| ATOM | 1048 | CG | LEU | A | 258 | 55.915 | 39.332 | 24.289 | 1.00 | 28.73 |
| ATOM | 1049 | CD1 | LEU | A | 258 | 54.508 | 39.297 | 24.871 | 1.00 | 30.02 |
| ATOM | 1050 | CD2 | LEU | A | 258 | 55.907 | 38.917 | 22.833 | 1.00 | 29.49 |
| ATOM | 1051 | N | CYS | A | 259 | 57.898 | 43.373 | 23.754 | 1.00 | 28.75 |
| ATOM | 1052 | CA | CYS | A | 259 | 58.206 | 44.743 | 24.142 | 1.00 | 28.59 |
| ATOM | 1053 | C | CYS | A | 259 | 57.122 | 45.669 | 23.617 | 1.00 | 28.15 |
| ATOM | 1054 | O | CYS | A | 259 | 56.827 | 45.670 | 22.423 | 1.00 | 28.23 |
| ATOM | 1055 | CB | CYS | A | 259 | 59.566 | 45.181 | 23.597 | 1.00 | 28.11 |
| ATOM | 1056 | SG | CYS | A | 259 | 60.079 | 46.808 | 24.215 | 1.00 | 29.44 |
| ATOM | 1057 | N | ILE | A | 260 | 56.525 | 46.443 | 24.518 | 1.00 | 28.54 |
| ATOM | 1058 | CA | ILE | A | 260 | 55.490 | 47.392 | 24.132 | 1.00 | 29.64 |
| ATOM | 1059 | C | ILE | A | 260 | 56.191 | 48.503 | 23.362 | 1.00 | 30.85 |
| ATOM | 1060 | O | ILE | A | 260 | 57.144 | 49.106 | 23.852 | 1.00 | 30.69 |

TABLE 7-continued

| ATOM | 1061 | CB | ILE | A | 260 | 54.786 | 47.985 | 25.361 | 1.00 | 29.60 |
| --- | --- | --- | --- | --- | --- | --- | --- | --- | --- | --- |
| ATOM C | 1062 | CG1 | ILE | A | 260 | 54.254 | 46.849 | 26.238 | 1.00 | 29.82 |
| ATOM C | 1063 | CG2 | ILE | A | 260 | 53.638 | 48.901 | 24.916 | 1.00 | 29.89 |
| ATOM C | 1064 | CD1 | ILE | A | 260 | 53.659 | 47.309 | 27.557 | 1.00 | 30.44 |
| ATOM N | 1065 | N | ASP | A | 261 | 55.702 | 48.760 | 22.156 | 1.00 | 31.00 |
| ATOM C | 1066 | CA | ASP | A | 261 | 56.266 | 49.756 | 21.257 | 1.00 | 32.38 |
| ATOM C | 1067 | C | ASP | A | 261 | 55.498 | 51.081 | 21.316 | 1.00 | 32.90 |
| ATOM O | 1068 | O | ASP | A | 261 | 54.361 | 51.162 | 20.859 | 1.00 | 32.73 |
| ATOM C | 1069 | CB | ASP | A | 261 | 56.252 | 49.151 | 19.846 | 1.00 | 33.58 |
| ATOM C | 1070 | CG | ASP | A | 261 | 56.773 | 50.088 | 18.783 | 1.00 | 35.13 |
| ATOM O | 1071 | OD1 | ASP | A | 261 | 57.544 | 51.012 | 19.104 | 1.00 | 35.01 |
| ATOM O | 1072 | OD2 | ASP | A | 261 | 56.415 | 49.874 | 17.604 | 1.00 | 35.63 |
| ATOM N | 1073 | N | SER | A | 262 | 56.121 | 52.112 | 21.888 | 1.00 | 32.69 |
| ATOM C | 1074 | CA | SER | A | 262 | 55.483 | 53.427 | 22.013 | 1.00 | 32.90 |
| ATOM C | 1075 | C | SER | A | 262 | 56.502 | 54.557 | 22.175 | 1.00 | 32.98 |
| ATOM O | 1076 | O | SER | A | 262 | 57.598 | 54.339 | 22.686 | 1.00 | 32.40 |
| ATOM C | 1077 | CB | SER | A | 262 | 54.529 | 53.423 | 23.213 | 1.00 | 33.69 |
| ATOM O | 1078 | OG | SER | A | 262 | 54.010 | 54.716 | 23.469 | 1.00 | 35.09 |
| ATOM N | 1079 | N | SER | A | 263 | 56.142 | 55.766 | 21.745 | 1.00 | 32.80 |
| ATOM C | 1080 | CA | SER | A | 263 | 57.048 | 56.906 | 21.872 | 1.00 | 33.15 |
| ATOM C | 1081 | C | SER | A | 263 | 56.985 | 57.508 | 23.276 | 1.00 | 33.32 |
| ATOM O | 1082 | O | SER | A | 263 | 57.932 | 58.151 | 23.722 | 1.00 | 35.72 |
| ATOM C | 1083 | CB | SER | A | 263 | 56.734 | 57.976 | 20.816 | 1.00 | 34.60 |
| ATOM O | 1084 | OG | SER | A | 263 | 55.370 | 58.352 | 20.845 | 1.00 | 37.69 |
| ATOM N | 1085 | N | ASP | A | 264 | 55.871 | 57.296 | 23.971 | 1.00 | 31.32 |
| ATOM C | 1086 | CA | ASP | A | 264 | 55.711 | 57.795 | 25.337 | 1.00 | 29.82 |
| ATOM C | 1087 | C | ASP | A | 264 | 55.158 | 56.664 | 26.203 | 1.00 | 29.45 |
| ATOM O | 1088 | O | ASP | A | 264 | 53.942 | 56.475 | 26.304 | 1.00 | 28.91 |
| ATOM C | 1089 | CB | ASP | A | 264 | 54.775 | 59.017 | 25.356 | 1.00 | 28.89 |
| ATOM C | 1090 | CG | ASP | A | 264 | 54.352 | 59.436 | 26.769 | 1.00 | 29.68 |
| ATOM O | 1091 | OD1 | ASP | A | 264 | 55.007 | 59.067 | 27.768 | 1.00 | 26.79 |
| ATOM O | 1092 | OD2 | ASP | A | 264 | 53.348 | 60.168 | 26.877 | 1.00 | 29.53 |
| ATOM N | 1093 | N | GLY | A | 265 | 56.071 | 55.914 | 26.815 | 1.00 | 27.82 |
| ATOM C | 1094 | CA | GLY | A | 265 | 55.692 | 54.796 | 27.662 | 1.00 | 27.73 |
| ATOM C | 1095 | C | GLY | A | 265 | 55.189 | 55.151 | 29.048 | 1.00 | 27.21 |
| ATOM O | 1096 | O | GLY | A | 265 | 54.751 | 54.269 | 29.784 | 1.00 | 27.06 |
| ATOM N | 1097 | N | PHE | A | 266 | 55.244 | 56.430 | 29.412 | 1.00 | 26.33 |
| ATOM C | 1098 | CA | PHE | A | 266 | 54.779 | 56.870 | 30.726 | 1.00 | 26.29 |
| ATOM C | 1099 | C | PHE | A | 266 | 53.265 | 56.989 | 30.574 | 1.00 | 27.35 |

TABLE 7-continued

| | | | | | | | | | |
|---|---|---|---|---|---|---|---|---|---|
| ATOM | 1100 | O | PHE | A | 266 | 52.707 | 58.086 | 30.516 | 1.00 26.16 |
| O | | | | | | | | | |
| ATOM | 1101 | CB | PHE | A | 266 | 55.403 | 58.222 | 31.071 | 1.00 26.18 |
| C | | | | | | | | | |
| ATOM | 1102 | CG | PHE | A | 266 | 55.499 | 58.503 | 32.553 | 1.00 27.83 |
| C | | | | | | | | | |
| ATOM | 1103 | CD1 | PHE | A | 266 | 54.770 | 57.754 | 33.481 | 1.00 26.01 |
| C | | | | | | | | | |
| ATOM | 1104 | CD2 | PHE | A | 266 | 56.305 | 59.541 | 33.017 | 1.00 26.81 |
| C | | | | | | | | | |
| ATOM | 1105 | CE1 | PHE | A | 266 | 54.846 | 58.040 | 34.843 | 1.00 27.31 |
| C | | | | | | | | | |
| ATOM | 1106 | CE2 | PHE | A | 266 | 56.385 | 59.833 | 34.373 | 1.00 27.03 |
| C | | | | | | | | | |
| ATOM | 1107 | CZ | PHE | A | 266 | 55.654 | 59.081 | 35.291 | 1.00 27.65 |
| C | | | | | | | | | |
| ATOM | 1108 | N | SER | A | 267 | 52.613 | 55.832 | 30.502 | 1.00 28.62 |
| N | | | | | | | | | |
| ATOM | 1109 | CA | SER | A | 267 | 51.176 | 55.751 | 30.282 | 1.00 29.12 |
| C | | | | | | | | | |
| ATOM | 1110 | C | SER | A | 267 | 50.490 | 54.634 | 31.061 | 1.00 29.52 |
| C | | | | | | | | | |
| ATOM | 1111 | O | SER | A | 267 | 51.036 | 53.543 | 31.231 | 1.00 27.59 |
| O | | | | | | | | | |
| ATOM | 1112 | CB | SER | A | 267 | 50.924 | 55.535 | 28.790 | 1.00 30.27 |
| C | | | | | | | | | |
| ATOM | 1113 | OG | SER | A | 267 | 49.593 | 55.132 | 28.534 | 1.00 33.40 |
| O | | | | | | | | | |
| ATOM | 1114 | N | GLU | A | 268 | 49.272 | 54.912 | 31.507 | 1.00 30.01 |
| N | | | | | | | | | |
| ATOM | 1115 | CA | GLU | A | 268 | 48.493 | 53.936 | 32.246 | 1.00 31.53 |
| C | | | | | | | | | |
| ATOM | 1116 | C | GLU | A | 268 | 48.208 | 52.753 | 31.328 | 1.00 31.63 |
| C | | | | | | | | | |
| ATOM | 1117 | O | GLU | A | 268 | 48.000 | 51.627 | 31.790 | 1.00 31.90 |
| O | | | | | | | | | |
| ATOM | 1118 | CB | GLU | A | 268 | 47.184 | 54.572 | 32.716 | 1.00 33.65 |
| C | | | | | | | | | |
| ATOM | 1119 | CG | GLU | A | 268 | 46.385 | 53.720 | 33.684 | 1.00 36.92 |
| C | | | | | | | | | |
| ATOM | 1120 | CD | GLU | A | 268 | 45.169 | 54.445 | 34.238 | 1.00 38.90 |
| C | | | | | | | | | |
| ATOM | 1121 | OE1 | GLU | A | 268 | 44.448 | 53.837 | 35.059 | 1.00 41.93 |
| O | | | | | | | | | |
| ATOM | 1122 | OE2 | GLU | A | 268 | 44.933 | 55.615 | 33.857 | 1.00 37.65 |
| O | | | | | | | | | |
| ATOM | 1123 | N | TRP | A | 269 | 48.212 | 53.007 | 30.022 | 1.00 30.66 |
| N | | | | | | | | | |
| ATOM | 1124 | CA | TRP | A | 269 | 47.960 | 51.950 | 29.053 | 1.00 32.73 |
| C | | | | | | | | | |
| ATOM | 1125 | C | TRP | A | 269 | 49.023 | 50.858 | 29.122 | 1.00 31.60 |
| C | | | | | | | | | |
| ATOM | 1126 | O | TRP | A | 269 | 48.717 | 49.678 | 28.951 | 1.00 32.00 |
| O | | | | | | | | | |
| ATOM | 1127 | CB | TRP | A | 269 | 47.890 | 52.520 | 27.632 | 1.00 34.13 |
| C | | | | | | | | | |
| ATOM | 1128 | CG | TRP | A | 269 | 46.705 | 53.411 | 27.401 | 1.00 38.84 |
| C | | | | | | | | | |
| ATOM | 1129 | CD1 | TRP | A | 269 | 46.723 | 54.759 | 27.170 | 1.00 39.63 |
| C | | | | | | | | | |
| ATOM | 1130 | CD2 | TRP | A | 269 | 45.325 | 53.021 | 27.383 | 1.00 40.48 |
| C | | | | | | | | | |
| ATOM | 1131 | NE1 | TRP | A | 269 | 45.442 | 55.229 | 27.009 | 1.00 40.70 |
| N | | | | | | | | | |
| ATOM | 1132 | CE2 | TRP | A | 269 | 44.565 | 54.185 | 27.134 | 1.00 40.74 |
| C | | | | | | | | | |
| ATOM | 1133 | CE3 | TRP | A | 269 | 44.657 | 51.800 | 27.553 | 1.00 41.39 |
| C | | | | | | | | | |
| ATOM | 1134 | CZ2 | TRP | A | 269 | 43.168 | 54.165 | 27.049 | 1.00 42.44 |
| C | | | | | | | | | |
| ATOM | 1135 | CZ3 | TRP | A | 269 | 43.266 | 51.780 | 27.469 | 1.00 42.63 |
| C | | | | | | | | | |
| ATOM | 1136 | CH2 | TRP | A | 269 | 42.539 | 52.957 | 27.219 | 1.00 42.95 |
| C | | | | | | | | | |
| ATOM | 1137 | N | GLN | A | 270 | 50.273 | 51.237 | 29.370 | 1.00 30.36 |
| N | | | | | | | | | |
| ATOM | 1138 | CA | GLN | A | 270 | 51.330 | 50.232 | 29.463 | 1.00 29.91 |
| C | | | | | | | | | |

TABLE 7-continued

| | | | | | | | | | |
|---|---|---|---|---|---|---|---|---|---|
| ATOM | 1139 | C | GLN | A | 270 | 51.197 | 49.444 | 30.764 | 1.00 29.40 |
| C | | | | | | | | | |
| ATOM | 1140 | O | GLN | A | 270 | 51.478 | 48.250 | 30.802 | 1.00 29.26 |
| O | | | | | | | | | |
| ATOM | 1141 | CB | GLN | A | 270 | 52.717 | 50.883 | 29.369 | 1.00 28.96 |
| C | | | | | | | | | |
| ATOM | 1142 | CG | GLN | A | 270 | 52.925 | 51.642 | 28.065 | 1.00 28.77 |
| C | | | | | | | | | |
| ATOM | 1143 | CD | GLN | A | 270 | 54.293 | 51.420 | 27.438 | 1.00 28.29 |
| C | | | | | | | | | |
| ATOM | 1144 | OE1 | GLN | A | 270 | 55.185 | 50.820 | 28.041 | 1.00 27.12 |
| O | | | | | | | | | |
| ATOM | 1145 | NE2 | GLN | A | 270 | 54.463 | 51.916 | 26.217 | 1.00 26.63 |
| N | | | | | | | | | |
| ATOM | 1146 | N | LYS | A | 271 | 50.763 | 50.113 | 31.828 | 1.00 30.02 |
| N | | | | | | | | | |
| ATOM | 1147 | CA | LYS | A | 271 | 50.579 | 49.437 | 33.107 | 1.00 31.43 |
| C | | | | | | | | | |
| ATOM | 1148 | C | LYS | A | 271 | 49.484 | 48.381 | 32.944 | 1.00 31.09 |
| C | | | | | | | | | |
| ATOM | 1149 | O | LYS | A | 271 | 49.618 | 47.257 | 33.419 | 1.00 30.76 |
| O | | | | | | | | | |
| ATOM | 1150 | CB | LYS | A | 271 | 50.181 | 50.433 | 34.202 | 1.00 33.38 |
| C | | | | | | | | | |
| ATOM | 1151 | CG | LYS | A | 271 | 49.911 | 49.770 | 35.552 | 1.00 36.04 |
| C | | | | | | | | | |
| ATOM | 1152 | CD | LYS | A | 271 | 49.607 | 50.779 | 36.655 | 1.00 37.85 |
| C | | | | | | | | | |
| ATOM | 1153 | CE | LYS | A | 271 | 49.404 | 50.068 | 37.993 | 1.00 40.25 |
| C | | | | | | | | | |
| ATOM | 1154 | NZ | LYS | A | 271 | 49.157 | 51.008 | 39.131 | 1.00 42.83 |
| N | | | | | | | | | |
| ATOM | 1155 | N | ILE | A | 272 | 48.409 | 48.752 | 32.257 | 1.00 31.55 |
| N | | | | | | | | | |
| ATOM | 1156 | CA | ILE | A | 272 | 47.291 | 47.841 | 32.018 | 1.00 31.85 |
| C | | | | | | | | | |
| ATOM | 1157 | C | ILE | A | 272 | 47.745 | 46.632 | 31.202 | 1.00 31.95 |
| C | | | | | | | | | |
| ATOM | 1158 | O | ILE | A | 272 | 47.433 | 45.490 | 31.544 | 1.00 31.04 |
| O | | | | | | | | | |
| ATOM | 1159 | CB | ILE | A | 272 | 46.139 | 48.565 | 31.278 | 1.00 31.97 |
| C | | | | | | | | | |
| ATOM | 1160 | CG1 | ILE | A | 272 | 45.463 | 49.551 | 32.235 | 1.00 32.25 |
| C | | | | | | | | | |
| ATOM | 1161 | CG2 | ILE | A | 272 | 45.137 | 47.552 | 30.730 | 1.00 32.38 |
| C | | | | | | | | | |
| ATOM | 1162 | CD1 | ILE | A | 272 | 44.456 | 50.473 | 31.570 | 1.00 32.51 |
| C | | | | | | | | | |
| ATOM | 1163 | N | THR | A | 273 | 48.492 | 46.890 | 30.133 | 1.00 30.63 |
| N | | | | | | | | | |
| ATOM | 1164 | CA | THR | A | 273 | 48.995 | 45.833 | 29.267 | 1.00 31.00 |
| C | | | | | | | | | |
| ATOM | 1165 | C | THR | A | 273 | 49.882 | 44.849 | 30.030 | 1.00 31.56 |
| C | | | | | | | | | |
| ATOM | 1166 | O | THR | A | 273 | 49.702 | 43.633 | 29.927 | 1.00 31.43 |
| O | | | | | | | | | |
| ATOM | 1167 | CB | THR | A | 273 | 49.796 | 46.422 | 28.084 | 1.00 30.85 |
| C | | | | | | | | | |
| ATOM | 1168 | OG1 | THR | A | 273 | 48.932 | 47.244 | 27.292 | 1.00 32.26 |
| O | | | | | | | | | |
| ATOM | 1169 | CG2 | THR | A | 273 | 50.366 | 45.311 | 27.208 | 1.00 30.97 |
| C | | | | | | | | | |
| ATOM | 1170 | N | ILE | A | 274 | 50.843 | 45.370 | 30.789 | 1.00 31.51 |
| N | | | | | | | | | |
| ATOM | 1171 | CA | ILE | A | 274 | 51.736 | 44.506 | 31.558 | 1.00 32.20 |
| C | | | | | | | | | |
| ATOM | 1172 | C | ILE | A | 274 | 50.927 | 43.738 | 32.603 | 1.00 32.56 |
| C | | | | | | | | | |
| ATOM | 1173 | O | ILE | A | 274 | 51.189 | 42.566 | 32.870 | 1.00 32.30 |
| O | | | | | | | | | |
| ATOM | 1174 | CB | ILE | A | 274 | 52.825 | 45.314 | 32.288 | 1.00 31.42 |
| C | | | | | | | | | |
| ATOM | 1175 | CG1 | ILE | A | 274 | 53.653 | 46.114 | 31.278 | 1.00 32.15 |
| C | | | | | | | | | |
| ATOM | 1176 | CG2 | ILE | A | 274 | 53.718 | 44.367 | 33.091 | 1.00 31.67 |
| C | | | | | | | | | |
| ATOM | 1177 | CD1 | ILE | A | 274 | 54.655 | 47.065 | 31.920 | 1.00 32.30 |
| C | | | | | | | | | |

TABLE 7-continued

| ATOM | 1178 | N | GLY | A | 275 | 49.941 | 44.410 | 33.189 | 1.00 | 32.77 |
| --- | --- | --- | --- | --- | --- | --- | --- | --- | --- | --- |
| ATOM | 1179 | CA | GLY | A | 275 | 49.110 | 43.775 | 34.196 | 1.00 | 33.56 |
| ATOM | 1180 | C | GLY | A | 275 | 48.351 | 42.578 | 33.653 | 1.00 | 34.04 |
| ATOM | 1181 | O | GLY | A | 275 | 48.245 | 41.546 | 34.320 | 1.00 | 34.05 |
| ATOM | 1182 | N | TRP | A | 276 | 47.822 | 42.714 | 32.443 | 1.00 | 33.68 |
| ATOM | 1183 | CA | TRP | A | 276 | 47.065 | 41.642 | 31.804 | 1.00 | 34.90 |
| ATOM | 1184 | C | TRP | A | 276 | 47.980 | 40.451 | 31.536 | 1.00 | 35.94 |
| ATOM | 1185 | O | TRP | A | 276 | 47.581 | 39.293 | 31.700 | 1.00 | 34.92 |
| ATOM | 1186 | CB | TRP | A | 276 | 46.469 | 42.134 | 30.485 | 1.00 | 35.21 |
| ATOM | 1187 | CG | TRP | A | 276 | 45.582 | 41.138 | 29.813 | 1.00 | 36.07 |
| ATOM | 1188 | CD1 | TRP | A | 276 | 44.237 | 40.972 | 30.002 | 1.00 | 36.67 |
| ATOM | 1189 | CD2 | TRP | A | 276 | 45.978 | 40.153 | 28.853 | 1.00 | 36.84 |
| ATOM | 1190 | NE1 | TRP | A | 276 | 43.772 | 39.944 | 29.212 | 1.00 | 36.48 |
| ATOM | 1191 | CE2 | TRP | A | 276 | 44.820 | 39.424 | 28.498 | 1.00 | 37.06 |
| ATOM | 1192 | CE3 | TRP | A | 276 | 47.201 | 39.814 | 28.255 | 1.00 | 36.59 |
| ATOM | 1193 | CZ2 | TRP | A | 276 | 44.848 | 38.376 | 27.572 | 1.00 | 37.28 |
| ATOM | 1194 | CZ3 | TRP | A | 276 | 47.230 | 38.772 | 27.336 | 1.00 | 37.26 |
| ATOM | 1195 | CH2 | TRP | A | 276 | 46.057 | 38.065 | 27.004 | 1.00 | 37.96 |
| ATOM | 1196 | N | ILE | A | 277 | 49.211 | 40.740 | 31.121 | 1.00 | 35.54 |
| ATOM | 1197 | CA | ILE | A | 277 | 50.181 | 39.690 | 30.835 | 1.00 | 36.20 |
| ATOM | 1198 | C | ILE | A | 277 | 50.562 | 38.933 | 32.109 | 1.00 | 37.31 |
| ATOM | 1199 | O | ILE | A | 277 | 50.646 | 37.703 | 32.106 | 1.00 | 37.04 |
| ATOM | 1200 | CB | ILE | A | 277 | 51.456 | 40.279 | 30.178 | 1.00 | 35.46 |
| ATOM | 1201 | CG1 | ILE | A | 277 | 51.112 | 40.828 | 28.791 | 1.00 | 35.23 |
| ATOM | 1202 | CG2 | ILE | A | 277 | 52.541 | 39.210 | 30.080 | 1.00 | 35.59 |
| ATOM | 1203 | CD1 | ILE | A | 277 | 52.273 | 41.503 | 28.081 | 1.00 | 35.42 |
| ATOM | 1204 | N | ARG | A | 278 | 50.787 | 39.666 | 33.194 | 1.00 | 38.07 |
| ATOM | 1205 | CA | ARG | A | 278 | 51.152 | 39.047 | 34.466 | 1.00 | 39.93 |
| ATOM | 1206 | C | ARG | A | 278 | 50.029 | 38.167 | 35.005 | 1.00 | 41.35 |
| ATOM | 1207 | O | ARG | A | 278 | 50.273 | 37.077 | 35.517 | 1.00 | 41.11 |
| ATOM | 1208 | CB | ARG | A | 278 | 51.489 | 40.120 | 35.502 | 1.00 | 39.44 |
| ATOM | 1209 | CG | ARG | A | 278 | 52.797 | 40.835 | 35.243 | 1.00 | 38.20 |
| ATOM | 1210 | CD | ARG | A | 278 | 53.989 | 39.927 | 35.511 | 1.00 | 38.69 |
| ATOM | 1211 | NE | ARG | A | 278 | 55.225 | 40.567 | 35.075 | 1.00 | 37.38 |
| ATOM | 1212 | CZ | ARG | A | 278 | 55.937 | 40.181 | 34.023 | 1.00 | 37.01 |
| ATOM | 1213 | NH1 | ARG | A | 278 | 55.547 | 39.141 | 33.297 | 1.00 | 35.28 |
| ATOM | 1214 | NH2 | ARG | A | 278 | 57.022 | 40.861 | 33.674 | 1.00 | 34.80 |
| ATOM | 1215 | N | GLU | A | 279 | 48.801 | 38.654 | 34.891 | 1.00 | 42.82 |
| ATOM | 1216 | CA | GLU | A | 279 | 47.634 | 37.922 | 35.369 | 1.00 | 45.18 |

TABLE 7-continued

| ATOM | 1217 | C | GLU | A | 279 | 47.353 | 36.655 | 34.559 | 1.00 | 45.03 |
| --- | --- | --- | --- | --- | --- | --- | --- | --- | --- | --- |
| C | | | | | | | | | | |
| ATOM | 1218 | O | GLU | A | 279 | 46.793 | 35.686 | 35.076 | 1.00 | 45.43 |
| O | | | | | | | | | | |
| ATOM | 1219 | CB | GLU | A | 279 | 46.417 | 38.858 | 35.355 | 1.00 | 47.47 |
| C | | | | | | | | | | |
| ATOM | 1220 | CG | GLU | A | 279 | 45.058 | 38.180 | 35.269 | 1.00 | 51.44 |
| C | | | | | | | | | | |
| ATOM | 1221 | CD | GLU | A | 279 | 44.757 | 37.662 | 33.873 | 1.00 | 53.84 |
| C | | | | | | | | | | |
| ATOM | 1222 | OE1 | GLU | A | 279 | 44.818 | 38.465 | 32.909 | 1.00 | 54.89 |
| O | | | | | | | | | | |
| ATOM | 1223 | OE2 | GLU | A | 279 | 44.460 | 36.454 | 33.740 | 1.00 | 54.90 |
| O | | | | | | | | | | |
| ATOM | 1224 | N | LYS | A | 280 | 47.755 | 36.655 | 33.294 | 1.00 | 44.19 |
| N | | | | | | | | | | |
| ATOM | 1225 | CA | LYS | A | 280 | 47.513 | 35.515 | 32.421 | 1.00 | 43.85 |
| C | | | | | | | | | | |
| ATOM | 1226 | C | LYS | A | 280 | 48.704 | 34.558 | 32.319 | 1.00 | 43.09 |
| C | | | | | | | | | | |
| ATOM | 1227 | O | LYS | A | 280 | 48.523 | 33.356 | 32.109 | 1.00 | 42.03 |
| O | | | | | | | | | | |
| ATOM | 1228 | CB | LYS | A | 280 | 47.133 | 36.030 | 31.027 | 1.00 | 45.44 |
| C | | | | | | | | | | |
| ATOM | 1229 | CG | LYS | A | 280 | 46.346 | 35.059 | 30.153 | 1.00 | 48.33 |
| C | | | | | | | | | | |
| ATOM | 1230 | CD | LYS | A | 280 | 47.213 | 33.959 | 29.575 | 1.00 | 50.41 |
| C | | | | | | | | | | |
| ATOM | 1231 | CE | LYS | A | 280 | 46.394 | 33.011 | 28.702 | 1.00 | 51.95 |
| C | | | | | | | | | | |
| ATOM | 1232 | NZ | LYS | A | 280 | 45.734 | 33.714 | 27.563 | 1.00 | 52.39 |
| N | | | | | | | | | | |
| ATOM | 1233 | N | TYR | A | 281 | 49.915 | 35.082 | 32.494 | 1.00 | 41.24 |
| N | | | | | | | | | | |
| ATOM | 1234 | CA | TYR | A | 281 | 51.121 | 34.268 | 32.369 | 1.00 | 39.92 |
| C | | | | | | | | | | |
| ATOM | 1235 | C | TYR | A | 281 | 52.095 | 34.338 | 33.535 | 1.00 | 39.29 |
| C | | | | | | | | | | |
| ATOM | 1236 | O | TYR | A | 281 | 53.103 | 33.636 | 33.538 | 1.00 | 38.90 |
| O | | | | | | | | | | |
| ATOM | 1237 | CB | TYR | A | 281 | 51.882 | 34.674 | 31.110 | 1.00 | 40.32 |
| C | | | | | | | | | | |
| ATOM | 1238 | CG | TYR | A | 281 | 51.108 | 34.542 | 29.823 | 1.00 | 40.12 |
| C | | | | | | | | | | |
| ATOM | 1239 | CD1 | TYR | A | 281 | 50.920 | 33.296 | 29.224 | 1.00 | 40.31 |
| C | | | | | | | | | | |
| ATOM | 1240 | CD2 | TYR | A | 281 | 50.595 | 35.668 | 29.181 | 1.00 | 40.13 |
| C | | | | | | | | | | |
| ATOM | 1241 | CE1 | TYR | A | 281 | 50.246 | 33.178 | 28.013 | 1.00 | 40.79 |
| C | | | | | | | | | | |
| ATOM | 1242 | CE2 | TYR | A | 281 | 49.918 | 35.560 | 27.973 | 1.00 | 40.17 |
| C | | | | | | | | | | |
| ATOM | 1243 | CZ | TYR | A | 281 | 49.750 | 34.314 | 27.393 | 1.00 | 41.11 |
| C | | | | | | | | | | |
| ATOM | 1244 | OH | TYR | A | 281 | 49.097 | 34.208 | 26.188 | 1.00 | 41.85 |
| O | | | | | | | | | | |
| ATOM | 1245 | N | GLY | A | 282 | 51.812 | 35.181 | 34.517 | 1.00 | 38.90 |
| N | | | | | | | | | | |
| ATOM | 1246 | CA | GLY | A | 282 | 52.733 | 35.306 | 35.629 | 1.00 | 39.41 |
| C | | | | | | | | | | |
| ATOM | 1247 | C | GLY | A | 282 | 54.044 | 35.871 | 35.105 | 1.00 | 40.43 |
| C | | | | | | | | | | |
| ATOM | 1248 | O | GLY | A | 282 | 54.044 | 36.689 | 34.184 | 1.00 | 39.10 |
| O | | | | | | | | | | |
| ATOM | 1249 | N | ASP | A | 283 | 55.163 | 35.432 | 35.671 | 1.00 | 40.95 |
| N | | | | | | | | | | |
| ATOM | 1250 | CA | ASP | A | 283 | 56.466 | 35.918 | 35.236 | 1.00 | 42.89 |
| C | | | | | | | | | | |
| ATOM | 1251 | C | ASP | A | 283 | 57.110 | 35.037 | 34.163 | 1.00 | 42.30 |
| C | | | | | | | | | | |
| ATOM | 1252 | O | ASP | A | 283 | 58.304 | 35.149 | 33.903 | 1.00 | 43.50 |
| O | | | | | | | | | | |
| ATOM | 1253 | CB | ASP | A | 283 | 57.407 | 36.046 | 36.440 | 1.00 | 44.35 |
| C | | | | | | | | | | |
| ATOM | 1254 | CG | ASP | A | 283 | 56.985 | 37.154 | 37.400 | 1.00 | 47.46 |
| C | | | | | | | | | | |
| ATOM | 1255 | OD1 | ASP | A | 283 | 57.019 | 38.341 | 37.000 | 1.00 | 47.96 |
| O | | | | | | | | | | |

TABLE 7-continued

| ATOM | 1256 | OD2 | ASP | A | 283 | 56.620 | 36.840 | 38.555 | 1.00 | 48.36 |
|---|---|---|---|---|---|---|---|---|---|---|
| O | | | | | | | | | | |
| ATOM | 1257 | N | LYS | A | 284 | 56.321 | 34.171 | 33.534 | 1.00 | 42.27 |
| N | | | | | | | | | | |
| ATOM | 1258 | CA | LYS | A | 284 | 56.843 | 33.283 | 32.494 | 1.00 | 41.83 |
| C | | | | | | | | | | |
| ATOM | 1259 | C | LYS | A | 284 | 56.953 | 33.968 | 31.134 | 1.00 | 40.43 |
| C | | | | | | | | | | |
| ATOM | 1260 | O | LYS | A | 284 | 57.689 | 33.518 | 30.256 | 1.00 | 40.67 |
| O | | | | | | | | | | |
| ATOM | 1261 | CB | LYS | A | 284 | 55.970 | 32.029 | 32.360 | 1.00 | 44.31 |
| C | | | | | | | | | | |
| ATOM | 1262 | CG | LYS | A | 284 | 56.142 | 31.005 | 33.480 | 1.00 | 47.22 |
| C | | | | | | | | | | |
| ATOM | 1263 | CD | LYS | A | 284 | 55.534 | 31.467 | 34.794 | 1.00 | 49.17 |
| C | | | | | | | | | | |
| ATOM | 1264 | CE | LYS | A | 284 | 55.602 | 30.352 | 35.837 | 1.00 | 51.28 |
| C | | | | | | | | | | |
| ATOM | 1265 | NZ | LYS | A | 284 | 54.892 | 30.695 | 37.108 | 1.00 | 52.23 |
| N | | | | | | | | | | |
| ATOM | 1266 | N | VAL | A | 285 | 56.204 | 35.045 | 30.950 | 1.00 | 37.55 |
| N | | | | | | | | | | |
| ATOM | 1267 | CA | VAL | A | 285 | 56.257 | 35.784 | 29.696 | 1.00 | 34.84 |
| C | | | | | | | | | | |
| ATOM | 1268 | C | VAL | A | 285 | 56.954 | 37.100 | 30.007 | 1.00 | 32.72 |
| C | | | | | | | | | | |
| ATOM | 1269 | O | VAL | A | 285 | 56.514 | 37.847 | 30.876 | 1.00 | 32.13 |
| O | | | | | | | | | | |
| ATOM | 1270 | CB | VAL | A | 285 | 54.846 | 36.045 | 29.142 | 1.00 | 34.53 |
| C | | | | | | | | | | |
| ATOM | 1271 | CG1 | VAL | A | 285 | 54.912 | 37.015 | 27.967 | 1.00 | 34.19 |
| C | | | | | | | | | | |
| ATOM | 1272 | CG2 | VAL | A | 285 | 54.224 | 34.722 | 28.698 | 1.00 | 35.84 |
| C | | | | | | | | | | |
| ATOM | 1273 | N | LYS | A | 286 | 58.053 | 37.364 | 29.307 | 1.00 | 31.33 |
| N | | | | | | | | | | |
| ATOM | 1274 | CA | LYS | A | 286 | 58.836 | 38.575 | 29.529 | 1.00 | 29.68 |
| C | | | | | | | | | | |
| ATOM | 1275 | C | LYS | A | 286 | 58.365 | 39.710 | 28.629 | 1.00 | 28.86 |
| C | | | | | | | | | | |
| ATOM | 1276 | O | LYS | A | 286 | 58.122 | 39.509 | 27.442 | 1.00 | 29.10 |
| O | | | | | | | | | | |
| ATOM | 1277 | CB | LYS | A | 286 | 60.318 | 38.281 | 29.276 | 1.00 | 30.15 |
| C | | | | | | | | | | |
| ATOM | 1278 | CG | LYS | A | 286 | 60.847 | 37.084 | 30.062 | 1.00 | 29.04 |
| C | | | | | | | | | | |
| ATOM | 1279 | CD | LYS | A | 286 | 60.622 | 37.263 | 31.558 | 1.00 | 28.26 |
| C | | | | | | | | | | |
| ATOM | 1280 | CE | LYS | A | 286 | 61.158 | 36.077 | 32.355 | 1.00 | 29.94 |
| C | | | | | | | | | | |
| ATOM | 1281 | NZ | LYS | A | 286 | 60.950 | 36.259 | 33.822 | 1.00 | 28.63 |
| N | | | | | | | | | | |
| ATOM | 1282 | N | VAL | A | 287 | 58.254 | 40.907 | 29.195 | 1.00 | 28.83 |
| N | | | | | | | | | | |
| ATOM | 1283 | CA | VAL | A | 287 | 57.786 | 42.050 | 28.427 | 1.00 | 28.30 |
| C | | | | | | | | | | |
| ATOM | 1284 | C | VAL | A | 287 | 58.482 | 43.361 | 28.793 | 1.00 | 27.68 |
| C | | | | | | | | | | |
| ATOM | 1285 | O | VAL | A | 287 | 58.459 | 43.792 | 29.942 | 1.00 | 28.41 |
| O | | | | | | | | | | |
| ATOM | 1286 | CB | VAL | A | 287 | 56.242 | 42.211 | 28.584 | 1.00 | 27.98 |
| C | | | | | | | | | | |
| ATOM | 1287 | CG1 | VAL | A | 287 | 55.874 | 42.312 | 30.049 | 1.00 | 29.20 |
| C | | | | | | | | | | |
| ATOM | 1288 | CG2 | VAL | A | 287 | 55.754 | 43.436 | 27.827 | 1.00 | 28.74 |
| C | | | | | | | | | | |
| ATOM | 1289 | N | GLY | A | 288 | 59.121 | 43.974 | 27.803 | 1.00 | 28.04 |
| N | | | | | | | | | | |
| ATOM | 1290 | CA | GLY | A | 288 | 59.786 | 45.246 | 28.025 | 1.00 | 26.66 |
| C | | | | | | | | | | |
| ATOM | 1291 | C | GLY | A | 288 | 58.762 | 46.345 | 27.815 | 1.00 | 26.11 |
| C | | | | | | | | | | |
| ATOM | 1292 | O | GLY | A | 288 | 57.721 | 46.105 | 27.203 | 1.00 | 25.68 |
| O | | | | | | | | | | |
| ATOM | 1293 | N | ALA | A | 289 | 59.044 | 47.541 | 28.323 | 1.00 | 25.08 |
| N | | | | | | | | | | |
| ATOM | 1294 | CA | ALA | A | 289 | 58.126 | 48.669 | 28.192 | 1.00 | 24.74 |
| C | | | | | | | | | | |

TABLE 7-continued

| ATOM | 1295 | C   | ALA | A | 289 | 58.906 | 49.955 | 27.935 | 1.00 | 25.55 |
| --- | --- | --- | --- | --- | --- | --- | --- | --- | --- | --- |
| ATOM | 1296 | O   | ALA | A | 289 | 60.115 | 50.007 | 28.151 | 1.00 | 26.30 |
| ATOM | 1297 | CB  | ALA | A | 289 | 57.288 | 48.813 | 29.460 | 1.00 | 22.88 |
| ATOM | 1298 | N   | GLY | A | 290 | 58.207 | 50.990 | 27.478 | 1.00 | 26.17 |
| ATOM | 1299 | CA  | GLY | A | 290 | 58.857 | 52.259 | 27.196 | 1.00 | 25.73 |
| ATOM | 1300 | C   | GLY | A | 290 | 58.137 | 52.974 | 26.069 | 1.00 | 26.32 |
| ATOM | 1301 | O   | GLY | A | 290 | 57.099 | 52.500 | 25.616 | 1.00 | 27.48 |
| ATOM | 1302 | N   | ASN | A | 291 | 58.677 | 54.095 | 25.592 | 1.00 | 25.49 |
| ATOM | 1303 | CA  | ASN | A | 291 | 59.932 | 54.659 | 26.086 | 1.00 | 24.28 |
| ATOM | 1304 | C   | ASN | A | 291 | 59.744 | 55.754 | 27.124 | 1.00 | 23.86 |
| ATOM | 1305 | O   | ASN | A | 291 | 58.738 | 56.465 | 27.115 | 1.00 | 22.00 |
| ATOM | 1306 | CB  | ASN | A | 291 | 60.729 | 55.245 | 24.919 | 1.00 | 24.80 |
| ATOM | 1307 | CG  | ASN | A | 291 | 61.287 | 54.184 | 24.008 | 1.00 | 25.31 |
| ATOM | 1308 | OD1 | ASN | A | 291 | 60.830 | 53.042 | 24.021 | 1.00 | 25.35 |
| ATOM | 1309 | ND2 | ASN | A | 291 | 62.278 | 54.555 | 23.202 | 1.00 | 24.45 |
| ATOM | 1310 | N   | ILE | A | 292 | 60.729 | 55.883 | 28.011 | 1.00 | 22.96 |
| ATOM | 1311 | CA  | ILE | A | 292 | 60.724 | 56.925 | 29.030 | 1.00 | 22.95 |
| ATOM | 1312 | C   | ILE | A | 292 | 62.077 | 57.636 | 28.986 | 1.00 | 23.91 |
| ATOM | 1313 | O   | ILE | A | 292 | 63.017 | 57.157 | 28.342 | 1.00 | 23.07 |
| ATOM | 1314 | CB  | ILE | A | 292 | 60.426 | 56.356 | 30.455 | 1.00 | 23.66 |
| ATOM | 1315 | CG1 | ILE | A | 292 | 61.301 | 55.139 | 30.770 | 1.00 | 22.82 |
| ATOM | 1316 | CG2 | ILE | A | 292 | 58.958 | 55.963 | 30.542 | 1.00 | 24.06 |
| ATOM | 1317 | CD1 | ILE | A | 292 | 62.734 | 55.478 | 31.158 | 1.00 | 23.86 |
| ATOM | 1318 | N   | VAL | A | 293 | 62.181 | 58.791 | 29.633 | 1.00 | 24.59 |
| ATOM | 1319 | CA  | VAL | A | 293 | 63.440 | 59.524 | 29.605 | 1.00 | 25.09 |
| ATOM | 1320 | C   | VAL | A | 293 | 63.902 | 60.057 | 30.944 | 1.00 | 25.38 |
| ATOM | 1321 | O   | VAL | A | 293 | 64.874 | 60.812 | 31.000 | 1.00 | 24.51 |
| ATOM | 1322 | CB  | VAL | A | 293 | 63.380 | 60.708 | 28.623 | 1.00 | 24.93 |
| ATOM | 1323 | CG1 | VAL | A | 293 | 63.283 | 60.192 | 27.196 | 1.00 | 24.14 |
| ATOM | 1324 | CG2 | VAL | A | 293 | 62.200 | 61.601 | 28.965 | 1.00 | 25.29 |
| ATOM | 1325 | N   | ASP | A | 294 | 63.209 | 59.686 | 32.018 | 1.00 | 25.36 |
| ATOM | 1326 | CA  | ASP | A | 294 | 63.610 | 60.140 | 33.342 | 1.00 | 25.43 |
| ATOM | 1327 | C   | ASP | A | 294 | 63.315 | 59.123 | 34.439 | 1.00 | 25.22 |
| ATOM | 1328 | O   | ASP | A | 294 | 62.705 | 58.082 | 34.188 | 1.00 | 24.53 |
| ATOM | 1329 | CB  | ASP | A | 294 | 62.966 | 61.500 | 33.678 | 1.00 | 26.32 |
| ATOM | 1330 | CG  | ASP | A | 294 | 61.456 | 61.424 | 33.890 | 1.00 | 26.90 |
| ATOM | 1331 | OD1 | ASP | A | 294 | 60.831 | 60.369 | 33.659 | 1.00 | 27.35 |
| ATOM | 1332 | OD2 | ASP | A | 294 | 60.884 | 62.456 | 34.291 | 1.00 | 28.46 |
| ATOM | 1333 | N   | GLY | A | 295 | 63.762 | 59.435 | 35.649 | 1.00 | 25.01 |

TABLE 7-continued

| ATOM | 1334 | CA | GLY | A | 295 | 63.561 | 58.540 | 36.774 | 1.00 | 26.69 | C |
| --- | --- | --- | --- | --- | --- | --- | --- | --- | --- | --- | --- |
| ATOM | 1335 | C | GLY | A | 295 | 62.112 | 58.224 | 37.083 | 1.00 | 26.45 | C |
| ATOM | 1336 | O | GLY | A | 295 | 61.778 | 57.086 | 37.408 | 1.00 | 25.94 | O |
| ATOM | 1337 | N | GLU | A | 296 | 61.243 | 59.225 | 36.991 | 1.00 | 27.48 | N |
| ATOM | 1338 | CA | GLU | A | 296 | 59.825 | 59.013 | 37.275 | 1.00 | 27.87 | C |
| ATOM | 1339 | C | GLU | A | 296 | 59.191 | 58.014 | 36.317 | 1.00 | 27.05 | C |
| ATOM | 1340 | O | GLU | A | 296 | 58.438 | 57.136 | 36.736 | 1.00 | 26.56 | O |
| ATOM | 1341 | CB | GLU | A | 296 | 59.066 | 60.340 | 37.211 | 1.00 | 31.37 | C |
| ATOM | 1342 | CG | GLU | A | 296 | 59.445 | 61.302 | 38.318 | 1.00 | 37.66 | C |
| ATOM | 1343 | CD | GLU | A | 296 | 58.542 | 62.513 | 38.368 | 1.00 | 42.29 | C |
| ATOM | 1344 | OE1 | GLU | A | 296 | 57.320 | 62.336 | 38.576 | 1.00 | 45.55 | O |
| ATOM | 1345 | OE2 | GLU | A | 296 | 59.050 | 63.643 | 38.196 | 1.00 | 45.27 | O |
| ATOM | 1346 | N | GLY | A | 297 | 59.492 | 58.155 | 35.030 | 1.00 | 25.33 | N |
| ATOM | 1347 | CA | GLY | A | 297 | 58.939 | 57.249 | 34.042 | 1.00 | 25.17 | C |
| ATOM | 1348 | C | GLY | A | 297 | 59.456 | 55.839 | 34.273 | 1.00 | 25.62 | C |
| ATOM | 1349 | O | GLY | A | 297 | 58.719 | 54.863 | 34.137 | 1.00 | 24.83 | O |
| ATOM | 1350 | N | PHE | A | 298 | 60.737 | 55.734 | 34.610 | 1.00 | 24.52 | N |
| ATOM | 1351 | CA | PHE | A | 298 | 61.343 | 54.434 | 34.880 | 1.00 | 25.70 | C |
| ATOM | 1352 | C | PHE | A | 298 | 60.631 | 53.751 | 36.043 | 1.00 | 26.22 | C |
| ATOM | 1353 | O | PHE | A | 298 | 60.219 | 52.595 | 35.946 | 1.00 | 26.55 | O |
| ATOM | 1354 | CB | PHE | A | 298 | 62.821 | 54.589 | 35.253 | 1.00 | 24.99 | C |
| ATOM | 1355 | CG | PHE | A | 298 | 63.432 | 53.322 | 35.785 | 1.00 | 24.97 | C |
| ATOM | 1356 | CD1 | PHE | A | 298 | 63.935 | 52.358 | 34.917 | 1.00 | 25.29 | C |
| ATOM | 1357 | CD2 | PHE | A | 298 | 63.410 | 53.047 | 37.150 | 1.00 | 25.62 | C |
| ATOM | 1358 | CE1 | PHE | A | 298 | 64.400 | 51.131 | 35.400 | 1.00 | 25.51 | C |
| ATOM | 1359 | CE2 | PHE | A | 298 | 63.871 | 51.822 | 37.645 | 1.00 | 25.63 | C |
| ATOM | 1360 | CZ | PHE | A | 298 | 64.364 | 50.863 | 36.766 | 1.00 | 23.87 | C |
| ATOM | 1361 | N | ARG | A | 299 | 60.504 | 54.478 | 37.149 | 1.00 | 26.18 | N |
| ATOM | 1362 | CA | ARG | A | 299 | 59.875 | 53.947 | 38.354 | 1.00 | 27.35 | C |
| ATOM | 1363 | C | ARG | A | 299 | 58.440 | 53.489 | 38.104 | 1.00 | 27.07 | C |
| ATOM | 1364 | O | ARG | A | 299 | 58.011 | 52.454 | 38.622 | 1.00 | 26.36 | O |
| ATOM | 1365 | CB | ARG | A | 299 | 59.916 | 55.000 | 39.468 | 1.00 | 28.99 | C |
| ATOM | 1366 | CG | ARG | A | 299 | 59.457 | 54.503 | 40.837 | 1.00 | 32.84 | C |
| ATOM | 1367 | CD | ARG | A | 299 | 59.794 | 55.518 | 41.926 | 1.00 | 35.60 | C |
| ATOM | 1368 | NE | ARG | A | 299 | 61.220 | 55.543 | 42.252 | 1.00 | 37.71 | N |
| ATOM | 1369 | CZ | ARG | A | 299 | 61.834 | 54.631 | 43.006 | 1.00 | 38.54 | C |
| ATOM | 1370 | NH1 | ARG | A | 299 | 61.150 | 53.616 | 43.519 | 1.00 | 37.82 | N |
| ATOM | 1371 | NH2 | ARG | A | 299 | 63.133 | 54.738 | 43.258 | 1.00 | 38.76 | N |
| ATOM | 1372 | N | TYR | A | 300 | 57.702 | 54.249 | 37.303 | 1.00 | 25.60 | N |

TABLE 7-continued

| ATOM | 1373 | CA  | TYR | A | 300 | 56.324 | 53.890 | 37.005 | 1.00 | 25.92 | C |
| --- | --- | --- | --- | --- | --- | --- | --- | --- | --- | --- | --- |
| ATOM | 1374 | C   | TYR | A | 300 | 56.249 | 52.543 | 36.286 | 1.00 | 26.46 | C |
| ATOM | 1375 | O   | TYR | A | 300 | 55.431 | 51.690 | 36.634 | 1.00 | 26.22 | O |
| ATOM | 1376 | CB  | TYR | A | 300 | 55.664 | 54.958 | 36.136 | 1.00 | 26.45 | C |
| ATOM | 1377 | CG  | TYR | A | 300 | 54.209 | 54.667 | 35.845 | 1.00 | 26.38 | C |
| ATOM | 1378 | CD1 | TYR | A | 300 | 53.222 | 54.911 | 36.803 | 1.00 | 27.42 | C |
| ATOM | 1379 | CD2 | TYR | A | 300 | 53.822 | 54.123 | 34.623 | 1.00 | 26.65 | C |
| ATOM | 1380 | CE1 | TYR | A | 300 | 51.881 | 54.621 | 36.546 | 1.00 | 27.66 | C |
| ATOM | 1381 | CE2 | TYR | A | 300 | 52.486 | 53.831 | 34.359 | 1.00 | 26.96 | C |
| ATOM | 1382 | CZ  | TYR | A | 300 | 51.525 | 54.083 | 35.321 | 1.00 | 27.35 | C |
| ATOM | 1383 | OH  | TYR | A | 300 | 50.207 | 53.804 | 35.045 | 1.00 | 28.84 | O |
| ATOM | 1384 | N   | LEU | A | 301 | 57.100 | 52.352 | 35.283 | 1.00 | 24.93 | N |
| ATOM | 1385 | CA  | LEU | A | 301 | 57.097 | 51.101 | 34.539 | 1.00 | 25.20 | C |
| ATOM | 1386 | C   | LEU | A | 301 | 57.727 | 49.962 | 35.343 | 1.00 | 24.99 | C |
| ATOM | 1387 | O   | LEU | A | 301 | 57.383 | 48.795 | 35.152 | 1.00 | 25.51 | O |
| ATOM | 1388 | CB  | LEU | A | 301 | 57.814 | 51.281 | 33.192 | 1.00 | 24.73 | C |
| ATOM | 1389 | CG  | LEU | A | 301 | 57.092 | 52.216 | 32.208 | 1.00 | 24.97 | C |
| ATOM | 1390 | CD1 | LEU | A | 301 | 57.901 | 52.348 | 30.920 | 1.00 | 24.19 | C |
| ATOM | 1391 | CD2 | LEU | A | 301 | 55.693 | 51.665 | 31.903 | 1.00 | 25.94 | C |
| ATOM | 1392 | N   | ALA | A | 302 | 58.642 | 50.300 | 36.243 | 1.00 | 25.01 | N |
| ATOM | 1393 | CA  | ALA | A | 302 | 59.284 | 49.289 | 37.077 | 1.00 | 26.34 | C |
| ATOM | 1394 | C   | ALA | A | 302 | 58.224 | 48.715 | 38.022 | 1.00 | 27.09 | C |
| ATOM | 1395 | O   | ALA | A | 302 | 58.068 | 47.495 | 38.140 | 1.00 | 27.29 | O |
| ATOM | 1396 | CB  | ALA | A | 302 | 60.426 | 49.911 | 37.872 | 1.00 | 25.08 | C |
| ATOM | 1397 | N   | ASP | A | 303 | 57.493 | 49.603 | 38.688 | 1.00 | 27.62 | N |
| ATOM | 1398 | CA  | ASP | A | 303 | 56.439 | 49.182 | 39.602 | 1.00 | 29.54 | C |
| ATOM | 1399 | C   | ASP | A | 303 | 55.335 | 48.444 | 38.853 | 1.00 | 29.82 | C |
| ATOM | 1400 | O   | ASP | A | 303 | 54.670 | 47.574 | 39.423 | 1.00 | 29.45 | O |
| ATOM | 1401 | CB  | ASP | A | 303 | 55.846 | 50.386 | 40.342 | 1.00 | 31.26 | C |
| ATOM | 1402 | CG  | ASP | A | 303 | 56.796 | 50.967 | 41.374 | 1.00 | 34.06 | C |
| ATOM | 1403 | OD1 | ASP | A | 303 | 57.678 | 50.226 | 41.863 | 1.00 | 35.03 | O |
| ATOM | 1404 | OD2 | ASP | A | 303 | 56.652 | 52.160 | 41.713 | 1.00 | 35.59 | O |
| ATOM | 1405 | N   | ALA | A | 304 | 55.145 | 48.786 | 37.579 | 1.00 | 28.20 | N |
| ATOM | 1406 | CA  | ALA | A | 304 | 54.124 | 48.148 | 36.748 | 1.00 | 28.48 | C |
| ATOM | 1407 | C   | ALA | A | 304 | 54.500 | 46.706 | 36.403 | 1.00 | 29.41 | C |
| ATOM | 1408 | O   | ALA | A | 304 | 53.644 | 45.919 | 35.981 | 1.00 | 30.01 | O |
| ATOM | 1409 | CB  | ALA | A | 304 | 53.913 | 48.943 | 35.467 | 1.00 | 29.13 | C |
| ATOM | 1410 | N   | GLY | A | 305 | 55.779 | 46.371 | 36.558 | 1.00 | 27.94 | N |
| ATOM | 1411 | CA  | GLY | A | 305 | 56.228 | 45.013 | 36.285 | 1.00 | 28.09 | C |

TABLE 7-continued

| | | | | | | | | | |
|---|---|---|---|---|---|---|---|---|---|
| ATOM | 1412 | C | GLY | A | 305 | 57.047 | 44.759 | 35.031 | 1.00 27.94 |
| ATOM | 1413 | O | GLY | A | 305 | 57.303 | 43.603 | 34.688 | 1.00 28.94 |
| ATOM | 1414 | N | ALA | A | 306 | 57.468 | 45.815 | 34.342 | 1.00 27.01 |
| ATOM | 1415 | CA | ALA | A | 306 | 58.259 | 45.655 | 33.118 | 1.00 26.21 |
| ATOM | 1416 | C | ALA | A | 306 | 59.530 | 44.833 | 33.371 | 1.00 25.71 |
| ATOM | 1417 | O | ALA | A | 306 | 60.172 | 44.983 | 34.409 | 1.00 26.47 |
| ATOM | 1418 | CB | ALA | A | 306 | 58.630 | 47.038 | 32.549 | 1.00 26.19 |
| ATOM | 1419 | N | ASP | A | 307 | 59.888 | 43.970 | 32.421 | 1.00 26.45 |
| ATOM | 1420 | CA | ASP | A | 307 | 61.087 | 43.135 | 32.549 | 1.00 26.38 |
| ATOM | 1421 | C | ASP | A | 307 | 62.351 | 43.883 | 32.137 | 1.00 26.11 |
| ATOM | 1422 | O | ASP | A | 307 | 63.459 | 43.517 | 32.523 | 1.00 26.90 |
| ATOM | 1423 | CB | ASP | A | 307 | 60.923 | 41.857 | 31.731 | 1.00 27.11 |
| ATOM | 1424 | CG | ASP | A | 307 | 59.967 | 40.887 | 32.387 | 1.00 29.35 |
| ATOM | 1425 | OD1 | ASP | A | 307 | 60.312 | 40.373 | 33.470 | 1.00 29.58 |
| ATOM | 1426 | OD2 | ASP | A | 307 | 58.873 | 40.656 | 31.837 | 1.00 30.28 |
| ATOM | 1427 | N | PHE | A | 308 | 62.174 | 44.916 | 31.324 | 1.00 24.79 |
| ATOM | 1428 | CA | PHE | A | 308 | 63.274 | 45.786 | 30.922 | 1.00 25.02 |
| ATOM | 1429 | C | PHE | A | 308 | 62.613 | 47.071 | 30.453 | 1.00 25.26 |
| ATOM | 1430 | O | PHE | A | 308 | 61.465 | 47.059 | 30.006 | 1.00 25.39 |
| ATOM | 1431 | CB | PHE | A | 308 | 64.194 | 45.142 | 29.855 | 1.00 24.16 |
| ATOM | 1432 | CG | PHE | A | 308 | 63.647 | 45.131 | 28.449 | 1.00 26.91 |
| ATOM | 1433 | CD1 | PHE | A | 308 | 63.601 | 46.297 | 27.686 | 1.00 26.51 |
| ATOM | 1434 | CD2 | PHE | A | 308 | 63.232 | 43.933 | 27.866 | 1.00 27.59 |
| ATOM | 1435 | CE1 | PHE | A | 308 | 63.157 | 46.273 | 26.368 | 1.00 27.45 |
| ATOM | 1436 | CE2 | PHE | A | 308 | 62.783 | 43.892 | 26.543 | 1.00 28.40 |
| ATOM | 1437 | CZ | PHE | A | 308 | 62.745 | 45.062 | 25.790 | 1.00 28.01 |
| ATOM | 1438 | N | ILE | A | 309 | 63.316 | 48.187 | 30.597 | 1.00 24.66 |
| ATOM | 1439 | CA | ILE | A | 309 | 62.737 | 49.469 | 30.227 | 1.00 24.56 |
| ATOM | 1440 | C | ILE | A | 309 | 63.565 | 50.185 | 29.171 | 1.00 24.22 |
| ATOM | 1441 | O | ILE | A | 309 | 64.781 | 50.319 | 29.304 | 1.00 23.11 |
| ATOM | 1442 | CB | ILE | A | 309 | 62.566 | 50.338 | 31.495 | 1.00 25.23 |
| ATOM | 1443 | CG1 | ILE | A | 309 | 61.544 | 49.662 | 32.419 | 1.00 24.51 |
| ATOM | 1444 | CG2 | ILE | A | 309 | 62.134 | 51.756 | 31.123 | 1.00 24.72 |
| ATOM | 1445 | CD1 | ILE | A | 309 | 61.450 | 50.243 | 33.802 | 1.00 25.49 |
| ATOM | 1446 | N | LYS | A | 310 | 62.881 | 50.643 | 28.125 | 1.00 23.39 |
| ATOM | 1447 | CA | LYS | A | 310 | 63.527 | 51.310 | 27.003 | 1.00 24.09 |
| ATOM | 1448 | C | LYS | A | 310 | 63.573 | 52.825 | 27.202 | 1.00 24.12 |
| ATOM | 1449 | O | LYS | A | 310 | 62.578 | 53.449 | 27.575 | 1.00 22.87 |
| ATOM | 1450 | CB | LYS | A | 310 | 62.788 | 50.945 | 25.713 | 1.00 25.57 |

TABLE 7-continued

| | | | | | | | | | |
|---|---|---|---|---|---|---|---|---|---|
| ATOM | 1451 | CG | LYS | A | 310 | 63.633 | 51.022 | 24.457 | 1.00 27.69 |
| C | | | | | | | | | |
| ATOM | 1452 | CD | LYS | A | 310 | 63.347 | 49.838 | 23.526 | 1.00 27.60 |
| C | | | | | | | | | |
| ATOM | 1453 | CE | LYS | A | 310 | 61.915 | 49.849 | 23.020 | 1.00 27.87 |
| C | | | | | | | | | |
| ATOM | 1454 | NZ | LYS | A | 310 | 61.614 | 51.110 | 22.280 | 1.00 28.37 |
| N | | | | | | | | | |
| ATOM | 1455 | N | ILE | A | 311 | 64.741 | 53.398 | 26.925 | 1.00 23.23 |
| N | | | | | | | | | |
| ATOM | 1456 | CA | ILE | A | 311 | 64.996 | 54.827 | 27.101 | 1.00 23.17 |
| C | | | | | | | | | |
| ATOM | 1457 | C | ILE | A | 311 | 65.173 | 55.586 | 25.794 | 1.00 21.87 |
| C | | | | | | | | | |
| ATOM | 1458 | O | ILE | A | 311 | 65.937 | 55.166 | 24.925 | 1.00 22.46 |
| O | | | | | | | | | |
| ATOM | 1459 | CB | ILE | A | 311 | 66.301 | 55.045 | 27.901 | 1.00 21.23 |
| C | | | | | | | | | |
| ATOM | 1460 | CG1 | ILE | A | 311 | 66.238 | 54.291 | 29.236 | 1.00 22.02 |
| C | | | | | | | | | |
| ATOM | 1461 | CG2 | ILE | A | 311 | 66.537 | 56.532 | 28.122 | 1.00 21.42 |
| C | | | | | | | | | |
| ATOM | 1462 | CD1 | ILE | A | 311 | 67.601 | 54.143 | 29.891 | 1.00 21.94 |
| C | | | | | | | | | |
| ATOM | 1463 | N | GLY | A | 312 | 64.484 | 56.712 | 25.662 | 1.00 24.32 |
| N | | | | | | | | | |
| ATOM | 1464 | CA | GLY | A | 312 | 64.666 | 57.510 | 24.467 | 1.00 24.57 |
| C | | | | | | | | | |
| ATOM | 1465 | C | GLY | A | 312 | 63.449 | 58.070 | 23.773 | 1.00 26.09 |
| C | | | | | | | | | |
| ATOM | 1466 | O | GLY | A | 312 | 62.559 | 57.332 | 23.356 | 1.00 25.55 |
| O | | | | | | | | | |
| ATOM | 1467 | N | ILE | A | 313 | 63.428 | 59.393 | 23.644 | 1.00 26.99 |
| N | | | | | | | | | |
| ATOM | 1468 | CA | ILE | A | 313 | 62.357 | 60.089 | 22.950 | 1.00 28.73 |
| C | | | | | | | | | |
| ATOM | 1469 | C | ILE | A | 313 | 62.968 | 61.275 | 22.215 | 1.00 30.51 |
| C | | | | | | | | | |
| ATOM | 1470 | O | ILE | A | 313 | 63.531 | 62.172 | 22.845 | 1.00 30.13 |
| O | | | | | | | | | |
| ATOM | 1471 | CB | ILE | A | 313 | 61.281 | 60.635 | 23.915 | 1.00 28.78 |
| C | | | | | | | | | |
| ATOM | 1472 | CG1 | ILE | A | 313 | 60.561 | 59.480 | 24.619 | 1.00 29.45 |
| C | | | | | | | | | |
| ATOM | 1473 | CG2 | ILE | A | 313 | 60.277 | 61.469 | 23.134 | 1.00 29.20 |
| C | | | | | | | | | |
| ATOM | 1474 | CD1 | ILE | A | 313 | 59.544 | 59.942 | 25.648 | 1.00 29.69 |
| C | | | | | | | | | |
| ATOM | 1475 | N | GLY | A | 314 | 62.865 | 61.264 | 20.888 | 1.00 33.20 |
| N | | | | | | | | | |
| ATOM | 1476 | CA | GLY | A | 314 | 63.385 | 62.357 | 20.087 | 1.00 36.88 |
| C | | | | | | | | | |
| ATOM | 1477 | C | GLY | A | 314 | 64.748 | 62.144 | 19.454 | 1.00 39.48 |
| C | | | | | | | | | |
| ATOM | 1478 | O | GLY | A | 314 | 65.102 | 62.843 | 18.499 | 1.00 40.62 |
| O | | | | | | | | | |
| ATOM | 1479 | N | GLY | A | 315 | 65.506 | 61.177 | 19.967 | 1.00 40.05 |
| N | | | | | | | | | |
| ATOM | 1480 | CA | GLY | A | 315 | 66.840 | 60.918 | 19.452 | 1.00 41.12 |
| C | | | | | | | | | |
| ATOM | 1481 | C | GLY | A | 315 | 66.950 | 60.152 | 18.146 | 1.00 42.12 |
| C | | | | | | | | | |
| ATOM | 1482 | O | GLY | A | 315 | 67.977 | 60.235 | 17.469 | 1.00 41.49 |
| O | | | | | | | | | |
| ATOM | 1483 | N | GLY | A | 316 | 65.906 | 59.409 | 17.790 | 1.00 42.04 |
| N | | | | | | | | | |
| ATOM | 1484 | CA | GLY | A | 316 | 65.924 | 58.640 | 16.555 | 1.00 42.81 |
| C | | | | | | | | | |
| ATOM | 1485 | C | GLY | A | 316 | 66.345 | 59.447 | 15.338 | 1.00 43.59 |
| C | | | | | | | | | |
| ATOM | 1486 | O | GLY | A | 316 | 66.029 | 60.633 | 15.227 | 1.00 44.04 |
| O | | | | | | | | | |
| ATOM | 1487 | N | SER | A | 317 | 67.056 | 58.800 | 14.419 | 1.00 44.63 |
| N | | | | | | | | | |
| ATOM | 1488 | CA | SER | A | 317 | 67.535 | 59.453 | 13.204 | 1.00 45.96 |
| C | | | | | | | | | |
| ATOM | 1489 | C | SER | A | 317 | 66.400 | 59.929 | 12.303 | 1.00 47.12 |
| C | | | | | | | | | |

TABLE 7-continued

| | | | | | | | | | | |
|---|---|---|---|---|---|---|---|---|---|---|
| ATOM | 1490 | O | SER | A | 317 | 66.554 | 60.897 | 11.561 | 1.00 | 46.76 |
| O | | | | | | | | | | |
| ATOM | 1491 | CB | SER | A | 317 | 68.436 | 58.503 | 12.412 | 1.00 | 45.33 |
| C | | | | | | | | | | |
| ATOM | 1492 | OG | SER | A | 317 | 67.704 | 57.391 | 11.925 | 1.00 | 44.82 |
| O | | | | | | | | | | |
| ATOM | 1493 | N | ILE | A | 318 | 65.266 | 59.240 | 12.363 | 1.00 | 49.21 |
| N | | | | | | | | | | |
| ATOM | 1494 | CA | ILE | A | 318 | 64.115 | 59.604 | 11.544 | 1.00 | 51.92 |
| C | | | | | | | | | | |
| ATOM | 1495 | C | ILE | A | 318 | 62.986 | 60.204 | 12.374 | 1.00 | 53.83 |
| C | | | | | | | | | | |
| ATOM | 1496 | O | ILE | A | 318 | 61.811 | 60.095 | 12.019 | 1.00 | 54.17 |
| O | | | | | | | | | | |
| ATOM | 1497 | CB | ILE | A | 318 | 63.581 | 58.381 | 10.754 | 1.00 | 51.77 |
| C | | | | | | | | | | |
| ATOM | 1498 | CG1 | ILE | A | 318 | 63.731 | 57.105 | 11.586 | 1.00 | 51.59 |
| C | | | | | | | | | | |
| ATOM | 1499 | CG2 | ILE | A | 318 | 64.339 | 58.237 | 9.441 | 1.00 | 51.61 |
| C | | | | | | | | | | |
| ATOM | 1500 | CD1 | ILE | A | 318 | 62.997 | 57.131 | 12.898 | 1.00 | 51.22 |
| C | | | | | | | | | | |
| HETATM | 1501 | N | CSO | A | 319 | 63.355 | 60.840 | 13.481 | 1.00 | 56.01 |
| N | | | | | | | | | | |
| HETATM | 1502 | CA | CSO | A | 319 | 62.387 | 61.468 | 14.371 | 1.00 | 58.61 |
| C | | | | | | | | | | |
| HETATM | 1503 | CB | CSO | A | 319 | 62.457 | 60.825 | 15.760 | 1.00 | 60.16 |
| C | | | | | | | | | | |
| HETATM | 1504 | SG | CSO | A | 319 | 60.983 | 61.106 | 16.793 | 1.00 | 64.08 |
| S | | | | | | | | | | |
| HETATM | 1505 | C | CSO | A | 319 | 62.708 | 62.957 | 14.481 | 1.00 | 59.03 |
| C | | | | | | | | | | |
| HETATM | 1506 | O | CSO | A | 319 | 63.754 | 63.331 | 15.008 | 1.00 | 58.88 |
| O | | | | | | | | | | |
| HETATM | 1507 | OD | CSO | A | 319 | 60.477 | 62.837 | 16.987 | 1.00 | 63.19 |
| O | | | | | | | | | | |
| ATOM | 1508 | N | ILE | A | 320 | 61.814 | 63.805 | 13.979 | 1.00 | 59.78 |
| N | | | | | | | | | | |
| ATOM | 1509 | CA | ILE | A | 320 | 62.028 | 65.250 | 14.034 | 1.00 | 60.48 |
| C | | | | | | | | | | |
| ATOM | 1510 | C | ILE | A | 320 | 61.159 | 65.875 | 15.125 | 1.00 | 60.65 |
| C | | | | | | | | | | |
| ATOM | 1511 | O | ILE | A | 320 | 60.074 | 66.397 | 14.856 | 1.00 | 60.82 |
| O | | | | | | | | | | |
| ATOM | 1512 | CB | ILE | A | 320 | 61.706 | 65.913 | 12.676 | 1.00 | 60.96 |
| C | | | | | | | | | | |
| ATOM | 1513 | CG1 | ILE | A | 320 | 62.500 | 65.221 | 11.562 | 1.00 | 61.17 |
| C | | | | | | | | | | |
| ATOM | 1514 | CG2 | ILE | A | 320 | 62.064 | 67.398 | 12.721 | 1.00 | 60.93 |
| C | | | | | | | | | | |
| ATOM | 1515 | CD1 | ILE | A | 320 | 62.196 | 65.738 | 10.167 | 1.00 | 61.13 |
| C | | | | | | | | | | |
| ATOM | 1516 | N | THR | A | 321 | 61.656 | 65.817 | 16.357 | 1.00 | 60.47 |
| N | | | | | | | | | | |
| ATOM | 1517 | CA | THR | A | 321 | 60.961 | 66.343 | 17.530 | 1.00 | 60.58 |
| C | | | | | | | | | | |
| ATOM | 1518 | C | THR | A | 321 | 60.288 | 67.701 | 17.323 | 1.00 | 60.31 |
| C | | | | | | | | | | |
| ATOM | 1519 | O | THR | A | 321 | 59.072 | 67.828 | 17.474 | 1.00 | 59.52 |
| O | | | | | | | | | | |
| ATOM | 1520 | CB | THR | A | 321 | 61.928 | 66.469 | 18.726 | 1.00 | 60.88 |
| C | | | | | | | | | | |
| ATOM | 1521 | OG1 | THR | A | 321 | 62.632 | 65.234 | 18.906 | 1.00 | 61.19 |
| O | | | | | | | | | | |
| ATOM | 1522 | CG2 | THR | A | 321 | 61.157 | 66.797 | 19.995 | 1.00 | 60.45 |
| C | | | | | | | | | | |
| ATOM | 1523 | N | ARG | A | 322 | 61.086 | 68.709 | 16.986 | 1.00 | 60.45 |
| N | | | | | | | | | | |
| ATOM | 1524 | CA | ARG | A | 322 | 60.581 | 70.063 | 16.776 | 1.00 | 60.85 |
| C | | | | | | | | | | |
| ATOM | 1525 | C | ARG | A | 322 | 59.375 | 70.172 | 15.850 | 1.00 | 60.80 |
| C | | | | | | | | | | |
| ATOM | 1526 | O | ARG | A | 322 | 58.401 | 70.849 | 16.176 | 1.00 | 60.73 |
| O | | | | | | | | | | |
| ATOM | 1527 | CB | ARG | A | 322 | 61.695 | 70.967 | 16.251 | 1.00 | 61.37 |
| C | | | | | | | | | | |
| ATOM | 1528 | CG | ARG | A | 322 | 62.696 | 71.397 | 17.305 | 1.00 | 62.07 |
| C | | | | | | | | | | |

TABLE 7-continued

| | | | | | | | | | |
|---|---|---|---|---|---|---|---|---|---|
| ATOM | 1529 | CD | ARG | A | 322 | 63.711 | 72.351 | 16.706 | 1.00 62.95 |
| ATOM | 1530 | NE | ARG | A | 322 | 64.504 | 73.029 | 17.726 | 1.00 63.47 |
| ATOM | 1531 | CZ | ARG | A | 322 | 65.442 | 73.931 | 17.458 | 1.00 63.65 |
| ATOM | 1532 | NH1 | ARG | A | 322 | 65.704 | 74.262 | 16.200 | 1.00 63.49 |
| ATOM | 1533 | NH2 | ARG | A | 322 | 66.115 | 74.504 | 18.445 | 1.00 63.65 |
| ATOM | 1534 | N | GLU | A | 323 | 59.437 | 69.522 | 14.693 | 1.00 60.59 |
| ATOM | 1535 | CA | GLU | A | 323 | 58.328 | 69.579 | 13.747 | 1.00 60.45 |
| ATOM | 1536 | C | GLU | A | 323 | 57.157 | 68.717 | 14.208 | 1.00 59.48 |
| ATOM | 1537 | O | GLU | A | 323 | 56.231 | 68.454 | 13.439 | 1.00 59.76 |
| ATOM | 1538 | CB | GLU | A | 323 | 58.781 | 69.116 | 12.359 | 1.00 61.67 |
| ATOM | 1539 | CG | GLU | A | 323 | 59.935 | 69.914 | 11.778 | 1.00 63.67 |
| ATOM | 1540 | CD | GLU | A | 323 | 60.259 | 69.515 | 10.348 | 1.00 64.69 |
| ATOM | 1541 | OE1 | GLU | A | 323 | 60.474 | 68.311 | 10.094 | 1.00 65.62 |
| ATOM | 1542 | OE2 | GLU | A | 323 | 60.301 | 70.407 | 9.476 | 1.00 65.47 |
| ATOM | 1543 | N | GLN | A | 324 | 57.194 | 68.284 | 15.464 | 1.00 57.92 |
| ATOM | 1544 | CA | GLN | A | 324 | 56.131 | 67.446 | 16.001 | 1.00 56.25 |
| ATOM | 1545 | C | GLN | A | 324 | 55.529 | 67.984 | 17.300 | 1.00 54.10 |
| ATOM | 1546 | O | GLN | A | 324 | 54.872 | 69.026 | 17.300 | 1.00 54.39 |
| ATOM | 1547 | CB | GLN | A | 324 | 56.653 | 66.022 | 16.206 | 1.00 58.06 |
| ATOM | 1548 | CG | GLN | A | 324 | 57.155 | 65.370 | 14.924 | 1.00 60.13 |
| ATOM | 1549 | CD | GLN | A | 324 | 57.820 | 64.027 | 15.164 | 1.00 61.81 |
| ATOM | 1550 | OE1 | GLN | A | 324 | 58.311 | 63.388 | 14.231 | 1.00 62.58 |
| ATOM | 1551 | NE2 | GLN | A | 324 | 57.838 | 63.590 | 16.419 | 1.00 62.80 |
| ATOM | 1552 | N | LYS | A | 325 | 55.754 | 67.278 | 18.404 | 1.00 50.55 |
| ATOM | 1553 | CA | LYS | A | 325 | 55.200 | 67.685 | 19.693 | 1.00 46.97 |
| ATOM | 1554 | C | LYS | A | 325 | 56.157 | 68.456 | 20.589 | 1.00 43.59 |
| ATOM | 1555 | O | LYS | A | 325 | 55.731 | 69.086 | 21.558 | 1.00 42.57 |
| ATOM | 1556 | CB | LYS | A | 325 | 54.703 | 66.463 | 20.467 | 1.00 47.99 |
| ATOM | 1557 | CG | LYS | A | 325 | 53.491 | 65.775 | 19.876 | 1.00 50.14 |
| ATOM | 1558 | CD | LYS | A | 325 | 53.077 | 64.618 | 20.773 | 1.00 50.62 |
| ATOM | 1559 | CE | LYS | A | 325 | 51.895 | 63.874 | 20.208 | 1.00 51.86 |
| ATOM | 1560 | NZ | LYS | A | 325 | 51.526 | 62.721 | 21.067 | 1.00 52.95 |
| ATOM | 1561 | N | GLY | A | 326 | 57.446 | 68.400 | 20.283 | 1.00 39.82 |
| ATOM | 1562 | CA | GLY | A | 326 | 58.399 | 69.103 | 21.118 | 1.00 36.97 |
| ATOM | 1563 | C | GLY | A | 326 | 58.613 | 68.383 | 22.439 | 1.00 35.12 |
| ATOM | 1564 | O | GLY | A | 326 | 58.842 | 69.015 | 23.473 | 1.00 33.70 |
| ATOM | 1565 | N | ILE | A | 327 | 58.510 | 67.056 | 22.412 | 1.00 33.10 |
| ATOM | 1566 | CA | ILE | A | 327 | 58.732 | 66.255 | 23.609 | 1.00 31.94 |
| ATOM | 1567 | C | ILE | A | 327 | 60.039 | 65.500 | 23.399 | 1.00 30.96 |

TABLE 7-continued

| | | | | | | | | | |
|---|---|---|---|---|---|---|---|---|---|
| ATOM | 1568 | O | ILE | A | 327 | 60.360 | 65.095 | 22.283 | 1.00 29.97 |
| O | | | | | | | | | |
| ATOM | 1569 | CB | ILE | A | 327 | 57.584 | 65.229 | 23.865 | 1.00 33.54 |
| C | | | | | | | | | |
| ATOM | 1570 | CC1 | ILE | A | 327 | 57.479 | 64.236 | 22.708 | 1.00 35.09 |
| C | | | | | | | | | |
| ATOM | 1571 | CG2 | ILE | A | 327 | 56.257 | 65.961 | 24.048 | 1.00 34.89 |
| C | | | | | | | | | |
| ATOM | 1572 | CD1 | ILE | A | 327 | 56.438 | 63.139 | 22.937 | 1.00 37.76 |
| C | | | | | | | | | |
| ATOM | 1573 | N | GLY | A | 328 | 60.807 | 65.322 | 24.463 | 1.00 29.65 |
| N | | | | | | | | | |
| ATOM | 1574 | CA | GLY | A | 328 | 62.058 | 64.606 | 24.312 | 1.00 29.68 |
| C | | | | | | | | | |
| ATOM | 1575 | C | GLY | A | 328 | 63.106 | 65.030 | 25.316 | 1.00 28.25 |
| C | | | | | | | | | |
| ATOM | 1576 | O | GLY | A | 328 | 62.838 | 65.825 | 26.220 | 1.00 27.09 |
| O | | | | | | | | | |
| ATOM | 1577 | N | ARG | A | 329 | 64.309 | 64.494 | 25.147 | 1.00 27.34 |
| N | | | | | | | | | |
| ATOM | 1578 | CA | ARG | A | 329 | 65.410 | 64.807 | 26.039 | 1.00 26.13 |
| C | | | | | | | | | |
| ATOM | 1579 | C | ARG | A | 329 | 66.674 | 64.258 | 25.404 | 1.00 25.89 |
| C | | | | | | | | | |
| ATOM | 1580 | O | ARG | A | 329 | 66.636 | 63.207 | 24.760 | 1.00 25.64 |
| O | | | | | | | | | |
| ATOM | 1581 | CB | ARG | A | 329 | 65.178 | 64.141 | 27.400 | 1.00 26.27 |
| C | | | | | | | | | |
| ATOM | 1582 | CG | ARG | A | 329 | 66.074 | 64.661 | 28.510 | 1.00 25.63 |
| C | | | | | | | | | |
| ATOM | 1583 | CD | ARG | A | 329 | 65.816 | 63.929 | 29.809 | 1.00 25.44 |
| C | | | | | | | | | |
| ATOM | 1584 | NE | ARG | A | 329 | 66.249 | 64.709 | 30.966 | 1.00 24.87 |
| N | | | | | | | | | |
| ATOM | 1585 | CZ | ARG | A | 329 | 66.203 | 64.269 | 32.218 | 1.00 26.41 |
| C | | | | | | | | | |
| ATOM | 1586 | NH1 | ARG | A | 329 | 65.754 | 63.048 | 32.475 | 1.00 25.65 |
| N | | | | | | | | | |
| ATOM | 1587 | NH2 | ARG | A | 329 | 66.577 | 65.058 | 33.216 | 1.00 26.64 |
| N | | | | | | | | | |
| ATOM | 1588 | N | GLY | A | 330 | 67.787 | 64.975 | 25.560 | 1.00 25.19 |
| N | | | | | | | | | |
| ATOM | 1589 | CA | GLY | A | 330 | 69.040 | 64.497 | 25.002 | 1.00 24.58 |
| C | | | | | | | | | |
| ATOM | 1590 | C | GLY | A | 330 | 69.218 | 63.063 | 25.469 | 1.00 24.73 |
| C | | | | | | | | | |
| ATOM | 1591 | O | GLY | A | 330 | 69.010 | 62.770 | 26.645 | 1.00 23.16 |
| O | | | | | | | | | |
| ATOM | 1592 | N | GLN | A | 331 | 69.617 | 62.174 | 24.566 | 1.00 24.37 |
| N | | | | | | | | | |
| ATOM | 1593 | CA | GLN | A | 331 | 69.763 | 60.757 | 24.909 | 1.00 24.78 |
| C | | | | | | | | | |
| ATOM | 1594 | C | GLN | A | 331 | 70.739 | 60.463 | 26.043 | 1.00 24.31 |
| C | | | | | | | | | |
| ATOM | 1595 | O | GLN | A | 331 | 70.466 | 59.610 | 26.889 | 1.00 23.63 |
| O | | | | | | | | | |
| ATOM | 1596 | CB | GLN | A | 331 | 70.162 | 59.947 | 23.667 | 1.00 25.13 |
| C | | | | | | | | | |
| ATOM | 1597 | CG | GLN | A | 331 | 70.073 | 58.430 | 23.863 | 1.00 25.46 |
| C | | | | | | | | | |
| ATOM | 1598 | CD | GLN | A | 331 | 68.633 | 57.917 | 23.958 | 1.00 28.00 |
| C | | | | | | | | | |
| ATOM | 1599 | OE1 | GLN | A | 331 | 68.391 | 56.774 | 24.355 | 1.00 29.62 |
| O | | | | | | | | | |
| ATOM | 1600 | NE2 | GLN | A | 331 | 67.679 | 58.756 | 23.586 | 1.00 26.29 |
| N | | | | | | | | | |
| ATOM | 1601 | N | ALA | A | 332 | 71.878 | 61.155 | 26.064 | 1.00 23.62 |
| N | | | | | | | | | |
| ATOM | 1602 | CA | ALA | A | 332 | 72.864 | 60.930 | 27.117 | 1.00 22.91 |
| C | | | | | | | | | |
| ATOM | 1603 | C | ALA | A | 332 | 72.283 | 61.243 | 28.492 | 1.00 23.37 |
| C | | | | | | | | | |
| ATOM | 1604 | O | ALA | A | 332 | 72.389 | 60.441 | 29.425 | 1.00 22.61 |
| O | | | | | | | | | |
| ATOM | 1605 | CB | ALA | A | 332 | 74.115 | 61.778 | 26.864 | 1.00 23.28 |
| C | | | | | | | | | |
| ATOM | 1606 | N | THR | A | 333 | 71.668 | 62.413 | 28.619 | 1.00 22.11 |
| N | | | | | | | | | |

TABLE 7-continued

| ATOM | 1607 | CA | THR | A | 333 | 71.075 | 62.815 | 29.878 | 1.00 | 22.48 |
| ATOM | 1608 | C | THR | A | 333 | 69.974 | 61.840 | 30.296 | 1.00 | 22.58 |
| ATOM | 1609 | O | THR | A | 333 | 69.857 | 61.492 | 31.470 | 1.00 | 21.18 |
| ATOM | 1610 | CB | THR | A | 333 | 70.493 | 64.238 | 29.785 | 1.00 | 23.93 |
| ATOM | 1611 | CG1 | THR | A | 333 | 71.547 | 65.160 | 29.457 | 1.00 | 24.95 |
| ATOM | 1612 | CG2 | THR | A | 333 | 69.865 | 64.645 | 31.119 | 1.00 | 23.81 |
| ATOM | 1613 | N | ALA | A | 334 | 69.176 | 61.401 | 29.329 | 1.00 | 21.99 |
| ATOM | 1614 | CA | ALA | A | 334 | 68.093 | 60.462 | 29.600 | 1.00 | 22.69 |
| ATOM | 1615 | C | ALA | A | 334 | 68.630 | 59.149 | 30.178 | 1.00 | 22.31 |
| ATOM | 1616 | O | ALA | A | 334 | 68.113 | 58.632 | 31.175 | 1.00 | 22.17 |
| ATOM | 1617 | CB | ALA | A | 334 | 67.315 | 60.186 | 28.319 | 1.00 | 22.40 |
| ATOM | 1618 | N | VAL | A | 335 | 69.663 | 58.604 | 29.548 | 1.00 | 22.74 |
| ATOM | 1619 | CA | VAL | A | 335 | 70.248 | 57.349 | 30.019 | 1.00 | 21.65 |
| ATOM | 1620 | C | VAL | A | 335 | 70.836 | 57.522 | 31.417 | 1.00 | 22.93 |
| ATOM | 1621 | O | VAL | A | 335 | 70.561 | 56.739 | 32.327 | 1.00 | 22.43 |
| ATOM | 1622 | CB | VAL | A | 335 | 71.360 | 56.864 | 29.062 | 1.00 | 23.64 |
| ATOM | 1623 | CG1 | VAL | A | 335 | 72.090 | 55.646 | 29.664 | 1.00 | 22.43 |
| ATOM | 1624 | CG2 | VAL | A | 335 | 70.750 | 56.502 | 27.712 | 1.00 | 22.06 |
| ATOM | 1625 | N | ILE | A | 336 | 71.644 | 58.562 | 31.590 | 1.00 | 22.47 |
| ATOM | 1626 | CA | ILE | A | 336 | 72.275 | 58.816 | 32.879 | 1.00 | 22.53 |
| ATOM | 1627 | C | ILE | A | 336 | 71.251 | 58.936 | 34.005 | 1.00 | 23.00 |
| ATOM | 1628 | O | ILE | A | 336 | 71.418 | 58.363 | 35.087 | 1.00 | 21.54 |
| ATOM | 1629 | CB | ILE | A | 336 | 73.132 | 60.097 | 32.810 | 1.00 | 22.52 |
| ATOM | 1630 | CG1 | ILE | A | 336 | 74.304 | 59.869 | 31.846 | 1.00 | 21.96 |
| ATOM | 1631 | CG2 | ILE | A | 336 | 73.639 | 60.476 | 34.199 | 1.00 | 23.53 |
| ATOM | 1632 | CD1 | ILE | A | 336 | 75.114 | 61.125 | 31.544 | 1.00 | 24.57 |
| ATOM | 1633 | N | ASP | A | 337 | 70.183 | 59.679 | 33.745 | 1.00 | 23.52 |
| ATOM | 1634 | CA | ASP | A | 337 | 69.146 | 59.880 | 34.750 | 1.00 | 23.90 |
| ATOM | 1635 | C | ASP | A | 337 | 68.406 | 58.575 | 35.066 | 1.00 | 23.59 |
| ATOM | 1636 | O | ASP | A | 337 | 68.220 | 58.212 | 36.234 | 1.00 | 22.64 |
| ATOM | 1637 | CB | ASP | A | 337 | 68.153 | 60.931 | 34.251 | 1.00 | 26.45 |
| ATOM | 1638 | CG | ASP | A | 337 | 67.150 | 61.326 | 35.301 | 1.00 | 28.83 |
| ATOM | 1639 | OD1 | ASP | A | 337 | 65.975 | 61.536 | 34.943 | 1.00 | 30.37 |
| ATOM | 1640 | OD2 | ASP | A | 337 | 67.539 | 61.437 | 36.483 | 1.00 | 32.41 |
| ATOM | 1641 | N | VAL | A | 338 | 67.982 | 57.870 | 34.024 | 1.00 | 22.38 |
| ATOM | 1642 | CA | VAL | A | 338 | 67.258 | 56.619 | 34.221 | 1.00 | 23.04 |
| ATOM | 1643 | C | VAL | A | 338 | 68.116 | 55.587 | 34.949 | 1.00 | 23.56 |
| ATOM | 1644 | O | VAL | A | 338 | 67.635 | 54.899 | 35.852 | 1.00 | 23.29 |
| ATOM | 1645 | CB | VAL | A | 338 | 66.776 | 56.030 | 32.875 | 1.00 | 22.58 |

TABLE 7-continued

| ATOM | 1646 | CG1 | VAL | A | 338 | 66.198 | 54.625 | 33.089 | 1.00 | 21.84 |
|---|---|---|---|---|---|---|---|---|---|---|
| C | | | | | | | | | | |
| ATOM | 1647 | CG2 | VAL | A | 338 | 65.707 | 56.941 | 32.269 | 1.00 | 21.24 |
| C | | | | | | | | | | |
| ATOM | 1648 | N | VAL | A | 339 | 69.383 | 55.489 | 34.559 | 1.00 | 23.76 |
| N | | | | | | | | | | |
| ATOM | 1649 | CA | VAL | A | 339 | 70.292 | 54.542 | 35.189 | 1.00 | 23.00 |
| C | | | | | | | | | | |
| ATOM | 1650 | C | VAL | A | 339 | 70.446 | 54.832 | 36.682 | 1.00 | 24.41 |
| C | | | | | | | | | | |
| ATOM | 1651 | O | VAL | A | 339 | 70.499 | 53.906 | 37.496 | 1.00 | 23.06 |
| O | | | | | | | | | | |
| ATOM | 1652 | CB | VAL | A | 339 | 71.677 | 54.563 | 34.497 | 1.00 | 23.80 |
| C | | | | | | | | | | |
| ATOM | 1653 | CG1 | VAL | A | 339 | 72.729 | 53.905 | 35.382 | 1.00 | 22.59 |
| C | | | | | | | | | | |
| ATOM | 1654 | CG2 | VAL | A | 339 | 71.588 | 53.822 | 33.164 | 1.00 | 22.47 |
| C | | | | | | | | | | |
| ATOM | 1655 | N | ALA | A | 340 | 70.512 | 56.110 | 37.045 | 1.00 | 23.21 |
| N | | | | | | | | | | |
| ATOM | 1656 | CA | ALA | A | 340 | 70.644 | 56.478 | 38.452 | 1.00 | 24.61 |
| C | | | | | | | | | | |
| ATOM | 1657 | C | ALA | A | 340 | 69.413 | 55.992 | 39.214 | 1.00 | 25.25 |
| C | | | | | | | | | | |
| ATOM | 1658 | O | ALA | A | 340 | 69.520 | 55.462 | 40.326 | 1.00 | 24.89 |
| O | | | | | | | | | | |
| ATOM | 1659 | CB | ALA | A | 340 | 70.783 | 57.992 | 38.591 | 1.00 | 25.22 |
| C | | | | | | | | | | |
| ATOM | 1660 | N | GLU | A | 341 | 68.243 | 56.168 | 38.608 | 1.00 | 24.78 |
| N | | | | | | | | | | |
| ATOM | 1661 | CA | GLU | A | 341 | 66.995 | 55.749 | 39.237 | 1.00 | 25.88 |
| C | | | | | | | | | | |
| ATOM | 1662 | C | GLU | A | 341 | 66.917 | 54.228 | 39.310 | 1.00 | 25.65 |
| C | | | | | | | | | | |
| ATOM | 1663 | O | GLU | A | 341 | 66.422 | 53.672 | 40.291 | 1.00 | 25.06 |
| O | | | | | | | | | | |
| ATOM | 1664 | CB | GLU | A | 341 | 65.799 | 56.283 | 38.449 | 1.00 | 26.19 |
| C | | | | | | | | | | |
| ATOM | 1665 | CG | GLU | A | 341 | 64.465 | 56.213 | 39.194 | 1.00 | 30.02 |
| C | | | | | | | | | | |
| ATOM | 1666 | CD | GLU | A | 341 | 64.419 | 57.128 | 40.411 | 1.00 | 33.39 |
| C | | | | | | | | | | |
| ATOM | 1667 | OE1 | GLU | A | 341 | 64.983 | 58.241 | 40.350 | 1.00 | 35.47 |
| O | | | | | | | | | | |
| ATOM | 1668 | OE2 | GLU | A | 341 | 63.804 | 56.744 | 41.424 | 1.00 | 35.11 |
| O | | | | | | | | | | |
| ATOM | 1669 | N | ARG | A | 342 | 67.403 | 53.566 | 38.265 | 1.00 | 25.58 |
| N | | | | | | | | | | |
| ATOM | 1670 | CA | ARG | A | 342 | 67.399 | 52.106 | 38.198 | 1.00 | 25.78 |
| C | | | | | | | | | | |
| ATOM | 1671 | C | ARG | A | 342 | 68.295 | 51.531 | 39.300 | 1.00 | 25.93 |
| C | | | | | | | | | | |
| ATOM | 1672 | O | ARG | A | 342 | 67.952 | 50.528 | 39.932 | 1.00 | 26.38 |
| O | | | | | | | | | | |
| ATOM | 1673 | CB | ARG | A | 342 | 67.878 | 51.651 | 36.803 | 1.00 | 24.64 |
| C | | | | | | | | | | |
| ATOM | 1674 | CG | ARG | A | 342 | 67.855 | 50.138 | 36.546 | 1.00 | 24.33 |
| C | | | | | | | | | | |
| ATOM | 1675 | CD | ARG | A | 342 | 69.100 | 49.431 | 37.092 | 1.00 | 23.54 |
| C | | | | | | | | | | |
| ATOM | 1676 | NE | ARG | A | 342 | 70.350 | 49.884 | 36.477 | 1.00 | 22.90 |
| N | | | | | | | | | | |
| ATOM | 1677 | CZ | ARG | A | 342 | 70.718 | 49.640 | 35.220 | 1.00 | 23.00 |
| C | | | | | | | | | | |
| ATOM | 1678 | NH1 | ARG | A | 342 | 69.934 | 48.943 | 34.406 | 1.00 | 21.73 |
| N | | | | | | | | | | |
| ATOM | 1679 | NH2 | ARG | A | 342 | 71.893 | 50.075 | 34.778 | 1.00 | 23.48 |
| N | | | | | | | | | | |
| ATOM | 1680 | N | ASN | A | 343 | 69.440 | 52.166 | 39.534 | 1.00 | 25.49 |
| N | | | | | | | | | | |
| ATOM | 1681 | CA | ASN | A | 343 | 70.355 | 51.697 | 40.571 | 1.00 | 27.07 |
| C | | | | | | | | | | |
| ATOM | 1682 | C | ASN | A | 343 | 69.774 | 51.944 | 41.964 | 1.00 | 27.92 |
| C | | | | | | | | | | |
| ATOM | 1683 | O | ASN | A | 343 | 69.976 | 51.150 | 42.887 | 1.00 | 27.27 |
| O | | | | | | | | | | |
| ATOM | 1684 | CB | ASN | A | 343 | 71.722 | 52.373 | 40.422 | 1.00 | 27.28 |
| C | | | | | | | | | | |

TABLE 7-continued

| ATOM | 1685 | CG | ASN | A | 343 | 72.457 | 51.921 | 39.171 | 1.00 | 28.20 |
| --- | --- | --- | --- | --- | --- | --- | --- | --- | --- | --- |
| C | | | | | | | | | | |
| ATOM | 1686 | OD1 | ASN | A | 343 | 72.178 | 50.844 | 38.634 | 1.00 | 27.39 |
| O | | | | | | | | | | |
| ATOM | 1687 | ND2 | ASN | A | 343 | 73.412 | 52.728 | 38.712 | 1.00 | 27.58 |
| N | | | | | | | | | | |
| ATOM | 1688 | N | LYS | A | 344 | 69.042 | 53.044 | 42.108 | 1.00 | 27.67 |
| N | | | | | | | | | | |
| ATOM | 1689 | CA | LYS | A | 344 | 68.402 | 53.376 | 43.374 | 1.00 | 29.76 |
| C | | | | | | | | | | |
| ATOM | 1690 | C | LYS | A | 344 | 67.313 | 52.334 | 43.617 | 1.00 | 29.60 |
| C | | | | | | | | | | |
| ATOM | 1691 | O | LYS | A | 344 | 67.162 | 51.810 | 44.726 | 1.00 | 30.86 |
| O | | | | | | | | | | |
| ATOM | 1692 | CB | LYS | A | 344 | 67.790 | 54.780 | 43.290 | 1.00 | 31.91 |
| C | | | | | | | | | | |
| ATOM | 1693 | CG | LYS | A | 344 | 67.158 | 55.286 | 44.574 | 1.00 | 37.21 |
| C | | | | | | | | | | |
| ATOM | 1694 | CD | LYS | A | 344 | 66.732 | 56.745 | 44.414 | 1.00 | 40.26 |
| C | | | | | | | | | | |
| ATOM | 1695 | CE | LYS | A | 344 | 66.241 | 57.339 | 45.725 | 1.00 | 42.77 |
| C | | | | | | | | | | |
| ATOM | 1696 | NZ | LYS | A | 344 | 66.010 | 58.812 | 45.594 | 1.00 | 44.75 |
| N | | | | | | | | | | |
| ATOM | 1697 | N | TYR | A | 345 | 66.564 | 52.023 | 42.564 | 1.00 | 28.67 |
| N | | | | | | | | | | |
| ATOM | 1698 | CA | TYR | A | 345 | 65.491 | 51.034 | 42.640 | 1.00 | 28.68 |
| C | | | | | | | | | | |
| ATOM | 1699 | C | TYR | A | 345 | 66.042 | 49.669 | 43.064 | 1.00 | 29.72 |
| C | | | | | | | | | | |
| ATOM | 1700 | O | TYR | A | 345 | 65.456 | 48.977 | 43.902 | 1.00 | 29.46 |
| O | | | | | | | | | | |
| ATOM | 1701 | CB | TYR | A | 345 | 64.816 | 50.896 | 41.280 | 1.00 | 27.98 |
| C | | | | | | | | | | |
| ATOM | 1702 | CG | TYR | A | 345 | 63.497 | 50.163 | 41.314 | 1.00 | 28.95 |
| C | | | | | | | | | | |
| ATOM | 1703 | CD1 | TYR | A | 345 | 62.325 | 50.822 | 41.684 | 1.00 | 30.04 |
| C | | | | | | | | | | |
| ATOM | 1704 | CD2 | TYR | A | 345 | 63.412 | 48.821 | 40.945 | 1.00 | 29.16 |
| C | | | | | | | | | | |
| ATOM | 1705 | CE1 | TYR | A | 345 | 61.099 | 50.165 | 41.677 | 1.00 | 30.92 |
| C | | | | | | | | | | |
| ATOM | 1706 | CE2 | TYR | A | 345 | 62.189 | 48.154 | 40.937 | 1.00 | 30.52 |
| C | | | | | | | | | | |
| ATOM | 1707 | CZ | TYR | A | 345 | 61.039 | 48.837 | 41.300 | 1.00 | 31.09 |
| C | | | | | | | | | | |
| ATOM | 1708 | OH | TYR | A | 345 | 59.820 | 48.205 | 41.256 | 1.00 | 32.41 |
| O | | | | | | | | | | |
| ATOM | 1709 | N | PHE | A | 346 | 67.162 | 49.281 | 42.467 | 1.00 | 29.90 |
| N | | | | | | | | | | |
| ATOM | 1710 | CA | PHE | A | 346 | 67.795 | 48.003 | 42.784 | 1.00 | 31.06 |
| C | | | | | | | | | | |
| ATOM | 1711 | C | PHE | A | 346 | 68.170 | 47.932 | 44.262 | 1.00 | 32.66 |
| C | | | | | | | | | | |
| ATOM | 1712 | O | PHE | A | 346 | 67.958 | 46.913 | 44.918 | 1.00 | 32.46 |
| O | | | | | | | | | | |
| ATOM | 1713 | CB | PHE | A | 346 | 69.051 | 47.814 | 41.932 | 1.00 | 30.74 |
| C | | | | | | | | | | |
| ATOM | 1714 | CG | PHE | A | 346 | 69.844 | 46.589 | 42.287 | 1.00 | 31.11 |
| C | | | | | | | | | | |
| ATOM | 1715 | CD1 | PHE | A | 346 | 69.329 | 45.319 | 42.053 | 1.00 | 29.91 |
| C | | | | | | | | | | |
| ATOM | 1716 | CD2 | PHE | A | 346 | 71.107 | 46.708 | 42.861 | 1.00 | 32.41 |
| C | | | | | | | | | | |
| ATOM | 1717 | CE1 | PHE | A | 346 | 70.061 | 44.177 | 42.383 | 1.00 | 30.76 |
| C | | | | | | | | | | |
| ATOM | 1718 | CE2 | PHE | A | 346 | 71.850 | 45.572 | 43.197 | 1.00 | 33.67 |
| C | | | | | | | | | | |
| ATOM | 1719 | CZ | PHE | A | 346 | 71.321 | 44.303 | 42.954 | 1.00 | 32.41 |
| C | | | | | | | | | | |
| ATOM | 1720 | N | GLU | A | 347 | 68.726 | 49.021 | 44.782 | 1.00 | 33.10 |
| N | | | | | | | | | | |
| ATOM | 1721 | CA | GLU | A | 347 | 69.130 | 49.072 | 46.182 | 1.00 | 36.04 |
| C | | | | | | | | | | |
| ATOM | 1722 | C | GLU | A | 347 | 67.933 | 49.020 | 47.127 | 1.00 | 35.98 |
| C | | | | | | | | | | |
| ATOM | 1723 | O | GLU | A | 347 | 68.032 | 48.491 | 48.235 | 1.00 | 35.44 |
| O | | | | | | | | | | |

TABLE 7-continued

| ATOM | 1724 | CB | GLU | A | 347 | 69.947 | 50.340 | 46.448 | 1.00 | 37.89 |
| --- | --- | --- | --- | --- | --- | --- | --- | --- | --- | --- |
| C | | | | | | | | | | |
| ATOM | 1725 | CG | GLU | A | 347 | 71.259 | 50.392 | 45.672 | 1.00 | 42.81 |
| C | | | | | | | | | | |
| ATOM | 1726 | CD | GLU | A | 347 | 72.257 | 49.319 | 46.102 | 1.00 | 46.57 |
| C | | | | | | | | | | |
| ATOM | 1727 | OE1 | GLU | A | 347 | 73.243 | 49.099 | 45.363 | 1.00 | 48.05 |
| O | | | | | | | | | | |
| ATOM | 1728 | OE2 | GLU | A | 347 | 72.071 | 48.702 | 47.177 | 1.00 | 48.54 |
| O | | | | | | | | | | |
| ATOM | 1729 | N | GLU | A | 348 | 66.802 | 49.560 | 46.687 | 1.00 | 35.06 |
| N | | | | | | | | | | |
| ATOM | 1730 | CA | GLU | A | 348 | 65.603 | 49.579 | 47.513 | 1.00 | 35.70 |
| C | | | | | | | | | | |
| ATOM | 1731 | C | GLU | A | 348 | 64.834 | 48.261 | 47.511 | 1.00 | 35.13 |
| C | | | | | | | | | | |
| ATOM | 1732 | O | GLU | A | 348 | 64.349 | 47.817 | 48.551 | 1.00 | 34.62 |
| O | | | | | | | | | | |
| ATOM | 1733 | CB | GLU | A | 348 | 64.633 | 50.671 | 47.043 | 1.00 | 37.06 |
| C | | | | | | | | | | |
| ATOM | 1734 | CG | GLU | A | 348 | 65.237 | 52.044 | 46.812 | 1.00 | 39.63 |
| C | | | | | | | | | | |
| ATOM | 1735 | CD | GLU | A | 348 | 64.207 | 53.056 | 46.324 | 1.00 | 40.78 |
| C | | | | | | | | | | |
| ATOM | 1736 | OE1 | GLU | A | 348 | 63.274 | 52.662 | 45.592 | 1.00 | 40.73 |
| O | | | | | | | | | | |
| ATOM | 1737 | OE2 | GLU | A | 348 | 64.340 | 54.251 | 46.660 | 1.00 | 43.08 |
| O | | | | | | | | | | |
| ATOM | 1738 | N | THR | A | 349 | 64.727 | 47.640 | 46.342 | 1.00 | 33.88 |
| N | | | | | | | | | | |
| ATOM | 1739 | CA | THR | A | 349 | 63.948 | 46.415 | 46.187 | 1.00 | 33.76 |
| C | | | | | | | | | | |
| ATOM | 1740 | C | THR | A | 349 | 64.713 | 45.121 | 45.922 | 1.00 | 33.08 |
| C | | | | | | | | | | |
| ATOM | 1741 | O | THR | A | 349 | 64.136 | 44.040 | 46.007 | 1.00 | 33.38 |
| O | | | | | | | | | | |
| ATOM | 1742 | CB | THR | A | 349 | 62.955 | 46.567 | 45.029 | 1.00 | 33.48 |
| C | | | | | | | | | | |
| ATOM | 1743 | OG1 | THR | A | 349 | 63.686 | 46.612 | 43.794 | 1.00 | 32.62 |
| O | | | | | | | | | | |
| ATOM | 1744 | CG2 | THR | A | 349 | 62.147 | 47.859 | 45.173 | 1.00 | 33.82 |
| C | | | | | | | | | | |
| ATOM | 1745 | N | GLY | A | 350 | 65.991 | 45.227 | 45.584 | 1.00 | 32.81 |
| N | | | | | | | | | | |
| ATOM | 1746 | CA | GLY | A | 350 | 66.762 | 44.035 | 45.283 | 1.00 | 31.80 |
| C | | | | | | | | | | |
| ATOM | 1747 | C | GLY | A | 350 | 66.481 | 43.557 | 43.865 | 1.00 | 31.19 |
| C | | | | | | | | | | |
| ATOM | 1748 | O | GLY | A | 350 | 66.976 | 42.515 | 43.440 | 1.00 | 31.53 |
| O | | | | | | | | | | |
| ATOM | 1749 | N | ILE | A | 351 | 65.687 | 44.327 | 43.125 | 1.00 | 30.11 |
| N | | | | | | | | | | |
| ATOM | 1750 | CA | ILE | A | 351 | 65.338 | 43.982 | 41.749 | 1.00 | 28.23 |
| C | | | | | | | | | | |
| ATOM | 1751 | C | ILE | A | 351 | 66.182 | 44.775 | 40.751 | 1.00 | 26.97 |
| C | | | | | | | | | | |
| ATOM | 1752 | O | ILE | A | 351 | 66.188 | 46.005 | 40.780 | 1.00 | 25.49 |
| O | | | | | | | | | | |
| ATOM | 1753 | CB | ILE | A | 351 | 63.859 | 44.308 | 41.442 | 1.00 | 30.29 |
| C | | | | | | | | | | |
| ATOM | 1754 | CG1 | ILE | A | 351 | 62.934 | 43.608 | 42.442 | 1.00 | 31.76 |
| C | | | | | | | | | | |
| ATOM | 1755 | CG2 | ILE | A | 351 | 63.533 | 43.901 | 40.008 | 1.00 | 30.03 |
| C | | | | | | | | | | |
| ATOM | 1756 | CD1 | ILE | A | 351 | 61.497 | 44.104 | 42.383 | 1.00 | 33.25 |
| C | | | | | | | | | | |
| ATOM | 1757 | N | TYR | A | 352 | 66.888 | 44.075 | 39.872 | 1.00 | 25.98 |
| N | | | | | | | | | | |
| ATOM | 1758 | CA | TYR | A | 352 | 67.699 | 44.747 | 38.862 | 1.00 | 25.54 |
| C | | | | | | | | | | |
| ATOM | 1759 | C | TYR | A | 352 | 66.955 | 44.707 | 37.541 | 1.00 | 25.29 |
| C | | | | | | | | | | |
| ATOM | 1760 | O | TYR | A | 352 | 66.696 | 43.631 | 37.002 | 1.00 | 24.79 |
| O | | | | | | | | | | |
| ATOM | 1761 | CB | TYR | A | 352 | 69.055 | 44.064 | 38.674 | 1.00 | 26.27 |
| C | | | | | | | | | | |
| ATOM | 1762 | CG | TYR | A | 352 | 69.950 | 44.807 | 37.696 | 1.00 | 25.26 |
| C | | | | | | | | | | |

TABLE 7-continued

| | | | | | | | | | |
|---|---|---|---|---|---|---|---|---|---|
| ATOM | 1763 | CD1 | TYR | A | 352 | 70.741 | 45.873 | 38.122 | 1.00 25.87 |
| C | | | | | | | | | |
| ATOM | 1764 | CD2 | TYR | A | 352 | 69.983 | 44.464 | 36.342 | 1.00 26.91 |
| C | | | | | | | | | |
| ATOM | 1765 | CE1 | TYR | A | 352 | 71.545 | 46.578 | 37.235 | 1.00 25.26 |
| C | | | | | | | | | |
| ATOM | 1766 | CE2 | TYR | A | 352 | 70.788 | 45.172 | 35.436 | 1.00 26.20 |
| C | | | | | | | | | |
| ATOM | 1767 | CZ | TYR | A | 352 | 71.568 | 46.226 | 35.895 | 1.00 25.73 |
| C | | | | | | | | | |
| ATOM | 1768 | OH | TYR | A | 352 | 72.394 | 46.918 | 35.030 | 1.00 24.57 |
| O | | | | | | | | | |
| ATOM | 1769 | N | ILE | A | 353 | 66.623 | 45.884 | 37.016 | 1.00 24.76 |
| N | | | | | | | | | |
| ATOM | 1770 | CA | ILE | A | 353 | 65.906 | 45.984 | 35.754 | 1.00 24.38 |
| C | | | | | | | | | |
| ATOM | 1771 | C | ILE | A | 353 | 66.813 | 46.507 | 34.648 | 1.00 24.63 |
| C | | | | | | | | | |
| ATOM | 1772 | O | ILE | A | 353 | 67.263 | 47.652 | 34.695 | 1.00 23.98 |
| O | | | | | | | | | |
| ATOM | 1773 | CB | ILE | A | 353 | 64.697 | 46.939 | 35.877 | 1.00 25.07 |
| C | | | | | | | | | |
| ATOM | 1774 | CG1 | ILE | A | 353 | 63.745 | 46.435 | 36.974 | 1.00 25.69 |
| C | | | | | | | | | |
| ATOM | 1775 | CG2 | ILE | A | 353 | 63.977 | 47.030 | 34.531 | 1.00 24.50 |
| C | | | | | | | | | |
| ATOM | 1776 | CD1 | ILE | A | 353 | 62.534 | 47.308 | 37.205 | 1.00 25.89 |
| C | | | | | | | | | |
| ATOM | 1777 | N | PRO | A | 354 | 67.111 | 45.667 | 33.642 | 1.00 24.90 |
| N | | | | | | | | | |
| ATOM | 1778 | CA | PRO | A | 354 | 67.974 | 46.100 | 32.537 | 1.00 24.20 |
| C | | | | | | | | | |
| ATOM | 1779 | C | PRO | A | 354 | 67.311 | 47.244 | 31.779 | 1.00 24.12 |
| C | | | | | | | | | |
| ATOM | 1780 | O | PRO | A | 354 | 66.089 | 47.268 | 31.641 | 1.00 24.10 |
| O | | | | | | | | | |
| ATOM | 1781 | CB | PRO | A | 354 | 68.085 | 44.846 | 31.669 | 1.00 24.27 |
| C | | | | | | | | | |
| ATOM | 1782 | CG | PRO | A | 354 | 67.941 | 43.720 | 32.681 | 1.00 23.16 |
| C | | | | | | | | | |
| ATOM | 1783 | CD | PRO | A | 354 | 66.802 | 44.229 | 33.536 | 1.00 24.40 |
| C | | | | | | | | | |
| ATOM | 1784 | N | VAL | A | 355 | 68.109 | 48.191 | 31.295 | 1.00 23.66 |
| N | | | | | | | | | |
| ATOM | 1785 | CA | VAL | A | 355 | 67.556 | 49.298 | 30.526 | 1.00 22.79 |
| C | | | | | | | | | |
| ATOM | 1786 | C | VAL | A | 355 | 68.210 | 49.322 | 29.158 | 1.00 23.11 |
| C | | | | | | | | | |
| ATOM | 1787 | O | VAL | A | 355 | 69.359 | 48.916 | 28.990 | 1.00 22.38 |
| O | | | | | | | | | |
| ATOM | 1788 | CB | VAL | A | 355 | 67.735 | 50.671 | 31.239 | 1.00 22.02 |
| C | | | | | | | | | |
| ATOM | 1789 | CG1 | VAL | A | 355 | 66.979 | 50.665 | 32.555 | 1.00 22.53 |
| C | | | | | | | | | |
| ATOM | 1790 | CG2 | VAL | A | 355 | 69.209 | 50.981 | 31.456 | 1.00 20.21 |
| C | | | | | | | | | |
| ATOM | 1791 | N | CYS | A | 356 | 67.454 | 49.794 | 28.178 | 1.00 23.23 |
| N | | | | | | | | | |
| ATOM | 1792 | CA | CYS | A | 356 | 67.906 | 49.842 | 26.802 | 1.00 23.04 |
| C | | | | | | | | | |
| ATOM | 1793 | C | CYS | A | 356 | 67.981 | 51.272 | 26.287 | 1.00 23.29 |
| C | | | | | | | | | |
| ATOM | 1794 | O | CYS | A | 356 | 67.023 | 52.025 | 26.414 | 1.00 22.76 |
| O | | | | | | | | | |
| ATOM | 1795 | CB | CYS | A | 356 | 66.924 | 49.035 | 25.940 | 1.00 25.03 |
| C | | | | | | | | | |
| ATOM | 1796 | SG | CYS | A | 356 | 67.126 | 49.192 | 24.147 | 1.00 25.41 |
| S | | | | | | | | | |
| ATOM | 1797 | N | SER | A | 357 | 69.126 | 51.647 | 25.727 | 1.00 22.98 |
| N | | | | | | | | | |
| ATOM | 1798 | CA | SER | A | 357 | 69.268 | 52.975 | 25.148 | 1.00 22.85 |
| C | | | | | | | | | |
| ATOM | 1799 | C | SER | A | 357 | 68.771 | 52.806 | 23.718 | 1.00 23.16 |
| C | | | | | | | | | |
| ATOM | 1800 | O | SER | A | 357 | 69.398 | 52.122 | 22.913 | 1.00 22.80 |
| O | | | | | | | | | |
| ATOM | 1801 | CB | SER | A | 357 | 70.724 | 53.428 | 25.138 | 1.00 21.98 |
| C | | | | | | | | | |

TABLE 7-continued

| | | | | | | | | | |
|---|---|---|---|---|---|---|---|---|---|
| ATOM | 1802 | OG | SER | A | 357 | 70.813 | 54.733 | 24.584 | 1.00 23.23 |
| ATOM | 1803 | N | ASP | A | 358 | 67.646 | 53.441 | 23.417 | 1.00 22.79 |
| ATOM | 1804 | CA | ASP | A | 358 | 67.020 | 53.333 | 22.109 | 1.00 24.60 |
| ATOM | 1805 | C | ASP | A | 358 | 67.090 | 54.614 | 21.279 | 1.00 25.62 |
| ATOM | 1806 | O | ASP | A | 358 | 66.466 | 55.616 | 21.617 | 1.00 25.58 |
| ATOM | 1807 | CB | ASP | A | 358 | 65.560 | 52.900 | 22.314 | 1.00 24.15 |
| ATOM | 1808 | CG | ASP | A | 358 | 64.776 | 52.816 | 21.026 | 1.00 25.77 |
| ATOM | 1809 | OD1 | ASP | A | 358 | 65.394 | 52.717 | 19.943 | 1.00 25.59 |
| ATOM | 1810 | OD2 | ASP | A | 358 | 63.530 | 52.833 | 21.111 | 1.00 25.33 |
| ATOM | 1811 | N | GLY | A | 359 | 67.860 | 54.562 | 20.193 | 1.00 28.47 |
| ATOM | 1812 | CA | GLY | A | 359 | 67.989 | 55.702 | 19.302 | 1.00 30.93 |
| ATOM | 1813 | C | GLY | A | 359 | 69.129 | 56.657 | 19.604 | 1.00 33.00 |
| ATOM | 1814 | O | GLY | A | 359 | 69.679 | 56.665 | 20.706 | 1.00 33.66 |
| ATOM | 1815 | N | GLY | A | 360 | 69.490 | 57.463 | 18.610 | 1.00 34.46 |
| ATOM | 1816 | CA | GLY | A | 360 | 70.551 | 58.434 | 18.793 | 1.00 35.68 |
| ATOM | 1817 | C | GLY | A | 360 | 71.968 | 57.960 | 18.533 | 1.00 36.49 |
| ATOM | 1818 | O | GLY | A | 360 | 72.905 | 58.740 | 18.671 | 1.00 38.41 |
| ATOM | 1819 | N | ILE | A | 361 | 72.146 | 56.696 | 18.169 | 1.00 36.80 |
| ATOM | 1820 | CA | ILE | A | 361 | 73.486 | 56.186 | 17.895 | 1.00 37.13 |
| ATOM | 1821 | C | ILE | A | 361 | 73.885 | 56.609 | 16.483 | 1.00 38.00 |
| ATOM | 1822 | O | ILE | A | 361 | 73.275 | 56.173 | 15.506 | 1.00 37.36 |
| ATOM | 1823 | CB | ILE | A | 361 | 73.543 | 54.640 | 17.980 | 1.00 37.20 |
| ATOM | 1824 | CG1 | ILE | A | 361 | 73.123 | 54.166 | 19.377 | 1.00 36.99 |
| ATOM | 1825 | CG2 | ILE | A | 361 | 74.951 | 54.153 | 17.666 | 1.00 37.15 |
| ATOM | 1826 | CD1 | ILE | A | 361 | 74.050 | 54.607 | 20.493 | 1.00 36.40 |
| ATOM | 1827 | N | VAL | A | 362 | 74.898 | 57.466 | 16.384 | 1.00 37.48 |
| ATOM | 1828 | CA | VAL | A | 362 | 75.373 | 57.940 | 15.088 | 1.00 38.82 |
| ATOM | 1829 | C | VAL | A | 362 | 76.707 | 57.292 | 14.735 | 1.00 38.61 |
| ATOM | 1830 | O | VAL | A | 362 | 76.916 | 56.862 | 13.599 | 1.00 39.64 |
| ATOM | 1831 | CB | VAL | A | 362 | 75.548 | 59.473 | 15.082 | 1.00 39.34 |
| ATOM | 1832 | CG1 | VAL | A | 362 | 76.006 | 59.946 | 13.701 | 1.00 41.47 |
| ATOM | 1833 | CG2 | VAL | A | 362 | 74.241 | 60.142 | 15.458 | 1.00 40.61 |
| ATOM | 1834 | N | TYR | A | 363 | 77.600 | 57.215 | 15.719 | 1.00 37.19 |
| ATOM | 1835 | CA | TYR | A | 363 | 78.921 | 56.624 | 15.530 | 1.00 36.38 |
| ATOM | 1836 | C | TYR | A | 363 | 79.131 | 55.425 | 16.447 | 1.00 34.11 |
| ATOM | 1837 | O | TYR | A | 363 | 78.471 | 55.303 | 17.477 | 1.00 32.33 |
| ATOM | 1838 | CB | TYR | A | 363 | 80.004 | 57.661 | 15.820 | 1.00 39.61 |
| ATOM | 1839 | CG | TYR | A | 363 | 79.918 | 58.894 | 14.957 | 1.00 43.43 |
| ATOM | 1840 | CD1 | TYR | A | 363 | 79.948 | 58.795 | 13.565 | 1.00 45.21 |

TABLE 7-continued

| ATOM | 1841 | CD2 | TYR | A | 363 | 79.824 | 60.162 | 15.527 | 1.00 | 44.88 |
| --- | --- | --- | --- | --- | --- | --- | --- | --- | --- | --- |
| C | | | | | | | | | | |
| ATOM | 1842 | CE1 | TYR | A | 363 | 79.889 | 59.933 | 12.761 | 1.00 | 47.51 |
| C | | | | | | | | | | |
| ATOM | 1843 | CE2 | TYR | A | 363 | 79.766 | 61.308 | 14.731 | 1.00 | 47.32 |
| C | | | | | | | | | | |
| ATOM | 1844 | CZ | TYR | A | 363 | 79.800 | 61.184 | 13.351 | 1.00 | 47.96 |
| C | | | | | | | | | | |
| ATOM | 1845 | OH | TYR | A | 363 | 79.755 | 62.310 | 12.556 | 1.00 | 49.68 |
| O | | | | | | | | | | |
| ATOM | 1846 | N | ASP | A | 364 | 80.059 | 54.548 | 16.079 | 1.00 | 32.88 |
| N | | | | | | | | | | |
| ATOM | 1847 | CA | ASP | A | 364 | 80.341 | 53.375 | 16.899 | 1.00 | 32.27 |
| C | | | | | | | | | | |
| ATOM | 1848 | C | ASP | A | 364 | 80.649 | 53.733 | 18.352 | 1.00 | 30.99 |
| C | | | | | | | | | | |
| ATOM | 1849 | O | ASP | A | 364 | 80.189 | 53.050 | 19.266 | 1.00 | 31.26 |
| O | | | | | | | | | | |
| ATOM | 1850 | CB | ASP | A | 364 | 81.531 | 52.574 | 16.351 | 1.00 | 34.38 |
| C | | | | | | | | | | |
| ATOM | 1851 | CG | ASP | A | 364 | 81.224 | 51.867 | 15.040 | 1.00 | 36.34 |
| C | | | | | | | | | | |
| ATOM | 1852 | OD1 | ASP | A | 364 | 80.081 | 51.396 | 14.850 | 1.00 | 37.26 |
| O | | | | | | | | | | |
| ATOM | 1853 | OD2 | ASP | A | 364 | 82.147 | 51.767 | 14.205 | 1.00 | 37.51 |
| O | | | | | | | | | | |
| ATOM | 1854 | N | TYR | A | 365 | 81.421 | 54.796 | 18.576 | 1.00 | 29.18 |
| N | | | | | | | | | | |
| ATOM | 1855 | CA | TYR | A | 365 | 81.776 | 55.153 | 19.949 | 1.00 | 27.62 |
| C | | | | | | | | | | |
| ATOM | 1856 | C | TYR | A | 365 | 80.571 | 55.537 | 20.796 | 1.00 | 27.21 |
| C | | | | | | | | | | |
| ATOM | 1857 | O | TYR | A | 365 | 80.638 | 55.497 | 22.019 | 1.00 | 25.96 |
| O | | | | | | | | | | |
| ATOM | 1858 | CB | TYR | A | 365 | 82.846 | 56.257 | 19.982 | 1.00 | 28.21 |
| C | | | | | | | | | | |
| ATOM | 1859 | CG | TYR | A | 365 | 82.351 | 57.679 | 19.854 | 1.00 | 29.19 |
| C | | | | | | | | | | |
| ATOM | 1860 | CD1 | TYR | A | 365 | 82.157 | 58.483 | 20.983 | 1.00 | 30.31 |
| C | | | | | | | | | | |
| ATOM | 1861 | CD2 | TYR | A | 365 | 82.135 | 58.242 | 18.602 | 1.00 | 30.72 |
| C | | | | | | | | | | |
| ATOM | 1862 | CE1 | TYR | A | 365 | 81.765 | 59.824 | 20.854 | 1.00 | 31.27 |
| C | | | | | | | | | | |
| ATOM | 1863 | CE2 | TYR | A | 365 | 81.746 | 59.568 | 18.464 | 1.00 | 32.19 |
| C | | | | | | | | | | |
| ATOM | 1864 | CZ | TYR | A | 365 | 81.565 | 60.353 | 19.587 | 1.00 | 32.87 |
| C | | | | | | | | | | |
| ATOM | 1865 | OH | TYR | A | 365 | 81.178 | 61.664 | 19.418 | 1.00 | 35.54 |
| O | | | | | | | | | | |
| ATOM | 1866 | N | HIS | A | 366 | 79.465 | 55.896 | 20.149 | 1.00 | 25.79 |
| N | | | | | | | | | | |
| ATOM | 1867 | CA | HIS | A | 366 | 78.253 | 56.229 | 20.888 | 1.00 | 26.00 |
| C | | | | | | | | | | |
| ATOM | 1868 | C | HIS | A | 366 | 77.757 | 54.963 | 21.582 | 1.00 | 25.36 |
| C | | | | | | | | | | |
| ATOM | 1869 | O | HIS | A | 366 | 77.091 | 55.035 | 22.616 | 1.00 | 24.64 |
| O | | | | | | | | | | |
| ATOM | 1870 | CB | HIS | A | 366 | 77.160 | 56.760 | 19.956 | 1.00 | 26.79 |
| C | | | | | | | | | | |
| ATOM | 1871 | CG | HIS | A | 366 | 77.409 | 58.148 | 19.455 | 1.00 | 28.37 |
| C | | | | | | | | | | |
| ATOM | 1872 | ND1 | HIS | A | 366 | 78.402 | 58.958 | 19.963 | 1.00 | 29.63 |
| N | | | | | | | | | | |
| ATOM | 1873 | CD2 | HIS | A | 366 | 76.774 | 58.880 | 18.510 | 1.00 | 28.28 |
| C | | | | | | | | | | |
| ATOM | 1874 | CE1 | HIS | A | 366 | 78.368 | 60.129 | 19.352 | 1.00 | 27.78 |
| C | | | | | | | | | | |
| ATOM | 1875 | NE2 | HIS | A | 366 | 77.390 | 60.108 | 18.466 | 1.00 | 29.94 |
| N | | | | | | | | | | |
| ATOM | 1876 | N | MET | A | 367 | 78.067 | 53.803 | 21.000 | 1.00 | 24.84 |
| N | | | | | | | | | | |
| ATOM | 1877 | CA | MET | A | 367 | 77.663 | 52.530 | 21.602 | 1.00 | 25.78 |
| C | | | | | | | | | | |
| ATOM | 1878 | C | MET | A | 367 | 78.401 | 52.385 | 22.927 | 1.00 | 24.73 |
| C | | | | | | | | | | |
| ATOM | 1879 | O | MET | A | 367 | 77.816 | 52.063 | 23.950 | 1.00 | 23.39 |
| O | | | | | | | | | | |

TABLE 7-continued

| ATOM | 1880 | CB | MET | A | 367 | 78.035 | 51.343 | 20.704 | 1.00 | 26.59 |
| --- | --- | --- | --- | --- | --- | --- | --- | --- | --- | --- |
| C | | | | | | | | | | |
| ATOM | 1881 | CG | MET | A | 367 | 77.291 | 51.272 | 19.369 | 1.00 | 30.31 |
| C | | | | | | | | | | |
| ATOM | 1882 | SD | MET | A | 367 | 77.849 | 49.839 | 18.398 | 1.00 | 32.89 |
| S | | | | | | | | | | |
| ATOM | 1883 | CE | MET | A | 367 | 77.037 | 50.144 | 16.824 | 1.00 | 32.21 |
| C | | | | | | | | | | |
| ATOM | 1884 | N | THR | A | 368 | 79.707 | 52.611 | 22.881 | 1.00 | 24.71 |
| N | | | | | | | | | | |
| ATOM | 1885 | CA | THR | A | 368 | 80.547 | 52.510 | 24.064 | 1.00 | 24.03 |
| C | | | | | | | | | | |
| ATOM | 1886 | C | THR | A | 368 | 80.063 | 53.484 | 25.135 | 1.00 | 23.45 |
| C | | | | | | | | | | |
| ATOM | 1887 | O | THR | A | 368 | 79.985 | 53.133 | 26.306 | 1.00 | 23.07 |
| O | | | | | | | | | | |
| ATOM | 1888 | CB | THR | A | 368 | 82.006 | 52.816 | 23.701 | 1.00 | 24.76 |
| C | | | | | | | | | | |
| ATOM | 1889 | OG1 | THR | A | 368 | 82.349 | 52.081 | 22.518 | 1.00 | 24.31 |
| O | | | | | | | | | | |
| ATOM | 1890 | CG2 | THR | A | 368 | 82.942 | 52.411 | 24.835 | 1.00 | 24.75 |
| C | | | | | | | | | | |
| ATOM | 1891 | N | LEU | A | 369 | 79.744 | 54.710 | 24.731 | 1.00 | 23.16 |
| N | | | | | | | | | | |
| ATOM | 1892 | CA | LEU | A | 369 | 79.249 | 55.722 | 25.666 | 1.00 | 24.00 |
| C | | | | | | | | | | |
| ATOM | 1893 | C | LEU | A | 369 | 77.939 | 55.308 | 26.335 | 1.00 | 23.72 |
| C | | | | | | | | | | |
| ATOM | 1894 | O | LEU | A | 369 | 77.797 | 55.411 | 27.551 | 1.00 | 23.10 |
| O | | | | | | | | | | |
| ATOM | 1895 | CB | LEU | A | 369 | 79.033 | 57.057 | 24.947 | 1.00 | 24.17 |
| C | | | | | | | | | | |
| ATOM | 1896 | CG | LEU | A | 369 | 80.281 | 57.884 | 24.624 | 1.00 | 26.48 |
| C | | | | | | | | | | |
| ATOM | 1897 | CD1 | LEU | A | 369 | 79.897 | 59.087 | 23.772 | 1.00 | 26.96 |
| C | | | | | | | | | | |
| ATOM | 1898 | CD2 | LEU | A | 369 | 80.943 | 58.342 | 25.926 | 1.00 | 26.87 |
| C | | | | | | | | | | |
| ATOM | 1899 | N | ALA | A | 370 | 76.986 | 54.837 | 25.533 | 1.00 | 22.35 |
| N | | | | | | | | | | |
| ATOM | 1900 | CA | ALA | A | 370 | 75.686 | 54.424 | 26.056 | 1.00 | 23.03 |
| C | | | | | | | | | | |
| ATOM | 1901 | C | ALA | A | 370 | 75.857 | 53.331 | 27.108 | 1.00 | 22.11 |
| C | | | | | | | | | | |
| ATOM | 1902 | O | ALA | A | 370 | 75.228 | 53.361 | 28.162 | 1.00 | 22.10 |
| O | | | | | | | | | | |
| ATOM | 1903 | CB | ALA | A | 370 | 74.803 | 53.917 | 24.917 | 1.00 | 21.13 |
| C | | | | | | | | | | |
| ATOM | 1904 | N | LEU | A | 371 | 76.707 | 52.361 | 26.805 | 1.00 | 21.79 |
| N | | | | | | | | | | |
| ATOM | 1905 | CA | LEU | A | 371 | 76.960 | 51.261 | 27.726 | 1.00 | 22.39 |
| C | | | | | | | | | | |
| ATOM | 1906 | C | LEU | A | 371 | 77.685 | 51.777 | 28.972 | 1.00 | 21.96 |
| C | | | | | | | | | | |
| ATOM | 1907 | O | LEU | A | 371 | 77.355 | 51.399 | 30.098 | 1.00 | 21.20 |
| O | | | | | | | | | | |
| ATOM | 1908 | CB | LEU | A | 371 | 77.803 | 50.186 | 27.030 | 1.00 | 21.70 |
| C | | | | | | | | | | |
| ATOM | 1909 | CG | LEU | A | 371 | 77.170 | 49.473 | 25.820 | 1.00 | 22.99 |
| C | | | | | | | | | | |
| ATOM | 1910 | CD1 | LEU | A | 371 | 78.221 | 48.634 | 25.112 | 1.00 | 24.60 |
| C | | | | | | | | | | |
| ATOM | 1911 | CD2 | LEU | A | 371 | 76.009 | 48.591 | 26.270 | 1.00 | 23.11 |
| C | | | | | | | | | | |
| ATOM | 1912 | N | ALA | A | 372 | 78.680 | 52.636 | 28.770 | 1.00 | 21.79 |
| N | | | | | | | | | | |
| ATOM | 1913 | CA | ALA | A | 372 | 79.437 | 53.182 | 29.894 | 1.00 | 21.89 |
| C | | | | | | | | | | |
| ATOM | 1914 | C | ALA | A | 372 | 78.534 | 53.993 | 30.812 | 1.00 | 23.49 |
| C | | | | | | | | | | |
| ATOM | 1915 | O | ALA | A | 372 | 78.720 | 54.004 | 32.032 | 1.00 | 22.41 |
| O | | | | | | | | | | |
| ATOM | 1916 | CB | ALA | A | 372 | 80.585 | 54.052 | 29.387 | 1.00 | 22.98 |
| C | | | | | | | | | | |
| ATOM | 1917 | N | MET | A | 373 | 77.550 | 54.675 | 30.231 | 1.00 | 22.86 |
| N | | | | | | | | | | |
| ATOM | 1918 | CA | MET | A | 373 | 76.632 | 55.471 | 31.039 | 1.00 | 23.45 |
| C | | | | | | | | | | |

TABLE 7-continued

| ATOM | 1919 | C | MET | A | 373 | 75.650 | 54.609 | 31.829 | 1.00 | 23.67 | C |
| --- | --- | --- | --- | --- | --- | --- | --- | --- | --- | --- | --- |
| ATOM | 1920 | O | MET | A | 373 | 74.913 | 55.119 | 32.665 | 1.00 | 24.88 | O |
| ATOM | 1921 | CB | MET | A | 373 | 75.884 | 56.474 | 30.159 | 1.00 | 23.86 | C |
| ATOM | 1922 | CG | MET | A | 373 | 76.792 | 57.571 | 29.612 | 1.00 | 25.21 | C |
| ATOM | 1923 | SD | MET | A | 373 | 75.984 | 58.618 | 28.385 | 1.00 | 26.48 | S |
| ATOM | 1924 | CE | MET | A | 373 | 77.324 | 59.787 | 28.016 | 1.00 | 26.43 | C |
| ATOM | 1925 | N | GLY | A | 374 | 75.635 | 53.302 | 31.572 | 1.00 | 23.45 | N |
| ATOM | 1926 | CA | GLY | A | 374 | 74.745 | 52.443 | 32.332 | 1.00 | 22.34 | C |
| ATOM | 1927 | C | GLY | A | 374 | 73.740 | 51.597 | 31.573 | 1.00 | 22.77 | C |
| ATOM | 1928 | O | GLY | A | 374 | 73.118 | 50.714 | 32.162 | 1.00 | 23.42 | O |
| ATOM | 1929 | N | ALA | A | 375 | 73.560 | 51.851 | 30.283 | 1.00 | 22.25 | N |
| ATOM | 1930 | CA | ALA | A | 375 | 72.614 | 51.051 | 29.509 | 1.00 | 22.62 | C |
| ATOM | 1931 | C | ALA | A | 375 | 73.143 | 49.625 | 29.389 | 1.00 | 23.21 | C |
| ATOM | 1932 | O | ALA | A | 375 | 74.329 | 49.416 | 29.134 | 1.00 | 23.32 | O |
| ATOM | 1933 | CB | ALA | A | 375 | 72.418 | 51.652 | 28.120 | 1.00 | 22.37 | C |
| ATOM | 1934 | N | ASP | A | 376 | 72.263 | 48.645 | 29.580 | 1.00 | 22.37 | N |
| ATOM | 1935 | CA | ASP | A | 376 | 72.661 | 47.244 | 29.478 | 1.00 | 23.13 | C |
| ATOM | 1936 | C | ASP | A | 376 | 72.750 | 46.840 | 28.012 | 1.00 | 23.56 | C |
| ATOM | 1937 | O | ASP | A | 376 | 73.624 | 46.064 | 27.624 | 1.00 | 23.83 | O |
| ATOM | 1938 | CB | ASP | A | 376 | 71.665 | 46.377 | 30.241 | 1.00 | 23.78 | C |
| ATOM | 1939 | CG | ASP | A | 376 | 71.596 | 46.756 | 31.706 | 1.00 | 24.06 | C |
| ATOM | 1940 | OD1 | ASP | A | 376 | 72.420 | 46.246 | 32.499 | 1.00 | 25.54 | O |
| ATOM | 1941 | OD2 | ASP | A | 376 | 70.734 | 47.586 | 32.062 | 1.00 | 23.75 | O |
| ATOM | 1942 | N | PHE | A | 377 | 71.841 | 47.355 | 27.193 | 1.00 | 23.34 | N |
| ATOM | 1943 | CA | PHE | A | 377 | 71.904 | 47.076 | 25.768 | 1.00 | 23.57 | C |
| ATOM | 1944 | C | PHE | A | 377 | 71.414 | 48.262 | 24.948 | 1.00 | 23.98 | C |
| ATOM | 1945 | O | PHE | A | 377 | 70.882 | 49.228 | 25.490 | 1.00 | 23.49 | O |
| ATOM | 1946 | CB | PHE | A | 377 | 71.168 | 45.778 | 25.385 | 1.00 | 23.30 | C |
| ATOM | 1947 | CG | PHE | A | 377 | 69.758 | 45.684 | 25.887 | 1.00 | 24.76 | C |
| ATOM | 1948 | CD1 | PHE | A | 377 | 69.495 | 45.318 | 27.203 | 1.00 | 26.77 | C |
| ATOM | 1949 | CD2 | PHE | A | 377 | 68.688 | 45.900 | 25.025 | 1.00 | 24.49 | C |
| ATOM | 1950 | CE1 | PHE | A | 377 | 68.180 | 45.163 | 27.652 | 1.00 | 26.00 | C |
| ATOM | 1951 | CE2 | PHE | A | 377 | 67.370 | 45.747 | 25.465 | 1.00 | 25.78 | C |
| ATOM | 1952 | CZ | PHE | A | 377 | 67.118 | 45.379 | 26.777 | 1.00 | 25.44 | C |
| ATOM | 1953 | N | ILE | A | 378 | 71.610 | 48.181 | 23.639 | 1.00 | 23.02 | N |
| ATOM | 1954 | CA | ILE | A | 378 | 71.278 | 49.271 | 22.738 | 1.00 | 23.35 | C |
| ATOM | 1955 | C | ILE | A | 378 | 70.335 | 48.846 | 21.621 | 1.00 | 23.49 | C |
| ATOM | 1956 | O | ILE | A | 378 | 70.502 | 47.778 | 21.045 | 1.00 | 24.62 | O |
| ATOM | 1957 | CB | ILE | A | 378 | 72.592 | 49.816 | 22.107 | 1.00 | 23.26 | C |

TABLE 7-continued

| | | | | | | | | | |
|---|---|---|---|---|---|---|---|---|---|
| ATOM C | 1958 | CG1 | ILE | A | 378 | 73.571 | 50.202 | 23.227 | 1.00 24.03 |
| ATOM C | 1959 | CG2 | ILE | A | 378 | 72.306 | 51.011 | 21.192 | 1.00 24.70 |
| ATOM C | 1960 | CD1 | ILE | A | 378 | 75.017 | 50.325 | 22.756 | 1.00 26.63 |
| ATOM N | 1961 | N | MET | A | 379 | 69.335 | 49.675 | 21.331 | 1.00 23.56 |
| ATOM C | 1962 | CA | MET | A | 379 | 68.418 | 49.374 | 20.238 | 1.00 23.95 |
| ATOM C | 1963 | C | MET | A | 379 | 68.755 | 50.340 | 19.109 | 1.00 24.40 |
| ATOM O | 1964 | O | MET | A | 379 | 68.915 | 51.540 | 19.338 | 1.00 23.43 |
| ATOM C | 1965 | CB | MET | A | 379 | 66.952 | 49.551 | 20.661 | 1.00 24.65 |
| ATOM C | 1966 | CG | MET | A | 379 | 65.968 | 49.319 | 19.508 | 1.00 24.74 |
| ATOM S | 1967 | SD | MET | A | 379 | 64.236 | 49.290 | 19.988 | 1.00 26.39 |
| ATOM C | 1968 | CE | MET | A | 379 | 64.115 | 47.609 | 20.644 | 1.00 27.00 |
| ATOM N | 1969 | N | LEU | A | 380 | 68.881 | 49.815 | 17.896 | 1.00 24.73 |
| ATOM C | 1970 | CA | LEU | A | 380 | 69.216 | 50.642 | 16.744 | 1.00 25.39 |
| ATOM C | 1971 | C | LEU | A | 380 | 68.334 | 50.345 | 15.545 | 1.00 25.28 |
| ATOM O | 1972 | O | LEU | A | 380 | 67.952 | 49.197 | 15.316 | 1.00 25.31 |
| ATOM C | 1973 | CB | LEU | A | 380 | 70.673 | 50.421 | 16.329 | 1.00 26.35 |
| ATOM C | 1974 | CG | LEU | A | 380 | 71.756 | 50.577 | 17.403 | 1.00 27.26 |
| ATOM C | 1975 | CD1 | LEU | A | 380 | 71.877 | 49.280 | 18.189 | 1.00 29.84 |
| ATOM C | 1976 | CD2 | LEU | A | 380 | 73.081 | 50.896 | 16.740 | 1.00 28.50 |
| ATOM N | 1977 | N | GLY | A | 381 | 68.034 | 51.388 | 14.778 | 1.00 25.23 |
| ATOM C | 1978 | CA | GLY | A | 381 | 67.221 | 51.232 | 13.584 | 1.00 27.24 |
| ATOM C | 1979 | C | GLY | A | 381 | 68.057 | 51.437 | 12.331 | 1.00 27.95 |
| ATOM O | 1980 | O | GLY | A | 381 | 68.330 | 50.493 | 11.592 | 1.00 28.13 |
| ATOM N | 1981 | N | ARG | A | 382 | 68.473 | 52.680 | 12.107 | 1.00 29.76 |
| ATOM C | 1982 | CA | ARG | A | 382 | 69.279 | 53.061 | 10.945 | 1.00 31.76 |
| ATOM C | 1983 | C | ARG | A | 382 | 70.494 | 52.150 | 10.748 | 1.00 32.08 |
| ATOM O | 1984 | O | ARG | A | 382 | 70.778 | 51.702 | 9.632 | 1.00 30.90 |
| ATOM C | 1985 | CB | ARG | A | 382 | 69.744 | 54.510 | 11.109 | 1.00 34.27 |
| ATOM C | 1986 | CG | ARG | A | 382 | 70.563 | 55.063 | 9.952 | 1.00 39.22 |
| ATOM C | 1987 | CD | ARG | A | 382 | 71.207 | 56.388 | 10.339 | 1.00 42.02 |
| ATOM N | 1988 | NE | ARG | A | 382 | 72.131 | 56.221 | 11.460 | 1.00 45.45 |
| ATOM C | 1989 | CZ | ARG | A | 382 | 73.260 | 55.518 | 11.399 | 1.00 47.01 |
| ATOM N | 1990 | NH1 | ARG | A | 382 | 73.610 | 54.920 | 10.267 | 1.00 48.07 |
| ATOM N | 1991 | NH2 | ARG | A | 382 | 74.033 | 55.399 | 12.471 | 1.00 47.88 |
| ATOM N | 1992 | N | TYR | A | 383 | 71.208 | 51.883 | 11.838 | 1.00 30.72 |
| ATOM C | 1993 | CA | TYR | A | 383 | 72.395 | 51.032 | 11.804 | 1.00 30.04 |
| ATOM C | 1994 | C | TYR | A | 383 | 72.136 | 49.699 | 11.098 | 1.00 29.56 |
| ATOM O | 1995 | O | TYR | A | 383 | 72.922 | 49.272 | 10.252 | 1.00 30.58 |
| ATOM C | 1996 | CB | TYR | A | 383 | 72.876 | 50.761 | 13.234 | 1.00 29.03 |

TABLE 7-continued

| | | | | | | | | | |
|---|---|---|---|---|---|---|---|---|---|
| ATOM | 1997 | CG | TYR | A | 383 | 74.100 | 49.878 | 13.329 | 1.00 | 28.59 |
| ATOM | 1998 | CD1 | TYR | A | 383 | 75.381 | 50.413 | 13.201 | 1.00 | 29.36 |
| ATOM | 1999 | CD2 | TYR | A | 383 | 73.975 | 48.505 | 13.538 | 1.00 | 28.86 |
| ATOM | 2000 | CE1 | TYR | A | 383 | 76.509 | 49.602 | 13.280 | 1.00 | 29.26 |
| ATOM | 2001 | CE2 | TYR | A | 383 | 75.097 | 47.683 | 13.617 | 1.00 | 28.40 |
| ATOM | 2002 | CZ | TYR | A | 383 | 76.360 | 48.240 | 13.486 | 1.00 | 28.60 |
| ATOM | 2003 | OH | TYR | A | 383 | 77.475 | 47.437 | 13.551 | 1.00 | 28.39 |
| ATOM | 2004 | N | PHE | A | 384 | 71.034 | 49.048 | 11.452 | 1.00 | 29.09 |
| ATOM | 2005 | CA | PHE | A | 384 | 70.679 | 47.757 | 10.872 | 1.00 | 29.81 |
| ATOM | 2006 | C | PHE | A | 384 | 69.991 | 47.843 | 9.510 | 1.00 | 30.44 |
| ATOM | 2007 | O | PHE | A | 384 | 70.102 | 46.922 | 8.701 | 1.00 | 30.80 |
| ATOM | 2008 | CB | PHE | A | 384 | 69.785 | 46.976 | 11.842 | 1.00 | 29.45 |
| ATOM | 2009 | CG | PHE | A | 384 | 70.511 | 46.460 | 13.057 | 1.00 | 28.89 |
| ATOM | 2010 | CD1 | PHE | A | 384 | 71.469 | 45.455 | 12.936 | 1.00 | 28.54 |
| ATOM | 2011 | CD2 | PHE | A | 384 | 70.237 | 46.980 | 14.322 | 1.00 | 28.04 |
| ATOM | 2012 | CE1 | PHE | A | 384 | 72.146 | 44.973 | 14.054 | 1.00 | 28.18 |
| ATOM | 2013 | CE2 | PHE | A | 384 | 70.905 | 46.506 | 15.446 | 1.00 | 27.99 |
| ATOM | 2014 | CZ | PHE | A | 384 | 71.864 | 45.500 | 15.313 | 1.00 | 27.33 |
| ATOM | 2015 | N | ALA | A | 385 | 69.286 | 48.940 | 9.258 | 1.00 | 31.37 |
| ATOM | 2016 | CA | ALA | A | 385 | 68.582 | 49.118 | 7.991 | 1.00 | 32.83 |
| ATOM | 2017 | C | ALA | A | 385 | 69.530 | 49.082 | 6.795 | 1.00 | 33.97 |
| ATOM | 2018 | O | ALA | A | 385 | 69.137 | 48.700 | 5.694 | 1.00 | 34.53 |
| ATOM | 2019 | CB | ALA | A | 385 | 67.815 | 50.433 | 8.004 | 1.00 | 31.76 |
| ATOM | 2020 | N | ARG | A | 386 | 70.779 | 49.482 | 7.018 | 1.00 | 35.25 |
| ATOM | 2021 | CA | ARG | A | 386 | 71.786 | 49.508 | 5.960 | 1.00 | 35.62 |
| ATOM | 2022 | C | ARG | A | 386 | 72.237 | 48.120 | 5.511 | 1.00 | 36.16 |
| ATOM | 2023 | O | ARG | A | 386 | 72.911 | 47.986 | 4.488 | 1.00 | 35.70 |
| ATOM | 2024 | CB | ARG | A | 386 | 73.027 | 50.272 | 6.428 | 1.00 | 36.74 |
| ATOM | 2025 | CG | ARG | A | 386 | 72.816 | 51.708 | 6.857 | 1.00 | 38.32 |
| ATOM | 2026 | CD | ARG | A | 386 | 74.090 | 52.191 | 7.536 | 1.00 | 40.83 |
| ATOM | 2027 | NE | ARG | A | 386 | 74.477 | 51.251 | 8.585 | 1.00 | 42.25 |
| ATOM | 2028 | CZ | ARG | A | 386 | 75.726 | 51.019 | 8.973 | 1.00 | 42.05 |
| ATOM | 2029 | NH1 | ARG | A | 386 | 76.737 | 51.661 | 8.401 | 1.00 | 41.85 |
| ATOM | 2030 | NH2 | ARG | A | 386 | 75.960 | 50.131 | 9.930 | 1.00 | 41.04 |
| ATOM | 2031 | N | PHE | A | 387 | 71.875 | 47.088 | 6.266 | 1.00 | 36.71 |
| ATOM | 2032 | CA | PHE | A | 387 | 72.309 | 45.740 | 5.928 | 1.00 | 37.28 |
| ATOM | 2033 | C | PHE | A | 387 | 71.442 | 44.973 | 4.938 | 1.00 | 38.78 |
| ATOM | 2034 | O | PHE | A | 387 | 70.249 | 45.233 | 4.779 | 1.00 | 38.34 |
| ATOM | 2035 | CB | PHE | A | 387 | 72.483 | 44.900 | 7.202 | 1.00 | 37.27 |

TABLE 7-continued

| ATOM | 2036 | CG  | PHE | A | 387 | 73.397 | 45.524 | 8.222  | 1.00 | 36.45 |
| ---- | ---- | --- | --- | - | --- | ------ | ------ | ------ | ---- | ----- |
| ATOM | 2037 | CD1 | PHE | A | 387 | 74.507 | 46.263 | 7.826  | 1.00 | 36.98 |
| ATOM | 2038 | CD2 | PHE | A | 387 | 73.152 | 45.364 | 9.584  | 1.00 | 36.75 |
| ATOM | 2039 | CE1 | PHE | A | 387 | 75.362 | 46.838 | 8.771  | 1.00 | 36.90 |
| ATOM | 2040 | CE2 | PHE | A | 387 | 73.998 | 45.931 | 10.536 | 1.00 | 35.15 |
| ATOM | 2041 | CZ  | PHE | A | 387 | 75.104 | 46.670 | 10.130 | 1.00 | 36.18 |
| ATOM | 2042 | N   | GLU | A | 388 | 72.081 | 44.013 | 4.280  | 1.00 | 39.94 |
| ATOM | 2043 | CA  | GLU | A | 388 | 71.442 | 43.155 | 3.294  | 1.00 | 41.27 |
| ATOM | 2044 | C   | GLU | A | 388 | 70.225 | 42.453 | 3.878  | 1.00 | 41.01 |
| ATOM | 2045 | O   | GLU | A | 388 | 69.216 | 42.268 | 3.195  | 1.00 | 40.68 |
| ATOM | 2046 | CB  | GLU | A | 388 | 72.453 | 42.111 | 2.809  | 1.00 | 42.64 |
| ATOM | 2047 | CG  | GLU | A | 388 | 71.901 | 41.064 | 1.853  | 1.00 | 46.30 |
| ATOM | 2048 | CD  | GLU | A | 388 | 71.435 | 41.660 | 0.542  | 1.00 | 47.81 |
| ATOM | 2049 | OE1 | GLU | A | 388 | 72.184 | 42.474 | −0.033 | 1.00 | 49.41 |
| ATOM | 2050 | OE2 | GLU | A | 388 | 70.326 | 41.310 | 0.081  | 1.00 | 50.01 |
| ATOM | 2051 | N   | GLU | A | 389 | 70.317 | 42.076 | 5.150  | 1.00 | 40.05 |
| ATOM | 2052 | CA  | GLU | A | 389 | 69.230 | 41.365 | 5.807  | 1.00 | 39.60 |
| ATOM | 2053 | C   | GLU | A | 389 | 68.002 | 42.182 | 6.200  | 1.00 | 39.15 |
| ATOM | 2054 | O   | GLU | A | 389 | 67.006 | 41.605 | 6.628  | 1.00 | 38.91 |
| ATOM | 2055 | CB  | GLU | A | 389 | 69.758 | 40.611 | 7.031  | 1.00 | 39.09 |
| ATOM | 2056 | CG  | GLU | A | 389 | 70.789 | 39.544 | 6.685  | 1.00 | 38.57 |
| ATOM | 2057 | CD  | GLU | A | 389 | 72.223 | 40.049 | 6.746  | 1.00 | 37.83 |
| ATOM | 2058 | OE1 | GLU | A | 389 | 72.453 | 41.267 | 6.600  | 1.00 | 38.50 |
| ATOM | 2059 | OE2 | GLU | A | 389 | 73.128 | 39.216 | 6.929  | 1.00 | 37.79 |
| ATOM | 2060 | N   | SER | A | 390 | 68.057 | 43.505 | 6.080  | 1.00 | 39.34 |
| ATOM | 2061 | CA  | SER | A | 390 | 66.879 | 44.303 | 6.417  | 1.00 | 41.26 |
| ATOM | 2062 | C   | SER | A | 390 | 65.839 | 43.965 | 5.343  | 1.00 | 42.43 |
| ATOM | 2063 | O   | SER | A | 390 | 66.193 | 43.713 | 4.192  | 1.00 | 42.09 |
| ATOM | 2064 | CB  | SER | A | 390 | 67.194 | 45.799 | 6.408  | 1.00 | 40.53 |
| ATOM | 2065 | OG  | SER | A | 390 | 67.514 | 46.256 | 5.111  | 1.00 | 44.02 |
| ATOM | 2066 | N   | PRO | A | 391 | 64.547 | 43.961 | 5.707  | 1.00 | 43.44 |
| ATOM | 2067 | CA  | PRO | A | 391 | 63.452 | 43.639 | 4.780  | 1.00 | 44.56 |
| ATOM | 2068 | C   | PRO | A | 391 | 63.123 | 44.645 | 3.678  | 1.00 | 45.93 |
| ATOM | 2069 | O   | PRO | A | 392 | 62.217 | 44.409 | 2.876  | 1.00 | 46.82 |
| ATOM | 2070 | CB  | PRO | A | 391 | 62.273 | 43.423 | 5.722  | 1.00 | 44.41 |
| ATOM | 2071 | CG  | PRO | A | 391 | 62.526 | 44.459 | 6.777  | 1.00 | 43.55 |
| ATOM | 2072 | CD  | PRO | A | 391 | 64.018 | 44.320 | 7.036  | 1.00 | 42.66 |
| ATOM | 2073 | N   | THR | A | 392 | 63.848 | 45.755 | 3.623  | 1.00 | 46.64 |
| ATOM | 2074 | CA  | THR | A | 392 | 63.573 | 46.767 | 2.612  | 1.00 | 47.66 |

TABLE 7-continued

| ATOM | 2075 | C | THR | A | 392 | 64.258 | 46.479 | 1.282 | 1.00 | 49.02 |
| --- | --- | --- | --- | --- | --- | --- | --- | --- | --- | --- |
| C | | | | | | | | | | |
| ATOM | 2076 | O | THR | A | 392 | 65.106 | 45.591 | 1.182 | 1.00 | 49.01 |
| O | | | | | | | | | | |
| ATOM | 2077 | CB | THR | A | 392 | 64.000 | 48.162 | 3.092 | 1.00 | 47.33 |
| C | | | | | | | | | | |
| ATOM | 2078 | OG1 | THR | A | 392 | 65.419 | 48.188 | 3.286 | 1.00 | 47.34 |
| O | | | | | | | | | | |
| ATOM | 2079 | CG2 | THR | A | 392 | 63.301 | 48.505 | 4.403 | 1.00 | 47.28 |
| C | | | | | | | | | | |
| ATOM | 2080 | N | ARG | A | 393 | 63.883 | 47.240 | 0.260 | 1.00 | 50.71 |
| N | | | | | | | | | | |
| ATOM | 2081 | CA | ARG | A | 393 | 64.456 | 47.061 | −1.066 | 1.00 | 52.75 |
| C | | | | | | | | | | |
| ATOM | 2082 | C | ARG | A | 393 | 65.795 | 47.757 | −1.219 | 1.00 | 53.23 |
| C | | | | | | | | | | |
| ATOM | 2083 | O | ARG | A | 393 | 65.993 | 48.876 | −0.743 | 1.00 | 52.80 |
| O | | | | | | | | | | |
| ATOM | 2084 | CB | ARG | A | 393 | 63.513 | 47.595 | −2.146 | 1.00 | 53.96 |
| C | | | | | | | | | | |
| ATOM | 2085 | CG | ARG | A | 393 | 62.189 | 46.865 | −2.283 | 1.00 | 56.12 |
| C | | | | | | | | | | |
| ATOM | 2086 | CD | ARG | A | 393 | 61.493 | 47.344 | −3.545 | 1.00 | 57.41 |
| C | | | | | | | | | | |
| ATOM | 2087 | NE | ARG | A | 393 | 61.452 | 48.802 | −3.587 | 1.00 | 59.49 |
| N | | | | | | | | | | |
| ATOM | 2088 | CZ | ARG | A | 393 | 61.357 | 49.518 | −4.702 | 1.00 | 60.61 |
| C | | | | | | | | | | |
| ATOM | 2089 | NH1 | ARG | A | 393 | 61.291 | 48.913 | −5.881 | 1.00 | 61.26 |
| N | | | | | | | | | | |
| ATOM | 2090 | NH2 | ARG | A | 393 | 61.337 | 50.842 | −4.636 | 1.00 | 61.38 |
| N | | | | | | | | | | |
| ATOM | 2091 | N | LYS | A | 394 | 66.713 | 47.077 | −1.894 | 1.00 | 54.19 |
| N | | | | | | | | | | |
| ATOM | 2092 | CA | LYS | A | 394 | 68.031 | 47.621 | −2.159 | 1.00 | 55.50 |
| C | | | | | | | | | | |
| ATOM | 2093 | C | LYS | A | 394 | 67.894 | 48.335 | −3.497 | 1.00 | 56.45 |
| C | | | | | | | | | | |
| ATOM | 2094 | O | LYS | A | 394 | 67.683 | 47.692 | −4.524 | 1.00 | 57.12 |
| O | | | | | | | | | | |
| ATOM | 2095 | CB | LYS | A | 394 | 69.053 | 46.492 | −2.277 | 1.00 | 55.00 |
| C | | | | | | | | | | |
| ATOM | 2096 | CG | LYS | A | 394 | 70.490 | 46.968 | −2.348 | 1.00 | 55.09 |
| C | | | | | | | | | | |
| ATOM | 2097 | CD | LYS | A | 394 | 71.417 | 45.863 | −2.824 | 1.00 | 54.69 |
| C | | | | | | | | | | |
| ATOM | 2098 | CE | LYS | A | 394 | 71.338 | 44.636 | −1.939 | 1.00 | 54.30 |
| C | | | | | | | | | | |
| ATOM | 2099 | NZ | LYS | A | 394 | 72.230 | 43.557 | −2.442 | 1.00 | 53.86 |
| N | | | | | | | | | | |
| ATOM | 2100 | N | VAL | A | 395 | 67.993 | 49.659 | −3.485 | 1.00 | 57.53 |
| N | | | | | | | | | | |
| ATOM | 2101 | CA | VAL | A | 395 | 67.860 | 50.432 | −4.712 | 1.00 | 58.92 |
| C | | | | | | | | | | |
| ATOM | 2102 | C | VAL | A | 395 | 69.139 | 51.181 | −5.061 | 1.00 | 60.04 |
| C | | | | | | | | | | |
| ATOM | 2103 | O | VAL | A | 395 | 69.813 | 51.718 | −4.183 | 1.00 | 59.84 |
| O | | | | | | | | | | |
| ATOM | 2104 | CB | VAL | A | 395 | 66.704 | 51.448 | −4.603 | 1.00 | 59.01 |
| C | | | | | | | | | | |
| ATOM | 2105 | CG1 | VAL | A | 395 | 65.392 | 50.713 | −4.362 | 1.00 | 58.97 |
| C | | | | | | | | | | |
| ATOM | 2106 | CG2 | VAL | A | 395 | 66.977 | 52.433 | −3.476 | 1.00 | 58.87 |
| C | | | | | | | | | | |
| ATOM | 2107 | N | THR | A | 396 | 69.467 | 51.213 | −6.350 | 1.00 | 61.16 |
| N | | | | | | | | | | |
| ATOM | 2108 | CA | THR | A | 396 | 70.668 | 51.896 | −6.818 | 1.00 | 62.32 |
| C | | | | | | | | | | |
| ATOM | 2109 | C | THR | A | 396 | 70.335 | 53.283 | −7.351 | 1.00 | 63.18 |
| C | | | | | | | | | | |
| ATOM | 2110 | O | THR | A | 396 | 69.646 | 53.421 | −8.363 | 1.00 | 63.24 |
| O | | | | | | | | | | |
| ATOM | 2111 | CB | THR | A | 396 | 71.367 | 51.099 | −7.934 | 1.00 | 62.19 |
| C | | | | | | | | | | |
| ATOM | 2112 | OG1 | THR | A | 396 | 71.668 | 49.780 | −7.464 | 1.00 | 62.83 |
| O | | | | | | | | | | |
| ATOM | 2113 | CG2 | THR | A | 396 | 72.662 | 51.785 | −8.343 | 1.00 | 62.42 |
| C | | | | | | | | | | |

TABLE 7-continued

| | | | | | | | | | |
|---|---|---|---|---|---|---|---|---|---|
| ATOM | 2114 | N | ILE | A | 397 | 70.834 | 54.305 | −6.665 | 1.00 64.15 |
| ATOM | 2115 | CA | ILE | A | 397 | 70.598 | 55.689 | −7.055 | 1.00 65.10 |
| ATOM | 2116 | C | ILE | A | 397 | 71.899 | 56.356 | −7.499 | 1.00 65.47 |
| ATOM | 2117 | O | ILE | A | 397 | 72.866 | 56.415 | −6.741 | 1.00 65.96 |
| ATOM | 2118 | CB | ILE | A | 397 | 70.003 | 56.495 | −5.884 | 1.00 65.41 |
| ATOM | 2119 | CG1 | ILE | A | 397 | 68.709 | 55.833 | −5.404 | 1.00 65.63 |
| ATOM | 2120 | CG2 | ILE | A | 397 | 69.736 | 57.930 | −6.320 | 1.00 65.84 |
| ATOM | 2121 | CD1 | ILE | A | 397 | 68.079 | 56.509 | −4.203 | 1.00 66.02 |
| ATOM | 2122 | N | ASN | A | 398 | 71.909 | 56.854 | −8.732 | 1.00 65.71 |
| ATOM | 2123 | CA | ASN | A | 398 | 73.073 | 57.526 | −9.307 | 1.00 65.41 |
| ATOM | 2124 | C | ASN | A | 398 | 74.417 | 56.895 | −8.945 | 1.00 64.56 |
| ATOM | 2125 | O | ASN | A | 398 | 75.353 | 57.592 | −8.551 | 1.00 64.63 |
| ATOM | 2126 | CB | ASN | A | 398 | 73.079 | 59.008 | −8.910 | 1.00 66.44 |
| ATOM | 2127 | CG | ASN | A | 398 | 73.115 | 59.215 | −7.405 | 1.00 67.59 |
| ATOM | 2128 | OD1 | ASN | A | 398 | 74.046 | 58.779 | −6.725 | 1.00 68.20 |
| ATOM | 2129 | ND2 | ASN | A | 398 | 72.099 | 59.891 | −6.878 | 1.00 67.87 |
| ATOM | 2130 | N | GLY | A | 399 | 74.508 | 55.576 | −9.082 | 1.00 63.47 |
| ATOM | 2131 | CA | GLY | A | 399 | 75.751 | 54.886 | −8.779 | 1.00 61.85 |
| ATOM | 2132 | C | GLY | A | 399 | 75.918 | 54.443 | −7.338 | 1.00 60.93 |
| ATOM | 2133 | O | GLY | A | 399 | 76.854 | 53.709 | −7.016 | 1.00 61.23 |
| ATOM | 2134 | N | SER | A | 400 | 75.019 | 54.882 | −6.464 | 1.00 59.70 |
| ATOM | 2135 | CA | SER | A | 400 | 75.096 | 54.511 | −5.056 | 1.00 57.96 |
| ATOM | 2136 | C | SER | A | 400 | 73.973 | 53.577 | −4.634 | 1.00 56.49 |
| ATOM | 2137 | O | SER | A | 400 | 72.793 | 53.898 | −4.774 | 1.00 56.56 |
| ATOM | 2138 | CB | SER | A | 400 | 75.079 | 55.761 | −4.174 | 1.00 57.95 |
| ATOM | 2139 | OG | SER | A | 400 | 76.286 | 56.488 | −4.305 | 1.00 58.53 |
| ATOM | 2140 | N | VAL | A | 401 | 74.351 | 52.414 | −4.118 | 1.00 54.54 |
| ATOM | 2141 | CA | VAL | A | 401 | 73.383 | 51.431 | −3.662 | 1.00 52.89 |
| ATOM | 2142 | C | VAL | A | 401 | 72.864 | 51.864 | −2.293 | 1.00 52.23 |
| ATOM | 2143 | O | VAL | A | 401 | 73.637 | 52.020 | −1.344 | 1.00 51.54 |
| ATOM | 2144 | CB | VAL | A | 401 | 74.027 | 50.038 | −3.550 | 1.00 52.97 |
| ATOM | 2145 | CG1 | VAL | A | 401 | 72.986 | 49.012 | −3.153 | 1.00 52.38 |
| ATOM | 2146 | CG2 | VAL | A | 401 | 74.670 | 49.660 | −4.876 | 1.00 52.77 |
| ATOM | 2147 | N | MET | A | 402 | 71.554 | 52.066 | −2.201 | 1.00 50.74 |
| ATOM | 2148 | CA | MET | A | 402 | 70.933 | 52.493 | −0.954 | 1.00 49.56 |
| ATOM | 2149 | C | MET | A | 402 | 69.878 | 51.490 | −0.509 | 1.00 48.15 |
| ATOM | 2150 | O | MET | A | 402 | 69.533 | 50.563 | −1.243 | 1.00 47.53 |
| ATOM | 2151 | CB | MET | A | 402 | 70.255 | 53.855 | −1.138 | 1.00 50.70 |
| ATOM | 2152 | CG | MET | A | 402 | 71.080 | 54.897 | −1.873 | 1.00 51.69 |

TABLE 7-continued

| ATOM | 2153 | SD | MET | A | 402 | 72.539 | 55.428 | −0.974 | 1.00 | 54.36 |
| --- | --- | --- | --- | --- | --- | --- | --- | --- | --- | --- |
| ATOM | 2154 | CE | MET | A | 402 | 71.840 | 56.729 | 0.054 | 1.00 | 52.69 |
| ATOM | 2155 | N | LYS | A | 403 | 69.380 | 51.683 | 0.708 | 1.00 | 45.93 |
| ATOM | 2156 | CA | LYS | A | 403 | 68.325 | 50.843 | 1.258 | 1.00 | 43.52 |
| ATOM | 2157 | C | LYS | A | 403 | 67.270 | 51.792 | 1.806 | 1.00 | 42.26 |
| ATOM | 2158 | O | LYS | A | 403 | 67.598 | 52.853 | 2.336 | 1.00 | 41.26 |
| ATOM | 2159 | CB | LYS | A | 403 | 68.856 | 49.937 | 2.373 | 1.00 | 43.98 |
| ATOM | 2160 | CG | LYS | A | 403 | 69.833 | 48.880 | 1.887 | 1.00 | 43.45 |
| ATOM | 2161 | CD | LYS | A | 403 | 69.570 | 47.521 | 2.524 | 1.00 | 43.42 |
| ATOM | 2162 | CE | LYS | A | 403 | 68.229 | 46.950 | 2.087 | 1.00 | 42.68 |
| ATOM | 2163 | NZ | LYS | A | 403 | 68.000 | 45.572 | 2.601 | 1.00 | 40.87 |
| ATOM | 2164 | N | GLU | A | 404 | 66.003 | 51.425 | 1.659 | 1.00 | 41.41 |
| ATOM | 2165 | CA | GLU | A | 404 | 64.927 | 52.275 | 2.144 | 1.00 | 41.08 |
| ATOM | 2166 | C | GLU | A | 404 | 64.881 | 52.222 | 3.661 | 1.00 | 39.67 |
| ATOM | 2167 | O | GLU | A | 404 | 65.181 | 51.192 | 4.265 | 1.00 | 38.02 |
| ATOM | 2168 | CB | GLU | A | 404 | 63.578 | 51.809 | 1.606 | 1.00 | 42.91 |
| ATOM | 2169 | CG | GLU | A | 404 | 63.610 | 51.221 | 0.214 | 1.00 | 46.16 |
| ATOM | 2170 | CD | GLU | A | 404 | 62.230 | 50.819 | −0.252 | 1.00 | 47.92 |
| ATOM | 2171 | OE1 | GLU | A | 404 | 61.469 | 51.711 | −0.685 | 1.00 | 48.56 |
| ATOM | 2172 | OE2 | GLU | A | 404 | 61.901 | 49.615 | −0.167 | 1.00 | 49.37 |
| ATOM | 2173 | N | TYR | A | 405 | 64.496 | 53.335 | 4.271 | 1.00 | 38.76 |
| ATOM | 2174 | CA | TYR | A | 405 | 64.390 | 53.402 | 5.717 | 1.00 | 38.34 |
| ATOM | 2175 | C | TYR | A | 405 | 63.347 | 54.438 | 6.094 | 1.00 | 37.84 |
| ATOM | 2176 | O | TYR | A | 405 | 63.499 | 55.622 | 5.796 | 1.00 | 38.50 |
| ATOM | 2177 | CB | TYR | A | 405 | 65.736 | 53.770 | 6.344 | 1.00 | 37.72 |
| ATOM | 2178 | CG | TYR | A | 405 | 65.698 | 53.826 | 7.855 | 1.00 | 37.96 |
| ATOM | 2179 | CD1 | TYR | A | 405 | 65.285 | 52.723 | 8.602 | 1.00 | 36.71 |
| ATOM | 2180 | CD2 | TYR | A | 405 | 66.072 | 54.982 | 8.539 | 1.00 | 38.07 |
| ATOM | 2181 | CE1 | TYR | A | 405 | 65.245 | 52.770 | 9.995 | 1.00 | 37.68 |
| ATOM | 2182 | CE2 | TYR | A | 405 | 66.036 | 55.038 | 9.931 | 1.00 | 38.31 |
| ATOM | 2183 | CZ | TYR | A | 405 | 65.621 | 53.929 | 10.650 | 1.00 | 37.39 |
| ATOM | 2184 | OH | TYR | A | 405 | 65.577 | 53.987 | 12.024 | 1.00 | 38.38 |
| ATOM | 2185 | N | TRP | A | 406 | 62.287 | 53.986 | 6.752 | 1.00 | 36.25 |
| ATOM | 2186 | CA | TRP | A | 406 | 61.221 | 54.885 | 7.160 | 1.00 | 35.74 |
| ATOM | 2187 | C | TRP | A | 406 | 60.829 | 54.630 | 8.608 | 1.00 | 35.35 |
| ATOM | 2188 | O | TRP | A | 406 | 60.906 | 53.499 | 9.092 | 1.00 | 34.84 |
| ATOM | 2189 | CB | TRP | A | 406 | 60.013 | 54.712 | 6.226 | 1.00 | 34.90 |
| ATOM | 2190 | CG | TRP | A | 406 | 59.374 | 53.345 | 6.257 | 1.00 | 33.53 |
| ATOM | 2191 | CD1 | TRP | A | 406 | 58.389 | 52.920 | 7.100 | 1.00 | 33.84 |

TABLE 7-continued

| ATOM | 2192 | CD2 | TRP | A | 406 | 59.679 | 52.232 | 5.405 | 1.00 | 34.08 |
|---|---|---|---|---|---|---|---|---|---|---|
| C | | | | | | | | | | |
| ATOM | 2193 | NE1 | TRP | A | 406 | 58.059 | 51.615 | 6.826 | 1.00 | 34.02 |
| N | | | | | | | | | | |
| ATOM | 2194 | CE2 | TRP | A | 406 | 58.835 | 51.167 | 5.791 | 1.00 | 33.93 |
| C | | | | | | | | | | |
| ATOM | 2195 | CE3 | TRP | A | 406 | 60.584 | 52.031 | 4.351 | 1.00 | 35.20 |
| C | | | | | | | | | | |
| ATOM | 2196 | CZ2 | TRP | A | 406 | 58.866 | 49.916 | 5.160 | 1.00 | 34.01 |
| C | | | | | | | | | | |
| ATOM | 2197 | CZ3 | TRP | A | 406 | 60.615 | 50.784 | 3.722 | 1.00 | 35.05 |
| C | | | | | | | | | | |
| ATOM | 2198 | CH2 | TRP | A | 406 | 59.758 | 49.744 | 4.132 | 1.00 | 34.39 |
| C | | | | | | | | | | |
| ATOM | 2199 | N | GLY | A | 407 | 60.421 | 55.691 | 9.295 | 1.00 | 36.13 |
| N | | | | | | | | | | |
| ATOM | 2200 | CA | GLY | A | 407 | 60.023 | 55.569 | 10.685 | 1.00 | 36.66 |
| C | | | | | | | | | | |
| ATOM | 2201 | C | GLY | A | 407 | 58.630 | 54.991 | 10.840 | 1.00 | 37.56 |
| C | | | | | | | | | | |
| ATOM | 2202 | O | GLY | A | 407 | 57.835 | 54.989 | 9.899 | 1.00 | 36.82 |
| O | | | | | | | | | | |
| ATOM | 2203 | N | GLU | A | 408 | 58.331 | 54.495 | 12.035 | 1.00 | 37.65 |
| N | | | | | | | | | | |
| ATOM | 2204 | CA | GLU | A | 408 | 57.022 | 53.917 | 12.316 | 1.00 | 38.92 |
| C | | | | | | | | | | |
| ATOM | 2205 | C | GLU | A | 408 | 55.950 | 54.998 | 12.390 | 1.00 | 40.20 |
| C | | | | | | | | | | |
| ATOM | 2206 | O | GLU | A | 408 | 54.756 | 54.704 | 12.374 | 1.00 | 40.37 |
| O | | | | | | | | | | |
| ATOM | 2207 | CB | GLU | A | 408 | 57.071 | 53.141 | 13.631 | 1.00 | 38.51 |
| C | | | | | | | | | | |
| ATOM | 2208 | CG | GLU | A | 408 | 57.848 | 51.845 | 13.535 | 1.00 | 37.66 |
| C | | | | | | | | | | |
| ATOM | 2209 | CD | GLU | A | 408 | 57.167 | 50.834 | 12.625 | 1.00 | 37.31 |
| C | | | | | | | | | | |
| ATOM | 2210 | OE1 | GLU | A | 408 | 56.048 | 50.392 | 12.960 | 1.00 | 37.35 |
| O | | | | | | | | | | |
| ATOM | 2211 | OE2 | GLU | A | 408 | 57.748 | 50.482 | 11.578 | 1.00 | 35.96 |
| O | | | | | | | | | | |
| ATOM | 2212 | N | GLY | A | 409 | 56.387 | 56.249 | 12.464 | 1.00 | 41.46 |
| N | | | | | | | | | | |
| ATOM | 2213 | CA | GLY | A | 409 | 55.455 | 57.358 | 12.544 | 1.00 | 43.94 |
| C | | | | | | | | | | |
| ATOM | 2214 | C | GLY | A | 409 | 55.111 | 57.955 | 11.193 | 1.00 | 45.38 |
| C | | | | | | | | | | |
| ATOM | 2215 | O | GLY | A | 409 | 54.268 | 58.844 | 11.105 | 1.00 | 45.63 |
| O | | | | | | | | | | |
| ATOM | 2216 | N | SER | A | 410 | 55.762 | 57.473 | 10.138 | 1.00 | 46.93 |
| N | | | | | | | | | | |
| ATOM | 2217 | CA | SER | A | 410 | 55.499 | 57.977 | 8.795 | 1.00 | 48.89 |
| C | | | | | | | | | | |
| ATOM | 2218 | C | SER | A | 410 | 54.184 | 57.394 | 8.293 | 1.00 | 50.59 |
| C | | | | | | | | | | |
| ATOM | 2219 | O | SER | A | 410 | 53.798 | 56.292 | 8.683 | 1.00 | 49.70 |
| O | | | | | | | | | | |
| ATOM | 2220 | CB | SER | A | 410 | 56.633 | 57.587 | 7.840 | 1.00 | 48.74 |
| C | | | | | | | | | | |
| ATOM | 2221 | OG | SER | A | 410 | 56.645 | 56.189 | 7.595 | 1.00 | 49.10 |
| O | | | | | | | | | | |
| ATOM | 2222 | N | SER | A | 411 | 53.495 | 58.137 | 7.433 | 1.00 | 52.78 |
| N | | | | | | | | | | |
| ATOM | 2223 | CA | SER | A | 411 | 52.224 | 57.674 | 6.890 | 1.00 | 55.38 |
| C | | | | | | | | | | |
| ATOM | 2224 | C | SER | A | 411 | 52.436 | 56.350 | 6.172 | 1.00 | 56.75 |
| C | | | | | | | | | | |
| ATOM | 2225 | O | SER | A | 411 | 51.559 | 55.487 | 6.154 | 1.00 | 57.17 |
| O | | | | | | | | | | |
| ATOM | 2226 | CB | SER | A | 411 | 51.656 | 58.710 | 5.917 | 1.00 | 56.02 |
| C | | | | | | | | | | |
| ATOM | 2227 | OG | SER | A | 411 | 52.569 | 58.984 | 4.868 | 1.00 | 56.98 |
| O | | | | | | | | | | |
| ATOM | 2228 | N | ARG | A | 412 | 53.621 | 56.195 | 5.591 | 1.00 | 58.21 |
| N | | | | | | | | | | |
| ATOM | 2229 | CA | ARG | A | 412 | 53.976 | 54.985 | 4.862 | 1.00 | 59.73 |
| C | | | | | | | | | | |
| ATOM | 2230 | C | ARG | A | 412 | 53.968 | 53.730 | 5.735 | 1.00 | 60.68 |
| C | | | | | | | | | | |

TABLE 7-continued

| ATOM | 2231 | O | ARG | A | 412 | 54.038 | 52.616 | 5.217 | 1.00 | 60.45 |
| --- | --- | --- | --- | --- | --- | --- | --- | --- | --- | --- |
| O | | | | | | | | | | |
| ATOM | 2232 | CB | ARG | A | 412 | 55.362 | 55.157 | 4.227 | 1.00 | 59.28 |
| C | | | | | | | | | | |
| ATOM | 2233 | CG | ARG | A | 412 | 55.870 | 53.925 | 3.502 | 1.00 | 59.26 |
| C | | | | | | | | | | |
| ATOM | 2234 | CD | ARG | A | 412 | 57.209 | 54.168 | 2.824 | 1.00 | 58.44 |
| C | | | | | | | | | | |
| ATOM | 2235 | NE | ARG | A | 412 | 57.669 | 52.964 | 2.141 | 1.00 | 57.93 |
| N | | | | | | | | | | |
| ATOM | 2236 | CZ | ARG | A | 412 | 58.797 | 52.874 | 1.445 | 1.00 | 57.94 |
| C | | | | | | | | | | |
| ATOM | 2237 | NH1 | ARG | A | 412 | 59.601 | 53.923 | 1.330 | 1.00 | 57.62 |
| N | | | | | | | | | | |
| ATOM | 2238 | NH2 | ARG | A | 412 | 59.120 | 51.727 | 0.863 | 1.00 | 58.08 |
| N | | | | | | | | | | |
| ATOM | 2239 | N | ALA | A | 413 | 53.865 | 53.902 | 7.050 | 1.00 | 62.54 |
| N | | | | | | | | | | |
| ATOM | 2240 | CA | ALA | A | 413 | 53.886 | 52.756 | 7.958 | 1.00 | 63.99 |
| C | | | | | | | | | | |
| ATOM | 2241 | C | ALA | A | 413 | 52.735 | 52.638 | 8.956 | 1.00 | 65.55 |
| C | | | | | | | | | | |
| ATOM | 2242 | O | ALA | A | 413 | 52.051 | 51.614 | 8.999 | 1.00 | 65.26 |
| O | | | | | | | | | | |
| ATOM | 2243 | CB | ALA | A | 413 | 55.212 | 52.736 | 8.712 | 1.00 | 64.03 |
| C | | | | | | | | | | |
| ATOM | 2244 | N | ARG | A | 414 | 52.533 | 53.676 | 9.764 | 1.00 | 67.81 |
| N | | | | | | | | | | |
| ATOM | 2245 | CA | ARG | A | 414 | 51.489 | 53.671 | 10.789 | 1.00 | 69.46 |
| C | | | | | | | | | | |
| ATOM | 2246 | C | ARG | A | 414 | 50.087 | 53.325 | 10.285 | 1.00 | 70.36 |
| C | | | | | | | | | | |
| ATOM | 2247 | O | ARG | A | 414 | 49.181 | 53.071 | 11.084 | 1.00 | 70.13 |
| O | | | | | | | | | | |
| ATOM | 2248 | CB | ARG | A | 414 | 51.446 | 55.026 | 11.509 | 1.00 | 70.05 |
| C | | | | | | | | | | |
| ATOM | 2249 | CG | ARG | A | 414 | 50.960 | 56.194 | 10.659 | 1.00 | 71.62 |
| C | | | | | | | | | | |
| ATOM | 2250 | CD | ARG | A | 414 | 50.711 | 57.418 | 11.534 | 1.00 | 73.27 |
| C | | | | | | | | | | |
| ATOM | 2251 | NE | ARG | A | 414 | 50.149 | 58.551 | 10.799 | 1.00 | 74.95 |
| N | | | | | | | | | | |
| ATOM | 2252 | CZ | ARG | A | 414 | 50.825 | 59.302 | 9.933 | 1.00 | 75.82 |
| C | | | | | | | | | | |
| ATOM | 2253 | NH1 | ARG | A | 414 | 52.102 | 59.047 | 9.682 | 1.00 | 76.36 |
| N | | | | | | | | | | |
| ATOM | 2254 | NH2 | ARG | A | 414 | 50.225 | 60.317 | 9.323 | 1.00 | 76.47 |
| N | | | | | | | | | | |
| ATOM | 2255 | N | ASN | A | 415 | 49.911 | 53.313 | 8.967 | 1.00 | 71.18 |
| N | | | | | | | | | | |
| ATOM | 2256 | CA | ASN | A | 415 | 48.617 | 53.001 | 8.364 | 1.00 | 72.52 |
| C | | | | | | | | | | |
| ATOM | 2257 | C | ASN | A | 415 | 48.712 | 51.666 | 7.617 | 1.00 | 73.18 |
| C | | | | | | | | | | |
| ATOM | 2258 | O | ASN | A | 415 | 48.989 | 51.638 | 6.416 | 1.00 | 73.46 |
| O | | | | | | | | | | |
| ATOM | 2259 | CB | ASN | A | 415 | 48.218 | 54.124 | 7.393 | 1.00 | 73.28 |
| C | | | | | | | | | | |
| ATOM | 2260 | CG | ASN | A | 415 | 46.759 | 54.059 | 6.982 | 1.00 | 73.50 |
| C | | | | | | | | | | |
| ATOM | 2261 | OD1 | ASN | A | 415 | 46.348 | 54.689 | 5.987 | 1.00 | 73.39 |
| O | | | | | | | | | | |
| ATOM | 2262 | ND2 | ASN | A | 415 | 45.957 | 53.314 | 7.742 | 1.00 | 73.08 |
| N | | | | | | | | | | |
| ATOM | 2263 | N | TRP | A | 416 | 48.482 | 50.563 | 8.329 | 1.00 | 73.62 |
| N | | | | | | | | | | |
| ATOM | 2264 | CA | TRP | A | 416 | 48.564 | 49.238 | 7.716 | 1.00 | 74.23 |
| C | | | | | | | | | | |
| ATOM | 2265 | C | TRP | A | 416 | 47.212 | 48.527 | 7.660 | 1.00 | 73.85 |
| C | | | | | | | | | | |
| ATOM | 2266 | O | TRP | A | 416 | 46.416 | 48.598 | 8.598 | 1.00 | 73.60 |
| O | | | | | | | | | | |
| ATOM | 2267 | CB | TRP | A | 416 | 49.593 | 48.374 | 8.468 | 1.00 | 74.70 |
| C | | | | | | | | | | |
| ATOM | 2268 | CG | TRP | A | 416 | 49.043 | 47.556 | 9.609 | 1.00 | 76.10 |
| C | | | | | | | | | | |
| ATOM | 2269 | CD1 | TRP | A | 416 | 48.308 | 46.405 | 9.516 | 1.00 | 76.57 |
| C | | | | | | | | | | |

TABLE 7-continued

| | | | | | | | | | |
|---|---|---|---|---|---|---|---|---|---|
| ATOM | 2270 | CD2 | TRP | A | 416 | 49.195 | 47.819 | 11.010 | 1.00 | 76.67 |
| C | | | | | | | | | | |
| ATOM | 2271 | NE1 | TRP | A | 416 | 47.996 | 45.936 | 10.770 | 1.00 | 76.56 |
| N | | | | | | | | | | |
| ATOM | 2272 | CE2 | TRP | A | 416 | 48.527 | 46.784 | 11.705 | 1.00 | 76.89 |
| C | | | | | | | | | | |
| ATOM | 2273 | CE3 | TRP | A | 416 | 49.830 | 48.828 | 11.747 | 1.00 | 77.37 |
| C | | | | | | | | | | |
| ATOM | 2274 | CZ2 | TRP | A | 416 | 48.477 | 46.729 | 13.102 | 1.00 | 77.40 |
| C | | | | | | | | | | |
| ATOM | 2275 | CZ3 | TRP | A | 416 | 49.780 | 48.772 | 13.138 | 1.00 | 77.75 |
| C | | | | | | | | | | |
| ATOM | 2276 | CH2 | TRP | A | 416 | 49.107 | 47.728 | 13.799 | 1.00 | 77.84 |
| C | | | | | | | | | | |
| ATOM | 2277 | N | GLU | A | 431 | 54.545 | 62.823 | 11.142 | 1.00 | 66.75 |
| N | | | | | | | | | | |
| ATOM | 2278 | CA | GLU | A | 431 | 54.941 | 62.244 | 12.421 | 1.00 | 66.57 |
| C | | | | | | | | | | |
| ATOM | 2279 | C | GLU | A | 431 | 56.245 | 61.460 | 12.283 | 1.00 | 65.93 |
| C | | | | | | | | | | |
| ATOM | 2280 | O | GLU | A | 431 | 56.929 | 61.185 | 13.270 | 1.00 | 66.27 |
| O | | | | | | | | | | |
| ATOM | 2281 | CB | GLU | A | 431 | 53.832 | 61.328 | 12.945 | 1.00 | 67.44 |
| C | | | | | | | | | | |
| ATOM | 2282 | CG | GLU | A | 431 | 52.495 | 62.032 | 13.143 | 1.00 | 68.98 |
| C | | | | | | | | | | |
| ATOM | 2283 | CD | GLU | A | 431 | 51.422 | 61.112 | 13.693 | 1.00 | 69.90 |
| C | | | | | | | | | | |
| ATOM | 2284 | OE1 | GLU | A | 431 | 51.073 | 60.126 | 13.010 | 1.00 | 70.49 |
| O | | | | | | | | | | |
| ATOM | 2285 | OE2 | GLU | A | 431 | 50.927 | 61.373 | 14.811 | 1.00 | 70.56 |
| O | | | | | | | | | | |
| ATOM | 2286 | N | GLY | A | 432 | 56.582 | 61.106 | 11.047 | 1.00 | 64.87 |
| N | | | | | | | | | | |
| ATOM | 2287 | CA | GLY | A | 432 | 57.803 | 60.367 | 10.786 | 1.00 | 63.17 |
| C | | | | | | | | | | |
| ATOM | 2288 | C | GLY | A | 432 | 58.332 | 60.728 | 9.414 | 1.00 | 62.04 |
| C | | | | | | | | | | |
| ATOM | 2289 | O | GLY | A | 432 | 57.658 | 61.423 | 8.654 | 1.00 | 62.22 |
| O | | | | | | | | | | |
| ATOM | 2290 | N | VAL | A | 433 | 59.533 | 60.262 | 9.085 | 1.00 | 60.59 |
| N | | | | | | | | | | |
| ATOM | 2291 | CA | VAL | A | 433 | 60.117 | 60.564 | 7.785 | 1.00 | 58.60 |
| C | | | | | | | | | | |
| ATOM | 2292 | C | VAL | A | 433 | 60.530 | 59.318 | 7.000 | 1.00 | 57.08 |
| C | | | | | | | | | | |
| ATOM | 2293 | O | VAL | A | 433 | 60.849 | 58.276 | 7.576 | 1.00 | 56.04 |
| O | | | | | | | | | | |
| ATOM | 2294 | CB | VAL | A | 433 | 61.336 | 61.508 | 7.930 | 1.00 | 58.79 |
| C | | | | | | | | | | |
| ATOM | 2295 | CG1 | VAL | A | 433 | 60.883 | 62.858 | 8.459 | 1.00 | 58.84 |
| C | | | | | | | | | | |
| ATOM | 2296 | CG2 | VAL | A | 433 | 62.359 | 60.901 | 8.867 | 1.00 | 58.98 |
| C | | | | | | | | | | |
| ATOM | 2297 | N | ASP | A | 434 | 60.507 | 59.446 | 5.676 | 1.00 | 55.12 |
| N | | | | | | | | | | |
| ATOM | 2298 | CA | ASP | A | 434 | 60.867 | 58.367 | 4.761 | 1.00 | 53.00 |
| C | | | | | | | | | | |
| ATOM | 2299 | C | ASP | A | 434 | 62.215 | 58.734 | 4.144 | 1.00 | 51.90 |
| C | | | | | | | | | | |
| ATOM | 2300 | O | ASP | A | 434 | 62.401 | 59.866 | 3.696 | 1.00 | 51.71 |
| O | | | | | | | | | | |
| ATOM | 2301 | CB | ASP | A | 434 | 59.799 | 58.250 | 3.667 | 1.00 | 53.31 |
| C | | | | | | | | | | |
| ATOM | 2302 | CG | ASP | A | 434 | 59.932 | 56.984 | 2.841 | 1.00 | 53.22 |
| C | | | | | | | | | | |
| ATOM | 2303 | OD1 | ASP | A | 434 | 59.210 | 56.862 | 1.830 | 1.00 | 53.79 |
| O | | | | | | | | | | |
| ATOM | 2304 | OD2 | ASP | A | 434 | 60.744 | 56.108 | 3.199 | 1.00 | 53.37 |
| O | | | | | | | | | | |
| ATOM | 2305 | N | SER | A | 435 | 63.153 | 57.792 | 4.106 | 1.00 | 50.14 |
| N | | | | | | | | | | |
| ATOM | 2306 | CA | SER | A | 435 | 64.471 | 58.098 | 3.560 | 1.00 | 48.49 |
| C | | | | | | | | | | |
| ATOM | 2307 | C | SER | A | 435 | 65.267 | 56.912 | 3.026 | 1.00 | 47.19 |
| C | | | | | | | | | | |
| ATOM | 2308 | O | SER | A | 435 | 64.748 | 55.809 | 2.862 | 1.00 | 46.05 |
| O | | | | | | | | | | |

TABLE 7-continued

| | | | | | | | | | |
|---|---|---|---|---|---|---|---|---|---|
| ATOM | 2309 | CB | SER | A | 435 | 65.304 | 58.806 | 4.627 | 1.00 48.72 |
| ATOM | 2310 | OG | SER | A | 435 | 65.451 | 57.976 | 5.768 | 1.00 49.51 |
| ATOM | 2311 | N | TYR | A | 436 | 66.545 | 57.169 | 2.765 | 1.00 46.20 |
| ATOM | 2312 | CA | TYR | A | 436 | 67.470 | 56.163 | 2.259 | 1.00 46.22 |
| ATOM | 2313 | C | TYR | A | 436 | 68.735 | 56.149 | 3.114 | 1.00 45.31 |
| ATOM | 2314 | O | TYR | A | 436 | 69.125 | 57.175 | 3.673 | 1.00 45.33 |
| ATOM | 2315 | CB | TYR | A | 436 | 67.858 | 56.481 | 0.812 | 1.00 48.04 |
| ATOM | 2316 | CG | TYR | A | 436 | 66.731 | 56.356 | −0.186 | 1.00 49.05 |
| ATOM | 2317 | CD1 | TYR | A | 436 | 66.236 | 55.106 | −0.555 | 1.00 49.71 |
| ATOM | 2318 | CD2 | TYR | A | 436 | 66.160 | 57.488 | −0.764 | 1.00 50.33 |
| ATOM | 2319 | CE1 | TYR | A | 436 | 65.198 | 54.987 | −1.476 | 1.00 50.76 |
| ATOM | 2320 | CE2 | TYR | A | 436 | 65.119 | 57.381 | −1.685 | 1.00 50.87 |
| ATOM | 2321 | CZ | TYR | A | 436 | 64.645 | 56.129 | −2.035 | 1.00 50.97 |
| ATOM | 2322 | OH | TYR | A | 436 | 63.614 | 56.019 | −2.940 | 1.00 52.36 |
| ATOM | 2323 | N | VAL | A | 437 | 69.361 | 54.980 | 3.217 | 1.00 44.07 |
| ATOM | 2324 | CA | VAL | A | 437 | 70.602 | 54.824 | 3.970 | 1.00 43.32 |
| ATOM | 2325 | C | VAL | A | 437 | 71.591 | 54.068 | 3.092 | 1.00 42.81 |
| ATOM | 2326 | O | VAL | A | 437 | 71.218 | 53.132 | 2.384 | 1.00 41.76 |
| ATOM | 2327 | CB | VAL | A | 437 | 70.401 | 54.034 | 5.290 | 1.00 42.99 |
| ATOM | 2328 | CG1 | VAL | A | 437 | 69.463 | 54.793 | 6.213 | 1.00 42.96 |
| ATOM | 2329 | CG2 | VAL | A | 437 | 69.868 | 52.645 | 4.997 | 1.00 42.44 |
| ATOM | 2330 | N | PRO | A | 438 | 72.873 | 54.460 | 3.133 | 1.00 43.06 |
| ATOM | 2331 | CA | PRO | A | 438 | 73.882 | 53.784 | 2.313 | 1.00 42.54 |
| ATOM | 2332 | C | PRO | A | 438 | 73.998 | 52.295 | 2.611 | 1.00 41.85 |
| ATOM | 2333 | O | PRO | A | 438 | 74.038 | 51.883 | 3.770 | 1.00 41.55 |
| ATOM | 2334 | CB | PRO | A | 438 | 75.162 | 54.554 | 2.641 | 1.00 43.10 |
| ATOM | 2335 | CG | PRO | A | 438 | 74.943 | 54.958 | 4.067 | 1.00 44.10 |
| ATOM | 2336 | CD | PRO | A | 438 | 73.501 | 55.422 | 4.056 | 1.00 42.97 |
| ATOM | 2337 | N | TYR | A | 439 | 74.034 | 51.491 | 1.554 | 1.00 41.03 |
| ATOM | 2338 | CA | TYR | A | 439 | 74.162 | 50.046 | 1.686 | 1.00 40.53 |
| ATOM | 2339 | C | TYR | A | 439 | 75.502 | 49.754 | 2.356 | 1.00 40.67 |
| ATOM | 2340 | O | TYR | A | 439 | 76.530 | 50.308 | 1.968 | 1.00 39.93 |
| ATOM | 2341 | CB | TYR | A | 439 | 74.108 | 49.393 | 0.303 | 1.00 40.18 |
| ATOM | 2342 | CG | TYR | A | 439 | 74.244 | 47.889 | 0.305 | 1.00 39.32 |
| ATOM | 2343 | CD1 | TYR | A | 439 | 73.339 | 47.086 | 0.998 | 1.00 40.13 |
| ATOM | 2344 | CD2 | TYR | A | 439 | 75.264 | 47.263 | −0.411 | 1.00 39.93 |
| ATOM | 2345 | CE1 | TYR | A | 439 | 73.445 | 45.697 | 0.975 | 1.00 40.31 |
| ATOM | 2346 | CE2 | TYR | A | 439 | 75.380 | 45.878 | −0.439 | 1.00 39.98 |
| ATOM | 2347 | CZ | TYR | A | 439 | 74.467 | 45.102 | 0.254 | 1.00 40.61 |

TABLE 7-continued

| ATOM | 2348 | OH | TYR | A | 439 | 74.576 | 43.731 | 0.226 | 1.00 | 41.51 |
|---|---|---|---|---|---|---|---|---|---|---|
| ATOM | 2349 | N | ALA | A | 440 | 75.485 | 48.885 | 3.361 | 1.00 | 40.76 |
| ATOM | 2350 | CA | ALA | A | 440 | 76.699 | 48.546 | 4.091 | 1.00 | 41.53 |
| ATOM | 2351 | C | ALA | A | 440 | 77.102 | 47.093 | 3.899 | 1.00 | 41.13 |
| ATOM | 2352 | O | ALA | A | 440 | 78.175 | 46.679 | 4.330 | 1.00 | 41.96 |
| ATOM | 2353 | CB | ALA | A | 440 | 76.507 | 48.842 | 5.580 | 1.00 | 40.70 |
| ATOM | 2354 | N | GLY | A | 441 | 76.239 | 46.320 | 3.251 | 1.00 | 41.41 |
| ATOM | 2355 | CA | GLY | A | 441 | 76.536 | 44.919 | 3.030 | 1.00 | 41.21 |
| ATOM | 2356 | C | GLY | A | 441 | 75.917 | 44.025 | 4.088 | 1.00 | 41.44 |
| ATOM | 2357 | O | GLY | A | 441 | 74.882 | 44.359 | 4.664 | 1.00 | 41.15 |
| ATOM | 2358 | N | LYS | A | 442 | 76.562 | 42.891 | 4.345 | 1.00 | 41.60 |
| ATOM | 2359 | CA | LYS | A | 442 | 76.097 | 41.917 | 5.329 | 1.00 | 41.97 |
| ATOM | 2360 | C | LYS | A | 442 | 76.237 | 42.410 | 6.771 | 1.00 | 40.70 |
| ATOM | 2361 | O | LYS | A | 442 | 77.189 | 43.112 | 7.114 | 1.00 | 41.12 |
| ATOM | 2362 | CB | LYS | A | 442 | 76.880 | 40.613 | 5.168 | 1.00 | 43.78 |
| ATOM | 2363 | CG | LYS | A | 442 | 76.859 | 40.049 | 3.756 | 1.00 | 46.44 |
| ATOM | 2364 | CD | LYS | A | 442 | 75.487 | 39.510 | 3.386 | 1.00 | 47.81 |
| ATOM | 2365 | CE | LYS | A | 442 | 75.159 | 38.260 | 4.179 | 1.00 | 48.88 |
| ATOM | 2366 | NZ | LYS | A | 442 | 73.844 | 37.682 | 3.783 | 1.00 | 51.00 |
| ATOM | 2367 | N | LEU | A | 443 | 75.285 | 42.020 | 7.611 | 1.00 | 39.20 |
| ATOM | 2368 | CA | LEU | A | 443 | 75.280 | 42.405 | 9.021 | 1.00 | 36.87 |
| ATOM | 2369 | C | LEU | A | 443 | 76.534 | 41.935 | 9.758 | 1.00 | 36.82 |
| ATOM | 2370 | O | LEU | A | 443 | 77.190 | 42.715 | 10.451 | 1.00 | 34.89 |
| ATOM | 2371 | CB | LEU | A | 443 | 74.032 | 41.829 | 9.703 | 1.00 | 35.37 |
| ATOM | 2372 | CG | LEU | A | 443 | 73.831 | 42.033 | 11.210 | 1.00 | 34.30 |
| ATOM | 2373 | CD1 | LEU | A | 443 | 72.354 | 41.880 | 11.554 | 1.00 | 34.00 |
| ATOM | 2374 | CD2 | LEU | A | 443 | 74.673 | 41.028 | 11.990 | 1.00 | 33.34 |
| ATOM | 2375 | N | LYS | A | 444 | 76.864 | 40.660 | 9.593 | 1.00 | 36.78 |
| ATOM | 2376 | CA | LYS | A | 444 | 78.016 | 40.052 | 10.256 | 1.00 | 37.95 |
| ATOM | 2377 | C | LYS | A | 444 | 79.303 | 40.880 | 10.292 | 1.00 | 37.79 |
| ATOM | 2378 | O | LYS | A | 444 | 79.801 | 41.211 | 11.371 | 1.00 | 36.54 |
| ATOM | 2379 | CB | LYS | A | 444 | 78.318 | 38.687 | 9.629 | 1.00 | 39.41 |
| ATOM | 2380 | CG | LYS | A | 444 | 79.374 | 37.896 | 10.380 | 1.00 | 43.18 |
| ATOM | 2381 | CD | LYS | A | 444 | 79.656 | 36.560 | 9.716 | 1.00 | 45.77 |
| ATOM | 2382 | CE | LYS | A | 444 | 80.661 | 35.762 | 10.527 | 1.00 | 47.73 |
| ATOM | 2383 | NZ | LYS | A | 444 | 81.910 | 36.539 | 10.764 | 1.00 | 49.70 |
| ATOM | 2384 | N | ASP | A | 445 | 79.839 | 41.207 | 9.120 | 1.00 | 37.04 |
| ATOM | 2385 | CA | ASP | A | 445 | 81.086 | 41.965 | 9.023 | 1.00 | 37.29 |
| ATOM | 2386 | C | ASP | A | 445 | 81.040 | 43.353 | 9.645 | 1.00 | 35.93 |

TABLE 7-continued

| ATOM | 2387 | O | ASP | A | 445 | 82.032 | 43.819 | 10.208 | 1.00 | 34.89 | O |
| --- | --- | --- | --- | --- | --- | --- | --- | --- | --- | --- | --- |
| ATOM | 2388 | CB | ASP | A | 445 | 81.512 | 42.095 | 7.558 | 1.00 | 39.90 | C |
| ATOM | 2389 | CG | ASP | A | 445 | 81.673 | 40.750 | 6.876 | 1.00 | 42.77 | C |
| ATOM | 2390 | OD1 | ASP | A | 445 | 82.442 | 39.906 | 7.389 | 1.00 | 43.80 | O |
| ATOM | 2391 | OD2 | ASP | A | 445 | 81.025 | 40.541 | 5.827 | 1.00 | 45.60 | O |
| ATOM | 2392 | N | ASN | A | 446 | 79.897 | 44.020 | 9.525 | 1.00 | 33.98 | N |
| ATOM | 2393 | CA | ASN | A | 446 | 79.739 | 45.359 | 10.075 | 1.00 | 33.10 | C |
| ATOM | 2394 | C | ASN | A | 446 | 79.657 | 45.330 | 11.596 | 1.00 | 31.88 | C |
| ATOM | 2395 | O | ASN | A | 446 | 80.257 | 46.167 | 12.272 | 1.00 | 30.91 | O |
| ATOM | 2396 | CB | ASN | A | 446 | 78.489 | 46.016 | 9.493 | 1.00 | 33.95 | C |
| ATOM | 2397 | CG | ASN | A | 446 | 78.683 | 46.454 | 8.051 | 1.00 | 35.61 | C |
| ATOM | 2398 | OD1 | ASN | A | 446 | 79.267 | 47.505 | 7.785 | 1.00 | 37.12 | O |
| ATOM | 2399 | ND2 | ASN | A | 446 | 78.207 | 45.641 | 7.116 | 1.00 | 34.41 | N |
| ATOM | 2400 | N | VAL | A | 447 | 78.911 | 44.371 | 12.131 | 1.00 | 31.04 | N |
| ATOM | 2401 | CA | VAL | A | 447 | 78.776 | 44.244 | 13.576 | 1.00 | 31.31 | C |
| ATOM | 2402 | C | VAL | A | 447 | 80.130 | 43.896 | 14.195 | 1.00 | 32.24 | C |
| ATOM | 2403 | O | VAL | A | 447 | 80.503 | 44.444 | 15.228 | 1.00 | 32.11 | O |
| ATOM | 2404 | CE | VAL | A | 447 | 77.740 | 43.160 | 13.949 | 1.00 | 30.45 | C |
| ATOM | 2405 | CG1 | VAL | A | 447 | 77.813 | 42.858 | 15.443 | 1.00 | 30.61 | C |
| ATOM | 2406 | CG2 | VAL | A | 447 | 76.336 | 43.642 | 13.587 | 1.00 | 30.05 | C |
| ATOM | 2407 | N | GLU | A | 448 | 80.863 | 42.988 | 13.559 | 1.00 | 32.57 | N |
| ATOM | 2408 | CA | GLU | A | 448 | 82.178 | 42.594 | 14.061 | 1.00 | 33.80 | C |
| ATOM | 2409 | C | GLU | A | 448 | 83.095 | 43.819 | 14.130 | 1.00 | 32.73 | C |
| ATOM | 2410 | O | GLU | A | 448 | 83.794 | 44.029 | 15.125 | 1.00 | 31.37 | O |
| ATOM | 2411 | CB | GLU | A | 448 | 82.798 | 41.529 | 13.148 | 1.00 | 37.00 | C |
| ATOM | 2412 | CG | GLU | A | 448 | 84.116 | 40.945 | 13.658 | 1.00 | 41.15 | C |
| ATOM | 2413 | CD | GLU | A | 448 | 84.710 | 39.904 | 12.714 | 1.00 | 44.90 | C |
| ATOM | 2414 | OE1 | GLU | A | 448 | 85.161 | 40.280 | 11.610 | 1.00 | 47.11 | O |
| ATOM | 2415 | OE2 | GLU | A | 448 | 84.720 | 38.705 | 13.075 | 1.00 | 47.09 | O |
| ATOM | 2416 | N | ALA | A | 449 | 83.086 | 44.630 | 13.076 | 1.00 | 31.13 | N |
| ATOM | 2417 | CA | ALA | A | 449 | 83.918 | 45.829 | 13.034 | 1.00 | 31.18 | C |
| ATOM | 2418 | C | ALA | A | 449 | 83.528 | 46.810 | 14.137 | 1.00 | 30.71 | C |
| ATOM | 2419 | O | ALA | A | 449 | 84.385 | 47.323 | 14.854 | 1.00 | 29.77 | O |
| ATOM | 2420 | CB | ALA | A | 449 | 83.802 | 46.506 | 11.674 | 1.00 | 31.83 | C |
| ATOM | 2421 | N | SER | A | 450 | 82.232 | 47.068 | 14.269 | 1.00 | 29.54 | N |
| ATOM | 2422 | CA | SER | A | 450 | 81.747 | 47.990 | 15.289 | 1.00 | 30.17 | C |
| ATOM | 2423 | C | SER | A | 450 | 82.130 | 47.528 | 16.694 | 1.00 | 30.40 | C |
| ATOM | 2424 | O | SER | A | 450 | 82.690 | 48.298 | 17.477 | 1.00 | 29.79 | O |
| ATOM | 2425 | CB | SER | A | 450 | 80.220 | 48.126 | 15.208 | 1.00 | 29.18 | C |

TABLE 7-continued

| ATOM | 2426 | OG | SER | A | 450 | 79.822 | 48.804 | 14.031 | 1.00 | 29.75 |
|---|---|---|---|---|---|---|---|---|---|---|
| ATOM | 2427 | N | LEU | A | 451 | 81.832 | 46.269 | 17.006 | 1.00 | 29.78 |
| ATOM | 2428 | CA | LEU | A | 451 | 82.123 | 45.734 | 18.330 | 1.00 | 30.57 |
| ATOM | 2429 | C | LEU | A | 451 | 83.614 | 45.586 | 18.620 | 1.00 | 31.46 |
| ATOM | 2430 | O | LEU | A | 451 | 84.022 | 45.603 | 19.781 | 1.00 | 30.55 |
| ATOM | 2431 | CB | LEU | A | 451 | 81.389 | 44.406 | 18.538 | 1.00 | 30.40 |
| ATOM | 2432 | CG | LEU | A | 451 | 79.858 | 44.540 | 18.505 | 1.00 | 30.16 |
| ATOM | 2433 | CD1 | LEU | A | 451 | 79.219 | 43.219 | 18.883 | 1.00 | 30.36 |
| ATOM | 2434 | CD2 | LEU | A | 451 | 79.409 | 45.640 | 19.466 | 1.00 | 30.38 |
| ATOM | 2435 | N | ASN | A | 452 | 84.430 | 45.440 | 17.580 | 1.00 | 32.01 |
| ATOM | 2436 | CA | ASN | A | 452 | 85.869 | 45.344 | 17.800 | 1.00 | 33.62 |
| ATOM | 2437 | C | ASN | A | 452 | 86.349 | 46.699 | 18.319 | 1.00 | 33.02 |
| ATOM | 2438 | O | ASN | A | 452 | 87.226 | 46.771 | 19.181 | 1.00 | 32.70 |
| ATOM | 2439 | CB | ASN | A | 452 | 86.615 | 44.988 | 16.510 | 1.00 | 35.58 |
| ATOM | 2440 | CG | ASN | A | 452 | 86.569 | 43.505 | 16.201 | 1.00 | 39.03 |
| ATOM | 2441 | OD1 | ASN | A | 452 | 86.531 | 42.669 | 17.109 | 1.00 | 41.67 |
| ATOM | 2442 | ND2 | ASN | A | 452 | 86.595 | 43.167 | 14.916 | 1.00 | 41.46 |
| ATOM | 2443 | N | LYS | A | 453 | 85.761 | 47.772 | 17.795 | 1.00 | 32.33 |
| ATOM | 2444 | CA | LYS | A | 453 | 86.125 | 49.115 | 18.225 | 1.00 | 32.17 |
| ATOM | 2445 | C | LYS | A | 453 | 85.642 | 49.343 | 19.655 | 1.00 | 30.92 |
| ATOM | 2446 | O | LYS | A | 453 | 86.344 | 49.949 | 20.459 | 1.00 | 29.86 |
| ATOM | 2447 | CB | LYS | A | 453 | 85.528 | 50.161 | 17.278 | 1.00 | 33.56 |
| ATOM | 2448 | CG | LYS | A | 453 | 86.172 | 50.131 | 15.889 | 1.00 | 37.25 |
| ATOM | 2449 | CD | LYS | A | 453 | 85.461 | 51.033 | 14.892 | 1.00 | 37.79 |
| ATOM | 2450 | CE | LYS | A | 453 | 85.502 | 52.490 | 15.316 | 1.00 | 39.41 |
| ATOM | 2451 | NZ | LYS | A | 453 | 84.804 | 53.342 | 14.314 | 1.00 | 40.64 |
| ATOM | 2452 | N | VAL | A | 454 | 84.447 | 48.849 | 19.966 | 1.00 | 29.21 |
| ATOM | 2453 | CA | VAL | A | 454 | 83.900 | 48.981 | 21.311 | 1.00 | 28.29 |
| ATOM | 2454 | C | VAL | A | 454 | 84.827 | 48.253 | 22.290 | 1.00 | 29.16 |
| ATOM | 2455 | O | VAL | A | 454 | 85.196 | 48.801 | 23.330 | 1.00 | 27.96 |
| ATOM | 2456 | CB | VAL | A | 454 | 82.478 | 48.368 | 21.408 | 1.00 | 28.44 |
| ATOM | 2457 | CG1 | VAL | A | 454 | 82.016 | 48.334 | 22.867 | 1.00 | 26.28 |
| ATOM | 2458 | CG2 | VAL | A | 454 | 81.499 | 49.188 | 20.571 | 1.00 | 27.61 |
| ATOM | 2459 | N | LYS | A | 455 | 85.209 | 47.024 | 21.945 | 1.00 | 28.54 |
| ATOM | 2460 | CA | LYS | A | 455 | 86.092 | 46.229 | 22.801 | 1.00 | 29.86 |
| ATOM | 2461 | C | LYS | A | 455 | 87.443 | 46.901 | 23.011 | 1.00 | 29.20 |
| ATOM | 2462 | O | LYS | A | 455 | 87.990 | 46.887 | 24.114 | 1.00 | 28.77 |
| ATOM | 2463 | CB | LYS | A | 455 | 86.322 | 44.838 | 22.202 | 1.00 | 30.13 |
| ATOM | 2464 | CG | LYS | A | 455 | 85.109 | 43.927 | 22.179 | 1.00 | 32.41 |

TABLE 7-continued

| ATOM | 2465 | CD  | LYS | A | 455 | 85.465 | 42.639 | 21.447 | 1.00 | 34.53 | C |
| --- | --- | --- | --- | --- | --- | --- | --- | --- | --- | --- | --- |
| ATOM | 2466 | CE  | LYS | A | 455 | 84.273 | 41.723 | 21.273 | 1.00 | 37.13 | C |
| ATOM | 2467 | NZ  | LYS | A | 455 | 84.641 | 40.530 | 20.457 | 1.00 | 38.19 | N |
| ATOM | 2468 | N   | SER | A | 456 | 87.985 | 47.483 | 21.946 | 1.00 | 29.06 | N |
| ATOM | 2469 | CA  | SER | A | 456 | 89.271 | 48.152 | 22.036 | 1.00 | 30.21 | C |
| ATOM | 2470 | C   | SER | A | 456 | 89.173 | 49.345 | 22.988 | 1.00 | 29.49 | C |
| ATOM | 2471 | O   | SER | A | 456 | 90.051 | 49.565 | 23.823 | 1.00 | 28.06 | O |
| ATOM | 2472 | CB  | SER | A | 456 | 89.722 | 48.617 | 20.650 | 1.00 | 31.84 | C |
| ATOM | 2473 | OG  | SER | A | 456 | 91.050 | 49.100 | 20.703 | 1.00 | 36.19 | O |
| ATOM | 2474 | N   | THR | A | 457 | 88.090 | 50.106 | 22.863 | 1.00 | 27.42 | N |
| ATOM | 2475 | CA  | THR | A | 457 | 87.872 | 51.265 | 23.717 | 1.00 | 27.12 | C |
| ATOM | 2476 | C   | THR | A | 457 | 87.689 | 50.822 | 25.163 | 1.00 | 26.61 | C |
| ATOM | 2477 | O   | THR | A | 457 | 88.174 | 51.476 | 26.087 | 1.00 | 26.73 | O |
| ATOM | 2478 | CB  | THR | A | 457 | 86.636 | 52.051 | 23.254 | 1.00 | 27.39 | C |
| ATOM | 2479 | OG1 | THR | A | 457 | 86.833 | 52.456 | 21.897 | 1.00 | 29.71 | O |
| ATOM | 2480 | CG2 | THR | A | 457 | 86.416 | 53.278 | 24.121 | 1.00 | 25.69 | C |
| ATOM | 2481 | N   | MET | A | 458 | 86.993 | 49.706 | 25.362 | 1.00 | 25.76 | N |
| ATOM | 2482 | CA  | MET | A | 458 | 86.791 | 49.197 | 26.708 | 1.00 | 25.74 | C |
| ATOM | 2483 | C   | MET | A | 458 | 88.145 | 48.903 | 27.349 | 1.00 | 26.35 | C |
| ATOM | 2484 | O   | MET | A | 458 | 88.373 | 49.229 | 28.518 | 1.00 | 24.96 | O |
| ATOM | 2485 | CB  | MET | A | 458 | 85.900 | 47.954 | 26.670 | 1.00 | 25.80 | C |
| ATOM | 2486 | CG  | MET | A | 458 | 84.427 | 48.318 | 26.457 | 1.00 | 25.05 | C |
| ATOM | 2487 | SD  | MET | A | 458 | 83.363 | 46.907 | 26.197 | 1.00 | 26.75 | S |
| ATOM | 2488 | CE  | MET | A | 458 | 83.422 | 46.109 | 27.816 | 1.00 | 25.98 | C |
| ATOM | 2489 | N   | CYS | A | 459 | 89.061 | 48.320 | 26.582 | 1.00 | 26.54 | N |
| ATOM | 2490 | CA  | CYS | A | 459 | 90.388 | 48.043 | 27.124 | 1.00 | 28.58 | C |
| ATOM | 2491 | C   | CYS | A | 459 | 91.144 | 49.331 | 27.465 | 1.00 | 27.83 | C |
| ATOM | 2492 | O   | CYS | A | 459 | 91.932 | 49.357 | 28.414 | 1.00 | 27.16 | O |
| ATOM | 2493 | CB  | CYS | A | 459 | 91.201 | 47.183 | 26.159 | 1.00 | 31.43 | C |
| ATOM | 2494 | SG  | CYS | A | 459 | 90.785 | 45.417 | 26.328 | 1.00 | 37.59 | S |
| ATOM | 2495 | N   | ASN | A | 460 | 90.913 | 50.393 | 26.696 | 1.00 | 27.31 | N |
| ATOM | 2496 | CA  | ASN | A | 460 | 91.554 | 51.678 | 26.978 | 1.00 | 26.88 | C |
| ATOM | 2497 | C   | ASN | A | 460 | 91.053 | 52.139 | 28.347 | 1.00 | 27.10 | C |
| ATOM | 2498 | O   | ASN | A | 460 | 91.792 | 52.748 | 29.122 | 1.00 | 25.93 | O |
| ATOM | 2499 | CB  | ASN | A | 460 | 91.168 | 52.744 | 25.942 | 1.00 | 27.20 | C |
| ATOM | 2500 | CG  | ASN | A | 460 | 91.839 | 52.542 | 24.595 | 1.00 | 30.02 | C |
| ATOM | 2501 | OD1 | ASN | A | 460 | 91.164 | 52.420 | 23.572 | 1.00 | 29.71 | O |
| ATOM | 2502 | ND2 | ASN | A | 460 | 93.170 | 52.524 | 24.583 | 1.00 | 29.98 | N |
| ATOM | 2503 | N   | CYS | A | 461 | 89.786 | 51.847 | 28.631 | 1.00 | 26.43 | N |

TABLE 7-continued

| ATOM | 2504 | CA | CYS | A | 461 | 89.162 | 52.233 | 29.891 | 1.00 | 26.78 | C |
| ATOM | 2505 | C | CYS | A | 461 | 89.394 | 51.232 | 31.024 | 1.00 | 26.46 | C |
| ATOM | 2506 | O | CYS | A | 461 | 88.900 | 51.426 | 32.134 | 1.00 | 27.65 | O |
| ATOM | 2507 | CB | CYS | A | 461 | 87.654 | 52.436 | 29.682 | 1.00 | 26.90 | C |
| ATOM | 2508 | SG | CYS | A | 461 | 87.253 | 53.712 | 28.445 | 1.00 | 29.55 | S |
| ATOM | 2509 | N | GLY | A | 462 | 90.139 | 50.168 | 30.739 | 1.00 | 26.72 | N |
| ATOM | 2510 | CA | GLY | A | 462 | 90.430 | 49.155 | 31.745 | 1.00 | 28.25 | C |
| ATOM | 2511 | C | GLY | A | 462 | 89.272 | 48.226 | 32.081 | 1.00 | 28.51 | C |
| ATOM | 2512 | O | GLY | A | 462 | 89.174 | 47.712 | 33.204 | 1.00 | 28.75 | O |
| ATOM | 2513 | N | ALA | A | 463 | 88.405 | 47.979 | 31.106 | 1.00 | 26.73 | N |
| ATOM | 2514 | CA | ALA | A | 463 | 87.239 | 47.136 | 31.335 | 1.00 | 26.80 | C |
| ATOM | 2515 | C | ALA | A | 463 | 87.198 | 45.909 | 30.435 | 1.00 | 27.34 | C |
| ATOM | 2516 | O | ALA | A | 463 | 87.350 | 46.018 | 29.218 | 1.00 | 27.58 | O |
| ATOM | 2517 | CB | ALA | A | 463 | 85.967 | 47.963 | 31.140 | 1.00 | 26.04 | C |
| ATOM | 2518 | N | LEU | A | 464 | 86.983 | 44.746 | 31.045 | 1.00 | 26.85 | N |
| ATOM | 2519 | CA | LEU | A | 464 | 86.896 | 43.489 | 30.308 | 1.00 | 27.73 | C |
| ATOM | 2520 | C | LEU | A | 464 | 85.447 | 43.057 | 30.121 | 1.00 | 26.69 | C |
| ATOM | 2521 | O | LEU | A | 464 | 85.169 | 42.119 | 29.379 | 1.00 | 27.47 | O |
| ATOM | 2522 | CB | LEU | A | 464 | 87.654 | 42.378 | 31.038 | 1.00 | 28.53 | C |
| ATOM | 2523 | CG | LEU | A | 464 | 89.176 | 42.386 | 30.902 | 1.00 | 31.51 | C |
| ATOM | 2524 | CD1 | LEU | A | 464 | 89.777 | 41.251 | 31.734 | 1.00 | 32.32 | C |
| ATOM | 2525 | CD2 | LEU | A | 464 | 89.545 | 42.218 | 29.442 | 1.00 | 31.92 | C |
| ATOM | 2526 | N | THR | A | 465 | 84.531 | 43.734 | 30.806 | 1.00 | 25.40 | N |
| ATOM | 2527 | CA | THR | A | 465 | 83.108 | 43.421 | 30.709 | 1.00 | 24.59 | C |
| ATOM | 2528 | C | THR | A | 465 | 82.320 | 44.716 | 30.749 | 1.00 | 24.19 | C |
| ATOM | 2529 | O | THR | A | 465 | 82.855 | 45.766 | 31.102 | 1.00 | 22.83 | O |
| ATOM | 2530 | CB | THR | A | 465 | 82.617 | 42.552 | 31.884 | 1.00 | 24.77 | C |
| ATOM | 2531 | OG1 | THR | A | 465 | 82.633 | 43.331 | 33.088 | 1.00 | 24.88 | O |
| ATOM | 2532 | CG2 | THR | A | 465 | 83.507 | 41.317 | 32.061 | 1.00 | 24.23 | C |
| ATOM | 2533 | N | ILE | A | 466 | 81.040 | 44.639 | 30.401 | 1.00 | 23.48 | N |
| ATOM | 2534 | CA | ILE | A | 466 | 80.200 | 45.825 | 30.410 | 1.00 | 22.77 | C |
| ATOM | 2535 | C | ILE | A | 466 | 80.004 | 46.343 | 31.839 | 1.00 | 23.62 | C |
| ATOM | 2536 | O | ILE | A | 466 | 80.103 | 47.545 | 32.082 | 1.00 | 22.96 | O |
| ATOM | 2537 | CB | ILE | A | 466 | 78.849 | 45.538 | 29.699 | 1.00 | 23.94 | C |
| ATOM | 2538 | CG1 | ILE | A | 466 | 79.113 | 45.363 | 28.194 | 1.00 | 22.77 | C |
| ATOM | 2539 | CG2 | ILE | A | 466 | 77.856 | 46.679 | 29.935 | 1.00 | 23.50 | C |
| ATOM | 2540 | CD1 | ILE | A | 466 | 77.886 | 44.941 | 27.377 | 1.00 | 24.77 | C |
| ATOM | 2541 | N | PRO | A | 467 | 79.742 | 45.448 | 32.809 | 1.00 | 23.36 | N |
| ATOM | 2542 | CA | PRO | A | 467 | 79.563 | 45.945 | 34.176 | 1.00 | 24.01 | C |

TABLE 7-continued

| ATOM | 2543 | C | PRO | A | 467 | 80.826 | 46.648 | 34.676 | 1.00 | 24.80 |
| --- | --- | --- | --- | --- | --- | --- | --- | --- | --- | --- |
| C | | | | | | | | | | |
| ATOM | 2544 | O | PRO | A | 467 | 80.753 | 47.640 | 35.399 | 1.00 | 24.96 |
| O | | | | | | | | | | |
| ATOM | 2545 | CB | PRO | A | 467 | 79.253 | 44.676 | 34.965 | 1.00 | 24.77 |
| C | | | | | | | | | | |
| ATOM | 2546 | CG | PRO | A | 467 | 78.516 | 43.843 | 33.954 | 1.00 | 24.81 |
| C | | | | | | | | | | |
| ATOM | 2547 | CD | PRO | A | 467 | 79.367 | 44.024 | 32.720 | 1.00 | 23.03 |
| C | | | | | | | | | | |
| ATOM | 2548 | N | GLN | A | 468 | 81.988 | 46.136 | 34.287 | 1.00 | 25.14 |
| N | | | | | | | | | | |
| ATOM | 2549 | CA | GLN | A | 468 | 83.233 | 46.754 | 34.713 | 1.00 | 26.45 |
| C | | | | | | | | | | |
| ATOM | 2550 | C | GLN | A | 468 | 83.394 | 48.121 | 34.042 | 1.00 | 25.99 |
| C | | | | | | | | | | |
| ATOM | 2551 | O | GLN | A | 468 | 83.909 | 49.062 | 34.650 | 1.00 | 26.63 |
| O | | | | | | | | | | |
| ATOM | 2552 | CB | GLN | A | 468 | 84.412 | 45.829 | 34.398 | 1.00 | 27.40 |
| C | | | | | | | | | | |
| ATOM | 2553 | CG | GLN | A | 468 | 85.759 | 46.390 | 34.791 | 1.00 | 29.99 |
| C | | | | | | | | | | |
| ATOM | 2554 | CD | GLN | A | 468 | 86.838 | 45.328 | 34.836 | 1.00 | 28.82 |
| C | | | | | | | | | | |
| ATOM | 2555 | OE1 | GLN | A | 468 | 86.952 | 44.501 | 33.934 | 1.00 | 27.62 |
| O | | | | | | | | | | |
| ATOM | 2556 | NE2 | GLN | A | 468 | 87.648 | 45.356 | 35.890 | 1.00 | 30.42 |
| N | | | | | | | | | | |
| ATOM | 2557 | N | LEU | A | 469 | 82.940 | 48.238 | 32.796 | 1.00 | 24.88 |
| N | | | | | | | | | | |
| ATOM | 2558 | CA | LEU | A | 469 | 83.014 | 49.507 | 32.081 | 1.00 | 24.40 |
| C | | | | | | | | | | |
| ATOM | 2559 | C | LEU | A | 469 | 82.093 | 50.527 | 32.753 | 1.00 | 24.98 |
| C | | | | | | | | | | |
| ATOM | 2560 | O | LEU | A | 469 | 82.447 | 51.702 | 32.898 | 1.00 | 25.34 |
| O | | | | | | | | | | |
| ATOM | 2561 | CB | LEU | A | 469 | 82.596 | 49.332 | 30.611 | 1.00 | 24.62 |
| C | | | | | | | | | | |
| ATOM | 2562 | CG | LEU | A | 469 | 82.396 | 50.625 | 29.799 | 1.00 | 24.32 |
| C | | | | | | | | | | |
| ATOM | 2563 | CD1 | LEU | A | 469 | 83.731 | 51.286 | 29.507 | 1.00 | 24.10 |
| C | | | | | | | | | | |
| ATOM | 2564 | CD2 | LEU | A | 469 | 81.681 | 50.298 | 28.497 | 1.00 | 23.72 |
| C | | | | | | | | | | |
| ATOM | 2565 | N | GLN | A | 470 | 80.914 | 50.077 | 33.168 | 1.00 | 24.91 |
| N | | | | | | | | | | |
| ATOM | 2566 | CA | GLN | A | 470 | 79.951 | 50.965 | 33.807 | 1.00 | 26.70 |
| C | | | | | | | | | | |
| ATOM | 2567 | C | GLN | A | 470 | 80.461 | 51.471 | 35.151 | 1.00 | 27.35 |
| C | | | | | | | | | | |
| ATOM | 2568 | O | GLN | A | 470 | 80.103 | 52.560 | 35.601 | 1.00 | 28.25 |
| O | | | | | | | | | | |
| ATOM | 2569 | CB | GLN | A | 470 | 78.614 | 50.238 | 33.961 | 1.00 | 27.04 |
| C | | | | | | | | | | |
| ATOM | 2570 | CG | GLN | A | 470 | 78.071 | 49.794 | 32.600 | 1.00 | 26.67 |
| C | | | | | | | | | | |
| ATOM | 2571 | CD | GLN | A | 470 | 76.805 | 48.981 | 32.688 | 1.00 | 27.02 |
| C | | | | | | | | | | |
| ATOM | 2572 | OE1 | GLN | A | 470 | 76.616 | 48.208 | 33.621 | 1.00 | 28.25 |
| O | | | | | | | | | | |
| ATOM | 2573 | NE2 | GLN | A | 470 | 75.934 | 49.135 | 31.696 | 1.00 | 25.90 |
| N | | | | | | | | | | |
| ATOM | 2574 | N | SER | A | 471 | 81.316 | 50.680 | 35.778 | 1.00 | 26.97 |
| N | | | | | | | | | | |
| ATOM | 2575 | CA | SER | A | 471 | 81.883 | 51.049 | 37.063 | 1.00 | 28.68 |
| C | | | | | | | | | | |
| ATOM | 2576 | C | SER | A | 471 | 83.122 | 51.944 | 36.928 | 1.00 | 28.52 |
| C | | | | | | | | | | |
| ATOM | 2577 | O | SER | A | 471 | 83.289 | 52.908 | 37.680 | 1.00 | 29.15 |
| O | | | | | | | | | | |
| ATOM | 2578 | CB | SER | A | 471 | 82.244 | 49.775 | 37.839 | 1.00 | 29.10 |
| C | | | | | | | | | | |
| ATOM | 2579 | OG | SER | A | 471 | 82.934 | 50.081 | 39.037 | 1.00 | 35.37 |
| O | | | | | | | | | | |
| ATOM | 2580 | N | LYS | A | 472 | 83.968 | 51.651 | 35.946 | 1.00 | 27.16 |
| N | | | | | | | | | | |
| ATOM | 2581 | CA | LYS | A | 472 | 85.224 | 52.390 | 35.782 | 1.00 | 28.51 |
| C | | | | | | | | | | |

TABLE 7-continued

| ATOM | 2582 | C | LYS | A | 472 | 85.293 | 53.531 | 34.778 | 1.00 | 27.51 |
|---|---|---|---|---|---|---|---|---|---|---|
| C | | | | | | | | | | |
| ATOM | 2583 | O | LYS | A | 472 | 86.232 | 54.323 | 34.818 | 1.00 | 26.25 |
| O | | | | | | | | | | |
| ATOM | 2584 | CB | LYS | A | 472 | 86.341 | 51.404 | 35.451 | 1.00 | 29.64 |
| C | | | | | | | | | | |
| ATOM | 2585 | CG | LYS | A | 472 | 86.461 | 50.273 | 36.453 | 1.00 | 32.63 |
| C | | | | | | | | | | |
| ATOM | 2586 | CD | LYS | A | 472 | 87.440 | 49.205 | 35.994 | 1.00 | 33.81 |
| C | | | | | | | | | | |
| ATOM | 2587 | CE | LYS | A | 472 | 88.868 | 49.704 | 35.997 | 1.00 | 35.59 |
| C | | | | | | | | | | |
| ATOM | 2588 | NZ | LYS | A | 472 | 89.815 | 48.590 | 35.715 | 1.00 | 35.49 |
| N | | | | | | | | | | |
| ATOM | 2589 | N | ALA | A | 473 | 84.322 | 53.617 | 33.876 | 1.00 | 26.09 |
| N | | | | | | | | | | |
| ATOM | 2590 | CA | ALA | A | 473 | 84.345 | 54.660 | 32.860 | 1.00 | 26.12 |
| C | | | | | | | | | | |
| ATOM | 2591 | C | ALA | A | 473 | 84.461 | 56.080 | 33.410 | 1.00 | 25.21 |
| C | | | | | | | | | | |
| ATOM | 2592 | O | ALA | A | 473 | 83.827 | 56.432 | 34.400 | 1.00 | 25.99 |
| O | | | | | | | | | | |
| ATOM | 2593 | CB | ALA | A | 473 | 83.106 | 54.553 | 31.971 | 1.00 | 26.24 |
| C | | | | | | | | | | |
| ATOM | 2594 | N | LYS | A | 474 | 85.290 | 56.882 | 32.749 | 1.00 | 24.98 |
| N | | | | | | | | | | |
| ATOM | 2595 | CA | LYS | A | 474 | 85.505 | 58.284 | 33.098 | 1.00 | 25.10 |
| C | | | | | | | | | | |
| ATOM | 2596 | C | LYS | A | 474 | 84.943 | 59.013 | 31.884 | 1.00 | 24.93 |
| C | | | | | | | | | | |
| ATOM | 2597 | O | LYS | A | 474 | 85.475 | 58.904 | 30.779 | 1.00 | 24.89 |
| O | | | | | | | | | | |
| ATOM | 2598 | CB | LYS | A | 474 | 87.000 | 58.549 | 33.278 | 1.00 | 25.31 |
| C | | | | | | | | | | |
| ATOM | 2599 | CG | LYS | A | 474 | 87.589 | 57.732 | 34.424 | 1.00 | 25.41 |
| C | | | | | | | | | | |
| ATOM | 2600 | CD | LYS | A | 474 | 89.078 | 57.470 | 34.242 | 1.00 | 26.81 |
| C | | | | | | | | | | |
| ATOM | 2601 | CE | LYS | A | 474 | 89.902 | 58.722 | 34.425 | 1.00 | 28.30 |
| C | | | | | | | | | | |
| ATOM | 2602 | NZ | LYS | A | 474 | 91.346 | 58.422 | 34.183 | 1.00 | 27.67 |
| N | | | | | | | | | | |
| ATOM | 2603 | N | ILE | A | 475 | 83.858 | 59.750 | 32.093 | 1.00 | 24.28 |
| N | | | | | | | | | | |
| ATOM | 2604 | CA | ILE | A | 475 | 83.169 | 60.408 | 30.986 | 1.00 | 25.91 |
| C | | | | | | | | | | |
| ATOM | 2605 | C | ILE | A | 475 | 83.103 | 61.924 | 31.100 | 1.00 | 25.77 |
| C | | | | | | | | | | |
| ATOM | 2606 | O | ILE | A | 475 | 82.519 | 62.453 | 32.042 | 1.00 | 26.40 |
| O | | | | | | | | | | |
| ATOM | 2607 | CB | ILE | A | 475 | 81.726 | 59.855 | 30.883 | 1.00 | 25.54 |
| C | | | | | | | | | | |
| ATOM | 2608 | CG1 | ILE | A | 475 | 81.763 | 58.319 | 30.868 | 1.00 | 26.29 |
| C | | | | | | | | | | |
| ATOM | 2609 | CG2 | ILE | A | 475 | 81.043 | 60.392 | 29.630 | 1.00 | 27.31 |
| C | | | | | | | | | | |
| ATOM | 2610 | CD1 | ILE | A | 475 | 80.394 | 57.657 | 30.959 | 1.00 | 25.53 |
| C | | | | | | | | | | |
| ATOM | 2611 | N | THR | A | 476 | 83.678 | 62.617 | 30.122 | 1.00 | 25.85 |
| N | | | | | | | | | | |
| ATOM | 2612 | CA | THR | A | 476 | 83.675 | 64.073 | 30.140 | 1.00 | 25.82 |
| C | | | | | | | | | | |
| ATOM | 2613 | C | THR | A | 476 | 82.795 | 64.688 | 29.067 | 1.00 | 25.93 |
| C | | | | | | | | | | |
| ATOM | 2614 | O | THR | A | 476 | 82.630 | 64.137 | 27.977 | 1.00 | 24.07 |
| O | | | | | | | | | | |
| ATOM | 2615 | CB | THR | A | 476 | 85.097 | 64.657 | 29.955 | 1.00 | 26.37 |
| C | | | | | | | | | | |
| ATOM | 2616 | OG1 | THR | A | 476 | 85.052 | 66.082 | 30.123 | 1.00 | 28.03 |
| O | | | | | | | | | | |
| ATOM | 2617 | CG2 | THR | A | 476 | 85.625 | 64.352 | 28.559 | 1.00 | 25.51 |
| C | | | | | | | | | | |
| ATOM | 2618 | N | LEU | A | 477 | 82.232 | 65.843 | 29.399 | 1.00 | 25.92 |
| N | | | | | | | | | | |
| ATOM | 2619 | CA | LEU | A | 477 | 81.406 | 66.596 | 28.472 | 1.00 | 27.45 |
| C | | | | | | | | | | |
| ATOM | 2620 | C | LEU | A | 477 | 82.433 | 67.442 | 27.722 | 1.00 | 27.85 |
| C | | | | | | | | | | |

TABLE 7-continued

| | | | | | | | | | |
|---|---|---|---|---|---|---|---|---|---|
| ATOM O | 2621 | O | LEU | A | 477 | 83.469 | 67.780 | 28.290 | 1.00 27.59 |
| ATOM C | 2622 | CB | LEU | A | 477 | 80.454 | 67.501 | 29.254 | 1.00 28.30 |
| ATOM C | 2623 | CG | LEU | A | 477 | 79.298 | 68.176 | 28.523 | 1.00 30.46 |
| ATOM C | 2624 | CD1 | LEU | A | 477 | 78.351 | 67.123 | 27.980 | 1.00 29.78 |
| ATOM C | 2625 | CD2 | LEU | A | 477 | 78.561 | 69.099 | 29.497 | 1.00 32.80 |
| ATOM N | 2626 | N | VAL | A | 478 | 82.167 | 67.771 | 26.462 | 1.00 29.07 |
| ATOM C | 2627 | CA | VAL | A | 478 | 83.095 | 68.592 | 25.686 | 1.00 31.32 |
| ATOM C | 2628 | C | VAL | A | 478 | 82.456 | 69.950 | 25.407 | 1.00 33.58 |
| ATOM O | 2629 | O | VAL | A | 478 | 81.248 | 70.044 | 25.212 | 1.00 32.21 |
| ATOM C | 2630 | CB | VAL | A | 478 | 83.480 | 67.912 | 24.348 | 1.00 32.07 |
| ATOM C | 2631 | CG1 | VAL | A | 478 | 83.857 | 66.462 | 24.604 | 1.00 32.68 |
| ATOM C | 2632 | CG2 | VAL | A | 478 | 82.342 | 68.018 | 23.341 | 1.00 34.67 |
| ATOM N | 2633 | N | SER | A | 479 | 83.274 | 70.997 | 25.385 | 1.00 35.26 |
| ATOM C | 2634 | CA | SER | A | 479 | 82.791 | 72.359 | 25.169 | 1.00 38.88 |
| ATOM C | 2635 | C | SER | A | 479 | 81.991 | 72.592 | 23.899 | 1.00 41.66 |
| ATOM O | 2636 | O | SER | A | 479 | 82.255 | 71.993 | 22.854 | 1.00 42.05 |
| ATOM C | 2637 | CB | SER | A | 479 | 83.963 | 73.339 | 25.174 | 1.00 38.14 |
| ATOM O | 2638 | OG | SER | A | 479 | 84.773 | 73.130 | 24.034 | 1.00 36.16 |
| ATOM N | 2639 | N | SER | A | 480 | 81.019 | 73.494 | 24.004 | 1.00 45.75 |
| ATOM C | 2640 | CA | SER | A | 480 | 80.169 | 73.865 | 22.881 | 1.00 50.07 |
| ATOM C | 2641 | C | SER | A | 480 | 81.035 | 74.534 | 21.819 | 1.00 52.24 |
| ATOM O | 2642 | O | SER | A | 480 | 80.834 | 74.346 | 20.617 | 1.00 51.90 |
| ATOM C | 2643 | CB | SER | A | 480 | 79.085 | 74.842 | 23.351 | 1.00 50.84 |
| ATOM O | 2644 | OG | SER | A | 480 | 78.323 | 75.323 | 22.258 | 1.00 52.94 |
| ATOM N | 2645 | N | VAL | A | 481 | 82.015 | 75.301 | 22.288 | 1.00 54.50 |
| ATOM C | 2646 | CA | VAL | A | 481 | 82.929 | 76.029 | 21.416 | 1.00 56.91 |
| ATOM C | 2647 | C | VAL | A | 481 | 84.004 | 75.136 | 20.803 | 1.00 58.08 |
| ATOM O | 2648 | O | VAL | A | 481 | 84.966 | 75.637 | 20.216 | 1.00 58.99 |
| ATOM C | 2649 | CB | VAL | A | 481 | 83.641 | 77.154 | 22.193 | 1.00 57.54 |
| ATOM C | 2650 | CG1 | VAL | A | 481 | 83.948 | 78.316 | 21.264 | 1.00 57.89 |
| ATOM C | 2651 | CG2 | VAL | A | 481 | 82.789 | 77.596 | 23.366 | 1.00 58.34 |
| ATOM N | 2652 | N | SER | A | 482 | 83.848 | 73.821 | 20.933 | 1.00 58.75 |
| ATOM C | 2653 | CA | SER | A | 482 | 84.838 | 72.896 | 20.393 | 1.00 59.46 |
| ATOM C | 2654 | C | SER | A | 482 | 84.252 | 71.737 | 19.593 | 1.00 60.06 |
| ATOM O | 2655 | O | SER | A | 482 | 83.245 | 71.896 | 18.902 | 1.00 60.14 |
| ATOM C | 2656 | CB | SER | A | 482 | 85.708 | 72.345 | 21.525 | 1.00 59.32 |
| ATOM O | 2657 | OG | SER | A | 482 | 86.717 | 71.486 | 21.025 | 1.00 60.01 |
| ATOM N | 2658 | N | ILE | A | 483 | 84.899 | 70.575 | 19.712 | 1.00 60.52 |
| ATOM C | 2659 | CA | ILE | A | 483 | 84.535 | 69.343 | 19.009 | 1.00 60.59 |

TABLE 7-continued

| ATOM | 2660 | C   | ILE | A | 483 | 85.319 | 69.317 | 17.701 | 1.00 | 60.24 | C |
| --- | --- | --- | --- | --- | --- | --- | --- | --- | --- | --- | --- |
| ATOM | 2661 | O   | ILE | A | 483 | 85.585 | 68.254 | 17.137 | 1.00 | 60.22 | O |
| ATOM | 2662 | CB  | ILE | A | 483 | 83.015 | 69.264 | 18.698 | 1.00 | 60.93 | C |
| ATOM | 2663 | CG1 | ILE | A | 483 | 82.227 | 69.079 | 19.997 | 1.00 | 60.99 | C |
| ATOM | 2664 | CG2 | ILE | A | 483 | 82.730 | 68.118 | 17.731 | 1.00 | 61.21 | C |
| ATOM | 2665 | CD1 | ILE | A | 483 | 80.725 | 69.039 | 19.804 | 1.00 | 60.52 | C |
| ATOM | 2666 | N   | VAL | A | 484 | 85.694 | 70.504 | 17.237 | 1.00 | 59.84 | N |
| ATOM | 2667 | CA  | VAL | A | 484 | 86.451 | 70.653 | 16.001 | 1.00 | 59.29 | C |
| ATOM | 2668 | C   | VAL | A | 484 | 87.845 | 70.049 | 16.151 | 1.00 | 58.69 | C |
| ATOM | 2669 | O   | VAL | A | 484 | 88.354 | 69.409 | 15.228 | 1.00 | 58.32 | O |
| ATOM | 2670 | CB  | VAL | A | 484 | 86.590 | 72.145 | 15.612 | 1.00 | 59.56 | C |
| ATOM | 2671 | CG1 | VAL | A | 484 | 87.372 | 72.277 | 14.311 | 1.00 | 59.65 | C |
| ATOM | 2672 | CG2 | VAL | A | 484 | 85.209 | 72.775 | 15.469 | 1.00 | 59.42 | C |
| ATOM | 2673 | N   | GLU | A | 485 | 88.456 | 70.254 | 17.316 | 1.00 | 57.53 | N |
| ATOM | 2674 | CA  | GLU | A | 485 | 89.790 | 69.725 | 17.584 | 1.00 | 56.68 | C |
| ATOM | 2675 | C   | GLU | A | 485 | 89.765 | 68.200 | 17.523 | 1.00 | 57.27 | C |
| ATOM | 2676 | O   | GLU | A | 485 | 90.758 | 67.565 | 17.164 | 1.00 | 56.78 | O |
| ATOM | 2677 | CB  | GLU | A | 485 | 90.277 | 70.170 | 18.969 | 1.00 | 54.83 | C |
| ATOM | 2678 | CG  | GLU | A | 485 | 91.732 | 69.794 | 19.274 | 1.00 | 52.09 | C |
| ATOM | 2679 | CD  | GLU | A | 485 | 92.168 | 70.183 | 20.682 | 1.00 | 50.97 | C |
| ATOM | 2680 | OE1 | GLU | A | 485 | 91.768 | 69.499 | 21.649 | 1.00 | 45.34 | O |
| ATOM | 2681 | OE2 | GLU | A | 485 | 92.911 | 71.180 | 20.820 | 1.00 | 51.44 | O |
| ATOM | 2682 | N   | GLY | A | 486 | 88.617 | 67.626 | 17.872 | 1.00 | 57.81 | N |
| ATOM | 2683 | CA  | GLY | A | 486 | 88.462 | 66.182 | 17.875 | 1.00 | 58.97 | C |
| ATOM | 2684 | C   | GLY | A | 486 | 88.580 | 65.524 | 16.515 | 1.00 | 59.51 | C |
| ATOM | 2685 | O   | GLY | A | 486 | 89.142 | 64.435 | 16.398 | 1.00 | 59.72 | O |
| ATOM | 2686 | N   | GLY | A | 487 | 88.045 | 66.176 | 15.487 | 1.00 | 60.19 | N |
| ATOM | 2687 | CA  | GLY | A | 487 | 88.118 | 65.620 | 14.146 | 1.00 | 60.96 | C |
| ATOM | 2688 | C   | GLY | A | 487 | 89.336 | 66.120 | 13.394 | 1.00 | 61.44 | C |
| ATOM | 2689 | O   | GLY | A | 487 | 90.170 | 66.831 | 13.957 | 1.00 | 61.56 | O |
| ATOM | 2690 | N   | ALA | A | 488 | 89.450 | 65.746 | 12.123 | 1.00 | 61.60 | N |
| ATOM | 2691 | CA  | ALA | A | 488 | 90.576 | 66.180 | 11.302 | 1.00 | 61.84 | C |
| ATOM | 2692 | C   | ALA | A | 488 | 90.446 | 67.683 | 11.068 | 1.00 | 62.10 | C |
| ATOM | 2693 | O   | ALA | A | 488 | 89.365 | 68.171 | 10.739 | 1.00 | 61.91 | O |
| ATOM | 2694 | CB  | ALA | A | 488 | 90.575 | 65.434 | 9.971  | 1.00 | 61.64 | C |
| ATOM | 2695 | N   | HIS | A | 489 | 91.541 | 68.417 | 11.240 | 1.00 | 62.27 | N |
| ATOM | 2696 | CA  | HIS | A | 489 | 91.499 | 69.863 | 11.049 | 1.00 | 62.65 | C |
| ATOM | 2697 | C   | HIS | A | 489 | 92.786 | 70.469 | 10.503 | 1.00 | 62.69 | C |
| ATOM | 2698 | O   | HIS | A | 489 | 93.887 | 70.008 | 10.809 | 1.00 | 62.31 | O |

TABLE 7-continued

| | | | | | | | | | |
|---|---|---|---|---|---|---|---|---|---|
| ATOM | 2699 | CB | HIS | A | 489 | 91.147 | 70.559 | 12.368 | 1.00 62.91 |
| C | | | | | | | | | |
| ATOM | 2700 | CG | HIS | A | 489 | 92.100 | 70.258 | 13.484 | 1.00 63.07 |
| C | | | | | | | | | |
| ATOM | 2701 | ND1 | HIS | A | 489 | 92.136 | 69.038 | 14.124 | 1.00 63.07 |
| N | | | | | | | | | |
| ATOM | 2702 | CD2 | HIS | A | 489 | 93.060 | 71.016 | 14.066 | 1.00 63.14 |
| C | | | | | | | | | |
| ATOM | 2703 | CE1 | HIS | A | 489 | 93.074 | 69.058 | 15.054 | 1.00 63.28 |
| C | | | | | | | | | |
| ATOM | 2704 | NE2 | HIS | A | 489 | 93.650 | 70.246 | 15.039 | 1.00 63.10 |
| N | | | | | | | | | |
| ATOM | 2705 | N | ASP | A | 490 | 92.626 | 71.513 | 9.695 | 1.00 62.96 |
| N | | | | | | | | | |
| ATOM | 2706 | CA | ASP | A | 490 | 93.747 | 72.234 | 9.101 | 1.00 62.99 |
| C | | | | | | | | | |
| ATOM | 2707 | C | ASP | A | 490 | 94.619 | 71.381 | 8.187 | 1.00 63.25 |
| C | | | | | | | | | |
| ATOM | 2708 | O | ASP | A | 490 | 95.824 | 71.609 | 8.066 | 1.00 62.96 |
| O | | | | | | | | | |
| ATOM | 2709 | CB | ASP | A | 490 | 94.593 | 72.857 | 10.210 | 1.00 63.04 |
| C | | | | | | | | | |
| ATOM | 2710 | CG | ASP | A | 490 | 93.789 | 73.797 | 11.086 | 1.00 63.29 |
| C | | | | | | | | | |
| ATOM | 2711 | OD1 | ASP | A | 490 | 93.394 | 74.879 | 10.597 | 1.00 62.95 |
| O | | | | | | | | | |
| ATOM | 2712 | OD2 | ASP | A | 490 | 93.539 | 73.447 | 12.259 | 1.00 63.21 |
| O | | | | | | | | | |
| ATOM | 2713 | N | VAL | A | 491 | 93.999 | 70.397 | 7.545 | 1.00 63.51 |
| N | | | | | | | | | |
| ATOM | 2714 | CA | VAL | A | 491 | 94.696 | 69.516 | 6.618 | 1.00 63.93 |
| C | | | | | | | | | |
| ATOM | 2715 | C | VAL | A | 491 | 93.743 | 69.145 | 5.489 | 1.00 64.46 |
| C | | | | | | | | | |
| ATOM | 2716 | O | VAL | A | 491 | 92.536 | 69.009 | 5.704 | 1.00 64.24 |
| O | | | | | | | | | |
| ATOM | 2717 | CB | VAL | A | 491 | 95.188 | 68.214 | 7.308 | 1.00 63.80 |
| C | | | | | | | | | |
| ATOM | 2718 | CG1 | VAL | A | 491 | 96.218 | 68.545 | 8.379 | 1.00 63.55 |
| C | | | | | | | | | |
| ATOM | 2719 | CG2 | VAL | A | 491 | 94.010 | 67.464 | 7.913 | 1.00 63.70 |
| C | | | | | | | | | |
| ATOM | 2720 | N | ILE | A | 492 | 94.287 | 68.996 | 4.287 | 1.00 64.85 |
| N | | | | | | | | | |
| ATOM | 2721 | CA | ILE | A | 492 | 93.486 | 68.633 | 3.125 | 1.00 65.38 |
| C | | | | | | | | | |
| ATOM | 2722 | C | ILE | A | 492 | 93.564 | 67.121 | 2.911 | 1.00 65.68 |
| C | | | | | | | | | |
| ATOM | 2723 | O | ILE | A | 492 | 94.423 | 66.665 | 2.123 | 1.00 66.09 |
| O | | | | | | | | | |
| ATOM | 2724 | CB | ILE | A | 492 | 93.974 | 69.375 | 1.854 | 1.00 65.44 |
| C | | | | | | | | | |
| ATOM | 2725 | CG1 | ILE | A | 492 | 93.922 | 70.887 | 2.084 | 1.00 65.23 |
| C | | | | | | | | | |
| ATOM | 2726 | CG2 | ILE | A | 492 | 93.101 | 69.001 | 0.661 | 1.00 65.46 |
| C | | | | | | | | | |
| ATOM | 2727 | CD1 | ILE | A | 492 | 94.390 | 71.707 | 0.900 | 1.00 65.68 |
| C | | | | | | | | | |
| TER | 2728 | | ILE | A | 492 | | | | |
| HETATM | 2729 | K | | K | 900 | 52.929 | 60.386 | 29.350 | 0.75 33.25 |
| K | | | | | | | | | |
| HETATM | 2730 | NA | | NA | 901 | 65.775 | 63.097 | 15.894 | 1.00 51.30 |
| NA | | | | | | | | | |
| HETATM | 2731 | P | | RVP | 602 | 67.806 | 55.192 | 15.010 | 1.00 32.06 |
| P | | | | | | | | | |
| HETATM | 2732 | O1P | | RVP | 602 | 67.447 | 55.106 | 13.566 | 1.00 33.43 |
| O | | | | | | | | | |
| HETATM | 2733 | O2P | | RVP | 602 | 68.618 | 53.993 | 15.386 | 1.00 33.48 |
| O | | | | | | | | | |
| HETATM | 2734 | O3P | | RVP | 602 | 68.589 | 56.489 | 15.335 | 1.00 32.27 |
| O | | | | | | | | | |
| HETATM | 2735 | O5* | | RVP | 602 | 66.564 | 55.260 | 15.998 | 1.00 32.66 |
| O | | | | | | | | | |
| HETATM | 2736 | C5* | | RVP | 602 | 65.601 | 54.207 | 15.962 | 1.00 31.36 |
| C | | | | | | | | | |
| HETATM | 2737 | C4* | | RVP | 602 | 64.521 | 54.418 | 16.985 | 1.00 30.66 |
| C | | | | | | | | | |
| HETATM | 2738 | O4* | | RVP | 602 | 63.766 | 55.605 | 16.540 | 1.00 29.94 |
| O | | | | | | | | | |

TABLE 7-continued

| | | | | | | | | | |
|---|---|---|---|---|---|---|---|---|---|
| HETATM C | 2739 | C3* | RVP | 602 | 63.437 | 53.370 | 17.179 | 1.00 | 29.26 |
| HETATM O | 2740 | O3* | RVP | 602 | 63.863 | 52.229 | 17.914 | 1.00 | 28.74 |
| HETATM C | 2741 | C2* | RVP | 602 | 62.343 | 54.162 | 17.832 | 1.00 | 30.26 |
| HETATM O | 2742 | O2* | RVP | 602 | 62.482 | 54.278 | 19.236 | 1.00 | 30.38 |
| HETATM C | 2743 | C1* | RVP | 602 | 62.434 | 55.486 | 17.067 | 1.00 | 31.26 |
| HETATM N | 2744 | N9 | RVP | 602 | 61.475 | 55.602 | 15.903 | 1.00 | 32.47 |
| HETATM C | 2745 | C8 | RVP | 602 | 60.989 | 54.694 | 14.978 | 1.00 | 33.70 |
| HETATM N | 2746 | N7 | RVP | 602 | 60.171 | 55.231 | 14.129 | 1.00 | 33.53 |
| HETATM C | 2747 | C5 | RVP | 602 | 60.084 | 56.544 | 14.468 | 1.00 | 34.69 |
| HETATM C | 2748 | C6 | RVP | 602 | 59.329 | 57.634 | 13.877 | 1.00 | 34.93 |
| HETATM O | 2749 | O6 | RVP | 602 | 58.592 | 57.567 | 12.906 | 1.00 | 35.34 |
| HETATM N | 2750 | N1 | RVP | 602 | 59.501 | 58.902 | 14.532 | 1.00 | 35.14 |
| HETATM N | 2751 | N4 | RVP | 602 | 60.883 | 56.810 | 15.574 | 1.00 | 33.87 |
| HETATM O | 2752 | O | HOH | 1 | 75.701 | 41.635 | 35.059 | 1.00 | 43.94 |
| HETATM O | 2753 | O | HOH | 2 | 74.079 | 38.696 | 40.465 | 1.00 | 55.18 |
| HETATM O | 2754 | O | HOH | 3 | 65.938 | 60.588 | 24.743 | 1.00 | 24.75 |
| HETATM O | 2755 | O | HOH | 4 | 90.376 | 44.734 | 34.332 | 1.00 | 58.18 |
| HETATM O | 2756 | O | HOH | 5 | 57.606 | 58.768 | 28.316 | 1.00 | 26.20 |
| HETATM O | 2757 | O | HOH | 6 | 73.742 | 57.520 | 36.339 | 1.00 | 22.08 |
| HETATM O | 2758 | O | HOH | 7 | 59.439 | 45.332 | 37.045 | 1.00 | 28.29 |
| HETATM O | 2759 | O | HOH | 8 | 66.630 | 48.045 | 39.016 | 1.00 | 24.24 |
| HETATM O | 2760 | O | HOH | 9 | 87.313 | 55.537 | 31.236 | 1.00 | 26.94 |
| HETATM O | 2761 | O | HOH | 10 | 79.723 | 41.990 | 29.591 | 1.00 | 24.41 |
| HETATM O | 2762 | O | HOH | 11 | 70.855 | 54.607 | 21.999 | 1.00 | 25.98 |
| HETATM O | 2763 | O | HOH | 12 | 75.110 | 45.838 | 32.838 | 1.00 | 30.43 |
| HETATM O | 2764 | O | HOH | 13 | 71.016 | 53.391 | 14.308 | 1.00 | 28.65 |
| HETATM O | 2765 | O | HOH | 14 | 75.872 | 56.829 | 34.478 | 1.00 | 29.47 |
| HETATM O | 2766 | O | HOH | 15 | 84.437 | 53.172 | 21.050 | 1.00 | 27.86 |
| HETATM O | 2767 | O | HOH | 16 | 76.208 | 43.857 | 31.117 | 1.00 | 21.58 |
| HETATM O | 2768 | O | HOH | 17 | 88.575 | 53.835 | 33.310 | 1.00 | 28.69 |
| HETATM O | 2769 | O | HOH | 18 | 78.805 | 48.189 | 37.292 | 1.00 | 30.37 |
| HETATM O | 2770 | O | HOH | 19 | 81.282 | 64.691 | 32.797 | 1.00 | 26.40 |
| HETATM O | 2771 | O | HOH | 20 | 74.258 | 59.955 | 37.886 | 1.00 | 35.26 |
| HETATM O | 2772 | O | HOH | 21 | 72.681 | 38.221 | 33.950 | 1.00 | 27.93 |
| HETATM O | 2773 | O | HOH | 22 | 56.779 | 57.580 | 38.836 | 1.00 | 33.24 |
| HETATM O | 2774 | O | HOH | 23 | 69.275 | 68.052 | 32.909 | 1.00 | 34.10 |
| HETATM O | 2775 | O | HOH | 24 | 58.760 | 51.196 | 23.042 | 1.00 | 28.36 |
| HETATM O | 2776 | O | HOH | 25 | 79.310 | 40.417 | 32.071 | 1.00 | 30.06 |
| HETATM O | 2777 | O | HOH | 26 | 77.754 | 54.034 | 34.410 | 1.00 | 31.27 |

TABLE 7-continued

| | | | | | | | | | |
|---|---|---|---|---|---|---|---|---|---|
| HETATM | 2778 | O | HOH | 27 | 64.140 | 56.432 | 20.380 | 1.00 | 35.64 |
| O | | | | | | | | | |
| HETATM | 2779 | O | HOH | 28 | 62.442 | 38.699 | 34.139 | 1.00 | 30.68 |
| O | | | | | | | | | |
| HETATM | 2780 | O | HOH | 29 | 65.481 | 36.753 | 34.839 | 1.00 | 29.52 |
| O | | | | | | | | | |
| HETATM | 2781 | O | HOH | 30 | 49.387 | 44.266 | 21.091 | 1.00 | 32.82 |
| O | | | | | | | | | |
| HETATM | 2782 | O | HOH | 31 | 74.171 | 50.758 | 36.345 | 1.00 | 35.61 |
| O | | | | | | | | | |
| HETATM | 2783 | O | HOH | 32 | 76.573 | 41.279 | 32.222 | 1.00 | 30.60 |
| O | | | | | | | | | |
| HETATM | 2784 | O | HOH | 33 | 87.348 | 67.083 | 31.015 | 1.00 | 29.38 |
| O | | | | | | | | | |
| HETATM | 2785 | O | HOH | 34 | 66.425 | 37.664 | 16.827 | 1.00 | 27.26 |
| O | | | | | | | | | |
| HETATM | 2786 | O | HOH | 35 | 59.765 | 51.154 | 9.792 | 1.00 | 31.75 |
| O | | | | | | | | | |
| HETATM | 2787 | O | HOH | 36 | 61.770 | 50.532 | 17.896 | 1.00 | 26.41 |
| O | | | | | | | | | |
| HETATM | 2788 | O | HOH | 37 | 65.804 | 58.780 | 21.469 | 1.00 | 36.21 |
| O | | | | | | | | | |
| HETATM | 2789 | O | HOH | 38 | 76.213 | 52.726 | 36.406 | 1.00 | 34.08 |
| O | | | | | | | | | |
| HETATM | 2790 | O | HOH | 39 | 59.631 | 51.746 | 16.407 | 1.00 | 31.30 |
| O | | | | | | | | | |
| HETATM | 2791 | O | HOH | 40 | 82.391 | 67.258 | 31.863 | 1.00 | 31.37 |
| O | | | | | | | | | |
| HETATM | 2792 | O | HOH | 41 | 70.252 | 33.623 | 27.556 | 1.00 | 35.71 |
| O | | | | | | | | | |
| HETATM | 2793 | O | HOH | 42 | 72.039 | 67.304 | 32.099 | 1.00 | 35.67 |
| O | | | | | | | | | |
| HETATM | 2794 | O | HOH | 43 | 53.140 | 51.705 | 38.165 | 1.00 | 31.55 |
| O | | | | | | | | | |
| HETATM | 2795 | O | HOH | 44 | 67.908 | 38.414 | 46.440 | 1.00 | 32.54 |
| O | | | | | | | | | |
| HETATM | 2796 | O | HOH | 45 | 58.797 | 45.284 | 6.070 | 1.00 | 39.86 |
| O | | | | | | | | | |
| HETATM | 2797 | O | HOH | 46 | 50.916 | 46.272 | 35.836 | 1.00 | 39.05 |
| O | | | | | | | | | |
| HETATM | 2798 | O | HOH | 47 | 48.468 | 54.286 | 36.992 | 1.00 | 37.90 |
| O | | | | | | | | | |
| HETATM | 2799 | O | HOH | 48 | 79.368 | 38.350 | 17.558 | 1.00 | 37.55 |
| O | | | | | | | | | |
| HETATM | 2800 | O | HOH | 49 | 65.917 | 31.312 | 26.738 | 1.00 | 40.60 |
| O | | | | | | | | | |
| HETATM | 2801 | O | HOH | 50 | 75.195 | 38.963 | 31.142 | 1.00 | 31.97 |
| O | | | | | | | | | |
| HETATM | 2802 | O | HOH | 51 | 51.201 | 58.619 | 25.886 | 1.00 | 40.51 |
| O | | | | | | | | | |
| HETATM | 2803 | O | HOH | 52 | 56.361 | 77.266 | 37.184 | 1.00 | 34.64 |
| O | | | | | | | | | |
| HETATM | 2804 | O | HOH | 53 | 75.373 | 38.767 | 8.255 | 1.00 | 34.82 |
| O | | | | | | | | | |
| HETATM | 2805 | O | HOH | 54 | 62.203 | 64.463 | 35.439 | 1.00 | 32.93 |
| O | | | | | | | | | |
| HETATM | 2806 | O | HOH | 55 | 67.513 | 69.374 | 38.251 | 1.00 | 43.30 |
| O | | | | | | | | | |
| HETATM | 2807 | O | HOH | 56 | 59.023 | 38.343 | 34.814 | 1.00 | 35.89 |
| O | | | | | | | | | |
| HETATM | 2808 | O | HOH | 57 | 61.282 | 73.583 | 39.232 | 1.00 | 39.52 |
| O | | | | | | | | | |
| HETATM | 2809 | O | HOH | 58 | 74.916 | 47.914 | 35.808 | 1.00 | 36.57 |
| O | | | | | | | | | |
| HETATM | 2810 | O | HOH | 59 | 62.673 | 61.732 | 37.514 | 1.00 | 33.12 |
| O | | | | | | | | | |
| HETATM | 2811 | O | HOH | 60 | 74.787 | 37.123 | 10.828 | 1.00 | 36.31 |
| O | | | | | | | | | |
| HETATM | 2812 | O | HOH | 61 | 87.050 | 70.287 | 23.795 | 1.00 | 40.37 |
| O | | | | | | | | | |
| HETATM | 2813 | O | HOH | 62 | 60.963 | 37.766 | 37.311 | 1.00 | 46.47 |
| O | | | | | | | | | |
| HETATM | 2814 | O | HOH | 63 | 74.898 | 62.998 | 19.440 | 1.00 | 40.44 |
| O | | | | | | | | | |
| HETATM | 2815 | O | HOH | 64 | 60.204 | 41.357 | 39.977 | 1.00 | 48.22 |
| O | | | | | | | | | |
| HETATM | 2816 | O | HOH | 65 | 83.322 | 55.796 | 16.450 | 1.00 | 32.01 |
| O | | | | | | | | | |

TABLE 7-continued

| | | | | | | | | | |
|---|---|---|---|---|---|---|---|---|---|
| HETATM | 2817 | O | HOH | | 66 | 74.375 | 34.757 | 40.315 | 1.00 36.09 |
| HETATM | 2818 | O | HOH | | 67 | 71.494 | 55.957 | 41.977 | 1.00 32.49 |
| HETATM | 2819 | O | HOH | | 68 | 59.957 | 50.992 | 20.176 | 1.00 43.21 |
| HETATM | 2820 | O | HOH | | 69 | 66.080 | 28.763 | 15.101 | 1.00 39.12 |
| HETATM | 2821 | O | HOH | | 70 | 50.588 | 31.847 | 16.621 | 1.00 43.31 |
| HETATM | 2822 | O | HOH | | 71 | 69.529 | 68.913 | 36.005 | 1.00 40.30 |
| HETATM | 2823 | O | HOH | | 72 | 73.768 | 64.532 | 30.646 | 1.00 40.71 |
| HETATM | 2824 | O | HOH | | 73 | 92.829 | 49.112 | 23.281 | 1.00 44.30 |
| HETATM | 2825 | O | HOH | | 74 | 70.278 | 54.233 | 17.770 | 1.00 32.36 |
| HETATM | 2826 | O | HOH | | 75 | 52.179 | 53.975 | 25.940 | 1.00 38.86 |
| HETATM | 2827 | O | HOH | | 76 | 70.150 | 32.823 | 38.265 | 1.00 49.16 |
| HETATM | 2828 | O | HOH | | 77 | 69.559 | 45.202 | 46.424 | 1.00 37.45 |
| HETATM | 2829 | O | HOH | | 78 | 81.658 | 38.524 | 24.274 | 1.00 39.74 |
| HETATM | 2830 | O | HOH | | 79 | 85.501 | 49.287 | 39.572 | 1.00 41.67 |
| HETATM | 2831 | O | HOH | | 80 | 43.313 | 43.736 | 23.528 | 1.00 38.76 |
| HETATM | 2832 | O | HOH | | 81 | 45.058 | 35.260 | 19.329 | 1.00 48.10 |
| HETATM | 2833 | O | HOH | | 82 | 86.888 | 47.694 | 13.726 | 1.00 42.11 |
| HETATM | 2834 | O | HOH | | 83 | 59.990 | 59.432 | 31.077 | 1.00 43.45 |
| HETATM | 2835 | O | HOH | | 84 | 65.702 | 28.237 | 26.872 | 1.00 41.07 |
| HETATM | 2836 | O | HOH | | 85 | 56.392 | 41.602 | 37.511 | 1.00 42.34 |
| HETATM | 2837 | O | HOH | | 86 | 89.958 | 53.438 | 35.939 | 1.00 44.28 |
| HETATM | 2838 | O | HOH | | 87 | 53.813 | 58.314 | 38.115 | 1.00 43.91 |
| HETATM | 2839 | O | HOH | | 88 | 54.846 | 33.441 | 37.762 | 1.00 45.87 |
| HETATM | 2840 | O | HOH | | 89 | 68.555 | 74.630 | 33.270 | 1.00 45.09 |
| HETATM | 2841 | O | HOH | | 90 | 46.075 | 48.997 | 27.411 | 1.00 39.29 |
| HETATM | 2842 | O | HOH | | 91 | 58.611 | 35.738 | 27.091 | 1.00 37.48 |
| HETATM | 2843 | O | HOH | | 92 | 65.536 | 61.610 | 38.426 | 1.00 47.43 |
| HETATM | 2844 | O | HOH | | 93 | 63.014 | 78.411 | 34.747 | 1.00 48.43 |
| HETATM | 2845 | O | HOH | | 94 | 69.402 | 35.849 | 7.804 | 1.00 43.16 |
| HETATM | 2846 | O | HOH | | 95 | 51.178 | 50.724 | 21.941 | 1.00 39.55 |
| HETATM | 2847 | O | HOH | | 96 | 85.871 | 39.272 | 22.557 | 1.00 42.34 |
| HETATM | 2848 | O | HOH | | 97 | 55.141 | 46.898 | 17.592 | 1.00 50.68 |
| HETATM | 2849 | O | HOH | | 98 | 54.804 | 53.900 | 40.431 | 1.00 53.97 |
| HETATM | 2850 | O | HOH | | 99 | 81.143 | 54.940 | 13.409 | 1.00 49.06 |
| HETATM | 2851 | O | HOH | | 100 | 60.601 | 30.026 | 22.828 | 1.00 51.45 |
| HETATM | 2852 | O | HOH | | 101 | 91.377 | 38.681 | 33.317 | 1.00 51.98 |
| HETATM | 2853 | O | HOH | | 102 | 50.491 | 32.970 | 12.092 | 1.00 45.61 |
| HETATM | 2854 | O | HOH | | 103 | 65.951 | 63.935 | 21.639 | 1.00 45.03 |
| HETATM | 2855 | O | HOH | | 104 | 92.613 | 40.981 | 20.428 | 1.00 51.23 |

TABLE 7-continued

| HETATM | 2856 | O | HOH | 105 | 66.842 | 34.584 | 37.015 | 1.00 | 49.51 |
|---|---|---|---|---|---|---|---|---|---|
| HETATM | 2857 | O | HOH | 106 | 79.154 | 37.014 | 24.773 | 1.00 | 43.76 |
| HETATM | 2858 | O | HOH | 107 | 72.247 | 31.318 | 24.007 | 1.00 | 40.85 |
| HETATM | 2859 | O | HOH | 108 | 60.754 | 51.022 | 46.130 | 1.00 | 52.32 |
| HETATM | 2860 | O | HOH | 109 | 45.352 | 44.922 | 33.115 | 1.00 | 39.72 |
| HETATM | 2861 | O | HOH | 110 | 43.049 | 56.846 | 35.553 | 1.00 | 56.39 |
| HETATM | 2862 | O | HOH | 111 | 93.844 | 47.843 | 37.235 | 1.00 | 47.50 |
| HETATM | 2863 | O | HOH | 112 | 72.886 | 49.728 | 42.684 | 1.00 | 42.85 |
| HETATM | 2864 | O | HOH | 113 | 44.622 | 43.340 | 15.564 | 1.00 | 48.15 |
| HETATM | 2865 | O | HOH | 114 | 56.638 | 31.718 | 23.687 | 1.00 | 50.30 |
| HETATM | 2866 | O | HOH | 115 | 75.960 | 53.691 | −1.202 | 1.00 | 54.62 |
| HETATM | 2867 | O | HOH | 116 | 63.275 | 58.904 | 18.617 | 1.00 | 44.23 |
| HETATM | 2868 | O | HOH | 117 | 58.451 | 52.848 | 43.791 | 1.00 | 49.56 |
| HETATM | 2869 | O | HOH | 118 | 54.165 | 41.889 | 6.948 | 1.00 | 52.21 |
| HETATM | 2870 | O | HOH | 119 | 49.652 | 53.672 | 24.234 | 1.00 | 60.78 |
| HETATM | 2871 | O | HOH | 120 | 53.791 | 55.765 | 20.073 | 1.00 | 41.34 |
| HETATM | 2872 | O | HOH | 121 | 82.081 | 63.415 | 21.222 | 1.00 | 39.55 |
| HETATM | 2873 | O | HOH | 122 | 59.793 | 54.194 | 20.862 | 1.00 | 39.76 |
| HETATM | 2874 | O | HOH | 123 | 91.395 | 41.899 | 35.234 | 1.00 | 47.28 |
| HETATM | 2875 | O | HOH | 124 | 78.660 | 72.133 | 28.009 | 1.00 | 48.50 |
| HETATM | 2876 | O | HOH | 125 | 76.816 | 36.477 | 6.733 | 1.00 | 59.31 |
| HETATM | 2877 | O | HOH | 126 | 51.697 | 56.879 | 39.951 | 1.00 | 56.83 |
| HETATM | 2878 | O | HOH | 127 | 73.160 | 41.047 | 42.151 | 1.00 | 46.35 |
| HETATM | 2879 | O | HOH | 128 | 78.361 | 33.624 | 16.246 | 1.00 | 47.03 |
| HETATM | 2880 | O | HOH | 129 | 65.071 | 63.965 | 35.876 | 1.00 | 40.53 |
| HETATM | 2881 | O | HOH | 130 | 75.546 | 70.802 | 31.702 | 1.00 | 43.13 |
| HETATM | 2882 | O | HOH | 131 | 45.695 | 41.554 | 13.117 | 1.00 | 46.21 |
| HETATM | 2883 | O | HOH | 132 | 74.770 | 75.486 | 30.649 | 1.00 | 50.17 |
| HETATM | 2884 | O | HOH | 133 | 61.457 | 33.492 | 27.149 | 1.00 | 38.92 |
| HETATM | 2885 | O | HOH | 134 | 78.747 | 70.267 | 25.631 | 1.00 | 47.28 |
| HETATM | 2886 | O | HOH | 135 | 67.587 | 59.325 | 38.812 | 1.00 | 44.68 |
| HETATM | 2887 | O | HOH | 136 | 56.460 | 34.436 | 25.338 | 1.00 | 50.36 |
| HETATM | 2888 | O | HOH | 137 | 87.425 | 55.130 | 37.159 | 1.00 | 57.77 |
| HETATM | 2889 | O | HOH | 138 | 62.549 | 55.054 | 1.389 | 1.00 | 52.64 |
| HETATM | 2890 | O | HOH | 139 | 63.046 | 39.459 | 6.185 | 1.00 | 33.80 |
| HETATM | 2891 | O | HOH | 140 | 52.457 | 45.986 | 7.697 | 1.00 | 51.12 |
| HETATM | 2892 | O | HOH | 141 | 68.162 | 53.372 | 47.262 | 1.00 | 59.06 |
| HETATM | 2893 | O | HOH | 142 | 54.370 | 73.869 | 39.160 | 1.00 | 53.30 |
| HETATM | 2894 | O | HOH | 143 | 58.332 | 49.599 | 44.654 | 1.00 | 56.73 |

TABLE 7-continued

| | | | | | | | | | |
|---|---|---|---|---|---|---|---|---|---|
| HETATM | 2895 | O | HOH | 144 | 57.914 | 66.131 | 38.178 | 1.00 | 50.57 |
| HETATM | 2896 | O | HOH | 145 | 69.153 | 44.094 | 0.472 | 1.00 | 58.32 |
| HETATM | 2897 | O | HOH | 146 | 70.955 | 57.555 | 14.580 | 1.00 | 42.14 |
| HETATM | 2898 | O | HOH | 147 | 64.290 | 80.942 | 33.633 | 1.00 | 50.16 |
| HETATM | 2899 | O | HOH | 148 | 71.059 | 63.093 | 33.999 | 1.00 | 48.63 |
| HETATM | 2900 | O | HOH | 149 | 68.250 | 44.131 | 48.927 | 1.00 | 56.50 |
| HETATM | 2901 | O | HOH | 150 | 53.995 | 61.899 | 36.136 | 1.00 | 38.46 |
| HETATM | 2902 | O | HOH | 151 | 61.723 | 64.570 | 38.471 | 1.00 | 57.73 |
| HETATM | 2903 | O | HOH | 152 | 72.479 | 45.867 | 47.190 | 1.00 | 59.67 |
| HETATM | 2904 | O | HOH | 153 | 72.416 | 63.521 | 16.449 | 1.00 | 43.93 |
| HETATM | 2905 | O | HOH | 154 | 72.663 | 61.263 | 18.483 | 1.00 | 55.81 |
| HETATM | 2906 | O | HOH | 155 | 78.290 | 65.312 | 33.155 | 1.00 | 53.08 |
| HETATM | 2907 | O | HOH | 156 | 94.608 | 53.219 | 22.065 | 1.00 | 52.11 |
| HETATM | 2908 | O | HOH | 157 | 75.671 | 73.066 | 28.735 | 1.00 | 53.82 |
| HETATM | 2909 | O | HOH | 158 | 75.598 | 67.940 | 32.952 | 1.00 | 59.45 |
| HETATM | 2910 | O | HOH | 159 | 75.773 | 35.559 | 27.231 | 1.00 | 45.26 |
| HETATM | 2911 | O | HOH | 160 | 97.730 | 48.875 | 26.955 | 1.00 | 50.24 |
| HETATM | 2912 | O | HOH | 161 | 95.855 | 46.417 | 27.517 | 1.00 | 51.32 |
| HETATM | 2913 | O | HOH | 162 | 94.096 | 48.923 | 26.023 | 1.00 | 51.83 |
| HETATM | 2914 | O | HOH | 163 | 91.721 | 50.895 | 35.397 | 1.00 | 58.59 |
| HETATM | 2915 | O | HOH | 164 | 92.397 | 47.915 | 34.455 | 1.00 | 52.43 |
| HETATM | 2916 | O | HOH | 165 | 97.410 | 43.546 | 26.476 | 1.00 | 59.63 |
| HETATM | 2917 | O | HOH | 166 | 90.165 | 38.748 | 36.119 | 1.00 | 56.38 |
| HETATM | 2918 | O | HOH | 167 | 94.316 | 37.414 | 34.403 | 1.00 | 54.53 |
| HETATM | 2919 | O | HOH | 168 | 43.075 | 36.122 | 24.970 | 1.00 | 55.92 |
| HETATM | 2920 | O | HOH | 169 | 67.736 | 76.231 | 16.895 | 1.00 | 56.81 |
| HETATM | 2921 | O | HOH | 170 | 71.677 | 32.859 | 30.158 | 1.00 | 52.78 |
| HETATM | 2922 | O | HOH | 171 | 68.554 | 30.002 | 38.857 | 1.00 | 54.82 |
| HETATM | 2923 | O | HOH | 172 | 73.000 | 33.391 | 26.251 | 1.00 | 47.75 |
| HETATM | 2924 | O | HOH | 173 | 68.812 | 31.473 | 26.121 | 1.00 | 56.59 |
| HETATM | 2925 | O | HOH | 174 | 63.228 | 31.574 | 25.697 | 1.00 | 48.31 |
| HETATM | 2926 | O | HOH | 175 | 62.682 | 33.531 | 30.030 | 1.00 | 49.27 |
| HETATM | 2927 | O | HOH | 176 | 65.167 | 31.555 | 29.683 | 1.00 | 55.99 |
| HETATM | 2928 | O | HOH | 177 | 56.336 | 48.164 | 14.845 | 1.00 | 48.86 |
| HETATM | 2929 | O | HOH | 178 | 78.620 | 50.501 | 10.475 | 1.00 | 62.38 |
| HETATM | 2930 | O | HOH | 179 | 84.701 | 43.066 | 9.965 | 1.00 | 56.01 |
| HETATM | 2931 | O | HOH | 180 | 77.072 | 52.215 | −3.925 | 1.00 | 52.09 |
| HETATM | 2932 | O | HOH | 181 | 81.505 | 72.460 | 16.927 | 1.00 | 56.81 |
| HETATM | 2933 | O | HOH | 182 | 56.776 | 62.766 | 36.110 | 1.00 | 35.88 |

TABLE 7-continued

| | | | | | | | | | |
|---|---|---|---|---|---|---|---|---|---|
| HETATM | 2934 | O | HOH | 183 | 52.708 | 50.106 | 19.084 | 1.00 | 46.95 |
| O | | | | | | | | | |
| HETATM | 2935 | O | HOH | 184 | 58.949 | 41.892 | 6.150 | 1.00 | 50.09 |
| O | | | | | | | | | |
| HETATM | 2936 | O | HOH | 185 | 66.279 | 40.996 | 3.132 | 1.00 | 51.65 |
| O | | | | | | | | | |
| HETATM | 2937 | O | HOH | 186 | 72.364 | 36.495 | 6.684 | 1.00 | 54.90 |
| O | | | | | | | | | |
| HETATM | 2938 | O | HOH | 187 | 64.663 | 41.304 | 7.894 | 1.00 | 34.55 |
| O | | | | | | | | | |
| HETATM | 2939 | O | HOH | 188 | 49.873 | 42.836 | 7.978 | 1.00 | 55.76 |
| O | | | | | | | | | |
| HETATM | 2940 | O | HOH | 189 | 57.589 | 27.901 | 17.205 | 1.00 | 55.94 |
| O | | | | | | | | | |
| HETATM | 2941 | O | HOH | 190 | 54.487 | 27.148 | 17.217 | 1.00 | 56.50 |
| O | | | | | | | | | |
| HETATM | 2942 | O | HOH | 191 | 74.055 | 29.387 | 14.028 | 1.00 | 55.18 |
| O | | | | | | | | | |
| HETATM | 2943 | O | HOH | 192 | 73.877 | 34.935 | 8.889 | 1.00 | 54.31 |
| O | | | | | | | | | |
| HETATM | 2944 | O | HOH | 193 | 64.874 | 25.940 | 14.827 | 1.00 | 47.78 |
| O | | | | | | | | | |
| HETATM | 2945 | O | HOH | 194 | 40.739 | 38.113 | 26.191 | 1.00 | 56.93 |
| O | | | | | | | | | |
| HETATM | 2946 | O | HOH | 195 | 81.037 | 48.857 | 11.250 | 1.00 | 51.13 |
| O | | | | | | | | | |
| HETATM | 2947 | O | HOH | 196 | 43.149 | 34.719 | 28.062 | 1.00 | 59.10 |
| O | | | | | | | | | |
| HETATM | 2948 | O | HOH | 197 | 63.348 | 58.590 | 43.529 | 1.00 | 57.64 |
| O | | | | | | | | | |
| HETATM | 2949 | O | HOH | 198 | 48.595 | 31.656 | 25.612 | 1.00 | 58.04 |
| O | | | | | | | | | |
| HETATM | 2950 | O | HOH | 199 | 58.778 | 58.864 | 41.117 | 1.00 | 54.64 |
| O | | | | | | | | | |
| HETATM | 2951 | O | HOH | 200 | 52.055 | 49.602 | 40.062 | 1.00 | 50.74 |
| O | | | | | | | | | |
| HETATM | 2952 | O | HOH | 201 | 55.370 | 44.532 | 39.918 | 1.00 | 58.59 |
| O | | | | | | | | | |
| CONECT | 202 | 2494 | | | | | | | |
| CONECT | 1501 | 1502 | | | | | | | |
| CONECT | 1502 | 1501 | 1503 | 1505 | | | | | |
| CONECT | 1503 | 1502 | 1504 | | | | | | |
| CONECT | 1504 | 1503 | 1507 | | | | | | |
| CONECT | 1505 | 1502 | 1506 | | | | | | |
| CONECT | 1506 | 1505 | | | | | | | |
| CONECT | 1507 | 1504 | | | | | | | |
| CONECT | 2494 | 202 | | | | | | | |
| CONECT | 2731 | 2732 | 2733 | 2734 | 2735 | | | | |
| CONECT | 2732 | 2731 | | | | | | | |
| CONECT | 2733 | 2731 | | | | | | | |
| CONECT | 2734 | 2731 | | | | | | | |
| CONECT | 2735 | 2731 | 2736 | | | | | | |
| CONECT | 2736 | 2735 | 2737 | | | | | | |
| CONECT | 2737 | 2736 | 2738 | 2739 | | | | | |
| CONECT | 2738 | 2737 | 2743 | | | | | | |
| CONECT | 2739 | 2737 | 2740 | 2741 | | | | | |
| CONECT | 2740 | 2739 | | | | | | | |
| CONECT | 2741 | 2739 | 2742 | 2743 | | | | | |
| CONECT | 2742 | 2741 | | | | | | | |
| CONECT | 2743 | 2738 | 2741 | 2744 | | | | | |
| CONECT | 2744 | 2743 | 2745 | 2751 | | | | | |
| CONECT | 2745 | 2744 | 2746 | | | | | | |
| CONECT | 2746 | 2745 | 2747 | | | | | | |
| CONECT | 2747 | 2746 | 2748 | 2751 | | | | | |
| CONECT | 2748 | 2747 | 2749 | 2750 | | | | | |
| CONECT | 2749 | 2748 | | | | | | | |
| CONECT | 2750 | 2748 | | | | | | | |
| CONECT | 2751 | 2744 | 2747 | | | | | | |
| MASTER | | 497 | 0 | 4 | 14 | 180 | 0 6 | 2951 | 1 30 39 |
| END | | | | | | | | | |

TABLE 8

Comparison of published IMPDH structures.

| Species | Resolution | R (R$_{free}$) in % | Missing residues | Heteroatoms | PDB ID |
|---|---|---|---|---|---|
| Human | 2.9 Å | 24.4 (27.0) | 2$^{nd}$ domain 130–139, 159–177, flap 400–448, end 499–514 | CPR, SAD | 1B30 |
| Hamster | 2.6 Å | 21.7 (28.5) | 2$^{nd}$ domain 121–177, flap 421–436 | K$^+$, XMP*, MPA | 1JR1 |
| Borrelia | 2.4 Å | 21.5 (26.8) | 2$^{nd}$ domain 92–129, flap 309–344 | SO$_4^+$ | 1EEP |
| *S. pyogenes* | 1.9 Å | 23.4 (25.8) | Flap 401–414, end 490–493 | IMP | 1ZFJ |
| *T. foetus* apo | 2.3 Å | 21.8 (26.5) | 2$^{nd}$ domain 102–221, loop 314–327, flap 413–431 | SO$_4^+$ | 1AK5 |
| *T. foetus* + XMP | 2.6 Å | 20.3 (26.4) | 2$^{nd}$ domain 102–221, loop 314–324, flap 413–431, end 484–503 | XMP | N/A |

* denotes covalent intermediate

TABLE 9

Data collection and refinement statistics.

| Structure | RMP | RMP + MPA |
|---|---|---|
| Wavelength (Å) | 0.97 | 0.97 |
| Resolution range (Å) | 50–1.90 | 50–2.15 |
| Resolution of outer shell (Å) | 1.90–2.02 | 2.15–2.28 |
| Current R (R$_{FREE}$) (%) | 24.3 (25.9) | 23.3 (26.5) |
| Unique reflections | 50,359 | 35,250 |
| Total observations | 1,289,813 | 620,781 |
| I/σ$_I$ overall/outer shell | 33.77/2.39 | 23.59/2.05 |
| R$_{sym}$ overall/outer shell (%) | 6.2/68.9 | 7.2/49.1 |
| Completeness overall/outer shell (%) | 99.9/100 | 94.0/79.5 |
| Degrees collected | 25 | 20 |
| Number of ordered water molecules | 211 | 120 |
| Deviation from ideal bond lengths (Å) | 0.005 | 0.006 |
| Bond angle RMSD (°) | 1.2 | 1.2 |
| Dihedral angle RMSD (°) | 22.7 | 22.6 |
| Improper angle RMSD (°) | 0.71 | 0.70 |
| Cell dimensions α = β = χ = 90°, a = b = c (Å) | 154.7 | 155.1 |
| Space group | P432 | P432 |
| Mosaicity (°) | 0.45 | 0.50 |

---

What is claimed is:

1. The crystalline complex comprising *T. foetus* IMPDH in complex with ribavirin monophosphate (1-β-D-ribofuranosyl-1,2,4-triazole-3-carboxamide monophosphate), having atomic coordinates set forth in Table 7.

2. The crystalline complex comprising *T. foetus* IMPDH in complex with ribavirin monophosphate and mycophenolic acid, having atomic coordinates set forth in Table 6.

* * * * *